US006537773B1

(12) United States Patent
Fraser et al.

(10) Patent No.: US 6,537,773 B1
(45) Date of Patent: *Mar. 25, 2003

(54) NUCLEOTIDE SEQUENCE OF THE MYCOPLASMA GENITALIUM GENOME, FRAGMENTS THEREOF, AND USES THEREOF

(75) Inventors: Claire M. Fraser, Potomac, MD (US); Mark D. Adams, N. Potomac, MD (US); Jeannine D. Gocayne, Silver Spring, MD (US); Clyde A. Hutchison, III, Chapel Hill, NC (US); Hamilton O. Smith, Towson, MD (US); J. Craig Venter, Potomac, MD (US); Owen White, Gaithersburg, MD (US)

(73) Assignees: The Institute for Genomic Research, Rockville, MD (US); Johns Hopkins University, Baltimore, MD (US); The University of North Carolina at Chapel Hill, Chapel Hill, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 46 days.

This patent is subject to a terminal disclaimer.

(21) Appl. No.: 08/545,528

(22) Filed: Oct. 19, 1995

Related U.S. Application Data

(63) Continuation-in-part of application No. 08/488,018, filed on Jun. 7, 1995, now abandoned, and a continuation-in-part of application No. 08/473,545, filed on Jun. 7, 1995, now abandoned.

(51) Int. Cl.[7] .................................................. C12Q 1/68
(52) U.S. Cl. .................. 435/69.1; 536/23.7; 536/24.32; 435/252.3; 435/320.1
(58) Field of Search .............................. 536/23.7, 23.1, 536/24.3, 24, 52; 435/69.1, 320.1

(56) References Cited

U.S. PATENT DOCUMENTS

| 5,064,754 A | 11/1991 | Mills ............................. 435/6 |
| 5,202,231 A | 4/1993 | Drmanac et al. ............... 435/6 |
| 5,219,726 A | 6/1993 | Evans ............................ 435/6 |
| 5,288,644 A | 2/1994 | Beavis et al. ................ 436/94 |
| 5,512,457 A | * 4/1996 | Lyman et al. ............... 435/69.5 |

FOREIGN PATENT DOCUMENTS

| EP | 0401979 | * 12/1990 |
| EP | 0 646 883 A1 | 4/1995 |
| WO | 94/04675 | * 3/1994 |

OTHER PUBLICATIONS

Sambrook et al Moleclar Cloning, Second Edition, Cold Spring Harbor Laboratory Press, 1989, p. 9.51, 1989.*
Voet et al Biochemistry, Second Edition, John Wiley & Sons, Inc., p. 683, second full paragraph, Jun. 1995.*
Rudinger (In Peptide Hormones, J.A. Parsons Ed. University Park press, Baltimore, See page 6, last paragraph, Jun. 1996.*
Bonner et al J. Mol Biol. 81: 123–135, Dec. 1973.*
SD Colman et al (1990) Molecular Microbiology 4: 683–687.*
JM Inamine et al (1989) Gene 82: 259–267.*
SN Peterson et al (1993) J Bacteriology 175: 7918–7930.*
Peterson et al., PNAS, vol. 92(25):11829–11833 (1995).
Reddy et al., J. Bact., vol. 177:5943–5951 (1995).
Fraser et al., Science, vol. 270:397–403 (1995).
GenBank Accession No: U39679 (XP–002089187) (Nov. 3, 1995).
Adams, M. D. et al., "A model for high–throughput automated DNA sequencing and analysis core facilities," *Nature* 368:474–475 (Mar. 1994).
Altschul, S. F. et al., "Basic Local Alignment Search Tool," *J. Mol. Biol.* 215:403–410 (1990).
Bailey, C. C. and Bott, K. F., "An Unusual Gene Containing a *dnaJ* N–Terminal Box Flanks the Putative Origin of Replication of *Mycoplasma genitalium*," *J. Bacteriol.* 176(18):5814–5819 (Sep. 1994).
Borodovsky, M. and McIninch, J., "Genmark: Parallel Gene Recognition for Both DNA Strands," *Computers Chem.* 17(2):123–133 (1993).
Brutlag, D. L. et al., "Blaze™: An Implementation of the Smith–Waterman Sequence Comparison Algorithm on a Massively Parallel Computer," *Computers Chem.* 17(2):203–207 (1993).
Colman, S. D., "Characterization of the genomes of *Mycoplasma pneumoniae* and *Mycoplasma genitalium*," Dialog File 35:Dissertation Abstracts Online, Accession No. 01142941 (1989).
Colman, S. D. et al., "Prevalence of novel repeat sequences in and around the *P1* operon in the genome of *Mycoplasma pneumoniae*," *Gene* 87:91–96 (1990).

(List continued on next page.)

*Primary Examiner*—James Ketter
*Assistant Examiner*—Richard Schnizer
(74) *Attorney, Agent, or Firm*—Human Genome Sciences, Inc.

(57) ABSTRACT

The present invention provides the nucleotide sequence of the entire genome of *Mycoplasma genitalium*, SEQ ID NO:1. The present invention further provides the sequence information stored on computer readable media, and computer-based systems and methods which facilitate its use. In addition to the entire genomic sequence, the present invention identifies protein encoding fragments of the genome, and identifies, by position relative to two (2) genes known to flank the origin of replication, any regulatory elements which modulate the expression of the protein encoding fragments of the *Mycoplasma genitalium* genome.

44 Claims, 23 Drawing Sheets

OTHER PUBLICATIONS

Figure 1:
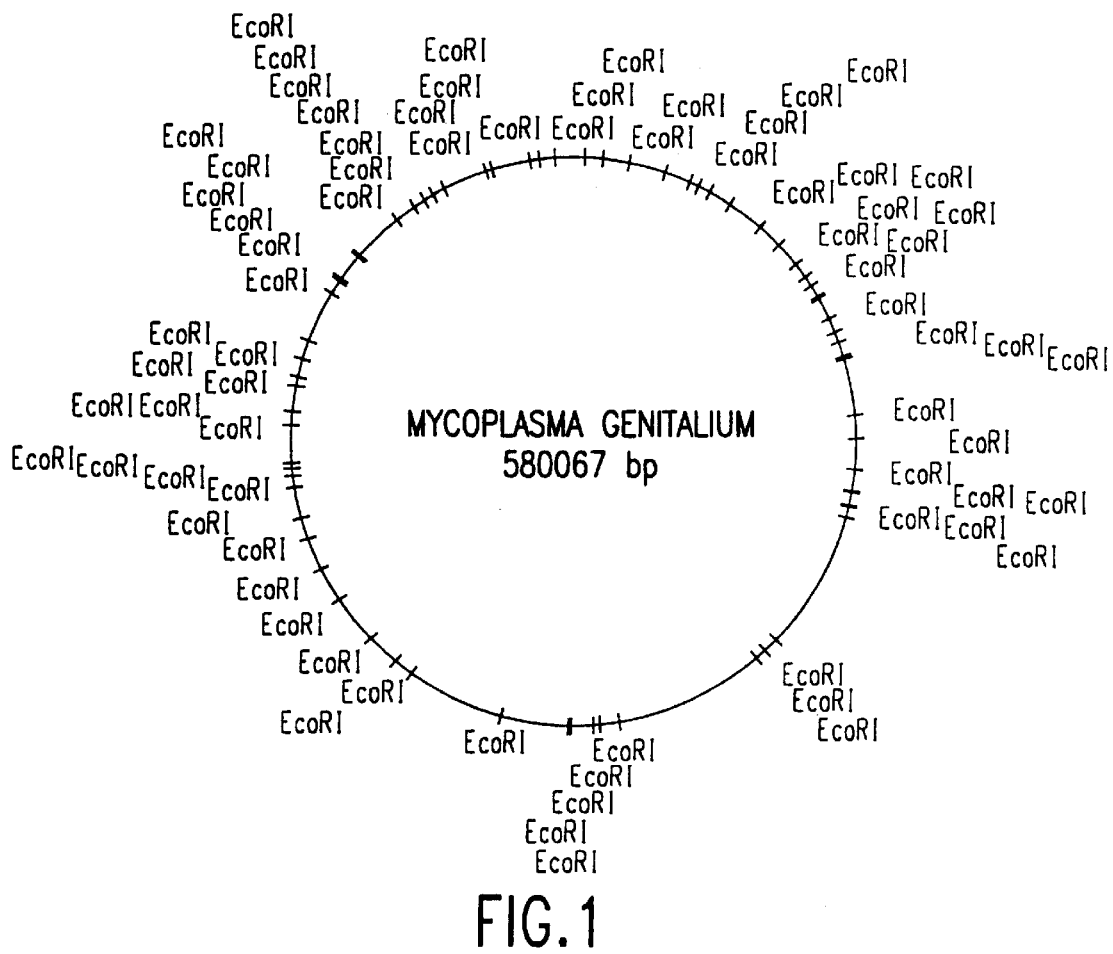
Figure 2:
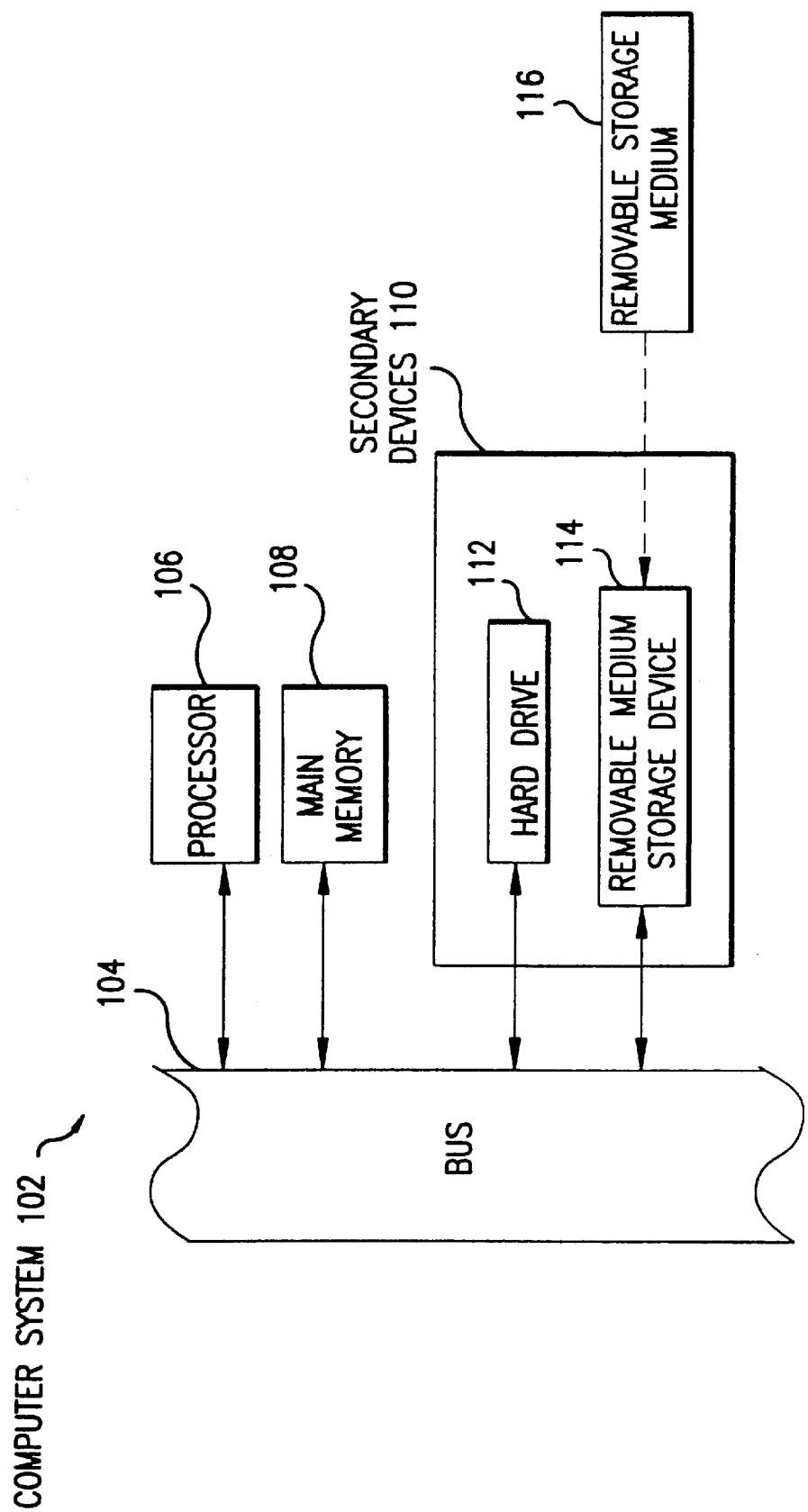

Colman, S. D. et al., "A physical map of the *Mycoplasma genitalium* genome," *Mol. Microbiol.* 4(4):683–687 (1990).

Dallo, S. F. et al., "Adhesin gene of *Mycoplasma genitalium* exists as multiple copies," *Microbial Path.* 10:475–480 (1991).

Dallo, S. F. et al., "DNA and Protein Sequence Homologies between the Adhesins of *Mycoplasma genitalium* and *Mycoplasma pneumoniae*," *Inf. Immun.* 57(4):1059–1065 (1989).

Dallo, S. F. et al., "Homologous regions shared by adhesin genes of *Mycoplasma pneumoniae* and *Mycoplasma genitalium*," *Microbial Path.* 6:69–73 (1989).

Dybvig, K., "Gene Transfer," in: *Mycoplasma: Molecular Biology and Pathogenesis*, Maniloff, J., ed., American Society for Microbiology: Washington, DC pp. 355–362 (1992).

Inamine, J. M. et al., "Nucleotide sequence of the *MgPa(mgp)* operon of *Mycoplasma genitalium* and comparison to the *P1(mpp)* operon of *Mycoplasma pneumoniae*," *Gene* 82:259–267 (1989).

Levy, J., "Sequencing the Yeast Genome: An International Achievement," *Yeast* 10:1689–1706 (Dec. 1994).

Loechel, S. et al., "A novel translation initiation region from *Mycoplasma genitalium* that functions in *Escherichia coli*," *Nucleic Acids Res.* 19(24):6905–6911 (1991).

Loechel, S. et al., "Nucleotide sequence of the *tuf* gene from *Mycoplasma genitalium*," *Nucleic Acids Res.* 17(23):10127 (1989).

Lucier, T. et al., "An Ordered Genomic Library of *Mycoplasma genitalium*," 93rd General Meeting of the American Society for Microbiology, Atlanta, Georgia, May 16–20, 1993, Abstract G–26 (1993).

Lucier, T. S. et al., "Construction of an ordered genomic library of *Mycoplasma genitalium*," *Gene* 150:27–34 (Dec. 1994).

Neimark, H. C. et al., "Pulse–field electrophoresis indicates full–length mycoplasma chromosomes range widely in size," *Nucleic Acids Res.* 18(18):5443–5448 (1990).

Nowak, R., "Venter Wins Sequencing Race—Twice," *Science* 268:1273 (Jun. 1995).

Peterson, S. N. et al., "A random sequencing approach for placing markers on the physical map of *Mycoplasma genitalium*," *Nucleic Acids Res.* 19(21):6027–6031 (1991).

Peterson, S. N., "Characterization and analysis of the *Mycoplasma genitalium* genome," Dialog File 35:Disseration Abstracts Online, Accession No. 0128135 (1992).

Peterson, S. N. et al., "A Survey of the *Mycoplasma genitalium* Genome by Using Random Sequencing," *J. Bacteriol.* 175(24):7918–7930 (1993).

Peterson, S. N. et al., "Genetic Map of the *Mycoplasma genitalium* Chromosome," *J. Bacteriol.* 177(11):3199–3204 (Jun. 1995).

Pyle, L. E. et al., "Pulsed–field electrophoresis indicates Larger–than–expected sizes for mycoplasma genomes," *Nucleic Acids Res.* 16(13):6015–6025 (1988).

Razin, S., "Molecular Biology and Genetics of Mycoplasmas (*Mollicutes*)," *Microbiol. Rev.* 49(4):419–455 (1985).

Richards, S. et al., "Sequence Map Gaps and Directed Reverse Sequencing for the Completion of Large Sequencing Projects," in: *Automated DNA Sequencing and Analysis*, Adams, M.D. et al., eds., Academic Press Inc.:San Diego (Jun. 1994).

Su, C. J. et al., "Genome Size of *Mycoplasma genitalium*," *J. Bacteriol.* 172(8):4705–4707 (1990).

Waterman, M. S., "Computer Analysis of Nucleic Acid Sequences," *Meth. Enzymol.* 164:765–812 (1988).

Yogev, D. and Razin, S., "Common Deoxyribonucleic Acid Sequences in *Mycoplasma genitalium* and *Mycoplasma pneumoniae* Genomes," *Internat. J. Systemat. Bacteriol.* 36(3):426–430 (1986).

\* cited by examiner

SUMMARY OF MYCOPLASMA GENITALIUM SEQUENCING PROJECT

| | |
|---|---|
| TOTAL TEMPLATES PREPARED | 5760 |
| TOTAL SEQUENCEABLE TEMPLATES | 5423 (94%) |
| TOTAL FORWARD REACTIONS COMPLETED | 4986 |
| TOTAL FORWARD REACTIONS WITH GOOD DATA | 4401 |
| AVG EDITED LENGTH OF FORWARD REACTIONS | 475 |
| SUCCESS RATE OF FORWARD REACTIONS | 88% |
| TOTAL REVERSE REACTIONS COMPLETED | 4860 |
| TOTAL REVERSE REACTIONS WITH GOOD DATA | 4071 |
| AVG EDITED LENGTH OF REVERSE REACTIONS | 444 |
| SUCCESS RATE OF REVERSE REACTIONS | 83.7% |

FIG.3

NUCLEOTIDE SEQUENCE OF THE MYCOPLASMA GENITALIUM GENOME, FRAGMENTS THEREOF, AND USES THEREOF

CROSS REFERENCE TO RELATED APPLICATIONS

This application is a continuation-in-part of application Ser. Nos. 08/488,018 and 08/473,545, both filed Jun. 7, 1995, both abandoned and both of which are hereby incorporated by reference.

STATEMENT AS TO RIGHTS TO INVENTION MADE UNDER FEDERALLY-SPONSORED RESEARCH AND DEVELOPMENT

Part of the work performed during development of this invention utilized U.S. Government funds. The U.S. Government may have certain rights in the invention-DE-FC02-95ER61962.A000; NP-838C; and NIH-AI08998,

BACKGROUND OF THE INVENTION

1. Field of the Invention

The present invention relates to the field of molecular biology. The invention discloses compositions comprising the nucleotide sequence of *Mycoplasma genitalium*, fragments thereof, and its use in medical diagnostics, therapies and pharmaceutical development.

2. Related Background Art

Mycoplasmas are the smallest free-living bacterial organisms known (Colman, S. D. et al., *Mol. Microbiol.* 4:683–687 (1990)). Mycoplasmas are thought to have evolved from higher gram-positive bacteria through the loss of genetic material (Bailey, C. C. et al., *J. Bacteriol.* 176:5814–5819 (1994)). *Mycoplasma genitalium* (*M. genitalium*)is widely considered to be the smallest self-replicating biological system, as the molecular size of its genome has been shown to be only 570–600 kp (Pyle, L. E. et al., *Nucleic Acids Res.* 16(13):6015–6025 (1988); Peterson, S. N. et al., *J. Bacteriol.* 175:7918–7930 (1993)). All mycoplasmas lack a cell wall and have small genomes and a characteristically low G+C content (Razin, S., *Microbiol. Rev.* 49(4):419–455 (1985); Peterson, S. N. et al., *J. Bacteriol.* 175:7918–7930 (1993)). Some mycoplasmas, including *M genitalium*, have a specialized codon usage, whereby UGA encodes tryptophan rather than serving as a stop codon (Inamine, J. M. et al., *J. Bacteriol.* 172:504–506 (1990); Tanaka, J. G. et al., *Nucleic Acids Res.* 19:6787–6792 (1991); Yamao, F. A. et al., *Proc. Natl. Acad. Sci. USA* 82:2306–2309 (1985)).

Mycoplasmas are widely known to be significant pathogens of humans, animals, and plants (Bailey, C. C. et al., *J. Bacteriol.* 176:5814–5819 (1994)). The metabolic systems of mycoplasmas indicate that they are generally biosynthetically deficient, and thus depend on the microenvironment of the host by characteristically adhering to host cells in order to obtain essential precursor molecules, i.e., amino acids, fatty acids and sterols etc. (Baseman, J. B., 1987. *Micoplasma Membranes*, Vol. 20. The Plenum Press, New York, N.Y.).

In particular, *M. genitalium*, a newly discovered species, is a pathogenic etiological agent first isolated in 1980 from the urethras of human males infected with non-gonococcal urethritis (Tully, J. G. et al., Lancet 1:1288–1291 (1981); Tully, J. G., et al., *Int. J. Syst. Bacteriol.* 33:387–396 (1983)). *M. genitalium* has also been identified in specimens of pneumonia patients as a co-isolate of *Micoplasma pneumoniae* (Baseman, J. B. et al., *J. Clin. Microbiol.* 26:2266–2269 (1988)). *M. genitalium* opportunistic infection has often been observed in individuals infected with human immunodeficiency virus type 1 (HIV-1) (Lo, S.-C. et al., *Amer. J. Trop. Med. Hyg.* 41:601–616 (1989); Lo, S.-C. et al., *Amer. J. Trop. Med. Hyg.* 41:601–616 (1989); Sasaki, Y. et al., *AIDS Res. Hum. Retrov.* 9(8):775–780 (1993)). Mycoplasmas can also induce various cytokines, including tumor necrosis factor, which may enhance HIV replication (Chowdhury, I. H. et al., *Biochem. Biophys. Res. Commun.* 170:1365–1370 (1990)).

A high amino acid homology exists between the attachment protein of *M. genitalium* and the aligned proteins of several human Class II major histocompatibility complex proteins (HLA), suggesting that *M. genitalium* infection may play an important role in triggering autoimmune mechanisms, thereby aggravating the immunodeficiency characteristics of acquired immune deficiency syndrome (AIDS) (Montagnier, L. et al., *C.R. Acad. Sci. Paris* 311(3):425–430 (1990); Root-Bernstein, R. S. et al., *Res. Immunol.* 142:519–523 (1991); Bisset, L. R. *Autoimmunity* 14:167–168 (1992)). A diagnostic immunoassay for detecting *M. genitalium* infection using monoclonal antibodies specific for some *M. genitalium* antigens has been developed. Baseman, J. B. et al., U.S. Pat. No. 5,158,870.

Due to its diminutive genomic size, *M. genitalium* provides a useful model for determining the minimum number of genes and protein products necessary for a host-independent existence. *M. genitalium* expresses a characteristically low number of base-pairs and low G+C content, which along with its UGA tryptophan codon, has hampered sequencing efforts by conventional techniques (Razin, A., *Microbiol. Rev.* 49(4):419–455 (1985); Colman, S. D. et al., *Gene* 87:91–96 (1990); Dybvig, K. 1992. Gene Transfer In: Maniloff, J. (ed.) *Mycoplasmas: Molecular Biology and Pathogenesis.*, Am. Soc. Microbiol. Washington, D.C., pp.355–362)). *M. genitalium* possesses a single circular chromosome (Colman, S. D. et al., *Gene* 87:91–96 (1990); Peterson, S. N. et al., *J. Bacteriol.* 175:7918–7930 (1993)). The characterization of the genome of *M. genitalium* has also been hampered by the lack of auxotrophic mutants and by the lack of a system for genetic exchange, precluding reverse genetic approaches. Thus, the sequencing of the *M. genitalium* genome would enhance the understanding of how *M. genitalium* causes or promotes various invasive or immunodeficiency diseases and to how best to medically combat mycoplasma infection.

Prior attempts at characterizing the structure and gene arrangement of the chromosomes of mycoplasmas using pulsed-field gel electrophoretic methods (Pyle, L. E. et al., *Nucleic Acids Res.* 16(13):6015–6025 (1988); Neimark, H. C. et al., *Nucleic Acids Res.* 18(18):5443–5448 (1990)), indicated that mycoplasmas have genomes ranging widely in size. Southern blot hybridization of digested DNAs of *M. genitalium* compared to the well-known human pathogen, *M. pneumoniae*, indicated overall low homology values of approximately 6–8% (Yogev, D. et al., *Int. J. Syst. Bacteriol.* 36(3):426–430 (1986)). However, high homologies have been reported between the adhesin genes of *M. genitalium* and *M pneumoniae* (Dallo, S. F. et al., *Microbial Path.* 6:69–73 (1989)). Initial studies at characterizing the genome of *M. genitalium* by comparison to the well-known *M. pneumoniae* species, indicated that both species have three (3) rRNA genes clustered together in a chromosomal segment of about 5 kb and form a single operon organized in classical procaryotic fashion, but differences exist between their respective restriction sites (Yogev, D. et al., *Int. J. Bacteriol*. 36(3):426–430 (1986)).

Restriction enzyme mapping of *M. genitalium* indicates that the genome is approximately 600 kb. Several genes have also been mapped, including the single ribosomal operon, and the gene encoding the MgPa cytadhesion protein (Su, C. J. et al., *J. Bacteriol*. 172:4705–4707 (1990); Colman, S. D. et al., *Mol. Microbiol*. 4(4):683–687 (1990)). The entire restriction map of the genome of *M. genitalium* has also been cloned in an ordered library of 20 overlapping cosmids and one λ clone (Lucier, T. S. et al., *Gene* 150:27–34 (1994)).

An initial study using random sequencing techniques to characterize the *M. genitalium* genome resulted in forty-four (44) random clones being partially sequenced; several long open reading frames were also found (Peterson, S. N. et al., *Nucleic Acids Rev*. 19:6027–6031 (1991)). Subsequent work using random sequencing of 508 random nonidentical clones has allowed sequence information to be compiled for approximately seventeen percent (17%) (100,993 nucleotides) of the *M. genitalium* genome (Peterson, S. N. et al., *J. Bacteriol*. 175:7918–7930 (1993)). Sequence information indicates that the diminutive genome of *M. genitalium* contains numerous genes involved in various metabolic processes. The genome is estimated to encode approximately 390 proteins, indicating that *M. genitalium* makes very efficient use of its limited amount of DNA (Peterson, S. N. et al., *J. Bacteriol*. 175:7918–7930 (1993)).

Several studies have been undertaken to sequence and characterize individual genes identified in *M. genitalium*. In particular, the medically important aspects of *M. genitalium* have helped to direct interest to those genes which determine the degree of infectivity and the virulence characteristics of the organism. The nucleotide sequence and deduced amino acid sequence for the MgPa adhesin gene, ie., the gene encoding the surface cytadhesion protein of *M. genitalium*, indicates that the complete gene contains 4,335 nucleotides coding for a protein of 159,668 Da. (Dallo, S. F. et al., *Infect. Immun*. 57(4):1059–1065 (1989)). Furthermore, subsequent nucleotide sequencing of the *M. genitalium* MgPa adhesin gene revealed the specific codon order for this important gene (Inamine, J. M. et al., *Gene* 82:259–267 (1989)). The MgPa adhesin gene also has been shown to express restriction fragment length polymorphism (Dallo, S. F. et al., *Microbial Path*. 10:475–480 (1991)). Nucleotide homology to the well-known highly conserved procaryotic origin-of-replication gene (gyrA) was noted for *M. genitalium* (Bailey, C. C. et al., *J. Bacteriol*. 176:5814–5819 (1994)). The highly conserved procaryotic elongation factor, Tu, encoded by the tuf gene, has been noted and sequenced for *M. genitalium*, and was found to contain an open reading frame encoding a protein of approximately 393 amino acids (Loechel, S. et al., *Nucleic Acids Res*. 17(23):10127 (1989)). The tuf gene of *M. genitalium* has also been determined to use a signal other than a Shine-Delgamo (ribosomal binding site) sequence preceding the initiation codon (Loechel, S. et al., *Nucleic Acids Res*. 19:6905–6911 (1991)).

SUMMARY OF THE INVENTION

The present invention is based on the sequencing of the *Mycoplasma genitalium* genome. The primary nucleotide sequence which was generated is provided in SEQ ID NO:1.

The present invention provides the generated nucleotide sequence of the *Mycoplasma genitalium* genome, or a representative fragment thereof, in a form which can be readily used, analyzed, and interpreted by a skilled artisan. In one embodiment, present invention is provided as a contiguous string of primary sequence information corresponding to the nucleotide sequence depicted in SEQ ID NO:1.

The present invention further provides nucleotide sequences which are at least 99.9% identical to the nucleotide sequence of SEQ ID NO:1.

The nucleotide sequence of SEQ ID NO:1, a representative fragment thereof, or a nucleotide sequence which is at least 99.9% identical to the nucleotide sequence of SEQ ID NO:1 may be provided in a variety of mediums to facilitate its use. In one application of this embodiment, the sequences of the present invention are recorded on computer readable media. Such media includes, but is not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

The present invention further provides systems, particularly computer-based systems which contain the sequence information herein described stored in a data storage means. Such systems are designed to identify commercially important fragments of the *Mycoplasma genitalium* genome.

Another embodiment of the present invention is directed to isolated fragments of the *Mycoplasma genitalium* genome. The fragments of the *Mycoplasma genitalium* genome of the present invention include, but are not limited to, fragments which encode peptides, hereinafter open reading frames (ORFs), fragments which modulate the expression of an operably linked ORF, hereinafter expression modulating fragments (EMFs), fragments which mediate the uptake of a linked DNA fragment into a cell, hereinafter uptake modulating fragments (UMFs), and fragments which can be used to diagnose the presence of *Mycoplasma genitalium* in a sample, hereinafter, diagnostic fragments (DFs).

Each of the ORF fragments of the *Mycoplasma genitalium* genome disclosed in Tables 1(a), 1(c) and 2, and the EMF found 5' to the ORF, can be used in numerous ways as polynucleotide reagents. The sequences can be used as diagnostic probes or diagnostic amplification primers for the presence of a specific microbe in a sample, for the production of commercially important pharmaceutical agents, and to selectively control gene expression.

The present invention further includes recombinant constructs comprising one or more fragments of the *Mycoplasma genitalium* genome of the present invention. The recombinant constructs of the present invention comprise vectors, such as a plasmid or viral vector, into which a fragment of the *Mycoplasma genitalium* has been inserted.

The present invention further provides host cells containing any one of the isolated fragments of the *Mycoplasma genitalium* genome of the present invention. The host cells can be a higher eukaryotic host such as a mammalian cell, a lower eukaryotic cell such as a yeast cell, or can be a procaryotic cell such as a bacterial cell.

The present invention is further directed to isolated proteins encoded by the ORFs of the present invention. A variety of methodologies known in the art can be utilized to obtain any one of the proteins of the present invention. At the simplest level, the amino acid sequence can be synthesized using commercially available peptide synthesizers. In an alternative method, the protein is purified from bacterial cells which naturally produce the protein. Lastly, the proteins of the present invention can alternatively be purified from cells which have been altered to express the desired protein.

The invention further provides methods of obtaining homologs of the fragments of the *Mycoplasma genitalium* genome of the present invention and homologs of the proteins encoded by the ORFs of the present invention. Specifically, by using the nucleotide and amino acid sequences disclosed herein as a probe or as primers, and techniques such as PCR cloning and colony/plaque hybridization, one skilled in the art can obtain homologs.

The invention further provides antibodies which selectively bind one of the proteins of the present invention. Such antibodies include both monoclonal and polyclonal antibodies.

The invention further provides hybridomas which produce the above-described antibodies. A hybridoma is an immortalized cell line which is capable of secreting a specific monoclonal antibody.

The present invention further provides methods of identifying test samples derived from cells which express one of the ORF of the present invention, or homolog thereof. Such methods comprise incubating a test sample with one or more of the antibodies of the present invention, or one or more of the DFs of the present invention, under conditions which allow a skilled artisan to determine if the sample contains the ORF or product produced therefrom.

In another embodiment of the present invention, kits are provided which contain the necessary reagents to carry out the above-described assays.

Specifically, the invention provides a compartmentalized kit to receive, in close confinement, one or more containers which comprises: (a) a first container comprising one of the antibodies, or one of the DFs of the present invention; and (b) one or more other containers comprising one or more of the following: wash reagents, reagents capable of detecting presence of bound antibodies or hybridized DFs.

Using the isolated proteins of the present invention, the present invention further provides methods of obtaining and identifying agents capable of binding to a protein encoded by one of the ORFs of the present invention. Specifically, such agents include antibodies (described above), peptides, carbohydrates, pharmaceutical agents and the like. Such methods comprise the steps of:

(a) contacting an agent with an isolated protein encoded by one of the ORFs of the present invention; and (b) determining whether the agent binds to said protein.

The complete genomic sequence of *M. genitalium* will be of great value to all laboratories working with this organism and for a variety of commercial purposes. Many fragments of the *Mycoplasma genitalium* genome will be immediately identified by similarity searches against GenBank or protein databases and will be of immediate value to Mycoplasma researchers and for immediate commercial value for the production of proteins or to control gene expression. A specific example concerns PHA synthase. It has been reported that polyhydroxybutyrate is present in the membranes of *M. genitalium* and that the amount correlates with the level of competence for transformation. The PHA synthase that synthesizes this polymer has been identified and sequenced in a number of bacteria, none of which are evolutionarily close to *M. genitalium*. This gene has yet to be isolated from *M. genitalium* by use of hybridization probes or PCR techniques. However, the genomic sequence of the present invention allows the identification of the gene by utilizing search means described below.

Developing the methodology and technology for elucidating the entire genomic sequence of bacterial and other small genomes has and will greatly enhance the ability to analyze and understand chromosomal organization. In particular, sequenced genomes will provide the models for developing tools for the analysis of chromosome structure and function, including the ability to identify genes within large segments of genomic DNA, the structure, position, and spacing of regulatory elements, the identification of genes with potential industrial applications, and the ability to do comparative genomic and molecular phylogeny.

BRIEF DESCRIPTION OF THE FIGURES

FIG. 1—EcoRI restriction map of the *Mycoplasma genitalium* genome.

FIG. 2—Block diagram of a computer system 102 that can be used to implement the computer-based systems of present invention.

FIG. 3—Summary of the *Mycoplasma genitalium* sequencing project.

FIG. 4—A circular representation of the *M. genitalium* chromosome. Outer concentric circle: Coding regions on the plus strand for which a gene identification was made. Second concentric circle: Coding regions on the minus strand for which a gene identification was made. Third concentric circle: The direction of transcription on each strand of the chromosome is depicted as an red arrow starting at the putative origin of replication. Fourth concentric circle: Coverage by cosmid and lambda clones. Nineteen cosmid clones and one lambda clone were sequenced from each end to confirm the overall structure of the genome. Fifth concentric circle: The locations of the single ribosomal operon and the 33 tRNAs. The clusters of tRNAs (trnA, trnB, trnC, trnD and trnE) are indicated by the letters A–B with the number of tRNAs in each cluster listed in parentheses. Sixth concentric circle: Location of the MgPa operon and MgPa repeat fragments.

FIG. 5A-5R—Gene map of the *M. genitalium* genome. Predicted coding regions are shown on each strand. The rRNA operon and tRNA genes are shown as described in the Figure key. Gene identification numbers correspond to those in Table 6.

FIG. 6—Location of the MgPa repeats in the *M. genitalium* genome. The structure of the MgPa operon (ORF1-MgPa gene-ORF3) in the *M. genitalium* genome is illustrated across the top. In addition to the complete operon, nine repetitive elements which are composites of particular regions of the MgPa operon were found. The coordinates of each repeat in the genome are indicated on the left and right end of each line. The repetitive elements are located directly below those regions in the operon for which there is sequence similarity. The percent of sequence identity between the repeat elements and the MgPa gene ranges from 78%–90%. In some of the repeats, the MgPa-related sequences are separated in the genome by a variable length, A–T rich spacer sequence (indicated in the figure by a line with the length of the spacer indicated in bp). In cases where no spacer sequence is shown, the composites of the operon are co-linear in the genome. In repeats 7 and 9, the order of the sequences in the repeats differs from that in the operon. In these cases, the order of the elements in each repeat in the genome is indicated numerically where element 1 is followed by element 2 which is followed by element 3, etc.

DETAILED DESCRIPTION OF THE PREFERRED EMBODIMENTS

The present invention is based on the sequencing of the *Mycoplasma genitalium* genome. The primary nucleotide sequence which was generated is provided in SEQ ID NO:1. As used herein, the "primary sequence" refers to the nucleotide sequence represented by the IUPAC nomenclature system.

The sequence provided in SEQ ID NO:1 is oriented relative to two genes (DNAA and DNA gyrase) known to flank the origin of replication of the *Mycoplasma genitalium* genome. A skilled artisan will readily recognize that this start/stop point was chosen for convenience and does not reflect a structural significance.

The present invention provides the nucleotide sequence of SEQ ID NO:1, or a representative fragment thereof, in a form which can be readily used, analyzed, and interpreted by a skilled artisan. In one embodiment, the sequence is provided as a contiguous string of primary sequence information corresponding to the nucleotide sequence provided in SEQ ID NO:1.

As used herein, a "representative fragment of the nucleotide sequence depicted in SEQ ID NO:1" refers to any portion of SEQ ID NO:1 which is not presently represented within a publicly available database. Preferred representative fragments of the present invention are *Mycoplasma genitalium* open reading frames, expression modulating fragments, uptake modulating fragments, and fragments which can be used to diagnose the presence of *Mycoplasma genitalium* in sample. A non-limiting identification of such preferred representative fragments is provided in Tables 1 (a), 1 (c) and 2.

The nucleotide sequence information provided in SEQ ID NO:1 was obtained by sequencing the *Mycoplasma genitalium* genome using a megabase shotgun sequencing method. The nucleotide sequence provided in SEQ ID NO:1 is a highly accurate, although not necessarily a 100% perfect, representation of the nucleotide sequence of the *Mycoplasma genitalium* genome.

As discussed in detail below, using the information provided in SEQ ID NO:1 and in Tables 1(a), 1(c) and 2 together with routine cloning and sequencing methods, one of ordinary skill in the art would be able to clone and sequence all "representative fragments" of interest including open reading frames (ORFs) encoding a large variety of *Mycoplasma genitalium* proteins. In very rare instances, this may reveal a nucleotide sequence error present in the nucleotide sequence disclosed in SEQ ID NO:1. Thus, once the present invention is made available (i.e., once the information in SEQ ID NO:1 and Tables 1(a), 1(c) and 2 have been made available), resolving a rare sequencing error in SEQ ID NO:1 would be well within the skill of the art. Nucleotide sequence editing software is publicly available. For example, Applied Biosystem's (AB) AutoAssembler™ can be used as an aid during visual inspection of nucleotide sequences.

Even if all of the very rare sequencing errors in SEQ ID NO:1 were corrected, the resulting nucleotide sequence would still be at least 99.9% identical to the nucleotide sequence in SEQ ID NO:1.

The nucleotide sequences of the genomes from different strains of *Mycoplasma genitalium* differ slightly. However, the nucleotide sequence of the genomes of all *Mycoplasma genitalium* strains will be at least 99.9% identical to the nucleotide sequence provided in SEQ ID NO:1.

Thus, the present invention further provides nucleotide sequences which are at least 99.9% identical to the nucleotide sequence of SEQ ID NO:1 in a form which can be readily used, analyzed and interpreted by the skilled artisan. Methods for determining whether a nucleotide sequence is at least 99.9% identical to the nucleotide sequence of SEQ ID NO:1 are routine and readily available to the skilled artisan. For example, the well known fasta algothrithm (Pearson and Lipman, *Proc. Natl. Acad. Sci USA* 85:2444 (1988)) can be used to generate the percent identity of nucleotide sequences.

Computer Related Embodiments

The nucleotide sequence provided in SEQ ID NO:1, a representative fragment thereof, or a nucleotide sequence at least 99.9% identical to SEQ ID NO:1 may be "provided" in a variety of mediums to facilitate use thereof. As used herein, provided refers to a manufacture, other than an isolated nucleic acid molecule, which contains a nucleotide sequence of the present invention, i.e., the nucleotide sequence provided in SEQ ID NO:1, a representative fragment thereof, or a nucleotide sequence at least 99.9% identical to SEQ ID NO:1. Such a manufacture provides the *Mycoplasma genitalium* genome or a subset thereof (e.g., a *Mycoplasma genitalium* open reading frame (ORF)) in a form which allows a skilled artisan to examine the manufacture using means not directly applicable to examining the *Mycoplasma genitalium* genome or a subset thereof as it exists in nature or in purified form.

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently know methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention.

By providing the nucleotide sequence of SEQ ID NO:1, a representative fragment thereof, or a nucleotide sequence at least 99.9% identical to SEQ ID NO:1 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403–410 (1990)) and BLAZE (Brutlag et al., *Comp. Chem.* 17:203–207 (1993)) search algorithms on a Sybase system was used to identify open reading frames (ORFs) within the *Mycoplasma genitalium* genome which contain homology to ORFs or proteins from other organisms. Such ORFs are protein encoding fragments within the *Mycoplasma genitalium* genome and are useful in producing commercially important proteins such as enzymes used in fermentation reactions and in the production of commercially useful metabolites.

The present invention further provides systems, particularly computer-based systems, which contain the sequence information described herein. Such systems are designed to identify commercially important fragments of the *Mycoplasma genitalium* genome.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of the *Mycoplasma genitalium* genome which match a particular target sequence or target motif. A variety of known algorithms are disclosed publicly and a variety of commercially available software for conducting search means are available and can be used in the computer-based systems of the present invention. Examples of such software includes, but is not limited to, MacPattern (EMBL), BLASTN and BLASIX (NCBIA). A skilled artisan can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments of the *Mycoplasma genitalium* genome, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzymic active sites and signal sequences. Nucleic acid target motifs include, but are not limited to, promoter sequences, hairpin structures and inducible expression elements (protein binding sequences).

A variety of structural formats for the input and output means can be used to input and output the information in the computer-based systems of the present invention. A preferred format for an output means ranks fragments of the *Mycoplasma genitalium* genome possessing varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments of the *Mycoplasma genitalium* genome. In the present examples, implementing software which implement the BLAST and BLAZE algorithms (Altschul et al., *J Mol. Biol.* 215:403–410 (1990)) was used to identify open reading frames within the *Mycoplasma genitalium* genome. A skilled artisan can readily recognize that any one of the publicly available homology search programs can be used as the search means for the computer-based systems of the present invention.

One application of this embodiment is provided in FIG. 2. FIG. 2 provides a block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage devices 110, such as a hard drive 112 and a removable medium storage device 114. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable medium storage device 114. The computer system 102 includes appropriate software for reading the control logic and/or the data from the removable medium storage device 114 once inserted in the removable medium storage device 114.

A nucleotide sequence of the present invention may be stored in a well known manner in the main memory 108, any of the secondary storage devices 110, and/or a removable storage medium 116. Software for accessing and processing the genomic sequence (such as search tools, comparing tools, etc.) reside in main memory 108 during execution.

Biochemical Embodiments

Another embodiment of the present invention is directed to isolated fragments of the *Mycoplasma genitalium* genome. The fragments of the *Mycoplasma genitalium* genome of the present invention include, but are not limited to fragments which encode peptides, hereinafter open reading frames (ORFs), fragments which modulate the expression of an operably linked ORF, hereinafter expression modulating fragments (EMFs), fragments which mediate the uptake of a linked DNA fragment into a cell, hereinafter uptake modulating fragments (UMFs), and fragments which can be used to diagnose the presence of *Mycoplasma genitalium* in a sample, hereinafter diagnostic fragments (DFs).

As used herein, an "isolated nucleic acid molecule" or an "isolated fragment of the *Mycoplasma genitalium* genome" refers to a nucleic acid molecule possessing a specific nucleotide sequence which has been subjected to purification means to reduce, from the composition, the number of compounds which are normally associated with the composition. A variety of purification means can be used to generated the isolated fragments of the present invention. These include, but are not limited to methods which separate constituents of a solution based on charge, solubility, or size.

In one embodiment, *Mycoplasma genatalium* DNA can be mechanically sheared to produce fragments of 15–20 kb in length. These fragments can then be used to generate an *Mycoplasma genitalium* library by inserting them into lambda clones as described in the Examples below. Primers flanking, for example, an ORF provided in Table 1(a), 1(c) or 2 can then be generated using nucleotide sequence information provided in SEQ ID NO:1. PCR cloning can then be used to isolate the ORF from the lambda DNA library. PCR cloning is well known in the art. Thus, given the availability of SEQ ID NO:1, Table 1(a), 1(c) and Table 2, it would be routine to isolate any ORF or other representative fragment of the present invention.

The isolated nucleic acid molecules of the present invention include, but are not limited to single stranded and double stranded DNA, and single stranded RNA.

As used herein, an "open reading frame," ORF, means a series of triplets coding for amino acids without any termination codons and is a sequence translatable into protein. Tables 1(a), 1(b), 1(c) and 2 identify ORFs in the *Mycoplasma genitalium* genome. In particular, Table 1(a) indicates the location of ORFs (i.e., the adresses) within the *Mycoplasma genitalium* genome which encode the recited protein based on homology matching with protein sequences from the organism appearing in parentheticals (see the fifth column of Table 1(a)).

The first column of Table 1(a) provides the "UID" (an arbitrary identification number) of a particular ORF. The second and third columns in Table 1(a) indicate an ORFs position in the nucleotide sequence provided in SEQ ID NO:1. One of ordinary skill in the art will recognize that ORFs may be oriented in opposite directions in the *Mycoplasma genitalium* genome. This is reflected in columns 2 and 3.

The fourth column of Table 1(a) provides the accession number of the database match for the ORF. As indicated above, the fifth column of Table 1(a) provides the name of the database match for the ORF.

The sixth column of Table 1(a) indicates the percent identity of the protein encoded for by an ORF to the corresponding protein from the orgaism appearing in parentheticals in the fifth column. The seventh column of Table 1(a) indicates the percent similarity of the protein encoded for by an ORF to the corresponding protein from the organism appearing in parentheticals in the fifth column. The concepts of percent identity and percent similarity of two polypeptide sequences are well understood in the art. For example, two polypeptides 10 amino acids in length which differ at three amino acid positions (e.g., at positions 1, 3 and 5) are said to have a percent identity of 70%. However, the same two polypeptides would be deemed to have a percent similarity of 80% if, for example at position 5, the amino acids moieties, although not identical, were "similar" (i.e., possessed similar biochemical characteristics). The eighth column in Table 1(a) indicates the length of the ORF in nucleotides.

Table 1(b) is a list of ORFs that have database matches to previously published *Mycoplasma genitalium* sequences over the full length of the ORF. The talbe headings for Table 1(b) are identical for Table 1(a) with the following two exceptions: (II) The heading for the eighth column in Table 1(a) (i.e., nucleotide length of the ORF) has been replaced with the following in Table 1(b): "Match_info". "Match_info" refers to the coordinates of the match of the ORF and the previously published Mycoplama genitalium sequence. For example, "MG002 (1–930 of 930) GB:U09251 (298–1227 of 6140)," indicates that for ORF MG002, which is 930 nucleotides in length, there is a database match to accession number GB:U09251, which has a total length of 6140 nucleotides. The ORF matches this accession from position 298 to 1227. (II) Where an ORF shows homology matches for both a previously published *Mycoplasma genitalium* sequence and a previously published sequence from a different organism, columns 3, 4, 5, and 6 of Table 1(b) respectively provide the accession number, protein name (and organism in parentheticals), percent identity and percent similarity for the "other organism," rather than for the previously published *Mycoplasma genitalium* sequence. (However, in this scenario, the accession number for the *Mycoplasma genitalium* sequence is still provided in column 8.)

Table 1(c) provides ORFs having database matches to previously published *Mycoplasma genitalium* sequences but only over a portion of the ORF. The table headings are the same as above for Table 1(b).

In Tables 1(a), 1(b) and 1(c), unique identifiers are used to identify the recited ORFs, (e.g., "MG123"). In the parent application Ser. Nos. 08/488,018 and 08/473,545, the recited ORFs are identified unsing the "MORF" identifier. Table 1(d) lists which of the new and old identifiers refer to the same ORF. For example, the first entry in Table 1(d) indicates that the ORF identifed as MG001 in the current application is the same ORF which was previously identified as MORF-20072 in parent application Ser. Nos. 08/488,018 and 08/473,545. Similarly, the third entry in Table 1(d) indicates that the ORF identified as MG003 in the current application is the same ORF which was previously identified as MORF-19818 and MORF-20073 in the parent applications.

Table 2 provides ORFs of the *Mycoplasma genitalium* genome which did not elicit a "homology match" with a known sequence from either *M. genitalium* or another organism.

Table 6 classifies each ORF according to its role category (adapted from Riley, M., *Microbiol. Rev.* 57:862 (1992)). The gene identification, the accession number from public archives that corresponds to the best match, the percent amino acid identity, and the length of the match in amino acids is also listed for each entry as above in Tables 1(a–c). Those genes in *M. genitalium* that also match a gene in *H. influenzae* are indicated by an asterisk (*). For the purposes of Tables 6 and 7 and FIG. 4, each of the MgPa repetitive elements has been assigned an MG number, even though there is evidence to suggest that these repeats may not be transcribed.

Table 7 sorts the gene content in *H. influenzae* and *M. genitalium* by functional category. The number of genes in each category is listed for each organism. The number in parentheses indicates the percent of the putatively identified genes devoted to each functional cetegory. For the category of unassigned genes, the percent of the genome indicated in parentheses represents the percent of the total number of putative coding regions.

Further details concerning the algorithms and criteria used for homology searches are provided in the Examples below.

A skilled artisan can readily identify ORFs in the *Mycoplasma genitalium* genome other than those listed in Tables 1(a), 1(b), 1(c) and 2, such as ORFs which are overlapping or encoded by the opposite strand of an identified ORF in addition to those ascertainable using the computer-based systems of the present invention.

As used herein, an "expression modulating fragment," EMF, means a series of nucleotide molecules which modulates the expression of an operably linked ORF or EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event. A review of known EMFs from Mycoplasma are described by (Tomb et al. *Gene* 104:1–10 (1991), Chandler, M. S., *Proc. Natl. Acad. Sci. USA* 89:1626–1630 (1992).

EMF sequences can be identified within the *Mycoplasma genitalium* genome by their proximity to the ORFs provided in Tables 1(a), 1(b), 1(c) and 2. An intergenic segment, or a fragment of the intergenic segment, from about 10 to 200 nucleotides in length, taken 5' from any one of the ORFs of Tables 1(a), 1(b), 1(c) or 2 will modulate the expression of an operably linked 3' ORF in a fashion similar to that found with the naturally linked ORF sequence. As used herein, an "intergenic segment" refers to the fragments of the Mycoplasma genome which are between two ORF(s) herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, an EMF will modulate the expression of an operably linked marker sequence. A more detailed discussion of various marker sequences is provided below.

A sequence which is suspected as being an EMF is cloned in all three reading frames in one or more restriction sites upstream from the marker sequence in the EMF trap vector. The vector is then transformed into an appropriate host using known procedures and the phenotype of the transformed host in examined under appropriate conditions. As described above, an EMF will modulate the expression of an operably linked marker sequence.

As used herein, an "uptake modulating fragment," UMF, means a series of nucleotide molecules which mediate the uptake of a linked DNA fragment into a cell. UMFs can be readily identified using known UMFs as a target sequence or target motif with the computer-based systems described above.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence. A review of DNA uptake in Mycoplasma is provided by Goodgall, S. H., et al., *J. Bact.* 172:5924–5928 (1990).

As used herein, a "diagnostic fragment," DF, means a series of nucleotide molecules which selectively hybridize to *Mycoplasma genitalium* sequences. DFs can be readily identified by identifying unique sequences within the *Mycoplasma genitalium* genome, or by generating and testing probes or amplification primers consisting of the DF sequence in an appropriate diagnostic format which determines amplification or hybridization selectivity.

The sequences falling within the scope of the present invention are not limited to the specific sequences herein described, but also include allelic and species variations thereof. Allelic and species variations can be routinely determined by comparing the sequence provided in SEQ ID NO:1, a representative fragment thereof, or a nucleotide sequence at least 99.9% identical to SEQ ID NO:1 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated.

Any specific sequence disclosed herein can be readily screened for errors by resequencing a particular fragment, such as an ORF, in both directions (i.e., sequence both strands). Alternatively, error screening can be performed by sequencing corresponding polynucleotides of *Mycoplasma genitalium* origin isolated by using part or all of the fragments in question as a probe or primer. Each of the ORFs of the *Mycoplasma genitalium* genome disclosed in Tables 1(a), 1(b), 1(c) and 2, and the EMF found 5' to the ORF, can be used in numerous ways as polynucleotide reagents. The sequences can be used as diagnostic probes or diagnostic amplification primers to detect the presence of a specific microbe, such as *Mycoplasma genitalium*, in a sample. This is especially the case with the fragments or ORFs of Table 2, which will be highly selective for *Mycoplasma genitalium.*

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the mRNA itself (antisense—Okano, *J. Neurochem.* 56:560 (1991); *Oligodeoxynucleotides as Antisense Inhibitors of Gene Expression*, CRC Press, Boca Raton, Fla. (1988)).

Triple helix—formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

The present invention further provides recombinant constructs comprising one or more fragments of the *Mycoplasma genitalium* genome of the present invention. The recombinant constructs of the present invention comprise a vector, such as a plasmid or viral vector, into which a fragment of the *Mycoplasma genitalium* has been inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK2223-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232–8 and pCM7. Particular named bacterial promoters include lac, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

The present invention further provides host cells containing any one of the isolated fragments of the *Mycoplasma genitalium* genome of the present invention, wherein the fragment has been introduced into the host cell using known transformulation methods. The host cell can be a higher eukaryotic host cell, such as a mammalian cell, a lower eukaryotic host cell, such as a yeast cell, or the host cell can be a procaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)).

The host cells containing one of the fragments of the *Mycoplasma genitalium* genome of the present invention, can be used in conventional manners to produce the gene product encoded by the isolated fragment (in the case of an ORF) or can be used to produce a heterologous protein under the control of the EMF.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the Genetic Code, encode an identical polypeptide sequence. Preferred nucleic acid fragments of the present invention are the ORFs depicted in Tables 1(a), 1(c) and 2.

A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polpeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level.

"Recombinant," as used herein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern different from that expressed in mammalian cells.

"Nucleotide sequence" refers to a heteropolymer of deoxyribonucleotides. Generally, DNA segments encoding the polypeptides and proteins provided by this invention are assembled from fragments of the *Mycoplasma genitalium* genome and short oligonucleotide linkers, or from a series of oligonucleotides, to provide a synthetic gene which is capable of being expressed in a recombinant transcriptional unit comprising regulatory elements derived from a microbial or viral operon.

"Recombinant expression vehicle or vector" refers to a plasmid or phage or virus or vector, for expressing a polypeptide from a DNA (RNA) sequence. The expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means host cells which have stably integrated a recombinant transcriptional unit into chromosomal DNA or carry the recombinant transcriptional unit extra chromosomally. The cells can be prokaryotic or eukaryotic. Recombinant expression systems as defined herein will express heterologous polypeptides or proteins upon induction of the regulatory elements linked to the DNA segment or synthetic gene to be expressed.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryatic and eukaryotic hosts are described by Sambrook, et al., in *Molecular Cloning: A Laboratory Manual*, Second Edition, Cold Spring Harbor, New York (1989), the disclosure of which is hereby incorporated by reference.

Generally, recombinant expression vectors will include origins of replication and selectable markers permitting transformation of the host cell, e.g., the ampicillin resistance gene of *E. coli* and *S. cerevisiae*TRP 1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may, also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1(Promega Biotec, Madison, Wis. USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant polypeptides and proteins produced in bacterial culture is usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

The present invention further includes isolated polypeptides, proteins and nucleic acid molecules which are substantially equivalent to those herein described. As used herein, substantially equivalent can refer both to nucleic acid and amino acid sequences, for example a mutant sequence, that varies from a reference sequence by one or more substitutions, deletions, or additions, the net effect of which does not result in an adverse functional dissimilarity between reference and subject sequences. For purposes of the present invention, sequences having equivalent biological activity, and equivalent expression characteristics are considered substantially equivalent. For purposes of determining equivalence, truncation of the mature sequence should be disregarded.

The invention further provides methods of obtaining homologs from other strains of *Mycoplasma genitalium*, of the fragments of the *Mycoplasma genitalium* genome of the present invention and homologs of the proteins encoded by the ORFs of the present invention. As used herein, a sequence or protein of *Mycoplasma genitalium* is defined as a homolog of a fragment of the *Mycoplasma genitalium* genome or a protein encoded by one of the ORFs of the present invention, if it shares significant homology to one of the fragments of the *Mycoplasma genitalium* genome of the present invention or a protein encoded by one of the ORFs of the present invention. Specifically, by using the sequence disclosed herein as a probe or as primers, and techniques such as PCR cloning and colony/plaque hybridization, one skilled in the art can obtain homologs.

As used herein, two nucleic acid molecules or proteins are said to "share significant homology" if the two contain regions which process greater than 85% sequence (amino acid or nucleic acid) homology.

Region specific primers or probes derived from the nucleotide sequence provided in SEQ ID NO:1 or from a nucleotide sequence at least 99.9% identical to SEQ ID NO:1 can be used to prime DNA synthesis and PCR amplification, as well as to identify colonies containing cloned DNA encoding a homolog using known methods (Innis et al., PCR Protocols, Academic Press, San Diego, Calif. (1990)).

When using primers derived from SEQ ID NO:1 or from a nucleotide sequence at least 99.9% identical to SEQ ID NO:1, one skilled in the art will recognize that by employing high stringency conditions (e.g., annealing at 50–60° C.) only sequences which are greater than 75% homologous to the primer will be amplified. By employing lower stringency conditions (e.g., annealing at 35–37° C.), sequences which are greater than 40–50% homologous to the primer will also be amplified.

When using DNA probes derived from SEQ ID NO:1 or from a nucleotide sequence at least 99.9% identical to SEQ ID NO:1 for colony/plaque hybridization, one skilled in the art will recognize that by employing high stringency conditions (e.g., hybridizing at 50–65° C. in 5×SSC and 50% formamide, and washing at 50–65° C. in 0.5×SSC), sequences having regions which are greater than 90% homologous to the probe can be obtained, and that by employing lower stringency conditions (e.g., hybridizing at 35–37° C. in 5×SSC and 40–45% formamide, and washing at 42° C. in SSC), sequences having regions which are greater than 35–45% homologous to the probe will be obtained.

Any organism can be used as the source for homologs of the present invention so long as the organism naturally expresses such a protein or contains genes encoding the same. The most preferred organism for isolating homologs are bacterias which are closely related to *Mycoplasma genitalium*.

Uses for the Composiftions of the Invention

Each ORF provided in Table 1(a), 1(b) and 1(c) was assigned to biological role categories adapted from Riley, M., *Microbiology Reviews* 57(4):862 (1993)). This allows the skilled artisan to determine a use for each identified coding sequence. Tables 1(a), 1(b) and 1(c) further provides an identification of the type of polypeptide which is encoded for by each ORF. As a result, one skilled in the art can use the polypeptides of the present invention for commercial, therapeutic and industrial purposes consistent with the type of putative identification of the polypeptide.

Such identifications permit one skilled in the art to use the Mycoplasma genitalium ORFs in a manner similar to the known type of sequences for which the identification is made; for example, to ferment a particular sugar source or to produce a particular metabolite. (For a review of enzymes used within the commercial industry, see *Biochemical Engineering and Biotechnology Handbook* 2nd, eds. Macmillan Publ. Ltd., N.Y. (1991) and Biocatalysts in Organic Syntheses, ed. J. Tramper et al., Elsevier Science Publishers, Amsterdam, The Netherlands (1985)).

1. Biosynthetic Enzymes

Open reading frames encoding proteins involved in mediating the catalytic reactions involved in intermediary metabolism, the biosynthesis of small macromolecular molecules, cellular processes and other functions includes enzymes involved in the degradation of the intermediary products of metabolism, enzymes involved in central intermediary metabolism, enzymes involved in respiration, both aerobic and anaerobic, enzymes involved in fermentation, enzymes involved in ATP proton motor force conversion, enzymes involved in broad regulatory function, enzymes involved in amino acid synthesis, enzymes involved in nucleotide synthesis, enzymes involved in cofactor and vitamin synthesis, can be used for industrial biosynthesis. The various metabolic pathways present in Mycoplasma can be identified based on absolute nutritional requirements as well as by examining the various enzymes identified in Table 1(a), 1(b) and 1(c).

Identified within the category of intermediary metabolism, a number of the proteins encoded by the identified ORFs in Tables 1(a), 1(b) and 1(c) are particularly involved in the degradation of intermediary metabolites as well as non-macromolecular metabolism. Some of the enzymes identified include amylases, glucose oxidases, and catalase.

Proteolytic enzymes are another class of commercially important enzymes. Proteolytic enzymes find use in a number of industrial processes including the processing of flax and other vegetable fibers, in the extraction, clarification and depectinization of fruit juices, in the extraction of vegetables' oil and in the maceration of fruits and vegetables to give unicellular fruits. A detailed review of the proteolytic enzymes used in the food industry is provided by Rombouts et al., *Symbiosis* 21:79 (1986) and Voragen et al. in *Biocatalyst in Agricultural Biotechnology*, edited J. R. Whitaker et al., *American Chemical Society Symposium Series* 389:93 (1989)).

The metabolism of glucose, galactose, fructose and xylose are important parts of the primary metabolism of Mycoplasma. Enzymes involved in the degradation of these sugars can be used in industrial fermentation. Some of the important sugar transforming enzymes, from a commercial viewpoint, include sugar isomerases such as glucose isomerase. Other metabolic enzymes have found commercial use such as glucose oxidases which produces ketogulonic acid (KGA). KGA is an intermediate in the commercial production of ascorbic acid using the Reichstein's procedure (see Krueger et al., *Biotechnology* 6(A), Rhine, H. J. et al., eds., Verlag Press, Weinheim, Germany (1984)).

Glucose oxidase (GOD) is commercially available and has been used in purified form as well as in an immobilized form for the deoxygenation of beer. See Hartmeir et al., *Biotechnology Letters* 1:21 (1979). The most important application of GOD is the industrial scale fermentation of gluconic acid. Market for gluconic acids which are used in the detergent, textile, leather, photographic, pharmaceutical, food, feed and concrete industry (see Bigelis in *Gene Manipulations and Fungi*, Benett, J. W. et al., eds., Academic Press, New York (1985), p. 357). In addition to industrial applications, GOD has found applications in medicine for quantitative determination of glucose in body fluids recently in biotechnology for analyzing syrups from starch and cellulose hydrosylates. See Owusu et al., *Biochem. et Biophysica. Acta.* 872:83 (1986).

The main sweetener used in the world today is sugar which comes from sugar beets and sugar cane. In the field of industrial enzymes, the glucose isomerase process shows the largest expansion in the market today. Initially, soluble enzymes were used and later immobilized enzymes were developed (Krueger et al., *Biotechnology, The Textbook of Industrial Microbiology*, Sinauer Associated Incorporated, Sunderland, Mass. (1990)). Today, the use of glucose-produced high fructose syrups is by far the largest industrial business using immobilized enzymes. A review of the industrial use of these enzymes is provided by Jorgensen, *Starch* 40:307 (1988).

Proteinases, such as alkaline serine proteinases, are used as detergent additives and thus represent one of the largest volumes of microbial enzymes used in the industrial sector. Because of their industrial importance, there is a large body of published and unpublished information regarding the use of these enzymes in industrial processes. (See Faultman et al., *Acid Proteases Structure Function and Biology*, Tang, J., ed., Plenum Press, New York (1977) and Godfrey et al., *Industrial Enzymes*, MacMillan Publishers, Surrey, UK (1983) and Hepner et al., *Report Industrial Enzymes* by 1990, Hel Hepner & Associates, London (1986)).

Another class of commercially usable proteins of the present invention are the microbial lipases identified in Tables 1(a), 1(b) and 1(c) (see Macrae et al., *Philosophical Transactions of the Chiral Society of London* 310:227 (1985) and Poserke, *Journal of the American Oil Chemist Society* 61:1758 (1984). A major use of lipases is in the fat and oil industry for the production of neutral glycerides using lipase catalyzed inter-esterification of readily available triglycerides. Application of lipases include the use as a detergent additive to facilitate the removal of fats from fabrics in the course of the washing procedures.

The use of enzymes, and in particular microbial enzymes, as catalyst for key steps in the synthesis of complex organic molecules is gaining popularity at a great rate. One area of great interest is the preparation of chiral intermediates. Preparation of chiral intermediates is of interest to a wide range of synthetic chemists particularly those scientists involved with the preparation of new pharmaceuticals, agrochemicals, fragrances and flavors. (See Davies et al., *Recent Advances in the Generation of chiral Intermediates Using Enzymes*, CRC Press, Boca Raton, Florida (1990)). The following reactions catalyzed by enzymes are of interest to organic chemists: hydrolysis of carboxylic acid esters, phosphate esters, amides and nitrites, esterification reactions, trans-esterification reactions, synthesis of amides, reduction of alkanones and oxoalkanates, oxidation of alcohols to carbonyl compounds, oxidation of sulfides to sulfoxides, and carbon bond forming reactions such as the aldol reaction. When considering the use of an enzyme encoded by one of the ORFs of the present invention for biotransformation and organic synthesis it is sometimes necessary to consider the respective advantages and disadvantages of using a microorganism as opposed to an isolated enzyme. Pros and cons of using a whole cell system on the one hand or an isolated partially purified enzyme on the other hand, has been described in detail by Bud et al., *Chemistry in Britain* (1987), p. 127.

Amino transferases, enzymes involved in the biosynthesis and metabolism of amino acids, are useful in the catalytic production of amino acids. The advantages of using microbial based enzyme systems is that the amino transferase enzymes catalyze the stereo-selective synthesis of only l-amino acids and generally possess uniformly high catalytic rates. A description of the use of amino transferases for amino acid production is provided by Roselle-David, *Methods of Enzymology* 136:479 (1987).

2. Generation of Antibodies

As described here, the proteins of the present invention, as well as homologs thereof, can be used in a variety procedures and methods known in the art which are currently applied to other proteins. The proteins of the present invention can further be used to generate an antibody which selectively binds the protein. Such antibodies can be either monoclonal or polyclonal antibodies, as well fragments of these antibodies, and humanized forms.

The invention further provides antibodies which selectively bind to one of the proteins of the present invention and hybridomas which produce these antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (Campbell, A. M., *Monoclonal Antibody Technology: Laboratory Techniques in Biochemistry and Molecular Biology*, Elsevier Science Publishers, Amsterdam, The Netherlands (1984); St. Groth et al., *J. Immunol. Methods* 35:1–21 (1980); Kohler and Milstein, *Nature* 256:495–497 (1975)), the trioma technique, the human B-cell hybridoma technique (Kozbor et al., *Immunology Today* 4:72 (1983); Cole et al., in Monoclonal Antibodies and Cancer Therapy, Alan R. Liss, Inc. (1985), pp. 77–96).

Any animal (mouse, rabbit, etc.) which is known to produce antibodies can be immunized with the pseudogene polypeptide. Methods for immunization are well known in the art. Such methods include subcutaneous or interperitoneal injection of the polypeptide. One skilled in the art will recognize that the amount of the protein encoded by the ORF of the present invention used for immunization will vary based on the animal which is immunized, the antigenicity of the peptide and the site of injection.

The protein which is used as an immunogen may be modified or administered in an adjuvant in order to increase the protein's antigenicity. Methods of increasing the antigenicity of a protein are well known in the art and include, but are not limited to coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)).

Techniques described for the production of single chain antibodies (U.S. Pat. No. 4,946,778) can be adapted to produce single chain antibodies to proteins of the present invention.

For polyclonal antibodies, antibody containing antisera is isolated from the immunized animal and is screened for the presence of antibodies with the desired specificity using one of the above-described procedures.

The present invention further provides the above-described antibodies in detectably labelled form. Antibodies can be detectably labelled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labelling are well-known in the art, for example see (Stemberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)).

The labeled antibodies of the present invention can be used for in vitro, in vivo, and in situ assays to identify cells or tissues in which a fragment of the *Mycoplasma genitalium* genome is expressed.

The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "*Handbook of Experimental Immunology*"4th Ed., Blackwell Scientific Publications, Oxford, England, Chapter 10 (1986); Jacoby, W. D. et al., *Meth. Enzym.* 34 Academic Press, N.Y. (1974)). The immobilized antibodies of the present invention can be used for in vitro, in vivo, and in situ assays as well as for immunoaffinity purification of the proteins of the present invention.

3. Diagnostic Assays and Kits

The present invention further provides methods to identify the expression of one of the ORFs of the present invention, or homolog thereof, in a test sample, using one of the DFs or antibodies of the present invention.

In detail, such methods comprise incubating a test sample with one or more of the antibodies or one or more of the DFs of the present invention and assaying for binding of the DFs or antibodies to components within the test sample.

Conditions for incubating a DF or antibody with a test sample vary. Incubation conditions depend on the format employed in the assay, the detection methods employed, and the type and nature of the DF or antibody used in the assay. One skilled in the art will recognize that any one of the commonly available hybridization, amplification or immunological assay formats can readily be adapted to employ the DFs or antibodies of the present invention. Examples of such assays can be found in Chard, T., *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the DFs or antibodies of the present invention; and (b) one or more other containers comprising one or more of the following: wash reagents, reagents capable of detecting presence of a bound DF or antibody.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or DF.

Types of detection reagents include labelled nucleic acid probes, labelled secondary antibodies, or in the alternative, if the primary antibody is labelled, the enzymatic, or antibody binding reagents which are capable of reacting with the labelled antibody. One skilled in the art will readily recognize that the disclosed DFs and antibodies of the present invention can be readily incorporated into one of the established kit formats which are well known in the art.

4. Screening Assay for Binding Agents

Using the isolated proteins of the present invention, the present invention further provides methods of obtaining and identifying agents which bind to a protein encoded by one of the ORFs of the present invention or to one of the fragments and the Mycoplasma genome herein described.

In detail, said method comprises the steps of:

(a) contacting an agent with an isolated protein encoded by one of the ORFs of the present invention, or an isolated fragment of the Mycoplasma genome; and (b) determining whether the agent binds to said protein or said fragment.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In *Synthetic Peptides, A User's Guide*, W. H. Freeman, N.Y. (1992), pp. 289–307, and Kaspczak et al., *Biochimistry* 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control.

One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251: 1360 (1991)) or to the mRNA itself (antisense—Okano, *J. Neurochem.* 56:560 (1991); *Oligodeoxynucleotides as Antisense Inhibitors of Gene Expression*, CRC Press, Boca Raton, Fla. (1988)). Triple helix-formation optimally results in a shut-off of RNA transcription from DNA, while antisense RNA hybridization blocks translation of an MRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition for use in controlling Mycoplasma growth and infection.

5. Vaccine and Pharmaceutical Composition

The present invention further provides pharmaceutical agents which can be used to modulate the growth of *Mycoplasma genitalium*, or another related organism, in vivo or in vitro. As used herein, a "pharmaceutical agent" is defined as a composition of matter which can be formulated using known techniques to provide a pharmaceutical compositions. As used herein, the "pharmaceutical agents of the present invention" refers the pharmaceutical agents which are derived from the proteins encoded by the ORFs of the present invention or are agents which are identified using the herein described assays.

As used herein, a pharmaceutical agent is said to "modulated the growth of Mycoplasma sp., or a related organism, in vivo or in vitro," when the agent reduces the rate of growth, rate of division, or viability of the organism in question. The pharmaceutical agents of the present invention can modulate the growth of an organism in many fashions, although an understanding of the underlying mechanism of action is not needed to practice the use of the pharmaceutical agents of the present invention. Some agents will modulate the growth by binding to an important protein thus blocking the biological activity of the protein, while other agents may bind to a component of the outer surface of the organism blocking attachment or rendering the organism more prone to act the bodies nature immune system. Alternatively, the agent may be comprise a protein encoded by one of the ORFs of the present invention and serve as a vaccine. The development and use of a vaccine based on outer membrane components, such as the LPS, are well known in the art.

As used herein, a "related organism" is a broad term which refers to any organism whose growth can be modulated by one of the pharmaceutical agents of the present invention. In general, such an organism will contain a homolog of the protein which is the target of the pharmaceutical agent or the protein used as a vaccine. As such, related organism do not need to be bacterial but may be fungal or viral pathogens.

The pharmaceutical agents and compositions of the present invention may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The agents of the present invention can be used in native form or can be modified to form a chemical derivative. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980).

For example, a change in the immunological character of the functional derivative, such as affinity for a given antibody, is measured by a competitive type immunoassay. Changes in immunomodulation activity are measured by the appropriate assay. Modifications of such protein properties as redox or thermal stability, biological half-life, hydrophobicity, susceptibility to proteolytic degradation or the tendency to aggregate with carriers or into multimers are assayed by methods well known to the ordinarily skilled artisan.

The therapeutic effects of the agents of the present invention may be obtained by providing the agent to a patient by any suitable means (i.e., inhalation, intravenously, intramuscularly, subcutaneously, enterally, or parenterally). It is preferred to administer the agent of the present invention so as to achieve an effective concentration within the blood or tissue in which the growth of the organism is to be controlled.

To achieve an effective blood concentration, the preferred method is to administer the agent by injection. The administration may be by continuous infusion, or by single or multiple injections.

In providing a patient with one of the agents of the present invention, the dosage of the administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered. The therapeutically effective dose can be lowered by using combinations of the agents of the present invention or another agent.

As used herein, two or more compounds or agents are said to be administered "in combination" with each other when either (1) the physiological effects of each compound, or (2) the serum concentrations of each compound can be measured at the same time. The composition of the present invention can be administered concurrently with, prior to, or following the administration of the other agent.

The agents of the present invention are intended to be provided to recipient subjects in an amount sufficient to decrease the rate of growth (as defined above) of the target organism.

The administration of the agent(s) of the invention may be for either a "prophylactic" or "therapeutic" purpose. When provided prophylactically, the agent(s) are provided in advance of any symptoms indicative of the organisms growth. The prophylactic administration of the agent(s) serves to prevent, attenuate, or decrease the rate of onset of any subsequent infection. When provided therapeutically, the agent(s) are provided at (or shortly after) the onset of an indication of infection. The therapeutic administration of the compound(s) serves to attenuate the pathological symptoms of the infection and to increase the rate of recovery.

The agents of the present invention are administered to the mammal in a pharmaceutically acceptable form and in a therapeutically effective concentration. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton Pa. (1980)). In order to form a pharmaceutically acceptable composition suitable for effective administration, such compositions will contain an effective amount of one or more of the agents of the present invention, together with a suitable amount of carrier vehicle.

Additional pharmaceutical methods may be employed to control the duration of action. Control release preparations may be achieved through the use of polymers to complex or absorb one or more of the agents of the present invention. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate agents of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

The invention further provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the agents of the present invention may be employed in conjunction with other therapeutic compounds.

EXPERIMENTAL

EXAMPLE 1

Overview of Experimental Design and Methods

1. Shotgun Sequencing Strategy

The overall strategy for a shotgun approach to whole genome sequencing is outlined in Table 3. The theory of shotgun sequencing follows from the application of the equation for the Poisson distribution $P_x = m^x e/x!$, where x is the number of occurrences of an event and m is the mean number of occurrences. To determine the probability that any given base is not sequenced after a certain amount of random sequence has been generated, if L is the genome length, n is the number of clone insert ends sequenced, and w is the sequencing read length, then $m=nw/L$, and the probability that no clone originates at any of the w bases preceding a given base, i.e., the probability that the base is not sequenced, id $p_0 = e^{-m}$. Using the fold coverage as the unit form, one sees that after 580 kb of sequence has been randomly generated, m=1, representing 1× coverage. In this case, $p_0 = e^{-1} = 37$, thus approximately 37% is unsequenced. A 5× coverage (approximately 3150 clones sequenced from both insert ends) yields $p_0 = e^{-5} = 0.0067$, or 0.67% unsequenced. The total gap length is $Le^{-m}$, and the average gap size is L/n. 5× coverage would leave about 48 gaps averaging about 80 bp in size. The treatment is essentially that of Lander and Waterman. Table 4 illustrates a computer simulation of a random sequencing experiment for coverage of a 580 kb genome with an average fragment size of 400 bp.

2. Random Library Construction

In order to approximate the random model described above during actual sequencing, a nearly ideal library of cloned genomic fragment is required. *M. genitalium* genomic chromosomal DNA was mechanically sheared, digested with BAL31 nuclease to produce blunt-ends, and size-fractionated by agarose gel electrophoresis. Fragments in the 2.0 kb size range were excised and recovered. These fragments were ligated to SmaI-cut, phophatased pUC18 vector and the ligated products were fractionated on an agarose gel. The linear vector plus insert band was excised and recovered. The ends of the linear recombinant molecules were repaired with T4 polymerase treatment and the molecules were then ligated into circles. This two-stage procedure resulted in a molecularly random collection of single-insert plasmid recombinants with minimal contamination from double-insert plasmid recombinants with minimal contamination from double-insert chimeras (<1%) or free vector (<1%). Deviation from randomness is most likely to occur during cloning. *E. coli* host cells deficient in all recombinant and restriction functions were used to prevent rearrangements, deletions, and loss of clones by restriction. Transformed cells were plated directly on antibiotic diffusion plates to avoid the usual broth recovery phase which allows multiplication and selection of the most rapidly growing cells. All colonies were picked for template preparation regardless of size. Only clones lost due to "poison" DNA or deleterious gene products would be deleted from the library, resulting in a slight increase in gap number over that expected.

In order to evaluate the quality of the *M. genitalium* random insert library, sequence data was obtained from approximately 2000 templates using the M13F primer. The random sequence fragments were assembled using The Institute for Genomic Research (TIGR) autoassembler software after obtaining 500, 1000, 1500, and 2000 sequence fragments, and the number of unique assembled base pairs was determined. The progression of assembly was plotted using the actual data obtained from the assembly of up to 2000 sequence fragments and compared the data that is provided in the ideal plot. There was essentially no deviation of the actual assembly data from the ideal plot, indicating that we had constructed close to an ideal random library with minimal contamination from double insert chimeras and free of vector.

3. Random DNA Sequencing

Five-thousand seven hundred and sixty (5,760) plasmid templates were prepared using a "boiler bead" preparation method developed in collaboration with AGTC (Gaithersburg, Md.), as suggested by the manufacturer. The AGTC method is performed in a 96-well format for all stages of DNA preparation from bacterial growth through final DNA purification. Template concentration was determined using Hoechst Dye and a Millipore Cytofluor. DNA concentrations were not adjusted and low-yielding templates were identified and not sequenced where possible. Sequencing reactions were carried out on plasmid templates using the AB Catalyst Lab station or Perkin-Elmer 9600 Thermocyclers with Applied Biosystems PRISM Ready Reaction Dye Primer Cycle Sequencing Kits for the M13 forward (-21M13) and the M13 reverse (RP1) primers. Dye terminator sequencing reactions were carried out on the lambda templates on a Perkin-Elmer 9600 Thermocyler using the Applied Biosystems Ready Reaction Dye Terminator Cycle Sequencing kits. Nine-thousand eight hundred and forty-six (9,846) sequencing reactions were performed during the random phase of the project by 4 individuals using an average of 10 AB373 DNA Sequencers over a 2 month period. All sequencing reactions were analyzed using the Stretch modification of the AB373, primarily using a 36 cm well-to-read distance. The overall sequencing success rate for M13-21 sequences was 88% and 84% for M13RP1 sequences. The average usable read length for M13-21 sequences was 485 and 441 for M13RP1 sequences.

The art has described the value of using sequence from both ends of sequencing templates to facilitate ordering of contigs in shotgun assembly projects. A skilled artisan must balance the desirability of both-end sequencing (including the reduced cost of lower total number of templates) against shorter read-lengths and lower success rates for sequencing reactions performed with the M13RP1 (reverse) primer compared to the M13-21 (forward) primer. For this project, essentially all of the templates were sequenced from both ends.

4. Protocolfor Automated Cycle Sequencing

The sequencing consisted of using five (5) ABI Catalyst robots and ten (10) ABI 373 Automated DNA Sequencers. The Catalyst robot is a publicly available sophisticated pipetting and temperature control robot which has been developed specifically for DNA sequencing reactions. The Catalyst combines pre-aliquoted templates and reaction mixes consisting of deoxy- and dideoxynucleotides, the Taq thermostable DNA polymerase, fluorescently-labelled sequencing primers, and reaction buffer. Reaction mixes and templates were combined in the wells of an aluminum 96-well thermocycling plate. Thirty consecutive cycles of linear amplification (e.g., one primer synthesis) steps were performed including denaturation, annealing of primer and template, and extension of DNA synthesis. A heated lid with rubber gaskets on the thermocycling plate prevented evaporation without the need for an oil overlay.

Two sequencing protocols were used: dye-labelled primers and dye-labelled dideoxy chain terminators. The shotgun sequencing involves use of four dye-labelled sequencing primers, one for each of the four terminator nucleotide. Each dye-primer is labelled with a different fluorescent dye, permitting the four individual reactions to be combined into one lane of the 373 DNA Sequencer for electrophoresis, detection, and base-calling. ABI currently supplies pre-mixed reaction mixes in bulk packages containing all the necessary non-template reagents for sequencing. Sequencing can be done with both plasmid and PCR-generated templates with both dye-primers and dye-terminators with approximately equal fidelity, although plasmid templates generally give longer usable sequences.

Thirty-two reactions were loaded per 373 Sequencer each day, for a total of 960 samples. Electrophoresis was run overnight following the manufacture's protocols, and the data was collected for twelve hours. Following electrophoresis and fluorescence detection, the ABI 373 performs automatic lane tracking and base-calling. The lane-tracking was confirmed visually. Each sequence electropherogram (or fluorescence lane trace) was inspected visually and assessed for quality. Trailing sequences of low quality were removed and the sequence itself was loaded via software a Sybase database (archived daily to a 8 mm tape). Leading vector polylinker sequence was removed automatically by software program. The average edited lengths of sequences from the ABI 373 Sequencers converted to Stretch Liners were approximately 460 bp.

Informatics

1. Data Management

A number of information management systems (LIMS) for a large-scale sequencing lab have been developed. A system was used which allowed an automated data flow wherever possible to reduce user error. The system used to collect and assemble the sequence information obtained is centered upon a relational data management system built using the Sybase RDBMS. The database is designed to store and correlate all information collected during the entire operation from template preparation to final analysis of the genome. Because the raw output of the AB 373 Sequencers is based on a Macintosh platform and the data management system chosen is based on a Unix platform, it was necessary to design and implement a variety of multi-user, client server applications which allow the raw data as well as analysis results to flow seamlessly into the database with a minimum of user effort.

2. Assembly

The sequence data from 8,472 sequence fragments was used to assemble the M. genitalium genome. The assembly was performed by using a new assembly engine (TIGR Assembler—previously designated ASMG) developed at TIGR. The TIGR Assembler simultaneously clusters and assembles fragments of the genome. In order to obtain the necessary speed, the TIGR Assembler builds a hash table of 10 bp oligonucleotide subsequences to generate a list of potential sequence fragment. The number of potential overlaps for each fragment determines which fragments are likely to fall into repetitive elements. Beginning with a single seed sequence fragment, the TIGR Assembler extends the current contig by attempting to add the best matching fragment based on oligonucleotide content. The current contig and candidate fragment are aligned using a modified version of the Smith-Waterman algorithm which provides for optimal gap alignments. The current contig is extended by the fragment only if strict criteria for the quality of the match are met. The match criteria include the minimum length of overlap, the maximum length of an unmatched end, and the minimum percentage match. These criteria are automatically lowered by the TIGR Assembler in regions of minimal coverage and raised in regions with a good chance of containing repetitive elements. Potentially chimeric fragments and fragments representing the boundaries of repetitive elements are often rejected based on partial mismatches at the ends of alignments and excluded from the current contig. The TIGR Assembler is designed to take advantage of clone size information coupled with sequencing from both ends of each template. The TIGR Assembler enforces the constraint that sequence fragments from two ends of the same template point toward one another in the contig and are located within a certain range of base pairs (definable for each clone based on the known clone size range for a given library). Assembly of the 8,472 sequence fragments of *M. genitalium* required 10 hours of CPU time on a SPARCenter 2000. All contigs were loaded into a Sybase structure representing the location of each fragment in the contig and extensive information about the consensus sequence itself. The result of this process was approximately 40 contigs ordered into 2 groups (See below). Because of the high stringency of the TIGR Assembler process it was found to be useful to perform a FASTA (GRASTA) alignment of all contigs built by the TIGR Assembler process against each other. In this way additional overlaps were detected which enabled compression of the data set into 26 contigs in 2 groups.

Achieving Closure

The complete genome sequence was obtained by sequencing across the gaps between contigs. While gap filling has occupied a major portion of the time and expense of other genome sequencing projects, it was minimal in the present invention. This was primarily due to 1) saturation of the genome as a result of the number of random clones and sequencing reactions performed, 2) the longer read lengths obtained from the Stretch Liners, 3) the anchored ends which were obtain for joining contigs, and 4) the overall capacity and efficiency of the high throughput sequencing facility.

Gaps occurred on a predicted random basis, as shown in Table 4, which illustrates simulated random sequencing. These gaps generally were less than 200 bp in size. All of the gaps were closed by sequencing further on the templates bordering the gaps. In these cases, oligo primers for extension of the sequence from both ends of the gap were generated using techniques known in the art. This gave a double standard coverage across the gap areas.

The high redundancy of sequence information that was obtained from the shotgun approach gave a highly accurate sequence. Our sequence accuracy was confirmed by comparing the sequence information obtained against known *M. genitalium* genes present in the GenBank database. The accuracy of our chromosome structure was confirmed by comparison of restriction digests to the known restriction map of *M. genitalium*. The EcoRI restriction map of *M. genitalium* is shown in FIG. 1 and expressed in tabular form in Table 5.

Identifying Genes

*M. genitalium* ORFs were initially defined by evaluating their coding potential with the program *Gene* Works using composition matrices specific to Mycoplasma genomic DNA. The ORF sequences (plus 300 bp of flanking sequence) were used in searches against a database of non-redundant bacterial proteins (NRBP). Redundancy was removed from NRBP at two stages. (1) All DNA coding sequences were extracted from GenBank (release 85), and sequences from the same species were searched against each other. Sequences having >97% similarity over regions >100 nucleotides were combined. (2) The sequences were translated and used to protein comparisons with all sequences in Swiss-Prot (release 30). Sequences belonging to the same species and having >98% similarity over 33 amino acids were combined. NRBP is composed of 21445 sequences from 23751 GenBank sequences and 11183 Swiss-Prot sequences from 1099 different species.

Searches were performed using an algorithm that (1) translates the query DNA sequence in all six reading frames for searching against a protein database, (2) identifies the protein sequences that match the query, and (3) aligns the protein-protein matches using a modified Smith-Waterman algorithm. In cases where insertion or deletions in the DNA sequence produced a frame shift error, the alignment algorithm started with protein regions of maximum similarity and extended the alignment to the same database match using the 300 bp flanking region. Regions known to contain frame shift errors were saved to the database and evaluated for possible correction. The role categories were adopted from those previously defined by Riley et al. for *E. coli* gene products. Role assignments were made to *M. genitalium* ORFS at the protein sequence level by linking the protein sequence of the ORFS with the Swiss-Prot sequences in the Riley database.

Detailed Description of Sequencing the Mycoplasma genitalium Genome, Genome Analysis and Comparative Genomics We have determined the complete nucleotide sequence (580,071 bp) of the *Mycoplasma genitalium* genome using the approach of whole chromosome shotgun sequencing and assembly, which has successfully been applied to the analysis of the *Haemophilus influenzae* genome (R. Fleischmann et al., Science 269:496 (1995)). These data, together with the description of the complete genome sequence (1.83 Mb) of the eubacterium *Haemophilus influenzae*, have provided the opportunity for comparative genomics on a whole genome level for the first time. Our initial whole genome comparisons reveal fundamental differences in genome content which are reflected in different physiological and metabolic capacities of *M. genitalium* and *H. influenzae*.

The strategy and methodology for whole genome shotgun sequencing and assembly was similar to that previously described for *H. influenzae* (R. Fleischmann et al., Science 269:496 (1995). In particular, a total of 50 μg of purified *M. genitalium* strain G-37 DNA (ATCC No. 33530) was isolated from cells grown in Hayflick's medium. A mixture (990 μl) containing 50 μg of DNA, 300 mM sodium acetate, 10 mM tris HCl, 1 mM EDTA, and 30 percent glycerol was chilled to 0° C. in a nebulizer chamber and sheared at 4 lbs/in$^2$ for 60 seconds. The DNA was precipitated in ethanol and redissolved in 50 μl of tris-EDTA (TE) buffer to create blunt ends; a 40 μl portion was digested for 10 minutes at 30° C. in 85 μl of BAL31 buffer with 2 units of BAL 31 nuclease (New England BioLabs). The DNA was extracted with phenol, precipitated in ethanol, dissolved in 60 μl of TE buffer, and fractionated on a 1.0 percent low melting agarose gel. A fraction (2.0 kb) was excised, extracted with phenol, and redissolved in 20 μl of TE buffer. A two-step ligation procedure was used to produce a plasmid library in which 99% of the recombinants contained inserts, of which >99% were single inserts. The first ligation mixture (50 μl) contained approximately 2 μg DNA fragments, 2 μg of SmaI+ bacterial alkaline phosphatase pUC 18 DNA (Pharmacia), and 10 units of T4 DNA hgase (GIBCO/BRL), and incubation was for 5 hours at 4° C. After extraction with phenol and ethanol precipitation, the DNA was dissolved in 20 μl of TE buffer and separated by electrophoresis on a 1.0 percent low melting agarose gel. A ladder of ethidium bromide-stained, linearized DNA bands, identified by size as insert (i), vector (v), v+i, v+2i, v+3i, etc. was visualized by 360 nm ultraviolet light. The v+i DNA was excised and recovered in 20 µl of TE buffer. The v+i DNA was blunt-ended by T4 polymerase treatment for 5 minutes at 37° C. in a reaction mixture (50 µl) containing the linerized v+i fragments, four deoxynucleotide triphosphates (dNTPs) (25 µM each), and 3 units of T4 polymerase (New England Biolabs) under buffer conditions recommended by the supplier. After phenol extraction and ethanol precipitation, the repaired v+i linear pieces were dissolvhed in 20 µl of TE. The final ligation to produce circles was carried out in a 50 µl reaction containing 5 µl of v+i DNA and 5 units of T4 hgase at 15° C. overnight. The reaction mixture was heated at 67° C. for 10 minutes and stored at −20° C.

For transformation, a 100 µl portion of Epicurian SURE 2 Supercompetent Cells (Stratagene 200152) was thawed on ice and transferred to a chilled Falcon 2059 tube on ice. A 1.7 µl volume of 1.42M β-mercaptoethanol was added to the cells to a final concentration of 25 mM. Cells were incubated on ice for 10 minutes. A 1 µl sample of the final ligation mix was added to the cells and incubated on ice for 30 minutes. The cells were heat-treated for 30 seconds at 42° C. and placed back on ice for 2 minutes. The outgrowth period in liquid culture was omitted to minimize the preferential growth of any transformed cell. Instead, the transformed cells were plated directly on a nutrient rich SOB plate containing a 5 ml bottom layer of SOB agar (1.5 percent SOB agar consisted of 20 g of tryptone, 5g of yeast extract, 0.5 g of NaCl, and 1.5 percent Difco agar/liter). The 5 ml bottom layer was supplemented with 0.4 ml of ampicillin (50 mg/ml) per 100 ml of SOB agar. The 15 ml top layer of SOB agar was supplemented with 1 ml of $MgCl_2$ (1M) and 1 ml of $MgSO_4$ (1M) per 100 ml of SOB agar. The 15 ml top layer was poured just before plating. The titer of the library was approximately 100 colonies per 10 µl aliquot of transformation.

One of the lessons learned from sequencing and assembly of the complete *H. influenzae* genome was that contig ordering and gap closure is most efficient if the random sequencing phase of the project is continued until at least 99.8%–99.9% of the genome is sequenced with at least 6-fold coverage. To calculate the number of random sequencing reactions necessary to obtain this coverage for the *M. genitalium* genome, we made use of the Lander and Waterman [E. S. Lander and M. S. Waterman, *Genomics* 2:231 (1988)] application of the Poisson distribution, where $p_x = e^{-nw/L}$. $p_x$ is the probability that any given base is not sequenced, n is the number of clone insert ends sequenced, w is the average read length of each template in bp, and L is the size of the genome in bp. For a genome of 580 kb with an average sequencing read length of 450 bp after editing, approximately 8650 sequencing reactions (or 4325 clones sequenced from both ends) should theoretically provide 99.85% coverage of the genome. This level of coverage should leave approximately 10 gaps with an average size of 70 bp unsequenced.

To evaluate the quality of the *M. genitalium* library, sequence data were obtained from both ends of approximately 600 templates using both the M13 forward (M13-21) and the M13 reverse (Ml3RP1) primers. Sequence fragments were assembled using the TIGR ASSEMBLER and found to approximate a Poisson distribution of fragments with an average read length of 450 bp for a 580 kb library, indicating that the library was essentially random.

For this project, a total of 5760 double-stranded DNA plasmid templates were prepared in a 96-well format using a boiling bead method. Ninety-four percent of the templates prepared yielded a DNA concentration ≧30 ng/µl and were used for sequencing reactions. To facilitate ordering of contigs each template was sequenced from both ends. Reactions were carried out on using the AB Catalyst LabStation with Applied Biosystems PRISM Ready reaction Dye Primer Cycle Sequencing Kits for the M13 forward (M13-21) and the M13 reverse (Ml3RP1) primers. The success rate and average read length after editing with the M13-21 primer were 88 percent and 444 bp, respectively, and 84 percent and 435 bp, respectively, with the M13RP1 primer. All data from template preparation to final analysis of the project were stored in a relational data management system developed at TIGR [A. R. Kerlavage et al., *Proceedings of the Twenty-Sixth Annual Hawaii International Conference on System Science* (IEEE Computer Society Press, Washington, D.C., 1993), p. 585] To facilitate ordering of contigs each template was sequenced from both ends. A total of 9846 sequencing reactions were performed by five individuals using an average of 8 AB 373 DNA Sequencers per day for a total of 8 weeks. Assembly of 8472 high quality *M. genitalium* sequence fragments along with 299 random genomic sequences from Peterson et al. (S. N. Peterson et al., *J. Bacteriol.* 175:7918 (1993)) was performed with the TIGR ASSEMBLER. The assembly process generated 39 contigs (size range: 606 to 73,351 bp) which contained a total of 3,806,280 bp of primary DNA sequence data. Contigs were ordered by ASM_ALIGN, program which links contigs based on information derived from forward and reverse sequencing reactions from the same clone.

ASM_ALIGN analysis revealed that all 39 gaps were spanned by an existing template from the small insert genomic DNA library (i.e., there were no physical gaps in the sequence assembly). The order of the contigs was confirmed by comparing the order of the random genomic sequences from Peterson et al. (S. N. Peterson et al., *J. Bacteriol.* 175:7918 (1993)) that were incorporate into the assembly with their known position on the physical map of the *M. genitalium* chromosome (T. S. Lucier et al., *Gene* 150:27 (1994); Peterson et al., *J. Bacteriol.* 177:3199 (1995)). Because of the high stringency of the TIGR ASSEMBLER, the 39 contigs were searched against each other with GRASTA (a modified FASTA (B. Brutlag et al., *Comp. Chem.* 1:203 (1993)). The BLOSUM 60 amino acid substitution matrix was used in all protein-protein comparisons [S. Henikoff and J. G. Henikoff, *Proc. Natl. Acad. Sci. USA* 89:1091 (1992)] to detect overlaps (<30 bp) that would have been missed during the initial assembly process. Eleven overlaps were detected with this approach which reduced the total number of gaps from 39 to 28.

Templates spanning each of the sequence gaps were identified and oligonucleotide primers were designed from the sequences at the end of each contig. All gaps were less than 300 bp; thus a primer walk from both ends of each template was sufficient for closure. All electropherograms were visually inspected with TIGR EDITOR (R. Fleischmann et al., *Science* 269:496 (1995)) for initial sequence editing. Where a discrepancy could not be resolved o a clear assignment made, the automatic base calls were left unchanged.

Several criteria for determination of sequence completion were established for the *H. influenzae* genome sequencing project and these same criteria were applied to this study. Across the assembled *M. genitalium* genome there is an average sequence redundancy of 6.5-fold. The completed sequence contains less than 1% single sequence coverage. For each of the 53 ambiguities remaining after editing and the 25 potential frameshifts found after sequence-similarity searching, the appropriate template was resequenced with an alternative sequencing chemistry (dye terminator vs. dye primer) to resolve ambiguities. Although it is extremely difficult to assess sequence accuracy, we estimate our error rate to be less than 1 base in 10,000 based upon frequency of shifts in open reading frames, unresolved ambiguities, overall quality of raw data, and fold coverage.

A direct cost estimate for sequencing, assembly, and annotation of the M. genitalium genome was determined by summing reagent and labor costs for library construction, template preparation and sequencing, gap closure, sequence confirmation, annotation, and preparation for publication, and dividing by the size of the genome in base pairs. This yielded a final cost of 30 cents per finished base pair.

Genomic Analysis

The M. genitalium genome is a circular chromosome of 580,071 bp. The overall G+C content is 32% (A, 34%; C, 16%; G, 16%; and T, 34%). The G+C content across the genome varies between 27 and 37% (using a window of 5000 bp), with the regions of lowest G+C content flanking the presumed origin of replication of the organism. As in H. influenzae (Fleischmann, R. et al., Science 269:496 (1995)), the rRNA operon in M. genitalium contains a higher G+C content (44%) than the rest of the genome, as do the tRNA genes (52%). The higher G+C content in these regions may reflect the necessity of retaining essential G+C base pairing for secondary structure in rRNAs and tRNAs (Rogers, M. J. et al., Isr. J. Med. Sci. 20:768 (1984)).

The genome of M. genitalium contains 74 EcoRI fragments, as predicted by cosmid mapping data (Lucier, T. S. et al., Gene 150:27 (1994); Peterson et al., J. Bacteriol. 177:3199 (1995)). The order and sizes of the EcoRI fragments determined from sequence analysis are in agreement with those previously reported (Lucier, T. S. et al., Gene 150:27 (1994); Peterson et al., J. Bacteriol. 177:3199 (1995)), with one apparent discrepancy between coordinates 62,708 and 94,573 in the sequence. However, re-evaluation of cosmid hybridization data in light of results from genome sequence analysis confirms that the sequence data are correct, and the extra 4.0 kb EcoRI fragment in this region of the cosmid map reflects a misinterpretation of the overlap between cosmids J-8 and 21 (Lucier, T. S., unpublished observation). The ends of each clone from the ordered cosmid library were sequenced and are shown on the circular chromosome in FIG. 4. The order of the cosmids based on sequence analysis is in complete agreement with that determined by physical mapping (Lucier, T. S. et al., Gene 150:27 (1994); Peterson et al, J. Bacteriol. 177:3199 (1995)).

Figure 4:
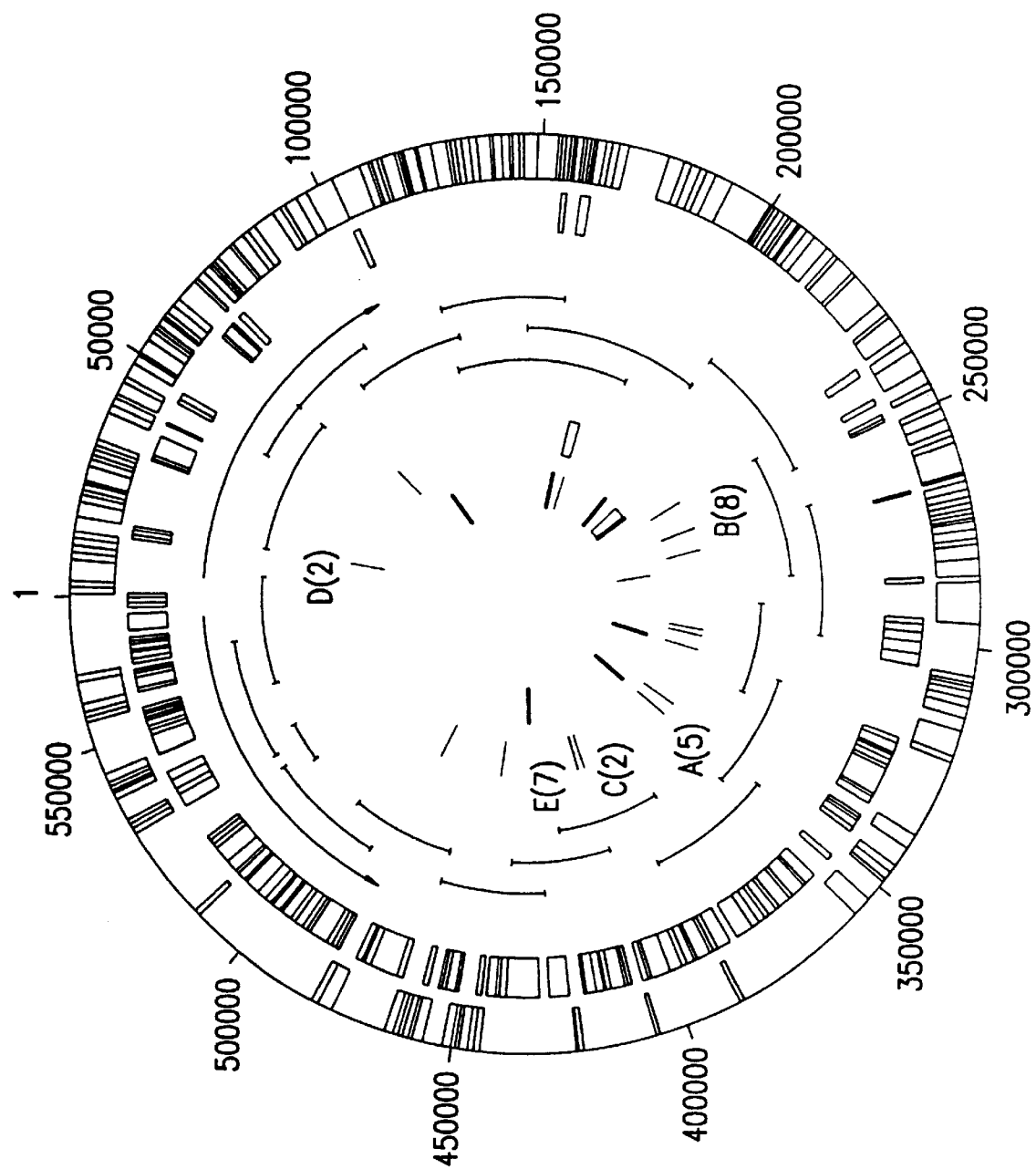
Figure 5A:
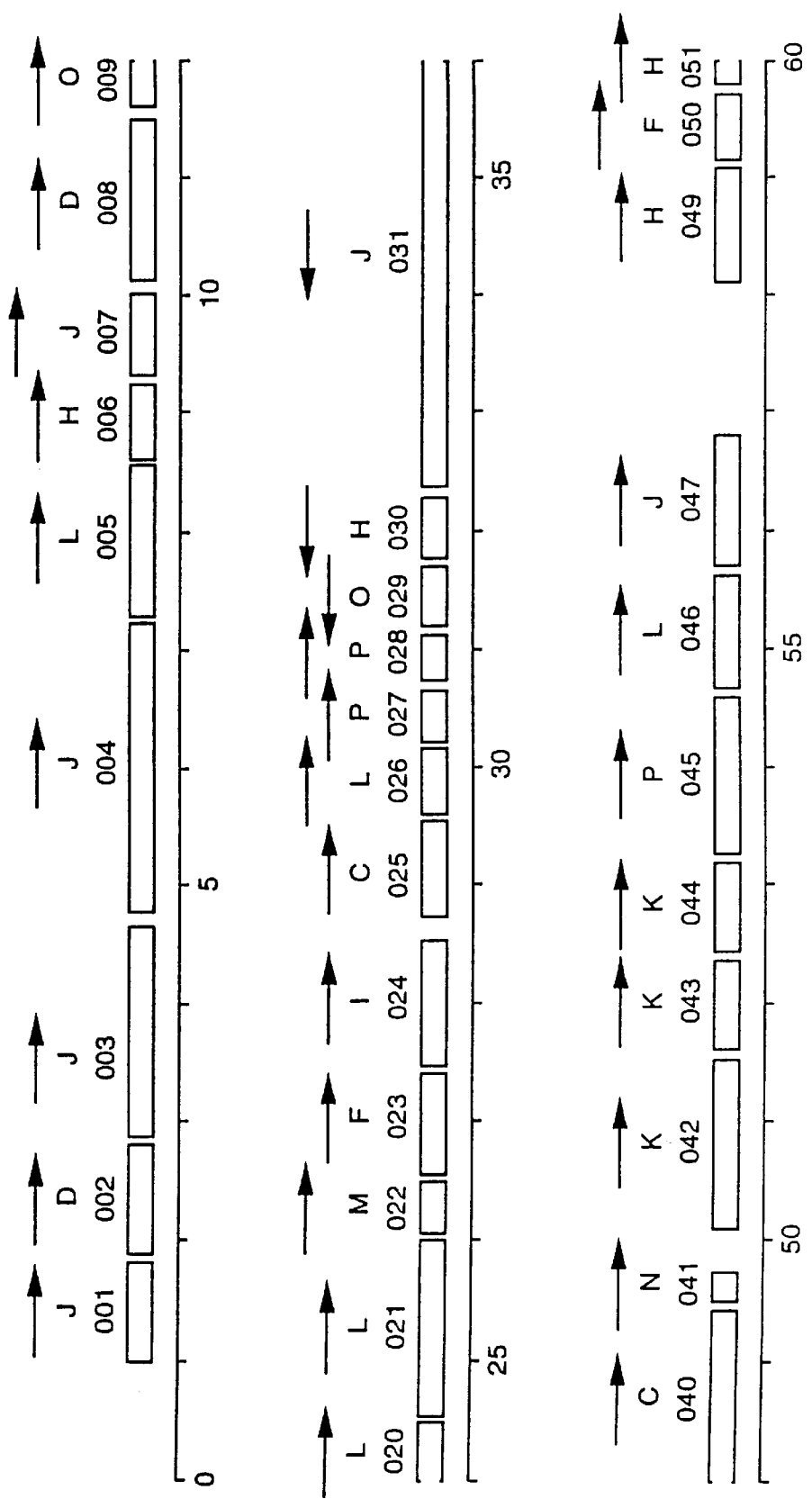
Figure 5B:
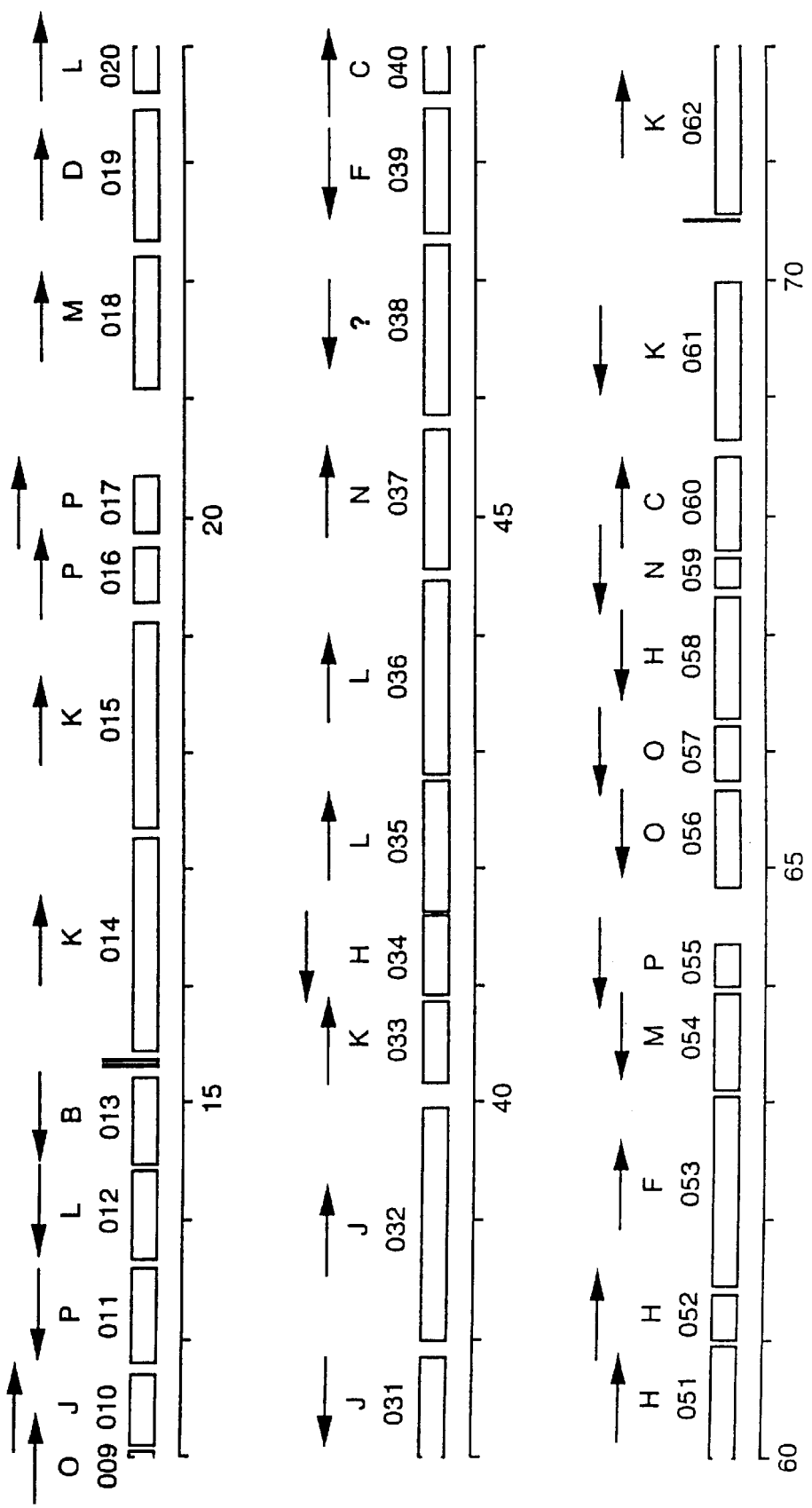
Figure 5C:
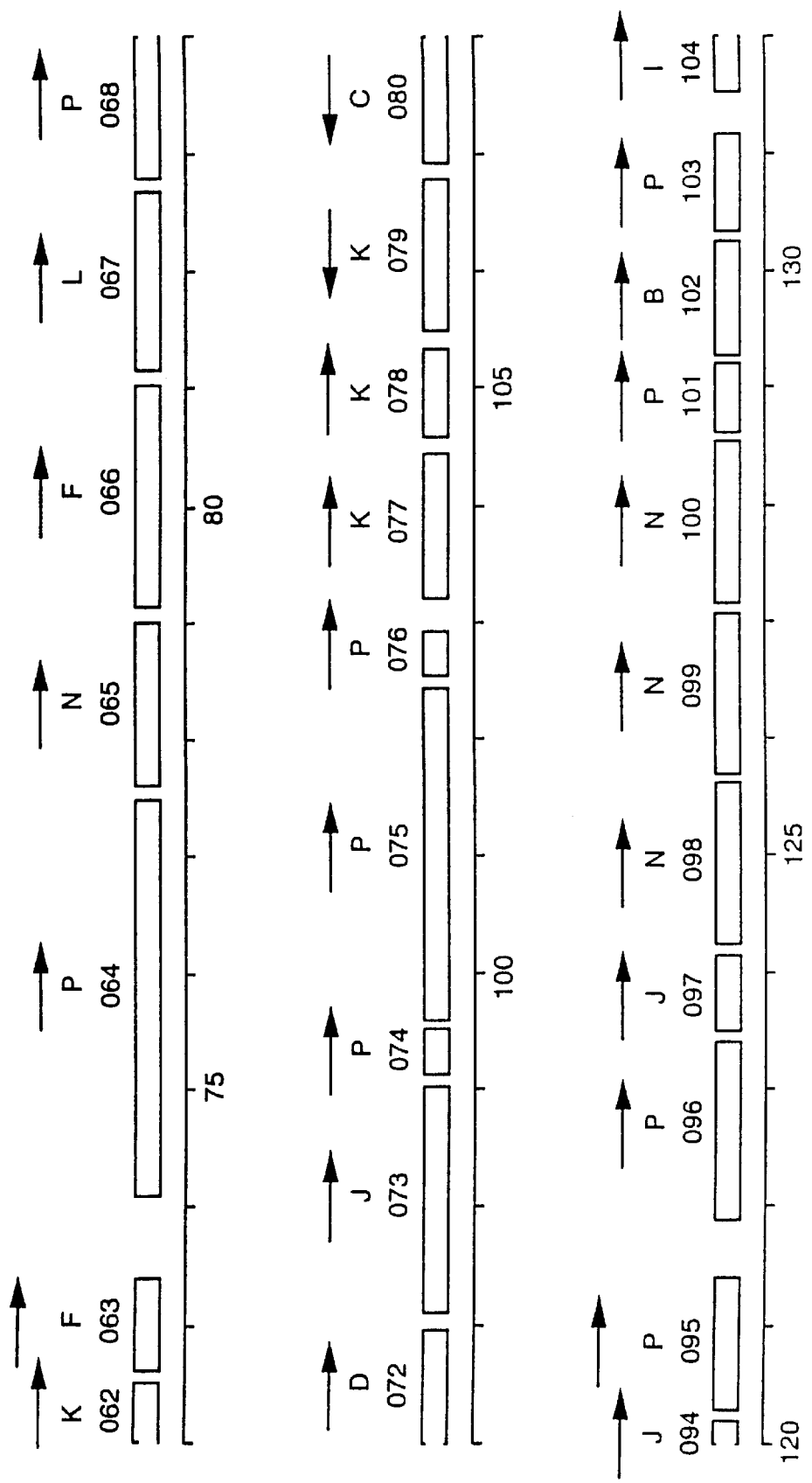
Figure 5D:
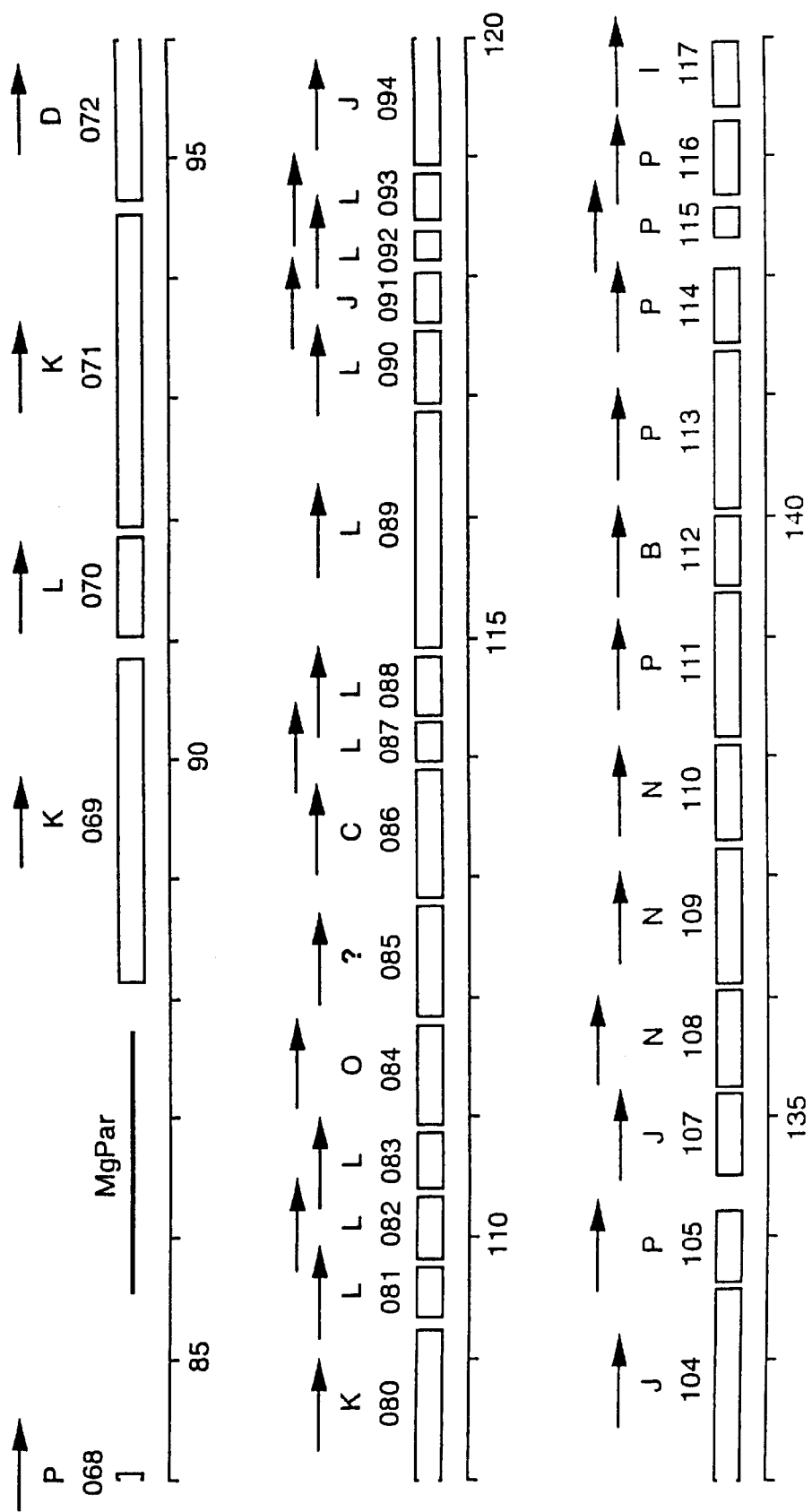
Figure 5E:
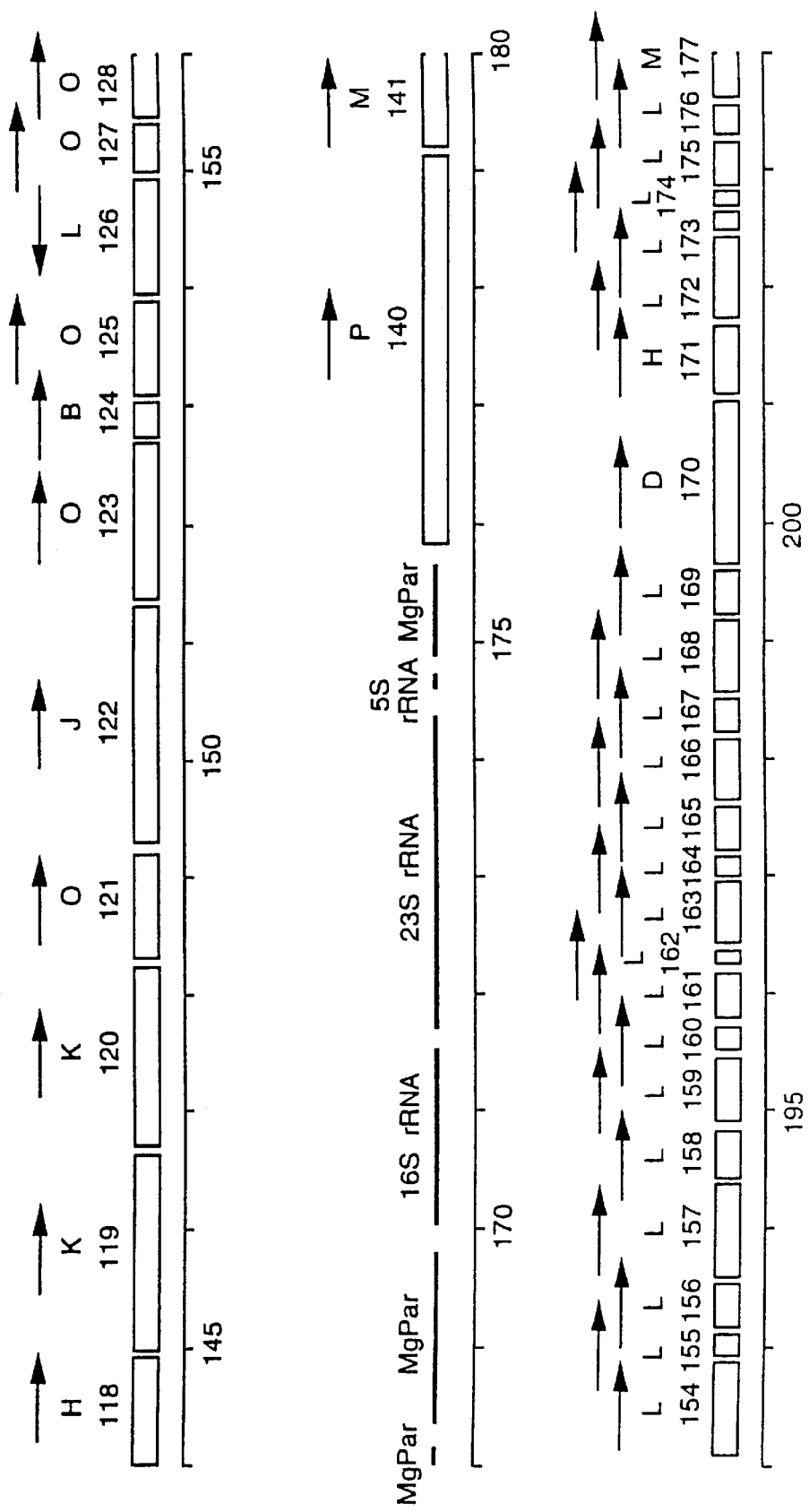
Figure 5F:
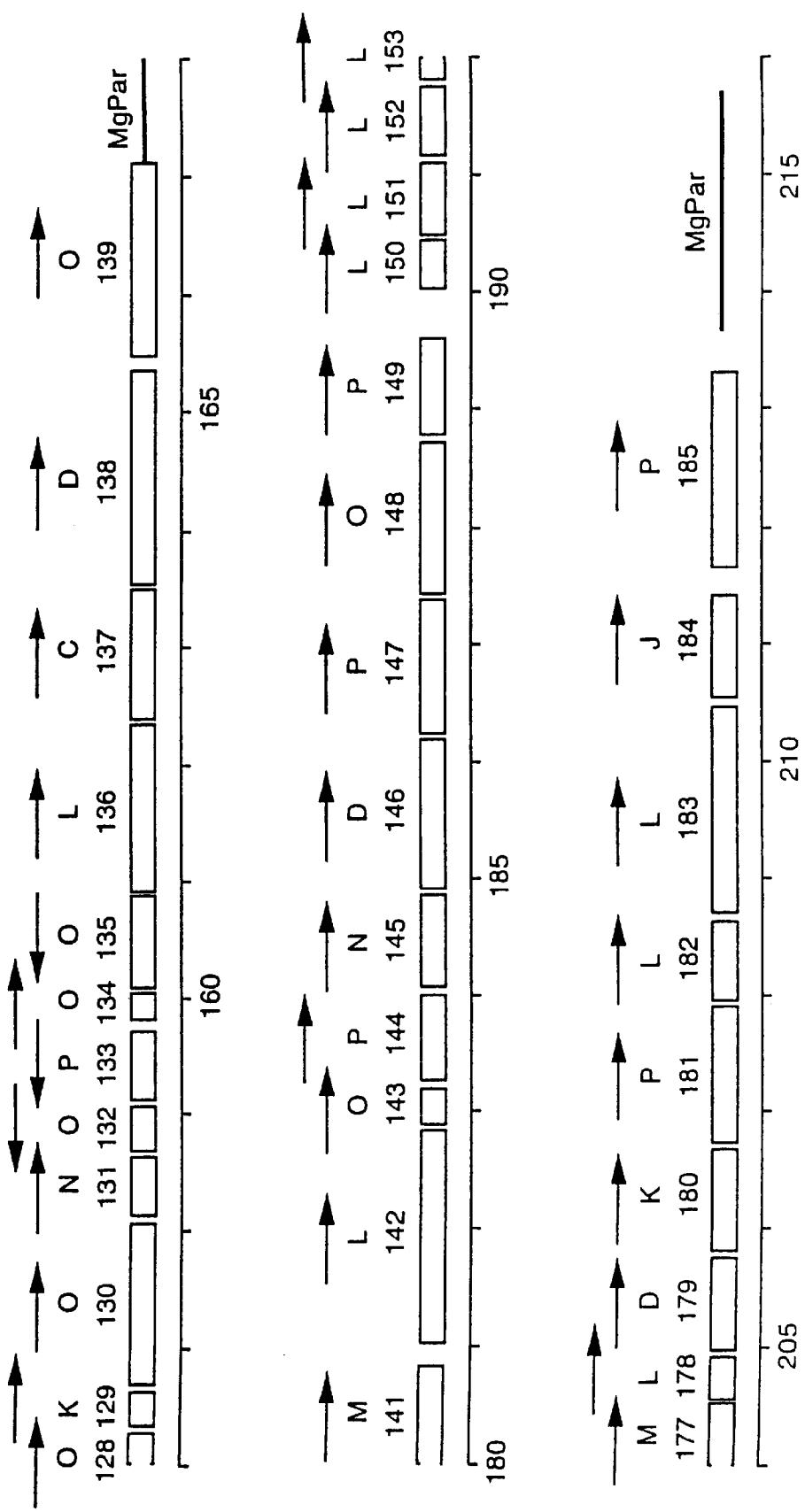
Figure 5G:
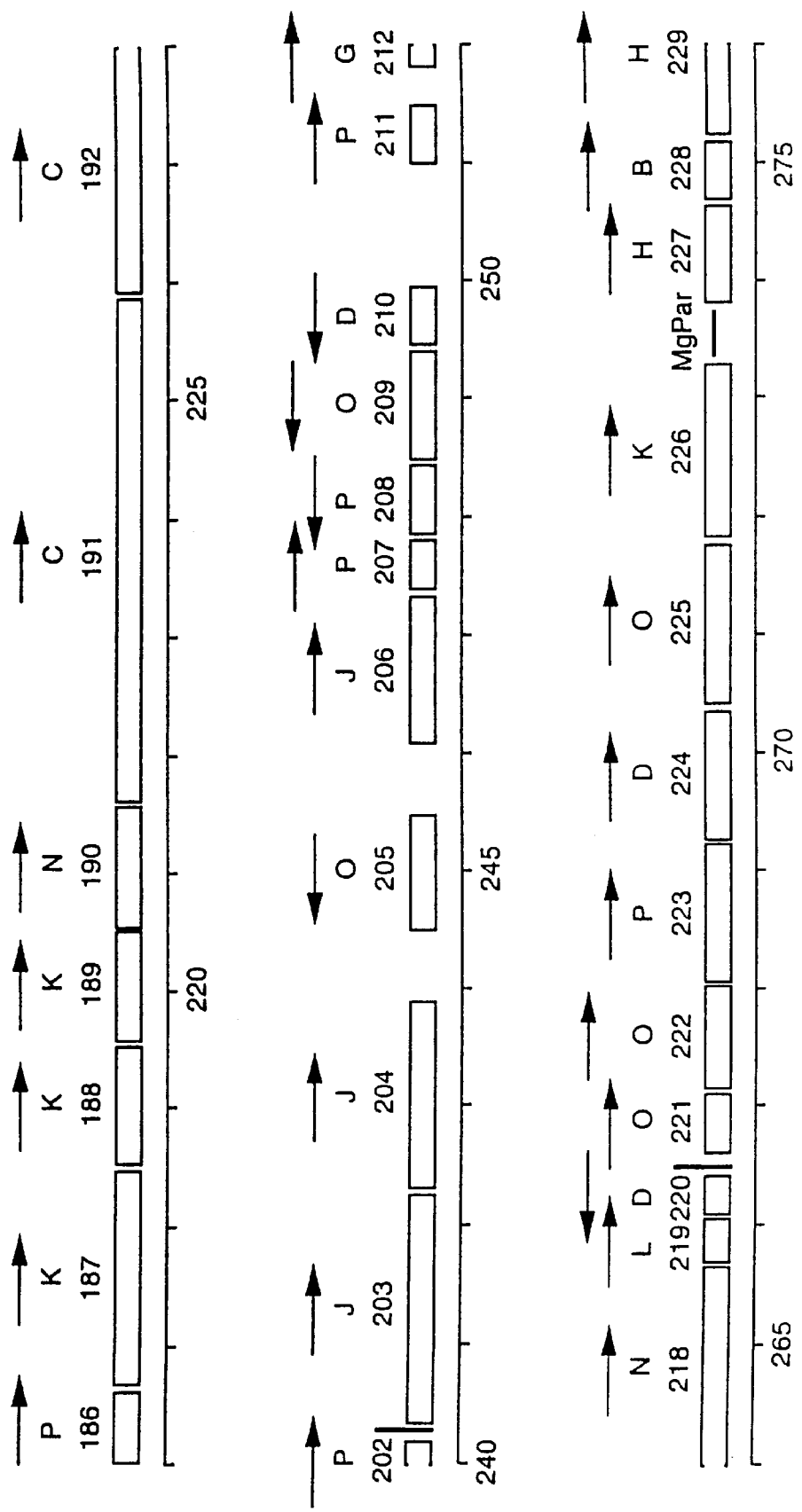
Figure 5H:
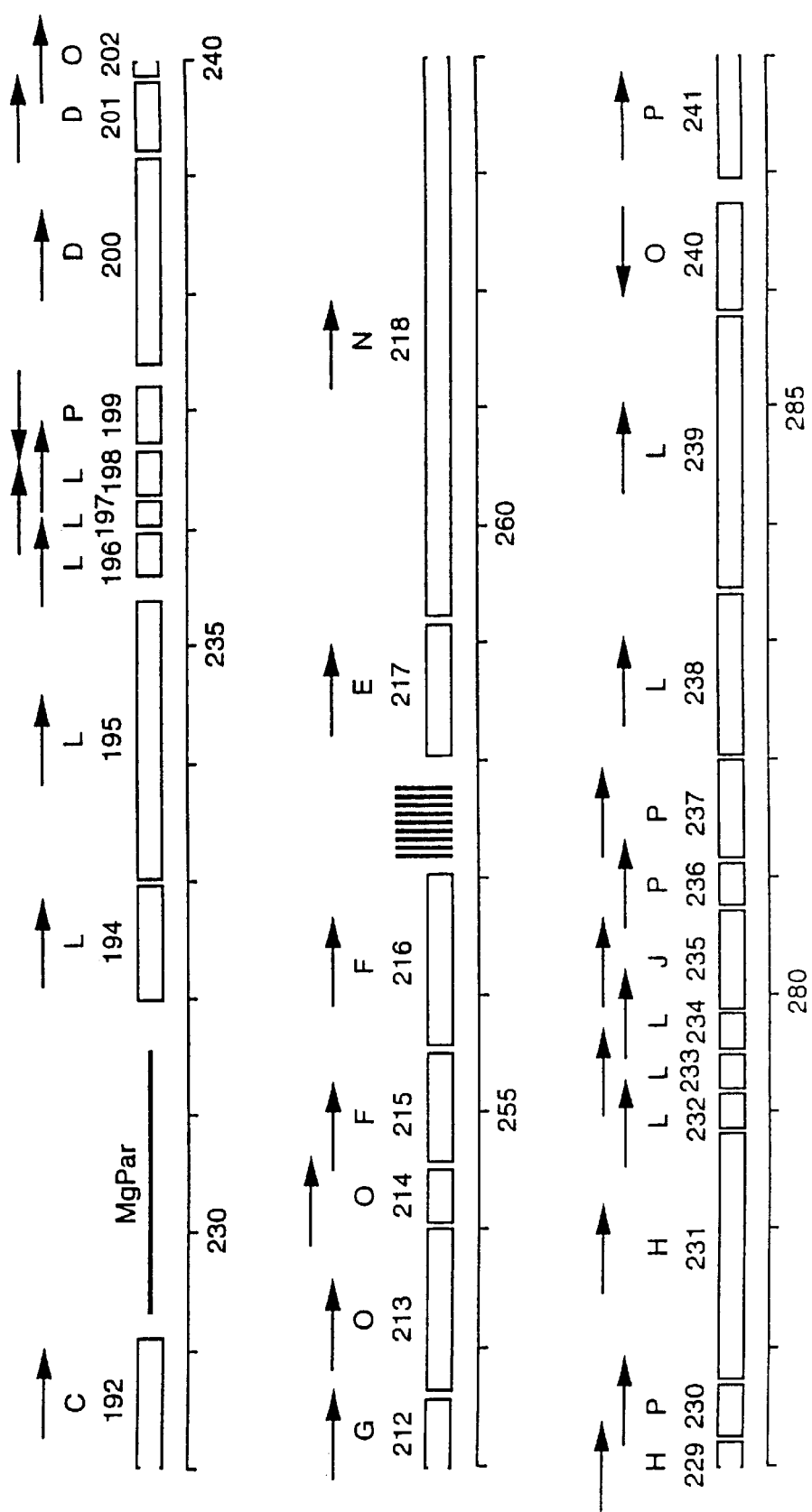
Figure 5I:
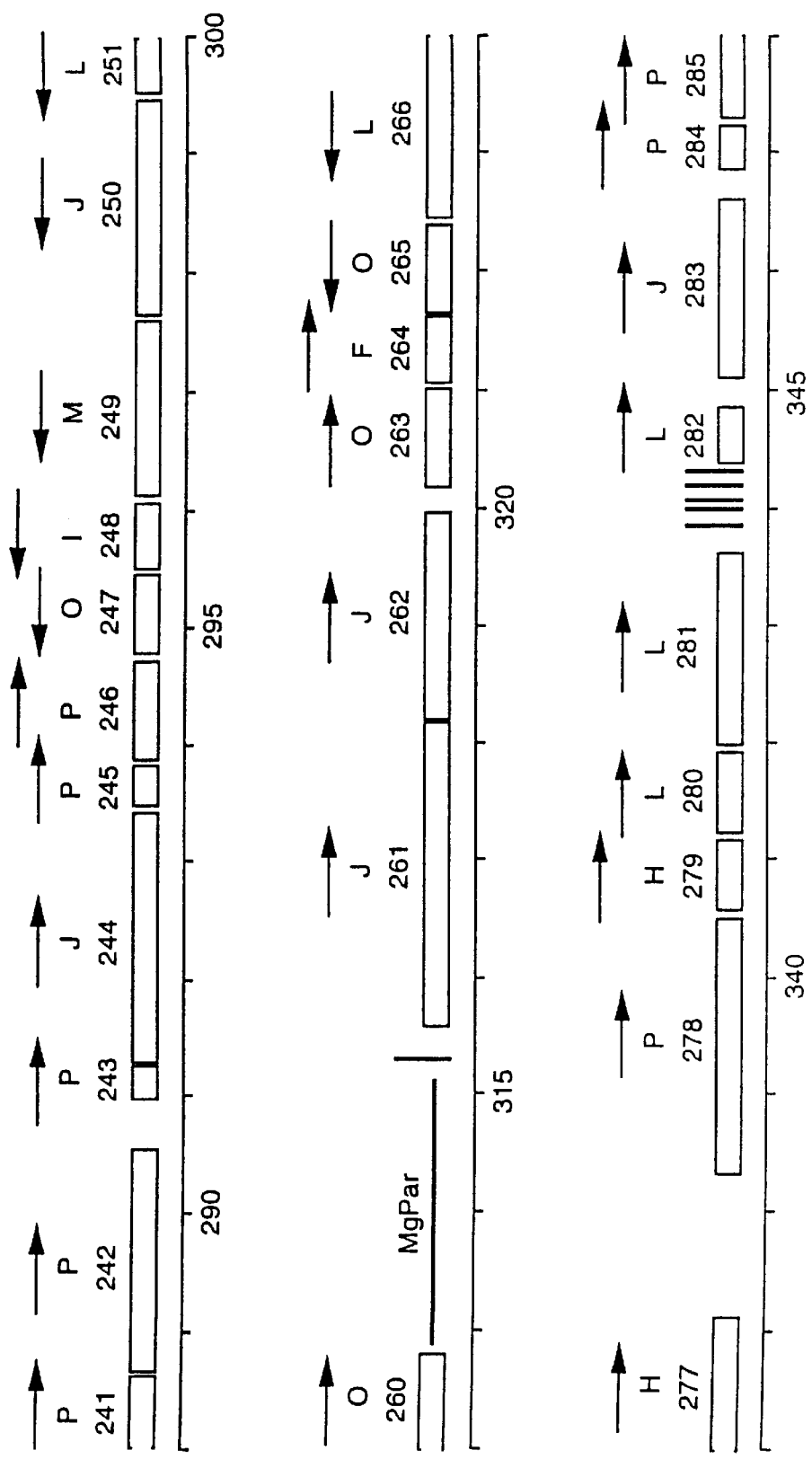
Figure 5J:
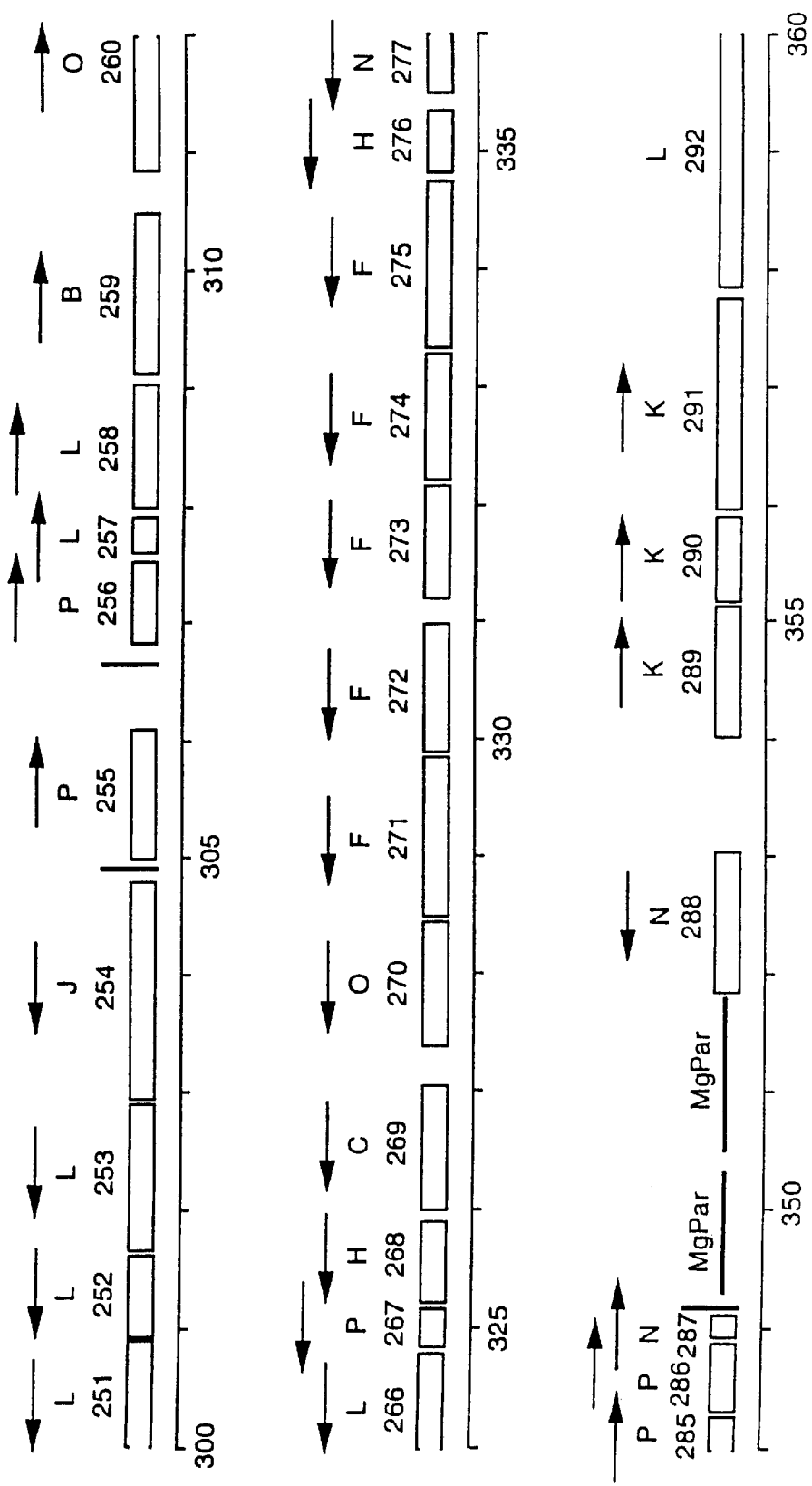
Figure 5K:
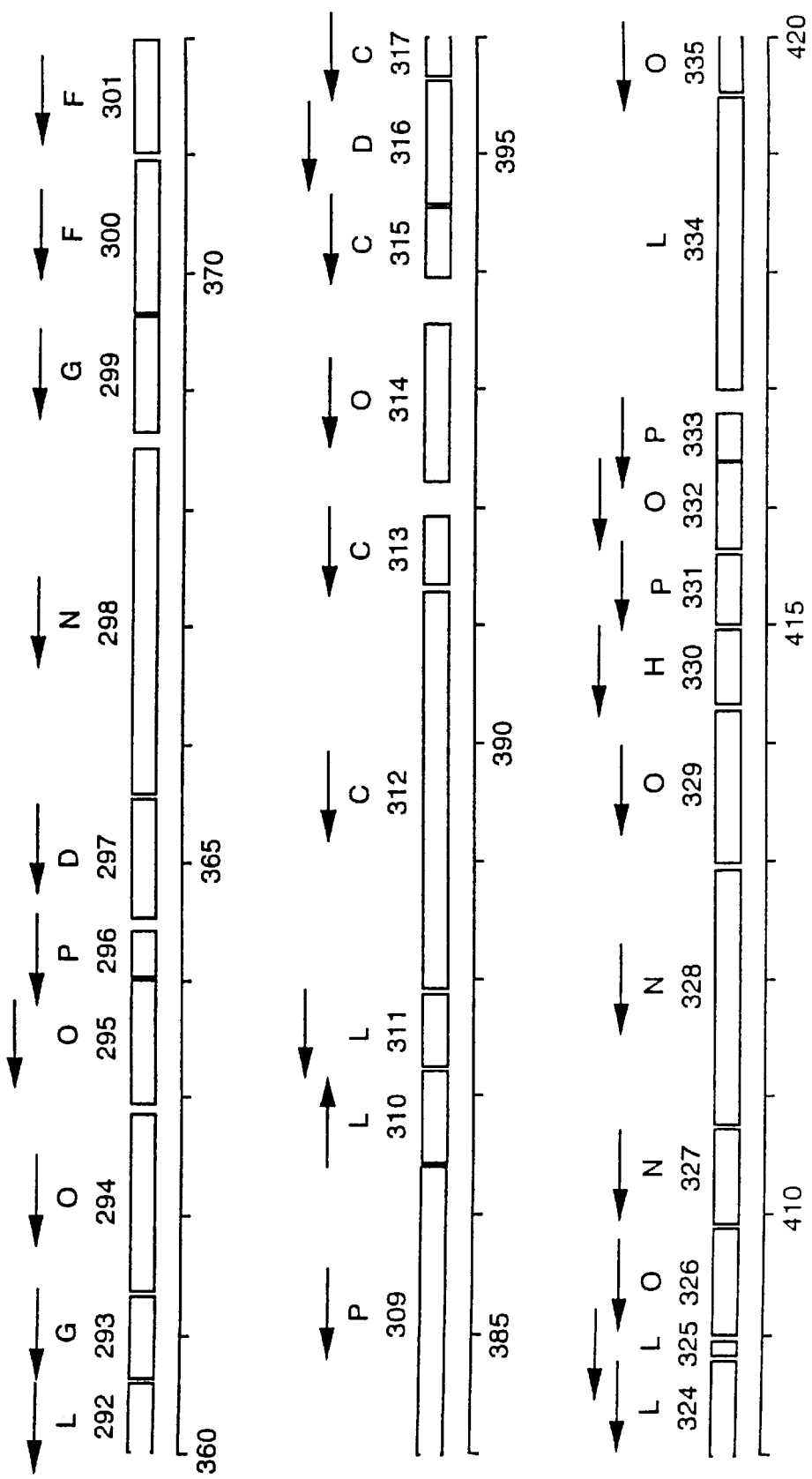
Figure 5L:
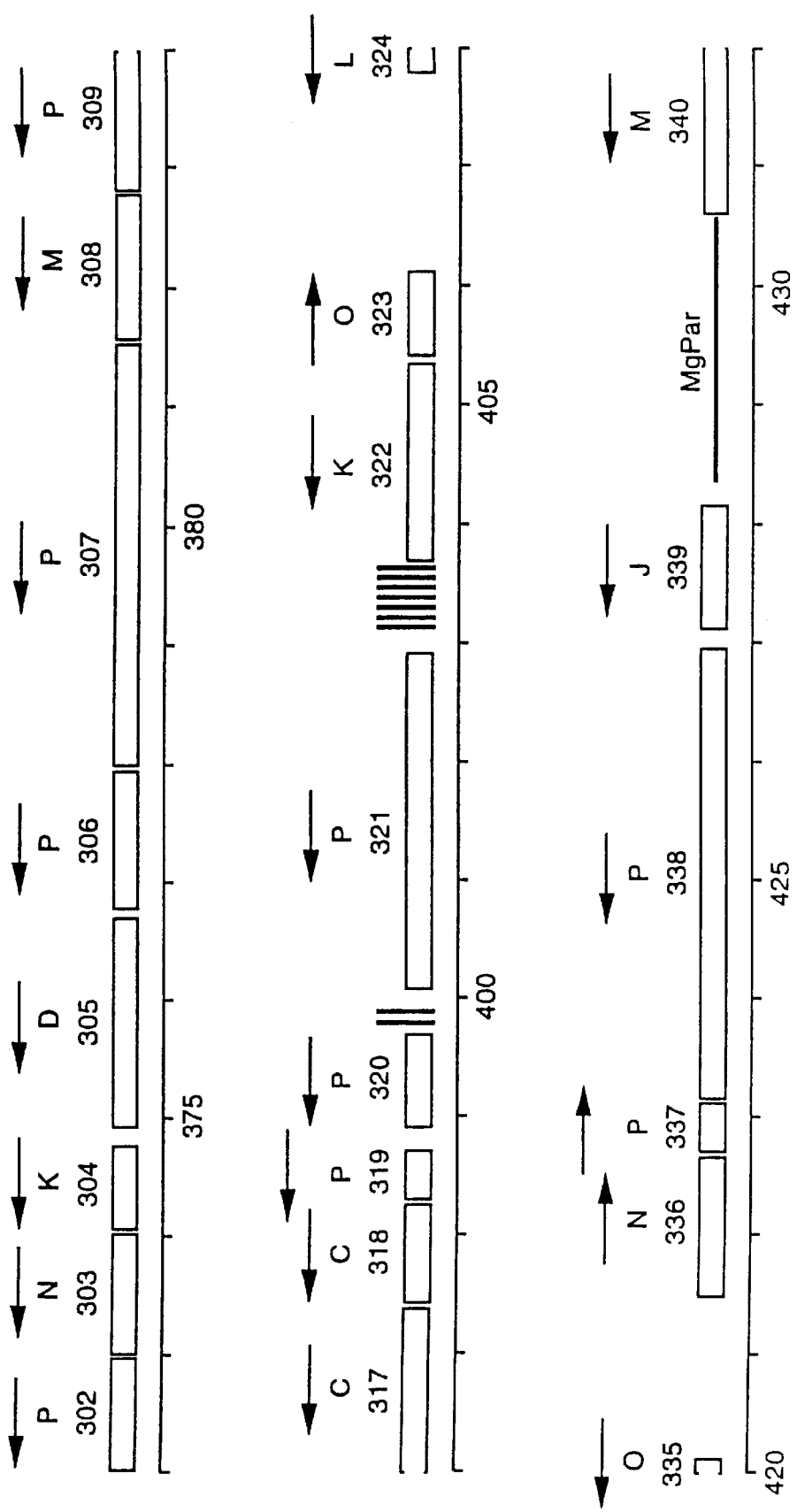
Figure 5M:
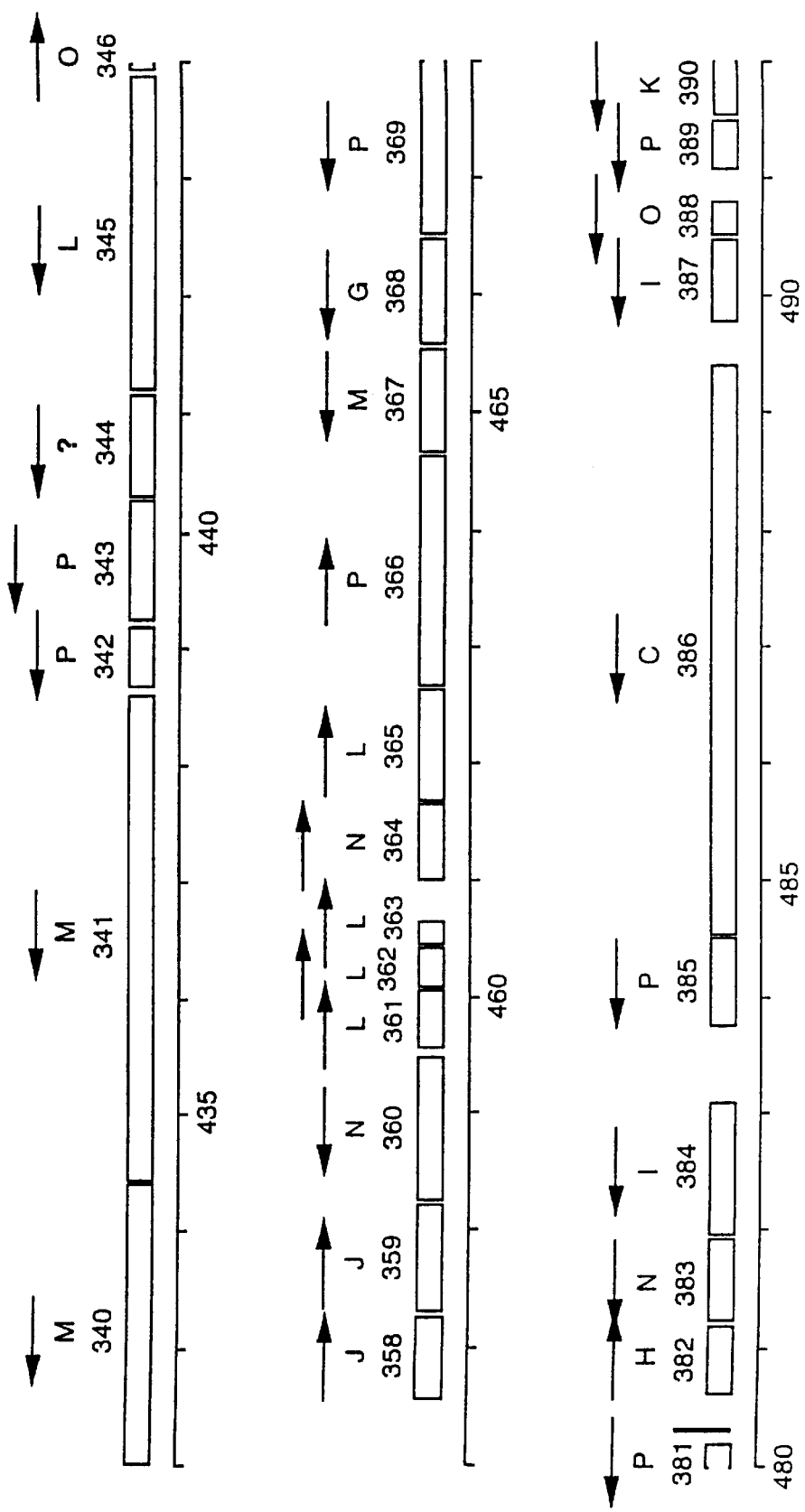
Figure 5N:
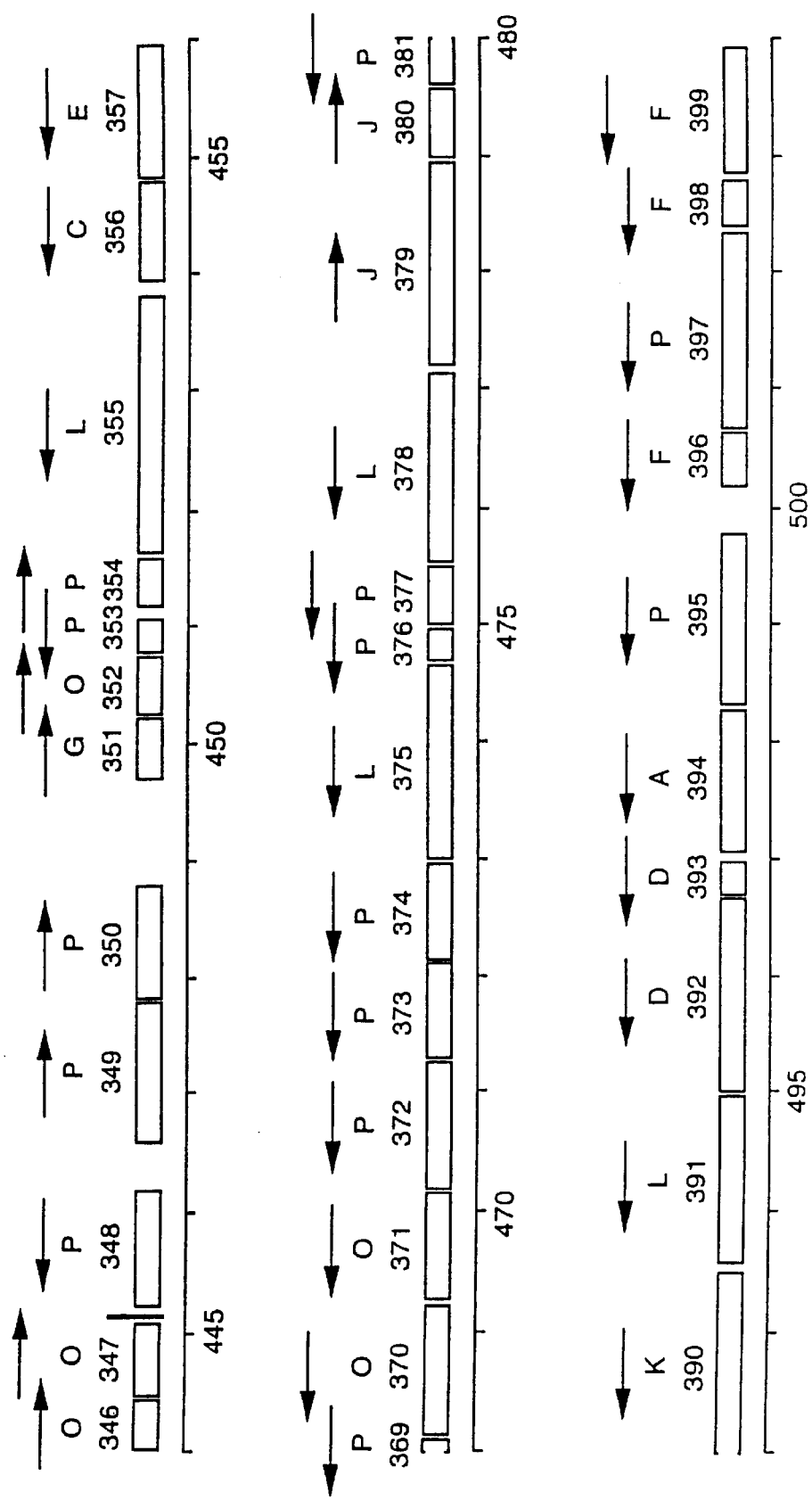
Figure 50:
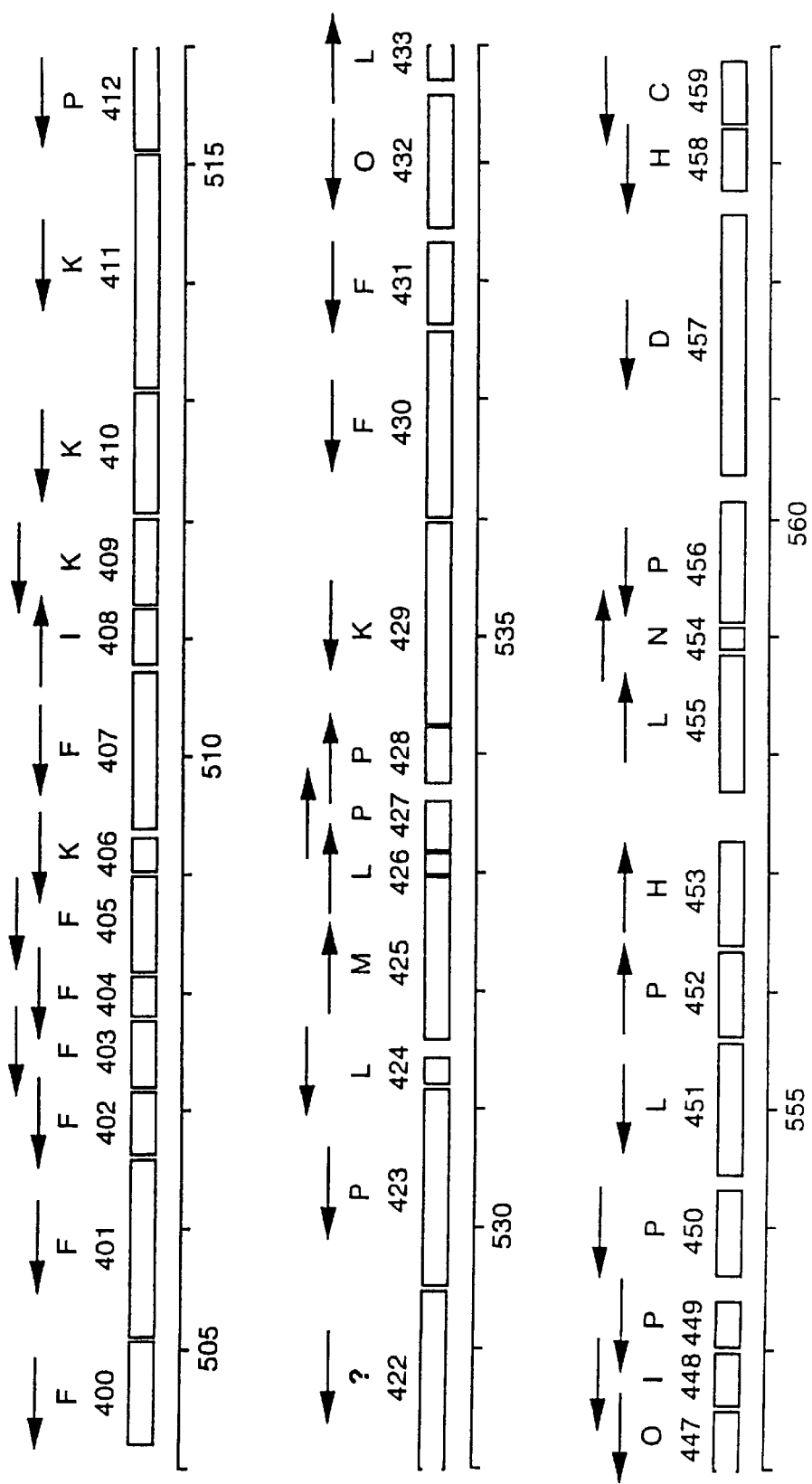
Figure 5P:
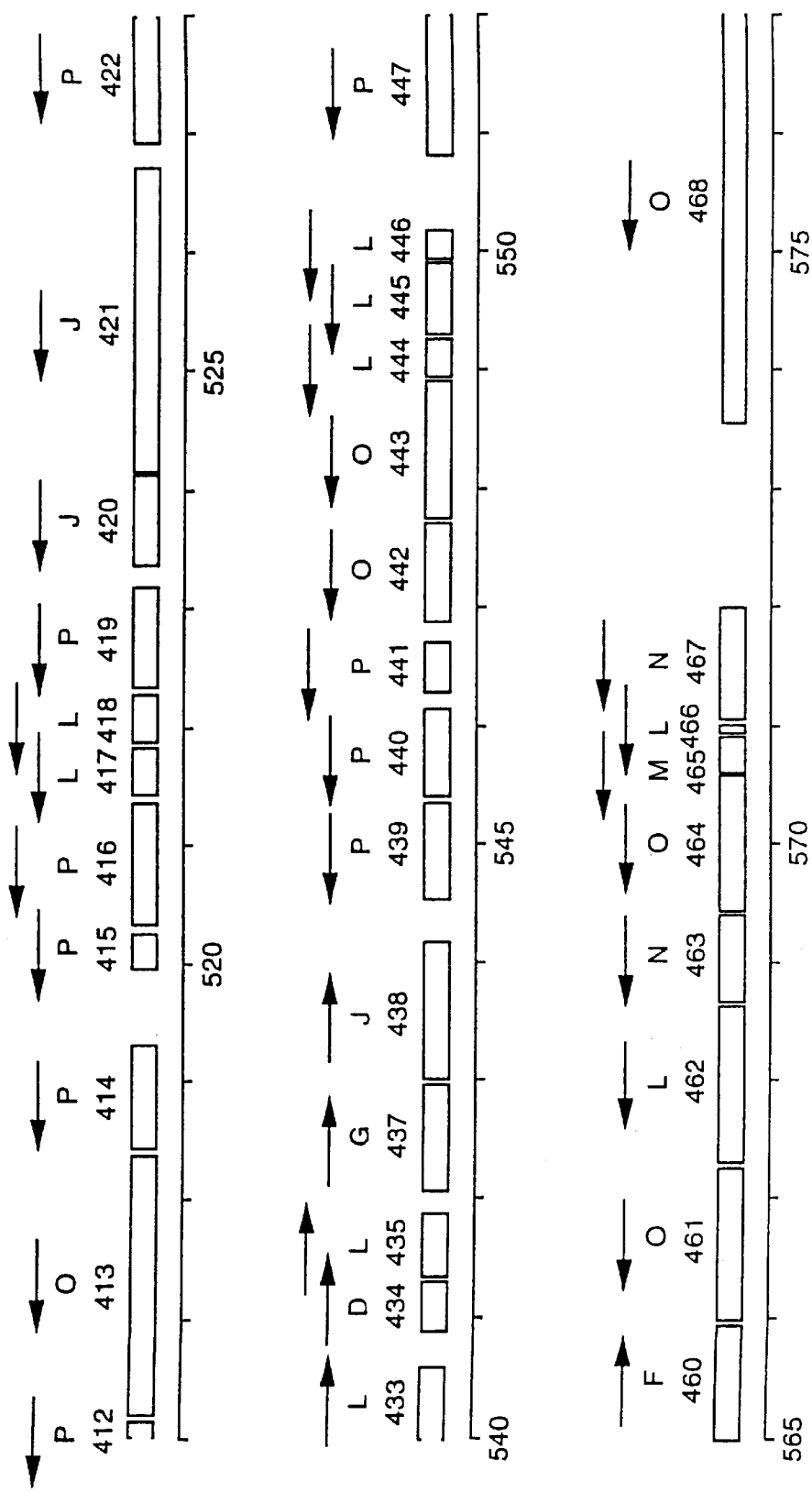
Figure 5Q:
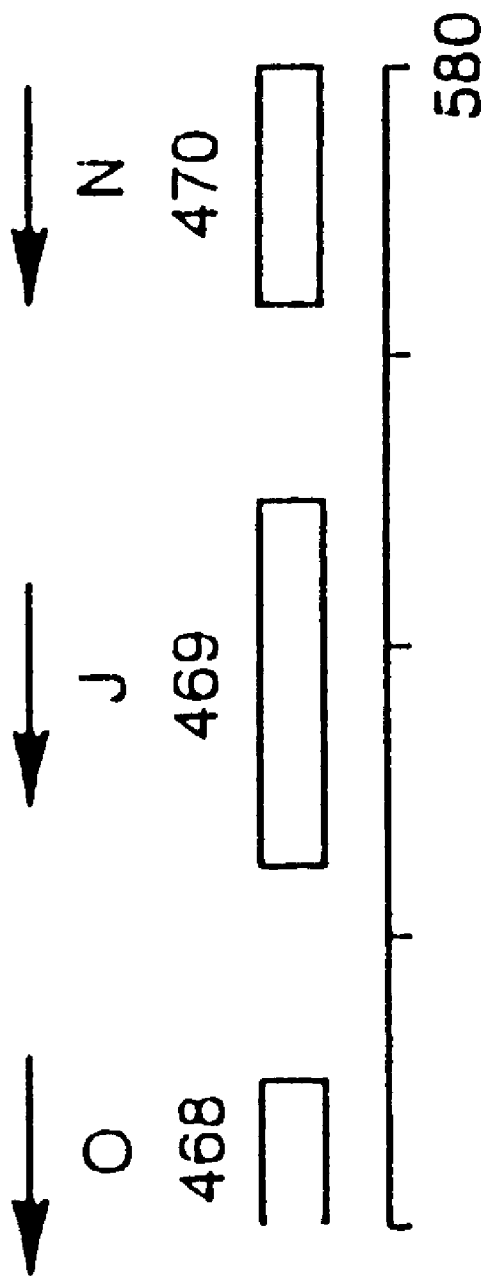
Figure 5R:
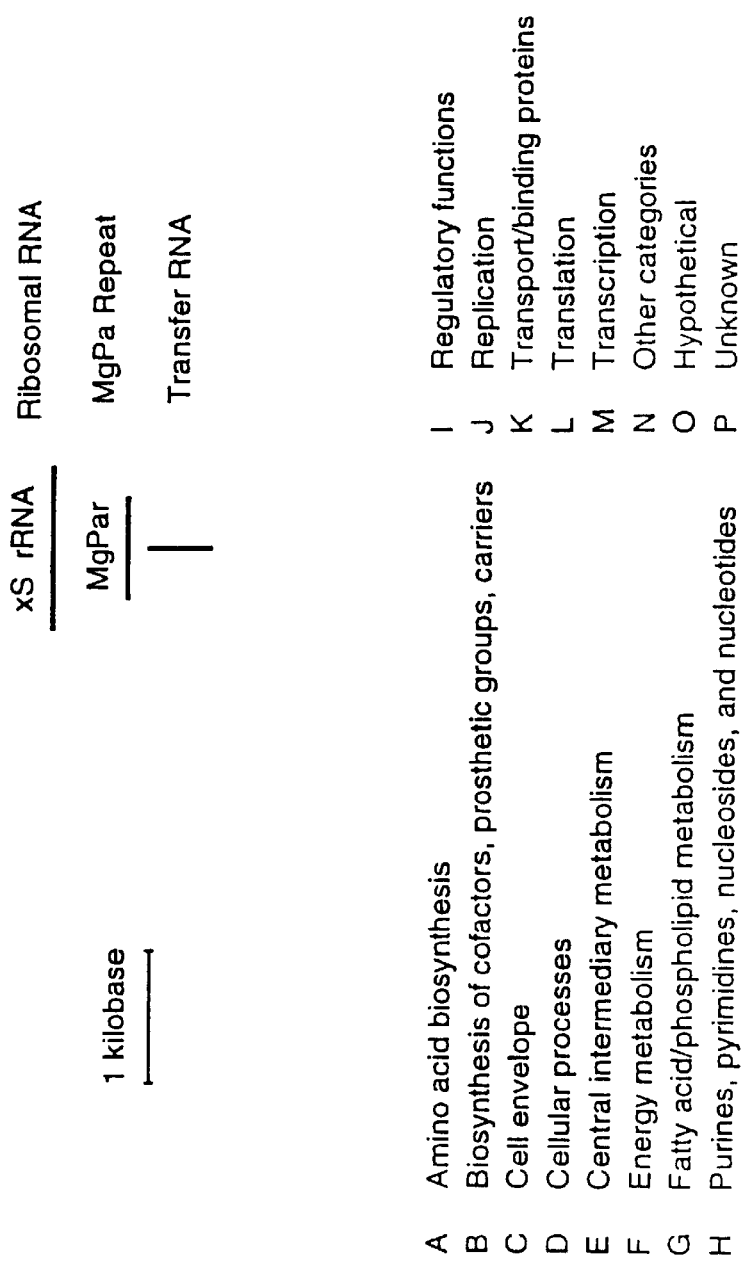

We defined the first bp of the chromosomal sequence of M. genitalium based on the putative origin of replication (Bailey & Bott, J. Bacteriol. 176:5814 (1994)). Studies of origins of replication in some prokaryotes have shown that DNA synthesis is initiated in an untranscribed AT rich region between dnaA and dnaN (Ogasawara, N. et al., in The Bacterial Chromosome, Krlica & Riley, eds., American Society for Microbiology, Washington, D.C. (1990), pp. 287–295; Ogasawara & Yoshikawa, Mol. Microbiol. 6:629 (1992)). A search of the M. genitalium sequence for "DnaA boxes" around the putative origin of replication with consensus "DnaA boxes" from Escherichia coli, Bacillus subtilis, and Pseudomonas aeruginosa revealed no significant matches. Although we have not been able to precisely localize the origin, the co-localization of dnaA and dnaN to a 4000 bp region of the chromosome lends support to the hypothesis that it is the functional origin of replication in M. genitalium (Ogasawara, N. et al., in The Bacterial Chromosome, Krlica & Riley, eds., American Society for Microbiology, Washington, D.C. (1990), pp. 287–295; Ogasawara & Yoshikawa, Mol. Microbiol. 6:629 (1992), Miyata, M. et al., Nucleic Acids Res. 21:4816 (1993)). We have chosen an untranscribed region between dnaA and dnaN so that dnaN is numbered as the first open reading frame in the genome. As seen in FIG. 4, genes to the right of this region are preferentially transcribed from the plus strand and to the left of this region, are preferentially transcribed from the minus strand. The apparent polarity in gene transcription is maintained across each half of the genome (FIGS. 4 and 5). This stands in marked contrast to H. influenzae which displays no apparent polarity of transcription around the origin of replication. The significance of this observation remains to be determined.

The predicted coding regions of M. genitalium were initially defined by searching the entire genome for open reading frames greater than 100 amino acids. Translations were made using the genetic code for mycoplasma species in which UGA encodes tryptophan. All open reading frames were searched with BLAZE (Brutlag, D. et al., Comp. Chem. 1:203 (1993). The BLOSUM 60 amino acid substitution matrix was used in all protein-protein comparisons (Henikoff, S. and Henikoff, J. G., Proc. Natl. Acad. Sci. 89:1091 (1992)) against a non-redundant bacterial protein database (NRBP) (Fleischmann, R. et al., Science 269:496 (1995)) developed at TIGR on a MasPar MP-2 massively parallel computer with 4096 microprocessors. Protein matches were aligned with PRAZE, a modified Smith-Waterman (Waterman, M. S., Methods Enzymol. 164:765 (1988)) algorithm. Segments between predicted coding regions of the genome were used in additional searches against all protein sequences from GenPept, Swiss-Prot, and PIR. Pairwise alignments between M. genitalium predicted open reading frames and sequences from the public archives were examined. Motif matches were annotated in cases where sequence similarity was confined to short domains in the predicted coding region. The coding potential of 170 unidentified open reading frames was analyzed with GeneMark (Borodovsky & McIninch, ibid, p. 123) which had been trained with 308 M. genitalium sequences. Open reading frames that had low coding potential (based on the Gene Mark analysis) and were smaller than. 100 nucleotides (a total of 53) were removed from the final set of putative coding regions. In a separate analysis, open reading frames were searched against the complete set of translated sequences from H. influenzae (GSDB accession L42023, see (Fleischmann, R. et al., Science 269:496 (1995))). In total, these processes resulted in the identification of 482 predicted coding regions, of which 365 were putatively identified (Twenty-three of the protein matches in Table 6 were annotated as motifs. These data matches were not full-length protein matches, but nonetheless displayed regions of significant amino acid similarity) and 117 had no matches to protein sequences from any other organism.

The 365 predicted coding regions that matched protein sequences from the public sequence archives were assigned biological roles. The role classifications were developed from Riley (Riley, M., Microbiol. Rev. 57:862 (1992)) and identical to those used in H. influenzae assignments (Fleischmann, R. et al., Science 269:496 (1995)). A separate search procedure was used in cases where we were unable to detect genes in the M. genitalium genome. Query peptide sequences that were available from eubacteria such as E.

coli, B. subtilis, M. capricolum, and H. influenzae were used in searches against all six reading frame translations of the entire genome sequence, and the alignments were examined. The possibility remains that current searching methods, an incomplete set of query sequences, or the subjective analysis of the database matches, are not sensitive enough to identify certain M. genitalium gene sequences.

One-half of all predicted coding regions in M. genitalium for which a putative identification could be assigned display the greatest degree of similarity to a protein from either a gram-positive organism (e.g., B. subtilis) or a Mycoplasma species. The significance of this finding is underscored by the fact that NRBP contained 3885 sequences from E. coli and only 1975 sequences from B. subtilis. In the majority of cases where M. genitalium coding regions matched sequences from both E. coli and Bacillus species, the better match was to a sequence from Bacillus (average of 62 percent similarity) rather than to a sequence from E. coli (average of 56 percent similarity). The evolutionary relationship between Mycoplasma and the Lactobacillus-Clostridium branch of the gram-positive phylum has been deduced from small subunit rRNA sequences (Maidak, B. L. et al., Nucleic Acids Research 22:3485 (1994)). Our data from whole genome analysis support this hypothesis.

Comparative Genomics: M. genitalium and H. influenzae

A survey of the genes and their organization in M. genitalium makes possible the description of a minimal set of genes required for survival. One would predict that a minimal cell must contain genes for replication and transcription, at least one rRNA operon and a set of ribosomal proteins, tRNAs and tRNA synthetases, transport proteins to derive nutrients from the environment, biochemical pathways to generate ATP and reducing power, and mechanisms for maintaining cellular homeostasis. Comparison of the genes identified in M. genitalium with those in H. influenzae allows for identification of a basic complement of genes conserved in these two species and provides insights into physiological differences between one of the simplest self-replicating prokaryotes and a more complex, gram-negative bacterium.

The M. genitalium genome contains 482 predicted coding sequences (Table 6) as compared to 1, 727 identified in H. influenzae (Fleischmann, R. et al., Science 269:496 (1995)). Table 7 summarizes the gene content of both organisms sorted by functional category. The percent of the total genome in M. genitalium and H. influenzae encoding genes involved in cell envelope, cellular processes, energy metabolism, purine and pyrimdine metabolism, replication, transcription, transport, and other categories is similar; although the total number of genes in these categories is considerably fewer in M. genitalium. A smaller percentage of the M. genitalium genome encodes genes involved in amino acid biosynthesis, biosynthesis of co-factors, central intermediary metabolism, fatty acid and phospholipid metabolism, and regulatory functions as compared with H. influenzae. A greater percentage of the M. genitalium genome encodes proteins involved in translation than in H. influenzae , as shown by the similar numbers of ribosomal proteins and tRNA synthetases in both organisms.

The 482 predicted coding regions in M. genitalium (average size of 1100 bp) cover 85% of the genome (on average, one gene every 1169 bp), a value similar to that found in H. influenzae where 1727 predicted coding regions (average size of 900 bp) cover 91% of the genome (one gene every 1042 bp). These data indicate that the reduction in genome size that has occurred within Mycoplasma has not led to an increase in gene density or a decrease in gene size (Bork, P. et al., Mol. Microbiol. 16:955 (1995)). A global search of M. genitalium and H. influenzae genomes reveals short regions of conservation of gene order, particularly two clusters of ribosomal proteins.

Replication. Two major protein complexes are formed during replication: the primosome and the replisome. We have identified genes encoding many of the essential proteins in the replication process, including M. genitalium isologs of the primosome proteins DnaA, DnaB, GyrA, GyrB, a single stranded DNA binding protein, and the primase protein, DnaE. DnaJ and DnaK, heat shock proteins that may function in the release of the primosome complex, are also found in M. genitalium. A gene encoding the DnaC protein, responsible for delivery of DnaB to the primosome, has yet to be identified.

Genes encoding most of the essential subunit proteins for DNA polymerase III in M. genitalium were also identified. The poiC gene encodes the α subunit which contains the polymerase activity. We have also identified the isolog of dnaH in B. subtilis (dnaX in E. coli) which encodes the γ and t subunits as alternative products from the same gene. These proteins are necessary for the processivity of DNA polymerase III. An isolog of dnaN which encodes the β subunit was previously identified in M. genitalium (Bailey & Bott, J. Bacteriol. 176:5814 (1994)) and is involved in the process of clamping the polymerase to the DNA template. While we have yet to identify a gene encoding the E subunit responsible for the 3'–5' proofreading activity, it is possible that this activity is encoded in the α subunit as has been previously described (Sanjanwala, B. and Ganesa, A. T., Mol. Gen. Genet. 226:467 (1991); Sanjanwala, B. and Ganesan, A. T., Proc. Natl. Acad. Sci. USA 86:4421 (1989)). Finally, we have identified a gene encoding a DNA ligase, necessary for the joining of the Okazaki fragments formed during synthesis of the lagging strand.

While we have identified genes encoding many of the isologs thought to be essential for DNA replication, some genes encoding proteins with key functions have yet to be identified. Examples of these are the DnaC protein mentioned above as well as Dnaθ and Dnaδ whose functions are less well understood but are thought to be involved in the assembly and processivity of polymerase III. Also apparently absent is a specific RNaseH protein responsible for the hydrolysis of the RNA primer synthesized during lagging strand synthesis.

DNA Repair. It has been suggested that in E. coli as many as 100 genes are involved in DNA repair (Komberg, A. and Baker, T. A., DNA Replication—2nd Ed., W. H. Freeman and Co., New York (1992)), and in H. influenzae the number of putatively identified DNA repair enzymes is approximately 30 (Fleischmann, R. et al., Science 269:496 (1995)). Although M. genitalium appears to have the necessary genes to repair many of the more common lesions in DNA, the number of genes devoted to the task is much smaller. Excision repair of regions containing missing bases (apurinic/apyriminic (AP) sites) can likely occur by a pathway involving endonuclease IV (info), Pol I, and ligase. The ung gene which encodes uracil-DNA glycosylase is present. This activity removes uracil residues from DNA which usually arise by spontaneous deamination of cytosine. This produces an AP site which could then be repaired as described above.

All three genes necessary for production of the uvr ABC exinuclease are present, and along with Pol I, helicase II, and ligase should provide a mechanism for repair of damage such as cross-linking, which requires replacement of both strands. Although recA is present, which in *E. coli* is activated as it binds to single strand DNA, thereby initiating the SOS response, we find no evidence for a lexA gene which encodes the repressor which regulates the SOS genes. We have not identified photolyase (phr) in *M. genitalium* which repairs UV-induced pyrimidine dimers, or other genes involved in reversal of DNA damage rather than excision and replacement of the lesion.

Transcription. The critical components for transcription were identified in *M. genitalium*. In addition to the a, b, and b-prime subunits of the core RNA polymerase, *M. genitalium* appears to encode a single a factor, whereas *E. coli* and *B. subtilis* encode at least six and seven, respectively. We have not detected a homolog of the Rho termination factor gene, so it seems likely that a mechanism similar to Rho-independent termination in *E. coli* operates in *M. genitalium*. We have clear evidence for homologs of only two other genes which modulate transcription, nusA and nusG.

Translation. *M. genitalium* possesses a single rRNA operon which contains three rRNA subunits in the order: 16S rRNA(1518 bp)-spacer (203 bp)-23S rRNA (2905 bp)-spacer (56 bp)-5S rRNA (103 bp). The small subunit rRNA sequence was compared with the Ribosomal Database Project's (Maidak, B. L. et al., Nucleic Acids Research 22:3485 (1994)) prokaryote database with the program "similarity_yank." Our sequence is identical to the *M. genitalium* (strain G37) sequence deposited there, and the 10 most similar taxa returned by this search are also in the genus Mycoplasma.

A total of 33 tRNA genes were identified in *M. genitalium*, these were organized into five clusters plus nine single genes. In all cases, the best match for each tRNA gene in *M. genitalium* was the corresponding gene in *M. pneumoniae* (Simoneau, P. et al., *Nuc. Acids Res.* 21:4967 (1993)). Furthermore, the grouping of tRNAs into clusters (tmA, trnB, trnC, trnD, and trnE) was identical in *M. genitalium* and *M. pneumoniae* as was gene order within the cluster (Simoneau, P. et al., *Nuc. Acids Res.* 21:4967 (1993)). The only difference between *M. genitalium* and *M. pneumoniae* observed with regard to tRNA gene organization was an inversion between trnD and GTG. In contrast to *H. influenzae* and many other eubacteria, no tRNAs were found in the spacer region between the 16S and 23S rRNA genes in the rRNA operon of *M. genitalium*, similar to what has been reported for *M. capricolum* (Sawada, M. et al., *Mol. Gen. Genet.* 182:502(1981)).

A search of the *M. genitalium* genome for tRNA synthetase genes identified all of the expected genes with the exception of glutaminyl tRNA synthetase. We expect that this gene is present in the *M. genitalium* genome, but we have not been able to identify it by similarity searches. The latest GenBank release (release 89) contains only a single entry for a glutaminyl tRNA synthetase from a bacterial species; this was from *E. coli*, a gram-negative organism only distantly related to Mycoplasma. In general, tRNA synthetase sequences from gram-positive organisms such as *B. subtilis* displayed greater similarity to those from *M. genitalium* than the corresponding sequences from *E. coli*, lending support to the notion that the similarity between the *E. coli* and *M. genitalium* glutaminyl tRNA synthetase may not have been high enough to be detected.

Metabolic pathways. The reduction in genome size among Mycoplasma species is associated with a marked reduction in the number and components of biosynthetic pathways in these organisms, requiring them to use metabolic products from their hosts. In the laboratory, *M. genitalium* has not been grown in a chemically defined medium. The complex growth requirements of this organism can be explained by the almost complete lack of enzymes involved in amino acid biosynthesis, de novo nucleotide biosynthesis, and fatty acid biosynthesis (Table 6 and FIGS. 5A-5R). When the number of genes in the categories of central intermediary metabolism, energy metabolism, and fatty acid and phospholipid metabolism are summed, marked differences in gene content between *H. influenzae* and *M. genitalium* are apparent. For example, whereas the *H. influenzae* genome contains 68 genes involved in amino acid biosynthesis, the *M. genitalium* genome contains only one. In total, the *H. influenzae* genome has 167 genes associated with metabolic pathways whereas the *M. genitalium* genome has just 42. A recent analysis of 214 kb of sequence from *Mycoplasma capricolum* (Bork, P. et al., *Mol. Microbiol.* 16:955 (1995)), a related organism whose genome size is twice as large as that of *M. genitalium*, reveals that *M. capricolum* contains a number of biosynthetic enzymes not present in *M. genitalium*. This observation suggests that *M. capricolum's* larger genome confers a greater anabolic capacity.

*M. genitalium* is a facultative anaerobe that ferments glucose and possibly other sugars via glycolysis to lactate and acetate. Genes that encode all the enzymes of the glycolytic pathway were identified, including genes for components of the pyruvate dehydrogenase complex, phosphotransacetylase, and acetate kinase. The major route for ATP synthesis may be through substrate level phosphorylation since no cytochromes are present. *M. genitalium* also lacks all the components of the tricarboxylic acid cycle. None of the genes coding for glycogen or poly-beta-hydroxybutryate production were identified, indicating limited capacity for carbon and energy storage. The pentose phosphate pathway also appears limited since only genes encoding 6-phosphogluconate dehydrogenase and transketolase were identified. The limited metabolic capacity of *M. genitalium* sharply contrasts with the complexity of catabolic pathways in *H. influenzae*, reflecting the four-fold greater number of genes involved in energy metabolism found in *H. influenzae*.

Transport The transporters identified in *H. influenzae* are specific for a range of nutritional substrates. Using protein transport as an example, both oligopeptide and amino acid transporters are represented. One interesting peptide transporter has homology to a lactococcin transporter (IcnDR3) and related bacteriocin transporters, suggesting the *M. genitalium* may export a small peptide with antibacterial activity. The *H. influenzae* isolog of the *M. hyorhinis* p37 high-affinity transport system also has a conserved lipid modification site, providing further evidence that the Mycoplasma binding-protein dependent transport systems are organized in a manner analogous to gram positive bacteria (Gilson, E. et al., *EMBO J.* 7:3971 (1988)).

Genes encoding proteins that function in the transport of glucose via the phosphoenolpyruvate:sugar transferase system (PTS) have been identified in *M. genitalium*. These include enzyme I (EI), HPr and sugar specific enzyme IIs (EII) (Postma, P. W. et al., *Microbiol Rev.* 57:543 (1993)). EIIs consist of a complex of at least there domains, EIIA, EIIB and EIIC. In some bacteria (eg, *E. coli*), EIIA is a soluble protein, while in others (*Bacillius subtilis*), a single membrane protein contains all three domains, EIIA, B and C. These variations in the proteins that make up the EII complex are due to fusion or splitting of domains during evolution and are not considered to be mechanistic differences (Postma, P. W. et al., *Microbiol. Rev.* 57:543 (1993)). In *M. genitalium* EIIA, B, and C are located in a single protein similar to the protein found in *B. subtilis*. In *Mycoplasma capricolum* ptsH, the gene which encodes for HPr, is located on a monocistronic transcriptional unit while genes encoding EI (ptsI) and EIIA (crr) are located on a dicistronic operon (Zhu, P. P. et al., *Protein Sci.* 3:2115 (1994); Zhu, P. P. et al., *J. Biol. Chem.* 268:26531 (1993)). In most bacterial species studied to date, ptsI,ptsH, and crr are part of a polycistronic operon (pts operon). In *M. genitalium* ptsH, ptsi and the gene encoding EIIABC reside at different locations of the genome and thus each of these genes may constitute monocistronic transcriptional units. We have also identified EIIBC component for uptake of fructose; however, other components of the fructose PTS were not found. Thus, *M. genitalium* may be limited to the use of glucose as an energy source. In contrast, *H. influenzae* has the ability to use at least six different sugars as a source of carbon and energy.

Regulatory Systems. It appears that regulatory systems found in other bacteria are absent in *M. genitalium*. For instance, although two component systems have been described for a number of gram-positive organisms, no sensor or response regulator genes are found in the *M. genitalium* genome. Furthermore, the lack of a heat shock σ factor raises the question of how the heat shock response is regulated. Another stress faced by all metabolically active organisms is the generation of reactive oxygen intermediates such as superoxide anions and hydrogen peroxide. Although *H. influenzae* has an oxyR homologue, as well as catalase and superoxide dismutase, *M. genitalium* appears to lack these genes as well as an NADH peroxidase. The importance of these reactive intermediate molecules in host cell damage suggests that some as yet unidentified protective mechanism may exist within the cell.

Antigenic variation. Numerous examples exist of microbial pathogens expressing outer membrane proteins that vary due to DNA rearrangements as a mechanism for providing antigenic and functional variations that influence virulence potential (Bergstrom, S. et al., *Proc. Natl. Acad. Sci.* 83:3890 (1986); Meier, J. T. et al., *Cell* 47:61 (1986); Majiwa, P. A. O. et al., *Nature* 297:514 (1982)). Because humans are the natural host for both *M. genitalium* and *H. influenzae*, it was of interest to compare mechanisms for generating antigenic variation in these organisms. In *H. influenzae*, a number of virulence-related genes encoding membrane proteins contain tandem tetramer repeats that undergo frequent addition and deletion of one or more repeat units during replication, such that the reading frame of the gene is changed and its expression altered (Weiser, J. N. et al., *Cell* 59:657 (1989)).

*M. genitalium* appears to use a different system for evading host immune responses. The 140 kDa adhesion protein of *M. genitalium* is densely clustered at a differentiated tip of this organism and elicits a strong immune response in humans and experimentally infected animals (Collier, A. M. et al., *Zbl. Bkt. Suppl.* 20:73 (1992)). The adhesion protein (MgPa) operon in *M. genitalium* contains a 29 kDa ORF, the MgPa protein (160 kDa) and a 114 kDa ORF with intervening regions of 6 and 1 nt, respectively (Inamine, J. M. et al., *Gene* 82:259 (1989)). Based on hybridization experiments (Dallo, S. F. and Baseman, J. B., *Microb. Pathog.* 8:371 (1990)), multiple copies of regions of the *M. genitalium* MgPa gene and the 114 kDa ORF are known to exist throughout the genome.

Figure 6:
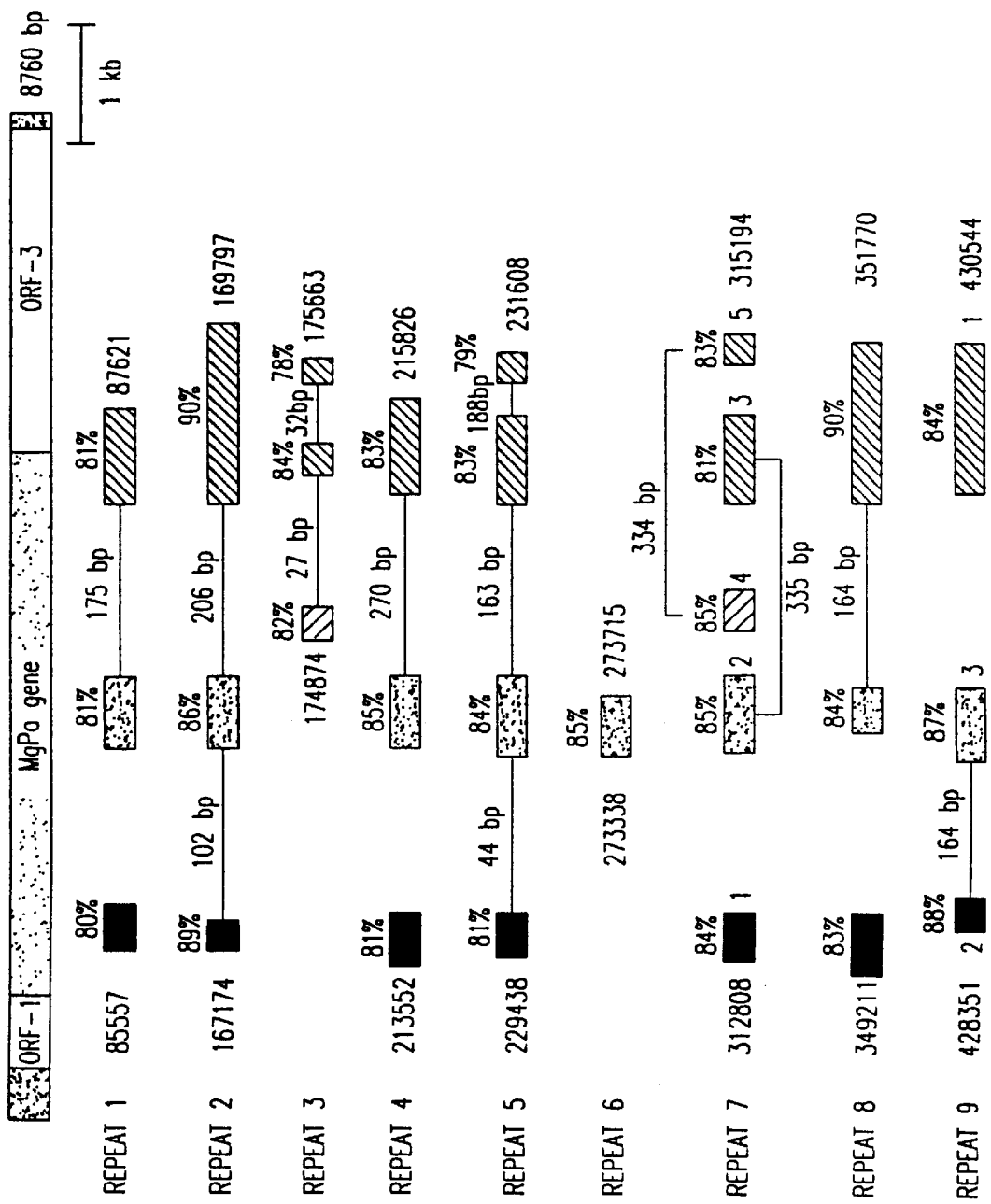

The availability of the complete genomic sequence from *M. genitalium* has allowed a comprehensive mapping of the MgPa repeats (FIGS. 4 and 6). In addition to the complete operon, nine repetitive elements which are composites of particular regions of the MgPa operon were found. The percent of sequence identity between the repeat elements and the MgPa gene ranges from 78%–90%. In some of the repeats, the MgPa-related sequences are separated in the genome by a variable length, A–T rich spacer sequence, as has previously been described (Peterson, S. N., PhD dissertation, Univ. No. Carolina 1992, Univ. Mi. Dissertation Services #6246). The sequences contained in the MgPa operon and the nine repeats scattered throughout the chromosome represent 4.5% of the total genonic sequence. At first glance this might appear to contradict the expectation for a minimal genome. However, recent evidence for recombination between the repetitive elements and the MgPa operon has been reported (Peterson, S. N. et al., *Proc. Natl. Acad. Sci. USA*, in press (1995)). Such recombination may allow *M. genitalium* to evade the host immune response through mechanisms that induce antigenic variation within the population. Since *M. genitalium* survives in nature by obtaining essential nutrients from its mammalian host, an efficient mechanism to evade the immune response may be a necessary part of this minimal genome.

The *M. genitalium* genome contains 93 putatively identified genes that are apparently not present in *H. influenzae*. Almost 60% of these genes have database matches to known or hypothetical proteins from gram-positive bacteria or other Mycoplasma species, suggesting that these genes may encode proteins with a restricted phylogenetic distribution. One hundred seventeen potential coding regions in *M. genitalium* have no database match to any sequences in public archives including the entire *H. influenzae* genome; therefore, these likely represent novel. genes in *M. genitalium*, and related organisms.

The predicted coding sequences of the hypothetical ORFs, the ORFs with motif matches and the ORFs that have no similarities to known peptide sequences were analyzed. The two programs used were the Kyte-Doolittle algorithm (Kyte, J. and Doolittle, R. F., *J. Mol. Biol.* 157:105 (1982)) with a range of 11 residues, and PSORT which is available on the WWW site http://psort.nibb.ac.jp. PSORT predicts the presence of signal sequences by the methods of McGeoch (McGeoch, D. J., *Virus Res.* 3:271 (1985)) and von Heijne (von Heijne, G., *Nucl. Acids Res.* 14:4683 (1986)), and detects potential transmembrane domains by the method of Klein et al. (Klein, P. et al., *Biochim. Biophys. Acta* 815:468 (1985)). Of a total of 201 ORFs examined, 90 potential membrane proteins were found. Eleven of them are predicted to have type I signal peptides, and five type II signal peptides. Using this approach, at least fifty potential membrane proteins were identified from the list of ORFs with known functions. This brings the total number of membrane proteins in *M. genitalium* to approximately 140.

To manage these putative membrane proteins, *M. genitalium* has at its disposal a minimal secretary machinery composed of seven functions: three chaperoning GroEL, DnaK and the trigger factor Tig (Pugsley, A. P., *Microbiol. Rev.* 57:50 (1993); Guthrie, B. and Wickner, W., *J. Bacteriol.* 172:5555 (1990), an ATPase pilot protein SecA, one integral membrane protein translocase (SecY), a signal recognition particle protein (Ffh) and a lipoprotein-specific signal peptidase LspA (Pugsley, A. P., *Microbiol. Rev.* 57:50 (1993)). Perhaps the lack of other known translocases like SecE, SecD, and SecF which are present in *E. coli* and *H. influenzae*, is related to the fact that *M. genitalium* has a one-layer cell envelope. Also, the absence of a SecB homologue, the secretory chaperonin of *E. coli*, in *M.* genitalium (it is also absent in *B. subtilis* (Collier, D. N. *J. Bacteriol.* 176:4937 (1994))) might reflect a difference between gram negative and wall-less Mollicutes in handling nascent proteins destined for the general secretory pathway. Considering the presence of several putative membrane proteins that contain type I signal peptides, the absence of a signal peptidase I (lepB) is most surprising. A direct electronic search for the *M. genitalium* lepB gene using the *E. coli* lepB and the *B. subtilis* sipS (van Dijil, J. M. et al., *EMBO J.* 11:2819 (1992)) as queries did not reveal any significant similarities.

There are a number of possible explanations as to why genes encoding some of the proteins thought to be essential for a self-replicating organism appear to be absent in *M. genitalium*. One possibility is that a limited number of proteins may have adapted to take on other functions. A second possibility is that certain proteins thought to be essential for life based on studies in *E. coli* are not required in a simpler prokaryote like *M. genitalium*. Finally, it may be that sequences from *M. genitalium* have such a low similarity to known sequences from other species that matches are not detectable above a reasonable confidence threshold.

Determination of the complete genome sequence of *M. genitalium* provides a new starting point in understanding the biology of this and related organisms. Comparison of the genes expressed in *M. genitalium*, a simple prokaryote, with those in *H. influenzae*, a more complex organism, has revealed a myriad of differences between these species. Fifty-six percent of the genes in *M. genitalium* have apparent isologs in *H. influenzae*, suggesting that this subset of the *M. genitalium* genome may encode the genes that are truly essential for a self-replicating organism. Notable among the genes that are conserved between *M. genitalium* and *H. influenzae* are those involved in DNA replication and repair, transcription and translation, cell division, and basic energy metabolism via glycolysis. Isologs of these genes are found in eukaryotes as well.

EXAMPLE 2

Production of an Antibody to a *Mycoplasma genitalium* Protein

Substantially pure protein or polypeptide is isolated from the transfected or transformed cells using any one of the methods known in the art. The protein can also be produced in a recombinant prokaryotic expression system, such as *E. coli*, or can by chemically synthesized. Concentration of protein in the final preparation is adjusted, for example, by concentration on an Amicon filter device, to the level of a few micrograms/ml. Monoclonal or polyclonal antibody to the protein can then be prepared as follows:

Monoclonal Antibody Production by Hybridoma Fusion

Monoclonal antibody to epitopes of any of the peptides identified and isolated as described can be prepared from murine hybridomas according to the classical method of Kohler, G. and Milstein, C., *Nature* 256:495 (1975) or modifications of the methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and modified methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2 (1989).

Polyclonal Antibody Production by Immunization

Polyclonal antiserum containing antibodies to heterogenous epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic than other and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al., *J. Clin. Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall (See Ouchterlony, O. et al., Chap. 19 in: *Handbook of Experimental Immunology*, Wier, D., ed, Blackwell (1973)). Plateau concentration of antibody is usually in the range of 0.1 to 0.2 mg/ml of serum (about $12_\mu M$). Affinity of the antisera for the antigen is determined by preparing competitive binding curves, as described, for example, by Fisher, D., Chap. 42 in: *Manual of Clinical Immunology*, second edition, Rose and Friedman, (eds.), Amer. Soc. For Microbio., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample.

EXAMPLE 3

Preparation of PCR Primers and Amplification of DNA

Various fragments of the *Mycoplasma genitalium* genome, such as those disclosed in Tables 1a, 1b, 1c and 2 can be used, in accordance with the present invention, to prepar PCR primers for a variety of uses. The PCR primers are preferably at least 15 bases, and more preferably at least 18 bases in length. When selecting a primer sequence, it is preferred that the primer pairs have approximately the same G/C ratio, so that melting temperatures are approximately the same. The PCR primers and amplified DNA of this Example find use in the examples that follow.

EXAMPLE 4

Gene expression from DNA Sequences Corresponding to ORFs

A fragment of the *Mycoplasma genitalium* genome provided in Tables 1a, 1b, 1c and 2 is introduced into an expression vector using conventional technology (techniques to transfer cloned sequences into expression vectors that direct protein translation in mammalian, yeast, insect or bacterial expression systems are well known in the art). Commercially available vectors and expression systems are available from a variety of suppliers including Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism, as explained by Hatfield et al., U.S. Pat. No. 5,082,767, which is hereby incorporated by reference.

The following is provided as one exemplary method to generate polypeptide(s) from cloned ORFs of the Mycoplasma genome fragment. Since the ORF lacks a poly A sequence because of the bacterial origin of the ORF, this sequence can be added to the construct by, for example, splicing out the poly A sequence from pSG5 (Stratagene) using BglI and SalI restriction endonuclease enzymes and incorporating it into the mammalian expression vector pXT1 (Stratagene) for use in eukaryotic expression systems. pXT1 contains the LTRs and a portion of the gag gene from Moloney Murine Leukemia Virus. The position of the LTRs in the construct allow efficient stable transfection. The vector includes the Herpes Simplex thymidine kinase promoter and the selectable neomycin gene. The Mycoplasma DNA is obtained by PCR from the bacterial vector using oligonucleotide primers complementary to the Mycoplasma DNA and containing restriction endonuclease sequences for PstI incorporated into the 5' primer and BglII at the 5' end of the corresponding Mycoplasma DNA 3' primer, taking care to ensure that the Mycoplasma DNA is positioned such that its followed with the poly A sequence. The purified fragment obtained from the resulting PCR reaction is digested with PstI, blunt ended with an exonuclease, digested with BglII, purified and ligated to pXT1, now containing a poly A sequence and digested BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). The protein is preferably released into the supernatant. However if the protein has membrane binding domains, the protein may additionally be retained within the cell or expression may be restricted to the cell surface.

Since it may be necessary to purify and locate the transfected product, synthetic 15-mer peptides synthesized from the predicted Mycoplasma DNA sequence are injected into mice to generate antibody to the polypeptide encoded by the Mycoplasma DNA.

If antibody production is not possible, the Mycoplasma DNA sequence is additionally incorporated into eukaryotic expression vectors and expressed as a chimeric with, for example, β-globin. Antibody to β-globin is used to purify the chimeric. Corresponding protease cleavage sites engineered between the β-globin gene and the Mycoplasma DNA are then used to separate the two polypeptide fragments from one another after translation. One useful expression vector for generating β-globin chimerics is pSG5 (Stratagene). This vector encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al. and many of the methods are available from the technical assistance representatives from Stratagene, Life Technologies, Inc., or Promega. Polypeptide may additionally be produced from either construct using in vitro translation systems such as In vitro Express™ Translation Kit (Stratagene).

TABLE 1(a)

| UID | end5 | end3 | db_match | db_match name | per_id | per_sim | gene_len |
|---|---|---|---|---|---|---|---|
| MG006 | 8552 | 9181 | SP:P00572 | thymidylate kinase (CDC8) {Saccharomyces cerevisiae} | 27.5862 | 51.7241 | 630 |
| MG009 | 11252 | 12037 | GB:D26185_1 02 | hypothetical protein (GB:D26185_102) {Bacillus subtilis} | 35.4331 | 55.1181 | 786 |
| MG010 | 12069 | 12722 | SP:P33655 | DNA primase (dnaE) {Clostridium acetobutylicum} | 25.731 | 53.2164 | 654 |
| MG012 | 14247 | 13573 | SP:P17116 | ribosomal protein S6 modification protein (rimK) {Escherichia coli} | 31.4961 | 54.3307 | 675 |
| MG013 | 15217 | 14399 | GB:D10588_1 | 5,10-methylene-tetrahydrofolate dehydrogenase (folD) {Escherichia coli} | 33.0472 | 53.2189 | 819 |
| MG015 | 17474 | 19240 | SP:P27299 | transport ATP-binding protein (msbA) {Escherichia coli} | 32.2382 | 57.4949 | 1767 |
| MG023 | 26478 | 27341 | GB:M22039_4 | fructose-bisphosphate aldolase (tsr) {Bacillus subtilis} | 45.9649 | 65.9649 | 864 |
| MG024 | 27345 | 28445 | GP:U02423_1 | GTP-binding protein (gtp1) {Escherichia coli} | 46.8401 | 67.658 | 1101 |
| MG032 | 36978 | 38975 | GB:M63489_1 | ATP-dependent nuclease (addA) {Bacillus subtilis} | 26.8293 | 54.2683 | 1998 |
| MG033 | 39242 | 39901 | GB:M99611_2 | glycerol uptake facilitator (glpF) {Bacillus subtilis} | 35.8974 | 55.3846 | 660 |
| MG034 | 40514 | 39876 | GB:M97678_5 | thymidine kinase (tdk) {Bacillus subtilis} | 48.1283 | 69.5187 | 639 |
| MG035 | 40543 | 41784 | GB:U00011_2 | histidyl-tRNA synthetase (hisS) {Mycobacterium leprae} | 30.7107 | 50.7614 | 1242 |
| MG038 | 46277 | 44754 | GB:L19201_168 | glycerol kinase (glpK) {Escherichia coli} | 46.8254 | 70.2381 | 1524 |
| MG039 | 47422 | 46271 | PIR:S48379 | glycerol-3-phospate dehydrogenase (GUT2) {Saccharomyces cerevisiae} | 43.2099 | 60.4938 | 1152 |
| MG041 | 49377 | 49640 | GB:L22432_2 | phosphohistidinoprotein-hexose phosphotransferase (ptsH) {Mycoplasma capricolum} | 48.8636 | 70.4545 | 264 |
| MG042 | 50060 | 51517 | GB:M64519_1 | spermidine/putrescine transport ATP-binding protein (potA) {Escherichia coli} | 41.9231 | 65.3846 | 1458 |
| MG043 | 51525 | 52379 | GB:M64519_2 | spermidine/putrescine transport system permease protein (potB) {Escherichia coli} | 26.5116 | 57.2093 | 855 |
| MG044 | 52366 | 53217 | GB:M64519_3 | spermidine/putrescine transport system permease protein (potC) {Escherichia coli} | 29.4574 | 58.1395 | 852 |
| MG046 | 54658 | 55602 | GB:M62364_1 | sialoglycoprotease (gcp) {Pasteurella haemolytica} | 36.6013 | 59.4771 | 945 |
| MG048 | 58310 | 56973 | SP:P37105 | signal recognition particle protein (ffh) {Bacillus subtilis} | 43.0206 | 66.1327 | 1338 |
| MG049 | 58117 | 59076 | GB:U14003_2 95 | purine-nucleoside phosphorylase (deoD) {Escherichia coli} | 44.7826 | 63.0435 | 960 |
| MG050 | 59083 | 59751 | GB:X13544_1 | deoxyribose-phosphate aldolase (deoC) {Mycoplasma pneumoniae} | 83.0357 | 91.5179 | 669 |

TABLE 1(a)-continued

| UID | end5 | end3 | db_match | db_match name | per_id | per_sim | gene_len |
|---|---|---|---|---|---|---|---|
| MG056 | 65731 | 64901 | GB:D26185_99 | hypothetical protein (GB:D26185_99) {*Bacillus subtilis*} | 30.2583 | 54.6125 | 831 |
| MG057 | 66249 | 65716 | GB:26185_104 | hypothetical protein (GB:D26185_104) {*Bacillus subtilis*} | 28.9017 | 28.9017 | 534 |
| MG067 | 81047 | 82594 | GB:D00730_1 | glutamic acid specific proteas (SPase) {*Staphylococcus aureus*} | 28.8462 | 48.0769 | 1548 |
| MG070 | 91065 | 91916 | SP:P34831 | ribosomal protein S2 (rpS2) {*Spirulina platensis*} | 34.8 | 55.2 | 852 |
| MG077 | 103104 | 104324 | SP:P24138 | oligopeptide transport system permease protein (oppB) {*Bacillus subtilis*} | 28.0528 | 58.4158 | 1221 |
| MG078 | 104320 | 105447 | SP:P26904 | oligopeptide transport system permease protein (dciAC) {*Bacillus subtilis*} | 33.4572 | 55.0186 | 1128 |
| MG079 | 105452 | 106657 | SP:P18765 | oligopeptide transport ATP-binding protein (amiE) {*Streptococcus pneumoniae*} | 47.9412 | 67.9412 | 1206 |
| MG081 | 109262 | 109672 | SP:P29395 | ribosomal protein L11 (RPL11) {*Thermotoga maritima*} | 51.7986 | 71.9424 | 411 |
| MG085 | 111790 | 112722 | PIR:S24760 | hydroxymethylglutaryl-CoA reductase (NADPH) {*Nicotiana sylvestris*} | 23.3216 | 46.1166 | 933 |
| MG086 | 112718 | 113863 | GB:L13259_2 | prolipoprotein diacylglyceryl transferase (lgt) {*Salmonella typhimurium*} | 29.1262 | 53.8835 | 1146 |
| MG091 | 117553 | 118032 | GB:U04997_2 | single-stranded DNA binding protein (ssb) {*Haemophilus influenzae*} | 21.7949 | 41.6667 | 480 |
| MG092 | 118025 | 118339 | GB:U14003_114 | ribosomal protein S18 (rpS18) {*Escherichia coli*} | 45.4545 | 68.1818 | 315 |
| MG093 | 118345 | 118794 | GB:M57623_1 | ribosomal protein L9 (rpL9) {*Bacillus stearothermophilus*} | 32.8859 | 56.3758 | 450 |
| MG099 | 125852 | 127282 | GB:M61151_1 | hydrolase (aux2) {*Agrobacterium rhizogenes*} | 32.1212 | 51.8182 | 1431 |
| MG106 | 134826 | 134149 | SP:P27251 | formylmethionine deformylase (def) {*Escherichia coli*} | 36.9369 | 68.4685 | 678 |
| MG107 | 134558 | 135334 | GB:L10328_14 | 5'guanylate kinase (gmk) {*Escherichia coli*} | 42.623 | 65.0273 | 777 |
| MG114 | 141345 | 142052 | GB:M12299_2 | phosphatidylglycerophosphate synthase (pgsA) {*Escherichia coli*} | 29.2994 | 57.3248 | 708 |
| MG118 | 143935 | 144954 | SP:P09147 | UDP-glucose 4-epimerase (galE) {*Escherichia coli*} | 34.0557 | 53.87 | 1020 |
| MG121 | 148238 | 149155 | SP:P32720 | hypothetical protein (SP:P32720) {*Escherichia coli*} | 30.8824 | 50.7353 | 918 |
| MG125 | 153081 | 153935 | GB:L10328_61 | hypothetical protein (GB:L10328_61) {*Escherichia coli*} | 31.9149 | 48.227 | 855 |
| MG126 | 154962 | 153922 | GB:M24068_1 | tryptophanyl-tRNA synthetase (trpS) {*Bacillus subtilis*} | 41.1585 | 61.5854 | 1041 |
| MG127 | 154998 | 155432 | SP:P19434 | hypothetical protein (SP:P19434) {*Streptomyces viridochromogenes*} | 25.9615 | 49.0385 | 435 |
| MG128 | 155443 | 156219 | GB:U00021_19 | hypothetical protein (GB:U00021_19) {*Mycobacterium leprae*} | 27.7027 | 49.3243 | 777 |
| MG129 | 156222 | 156572 | GB:U12340_1 | PTS glucose-specific permease {*Bacillus stearothermophilus*} | 25.4545 | 51.8182 | 351 |
| MG130 | 156565 | 158016 | GB:M91593_1 | hypothetical protein (GB:M91593_1) {*Mycoplasma mycoides*} | 30.6773 | 55.7769 | 1452 |
| MG131 | 158022 | 158243 | GB:M21161_3 | hypothetical protein (GB:M31161_3) {*Spiroplasma citri*} | 21.5909 | 56.8182 | 222 |
| MG132 | 159005 | 158583 | SP:P3203 | hypothetical protein (SP:P32083) {*Mycoplasma hyorhinis*} | 30.0971 | 56.3107 | 423 |
| MG136 | 160962 | 162431 | GB:D26185_144 | lysyl-tRNA synthetase (lysS) {*Bacillus subtilis*} | 45.6212 | 68.4318 | 1470 |
| MG137 | 162376 | 163587 | GP:L41518_4 | dTDP-4-dehydrorhamnose reductase (rfbD) {*Klebsiella pneumoniae*} | 32.1622 | 55.9459 | 1212 |
| MG139 | 165470 | 167176 | GB:L18927_2 | hypothetical protein (BG:L18927_2) {*Bachnera aphidocola*} | 28.5714 | 62.8571 | 1707 |
| MG143 | 182853 | 183188 | SP:P09170 | hypothetical protein (SP:P09170) {*Escherichia coli*} | 25 | 53.7037 | 336 |
| MG145 | 184055 | 184861 | GB:M35367_1 | protein X {*Pseudomonas fluorescens*} | 29.0698 | 48.4496 | 807 |
| MG148 | 187304 | 188530 | GB:L18965_6 | hypothetical protein (GB:L18965_6) {Thermophilic bacterial sp.} | 25.2874 | 52.8736 | 1227 |
| MG150 | 190048 | 190365 | SP:P38518 | ribosomal protein S10 (rpS10) {*Thermotoga maritima*} | 48.913 | 71.7391 | 318 |
| MG152 | 191145 | 191777 | SP:P28601 | ribosomal protein L4 (rpL4) {*Bacillus stearothermophilus*} | 39.2345 | 63.1579 | 633 |
| MG153 | 191784 | 192101 | SP:P04454 | ribosomal protein L23 (rpL23) {*Bacillus stearothermophilus*} | 38.7097 | 62.3656 | 318 |
| MG154 | 192104 | 192958 | SP:P04257 | ribosomal protein L2 (rpL2) {*Bacillus stearothermophilus*} | 58.7814 | 72.4014 | 855 |
| MG155 | 192961 | 193221 | GB:X02613_6 | ribosomal protein S19 (rpS19) {*Eschenchia coli*} | 58.6207 | 77.0115 | 261 |
| MG156 | 193227 | 193658 | GB:M74770_4 | ribosomal protein L22 (rpL22) {Mycoplasma-like organism} | 49.0385 | 67.3077 | 432 |

TABLE 1(a)-continued

| UID | end5 | end3 | db__match | db__match name | per_id | per_sim | gene_len |
|---|---|---|---|---|---|---|---|
| MG157 | 193664 | 194467 | SP:P02353 | ribosomal protein S3 (rpS3) {*Mycoplasma capricolum*} | 46.729 | 67.2897 | 804 |
| MG158 | 194476 | 194889 | SP:P02415 | ribosomal protein L16 (rpLl6) {*Mycoplasma capricolum*} | 63.5037 | 78.1022 | 414 |
| MG159 | 194892 | 195491 | SP:P38514 | ribosomal protein L29 (rpL29) {*Thermotoga maritima*} | 41.6667 | 65 | 600 |
| MG160 | 195494 | 195748 | SP:P10131 | ribosomal protein S17 (rp517) {*Mycoplasma capricolum*} | 51.1905 | 67.8571 | 255 |
| MG161 | 195754 | 196120 | SP:P04450 | ribosomal protein L14 (rpL14) {*Bacillus stearothermophilus*} | 63.1148 | 86.0656 | 366 |
| MG162 | 596123 | 196446 | SP:P04455 | ribosomal protein L24 (rpL24) {*Bacillus stearothermophilus*} | 44.5783 | 66.2651 | 324 |
| MG163 | 196455 | 196994 | SP:P08895 | ribosomal protein L5 (rpL5) {*Bacillus stearothermophilus*} | 57.5419 | 77.095 | 540 |
| MG164 | 197000 | 197182 | GB:X06414__15 | ribosomal protein S14 (rpS14) {*Mycoplasma capricolum*} | 70.4918 | 83.6066 | 183 |
| MG165 | 197179 | 197601 | SP:P04446 | ribosomal protein S8 (rpS8) {*Mycoplasma capricolum*} | 46.875 | 71.0938 | 423 |
| MG166 | 197611 | 198162 | SP:P04448 | ribosomal protein L6 (rpL6) {*Mycoplasma capricolum*} | 46.9945 | 66.6667 | 552 |
| MG167 | 198167 | 198511 | GB:M57624__1 | ribosomal protein L18 (rpL18) {*Bacillus stearothermophilus*} | 42.9825 | 57.8947 | 345 |
| MG169 | 199160 | 199609 | SP:P10138 | ribosomal protein LIS (rpL15) {*Mycoplasma capricolum*} | 41.8919 | 66.2162 | 450 |
| MG170 | 199612 | 201036 | SP:P10250 | preprotein translocase secY subunit (secY) {*Mycoplasma capricolum*} | 38.7892 | 68.1614 | 1425 |
| MG171 | 201033 | 201674 | GB:M88104__2 | adenylate kinase (adk) {*Bacillus stearothermophilus*} | 32.2115 | 57.6923 | 642 |
| MG172 | 201680 | 202423 | GB:D00619__5 | methionine amino peptidase (map) {*Bacillus subtilis*} | 36.2903 | 58.4677 | 744 |
| MG173 | 202426 | 202635 | GB:M26414__1 | initiation factor 1 (infA) {*Bacillus subtilis*} | 48.5294 | 67.6471 | 210 |
| MG174 | 202649 | 202759 | SP:P38015 | ribosomal protein L36 (rpL36) {*Chlamydia trachomatis*} | 78.3784 | 83.7838 | 111 |
| MG177 | 203516 | 204499 | GB:M26414__5 | RNA polymerase alpha core subunit (rpoA) {*Bacillus subtilis*} | 39.3939 | 65.9933 | 984 |
| MG178 | 204515 | 204515 | GB:M26414__6 | ribosomal protein L17 (rpL17) {*Bacillus subtilis*} | 34.7826 | 59.1304 | 369 |
| MG179 | 204873 | 205694 | SP:P11599 | haemolysin secretion ATP-binding protein (hlyB) {*Proteus vulgaris*} | 34.5992 | 62.0253 | 822 |
| MG187 | 216762 | 218516 | GB:M77351__7 | ATP-binding protein (msmK) {*Streptococcus mutans*} | 40.5325 | 65.6805 | 1755 |
| MG188 | 218522 | 219508 | GB:M77351__4 | membrane protein (msmF) {*Streptococcus mutans*} | 22.4719 | 51.6854 | 987 |
| MG189 | 219435 | 220436 | GB:M77351__5 | membrane protein (msmG) {*Streptococcus mutans*} | 27.1429 | 52.8571 | 1002 |
| MG196 | 135635 | 236057 | GB:X16188__1 | translation initiation factor IF3 (infC) {*Bacillus stearothermophilus*} | 31.3433 | 62.6866 | 423 |
| MG197 | 236063 | 236239 | PIR:S05347 | ribosomal protein L35 (rpL35) {*Bacillus stearothermophilus*} | 60 | 72.7273 | 177 |
| MG198 | 236245 | 236616 | SP:Q05427 | ribosomal protein L20 (rpL20) {*Mycoplasma fermentans*} | 57.5221 | 73.4513 | 372 |
| MG201 | 239163 | 239813 | GB:M84964__2 | heat shock protein (grpE) {*Bacillus subtilis*} | 31.677 | 49.6894 | 651 |
| MG205 | 245596 | 244568 | GB:M84964__1 | hypothetical protein (GB:M84964__1) {*Bacillus subtilis*} | 30.9942 | 58.1871 | 1029 |
| MG213 | 252579 | 253991 | GB:L09228__16 | hypothetical protein (GB:L092281__16) {*Bacillus subtilis*} | 27.1186 | 54.661 | 1413 |
| MG214 | 253978 | 254598 | GB:L09228__17 | hypothetical protein (GB:L092281__17) {*Bacillus subtilis*} | 34.8571 | 59.4286 | 621 |
| MG215 | 254620 | 255588 | SP:P20275 | 6-phosphofructokinase (pfk) {*Spiroplasma citri*} | 39.441 | 63.0435 | 969 |
| MG217 | 258040 | 259155 | SP:P29126 | bifunctional endo-1,4-beta-xylanase xyla precursor (xynA) {*Ruminococcus flavefaciens*} | 37.5839 | 48.9933 | 1116 |
| MG219 | 265596 | 266039 | GB:M87491__1 | IgA1 protease {*Haemophilus influenzae*} | 32.2314 | 51.2397 | 444 |
| MG220 | 266382 | 266077 | GB:Z26883__1 | pre-procytotoxin (vacA) {*Helicobacter pylori*} | 36.1446 | 51.8072 | 306 |
| MG222 | 267080 | 268006 | GB:D10483__63 | hypothetical protein (GB:D10483__63) {*Escherichia coli*} | 35.1974 | 56.5789 | 927 |
| MG224 | 269249 | 270355 | GB:U06462__1 | cell division protein (ftsZ) {*Staphylococcus aureus*} | 30.8824 | 50.7353 | 1107 |
| MG234 | 279491 | 279802 | GB:K02665__2 | ribosomal protein L27 (rpL27) {*Bacillus subtilis*} | 64.3678 | 80.4598 | 312 |
| MG235 | 279798 | 280670 | SP:P12638 | endonuclease IV (nfo) {*Escherichia coli*} | 29.368 | 51.3011 | 873 |

TABLE 1(a)-continued

| UID | end5 | end3 | db_match | db_match name | per_id | per_sim | gene_len |
|---|---|---|---|---|---|---|---|
| MG245 | 293446 | 293940 | GB:M12965_1 | hypothetical protein (GB:M12965_1) {*Escherichia coli*} | 33.8462 | 56.9231 | 495 |
| MG247 | 295484 | 294768 | SP:P31056 | hypothetical protein (SP:P31056) {*Escherichia coli*} | 32.973 | 56.2162 | 717 |
| MG248 | 296127 | 295474 | GP:U17284_2 | major sigma factor (rpoD) {*Listeria monocytogenes*} | 28.4848 | 51.5152 | 654 |
| MG251 | 700802 | 299465 | GB:L081061_1 | glycyl-tRNA synthetase {*Bombyx mori*} | 35.8974 | 56.1772 | 1338 |
| MG252 | 301550 | 300825 | GP:Z33076_2 | rRNA methylase {*Mycoplasma capricolum*} | 38.8626 | 59.7156 | 726 |
| MG253 | 302839 | 301556 | GB:D26185_156 | cysteinyl-tRNA synthetase (cysS) {*Bacillus subtilis*} | 34.3458 | 56.3084 | 1284 |
| MG257 | 307635 | 307925 | GB:L19201_78 | ribosomal protein L31 (rpL31) {*Escherichia coli*} | 37.3134 | 61.194 | 291 |
| MG258 | 307928 | 309004 | GB:M11519_1 | peptide chain release factor 1 (RF-1) {*Escherichia coli*} | 43.1677 | 66.4596 | 1077 |
| MG259 | 309008 | 310375 | GB:D28567_2 | protoporphyrinogen oxidase (hemK) {*Escherichia coli*} | 30.5732 | 54.1401 | 1368 |
| MG260 | 310509 | 312803 | GB:Z32651_1 | hypothetical protein (GB:Z32651_1) {*Mycoplasma pneumoniae*} | 57.1429 | 71.4286 | 2295 |
| MG262 | 318330 | 319202 | GB:L11920_1 | DNA polymerase 1 (polI) {*Mycobacterium tuberculosis*} | 29.9419 | 47.9651 | 873 |
| MG264 | 321044 | 321637 | GB:M64324_1 | 6-phosphogluconate dehydrogenase (gnd) {*Escherichia coli*} | 29.8507 | 47.7612 | 594 |
| MG265 | 322412 | 321579 | GB:L10328_61 | hypothetical protein (GB:L10328_61) {*Escherichia coli*} | 27.193 | 48.6842 | 834 |
| MG268 | 325877 | 325194 | GB:U01881_2 | deoxyguanosine/deoxyadenosine kinase(I) subunit 2 {*Lactobacillus acidophilus*} | 29.5181 | 49.3976 | 684 |
| MG270 | 328442 | 327435 | GB:U14003_297 | hypothetical protein (GB:U14003_297) {*Escherichia coli*} | 38.2838 | 57.7558 | 1008 |
| MG272 | 330984 | 329833 | GB:M81753_3 | dihydrolipoamide acetyltransferase (pdhC) {*Acholeplasma laidlawii*} | 45.1524 | 62.0499 | 1152 |
| MG273 | 332214 | 331237 | GB:M81753_2 | pyruvate dehydrogenase E1-beta subunit (pdhB) {*Acholeplasma laidlawii*} | 55.0314 | 76.7296 | 978 |
| MG274 | 333308 | 332235 | GB:M81753_1 | pyruvate dehydrogenase E1-alpha subunit (pdhA) {*Acholeplasma laidlawii*} | 42.9825 | 61.1111 | 1074 |
| MG277 | 338323 | 335414 | GB:L16960_2 | spore germination apparatus protein (gerBB) {*Bacillus subtilis*} | 31.2 | 55.2 | 2910 |
| MG280 | 341920 | 341177 | GB:Z35086_1 | sensory rhodopsin II transducer (htrII) {*Natronobacterium pharaonis*} | 15.7143 | 46.6667 | 744 |
| MG288 | 353034 | 351793 | GB:L04466_1 | protein L {*Peptostreptococcus magnus*} | 31.1475 | 50.8197 | 1242 |
| MG290 | 355119 | 355853 | SP:P15361 | ATP-binding protein P29 {*Mycoplasma hyorhinis*} | 32.3009 | 58.8496 | 735 |
| MG292 | 360592 | 357893 | GB:J01581_1 | alanyl-tRNA synthetase (alaS) {*Escherichia coli*} | 33.8403 | 55.64 | 2700 |
| MG295 | 364022 | 362922 | SP:P25745 | hypothetical protein (SP:P25745) {*Escherichia coli*} | 34.7107 | 57.0248 | 1101 |
| MG299 | 369694 | 368735 | SP:P39646 | phosphotransacetylase (pta) {*Clostridium acetobutylicum*} | 44.6541 | 63.522 | 960 |
| MG303 | 373998 | 372928 | GB:M61017_1 | membrane transport protein (glnQ) {*Bacillus stearothermophilus*} | 31.982 | 54.955 | 1071 |
| MG304 | 374741 | 373983 | GB:U13043_1 | membrane associated ATPase (cbiO) {*Propionibacterium freudenreichii*} | 30.0448 | 53.8117 | 759 |
| MG310 | 386462 | 387265 | GB:D11037_1 | proline iminopeptidase (pip) {*Bacillus coagulans*} | 29.2079 | 51.4851 | 804 |
| MG311 | 387892 | 387278 | GB:M59358_1 | ribosomal protein S4 (rpS4) {*Bacillus subtilis*} | 43 | 65.5 | 615 |
| MG313 | 392023 | 391397 | GP:L38997_5 | cytadherence-accessory protein (hmwI) {*Mycoplasma pneumoniae*} | 53.8462 | 79.8077 | 627 |
| MG315 | 394550 | 393660 | GP:L38997_3 | cytadherence accessory protein (hmwI) {*Mycoplasma pneumoniae*} | 44.3878 | 69.898 | 891 |
| MG316 | 395583 | 394477 | GB:L15202_4 | competence locus E (comE3) {*Bacillus subtilis*} | 30.4933 | 52.4664 | 1107 |
| MG322 | 405398 | 403725 | GB:D17462_11 | Na+ ATPase subunit J (ntpJ) {*Enterococcus hirae*} | 31.0811 | 56.3063 | 1674 |
| MG323 | 405455 | 406135 | GB:D37799_6 | hypothetical protein (GB:D37799_6) {*Bacillus subtilis*} | 27.5701 | 54.2056 | 681 |
| MG325 | 408953 | 408795 | SP:P23375 | ribosomal protein L33 (rpL33) {*Bacillus stearothermophilus*} | 58.1395 | 69.7674 | 159 |
| MG326 | 409857 | 408973 | GB:Z18629_1 | hypothetical protein (GB:Z18629_1) {*Bacillus subtilis*} | 27.0758 | 52.7076 | 885 |
| MG329 | 414318 | 412975 | GB:U00021_5 | hypothetical protein (GB:U00021_5) {*Mycobacterium leprae*} | 32.1839 | 54.2529 | 1344 |
| MG332 | 416329 | 415613 | GB:D10165_3 | hypothetical protein (GB:D10165_3) {*Escherichia coli*} | 26.9231 | 49.1453 | 717 |

TABLE 1(a)-continued

| UID | end5 | end3 | db_match | db_match name | per_id | per_sim | gene_len |
|---|---|---|---|---|---|---|---|
| MG346 | 443922 | 444419 | GB:M65289_3 | hypothetical protein (GB:M65289_3) {Bacillus stearothermophilus} | 37.9747 | 60.1266 | 498 |
| MG347 | 444413 | 445042 | SP:P32049 | hypothetical protein (SP:P32049) {Escherichia coli} | 28.4615 | 46.9231 | 630 |
| MG351 | 449665 | 450216 | SP:P37981 | inorganic pyrophosphatase (ppa) {Thermoplasma acidophilum} | 38.8535 | 61.7834 | 552 |
| MG355 | 453757 | 451616 | GB:M29364_2 | ATP-dependent protease binding subunit (clpB) {Escherichia coli} | 47.7337 | 70.6799 | 2142 |
| MG356 | 454753 | 453914 | GB:M27280_1 | lic-1 operon protein (licA) {Haemophilus influenzae} | 27.7778 | 56.25 | 840 |
| MG359 | 457347 | 458267 | GB:M21298_2 | Holliday junction DNA helicase (ruvB) {Escherichia coli} | 34.6939 | 64.966 | 921 |
| MG360 | 459495 | 458263 | SP:P14303 | UV protection protein (mucB) {Salmonella typhimurium} | 22.0859 | 48.1595 | 1233 |
| MG363 | 460497 | 460667 | GB:M29698_2 | ribosomal protein L32 (rpL32) {Escherichia coli} | 48.1481 | 62.963 | 171 |
| MG364 | 461015 | 461686 | GB:M95954_1 | mobilization protein (mobl3) {Leuconostoc oenos} | 30.8725 | 53.6913 | 672 |
| MG367 | 465434 | 464649 | GB:X02673_1 | ribonuclease III (rnc) {Escherichia coli} | 30.1724 | 65.5172 | 786 |
| MG380 | 478999 | 479574 | GB:L10328_105 | glucose inhibited division protein (gidB) {Escherichia coli} | 24.8276 | 51.7241 | 576 |
| MG382 | 480691 | 481329 | SP:P31218 | uridine kinase (udk) {Escherichia coli} | 34.4828 | 62.5616 | 639 |
| MG383 | 482075 | 481332 | GB:M15811_1 | sporulation protein (outB) {Bacillus subtilis} | 36.3636 | 54.9784 | 744 |
| MG384 | 483369 | 482071 | GB:M24537_2 | GTP-binding protein (obg) {Bacillus subtilis} | 39.627 | 62.0047 | 1299 |
| MG387 | 490711 | 489842 | SP:P37214 | GTP-binding protein era homolog (spg) {Streptococcus mutans} | 27.3859 | 51.0373 | 870 |
| MG396 | 500719 | 500264 | GB:M80797_2 | galactosidase acetyltransferase (lacA) {Streptococcus mutans} | 40.5797 | 57.971 | 456 |
| MG398 | 502823 | 502425 | SP:P33255 | ATP synthase epsilon chain (atpC) {Mycoplasma gallisepticum} | 36.9231 | 55.3846 | 399 |
| MG402 | 507201 | 506674 | SP:P33254 | ATP synthase delta chain (atpH) {Mycoplasma gallisepticum} | 33.9181 | 58.4795 | 528 |
| MG403 | 5107820 | 507197 | SP:P33256 | ATP synthase B chain (atpF) {Mycoplasma gallisepticum} | 36.5979 | 66.4948 | 624 |
| MG404 | 508131 | 507826 | SP:P33258 | ATP synthase C chain (atpE) {Mycoplasma gallisepticum} | 50 | 74.359 | 306 |
| MG407 | 510836 | 509463 | GB:L29475_4 | enolase (eno) {Bacillus subtilis} | 54.0793 | 74.1259 | 1374 |
| MG408 | 510903 | 511373 | SP:P14930 | pilin repressor (pilB) {Neisseria gonorrhoeae} | 49.2188 | 68.75 | 471 |
| MG409 | 512050 | 511376 | GB:L10328_88 | peripheral membrane protein U (phoU) {Escherichia coli} | 27.027 | 48.6486 | 675 |
| MG420 | 524144 | 523365 | GB:D26185_8 | DNA polymerase III subunit (dnaH) {Bacillus subtilis} | 49.115 | 68.5841 | 780 |
| MG424 | 531479 | 531222 | SP:P05766 | ribosomal protein S15 (BS18) {Bacillus stearothermophilus} | 48.1481 | 71.6049 | 258 |
| MG426 | 533040 | 533231 | GB:L12244_2 | ribosomal protein L28 (rpL28) {Bacillus subtilis} | 36.0656 | 59.0164 | 192 |
| MG429 | 536036 | 534321 | GB:M69050_2 | PEP-dependent HPr protein kinase phosphoryltransferase (ptsI) {Staphylococcus carnosus} | 46.4789 | 66.5493 | 1716 |
| MG430 | 537563 | 536043 | GB:L29475_3 | phosphoglycerate mutase (pgm) {Bacillus subtilis} | 45.1866 | 62.4754 | 1521 |
| MG432 | 539546 | 538353 | SP:P27712 | hypotheticai protein (SP:P27712) {Spiroplasma citri} | 28.436 | 48.8152 | 1194 |
| MG433 | 539632 | 540525 | GB:M31161_2 | elongation factor Ts (tsf) {Spiroplasma citri} | 39.0572 | 62.6263 | 894 |
| MG434 | 540848 | 541237 | GB:D26562_56 | mukB suppressor protein (smbA) {Escherichia coli} | 40.8696 | 61.7391 | 390 |
| MG435 | 541240 | 541788 | GB:D26562_57 | ribosome releasing factor (frr) {Escherichia coli} | 34.9112 | 57.3965 | 549 |
| MG438 | 543004 | 544152 | GB:J01631_1 | restriction-modification enzyme EcoD specificity subunit (hsdS) {Escherichia coli} | 24.5734 | 45.7338 | 1149 |
| MG442 | 547690 | 546881 | GB:U00021_5 | hypothetical protein (GB:U00021_5) {Mycobacterium leprae} | 26.8966 | 42.069 | 810 |
| MG443 | 548849 | 547665 | GB:D16311_1 | hypothetical protein (GB:D16311_1) {Bacillus subtilis} | 26.1818 | 52 | 1185 |
| MG444 | 549224 | 548868 | SP:P30529 | ribosomal protein L19 (rpL19) {Bacillus stearothermophilus} | 49.1071 | 69.6429 | 357 |
| MG445 | 549903 | 549211 | SP:P36245 | tRNA (guanine-N1)-methyltransferase (trmD) {Salmonella typhimurium} | 40.8072 | 64.1256 | 693 |
| MG446 | 550172 | 549906 | SP:P21474 | ribosomal protein S16 (BS17) {Bacillus subtilis} | 48.7805 | 64.6341 | 267 |

TABLE 1(a)-continued

| UID | end5 | end3 | db_match | db_match name | per_id | per_sim | gene_len |
|---|---|---|---|---|---|---|---|
| MG448 | 552897 | 552448 | GB:Z33052_1 | pilin repressor (pilB) {*Mycoplasma capricolum*} | 53.4884 | 72.093 | 450 |
| MG454 | 557770 | 557306 | SP:P23929 | osmotically inducible protein (osmC) {*Escherichia coli*} | 28.4091 | 51.1364 | 465 |
| MG457 | 562602 | 560497 | GB:D26185_132 | cell division protein (ftsH) {*Bacillus subtilis*} | 49.7445 | 68.1431 | 2106 |
| MG461 | 566203 | 564929 | GB:X73124_94 | hypothetical protein (GB:X73124_94) {*Bacillus subtilis*} | 40 | 64.2857 | 1275 |
| MG464 | 569554 | 568400 | GB:D14982_3 | hypothetical protein (GB:D14982_3) {*Mycoplasma capricolum*} | 32.3699 | 53.7572 | 1155 |
| MG465 | 569912 | 569529 | GB:D14982_2 | RNaseP C5 subunit (rnpA) {*Mycoplasma capricolum*} | 40 | 58.75 | 384 |
| MG466 | 570027 | 569884 | GB:L10328_67 | ribosomal protein L34 (rpL34) {*Escherichia coli*} | 67.3913 | 80.4348 | 144 |
| MG470 | 580030 | 579224 | GB:D26185_55 | SpoOJ regulator {*Bacillus subtilis*} | 27.8884 | 53.3865 | 807 |

TABLE 1(b)

| UID | end5 | end3 | db_match | db_match name | per_sim | per_id | match_info |
|---|---|---|---|---|---|---|---|
| MG002 | 1829 | 2758 | SP:P35514 | heat shock protein (dnaJ) {*Lactococcus lactis*} | 40 | 61.6667 | MG002(1–930 of 930)<br>GB:U09251(298–1227 of 6140) |
| MG003 | 2846 | 4795 | GB:U09251_3 | DNA gyrase subunit B (gyrB) {*Mycoplasma genitalium*} | 99.3846 | 99.3846 | MG003(1–1950 of 1950)<br>GB:U09251(1315–3264 of 6140) |
| MG004 | 4813 | 7320 | GB:U09251_4 | DNA gyrase subunit A (gyrA) {*Mycoplasma genitalium*} | 99.8804 | 99.8804 | MG004(1–2508 of 2508)<br>GB:U09251(3282–5789 of 6140) |
| MG191 | 221571 | 225902 | SP:P20796 | attachment protein, MgPa operon (mgp) {*Mycoplasma genitalium*} | 100 | 100 | MG191(1–4332 of 4332)<br>GB:M31431(1066–5397 of 8760) |
| MG192 | 225907 | 229062 | SP:P22747 | 114 kDa protein, MgPa operon (mgp) {*Mycoplasma genitalium*} | 100 | 100 | MG192(1–3156 of 3156)<br>GB:M31431(5402–8557 of 8760) |
| MG232 | 278904 | 279203 | SP:P26908 | ribosomal protein L21 (rpL21) {*Bacillus subtilis*} | 37.8947 | 65.2632 | MG232(1–300 of 300)<br>GB:U02141(138–437 of 827) |
| MG233 | 279199 | 279495 | GP:U02141_2 | ribosomal protein L21 homolog {*Mycoplasma genitalium*} | 100 | 100 | MG233(1–297 of 297)<br>GB:U02141(433–729 of 827) |
| MG287 | 348882 | 349133 | SP:P04686 | nodulation protein F (nodF) {*Rhizobium leguminosarum*} | 34.9398 | 56.6265 | MG287(1–252 of 252)<br>GB:U01810(152–403 of 917) |
| MG417 | 521868 | 521473 | SP:P07842 | ribosomal protein S9 (rpS9) {*Bacillus stearothermophilus*} | 51.9685 | 71.6535 | MG417(1–396 of 396)<br>GB:U01744(127–522 of 620) |

TABLE 1(c)

| UID | end5 | end3 | db_match | db_match name | per_sim | per_id | match_info |
|---|---|---|---|---|---|---|---|
| MG001 | 1026 | 1826 | GB:U09251_1 | DNA polymerase III beta subunit (dnaN) {*Mycoplasma genitalium*} | 100 | 100 | MG001 (507–801 of 801)<br>GB:U09251 (1–295 of 6140) |
| MG005 | 7295 | 8545 | GB:D26185_77 | seryl-tRNA synthetase (serS) {*Bacillus subtilis*} | 42.615 | 66.3438 | MG005 (1–377 of 1251)<br>GB:U09251 (5764–6140 of 6140) |
| MG005 | 7295 | 8545 | GB:D26185_77 | seryl-tRNA synthetase (serS) {*Bacillus subtilis*} | 42.615 | 66.3438 | MG005 (16–337 of 1251)<br>GB:U02210 (1–322 of 322) |
| MG007 | 9157 | 9918 | GB:D26185_83 | DNA polymerase III subunit (dnaH) {*Bacillus subtilis*} | 22.695 | 45.3901 | MG007 (762–711 of 762)<br>GB:U02216 (270–321 of 321) |
| MG008 | 9924 | 11249 | GB:D26185_60 | thiophene and furan oxidizer (tdhF) {*Bacillus subtilis*} | 31.9101 | 59.7753 | MG008 (264–1 of 1326)<br>GB:U02216 (1–264 of 321) |
| MG011 | 13565 | 12705 | — | — | — | — | MG011 (473–767 of 861)<br>GB:U02257 (2–296 of 296) |
| MG014 | 15556 | 17424 | SP:P27299 | transport ATP-binding protein (msbA) {*Escherichia coli*} | 28.0702 | 52.6316 | MG014 (1005–678 of 1869)<br>GB:U02235 (1–326 of 326) |
| MG018 | 21063 | 22343 | SP:P32333 | helicase (mot1) {*Saccharomyces cerevisiae*} | 36.6972 | 60.0917 | MG018 (1281–1067 of 1281)<br>GB:U01723 (89–304 of 304) |
| MG018 | 21063 | 22343 | SP:P32333 | helicase (mot1) {*Saccharomyces cerevisiae*} | 36.6972 | 60.0917 | MG018 (409–105 of 1281)<br>GB:U02179 (1–305 of 305) |
| MG018 | 21063 | 22343 | SP:P32333 | helicase (mot1) {*Saccharomyces cerevisiae*} | 36.6972 | 60.0917 | MG018 (592–896 of 1281)<br>GB:U01757 (1–305 of 305) |
| MG019 | 22388 | 23554 | SP:P35514 | heat shock protein (dnaJ) {*Lactococcus lactis*} | 33.9779 | 51.105 | MG019 (44–1 of 1167)<br>GB:U01723 (1–44 of 304) |
| MG020 | 23541 | 24464 | GB:Z25461_2 | proline iminopeptidase (pip) {*Neisseria gonorrhoeae*} | 37.5439 | 55.7895 | MG020 (723–924 of 924)<br>GB:U02229 (1–202 of 333) |
| MG021 | 24467 | 26002 | GB:D26185_101 | methionyl-tRNA synthesase (metS) {*Bacillus subtilis*} | 37.5494 | 58.8933 | MG021 (1–129 of 1536)<br>GB:U02229 (205–333 of 333) |

TABLE 1(c)-continued

| UID | end5 | end3 | db_match | db_match name | per_sim | per_id | match_info |
|---|---|---|---|---|---|---|---|
| MG021 | 24467 | 26002 | GB:D26185_101 | methionyl-tRNA synthetase (metS) {Bacillus subtilis} | 37.5494 | 58.8933 | MG021 (1318–1527 of 1536) GB:X61513 (1–209 of 209) |
| MG022 | 26035 | 26469 | GB:M21677_1 | RNA polymerase delta subunit (rpoE) {Bacillus subtilis} | 28.6765 | 49.2647 | MG022 (254–1 of 435) GB:U01721 (1–254 of 299) |
| MG025 | 28651 | 29544 | GP:Z47767_4 | TrsB {Yersinia enterocolitcia} | 27.551 | 54.0816 | MG025 (514–894 of 894) GB:U02253 (1–381 of 649) |
| MG026 | 29551 | 30120 | GP:U14003_62 | elongation factor P (efp) {Escherichia coli} | 26.3804 | 47.2393 | MG026 (1–93 of 558) GB:U02253 (388–649 of 649) |
| MG029 | 31702 | 31145 | GP:L19300_1 | hypothetical protein (GB:L19300_1) {Staphylococcus aureus} | 27.027 | 45.045 | MG029 (1–93 of 558) GB:U01773 (210–302 of 302) |
| MG030 | 32324 | 31707 | GP:Z27121_3 | uracial phosphoribosyltransferase (upp) {Mycoplasma hominis} | 44.9275 | 66.6667 | MG030 (414–618 of 618) GB:U01773 (1–205 of 302) |
| MG031 | 36713 | 32361 | GP:U06833_1 | DNA polymerase III (polC) {Mycoplasma pulmonis} | 38.0303 | 59.3182 | MG031 (1473–1701 of 4353) GB:U01807 (1–229 of 229) |
| MG031 | 36713 | 32361 | GP:U06833_1 | DNA polymerase III (polC) {Mycoplasma pulmonis} | 38.0303 | 59.3182 | MG031 (2923–3309 of 4353) GB:U01712 (1–387 of 387) |
| MG031 | 36713 | 32361 | GP:U06833_1 | DNA polymerase III (polC) {Mycoplasma pulmonis} | 38.0303 | 59.3182 | MG031 (3330–3676 of 4353) GB:U02208 (1–347 of 347) |
| MG036 | 41777 | 43426 | SP:P36419 | aspartyl-tRNA synthetase (aspS) {Thermus aquaticus} | 40.8582 | 62.8731 | MG036 (1115–1650 of 1650) GB:U01814 (1–532 of 1006) |
| MG036 | 41777 | 43426 | SP:P36419 | aspartyl-tRNA synthetase (aspS) {Thermus aquaticus} | 40.8582 | 62.8731 | MG036 (1407–1638 of 1650) GB:X61511 (1–232 of 232) |
| MG036 | 41777 | 43426 | SP:P36419 | aspartyl-tRNA synthetase (aspS) {Thermus aquaticus} | 40.8582 | 62.8731 | MG036 (1412–1160 of 1650) GB:X61523 (1–252 of 252) |
| MG037 | 43402 | 44751 | GP:U02020_1 | pre-B cell enhancing factor (PBEF) {Homo sapiens} | 34.3164 | 52.2788 | MG037 (1–500 of 1350) GB:U01814 (508–1006 of 1006) |
| MG040 | 47581 | 49353 | SP:P29724 | membrane lipoprotein (tmpC) {Treponema pallidum} | 30.8594 | 48.0469 | MG040 (1341–1552 of 1773) GB:U02125 (1–212 of 212) |
| MG045 | 53205 | 54653 | — | — | — | — | MG045 (381–4 of 1449) GB:U02166 (1–378 of 378) |
| MG047 | 55589 | 56737 | SP:P30869 | S-adenosylmethionine synthetase 2 (metX) {Escherichia coli} | 43.6111 | 60.5556 | MG047 (787–1070 of 1149) GB:U02123 (1–284 of 284) |
| MG051 | 59741 | 61003 | GB:L13289_3 | thymidine phosphorylase (dcoA) {Mycoplasma pirum} | 52.7316 | 73.6342 | MG051 (1161–1263 of 1263) GB:U02191 (1–103 of 183) |
| MG052 | 61015 | 61404 | GB:L13289_4 | cytidine deaminase (cdd) {Mycoplasma pirum} | 38.2114 | 64.2276 | MG052 (1–69 of 390) GB:U02191 (115–183 of 183) |
| MG052 | 61015 | 61404 | GB:L13289_4 | cytidine deaminase (cdd) {Mycoplasma pirum} | 38.2114 | 64.2276 | MG052 (320–390 of 390) GB:U02108 (1–71 of 212) |
| MG053 | 61407 | 63056 | GB:L13289_5 | phosphomannomutase (cpsG) {Mycoplasma pirum} | 38.7868 | 58.0882 | MG053 (1–140 of 1650) GB:U02108 (74–212 of 212) |
| MG054 | 63986 | 63039 | GB:D13303_4 | transcription antitermination factor (nusG) {Bacillus subtilis} | 30.8571 | 51.4286 | MG054 (688–44 of 948) GB:U01710 (1–645 of 645) |
| MG054 | 63986 | 63039 | GB:D13303_4 | transcription antitermination factor (nusG) {Bacillus subtilis} | 30.8571 | 51.4286 | MG054 (948–719 of 948) GB:U02236 (45–274 of 276) |
| MG055 | 64361 | 63993 | — | — | — | — | MG055 (1–326 of 369) GB:U02240 (23–348 of 348) |
| MG058 | 67121 | 66231 | GB:D26185_114 | phosphoribosylpyrophosphate synthetase (prs) {Bacillus subtilis} | 44.4089 | 63.5783 | MG058 (72–1 of 891) GB:U01693 (1–72 of 350) |
| MG059 | 67644 | 67210 | GB:D12501_1 | small protein (smpB) {Escherichia coli} | 32.5581 | 62.0155 | MG059 (435–247 of 435) GB:U01693 (161–350 of 350) |
| MG060 | 67651 | 68541 | SP:P26401 | lipopolysaccharide biosynthesis protein (rfbV) {Salmonella typhimurium} | 36.0656 | 59.8361 | MG060 (723–396 of 891) GB:U02262 (1–328 of 328) |
| MG061 | 69908 | 68526 | GB:M89480_4 | hexosephosphate transport protein (uhpT) {Salmonella typhimurium} | 30.9091 | 57.2727 | MG061 (1273–613 of 1383) GB:U01705 (1–661 of 661) |
| MG062 | 70531 | 72570 | SP:P20966 | fructose-permease IIBC component (fruA) {Escherichia coli} | 42.723 | 60.5634 | MG062 (439–761 of 2040) GB:U02138 (1–323 of 323) |
| MG063 | 72668 | 73432 | SP:P23539 | 1-phosphofructokinase (fruK) {Escherichia coli} | 26.3158 | 51.5038 | MG063 (363–626 of 765) GB:U01777 (1–264 of 264) |
| MG065 | 77686 | 79083 | GB:X75422_1 | heterocyst maturation protein (devA) {Anabaena sp.} | 35.2941 | 59.7285 | MG065 (1398–1176 of 1398) GB:U02154 (133–354 of 354) |
| MG066 | 79090 | 81033 | SP:P27302 | transketolase 1 (TK 1) (tktA) {Escherichia coli} | 32.5617 | 54.9383 | MG066 (126–of 1944) GB:U02154 (1–126 of 354) |
| MG068 | 82621 | 84042 | — | — | — | — | MG068 (1244–919 of 1422) GB:U02162 (1–326 of 326) |
| MG069 | 88228 | 90951 | SP:P20166 | phosphotransferase enzyme II, ABC component (ptsG) {Bacillus subtilis} | 43.1596 | 61.0749 | MG069 (1127–849 of 2724) GB:U02207 (1–279 of 279) |
| MG071 | 91924 | 94545 | SP:P37278 | cation-transporting ATPase (pacL) {Syncchococcus sp.} | 34.3897 | 57.277 | MG071 (1470–1209 of 2622) GB:X61532 (1–262 of 262) |
| MG072 | 94535 | 96952 | GB:D10279_2 | preprotein translocase (secA) {Bacillus subtilis} | 43.6601 | 66.7974 | MG072 (2269–2418 of 2418) GB:U01743 (1–150 of 365) |
| MG073 | 96933 | 98900 | SP:P07025 | excinuclease ABC subunit B (uvrB) {Escherichia coli} | 47.9751 | 67.2897 | MG073 (1–235 of 1968) GB:U01743 (131–365 of 365) |
| MG073 | 96933 | 98900 | SP:P07025 | excinuclease ABC subunit B (uvrB) {Escherichia coli} | 47.9751 | 67.2897 | MG073 (1584–1240 of 1968) GB:U01698 (1–345 of 345) |
| MG073 | 96933 | 98900 | SP:P07025 | excinuclease ABC subunit B (uvrB) {Escherichia coli} | 47.9751 | 67.2897 | MG073 (305–694 of 1968) GB:U02119 (1–391 of 391) |

TABLE 1(c)-continued

| UID | end5 | end3 | db_match | db_match name | per_sim | per_id | match_info |
|---|---|---|---|---|---|---|---|
| MG074 | 98906 | 99316 | — | — | — | — | MG074 (369–411 of 411)<br>GB:U01715 (1–43 of 576) |
| MG075 | 99383 | 102454 | — | — | — | — | MG075 (1–467 of 3072)<br>GB:U01715 (110–576 of 576) |
| MG075 | 99383 | 102454 | — | — | — | — | MG075 (1206–804 of 3072)<br>GB:U02251 (1–403 of 403) |
| MG075 | 99383 | 102454 | — | — | — | — | MG075 (1927–2210 of 3072)<br>GB:U01749 (1–284 of 284) |
| MG075 | 99383 | 102454 | — | — | — | — | MG075 (2841–2422 of 3072)<br>GB:U01775 (1–420 of 420) |
| MG080 | 106660 | 109203 | SP:P18766 | oligopeptide transport ATP-binding protein (amiF) {Streptococcus pneumoniae} | 46.6403 | 67.1937 | MG080 (2268–1954 of 2544)<br>GB:U02129 (1–315 of 315) |
| MG080 | 106660 | 109203 | SP:P18766 | oligopeptide transport ATP-binding protein (amiF) {Streptococcus pneumoniae} | 46.6403 | 67.1937 | MG080 (951–646 of 2544)<br>GB:U01758 (1–306 of 306) |
| MG082 | 109675 | 110352 | SP:P04447 | ribosomal protein LI (rpL1) {Bacillus stearothermophilus} | 48.1982 | 67.5676 | MG082 (446–170 of 678)<br>GB:U02113 (1–278 of 278) |
| MG083 | 110355 | 110921 | GB:L32144_1 | peptidyl-tRNA hydrolase homolog (pth) {Borrelia burgdorferi} | 38.2166 | 57.3248 | MG083 (567–220 of 567)<br>GB:U02185 (26–373 of 373) |
| MG084 | 110917 | 111786 | SP:P37563 | hypothetical protein (SP:P37563) {Bacillus subtilis} | 28.125 | 46.3542 | MG084 (30–1 of 870)<br>GB:U02185 (1–30 of 373) |
| MG084 | 110917 | 111786 | SP:P37563 | hypothetical protein (SP:P37563) {Bacillus subtilis} | 28.125 | 46.3542 | MG084 (794–870 of 870)<br>GB:U01783 (1–77 of 269) |
| MG087 | 113895 | 114311 | SP:P09901 | ribosomal protein S12 (rpS12) {Bacillus stearothermophilus} | 75.3731 | 82.0896 | MG087 (417–349 of 417)<br>GB:U02212 (326–394 of 394) |
| MG088 | 114331 | 114795 | SP:P22744 | ribosomal protein S7 (rpS7) {Bacillus stearothermophilus} | 64.9351 | 81.1688 | MG088 (305–1 of 465)<br>GB:U02212 (2–306 of 394) |
| MG089 | 114808 | 116871 | SP:P13551 | elongation factor G (fus) {Thermus aquaticus} | 59.2105 | 78.0702 | MG089 (1878–1540 of 2064)<br>GB:U02180 (1–339 of 340) |
| MG089 | 114808 | 116871 | SP:P13551 | elongation factor G (fus) {Thermus aquaticus} | 59.2105 | 78.0702 | MG089 (1885–2064 of 2064)<br>GB:U02136 (1–180 of 410) |
| MG089 | 114808 | 116871 | SP:P13551 | elongation factor G (fus) {Thermus aquaticus} | 59.2105 | 78.0702 | MG089 (687–1374 of 2064)<br>GB:U01722 (1–688 of 688) |
| MG090 | 116926 | 117549 | SP:P02358 | ribosomal protein S6 (rpS6) {Escherichia coli} | 23.8636 | 44.3182 | MG090 (1–176 of 624)<br>GB:U02136 (235–410 of 410) |
| MG094 | 118847 | 120184 | SP:P03005 | replicative DNA helicase (dnaB) {Escherichia coli} | 33.105 | 55.0228 | MG094 (1068–731 of 1338)<br>GB:U01803 (1–336 of 336) |
| MG094 | 118847 | 120184 | SP:P03005 | replicative DNA helicase (dnaB) {Escherichia coli} | 33.105 | 55.0228 | MG094 (228–1 of 1338)<br>GB:U02158 (1–228 of 301) |
| MG095 | 120191 | 121384 | — | — | — | — | MG095 (355–759 of 1194)<br>GB:U01787 (1–403 of 403) |
| MG096 | 121939 | 123519 | — | — | — | — | MG096 (1–309 of 1581)<br>GB:U01713 (58–366 of 366) |
| MG096 | 121939 | 123519 | — | — | — | — | MG096 (361–531 of 1581)<br>GB:U01762 (1–171 of 171) |
| MG097 | 123579 | 124313 | GB:D13169_3 | uracil DNA glycosylase (ung) {Escherichia coli} | 32.5688 | 31.8349 | MG097 (220–694 of 735)<br>GB:U02201 (1–475 of 475) |
| MG098 | 124416 | 125846 | GM:M74170_2 | p48 eggshell protein (p48) {Schistosoma mansoni} | 23.0769 | 47.9853 | MG098 (1260–831 of 1431)<br>GB:U01782 (1–431 of 431) |
| MG098 | 124416 | 125846 | GM:M74170_2 | p48 eggshell protein (p48) {Schistosoma mansoni} | 23.0769 | 47.9853 | MG098 (134–467 of 1431)<br>GB:U01701 (1–334 of 334) |
| MG100 | 127278 | 128708 | GP:L22072_1 | PET112 protein {Saccaromyces cerevisiae} | 30.8696 | 54.1304 | MG100 (533–238 of 1431)<br>GB:U01799 (1–296 of 296) |
| MG101 | 128686 | 129351 | — | — | — | — | MG101 (89–398 of 666)<br>GB:U02103 (1–309 of 309) |
| MG102 | 129347 | 130291 | GB:J03762_1 | thioredoxin reductase (trxB) {Escherichia coli} | 38.5906 | 59.396 | MG102 (45–367 of 945)<br>GB:U02197 (1–322 of 322) |
| MG103 | 130284 | 131123 | — | — | — | — | MG103 (623–256 of 840)<br>GB:U02170 (1–368 of 369) |
| MG104 | 131384 | 133558 | GB:U14003_91 | virulence associated protein homolog (vacB) {Escherichia coli} | 29.2335 | 52.2282 | MG104 (215–491 of 2175)<br>GB:U01795 (1–277 of 277) |
| MG108 | 135337 | 136116 | SP:P35182 | protein phosphatase 2C homolog (ptc1) {Saccaromyces cerevisiae} | 27.5362 | 52.1739 | MG108 (780–598 of 780)<br>GB:U02111 (33–215 of 215) |
| MG109 | 136179 | 137264 | PIR:S36944 | protein serine/threonine kinase {Arabidopsis thaliana} | 33.7398 | 52.0325 | MG109 (425–786 of 1086)<br>GB:U01720 (1–362 of 362) |
| MG109 | 136179 | 137264 | PIR:S36944 | protein serine/threonine kinase {Arabidopsis thaliana} | 33.7398 | 52.0325 | MG109 (781–1084 of 1086)<br>GB:U01748 (1–303 of 303) |
| MG110 | 137380 | 138087 | GB:U14003_76 | hypothetical protein (GB:U14003_76) {Escherichia coli} | 28.5714 | 54.1126 | MG110 (140–242 of 708)<br>GB:X61518 (1–102 of 102) |
| MG110 | 137380 | 138087 | GB:U14003_76 | hypothetical protein (GB:U14003_76) {Escherichia coli} | 28.5714 | 54.1126 | MG110 (670–378 of 708)<br>GB:U01714 (1–293 of 293) |
| MG111 | 138105 | 139403 | SP:P13376 | phosphoglucose isomerase B (pgiB) {Bacillus stearothermophilus} | 34.8235 | 53.6471 | MG111 (1–98 of 1299)<br>GB:U01747 (38–135 of 135) |
| MG112 | 139396 | 140022 | GB:M64173_3 | D-ribulose-5-phosphate 3 epimerase (cfxEc) {Alcaligenes cutrophus} | 33.1361 | 53.8462 | MG112 (207–473 of 627)<br>GB:U02181 (1–267 of 267) |

TABLE 1(c)-continued

| UID | end5 | end3 | db_match | db_match name | per_sim | per_id | match_info |
|---|---|---|---|---|---|---|---|
| MG113 | 140039 | 141406 | GB:M33145_1 | asparaginyl-tRNA synthetase (asnS) {*Escherichia coli*} | 41.4579 | 64.2369 | MG113 (1231–941 of 1368) GB:U01692 (1–291 of 291) |
| MG115 | 142314 | 142550 | SP:P31131 | hypothetical protein (SP:P31131) {*Escherichia coli*} | 32.6087 | 50 | MG115 (198–237 of 237) GB:U02127 (1–40 of 234) |
| MG116 | 142562 | 143314 | — | — | — | — | MG116 (1–183 of 753) GB:U02127 (52–234 of 234) |
| MG119 | 144972 | 146663 | GB:M59444_2 | methylgalactoside permease ATP-binding protein (mglA) {*Escherichia coli*} | 33.1984 | 57.6923 | MG119 (1660–1692 of 1692) GB:U02147 (1–33 of 301) |
| MG119 | 144972 | 146663 | GB:M59444_2 | methylgalactoside permease ATP-binding protein (mglA) {*Escherichia coli*} | 33.1984 | 57.6923 | MG119 (192–1 of 1692) GB:U02149 (1–192 of 681) |
| MG120 | 146673 | 148232 | SP:P36948 | ribose transport system permease protein (rbsC) {*Bacillus subtilis*} | 27.4809 | 51.9084 | MG120 (1–259 of 1560) GB:U02147 (43–301 of 301) |
| MG122 | 149198 | 151324 | GB:L27797_2 | DNA topoisomerase I (topA) {*Bacillus subtilis*} | 38.9222 | 59.7305 | MG122 (1193–1443 of 2127) GB:U02134 (1–251 of 251) |
| MG122 | 149198 | 151324 | GB:L27797_2 | DNA topoisomerase I (topA) {*Bacillus subtilis*} | 38.9222 | 59.7305 | MG122 (1578–1971 of 2127) GB:U02242 (1–394 of 394) |
| MG123 | 151305 | 152717 | GB:M91593_1 | hypothetical protein (GB:M91593_1) {*Mycoplasma mycoides*} | 23.9837 | 50.4065 | MG123 (1413–1236 of 1413) GB:U01796 (114–291 of 291) |
| MG124 | 152767 | 153072 | GB:J03294_1 | thioredoxin (trx) {*Bacillus subtilis*} | 36.0825 | 65.9794 | MG124 (64–1 of 306) GB:U01796 (1–64 of 291) |
| MG133 | 159669 | 158986 | — | — | — | — | MG133 (1–110 of 684) GB:U02144 (237–345 of 345) |
| MG133 | 159669 | 158986 | — | — | — | — | MG133 (435–673 of 684) GB:X61537 (1–238 of 238) |
| MG134 | 159797 | 160096 | GB:M38777_3 | hypothetical protein (GB:M38777_3) {*Escherichia coli*} | 28.5714 | 57.1429 | MG134 (109–1 of 300) GB:U02144 (1–109 of 345) |
| MG135 | 160913 | 160074 | PIR:E22845 | hypothetical protein 4 (GP:Z33006_1) {*Trypanosoma brucci*} | 30.7692 | 55.9441 | MG135 (485–782 of 840) GB:U02114 (1–298 of 298) |
| MG138 | 163590 | 165383 | GB:K00426_1 | GTP-binding membrane protein (lepA) {*Escherichia coli*} | 47.5465 | 70.5584 | MG138 (1237–938 of 1794) GB:U02133 (2–301 of 301) |
| MG138 | 163590 | 165383 | GB:K00426_1 | GTP-binding membrane protein (lepA) {*Escherichia coli*} | 47.5465 | 70.5584 | MG138 (1318–1794 of 1794) GB:U01745 (1–477 of 524) |
| MG138 | 163590 | 165383 | GB:K00426_1 | GTP-binding membrane protein (lepA) {*Escherichia coli*} | 47.5465 | 70.5584 | MG138 (323–591 of 1794) GB:X61521 (1–269 of 269) |
| MG140 | 175807 | 179145 | — | — | — | — | MG140 (1–41 of 3339) GB:U02110 (178–218 of 218) |
| MG140 | 175807 | 179145 | — | — | — | — | MG140 (2727–2429 of 3339) GB:U01730 (1–297 of 297) |
| MG140 | 175807 | 179145 | — | — | — | — | MG140 (3302–2994 of 3339) GB:U02156 (1–308 of 308) |
| MG140 | 175807 | 179145 | — | — | — | — | MG140 (382–834 of 3339) GB:U01729 (1–454 of 454) |
| MG140 | 175807 | 179145 | — | — | — | — | MG140 (834–616 of 3339) GB:X61512 (1–220 of 220) |
| MG140 | 175807 | 179145 | — | — | — | — | MG140 (880–1182 of 3339) GB:U01742 (1–303 of 303) |
| MG141 | 179153 | 180745 | SP:P32727 | N-utilization substance protein A homolog (nusA) {*Bacillus subtilis*} | 30.8743 | 53.8251 | MG141 (223–871 of 1593) GB:U01778 (1–652 of 652) |
| MG142 | 181007 | 182863 | GB:M34836_1 | protein synthesis initiation factor 2 (infB) {*Bacillus subtilis*} | 46.0292 | 64.6677 | MG142 (265–393 of 1857) GB:U01765 (1–129 of 129) |
| MG144 | 183216 | 184052 | — | — | — | — | MG144 (190–420 of 837) GB:U02121 (1–231 of 231) |
| MG146 | 184877 | 186148 | GB:X73141_2 | hemolysin (tlyC) {*Serpulina hyodysenteriae*} | 26.2712 | 52.1186 | MG146 (1272–1174 of 1272) GB:U02223 (19–117 of 117) |
| MG149 | 188609 | 189451 | — | — | — | — | MG149 (843–765 of 843) GB:U02135 (182–260 of 260) |
| MG151 | 190372 | 191142 | SP:P10134 | ribosomal protein L3 (rpL3) {*Mycoplasma capricolum*} | 42.5926 | 61.5741 | MG151 (528–1 of 771) GB:U02153 (1–527 of 543) |
| MG168 | 198519 | 199151 | GB:M57621_1 | ribosomal protein S5 (rpS5) {*Bacillus stearothermophilus*} | 55.9748 | 72.327 | MG168 (505–633 of 633) GB:U01726 (1–129 of 260) |
| MG175 | 202762 | 203133 | GB:M26414_3 | ribosomal protein S13 (rpS13) {*Bacillus subtilis*} | 63.3333 | 82.5 | MG175 (22–372 of 372) GB:U01733 (1–351 of 600) |
| MG176 | 203136 | 203528 | GB:X02543_2 | ribosomal protein S11 (rpS11) {*Escherichia coli*} | 47.7876 | 69.9115 | MG176 (1–247 of 393) GB:U01733 (354–600 of 600) |
| MG180 | 205682 | 206593 | GB:M61017_1 | membrane transport protein (glnQ) {*Bacillus stearothermophilus*} | 37.3832 | 63.0841 | MG180 (249–1 of 912) GB:U01754 (1–248 of 265) |
| MG180 | 205682 | 206593 | GB:M61017_1 | membrane transport protein (glnQ) {*Bacillus stearothermophilus*} | 37.3832 | 63.0841 | MG180 (912–784 of 912) GB:U01750 (167–295 of 295) |
| MG181 | 206589 | 207848 | — | — | — | — | MG181 (171–1 of 1260) GB:U01750 (1–171 of 295) |
| MG182 | 207844 | 208575 | SP:P07649 | pseudouridylate synthase I (hisT) {*Escherichia coli*} | 27.0042 | 45.1477 | MG182 (1–308 of 732) GB:U02176 (70–377 of 377) |
| MG182 | 207844 | 208575 | SP:P07649 | pseudouridylate synthase I (hisT) {*Escherichia coli*} | 27.0042 | 45.1477 | MG182 (732–383 of 732) GB:U02100 (31–380 of 380) |
| MG183 | 208568 | 210388 | GB:Z32522_1 | oligoendopeptidase F (pepF) {*Lactococcus lactis*} | 30 | 50.6667 | MG183 (27–335 of 1821) GB:U02198 (1–309 of 309) |

TABLE 1(c)-continued

| UID | end5 | end3 | db_match | db_match name | per_sim | per_id | match_info |
|---|---|---|---|---|---|---|---|
| MG183 | 208568 | 210388 | GB:Z32522_1 | oligoendopeptidase F (pepF) {Lactococcus lactis} | 30 | 50.6667 | MG183 (38–1 of 1821) GB:U02100 (1–38 of 380) |
| MG184 | 210392 | 211342 | GB:M97479_2 | methyltransferase (ssolM) {Shigella sonnei} | 42.5249 | 67.4419 | MG184 (520–719 of 951) GB:U02115 (1–200 of 201) |
| MG190 | 220479 | 221561 | PIR:JS0068 | 29 kDa protein, MgPa operon (mgp) {Mycoplasma genitalium} | 62.0833 | 82.0833 | MG190 (28–1083 of 1083) GB:M31431 (1–1056 of 8760) |
| MG194 | 232007 | 233029 | GB:V00291_5 | phenylalanyl-tRNA synthetase beta-subunit (pheS) {Escherichia coli} | 35.0769 | 56.3077 | MG194 (194–359 of 1023) GB:U02120 (1–166 of 166) |
| MG195 | 233036 | 235453 | SP:P17922 | phenylalanyl-tRNA synthetase beta chain (pheT) {Bacillus subtilis} | 25.4597 | 49.0806 | MG194 (2044–2396 of 2418) GB:U021763 (1–353 of 353) |
| MG200 | 237346 | 239148 | GB:L36455_1 | heat shock protein (dnaJ) {Coxiella burnetii} | 33.5938 | 51.5625 | MG200 (842–1227 of 1803) GB:U02163 (2–387 of 387) |
| MG203 | 240322 | 242220 | GB:U25549_1 | topoisomerase IV subunit B (parE) {Mycoplasma genitalium} | 100 | 100 | MG203 (1216–1899 of 1899) GB:U25549 (1–684 of 2124) |
| MG204 | 242223 | 244565 | GB:U25549_2 | topoisomerase IV subunit A (parC) {Mycoplasma genitalium} | 99.7912 | 99.7912 | MG204 (1–1438 of 2343) GB:U25549 (687–2124 of 2124) |
| MG204 | 242223 | 244565 | GB:U25549_2 | topoisomerase IV subunit A (parC) {Mycoplasma genitalium} | 99.7912 | 99.7912 | MG204 (1950–1641 of 2343) GB:U02155 (1–308 of 308) |
| MG206 | 246127 | 247422 | SP:P14951 | excinuclease ABC subunit C (uvrC) | 28.0872 | 51.0896 | MG206 (738–399 of 1296) GB:U02182 (1–341 of 341) |
| MG208 | 248492 | 247905 | — | — | — | — | MG208 (585–162 of 588) GB:U01785 (1–423 of 423) |
| MG209 | 249402 | 248479 | SP:P23851 | hypothetical protein (SP:P23851) {Escherichia coli} | 30.4498 | 55.0173 | MG209 (730–372 of 924) GB:U02214 (1–359 of 359) |
| MG210 | 249947 | 249405 | GB:M83994_1 | prolipoprotein signal peptidase (lsp) {Staphylococcus aureus} | 32.3944 | 52.1127 | MG210 (1–116 of 543) GB:U01759 (196–311 of 311) |
| MG212 | 251780 | 252583 | GB:L21861_1 | 1-acyl-sn-glycerol-3-phosphate acetyltransferase (plsC) {Borrelia burgdorferi} | 32.1429 | 60.7143 | MG212 (7–315 of 804) GB:U02160 (5–313 of 313) |
| MG216 | 255594 | 257117 | GB:L07920_2 | pyruvate kinase (pyk) {Lactococcus lactis} | 35.3319 | 57.6017 | MG216 (1118–790 of 1524) GB:U01798 (1–329 of 329) |
| MG218 | 259176 | 264590 | PIR:S37536 | no score generated-score shown is bogus | −1 | −1 | MG218 (1669–1977 of 5415) GB:U02165 (1–309 of 309) |
| MG221 | 266626 | 267087 | SP:P22186 | hypothetical protein (SP:P22186) {Escherichia coli} | 28.8732 | 56.338 | MG221 (337–49 of 462) GB:U02195 (1–290 of 290) |
| MG225 | 270404 | 271870 | GB:U14003_71 | hypothetical protein (GB:U14003_71) {Escherichia coli} | 21.9565 | 48.0435 | MG225 (1467–1409 of 1467) GB:U02264 (289–347 of 347) |
| MG226 | 271938 | 273314 | GB:D26562_11 | aromatic amino acid transport protein (aroP) {Escherichia coli} | 24.5902 | 47.2131 | MG226 (221–1 of 1377) GB:U02264 (1–221 of 347) |
| MG227 | 273789 | 274649 | SP:P13954 | thymidylate synthase (thyA) {Staphylococcus aureus} | 56.5972 | 75.3472 | MG227 (577–861 of 861) GB:U01718 (1–285 of 439) |
| MG228 | 274652 | 275131 | GB:X60681_1 | dihydrofolate reductase (dhfr) {Lactococcus lactis} | 33.1288 | 59.5092 | MG228 (480–385 of 480) GB:U02137 (174–269 of 269) |
| MG229 | 275140 | 276159 | SP:P17424 | ribonucleotide reductase 2 (nrdF) {Salmonella typhimurium} | 50 | 70.0637 | MG229 (1020–697 of 1020) GB:U01739 (22–344 of 344) |
| MG231 | 276646 | 278808 | GB:X73226_1 | ribonucleoside-diphosphate reductase (nrdE) {Salmonella typhimurium} | 54.1193 | 73.1534 | MG231 (2122–2163 of 2163) GB:U02141 (1–42 of 827) |
| MG237 | 281078 | 281959 | — | — | — | — | MG237 (647–882 of 882) GB:U01774 (1–236 of 289) |
| MG238 | 281992 | 283323 | GB:M34066_1 | trigger factor (tig) {Escherichia coli} | 24.6193 | 47.9695 | MG238 (420–648 of 1332) GB:U01772 (1–229 of 229) |
| MG239 | 283395 | 285779 | SP:P37945 | ATP-dependent protease (lon) {Bacillus subtilis} | 43.6268 | 65.8344 | MG239 (1818–1449 of 2385) GB:U02148 (1–370 of 370) |
| MG240 | 286657 | 285782 | GB:M91593_1 | hypothetical protein (GB:M91593_1) {Mycoplasma mycoides} | 27.8195 | 53.3835 | MG240 (876–598 of 876) GB:U01734 (27–305 of 305) |
| MG242 | 288752 | 290641 | — | — | — | — | MG242 (886–543 of 1890) GB:U02194 (1–344 of 344) |
| MG244 | 291332 | 293440 | GB:M99049_1 | DNA helicase II (mutB1) {Haemophilus influenzae} | 36.0078 | 55.9687 | MG244 (829–1035 of 2109) GB:X61517 (1–207 of 207) |
| MG249 | 297604 | 296114 | SP:P33656 | RNA polymerase sigma-A factor (sigA) {Clostridium acetobutylicum} | 43.6842 | 66.0526 | MG249 (970–666 of 1491) GB:X61535 (1–306 of 306) |
| MG250 | 299472 | 297652 | GB:M10040_1 | DNA primase (dnaE) {Bacillus subtilis} | 27.2727 | 52.2078 | MG250 (1530–1821 of 1821) GB:U01771 (1–292 of 572) |
| MG250 | 299472 | 297652 | GB:M10040_1 | DNA primase (dnaE) {Bacillus subtilis} | 27.2727 | 52.2078 | MG250 (648–231 of 1821) GB:U02146 (1–418 of 418) |
| MG254 | 304823 | 302847 | GB:M24278_1 | DNA ligase (lig) {Escherichia coli} | 38.2263 | 59.3272 | MG254 (1429–1722 of 1977) GB:U02152 (1–294 of 294) |
| MG254 | 304823 | 302847 | GB:M24278_1 | DNA ligase (lig) {Escherichia coli} | 38.2263 | 59.3272 | MG254 (37–367 of 1977) GB:U01761 (1–330 of 330) |
| MG255 | 304999 | 306093 | — | — | — | — | MG255 (726–1095 of 1095) GB:U02164 (1–370 of 370) |
| MG255 | 304999 | 306093 | — | — | — | — | MG255 (729–400 of 1095) GB:U02174 (1–333 of 333) |
| MG261 | 315699 | 318320 | GB:M19334_4 | DNA polymerase III alpha subunit (dnaE) {Escherichia coli} | 31.9115 | 55.7662 | MG261 (2442–2159 of 2622) GB:U01738 (1–284 of 284) |
| MG263 | 320175 | 321047 | GB:L10328_61 | hypothetical protein (GB:L10328_61) {Escherichia coli} | 27.8008 | 47.7178 | MG263 (828–489 of 873) GB:U01764 (1–340 of 340) |

TABLE 1(c)-continued

| UID | end5 | end3 | db_match | db_match name | per_sim | per_id | match_info |
|---|---|---|---|---|---|---|---|
| MG266 | 324809 | 322434 | GB:M88581_1 | leucyl-tRNA synthetase (leuS) {Bacillus stearothermophilus} | 43.401 | 64.2132 | MG266 (78–287 of 2376) GB:U01780 (1–210 of 210) |
| MG266 | 324809 | 322434 | GB:M88581_1 | leucyl-tRNA synthetase (leuS) {Bacillus stearothermophilus} | 43.401 | 64.2132 | MG266 (957–622 of 2376) GB:U02167 (1–336 of 336) |
| MG269 | 327050 | 326031 | GB:D90354_1 | surface protein antigen precursor (pag) {Streptococcus sobrinus} | 25.5144 | 47.3251 | MG269 (239–1 of 1020) GB:U02215 (1–239 of 366) |
| MG271 | 329826 | 328456 | SP:P11959 | dihydrolipoamide dehydrogenase (pdhD) {Bacillus stearothermophilus} | 38.3592 | 62.306 | MG271 (914–1214 of 1371) GB:U01784 (1–301 of 301) |
| MG275 | 334772 | 333339 | SP:P37061 | NADH oxidase (nox) {Enterococcus faecalis} | 39.229 | 62.1315 | MG271 (914–1214 of 1371) GB:U01786 (4–84 of 280) |
| MG276 | 335397 | 334858 | GB:M14040_1 | adenine phosphoribosyltransferase (apt) {Escherichia coli} | 34.3373 | 58.4337 | MG276 (540–430 of 540) GB:U01786 (170–280 of 280) |
| MG278 | 338366 | 340525 | GB:X72832_5 | strigent response-like protein (rel) {Streptococcus equisimilis} | 29.1339 | 55.1181 | MG278 (391–697 of 2160) GB:U01770 (1–308 of 308) |
| MG281 | 343702 | 342035 | — | — | — | — | MG281 (748–1051 of 1668) GB:U01706 (1–303 of 303) |
| MG282 | 344849 | 344367 | SP:P27640 | transcription elongation factor (greA) {Rickettsia prowazekii} | 40.146 | 65.6934 | MG282 (483–356 of 483) GB:U02104 (187–314 of 314) |
| MG283 | 345181 | 346629 | GB:M97858_1 | prolyl-tRNA synthetase (proS) {Escherichia coli} | 22.6562 | 46.0938 | MG283 (839–1183 of 1449) GB:U02205 (1–346 of 346) |
| MG285 | 347214 | 348254 | — | — | — | — | MG285 (315–493 of 1041) GB:U02266 (1–180 of 180) |
| MG289 | 354023 | 355156 | SP:P15363 | high affinity transport system protein P37 (P37) {Mycoplasma hyorhinis} | 35.7798 | 58.4098 | MG289 (105–1 of 1104) GB:U02132 (1–105 of 571) |
| MG291 | 355846 | 357474 | SP:P15362 | transport system permease protein P69 (P69) {Mycoplasma hyorhinis} | 27.9159 | 54.8757 | MG291 (1216–1629 of 1629) GB:U01768 (1–415 of 705) |
| MG291 | 355846 | 357474 | SP:P15362 | transport system permease protein P69 (P69) {Mycoplasma hyorhinis} | 27.9159 | 54.8757 | MG291 (279–1 of 1629) GB:U02171 (1–279 of 346) |
| MG293 | 361384 | 360653 | SP:P37965 | glycerophosphoryl diester phosphodiesterase (glpQ) {Bacillus subtilis} | 30.3965 | 55.9471 | MG293 (357–41 of 732) GB:U02118 (1–317 of 317) |
| MG294 | 362801 | 361380 | GB:L19201_18 | hypothetical protein (GB:L19201_18) {Escherichia coli} | 23.1013 | 46.2025 | MG294 (256–592 of 1422) GB:U02243 (1–337 of 337) |
| MG297 | 365574 | 364537 | GB:U00039_18 | cell division protein (ftsY) {Escherichia coli} | 36.1371 | 57.9439 | MG297 (1–57 of 1038) GB:U02177 (215–271 of 271) |
| MG298 | 368529 | 365584 | GB:M34956_1 | 115 kDa protein (p115) {Mycoplasma hyorhinis} | 33.4059 | 57.5626 | MG298 (2743–2946 of 2946) GB:U02177 (1–205 of 271) |
| MG300 | 370962 | 369715 | SP:P36204 | phosphoglycerate kinase (pgk) {Thermotoga maritima} | 51.2887 | 70.6186 | MG300 (1–167 of 1248) GB:U02178 (167–333 of 333) |
| MG300 | 370962 | 369715 | SP:P36204 | phosphoglycerate kinase (pgk) {Thermotoga maritima} | 51.2887 | 70.6186 | MG300 (935–609 of 1248) GB:U02226 (1–326 of 326) |
| MG300 | 370962 | 369715 | SP:P36204 | phosphoglycerate kinase (pgk) {Thermotoga maritima} | 51.2887 | 70.6186 | MG300 (939–1243 of 1248) GB:U02234 (1–305 of 305) |
| MG301 | 371962 | 370952 | GB:X72219_1 | glyceraldehyde-3-phosphate dehydrogenase (gap) {Clostridium pasteurianum} | 56.0606 | 73.0303 | MG301 (244–1 of 1011) GB:U02213 (1–244 of 364) |
| MG301 | 371962 | 370952 | GB:X72219_1 | glyceraldehyde-3-phosphate dehydrogenase (gap) {Clostridium pasteurianum} | 56.0606 | 73.0303 | MG301 (835–1011 of 1011) GB:U02178 (1–177 of 333) |
| MG302 | 372946 | 371996 | — | — | — | — | MG302 (951–865 of 951) GB:U02213 (278–364 of 364) |
| MG305 | 376705 | 374921 | GB:D30690_3 | heat shock protein 70 (hsp70) {Staphylococcus aureus} | 57.4359 | 75.8974 | MG305 (1382–1055 of 1785) GB:U02204 (1–327 of 327) |
| MG307 | 381507 | 377977 | — | — | — | — | MG307 (3175–2042 of 3531) GB:U01767 (1–1134 of 1134) |
| MG308 | 382724 | 381495 | SP:P23304 | ATP-dependent RNA helicase (deaD) {Escherichia coli} | 23.0986 | 48.169 | MG308 (1–89 of 1230) GB:U02200 (276–364 of 364) |
| MG309 | 386408 | 382734 | — | — | — | — | MG309 (3410–3675 of 3675) GB:U02200 (1–266 of 364) |
| MG312 | 391334 | 387918 | GB:U11381_1 | cytadherence-accessory protein (hmw1) {Mycoplasma pneumoniac} | 39.3235 | 60.6765 | MG312 (2541–2160 of 3417) GB:U02261 (1–382 of 382) |
| MG314 | 393633 | 392305 | GP:L38997_4 | hypothetical protein (GP:L38997_4) {Mycoplasma pneumoniac} | 51.4477 | 71.4922 | MG314 (514–206 of 1329) GB:U02151 (1–309 of 309) |
| MG317 | 397426 | 395627 | GP:M82965_1 | cytadherence-accessory protein (hwm3) {Mycoplasma pneumoniac} | 41.1458 | 59.8958 | MG317 (1329–1542 of 1797) GB:U02267 (1–214 of 214) |
| MG317 | 397426 | 395627 | GP:M82965_1 | cytadherence-accessory protein (hwm3) {Mycoplasma pneumoniac} | 41.1458 | 59.8958 | MG317 (509–169 of 1797) GB:U02224 (1–341 of 341) |
| MG317 | 397426 | 395627 | GP:M82965_1 | cytadherence-accessory protein (hwm3) {Mycoplasma pneumoniac} | 41.1458 | 59.8958 | MG317 (73–1 of 1797) GB:U01716 (1–73 of 325) |
| MG318 | 398280 | 397441 | GB:J04151_1 | fibronectin-binding protein (fnbA) {Staphylococcus aureus} | 24.6154 | 43.0769 | MG318 (840–604 of 840) GB:U01716 (91–325 of 325) |
| MG319 | 398833 | 398300 | — | — | — | — | MG319 (423–1 of 534) GB:U01769 (1–426 of 541) |
| MG320 | 399797 | 398940 | — | — | — | — | MG320 (371–781 of 858) GB:U01700 (1–410 of 410) |
| MG324 | 408792 | 407731 | GB:D00398_1 | aminopeptidase P (pepP) {Escherichia coli} | 30.531 | 54.4248 | MG324 (883–1062 of 1062) GB:U01717 (1–181 of 223) |

TABLE 1(c)-continued

| UID | end5 | end3 | db_match | db_match name | per_sim | per_id | match_info |
|---|---|---|---|---|---|---|---|
| MG324 | 408792 | 407731 | GB:D00398_1 | aminopeptidase P (pepP) {*Escherichia coli*} | 30.531 | 54.4248 | MG324 (889–1062 of 1062) GB:U01755 (2–175 of 217) |
| MG327 | 410676 | 409873 | SP:P26174 | magnesium-chelatase 30 kDa subunit (bchO) {*Rhodobacter capsulatus*} | 26.7281 | 51.1521 | MG327 (782–533 of 804) GB:U02232 (1–250 of 250) |
| MG328 | 412933 | 410666 | GB:X62467_1 | protein V (fcrV) {*Streptococcus sp.*} | 27.5434 | 48.3871 | MG328 (339–53 of 2268) GB:U02188 (1–287 of 287) |
| MG328 | 412933 | 410666 | GB:X62467_1 | protein V (fcrV) {*Streptococcus sp.*} | 27.5434 | 48.3871 | MG328 (817–462 of 2268) GB:U02203 (1–356 of 356) |
| MG330 | 414975 | 414325 | SP:P38493 | cytidylate kinase (cmk) {*Bacillus subtilis*} | 40.3756 | 61.0329 | MG330 (537–226 of 651) GB:U02241 (1–312 of 314) |
| MG334 | 419480 | 416970 | SP:Q05873 | valyl-tRNA synthetase (valS) {*Bacillus subtilis*} | 38.5629 | 60.5988 | MG334 (1109–781 of 2511) GB:U02202 (1–330 of 330) |
| MG334 | 419480 | 416970 | SP:Q05873 | valyl-tRNA synthetase (valS) {*Bacillus subtilis*} | 38.5629 | 60.5988 | MG334 (2400–2511 of 2511) GB:U02249 (1–112 of 305) |
| MG335 | 420045 | 419473 | SP:P38424 | hypothetical protein (SP:P38424) {*Bacillus subtilis*} | 34.5238 | 61.3095 | MG335 (1–95 of 573) GB:U02190 (200–294 of 294) |
| MG336 | 421467 | 422690 | GB:U00013_6 | nitrogen fixation protein (nifS) {*Mycobacterium leprac*} | 26.2295 | 47.2678 | MG336 (990–719 of 1224) GB:U02256 (1–272 of 272) |
| MG337 | 422697 | 423110 | — | — | — | — | MG337 (414–151 of 414) GB:U01709 (35–297 of 297) |
| MG338 | 426915 | 423103 | — | — | — | — | MG338 (1–251 of 3813) GB:U02269 (65–315 of 315) |
| MG338 | 426915 | 423103 | — | — | — | — | MG338 (1304–917 of 3813) GB:U02221 (1–388 of 388) |
| MG338 | 426915 | 423103 | — | — | — | — | MG338 (3342–3067 of 3813) GB:U0222 (1–388 of 388) |
| MG338 | 426915 | 423103 | — | — | — | — | MG338 (3722–3813 of 3813) GB:U01709 (1–42 of 297) |
| MG339 | 428115 | 427096 | GB:L25893_1 | recombination protein (recA) {*Staphylococcus aureus*} | 46.5986 | 69.3878 | MG339 (372–93 of 1020) GB:U01704 (1–279 of 279) |
| MG340 | 434458 | 430583 | SP:P00577 | DNA-directed RNA polymerase beta' chain (rpoC) {*Escherichia coli*} | 44.4828 | 66.0345 | MG340 (1294–999 of 3876) GB:X61534 (1–295 of 295) |
| MG340 | 434458 | 430583 | SP:P00577 | DNA-directed RNA polymerase beta' chain (rpoC) {*Escherichia coli*} | 44.4828 | 66.0345 | MG340 (1519–1289 of 3876) GB:X61528 (1–231 of 231) |
| MG340 | 434458 | 430583 | SP:P00577 | DNA-directed RNA polymerase beta' chain (rpoC) {*Escherichia coli*} | 44.4828 | 66.0345 | MG340 (3444–3083 of 3876) GB:U02169 (1–361 of 361) |
| MG340 | 434458 | 430583 | SP:P00577 | DNA-directed RNA polymerase beta' chain (rpoC) {*Escherichia coli*} | 44.4828 | 66.0345 | MG340 (3772–3876 of 3876) GB:U01766 (1–105 of 467) |
| MG340 | 434458 | 430583 | SP:P00577 | DNA-directed RNA polymerase beta' chain (rpoC) {*Escherichia coli*} | 44.4828 | 66.0345 | MG340 (426–66 of 3876) GB:U01797 (1–361 of 361) |
| MG341 | 438640 | 434471 | GB:L24376_3 | RNA polymerase beta subunit (rpoB) {*Bacillus subtilis*} | 46.5338 | 67.5043 | MG341 (1–107 of 4170) GB:U02230 (217–323 of 323) |
| MG341 | 438640 | 434471 | GB:L24376_3 | RNA polymerase beta subunit (rpoB) {*Bacillus subtilis*} | 46.5338 | 67.5043 | MG341 (1932–1595 of 4170) GB:U01737 (1–338 of 338) |
| MG341 | 438640 | 434471 | GB:L24376_3 | RNA polymerase beta subunit (rpoB) {*Bacillus subtilis*} | 46.5338 | 67.5043 | MG341 (2833–3201 of 4170) GB:U01735 (1–369 of 369) |
| MG342 | 439236 | 438733 | — | — | — | — | MG342 (381–504 of 504) GB:U02230 (1–124 of 323) |
| MG342 | 439236 | 438733 | — | — | — | — | MG342 (386–65 of 504) GB:U02231 (1–322 of 322) |
| MG343 | 440355 | 439318 | — | — | — | — | MG343 (108–452 of 1038) GB:U01811 (1–345 of 345) |
| MG344 | 441180 | 440362 | GP:U17036_2 | lipase-esterase (lip1) {*Mycoplasma mycoides*} | 26.6667 | 47.5 | MG344 (575–767 of 819) GB:U02222 (1–193 of 193) |
| MG345 | 443878 | 441194 | SP:P00956 | isoleucyl-tRNA synthetase (ileS) {*Escherichia coli*} | 33.2963 | 56.2708 | MG345 (1115–782 of 2685) GB:U02196 (1–334 of 334) |
| MG345 | 443878 | 441194 | SP:P00956 | isoleucyl-tRNA synthetase (ileS) {*Escherichia coli*} | 33.2963 | 56.2708 | MG345 (1811–2134 of 2685) GB:U02254 (1–324 of 324) |
| MG348 | 446165 | 445200 | — | — | — | — | MG348 (166–459 of 966) GB:U01781 (1–292 of 292) |
| MG352 | 450222 | 450719 | GB:U11883_2 | hypothetical protein (GB:U11883_2) {*Bacillus subtilis*} | 33.3333 | 56.7901 | MG352 (366–498 of 498) GB:U02237 (1–133 of 310) |
| MG353 | 451048 | 450722 | — | — | — | — | MG353 (327–153 of 327) GB:U02237 (136–309 of 310) |
| MG357 | 455947 | 454769 | GB:L17320_2 | acetate kinase (ackA) {*Bacillus subtilis*} | 42.6735 | 65.5527 | MG357 (342–131 of 1179) GB:X61531 (1–211 of 211) |
| MG358 | 456590 | 457369 | GB:M21298_1 | Holliday junction DNA helicase (ruvA) {*Escherichia coli*} | 26.2411 | 42.5532 | MG358 (350–87 of 780) GB:U02233 (1–265 of 265) |
| MG361 | 459615 | 460100 | SP:P29394 | ribosomal protein L10 (rpl10) {*Thermotoga maritima*} | 29.8137 | 61.4907 | MG361 (274–486 of 486) GB:U02206 (1–213 of 345) |
| MG362 | 460126 | 460491 | SP:P02394 | ribosomal protein L7/L12 ('A' type) (rpL7/L12) {*Bacillus subtilis*} | 47.5 | 70 | MG362 (1–107 of 366) GB:U02206 (239–345 of 345) |
| MG365 | 461682 | 462614 | GB:X63666_2 | methionyl-tRNA formyltransferase (fmt) {*Escherichia coli*} | 24.43 | 50.8143 | MG365 (292–1 of 933) GB:U02238 (1–292 of 349) |
| MG368 | 466410 | 465427 | GB:M96796_1 | fatty acid/phospholipid synthesis protein (plsX) {*Escherichia coli*} | 28.972 | 52.3364 | MG368 (227–1 of 984) GB:U01791 (1–227 of 326) |

TABLE 1(c)-continued

| UID | end5 | end3 | db_match | db_match name | per_sim | per_id | match_info |
|---|---|---|---|---|---|---|---|
| MG369 | 468083 | 466413 | — | — | — | — | MG369 (1146–1446 of 1671) GB:U01763 (1–300 of 300) |
| MG370 | 469123 | 468155 | SP:P23851 | hypothetical protein (SP:P23851) {*Escherichia coli*} | 26.9531 | 48.8281 | MG3370 (240–599 of 969) GB:U02220 (1–360 of 360) |
| MG371 | 470084 | 469113 | GB:D26185_10 | hypothetical protein (GB:D26185_10) {*Bacillus subtilis*} | 25.8065 | 47.0046 | MG371 (349–689 of 972) GB:U02263 (1–341 of 341) |
| MG374 | 472891 | 472070 | — | — | — | — | MG374 (1–178 of 822) GB:U02250 (159–337 of 337) |
| MG375 | 474578 | 472887 | GB:M36594_1 | threonyl-tRNA synthetase (thrSv) {*Bacillus subtilis*} | 38.7097 | 60.7527 | MG375 (1048–1389 of 1692) GB:U02130 (1–342 of 342) |
| MG375 | 474578 | 472887 | GB:M36594_1 | threonyl-tRNA synthetase (thrSv) {*Bacillus subtilis*} | 38.7097 | 60.7527 | MG375 (1530–1692 of 1692) GB:U02250 (1–163 of 337) |
| MG378 | 477139 | 475529 | SP:P35868 | arginyl-tRNA sythetase (argS) {*Corynebacterium glutamicum*} | 33.6406 | 56.9124 | MG378 (1394–1047 of 1611) GB:U01740 (1–319 of 319) |
| MG378 | 477139 | 475529 | SP:P35868 | arginyl-tRNA sythetase (argS) {*Corynebacterium glutamicum*} | 33.6406 | 56.9124 | MG378 (765–456 of 1611) GB:U02168 (1–309 of 309) |
| MG379 | 477168 | 479003 | GB:L10328_106 | glucose inhibited division protein (gidA) {*Escherichia coli*} | 40.7346 | 61.9366 | MG379 (900–1184 of 1836) GB:U01812 (1–285 of 285) |
| MG385 | 484699 | 483992 | — | — | — | — | MG385 (234–6 of 708) GB:U02112 (1–229 of 229) |
| MG385 | 484699 | 483992 | — | — | — | — | MG385 (523–708 of 708) GB:U02239 (1–186 of 320) |
| MG385 | 484699 | 483992 | — | — | — | — | MG385 (528–259 of 708) GB:U02246 (1–270 of 270) |
| MG386 | 489552 | 484705 | GB:U11381_1 | cytadherence-accessory protein (hmw1) {*Mycoplasma pneumoniac*} | 31.1755 | 49.4037 | MG386 (1294–1628 of 4848) GB:U02175 (1–335 of 335) |
| MG386 | 489552 | 484705 | GB:U11381_1 | cytadherence-accessory protein (hmw1) {*Mycoplasma pneumoniac*} | 31.1755 | 49.4037 | MG386 (2274–1991 of 4848) GB:X61519 (1–283 of 284) |
| MG386 | 489552 | 484705 | GB:U11381_1 | cytadherence-accessory protein (hmw1) {*Mycoplasma pneumoniac*} | 31.1755 | 49.4037 | MG386 (3247–3420 of 4848) GB:U02126 (1–174 of 174) |
| MG386 | 489552 | 484705 | GB:U11381_1 | cytadherence-accessory protein (hmw1) {*Mycoplasma pneumoniac*} | 31.1755 | 49.4037 | MG386 (3842–4196 of 4848) GB:U02192 (1–355 of 355) |
| MG386 | 489552 | 484705 | GB:U11381_1 | cytadherence-accessory protein (hmw1) {*Mycoplasma pneumoniac*} | 31.1755 | 49.4037 | MG386 (767–1281 of 4848) GB:U02245 (2–515 of 515) |
| MG388 | 491004 | 490702 | GB:U00016_19 | hypothetical protein (GB:U00016_19) {*Mycobacterium leprae*} | 30.9278 | 56.701 | MG388 (285–1 of 303) GB:U02265 (1–285 of 339) |
| MG389 | 491530 | 491150 | — | — | — | — | MG389 (320–129 of 381) GB:U01813 (1–192 of 192) |
| MG390 | 493516 | 491537 | SP:P37608 | lactococcin transport ATP-binding protein (lcnDR3) {*Lactococcus lactis*} | 22.3421 | 46.5331 | MG3390 (1395–1744 of 1980) GB:U02218 (1–350 of 350) |
| MG390 | 493516 | 491537 | SP:P37608 | lactococcin transport ATP-binding protein (lcnDR3) {*Lactococcus lactis*} | 22.3421 | 46.5331 | MG3390 (1400–1174 of 1980) GB:U02248 (1–227 of 227) |
| MG391 | 494967 | 493627 | GB:D17450_1 | aminopeptidase {*Mycoplasma salivarium*} | 41.2921 | 60.3933 | MG391 (1–217 of 1341) GB:U02268 (256–472 of 472) |
| MG391 | 494967 | 493627 | GB:D17450_1 | aminopeptidase {*Mycoplasma salivarium*} | 41.2921 | 60.3933 | MG391 (412–735 of 1341) GB:U01801 (1–324 of 324) |
| MG391 | 494967 | 493627 | GB:D17450_1 | aminopeptidase {*Mycoplasma salivarium*} | 41.2921 | 60.3933 | MG391 (412–735 of 1341) GB:U01802 (1–324 of 324) |
| MG392 | 496615 | 494987 | GB:L10132_2 | heat shock protein (groEL) {*Bacillus stearothermophilus*} | 51.5209 | 71.4829 | MG392 (1394–1629 of 1629) GB:U02268 (1–236 of 472) |
| MG392 | 496615 | 494987 | GB:L10132_2 | heat shock protein (groEL) {*Bacillus stearothermophilus*} | 51.5209 | 71.4829 | MG392 (181–1 of 1629) GB:U02252 (1–181 of 296) |
| MG393 | 496960 | 496631 | GB:D17398_1 | heat shock protein 60-like protein (PggroES) {*Porphyromonas gingivalis*} | 39.5604 | 54.9451 | MG393 (330–231 of 330) GB:U02252 (197–296 of 296) |
| MG394 | 498306 | 497089 | SP:P06192 | serine hydroxymethyltransferase (glyA) {*Salmonella typhimurium*} | 55.303 | 70.7071 | MG394 (328–683 of 1218) GB:U02131 (1–356 of 356) |
| MG395 | 499890 | 498319 | — | — | — | — | MG395 (457–116 of 1572) GB:U02260 (1–342 of 342) |
| MG395 | 499890 | 498319 | — | — | — | — | MG395 (763–979 of 1572) GB:X61530 (1–217 of 217) |
| MG399 | 503976 | 502831 | SP:P33253 | ATP synthase beta chain (atpD) {*Mycoplasma gallisepticum*} | 80.9524 | 89.418 | MG399 (447–852 of 1146) GB:U01752 (1–406 of 406) |
| MG400 | 505099 | 502831 | SP:P33257 | ATP synthase gamma chain (atpG) {*Mycoplasma gallisepticum*} | 37.9433 | 62.0567 | MG400 (160–711 of 837) GB:U01703 (1–552 of 552) |
| MG401 | 506655 | 505102 | SP:P33252 | ATP synthase alpha chain (atpA) {*Mycoplasma gallisepticum*} | 63.3911 | 79.5761 | MG401 (973–1554 of 1554) GB:U01727 (1–583 of 598) |
| MG405 | 509012 | 508137 | GB:X64256_2 | adenosinetriphosphatase (atpB) {*Mycoplasma gallisepticum*} | 36.4261 | 63.9175 | MG405 (75–1 of 876) GB:U01728 (1–75 of 299) |
| MG406 | 509319 | 508981 | SP:P15362 | transport system permease protein P69 (P69) {*Mycoplasma hyorhinis*} | 40 | 57.1429 | MG406 (339–84 of 339) GB:U01728 (44–299 of 299) |
| MG410 | 513042 | 512056 | GB:L10328_89 | peripheral membrane protein B (pstB) {*Escherichia coli*} | 50.813 | 70.3252 | MG410 (301–941 of 987) GB:U01707 (1–640 of 640) |
| MG411 | 514991 | 513030 | GB:X75297_1 | periplasmic phosphate permease homolog (AG88) {*Mycobacterium tuberculosis*} | 30.7692 | 56.2753 | MG411 (406–632 of 1962) GB:U01746 (1–227 of 229) |
| MG412 | 516124 | 514994 | — | — | — | — | MG412 (252–1 of 1131) GB:U01702 (1–252 of 313) |

TABLE 1(c)-continued

| UID | end5 | end3 | db_match | db_match name | per_sim | per_id | match_info |
|---|---|---|---|---|---|---|---|
| MG412 | 516124 | 514994 | — | — | — | — | MG412 (675–563 of 1131) GB:U02101 (1–113 of 113) |
| MG413 | 518389 | 516248 | GB:L22432_4 | hypothetical protein (GB:L22432_4) {*Mycoplasma capricolum*} | 25 | 54.1667 | MG413 (1179–701 of 2142) GB:U01699 (1–480 of 480) |
| MG413 | 518389 | 516248 | GB:L22432_4 | hypothetical protein (GB:L22432_4) {*Mycoplasma capricolum*} | 25 | 54.1667 | MG413 (1535–1230 of 2142) GB:U01804 (1–305 of 305) |
| MG414 | 519355 | 516248 | — | — | — | — | MG414 (438–154 of 917) GB:U01695 (1–285 of 285) |
| MG416 | 521414 | 520371 | — | — | — | — | MG416 (1–39 of 1044) GB:U01744 (580–618 of 620) |
| MG416 | 521414 | 520371 | — | — | — | — | MG416 (7–351 of 1044) GB:U02102 (1–345 of 345) |
| MG418 | 522314 | 521877 | SP:P02410 | ribosomal protein L13 (rpL13) {*Escherichia coli*} | 41.3043 | 70.2899 | MG418 (321–438 of 438) GB:U01744 (1–118 of 620) |
| MG421 | 526696 | 524153 | SP:P07671 | excinuclease ABC subunit A (uvrA) {*Escherichia coli*} | 47.7541 | 68.5579 | MG421 (1693–1393 of 2544) GB:X61514 (1–301 of 301) |
| MG422 | 529493 | 526989 | — | — | — | — | MG422 (2274–2101 of 2505) GB:U02117 (1–174 of 174) |
| MG422 | 529493 | 526989 | — | — | — | — | MG422 (2439–2505 of 2505) GB:U02172 (1–67 of 318) |
| MG422 | 529493 | 526989 | — | — | — | — | MG422 (35–1 of 2505) GB:U02228 (1–35 of 304) |
| MG423 | 531216 | 529534 | — | — | — | — | MG423 (1434–1197 of 1683) GB:X61510 (1–238 of 238) |
| MG423 | 531216 | 529534 | — | — | — | — | MG423 (161–413 of 1683) GB:X61524 (1–252 of 255) |
| MG423 | 531216 | 529534 | — | — | — | — | MG423 (1683–1455 of 1683) GB:U02228 (76–304 of 304) |
| MG425 | 531668 | 533014 | SP:P23304 | ATP-dependent RNA helicase (deaD) {*Escherichia coli*} | 32.4121 | 58.0402 | MG425 (989–769 of 1347) GB:U01805 (1–220 of 220) |
| MG431 | 538290 | 537559 | GB:L27492_1 | triosephosphate isomerase (tim) {*Thermotoga maritima*} | 39.7541 | 61.8852 | MG431 (463–732 of 732) GB:U02109 (1–270 of 277) |
| MG437 | 542067 | 542981 | GB:M11330_1 | CDP-diglyceride synthetasae (cdsA) {*Escherichia coli*} | 38.0165 | 55.3719 | MG437 (679–378 of 915) GB:U02189 (2–303 of 303) |
| MG441 | 546707 | 546300 | — | — | — | — | MG441 (20–318 of 408) GB:U02128 (1–299 of 299) |
| MG447 | 552444 | 550804 | GB:L08897_1 | hypothetical protein (GB:L08897_1) {*Mycoplasma gallisepticum*} | 34.058 | 55.0725 | MG447 (319–645 of 1641) GB:U01788 (1–327 of 327) |
| MG451 | 555612 | 554431 | SP:P13927 | elongation factor TU (tuf) {*Mycoplasma genitalium*} | 100 | 100 | MG451 (927–586 of 1182) GB:U02255 (1–342 of 342) |
| MG453 | 556435 | 557310 | GB:L12272_1 | UDP-glucose pyrophosphorylase (gtaB) {*Bacillus subtilis*} | 48.0287 | 65.233 | MG453 (491–181 of 876) GB:U02258 (1–311 of 311) |
| MG455 | 557724 | 558944 | GB:M77668_1 | tyrosyl tRNA synthetase (tyrS) {*Bacillus stearothermophilus*} | 38.539 | 61.7128 | MG455 (604–362 of 1221) GB:U02247 (5–247 of 247) |
| MG456 | 559941 | 558940 | — | — | — | — | MG456 (256–568 of 1002) GB:U01790 (1–312 of 312) |
| MG458 | 563307 | 562783 | SP:Q02522 | hypoxanthine-guanine phosphoribosyltransferase (hpt) {*Lactococcus lactis*} | 38.3721 | 66.8605 | MG458 (295–24 of 525) GB:U02193 (1–272 of 272) |
| MG459 | 563818 | 563312 | GB:M64978_2 | surface exclusion protein (prgA) (Plasmid pCF10) {*Enterococcus faecalis*} | 28.3582 | 49.2537 | MG459 (330–1 of 507) GB:U01725 (1–330 of 638) |
| MG460 | 563991 | 564926 | SP:P33572 | L-lactate dehydrogenase (ldh) {*Mycoplasma hyopneumoniae*} | 50.3226 | 67.7419 | MG460 (1–136 of 936) GB:U01725 (503–638 of 638) |
| MG462 | 567638 | 566187 | GB:M55072_1 | glutamyl-tRNA synthetase (gltX) {*Bacillus stearothermophilus*} | 42.887 | 65.272 | MG462 (1452–1081 of 1452) GB:U02122 (9–379 of 379) |
| MG463 | 568404 | 567628 | GB:D26185_105 | high level kasgamycin resistance (kagA) {*Bacillus subtilis*} | 35.6164 | 53.8813 | MG463 (777–409 of 777) GB:U01719 (36–405 of 405) |
| MG467 | 570988 | 570056 | GB:X75422_1 | heterocyst maturation protein (devA) {*Anabaena sp.*} | 39.899 | 63.1313 | MG467 (40–352 of 933) GB:U01741 (1–313 of 313) |
| MG469 | 578578 | 577268 | SP:P34028 | chromosomal replication initiator protein (dnaA) {*Spiroplasma citri*} | 30.9469 | 57.2748 | MG469 (845–547 of 1311) GB:U02259 (1–299 of 299) |
| MG469 | 578578 | 577268 | SP:P34028 | chromosomal replication initiator protein (dnaA) {*Spiroplasma citri*} | 30.9469 | 57.2748 | MG469 (855–1206 of 1311) GB:U02145 (1–352 of 352) |

TABLE 1(d)

| UID | Old_id(s) |
|---|---|
| MG001 | MORF-20072 |
| MG002 | MORF-19817 |
| MG003 | MORF-19818 MORF-20073 |
| MG004 | MORF-19819 MORF-20074 |
| MG005 | MORF-20075 |
| MG006 | MORF-20076 |
| MG007 | MORF-19820 |
| MG008 | MORF-20077 |
| MG009 | MORF-20078 |
| MG010 | MORF-20079 |

TABLE 1(d)-continued

| UID | Old_id(s) |
|---|---|
| MG011 | MORF-19821 MORF-19822 |
| MG012 | MORF-20080 |
| MG013 | MORF-19823 MORF-20080 MORF-20081 |
| MG014 | MORF-20082 |
| MG015 | MORF-20084 |
| MG016 | MORF-19824 |
| MG017 | MORF-19825 |
| MG018 | MORF-20085 |
| MG019 | MORF-20086 |
| MG020 | MORF-20088 |
| MG021 | MORF-20089 |
| MG022 | MORF-20091 |
| MG023 | MORF-20092 |
| MG024 | MORF-19826 MORF-20093 |
| MG025 | MORF-20094 |
| MG026 | MORF-20095 |
| MG027 | MORF-19827 |
| MG028 | MORF-19828 |
| MG029 | MORF-19829 |
| MG030 | MORF-20096 |
| MG031 | MORF-19830 MORF-20097 |
| MG032 | MORF-20099 |
| MG033 | MORF-20100 |
| MG034 | MORF-20101 |
| MG035 | MORF-20102 |
| MG036 | MORF-20103 |
| MG037 | MORF-20104 |
| MG038 | MORF-20105 |
| MG039 | MORF-19831 MORF-20106 |
| MG040 | MORF-20107 |
| MG042 | MORF-19832 MORF-20108 |
| MG043 | MORF-20110 |
| MG044 | MORF-20111 |
| MG045 | MORF-19833 |
| MG046 | MORF-20112 |
| MG047 | MORF-20113 |
| MG048 | MORF-19834 MORF-20114 MORF-20115 |
| MG049 | MORF-20114 MORF-20115 |
| MG050 | MORF-20117 |
| MG051 | MORF-19835 MORF-20118 |
| MG052 | MORF-20119 |
| MG053 | MORF-20120 |
| MG054 | MORF-20120 MORF-20121 |
| MG055 | MORF-19836 |
| MG056 | MORF-20122 |
| MG057 | MORF-20123 |
| MG058 | MORF-20124 |
| MG059 | MORF-20124 MORF-20125 |
| MG060 | MORF-20126 |
| MG061 | MORF-19838 |
| MG062 | MORF-19839 MORF-20127 MORF-20128 |
| MG063 | MORF-19840 MORF-20128 |
| MG064 | MORF-19841 MORF-19842 |
| MG065 | MORF-19843 MORF-20129 |
| MG066 | MORF-19844 MORF-20130 |
| MG067 | MORF-19845 |
| MG068 | MORF-20131 |
| MG069 | MORF-19847 MORF-20135 |
| MG070 | MORF-20136 |
| MG071 | MORF-19848 MORF-19849 MORF-19850 MORF-19851 MORF-20137 |
| MG072 | MORF-19852 MORF-19853 MORF-19854 MORF-20138 |
| MG073 | MORF-20139 |
| MG074 | MORF-19855 |
| MG075 | MORF-19856 MORF-19857 |
| MG076 | MORF-19858 |
| MG077 | MORF-20140 |
| MG078 | MORF-19859 MORF-20141 |
| MG079 | MORF-20142 |
| MG080 | MORF-20143 |
| MG081 | MORF-20144 |
| MG082 | MORF-20145 |
| MG083 | MORF-20146 |
| MG084 | MORF-20147 |
| MG085 | MORF-20147 MORF-20148 |
| MG086 | MORF-19860 MORF-19861 |
| MG087 | MORF-20149 |
| MG088 | MORF-20150 |
| MG089 | MORF-20151 MORF-20152 |
| MG090 | MORF-19862 |
| MG091 | MORF-20153 |
| MG092 | MORF-20154 |
| MG093 | MORF-20155 |
| MG094 | MORF-20156 |
| MG095 | MORF-19863 |
| MG096 | MORF-20157 |
| MG097 | MORF-20158 |
| MG098 | MORF-20159 |
| MG099 | MORF-19864 MORF-20160 |
| MG100 | MORF-19865 MORF-20161 |
| MG101 | MORF-19866 |
| MG102 | MORF-20162 |
| MG103 | MORF-19867 MORF-19868 |
| MG104 | MORF-20163 |
| MG105 | MORF-19869 |
| MG106 | MORF-20164 MORF-20165 |
| MG107 | MORF-20164 MORF-20165 |
| MG108 | MORF-20166 |
| MG109 | MORF-20167 |
| MG110 | MORF-20168 |
| MG111 | MORF-20169 |
| MG112 | MORF-20170 |
| MG113 | MORF-19870 MORF-20171 MORF-20172 |
| MG114 | MORF-20171 MORF-20172 |
| MG116 | MORF-19871 |
| MG117 | MORF-19872 |
| MG118 | MORF-20173 |
| MG119 | MORF-19873 MORF-20174 |
| MG120 | MORF-19874 |
| MG121 | MORF-19875 MORF-20175 |
| MG122 | MORF-20176 |
| MG123 | MORF-19876 |
| MG124 | MORF-20177 |
| MG125 | MORF-19877 |
| MG126 | MORF-20178 |
| MG127 | MORF-20179 |
| MG128 | MORF-20180 |
| MG129 | MORF-20181 |
| MG130 | MORF-20182 |
| MG132 | MORF-20183 |
| MG133 | MORF-19878 |
| MG134 | MORF-20184 |
| MG135 | MORF-20185 |
| MG136 | MORF-20186 MORF-20187 |
| MG137 | MORF-20186 MORF-20187 |
| MG138 | MORF-20188 |
| MG139 | MORF-19879 |
| MG140 | MORF-19884 |
| MG141 | MORF-19885 MORF-20192 |
| MG142 | MORF-19886 MORF-20193 |
| MG143 | MORF-20194 |
| MG144 | MORF-19887 |
| MG145 | MORF-20195 |
| MG146 | MORF-20196 |
| MG147 | MORF-19888 MORF-19889 |
| MG148 | MORF-19890 |
| MG149 | MORF-19891 |
| MG150 | MORF-19893 MORF-20197 |
| MG151 | MORF-19893 MORF-20198 |
| MG152 | MORF-19895 MORF-20199 |
| MG153 | MORF-19894 |
| MG154 | MORF-19896 MORF-20200 |
| MG156 | MORF-19897 |
| MG157 | MORF-20201 |
| MG158 | MORF-20202 |
| MG159 | MORF-19898 |
| MG161 | MORF-19900 MORF-20203 |
| MG162 | MORF-19899 MORF-19900 |
| MG163 | MORF-20204 |
| MG165 | MORF-20205 |
| MG166 | MORF-19901 MORF-20206 |
| MG167 | MORF-19901 MORF-20207 |
| MG168 | MORF-19902 MORF-20208 |

TABLE 1(d)-continued

| UID | Old_id(s) |
|---|---|
| MG169 | MORF-20209 |
| MG170 | MORF-20210 |
| MG171 | MORF-20211 |
| MG172 | MORF-20212 |
| MG175 | MORF-20213 |
| MG176 | MORF-20214 |
| MG177 | MORF-19903 MORF-20215 |
| MG178 | MORF-20216 |
| MG179 | MORF-19904 MORF-20217 |
| MG180 | MORF-20218 |
| MG181 | MORF-19905 |
| MG182 | MORF-20219 |
| MG183 | MORF-20219 |
| MG184 | MORF-20220 |
| MG185 | MORF-20221 |
| MG186 | MORF-19907 |
| MG187 | MORF-19908 MORF-19909 MORF-20225 |
| MG188 | MORF-20226 MORF-20227 |
| MG189 | MORF-20226 MORF-20227 |
| MG190 | MORF-20228 |
| MG191 | MORF-19910 MORF-19911 MORF-20229 |
| MG192 | MORF-19911 MORF-19912 MORF-20230 |
| MG194 | MORF-19913 MORF-20234 |
| MG195 | MORF-20235 |
| MG196 | MORF-20236 |
| MG199 | MORF-19914 |
| MG200 | MORF-19915 MORF-20237 |
| MG201 | MORF-19916 MORF-20239 |
| MG202 | MORF-19917 |
| MG203 | MORF-19918 MORF-19919 MORF-20240 |
| MG204 | MORF-20241 MORF-20242 |
| MG205 | MORF-20243 |
| MG206 | MORF-20244 |
| MG207 | MORF-19920 |
| MG208 | MORF-19921 |
| MG209 | MORF-20245 |
| MG210 | MORF-20246 |
| MG211 | MORF-19922 |
| MG212 | MORF-19924 MORF-20247 MORF-20248 |
| MG213 | MORF-20248 |
| MG214 | MORF-20249 |
| MG215 | MORF-20250 |
| MG216 | MORF-20251 |
| MG217 | MORF-20252 |
| MG218 | MORF-19926 MORF-19927 MORF-20253 |
| MG219 | MORF-19928 MORF-19930 MORF-20253 |
| MG220 | MORF-19931 |
| MG221 | MORF-20255 |
| MG222 | MORF-20256 |
| MG223 | MORF-19932 |
| MG224 | MORF-20257 |
| MG225 | MORF-20258 |
| MG226 | MORF-20259 |
| MG227 | MORF-20260 |
| MG228 | MORF-19933 |
| MG229 | MORF-19934 MORF-20261 |
| MG230 | MORF-19935 |
| MG231 | MORF-20262 |
| MG232 | MORF-20263 |
| MG234 | MORF-20264 |
| MG235 | MORF-19936 MORF-20265 |
| MG236 | MORF-19937 |
| MG237 | MORF-19938 |
| MG238 | MORF-19939 MORF-20266 |
| MG239 | MORF-20267 |
| MG240 | MORF-20268 |
| MG241 | MORF-19940 MORF-19941 MORF-19942 |
| MG242 | MORF-19943 |
| MG243 | MORF-19945 |
| MG244 | MORF-20269 |
| MG245 | MORF-19946 |
| MG246 | MORF-19947 |
| MG247 | MORF-20270 |
| MG248 | MORF-19948 |
| MG249 | MORF-19949 MORF-20271 |
| MG250 | MORF-20272 |
| MG251 | MORF-19950 MORF-20273 |
| MG252 | MORF-20274 |
| MG253 | MORF-20275 |
| MG254 | MORF-20276 |
| MG255 | MORF-19951 MORF-19952 |
| MG256 | MORF-19953 |
| MG258 | MORF-19954 MORF-20277 |
| MG259 | MORF-20278 |
| MG260 | MORF-19955 MORF-19956 MORF-20279 |
| MG261 | MORF-19958 MORF-20282 |
| MG262 | MORF-20283 |
| MG263 | MORF-20285 |
| MG264 | MORF-20286 MORF-20287 |
| MG265 | MORF-20286 MORF-20287 |
| MG266 | MORF-20288 |
| MG267 | MORF-19959 MORF-19960 |
| MG268 | MORF-20290 |
| MG269 | MORF-20291 |
| MG270 | MORF-20292 |
| MG271 | MORF-20293 |
| MG272 | MORF-19961 MORF-19962 MORF-20294 |
| MG273 | MORF-20295 |
| MG274 | MORF-20296 |
| MG275 | MORF-20297 |
| MG276 | MORF-20298 |
| MG277 | MORF-19963 MORF-20299 |
| MG278 | MORF-19964 MORF-20300 |
| MG279 | MORF-19965 |
| MG280 | MORF-19966 MORF-20301 |
| MG281 | MORF-19967 MORF-19968 |
| MG282 | MORF-20302 |
| MG283 | MORF-20303 |
| MG284 | MORF-19969 MORF-19970 MORF-19971 |
| MG285 | MORF-19969 MORF-19970 MORF-19971 |
| MG286 | MORF-19972 |
| MG288 | MORF-20306 |
| MG289 | MORF-20307 |
| MG290 | MORF-20308 |
| MG291 | MORF-20309 |
| MG292 | MORF-20310 |
| MG293 | MORF-20311 |
| MG294 | MORF-19974 MORF-20312 |
| MG295 | MORF-20313 |
| MG296 | MORF-19975 |
| MG297 | MORF-20314 |
| MG298 | MORF-19976 MORF-20315 |
| MG299 | MORF-20316 |
| MG300 | MORF-20317 |
| MG301 | MORF-19977 MORF-20318 |
| MG302 | MORF-19978 |
| MG303 | MORF-20319 |
| MG304 | MORF-20320 |
| MG305 | MORF-19979 MORF-20321 |
| MG306 | MORF-19980 |
| MG307 | MORF-19981 MORF-19982 |
| MG308 | MORF-20323 |
| MG309 | MORF-19983 MORF-19984 |
| MG310 | MORF-20324 |
| MG311 | MORF-20325 |
| MG312 | MORF-20326 |
| MG314 | MORF-19985 MORF-19986 |
| MG315 | MORF-19987 MORF-19988 MORF-20327 |
| MG316 | MORF-19988 MORF-20327 |
| MG317 | MORF-20328 MORF-20329 |
| MG318 | MORF-19989 MORF-19990 |
| MG319 | MORF-20330 |
| MG320 | MORF-19991 |
| MG321 | MORF-19992 |
| MG322 | MORF-19993 MORF-20331 |
| MG323 | MORF-19994 MORF-20332 |
| MG324 | MORF-19995 MORF-20333 |
| MG326 | MORF-20334 |
| MG327 | MORF-20335 |
| MG328 | MORF-19996 MORF-20336 |
| MG329 | MORF-19997 MORF-20337 |
| MG330 | MORF-20338 MORF-20339 |
| MG331 | MORF-20339 |
| MG332 | MORF-20340 |

TABLE 1(d)-continued

| UID | Old_id(s) |
|---|---|
| MG333 | MORF-19998 |
| MG334 | MORF-20341 |
| MG336 | MORF-20343 MORF-20344 |
| MG337 | MORF-19999 |
| MG338 | MORF-20000 |
| MG339 | MORF-20001 MORF-20345 |
| MG340 | MORF-20006 MORF-20348 |
| MG341 | MORF-20349 |
| MG342 | MORF-20350 |
| MG343 | MORF-20007 |
| MG344 | MORF-20008 |
| MG345 | MORF-20351 |
| MG346 | MORF-20352 |
| MG348 | MORF-20009 |
| MG349 | MORF-20010 |
| MG350 | MORF-20011 |
| MG351 | MORF-20353 |
| MG352 | MORF-20354 |
| MG353 | MORF-20355 |
| MG354 | MORF-20013 MORF-20014 |
| MG355 | MORF-20015 MORF-20016 MORF-20356 |
| MG356 | MORF-20357 |
| MG357 | MORF-20358 |
| MG358 | MORF-20017 MORF-20018 MORF-20019 MORF-20359 |
| MG359 | MORF-20019 MORF-20359 MORF-20360 |
| MG360 | MORF-20361 |
| MG361 | MORF-20362 |
| MG362 | MORF-20363 |
| MG364 | MORF-20364 |
| MG365 | MORF-20020 MORF-20365 |
| MG366 | MORF-20021 |
| MG367 | MORF-20366 |
| MG368 | MORF-20022 MORF-20366 MORF-20367 |
| MG369 | MORF-20022 MORF-20023 |
| MG370 | MORF-20368 |
| MG371 | MORF-20368 MORF-20369 |
| MG372 | MORF-20370 |
| MG373 | MORF-20024 |
| MG374 | MORF-20025 |
| MG375 | MORF-20371 |
| MG376 | MORF-20026 |
| MG377 | MORF-20027 |
| MG378 | MORF-20372 |
| MG379 | MORF-20373 |
| MG380 | MORF-20374 |
| MG381 | MORF-20028 |
| MG382 | MORF-20375 |
| MG383 | MORF-20376 |
| MG384 | MORF-20029 MORF-20377 |
| MG385 | MORF-20031 MORF-20378 |
| MG386 | MORF-20032 MORF-20379 MORF-20381 |
| MG387 | MORF-20382 |
| MG388 | MORF-20383 |
| MG389 | MORF-20033 |
| MG390 | MORF-20034 MORF-20384 |
| MG391 | MORF-20034 MORF-20035 MORF-20385 |
| MG392 | MORF-20036 MORF-20037 MORF-20386 |
| MG393 | MORF-20038 |
| MG394 | MORF-20387 |
| MG395 | MORF-20039 |
| MG396 | MORF-20388 |
| MG397 | MORF-20040 MORF-20041 |
| MG398 | MORF-20042 |
| MG399 | MORF-20389 |
| MG400 | MORF-20390 |
| MG401 | MORF-20043 MORF-20391 |
| MG402 | MORF-20392 |
| MG403 | MORF-20393 |
| MG404 | MORF-20394 |
| MG405 | MORF-20395 MORF-20396 |
| MG406 | MORF-20395 MORF-20396 |
| MG407 | MORF-20044 MORF-20397 |
| MG408 | MORF-20398 |
| MG409 | MORF-20045 |
| MG410 | MORF-20046 MORF-20399 |
| MG411 | MORF-20400 |
| MG412 | MORF-20047 |
| MG413 | MORF-20401 |
| MG414 | MORF-20048 |
| MG415 | MORF-20049 |
| MG416 | MORF-20050 MORF-20051 |
| MG417 | MORF-20402 |
| MG418 | MORF-20052 |
| MG419 | MORF-20053 |
| MG420 | MORF-20403 |
| MG421 | MORF-20404 |
| MG422 | MORF-20054 MORF-20055 |
| MG423 | MORF-20056 |
| MG425 | MORF-20406 |
| MG427 | MORF-20057 |
| MG428 | MORF-20058 |
| MG429 | MORF-20059 MORF-20407 |
| MG430 | MORF-20408 |
| MG431 | MORF-20409 |
| MG432 | MORF-20410 |
| MG433 | MORF-20411 |
| MG435 | MORF-20060 MORF-20412 |
| MG436 | MORF-20060 MORF-20412 |
| MG437 | MORF-20413 |
| MG438 | MORF-20414 |
| MG439 | MORF-20061 |
| MG440 | MORF-20062 |
| MG441 | MORF-20063 |
| MG442 | MORF-20415 |
| MG443 | MORF-20064 |
| MG444 | MORF-20065 MORF-20416 |
| MG445 | MORF-20417 |
| MG447 | MORF-20418 |
| MG448 | MORF-20419 MORF-20420 |
| MG449 | MORF-20419 MORF-20420 |
| MG450 | MORF-20066 |
| MG451 | MORF-20421 |
| MG452 | MORF-20067 |
| MG453 | MORF-20422 |
| MG454 | MORF-20423 MORF-20424 |
| MG455 | MORF-20423 MORF-20424 |
| MG456 | MORF-20068 |
| MG457 | MORF-20069 MORF-20425 |
| MG458 | MORF-20426 |
| MG459 | MORF-20070 |
| MG460 | MORF-20427 |
| MG461 | MORF-20428 |
| MG462 | MORF-20429 |
| MG463 | MORF-20430 |
| MG464 | MORF-20431 |
| MG467 | MORF-20432 |
| MG468 | MORF-20283 |
| MG469 | MORF-20434 |
| MG470 | MORF-20071 MORF-20435 |

TABLE 2

| UID | end5 | end3 | gene_len |
|---|---|---|---|
| MG016 | 19253 | 19756 | 504 |
| MG017 | 19825 | 20352 | 528 |
| MG027 | 30092 | 30544 | 453 |
| MG028 | 30547 | 31149 | 603 |
| MG064 | 74066 | 77683 | 3618 |
| MG076 | 102870 | 102457 | 414 |
| MG105 | 133569 | 134168 | 600 |
| MG117 | 143310 | 143951 | 642 |
| MG147 | 186138 | 187262 | 1125 |
| MG185 | 211445 | 213547 | 2103 |
| MG186 | 216017 | 216766 | 750 |
| MG199 | 237094 | 236594 | 501 |
| MG202 | 239826 | 240191 | 366 |
| MG207 | 247523 | 247906 | 384 |
| MG211 | 250997 | 251437 | 441 |
| MG223 | 268011 | 269243 | 1233 |

TABLE 2-continued

| UID | end5 | end3 | gene_len |
|---|---|---|---|
| MG230 | 276166 | 276624 | 459 |
| MG236 | 280663 | 281082 | 420 |
| MG241 | 286884 | 288743 | 1860 |
| MG243 | 290976 | 291323 | 348 |
| MG246 | 293936 | 294778 | 843 |
| MG256 | 306819 | 307586 | 768 |
| MG267 | 325157 | 324813 | 345 |
| MG279 | 341181 | 340528 | 654 |
| MG284 | 346853 | 347248 | 396 |
| MG286 | 348260 | 348847 | 588 |
| MG296 | 364414 | 364028 | 387 |
| MG306 | 377974 | 376796 | 1179 |
| MG321 | 402922 | 400121 | 2802 |
| MG331 | 415622 | 414987 | 636 |
| MG333 | 416716 | 416339 | 378 |
| MG349 | 446576 | 447787 | 1212 |
| MG350 | 447790 | 448722 | 933 |
| MG354 | 451197 | 451607 | 411 |

TABLE 2-continued

| UID | end5 | end3 | gene_len |
|---|---|---|---|
| MG366 | 462619 | 464619 | 2001 |
| MG372 | 471234 | 470080 | 1155 |
| MG373 | 472066 | 471224 | 843 |
| MG376 | 474892 | 474581 | 312 |
| MG377 | 475479 | 474901 | 579 |
| MG381 | 479570 | 480223 | 654 |
| MG397 | 502420 | 500723 | 1698 |
| MG415 | 520238 | 519929 | 310 |
| MG419 | 523215 | 522355 | 861 |
| MG427 | 533270 | 533692 | 423 |
| MG428 | 533806 | 534318 | 513 |
| MG436 | 542092 | 541739 | 354 |
| MG439 | 545378 | 544563 | 816 |
| MG440 | 546154 | 545381 | 774 |
| MG449 | 553295 | 552864 | 432 |
| MG450 | 554269 | 553559 | 711 |
| MG452 | 555665 | 556447 | 783 |
| MG468 | 318330 | 319202 | 873 |

The Nucleotide Sequence of the *Mycoplasma genitalium* Genome

```
   1 TAAGTTATTATTTAGTTAATACTTTTAACAATATTATTAAGGTATTTAAA
  51 AAATACTATTATAGTATTTAACATAGTTAAATACCTTCCTTAATACTGTT
 101 AAATTATATTCAATCAATACATATATAATATTATTAAAATACTTGATAAG
 151 TATTATTTAGATATTAGACAAATACTAATTTTATATTGCTTTAATACTTA
 201 ATAAATACTACTTATGTATTAAGTAAATATTACTGTAATACTAATAACAA
 251 TATTATTACAATATGCTAGAATAATATTGCTAGTATCAATAATTACTAAT
 301 ATAGTATTAGGAAAATACCATAATAATATTTCTACATAATACTAAGTTAA
 351 TACTATGTGTAGaATAATAAATAATCGATTAAAAAAATTTTATTTATCT
 401 GAAACATATTTAATCAATTGAACTGATTATTTTCAGCAGTAATAATTACA
 451 TATGTACATAGTACATATGTAAAATATCATTAATTTCTGTTATATATAAT
 501 AGTATCTATTTTAGAGAGTATTAATTATTACTATAATTAAGCATTTATGC
 551 TTAATTATAAGCTTTTTATGAACAAAATTATAGACATTTTAGTTCTTATA
 601 ATAAATAATAGATATTAAAGAAAATAAAAAAATAGAAATAAATATCATAA
 651 CCCTTGATAACCCAGAAATTAATACTTAATCAAAAATGAAAATATTAATT
 701 AATAAAAGTGAATTGAATAAAATTTTGGGAAAAAATGAATAACGTTATTA
 751 TTTCCAATAACAAAATAAAACCACATCATTCATATTTTTAATAGAGgCA
 801 AAAGaAAAAGAAATAAACTTTTATGCTAACAATGAATACTTTTCTGTCAA
 851 ATGTAATTTAAATaAAAATATTGATATTCTTGAACAAGGCTCCTTAATTG
 901 TTAAAGGAAAAATTTTTAACGATCTTATTAATGGCATAAAAGAAGAGATT
 951 ATTACTATTCAAGAAAAAGATCAAACACTTTTGGTTAAAACaAAAAAAAC
1001 AAGTATTAATTTAAACACAATTAATGTGAATGAATTTCCAAGAATAAGGT
1051 TTAATGAAAAAAACGATTTAAGTGAATTTAATCAATTCAAAATAAATTAT
1101 TCACTTTTAGTAAAAGGCATTAAAAAAATTTTTCACTCAGTTTCAAATAA
1151 TCGTGAAATATCTTCTAAATTTAATGGAGTAAATTTCAATGGATCCAATG
1201 GAAAAGAAATATTTTAGAAGCTTCTGACACTTATAAACTATCTGTTTTT
1251 GAGATAAAGCAAGAAACAGAACCATTTGATTTCATTTTGGAGAGTAATTT
1301 ACTTAGTTTCATTAATTCTTTTAATCCTGAAGAAGATAAATCTATTGTTT
1351 TTTATTACAGAAAAGATAATAAAGATAGCTTTAGTACAGAAATGTTGATT
1401 TCAATGGATAACTTTATGATTAGTTACACATCGGTTAATGAAAAATTTCC
1451 AGAGGTAAACTACTTTTTTGAATTTGAACCTGAAACTAAAATAGTTGTTC
1501 AAAAAAATGAATTAAAAGATGCACTTCAAAGAATTCAAACTTTGGCTCAA
1551 AATGAAAGAACTTTTTTATGCGATATGCAAATTAACAGTTCTGAATTAAA
1601 AATAAGAGCTATTGTTAATAATATCGGAAATTCTCTTGAGGAAATTTCTT
1651 GTCTTAAATTTGAAGGTTATAAACTTAATATTTCTTTTAACCCAAGTTCT
1701 CTATTAGATCACATAGAGTCTTTTGAATCAAATGAAATAAATTTTGATTT
1751 CCAAGGAAATAGTAAGTATTTTTTTGATAACCTCTAAAAGTGAACCTGAAC
1801 TTAAGCAAATATTGGTTCCTTCAAGATAATGAATCTTTACGATCTTTTAG
1851 AACTACCAACTACAGCATCAATAAAAGAAATAAAAATTGCTTATAAAGA
1901 TTAGCAAAGCGTTATCACCCTGATGTAAATAAATTAGGTTCGCAAACTTT
1951 tGTTGAAATTAATAATGCTTATTCAATATTAAGTGATCCTAACCAAAAGG
2001 AAAAATATGATTCAATGCTGAAAGTTAATGATTTTCAAAATCGCATCAAA
```

| The Nucleotide Sequence of the *Mycoplasma genitalium* Genome |
|---|
| 2051 AATTTAGATATTAGTGTTAGATGACATGAAAATTTCATGGAAGAACTCGA |
| 2101 ACTTCGTAAGACCTGAGAATTTGATTTTTTTTCATCTGATGAAGATTTCT |
| 2151 TTTATTCTCCATTTACAAAAAACAAATATGCTTCCTTTTTAGATAAAGAT |
| 2201 GTTTCTTTAGCTTTTTTTCAGCTTTACAGCAAGGGCAAAATAGATCATCA |
| 2251 ATTGGAAAAATCTTTATTGAAAAGAAGAGATGTAAAAGAAGCTTGTCAAC |
| 2301 AGAATAAAAATTTTATTGAAGTTATAAAAGAGCAATATAACTATTTTGGT |
| 2351 TGAATTGAAGCTAAGCGTTATTTCAATATTAATGTTGAACTTGAGCTCAC |
| 2401 ACAGAGAGAGATAAGAGATAGAGATGTTGTTAACCTACCTTTAAAAATTA |
| 2451 AAGTTATTAATAATGATTTTCCAAATCAACTCTGATATGAAATTTATAAA |
| 2501 AACTATTCATTTCGCTTATCTTGAGATATAAAAAATGGTGAAATTGCTGA |
| 2551 ATTTTTCAATAAAGGTAATAGAGCTTTAGGATGAAAAGGTGACTTAATTG |
| 2601 TCAGAATGAAAGTAGTTAATAAAGTAAACAAAAGACTGCGTATTTTTTCA |
| 2651 AGCTTTTTTGAGAACGATAAATCTAAATTATGGTTCCTTGTTCCAAACGA |
| 2701 TAAACAAAGTAATCCTAATAAGGGCGTTTTTAACTATAAAACTCAGCACT |
| 2751 TTATTGATTAAAAAACCTTTCATTTTTAATGTGTTATAATTATTGTTAT |
| 2801 GCCATAAATTTAGTTTGTGGCAAAAGCTTCTGTACTGTTTATTTAATGGA |
| 2851 AGAAAATAACAAAGCAAATATCTATGACTCTAGTAGCATTAAGGTCCTTG |
| 2901 AAGGACTTGAGGCTGTTAGAAAACGCCCTGGAATGTACATTGGTTCTACT |
| 2951 GGCGAAGAAGGTTTGCATCACATGATCTGAGAGATAGTAGACAACTCAAT |
| 3001 TGATGAAGCAATGGGAGGTTTTGCCAGTTTTGTTAAGCTTACCCTTGAAG |
| 3051 ATAATTTTGTTACCCGTGTAGAGGATGATGGAAGAGGGATACCTGTTGAT |
| 3101 ATCCATCCTAAGACTAATCGTTCTACAGTTGAAACAGTTTTTACAGTTCT |
| 3151 ACACGCTGGCGGTAAATTTGATAACGATAGCTATAAAGTGTCAGGTGGTT |
| 3201 TACACGGTGTTGGTGCATCAGTTGTTAATGCGCTTAGTTCTTCTTTTAAA |
| 3251 GTTTGAGTTTTTCGTCAAAATAAAAAGTATTTTCTCAGCTTTAGCGATGG |
| 3301 AGGAAAGGTAATTGGAGATTTGGTCCAAGAAGGTAACTCTGAAAAAGAGC |
| 3351 ATGGAACAATTGTTGAGTTTGTTCCTGATTTCTCTGTAATGGAAAAGAGT |
| 3401 GATTACAAACAAACTGTAATTGTAAGCAGACTCCAGCAATTAGCTTTTTT |
| 3451 AAACAAGGGAATAAGAATTGACTTTGTTGATAATCGTAAACAAAACCCAC |
| 3501 AGTCTTTTTCTTGAAAATATGATGGGGATTGGTTGAATATATCCACCAC |
| 3551 CTAAACAACGAAAAAGAACCACTTTTTAATGAAGTTATTGCTGATGAAAA |
| 3601 AACTGAAACTGTAAAAGCTGTTAATCGTGATGAAAACTACACAGTAAAGG |
| 3651 TTGAAGTTGCTTTTCAATATAACAAAACATACAACCAATCAATTTTCAGT |
| 3701 TTTTGTAACAACATTAATACTACAGAAGGTGGAACCCATGTGGAAGGTTT |
| 3751 TCGTAATGCACTTGTTAAGATCATTAATCGCTTTGCTGTTGAAAATAAAT |
| 3801 TCCTAAAAGATAGTGATGAAAAGATTAACCGTGATGATGTTTGTGAAGGA |
| 3851 TTAACTGCTATTATTTCCATTAAACACCCAAACCCACAATATGAAGGACA |
| 3901 AACTAAAAAGAAGTTAGGTAATACTGAGGTAAGACCTTTAGTTAATAGTG |
| 3951 TTGTTAGTGAAATCTTTGAACGCTTCATGTTAGAAAACCCACAAGAAGCA |
| 4001 AACGCTATCATCAGAAAAACACTTTTAGCTCAAGAAGCGAGAAGAAGAAG |
| 4051 TCAAGAGGCTAGGGAGTTAACTCGTCGTAAATCACCTTTTGATAGTGGTT |
| 4101 CATTACCAGGTAAATTAGCTGATTGTACAACCAGAGATCCTTCGATTAGT |
| 4151 GAACTTTACATTGTTGAGGGTGATAGTGCTGGTGGCACTGCTAAAACAGG |
| 4201 AAGAGATCGTTATTTTCAAGCTATCTTACCCTTAAGAGGAAAGATTTTAA |
| 4251 ACGTTGAAAAATCTAACTTTGAACAAATCTTTAATAATGCAGAAATTTCT |
| 4301 GCATTAGTGATGGCAATAGGCTGTGGGATTAAACCTGATTTTGAACTTGA |
| 4351 AAAACTTAGATATAGCAAGATTGTGATCATGACAGATGCTGATGTTGATG |
| 4401 GTGCACACATAAGAACACTTCTCTTAACTTTCTTTTTTCGCTTTATGTAT |
| 4451 CCTTTTGGTTGAACAAGGCAATATTTTTATTGCTCAACCCCCACTTTATAA |
| 4501 AGTGTCATATTCCCATAAGGATTTATACATGCACACTGATGTTCAACTTG |
| 4551 AACAGTGAAAAAGTCAAAACCCTAACGTAAAGTTTGGGTTACAAAGATAT |
| 4601 AAAGGACTTGGAGAAATGGATGCATTGCAGCTGTGAGAAACAACAATGGA |
| 4651 TCCTAAGGTTAGAACATTGTTAAAAGTTACTGTTGAAGATGCTTCTATTG |
| 4701 CTGATAAAGCTTTTTCACTGTTGATGGGTGATGAAGTTCCCCCAAGAAGA |
| 4751 GAATTTATTGAAAAAAATGCTCGTAGTGTTAAAAACATTGATATTTAATT |
| 4801 TGGTTAGTATAAATGGCAAAGCAACAAGATCAAGTAGATAAGATTCGTGA |
| 4851 AAACTTAGACAATTCAACTGTCAAAAGTATTTCATTAGCAAATGAACTTG |
| 4901 AGCGTTCATTCATGGAATATGCTATGTCAGTTATTGTTGCTCGTGCTTTA |
| 4951 CCTGATGCTAGAGATGGACTTAAACCAGTTCATCGTCGTGTTCTTTATGG |
| 5001 TGCTTATATTGGTGGCATGCACCATGATCGTCCTTTTAAAAAGTCTGCGA |
| 5051 GGATTGTTGGTGATGTAATGAGTAAATTCCACCCTCATGGTGATATGGCA |
| 5101 ATATATGACACCATGTCAAGAATGGCTCAAGACTTTTCATTAAGATACCT |
| 5151 TTTAATTGATGGTCATGGTAATTTTGGTTCTATAGATGGTAGACCTG |
| 5201 CTGCACAACGTTATACAGAAGCAAGATTATCTAAACTTGCAGCAGAACTT |
| 5251 TTAAAAGATATTGATAAAGATACAGTTGACTTTATTGCTAATTATGATGG |
| 5301 TGAGGAAAAAGAACCAACTGTTCTACCAGCAGCTTTCCCTAACTTACTTG |
| 5351 CAAATGGTTCTAGTGGGATTGCAGTTGGAATGTCAACATCTATTCCTTCC |
| 5401 CATAATCTCTCTGAATTAATTGCGGGTTTAATCATGTTAATTGATAATCC |
| 5451 TCAATGCACTTTTCAAGAATTATTAACTGTAATTAAAGGACCTGATTTTC |
| 5501 CAACAGGAGCTAACATTATCTACACAAAAGGAATTGAAAGCTACTTTGAA |
| 5551 ACAGGTAAAGGCAATGTAGTAATTCGTTCTAAAGTTGAGATAGAACAATT |
| 5601 GCAAACAAGAAGTGCATTAGTTGTAACTGAAATTCCTTACATGGTTAACA |
| 5651 AAACTACCTTAATTGAAAAGATTGTAGAACTTGTTAAAGCTGAAGAGATT |
| 5701 TCAGGAATTGCTGATATCCGTGATGAATCCTCTCGAGAAGGAATAAGGTT |
| 5751 AGTGATTGAAGTAAAACGCGACACTGTACCTGAAGTTTTATTAAATCAAC |
| 5801 TTTTTAAATCAACAAGATTACAAGTACGCTTCCCTGTTAATATGCTTGCT |
| 5851 TTAGTTAAAGGGAGCTCCTGTACTTCTCAACATGAAACAAGCTTTGGAAGT |

-continued

The Nucleotide Sequence of the *Mycoplasma genitalium* Genome

```
5901  ATATCTTGATCATCAAATTGATGTTCTTGTTAGAAAAACAAAGTTTGTGC
5951  TTAATAAACAACAAGAACGTTATCACATTTTAAGCGGACTTTTAATTGCT
6001  GCTTTAAATATTGATGAGGTTGTTGCAATTATTAAAAAATCAGCAAATAA
6051  CCAGGAAGCAATTAATACATTAAATACAAAGTTTAAGCTTGATGAAATTC
6101  AAGCTAAAGCAGTTCTTGACATGCGTTTAAGGAGCTTAAGCGTACTTGAA
6151  GTTAACAAACTTCAAACTGAACAAAAAGAGTTAAAAGATTCAATTGAATT
6201  TTGTAAGAAAGTGTTAGCTGATCAAAAATTACAGCTAAAAATAATCAAAG
6251  AGGAATTGCAAAAAATCAATGATCAGTTTGGTGATGAAAGAAGAAGTGAA
6301  ATTCTCTATGATATCTCTGAGGAAATTGATGATGAATCATTGATAAAAGT
6351  TGAGAATGTAGTGATAACTATGTCTACAAATGGTTATCTAAAAAGGATTG
6401  GAGTTGATGCTTATAATCTTCAACATCGTGGTGGAGTTGGGGTTAAAGGG
6451  CTAACTACTTATGTTGATGATAGTATTAGTCAATTATTGGTCTGTTCAAC
6501  TCACTCTGACTTATTATTTTTTACTGATAAGGGTAAGGTTTATAGAATTA
6551  GAGCTCATCAAATTCCCTATGGTTTTAGAACAAATAAAGGTATTCCCGCT
6601  GTTAACTTAATCAAAATTGAAAAGGATGAAAGAATTTGTTCATTGTTATC
6651  TGTTAATAACTATGATGATGGTTATTTCTTTTTCTGTACTAAAAATGGAA
6701  TTGTTAAAAGAACGAGCTTGAATGAATTCATCAACATCTTAAGTAATGGT
6751  AAGCGGGCTATATCTTTTGATGATAATGACACTTTGTATTCAGTAATTAA
6801  AACCCACGGAAATGATGAGATTTTTATTGGTTCTACCAATGGATTTGTTG
6851  TTCGCTTCCATGAAAATCAACTCAGAGTTCTTTCAAGAACAGCAAGAGGT
6901  GTATTTGGTATCAGTTTAAATAAAGGAGAATTTGTTAATGGACTATCAAC
6951  TTCAAGCAACGGTAGCTTACTTTTATCAGTCGGTCAAAATGGAATAGGTA
7001  AATTAACGAGCATAGATAAATATAGACTCACAAAACGTAATGCTAAGGGA
7051  GTTAAAACTCTAAGGGTTACTGATAGAACAGGCCCTGTTGTTACAACAAC
7101  CACTGTTTTTGGTAATGAGGATCTTTTAATGATTTCCTCTGCTGGTAAAA
7151  TTGTGCGTACCAGTTTACAAGAACTTTCAGAACAAGGTAAAAACACTTCT
7201  GGTGTTAAGTTAATTAGATTAAAAGATAATGAACGTTTAGAAAGAGTAAC
7251  TATCTTTAAAGAAGAGTTAGAAGACAAAGAAATGCAACTAGAAGATGTTG
7301  GATCCAAACAAATTACGCAATAACTATGATTTCTTTAAAAAGAAACTGTT
7351  AGAAAGAAATGTAAATGAGCAATTATTAAATCAGTTTATTCAAACTGATA
7401  AACTAATGCGCAAAAACTTGCAACAACTTGAACTTGCTAACCAAAAACAA
7451  AGCTTGTTGGCAAAACAAGTTGCTAAGCAAAAAGATAATAAAAAGCTATT
7501  AGCTGAATCAAAAGAACTTAAGCAGAAGATTGAAAACTTAAATAATGCTT
7551  ATAAAGATTCACAAAACATTAGTCAAGATTTACTTCTAAATTTTCCTAAT
7601  ATTGCTCATGAATCAGTTCCTGTTGGTAAAAATGAATCAGCAAACTTAGA
7651  ACTTCTTAAAGAAGGGAGAAAACCAGTTTTTGATTTCAAACCTTTACCAC
7701  ATCGAGAGTTATGTGAAAAGTTAAATTTAGTTGCTTTTGATAAAGCTACT
7751  AAGATTAGTGGAACTAGGTTTGTTGCATATACAGATAAAGCAGCTAAACT
7801  ACTTAGAGCGATAACTAATCTAATGATTGACCTTAATAAAAGCAAGTATC
7851  AAGAATGAAACCTGCCAGTTGTTATTAATGAATTAAGTTTAAGATCAACC
7901  GGACAACTACCTAAGTTTAAAGATGATGTTTTTAAACTAGAAAACACCCG
7951  TTATTATCTTTCTCCAACTTTAGAGGTACAACTTATCAATTTACATGCTA
8001  ATGAAATTTTTAATGAAGAAGATTTACCTAAATACTACACTGCAACAGGT
8051  ATTAACTTTCGTCAAGAAGCGGGTAGTGCTGGTAAACAAACCAAAGGAAC
8101  TATTAGATTGCATCAGTTTCAAAAAACTGAGTTAGTTAAGTTTTGTAAAC
8151  CTGAAAATGCTATCAATGAATTGGAAGCAATGGTTAGAGATGCTGAACAA
8201  ATCTTAAAGGCACTTAAGTTACCTTTTAGAAGGTTATTGTTATGTACTGG
8251  TGATATGGGCTTTAGTGCTGAAAAAACATATGATCTTGAAGTTTGAATGG
8301  CAGCTAGCAATGAATATCGTGAAGTTTCTTCTTGTTCATCTTGTGGTGAT
8351  TTTCAAGCAAGAAGAGCTATGATTCGTTACAAAGATATTAACAACGGTAA
8401  AAACAGTTATGTTGCTACTTTAAATGGAACAGCATTATCTATTGATAGAA
8451  TTTTTGCTGCAATTCTAGAAAATTTTCAAACAAAAGATGGCAAAATTCTT
8501  ATCCCACAAGCATTAAAAAAATACCTTGATTTTGACACAATCAAGTAATT
8551  TATGAATAAAGGTGTTTTTGTTGTTATTGAAGGAGTTGATGGAGCGGGCA
8601  AAACTGCTTTAATTGAAGGTTTTAAAAAACTTTATCCAACTAAGTTTTTG
8651  AACTATCAACTTACTTATACTAGAGAACCTGGTGGTACTTTGTTAGCTGA
8701  AAAAATTCGTCAACTTCTTTTAAATGAAACAATGGAACCTCTAACTGAAG
8751  CTTATTTGTTTGCCGCAGCTAGAACTGAACATATCAGTAAGCTAATTAAA
8801  CCAGCAATTGAAAAGAACAACTAGTTATTTCAGATAGATTTGTTTTCTC
8851  TAGTTTTGCATACCAAGGATTAAGCAAAAAAATAGGCATTGATACAGTAA
8901  AACAGATTAATCATCATGCGTTAAGAAATATGATGCCAAACTTTACCTTT
8951  ATTTTGGATTGCAATTTTAAAGAAGCATTACAAAGGATGCAAAAGCGTGG
9001  TAATGATAATCTTCTTGATGAATTTATTAAAGGAAAGAATGATTTTGATA
9051  CAGTTCGTTCTTATTATTTAAGCTTAGTTGATAAAAAAAACTGTTTCTTG
9101  ATTAATGGTGATAATAAACAAGAACACCTAGAGAAATTTATTGAATTGTT
9151  AACAAGATGCTTACAACAACCCACGCATTACTAATCATTCAAAGAAAAGG
9201  TAGTTTCTTAAAACCTTTTCTTGATAATTATCTTACTAGTATTGTTTGTG
9251  AAAAACAAAAATGGTTGCAAAAAGTGTATAAACTGTTTGGAAATTCTCAAT
9301  AATAAATACAACAGCTTATATTGATTTGATCAAATTAATCCTTTCAAAAG
9351  AGAAAATGCCCTTCAGTTAGCAAGAATTTTTAACCGTGAAAGAACAAGTG
9401  TAAACAATAAAAATATTTATCTAATTGAAGAAATTGAAAAATTAAGCAGT
9451  AATTCTATAAATAGTTTATTGAGACTAGTTGAAGATAGTCCGATAAATAG
9501  TTATGGTATTTTTACAACTAAAAATGAAAGTTTAATTCTTTCCACTTTTT
9551  TAAGTAGAGTACAGAAAGTAGTTTTAAAAAAAGCTAGTAAAGTTCCTTTT
9601  AAAGTAAGCAAAAATGATCAAGAAATTATTACAAGTTTTTTTACTGTAGA
9651  TGAACAAATTGAAGCAATTGAAAATGGAAGTTTTAACCGTTTCAAAATTA
9701  TCTTAGATGCATGTTTAAACAAAAAAACAGGTACAGAACAAATTTATCAT
```

-continued

| The Nucleotide Sequence of the *Mycoplasma genitalium* Genome |
|---|
|  9751 GCTTGACAAATTTTTAGAGATTTTTCTAATAGTGAAATTGCTCAGTTAAT |
|  9801 TACTCTAATAATTAATAAAACTGAAAATATAGATAAAAAATCAATTTTGT |
|  9851 TTAATTGTTTAAAAGTTTTGCCATATAATCCTCCAAAATCCACTTTGTTT |
|  9901 GCTAATTTAGTTAGTTGATAGTTATGAAAAGCGAAATTAATATTTTTGCA |
|  9951 CTAGCAACTGCACCTTTTAATAGTGCATTACATATTATTAGGTTTTCTGG |
| 10001 TCCTGATGTTTATGAGATTTTAAACAAGATAACTAATAAAAAAATAACAA |
| 10051 GAAAAGGGATGCAAATTCAACGCACATGGATAGTTGATGAAAACAATAAG |
| 10101 CGAATTGATGATGTGCTATTATTTAAATTTGTCTCTCCAAATTCTTATAC |
| 10151 AGGAGAAGATTTAATTGAAATTTCTTGTCATGGTAACATGTTGATCGTTA |
| 10201 ATGAAATTTGCGCACTTCTTTTAAAAAAAGGAGGTGTTTATGCCAAACCT |
| 10251 GGTGAATTTACCCAAAGGAGTTTTTTAAATGGAAAAATGAGTTACAACA |
| 10301 AGCTAGTGCTGTAAATAAATTGATTTTATCTCCTAACTTATTAGTTAAAG |
| 10351 ATATAGTCTTAAATAATTTAGCGGGTGAAATGGATCAACAATTAGAACAA |
| 10401 ATAGCTCAACAAGTTAATCAATTAGTAATGCAAATGGAAGTAAACATTGA |
| 10451 TTATCCAGAATATCTTGATGAACAAGTAGAACTATCAACTTTAAATAATA |
| 10501 AAGTTAAATTGATTATTGAAAAGCTTAAAAGAATTATTGAAAATAGTAAA |
| 10551 CAACTCAAAAAACTTCACGATCCTTTTAAAATTGCCATTATAGGCGAAAC |
| 10601 TAATGTAGGTAAATCTTCTTTACTCAACGCTTTATTAAATCAAGATAAAG |
| 10651 CGATAGTTTCAAATATTAAAGGTAGTACACGCGATGTTGTTGAAGGGGAT |
| 10701 TTCAATTTAAATGGTTATTTAATCAAGATCTTAGATACTGCAGGTATCCG |
| 10751 TAAACATAAAAGTGGGCTTGAAAAAGCAGGAATTAAAAAAAGCTTTGAAT |
| 10801 CTATAAAGCAAGCTAATTTGGTTATTTATCTTTTAGATGCAACACATCCA |
| 10851 AAGAAAGATCTTGAATTAATTAGTTTTTTTAAGAAAAATAAAAAGGATTT |
| 10901 TTTTGTTTTCTATAACAAAAAGATTTAATTACAAATAAGTTTGAAAATA |
| 10951 GTATTTCTGCAAAGCAAAAAGATATTAAAGAATTAGTTGATTTATTAACT |
| 11001 AAATATATTAACGAGTTTTATAAAAAAATAGATCAAAAAATCTATCTGAT |
| 11051 TGAAAATTGACAGCAAATTTTAATTGAAAAAATTAAAGAACAATTAGAAC |
| 11101 AGTTTTTAAAGCAACAAAAAAATATTTATTTTCGATGTTTTAGTTACC |
| 11151 CATCTAAGAGAAGCTCAACAAGATATTCTTAAACTACTAGGTAAGGATGT |
| 11201 AGGTTTTGATTTAGTTAATGAAATTTTAATAATTTTTGTTTAGGAAAAT |
| 11251 AATGGAATACTTTGATGCACATTGTCATTTAAATTGTGAACCTTTACTGA |
| 11301 GTGAAATTGAAAAAAGCATCGCTAATTTCAAATTAATTAATTTAAAAGCA |
| 11351 AATGTTGTAGGTACAGATTTGGATAATTCTAAAATTGCTGTTGAATTAGC |
| 11401 TAAAAAATATCCTGATCTTTTAAAAGCAACCATAGGTATCCATCCAAATG |
| 11451 ATGTTCATTTAGTTGATTTTAAAAAGACAAAAAAACAACTTAATGAACTA |
| 11501 TTAATAAATAACAGAAATTTCATAAGTTGTATTGGTGAATATGGTTTTGA |
| 11551 TTATCACTACACAACAGAATTTATTGAATTGCAAAACAAATTCTTTGAGA |
| 11601 TGCAATTTGAAATAGCTGAAACTAATAAATTGGTTCACATGCTTCATATT |
| 11651 CGTGATGCTCATGAAAAAATTTATGAAATATTAACAAGATTAAAGCCAAC |
| 11701 TCAACCTGTGATTTTCATTGTTTCAGTCAAGATATAAATATTGCTAAAA |
| 11751 AGCTACTATCATTAAAAGATTTAAATATTGACATCTTCTTTTCTATCCCA |
| 11801 GGGATAGTTACTTTTAAGAATGCTCAAGCATTACATGAAGCTTTAAAGAT |
| 11851 TATTCCTAGTGAATTACTTTTAAGTGAAACTGACTCACCGTGATTAACCC |
| 11901 CTTCTCCTTTTCGAGGCAAAGTTAACTGACCTGAATATGTAGTTCATACT |
| 11951 GTTAGCACTGTTGCTGAAATAAAAAAAATAGAAATTGCTGAAATGAAGCG |
| 12001 AATTATTGTTAAAAATGCAAAAAAATTATTTTGACATTAAAAGTTAAATA |
| 12051 AAGCAATTTATTTAACAAATGGATGTTAGAACTGAAAGATTAAACGAATT |
| 12101 GTTTTTTGTTTATCATAAAAACTTAAAAAATCAATCTAAATCTAAATATA |
| 12151 GCAGAGCAGTTAATTACTTAAAAAGGCGTGGATTCAATTTACAAGATTTT |
| 12201 TTAAAAGTTGGGGGTGGTGTTGGTTATTTACAAAATAAAGAATGATTAAA |
| 12251 TTTACCTTTATACAGTTTTGATGGTAATTTAATTGGTTTTCTAAACAGAA |
| 12301 AAGTTAGTTATAAAAAGGAATTTTTATATACACCTTTTAATAAACCTCCT |
| 12351 TCAAAGAGCGAAGCTTTTGTAGGACTCAGAGAATTAGTTATTAAAGACAA |
| 12401 TAGCATATATCTTGTTGAAGGTGATTTTGACTGGTTAGCTTTTCGCAAAG |
| 12451 CAGGTATATTAAATTCTCTTCCTCTTTGTGGTTTGACTATTTCAAATCAA |
| 12501 CAAGTTCAATGATTAAAACAAAAAAAGATTAAAAAGATTTTTATCTGTTT |
| 12551 TGATAATGATTAGCTGGAAAGAATGGAGCAAAAAATTTAAAGAATATC |
| 12601 TAACTAAGCAAGGATTATAACAAAAGTTATAGAAATTAAAGCTGCCGCA |
| 12651 AAAGACTGAAATGATTTGTTTTTATTAAACAACTCAAATTGATCAGCGGT |
| 12701 TTTAACTAATCAACTTCTTTTTTAAGAATTTTTAAATTTACTAATAATT |
| 12751 GTTCTGATAATTATTTTAGTGATATTTAAATCTGGACAAAGCTGAACTAA |
| 12801 AGCTCTCGCACCAGCAGCATCTTCAATTTCATTAACAATAACCCTATTAT |
| 12851 ATCTATTTAAAAAGAAGTCAATAGCATAATAACCTTCCCTTAGGCGTTTA |
| 12901 GCTATTTTCTTTATTTTTCTTTTAGTAAATCACTTTAATTTAAACAAGGA |
| 12951 AACTTCAGCACCTTGTGAAAAGTTAGCTTTAAATTGATTAGCATTAGAAA |
| 13001 TTTTTTTAATAACTTTAATTATTTTTCCAAACAAAATATAAGCACGATAT |
| 13051 TCAACTGTGCCAATTGATAAAAAAGGTTGAACAATTCATTCTGTTGCATT |
| 13101 TTCAATGTTTAAATGTTTGATCTCGTCAGCACTATTAACTAAATGTACAT |
| 13151 CTTTTCCACCGTGTGAATTACGTTTCTTAACGATGACAGGAAATGATTTG |
| 13201 ATTGTTTCTTTACTAAGAAGAGAAGAATTGACAGTTAGAAATCTATTTTG |
| 13251 TTTTAATCATTTATATGTTTCGTATTTATCGTTTGCTATAAAAACAACAT |
| 13301 TAAAAGGATTAACTAAAAAAGTATTTATTTGATTATTGGTTTTTAAAAAA |
| 13351 TCTACTTTTCTTGAACGATTTAAAATCAATTCAGCTTCATTAATTTTAGC |
| 13401 TTCGAAATTAATGTCTTTATTTTCAAGTAATAAGACTTCAGCATTTAGTT |
| 13451 TTTTCTTTTGTAATTCCTTGATTAGACTTAAAGCAAATGTTTGATTTTTT |
| 13501 TCAAAATCATCCTTGTTGTCATAAACAACTAATGCTTTTCTGTTTTTTAA |
| 13551 TTTAATTTTTCCCATTAATCTAAATTGCTTTTAAAAGCTCAATTGCAAGA |

-continued

The Nucleotide Sequence of the *Mycoplasma genitalium* Genome

```
13601  TTAGTATTTAAATACATTGAGCTTCTTGTTAATTGCACATTAGGATTTAC
13651  TTCACAAAAGATCAATGATCTGTCTTGATCAAACAAAAAATCAATACCGC
13701  AATAAAAAAGTTGCATTACTTTACTAATTTTAACTGCTAAATTTTCTTGT
13751  TCCTTATTCAAAAAAAAGCGTTCTGCCTTTGCCCCTTTATTGAGATTAGA
13801  ACGAAAATCACTATTATTAGTTGTATGTAAAGCACCTATAACTTTATTGT
13851  TCACAACAATAACTCTTACCGATTCACCTTTAGAGCAAGTAATGTATTTT
13901  TGCACAATTGCTTGTTGATTAAAAGACATTAAAGTTTTTCTTAATTTTTG
13951  TTCATCTAAACACAAAAAAACATAATCACCAAAAGAACCAAAAACACTTT
14001  TAACAATAACAGGAAACTCCATACTTTGTTTTATTTGATTAATAAAAACA
14051  TCGAGCATTACTGGATTTCACTCCCTGTCAAAATTTTGAGGTCCTAAAAG
14101  TGTTTTAATCTGCTTTATGAATGGATATTGTGCAATGATAGCGTGACTAA
14151  GTCCTTTATTATCTGCATTGTTAATTCCAATTGAACTGTTAATTACTTCA
14201  AAACCATTGCTTTCTAGTCATCTAGCTAAAGCAATATTTTTATCCATAAA
14251  AAGAATTTTGTTGGATATGAAGGGTAAATTTGCTTTTGCTTTAGTTGTAT
14301  TAATATCAAAACTAGTAAAGAATTTTAGTTCTATATCTAACTCTTCACTA
14351  GCATTTTTTAAAAGTTGAGTTTGATTTAATTTAGAGCTAATTGGATTAAA
14401  TGCTGGATTGTAAACAACGTTTATTTTTTCATGCAATATTCAAAGATTT
14451  TTTATTATTGCTAAAACTGTAAAAGGGCCAACACCGCCAGGCGTTTTAGT
14501  TCATCATCTAGCTTTTTTTTCAATGCCTTCAGGATTTATATCACCACAAA
14551  GTTTATTTTGCTTGTTTCTTGAAACACCTATATCAAATAAAATAACTCCT
14601  TTTTTAAAGTTTTTAGCTTGAAAAAAATGAGATTTTCCAATAGCAGTAAA
14651  AACTATATCAGCACTTTTAATCAATTCAAATGTATTTGGAGTATCTTTAT
14701  CGCATGCTTGAACTTTATAACCACTAGTTTTTAAAAATTCATAAATAGGT
14751  TTGCCACCAGTTATTCCCAAACCTACCACAACAATTTTTTGATTATTAAA
14801  TTCAAGGTTAAATAGTTCTTTTAGTGTTATTATAGCTTCAACTATACAAG
14851  GTTTAATTTCAGCCAAATGATTAGTTGTTAAACCATCAACATCTTTTAAA
14901  GGATTAATTGCTTCTAGTAGTGAGTTTTTATCTAAGTGTGGATAAACTGG
14951  CAATTGCAAATGATACCAGTAACATTTACATCATGATTTAAACTAATTA
15001  TTTTTTCTATTAACTCTGCTTGAGTTATTTGATTAGATAGTTTAATTAAT
15051  TCACTTTTTGCTCCTACAGTGTTACAAGCAATAaGTTTTTGTTTAATAAA
15101  ACTGTCTGATGAATCATCATCATTAGCTTGAATAATCACTAACTTACATT
15151  TTGATCAATCAAAATTCTTGTAAGTTTCTAAGATTGATTGCGCTTTTAGT
15201  TTTCCATCAAATGACATCTTATTTTGCCTAATATAAAACAAAACGTCTAA
15251  CTTCTTATTTATGCAAAGGTAAGTTAGACGTTGGAATTCTTTAATGGTGG
15301  AGATGAAGGGTCTCAAACCCTCAACCTCCTGAGTGCAAATCAGGTGCTCT
15351  ATCAGTTGAGCTACATCCCCATTATTGGTGGAAGTAAATGGACTTGAACC
15401  ATCGACCTCACCCTTATCAGGGGTGTGCTCTAACCAACTGAGCTATACTT
15451  CCAAGCATAATCCTAAGGGTATTTAACTAATTATTATAACAATTTTAATT
15501  TAACCAAAATACCCCTCGAATTTTAACAGTTTTTATAATCAAAACAGCTA
15551  ATTTTATGGGGCTTGTTTTAAAAGAATTTAACAATAAAATAAGAACAGCA
15601  TTAATTCTCGCTCCTTTTTTCACTTTCGCTCAGATAGTGATTGATTTAAT
15651  CATTCCTTCTTTTTTAGCAAGTGCTATTTCAGTTGTGTTTTCAATTGATA
15701  AATTAAAACAGGATGAGTCAGGCGGAAAGACAATTTCAGTTGATTTTATT
15751  GGTGGGGCTAATATTAATTTTGCTAATGTAAGAGAAGCGCAAATAGTTTT
15801  AGCAACCACAGTTATTTTACTTGCATTATGTGGACTTTTTTTGGTCTAA
15851  TATCTATTTATTGTGCAAGTTATGTTTCAGCAAACACTTCTTTTCTATTA
15901  AGAAAAAAGATCTTTGCAAAATTAATGCGAATCACAACCCCATCACATGA
15951  CCATTATGGTTCTTCTACTTTATTAGTTAGATTAACAAATGATGTTTATT
16001  TGATGGAGGTAATTGCTTTTGATTTTTTAAGGCTAATTATTCGTGCTCCG
16051  CTTTTGTTTATAGGTGGATTAGTGTTTGCAGTAACTACAAATCAAGATAT
16101  GTCAATATCTTTACTAATTACTTTTCCTTTGATTCTTTTGGTAATTGGTA
16151  TTCTAAACCGTAAATCTATTCCTTTATTTAAAGAAAATCAAAAATCAGTT
16201  GATAAGATAAATGAAAGAGTAGAAGAAGATGTTTCAGGTTATAAAGTAAT
16251  TCAATCTTTTAATCTTCATTCCTTTACAAATAACAAATTTAAGATTGCAA
16301  ATGAAGGATGAAAAAAGAATAGTACAAGTTCTTTATTTATAAACTCACTT
16351  AACATTCCATTTACCTTTTTTTAAGCAGTTTAACTATTATTATTGCTCT
16401  ACTATTAGTTTTTCAATTAGATAGTAGTGTTTCAGTTGACCCATTACCGC
16451  AGGATGCAGCTATTAGACCTAATATCTTTGCTTTTTTCCAATATAACTTT
16501  TACATTGTTTTAGGGTTTATCTTAACCTCTTTAACAATGGTGAACTTTAA
16551  TCGTTCTAGAGTTGCACTAGGCAGAATTAAAGATATTTTATCTCAGCCTG
16601  AAATAAAAACTATTACAAATAAAGATCAAAAAGAATTATTACCTACCTTG
16651  GAGTTTAGAAATATCTCTTTTGGTCTTGGCAATAAGAACAATAACAATTT
16701  TTTACAAAATCTTAGTTTTAAATTTGAAGCATATAAAACATATGGTATTG
16751  TTGGGCCTACAGGCTCTGGAAAATCTTTAATTGCTAACATTATCGGTGGT
16801  TTATATGAGCCTAATGAGGGTGAAATTCTCATTGGTGGGGAGAAAATTCA
16851  ATCTATTGACAGTTTATATCTATCAGAAATGATAGGAATTGTTTTCCAAC
16901  AAAACATCCTTTTTAAAGGAACAATTTCTTCTAATATAAAAATTGGTATT
16951  GAAACTAGAAGTGATTGAAAGAATCAATCTGATTTACAAAAGAATGAAGC
17001  GATGAAAAACGCAGCTAAAATAGCTTGCGCTGACACCTTTATTGAAAAGT
17051  TTTCTGATAGTTATGATCACAATGTTGAACAGTTAGGTAAAAACTTATCT
17101  GGTGGACAAAAACAAAGAGTTGCTATTGCAAGAACTTTAATTACAAAACC
17151  AAGAATTTTAGTTTTTGATGATAGTATGAGTGCTCTTGATGCTCTAACTG
17201  AAAAAAAGTAAGAGAAAATATTGAAATGATTTAAAGCTAACTACCAAA
17251  ATCATTATTAGTCAAAACATTAATTCAATTAAACACGCAGATAAAATTTT
17301  GGTAATTGATAATGGCAGAATTGTTGGTTTTGATAGTGATCAAAAGCTAA
17351  TGAAAAATTGTTCACTTTATCAAAAGATGAAAGAATCTCAAAAAGATTTG
17401  GGAGGTGATTTTGATGCAGTTAACTAGTGTAAAACCAAGTTCTTGAAAGA
```

-continued

The Nucleotide Sequence of the *Mycoplasma genitalium* Genome

```
17451  TTTTAAAGAGATTAATTACTTCAATGGAAGGAAGTTGAAGTTATAAATTA
17501  CTTTATGTTTTTTGTGTATAGTTCTTGGTATTTTATATGGAATTGCTAA
17551  CCCTATCTTATTAGCACAAGGTCTTGGTTTTATTTTTCCTATTACTAGTA
17601  GTAATGGTCGTGCTGTTGACTCAATATATTCATTAATTTACCCAACAAAT
17651  TTAAATGTATTCATTAGGCTCACAATTGTGAGCGTAACTGTTTTTGTAGC
17701  TTATGCATTAATCTTTGTATTTAATGTAGCGCAAAACTATGTAGGGATTA
17751  AACTTTACCAACAAACATGTGCTACTTTGCGTTGAAAGGCATATTTAAAA
17801  ATGCAGAGTATGTCAACCAGCTTTTTTGATACGCAAAATAATGGTGATCT
17851  TATGAGTAGGTTAACTAATGATATGTATAACATTGATAACCTATTCACTC
17901  AAGCTGGTGGACAAGCTATTCAAAGTTTGTTTAATATTTTAACAACCTCA
17951  GTATTAATATTTTATTAAGCCCAGTTATTGCACTTATTTCACTTTCAAT
18001  TTTAGCTACATTAATTACTTTTTCTTTTGCCTTTCTAAAGAAATCAAAAA
18051  CTTCATATAGTCAAGTACAAAATAATTTGGGTGATATGTCTGGTTATATT
18101  GAAGAGGTTTTAACTAATCATAAGGTTGTTCATGTCTTGAAGTTGCAAGA
18151  GATAATGATTAAGGATTTTGATCAATACAACAAATCAATGATCAAACCAA
18201  CTGTAAGAGGGAATACATATTCGATCTTTCTTTTTTCTTGGTTTGGTTTT
18251  ATATCAAATATTACTTATCTGGTTTCTATATCAATTGCTACTGCTTTTAG
18301  TGTTAATTCTATTCCTTCATTTGGAATTAGTGTTATTAACTATTCATTCA
18351  TGTTGTCTTACATTGCTTCTTTAAGGCAAATAACTTTAGCATTAGATCAA
18401  ATCTTTACCCTTTGAAACTTAGTTCAATTAGGGGTTGTTAGTGCAGAAAG
18451  AGTATTTAAGGTATTAGATCTTAATGTAGAGAAAGATACTGCTACTATTG
18501  ACAAATTACCTGATATTAAAGGTAATATAAGGTTTGAAAATGTAGCATTT
18551  GGTTACAATAAAGATAAACCTACTTTAACAGGAATTAACTTTAGTGTTAA
18601  ACATGGAGATGTAGTTGCAATAGTAGGTCCTACAGGAGCTGGTAAATCAA
18651  CTATTATTAATCTATTGATGAAATTCTATAAACCTTTTGAAGGAAAGATT
18701  TATATGGATAACTTTGAAATTAGTGATGTAACTAAAAAAAGCATGAAGAGA
18751  AAAGATTTCTATAGTATTACAAGATTCATTCTTATTTAGCGGCACAATTA
18801  AAGAAAATATTCGTTTAGGCAGACAGGATGCTACTGATGATGAGATTATC
18851  GCTGCATGTAAAACTGCTAATGCTCATGATTTCATCATGCGTTTACCAAA
18901  AGGATATGACACTTATATTTCCAATAAAGCAGATTATCTTTCTGTTGGTG
18951  AAAGGCAATTATTAACAATTGCCAGAGCAGTAATCCGTAATGCTCCAGTT
19001  TTGCTCTTAGATGAAGCAACTAGTTCAGTTGATGTCCATTCAGAAAAATT
19051  AATTCAAGAATCAATAGGAAGGTTAATGAAAAATAAAACTTCTTTTATAA
19101  TTTCTCATCGTCTTTCAATTATTCGTGATGCAACATTAATAATGGTTATT
19151  AATGATGGTAAAGTACTTGAAATGGGTAATCATGATCAGCTGATGAAACA
19201  AAATGGATTTTATGCACGTTTAAAACAATCTTCGGTTCGTTAATAAATTC
19251  TAATGACTGTTGCTGAAATTAAAAAACTTGCATTAAATAATCAGGTATTT
19301  AATGAAGCAAAAGCGCTTTTAGAAAAAGGTAATGTTATTTTTCCAAAAAA
19351  ATTCTTAAAGCGAAAGAAGATCATTATTGAAGTATTAGATGGTAAGGTTT
19401  TTAAGGTTCAAATTAATTTAAAAACCGCTGCTGCACACTTGGATTGTAGT
19451  TGCTCTAATGATAAGCAAAATTGCGTTCATATAATTGCAGCGCTTTTGAA
19501  ATATAATGaTCTAAAAAATCAAGATAACAAAGAATTTGACCTTAATAAAG
19551  CCGATAAATTAGAGTGCAAAGAAGTTGAAATTcTAATTGaAAATGTTAGC
19601  TTAGCAATTGTTAATGGCAGCtGaAAATTAAAGATAGGTTTTGTAATTAA
19651  TATTGATAAAGTTCAAAcTAAtACAACTGCTTTACGTTTTTATTGTTGTG
19701  ATAATAAAGATGTTTATTTTCTACATACTGAAGATGAAcACTTTTCAGGA
19751  TTGCTTTAGATAAATTTAATAGTGTTGAAAGACaAACATTATTAATTTTT
19801  GATCAGCTAAATAAAACAAAGCAAATGCAATATGAAAATAACAGTTTGCT
19851  TTTTAATTTAGATCAATTCCTAAGCCTAGTTAAGGAAGTTAAAAAACCTT
19901  CATTATTCTTATTAAATGAGGATAAAACTGACAATATTCTTTTCTTAAGA
19951  AGTCAACATAAAATCAATGGATTAAGCCACGTTTGTGGTTTTTTAAATAA
20001  TAAGGTTTTTGATTTTGTATCCTACAATGAAAAAACTAAGCAAATTGTTT
20051  TACGCTTAGCTTATCTTAATAAGTTCACTGATTTTAAATTTCCATACAAC
20101  ATTAACATCTATAAACTTGCTTTTGGAGAAACATTATTTTTCCATTTTTT
20151  AATCCATTTAAAAATGAATGGTTTTAAAAACATCTTTTTTCAAAGTGATG
20201  TTGTTATTGTTAAGGAAAGTGAATATCTACCTAAGATGTTTTTGACTATT
20251  GAATTTAATACACAAAAAAACAAGTTTATAACTGATGCTTTTTTTAAATA
20301  TAAGAATAAAAATAGCAATACTTTAACAACTGTTTACCCCCATCGCTATA
20351  CTTAGCTCAAAAAACTAATACATCAAACTTCAACCGTTTACTTTTTTATG
20401  AACAAGCACTACAAAGGTTTTATGAAGAATTATTTCAAATAGATTATTTA
20451  AGAAGATTTGAAAACATTCCCATTAAAGATAAGAATCAAATTGCGCTTTT
20501  TAAAACTGTTTTTGATGATTACAAAACCATTGATTTAGCAGAATTGAAAC
20551  TTACAAGTAATCTCTTAAATTACAAACAGTTACATTTTTCAATAAGTGAT
20601  ATTAAAGCTTTAAAAAATTGAAGATAGACAACTAAAAATTGAATTTAAAGC
20651  TGGCGGGATAGATCTAAAGTTAATTAAAAGTGTTTTAAGTAACTACTATA
20701  AGGGTAATGCTATTTGTATTGGTGAAGATGGTTGATATGATTTGAACGAT
20751  GAAAATGCTAAAGCACTAATTTCATTTTGGAGTCAAATTGACTTAAGAAA
20801  TGCTACTTGTGATGCTAATAACAATTTGCTTCTTGCTAAATACCACTTGT
20851  TTGAAGTTGTAGATACTATTAGTAAATACACTGATGTAACTAATTTATTA
20901  GATGAAAAAACAGCCTTACAATTAAAAATAGCTAGTGAAAATCAATTTCA
20951  TCTTTCGTTAGATAATAACCAAATTAATAACTTACGCAAATATCAAAAAG
21001  AAGGAGTTAAATGGATAAGGGCATTAGAAGATAATCAGTTTGGTGGAATT
21051  TTAGCAGATGAAATGGGGTTAGGTAAAACTGCTCAAGTGATCTTTGCAAT
21101  GCTGGATAGTTATCAATCAACAAAATCACTTTTACCTAGTTTAATTATCG
21151  TTCCAGCATCCTTACTCTTAAATTGAAAAAGTGAGTTCCAAAAGTTTGCA
21201  CCTCATGTGAAAATAGTTACTGCTAATGGCAATTTTAAAGAACGCTCGCA
21251  GGTATATGAATCATTAAAAAATCAGATTTTGTTAATGAGTTTTAATGTCT
```

-continued

The Nucleotide Sequence of the *Mycoplasma genitalium* Genome

```
21301 TAAGAAGTGATATTAAATGAATATCTCAAAAAAAGTTCCATTATGTAGTA
21351 ATTGATGAAGCACAAGGAATCAAAAATGAAAATTCTACTGTAACAAAAGC
21401 CGCTAAAAAAATTAAAGGTAATTTTTGCTTAGCACTTACCGGTACTCCTA
21451 TTGAAAATCGTTTGCTTGATCTTTGATCTTGTTTTGATTTTGTTTTACCA
21501 AATTTCCTTGGTAATAAAAAACAGTTTTCAGATCAATTTGAAAAAGAAAA
21551 AAATGATGAAAGCTTTCAAAAATTAATGAAAAAAACGAGTCCTTTTATTT
21601 TAAGAAGGACTAAAAATAAAGTTTTAAAAGAACTACCTAAAAAAATTATT
21651 ACTGATATCTATGTTGAACTTAGTGAAGAACATCAAAAACTGTATGATAA
21701 ACAAAAAACAGATGGTTTGAAGGAGATTAAAGAAAGTGATGCTAAAAATG
21751 CTTTAAATATCCTTAGTTTAATCTTGAAATTAAGGCATATTTGTAGCTTA
21801 GTTAAAGACAATGATGTTAATGATTTTGAAGATAATTCCAAAGCTAATGC
21851 AGCTTTAAACATTATTTATGAAGCACTTGAAAATAAACGCAAAGTTATTT
21901 TGTTTACTCAATTTTTAGATGTAATTGATTGTTTTAAGCAAACTTTAAAA
21951 AATCAAAAGATTGATCACCTGGTATTTGATGGTAGAAAAACTGTGAAGAA
22001 TAGAAACACTATTATCCAGAAGTTCAATAGTGCTAAAGAACCTTGTGTGA
22051 TGCTAGCTTCTTTAAAAGCTGGTGGAGTTGGTATTAACTTAACTGCTGCT
22101 GAAGTTGTTATTCATTTTGATGTGTGATGAAACAGTGCTGTTGAAAATCA
22151 AGCAACTGATAGAGCACATCGTATTGGTCAAAGTAAAACTGTACAAGTTT
22201 ATAGAATTATTGCTAAAAATACTATTGAAGAGCGAGTTTGTCAAGTTCAG
22251 AATCAGAAACAAGAACTTGTTAAAAAAACCTTGGTTGAGGATGTAAATTT
22301 CTTTAAATCTCTTTCACATGAAGAACTCTTAAAGCTTTTTGAATAAAGCA
22351 AGAATTATAATTAACACTCTAAGGATGCAAGTGATAAATGGCTGCTGGTA
22401 AAAGGGATTATTATGAAGTTCTAGGGATATCTAAAAACGCTAGTTCTCAA
22451 GACATAAAAAGAGCTTTTAGAAAGCTTGCAATGCAATATCACCCCGATCG
22501 TCATAAAGCAGAAAATGAAACTACTCAAAAACAAAATGAGGAAAAGTTTA
22551 AAGAGGTTAATGAAGCATATGAAGTTCTAAGTGATGAAGAAAAACGTAAG
22601 CTTTATGACCAGTTTGGTCATGAAGGGTTAAATGCTTCTGGTTTTCATGA
22651 AGCAGGGTTTAATCCTTTTGACATCTTTAATAGTGTTTTTGGTGAGGGAT
22701 TTTCCTTTGGAATGGATGGTGATTCACCATTTGATTTCATTTTTAATCGT
22751 TCTAAAAAACGTCAACAACAAATTGTTGTTCCCTATAACCTTGATATTGC
22801 TTTAGTAATTGAAATTAACTTTTTTGAAATGACTAATGGTTGCAACAAAA
22851 CCATCAAATATGAAAGAAAAGTTTCATGTCATAGTTGTAATGGTTTTGGC
22901 GCTGAAGGCGGGGAAAGTGGATTGGATCTTTGTAAGGATTGTAATGGCAA
22951 TGGTTTTGTTATTAAAAACCAACGTTCTATCTTTGGAACCATTCAATCCC
23001 AAGTCTTGTGTTCAACTTGCAATGGACAAGGAAAACAAATTAAAGTTAAG
23051 TGCAAAACTTGTCGTTCTAACAAATACACTGTTACCAATCAAATTAAAGA
23101 GATTAATATTCCAGCAGGAATGTATAGTGGTGAAGCTTTAGTTGATGAAA
23151 GTGGTGGTAATGAATTTAAAGGTCACTATGGAAAATTAATCATTCAAGTG
23201 AATGTATTGGCAAGTAAGATTTTCAAACGTAGTGATAATAATGTTATTGC
23251 CAATGTTTTAGTAGATCCAATGGTTGCTATAGTTGGTGGGGTAATTGAAC
23301 TACCTACTCTTGAAGGGATTAAAGAATTTAATATTAGACCAGGCACTAAG
23351 AGTGGCGAACAGATTGTTATTCCTAACGGTGGGATTAAATTCTCAAAGAG
23401 TTTTAAAAGAAAAGCTGGGGACTTAATCATTATTATTAGTTATGCACGTC
23451 CTTGTGAATACACTAACTTAGAATTGAAAAAATTACGTGAGTTTATCAAA
23501 CCTAATCAAGAGGTTAAACAATATTTAAATACTTTAAAAAATGAATACAA
23551 AACTTAATGTAAAAGGTTATCTAAATGTTGGTGATAACCATCAACTTTAT
23601 TACTGAACACAAGGAAATCCTAATGGTAAACCGGTTTTGTATATCCATGG
23651 CGGACCTGGTTCTGGTACTGATGAAGGATGTTTAAAGTATTTTGATCTTG
23701 AAACAACTTGGATTATTTTATTAGATCAAAGAGGTTGTGGTAAGAGTAAG
23751 ACTAATGATATCTTTTATGAAAATAACACTGATAAATTAGTTAGTGATTT
23801 TGAAATTTTACGTCAAAAATTAAACATTAAAAACTGAACACTCTTTGGTG
23851 GTAGTTGGGGTTCTGCACTTGCTTTAGTTTATGCAATTAAACACCCACAA
23901 GTAGTTGATAAGATCTTTTTAAGAGCACTTTTTTTAGCTAGAGAAAAAGA
23951 CTGATCTGAAGCTTTAATGGGATTAGGAAAAATGTTTTATCCTTATGAAC
24001 ACCAACGCTTTATGGATAGTATTCCTAAAGCTTATCAGAACAGTTATGAA
24051 CAAATTGTTAACTACTGTTATGATCAATTTCAAAATGGTGATGAATCAAC
24101 CAAAGAAAAACTTGCTAAAGCTTGGGTGGATTGAGAATCAACATTACTTT
24151 CACCTATTAACaAAATTCATTCAACAGCaACAGACTTTAAATTAGTTGAA
24201 AAACTAGCTTTATTGGAATGTCACTATGCAGTTAATAAAAGTTTTTTGGA
24251 TGAAAACTTCATTCTAGATAACATTAGTGTTCTTAAAAATAAAAGTATTT
24301 ATTTGGCTCATGGTAGATTTGATCTGATCTGTCCTTTATATCAACCATTA
24351 GCATTAAAACAAGCATTCCCTGAATTACAACTTTATGTAACCAATAATGC
24401 TGGTCATAGTGGTAGTGATGCTAATAATTTAGCAACTATAAAACACCTTT
24451 TAAAAACTTACCTTTAATGAAGCGTTGTTATATTACAACCCCTATCTACT
24501 ACGCATCAGGTAAGCCACACATAGGTCATGCTTTTACCACTATTTTGGCG
24551 GATGTAATTAAGCGTTTTAAAATCCAAAACGGATATGAGGCTTTTTTGCT
24601 TGTTGGCAGTGATGAACATGGCAATAAAATAGAAAGTAAAGCTAAAAGTT
24651 TAAATTTAGATCCTAAAACATTTGTTGATATTAACGCTCAAGCTTTTAAG
24701 TTAATGTGAAAGACCCTTAATATTAGTTTTGATCACTTTATTAGAACAAC
24751 TGATGAAATCCATAAACAACAAGTTCAAAAAACATTTCAAGATTTATATG
24801 ACAAAAAACTAATTTATCAAAGTGAATGAAAAGGGGCATATTGTGTTGAG
24851 TGTGAACAAAATTACTTTACTTTTAATAAACAAACAATGTTATGTGAAAT
24901 AGGTCATAATCTCAGTCTTGTCCAAGAACCTTGCTGATTTATTTCTTTTT
24951 CTTCTACTAAAAATTGAATTGAAACAACGATAGGAAAAAATCAACTTAAC
25001 ATTATTCCTAAATCACGTGCTTCTGAATTAAAAAATAACTTTATAAACAA
25051 TGGTTTAAACGATTTAGCATTAACAAGAAAAAATGTTACTTGAGGAATAA
25101 AAGTTCCTTTTGATCCAAATCAAACAATCTATGTTTGGTTTGATGCATTG
```

| The Nucleotide Sequence of the *Mycoplasma genitalium* Genome |
|---|
| 25151 TTTTCTTATATCACCAATTTAGGATTTAGAAATGGTGATCCTAATTTTAT |
| 25201 AAAGTGATGAAATAATGACAATAAAGAAAGAGAAGTTATCCATCTTATAT |
| 25251 CACGTGAAATCACCAGATTTCACTGCATCTATTGACCGATTTTTCTACAC |
| 25301 TTACTTGATATTAAGTTACCAACCCAATTTTTATCACATGGCTGGATAGT |
| 25351 TGATGGTGAAGGGAGAAAGATGTCAAAATCTTTAAACAACGTTATCTCTC |
| 25401 CAGAACAATTAATTGATCAATTTGGTGTTGATGGTACAAGATATTGTTTA |
| 25451 TTAAAAGAGATGCGTTTAGATAAAGATAATCGTTGTAGTGTTAGCATCTT |
| 25501 AAAAGAGATTTATAATGCTGATCTTGCCAATAGTTTTGGAAACCATGTTT |
| 25551 CACGTACTTTTGGCATGATTAAAAAGTATCTAAACGGCAAATTAGAATAC |
| 25601 CAAATTATTACTGATAATGCACTTCAAAAAATAATGATTTTAATAGATGA |
| 25651 ATCAATCGTTCAATTTGATCATTACTTTAACAGTTATGAATTTTATAGAG |
| 25701 CGATTAATCTACTTTTAAAAATTGTTTTTGAATTAAGTAAATTAATTGAT |
| 25751 GATTTCAAACCATGAGAATTGTTTAAAAATCAGGAATTCTCACTTTTAAA |
| 25801 ACAACTACTTTTTACTTGTGTTAGGTGTGTGCAGGTATGCTATGTGTTGT |
| 25851 TAACACCTATCTTAGTAAATACTGCTTCAAAAGTTTTTCATTTATTTAAT |
| 25901 TTCGCTGATGATGCCTGTAGAAAAGATCAATTAAGAGATGCAACTTTATT |
| 25951 AAAAAAAATTATTATCTCTAATTCAATGGAAGTTTTATTTAAAAGAGTAG |
| 26001 ATTAAGAAAAGTAGTATTAGAATTTTATTGATTTATGCAATTAGAGTACC |
| 26051 TCAATCTTATTTCTCAAGCTAAAGTTATTGCAGAAAAACAATTTAAAGCT |
| 26101 AACCCTTTTTCTTTTGAAACAATTTGAAAAGAAGTAGTTAAACATTTCAA |
| 26151 GATTTCAAAACAAGATGAACCAAGCTTAATTGGTCGTTTTTATCAAGATT |
| 26201 TTCTTGAGGATCCTAACTTTGTCTATTTAGGTGATAGAAAATGAAAACTT |
| 26251 CGTGATTTTATGAAGTTTGATGAATGGACAAGATATCACAATCTATGTT |
| 26301 TGTTACAAAGGAGATTTTTGAAGAAGGTTATGAAGATCTTTCCAATAAAA |
| 26351 AAGTAGAACCTGAGGAAGGAGTTGGTGATTTCATTATGGGAAATGATGGT |
| 26401 GATGACAATGAAACTGGCAGTGAAATAGTACAAGGTTTAATTAATGATTC |
| 26451 ATTCAGTGAGGAAAATCAATAGTAGATATGCTTGTTAACTTTAAATTGAT |
| 26501 GCTTCAAAAAGCAAAGCTAGGTAAATATGCAATCCCTCACATTAACATCA |
| 26551 ATAACTATGAATGGGCCAAAGCTGTTTTAACAGCAGCAAATCAAGCTAAT |
| 26601 AGCCCAATTATTGTTTCAGTATCTGAAGGTGCTTTAAAGTACATGTCTGG |
| 26651 TTATAGTGTTGTTATCCCGCTTGTTAAGGGTTTAATTGAATCACTAAGTG |
| 26701 TTAAAGTACCAGTGACATTACATTTAGATCATGGTAGTTATGATGCATGT |
| 26751 ATCCAAGCATTACAGGCTGGATTTAGTTCAGTAATGTTTGATGGTTCACA |
| 26801 TTTACCATTTGAAGAAAATTTCAATAAATCTAAAAAGTTAATAGAGATAG |
| 26851 CACAAAAAACAAATGCTTCTGTTGAACTTGAAGTTGGTACTATTGGTGGA |
| 26901 GAAGAAGATGGTGTTATAGGACAAGGTGAGTTAGCTAATGTTGATGAATG |
| 26951 TAAACAAATCGCTAGTTTAAAACCAGATGCTTTAGCAGCAGGAATTGGTA |
| 27001 ATATCCATGGTATCTATCCTAAGAATTGAAAAGGATTAAACTTTCCTTTG |
| 27051 ATTGAAACAATATCAAAAATTACTAACTTACCCTTAGTTTTACATGGTGG |
| 27101 CTCTGGAATCTTAGAAAATGATGTTAAAAAAGCAATTAGTTTAGGGATTT |
| 27151 GCAAACTAAATATTAATACTGAGTGTCAATTAGCATTTGCACATGAAATT |
| 27201 AGAAAATACATTGAATCAAATAAAGACTTGGATCTTAACAAAAAAGGTTA |
| 27251 TGATCCTAGAAAACTTTTAAAAGAACCTACTCAAGCAATTGTTGATACTT |
| 27301 GCTTGGAAAAGATTGATTTGTGTGGTTCTAGAAATAAAGCATAGATGTTA |
| 27351 AGTGCAGGGATAGTTGGTTTACCTAATGTTGGTAAGTCAACTTTATTTAG |
| 27401 TGCTATTACTAATTTGCAAGTTGAAATAGCAAACTATCCTTTTGCAACTA |
| 27451 TAGAACCTAATACTGGCATTGTTAATGTTAGTGATGAGAGATTAGATAAA |
| 27501 TTAGCTAGCTTAATTAATCCTGAAAAGATAGTTTATACAACCTTTCGTTT |
| 27551 TGTTGATATAGCAGGTCTTGTTAAAGGCGCCAGTCAAGGTCAAGGATTGG |
| 27601 GTAATCAATTCTTAGCAAACATCCGTGAAGTGGATTTAATTTGTCATGTT |
| 27651 GTAAGATGTTTTCAAGATAAAAAAAATTGTTCATGTTAACAATACAATAGA |
| 27701 TCCTGTTTTTGATTTTGAAATTATTGTTAATGAACTAATCCAAGCTGATT |
| 27751 TTGAATTAATAACAAACAGAATCGGCAAGCTTAAAAGAAAAGCTGAATCA |
| 27801 GGTGATAAAATCGCTAAAGAAGAGTTTGTATTACTTGAAATTGTTTTAAA |
| 27851 TGGATTAAAACAAGGTCAAATGCCCATTCAGACTCTAAGTGAAAGTGAAT |
| 27901 TGAAAACAATTAAATCACTTAATCTATTAACAGCTAAACCTATTCTAATA |
| 27951 GTAGCCAATGTATCTGAGAATGACTTATTAAACCTTGATAATAATGAAGC |
| 28001 TTTAAAAAAATTGAATGCTTTTCTTGATCAAAAAAAGATTCCCAAGGCAA |
| 28051 TCACAGTTTGTTCTTTAATTGAAAAAGAATTAAGCGGTTTGAAATTAGAA |
| 28101 CAACGTCAATACTTTTTGGATGAACTTGGCTTAAAAAATTATTCAGGTTT |
| 28151 AAACCGAGTAATTCAAGCTGCATATCAAACTTTAAACCTTTGGTCTTTTT |
| 28201 TTACTTTTGGTAAAAAAGAAGTTAGAGCATGAACATTTAAAAAGGGTTGA |
| 28251 AATGCTCCTCAGTGTGCTGGGCAAATTCATTCTGATTTTGAAAAAGGATT |
| 28301 TATTAAAGTTGAAGTAATTAGTTGAGATCAATTGTTTGCAATGAAATCTT |
| 28351 TACAAGAAGCTAAAAAACAAGGTTTGATAAGATTGGAAGGCAAAAATTAC |
| 28401 TTAATAAAAGATGGTGATGTTTGTAACTTTAAATTTAACGTCACTTAAAA |
| 28451 ATTAATCTATTTTCAAAATGAGTTTTTTCAACATTTATTAATTAAAAATT |
| 28501 AATGCTTTTTAAAGTTGAATCTTAATTCATTTTTCAATACTTTTTTAGGC |
| 28551 TTCCTATTCTTTAATTAAATTAATACGCTTTTCTAAAAGTAAAAGTTAAG |
| 28601 AAAAGTACTTTTATTCAAACAAAAACGTTTTTATAATTTTAGAGATAGTT |
| 28651 GTGCCAAGTAAGTATTTATTCACCGTTATAATTCCAACATACAATTGTTG |
| 28701 TCAATACATAAAAAAGGCATTAGATTCATTGCTTTTACAGAATGAATATT |
| 28751 TTTTAAAAACACAAGTACTAATAGTTAACGATGGTTCACTAGACAATACT |
| 28801 AAGGAAGTTGTTAGTGACTATTTAATAAAGTACTCCAATATTAGTTATTT |
| 28851 TGAAAAAACTAATGGTAATTGGGGTAGTGTTATTAACTATGTTAAAAAAA |
| 28901 ATAAATTAGCCTTAGGTCAATATATTACTGTTTTAGATAGCGATGATTAT |
| 28951 TTTTTAAAAGATAGTTTTAAAAAAGTGGCTCGTTTCTTTGGCCATGACAT |

-continued

The Nucleotide Sequence of the *Mycoplasma genitalium* Genome

```
29001  GATCATTGGCGCTTTTTATTGTTATATTAATGAAAATAAAACTCGTTTTT
29051  TAAAACCTTATTTCGGTAAGACTGGTGTTATTAAAGAACATACCAAATTA
29101  AGAACCCCCCATTCCCAACCTATTGCTAAATTTTACAGTAATAAACTTTT
29151  CTATGAACTACATGATCTTAAGGAAAAGTTATTCTTCCAGGATTGTTTAA
29201  TGTATCACGATGCTATTAACAGAGTTGAAAGTGTTTTTTATTTGCGAGAG
29251  CCTTTAGCAGTTTGGTTTTCTACAAGACCTGGCAATTCTACAACAACTTC
29301  TTGAGAAAATCCAATAAATTTAATGCTTGGTGTGAAATTCTCCAAAAAA
29351  TGAATTTGTATGGAGCTGGGATAGTAATCTACATCTATACTATGCTACCT
29401  GGATTTCTAAAACAACTAAAGAAAAAACAACTAATACTGAATTTGAACCA
29451  TAAACCAGCTTACACTTGATTACCTAAACCTTTAGCGTTTATTTTTGGTG
29501  GTTTAATGGCATTTAAAACCAGAAAATACATTAAATATCCTAAGTAATTT
29551  ATGGCAGAAATGATAGAAGCAAAAAATCTTCGTAATGGGCAAACCATCTT
29601  CGGTCCTAACAAAGAGATTTTATTAGTACTGGAAAATACATTTAACAAA
29651  CCGCAATGCGCCAGGGAATTGTTAAAACTAAAGTTAAAAACTTAAGAACT
29701  GGGGCTATTGTTTGGCTTGAATTTACTGGTGACAAATTAGAACAAGTAAT
29751  TATTGATAAGAAAAAAATGAATTTCTTATACAAAGATGGTAATAACTTTG
29801  TTTTTATGGATCAAAAAGACTACAGTCAGATTGAGATTAATGAAAAAAAA
29851  TTAGAGTGGGAAAAAAATTTCATTACTGAAGAAATTGAAGTTACTGTTAT
29901  TACTTATCAAGATGAAATTCTAGGAGTTAATTTACCTGATTTAGTTCCTA
29951  TTGAAGTTGAGTTTGCTGAAGATGCTATTCAGGGCAATACTGCTAACATG
30001  GCAAGAAAAAAGCACGCCTTGTAACTGGTTATGAACTTGATGTACCCCA
30051  ATTTATTAATACTGGTGATAAGATTGTAATTGCCACTGTTGATGGCAATT
30101  ACCGTGAAAGGTTAACAAATAAATTAACTAGAACCCAAAGACGAATTGC
30151  TGTAGTGGAATTTATCTTTTCTCCTCTTTTTCTTACCTAAAGAAGCTG
30201  AAGTTATTCAAGCAGATTTTTTAGAGTATGATACTAAAGAACGACAACTA
30251  AATGAATGACAAAAACTAATTGTTAAAGCATTTAGTGAAAATATCTTCTC
30301  TTTTCAAAAGAAAATTGAAGAACAACAATTGAAAAATCAATTAGAAATTC
30351  AAACTAAATACAATAAAATATCAGGAAAAAGATTGATCTTTTAACTACT
30401  GCAGTTGTTTTATGTGCACTTAGTGAACAAAAGGCACATAATACTGATAA
30451  ACCACTTTTAATTAGTGAGGCATTGTTGATTATGGATCATTATTCACAAG
30501  GTGCTGAAAAAAAACAAACTCATGCTTTATTAGATAAGCTCTTGTAATGA
30551  AACGTAACTGAAGACAACACTATAATGTTTTTTAGCTAATCTAGTTTTA
30601  GTATTTGGCTTTGCTTTAAATATTTTGGTTGCAAAACAATCTTTAAATAA
30651  CACAACGCCCCAGTTCAGGTTTTGTTTGTAACTCCTTTTCTTGGCGTTG
30701  TCATAGGTGCTGTTCTCTATTTTTTTGATGTTAAGTGGTTTTTAATTGAC
30751  TATCCATACAAGAAATTTCACTTTCAAAAAAAATGAGCAATTGTTTATTT
30801  ATCAGGGGTTATTGTATTTTTTTAAATGTTTTAATTGGAGTAGTTTTAC
30851  TTGTTGTAATGGTTAATTACATTACTAACCAAATTCTTGAAAGGGAAATT
30901  GAAAGATTATTTACAAATTCATTACCTTATTTATGATCAACAACAGGAAC
30951  TAGTATTGTTTTAAGTCTTATTAGTATAGGAATGAGTAAAACTGCACATT
31001  TTTTTATTGATATAGAGATTTTGAAAGCCAAAAAAGGAGAACCCACTGAT
31051  CCTAATAAAACTGATAATAGAGCAGTTGTTATTAATCTTGATGAGAATAA
31101  AAAGAATGAAAAAGaACAGTCCCCTCCTTCTGCAGAAATGACTAGTCTTT
31151  AATTTCACTACCAAATAACCTTTTATGaACAAGCTCATTTAAAGTGTTAT
31201  CTTTTAAAAAAGTGCACACAATAACTGTTGCAAATTCCAAAGCACAACCA
31251  GCACTTCTTGCTGTTATTAATTTATTTGCTACTGTTACTTTTGCTGTTGA
31301  TCTGTTTTCAGACATAACTAAATTTGGGTTTGGAAAAGAAGAATAGATCT
31351  CATCTTTAGTGATAATACCATGTTTAAATAGAACATTCGGTGTGTCACAA
31401  ATAGCAAAAAGATAAAGGTTATTTACTTTGAAATAATTAATTGTTTTAAG
31451  CAGTTTTTCATCTTTATCTAAGTGTTTTGTAGCTCCTATTCCACCGGGAA
31501  TATAAACTGCATCAAATTCTGATAAGTTAATGGTGTTGACAATATTGTTA
31551  ACTTCAACAACACCATTACTAGCAGTTATCTTTTTTAATGAATGGTGATA
31601  ACATGTTGTTTGTATTGTTTTAATGAAACTAAATACAACCATTACATTAG
31651  TATATTCAACATCATTCATCTCTGGATAGACAATAACAAGTATCTTTTTC
31701  ATTTTATTTAGTACCAAATAAACGGTCCCCAGCATCACCAAGACCAGGGA
31751  TTATGTATCTATTGTCATTTAACTTTTCATCAATTGCTGCAAGAAATATA
31801  TCAACATGAGGATGCATTTTTtCTACTTTATTAATTCCTTCAGGTGCTGC
31851  TACTATAGCAATAACACTAATTTTGATAGGTTTATCTTCTTTAATAGATT
31901  TAATAGCAGTTAACAATGTAGTTCCAGTAGCAAGCATAGGATCAAGAATA
31951  ATAACATGTGAATCAGAGATGTTTTCAGGCATCTTTTTATAGTATGAAAT
32001  TACACTGGTTGTTTGGGTTTGACGATAGATTCCTAAATGACCAACTCTGA
32051  TTTTATCTGAATAGCGAACAATAGCATCAATCATTCCAAGTCCAGCACGC
32101  ATAATAGGTACAAGAACAATGTCATTTTTTAATTTGTAGCCCTTTGTTTT
32151  AGCAAAGGGAGTTTCAACTTCAACTGTTGCTAGTGGTAGCTGTTTAGTTG
32201  CTTCAAAAAAGAGTAATGAAGTGATTTGATTCAAGGCCATGCGAAACTGG
32251  GAGGTTGTTGTATTTTTATCACGCAGTTTTGTCAATTCATTCAAGATTAA
32301  AGCATGTTGAACTTTTTTATCACGTTAGTTATCTTTAAATAAGTTTAAA
32351  CTAAAAATTAGTTGAAAAGTTTATGATCATCTTGATGTTCAAATTCATCA
32401  AACAGTTGTAATTGTTCCATCGTTTCAACGTGTTTTTTAGTAATTTTGGT
32451  TCTTTTTTTGAAATCATTTAAGGAAGCAAATGGTTTTTCATTTCTTGCTT
32501  CTACAATTGAAGAAGCTACCGCTTCTCCCATTCCTGGAATAGTGATGAAA
32551  GGCGCAATTAAAACACCATTATGTTCAACAAACATCCTTGCATTAGAGTT
32601  TTGAATAGAGATTTGTTGCAACTTTATATTGCGTGCCATCATTTCTAAAT
32651  AAACTTCATAACTTGTTAAAAGCTCCGCTTCTTTTGGTTTAATCTTTTTT
32701  ATTCTGTAAAGCTTATTAAGTTCATCTAAACGGTTTTTAATAAATTCATA
32751  CCCTTTTTCAAAACCATTAATATCATGTTCCTTTAGTTTGAAACTTAATA
32801  AACAAGCATAGTAACTCAAAGGGTGATAAAGCTTAAATCAAGCAATTCTT
```

-continued

| The Nucleotide Sequence of the *Mycoplasma genitalium* Genome |
| --- |
| 32851 CAAGCCATTAAAACATAAGCTGCAGCATGTGCCTTAGGGAATAGATAATT |
| 32901 AATTTTTAAACAAGCATTAATCCAATATTGTTCAACACCACAGTTTTGCA |
| 32951 TCAGGCTAACTTCTTTAGCATTTACTTTAATACCTTTTCTTACTTTTTCC |
| 33001 ATGATTTCAAAAGCATCTTTTGCTTGCATCCCTTTATTAATTAGATAAAG |
| 33051 CATGATGTCATCTCTACAAGCAATTACATCTCTTAAAGTTAACCTATTGC |
| 33101 TTTTAATTAGTTTTTGTGCATTATCTGCTCACACGTTTTTACCATGGCTT |
| 33151 AATCCTGAAACTCTAATTAAGTCAGCAAAGTCTTTAGGTTTTGTCTGTTC |
| 33201 TAAAATTTTTCTAACAAATTTAGTCCCAAATTCAGGGATACCAACCGCTC |
| 33251 CTGTAACTTCATCAACAATGCCTGGTTTTAGGTTTAATGGTTTGTTTGAA |
| 33301 GAAAACATCGAAATTAAGTTCTTATCAAAGTGAGGGATATTTTGGGGATT |
| 33351 TATCTTAGTTAGATCAGCTAAGTGCTTTAACATTGTTGGATCATCTTGAC |
| 33401 CTAAGATATCAAGTTTTAATATGGCATCACCTAATGCATCATATTCAAAA |
| 33451 TGGGTGGTCTTTCATTCACTTTCAACATCATCTGCTGGAAAACCACAGGG |
| 33501 AGTAAATTCATAAACAGAATGATCACTAGGAAAGATCATAATTCCCCCTG |
| 33551 GATGTTGCCCTGTTGTTCTCTTAATTCCTATAAGCTTTTGTTTAAATCTT |
| 33601 TCAATTTCAGCAGTAGTTGCAAGATCAACACGTTTAATGATTTCAAAATA |
| 33651 GTTTCTAGCATAACCATAAGCAGTTTTTTCAGCAACTGTTGCAATTGTTC |
| 33701 CTGCCCTGAAGGTGTTATTAACTCCAAATAATTTTCTGACATAATCATGG |
| 33751 GCTTTAGCTTGATATTCGCTAGAAAAATTAAGATCGATATCAGGAATTTT |
| 33801 ATCACCAGAAAAACCCATAAAAGTAGCAAAAGGAATGTTATGACCATCAC |
| 33851 CTTTGAAACTTGCTTTTTCATGGCATTTAGGACAATCACGAATCATCAAA |
| 33901 TCATATCCATCATCAACACTGTCACTAACTTCAAAGTAATGACATTGTTC |
| 33951 ACAAAGATAATGAGCAGCTAATGGATTGATTCTGATATACCAATTAAAT |
| 34001 TAGCAATTAAAGAAGAGCCTATAGAACCACGTGGACCTACAAAATAACCA |
| 34051 TCTTTAACAGATTGTTCTACTAATAGATGGGAAATTCAAAAGACAATTCC |
| 34101 AAAACCATTACTAATGATTGCATTTAGTTCTTTTTCAATTCTTTCCTTAA |
| 34151 TAAGTTTAGGTAAATTTTTACCATACCTTTTTTCAGCTTGTTTTCAAGTT |
| 34201 TTATCAATTAATTTTTGGTTAGAATCTTGCATCACTGGTGGATAAAGCTT |
| 34251 GTTTTTAGTTGGTACTAATTCATTTAAGTCAAGTAGCTTCACTATCTTAT |
| 34301 TAGTGTTTTCAACGACTAATTTATAGGCAATATCTTCTCCTAAAAAACTC |
| 34351 ATTCTTTTTAGCATCTCATCAGTGGTGTGAAGAAATACTTCAGGAACGGT |
| 34401 TTGTTCTTTTTCTTTATTGTTAAAGTGTCTATGTCATTTCCCACCTAAGC |
| 34451 CCTTAGCACAAACTATTGCCTTATAATATTCATTTTCCCAAGGATGGATA |
| 34501 AAGTAAGCATCAGATGCAACAGCAACTAATTCTTAAGTTTTGTTGCTGT |
| 34551 TTTGATAACTAGTTTGATTGCATCATTAATAAGTTCTTTTTTCAGTCCTT |
| 34601 CACGTAGTGTATAACCAAGGTAAGCATTGGGTTGTGAAATAAGCACAAAG |
| 34651 TCAACTTTTTCAATTGCTTTTTCAAGTTCATTAATTGGTTTTGTTAATGC |
| 34701 AGCTTTAAAGATGTCACCCTGAACAGGGTTTTCTGTTAATAAAAAAGATT |
| 34751 TTCTAAATTTAGCTAAGCTGCTAGCTAAAACTAATGGTCTGTTAGCATTA |
| 34801 TGATCTGTTAATGCAATTGATAACATCTCATATAGGTTTTGAAAGCCCCG |
| 34851 TTGGTTTTTTACATAAACGATTGCTGTGTTTGTAAATACCCTTTTCATCA |
| 34901 GATCAATTTGACACTTTTTATTTAGGTTTTGATCTATCTCTGTTAAGGTA |
| 34951 TTAATACCCATTTCTTTTAACTGCTTTTTAAAGTAAAAGAAAACTTTTTT |
| 35001 TAAAGCTTCTGTATCATATTCAGCACGGTGTAATCTTTCATCATCAAATT |
| 35051 CAAGTTTTAGTTTAGAACAAATATTGCTTAAAGTATGGGATGAAAACAAG |
| 35101 GGATTCAATGCTCATGATAAACATAAGGTATCAATCAGTGGGTTGTTAA |
| 35151 TGGTTTGATGTTGTATTTTTCAAATTGAGTTTGCAAAAAGGGTAAATCAA |
| 35201 AATTAATACCATTATGAGCTACCATAACACAATCATCTAGATAATTTCTT |
| 35251 ATCTTTTCTAAACCTTGCTGTTGATCAATACCGCCTTCAAGCATCTCATC |
| 35301 AGTTATTTTGGTGATTTCAGTGATTGTTTTTGGGATAGGTTTGTCAATTT |
| 35351 TTAAAAAGAATTGCTGATGATCTATCTCGCTGTTATTCTTAATTTTGCGT |
| 35401 GCTGAAAACTCAATAACATCATCATACCTACCATGTAATCCAGTGGTTTC |
| 35451 AATATCAAAAATAACAAAGGTGGCATCACTTAACTTAGTGTTATCTGGGT |
| 35501 TGTGAACAATTTTGATGTGATCATCAGTTAAGTTGAATTCCAAACCATAG |
| 35551 ATAGCTTTAAATCATATTTTTAGCCACTTCATAAAACTTGGGATAAAT |
| 35601 ATGGATATTATCTTTATCTGTAACAGTTATTGCTTTTCAACCTCTTTCTT |
| 35651 TAGCAAACTGTGCATATTCTTCAATGTCATTGATACCATCAAAAGCAGTC |
| 35701 ATTTTAGTATGAAAAACTAACTCCACTCGCTTTTGTTTGATAAATCTAA |
| 35751 CCTTTTATAGTTATTAGGTATTTCAACAGGATTTATCTCTCTAACAATTC |
| 35801 CATATAAGATTTGAGTATTAGGGTCACGTTCTACTTGGATATGGGCTTTT |
| 35851 ATCCAATTGCCAATAGTAATTCCTTCAATCTTTTTTTCATCAGTATAGGA |
| 35901 TCATTTCAAAATTAACGATCCACCTAATTGAAAATCAGTTACATAGATAT |
| 35951 TAAGTGTTTTTTTACCAGTTAAACTTTCATGGGTTTTTAATTCAAAGATT |
| 36001 TGCCCAATAATCTTGACATCATCGATCTGTTGGTTAATCTTGTGGATAGG |
| 36051 GATAAATTCTGTTGCAAATACCTTTGTTTCAAACTGCTTATCATATTGAG |
| 36101 AAACAGTTACAGCTTTTACTTTTAATTTAGATTCATTTTTATCAATAGGA |
| 36151 TAAAGTGCAATGAAGTTAAAGTTTTTAAAACCAGCATTATTCATCCAAAA |
| 36201 AATGAAAGATTTACTTTTTTGAACTAATCATTCAGTTAATTCTTTGGTTT |
| 36251 GACATTGTGCTTTTAATTCGTCATTTTCATAACTAAGAAAATTGGGATTA |
| 36301 CTTAACTCTTGTTCAATGAGAATTTTGTATTTCTTATCTTTTGAAAAGAA |
| 36351 ACTGTGAAAATAGTCTTTAATAATAGCTATCGTTACAGAAGAAAAACTAT |
| 36401 TTTTTGATTTAAAGAATGGCTCATTCTCCTTAAAGGTAATGGTAAGTTTA |
| 36451 AAAGATTCATTATCAGCTTTAAATCCCTCATTTAATTCATTAAATCCTTC |
| 36501 ATATAAAGCATTTCAAATATCAATAGTTAAAGGGCGACTAATAGTTATTG |
| 36551 CAAATAGAAAAACCTTCTCTTCAATATATTTATTAAAGTAAATTGATTCA |
| 36601 ATCCTTTCAATTAAGCTGTTAAGCTCATTGTGGTCAAGGATATTGTTATC |
| 36651 TATCAAAAAATTGGAGAGTGCAAGAACCTTTTTATCTTTTTCATTCTCAA |

-continued

The Nucleotide Sequence of the *Mycoplasma genitalium* Genome

```
36701  GATTAAATACCATAAGCGTTTATTAAAAAAATCAAAATAAAAGATCGAAA
36751  TTTATCAATAATTATTTTTAGTTTTAGCCACTTTTTCGTAAAAAAAAAAA
36801  AAAAAAAAGCAGTTTTTGCTATTTTAGACTAAAAGTGGTTATATACCAAA
36851  ATTTAAACCTTCTTTTGGTTAGTTCTTACTAACAGTTTTAAATGTTACAC
36901  AAGTTTTTCAAAGTGTGAATTTAAAAACTTCAAATAGTTGTTTATTCTGT
36951  ATCTAATTAACCTTTAATCTTTCAATAATGAAAACAATTCATARACTATT
37001  TTTAGGTCTTTGTTTACCCGCAACATTAGGTCCTTTACTTGGAATTGTTG
37051  TTACAAATACTGACCAAAGTATTAAGTTTACAAGCAAATCAAATTCGATT
37101  AATAAGAATAACCAAAATAAAGAGTTGGCTCTACTTAGAGATAATTTGAT
37151  GAACGAAGCGAAAGTTGATGAACCACTTTCCTTTGAAAAACGGTTTGAAA
37201  ACTTTAAAAATAAGTATAGTGATATACATAGCTTAAATAACAGTGTTTTT
37251  TCACTTCATGACGTTTATGACTTATTAGGTGGATTTAAACAATCATTGAC
37301  AACATTTTTGATGAAGTGATTGCCCAACAACAAAAGATCAAGGATGCAG
37351  ATAAGATCTTTCCAAGTACTAAAGATAATCCACCTAAAGAAGAAAATCCT
37401  AATGTTTTAGATACACTAGCTAACTACCAAGGAGCAGGATTTTTCCCTAG
37451  TTTAGGTAAAAATGGTTTTAATTTACCTGAAGCAGTGTTCCAAAATTTCA
37501  CTGATTTTAGGATTAATGACTACAAGATTAAAAATTTTAATGTTGATCTT
37551  GTTAGTGAAAATGACATTATTAAACATGATAAAGTTCGTTATGCTTTTGA
37601  AGTTAAGTTCAATATTGCTTTAGTTTTATCTATTAATAAGTCAAATGTTG
37651  ATTTTGACTTTGATTTCATTTTAAAGACTGATAATTTCTCAGACATTGAA
37701  AACTTTAATGAAATTTTCAACAGAAAACCTGCTTTACAATTTCGTTTTTA
37751  TACCAAGATCAATGTACATAAGTTAAGTTTCAATGGTAGTGATTCCACTT
37801  ACATTGCCAATATCTTGTTACAAGATCAGTTCAACCTATTAGAAATTGAT
37851  TTAAATAAATCTATTTATGCATTAGATCTTGAAAATGCTAAAGAACGCTT
37901  TGATAAGGAATTTGTTCAACCTCTTTATCAAAAACGACGTGAAGCAAAGC
37951  TTGCTTGAGAAGAAGAACAGAGACGCATTGCTGAAGAACAACGTAGACAA
38001  GAAGAGGAGAGAGCTAGAATCTTAAAAGAGTTAAAAGAAAAAGCTGAGAA
38051  AGATAAAAGAGTTAAAGAAGCACAAAACAACCTTCAAAAAGCACTTGGTA
38101  ACTTAGATACTTTCTTTAACTTCTTTAGCAGTGGTCAAGATAGAGTTTTA
38151  CTTGGTTTTGATCCAAATAAATACAATGTGCAAACTCGTGAAGGTTTGTT
38201  TAAAGCATTACAAATTTCCTATTCTAACTTCAAAACTTGAACATTCTATA
38251  TCTCCTTGTTGGGGTGAAAAGAAGGTAGTGTTAAACTGTTGAAAAAACCT
38301  ATCTGAAATGCCTTGAGAGATGATAAAGCATTTCAATATGCTTTTGGTTT
38351  AGGTCCAAATACTTCTGAACAACAACTTGGTAGAGTAACCCTACCTGGTT
38401  ATGGTTATGAAGGAATTAGAATGAGTGATTGGTTGAGGTGAGCATTGGGT
38451  TACTATACTAGTTTCACTTTAAGTCCACCTAAAAATGTTGAAGCTAATCT
38501  TATAGGTGATGCTAATGATAAAAAACACATTTGAATCTCACCTCATACTT
38551  TCAAATTAAACAGAGAGTATGGTGATGGTGAAAGATTCAAAGGTAAAGCA
38601  TATCGTTTTAAACTATCAATAAGTTTTGAACTAGAAGGTCATTTAACTGC
38651  CCACTGATGAACAATTGCCTTTAGAGGTAGTATTCCTGGAAGCTGAAGTG
38701  GTAAGTTAAGAGTTACCCATGAGTTTGATGGTGATGTGCCTTACTATAGA
38751  TTACATACAACTCCACCACAATATCGTTTAACTGATGATATGAAATTATT
38801  GTTTGTTCCGCACAGTATCCAAAGGGTAACTGCAGTTGGTAATGAAAGCA
38851  TTAATGGTCTTCTCAGATCACAAAAACCTTCATAACTTGGAACGTCAATCA
38901  TATGAAGCGACTGCTCCTATTGATTTAATATCATATATGCTTTATGCAAT
38951  TAGTGATAAAAAACCACCTCAAAAATAAGTTTTATATCATTAACGTTTAA
39001  ATAAATATTATTGCTAAGATTACTTTAAACTTGTTAGCAAACTTTAATCA
39051  TTTTTTAGCTAAATTAAACAACCAGTTAATTAGTAAACAGTTCCAGAATT
39101  AAAATCAAATATTAGTTAGTTTTTATTTTGTATTTTCAAAATTCTACTCA
39151  ATTAGGATGATGGTTTCTTGCTGAATTGATAGGAACATTTATCCTAATTA
39201  TCTTTGGTAATGGTGCAGTTGCCCAAGTTAATTTAAAGAAGATGGCTACA
39251  AGTGAAACAAAAGCCAAGTTTTTAACAGTTGCACTTACTTGAGGAATAGG
39301  TGTTTTATTTGGTGTTTTAACTGCTAATGCTATCTTTAAGGGTAGTGGTC
39351  ATTTAAACCCTGCTATATCATTATTTTATGCAATTAATGGCAGTATCAAA
39401  TCACCTACTGCATTAATATGACCTGGTTTTGTAATTGGGATTTTAGCTCA
39451  ATTCTTAGGTGCAATGATAGCTCAAACAACACTTAACTTTTTATTTTGAA
39501  AACAACTATCATCAACCGATCCACAAACAGTTCTAGCAATGCATTGTACA
39551  AGTCCTAGTGTATTTAACATTACTAGGAATTTTCTAACTGAATTTATTGC
39601  AACTTTAATATTGATAGGTGGAGTTGTTGCTGCTAGTCACTTTCTTCATA
39651  ACAACCCAAACTCTGTTCCTCCTGGATTTATGGGGCTTTGATTGGTTGCT
39701  GGGATTATTATTGCTTTTGGTGGCGCTACAGGCTCCGCAATTAATCCTGC
39751  AAGGGATTTGGGAACTAGAATTGTGTTTCAATTAACTCCAATTAAAAATA
39801  AGGATGCGAATTGAAAGTACAGCTGAATTCCAGTAATTGCTCCTTTATCT
39851  GCAGGATTAGTTTTATCAATAATTATTGGGTTTTCCCCTGCACCTGTTCT
39901  TTAAAGTTTTTGGTTTTAACAGTAACGTGCTTTTTAGTTAAAAATGAGTG
39951  GTGCAGTTTGCATCTAGCTTCATAAGCTTCTGCATCACCAATTAAGACAA
40001  GGTTATCATTAGTATTTTTATTTACTAGTCTTTGGGTTCGTTGTGCTAAA
40051  CTACCACAAACATTGCAAATAGCATCAAGTTTATTAACTACATCAGCTAT
40101  TGCTAAAAGTTGGGGAATACAACCAAAAGGCTCAGCTCTAAAATCAGTAT
40151  CAAGCCCAGAAATAATTACATTTGTTCCTATCTCATTGAGAGTTGTAACA
40201  ACTTCTATAATCTCATTTGAAAAGAATTGTGCTTCATCAATGGCAACAAT
40251  TTGATAGTTTTTATCAACTAAGTGATCATAGATCTCAAAAGGAGAATTAA
40301  TAGTTATTGCTTGATCATATTCACCGTTGCGTGATTTGACAATATTAGTT
40351  TGTCTAGTATCAATTATTGGTTTGAAGATAACAACTGAAATTTTGGCTAT
40401  CTTTCACCGTTTTATTTTGTGAAGTAATTTCTCTGTTTTTCCAGAAAACA
40451  TTGGGCCACAAATAACTTCAGTTCAGCCCTTTTTGGTTTGAAAAGATGGT
40501  TGATATTTACCCATATAATTTCGAAATTATAATTAATGACACATGAACTT
```

-continued

| The Nucleotide Sequence of the *Mycoplasma genitalium* Genome | |
|---|---|
| 40551 | CTTGCAAAAACCAAGGGGAGTTAAAGATTGGTTTGGTGATGAATTAGTTT |
| 40601 | ATTTTAATTGGATTGTTAAAAAAATAAGATCTTTAGCATTTAATTGGGGT |
| 40651 | TTTAGTGAAGTTAAAACTCCGTTGTTTGAAAATGCACAACTTTTTCAAAG |
| 40701 | ATCTAATGCTAATGCTGATATTGTTCAAAAAGAACTATACCAGTTTTTTG |
| 40751 | ATAAATCTCAAAGAGAATTAGCTTTAAGACCTGAAGCTACTACACCAATA |
| 40801 | GTAAGACTTGCTTGTGAAAACAAATTAATGCAAGAAGCAAATTTTCCCTT |
| 40851 | AAAGTTATTTTGCATTGGTTCAATGTATCGTTATGAACGTCCACAAAACA |
| 40901 | ATAGGTTTCGTGAACATTGGCAATTTAGTTGCGAAGTATTTGGTTTTTCC |
| 40951 | AACCTGTTTATCTTTTTAGATACACTTTTGTTTGCTAACTCTTTGCTTGA |
| 41001 | AGCACTTGGAATTACTGGATATGTGCTTAAAATTAATAATCTTGCTAACT |
| 41051 | TTGAAACACTTAGTAAGTGAAATAAAGCCCTAAAAGATTATTTAACTCCA |
| 41101 | TATAAATTAGAACTAACTGAGCTTTCTCAAAAAAGATTAGAAAAAATCC |
| 41151 | TTTGAGAATTTTAGATGACAAGATAGATCAAAAAAAATCATTTGTTAAAA |
| 41201 | ATGCTCCTAAAATTACTGATTTTTTAGATGCAAGTGCAAAACAAGATTCA |
| 41251 | GAATTGTTAAAAACACAACTAAAAAAACACAATATTAGTTTTGAATGAAC |
| 41301 | AGACAATCTAGTTAGAGGATTGGATTACTATACTGGATTTGTGTTTGAAT |
| 41351 | ATGTAAAAAATCAAGACACAATTTTAGCAGGTGGAGTTTATGATAACTTA |
| 41401 | GTTGAAGAATTAAGTAGTAATCCAACTCCCGCATTAGGTTTTGCTTGTGG |
| 41451 | AATTGAACGGTTAATTAACTGTTTAGAAATTGATAAAAAAGCATTTATTT |
| 41501 | TGAATACTAAACCAAAGCAGATGTTAGTAATTTGCTTATTTGAAGAAGCG |
| 41551 | CTTGAAGAATTGGTTTGACTAGCTAAATTATGAAGGGAATATAACCAAGT |
| 41601 | AACTATTTATCCTAAGGTTATTAAAGTTGATAATGGGATTAGATTAGCAA |
| 41651 | ATCGCTTGGGTTATACTTTCATTGGCATTGTTGGAAAAACTGATTTTGAC |
| 41701 | AAAAAAGCTATTACAATCAAAAACTTAGTATCTAAACAACAGACCATTTA |
| 41751 | CACTTGAAATGAACTTGGAGAACGAAATGTGTTTTAACCAACGAATTTTA |
| 41801 | ATTGGCTCAATTTCAACTGAACAACTCAATAAAACAATAGTTATTATTGG |
| 41851 | GTGAATTAAACGGATTAAAAAGTTAGGTGAAATTAACTTTATTATCGTTG |
| 41901 | GTGATAAATCAGGAACTATCCAAGTAACTTGCAAAGATAAAGAACAGATT |
| 41951 | CAACAACTTACAAGAGAAGACATAGTTATTGTTAAAGCCAAATTACAACG |
| 42001 | CTTAGATAGTGTTAGATTTGAACTGATAAATCCAACTATTAAACTTTTTT |
| 42051 | CAAAGTCAAAAACTCCTCCTTTAATTATTGAAGATGAAACTGATGCTTTA |
| 42101 | GAAGAAGTTAGGTTAAAATACCGTTACCTTGATCTGAGAAGACGTTTGAT |
| 42151 | GCAAAAACGATTGTTATTGCGTCATCAATTTATATTAGCAATTCGTAACT |
| 42201 | GATTTAACCAGCAGGGTTTTATTGAAATAGAAACACCTACCTTATCCAAA |
| 42251 | TCAACTCCTGAGGGAGCACAAGACTTTTTAGTTCCTGCAAGAATTAGAAA |
| 42301 | AGATTGTTTTTATGCTTTAGTTCAAAGTCCACAAATCTATAAGCAGCTCT |
| 42351 | TAATGATTGCAGGAGTTGAAAAATATTTTCAAATTGCAAGGGTCTATCGT |
| 42401 | GATGAAGATAGCAGAAAAGATCGTCAACCAGAACACACACAAATTGATTT |
| 42451 | CGAGATCTCTTTTTGTAACCAAAAAATGATTATGAATCTAGTTGAAAAAC |
| 42501 | TCTTTTTTAGTGTTTTCTTAGATGTTTTTCAAATCAAAATAAAAAAGACT |
| 42551 | TTTCCTGTTTTTAAATTTTCAGAACTTTTTGAAAGATTTGGTAGCGATAA |
| 42601 | ACCAGATTTACGTTATGGTTTTGAAATAAAAGATTTCACCTCGCTTTTTC |
| 42651 | AAGATCATCAGAATCAGTTCACTAAATTAATTGAAGCAAAAGGCATTATT |
| 42701 | GGTGGTATTGAACTTACTAATATTGAGTTAAGTACAGACAAAATTAAAGC |
| 42751 | ATTAAGAAAAATTGCTAAGGACCATGATGTGAGTTTAGAAGTTCATAATA |
| 42801 | AAAATAATTCAACATTAAAAACTTCAATTAAATGTGATGAAAAAAACACT |
| 42851 | CTTCTGTTAGTAGCAAATAAATCTAAAAAGAAGGCATGAACTGCTTTAGG |
| 42901 | AGCAATTAGAAATGAGTTGAAATACCACTTGGATATTGTCAAACCTAACC |
| 42951 | AATACAGCTTTTGTTGAGTTGTTGATTTCCCTCTCTATGATTTTGATGAG |
| 43001 | AAAACAAATCAGTGAATATCAAATCACAACATCTTTTCAAAACCTAAACA |
| 43051 | AGAATGAATTGATAATTTTGAATCAAATAAAAACGAAGCATTAAGCGAAC |
| 43101 | AGTTTGATCTTGTTTTAAATGGTTTTGAAATTGGTAGTGGTTCAATAAGA |
| 43151 | ATTAATGATCCAATTGTTCAAAAAAGACTAATGAATTCTTTGAACATTGA |
| 43201 | CCCAAATAAGTTTGCTTTTCTTCTAGAAGCTTATCAATATGGTGCTCCTG |
| 43251 | TTCATGGTGGAATGGGACTAGGTATTGATCGTTTAATGATGATTCTTAAT |
| 43301 | CAAACTGATAACATCAGAGAAGTAATCGCTTTTCCTAAGAATAATCATGG |
| 43351 | TATTGAAGTCCATACAAACGCTCCTGATAAAATTGACAAAGAGGAGGTTA |
| 43401 | AATGATGGATAAAAGAACTAGTGAAATAGAGTTTCACTTAAAGAATCTTT |
| 43451 | TGGCTTGTGATGCATATAAACTTTCACACCGTTTAATGTATCCACAAGAT |
| 43501 | ACACAAAACCTTTATAGTATGTTAACTGCAAGAGGTGTTTATGGTGATTT |
| 43551 | TAAGGAGTTTGTTTGAAACCATGATTTTGCTAAAGAGATCCTTTTGAATG |
| 43601 | TATTTAATGGTTTTGTAAACAGTGTAATTGAAGTTAAAAAAAACAAATTG |
| 43651 | CTAGCTGCAGCATTGACAGATAAATTAGTTAGTGTTTTTAATGATCATGA |
| 43701 | ATTGGCTAATGAATTCACACAACACATCTGTCATTTAGCTAGTTTCTTAG |
| 43751 | AGAAAAATAAAAAAATGCCGTTAGTTGCAAAGATCCATGAAAGTGATCAA |
| 43801 | TCATTACCATTTAGAACTCCTTTAATAACTATAGAAGGAGTTGAAAATAT |
| 43851 | TCCAAACAACTTTGTATGGTTAGTTAATTACTTTGAAACTGTACTTCTAG |
| 43901 | AAAACATTTGGTTGTTTCAAACTGCTTCTACAGTTGCTAAAAGAATTAAA |
| 43951 | TCTTTACTTGAAAAATATGCTAAAGAAACCGCAGATGAAACAAGTTTTAT |
| 44001 | TAATTTTCAATGCCACGACTTTAGTATGCGGGGCATGAGTAGTTTGCAAA |
| 44051 | GTGCTTTGTATGTTGCTAGAGCACACTTGCAATACTTTACTGGAAGTGAC |
| 44101 | ACGATCTTAGGTGGGGATAATTCTCGTTCAATTTTAGCTTCTGAACATTC |
| 44151 | AGTGATGTGCGCAGATGGTAGTAAACATGAATTGAAAACTTTTCAACGTT |
| 44201 | TATTGGAAAAGTTTAAAGATAAAAAACTTTCTTTAGTGATTGATTCTTAT |
| 44251 | GACATGTGAAATGTCCTTGATAACATTATTCCAAGGTTAAAAAACTTAAT |
| 44301 | CTTAATGCGTGGTGCTACGCTTTATTTGCGTGCTGATTCTGGTAATTATC |
| 44351 | AAACTCTTATTTGCAATCCTAATTACAAAAAGCAAGATAAAAGTACATGA |

-continued

The Nucleotide Sequence of the *Mycoplasma genitalium* Genome

```
44401  GCAATGATCGATTACTTAGATCATCATTTTAGTTCAACTATAAATAAAAA
44451  AGGTTATAAGGTTTTAAACAAGAAAATTGGCATTATTTATGGTGATGGAA
44501  TCAcCTATCAAAAGATAGAATGGATCTTAAATTGTTTAAAAAACCATGGT
44551  TATTGTtCTTCAAACATTATTTTTGGAGTTGGTAGTAGCACTTATCAAAA
44601  TTTAAACCGTGATACTTTAGGTTTTGTATACAAATTGACTGCTATTAAAA
44651  GAAATAATAGATGGATAGGCGTTAAAAAAACTCCCATAACTGATCTATCT
44701  AAAAGTTCAAAAGGCGGTAGATATAAAACAAAGCGATTAATTACAGTTTA
44751  TTAATCAATTTCTTTCCATTTTAAAGCACGTTCAACTGCTTTATGTCAAC
44801  TGTTAATTTTGGTTTTTCTTATGTTTGGGTCCATAGTGCTTTTGAACTTT
44851  TTATCAAGAGTAGTGAGTTTTTCAAGTTGATGAATGTCTTTTCAAAATCC
44901  ACAAGCAAGTCCAGCTAAAAAACAAACACCAACTGCAGTGGTTTCTTTAT
44951  TTTTAGGGATAGAAACAATTACATCTGCAATATCAGCTTGAAACTGCATT
45001  AAATAGTTTGATTTAACAATCCCCCATCAGCTTTAATGCTAGTAATCTT
45051  ATAGCCTAGATCACTTGCCATTGCATTTAATAAATCATTAGTTTGAAAAG
45101  CAATTGACTCTAAGCTAGCTTTTACTATGTGCTCTCTTTTAGTGCTTGCT
45151  TCAATTCCTAAGATAATACCCCTAGCACTAGCATCTCATCAAGGAGCTCC
45201  AAGTCCACTGAAAGCTGGTACAAAAACTAGGTTTTGTTCATTTTCTTTTG
45251  CAAGTTCTGCATAAAAATCACTTTCCTTTTCTGAATAGATAATTTTTAAT
45301  GCATCCCTTAACCATTTTATAGCCGCACCCGCTACAAACACACTACCTTC
45351  CAATGCATATACAGGTGGATGATTTTCTAGTTGCCATGCTACTGTTGTGA
45401  GCAGATTGTGCTTTGAGAGTGTTGGTTTATCACCAATGTTCATGAGTACA
45451  AAACATCCAGTACCATAGGTATTTTTTACCATTCCAGGTTCAGTACAGAG
45501  TTGACCAAACAAAGCTGCTTGCTGGTCTCCTAAAACTGCTCTAATTGGTA
45551  CAATACCTTTAGCATTACTAGATCAGTGATTAGTTTCAATATCACCAAAG
45601  TAAGCATTGGAACTCAGAACTTTAGGTAAGATTGAAACTGGTACTTCAAA
45651  TAAATCACATAACTCTTTGGATCACTCCATTTTGACAATGTCAAATAAAA
45701  GAGTTCTTGAAGCATTTGAAACATCTGTAACATGCATTTTTCCATTAGTT
45751  AGTTTTCAGATTAATCAGCTATCAATGGTGCCAAATAACAACTTTTTTTG
45801  CTCCATTAGTTTCTTTGCTAAAGGAACATTTTTTAAGATTCAAGCTATCT
45851  TAGTAGCACTAAAATAGGGGTTAATAGGTAATCCAGTTTTTTGTTTTACT
45901  TTGGTTTGGATTAACTTATCCTCATTGAATTTTTGACATAGTGCTGCAGT
45951  TCTTTGATCCTGTCAAACGATGGCATTATAAACAGGCAAACCATTTTCTT
46001  TATTTCATAAAACTATTGTTTCTCTTTGATTGGTAATACCAACTGCAATC
46051  ACTTCATGAGATTTGATTTGTGCTTTATTTTTAGCACTTTGCATGGTAGC
46101  TAGTTGGGCTGATCAAATTTCTAGTGGATCTTGTTCAACTCAACCACTAT
46151  TAGGAAAAAAAGTGTTAAATTCGTTTTGTGCTATTGCTATTTGGTTAAGA
46201  TTGTGATCAAAAACAATTGATCGACAAGAACTAGTACCTTCATCTAAGGC
46251  AATAATGTATTGTTTTTTAGATCCATGATAAGTTGTAATTAGGATTTCA
46301  ATTTATCTTCTTTTTTAACTTTAAATTAAGGAGTTCAACTGCTCTCTTAG
46335  CACCCTGAAAAAATTGCTTACATACACAAAAALAAGAGCAATGGAGTTAA
46351  CAATAGCAGGACTTGATGTTAAACCAGGGGATTTCATGCCACCAAGGATG
46401  ATAAAGTTAGGATTGCTTTTTGCTGTTCTAATAACAAAGTCATTTGTTTC
46451  AATATCAATAGCTCTTGAACCTGCAAAACTATAAATACTATTTTCAAATT
46501  GCAATGAAGGAACCATTTTTTTACCAATAGTTTTAATTTGGTTAATTGAA
46551  TCTAAATCTATGGAACGAGTTTTGTTTTTTTCAATTCCCTCAACTGCATT
46601  AGGTCCCACAAGGATATTACCATCTAACATCTCAGCAACAACTACTCCCT
46651  TACCATGGATAGTAGGTACCATAAAAATAATTGTGTTAATCTTAAGGTTG
46701  TTTTGATTTTTTAAAACTAGATATTGTCCTTTTCTTGTTGTTTGTTTAAA
46751  ATTATCAACTTGTGTAGTTTCTGCTAGTCAATCTGCATAATGACCAGCTG
46801  CATCAATTAACTTTTTGGTTTTAAATTGTGGTGTTGTTTCATTGTTAATA
46851  AAAACTAAAAAATCATCATCAGAATCTATTTCAATTTTTGTAACTTTTT
46901  ATTTGAGTAGATGGCAACATTGTTTTGTAAACTAGCAAGGGCTAAACACT
46951  TGGTTGCAATTAAAGGGTCAATTAGTCAACTACCTTCAACTTTTAAACTA
47001  GCTACTACATTTGGATTGATAAACGGTTCTTGCAATAAAGTTTGTTGTTG
47051  ATCTAATATTTGAATGTTTTCAACAGGAATTGAGTTTTTAATTCCCCTTT
47101  CTTTTAACAAATTTAATTGAAGTTTTTCTTCATTGTTGAAAGCAACAATT
47151  AAAGTAGCAATTTTTTTCCTTGGGAAGATTAGTTTTTTAAATCAATCCTC
47201  AATTCAGATTTTTCTCCCTAAGATGTTGTATTTGGCAGTTAGCTTATTAG
47251  GATTAGGATCAATTCCTGAATGGATTACACCACTGTTAGCCTGCGAAGTT
47301  TCACAACCCAAAAAAGCATTTTTTTCTAAAAGTGCAACTTTTAATTTATA
47351  TTGGCTGAGTTCATATGCACAACTAGTACCGATGACACCCCACCCACAA
47401  TTAAAACGTCAATTGTTTGCATTAATTAATCTTCTAGTATTTAGTTAGTT
47451  ATTTTGCAAAAAAGGATTAGTTTTATAGTTGTGATTTACTTTTTGGTATC
47501  TCTATAAAAAGTAGTATCAAACATTTTTTATCTTTTGATTTCTTTTTAC
47551  TAAAAATAATTAGCTAAAATACCGTCATATATGGGAAAGCTATTATTTGG
47601  TAAGTTAGTTTTTAAAAAGAGCTTGTTTTTACTGAGTGGTATGAGCAGTT
47651  TAGCAGTTTTTTTAACTGCATGTGGGGCTACCAAAATATTTGATTCCTCT
47701  GTACAGCTATTAGTGTCAGATAACTTTTCCACACTTGCTGATAAATCATT
47751  TTCACAAATGTCCTATGAAGGAATCAGGAGCTTTTTTAAAAAAAGTAAGG
47801  GTGTTGATTTACCTGAAGCAGATAGTTCACAATTACAAGAAGGCAATGGC
47851  TTGTGAAAACGTCCTGGTTTTACATTAAGTGATAGAATTGCTACTTTTAA
47901  TAACATCAAAAATGATGGCTCTGATGTTATTGTTGCAACAGGTTTTAACC
47951  AACAAGAATCACTTCAAGCAATTACTTCTGATGACATTAGGTTTCAAAGT
48001  GATAAAGAAAGCTTAGCTAAAACAGGTTTTATTTTTGTTGATGGAGCTAT
48051  TGAAAAGGAGTTTAATAAAAGAAATGGTGTTCCTCAATTTAAGTCAACTC
48101  CTACCAATATCTCATCAGTTGCTTTTAGAAGTGATGATGGTTCTTTTTTA
48151  ACTGGAGTTGCTACTGCAGTTTACTTAAATCTTAACCAAGAATATTTCCT
```

-continued

The Nucleotide Sequence of the *Mycoplasma genitalium* Genome

```
48201  TGATAAAAGTGGTTGGTCAACTAATAGTAGTAATAATAACGAACTAACTG
48251  TAAGTGGTTTTGTAGGTATTGCTCTACCTTCAACGCTTTCTTTTCTAAAT
48301  GGTTTTCGACTAGGTATTGCTTATTTTAATGAAGTGATTTATAAACATTT
48351  AAGCGATGCACAAGATTCATCTGCACAAGTGACCACTTCTAAACAAACTG
48401  TTTTAAAACAACTTCAAGTTGCAAATGGTGAAAAAAGGATTAAAAAGATT
48451  AAATGGATTTCACCAAAACAAGGAAGTGATGGAGAAACTATAAACATTCA
48501  AGATCACCAATCAGGTTCTTTTTCAGATACTGAACCTAGAGCAATAACAA
48551  TAGCTAATAATTTAATTGATAAAGGAGTTAATGCTATCATTCCTATTGCT
48601  GGACCACAAACGAATTTAGTGGTTACTCAAATTGCTAGAAGACAAGCCCA
48651  TACTGCAGTTATTGGCGTTGATAGTGCACAGGAATTGCTAGATATTAATA
48701  TTGATGCTCCAAATAAAGATAAGTTAAAAATGGGGAATAAAAAGATTATT
48751  CCCTTCTCTTCTATTAAGGCTTTGGATGTTGCTGTTGAAAGTATCTTATC
48801  AACATTAGAAAAAGGTTCCAGCCAAATGGTTATCAAGGCTTTGGATATA
48851  ACAACATAGGTACAGTGAAAAACAACTCTGTTGGGGTTAGTGAAGCAGGT
48901  TATGAATTTTTAATAGATCCTGTTTTTTGAAAAAATACTAGTTCAATGCA
48951  AGCTATGTCTTTATCAGCAAGTCTAAAAGCTAATGCAGCATCTTCATCAG
49001  ATAATAAGAAAAAATTATCAGAAGTTGCTACTAAGAAAAATGAAAACGGT
49051  TCGACAAAAAATGGTAGTAATGACATCATTGACAAATATGCCAAACTCTT
49101  AACAAAATCTAGTTCTTCAACTAGTATGAGAAACGGTAGTTCAGATAGCA
49151  ATCAACAGAATTTTAAAACAACAGATAATGATGGTGATTGAACTATTGTT
49201  GGTGATGAATTAGGTAAATATAAGTCTAGTGAACTGCCTATTTTTACAGG
49251  TAGTTCTTCATACCCAACTTTTCAAACTGAAGCACAAAATGTTTTAGATG
49301  GTGGAGCGAATGTTGCTTCAACACAAGGCTTTAAATGAAGCTTTAAACAA
49351  ATTTAGAATTTTGATTACTTAAAGATATGAAAAAATTTCAAGCAGTTATT
49401  AAAGACCCAGTGGGAATTCACGCACGTCCTGCTTCTATCCTTGCAAGTGA
49451  GGCTAGTAAGTTTAAATCTGAACTTAAACTGGTAGCTCCAAGTGGTGTTG
49501  AAGGTAATATTAAATCAATTATTAACTTAATGTCTTTAGGAATTAGACAT
49551  AATGACAACATTACTATCAAAGCAGATGGAGCTGATGAAGAAGAAGCTTT
49601  AGCAGCTATTAAAGCTTGTCTTGAAAAAAATAAAGTTATCTAACTTAGCA
49651  TATTTTAATCAATTAAATCTGTTTATTTTTTAATAGTAAAAACACAATTT
49701  AACCTTGTTTCTATTTAACAAAATTGGTTTGAAAAAGGCTATCAATTTTG
49751  CTGTAAAAAATTAAGATATTTTTATCAAAAATTAGCATAAAAAATTGTT
49801  ATACTAATTAACGTTTTTTATTGAAAATTAAGTATTTAAATTGAACGaAC
49851  ATTCTTTAATTGAAATTGAAGGTTTGAACAAGACCTTTGATGATGGTTAT
49901  GTTTCTATAAGAGACATTAGCCTAAATATTAAAAAAGGCGAATTTATTAC
49951  TATTTTAGGCCCTTCTGGTTGTGGTAAAACTACCCTGTTGAGGTTATTAG
50001  CTGGATTTGAAGATCCTACTTATGGCAAGATCAAAGTTAATGGTATTGAC
50051  ATTAAAGACATGGCAATCCATAAGCGTCCTTTTGCGACAGTTTTTCAAGA
50101  CTATGCTTTATTTTCCCATCTAACTGTTTATAAAAACATTGCTTATGGTC
50151  TGAAGGTAATGTGAACAAAGTTAGATGAAATTCCAAAACTTGTAAGTGAT
50201  TATCAAAAGCAACTTGCTCTTAAGCATTTAAAGCTAGAAAGAAAAATAGA
50251  GCAGTTACAAAAAAACAATTCTAATGCTCAAAGAATAAAGAAATTAAAGG
50301  AAAAATTACAAAAACTTTTAGAAATTAACAAACAAAAAGTTATTGAGTTT
50351  GAAAATAAAGAAAAACTACGTAGAGAAGATATTTACAAGAATTTAGAGCA
50401  ATTAACAAAAGAATGGGATCTACTTTCTCAAAAGAAACTAAAAGAAGTTG
50451  AACAACAAAAACAAGCAATTGATAAAAGTTTTGAAAAAGTAGAGAATAAA
50501  TACAAAAAAGATCCTTGGTTTTTTCAACACAGTGAAATACGTTTAAAACA
50551  ATATCAGAAGAAAAAAACTGAGTTGAAAGCTGATATTAAAGCAACAAAGA
50601  ACAAAGAACAAATCCAAAAATTAACTAAAGAACTTCAAACCTTAAAACAA
50651  AAATACGCTAATAAAAAAGCAATTGACAAAGAGTATGACAAATTAGTTGT
50701  AGCTTACAATAAGAAAGACTATTGAACTTCTTATTGAGAAACATACACAC
50751  TTCAACAAAAAGAAGCTTTTGAAAAACGTTATCTTTCAAGAAAACTAACT
50801  AAAGCTGAACAAAATAAAAAAGTTAGTGATGTTATTGAAATGGTTGGTTT
50851  AAAAGGTAAAGAAGATCGTTTGCCTGATGAATTATCAGGGGAATGAAAC
50901  AAAGAGTTGCTTTAGCACGTTCTTTAGTAGTAGAACCTGAAATTCTTTTA
50951  TTAGATGAACCATTATCTGCACTTGATGCAAAGGTTAGAAAGAATTTACA
51001  AAAAGAATTACAACAGATTCATAAAAAAAGTGGATTGACTTTTATCTTAG
51051  TAACTCATGATCAAGAAGAGGCTTTAGTTTTATCAGATCGGATAGTGGTT
51101  ATGAATGAGGGAAACATCTTACAAGTTGGTAATCCTGTTGATATTTATGA
51151  CTCTCCTAAGACTGAATGAATTGCTAATTTCATTGGTCAAGCTAACATCT
51201  TTAAAGGTACTTATTTAGGAGAAAAAAAGATTCAGTTACAGAGTGGTGAA
51251  ATCATTCAAACTGATGTTGATAATAACTATGTTGTAGGTAAGCAATATAA
51301  GATCTTAATTCGTCCTGAAGACTTTGATCTTGTTCCTGAAAATAAAGGTT
51351  TTTTTAATGTTCGTGTTATTGATAAAAACTACAAAGGATTGCTTTGAAAG
51401  ATAACCACACAATTAAAAGATAACACTATTGTTGATTTGGAGAGTGTTAA
51451  TGAAGTTGATGTAAATAAGACCTTTGGTGTTTTATTTGATCCTATAGATG
51501  TTCATTTAATGGAAGTTTAACAAGATGCACATTAAGAaAAAATACTGACT
51551  TCTGCTCCCCTTCTTTTTATTAATGACAATCTTCTTTATTATTCCAATGG
51601  CATGGATTATTGTTAGTGGATTACAAAGTGAAGATGGGGCTAGTATTAGT
51651  CAAAAATATGAACCACTTGTTAGTGGCTTAGGTTTTTTTAACAGTTTCTG
51701  AACCAGTTTGTGGATCTCAATAGTGACTGTAATTGTTGCATTGTTGTTTT
51751  CTTTTCCTTTTTGTTACTTTCTCTCCCAATCAAAAAACAAAATTTTTAAA
51801  GCGTTTGTTATTTCAATTGCAACAGTTCCTATTTGAAGTAGTTTTCTTAT
51851  TAAGTTAATTGGATTGAAAACCCTACTTGATTTATTAATTGGACTTTCTT
51901  TAAACAGAGTTGGTGATAACAACTTAACTTTTGGTTCAGGATATACCTTA
51951  CTTGGAACAATTTATCTGTTTACTCCTTTTATGTTTTTACCACTTTATAA
52001  CCACTTCTGTGTTTTACCTAAAAACTTGTTGTTAGCTAGTCAAGATTTGG
```

-continued

The Nucleotide Sequence of the *Mycoplasma genitalium* Genome

```
52051 GTTATAACTGGATTTACAGCTTTGTGAAAGTAGTAATTCCTTTTTCTAAA
52101 ACCGCAATGTTATCAGGAATTGCTTTAACTTTTTTCCCTGCTTTAACTTC
52151 AGTTGCAATTGCTCAGTTTTTAGATAACTCTAACCAAGCCGAAACCCTTG
52201 GTAACTACATATTTACCTTGGGTAATAATGGTTATGATAGTGCAATTGAA
52251 AGAGGCAGAGCTGCTGGAGCAATTATTATTGCTGCTTTAATTACTTTTGC
52301 AATTTACTTTACTGTTGTTTTTTTGCCTAAAATTGTCCGTATTGTTCATA
52351 ACAAATGAAAACAACATGAAAAAGCATTTTAAGAATTTAATTAAAAACAG
52401 TTATTTCTTTCTGTTAATAACTTTAATCTATTTACCACTTTTAATAGTTG
52451 TACTTGTTAGTTTAAACGGTTCTTCTTCAAGAGGAAATATAGTGCTTGAT
52501 TTTGGTAATGTTTTAAATCCTAATCCTGATTCTAAATCTGCTTATTTAAG
52551 ATTAGGTGAAACTGATTTTGCAACACCACTAATAAATTCAATCATTATAG
52601 GTGTGATCACTGTTTTAGTGTCTGTTCCTATTGCTGTTATCAGTGCGTTT
52651 GCGCTTTTAAGAACAAGGAATGCTTTAAAAAAGACAATCTTTGGAATTAC
52701 TAATTTTTCTTTAGCAACTCCTGATATTATTACTGCTATCTCTTTAGTGT
52751 TGTTATTTGCTAACACTTGATTAAGTTTTAACCAGCAGTTAGGTTTTTTT
52801 ACCATTATTACTTCCCATATCTCTTTTTCAGTGCCTTATGCATTGATTTT
52851 GATTTACCCTAAAATTCAAAAATTGAATCCTAATTTAATTCTTGCTTCTC
52901 AAGATTTAGGCTATTCGCCTTTAAAAACTTTTTTCCATATTACTCTACCT
52951 TATCTAATGCCAAGTATTTTTTCAGCAGTACTAGTAGTATTTGCAACTAG
53001 TTTTGATGATTATGTAATTACCTCTTTAGTACAAGGATCAGTAAAAACTA
53051 TAGCAACTGAACTCTATTCATTTAGAAAAGGAATTAAAGCATGGGCAATC
53101 GCCTTTGGGTCTATTCTCATATTGATTAGTGTCTTAGGAGTCTGTTTAAT
53151 AACCCTGCAAAAGTATTTAAGGGAAAAAAGAAAGGAAATAATCAAAATAA
53201 GACAATGAAAkAACAGTTAAAATATTGCTTTTTCTCACTTTTTGTTAGTC
53251 TCTCATCAATATTGAGTAGTTGTGGTTCAACAACATTTGTACTAGCTAAC
53301 TTTGAATCTTATATTTCGCCCTTATTGCTAGAAAGAGTACAAGAAAAACA
53351 TCCCTTAACTTTCTTGACTTATCCTAGTAATGAAAAACTAATTAATGGTT
53401 TTGCTAACAACACTTATTCAGTAGCAGTAGCATCTACTTATGCAGTTAGT
53451 GAATTGATAGAAAGGGATCTATTATCACCAATAGATTGAAGTCAGTTTAA
53501 TCTGAAAAAAAGTAGTAGTTCAAGTGATAAAGTAAATAATGCCAGTGATG
53551 CAAAGGATTTGTTTATTGATTCAATTAAAGAGATCAGTCAACAAACCAAA
53601 GATAGTAAAAACAATGAATTACTGCATTGAGCAGTTCCTTATTTTCTTCA
53651 AAACTTAGTGTTTGTTTATCGTGGTGAAAAAATTAGTGAACTTGAACAGG
53701 AAAATGTTTCATGAACTGATGTAATTAAAGCAATTGTGAAACACAAAGAT
53751 CGCTTTAATGACAATAGGTTAGTTTTCATTGATGATGCTAGAACGATCTT
53801 TTCACTTGCTAACATCGTTAATACTAACAACAATTCAGCTGATGTTAATC
53851 CAAAGGAAGATGGAATTGGTTATTTCACTAATGTCTATGAAAGCTTTCAA
53901 AGACTTGGATTAACAAAATCTAATTTAGATAGTATCTTTGTTAATTCTGA
53951 TTCCAATATTGTGATCAATGAATTGGCAAGTGGTAGAAGACAAGGAGGAA
54001 TTGTTTACAATGGTGATGCAGTGTATGCTGCATTGGGCGGTGATTTACGT
54051 GATGAATTGAGTGAAGAACAGATTCCTGATGGGAACAACTTTCACATTGT
54101 GCAACCCAAAATTTCCCCAGTTGCTTTAGATCTTTTGGTTATCAATAAAC
54151 AACAATCTAATTTTCAAAAAGAAGCACATGAGATCATTTTTGATCTTGCT
54201 TTGGATGGTGCTGATCAAACTAAAGAACAGTTAATTAAAACTGATGAAGA
54251 ATTGGGTACTGATGATGAAGACTTTTACTTAAAAGGAGCGATGCAAAACT
54301 TTAGTTATGTGAACTATGTTTCACCATTAAAAGTAATATCTGATCCAAGT
54351 ACTGGAATAGTCAGTTCCAAAAAGAATAATGCTGAAATGAAAAGTAAACA
54401 AATGTCAACTGATCAAATGACTAGTGAAAAAGAATTTGATTATTACACTG
54451 AAACACTTAAAGCATTATTAGAGAAAGAAGATAGTGCAGAATTAAATGAA
54501 AATGAAAAAAAACTAGTTGAAACCATTAAGAAAGCTTACACTATTGAAAA
54551 AGATAGTTCAATTCGGTGAAACCAATTGGTCGAAAAACCAATTTCTCCCT
54601 TACAACGTAGTAATTTATCGTTATCTTGATTAGACTTTAAATTACACTGG
54651 TGATAATATGGAACAACCGTTGTGTGTTTAGGGATTGAAACAACCTGTG
54701 ATGACACAGGTCTTAGTATTGTCATTGATCAAAAAATCAAGAGTAACATT
54751 GTTATCTCTTCTGCTAACTTACATGTAAAAACAGGAGGAGTTGTACCTGA
54801 AATTGCAGCACGATGCCACGAACAAAATCTCTTTAAAGCAATAAGAGATT
54851 TAAATTTTGAGATAAGAGATTTATCTCACATTGCTTATGCATGTAATCCT
54901 GGGTTAGCAGGATGTTTACATGTGGGAGCCACTTTTGCTAGAAGCTTAAG
54951 TTTCTTATTAGACAAACCATTGTTACCCATCAACCATCTTTATGCGCATA
55001 TCTTTTCTTGTTTAATTGATCAAGATTTAAATAAGCTGCAATTACCAGCA
55051 TTAGGCCTTGTAATTTCAGGTGGACATACTGCCATTTATCTAGTTAAATC
55101 ATTTTATGAACTTGAACTAATTGCTGAAACTAGTGATGATGCAATTGGTG
55151 AAGTTTATGACAAGATAGGCAGAGCAATGGGCTTTGATTATCCTGCTGGT
55201 AGTAAAATTGATAGTCTTTTTAATAAAGAATTAGTTAAACCTCACTATTT
55251 CTTTAAACCTTCTACTAAGTGAACTAAGTTTTCCTATTCTGGTTTAAAAT
55301 CTCAGTGTTTAAACAAGATTAAACAAATAAGTGCTAATAAAACCCGAATT
55351 GATTGGAGTGAATTAGCATCCAATTTTCAAGCTACTATTATTGATCATTA
55401 CATTGATCATGTTAAAAATGCAATTAAAAAAATTTGCCCCTAAAATGTTGT
55451 TAGTAGGAGGTGGAGTTAGTGCCAATTCTTATCTATCTAACAGAATTAGT
55501 ACATTAAATTTACCCTTTTTAATTGCTGATAGCAAATACACCAGTGATAA
55551 TGGAGCAATGATTGGTTTTTATGCATCACTTTTAATTAATGGCGATAAGA
55601 ATTAAAAGTACAAGAGTTGGTAGATTTGTTTCTGAATCAGTGGGATTAGG
55651 TCATCCTGATAAAATTTGTGATCAGATTGCAGATAGTATCTTAGACCAAT
55701 GTTTACTACAGAGTAAAACTAGTCATGTAGCATGTGAAGTCTTTGCTTCT
55751 AAAAACCTTATTTTAATAGGTGGTGAGATTTCAACAAGTGGCTATGTTGA
55801 TGTTGTTCAAACTGCTTGAAGAATTTTAAGAAATTTAGGTTACAACGAGA
55851 CTGATTTCAGTTTTTTAAGCTGTATCAACAACCAATCACTAGAAATTAAT
```

-continued

| The Nucleotide Sequence of the *Mycoplasma genitalium* Genome | |
|---|---|
| 55901 | CAAGCAGTTTTAAAAAATAATGAGATTAATGCAGGAGATCAAGGCATTAC |
| 55951 | TGTTGGTTATGCAGTGAATGAAACAAAGCAACTAATGCCTTTAGGAGTTT |
| 56001 | TACTAGCACACTCGTTTTTAAAACAAGCAGAAAAACTAACAAAACAATTT |
| 56051 | GATTTTTTAAAAAATGATATGAAAAGTCAAGTGGTTTTAAACTACAGTTT |
| 56101 | AAACCAAGTTGAATGTGAAGAAGTTTTACTATCAATTCAACACACTAATG |
| 56151 | CTATTAGTTTAACAGAATTGAGAAAAGTGATTGAAAATAATGTAATTCTA |
| 56201 | CCTGTTTTAAACCAATATGGTTTTCAAGATAAAAAGCCAACTTGTTTAGT |
| 56251 | GAATCCTGGTGGTTCTTTTGTTTTAGGTGGACCTATGGCAGATACTGGAC |
| 56301 | TAACTGGTAGAAAAATCATTGTTGACACCTATGGTCCATATGCTCACCAT |
| 56351 | GGTGGTGGTAGCTTTAGTGGCAAAGATCCTAGTAAGGTGGATAGAACAGG |
| 56401 | TGCTTATTTTGCACGTTTTATCGCAAAACATATTGTAAGTTTAGGCTGGG |
| 56451 | CCAGTGAGTGTGAAGTCAGTATTAGCTGAGTCTTTTCAAAACCCAATCCA |
| 56501 | CAATCTATTACTGTTAAGTGTTTTAACACTAACATACAGTATGATGAAGT |
| 56551 | GTTAATTAATAGAGTTGTAAATAACTATTTCAACTGATCGATTACTAAAA |
| 56601 | TTATTGACAAGCTAAAATTACTTGATTTTGTTAAGTATTCTGATTATGCA |
| 56651 | GTTTATGGaCATTTTGGTAATGATCTTTCACCATGAGAACAGCCCACTGA |
| 56701 | ATTGGATAAATTAGAATGCTTAATCAAAAATTTCCATTAGATCCTAATAA |
| 56751 | AAAAAAGGAACAACAAGGCGTAGTAAAACCAAATCTACCGGTTGTTAAAG |
| 56801 | AAAAGAAAAAACAGCCATTTAAAAAACCAAATTGGAGTGAATTTAAGCTG |
| 56851 | TTCAACTTTTTTAAAAAGCACACTTATTTTTGCTTGGTTGTATTAGCTTT |
| 56901 | TCTTATCTTGATTATTTTACTTAGCAGCTTATTTGCTATTCCACTTAGCC |
| 56951 | AAATACCTTCAAGTACTGTTTAAAAGAATTGTCCAAATCCACCAAACGGG |
| 57001 | TTACTACCTGTTTTTAATAGTTTACCCATTTCTGTTGCTTTTAGTTGCAT |
| 57051 | CTTATTTCATTCCTTCATCAGTTTGTTTAACTCATCCATTTTTCTCCCTG |
| 57101 | AACCTTTTATGATGCGCTGTTTTCTATTAGGATCACGATTAATTAATTTG |
| 57151 | GGATGTCTCCTTTCTTCTCTAGTCATAGAGTTAATTAAAACCTTTCATAG |
| 57201 | TTCAATTTTGTTTTCAATTAATTCAGCATTTTCTTCTGATACAGAAAAGT |
| 57251 | TAGCAGGCAACATTTTTATCAGTGaACTGACACTTCCCATTTTGTGCATT |
| 57301 | TGTTGCATGTAGATCAAAAGATCTTCTAAATCCATTTTTCCCAAAAACAT |
| 57351 | CTTGCTGATGGTTTTAGTTAAATCTTTTTTATCAAAAACTTGTTCAGCTT |
| 57401 | TTTCAACTAAACTCATTACATCACCCAAACCTAAGATCCGATTGGCTATC |
| 57451 | CTTTCAGGATGAAATTGTTCCAATCCATCTAATTTTTCAGAAACACCAAT |
| 57501 | TAATTTAATGGGTACTTGTAAAAGTGAAGCTAATGAAAGTGCAGCTCCTG |
| 57551 | CTCTAGCATCACTGTCTAATTTACTGATAATAAATCCAGTTAGTTTTAAA |
| 57601 | CGTTTGTGGAACGTTTGAGCAACATTGATAATTTCCTGACCGCTTAATCC |
| 57651 | ATCTACTACCATGATAATTTCATCAGGATTTAATTCATTTTTAACACTTA |
| 57701 | CCAATTCATCCATTAATGTTTCATTTGTTTGTAATCTACCAGCGGTATCA |
| 57751 | CAAATGATTGTTTGACATTTTGCAGTTTTAAAAGCACTGAGTGCTGCTTT |
| 57801 | TGTTGTTTTAGCAACTGGTTGAGTGCCTTGTGCAAAAAATACGCTGTTAG |
| 57851 | TTTGTTGTGAAAGCGTTTCAAGTTGTTCAATGGCAGCGGGTCTGTAGATG |
| 57901 | TCCAAGCCTACTAACATTGTTTTTTGCTTGTATTTCTTTTCAAGTCAATA |
| 57951 | AGCTAGTTTGCCACAAGTTGTTGTTTTACCTGATCCTTGTAAACCAACCA |
| 58001 | TCATTATTTTTAAAGGTCTTTTTTCATTTAGTTCTTGGTTGGGTTGGCTT |
| 58051 | AAGATATTAATTAGTTCTGTTTTGATTGTTTTTAATAGAGACTTTTGCAA |
| 58101 | ATCTTGACCAGGTTCAATGGTTTGTCCTACTGTTTTATCTCTAATTGCTT |
| 58151 | TGATGAAATTTTTAACAACAAGCAGGTTAACATCAGCATCAAGCAATGCA |
| 58201 | ATTCTAATCTCTTTTAGAACTAACTCTACATCTTTCTCAGTGATCGTTTG |
| 58251 | AGCGTTAATTTTTTTTTGCATCGTGCGCATAACGATGCTTGATAACATTG |
| 58301 | CTTTGAACATGATTTTTAATTATTTATTATTAAATAATGTTTTAATAAAA |
| 58351 | CAATATTGCAATATGACCCCACATATAAGTGCTAAGAAAGATGACATTAG |
| 58401 | CAAAGTTGTTTTAATGCCAGGTGATCCATTGAGAGCTAAATGGATAGCTG |
| 58451 | AGCAATTCTTAGATCAAGCTAAATTAGTCAATGAAGTGAGGGGAATGTTT |
| 58501 | GCTTATACTGGGCAGTATAAATCTAAAACAGTTACAGTAATGGGCCATGG |
| 58551 | AATGGGGATCCCTTCTATTGGAATTTATTCATATGAGTTGATGAATTTTT |
| 58601 | ATGAGGTTGAAACTATCATTAGAATCGGAAGTTGTGGTGCTTTAGCACCG |
| 58651 | CAATTAAAATTAAAAGATCTTGTTATTGCTTCAAAAGCATGAAGTGAGTC |
| 58701 | TATTTATGCTAAAGACATGGGTGTTGAAATTCCAGAAGATAAGATCTTAT |
| 58751 | TTGCAACAAGTTCTTTAGTGGAATTAGCAAAAGAAACTGCGATTAAGAAC |
| 58801 | AAGCTTGATTTTCATGAAGGATTAGTATTTTGTGAGGATGCTTTTTATCA |
| 58851 | AACTAGAAAAGATGTAATTAGTCTTGCTAAAGAAAAAAATAGTTTAGCAG |
| 58901 | TTGAAATGGAAGCACATGCACTTTATGCTAATGCAATCCTGTTGAAGAAA |
| 58951 | AAAGCACTTACACTCTTAACAGTATCTGATTCTCTAGTAACTCATGAAGC |
| 59001 | ACTTAGTTCTGAATTAAGACAAAAGTCATTTAAGCAAATGGCTTTATTAG |
| 59051 | CACTTGAAATGACTCAAAAACTAATCTAATCTATGAAATTAGAATACAAC |
| 59101 | CGGATTATTGATAGCACCTTAGTCAAAGCTGATACGCTTCCCCATGAAAT |
| 59151 | AGATACTTTATGTGCTGATGCTCATAAATACCAGTTTTTTGCAGTGTGTG |
| 59201 | TTAATCCTAGTTATGTTAGTTATGCTAAAAACATCTTGAAAAATACTGCA |
| 59251 | GTTCAACTCTGTTGTGTTGTTGGTTTCCCCTTAGGACAAACAACCCAAAA |
| 59301 | ACAGAAGGTATATGAAGCTAAGATTGCTATTAAAGAGGGAGCGGATGAAA |
| 59351 | TTGATATGGTAATGAATATTGCTGAGTTTAAAAAACGTTGTGCTTGTGTT |
| 59401 | ATTACTGAAATTAGAGCTGTTAAAAAAGTGTGTGGCAAGCGTAAATTAAA |
| 59451 | AGTAATTATTGAAACTGCACTTTTAACAAATGATGAAATCAAAGATGCAG |
| 59501 | TTAATGTTTGCATTGATGGCAATGCAGATTATGTTAAAACTTCCACTGGT |
| 59551 | TTTTCTTTCCGTGGTGCATCTTTAGAAGATGTTCAGATTATGAATAATGC |
| 59601 | TGCAGCAAATTTAATTAAAATCAAAGCTTCAGGTGGGATTAAAACAGCAA |
| 59651 | AGCAATTTATAGATTTATTTCAAGCTGGAGCTAGTAGAATTGGAACTTCA |
| 59701 | AATGCGGTCCAAATAATGCAAGAATTAAAAAAAATGAACCATGAATATCA |

-continued

| The Nucleotide Sequence of the *Mycoplasma genitalium* Genome |
|---|
| 59751 TTAATTTAATTAATAAAAAACAACGCGGAAAAGCTTTAAATTTAGCTGAA |
| 59801 ATCAATTGGTTTGTTAATGCTGTTTTAAACAAAACCATTGCTGATTATCA |
| 59851 AATTACTGCATTTTTGATGGCTATTTGGTTTAAAGGGATGAACCCAAATG |
| 59901 AACTTTTTTATTAACAAAAGCAATGGTGGATACTGGTGAAATTATTAAG |
| 59951 TTTAATCACCATGGCAAGATTAGTGTTGATAAACATTCAACTGGTGGTAT |
| 60001 TGGTGATAAGGTTTCTTTAGCATTGGTTCCTATCTTAACTAGTTTAGGAT |
| 60051 TTAGTGTTGCTAAATTATCAGGAAGAGGCCTTGGTTATACTGGTGGAACA |
| 60101 ATTGATAAATTAGAAGCAGTTGGAGTTAAAACAGAATTAACTGACCAACA |
| 60151 AGCACAAGCATGTTTAGATAAAAATGATTGTTTTATCATCGGACAAAGTA |
| 60201 AGGACATCGCACCAGTTGATAAAGTACTTTATGGTTTAAGAGATATTACT |
| 60251 GGAACAGTTGATAGTTTGCCTTTAATTGCATCTAGTATTATGTCTAAAAA |
| 60301 GCTAGCAGTTATGAACGAGTATATTTTCATTGATCTTAAATATGGAAAAG |
| 60351 GTGCCTTTTGTAAAACTAAGAAAATTGCTAACGAACTTGCAAAACTGATG |
| 60401 CAAAGTATTGCTAAAAGTTTTAAAAGAAAGCTGTCTGTTAAATTAAGTGA |
| 60451 TATGAATCAAGTACTTGGTAAAGCTGTTGGCAATGTAATTGAAGTTAATG |
| 60501 AAGCTGTTAACTTTCTAAAACAAGATTTAGATCAAGTAGGACAAGATTTT |
| 60551 ATTGATTTAATGCAAACAATTGTTATTAACATTCTACTTGAAACAAAACA |
| 60601 AGCAAAAACCAAACAAAAGGCTATTGAACTTTATCAGGATGTTTTAACTA |
| 60651 GTAAAAAAGCATGAAATCGCTTTTTATCTTTTATTGAATCTCAAGGAGGA |
| 60701 AATGTTGAATTATTTACTCAAAAAGAAGGTTTTTTTAAACCTAAGTATAA |
| 60751 GGCATCTATAAAAGCTGAAAAAAGTGGTATACTACATTTTACTGATCCAA |
| 60801 TTGATTTAGCTAAAATTGGGATTAATCTAGGGGCAGGTAGGATGAAGAAA |
| 60851 ACAGATCAAATTGATCCAATGGCAGGGTTATTTTTAATGAAAAAAGATAA |
| 60901 TGAGTCTGTGGCAGTTGGAGACACTGTATTAAACCTGTATAGTTCTAGTC |
| 60951 CTATTAGCAATGAATATATCTCTGCTGCTCAAAAAACAATAATTATTAAT |
| 61001 AAATAAAAATTCCTATGAAGGTGAATTTAGAGTGGATAATTAAACAGTTA |
| 61051 CAAATGATAGTTAAAAGAGCATATACTCCCTTTTCTAACTTTAAAGTTGC |
| 61101 ATGTATGATTATTGCTAACAACCAAACTTTTTTTGGAGTTAACATTGAAA |
| 61151 ATTCTTCCTTTCCAGTAACTTTGTGTGCTGAAAGAAGCGCCATTGCTAGC |
| 61201 ATGGTTACAAGTGGTCATAGGAAAATTGATTATGTTTTTGTTTACTTCAA |
| 61251 TACTAAAAATAAGAGTAACTCACCCTGTGGAATGTGCAGACAAAACTTAC |
| 61301 TGGAATTTTCCCATCAAAAAACAAAGCTTTTTTGTATTGATAATGATAGT |
| 61351 AGTTATAAACAATTTTCCATTGATGAATTATTAATGAATGGTTTTAAAAA |
| 61401 GAGCTAATGGATAAACTTAGATTAGAAGTTGAAAGATGGTTAAATCATCC |
| 61451 TAATGTTAATTGGGAGTTAAAACAACAAATTAAGGAGTTGAATGAATCAG |
| 61501 AAATTCAAGAACTTTTTAGTTTGGAAAAACCTTTATTTGGCACTGCAGGT |
| 61551 GTAAGAAACAAAATGGCACCAGGTTATCATGGTATGAATGTTTTTTCTTA |
| 61601 TGCCTATTTGACCCAAGGTTATGTTAAGTACATTGAATCCATCAATGAAC |
| 61651 CAAAGCGTCAACTACGGTTTTTAGTAGCACGTGATACAAGAAAAAATGGT |
| 61701 GGTTTATTTTTAGAAACGGTTTGTGATGTAATTACATCTATGGGTCATTT |
| 61751 GGCTTATGTGTTTGATGATAACCAGCCAGTTTCAACACCTCTAGTGTCCC |
| 61801 ATGTCATTTTTAAATATGGTTTTAGTGGAGGTATTAATATCACAGCTAGC |
| 61851 CATAACCCTAAAGATGATAATGGTTTTAAGGTTTATGATCATACTGGTGC |
| 61901 ACAGCTTTTAGACACACAAACAAACCAATTGTTAAGTGATTTACCTTGTG |
| 61951 TTACATCTATGCTAGATTTGGAATTACAACCAAATCCAAAGTTTGTCCAT |
| 62001 ACTCTTGACAATGAAAAGGTTTATAAAAACTATTTCAGAGAGTTGAAAAA |
| 62051 GGTGTTGGTTATTAACAACAACAATTTCAAAGACATTAAGGTAGTTTTTA |
| 62101 GTGGGCTTAATGGGACTTCAGTTTGCTTAATGCAACGCTTTTTAAAGTAC |
| 62151 CTTGGTTATAGCAATATTATCAGTGTTGAGGAACAAAATTGGTTTGATGA |
| 62201 GAATTTTGAAAATGCTCCTAACTTAAATCCAGAGTATAAAGATACATGGA |
| 62251 TATTAGCACAAAAAATATGCTAAGAAAAATAATGCTAAGTTAATTATTATG |
| 62301 GCAGACCCTGATGCTGATAGATTTGCAATTGCAGAGTTAAATAATAATCA |
| 62351 ATGACATTATTTTTCAGGTAATGAAACAGGAGCAATTACTGCTTACTATA |
| 62401 AACTTAATCATAAGGTTTTTAAATCACCTTACATTGTCTCAACTTTTGTC |
| 62451 TCAACTTATTTGGTAAATAAGATTGCTAAAAGATATGGCGCTTTTGTGA |
| 62501 TAGAACCAATGTTGGTTTTAAGTACATTGGTCAAGCAATTAATGAGTTAT |
| 62551 CACAAACAAACGAATTAGTTGTTGGTTTTGAAGAGGCAATTGGTTTAATA |
| 62601 ACTAGTGATAAATTAAACCGCGAGAAAGATGCTTATCAAGCTGCTGCATT |
| 62651 ATTGCTTGAGATTGCTAGACATTGCAAAGAACAAAACATCACGCTTTTAG |
| 62701 ATTTTTATAAAAGAATTCTTTCTGAGTTTGGTGAATATTTCAATTTAACA |
| 62751 ATATCTCATCCCTTTAAAGCTACTGCTACTGATTGAAAAGAAGAGATTAA |
| 62801 AGCTTTATTTAATCAACTTATAAATGCTAATTTAACTGAAGTGGCTGGTT |
| 62851 TTAAAGTAGTTAAAGTCCATCTTGATAAACAAACAAATATCTTAGATGTT |
| 62901 GGTTTTGAAAATGGCTGGGTTAAATTCCGCTTTTCAGGTACTGAACCTAA |
| 62951 ATTGAAATTTACTTTGACCTAACTAATGGCACTAGAGAGGCTCTAGAAA |
| 63001 AGCAAGCTAAGAAAATTTATAAATTCTTTGTAAATTTACTCAAACTCAAC |
| 63051 AAAGCTTAAATTTTCTAAAGGTAAGTTAATTAATTGGGTTTTAGATGTTA |
| 63101 ATTCTATCTCTACAACTGCTTTGTTAACTGTACCTTGATAAAGTGCTTTT |
| 63151 ATCTGTCCTTGAACATGAATAGTATCAGTTAAATGTACCTCTACTAAATT |
| 63201 ACCAACACTAAATTCAAAGAGTTGTTCAACTTTATTGTCAGTATCAAGAA |
| 63251 TTTCATATTTGCCCAAAAAAGGAACTAATACTGATGGATCAAGTTTGGTT |
| 63301 TGCTCACTTTGAATAATCGTTGCTTTTTCTTTCCATTCATCTTGTTCTTG |
| 63351 ACTATTTTGTAGTTTTTTAAAAGCTTCTTTTAGTTTTTCAGCATCAACAA |
| 63401 TTTCTGAATCTTCATCCTCTTTTGGTTTTGAATGGCTTGTTTTTGTTTT |
| 63451 AAGATATATTGAAATTTTTCATCAAATTTATCACTGTCCATTTCAATAAT |
| 63501 GGCAGTATTTGTTAGCATAATTCGTTTGCTAGGATTGATTGATATCCCTT |
| 63551 TAAGCATTTGTTCTAAATTATTAGCATCTTTTTCATCTAAAGGGATAGGT |

-continued

The Nucleotide Sequence of the *Mycoplasma genitalium* Genome

```
63601 AAAGCACCCCTGCCAGAAGAACCTACTATGCCAGTGATCCCAGGGAAGTT
63651 ACGAACAATTCTTCAAGCATCTTCACTATAAATCATCTTTATGTAGATGT
63701 ATCTACCAAGGAGATTTTTTTCACTAATTTTTACCCTAAGATAACGGTAA
63751 TCATCAAGAACAAACCATTTGTTAAAAGTAGTGTTCTTTAAGGAACGAGG
63801 AAGTTTTCCTGATTTTAATGAATAAACTTCTTCATGAACTTCCCTTTCTT
63851 TTAGAACTTTAACATCAACAATCTCATGATTAAATCCTAAAGCTTGAATT
63901 TTAGCTTTTAGATTTTTTACAACAGCTTCATCTTTAATACTAACAGGAGC
63951 TACATACCACTTTGGTGTTAATTCACTAGCTTGCATAAATTAATTTTTAA
64001 ATATTCCCAACGTAATTAACAATTGATTGATACCAAAAAAGATTCCTACC
64051 ATCAGTCCACTAACTAGCAAAATTAAAAGAAAAATTATGATAAGTTGTCT
64101 ACCTTTTACTCAAACAATTTTGTTGATCTCTTTATCAACTCCAAATCATA
64151 AATTAACAATTCGTTTTTTAAAAGGAAGCTTGGGTTTCTTTTCCTTTGCT
64201 AAACTTTCATGCTTTTCTTTTTCTTTAGTTCTTTCCTTATCTTTACTTTT
64251 CTTGGCTTCTGTTCTAAGTTTGAGCTGTTTATGTAACTCATGAATTGAAG
64301 CATCATCATAAGCAGTTAGCTTTTCCTTCTTTTTAAAGCTAAAAGGCAGT
64351 TTTTTTTCCATGGCTTTTTAAAAAGAATCTAGATGCTTAGTTTTTTGATT
64401 GCACTGCTTGCAGTACTTGTTGATGATAAGTCGCTGCAAAGGTTGTTTTG
64451 TTCACCGTTTTACATAGTTACGACTTAAACAGTCTTGACAGACAAAAATA
64501 ATCTTTTTGCGCAACTTCAGTAGCAAATTATAAATTATCTGCTTGTTTTA
64551 CTAATTTAATCTTTTGATAGCAATAGAGCTGTAAAAGGCCAAAGGGTAAA
64601 AAACAAGATCAGTGTAGAATTTTTTTGAATTTAGGTTCAATATTTTCACA
64651 TGCAGTATTAATTGTTTTTCAAATCATTATGCTGATAACTAACTGGATGA
64701 TCATAAAACAGATAGCAAAAACTCCTAAAACAATTAAAACTGCTCGTAAA
64751 TTAAAAAAAATAGGATCACTTCTAATTGCACTTAAACTAGCTTTTCTAAT
64801 TAAATCAAAGATGATACCAATCCCTACTAAAGAGATAATACAAACTAAAA
64851 AAAAGATACTAATTAACAAAAGAATCTCATTAAGGTTATGGAGTTTTTA
64901 AATACTTTCATGGAAAAGTGTATAGAGCATACTTGATTTTAAATGCATTT
64951 TTTTAGCTAAATAATTGCATGCATCTTTTAACTTAACACCAATATCCATT
65001 AACTTCTTTATTTCATATACTAAGTATTGATTGGAAGATAATGTTTGGTG
65051 ATTAATATTTTGATTATCAATAACAATTACAAATTCTCCTTTTAAAGTGA
65101 TGTCAGGTAAAGTGTTTTCACTGGTGTTAAATCAATAATGTGATTCATGT
65151 AACTTAGTTAATTCTCTTCCTATAAAAACGTCATTGTTTTTAAAACATT
65201 TTTCACAGTTTCTAAAGTATTTtCTAACCTATGCACTGCTTCAAAAAAAA
65251 CGATAGTGCTTTTCTGATTTTGATAGGTACTTAAATAATTTTTGAGCTGA
65301 TTTTGTTTGTGACTTAAAAAACCTAAAAACAAAAGTGGTGTTGTTTTAAA
65351 ACCACTAGTGATCAATCCACACATTAATGCACTAGGACCATTAATAACTT
65401 CGATTCTTATCTCCTTATTTTTTGATATGATCCAATTAATCATTTCATTA
65451 CCAGGATCAGATAAACTAGGATAACCTGCATCACTAACAAGACAACACTT
65501 AAAGTTAGTTATAAATTCCTCAGCAAAAGTTAAATTCTGTTTTTCTTTAA
65551 AACTGTTGTTAATAACAAACTTTTTTTGCTTGCAATCAATGTTGAGTAAA
65601 TCCAGCATTTTTCTTGTTACTCTACTATCTTCACAGAATAACACTTCACA
65651 ATCTTGTAACGCTTTTTTAGCTCTTTCACTTATCTCTTGAATATTACCAA
65701 TTGGTGTAGCAACTACTTTAAGTGTTTTCATACATCTTGAAAAGTTAGAT
65751 TTAATAAGTTAAGTTTTTTAAATAGTTGCTTGTGGTTAAAATAAGGTAAA
65801 TTAAGATTATTGCATAAAAGTAATCGCTTTTTCTTATCATTTAACTTTAA
65851 GCTTAAATACTGATCTCATAATATGCTTTGATTAGCATTTTTTGTGATTG
65901 CAACACGATTATTTAAAGCAGCAATTAAAGCACTAGTTTCCATTTCAGCA
65951 ATACCAGCTTTTTTAGCGTTTTTTAACCTTGCATTCATATCAACATAACA
66001 GTTGTAATAGTTTGTTAGATGTTGTTCTAATTTACTTCTAATCTTTTTGC
66051 CTTGTTGATCTGGATCTAATAACAAGATAACAGTTTGCTTTTCACTGATT
66101 TTTTTAATTAGGTTAATAGTTTCTTTTTTTAAAGCTGAACCATTTGTTGT
66151 AATTACATCTACATCAAAAATTTGCTGTAATTTAGCTTGGTCAGTTTTAC
66201 CCTCACAAACAATTACCCCATCAATTTTTATACGTGCTTTTTGATCCATT
66251 CAATGTGACGTTCATATATTGCAGAAACTGATAAGCTGTTAGCGTAACAC
66301 AGAACAACCTCTTCATATAAAGATGCTAGATCAACTACTTCAAACTGCTT
66351 TACAGCTTTAAACTTATATTGAGGAATAGAGTTTGATACAAACAAGAAAT
66401 CAATTAGTTTTTGATCAAATGCTTCCATAAACTTTTGTTCTGCATCATTG
66451 TTAAACAAACCATGAGTTGCCATTACACACACTTTTTTAGCTTGTTCTTT
66501 TTGTAATAGCTTGGCTGCTGCAATTACTGTACCACCAGTATCTATCATGT
66551 CATCAACTATTAAaCAGTTTTTATTTTTCACTTCACCTAAAACATTAATT
66601 GATTCAGCAACATTATGAGATGGTCTTCTTTTATCAATAATGGCTAATGG
66651 TAGTTCTAGTGTATTTGCAATTAACCTTGCTCTTTTAACCCCACCATAAT
66701 CAGGGGAAACAACCACCAAGTCTTTTTTACCAAGTAGTTCTATAACTCTA
66751 AAAAGAAAGATGTGATAAGTTCTTAAAGAATCAACGGGAATATCAAAAAA
66801 ACCTTGGGTTTGATCACTATGAATGTCAGTTAGAACAACCCTGTTAGCAC
66851 CTGCTTTTGTTAACATATCAGCAATCAATTTACTGGTAATTGGTTCTCTT
66901 CCTTTTGTTTTCTATCTTGTCTTGCATATCCATAATAGGGTAGAATGGC
66951 AGTAATACTTTTAGCACTACCTCTTTTCAATGCATCAATAGCAATTAAAA
67001 GTTCCATTAAGCTATCGTTAACATTAGGACAGGTTGATTGAAAAATATAG
67051 ATATCTTTGTTACGAACTGATTCATCAAAACGGATATAAGtTTCACCATC
67101 AGCAAAGTGTTCGCAAACCATTTTGCCCTCTGAAATATTTAGTTTTTTGC
67151 AGATATTTTCAACCAGTGTTTTGCTTTTAGATAAACTAAAAATAACGTGC
67201 TTTTTATTATCGATACTCAGCTTCAAGCTCGCGTCGGATTGTTTTCTTTT
67251 TAATAGTTTCACGTTTGTCAAATTTCTTTTTAGGTTTTGCCAATCAAATT
67301 TCCACTTTAATTTTGCCATTTCTAAAGAATACTTTACTTGGGATTACAGA
67351 TAAAGATTGTTGTTGTTTTTTATTGATAATTTGTTTAATTTCATGTTTAT
67401 TTAATAAAAGTTTCTTAATTCTATCTGAAGCGTGATTTAATGGACCTGCA
```

-continued

The Nucleotide Sequence of the *Mycoplasma genitalium* Genome

```
67451 AAACTATAAGGTGGAATAGTGAACTGTTCTAAAAAAAGCTCATTGTTTTT
67501 AACAAAAACATAAGCTTCTTTTAAACTACCTTGACCTAAACTTAAAGCTT
67551 TAACTTCACTTCCTTTTAAAACTATTCCAGCACAATAAGATTCCATTAAA
67601 TGATAGTCATATTTAGCCTTAGGATTGTTAACAAGAATTAACATTTATCA
67651 ATGAAATTATCTGTAATTATACCTACTTACAATTGTGCATCATTTATTGA
67701 AAAAGCAATTAATTCAATTGTTAAAAATAGACCTAATGATTTGGAAATAG
67751 AAGTTTTAATTATTGATGATGGATCAATTGACAATACTAACAAAGTTATT
67801 AAGAAAATTCAAGACCAAATTAATAATTTAACTTTGCAGTATTTTTACAA
67851 AAGTAATGGTAACTGGGGTAGTGTTATTAATTATGTTAGAAACAATAAAC
67901 TAGCAAAAGGGGAATGAGTAACAGTATTGGATAGTGATGACATTTTTTCA
67951 AAAAAAACAATTTCTATTTTTCAAAAATATGCCCAAAAACAAAGATATGA
68001 TGCGATTATTTTTGACTACTATAAATGCTGAAAAAAGTTTTTGTGAAAAA
68051 TTCCTACCTATGCAAGGTTTAGAAAAGAAATTAAAGGTGAATTGAAAAAA
68101 CAAACACCTTTTTGTATTCCCTTAGCTAAGTTTTTTAAAAATGAGGTTTT
68151 CTATCAACTTCCTAAACTAAGAGAAAATGTTGGTTTTCAAGACGCTATTT
68201 ATACGATGCATGCATTACAAATTGCAAATAATGTTTTCCATGTTTCTAAA
68251 GCTGGAGGATATTACTTTTTTAAAAGGGTAGGTAACTCTATGAGTATCCC
68301 TTGACACAGTTCTAGGTTTGATATTGAAGTACAAATCTGCAAGGATCTGA
68351 TTGAAAATAATGCGCAAGAGATCGCTTTAGTGCATTTACTTCGTTTAAAA
68401 TTTCGTAATTTAGTTGATGATAAAAAGATTAAATTTACAGTTAAAAGAGA
68451 CTTTTGTTTTAGTGGTTTTAGTTGGTATAGTAGGTTAATTTTATCTCTGA
68501 TGTATAACTTCTGATTGAAACGTTATTTCAACAGTTCTGAATAACGATTT
68551 TTTTGCTTATTTGCAATTACAAACTGTCATTCATTGAGTTTTCATTTTCT
68601 TGTCATTTCCTGAACCAATTGATCACCATCTTTAATCCAACAAGCAGGAA
68651 AGAACTTAACAATTAGGTTTGCTAGTGCAATAAGTCCTAAGAAGAAAACA
68701 ATACTTACAATTACCCCTGGTAAAATACTTGTACCTTTTCCTTGAATTAA
68751 AACAGGCGCTTGGAGAAATACTGATTGGGTAATGTCAAATAAGGTGTAAG
68801 CAATATAACCAAAGCCCCAACAAAATCCAAAAGAATAGGAAGTTCATTC
68851 TTCTTGTAATCTTTAAATTCATATGGCAGGATTAAATTTGAACTTGATAA
68901 ACTCCAAGCAAATGCACCACCGATAAATGAAAAGATACTAATTAAAGCAA
68951 ACCCAGCTGCACTACCAATACCAAGTGTTGCTGCAAACATGATGATTATA
69001 AGCAATACCACTATGTTAGCTGTTAATAAGAAGTGCATTCACCTCTTCTT
69051 GTCATAAATGGTTTTATTAAATGGTGAAAAAACAACAAAGCCCAAAGCAT
69101 AACCAATAACTCAAAAAATAGCAAGTGTTGCTAAACCTGTTGTGTACACA
69151 CCAGTACTTATCAAACCATTTGATCCTGATGGGGAAACAGTTTGCAAGAT
69201 GCTAAATCAAGCTGGAGTTAACGGATTGACTATTAGTATTAAAACTATGC
69251 CATAAACACCAATTAATTTTCATGTTGTTTTATTCTTTAAGATATCTATG
69301 GATTTTGGTTGAGTAGTTAAACTCATATTTTCCTTAGTTTGCTTTTGAGG
69351 AAAGATGTGATCTATCTTGCTTTCAAACCATAAAAATAAACATAAGTTAG
69401 CAAACACAACCAAAATCATCACAGTCATAATGTAAACCCAGTATTGAGAG
69451 GCTACTTGTTGAACTTGTTCAAATAAAAACGGTGTGAAAACTACTGCAAT
69501 CCCAATGTTAAAACCCCAAAGGTTAGCATTAGATAGGATTGATTTTTTTC
69551 TGTTTGAAGAAAGATTAGCAATTGCTGGTTGAGTATAAACTACTAAGGTA
69601 GTTCCACCAATAGCAATTGTGCTTCTAAAGATAATAAACAATGCATAACC
69651 AGTAATTGATGCAGCTGTACCAATACTATTACCATCCAAACCCTTAATAA
69701 GTTCAACACTTGTTCCATCTGCAAGCATCGTTTTACCATTGATCATCACC
69751 GGTCCAAGTAATTGACCCACTTGTAAATTGCTACTTAGTGAACTTAATTG
69801 AGTTTTTACTGAATCTGATAAAGGTCTTAATAAAGTTAATTGATTATGAC
69851 CATTCAAAGGGTCTCCTATAATAAGAAAGGGAAAACAAACACACATGATT
69901 CCCATCATGATTAAAACCGCATAACGATAACCAAATTTCAAAACAACAAC
69951 TCCACAAAGAATAGAACCTACTGCTCTCAATAAAGTGATAGTTCAGTTGG
70001 TGGAAGATGTGGCTATTTGCCCAGCATTTTCAGTAAAGAAAGAACTTAAC
70051 CAACCACTGTACTGTGGTAAAGTGGTGGTTGATTGAGTAAGTATACCAGT
70101 TGGTTTACCACTAATTCGATCAATTACAAACCATTCAACTACAAACAATA
70151 GATACCCAAAAATTACTATGATCCACAGGGTAATAAGTTTCAGATCACTT
70201 ACTTTTTTTTGACTTTTATTTTCCACAAATTAAGACAGAATTTACATTAG
70251 ACTAATTTTAAAAGCTGTAGCTAATTGTTTTTTAGAACAAACTGAATCAA
70301 AGAATTTGAAATTGTCTTTCATTGTTAACAGCATTTAACAACAAAATTGA
70351 ATAAAAATAAAAAACAGACCCTGATGGTCTGTTGGATATTTAATGGCGGA
70401 AGCGGTGGGATTCGAACCCACGCACCGTAGAACGATCTAACACCTTAGCA
70451 GGGTGTCCTCTTAACCACTTGAGTACGCTCCCAGTTTGTTGTTAAATTTA
70501 TTATAAATATGCAACTAATTAGCGCTTTAGATGTTTAAAAATTTATTAAG
70551 ACCATCCCTATTTTTTAACTGGAGCCAAAAAACATTTAAAAATAAATTTT
70601 CGTTTTTAAAACAAGCAGCAAATGCATTACAAAAACAGGCTGTTATCAAT
70651 GATAACAATGTTGCATTTGAAGCTTTAAAAAAGCGTGAAGAAGAGATTAC
70701 AACTGGAATTATTACTAGTTTAGCTTTACCTCACTTACAAAGTCAAAGTG
70751 TTATAGAACCTTTTGTTGCTGTATTTAAGGTTAAAAACTTAGATTGACAA
70801 TCATTAGATCAAAAACCAGTTAAATTGATATTTTTAATTGGTGTTCTTGT
70851 TGACAAAACCAATTTGCATCTTGATTTCATTAGTAACTTTTCCAAGTTAA
70901 TGTTGAATGAAACATTTGCAAGTAAGGTTTTAAATGTCACTAGCTATAAC
70951 GGCTTGATTAAACTAATTGATCTTTTTAACCAACAAAAAGTGCAAGACCA
71001 ACCAGCTGTTGAAACAAAAAAAGAGTATGACTTTGTTGCTGTAACAGCAT
71051 GCCCAACTGGCATTGCCCATACTTTCATGGCTAAAGAAGCGTTGGAAGCA
71101 TTTGCAAAAAAGCATAACTTATATGTAAAAGTTGAAACTCAAGGTACAGA
71151 TGGGATACAAAATCAACTTACAAGTGACGATATTAATAACGCTAAAGGTG
71201 TTATTCTTGCTTGTGATCGTTTAATTGATTTCTCTAGGTTTTATGCAAAT
71251 AAGAATGTGATTGAAGTGTCAACTACTAAAGCCATTAAAAAACCTGATGA
```

-continued

The Nucleotide Sequence of the *Mycoplasma genitalium* Genome

```
71301 GGTGTATGAATTAATTAAAAACCAAAAGGGTAAACAGCTTGCAAATAGTG
71351 CTAAACCAACTAATCAAACCCAATTAGCTGAAAGTGAAGGGGAATTCAAC
71401 TTTAATAATTTTCACAAGCGGATTTATCGTGCCATTTTAAGTGGTGTTTC
71451 TTACATGCTACCATTCGTTGTTTTTGGTGGGATATTAATTGCACTCTCTT
71501 TTCTAATTGATATAAATAACGCTAATAATGCTGGTGGTAACTTTGGCACA
71551 ATTAATCCTGTTGCTAACTGGTTAAATAAGCTAGGAGGAATTTCCTTTAG
71601 TTTAATTGTTCCTATCTTATCTGCATACATTGCATATGCATTGGTATCAA
71651 GACAGGGATTATTACCTGGTTTTGTTGTTGGTTTAATCTCTTCAGGACAA
71701 TTTTTATTARATATTGTTCTGACCAATGGAACAATTGAATGGTTAGCACC
71751 ATCACAAGTATCAAGTGGCTTTTTTGGTGCTATCTTTGGAGGACTTTTGA
71801 GTGCTTGCTTAATAATTGTTCAACAAAACTACATCTATAAAAAATTACCT
71851 CAATCTTTGCAGGGAATTAAAAACATCTTGTTTATTCCCTTGTTTGGTAC
71901 TTTATTCACTGCTGGTTTATTTTGGGTTATTAACATTCCTTTAATTTATC
71951 TAAACTATGGATTAAGTCTGTTTTTAAATATTATGAACAGCCCTATCCTA
72001 GCACCTTTACTTGGTTTTGTAATTGGGTTGATGATGTGCTTTGATTTAGG
72051 GGGGCCAATTAATAAAGCAGCTTATGTTTTTGGTGTTGTTTCTTTACAAA
72101 ATCAAAATGCAGGAACAATTTCGATGGCTGCAGCTATGCTATCAGGGATG
72151 GTACCTCCTTTATCAATTGCTTTGGCAGCTTCCATTCGAAAGAGCTGCTT
72201 TGATAAACAGGAATTACCTGCAGCTTATGCTTGTTATCTGATGGGATTGA
72251 GTTTTATTAGTGAAGGTGCTATCCCATTTGTTGTTAAAAAACCTAAGGTG
72301 ATGTTAACTGCTAACTTAATTGCTGGAGCAATTTGTGGAGCATTAACAGG
72351 AGCATTTGCCTTATCAATTCGTGCTCCTCATGGCGGTGTTTTTGTGTTTG
72401 CACTTTTAAAAACTACTTTACAAGGGATTGAAGGAGCTACATTACAAACT
72451 GGAGTTGGCATTGGTTTGGCATTGGTTTGTTTAATAATTAGTATGATAGT
72501 TGGTAGTAGTATTATCATTGGCTATGACTTGATTGCAAAACATAACCAAA
72551 GAAAGCAAAATCTGAATAGTTAATTACGCTTGCGCAATTGATTATTATGT
72601 TGATTTAAACAAGCAAAAAAATAGTGTTTTAATACCTGGTGGTAAGGGGA
72651 TTAATGTTGCTATTGTAATGAAATCACTTGGTTTTGATCCAACTGTCATT
72701 ACTTTTTTGGGACAACCCACTAAAAACTTATTTTTAGAGTTGGTAAAACC
72751 TTATGATCTAAATATAGTTAGCTTCATTTCTGAAACTAAAACAAGAATTA
72801 ACCTTAAGTTATTAAAAGATGAAAAAACTACTGAAATTAATGATTTAAGT
72851 CCTTTAATAACAGATGCTAATCTAACTGAATTGTTAACTTTTTTAAAAGC
72901 TAATGTTAAGAATAATGATTTGGTTATCATCAACGGAAGATTTAAATTTG
72951 AAGCTTTAGAAAAAGTTCTAAACTTGGTCTTTACATTAACAGAAAATGTG
73001 GTTATAGATGTTGATGAAAGCAAAATGTTAACGCTTTTAAATCAGTCTAA
73051 ACCACTAGTTATGAAACCTAACATTGATGAGTTTCAAACTATGATTAATA
73101 CTTTTTTTCACGATCAACAAAGCTTAATAGCAGCAATTAAAAAATTTCAT
73151 TACTGTAAGCTCTTATTATTATCTGATGGTGACAAAGGAGCTTATCTTTT
73201 TGATCAGAATAAGTTATTGTTTGTAAGTTCTATCACTCCTAAACAAGTAG
73251 TTAGCACCACAGGAGCAGGTGATACTTTGTTGGCAGTTTTTTTAGCAAAT
73301 TTGATTCTAAAGGTAGATTTAAAAACTGCTTTGATTAAAGCAACTAACTA
73351 TGCAAGTGCAACAATTAGTAAGTTAGGTGTTGTTGATAGTAAAGACAAAA
73401 TTAGTGTTATAACCCCAAAAAGTTACTATTTATAATTAATATTTGATGGT
73451 AAAAAGAAAGCGAAAGCCTAAGCTTAATTCGCGTAATATTTTAACTATCC
73501 AGATTGTTTTAACAATCTTTAGTATGATCTTTTTTCTTACTTTGCTATCT
73551 TTAATCTTGTTTTTGAGTTTGCAAAGTAATTTAGCTACAGCTTTAGTTGA
73601 AAACAGAAATAAAGCTGTGGAACTTGTAGATAACATTGTCTTTTTTTAAA
73651 AGAACTGATTTTTAAATTTGTCTCTGACTAATTTATTAGTGTGTTAAACC
73701 TAATTAAAAATGTTATTCGTTCTTTAAAGAGTGCTAAGATTGCTTTAATA
73751 GCGTTAACTTTTTTAATTTTTGTTGCTGTTGGTGGTTTTGTGTTGTTAAA
73801 TAACACAGTTAATAATTTTAACGCTGCTTTTAACTATGTCACCCACACTG
73851 GTAAATTAAGCAATGCCATCATTAATGAGCGTTATGACTTTGGTAAATTA
73901 GAGTTTCAAGAACAGACCAATAATTCTCAGAATAGTAGCGACAGTTTTAC
73951 TTTAACTTTAACTAATGATTCAAGAACAAGTTTTATTAATAATGCCTTGA
74001 GAACTAACCCTTCTTTGTATGAAGGATTAGTAACCCAAACTTTTAGCTAT
74051 CAAAACAAAACTGAAATGACTGAAAAAACCAATATAGTTAATCAGTCTAA
74101 AATTATTGCTGCTAACAATCTTAACAATGCATTAAGTAAAGATAAACAGC
74151 TCTTAGTTTCAGGTCAACTTGAAAAACTAAATGCTGTTTTTCGGGAATAT
74201 AAAGCTATTAATATTACTGACAAAAGTGTTTTTAAAAAATTGATAGTATC
74251 AGAACCTAATGATTTGGTAAATAGCCTAGTTATTTTTGATGGTCAAAATT
74301 TATCTAGCTCCAAACAAAGTGATTTCAATAATTTTTTAAATCAATTTAAC
74351 GAAATTAAATCAAAGGGTAAAGATAATTTAAGTACTACTTTAAAAACTGG
74401 GCAGTATCAGGCATTTTTACAAACTCTTTTTGATTATGCTCAAGCGAGTG
74451 AAACAACATTAAAAGATCAGCTTCAAAAGTTAATTTCAAATCCAGATTCA
74501 AGTGAAACAAATCAGGTTAAAAATCTCTTTGATACTCCAAGTACGCTTAC
74551 TAATATTGGGGGTCAATTAACCTTACAATGAACAGAAAATAGCCTAACAA
74601 AACAGATAGTTATCTTTGATCCTAGTAGTTATGAAACAATAGTCGCTCCT
74651 GGTAACTGAACTTATCAACAACAATTAGGTAAAGAAGTTTATCCTGATAT
74701 TAACAACTGAGAAAGTATTAAAAAACTACCACTTGAACAATTTGAAAGTG
74751 AATTTTTAAAAATTGATCAAAAGTATAAGATCAGTATTGATAATATCGAT
74801 TATTTAGTTATTGGGGTTGGAATTAGTCCAGATTTTGTTTATCCTGTTTT
74851 TAGTGCATCTTTAATTGTTCCTAACATTGAAAATGAACAACTTTACTATG
74901 TTAACCAAACTGGATATGAAAGAACTTTTTCCTCTTTTTTAACAAATCCA
74951 GTTGAAACAGCAATAGTAGCAAGATTGATTAATCTTGAAAGTGATCTTAA
75001 TACTATCAACCAGTGAGCTGTTGAAAACATGTCATGACCAACAAACATTA
75051 AAGCTGCATACAGTAGTTCTGATACCACTAATATTTTGAATTTATTAGCA
75101 GCAAGAACAGTTTTTATCCCTAATCTAATTAACACAATTAATTTAGTGGC
```

-continued

The Nucleotide Sequence of the *Mycoplasma genitalium* Genome

```
75151 TTTGTTTTTAACTATTGCTATCCTAACTGTTGCTATAATTGTCAGCATTT
75201 TAATCCTGATTAGTTATTTAAAGAAAAACACTGAGCAAATTGGCATTTTA
75251 AAAGCAAATGGGTTAAGTGGTAAAAAGATTAACCTTAGCTTGTTAATCTT
75301 TGGGTTAATTCCTGCTATAGTAGGTGCTATTTCTGGATATAGCTTTGGAA
75351 TTGGATTTCAAGACGTAGCTATTCATCTATTTAGTAACTATTGATTTATA
75401 CCAACAGCAACATCAAGTTTTTCAGTAGTAGGATTGTTGTTTTTTCACT
75451 GTTTGTTATCTTAATTATGAGTAGTATATCGCTTTTAGTGGGATCAATTA
75501 TCTTAAAGAAGGATGTTGTAAAGATTTTAAAGCATGACAGTGAATTTAAA
75551 GTTTCAAGATTAGGACTTAGTTCTAAGAAATTGTTTGCTAGGTTTGGTAT
75601 TATGACCAGGTTTAGAGTAGCATTAGCATTTAACGCTCCTTGAAAATTAG
75651 TTTTTCTAACCTTGATGAGTTCATTTACAATGATGATTTTAAACCTTAGT
75701 TTTGCAACTAAAGATAGCTTTGAAAATGCTCAATCAAAAACTAATTTAAC
75751 TAATCAGAACCACCAATATGAATTTGAACTCGCTTCAGCAACAACACAAA
75801 GTGGTTTATTGAAGTGACAGTTATTTGCAGAACTAGGTACAACTGATAAA
75851 AGAAGTGAAAGTAGTGTAAAGCTTGCAAATAAAAGGATGGATATTAGTAA
75901 TGTTGATGCATCTAAAGATTGAAAGAACCAACAAGTAATTAATTTTTTAA
75951 GCGATGCTAGTGGCTTTAGTAATGATTTAAATTACCTTGAAAACATTGTT
76001 CAATCCAAGATAGGTTTAGACTATTCATTGGGATTTAACAATATTGTTTC
76051 AAATCCCTGAAGGTTAAGTGAAACATTAATGCCAACTAACCAAGCATCTG
76101 CTTCCAACACTGCTTTTCAAAATTTTTTAAAAGCAATCATTACTATAAAT
76151 CCAAGCCAAGGATCGCAATTCATTAAACAAACCCAAGATCCATTAACAAA
76201 AAGATTTATCTATGCAATTGACAGTGATAAGGCATTAAAAAATAATAATG
76251 AACAAAACGGTTCCCAAAACCACTTAACTTTAAATGATGATTTTGCTAAA
76301 TTTCTCTACAGTCAATTTGAATTAATTAAAAAGAGTGGGAATGCAAGTAA
76351 TGAAGATTTAAATGCAATTGATTTTGAAAACCCCCAAACAATCAGAGATT
76401 TTTACAACAAGTACAATGCTTTACCACCATTAGATTACAAACTTAGCTTT
76451 AATGTAATAGGTTTACCCAAAGAGACAATTGCTGGACAAATTGACACCCC
76501 TAAGTATGGATTTTTAACCCTTCATGGTGAATATCAAAATACTCCTATCA
76551 AGATTAAAGGTATTAAAGATTGAAAAGATAAAGTGGATAATTTAGGTCCA
76601 GTTTTGAGTGATCAAAACAACCACATTATTAATCAAGAATTGTTTAAAAA
76651 TTATTCTTTTGATCCTTTGATAGTTAACAATTCTGCTGCAAAAAAATACC
76701 AACTTGCAATAGGTAGTGAGATTAATATTGCAGTTAACAACAGCTTCAAA
76751 CGGATTGACAATAAGATCATTAATCAAGATCCTTTAGTGAATGCTACCTT
76801 TAGAGTTGTAGGGATTAACAATTCCGCTCATGATCCTGAATTTTTCACTA
76851 GTTATAGTACTGCTTTTAAAGTATTGGAATATCCCAATGAATGGTTCGTA
76901 AAAAAACTTCCATTTAATAGCTTCTATGCTAATTCGCTTTTAAGTTTTGT
76951 TCAATCTACTTCGCTATTTTCTGAATCTGGTATTTTTCCTGCTACTAGTA
77001 GTTTTTCAACTAATAACACTGTACTTGTTGAGTTAATTAAAAAAACCATT
77051 AATTACAAGAATGGTCAAATGAATCAAACTTCAAGTAATGACTCTTCTAA
77101 GAAAGAAAATTACCAAAAATTGCAAAAAGCATTAGGAATATCAACTGATT
77151 TGGAGATTAGTAAAGTTAATGAATATGTTGCTATCTTAGCAAGGGTTTAT
77201 AATGGTTTACCTTACAACTCTACTATTAGCTTTATTAGCAATGTTGCTGC
77251 TAACAACGCTTTATTTGGAAATATTGCTAACACCACCAAGCAGATTCAAG
77301 CTGTTGTAATTGCAGTGATTATTCCTATAATCATGTTGATTATTCTTTTG
77351 GTTTCAACTACCTTAATTCAAGAGTTGAAAAAAATTGCTATTAGATTAAA
77401 AGCATTGGGATATTCCAATTTAAAAATTCTCGCTTCATTTTTATCAATAT
77451 ACATCCCTTTATTTGCCTTTGGTTTGTTGATTTCTATCCCCTTTTCTATC
77501 TATCTAATTGCACTACATAATGAGGTAATTTTTGCAAGCTCATCGATCTT
77551 TTTAGATGCTTTTTTAAGTTTTGAAAGTGCAATTGGTTCAATGTTAGTTT
77601 TACTAGCGGTTTTATCAATTACCTTTGTGTTGAATTGATTAGAGTTGAAC
77651 AAAATTAAGATTGACAAGGAAATCAAAAACTCCTAATGGATTTTTTCTCT
77701 TTAAACAAAATCATAAAACCCAACCAGAAATTCACTAGTAATGAAGCTGA
77751 ATTTCTACAGATAGCTACTGATTATTTGGAGGAAAGTCAAAACTATCTTC
77801 AAAAGGGTTTAAAGCAATTAAAAAAAGAATATAAAAGATCCATTATTTAT
77851 AACCCTAACCTTGAATATAAACGCTTTGTTAAATGAAAAGAAAATTTCAC
77901 TGAAACATTTGAAAGTTATTATGACAGGTTTTTTATTACCAAATACAACC
77951 ATTATTCACTAAGCTTACTTTTTAGCTTATTAATGAACAGATTGAAACA
78001 GTTATTGCTAGTTACAACTCATTTCTAAATGAGCATAATAAGTTAGCTTT
78051 TAATAAAGTTAGTTTTAGTTTTGAAAAGAAACTTTTTGAAGCTACACAAC
78101 AGTTTAATAACTTAGAAAAAAACACTGCTATTAGTGATGATTTACCGCTC
78151 CAGTTTAAAGTTAGAACAACTCAACTAAAAGCCCAAAGAGAAAGGGAATT
78201 GAAGAACTTGTTGAATAAAATCAAGCTTAAAAATTTAAGTGAAAAAAAAC
78251 AAGAAATTTTGTTAAATAACTGGTTTAATAGCAACGAACGTTTGTTTTTA
78301 AAAAATGAAGTGAAAAAGGTTAATTGACTAAACTCGCCAAGACAAAAACA
78351 ACAAGCAGCTCAAATTGATGATCAAAACATTATTGAATTGAAAAATGTGT
78401 ATAAATACATCACTAATGGCATTACTACAAATGCAGTTCTTAAAGGAGTT
78451 GATCTTGCCATTAAAAGTCATGATTTTATTGTGATTTTAGGCCCTTCAGG
78501 ATCTGGTAAAACCACATTACTAAACATTATTTCAGGGATGGATAGAGCTT
78551 CTAGTGGTAGTGTTATTGTCAATGGTTATAACATGATTTGTTTAAATGAT
78601 AGAAAGCTCACTAAATTCCGTCAAAAGTATGTTGGTTACATCTTTCAACA
78651 ATACGGTTTATTACCTAATTTAACAGTTAGAGAAAACATTGAGATAGGAG
78701 CAAATCTTCAACCAGATCCTAGTAAAAGGATCAGCATTGATGCACTTTTA
78751 GAAGCGGTTGGGATGGATAGTTTGCAAAAGAAGCTTCCTAATGAATTGAG
78801 TGGTGGGCAACAGCAACGTGTTTCCATTGCAAGAGCTTTTGCTAAAAACC
78851 CCTTATTAATTTTTGGTGATGAACCTACTGGGGCACTTGATCTTGAGATG
78901 ACCCAAATTGTTTTAAAACAGTTTTTAGCAATTAAAAAGCGTTATCAAAC
78951 GACAATGATTATTGTTACCCACAACAATTTAATTGCTAACTTAGCTGATT
```

-continued

| The Nucleotide Sequence of the *Mycoplasma genitalium* Genome |
|---|
| 79001 TAGTTATCTATGTAGCAGATGGAAAAATAAAATCACTACACAGGAACTTA |
| 79051 AATCCTAAACAGGTTGAAGAGATCCATTGAATTTAGATTATGAAATACTT |
| 79101 ATATGCCACTCAACACCTTACTTTAAATGCTATTAAGCATGCTAAGGGAG |
| 79151 GACATGTTGGCATGGCCATTGGTGCAAGTCCTATCTTATTTAGTTTATTT |
| 79201 ACTAAACACTTTCACTTTGATCCTGACCAACCAAAGTGGATCAACAGAGA |
| 79251 TCGCTTTGTTTTAAGTGCTGGCCATGGTAGCATGGCATTATATTCAATTT |
| 79301 TCCATTTTGCCGGACTTATTTCTAAACAAGAGATCTTACAGCATAAACAT |
| 79351 GGTCAAATTAACACTTCTTCCCATCCTGAATATGCTCCAAATAACTTCAT |
| 79401 AGATGCATCAACAGGCCCTTTAGGTCAAGGCTTTGGCATGGCAGTTGGCA |
| 79451 TGGTGTTAGCACAAAAGTTATTAGCTAATGAATTTAAAGAGCTAAGTGAT |
| 79501 AAATTGTTTGACCATTACACCTATGTGGTTGTTGGGGATGGAGATCTACA |
| 79551 GGAGGGGGTTAGTTATGAAGTTAGTCAAATTGCTGGGTTATATAAATTAA |
| 79601 ATAAACTAATTGTGCTTCATGATTCAAATAGAGTGCAAATGGATAGTGAA |
| 79651 GTAAAAAAAGTTGCTAATGAAAATCTAAAGGTTAGGTTTGAAAACGTTGG |
| 79701 TTGGAATTACATCCATACTGATGATCAACTAGAAAATATTGATCAAGCTA |
| 79751 TTATTAAAGCCAAACAATCAGATAAGCCAACTTTTATTGAAGTGAGAACA |
| 79801 ACTATTGCTAAAAACACCCACCTTGAAGATCAGTATGGAGGACATTGGTT |
| 79851 TATTCCCAATGAAGTGGACTTTCAACTTTTTGAGAAAAGAACAAATACTA |
| 79901 ACTTTAACTTTTTTAATTATCCAGATAGTATTTACCACTGATTCAAACAA |
| 79951 ACTGTTATTGAAAGACAAAAACAAATTAAAGAAGATTACAACaATTTGCT |
| 80001 AATTTCTCTTAAAGACAAACCACTTTTTAAAAAATTTACTAATTGGATTG |
| 80051 ACAGTGATTTTCAAGCCCTTTATCTTAACCAACTAGATGAAAAGAAAGTA |
| 80101 GCAAAAAAAGATAGTGCTACTAGAAACTATTTAAAAGATTTTTTAAACCA |
| 80151 AATTAATAATCCTAATTCCAACTTGTATTGCTTAAATGCTGATGTATCAC |
| 80201 GTTCTTGTTTTATCAAGATAGGTGATGATAATCTCCATGAAAATCCTTGT |
| 80251 TCTAGAAATATCCAAATAGGAATTAGGGAGTTTGCAATGGCAACAATAAT |
| 80301 GAATGGTATGGCACTTCATGGTGGTATTAAAGTGATGGGTGGTACTTTTT |
| 80351 TAGCATTTGCTGATTATTCAAAGCCAGCAATTCGCTTAGGTGCATTAATG |
| 80401 AACTTACCAGTATTTTATGTTTATACCCATGACTCTTATCAAGTAGGGGG |
| 80451 TGATGGTCCTACTCATCAACCCTATGATCAACTACCAATGTTAAGAGCAA |
| 80501 TTGAAAATGTTTGTGTATTTCGTCCTTGTGATGAAAAGGAAACTTGTGCT |
| 80551 GGATTTAACTATGGTCTTTTAAGTCAAGATCAGACAACTGTTTTGGTTTT |
| 80601 AACACGTCAACCCTTAAAATCCATTGATAACACTGATAGTTTAAAAACAC |
| 80651 TGAAGGGTGGTTATATCCTTTTGGATAGAAAACAACCTGATTTAATTATT |
| 80701 GCTGCTAGTGGTAGTGAAGTGCAACTTGCAATAGAGTTTGAAAAAGTTTT |
| 80751 AACTAAACAAAATGTAAAGGTAAGAATTCTGTCAGTTCCCAATATAACTT |
| 80801 TACTTTTAAAACAAGATGAAAAATATCTAAAGAGTTTATTTGATGCTAAC |
| 80851 AGTTCACTTATCACCATAGAAGCTAGTAGTAGCTATGAGTGGTTTTGCTT |
| 80901 TAAGAAGTATGTTAAAAACCATGCTCATTTAGGAGCTTTTAGTTTTGGTG |
| 80951 AATCTGATGATGGAGATAAAGTTTATCAGCAAAAAGGGTTTAATCTGGAA |
| 81001 AGGTTAATGAAAATATTTACTTCCCTAAGAAATTAAAATTATCTTAATGT |
| 81051 TGTATAGGTTTTGAAAAACAGGATTGGCAATTTTTATGCCTGGTTGCATC |
| 81101 TTACTTTCATCCTGTTCTTTTAGAAGTTATATCCCAACTCCTAGTTTAAG |
| 81151 AAATACTGTTGGTAATCACAACAGTTATGTTAATAATACTGTCCCTAAAA |
| 81201 ACAATTTTTATGAAAAGTTTTATGATCTAACTTTTGCTTTAAATTTCACT |
| 81251 AATCAGAAAACTCAAGAGTTTGGTACTGGTTGGTTAATTGACTGAAAAGG |
| 81301 AGATGAAACTAAAGATCTTAATACATTAACTATTGCTAGTTCTTCTATTA |
| 81351 TTTCCTCTGTAAGTAATCATTCTTTAAAAGAAAAACAAGATGACAAGCTT |
| 81401 TTTATTGCTTATATTGCCACCAATTTACATCTGATAGATGGTTTAAAGAA |
| 81451 TGATCATGATTATCAACCATACAATAAAGATGGAAATGGTCTTAGTTTTC |
| 81501 CATTTGATCAAAAAACCCAATCATTCTTATTGGGTAGGTTTGCCAATCCT |
| 81551 AAGATAAATTCCAAACCAGAAGAGATGAACTACCAAGTTCAAACTCGTTT |
| 81601 AAAACAAGATGCAATGGTGTTTATCCAAACCAGTACTTTACCTAAAACTG |
| 81651 CTTATGCAGGAATTGATCCTATTAACTTTGATTACCATGAAACTAGTGAT |
| 81701 GAGAGTGGATTTTGAACTAAAAAACAAAGCACTGCAAACTTCCCTAGAAC |
| 81751 AAGAACATTAAAAAGTTATGCTGATTTTGCAGTTTTAGAGGTACCCTTAT |
| 81801 TCTTAGATAATGCTAATGATGCCAAGATTTATCAAGAGTGAATTAGACCA |
| 81851 GCAGTTCAAGCTTATAAGGAGCTAGGGGATGTTGAAAATATTTTGCTAA |
| 81901 AACCCCATACGCTGAATATATTAATAACACCTACTACTTATTGGGTTATC |
| 81951 CTGTTACTAATAACAATAAGTATCAGTTTATCTTAGGTCAAGATGAAAAG |
| 82001 TGAAAGTTTTCTCAACAAACTTCTGTATTAAAGCACTATCAAAAACAACC |
| 82051 TCTTCAACAAAGAACAGTTTATGTTGAACGTGATGATGGTCTTCCTACAT |
| 82101 TAACTTTTAATGAAGATAAACTCACTCATGTTCAAGGTACTGATCTAATT |
| 82151 AATGTTGATCAGATTACCGATACTAATTTAGGAAATGGCTTAATAAATTA |
| 82201 TGCTGGTTTATCACGCTTTACTTTAAGCTATCACAATGTTGAATATAAGT |
| 82251 TATTTGGTTATGGCACTATTTTAAATAATACTAATTTTCCAGGTGGATCT |
| 82301 TCTGGTAGTGCTGTTTTCAACAAGGAAAAACAACTAACAAGTATTTACTT |
| 82351 TGGTTCACTGATTAATGTAACAACTGGAAATAACAGGAATGTTAATTTAG |
| 82401 GTTTGGGTCAAATTCTTCGTACTTATAACACTAATAATAGTAAGCACAGT |
| 82451 GCACCATCATCATATGATTTAATTTTTGGTGATAAAAACACCATCAAGTT |
| 82501 TTATGCACAGTTTGCAAAAGAAAAGCAAACTCATCTTTGAAATAAAATTC |
| 82551 AAACATCTGTTAACTCTTCAATCAGCTTTTACAAAGACAAAAAATAATAA |
| 82601 TTAACTAACAATTTGTATTTGTGTTAAGACGTTATCTAACTCTGAGTTTT |
| 82651 TCTAGCTTGCTTTTATTAGCACTGCTGTTTTAACAGGCTGTTCTTTTGT |
| 82701 TAGACCACAATTTCGCAGGGGCTTTAGAACCCAGTTTAAAATTAACTCTA |
| 82751 TTCCAACTGTTAGTGATCCTTATCACATTAACTACGACTTAACTTTTTCA |
| 82801 TTAAACTTTGCTTCCAACAAAAGAAATACTTATGGTACTGGTTGGTTAAT |

-continued

| The Nucleotide Sequence of the *Mycoplasma genitalium* Genome |
|---|

```
82851  TGATTGGAAAGGAGATGAAAATAACCCTGAGaAAAATGATCCTTTTAAAG
82901  TTTATTTAGCTACTAACCtCCATGTGATAGATGCTTTAAGAAATAATAAT
82951  GACTATGAACCATATAACAAGGATAGTAATAACCAAGCTTTTAATAGTGA
83001  AGAGATCACTAGGTTCTTTTCTATAGGTAAATACACATATCCTAGTATTT
83051  TTAGTGAATTAAATTTCATTATCAATGCTAGAGAAGCGTTTGTTTCGATT
83101  CAAACCTCTACTATTCCTAAAACTGCTTATGCTGCTGTTAACTTTGTTGA
83151  AACACAAGGAGAGGATGAAAGTTATACAGATTCATTATCAACTGATAATA
83201  AAAGAGATATTTATGCGGATTTTGCTGTGATAGAAATTCCCTTATTCTTA
83251  ACTAACCATCGCGATTATCAAGTATTTAATGAATTTATTAAACCAGCAAT
83301  AGAAACATACAAACAACTAGGAAACTCTTCCTTTGAAAAAAAACAACTAG
83351  ATCAACATAAAAACGACAACTTTTACATGTTAGGTTATCCTTTGGTTGAG
83401  AGTAGCATAGATGCTCTAATTTTGAACCAAAGAAGACAGTACAATAACAG
83451  TTATACTGAAAAATATACTCCTCAAACTTTAACCAAAGATCAACGTACCA
83501  TTGACTTAAGCAGAGAAGTTCCTACTTTAATTCAGAACAAAACAGAAAAC
83551  TCTACAGGAAGTCAATTACTAGTAAATCAATCTTTAAGTAGTACATCTGA
83601  AGGGATTATTGAATTTATTAAGTTACCTGAATTTAAACTCAATTATCATA
83651  ATAAAAGTTACCGTCAATATGGTAGAGGTTTTGCTCTACAAAACACTAAC
83701  TTTAGACCAGGTTCTTCAGGAACTTTAATGTTAAATAACCAAAAACAGAT
83751  AGCAGGTATTTATTTTGGTGTTTTAGATTTTGGAGAAGATGTAAGTTTAA
83801  TGAGTAACATTGGCGTTGGACAAATTCTTCGTGTTCCTCAAAAGAACAAT
83851  ACTAGAAATAGATCAATTGCTACTAATAAAAGCAACTATGATTTGATCTT
83901  TGGTGATAGCAATACAACTAACTTTTATGCAAAATTTGCTAGACAAAATA
83951  ACACCCATCTTTATCAGATGATTTCAAATAGTAAAGATACAAAATTAAAG
84001  TATGTGAATACTGTTGAAAAAACAGTAAAAGCTAGTATTAAATAAAACAA
84051  AATAGTGACTTTCTTTTTTTATACTCATAAAAATGGAAAATCAAACAGT
84101  TGTAGTTCTGTAAAAGAAAAAGAGTTATATAATCCAAAAAAGCCTTTTCT
84151  TTTTGCGGTAATTTCTTTCTTTGTTTTCATAATATTTTTTGCTTTAGCAG
84201  GTTCATTTACCAAATTTGCATTAGAAGAAAGCAGGGGTTATAGTTTTCTT
84251  GTTATTGTCTGTTATCTTCTAGGAACAGTTTGTTTTTTTGTTTTTATCTA
84301  TTTTTGGTTTTGATTCTTATCTGAATTTTTTGCAAATAGAGTTCTAGTTA
84351  AGTTATGAGATTTACCTACTAAAAAGAGAAGAAAAAGACATGCAAAAAAA
84401  CAAAGATAATTAGTTAAGTTTTAATAACTCAGTTGGCAAATAAATTAGGG
84451  AGTTATTAGAACGCTATTTTTATTAATTTAAGTGTTTGTTTAAAATTTA
84501  TTAAGTACTTTTTTAACTTGTTAAAAAAGTAGTTATTTTATTAGTTGGAA
84551  AGTGCAAAAAGAATTAAATATTTCAAATGATAAAAAGACTTGTTTAAATG
84601  AAATAGAAACAAGCAAAGTTAAATTTCTAACAACAACTTTAATTTTGTTG
84651  TGATCAATATTAATAACACTCTTAGTTGTTGTTAGTGTATTAGCATTTAA
84701  TTTCATTTTATTAGGATCTACTAAACAAGGATTACCAAATACCAATGAAA
84751  TAGAGACACTAAAAAGTTCATTAGCCTTGCAATTATCACAAAATGGTGTG
84801  ATCTTATCAATAGCACTACTTGCTTTTTTTAGTTGGATGGCAATTGTTGG
84851  AATTCACAGCTTTTTAGTTGGAATTTTAGTTAATCATCAAACACTTAAAA
84901  TAAGTAAAAAGTATGTTATTTTAGGTTCGATTTTTCCAATTATGGCATTA
84951  ACAAATACTcTGTAATTAGAAAAAAATTAAAAGCTTTATTAGGAGAGGGT
85001  AAGGTTCAAAAAGGACTCaAAGTTTTAACTATTAGTTTTATTTGTGTTTG
85051  AAGCTTGCAATTGATAATAGGCTTTTTTGTATGACTTTTTCCTTATGCTG
85101  GTGAGGCAGGAATTAATATAGGAATTAATTTATCTATTTTTAATTTGGCT
85151  CAGTTAGTAGGCTCAGATATAAATGTAATAACTTACTTTACAACTTTTTT
85201  AACGCTGCTTTTTGCATTTCTTTCATGAGCCGTATTGCATGTTTTAGCTT
85251  GCTTTATTTTGGTACATTTGACTATTTATAAACAACAAGAATGAATAAAA
85301  ATTAAAGCTATTTACATTTTGGCTTTAACCTTAATTGATTTAATGGGTTT
85351  AATTTTGGCTTTTGGTATTATTGTTGTTAACAATACAAATTCTTCAAGTG
85401  TTGATGCAAAATCAAATTCCTTAGCATTAATTTTTAAGTTCATTTATTTT
85451  GGTAGTTCTATAGCAGCCTTTTTAACAGTTTTAAGTTTTGCTAGTTCAGT
85501  TGCTTTACTTGTCAATTTAATAAAAAAAGATAAGGGATTAACCTTAAAAA
85551  ATTAGTTAACCTCCCCCAACCTCTATTTTCTGTTACTAGTGCCTAAGGTG
85601  GTATTGGAGTATCACAAGCTCAGTAAGGATGTAGTCAAAGAGAGTTTGGG
85651  GGTGGATACATCAGGTTCAACTTTTGATCCAACTAAAAGGTTGAAAAAAG
85701  ATAGTCCAATGAAGGATTCAAACAAAGACAGTGAGAAACTCACCGAAGCA
85751  ACTGCTTCATCCATGAGTAGTGGTGGGGCTACATCCACTCGCAAGGCCCT
85801  CAAGGTTGAGGTGGAGAAACAAAGTGGATCAACTGATTCACTTTTAAAAA
85851  ACGACTTTGCTAAAAAGCCACTAAAGCATAAAGAAAATAGTGGGGAGGTG
85901  AAGTTGGATGCGAGTGGGGAGTTTGCCAATGATAAAGCCTGAAAACCGGT
85951  GTTGAAAACAGATGAGATAACAAGAGAGAGGGGATGGGGCGACTTAGA
86001  CTTTCTCCCCTGAATCGGCAATGGTTATTCCTTCTCCAACTCCCCCTCCC
86051  CTTCTTCTTCTTCTTCTACTACTTCTACTTCCTCTTCTACCCCACTCCCC
86101  ACTTTTTCTAACATCAATGTTGGGGTTAAATCAATGATCACTCAACACTT
86151  AAATCAGCAAAACACCCGGTGGGTGTTTACCCCTAACTCTTCACCAGACA
86201  TCTGAACGGGAGCAGGGTATCGCAAGGGTTCATCAAACACCAACGGCATT
86251  CCCTTCGACCAGGTGAAACCTAGCAATAATAGTCAACAGTTTAATCCCAA
86301  TTCAGATGATAATAAAGTCACTTCAGGTGGCTCCTCCAAACCAACCACCT
86351  ACACCCATTTACCCAACAGTATCAGTCCCACCAGTGACTGGATCAATGCG
86401  TTGACTTTCACTAATAAGAATAACCCGCAAAGAAACCAACTGTTGCTCAG
86451  AGCACTGTTAGGAACGATCCCGGTATTGATCAATAAGAGTGGAGGAAGTG
86501  GGAATGAGTTTACCCATACGAGTGAGCAGCAGTGAAACGAAACAGATAAA
86551  TTAGGAGGTAACCTCCCGGGGTTTGGGAGGTGAATGGCGGTTTTTACCC
86601  AGTTTTACTTATTTAATAGTTAAAAAAGCTTTAGATTTTTATCAAATTTT
86651  TATCTATTTAATATTTAAGAAAGTCGCAAATTTTTATCAGTTTATTGGTC
```

-continued

The Nucleotide Sequence of the *Mycoplasma genitalium* Genome

```
86701  AAAGAAGTCGCAAATTTTTCTTAGTTTTTTATTTGCTTAATGGTTAAAAA
86751  AGCGTTAGTTTTTACCTTTATTTAATTAATAAACTTCGCCACCCCCATCA
86801  CCGATTCTAAGGCTGATCTGGTTAGTTTGGCACAACTAGATGATTCCTAT
86851  CAAATCTCCGACCAAACCATCCATAACACCAACCTGTTTGTGTTGTTCAA
86901  GTCCAAGGATGTGAAGCTTACATATAGTTCAAGTGGCTCAAATAACCAGA
86951  TTAGTTTTGATTCAACTAGTCAAGCTAACAAACCCGCCTACATCGTTGAA
87001  TTTACTAATTCCACCAACATTGGCATCAAGTGAAGCGTGGTGAAAAATA
87051  TAAGTTAGATGTGCCAAGTGTTTCAACAACCATGAACCAAGTGTTGCAAG
87101  AATTGATCCTTGAACAACCTTTGACTAAGTATACGCTTAATAGTAGTTTG
87151  GCCAAAGAGAAGGGCAAAAGCCAAAGGGAGGTGCATCTGGGTTCAAATTC
87201  AAATCAGTGACGATCGATGCGTGACCAACACGGCTTAAACAACAATCCCA
87251  GCCCAAATGCTTCAACTGGATTTAAACTCACTACCGGCAACGCATATAGA
87301  AAACTAAGTGAGTCCTGACCAATTTATCAACCAATTGATGGGACCAAGCA
87351  GGGCAAAGGGAAGGATAGTAGTGGGTGGAGTTCAACTGAAGCAACAACGG
87401  CAAAAAATGATGCGCCCAGTGTTTCTGGAGGGAGATCATCAGATCAAAGT
87451  AATAAATTCACCAAGTACCTCAACACCAAGCAAGCATTGGAAAGGATCGG
87501  TATCTTGTTTGAAAGTAATGGAGAGGCGAGGAATGTTGTTAGCCTCCTTC
87551  CTCTACTTTCAACCCAACAAGGTGAAAAGTGGTCAATACCAAACCACCAA
87601  CACCTACAACAAGTTAATTGAACCTGACAAGTGACAATCAAGTAGTGATT
87651  TGAACAATATGACCAACTTGTTAAAACTCCTAACAACTAAAAATGTGAAA
87701  GCAAAGTTGGGGAAGACAGCCCAATCTCAGGAAAATAGTGGGGGGTGAA
87751  ATGATAAAAATGTTTTTAAATAACTACATTAATTCTCTTAAACTTACTAA
87801  ATTATTTTTCCATTTCGAACTATTATTTGAAAAAAGTTATTAATTGCAAG
87851  TTGATAAAGAAAATGAAGCAAAATAACAAGAAAGAATTATCTAAATTTAA
87901  ATAGACTAGAATTAAATTAAGACCAAAATGTTGCATGCAAACAACATATG
87951  CTCTTTTAGTTGTTTTTGGAATTTTATTAGTTCTAATTGGACTAGGATTT
88001  TTATTTTGAGCTTTAAAAATTTCACTTAAAGAACAAAAGAAAGGTCAAAT
88051  TACTAATGATTTGACTTCCAATAACTCACTTAAAAATGAAGTTCCTAGAG
88101  GGAGTTGATGAAAAAGAAACAACAAATTAGTTTTATTTTTGCTTGCAATA
88151  GTTTTTTTAATGCTAGGAATAGGTGGACTTGTTTCCCTTCCTAAGCTGTT
88201  TGGTTAATAAAATTTAGTAGTTTTAAAATGCAGATTAGTTTAGTTAAAAT
88251  CCGCAATAAGTTTAAACAAAGAAACCGTGGTTCTTTTCGTCAGTGAGTTG
88301  GTAAGCTTTCCAACGGTTTGATGATCCCTATTGCAGTTTTGCCTTTAGCA
88351  GGTATTTTTTTAGGAATCGGTGATGCCATTTCTTCCAATTCATCTGGCAT
88401  TGTTGGTGTGAAATTTTTTGGTGAATTTATTAAACAAGGTGGTAATGTAG
88451  TTTTTGCTAACTTACCTATTTTGTTTGCAGTTGCAATTGCGATCACCTTT
88501  TCTCAAGATGCAGGGGTTGCTGGATTTTCTGCTTTTGTTTTTGGGCCAC
88551  AATGAACGCGTTTATGAGTTCATTAATTATTCCTGTTGATGCAAATAATA
88601  CTGCTTCAGGTTATAACATCCTTTATTGAAAAGCAGTACCTCAGTCAGCA
88651  ATTGCTTCTACTTTAGGATTAAATTCACTTTCAACTTCAGTTTTTGGTGG
88701  GATTATAGTAGGGGCTTTAACTGCATATTTATATAACAAGTTTTATGCAA
88751  TTAGATTGCCTGATGTAATTGGGTTTTTTAGTGGTACTAGGTTTGTTCCT
88801  ATTATTTGTATGACTATTGCTATTCCAGTAGCATTACTTTTATTGATGGT
88851  TTGACCTGGTGTTTCTATCTTATTAAATTTAATAGGAACTGGGCTTGGAA
88901  TCTTAGGTGGAAGAGGATATGGTGCTAACAGTTTAATCTTTGGATATATA
88951  GAAAGAGCACTAATTCCTTTTGGAGTACATCATGCCTTTTATGCACCATT
89001  ATGATATACAAGTGCAGGCGGTAGTTTGCAAGAAATTGCAAATCAACAAG
89051  TTTGGATTAGAGCTCCTGGTAGTGATTATGTAACCAGAGTGATAGGTTGA
89101  GAAGATTTTAATACTCCAGGAAAATGAGTTATTCCTGCTGCTTTAGCTAA
89151  TGGAACAAGTGGAATGATGAATGGAGCTACTACAACAGGACAAGATAGTA
89201  CATCTGCACTTTCAAAATACATGAGTAAAGAATCAACAAACTTTCTAAGT
89251  TGAAAAGAACTTGTTGATGGTCTTACACGTAAAGGTAACTTTGATGAATT
89301  GGCTAAAAACGGTTTATTAGATGGTTCTAACAAGATTTGAATTGGTTTAA
89351  ACCAGTCAGGGATCTTAGGTAAAAAAGTACTGTTAAGTGATGGTAAGGAC
89401  TACACTATTACCTTTAAAACTTTTGCTAACACCACGCCAACATTCTGAAG
89451  CCATGGTGCTCATGCACTTTTACCAATTAGTGGAACTCCAAGTGCAATAA
89501  CTAATGGAGTTACTGTTAATGGTACTGCTAATTCTAAAACCTATAATGTC
89551  AGTCAGTTCACTGTTGCAGTTCCTTCTTTAAACCCAGCACAATATTCCCA
89601  AGGTAAATTCCCATTCATGCTAATTGAATTCCAGCAGCTGGACTTGCAA
89651  TGATCTTAGCTGCTCCTAAGGGTAGAAGAAAAGAAGCTAGTTCTATTATT
89701  GGTAGTGCTGCATTCACTAGTTTTCTAACAGGGATCACCGAACCTTTTGA
89751  ATTTACCTTTCTTTTCTTAGCACCATGGTTATTCTATGGTATCCACGCTG
89801  TATTAGCTGCAGTAAGCTTTTGATTAATGAACTTATTGAGTGCTAACGTT
89851  GGACAAACCTTCTCAGGTTCTTTCATTGACTTTATCTTGTATGGGCTTT
89901  ACCTGATGGTAGGGGTTGATTAGCAAACTCTTACTTAGTACCTATTATTG
89951  GTATCTTTTTAGCATTGATTTATTTCCCTACCTTCTATTTCTTGACAATT
90001  CGCTTTAACTTAGCAACTCCTGGTAGAGGTGGTAAGTTAATTACTAAAAA
90051  GGAATATTTAGCAGCAAAAGCAGCTCAAAAAACTGATCAAACTACTAACA
90101  CTAACTTTAATCAAACCCAAATTGAAGCTGGTATGTTACTAAGAGCTTAT
90151  GGTGGAAGTGAAAACATTGCTGAATTAGGGGCTTGCATTACTAAATTAAG
90201  AGTAACAGTTAAAAACCCTGAACTTGTTAATGAAACTATTATTAAAGACT
90251  TGGGAGCAGCTGGGGTAATGCGTACCACTCCAACATTCTTTGTAGCAGTG
90301  TTTGGTACTCGAGCTGCTGTTTATAAATCAGCAATGCAAGATATTATCCA
90351  AGGCAAAGTAAATTGAACAGAGTTGCAAAAAGTCTTAGATAAAAATGATA
90401  GTACTGTTGAAAAACCAGAAATAAAACCAACCCCAGTTTTAAAAGTTCAA
90451  GATGAAATTGTGATCCTCTCACCAGTTAATGGCACCTTAAAACCGCTCAC
90501  CCAAGTTCCTGATGATACCTTCAAAAATCGTTTGGTAGGAGATGGAATTG
```

-continued

The Nucleotide Sequence of the *Mycoplasma genitalium* Genome

```
90551 CTATCTTACCTAGCGATGGGCACTTCAAAGCACCAGGTGATGTGGGTGTG
90601 AAAACTGAACTTGCTTTCCCTACTGGTCATGCCTTTATCTTTGATGTTGA
90651 TGGTGTGAAAGTAATGCTTCACATTGGGATTGATACAGTAAAAATTAATG
90701 CTGATAAAAAACCAGGGGAACAACTTGAAGTGTTTGATGTAAAAACAAAA
90751 CAAGGAGAATACACTAAATTAAAGAGTGAAAGTGTTGTTGAAGTTGATTT
90801 AAAGAAACTTAAACGAAAGTATGATCCAATCACTCCTTTCATTGTGATGC
90851 AAGAATCACTTGATAACTTCAAGTTGGTGCCAATTCGCCAACGTGGTGAA
90901 ATTAAAGTTGGCCAACCTTTATTTAAACTAATTTATAAAGATAAGAAGAG
90951 TTAATCAATAAAACTCGATAATAACTAAAAGCCATAAAACCTTGGTTTTG
91001 TGGTTTTTAGCTTGTTTATAACAATATTATTGCAGTTTTACTGCATAATG
91051 TAAAATTACACAGCATGTCAGATACAAATACTGAAAAACCTGAGTTAGTT
91101 TCCCTTAATAAGTTAAGTGAGATGCGCACTAACATCGGGATGGTTAAACG
91151 TTATTGAAACCCAAAGATGGGATTCTTTATCGAACCTGAACGTAAGCATA
91201 ATAACGATTTATTGAAGCTTGATCTACAGTACCAAGCGTTAAAAACTGCT
91251 TATAACTTCATTAAGGATGTTGTTAAAAATCACGGACAAATCCTTTTTGT
91301 TGGAACAAAGAATGATTATGTTAAAAAACTGGTAATTGATATTGCTAAAA
91351 GAGTTAATGTTGCATATATTACCCAGCGCTGATTAGGTGGTACTTTAACT
91401 AACTTTAAAACCCTTTCTATCTCAATTAACAAACTCAATAAATTAGTTGA
91451 ACAGCAAAAGCAAAATGCAAATGATCTAACCAAGAAAGAAAACCTGTTAC
91501 TTTCAAGAGAGATTGAAAGACTTGAAAAGTTCTTTGGTGGGGTCAAAAAT
91551 TTAAAAAGACTTCCTAATCTAATAGTTATAGATGATCCTGTTTATGAAAA
91601 AAATGCAGTTTTAGAAGCAAACAGCTTAAAAATCCCTGTTGTGGCACTAT
91651 GCAACACCAACACCAATCCAGAGCTAGTTGACTTTATTATTCCAGCTAAT
91701 AACCACCAACCCCAAAGTACTTGTTTATTGATGAATTTACTAGCAGATGC
91751 GATAGCAGAAGCGAAGGGTTTTGAAACCTTGTATGCTTACAAACCAGATG
91801 AACAGATCCAAATTGAAATTCCTCCCAAACAAGAACGCCAAGTTATTAAC
91851 CGTTCCAATACCAGAAACATCACTAACCAGCGCTTAAACATTAACCGTCA
91901 ACAACAAGAAACTTTATAGAGCAGTGAACAGTTGAACAGGACTTAGTGAA
91951 CAAGCGGCAATTAAAAGTCGTCAAGAACATGGTGCTAATTTTCTTCCTGA
92001 GAAAAAAGCTACCCCTTTTGGTTGTTATTTCTTCAACAATTTAAAAGTT
92051 TAGTTGTTATTCTTTTACTGCTAGCTAGCTTGTTATCGTTTGTAGTTGCT
92101 ATTGTCAGTGGTTTGAGAAGTAACTGAAACTTTAACCATGATCTGATTAT
92151 TGAATGGGTTCAACCTTTTATTATCTTATTAACTGTTTTTGCCAATTCAC
92201 TAATTGGTTCTATCCAGGAATTTAAAGCCCAGAAATCTGCTAGTGCTTTA
92251 AAGTCCTTGACAAAGTCTTTCACAAGGGTTTTTAGGAATGGTGAATTAAT
92301 TAGCATTAATGTTAGTGAAGTTGTTGTAGGAGATATTATTTTTGTTGATG
92351 CAGGAGATATTATCCCTGCTGATGGCAAATTACTACAGGTTAATAACTTA
92401 CGTTGTTTGGAAAGCTTTTTAACTGGTGAATCAACTCCAGTTGATAAGAC
92451 TATTGATAGCAATGAAAAAGCTACTATTCTTGAACAGACAAACTTAGTTT
92501 TTTCAGGGGCACAAGTAGTTTATGGTAGTGGCGTTTTTCAAGTGGAAGCA
92551 GTTGGGATTAAAACCCAAGTTGGAAAAATTGCTAAAACTGTTGATGATAG
92601 TGTAACTAAACTCTCACCCTTACAACAAAAACTAGAGAAGATAGGAAAGT
92651 GATTTAGTTGGGTTTGGGCTTGGTCTTTTTGCTGTAGTTTTTCTTGTCCAA
92701 ACTGCTTTATTAGGATTTGATAATTTCACTAATAACTGATCAATAGCTTT
92751 AATTGGTGCTATTGCGCTTGTTGTTGCAATTATCCCTGAAGGGCTTGTTA
92801 CTTTTATTAATGTGATCTTTGCATTAAGTGTGCAGAAACTAACTAAGCAA
92851 AAAGCCATTATTAAGTATTTATCAGTAATTGAAACACTTGGATCAGTACA
92901 AATTATCTGTACTGATAAAACTGGTACTTTAACCCAAAACCAGATGAAAG
92951 TTGTCGATCACTTCTGTTTTAATTCAACAACCCAAACTGATCTAGCAAGA
93001 GCATTGTGCTTGTGTAATAATGCTTCTATTTCCAAAGATGCTAATAAAAC
93051 AGGTGATCCTACTGAAATTGCTCTCTTGGAATGAAAAGATCGCAGTCAAT
93101 TAGATTTAAAAACCTATTACAGGGTTTATGAAAAAGCCTTTGATTCAATC
93151 AGAAAACTTATGACAGTTGTTGTTCAAAAAGACAACCGCTTCATTGTGAT
93201 TGTTAAAGGTGCTCCTGATGTGTTATTACCATTATGTAATAACGTTCAAA
93251 ATGAAGTAAAGAACATTGAAAACTTACTTGATCAAAGTGCTGGTCAAGGC
93301 TTGCGTACCTTAGCAGTTGCTTTAAAGGTTTTATATAAGTTTGATCAAAA
93351 CGATCAGAAGCAAATTGATGAACTTGAAAACAACCTTGAATTCCTTGGGT
93401 TTGTTAGTTTACAAGACCCACCAAGAAAAGAAAGTAAGGAAGCGATTTTA
93451 GCGTGCAAGAAAGCTAATATAACCCCAATAATGATTACAGGGGATCATCT
93501 TAAAACTGCAACTGTAATTGCTAAAGAGTTAGGCATTTTAACTTTAGATA
93551 ATCAAGCAGTTTTAGGTAGCGAACTAGATGAAAAGAAGATCTTGGATTAC
93601 AGGGTATTTGCTAGAGTAACTCCCCAACAAAAATTAGCCATTGTTAGTGC
93651 TTGAAAAGAAGCGGGATTTACAGTTAGTGTTACTGGTGATGGGGTGAATG
93701 ACGCACCTGCATTAATCAAGAGTGATGTAGGGTGTTGTATGGGGATTACT
93751 GGGGTTGATATTGCAAAAGATGCTAGTGATCTGATTATTAGTGATGATAA
93801 TTTCGCTACTATAGTAAATGGTATTGAGGAGGGTAGAAAAACTTTTTTAA
93851 CTTGTAAACGAGTTTTATTAAACCTGTTTTTAACTTCAATTGCAGGAACA
93901 GTTGTAGTTTTATTAGGACTATTCATCTTAGGACAAGTTTTTAAAACTAA
93951 TTTATTACAACAAGGTCATGACTTTCAGGTGTTTAGTCCTACCCAACTGC
94001 TAATTATTAACTTGTTTGTTCATGGTTTTCCTGCTGTTGCATTAGCAGTA
94051 CAACCTGTTAAAGAAAAATTGATGGTAGGTAGTTTTTCTACTAAAAATCT
94101 GTTTTACAACCGCCAGGGATTTGATTTAATCTGACAATCACTATTCTTAA
94151 GCTTTTTAACTTTATTGTTCTATAGCTTAGGAATTATATATGCAATTAAT
94201 AACCGTGATTTACAAACTAGCGGGGATCTAATTAATCGTGCTGGATCAAC
94251 GTGCGGTTTTTTATTTTGGGTGCTAGTGCTGCTTTAAACTCATTAAACC
94301 TAATGGTAGATAAACCATTGCTTATGACAAACCCTTGGTTTTTTAAGTTA
94351 GTTTGAATAGGTTCACTTGCTTCTATACTGGTATTTTATTGATCATCTT
```

-continued

The Nucleotide Sequence of the *Mycoplasma genitalium* Genome

```
94401 TATCAACCCTTTAGGGTTAGTGTTTAATGTCTTGCAAGATTTAACTAATC
94451 ACCCAGTTTTAATAAGCTATAGTTTTGGGGGAGTTATTTTGTATATGGGG
94501 ATGAATGAAGTTGTTAAACTTATTAGATTAGGTTATGGCAATATTTAACT
94551 TCCTTAAGTTAATTTCACCCAAAAACAGAATTCTCAGTAAGGCAAATAGG
94601 ATTGCCAGTGAGGTTGAGAGTTATAAAAACTACTACCGTAACTTAACTGA
94651 TCAACAGTTATTTGAAGAGTCAAATAAACTAGTTGATCTTGTCACTAAGC
94701 AAAATTACACCATTCTAGATGTTTGTGTTGCTGCACTTGCTTTAATTAGA
94751 GAAGTGGTTTACCGTGAGACTGGTGAATTTGCATATAGGGTGCAGATCAT
94801 AGGAGCTTTTATTGTTTTAAGTGGTGATTTTGCTGAGATGATGACTGGTG
94851 AAGGTAAGACCTTAACCATTGTTTTAGCAGCATACGTTTCTGCACTTGAA
94901 AAGCGTGGTGTGCATGTTGTTACTGTTAATGAATATCTAGCTCAAAGGGA
94951 TGCTAATAATGCAATGAAGATCTTAAAACGGGTTGGGATGAGTGTCGGTT
95001 GTAACTTTGCTAATCTCTCCCCTCAGCTAAAACAAGCTGCATTTAATTGC
95051 GATGTTACCTACACCACTAACAGTGAACTGGGGTTTGATTATCTTAGAGA
95101 TAACATGGTCCACAGTTATCAAGATAAGAAGATCAGAGAGTTGCACTTTG
95151 CAATAGTTGATGAAGGTGATTCAGTTTTAATTGATGAGGCGCGAACGCCT
95201 TTAATTATTTCAGGTCCTAGTAAAAATGAGTTTGGGTTATATGTTGCAGT
95251 TGATCGATTTGTTAAATCATTAACTGAACAGGAGTTTAAGATTGACCCTG
95301 AATCACGTGCTGCTTCTTTAACTGAACTTGGGATTAAAAAAGCAGAGCAA
95351 ACATTTAAAAAAGAAAACCTTTTTGCTTTGGAAAACAGTGATCTTTTTCA
95401 CAAGATCATGAATGGTTTGACTGCTGTGAAAGTTTTTGAACAGGGCAAAG
95451 AGTACATTGTTCGTGATGGCAAGGTTTTAATTGTTGATCACTTTACAGGT
95501 AGGATATTGGAAGGGAGAAGTTACAGTAATGGCTTACAACAAGCTGTACA
95551 AGCCAAAGAATATGTTGAGATAGAACCTGAAAATGTGATAGTAGCTACCA
95601 TTACCTACCAATCCTTCTTTAGGCTATACAACCGCTTAGCAGCAGTATCA
95651 GGTACTGCTTTAACTGAATCAGAGGAGTTTCTCAAGATTTATAACATGGT
95701 TGTAGTACCAGTGCCAACTAACCGTCCTAACATCAGAAAAGACCGTTCTG
95751 ATAGTGTATTTGGTACCCCACAAATTAAGTGAATGGCAGTTGTTAAAGAG
95801 ATAAAAAAGATCCATGAAACTTCTCGACCTATTCTGATTGGAACTGCTAA
95851 CATAGATGATTCTGAACTCTTACATAATCTGTTACTAGAAGCTAATATTC
95901 CCCATGAGGTTTTAAATGCTAAAAACCATTCAAGAGAAGCGGAGATAGTA
95951 ACTAAAGCAGGACAGAAGAATGCAGTTACTATTTCAACTAACATGGCTGG
96001 AAGAGGAACTGATATCCGTTTAGGTGAAGGGGTTGCTGAAATGGGTGGTC
96051 TTTATGTATTGGGAACTGAAAGAAATGAGTCAAGAAGGATTGATAACCAA
96101 CTAAGAGGGAGAGCTGCTAGACAAGGTGATAAAGGGGAAACTAAGTTCTT
96151 TATCTCACTAGGTGATTCATTGTTTAAACGTTTTGCTCATGACAAGATTG
96201 AAAGAGCGATTAGCAAATTAGGTAATGAAACATTTGACAGTGCCTTCTTT
96251 TCCAAAATGTTAAGTAGAACCCAAAAACGGGTGGAAGCAATTAACTTTGA
96301 CACTAGAAAAAACCTGATTGATTATGACCATGTTCTTGCAAGTCAAAGGG
96351 AATTGATTTACAAACAACGTGATAAGTTTTTATTAGCAAACGATTTAAGT
96401 GAAATGATCGACAAAATGCTAGAAAAGTTTGTACAACAGTTTTGTGATCA
96451 ATATAGAAACCAAAAGAACCAAAACTTAATTAATCACATTGCACTAGCAG
96501 AAGCTTTAAATCTTGAGATGAACATGCAAAACACCATTAATCCAAAGGTG
96551 TTTGAAAACATGACTTTTGATGTTGCTGTTGATAAAACCCGTAACTTAGT
96601 AGCTAAAAAGATTAGTGATAAAGTTAATGTTTTGACCAAACCAATTGCTT
96651 TAAACAGGTTTCGTGACATTATCATAACTTCGATGGATAAACATTGAACT
96701 GAACACTTGGATAGTGTTTTTAAGTTAAGAGAAGGGGTTGTACTTCGTTC
96751 TATGGAACATACGAGTCCTTTAAATGTTTACATTAAAGAAACAGATATCC
96801 TTTTTAAAACAATGTTGCAAAAGATTGCTCAAGATGTCATTGTGCAAATT
96851 GCTAACCTCACAACTTCCAGATGAATTTGATCATAGCTTAATGCAAGCCAA
96901 TGCTTTAAAGAAACTAGCAGCAATTAAAGCAGATGAAAAATCAAACCAAG
96951 AGTAATAGTTTATTTCAACTTTCCACTAACTATATACCTACTGGTGATCA
97001 ACCTGAAGCAATTAAGAAATTATCAGAATTTAAAACTAAGCAGCAGGTTT
97051 TATTGGGGCCACAGGCACAGGTAAAACCTTTACAATTGCTAATGTAATT
97101 CAAAACAGCCAACTCCCAACAGTTGTTATTGCTCATAACAAAACCCTAGC
97151 AGGTCAACTCTTCAATGAATTAAAGCAACTGTTTCCTAAAAATGCAGTTG
97201 AATATTTTATCTCTTACTTTGATTTTTATCAACCTGAAGCTTACTTACCC
97251 AGTAAAGGGATCTACATTGAAAAAAGTGCTACAGTCAATGAAGCGATTAA
97301 ACGCTTAAGAGTCTCAACACTGCATTCACTTTCAACAAGAAAAGATGTTA
97351 TTGTAGTAGGTTCTGTTGCTAGTATTTATCCCACCTCATCTCCCAGTGAT
97401 TTTGTTAAGTATTGCTTGTGGTTTGTGGTTGGCAAAGATTATGATTTGAA
97451 AACCATTAAAGATAGGTTAGTTAGTCTTAACTATGTTGTTAATAAACAAC
97501 AATTAACCCCAGGAAAATTTCGCTTTCAGGGTGATGTTTTGGAGGTATTT
97551 CCTGGTTACAGTGATGCTTTTGTGATCAGAATCTCCTTTTTTGATACTAA
97601 AGTAGAACAAATTTGTCAAATTGACCCACTAACAAATAAGATTTTAAACC
97651 AACTCTTTGAGATTAAGATAGGTCCTGCTGATGAATATGTTGTAAACCAA
97701 TCTGATCTTGATATAGCAATTAAAAAATATTAAACAAGAACTTCAGGAACG
97751 AGTTAATTATTTCAATAAGCAAAATCTTGTTGAAAGAGCACAACGTTTAG
97801 CCACCATTACTAACCATGATCTCAATGATCTGAAGGCTTGGGGATTTTGT
97851 AGTGGAGTTGAAAACTATGCTAGACACTTAGAGTTGAGGATGGCTAACTC
97901 AACCCCTTACAGTATCTTTGATTATTTTAAGGGGGATTGGTTACTGGTTA
97951 TTGATGAATCACACCAAACTTTACCGCAACTTAATGGGATGTATAACACT
98001 GATCTTTCAAGAAAGCAAAGCTTAATTGATTATGGTTTTCGACTCCCCTC
98051 TGCACTTGATAACAGACCGCTCTCATTTGCTGAATTACAACAAAAAATGC
98101 AAAAAGTTATTTATGTTTCAGCAACTCCAAGAGATAAAGAGATTAGTTTA
98151 AGTCAGAATAATGTCATTGAACAGTTAGTTAGACCAACTTACTTGGTTGA
98201 TCCTATTATCGTTGTTAAACCAAAAGATAACCAGGTGGAGGATCTCATTG
```

-continued

The Nucleotide Sequence of the *Mycoplasma genitalium* Genome

98251 AAGAGATTATCAACCAACGCCAAAACAACACAAGAACATTTGTTACTGTT
98301 TTAACTATTAAGATGGCTGAAAACCTCACTGAATACTTAAAGGAACGCAA
98351 AATTAAAGTTGCCTATATCCATAAGGACATTAAAGCATTGGAACGTTTAT
98401 TGTTAATTAATGACCTGAGAAGAGGTGAATATGAGTGTTTAGTTGGGATT
98451 AACCTTTTAAGAGAAGGGTTAGATGTCCCTGAAGTTGCTTTAGTTTGTAT
98501 CTTTGATGCAGATATCCCAGGACTACCTAGGGATGAGAGAAGTTTAATCC
98551 AGATTATTGGACGTGCTGCTAGAAATGAACATGGTCGAGTTGTTATGTAT
98601 GCTAACCATGTTACTGAACAGATGCAAAAAGCCATTGATGAAACCAAAAG
98651 AAGAAGAACTGTTCAAATGGAATATAACAAGCTACATAATAAGACACCAA
98701 AAACAGTTGTTAAACCCCTTACCTTTGTTCAACCAATCAAATTAAAAGCT
98751 AAGAGTAATGCAGAAAAAAATGCTGCATTAATCAAACAATTAACCAAAGA
98801 AATGAAGAAAGCAGCAGCTAATCAAAATTATGAACTTGCCATTGAGATTA
98851 GAGATTCCATATTTGAATTGGAAAAAGAAATTGGTAGTAAAATTAAAGTA
98901 TAGCAATGCGACAGTTTATTAAGCTTAGCCTCTTAGTCTTTGTCTTGCTT
98951 TTCTTAAGTGAACTTATCTGTAGGTTCTCTTTACGCTTAGTAAATTCTAT
99001 TAAAGCGAGATATAAATCTTCAGTATTTCCTACACTGCTTGTTGCTAT
99051 TTTTAAAGAGTTTTCAAAACTTTTCTAATGCTTTTCAGAAGTTAGCTAAC
99101 TGGGTATTTTGATTTGAAAATGATGTTAATGAACTGTTATCTATCTTTTA
99151 CTTTAACTTTGATCAGAAGAGTGAAAAAGTAGATTACAACTTCTTTAATG
99201 GTTATAAAGTTACTGCTCAAAAAGTAGTTGAAAAAGAACAGTTATTAACT
99251 TGTAAGTTAAGTGATTACTACCGTTTATTTAGAGATAAAACCTTTTGATT
99301 TGAACTTATCAACAACTAATAAGATCCTTATTGGCTGTTTAAGTTTGCTC
99351 TCTTTATAAATTCATAACTTTTCTCTTAACATATGAAATTAAGTACAATA
99401 ACTACTATCTGCTTGTCAATATCTGGTGCTTTTGGTACTACTGCAATTGC
99451 TTTACCAACTACAGTAGCATTGTTAAAAAACCACCAACAGCAAAACACTG
99501 AAAAACAACAAAACCCGATTAAAGATATCCGCTTTGGTTTAAACAATGTA
99551 CAGGTTCCAAATACCATTCCGtTACACCAAACTGTGGTTGAAGTGACCAA
99601 CAACAAAGCAATTGTTGATTACAAAGATGCACCCCAAAAATTCTTTTTAG
99651 CTAAAAGTGCGTTAAATAATAAACTCCAAGTTGAGTTTGATAAGTTCTTG
99701 TTAAGAACAGGAGTGATTAATGCTTTAAATGCAGATTTGAAAGAATGGAT
99751 AGACCAAACATTATTTATCCCCAATCAAAGTTTTTTTGATCTTAGTGCTA
99801 ATAAACTCAATTTAACTTTGTCAAATCAAAGCGAAGTGAGTTTAGATCTT
99851 GAGTTTATTTTTACTAACTTTAGTGATAAAAATCAACCATTAAAACTCCC
99901 CTTTGATGGTAGTGTGGTGGTTAATGCTAACGAGTCATACACCTATTCAG
99951 TTAAAGCAACACTACAGAAACTAAAAGTATTGACTTATTCAAGAGCAGAT
100001 CATTCTGTAGGGATTAGTTATGCAATACCAACAGTGAGTTTAAATGGCAA
100051 AACTCAAAATGACTTTAGTTTTAACCCCTTTAAAAGTAATATTAACTTTG
100101 CTTTCAAAAATGTCTACAATGCTTTAAATCCGTTTGAAGCACAACAATAC
100151 CTGGTTGGCCAAGGTAAGTTTTTAAACCAAAAAGTTAATGCTGATGATGT
100201 TAAAAATGACATTAATAATCACATTGAAACCCAGTTTAATGTTGCTAAAA
100251 TCACAGCAACTCTTTTAGGAAAAGCTTTTAAGCAGTTTGGTGAACATAAA
100301 AATGGTCAACCACTTTCACTTTTAAAAGTACTAAGTGGATTAAACAATGA
100351 GTTTAAACAACTCTTTAATTATGTCAGACCTGGTTTAGGTGATTTTGTTA
100401 GTGATTTAATCCAAAGCTCCAGTCAATCAAGTAATAAAAAAACTGTTTAC
100451 CAGCTATTATTTGAAAACAAGACAACAATTATCCACTTGTTGCAAGATCT
100501 TAATATTAGTGAACTGAACTCTGTTTTACCAGTTGTTGATATTTTGTTTG
100551 AAGGGATTAACAGTGCAGAATCACTATACCAAAGGATCCAATCATTTAAG
100601 GATTTAATTGTTCCTGCTTTAAAAGCTGATAAGCAACTTAAGAGCTTAGA
100651 AGCGATTATTTTAGCAGTTTTAGACAATCCTAATACCTATGTTTTTGATC
100701 TTGTTTACCAAAACAAATCGATTCTGTTTAATTTGTTAAGTGATTTTCTT
100751 AAAAACACCGCAAACACTTTACCATTTCTTCAAGAACAGTTTGATATTGT
100801 TAACCACTTATTTGCCAATGAAGCGATCTTTGATCTGTTTTCCAATGCTG
100851 ACTTTGTTGAGAAGATTGCTGATCTTTTTTTAGCAAAACAAAAGGTACAA
100901 GAAGTTAATAATGATGGAACTAAATCAACAAAAATTGTTGATTCGATTTT
100951 AGTTGCTACCCTTAAGGGTTTAGTTGGTGATCAGCTCAGTTCAATCACTG
101001 AACTGTTAAACATCTATATCTTTGAAAATGAATTTTTAAACAGAAATGAT
101051 AGTAATAGTTCAGTTAAAAAACAACAAACTGATAGTCTAAAAAATCTGTT
101101 TAGCGTAATTGGTGATATTTTAAGTGAGACCAATGTTAACAAGATCACTT
101151 TACACGCAGTTAAAAATAATGAACTTCTTTCGTTAGTTGAAACAGCTTCA
101201 ACACTAAAAATTAAACATCTTAATGTTCAATACAAAGTTTTAGTTGATAA
101251 GTTTGAATTGAAAAACAGTTTCATTAAGGAACTATTAAATTTTTTCCCAG
101301 ATACTAAAGATATCACCCCAACTATTAAAAAGGTACTGTTTGAAAGTGAA
101351 AATTATAAAACACTCCGTAAGAAGTATGAAAATGAAGGGTTCCCAGGTTA
101401 TCACTGGGCTAAGTTCATTGTCCCAGGTACCTTCAATTCTGCTGAAAACA
101451 CTTTCTATTCTGCTATTGATAAAACTAAATCAATTCGCGATCTGTTTGCT
101501 GACATGTTATTTGGTAAGAGTTTAGAGAGTGTTAATGACAGTGATAGTTT
101551 TATCAAAATTAATGGTTCATTTACATTAAAGTACCACGGTGATAACTTAA
101601 ATTTACTCCCTAACTACCACTCATTAATCACTAAGAATGTTGGTTATCAA
101651 ATAGTTAATGTTAATTTTCATATTGATGCAAGATTGCTAACTGCAGAACT
101701 ACAAAACACGGTATTTTCAAATCCAAAACCAGTTATTAAATCACCTGTTG
101751 AACTCTCCAAATCCTTATTTGAAGTTTGAAAGACTATCTTTGAAAACTCA
101801 GTTAACCAAATCTTAAAAAAAGAATATACTTTCAAAGATAATCTAAAGTT
101851 CTTTCCTTTTAAAGCTGATGGCTCCTCGCGCTTAGAATTTGATCTATCAA
101901 AACCTGATCAACGTGTTATTCCTTTTGCTTTTGTTGATGGTTATCAATTC
101951 CAACTAAAAAAAGAGTTAATTCCTAACAAAGAAACAAAAAAAGAAGCTAA
102001 TTCTTCACCAGTTTTAAAGCTTTATGATGCAGTTAAAAGAAACGATAGAC
102051 AATATCGTCCTAATCACCACCATGATGATCTGAGAAACTATCCTAGCCTT

-continued

| The Nucleotide Sequence of the *Mycoplasma genitalium* Genome |
|---|
| 102101 AAATCTCAACTAGAACTTATATTAAACCTTGGTGATAAGCTTAAAGCTAA |
| 102151 TAATGATTTTATAGATGACACTGTTGTTAATGCTTTGCAATATAAAACTA |
| 102201 GTTTTAAATCTACTCTAAAAGTTAACAGTTTAGGAATTCCTATTAACCTT |
| 102251 TTCTTTTTCACATTGTGACTTAAATTTAACTTAGAAATTCCAATTGACGG |
| 102301 TTCATTAACATTAACATCCGTTAATGTTGTTTTCCCATACAGTTTGTATG |
| 102351 ATACTAGTTCAAATGAATTTACAAGGATAGTCGATCGCTTAAATTTCACT |
| 102401 GATACCAACTTCTATCTAAAAGATGCATTTCCTAATTTCTGGTTTGTTGG |
| 102451 TTTCTAGAGTAATGAAACTAAACCACTAACTAAACTACCAACTAGATAAA |
| 102501 CAATCAAGTTCATCCACCAAAACCCACTAGTTTTTTGTCTGTAAGTTGCA |
| 102551 CTTTGATCTTGATATTGATTAAAACTAACTAATGGTTTTGCATAAACACT |
| 102601 ACCTAACTTAAGATATCTGTTAAACTTACTAATTTCATACCGCATTCCAT |
| 102651 CACAAGTTTTTAAACGGAATATCCCCTGTAAACAAACAAGTAATAAGTTA |
| 102701 ACAAAAAAGCTAGTTAGTACTGAaTTTTTAACAACCACTGTAAAATTGGT |
| 102751 TGACTTGTGAAAATAAATAGTAATGTTTAAGATCAAAAAGAAAAGGATTA |
| 102801 GATAAAATACGCTAACAACTATCCCACCATACTCAGCTTTATTACTGTTT |
| 102851 TTGTTTTGATTTAAAACCATCTAGTAATCGTTATTAGTATCATTTTTTTA |
| 102901 TAAAATAATCAAGAACATCAGCACATGATCTTTATCACTAAATTTATGTT |
| 102951 TGGTTTCAAATGAAGTTGGATTATAAATCCTGCTTTATTGTAATCATGCT |
| 103001 TTAGATTTAGAAGCTGGTTACTTTTGTTTCAGGTAACCAGTACCATTTCC |
| 103051 AAAAAACTGAGAACCTGAAAAAACAGGTTCTTTTTTTATTTCTATTTAG |
| 103101 TAAATGTTCAAGTATATTCTTAAACGATTAGGACTAGCAGTAGTTGCGAT |
| 103151 GTTTATCGTAATGTCTATAGTCTTCTTTTTAGTGAACGCTACTGGTAATG |
| 103201 TTCCCTTGTCAGCCACTTCTGCAAGAGATATTGCTGCAGTGCAAGCACAA |
| 103251 CTACAAGAGTTTGGGTTTAATGACCCTATTATAGTTAGGTATTTTCGCTA |
| 103301 TTGAGCTAAGCTATTTTCCTTTCAAGCTGATGCTTTAGGAATTTATTATG |
| 103351 CAAACCCTAACCAAACAATTGGTGAGATTGTGTTTGCAAGAGTACCAAAT |
| 103401 ACCTTATATGTGGTTTTAATCTCTTTTTTAATTGGTTCATTGCTAGGGAT |
| 103451 CTTTTTAGGGATGGTTTCAGGATTGAATAGAGGGAAGTTTTTAGATGCAG |
| 103501 CAATTAATGTGTTGGTAGTTTTATTTGTATCTATTCCTTCATTTGTAGTG |
| 103551 GGATTAGGGTTACTTAAACTAGCAGGATTTTTAAATCTACCACCACGGTT |
| 103601 TATTAACTTTGATGATGCTTTTTTTAGCTTTGATCGTTTCTTGCTTGCAT |
| 103651 CAATTATCCCGATCCTTTCATTGGTCTTCTATTCATCAGCTGCTTTTACA |
| 103701 TACAGGATTAGAAATGAGGTGGTGGAAGTGATGAATCAAGACTATATTAA |
| 103751 AACTGCAAAAAGTAAGGGACTTGGGATGTTTGCTGTAGCTAGGTATCATA |
| 103801 TCTTTAGAAACTCGATTATTCCTTCTATTCCCTTGTTTGTATTTGGAATC |
| 103851 TCAGGTGCTTTTTCAGGTGGATTTATTATTGAGTCTTTGTTTGGAGTACA |
| 103901 AGGGGTATCTAGGATCTTAATTGATTCAGTGCAAGTTAATGAAACTAACA |
| 103951 TGGTAATGTTTAATATCTTGTTTATCCAAGGGATTCCCTTATTAGCAAGT |
| 104001 GTCTTTATTGAATTTATCTATGTTTTAGTTGATCCTAGAATTAGGATTGC |
| 104051 AAATAGTTCTAATGTTAGCTTATTAACTAAGTTAAAGTTCTTAAGTTCAA |
| 104101 GACACCAATGGTTAATGAAGTGAAACAAGATTAACAGTGATAATGCCCAA |
| 104151 AATATTGTGTTTAACTCGCCACTGCACCACCAGCTATTAGAACTCAATGC |
| 104201 AATTGATTACAAAACAAAAACAGTTCAACTAACAACTGAACAAAAAACTG |
| 104251 CTCTCAATATCAGTGCAACTGCTAACTTTATCTTACTTGGTAACAAGTGT |
| 104301 TTAAAACTCAAAACAATCCATGGATAGAAATAAAAGTTTTGACCCTAACT |
| 104351 TATTTAAAAGGGTTGATATCAACTTATTAAAGCGAAATGATCAGCTTATT |
| 104401 GGTAAACCAACTACCAATTCAATAGAAATTATCAAGCGCTTGTTTCAAAA |
| 104451 CAAGTGGGCCATCTTATTTTTTCTTTTAATAGTTGTTATTGTGCTATTAG |
| 104501 CAATTATTGTGCCTTTAACTTCCCCTTTTTCAGCAGTAACTCCTGTTTCA |
| 104551 ACCAATGCCTTAGCACAAAATCTACQACCACGGTACTTATGGCATAAACC |
| 104601 AGGTGACATTTTAGTTCATAAGATTACAGCAAGATCAATTGCTGAAATCT |
| 104651 CTCAAGCTAGTGGAGTTTTAGTAGGAACATTACCTAGTGCAAATAGTAAT |
| 104701 CCCTTAGCAACTAATGTCCAGTATGATATTGCTCCTTTTCAACTCCAAGA |
| 104751 ATTGCGTAATTATTTCCCTTTATTGGGGACTAATGGACTTGGGATTGATA |
| 104801 TTTGAACCTTGTTGTGAGCTTCTGTTGCCAAGTCATTGTGAATTGCAGTA |
| 104851 GTAGTAGCAATTATAGCAATGGTGTTTGGAACCATTTATGGAGCGGTTGC |
| 104901 TGGAAGCTTTGTTGGACATATGGCTGATAACATTATGAGTAGGATCATTG |
| 104951 AGATTATTGATATAGTCCCTTCTATTCTTTGAATTATTGTCTTAGGAGCT |
| 105001 ACATTCCGCTTTGGTGGGGTTAAACAATTTGATGATAGTGTTGTAATCTT |
| 105051 TACTTTAATCTTTGTGTTTTGAACATGACCTGCTACTACAACCAGAATTT |
| 105101 ACATTTTGAAAAACAAAGATACAGAGTACATCCAAGCAGCTAAGACCCTA |
| 105151 GGGGCACACCAAATCAGAATTATCTTTGTTCATATGTTACCTGTTGTATT |
| 105201 TGGGAGATTAGCTGTTGTGTTTGTTAGTTTAATCCCAGCAGTTATTGGTT |
| 105251 ATGAAGCTTCCTTAGTTTTCCTTGGGTTAAAACCAGCTACTGATATTGGC |
| 105301 TTAGGGGCACTTTTAAACCAAGTAACTTCAAGTGATAATGTAGCTTTAAT |
| 105351 CTTAAGTTCGATTGTTAGCTTTGCAGTTTTAACAGTAGCAGCTAGAACAT |
| 105401 TTGCTAATGCTTTAAATGATGCAATTGACCCTAGGGTTGTAAAACGATAA |
| 105451 AATGGCACTTAAAAGAAGTAATTTCTTTGTTGATAAAGACCAACAACTAA |
| 105501 AGGATAATTTGATCTTAGACATCACTGATTTACATGTTAACTTTAAGGTT |
| 105551 AAAGATGGGATCTTACATGCTGTTAGAGGGATTGATCTTAAGGTAGAGAG |
| 105601 GGGTAGTATTGTAGGGATTGTAGGTGAATCAGGCAGCGGTAAATCAGTGA |
| 105651 GTGTTAAATCAATTATTGGTTTTAATGACAATGCACAAACTAAAGCCAAA |
| 105701 CTGATGAACTTTAAAAACGTTGATATTACCAAACTAAAGAAACACCAGTG |
| 105751 GAAGTATTATAGAGGGACATATGTCTCTTATATTTCCCAAGACCCATTGT |
| 105801 TTTCTCTAAACCCAACAATGACGATAGGAAAACAAGTAAAAGAAGCGATT |
| 105851 TATGTGGCTTCAAAAAGAAGGTATTTCCAAGCTAAATCAGACTTAAAATT |
| 105901 TGCTTTATCAAATAAGGAGATTGACAAAAAAACTTATAAAAGTAAACTAA |

-continued

| The Nucleotide Sequence of the *Mycoplasma genitalium* Genome |
| --- |
| 105951 AAGAGATCAAACAAACCTACCAACAAAAAATAAAACCTATCAATGTAGAG |
| 106001 AAAAAAACCTTAGAGATCCTGCAGTTCATTGGTATTAATGATGCCAAGAA |
| 106051 ACGTTTAAAGGCATTCCCAAGTGAGTTTTCAGGAGGGATGAGACAGAGAA |
| 106101 TTGTGATTGCTATTGCAGTAGCAACTGAACCTGATTTAATTATTGCTGAT |
| 106151 GAACCTACTACTGCACTTGATGTAACTATTCAAGCTAAGGTATTAACTTT |
| 106201 AATTAAACAACTCCGTGATCTACTTAATATCACTATTATCTTTATTAGTC |
| 106251 ACAATATCTCTTTAATTGCTAATTTCTGTGACTTTGTTTATGTTATGTAT |
| 106301 GCAGGGAAAATTGTAGAACAGGGTCTGGTTGAAGAGATCTTTACAAATCC |
| 106351 ACTCCATCCCTATACATGGGCATTGATTTCTTCAATTCCTGAACAGAAAG |
| 106401 ATAAAAACAAACCACTAACTTCTATCCCTGGAGTTATTCCTAACATGTTA |
| 106451 ACCCCACCAAAGGGTGATGCTTTCGCTAGTAGAAACCAATATGCTCTAGC |
| 106501 AATTGACTTTGAATACCATCCACCCTTTTTTGAAGTTACTAAAACCCATA |
| 106551 AAGCAGCAACTTGATTGCTGCATCCCCAAGCCCCTAAAGTTGAACCACCT |
| 106601 CAAGCGGTTATTGATAACATTACCTTAACCAAAAAAGCACTGCAATTTAA |
| 106651 AGATCAATAATGGAAAACCAAACACAAAAAAACCACTTGTTAATGTTAA |
| 106701 GGCTTTGAGCATGATGTTCAAGGTCAGAGGAACTCTTTTTAAAGCCCTTG |
| 106751 ATGAAATTGGTTTTACTGTTAATGAAGGGGACTTCTTTGGGGTTATTGGT |
| 106801 GAGAGTGGTAGTGGTAAATCAACCACGGGAAAATGTTTGATTAGATTAAA |
| 106851 CATTCCTAGTGGTGGAAAGATTGAGATTGCCAACCACTTACTCTCAGGAA |
| 106901 AAAAACTTACTAAAGAGAATAACCAGTGGTTAAAACAAAACATCCAAATG |
| 106951 GTGTTTCAAGACCCTTATTCATCTATTAACCCTACTAAAAATGTGCTAAC |
| 107001 TGTGATTTCAGAACCGCTGGTAATTAGTAAAACTGTTTTTGGGGAAACAA |
| 107051 AACAATACTTAAAGAGTTTGCAAAAGCTCTCTTTTAAAGTAAAGAAAACA |
| 107101 TTGTTAAGGAATGATATTGAACTTGAAACCAAGTTTCACAATAACTTTTT |
| 107151 TAAAACCGTTATTAAGCAAATTAATGAATCATTGTTTAACTTTGAAGATC |
| 107201 TTGATTACAAGGATTTAAAACCATCACATTTAAGGCAAAGAATCATAAAT |
| 107251 GAAACAGATAAATTCATTGAAAAAATTAGAAGTGAGTTTGCCCTTTTTTA |
| 107301 TGATTTTTATGCTAACCAATCAGTACCCTTGCAAAAGGCATTAGATGATG |
| 107351 CGAATTCCTCTTTAACACCATCTAGTGTTATTGAGTTAAAAAACCAGTTA |
| 107401 AAAGCATTACAAAAACAAGCAAAGATTTCAAAGGCAGCATGGGATATTTT |
| 107451 ACAAGCCCTAAAGCAAAACCAAAAGGAGTTGAAAGATTATGAAAATTATG |
| 107501 TCCATTTTGAACTCCAAAAAAAGCCACGAATCTATCTTAATACCTGACTT |
| 107551 TTAACAACCAAAAGCTACATTAAAGATTCCAAGCAAAACATGCAGCTTAC |
| 107601 TGATGATATCTTTGCTTTTTCATATAACAGTATGGTTGACAAGAAAAGAA |
| 107651 ACTTGGTTTTAATTCTTTCTAAATACTATAAGCTGTTACCTTATTTCTAT |
| 107701 GACCAATCAGTATTTGATAATGCTGATCAATTTGATGAAATTGCTAACCT |
| 107751 TATCTTTTTTGATTTAGTTGAAACATTGCTTGGTGTAACTAGTTTATTTA |
| 107801 ATGATGCATTAGCAGCTGATAAAGTCCCACTAATTAAGTTTGCTAAGTTC |
| 107851 TTAAATAAGTTATGTGACTTGCGCTTTTTAACCTTAAAAAAGAGCTTTAA |
| 107901 AAAAACAAGAGTAAGTTGTAGCTTTAGTTTTAACAGTGAACCTGAAATCT |
| 107951 TGTTTGCCAACAGCTGCTATGATTTGCAACAAATGCCTCAAATCATTAAA |
| 108001 CCCTTTTGAGAGAAGCTTTTTAATGAACAGAACTACCAAAAGATTATTGA |
| 108051 TTCAGTTTCAAGACTGAATGTAATGATTGCAAATTACATTACCAAAGCTT |
| 108101 TTGAAATTAAAAAAACTATTGATGAAAAACTAAGGGAGTTTAAACAACAA |
| 108151 AATTTAGCTTTAAAAAAAGCTTATTCAGCTAACAAGAAAAGTGAGGCAAA |
| 108201 CAAAGCTTCCATTAATGAGTTAAAAGTCAATTTAAAAACACTTAAAAAAC |
| 108251 AGCTTAAACAAGAGAAAAATACTACTAAAAAAACAATCAAAAAAGGAATTA |
| 108301 AAACCACTTTTAAAGAACACCATACTGCTTTAAAACTCCATGATGAGTT |
| 108351 TAACCATGATTTACGCAAGTGGTTCAAAAAACTTAACTTTATGGTTAAGA |
| 108401 AATACAACCGACTGGAAAACAGCCAGAAAAGTTTTGTTTAGTTAAAAAG |
| 108451 TTAAAAGCGCTTTTCAAAAAACAGGATGAAACACTGCAAAGTGAATTAAG |
| 108501 ACCAAAACTAAAAACATTTGGTGTAATTAACTTTGAGTACAAACGTGCAG |
| 108551 TCAAAGAGTCCAATGTCTTTCGATTGGTGCATTTTGCTAAAAATATCTTT |
| 108601 AAACCATTCTTGTTTTTTAACCTCACCAAGATTTTTATGAGAAATAAGGT |
| 108651 CTATGAAGCACTTGATAGTGTTGGTTTAAAAAGAGAACATGCTTACAGAT |
| 108701 ACCCCCATGAATTTTCAGGCGGACAAAGACAAAGAATTGCTATTGCCCGT |
| 108751 GCTTTAATCACTAAACCCAAACTGATTATTGCAGATGAATTGATTAGTGC |
| 108801 ACTTGATGTTTCTATCCAAGCCCAAGTTATTAACATCTTGARAGACTTGG |
| 108851 CTAAAAAACACAACTTAACTGTGCTTTTCATTGCCCATGATTTATCAATG |
| 108901 GTGCAAACTGTTTGTAACCGTTTGATCATTATGCATAGGGGCAAGATTGT |
| 108951 TGAACGGGCAGTGTGGATGAGATCTTTTCAAATCCAGTTCATCCCTACA |
| 109001 CCCGTTCCCTAATAAAAGCATCTCCTAAGTTAAGCAAAATCAATGTTGAT |
| 109051 CTCGCTTCTTTTGATGAAAACTTCACTTATGATAGTGATTATTCACTAAC |
| 109101 CAATATGCCCTTTTATATTAAAGTTCCTAACAGTGAAGAACATGAACTTT |
| 109151 ACTGTACTCAAAAGCAATTTGATAGTTGAATCAAAGAGGCTACGCCGATA |
| 109201 AATTAATTTAAAATTTTCCAAAAATGTGGGAGCTAATTAAGCGTTTGTAC |
| 109251 CACAGCAAAATATGGCTAAAAAAACAGTTACAAGAATCGCTAAGATTAAC |
| 109301 CTAATTGGCGGACAAGCAAAACCTGGCCCTGCGCTTGCTTCTGTAGGGAT |
| 109351 TAATATGGGTGAGTTTACCAAACAATTTAATGAAAAAACCAAGGATAGAC |
| 109401 AAGGTGAAACGATCCCTTGTATAATCACTGCTTTTAACGATAAATCATTT |
| 109451 ACTTTTGTCTTAAAAACTACCCCTGTTAGTAACTTAATTAAACAAGCTGC |
| 109501 TAAACTAGAAAAAGGTGCTAAAAATGCAAAAACTATTGTTGGAAAAATCT |
| 109551 CCTTACAACAAGCTAAGGAGATTGCGCAATACAAGTTAGTTGATCTTAAT |
| 109601 GCTAACACAGTTGAAGCAGCATTAAAAATGGTGTTAGGTACAGCTAAACA |
| 109651 GATGGGAATAGAGGTAACTGATTAATGAAAAACTATCAAAAGGATGCA |
| 109701 AGCTGTTACCAAGCTCATTGATAAAAACAAACTTTATCCTATCCAAGAAG |
| 109751 CATTTGAATTAATTAAAAAAACAGCAATTACTAAGTTTGTCAGTTCAGTT |

| The Nucleotide Sequence of the *Mycoplasma genitalium* Genome |
|---|
| 109801 GATATTGCTGTTAGTTTAAACCTTGATACTACTAAAGCTGAACAACAGTT |
| 109851 AAGAGGTGCAATTGCTTTTCCTTTTAGTATTGGTAAATCTATCAGAATTT |
| 109901 TAGCTATCACTGATGATGAGAAAAAAGCTAGTGAAGCAGGTGCTGATTTT |
| 109951 GTTGGTGGGCTTGATAAGATAGAAGCGATAAAAAATGGCTGATTAGATTT |
| 110001 TGATCTAATTATCACTTCTCCCAAGTTCATGGGAGCATTAGGTAAACTAG |
| 110051 GAAAACTATTAGGAACCAGGGGATTGATGCCAAACCCAAAAACTGAAACA |
| 110101 GTTACTGATGATGTAGTTAGTGCTATTAAAGCTTATAAAAAGGGTAAGAA |
| 110151 AGAATATCGAACTGATTCATTTGGCAACATCCACCTCTCTTTAGGTAAAA |
| 110201 CAGATACCAAAACTGAGCACTTGGTTGCTAATGCCATGCGTTTAATAGAT |
| 110251 TTAATTAAGTCTAAACGTCCTAGCACAGTCAAAGGTACTTACATTAAAAA |
| 110301 TATTGCTTTGACAACAACAATGGGACCAAGTTTAAAAGTAAAGCTACCTG |
| 110351 ATTAATGCCCACCTATAAACTAATTGTTGGTTTAGGTAACTTAGGTAAAA |
| 110401 AGTATGAGAAAACTCGCCATAATGCTGGTTTTATGGTGTTAGATAGACTA |
| 110451 GCTAGTTTATTCCACTTAAACTTTGATAAAACCAACAAGTTAGGTGATTA |
| 110501 TCTTTTTATTAAAGAAAAAGCAGCAATCTTAGCAAAACCTGCTACCTTTA |
| 110551 TGAATAATAGCGGTCTTTTTGTGAAATGGTTACAAGATCACTTTCAAATT |
| 110601 CCGCTTGCAAACATAATGATAGTCCATGATGAAATAGCGTTTGATTTGGG |
| 110651 AGTAATTAGGCTTAAAATGCAAGGGAGTGCTAACAATCATAATGGCATAA |
| 110701 AATCAGTAATTAGACATTTAGATACTGAACAGTTCAATCGTTTACGCTTT |
| 110751 GGGATTAAATCACAAAATACGAGTAACATATTGCATGAACAGGTAATGAG |
| 110801 TGAATTCCAGAATAGTGAACTGACTAAACTGGAAGTTGCGATTACAAAGT |
| 110851 CTGTTGAACTGTTGAAGCGTTATATTGAAGGAGAAGAGTTACAAAGGTTA |
| 110901 ATGGAATATTATCATCATGGCTAGTGAAAAACAATATATAGCAGGGGTTT |
| 110951 CAGGTGGATCTGATTCAATGCTAATGCTTAAACTTTACCAAAAGAAGATT |
| 111001 GCTTGTGTTGTTCATGTCAATTACAACACQAGATCAACCTCATTACGTGA |
| 111051 TCAAAAGTTAGTAGAACAATATTGTCAAAAATTAAATATTCCACTGGTTG |
| 111101 TTCACACTGTTGATCCTGATCTAGTTTGAAAGAAGAACTTTCAAAATCAG |
| 111151 GCACGGAAAATCCGCTTTGATCAGTTTAAAAAGACTGCAAAGCTATACCA |
| 111201 GACCAACAAGTTATTATTAGCTCATCACCGTGATGATTTCATTGAGCAGG |
| 111251 CCAAAATGCAACTAGATGCAAAAAAACGTGCTGTTTACTATGGGATTAAA |
| 111301 ACCAGGTGTGAATTGTATGGTTTGAAAATCTACCGTCCCCTAATGAAATA |
| 111351 CTGAAAAGATGAAATCATTGCCCTCTGTAGACAAGACCATATCCCTTATG |
| 111401 AGATTGATGAAACTAACAAGTTACCTATTTATAAGCGCAATGAAGTGAGG |
| 111451 TTAGAGATAGAAAAATGGTCTAAAATCGAAAAAGAACAGTTTTATATTGC |
| 111501 TATCTGTGCAATGAACAAAACAATTGCTCAAAAACTGTTTGTATTAATGA |
| 111551 AAAAAGCTAAAAAATGGTTATTACAACCTGATGTTAGGGAATTGAAACGG |
| 111601 TTTTCAATTATTGATCAAAAACAGTTAATTTATAGCTATCTTATTTATCA |
| 111651 CAAGATTAATGTTAATGGTGAGAAAATTGATGCTATCCTTGATTTTATCC |
| 111701 AACCTAGTCAACAAAAACAATACCGCTTGCAAAACGATATCTTTTTGATG |
| 111751 GTGAAAAACCAGTGTTTAGCACTTTTATACAAAAGCTAAATGAAACATTT |
| 111801 AACTGTCAAAGCATTAGTTTTGCAATTTAATGATTGTATCCAACTCATTG |
| 111851 ATGGTAAAAACAACATAGATAATGTGATTACTATCCCTGGGTTAAAAAGG |
| 111901 AGTGTTTTTGAACTATTAGGACTATTTTGTAAGCCAATTGGTTCAGTTGC |
| 111951 TATTTTAGGTAAACGTGAATTTATTTTTTTAAATCAAAAGCCAGTTGAGC |
| 112001 AACAGAAAAAGATTATTGCAAACCTCTTGAAACTCAAACCACCTGCAGTT |
| 112051 ATTCTAACCAAGTCATTTCTTGATTGTGGTGTTTTGTTAGCTGTTAATCA |
| 112101 AACTTATCAAGTTCCTATTTTAAAAACTAACTTGTTTTCAACTGAACTCT |
| 112151 CTTTTACTGTTGAAACCTATATTAACGAGCAATTTGCTACTGTTCAAAAG |
| 112201 TTACATGGGGTTTTACTTGAAATCTTTGGTGTTGGGGTATTTTTAGAAGG |
| 112251 AAAGAGTGGGATTGGTAAATCTGAAAGTGCTTTAGATTTAATTAATAAAA |
| 112301 ACCACCTTCTAATAGGTGATGATGCTATTGAGATCTACAGATTAGGCAAT |
| 112351 AGGTTATTTGGTAGAGCACAAGCACTGGCAAAAGGCTTTATGGAGATTAG |
| 112401 AGGTCTTGGCATCATTAATATTGAACGTGCTTATGGGTTACAGATTACAA |
| 112451 AAGAACAAACTGAAATCCAACTAGCAATTAGTTTGTTGAGTTTAGAGGAG |
| 112501 AAAAACAACGCTAGTTTTGAGCGCTTAGGCAGTGATTTAAAACTAAAAAA |
| 112551 TCTGCTTGGGGTTAAGATTAGTTACTATCAGATCCCTATCTCTTCAGGTA |
| 112601 GAAAAACAAGCGAAATTATTGAAAGTGCAGTAATCGATTTTAAACTTAAG |
| 112651 AAAAGTGGTTACAATTCAGCAAACGAGTTTATCTTAAAGCAACGTGCCAT |
| 112701 GTTAGAAGAACAAACTGATGAATAGACCAAGTTGATCAACTGCATTTAAT |
| 112751 ATTGGTGGTGGATTTCCCATCCAGTGGTATGGGATCATTGTCTCAATTGG |
| 112801 CATTATTTTTGCCATTTTAATGTTTGTCTTTAAACTGATTTATTGTTACA |
| 112851 AATTACAAGACAACAGTTTTTATTTTTTATCTTTATTGCTGTTTTAACG |
| 112901 ATGGTTTTAGGCGCTCGCCTCTGGTCATTTGTAATTGGTGATTCCAATTT |
| 112951 TGCTAACAACAATTTCTTTGATTTTCGTAACGGTGGATTGGCCATTCAGG |
| 113001 GTGGGATTTTGTTAACCAGTATTGTCGGAGTAATCTATTTCAACTTCTTT |
| 113051 TTAAATAGTAAGACCAATAAAACCAAAACGATTGCTGAATTACTGAATAA |
| 113101 TAAGAATGAAATAAAAGCTGTTTATGTTGAAAGAAATATCTCTGTTCTAG |
| 113151 TGATGTTAGATCTGATTGCTCCTTGTGTTTTAATTGGTCAAGCAATTGGC |
| 113201 AGATGGGGTAATTTTTCAACCAAGAAGTTTATGGGTTTGCTTTAGCTGG |
| 113251 AACAATGAATGATCCCCAAGCATTGGCTAATACCCAGTGGGATTTTTAA |
| 113301 AGATCTTAATGCCTAAGGTTTGGGATGGGATGTGGATTGATGGTCAGTTT |
| 113351 CGCATTCCGCTCTTTTTAATTGAGTCATTTTTTAACACTATTTTCTTTGT |
| 113401 GTTAATTTACTTTGTAATGGATTTTATTAGGGGAGTTAAAAGTGGCACAA |
| 113451 TTGGTTTTAGTTATTTTCTTGCTACTGGAATCATTCGTTTAATCTTGGAA |
| 113501 AACTTTAGAGACCAAACCTTTTATTTTCAAACTTCAATAACCACTAGTAT |
| 113551 TTTGTTTATTGTCGTTGGTATTTTAGGAATTTTTATTGCCAGTTTATCC |
| 113601 ATGTCAAATTAAGAAATTACTTCTGAACTTATTTCTTCTTTATGCCTTT |

-continued

The Nucleotide Sequence of the *Mycoplasma genitalium* Genome

```
113651  TATAAAGTAGCTGCTTTTTTCACTACACTTTTTTTGAATAACAGAAAGCA
113701  AATGGCACAACAGAAGTTTGCTTTTTATGAAAAATCACTTCCCAATAAGA
113751  AGCGTTCTTTTTTTGAAATGAAGTATTACAATGATGTAACAACACCCAAA
113801  ATTTATCGTTTAACTGATCAGGAAATGAAGTTATTTGATAAATTAGAGGC
113851  AGTTACAACCAGCTAGATTTTGTTAGAATACTTCAGTTGTCTATATGGCT
113901  ACAATAGCGCAATTAATTAGAAAACCACGCCAAAAAAAGAAGGTTAAATC
113951  AAAGTCACCTGCACTCCATTATAACCTCAACCTTTTAAACAAAAAAACTA
114001  CCAATGTTTACTCACCACTAAAGCGTGGTGTTTGCACCAGGGTTGGCACC
114051  ATGACCCCCAGAAAACCTAATTCTGCACTAAGAAAGTATGCTAAGGTTAG
114101  ACTTACAAATGGCTTTGAAGTACTTGCTTATATCCCAGGAGAAGGTCATA
114151  ACCTACAAGAACACAGTGTTACTTTATTAAGGGGGGTAGAGTAAAAGAT
114201  CTCCCTGGAGTTAGATACCATATTGTTCGTGGTACTTTAGATACAGTTGG
114251  TGTTGACAAAAGAAGACAACAACGTTCTGCATATGGCGCTAAAAAACCAA
114301  AACCAAAATCTTAACTTGATCAGTTAAATAATGAGAAAAAATCGTGCTTT
114351  AAAAAGAACTGTTTTACCCGATCCTGTTTTTAACAACACACTGGTTACAA
114401  GGATTATTAATGTCATCATGAAAGATGGCAAGAAGGGTTTAGCACAACGC
114451  ATCTTGTATGGTGCTTTTGAGATCATTGAAAAACGCACCAACCAACAACC
114501  TTTAACTGTCTTTGAAAAAGCAGTTGATAATGTTATGCCCCGCTTAGAGT
114551  TAAAAGTGAGAAGAATTGCTGGTTCTAACTACCAAGTACCAACTGAAGTT
114601  CCCCCTGACAGAAGGATTGCTTTAGCACTAAGATGGATTGTGATCTTTGC
114651  TAACAAAAGAAATGaAAAAaCAATGCTTGAACGTGTTGCTAATGAAATTA
114701  TTGATGCTTTTAATAACACGGGTGCTAGTGTTAAAAAGAAGGATGATACT
114751  CACAAGATGGCAGAAGCTAACAAAGCCTTTGCCCACATGCGTTGGTAGTT
114801  ATTTATTATGTCAAGAACAGTTGATTTAAAAAACTTCCGTAACTTTGGCA
114851  TTATGGCCCATATTGATGCTGGGAAAACCACCACATCAGAACGTATTTTG
114901  TTCCATTCAGGTAGAATTCACAAGATTGGTGAAACCCATGATGGTGAATC
114951  AGTGATGGACTGGATGGAACAAGAAAAAGAAAGGGGTATTACTATCACCT
115001  CTGCAGCCACTTCAGTGAGCTGAAAAAACTGCAGCTTAAACTTGATTGAC
115051  ACTCCTGGCCATGTTGACTTTACAGTTGAAGTGGAGCGTAGCTTAAGGGT
115101  TTTGGATGGAGCAATTGCGGTATTGGATGCTCAAATGGGAGTAGAACCAC
115151  AAACTGAAACAGTATGAAGACAAGCTTCACGCTATGAAGTACCACGGGTA
115201  ATCTTTGTTAATAAGATGGATAAAACCGGTGCTAACTTTGAGCGCTCTGT
115251  TTTATCAATTCAACAACGCTTGGGAGTGAAAGCTGTTCCTATTCAATTTC
115301  CCATAGGTGCTGAAAATGATTTCAATGGCATCATTGATATCATCACTAAA
115351  AAAGCTTATTTTTTTGATGGTAATAAAGAGGAAAATGCTATTGAAAAACC
115401  AATTCCTGAACAGTATGTTGATCAAGTTGAAAAACTTTACAACAACTTAG
115451  TTGAAGAAGTTGCTAGTTTAGATGATCAACTCATGGCTGATTATCTAGAT
115501  GGTAAACCAATTGAAATTGATGCAATTAAAAAATGCAATTAGAAACGGGGT
115551  AATTCACTGTAAGTTTTTCCCGGTATTGTGTGGTTCAGCATTTAAAAACA
115601  AGGGAATTAAACTCTTACTTGATGCAGTGGTTGATTTTCTCCCTTCACCT
115651  GTTGATGTCCCACCTGCTAAAGCAATTGATGCAAACAACAAAGAGATATC
115701  TATTAAAGCTAGTGATGATGCTAACTTTATTGGCTTAGCATTTAAAGTTG
115751  CTACTGATCCTTTTGTTGGTAGATTAACTTTTATTAGGGTTTATGCAGGA
115801  GTTTTAAAATCTGGTTCTTATGTTAAGAATGTTAGAAAAAACAAAAAGGA
115851  AAGGGTATCACGTTTAGTGAAAATGCACGCACAAAATCGCAATGAAATTG
115901  ATGAAATTAGAGCAGGGGATATCTGTGCAGTAATTGGCTTGAAAGATACT
115951  ACTACTGGAGAAACTTTAACTGATGATAAGCTTGATGTGCAACTAGAAGC
116001  AATGCAATTTGCTGAACCAGTGATCTCTTTAGCAGTAGAACCTAAAACTA
116051  AAGCAGATCAGGAAAAGATGTCAATTGCTTTATCAAAACTAGCAGAAGAA
116101  GATCCTACTTTTAAAACCTTTAGTGATCCTGAAACAGGGCAAACTATTAT
116151  TGCTGGAATGGGTGAGTTACACCTTGATATCTTAGTTGATAGGATGAAAC
116201  GTGAATTTAAGGTAGAAGTTAACATTGGTGCACCTCAAGTTAGCTTTCGT
116251  GAAACCTTTAAATCAACTAGTGAAGTTGAGGGTAAATACATCAAACAATC
116301  AGGTGGTAGAGGTCAATATGGACATGTTAAAATCCGTTTTGAACCTAATA
116351  AAGATAAGGGCTTTGAATTTGTTGATAAGATTGTGGGCGGAAGGATTCCA
116401  AGGGAATATATTAAACCAGTTCAAACTGGTCTTGAAAATGCAATGAATTC
116451  AGGTCCTTTAGCAGGTTACCCAATGATTGATATTAAAGCTACCTTATTTG
116501  ATGGTTCTTTCCATGAAGTTGACTCAAGTGAAATGGCTTTTAAAATTGCT
116551  GCATCCTTAGCTTTAAAAGAAGCAGGTAAACAATGTAACCCAGTTTTACT
116601  TGAACCTATTATGGCAATAGAAGTTACTGTACCTGAACAGTACTTTGGGG
116651  ATACAATGGGTGATATCAGTTCAAGAAGAGGGATCATTGAAGGTACTGAA
116701  CAACGTGATAATGTTCAACTAATAAAAGCAAAAGTACCTTTAAAAGAGAT
116751  GTTTGGTTATGCCACTGATTTACGCTCTTTTTCCCAAGGTAGGGGTAATT
116801  ATGTAATGCAATTTAGCCATTATGCTGAAACTCCTAAAAGCGTTGTTAAT
116851  GAGATAATTGCTAATAAAAAATAGATACTTAATAAAAATATAACTTTACT
116901  CAATGAGTTTTTCCAAAAAGTTTTTATGCACTACAATATCATTCTTTTAG
116951  TTGATGGTACGCTTAGTTTAGAACAAGCTAACCAAGTTGAACAAAAACAC
117001  CAAAAATTGCTTGAAAAGGCAACTGAATTTAAAAGTGAATACTTAGGTTT
117051  AAAAGAGTTGGCTTACCCCATTAAAAAGCAACTTTCTGCTCACTATTACA
117101  GATGGAGTTTTCATGGTGAAAGCAATTGTACTAAGGAGTTTAAAAGAGCT
117151  GCTAACATCAATAAGCAGATAATAAGAGAGTTAATTATTAACAGAGAAAA
117201  AGACTATGGTTATTTAGGTTCAGTTAACCCTAAAAAAACAACAACTGTCTT
117251  TGCAGAAGCTAACCAAGTATAATGAGATTATTGCTAGTGAAAATAATCCT
117301  GATAACCCAGATGCGCCTGTCACTTCTGGTCTAGCTTCTGTTAAACCACG
117351  GCTATCAAGAGTTGAAAAACAAAAGGAACGTGAACTTGAAAAGTGAACGG
117401  TTGTTCACCAATCAGGTAACTTTGATACTGTACAGATCAATCCTTATCGT
117451  CCTAGGATAAAACGCTTTTTACAAAACAACCAACAAACCTCCCAAGCTAA
```

-continued

The Nucleotide Sequence of the *Mycoplasma genitalium* Genome

```
117501  TAATAACCAACCTCGTTTTCAAAATCAATTTAAAAAAGGAGCAAAACCTT
117551  AGATGAACCGGGTCTTCTTGTTTGGTAAACTCAGTTTTACTCCCAACCGT
117601  TTACAGACAAAAAATGGTACGTTAGGAGCTACTTTTTCCATGGAATGTCT
117651  TGATTCCAGTGGTTTTAATAATGCCAAATCATTCATTAGAGTAACTGCTT
117701  GAGGTAAAGTTGCTAGTTTTATTGTTGCTCAAAATCCTGGGGTGATGCTT
117751  TTTGTAGAAGGAAGATTAACTACATATAAAATTACTAACAGTGAAAATAA
117801  AAACACCTATGCTTTACAAGTAACTGCTGATAAGATCTTTCATCCTGATG
117851  AAAAAACTACCAATGAAGAACCTATTAAATCAACTGTAGTTGATTCACCC
117901  TTTATGAATCCCAAAGCAAGTGTTACAGAAGCTGAGTTTGAACAAGCATT
117951  CCCCCATCAAGATGAAACTGATTTTAACAACATTACCCCTATATTTGAAA
118001  ATGATGTCCAACTAGAGGAGGAAAGTGATGATTAATAAAGAACAGGATTT
118051  AAACCAATTAGAAACCAACCAAGAACAGAGTGTTGAACAAAACCAAACTG
118101  ATGAAAAGCGCAAGCCAAAACCAAACTTTAAAAGAGCAAAAAAATATTGT
118151  CGATTTTGCGCCATAGGTCAACTAAGGATTGATTTTATTGATGATTTGGA
118201  AGCAATCAAACGCTTTCTCAGTCCCTATGCAAAGATTAATCCTAGAAGAA
118251  TTACAGGTAATTGCAACATGCACCAACGTCATGTAGCTAATGCTCTAAAA
118301  CGAGCACGTTACCTAGCTTTAGTGCCATTTATTAAAGATTAAATATGAAG
118351  ATAATTTTGAAGCAAGATGTTGCTAAATTAGGCAAGCGGTTTGATGTTGT
118401  TGAAGTTAAAGATGGGTTTGCTATCCATTTTTTATTTCCCAAAAAACTAG
118451  CTGCACCTTTAACAAAGAAAGCAATTGCTAACCGTGATTTGTTTTTAAAA
118501  CAACAACAAGAACAATACCAAAAAAATCGTGCCTTAGCTGAAAAATTGAA
118551  ACTAGTAATTGAACAAACACCATTAACTTTTCAACTCAAACAACACGATG
118601  GCAAGCCATATGGTTCAATCATCACCAAACAAATAATTAATTTAGCAAAA
118651  CAACAAAGACTTGATTTACAGCGCTTTATGTTTAAAGATAATGTGCGCTT
118701  ACAGTTTGGTGAACACAAACTAATTTTGCACCTTTTTGAGGAGATAACTG
118751  CAACTTTAACTGTTATAGTGAACCCTGAAAATGGGACAACAACTAGTTTT
118801  TAAATATGCAAATGATAGCAACATTGAACGTGCAAAGACGTTTGATGC
118851  AAGCAGTTGCTCAAAACAGTGAGGGCATTGATCTAATTTTCAATAAACTT
118901  GAACCAATTGATTTTTTTGCAACCCCTTTCAAACTCATTTTTCAAACTGC
118951  AAAAGAAAACTACCAATTAAATAACCCTATTATTGGTTCTGGTTTACTAG
119001  AAGCGGTTAAGTTTAAACTTGATGCTAATGATCAATCCACTAAAAGTGAA
119051  CTTGAAATTTTATTCACAAAGATCTTATTAATCCGTTTACCACCTAACCA
119101  AACAGAGATTAAAACACTGGTTGATGTTGTTAAAAAAGCTTCTATTTTTC
119151  GCAGGTTACAACAGTTTGCTAAGCGTGTTTACAACGAGGAATTTAAGTTA
119201  AAAGAAGATCGTTTTGAAGGCTATTTACAAGCTATTCAAGATGATTTTGT
119251  CAAGATTATCCACAGTGCTTTTAGTAACATCTTTGCTTTTAGCTATGATG
119301  AGATTGCCAATCAAGAGGAAGCATTAATTAAAAAGGTTCACCGTGGGGAA
119351  TTGATCATCAGTGGACTTTCAAGTGGATTTTTAAAATTAGATCAACTTAC
119401  ATCAGGTTGAAAACCAGGAGAGTTAATAGTAATAGCAGCTCGCCCAGGTA
119451  GAGGTAAAACTGCCCTTTTGATTAATTTTATGGCTAGTGCAGCTAAACAA
119501  ATTGATCCTAAAACTGATGTGGTCCTCTTCTTTAGTTTAGAGATGCGTAA
119551  CCGGGAAATTTACCAAAGGCACTTAATGCATGAAAGTCAAACTAGTTACA
119601  CACTAACCAACCGGCAAAGGATTAATAATGTCTTTGAAGAGTTAATGGAA
119651  GCATCTTCAAGGATCAAAAACTTACCTATTAAACTCTTTGATTACAGTAG
119701  TTTAACACTCCAAGAGATCAGAAACCAAATTACTGAAGTGAGTAAAACCA
119751  GTAATGTTAGGTTAGTAATTATTGACTATTTACAACTTGTTAATGCTTTA
119801  AAAAATAACTATGGTTTGACAAGACAACAAGAAGTGACAATGATCTCTCA
119851  ATCACTTAAAGCATTCGCTAAGGAGTTTAATACCCCTATTATTGCTGCAG
119901  CTCAACTTTCTAGAAGGATTGAAGAAAGGAAAGATTCCAGACCAATTCTT
119951  TCTGATTTAAGAGAATCAGGTTCAATTGAACAGGATGCGGATATGGTTTT
120001  ATTTATCCATAGAACTAATGATGATAAAAAAGAACAGGAAGAGGAGAACA
120051  CAAACTTGTTTGAAGTGGAGCTTATCTTAGAAAAGAACAGAAATGGTCCC
120101  AATGGCAAAGTTAAACTAAACTTTCGCAGTGACACTTCTTCTTTTATTAG
120151  TCAATATTCCCCTAGTTTTGATGACCAATACAGTTAATTATGAAACTGA
120201  AGTTTTACAAACTACCTTTAATTACTACAGCATTTAGTTTTGTATTTTTA
120251  ACTGCTTGTTCAACACCCCAATCTTCCTTTTTTCTCCCTGCACAAACAAC
120301  TATTAGTACTTTAAAAATTAATGGTATGGAAAACAAAACAGGTTATTTTC
120351  TTGAAACGCAGCGTTCTCGTGGTAGTTACAATCCCACCGCTTCACTTACT
120401  ATGATTAAGTTAGGAGATGAAAAAGAGTTTAAAAACGTAGATACAACCAA
120451  GCAAGATGAAGTTTTGTTTGCCAACATTTATGGTGGAATCTCTTCATTGC
120501  TTAACTTCAGAATTATCCAACCGATGTTAACCTACTGAAACTTAGTTAAC
120551  AACTCATTAAGTCAGATTGGTAGTACTAATGACTTAATTACATTCAAAGA
120601  TAGTGGATATAAAGATCAACTTGCAAAAGCGCTTGCTAACAATCTCATAG
120651  TTGCTGATGAAGGTAATAATAACTTTTGGTTTGGTTTAAAAGCCCTAAAG
120701  TTTGATACGGTTAAACTCCAAGCTAATAATACTGCTACTAGTTCAACAAG
120751  AGCTTCAACTACTCAAAATACTAATAATAAGATTGATGCACGTGAAAAAA
120801  TCACCATTAATGGGAATGGTGGAACAAATAATGATCAAAATGCTACTGTT
120851  CAAAAGTTGATAGGTATTGAAAATATTGAAGTTGAGTTTAGCTTTGTTAA
120901  AACTGGTTTTAATGGAAATGAGATTAAGTTTGAAGATTATGTAACAGATT
120951  CTTCCCCCACAACATCTTTATTAAAGCAAGTTTGAAAAAGTAAGTGAAAT
121001  ACCGAGTTGACCCACACCAGCTTTAAATTCAAACTCAATTCTTTCAATGT
121051  TTTGTTAACTTATCAATTGGAAGCAAACCAAAAAAGCCAATATCTTCCCA
121101  ATGGCTTTAGCTTTCTTTTTCCATCTAATTTAGAAGGAAAGATAGATAGT
121151  TCAAAAAGCTATTGAAACAATCTTGTTGATTTTTCAAAAAGAACCACAAA
121201  TGAAGAGAACACAATGCTACTAACTGATTTGCAAAAGAAACAAGATCAAG
121251  TGAATCGGTTTGTTGGTTTTATTGGTCAAAACCACTTTACTTTAAGTGCT
121301  AACAGCATTAATGAAAAGCAGTTTAACGATGCTAGTACTGCTGATTTTTT
```

-continued

| The Nucleotide Sequence of the *Mycoplasma genitalium* Genome |
|---|
| 121351 TAAAGCAATCTTTCAAAAAGTGAGTATCAATGAATAACAATTTTAGCCAT |
| 121401 TCAGTTTTGAAAAGAAAAGTTTAAATTAATGGTAAAATTATTCATTAAAC |
| 121451 TTTCCTTGTTAGTTGTAGTTTTCAATACTGTTTGTATTTCGAAGTTCATT |
| 121501 TTAAAAAATTCGTAGTTCTAGATCTTTAAAATATGTTATTTAATTGTCTT |
| 121551 TTTTAATTTCATAAATTGTTTGAAAACACARAAAAATATCTTTAAGGTCA |
| 121601 AGGCCTTACTACTTTCACTTTTTTCTGCTGCTGTTACCATCACTATTTTT |
| 121651 GCTTTACCTATCTTTGCAAACAATGGTTCTAAAACTGATTTAGGTTTGCT |
| 121701 TTCTAAAAATAGTGCTGATTTTTTAGGTAGTTCAAAAAGAAGTCTTGCTG |
| 121751 GCTTTGATACTCCTTTTAGTCCAGATAACCTCCAGTATTTAGAAAAAGAA |
| 121801 ACTGATTATGATCAGAACTTTAAAAGTTTTACTGAAAAGTTTAAAGATGA |
| 121851 AxAAATAACTAACAACCAACTTGGTATTGTTGATATCTATAACTTATTCA |
| 121901 GTGGTTTTCACAAGAGTGTCAAAAGCACAGTTGACTTAATGAACCAACTG |
| 121951 CAAAAGCAAGTTGAAGCTGCTAATGCTATCTTCCCAGTTGATGATGCTTT |
| 122001 TGTTAAATTACCTAAAGTACCTACTGAATTATTTAAGTTAGTTGATGATA |
| 122051 ATGTCTTTCCTAAGTTAAATCCTAAGGGCTTAAATATCTCTGATAATATT |
| 122101 GCTGCACTTTTTGAAAGATATAACCTTAAATCGATTGAACTTAAGAACTT |
| 122151 TGACTTAGCTTTCTTGAGAAAAGCTGATGTAATTATCAAAGACAAGGTTC |
| 122201 GATATAACTTTGAGATGCAAATGCAGTTTCAAACTGTTTATGTTGGTGGA |
| 122251 GGGAATACCGTTATTAACTTAGACTTTACTTTAAAAGCCCAAACCGTTAA |
| 122301 CTTTGCTAACCTCCAAGATTTACAAAACACTTTTGTTAAAGTTGGTAATG |
| 122351 ATCTTTCCACCCAACTCTTTTGGATTCCAACTGTTAATAAATTAACTGAT |
| 122401 AATGCAGGTAATGATCTTACCCATATTGCTAAAACTGTGATTGGTGAATC |
| 122451 GTTTTTCCAAACCAATGTTAACTTAGCTAAATCAGTTATTGAATATGATA |
| 122501 AGGTTCAACCATTGGTTAAACAAGCTTTTGAAGAGCGAGTTTTAACTCCT |
| 122551 TTCAAAAAGGAAAGAGAAGCTGCTAAAAAAGCTTATGAAGAAGAACAACG |
| 122601 TCGCTTGGAAGAGGAACGTAAGCGTCAACTAGAAGAGCTAAGGAGAAGAG |
| 122651 AAGCTGAGGAGAAAAGAAAAGCTGAAGAAGCAAAACGAAATCAAGAAAAA |
| 122701 GCACGCAGAGAAAGAGAAGCTTATGAAAAATCATTTAACTCCTTTAAAGA |
| 122751 CTTTAAATTTTACTGGTTAACTAAAGGTAAAGATGTTACTAAAAAAGCTG |
| 122801 ATTTAATTGATGCACTTAAAACCGCTATTGCTACACCAGCATACAGAAAT |
| 122851 AGAACATTCTCTTTATTAATCAAAGGTTTTGCTAGTGGAGTTGAACGTTA |
| 122901 TTTCAACGCTAACAAGAATGATAAAGAGTTGAAAAAACTTGCATTTGGTG |
| 122951 AAAAAGGGATCCAATTCCCTAGAGCAGATGCTGGGGTAAATGGTCTTTAC |
| 123001 ATGAGTAATTTTTTGAGGCATGAATTGACAAGCAAAGCAAAATTTTCACT |
| 123051 TAACCTAAAAGATATAAAAGTTGAAAATACGGTTGAAGATACTCAATTGT |
| 123101 ATTGGAAGGATAATGGCATTCATTTAAAGCAAGCCAATCCTTATAAATTC |
| 123151 AATCTAAATATCAAGATCAAGTACAACGGCTGGTATAATGTCCACTGGTG |
| 123201 AAACTGGCTCCCTGCTAAAATTTTAGGGATTCCTACAGACTGAAGTGGTG |
| 123251 AGATGAATTTAACATTTGTTGTCAACGGTGACCTATCAGAAATTGTTGAT |
| 123301 AAACATGATTACCCTGGTACTTTCTTTCAATTTACCGATAAAAATGAATT |
| 123351 GCTATTTACCTTAGCAGTTAGAGAACAAATTAAGGTTGATAATAATCATT |
| 123401 TTATGGGTCTGTTAAAAAGCCAAAACCTTCATAATCTTCAGCTTGCTTCT |
| 123451 GGTGCTACAAAACCTCCTGTTGTTGATTTAGCTAGTTATTTCCACTTTGT |
| 123501 ATTATTGACTGAAAAATCTTAATCTATTAAGAAATTTTTGATCAGTTACT |
| 123551 TTTACCTAGATAAATTTAAAGTTTATTTGTGGTAATGGATGATCTATTCC |
| 123601 AAAGAATGGTTAGCTGTGTTCTACCGTCATGAAGAGCTTTTATTGATGAG |
| 123651 GAAGTTAAAAAACCTTATTTTCAAGCTTTATTAGAAAAATTAAAGGCTTT |
| 123701 AAAAGCAACAATAATTCCAAAACCAGAACTTATTTTCCGTGTTTTTAGCT |
| 123751 TCTTTAAGCCAATTGATACAAAGGTAATTATCTTTGGTCAAGATCCCTAT |
| 123801 CCTAGTCCTAATGATGCTTGTGGACTTGCTTTTGCATCCAATAATTCCAA |
| 123851 AACCCCTGCCAGCTTAAAAAGAATAATTTTACGTTTAGAAAAAGAATATC |
| 123901 CTTCGCTTAAACAAGAAAGTAGTTGACAACAAAACTTCCTATTGAATTGA |
| 123951 GCAGAACAGGGCGTTTTATTACTAAATGGAATTTTAACAACTACTGTATT |
| 124001 TATACGCAACGCCCATAAAAATTGGGGTTGGGAGGAGTTTAACTGTAATT |
| 124051 TGCTAACTTTTCTAAAkAATCAAAACATTAAACCGCTGTTGGTATTTCTG |
| 124101 GGTGTTCAAACTAAAAACTTTGTTGTTAAGAGTATTGGTAATGTTGATGG |
| 124151 ATTTGAGCATTTATCATATCCCCATCCCTCACCACTAAGTGGTAATTTGT |
| 124201 TTCTAACAAACCCTAACGATCTGTTTAAAACAATTAACAATTGGTTGAAA |
| 124251 CAACATAACCAAAAAATAATTAACTGAGCAGTTGTTAAAAATGCTAGTTT |
| 124301 TGACCAATTAAGTTAATTAAAAACAAAGCTGTAGTTGACACTTGTTTATT |
| 124351 GATTAGAAAAACAACAACCTTGTAAAATTATTTAACTAAGTGATTATTAC |
| 124401 TTAATTGCACTTTAGATGGGAGAGATTAAAAATACTGCACCAACAAGCGA |
| 124451 TATTTCCACTTCAGGATTTATCTATTTTGCAGTTGTTTTCTAATCATTA |
| 124501 TAGTCTATCTTTTTTTTAAAAACATTCTCTTTTTGTTCTTCTTTAAAAGA |
| 124551 TATCCTAAAAACACACCTAAAATTGGGGTTAGCAATATTACTACTATTGC |
| 124601 TATGATTATTGCTGTTGCTGTATCTGTTGTTTTGGTCTTAATGGCTTTAG |
| 124651 CAGGGGGGTTAACAGCAGCGCTGTTCCGTGGTTATCCTGGGTTCCGTGTT |
| 124701 ACCTTAGAGTTAATTCTAGTGAAGATTTCAGGACTTTTATTTGGTCCTAT |
| 124751 AATTGGTATTTTTTCAGCAGCTACCATTGACTTTTTAACTGTTATTTTTT |
| 124801 CAGGTGGGGTGTTTAATATTGGTTATGTTTTAGGAGCAATCCTAACGGGA |
| 124851 ATGATTGCTGGAATTTTACGTGAAGTTTTAATTTCAACTTCTTTTTTAAA |
| 124901 TAACAAAACTTTAAGTGATTTTGCCTATCTTGTTTTATCAGTGGGGATGG |
| 124951 TATTTGCCAGTTTTTTAGTAACCCAGTTTTTTGTTATCTCAGTTACCCAA |
| 125001 AACTTATCAGCATTTCAAAGTAATGATCAAATTGTTTTACGTTTTAACGC |
| 125051 CTCACCTTTAAATTTCAGTATCTCATTGCAAAGATATGTTCAAATTATTT |
| 125101 TCTATTTTGCGATGGTTGTAATCATCACAATGGTAGTACTTTACTTTGTT |
| 125151 TGAATAATCAAGCAAAAGCACTTTAACTATGCTTATTCCAAGTTTTTCTT |

| The Nucleotide Sequence of the *Mycoplasma genitalium* Genome |
|---|
| 125201 TCGTAGATATAAACATGCTAATCACCAATTTACCTTATTTGTGTTAACAA |
| 125251 AAGAAAACTGGTTTTATCTAATTCTGAATGTAATTACATTAGCAACCACC |
| 125301 AGTTTGCTAATGATTAACATTGCATTTATTCCTATCTTTGATACCCAAAC |
| 125351 AACTGGACAAACTTATGATTTTTGATTATTAGTTAGATTATTGTTTGCTC |
| 125401 CTTTGATCTTCTTACTTGATATTATTGTTATCTATCCAATCTTGTTATTG |
| 125451 TTAACCCCAATCATGTTAAAAGGGTTTAAAACAGTAGCATCAGAAACCCA |
| 125501 AACAAAAGGAATCAAAAAGAGTTTTTCAGATATGCAAAGCTTAATTATGC |
| 125551 CCAATGTTATTAGTCACAAAAAACAGCAGTTAATTAGAAAAGAGATGCAA |
| 125601 CAGTTAGCAAAAACAATCAGAATTGATTTATCAGACAAAGAAGTGGATGC |
| 125651 ACTTGTTGAAGAGTTTAAAGAGATCACAAAGAGTTTTAATAAGGTAACTA |
| 125701 AAATTGATACCACTAATGTTCAACCGATGTACGCTCCATTTGAATTTAGT |
| 125751 CCAACCCCACTAAGAAAAGATAAACCAGTAGTTGATAAACACGCTAAGCA |
| 125801 ACTACTTAATAACTGTTGTGAAGTTAAAACAGGTTTTGTAAAGGTATAGT |
| 125851 TGTGCGATCAAATATTTTAAGTCTCAGGGCGATACTTGATAAAAAACCTA |
| 125901 GTGCCATTAACGATGTTTTAACATCAATTAATGCAAAGATAGAACTGAAT |
| 125951 AAATCAAGTAATTTTTTATTGAAAAATACTGTTGAAATTTATTCAAAAAA |
| 126001 AATTAATAAAAGTGATGAAAAGATTCTGCTAAATAACATCCCTTATGTTT |
| 126051 TGAAAGATAACATCGCTACTAAAGATATTGTCACCACTGGTGGTTCTTTG |
| 126101 TTTTTAAAAAACTATCTTCCCCCTTTTTCAGCAACTGTGTTTGAACTGTT |
| 126151 AGAAATGAATGGCGCGTTGCTTGTTGGTAAAGCTAATATGGATGAATTTG |
| 126201 GCTTAGGTGGAACAGGTAGTTATTCTGCTTTTGGTGTTGTTCATCACCCT |
| 126251 GAAAATTCCAGTTTAATTGCAGGTGGTTCTTCCTCAGGTTCAGCTTACGC |
| 126301 AGTTGCTAAAGACATTGTTCCTTTTTCCATTGCAACTGACACTGGTGATT |
| 126351 CGATTAGAAGACCTGCTAGTATCTGTAATGTTGTTGGCTTTAAACCAACT |
| 126401 TATGGTTTGATATCACGTAATGGGGTATTTCCATATGCCCCAAGTATGGA |
| 126451 CCATGTGGGGATATTTGCTAAGTTTGTTAGTGATATTGCCATTGTTAGTG |
| 126501 ATGTTGTTATTAAACATGATAAAACTGATTTTTCTTCCCAAAAATCACCT |
| 126551 GATGAAAACCAGTTTTTCAATGAGTTGGCCATTCCCTTTACAAGATCAAT |
| 126601 TCGCTTCGGTTATTTAAAACCACTAGAAAAACTGTTTAACAAACACCTCC |
| 126651 AAAAAAAATGAAATAATCTCAAAAAAACCTTAGAACAAAAAACTACCAG |
| 126701 TTGATTCCACTTGATTTTGATGTGGAACTTCTCAAAGTAATTGATTCTAT |
| 126751 TTACAAAATAATTAGTTATAGCGAAGCAGTTAGTTGTTATAGTAATTTAA |
| 126801 CTGGCATTGTCTTTGGTCAAAAGGTGTTTGAACCTAATTCACCAAGTAAT |
| 126851 TTTGATCAAACTATTACCAGAAACAGAGATCAGTTTTTAGGTAAACAACT |
| 126901 AAAAAGAAGATTTGTAATAGGGGCATTTGCAACTGATGAGAAGAATTTTG |
| 126951 AAAAGTACTTTGAAAAAGCTCAGAAAATAAGAAGAGTCTTAGTGGATAAC |
| 127001 TTTCTGAATCTCTTTAGTGATGTTGATTTTGTATTATCACCAAGCGCTTC |
| 127051 TTGTTTTGCTAGTACCATTGAAGATATTCAAGCTAATAAGCCATATACAA |
| 127101 ACATTATTGATGACTTTTTACAATTAGCTAATTTTGCTGGTAGCCCTTCT |
| 127151 ATAACTATCCCTTGGTTAGTTCAAACAAAAGACCAAACAATTGGTTTAAG |
| 127201 TATTAGTGCTAACTGTTTTGAAGATAAAAAACTCTTACAAATTGCTTATT |
| 127251 GATTTGAACAACTTTTTGATTTAAACCATGATTAATTTTGAAGCGATTAT |
| 127301 TGGAATTGAAGTCCATGTAGTTTTAAATACTGCTAGCAAGATGTTTTCAA |
| 127351 AAGCACCTAACCGCGTTGATAATCAAAAAATCAATCATTTTATTGACCCA |
| 127401 ATAGATTTAGGTTTACCAGGCACTTTGCCTCAAGTTAATGAGTTAGCAGT |
| 127451 TTACAAGGCATTATTATTAGCTGATGCATTAAAAATGAAGACAGTAACAA |
| 127501 ATAAACTTGTTTTTGATCGAAAGCACTATTTTTATCAGGACTTACCTAAG |
| 127551 GGTTTTCAAATCACCCAACAAAATTATCCTTTTGCTAAAAATGGTGTAGT |
| 127601 TACCATTAATGTTGATGCTATTGAAAAACCAATTTATATTGACCGGTTTC |
| 127651 ATTTGGAGGAAGATACTGCCAAACAACACTTTAACCATGACCAAATTCTG |
| 127701 CTTGATTTTAATAGGTGTGGTGCACCTTTAATTGAAGTTGTTACTCTTCC |
| 127751 TGTTATCAACACTGCAAAAGAAGCGAAAGCCTACCTACAGAAGTTGAGAC |
| 127801 AAATTCTGATTGTTAACAATATCTCCAATGCCAAATTGGAAGATGGTTCA |
| 127851 ATGCGGAGCGATTGCAATGTTTCAGTACGTTTAAAAGGTCAAAGGCAACT |
| 127901 AGGAACTAAAATTGAAATTAAAAACATCAACTCACTTAATAATGTTGAAA |
| 127951 AAGCGATTGATCTTGAGATTAACCGCCAAGTTAAAGCACTTATTAATGGT |
| 128001 GAAACCTTGAGTCAAGCAACTTTAAGCTTTGATGATAAAACCAACAACAA |
| 128051 TGTTTTTATGAGAAAAAAAGACAATACGATTGACTATAGGTACTTTATTG |
| 128101 AACCTAACATCATGACTAGTAATATTGATGATTTATTATTAGAAAAACCT |
| 128151 GTTGCTTTTCAGTTAGAACAGTTTCAAAAAGAACTAATTGATAGTAATGT |
| 128201 CAATCCTCAATTAGTCCAATTAGTAGTTGATGATGCAACTATCTTTAGTG |
| 128251 CTTTTCAAACTATTAATAGTGTGATTAAAAACCCCCAAGAAACCATCAGG |
| 128301 TGGTTATGTATTGAACTAATAGGTCAACTCAATAAAACCAACAGTTCATT |
| 128351 AACAGCTAATTTAATTCAAGATCTAATTACCCTAATTGAAATGCTAAAAG |
| 128401 CAGCAAAGGTTAACCAAAAACAAGCTAAGCAGTTAATTACTTTAATGATT |
| 128451 GAAACTAAAAAAGATCCAAATCGCTAGCTAAGCTCCATAATTTAGAGCA |
| 128501 AATTACTGATCCAAAAGAGTTACAAAAGATCATTAAAAAAATCTTTCAGG |
| 128551 AAAATGAAAAAGAGATCCTGAAAAACATTGATAGAATTGAACGGATTCAA |
| 128601 AAGTTAATTATTGGTCAAGTTATGCATAAGACCAATAATCGAGCAAACCC |
| 128651 CCAACAAGTTTTTATAATTGTTGAAAATATGCTTCATGAAGTTCGGGAAA |
| 128701 GAGATAGCTSAAAAAAATCAAATTATTTATCGCTATATAATCCTTAAAAT |
| 128751 TCAAAGCTTTGAATGACCTGCTAACACCCGTATCTTCTCAGAACGCCAAC |
| 128801 TAGAAATCCGTTTCAACTCCTCACGGAGTCAAATTCGCTCTGTTCTCGCT |
| 128851 ACGCTTTTAAACAAAAATATAATCCGCTACACTAAAAATACCCCTGGTTA |
| 128901 TTTTGTGTGTAAAGATGTAGGCTTTAGTTTTTTTCATAAAACCCAGGATA |
| 128951 ATCTGAAGGTGAAATATGCTAAACTTTCAACTTTGATTAAAAAGCTGTTA |
| 129001 TCACAGGATGATGCTAGTGTTTTTGCCAATATTGACAGTACTGTGCACCT |

-continued

| The Nucleotide Sequence of the *Mycoplasma genitalium* Genome |
|---|
| 129051 TGATAAATTTAAGGGAATTGAAGCTAAGTTTTTTGATGAGAATAAAAAAC |
| 129101 ACTTTTTAAACGTTTGTTTTTTGCTAAAGATGATATTTTAAACATCCTT |
| 129151 GATGAAAACAACCTCCAGCAACAGTTCTTCAGGGAGTTTGCTTACAATGG |
| 129201 GATTGCTATTGAAAAACGTCATTGTGTTACCTCTGTTGACAAGGAAAGTG |
| 129251 GGTGCTTGGTGATGTATGACATGTATTATGATGACAATGATAATTTTGTA |
| 129301 GTTGCTAGCAAAAGTAACTTCCTTAACCCTGAATTGAAAGTAATCAATGC |
| 129351 TTAAAGTGAATGCTGATTTTTTAACTAAAGATCAAGTTATCTATGATTTA |
| 129401 GTGATAGTAGGTGCTGGCCCTGCTGGGATTGCTAGTGCCATTTATGGTAA |
| 129451 ACGTGCTAACTTAAATTTAGCAATTATTGAAGGAAACACTCCAGGAGGGA |
| 129501 AGATAGTAAAAACTAACATTGTGGAAAACTATCCTGGTTTTAAAACCATA |
| 129551 ACTGGTCCTGAATTAGGTCTTGAGATGTACAACCACTTGTTAGCATTTGA |
| 129601 ACCAGTTGTTTTTATAACAACTTAATCAAAATTGATCATCTTAACGATA |
| 129651 CATTCATCTTGTATTTAGATAACAAAACGACAGTTTTTAGCAAAACTGTT |
| 129701 ATCTATGCAACAGGGATGGAAGAGAGAAAACTTGGCATTGAAAAGGAAGA |
| 129751 TTATTTTTATGGTAAAGGGATTAGTTATTGTGCTATTTGTGATGCGGCTC |
| 129801 TTTACAAAGGTAAAACAGTTGGTGTTGTAGGAGGAGGTAATTCTGCAATA |
| 129851 CAGGAAGCAATTTATCTTTCAAGTATTGCTAAAACAGTTCACCTTATTCA |
| 129901 CAGACGTGAAGTGTTTAGAAGTGATGCATTACTAGTTGAAAAATTAAAAA |
| 129951 AAATTAGTAATGTAGTTTTTCATTTAAATGCTACTGTAAAACAGTTAATA |
| 130001 GGTCAAGAAAAGCTCCAAACTGTTAAATTGGCAAGCACAGTTGATAAATC |
| 130051 AGAAAGTGAAATTGCAATTGATTGTCTCTTTCCTTACATAGGCTTTGAAA |
| 130101 GTAATAACAAGCCAGTTTTAGATCTTAAGCTTAATTTAGATCAAAATGGT |
| 130151 TTTATTTTAGGAGATGAAAATATGCAAACTAACATTAAGGGTTTTTATGT |
| 130201 TGCTGGGGATTGTAGAAGTAAATCATTCCGGCAAATTGCCACTGCAATTA |
| 130251 GTGATGGGGTAACAGCTGTTTTAAAGGTTAGGGATGACATTTAGTACACA |
| 130301 GATTAAAGCTGAACTGGTCCAAAACAAATTAATTGATAAACACTGAAATG |
| 130351 TCTTTTTAGCAGGTTTTTTTCAAAACAACTTAAAGCTACTTTACAACCGT |
| 130401 AACTGAAGTTTTAAAGTGCAATCTGAAGCATTAAAGGAACAATTTGTTCA |
| 130451 AAATCTTAAGTTTGACTTTAAGACAAAAGCTAGTAAGAAATACTTTCTTT |
| 130501 TTGAGTTTAATGCAGATATTAACGTAATTAACACTCTTTTAAAACTTGAT |
| 130551 GTGACAACTAGTGAATTGGTAGTTAAACAAGTTTATCTCATTGCTGCTTT |
| 130601 TTTAAGTGGAGGTAGTGTTAGTGATTTAATAAACTCCAATAACTTTCACT |
| 130651 TGCAAATCAGTTCCAACAATGAGTTTCAAATTCAACAACTTTTAAAATTG |
| 130701 TTTAGTTTTTTTAAAAAAACAGTTAAACAAAACCAGTTAGTTGTTTATCT |
| 130751 TAAAAGTTATGAAAAGATCTGTAATTTTTAAAACTGATTCAAGCCTTTG |
| 130801 ATGGTTATCTTGCTTTTGAAAATAAGCAACTAGAGAAAAGTTTTACTTTA |
| 130851 AACCAGTTAAGAAAAAGTAATTTGGAAGTTGCTAACTTAATGAAGACAAT |
| 130901 CAGATCTAATAATCAAACTAATCAACTCCAACTAAAATCATTTATTAAAA |
| 130951 GTAGTAGTTTTGCAAAAAGACCGCTTAATTTTCAGCGTTATTGCTTAATT |
| 131001 AAAAGTGATCATCCTGATTGATCTTTAGAACAGATAGCAAACTTTTTTTT |
| 131051 CACAAAATATAACATAAAGATTAGCCGCAGTGGAATCCAACATTTTAGTG |
| 131101 TTAATCTAAAAAAACTATGCCAGTAGTTTAAAATTAGTTCAACAAGCAATG |
| 131151 CATCCAATCCAAATAGTAATGTTCATTATGGCTGTTATCTGTTTAATTAT |
| 131201 TGGACTTTTGCTTTCTAACCATGGTTCTACTGGAGGATTAGCTTCTCTAT |
| 131251 CAGGTCAGGACTTGGAGATCTTTCGTAAAACCAAAGATAGGGGTTTTGTA |
| 131301 AAGATCTTACAGATTATCATGTTTATCTTAGTAGTTTTATTTTTAATTCT |
| 131351 TGGGTTGATATTTAGTTTTGCACCAAGATAACAATGAAGGTTTTAACTGA |
| 131401 ACTCCAAAAGCAGATATTTACCATTGTCAAAAAGGAAAATGGTAAACCTA |
| 131451 TTCCCCCTGGAATAGTGGTAAGAATGATGGAAAATAGTCCTAATTTTCCA |
| 131501 GGTAAACATCTCATCTATCGGGCCATTGATGATCTGCTTGATTGAGCCAT |
| 131551 CTTAAGGAAAGCTGGTGGGGTTACAAACCAGCTATTAGTTAACTATGAAC |
| 131601 CTGCTGAGCCTTTACTTGATAAAAAACTACAAGGGATTTTAACCTTAGGA |
| 131651 AATAAGAATAGTGGTTTTATCCGCTCTTTGGATGATGATAAAACTGTGTA |
| 131701 TTATGTCCATTACTCTAATTTAACTGGAGCTTTAGATGGGGATCTTGTGG |
| 131751 AGTTTTGTAAATTAGATAAACCCCAATTTGGTGATAAGTTTGATGCTGCA |
| 131801 GTTATTACTATTCTAAAAAGAGCAAGAATCTTGTATGCAGGTAATTTTTT |
| 131851 AGTAGATCAAAATGAGTTTGCCTTGGAATACAAAATTGTTGCTGATAACC |
| 131901 CTAGATTTATTTAACTATGATTGTAAATCCTGATTCTATCCCAAATAAC |
| 131951 TTAGCATCTAACACCAAGATAGCTTTTCAAATTGATGAGTATGATCCTGA |
| 132001 TAACAACTTATGTAAGGTTTCTGTACAACAAGTTTTGGGTAACAATGATG |
| 132051 ATCCGCTAATTAATATAAAAGCAATCATGTTGGACAATTCCATTGTCTTT |
| 132101 GAAACTAACGATGTAGTTGAACAGCATGCTAACAAGTTAAGTTTTGATAC |
| 132151 TGAAGAACAACATAAAGCTTACCGTCAGGATTTAACTGATTTAGCTTTTG |
| 132201 TGACTGTTGATCCTACAACATCAAAAGACCTTGATGATGCTATTTATGTC |
| 132251 AAAACAATACCAACAGGTTTTGTGCTTTATGTAGCTATTGCTGATGTTGC |
| 132301 ACACTATGTTAATAGAAATAGTGAAATAGACATTGAAGCAAAACACAAAA |
| 132351 CAAGCTCAATCTATCTACCTGGTCATTATGTTGTGCCCATGCTACCTGAG |
| 132401 CAATTGTCAAATCAGCTCTGTTCTTTAAATCCAGCACAAAAACGTTATGT |
| 132451 TGTTGTTTGTGAGATTAGTTTTGATAATCAGGGAAGGATTAAAACAAACA |
| 132501 AGCTTTACCCAGCAACAATTATTTCCAAAAATCGTTTTAGCTATGATCAG |
| 132551 GTTAACAAGTGGTTAAATAATAAATCAGAATTAAACTGTGATGAAACAGT |
| 132601 TATCAACAGCTTAAAAGCAGCTTTTACACTAAGTGATCTAATTCAAGCGC |
| 132651 AACGTCAAAAACGCGGTACAATTGATCTTTCACACAAAGAAACTGAGATA |
| 132701 GTTGTTGATGAACATTATTTTCCCATTAAGATAAATTTTTTGGTTCACGA |
| 132751 TAAAGCTGAAACCATGATTGAAAATCTCATGGTAGTGGCCAATGAGACAG |
| 132801 TTGCTTGGGTGTTAACTAACAACAAAATTGCTTTACCATACAGAGTTCAC |
| 132851 CCAAGACCAAGCAAAAAGAAGTTACAAAGTTTGATTGAAACAGTTGGTGA |

-continued

The Nucleotide Sequence of the *Mycoplasma genitalium* Genome

```
132901 GTTGAACATAACTAAACCCCAATTTAACTTAGATACTGTCACTTCAAGCC
132951 AAATAGCTAGCTGATTAAATGAAAACAAAGATAATCCTAGTTATGAGATC
133001 TTTGTAATCCTCTTATTAAGAACACTAGGCAAAGCTTTTTATAGTGTTAA
133051 TCCCCTGATGCACTTCAGCATTGGTTCTAACCACTATACCCACTTTACTT
133101 CACCGATTAGAAGGTATATAGATCTAACCATTCACAGGTTGTTGTGAATG
133151 CATCTTTTTACTCCCGATCAATTCACTGATAATGAAAGAGATCAACTCAA
133201 ACAAGAGTTGGAAAAAATTGCTGATACAGTTAATGATACAGAGATTAAAA
133251 TTATCAATTGTGAAAGAAATGCCAATGATTATCTAACAACGCTGTTATTA
133301 TCAAAACAAATTGGCAAAACCTTCAGCGGATTTATTTCAGCAATTACTAG
133351 CTTTGGAATTTTTATGAGAATGGATGAAAATAACTTTGATGGGTTAATCA
133401 AAATTACAACTATCCCTGATGATTTCTTTATTTTTGAAAAGGAAAAAATG
133451 GTATTGAAAGGAAGAAAAACTAATAAGGTTTATAAAATTGGCGATCGTTT
133501 GGAAGCTAAACTAAGTGAGATTGATTTCATCCAAAAACGTGCTATTTTAA
133551 CACTCATATAATTAGCCAATGGTTGTTAATATCCTGCTTTTTATTACCCT
133601 TATTTTTTTACTTTTACTGTTTGTTTTTTTAATTGCTTTTGCATTTCTAA
133651 ACAAACGGGTTAGAAATTATGTTGTACGTACTTGAACTAGTGTTTTCAGT
133701 AAGTCCAAACAAAACCTTGATAAAAAGAACTTTTTTGACAATTTAACTTC
133751 AACTTTATTAAGACTTTCAGTTGATAAAATTGGGGCTATTATTGCCATTG
133801 AAAAACGTGATTCACTTGAACCTTATATCAACATTGGTTATCGGGTTAGT
133851 TCTGATTTTTCCCCTGAACTGTTAGTTACTATTTTTTACAACAAATCATC
133901 TCCTTTACATGATGGAGCGGTGATTGTTAGAGATTACAAAATTATTAGTG
133951 TCTCTTCTTACTTTCCAATGACAAGACAATTAATTGATGTTTCATATGGT
134001 TCAAGACACAGAAGTGCCTTGGGATTAAGTGAAAAGTCTGATGCAGTTGT
134051 TTTTATTGTTAGTGAAACAACTGGTAAAATATCAGTTGCTTTAAAAGGGG
134101 TTATTAAAACCTTGTCTTCCAACTCAGATAGGTTGCAAGATGAAATTATC
134151 CATTACTTGTCTTCAAAGTAGGATTAATCACTTTTCATTCTGGTTTTTTA
134201 AACCATGGATTCAAAGGGTTAATTCTTTGGTAAAAAAAGCGTCCCTGTAA
134251 GTGATCAAATTCATGCTGTAAACACATTCCAAATAGTCCAGTTGCTTTAA
134301 TGGTAATCTCTTTTTTTTCAAACCAATCATAACCTTTAATAGTGATCCAT
134351 TCACTACGAATTACATAACCTTTGTGCTGCTTTTTAACACTTAAACACCC
134401 CTCACCACTTTCTAAAAATGCTTTATTTTCACTTTGATCAATAATTTTAG
134451 GATTGATCAGTAGGCACTTTTTTTCTTTGTTTAAATCATTGAGGTGGATG
134501 TAAAACAGTTGTTTTCAATAGCCAATCTGGTTAGCAGCTATCCCAATTCC
134551 TGGAATAATGTCATATTCTTGTGCTTTACCATCATATGAAGCATCAACAT
134601 ATGCAATCATCTTTTTAATACAGGTTTCAATTTGCTCATCTATTGGAAAA
134651 TTAACAGCTTCAGTTGGCTTGTTAATCAAAGCATTATCATCAAAAACAAG
134701 CCAAGTTTTAGTTGGTTGAAAAGTCATTGATAAAAACAGTAAAGTTAAAA
134751 TTATTCTAACAATTGAAGTGAACAATCAGGGGAGAATTTTTGTCATTACT
134801 GGTCCTAGCGGTGTTGGCAAAAGCACCCTTGTTAAAGCCTTATTAGATCA
134851 TTTCAAAGaACAACTGTTCTACAGTATCTCTGCAACTACAAGAAAAAAGC
134901 GCATTAGTGAAAAAGAGGGAATTGATTATTTTTTTAAAGATAAAGATGAG
134951 TTTGAAAACTTAATAAAACAAGATGCTTTCATTGAATGGGCTTGCTATAA
135001 TAACCATTATTATGGAACGCTCAAGTCTCAAGCTGAACAAGCAATTAAAA
135051 GCGGAATTAATTTAATGCTTGAAATTGAGTATCAAGGTGCTTTACAGGTT
135101 AAAAGTAAATATCCTCATAACGTTGTTTTAATTTTCATTAAACCACCTTC
135151 AATGCAAGAGTTGTTAAAACGTTTAAAAAAGCGTAATGATGAAGATGAAA
135201 CCACAATTAAAAAACGTTTAGAACAAGCTAAGATAGAGTTTCAACAGATT
135251 GATAATTTTAAGTATGTTGTCACTAACAAAGAGTTTGATAAAACCCTTAA
135301 TGAGTTGAAATCAATCTTACTATCTGAGTTTATTTAATGCAAGCTGCTAA
135351 TGATCATTTCTTTACCGGTTTATCAAAAAAAGGTCCTGTAAGAAAGGAAA
135401 ATCAGGACTTTTATGGATTTAGTTTTAATCAAAATAACCTACTAATAGTT
135451 GTTTGTGATGGTCTTGGTGGTTATAAGGGTGGCAAGATTGCTAGTAACTT
135501 AGTAGGTAAACTCTTTCTTAGTTTATTTGAAGGTTTTGAATTTAACCAGT
135551 GAGATGAAACTACAGTTAAAAAGTGGTTTGAAAATACTTTAATACAAGCA
135601 CGCTTTCAACTAGAAAATTGTTTTCAAACAGTTTATGAAGCACAAATCCA
135651 GTTTGCTAGGATGGCTAGCACCTTGGTCTTGGGAATTTTAACTAAAAGTG
135701 ATATTTATATCTTTTGAATTGGTGATTCCAGAGCTTACTTATTATTTGAA
135751 AACCAAGCTAAGTTAGTTACTAAGGATCACAATCTTTATAACCAGTTAGT
135801 TGCTATGAATGCTGATGAGAAATTACTTTTAAGTTATTCTAATCAACTTT
135851 TAGCATTAACAAATACTATTTCCAAAGAAACAAAAAGACCATTAGTTTAT
135901 GGTTTTTATAACACAAAAATTGAACAACAAGAATTTTTATTATTGTGTTC
135951 TGATGGACTTTATAACTTTGTTGAAAAAGAGCTTTTTTTTGAAATTATCA
136001 CTAATTCTAAAAACCTAAAACAAGCAGTGTTTAATCTTTATAGAAAAAGT
136051 ATTGAAAATGCAAGTAATGATAATATTACTGCTGCCCTTGTTAATCTGCA
136101 AAAATGGAAGCAATCTTAAAGATAGGTGATATTGTTGAAAATAAGTATCA
136151 AATTGAAAAGCTTTTAAATAGGGGTGGGATGGATTCCTATCTTTTTTTAG
136201 CAAAAAATTTGAACTTAAAAAACTATGGACCAGTTCAPAAAAAACAGTAT
136251 GGACACTTAGTTTTAAAGGTGGTTCLAAAAAATCCTAAGATTAATGAAAA
136301 TAATTGGAAAAAGTTCCTTGATGAAATGGTAACCACAACTAGAGTGCACC
136351 ATTCTAACCTAGTGAAAAGTTTTGATGTGGTGAACCCTTTTTTGAAAATA
136401 GTTCGTGGTAATAAAACAATTGCTCTCAATCAGATAGTGATGATTGCAAT
136451 GGAGTATGTTGATGGCCCTTCTTTAAGACAATTGCTTAACAGAAAAGGCT
136501 ACTTTAGTGTTAGCGAAGTAGTTTATTACTTTACAAAGATAGTAAAAGCC
136551 ATTGATTATCTCCACAGTTTCAAGCACCAAATTATCCACCGTGATCTTAA
136601 ACCTGAAAACATCTTATTTACTAGTGATTTAACTGATATTAAACTATTAG
136651 ATTTTGGCATTGCTTCAACAGTAGTTAAAGTTGCTGAAAAAACCGAAGTT
136701 TTAACTGATGAAAATTCACTGTTTGGCACAGTTAGTTATATGATTCCTGA
```

The Nucleotide Sequence of the *Mycoplasma genitalium* Genome

```
136751 TGTTTTGGAAAGCACAGTTAATAAAGCTGGTAAAAAGGTTAGAAAACCAC
136801 CCAATGCCCAGTATGATATCTACTCGTTAGGAATTATTCTATTTGAGATG
136851 TTAGTTGGTAGAGTTCCATTTAACAAGTCAATTAACCCCAACAAGGAAAG
136901 AGAAACAATCCAAAAAGCACGCAATTTTGACTTACCTTTAATGCAAGCAA
136951 CTAGAAGTGATATCCCAAATAGCTTAGAAAATATTGCTTTTCGTTGTACT
137001 GCTGTGAAAAGAGAAAACAATAAGTGACTTTACAGTTCCACAAAAGAACT
137051 TTTAGAAGATTTGGCGAATTGAGAAAATGAACAAGCGATGATTAAACCTG
137101 CTAATGAAAGGGTTTTAGAAGGGCAGGTGGAAATTAGAGAAATGATGCTT
137151 GAAAAGCCCTTAGCTTGGTATTTCAAAACTTGAGCCTTATCAATCTTTAC
137201 TATCGTTTTTATAGGGTTAATTATTGCTGCAATAGTTCTTTTATTAATTT
137251 TTAATGCCAGATTCTAACTTTGGGATAGTGCTTCAGTCATTAGCAAAACA
137301 ATGCAAAGTATTTTGGAATAACCAGATAATAACTGCTTTTCCTCAAAAGA
137351 AGTTACAGTGAAAAAATGATTTTAAGTTGATGGTTGGTGATAGGGTTCAA
137401 CTTGAAGATGGTGCGATCACTAAAGTTTTAGCTAGAAAAAATGAACTTAC
137451 AAGACCAAGGGTTGCTAATGTTGATCAGATTGTTTTAATCCAATCACTAG
137501 TTCAACCTAAGATTAACTGAATTCAACTGTTGAAATTATTGGTATATTTC
137551 AATGCTAAATTAATTGATGAAATACCTATTTTAATAACAAAAACAGACCT
137601 TGATTTTGATCCAATGGAAAAACAAAAGTTAATCGATTTAAAACAGTTTA
137651 ACTATCAGTTATTTTTTGTTTCTAAAAATGAACCACTACCTTCAGAATTA
137701 ATCGATATTTTTAGTAAAAAACTAAGTGTTTTTACAGGTCAATCTGGTGT
137751 TGGTAAATCTAGCTTAATTAATCGTTTAGATCCTTCTTTAAAACAAAAGA
137801 TTCAAGCCTTATCAGTTAATAAATTTGGTAAGAATACCACTACTAAAACA
137851 ACACTTTTTTCATTTAGAGGCGGTTTTATTTGTGACACCCCTGGTTTTAA
137901 TGTAATTTCTATTAAAAACCTCAAAATTTTAGCAGCCCAACACTTTGTTG
137951 GTTTTCAGAAAATGATTAGTAAGTGTCATTTTTCTAACTGTTATCATCAG
138001 TATGAAAAAGATTGCTTTGTAACCACAAGTGTTATGAAAAACAGATATCC
138051 TTCGTGATTGTATGAGAAGTATAGAAAAATGATTAATTAAAATCAACTGC
138101 AAAAGTGTTTATGAGTGATAAATTATTAACAATTGACTTAAGTCATGTTT
138151 ATGGATTTGATAAAGAAATTATTTTTAAGAAATACCAAAAAAAAGTAGAT
138201 CAAATTCACCAAGATTTTCTAGCTCATAAACTTGCTGATGGTCACATGAC
138251 TGGGTGGTATGACCAACCTGATCAAAACCACCAATTCCTTTTAAAAACCA
138301 TTAATCAAATTGACAAAAAGTTTAAAAGTTTAAAAGTAACTGACATTGTT
138351 TATGTTGGTATTGGTGGTTCTTTTACTGGTATTAAAACAGTTTTAGATTT
138401 CTTAAAACCAAAACAAAGAACAGGATTAAAAATCCACTTTGTCCCTGACC
138451 TTTCTGCTTTTCAAGCTGCAAGTGTTATTAAGGAAATTAAAAATAAATCA
138501 TGGGCTCTAATTACCACTTCTAAGTCTGGTAGAACCCTAGAACCAGCACT
138551 GAATTTCCGCATTTTTAGAAACTTATTAAACAAGCGTTATGGCAACAAAC
138601 ACTACCAAAGAGTAGTTGTTATTACTGATGAAAAAAAGGGATTACTAACC
138651 AAAATGGCATCAAATCATGGTTACCAAAAGTTAGTTATTGATTCAAATAT
138701 CGGTGGGCGTTTTCAACTCTATCTCCTGCTGGTTTGTTACTAGCCAAAC
138751 TTTTTGGTCATGATCCTAAGGCCATCTTAAAAGGAACATTACAAGCCAAA
138801 AAGGATTTGCAAACAACTTCACTTGAAAACAATTCTGCATACCTTTATGC
138851 AGTAGTTAGACATTGACTATACACCACAAAAAAATTCAAAATTGAAGTTT
138901 GCATTGCTTATCACAGTTTGTATGAATATTGTTATTACAGCATCGACAA
138951 CTTTTTGGTGAATCAGAAGGTAAGAACGATAAATCTTTATTTCCTACTTT
139001 TTCGATTTTTACTGTTGACTTACACTCAATGGGACAACTCTATCAAGAAG
139051 GGGAAAAAGTGTTTTTTGAAACAGTAATTGATGTTAAAAATCCACTTGTT
139101 AATATTAATTTACCTCCATCTGATTTTGACAATGATGATGAACTTGATTT
139151 CTTGTTAGATAAAAGCTTAAATGAGATTTCAGATGTTGCAATTGATTCAG
139201 TTATTAAAGCGCACTACCAAGCAAATGTAAGCATTATTAAATTAACTTTA
139251 AAAGAACAATCTGCATTTATGTTTGGTTATTTTTACTTTTGACTCTCTGT
139301 TGCTACAGTGATGAGTGGATCATTATTAGGGCATAATGTCTTTAATCAAC
139351 CTGGCGTTGAAGTTTATAAAAAGTTAATGTTTGAAAAACTAAGAAGTGGC
139401 CACTAAGGTTGTTTTTTCACTCTTACCACTTTTAAATAGGTTTGACAAGT
139451 CACTTTTAGAAAGTTACTTTCAAGATGGATTGAGGTTAATCCATTATGAT
139501 GTGATGGACCAATTTGTTCATAATACTGCTTTTAAAGGTGAATATTTGGA
139551 TGAATTGAAAACAATAGGTTTTGATGTTAATGTCCATTTAATGGTGGAAC
139601 AGATCATCCCTCAAATAAATTTTTATCTTCACAACCTAATGTGAAAAGG
139651 ATTTCGTTTCATGTTGAACCATTTAGTTTTTGCAAAGATTAAAGAACTAAT
139701 CCAACTAGTTAAAGAAAATGGTAAAGAAGTTGGTCTTGCTTTTAAATTTA
139751 CAACCAATTTACAACTATACCAACCATTTTTTACAACCATCGACTTTATC
139801 ACTTTAATGAGTGTTCCTCCTGGTAAAGGTGGTCAAGCTTTTAACGAAGC
139851 TGTTTTTACAAATTTAAAGATTGCTAACCATTACAACTTGAAAATTGAGA
139901 TTGATGGTGGGATTAAAGTTAATAACATTGATCAAATTAAAGCCTTTGTT
139951 GATTTCATTGTAATGGGAAGTGGCTTTATAAAATTAGAGCAGTGGCAACG
140001 TCAAAAATTGTTGCAAACAATCTAATTAAACTTTATTGATGAAATCAGTT
140051 ACAGTCAAGCAGTTACTACAAACCCCACGAAAATTTAATAACAAGCAGAT
140101 TAAACTATCAGGTTGGGTTAAAAATAAACGTGCTAGTGCTAACATCATCT
140151 TTCTAGCAATTAGTGATGGCTCTAGTATTAATACCCTACAAGCAGTAGTA
140201 AAACAAGAAGATAACCCCCAGGTTTTCTCACTGTTACAAACTGTTAATTT
140251 AGCAAGTGCTGTTATGGTTTGAGGGGAAATTATCTTAACCCCAAAAGCTA
140301 AACAACCACTGGAGTTGAAATTAAAGCAGGTGAGTTTATTAGCACAAGCA
140351 GAGTCTGATTATCCACTGCAAAAAAAAGAACATAGTCAAGAGTTTTTTAG
140401 AAGTAATGCGCATCTAAGAGTAAGAGCAAAAACTTACTTTGCAGTGATGA
140451 AAATAAGGAGTGTTTTGTCACACGCAATCTTTGAATACTTCTTTAAAAAT
140501 GATTTTATCTTAGTGCAAAGCCCTATTTTAACTAGTAATGATTGTGAGGG
140551 AGCGGGGAAACATTTGTAATTAAAGATAGTGAAACTTTTTTTAATAAAA
```

-continued

The Nucleotide Sequence of the *Mycoplasma genitalium* Genome

```
140601 CGACTTTTTTAACAGTAAGTGGCCAGTTTGGAGCAGAAGCTTTTGCGCAA
140651 GCATTTAAAAAGGTTTTCACCTTTGGTCCTACTTTCAGAGCTGAAAAATC
140701 CCATACTAATCGTCATCTTAGTGAGTTTTGGATGATCGAACCTGAAATTG
140751 CATTTGCTAACTTAAAAGATTTAATGCAGTTAATACAAAACCTAATTAAA
140801 TTCTTAATTAAAAAAGTGATGGAAAATGCTAGTGATGAACTAAATGTTTT
140851 AGCAAAGCAATTTAGCAATGACATTATTAGCAACTTAAAGACAATCATTA
140901 GTACTAAAAAATTTCCAATCATTGAATACAGCAAAGCATTAGCGATTCTA
140951 AAGGAATCTAGTGATACAAAAAAAACTAATTTTGAACTAAACGACTTTAG
141001 TTTTGGTATTGACTTAAAAACAGAACATGAACGCTTTTTGTGCGAACAAT
141051 ATTTTCAAAATCAACCGCTTTTTGTTATTAACTATCCAAAGGAGTTAAAG
141101 GCATTTTACATGAAAACAAATACTGACAATAAAACTGTTGCTGCAGTTGA
141151 TCTTTTATTACCAAAGATTGGTGAGATTTGTGGGGAAGTGAAAGGGAAA
141201 GTGATTTAAACCAACTTAAGAATAGGTGTCAATCTTTAAACATTGACACA
141251 AAAAGTTTGAACTGATATCTTGATATGAGGAAATGGGGTTATTTTGCTAG
141301 TGCAGGTTTTGGTTTGGGCTTTGATAGATTATTAGCTTATATATGTGGAT
141351 TGGAAAACATCAGAGATGCTATTCCCTTTCCCCGTGTACATGGCACCATT
141401 AACTTCTAAATTCGCTGCTTATAAAAAAAAGATTGCAAACTGGTTAACAG
141451 TTTACAGAATTTTTATTGCTTTACCTACTATTATTTTTATTGCTTTAGAT
141501 AATCAACTAGGAGTTTTAGCTAACTTTTCTGTTGGTGCAATTAGCATTAG
141551 TTTACAGATCAGTTTATTGATTGGAGGATTTTTGTTTTTAACTGCAGTTA
141601 TATCAGATTATTTAGATGGATATTTAGCAAGAAAATGGCTAGCAGTTTCT
141651 AACTTTGGTAAATTATGAGACCCCATTGCTGATAAAGTGATTATCAATGG
141701 TGTTCTTATTGCACTAGCGATTAATGGATATTTTCACTTTAGCTTATTAA
141751 TTGTTTTTATAGTCCGTGATCTTGTGTTGGATGGAATGCGGATTTATGCT
141801 TATGAGAAAAAGGTGGTTATTGCTGCTAACTGACTTGGAAAATGAAAAAC
141851 TATCATGCAGATGGTTGGTATTGTTTTTAGTTGTTTTGTTTGGAGTTTTA
141901 AACAAAGTGAAATAGCTTCTTTGAATAGTGGACTGTTCTTTTGATTACTA
141951 ACTCAACTGCCATATTATTTAGCAGCAGTTTTTTCAATTTGGTCTTTCAT
142001 TGTTTATAACATCCAAATATATCAGCAACTAAAGGCTTATAACTCCAAGT
142051 TATAATCCTTATTAGGCATTGGAATAACTTTGTTTGCCAATTTAATAGCA
142101 GAAAAACTCCAAAAGTTACAACTTAGTGTTGCAACAGCTGAATCAGTTAC
142151 TGGTGGCTTATTAGCTCATTGTTTAACTTCCATTGATGGTGCTTCTAACT
142201 ATTTTAATGGCGGTGTTATTGCTTACAATAACCAAGTTAAGATTAACTTA
142251 CTGAATGTTCAATCCTCCACAATTGCAAACCATGGGGCAGTTTCCAGTTT
142301 CTGTGCTAGGGAGATGGCAGTTGGGGTTAAACAAAAGTTTCAAGCTGATG
142351 TGGGTATTGCTTGCAGTGGGATAGCAGGTAGTAAAGCAGTTGAAAATAAA
142401 GCAATAGGATTACTTTTTTTCTGTATTATTATAGGAAATAAGGCTTATGA
142451 TTTTGAGTTTGAAATGAACCAAAATAATCGTAAGGATAACATTGAATTAT
142501 TTACCAATAAGATCTTGGAATCTTTCCACTATTTGTTAACAAAGCTAGCT
142551 TAATCTAAGTTATGAAACGTACTTTAAATATAGGTATTGTTTTGTGTGAA
142601 AATTTTCTTTCAGACCAACAAAATGCTGTTGATAGTTACACCCAAGTTTA
142651 TGAAGATGTTAGGATGTTTGAATTTGGGTTAAAACTCTTTCAATCATTAC
142701 CTTTTAACATCCAAGAAACCCTTATATTTTGTAATGCTGAACAACATAAA
142751 ATAGTTGATAAAGCTGCTAAAAAATACAAAAACACTACTGTGTTTTTTTC
142801 ACGTGATACTGATGTAGCTAATGTTTATGAAGCTAAGGTATTTATCCAAG
142851 AAAAATACAAATTAACCCAAGATTACAAAAAAAGAGGTGTTAGCTCTTAT
142901 TATGACAGCTGTTGCTTTATCTTAATTGAAGCGAATCGTCCATTAACTGC
142951 AATAAAGACAGTTAAAAGTGTTTATGAAAAAGCACTGATAGAAAAAGCAG
143001 CTATTGCAGTATTACCATATAATGGTACACTAATGAATGGTAACAATGAT
143051 GTTGTCTTTAGCCACTTGCAAGATAAAAATAGGTTTAACTATTGAAAACA
143101 AAGCAAGGCTTATGAAGTACAATACCCCCAAGCATATACTTTAAATAAAC
143151 TTAATCAGTTTTCAAAACAGCAATTTCTAAGGGCTAGAAGTATGTTGGAC
143201 TTAATGAAGATTTCTAATAAATCACCCTTAAGTATTGTTGATGGTAGTGC
143251 TTATGCTTTTAGGGTTGTTACCAACCTTGATTTTGAAATTTATTAGGTA
143301 TTTTAAAAAATGGATAAAAATATTTTTCAATTAGTACAAAGTTTTGCTAA
143351 AACGCAAAATGTGCGAGCTAATTACACCTCACAAGACAAAAATATTAGTT
143401 TAGATTTTGTTAGTTTTGAAACAGTTAGTCAATCACTAACAGGTTTTCTA
143451 ATTTTTAATAATTTCAATAAATTGTTACAACTAATTGAACTGATAAAACA
143501 AAAGCAAACATGATTATATGTAGATCAGCTCTGAATTGTTGATCTTTCCA
143551 ATAACAAAGCCTTAACTGATGCTACTGTTTGGATTATTAAACAAGAAAAA
143601 TTGCCTGTTTCAGTTGCGGCTTTTAGCAACCAACAACTCAACCAAGTTTA
143651 TCGCAATTCATCCACAAGTCCTTTGTATCTTAGTTATGTCAAACCAATCG
143701 AAGTTCAACAATTTTTTACACTTTCTCCATCCATTAACAATAATCCTTTT
143751 TTAAATCAAAATCCTTTAACTGAATCACCATTTGATAACAATAATCAGCT
143801 GTTTCAAGCAACAAAGAGCGTTGAACCTTCAATGGAAACAATGGAATTTT
143851 CCCGGTTTATGGATGAATTTGATCAGATTACAAAGAACTTTTCTGATATA
143901 GAGCTTGAACCTATGCAATTCACCCAAAGTTTTGATGATTGGAGCAAAGA
143951 CTAGGGTTGCAATAGTTGGCGGGATTGGTTACATAGGTAGTTGTTTTGCT
144001 AGTTTTATCAAAGAACAAAATGATAAGCTAATTGTTACTGTTATTGATAA
144051 CAACAAAAATAACCATGTAATTAAACTCTTAAAAAAGATTGGAATTGAAT
144101 TCTATTTTGCTGATTTACTAGATAGACATAAGCTAACTGAAGTAATTGCA
144151 GCAATTCAACCTGATGTGGTATTTCACTTTGCTGCTAAAACAAGTGTAAG
144201 TGAATCAGTACATAATCCATTGAAGTACTTTGATTGCAATGTAATTGGTA
144251 CTTTAAACCTAATTAGTGCAATTAGTAACTTACAGAAGCCAATTAAATTA
144301 TTTTTCGCTTCTAGTGCTGCAGTGTATGGTCAAACAACTAATAGTTACAT
144351 TAGTGAAGAGATTGTAATAACTGAAACACAAGCAACCAATCCTTATGGAT
144401 TGAGTAAGTTTTTAGATGAATTAATCTTAAATGCAGTTGCCAAAAATAGT
```

-continued

The Nucleotide Sequence of the *Mycoplasma genitalium* Genome

```
144451 CAACTACAAGTTGTTTGCTTACGCTTTTTTAATGTGGCAGGTGCAATTCT
144501 GCCATTTGGTAATTTTAATGGTAATACCACGCTTTTAATTCCTAACTTAG
144551 TAAAAGCCTTTTTAAAACAAACTCCCTTTTTTTATATGGCAATGATTAT
144601 GCAACTAAGGATGGTAGTTGCATAAGAGATTACATCCATGTTTATGATAT
144651 ATGTAATGCTCATTTCTTATTATGAAAGTGGTTAAATGATCATCGCCAA
144701 TTAAATTTGAAACCTTTAACTTGGGGAGTGGGATAGGAACTTCTAATTTA
144751 GAAGTTATTGATATTGCTAAAAAAGTGTTTTATCCTAGTAGATTAAATTT
144801 AGAAATTAGACCAAAAAGAAGCTGAGATCCAGCAATTTTAGTAGCAAATG
144851 TTGCTAAAGCAAAACAAACCTTTCAATTCAAAATAACGCGTAATTTGAAA
144901 GATATGATAAGTGATGAGCGTAATTTTTATGAGAATTTTTATAATGACGC
144951 TTATTAAGTGGTGTTTAATTAATGGAAAAAGTTGCCTTCAAAATGGAGCA
145001 TATCTCCAAAAGTTTTGACAATGGCAAAATTAAGGCTAATGTTGATGTTA
145051 GCTTAGTTGTTTATGAAAATACTGTCCACACCATTTTGGGGGAGAATGGT
145101 GCAGGAAAATCAACCCTGACTTCGATTTTATTTGGTTTATATAAACCTGA
145151 TAGTGGCAAGATCTTTATTGGTGAAAAGCAAGTAAATTTTAAATCTTCTA
145201 AAGATGCAGTAAAACATAAAATCGGAATGGTGCACCAGCACTTTAAGTTA
145251 ATAGAAAACTACACGGTTTTAGATAACATCATTCTAGGGAATGAAAGTAG
145301 GTTTGGGTTTTTACCTTTAATTAATCGTAAAGTAAGTGAAGCAAAGATTA
145351 AAACCATCATGGAAAAATATGGAATCTTTGTTGATCTTAAACAAAAAGTT
145401 AGTAACTTAACAGTAGGTCAGCAACAACGGGTTGAGATCCTAAAGGTTTT
145451 ATTTCGTGATAGTAATATCCTTATCTTTGATGAACCCACTGCAGTTTTAA
145501 GTGATCTTGAAATTCAAAACTTTCTCAAGATTATTGCTAACTTTAAAAAG
145551 CTAGGAAAAACAATTGTTTTAATCTCTCATAAATTAAATGAAATTAAACA
145601 AGTTGCTGATACAGCTACTGTCTTAAGACTTGGCAAGGTAGTTGGTAGTT
145651 TTGATGTTAAAACAACACCAGTTGATAAGATTGCGCTTTTAATGATGGGC
145701 AAAGAGTTAAAACAAACTAAAAACACCACAGATTTTGTTGCTAAAGATGA
145751 ACCTGTTTTAAAAGTTCAAAACCTGAATTTGTTTCTCAATAAATCTTTAG
145801 CATACAAGTTCTTAGTGAGGTGCAATAACATCCATAAAGCCCAACAAATT
145851 AAGAAAAATAAACCATTAAAAGACTTATGGATAATTAGTTTTTTAAATAA
145901 ACTAACCACCAGTAACAAAACCCCTAAATTAGTAAAAGGCTTGATTAATA
145951 AGTTAGGACTTTCCTATCAAGAAAATACAGATGAAACCATTAGTTTTGCT
146001 ATCCATAAGGGAGAAATTTTTGCTATTGCTGGGGTTGAGGGTAATGGTCA
146051 AAGTCAGCTTGTTAATTTAATTTGTGGAATTGAAAAAGCTGCTAGTAATA
146101 AGTTAATTTTTAACAATATTGATATCTCAAGATGATCAATTAGAAAACGG
146151 ATTAATGCTGGGATTAGTTTTGTTTTGGAAGATAGACATAAATATGGCTT
146201 GATCTTAGATCAAACCGTGAGGTTTAATACGGTTAATAACCAGATTAATA
146251 ACCGTCCTTTTAGTAGTTGAAACTTTTTAAAACCAATGGAGATTGCTCTT
146301 TATAGCAACACTATTATTAAAAAGTTTGATGTTAGGGGCAGTGCTGAGGG
146351 TAGTGCTGTTGTAAGAAGACTTTCAGGTGGTAATCAACAGAAACTAATTA
146401 TTGGTCGAGAAATGACCAAACAAAATGACCTTTTGGTGTTAGCACAAGTA
146451 ACCAGAGGCCTTGATATTGGTGCTATTGCTTTTATCCATGAAAACATCTT
146501 ATTAGCTAAAGCTAATAATAAAGCTATCTTATTGGTTTCATATGAACTTG
146551 ATGAGATCTTAGCACTTGCTGATACAGTGGCTGTTATCAATAAGGGGAGA
146601 ATAGTTGGTATGGGAAAAAGAGATTTAATGGATCGCCAATCGATAGGTAG
146651 ATTAATAATGCAATAAAAGACTATGACAATGTGGCAATTTAAAAGTTACT
146701 TTAAACACCACCTGGTGTTTGAAAAGACCGATTTTTACATAGCTCTGAG
146751 AAACAAATGCAAAGAAGAAGTATCCTCTCTTCAGTGGTTTTGATAATCCT
146801 CTCTTTTCTTATATCGTTTTTACTGATTATTTCAATTCCTGGAGGTAGAG
146851 GTGCGAGCTTCTTTGCACTGTTTACTAAGTTATTTTTAGATAACACTAAT
146901 ACTGAAAATTTCTTAAGACAGATTGCTATTTATATCCTAGCTGGATTAGC
146951 ATTTAGTTTCTGTATGAGTGTTGGTATTTTCAACATTGGTATCTCAGGGC
147001 AGATGATGGCTGGAGCCATCTTTGGGTTTTTAATGATTCTCAAGGTGTTT
147051 CCAAGTTCATTTCGACCTGGTTTTGGAGGTCAGATTATTACTGTATTATT
147101 GATGGTAATAGGTAGTGTTAGTGTGGCAGTTGTTGTTGCAACTTTAAAGA
147151 TTTTTTTCAAGGTTAATGAAGTTGTAAGTGCAATTATGTTGAACTGAATT
147201 GTAGTGCTTATTAGTGCTTATTTAGTAGAGACTTACATTAAAGATAATAG
147251 TGGGGGTACAGCCCAATTCTTTTCCTTACCACTCCCTGATGAATTTGCTT
147301 TATATAACtTCTCTCCTTTAACAAAAAAGTTTGGTTGATTAGCTTCACTT
147351 ATTATTGCTTTCATTAGTGTTATTATTGTGGCAGTAGTATTAAAATACAC
147401 AGTTTTTGGACACAAATTAAAGTCAATTGGCAGTAGTGTATTTGGTTCTC
147451 AGGCAATGGGTTTAATGTTAGAAAATACCAGTTCTTATCGTTTATTATC
147501 TCAGGAATTTTATCAGGACTATTAGCAACGGTTGTTTACACTGCATCAAC
147551 TGAAAAAGTATTGACATTTAACAATGTTGGGGATAGTGCTATTTCAGCAG
147601 TACCAGCTACTGGTTTTGATGGGATTGCGATTGGTTTAATTGCTTTAAAT
147651 AACCCCTTTAGGATTGTTATTGTTTCTGTTCTTATTGCTTTTGTTAACAT
147701 TGGGGCAAGACCTGCTAATTTAAACCCTAATACTGCTAGTTTAGTTTTAG
147751 GAATCATGATGTATTTTGCTGCACTTTATAACCTAATGGTTTACTTTAAA
147801 CCATGAAGATACCTAGTGAAGCTGAACATTGGAAAGATAAATCTCACCAC
147851 ATATGAAACATATGAAAACAAACTAGCTGCTAACCTAGAGTGACTAAGTT
147901 TCCAACGCTTCTTGTCAAAACAGAAAAAAAGAATGACAAAACTAAATTT
147951 AATTGGTTTGATACTAGTTTATTTGAACAATATGCAAAAAACAAACAAGA
148001 AATTGTTCAAGAATACCATCACAATTGTGCAACTAATTTAATTGCTTGGT
148051 GATTGAATGCAATCCAAAGTGGCAATATTAAACCTTCAACTACTTTTAAG
148101 TTGGAATTTGTTAATTTTAAACACCAACAGAAGTTTGTATTAAATTGGTT
148151 TAAAAATGAAAGTGAATCACTGCGTGATTTCCAATCACAGTTTGAGAGAA
148201 TCAATAAGTTAGTGGAAAGGGAGTTTGTTAAGTAACAATGTTAAGTTTAG
148251 CACAATTAGAAAGTTGGTTTTTTATCGCTCCAGCACTGCTTTTAGCAGTA
```

-continued

The Nucleotide Sequence of the *Mycoplasma genitalium* Genome

```
148301 TTGAGTGGTTATCTCGCTGAACGCGTTGGGATCATTAATATTGCTATTAA
148351 TGGTGGAATGGTGTTTGGTGGGTTATTTATGGCACTCTTATCGTATGGAT
148401 TTACAAATAACTTAAATCAATCCGCTCCCTCCTGATCACTATTTATCACC
148451 ATTCCCTTATCAGTTTTATTTAGTAGTGTTATAGGTTGTTTATTTGCACT
148501 AGCAGCAGTTAAGTTAAGAGCAGATCATGTTATTGTGGGAACTGGGATTA
148551 ACTTGTTGGCTAGCGGAATTACCCTTTTTATTAGTCAGAATGCTGCTAGT
148601 TTGTTTTCCGATACTACCTTAAGAGTAAGGTACTTATTTCCCATCCAAAC
148651 TACTGTTAGTATAGAAGCAATTGGTGTGTTTGTTTTTAGTTTACTTCTGA
148701 TTGGGTTTGTATGGTACTTGATGAGTTTTACTAAAACTGGGTTGAGATAC
148751 CGTGCGGTAGGTGAGAATCCTAATGTAATTGATACCCAAGGGATTAGTGT
148801 TTACAAATACCAATGGATAGGCGCAATTTGTTCAATGATGGTAGCTGGAT
148851 TGAGTGGTAGTTTGTTTGTTTTAAGTGTTTCTAACTTTCCCTTTAACAGC
148901 GGAGATGTAAATGGCTTGGGTTTTATTGCTATTGCCATTATGATTATCTC
148951 AATGTGAAGAATTATCCCTAGCATCTTTATTGGGTTAATCTTTGCATATG
149001 CCTATGTTTTTACCAATAGTCAAATAGGATCTAATAGTAATTCCTACTTG
149051 TTAAGAACGATCCCTTTCATCATCTCATTACTAGTAATGTTGTTATTTGG
149101 TTTTCTTAATGTTGCCCCAAAAAATATAGGTAAACATTTTGACAAGGGTT
149151 TAAGATAAACAAAAACCTTATTTATAGTTAAGTAAGTaGTTTTATTAATG
149201 ATTAAAAACCTGGTGGTGATTGAATCACCCAATAAAGTTAAAACATTAAA
149251 ACAATATCTTCCTAGTGATGAATTTGAGATAGTCTCAACCGTTGGTCACA
149301 TCAGAGAAATGGTGTATAAAAACTTTGGTTTTGATGAAAATACCTATACC
149351 CCTATCTGAGAAGATTGAACTAAAAATAAACAGAAAAATCCCAAACAGAA
149401 ACACCTGCTCAGTAAGTTTGAGATCATCAAATCAATCAAAGCTAAAGCTA
149451 GTGATGCACAAAACATTTTTTTAGCTTCTGACCCTGATAGAGAAGGGGAA
149501 GCCATCTCTTGGCATGTCTATGATTTATTGGATCAAAAAGATAAAGCTAA
149551 GTGCAAACGAATCACTTTCAATGAGATCACTAAAAAAGCAGTAGTAGATG
149601 CATTAAAACAACCGCGTAACATCGATCTTAACTGGGTTGAAAGTCAGTTT
149651 GCCCGCCAAATCCTTGACAGGATGATAGGTTTTAGATTATCAAGATTATT
149701 AAATAGTTATCTGCAAGCAAAGTCTGCAGGTAGAGTTCAATCAGTGGCTT
149751 TGCGCTTTCTTGAGGAAAGAGAAAAGGAGATAGCTAAGTTTGTTCCGCGT
149801 TTTTGGTGGACAGTTGATGTTTTATTAAACAAAGAAAATAACCAAAAAGT
149851 AGTTTGTGCAAACAAGTCTATTCCTTTGGTTTTAAGAGAAATTAACCCTG
149901 AATTAAGTGCTAGTTTAAAACTGGATTTTGAAGCTGCTGAAAACGTATCA
149951 GGAATTGACTTTTTAAATGAAGCTTCAGCAACCAGATTTGCCAACCAACT
150001 GACTGGCGAATATGAAGTTTATTTTATTGATGAACCTAAGATTTACTATT
150051 CATCTCCAAACCCAGTTTATACCACCGCTTCACTTCAAAAGGATGCAATT
150101 AATAAGTTAGGATGGTCTTCCAAAAAAGTAACAATGGTGGCCCAAAGACT
150151 GTATGAAGGGATTAGTGTTAATGGGAAACAAACTGCATTAATTAGTTATC
150201 CAAGAACTGATTCAATTAGGATTTCAAACCAATTTCAATCAGAGTGTGAA
150251 AAGTACATTGAAAAGGAGTTTGGAAGTCATTATTTAGCTGATAAAAATAA
150301 GTTAAAAAGACATAAAAAGGATGAGAAAATCATCCAAGATGCCCATGAAG
150351 GGATCCATCCTACTTACATTACTATTACCCCCAATGATCTGAAAAACGGG
150401 GTGAAACGCGATGAGTTTCTCCTTTATCGTTTAATATGGATTAGAACAGT
150451 TGCTAGTTTAATGGCAGATGCTAAAACATCAAGAACTATTGTTCGTTTTA
150501 TAAACCAAAAAAACAAGTTTTATACCTCTTCAAAATCACTTTTATTTGAT
150551 GGTTATCAAAGGTTATATGAAGAGATTAAACCTAATACTAAAGATGAACT
150601 TTACATTGATCTTAGTAAGCTTAAAATTGGTGATAAATTTAGTTTTGAAA
150651 AGATCAGCGTTAATGAGCATAAAACCAACCCACCACCACGTTACACCCAA
150701 GCTAGTTTAATTGAAGAGCTTGAAAAATCTAACATCGGTCGTCCCTCTAC
150751 TTATAACACTATGGCCAGTGTTAATCTAGAAAGGGGCTATGCTAACTTAG
150801 TGAACCGATTTTTTTATATCACTGAGCTTGGTGAAAAAGTTAATAATGAA
150851 CTTTCCAAGCATTTTGGGAATGTAATTAATAAAGAATTTACCAAGAAGAT
150901 GGAAAAATCTTTGGATGAAATTGCTGAAAACAAAGTAAACTATCAAGAAT
150951 TTCTTAAGCAGTTTTGAACAAATTTTAAATCTGATGTTAAACTAGCTGAA
151001 AATTCAATTCAAAAAGTGAAAAAGGAAAAAGAATTGGTTGAAAGAGATTG
151051 TCCTAAATGTAATCAACCGTTGGTATATCGTTACACCAAAAGAGGTAATG
151101 AGAAGTTTGTTGGTTGTAGTGATTTTCCTAAGTGTAAATACAGTGAGTTT
151151 AGTAATCCTAAACCAAAACTAACCTTGGAAACACTTGATGAATTGTGTCC
151201 TGAGTGTAACAATAAACTGGTTAAGAGGAGAACTAAATTTAACGCTAAAA
151251 AGACCTTTATAGGTTGCAGTAATTTCCCTAACTGCCGTTTTATCAAAAAG
151301 GATAATGCTGCTGAATTTAAACAATAACAGCGTTCTTATTGTTGCGTTTG
151351 TAATTGTTTCTTTATTCTTTCTAATAATTGTTGGGTTTGCTTTAAATTTA
151401 GCAATTGCTTTTTCACTCCATTTAAAGCAGAATAAAAATAACAAAAAATA
151451 CATCTTAAATGACCAACAGATCCAGTTAAGATTAACTGAAAAACAAGCCC
151501 AATTAACAACTTTACTTAACTTTTATCAACAAAAAATTGAAAGTGTAAAC
151551 AGAGAAAAAGTTGGTTAGAAAGTCAGTTACAGGTAATTGATAAAAAGGA
151601 TTTAAAGCAAGCGCAAAAGTTAACTTTACATTTAAAAAAAAGACCAAATAT
151651 TAGCTCAACTTAATGAAAAGCTGATTCAAAAAAAAAGTTGATCAGCCTTTA
151701 GTTAATGAACTACAGAAAACCAAACTTTCCTATCTTGAAAGGTTAGTTGA
151751 TCAAAAGATTAAACTCAGTGAAAATAATTTCAAAAGTGCTTTTCTTAAAA
151801 CGAAGGTAAAAGAGACAGCATTTAATATCTTTGCAGCTAAAAACAAGGTG
151851 AACTGGGAGTATTTTAAACAGGTGTGTGATGCTGATTGCACTTTAAAAAA
151901 CTTAGAAGATGAAGTGGAAATTACTTTTTCTAATTGGAGTTATTTGAGAA
151951 GGATGCAAGCTCTATTAGCGTTTGAAAAACTAATTAGCAAAATCAAACA
152001 GTCAAAATTAATGAATTGGTTATTAATGAAACTTTAGATGAAGTGAAAAA
152051 CGAAATTAGCCAAACTGCTTTTCAAGCGGGTGAAAAAATAGTTAAGGAAT
152101 TTCAGATAACTAATTTTAAACGAGCAAATTACCAGACTAATTGGCTTGCAA
```

-continued

The Nucleotide Sequence of the *Mycoplasma genitalium* Genome

```
152151 AAATACTATTTTGGCACTGATCAGCTCAATCTCTTAGAACTCGCGGTATT
152201 AACAACCAAATTAGTAATTTTACTGAACAAAAAGTTCAAACTAGATTTAG
152251 ATTTAGAACTTCTTAAAGCAGCTAGCTTGTTTAACTATTTAAAGTGAGTA
152301 GATAATAACCAGTTCTTTCAAATATTAAACACAAAACTTAACCAGCTTTT
152351 AATTAGTGATCAAGTTATTGCAATCATCCAACAACAAGAACTTAGTTTTT
152401 ATCCTGATCAGTATGGGATGTTAATTAATGGAGTGAAAACAATGATTAGA
152451 GAGCATAACACCATTGATTTTGAAAAACTGGTTTTTCTCAACTCAACAAA
152501 ACTTATTGATAATTTTTATCTCTATGATTTAAATATGATCCATGCAGTTG
152551 AATATAACAACTGCTTTTATTACTTTGTTAGTGTTAAACCCTTTGAGATT
152601 AAGTCATTAGCAGAACTTGATCTTTTTGTTGTTTTGTTAAAAACTTTTTT
152651 AGCTAAAAAGCAAAAGCAAAATCCAAAAGCGGTTAAACTGTTTATCACTA
152701 CCAAAATTTTAGCGATCTAATTACATTAGATTTTATTAGAATTGTTTCAA
152751 CTAATAAATTGGCCTTATGGTAACAGAAATTAGAAGTCTTAAACAACTTG
152801 AAGAGATCTTTTCAGCTAAGAAAAATGTTATTGTTGACTTTTGAGCAGCA
152851 TGATGTGGTCCTTGTAAACTAACCAGCCCTGAGTTTCAAAAAGCAGCAGA
152901 TGAATTTAGTGATGCTCAGTTTGTTAAGGTTAATGTTGATGATCATACTG
152951 ATATAGCAGCAGCTTATAACATTACCTCTTTACCAACTATTGTTGTTTTT
153001 GAAAACGGGGTTGAAAAAAAGAGAGCCATTGGCTTTATGCCAAAAACCAA
153051 AATTATTGATCTTTTCAATAACTAAAGTCCATGATTGATCTGCTTGGTTT
153101 GGATCTGGATGGAACGTTATTATCTAAAACTAAAAAAATTAACAATCCAT
153151 CAAAATTAGCATTAACTAATTTAATTGCTAAAAAACCAAGTTTAAAGGTG
153201 ATGATTTTAACTGGTAGATCAGTTTTTTCTACTCTAAAACACGTTGAAAA
153251 GCTGAACAGTTTGTTTAAAAAACCAATTGTTGATTATTTTTGTTGTTATG
153301 GGGGTGCTAAACTTTATCAAATTGAAGCAAATAAGCCACAAGAAAGATAC
153351 AAGTTTTGCTTGGAAAACAGTGTTGTTGAAACTACCTTTAGTATTATCAA
153401 AAAACACCGCGGATTATGTTTAGCTTACTTAGATAGTTATGTCTCTCCTT
153451 ACCTTTGTTTAGCTGGTAACAAGCTCCTTGGGTGGTTCACTAAATACTTT
153501 TGGTATAGAAAAAGGTGTGTGTTTTTTAACCAGAACCATTTAAAACAAGG
153551 TATTCTAAAGATTAGTGTTTACTTTTTAAGTGCAAAAAGGTGTAAzAAAG
153601 TTTATGAAATCTTAAAAAATACCTTTCAAGAAAAGGTTAATGTTTTAAGT
153651 TTTTCTAATAATTTAATTGAGATAACTCATCATGATGCTAATAAGGGTTA
153701 TGCAATTGAATATATGGCCAAAAGAGAACAACTTTCACTTAATAGAATAG
153751 CAGTTATTGGTGATTCTTGAAATGATTATGCAATGTTCAAAAAAGCTAAA
153801 TATTCCTTTGCAATGTCAAATCCCCTTCCCAGTTAAAATTAATTGCTAC
153851 CAATACCAGTAACAAAACCAACCGTTACCGCTTTAGTACCTTACTTAATT
153901 TAATTAGTGAAACAATCATTAATCAAAAAGCTGATTAGATGTTAAACCAA
153951 ATGCTTTATAAAACATTTTTAATGTTTCATCAGCAACTTTTTTAGCTTGG
154001 TTTTTACCATCATTTAGGACTTTTAATACCATTTCATCAGTAATTTGTGC
154051 TTTTTTTAAATTTAAGTGATTCTATGACATTAATAACAGCACTACTGAGGT
154101 CATTCTTTAAATCTAAATAACTTTTATTCTGATAATATTTAACAAGATCA
154151 GAGCCGATTTTTTTACTTAAATTATGGTTAACTTCTTCTTTTAAAAGTGC
154201 AGTTAAAATAACAAGTAAATTAGTAACACCAGGTTGGGTTTTTTAGCAA
154251 AACGAATCTTATTAAAACTATCAGTTGTGGCTTTGCGCACTTTTTTGATG
154301 ATTGTTTCTTTACTATCATCCAGATAGATAACACCATTTTGATCAGGATT
154351 TGATTTGGACATCTTTTTTAAAGGATTTGATAGATCCATGATCCTGTTGG
154401 TATCTTTGTTTTCTATAAATACAGGTAATTTCAGTTTTAACTTAAATTTT
154451 TTTGCTACACGTTTAGCTAAATCATTGGTTAATTCCAAGTGCTGCTTCTG
154501 ATCATTACCAACTGGAACAATATCAGGTTGATAAAGCAAGATATCAGCAG
154551 CCATTAACACTGGGTAAGTTAACAAACCAGTTGGGATAGTAATGGTGTTA
154601 TTACTATTTCTTTTTTGCGCTAATTTCTTTGTTTTAAATTGGGTCATTCT
154651 TTGTAATTCACCTAGATTACTTTGTGTCAGCATTAGATAACCTAACATGG
154701 TATGTTCCATCAGATCACTTTGTAAAAATAAGTTCACTTTTCCATAATCA
154751 AGTCCTAGTGCTAATAAAGTTTTAACAAGTTGCAAGTTGTTATCTTTGAG
154801 CATTGTTGGTTCAAAATCAACAGTAATAGCATGAAGATCAGCAACAAATA
154851 AAAACAGTTGGTATTGACTTTGGAGTTGTTTTAAACCTTGCATTACGCCA
154901 AGAAAGTTACCTAGGTGTTGTCTTCCAGAAGCTTGAATCCCTGTAATTGC
154951 GCGCTTTATCATTATTAGAATTGATAGGGTAATTAAAGGTTATTTTAATG
155001 AAAAAAGCGGGTAAAAAAAATAGTGATGCAGGTAAGACTTTTATCTTAAT
155051 CTCATCATCCTGTTCATCCTGTCAGAAAGCCATTGAGTTTTTTGATCAAA
155101 ACAAAATTAGCTATGTTGTTGAGAATTTTTATAAAAAACCAATTAGTGAT
155151 AAGCGTTTTAAAGATATTTTAAGTCTTAGTGAGGATGGTACTGAAAGTTT
155201 GTTTTCCAAACGTGCTGATCAGATTAAAGCaACTAACAGTGTTAGTGTTG
155251 AAGAGTTGAGTATCAGTGAATTAATTAAGCTAGTTAGAGAACGTCCTTCT
155301 TTACTAAGAAGGCCTATTATCATCCAATATAATTCTTCAGGAATTCCTAA
155351 AAGGATGCGAATTGGTTATAACTCATCTGAATTAAGGTCTTTGAGCGTA
155401 AACTAATAGAACCAAAGCCTATAATACAACAATAACATCTAAATGAAATA
155451 CAAAATTTTTGCTTCCACAACGCCCCAAACTGAACCTGTTCTCAATAAGT
155501 TAAGAGCAGTTTTAAAAACTTGGCAAGCGGTTGAGAATGGTTATGAATAT
155551 GTGTTTGTTTAGGTGGGGATGGTTTTTTTGTTTCCACACTTGCTAACTA
155601 TAACTGTGATAGTTGTAAGGTAGTTGGTATCAATACTGGCCACATTGGTT
155651 TTTACACTTCTTTTAATGGAGATGATCTTGATGAAAATTTCATTTCAAAA
155701 CTAACTAGCTTTGAGTTTAAAAAGATTAATTTACTGGAAGTGAAAACTAA
155751 AAACCACAGTTTCTTAGTTTTAAATGAACTTGCAGTTTACACCAACACTG
155801 CATATCCAATTAACATCTTTATTGATGATAACCACTGGGAATCATACCGC
155851 GGTTCAGGGTTGCTAATTGGCCCAAGAACAGGTTCAACTGCCCTAGCAAA
155901 ATCTGCTAAGGGAGCGGTTATCTTTCCAAATGTTGATGTTGTTCAAATTA
155951 TTGAACTAAACCCCTTATTACATCCCAACCAAATCACAATTCAATCTCCG
```

-continued

| The Nucleotide Sequence of the *Mycoplasma genitalium* Genome |
|---|
| 156001 ATTATTCTGCCAATGCAAACCAAGGTTGAATTTAGGATCAAAAAAGCTTT |
| 156051 TAAAGCAGAGCAATTTCCCAATTTTTATGCAGATGGAATCAAGCTTGATT |
| 156101 TAAAAAATGAAGATACCAGTATTAGCTTTCAGTTGGTTTTATCAAGATCA |
| 156151 ATGTTTCACGCTTCTTTAAAAACTAAGGATTTTATTGATAAACTAAATC |
| 156201 AACTTTTATTAAGCAAAGCTAATGAAATGGTTGTTGTGATTGGGTTATAT |
| 156251 TTTTAGTTTTGGTTTACTCTATCTTTGGATAGTAAAAAAATCAAAACAAA |
| 156301 TTGCTCAACAACCTAACACAAAACTGGTTGAATCAACTTCTATTCCTTTT |
| 156351 AAAGTTAAGGACTTTGTTAGTGCTTGTGGTGGTAAGGAAAATTTTGTTAA |
| 156401 TATAAAAACAACACCAACTCAATTAATAGTTACTTTTAAAGATGTTAACT |
| 156451 CAGTGAGCTTAACAAAGCTTAATGCGCTTAATATCAAAGGAATTAACAAA |
| 156501 AACCAAAACCAATTTCGTTTTGTACTTGGTAACTTTGTAAATGAATTGAA |
| 156551 AAAAAAGATAGAAGATGAACAATAACATTACTAACAGTATTGCCCAATTG |
| 156601 TTTTTCAACACTTCTTTCTTTGCTTTCTGTTTTTAATCATTATTGCGTT |
| 156651 TAATTTATGCTTGTTTGCCTATCTTTATTTTCAGTACCGAATTTATAAGA |
| 156701 AAAACCCTAAAAAAGCTAACAACTTTAAAGCGAATGAATATGAAAAAATT |
| 156751 AAGCTATTAAAAAACCAAAATTTCACTGAAAGTAATAAATTAATTGCAAC |
| 156801 AACTAATGAGTTAAATGAACTTACTAGTCAGCTAGATAATATCTTGGTTA |
| 156851 GGATTATCAACAAACCACTAGCAAAGTTAGTTAATGATTTTTTAGATGAA |
| 156901 CAGATTAAACAGATAGTTAAGCTAGATAAAAACAGTTCTGATTTTCACTC |
| 156951 AGAAAGTGATAACCTCCCTTTTTATACCAAACTCTTTAATGATTTTCACT |
| 157001 TTGGTGTTGATAAATTAATAAACATTAACATAAAAAACCCTCTTTATAAC |
| 157051 TGGGTTTATAGCCCCAGTTTTTTAATTAGTGAAAGTGATTTTCGCAAGCT |
| 157101 TAATGGTATTAGTGGTATCAATAAAAAGCTTTTGGTTGAAAAACTTAGAA |
| 157151 TTGAAGACATTGTGTTTACAGATCTAAACAAAAAGTATGAAGTTAATGTC |
| 157201 TTGACAGAAAGTCCTATTAAAGCACAAAAAACAGTGTTAACTGTGCGCAA |
| 157251 TATCCTGATGAACGATTATGTTGATAATGAAAGGATTGAATCATATGTCC |
| 157301 AACAAGCTAACTTCTTTTTTACTGAGCACTGTAAAAAGATCGGTAAAGAG |
| 157351 ATCTTAGAATCACTTAATATTTTTATCTCAAGTAGTTCACTACACCGTCA |
| 157401 TTTTTGGCTTTTTAGCATTTCGCTATTCATTTGGACAAAATGTCTTATCCC |
| 157451 ATAGCCTTGAAACTGCATTTTTAACTGCCCACTTAGCAGCTTTAATAGAA |
| 157501 CTTGATAGTGAACTGAGTTTAAAGTGTGGATTGCTCCATGATATTGGTAA |
| 157551 ATCTAATGATGATAATGGTAAAGAGAGCCATACGATTACAGGCGCTAAAC |
| 157601 TCGCTGAGCAATTTCAACTACCTGATGACATTAAATACACAATTGCTAAC |
| 157651 CACCACAATAAACATATTGACAATACCTATTGTCGTTTAACACAAATTGC |
| 157701 TGATAAACTATCTGCTGCTAGAATTGGTGCTAGAAGTGATAGTTCGCTTC |
| 157751 TTTTTAAACAACTAAAAGATGAGTTGAAAAGATTGTTGATAAAACTATT |
| 157801 AATAATTTTCATACAACGATCTTACTAGGTCAAAGTGGTAGAAGGTTAAT |
| 157851 GATTTGACTTGAAACTAAAAACCAAAATCAACTGTTAAGTAATGAGCAAA |
| 157901 TTATTGAAATGGTTGAAAAGATTAAAGCTGAAATTGCTAAGAATCCAATT |
| 157951 ACAAATCACTTCCCTATTAAAGTTGTAATTAGATATAACTTTGAACACAG |
| 158001 TTTTAACACCAAAAGCTAAGGATGCAATACAGTGCTTTAATACCACTTTT |
| 158051 TATATTACTAATTAGCTTAGTATTATTTTGTTTCAGCTTTAGAAAAAATC |
| 158101 AAAGTGAAAATCAGATAGTGAAAATCTTATTTTTTGCTTATTGCATCGAT |
| 158151 TTTTTAGCTTTAATTCTTGCTGTAATGTTGCTCACTTTTTTAAGTCATGG |
| 158201 GTTGTTAAGTTTAGCGATTTTAATCCCTGTCTTAGTTTTTCAATAATAAT |
| 158251 GTTTTTTGTTATGGTTATTAGTCACTATCCCCTTATGAAAAGACTATTTG |
| 158301 GAAATTAAAATTCTAAGTACCATGGAGTTGAAAACCCCTAACTTTAAGCT |
| 158351 AATTGATGAAAAGATTGCTGAATTTAATAAGAGTAATGAAAACCTGATTG |
| 158401 TAAAACTACTTCAAAAAGAAAAGGAATTTGCCACAAACCAAGTTACTGTT |
| 158451 CAGTTTGATACTCAGTCAAAAAAGTCAGAAGAAGTGAAAAAACCTAGTAA |
| 158501 AAAAAATACTGAAAAGTTATCACTTTCTAACAGTAGTTATGGCAGTTAATT |
| 158551 TGCTAATAACTGTTGGTTGATAGTTGGCTTAATTTTTGCTTTCAGATAT |
| 158601 TAGTTGGTAGTTTTCTTCTAAGGAACGTTTGTTGGTTTTATTGACATTAT |
| 158651 AGCCAAACCCTTTACCAGTTTCATATTTGGGTACTATGTGTAAGTGAAAA |
| 158701 TGAAAAACCACTTGACCTGCAATTGCCCCTTCATTAGAAACATAGTTTAA |
| 158751 ACCAGATGGTTTTAGTGTCATCTTTAGTTTTAAAGCGATTTGTTTTGCTA |
| 158801 ATAAACTAACTGCTTGTAACTCTTTTTGATCAGTTGAAGAAAAATCAACT |
| 158851 GCATGTTTTTTAGGGATTACTAAAGTATGACCATCAGCTACAGGAAAAGC |
| 158901 ATCTAAAAAAGCAATGGCATGCTCATTTTCTCCAATTTTATAGGATGTAA |
| 158951 TTGAACCTTGAACAATATCACAAAAGATACAACTACTTGTGGTGTTTTTT |
| 159001 TCCATAGTAATGGTTATTTATAACAAAAAGCATTCATAAGATTAAAAACA |
| 159051 TTGATGCAAAAATAGGGATTGATCAAATCCAAACATAACTGTTATATTTA |
| 159101 GTTTGCGTAAAAAATCCATTACACTGAATAGGAGTTTTCACCATTATCCCA |
| 159151 AACATTTAAAAATGGAATAGTTTGGAGATAAAAAGCATAGATACTGGGAT |
| 159201 AAATGCCTGCTTTTAAAAGAAAGGATTGCAAATTCCTTGGCGGTTTGATA |
| 159251 AATTTATAAGTTTTAAAAAGTAATCCAACATAAATAAAGTAAAACAACGG |
| 159301 ATGGATAACATGGAGTAATAGCTCTGAAAAAGCATTCCAGTCATTAATAA |
| 159351 AAGAACCATTAAAACTATATGGTAATTGCGTTGTTATAGTTGAAAACCAA |
| 159401 CCCTGTACATCAGGTTCTATATTAACAATACCTGTGAAGCGTGATAAAGC |
| 159451 ATAAAAGTTAAAGAAAATAACTGTAAAAACTAGATAACCTGTAACACTTA |
| 159501 AAACCAGTGAACTGTTTTCAAATCATCTGCTTTTATGGTTAAGAAAGTAG |
| 159551 TATCATACTAAAAAGATTGCAAGGCTATTACTTTGGTAAGTAAAAGTATC |
| 159601 AAAATTAGTAAACCAAATCAGGCTCATTTGACCACTGTTAGCAACACTAA |
| 159651 TCAGTGCAGTAATCACCATAAAGATTTGGGTGAATAGTGAAAAAGGTGCT |
| 159701 AGAAAAATTAAATAATAATCGCATTTATTGTTAAGATAAAAGCAACGGTA |
| 159751 AAAAATTCCAATTGATTTTTTAAGCACGATTTTTATTTAATGATATATGA |
| 159801 GTTTTAAAAAGATTGCTGAAATGATGCGTCAAGCAGAACGAGAAACTAAG |

-continued

The Nucleotide Sequence of the *Mycoplasma genitalium* Genome

```
159851 AAAAAAACATTAGCGTTTGAACAACAAGCCTTTGAATACAACTATAAAAA
159901 TGGTGCGATTAAGATCACTATTTTAGGTGATCTTACACTTAAATCAATTA
159951 ACATCGATCCTGTTTTGATTGATGCAAGTGACAAAGTTATTCTAGAGGAG
160001 ATGATTATAGAAGCTACTAATGAAGCGGTTAGTGATGTGAAAACCAAGTA
160051 TGATAACTTAGTTGAGAAAACTATGCCAAAAGTTCCAGGTCTTTTCTAAT
160101 TAGATTTTCTTTTTTAATAAAGATCTTATCCTTTTTCATTTCCATAAATG
160151 TAGGGATATTAGCAAAGAGTGTCATTAGTAAAATTGCAACATAACTTAAA
160201 CTAAAGCCCACAATAAACACAAGTTGTGGATCACTATTGCTTAAGTTAAG
160251 AAAGGTCGCCACATTTTTATATTCACCATTAGTTCAATCACTTGCTAAGA
160301 TACCAGTTGTATTACCTGTGATCTGGCCCTTAAACACAGATACCATCAAA
160351 GCTACATAACTAAAGTAAATTAGAGCAAACACATGGATATAGAAAAATGA
160401 GATTAAAGAAAAACAGTTATCCCACAAGATAATTGCTAAGCTTACAAGTA
160451 AACTGAGAAAATGCATCATGAAATAAATCTGGTTATTTCCTGTACCAACA
160501 AAGATGAAATTCACAATATCTTGTTCATTAACAGGTGTAAAAATTAGTTC
160551 ACCAAAAGAGTAACCAAAGCTCCAATAACCCAAAAACAGCTAACACCC
160601 CACTAATCTTTTTTTGCTTTAAAAAGACAAACACTGGCGCAATAACAGCA
160651 AAAAATGGACAAAGATCTAATAAAAATATCCTACTTAGTCGTAGTGAATC
160701 TAAATTTTGTGAAGATTGGGAATTTTGTCCATAAACATCAGGGAATAAAT
160751 AAATAATCTGCCTACCAAAAAAAACATAGACAAACAGTACAATGGCTAGT
160801 ACTTGAATTAGATAGAACCTAATCTTTAGTTTTCGAACTAAAGGAGTAAA
160851 AGCTAAAACAGAAATTACACCAGCAATAATAAGGATGATGACAAGGTAGT
160901 TAAGTGTCTGCATTACTTATTGCTTAAAATTAAGATAAATAATTTTCCAA
160951 TTTTGTTTTCAATGAGTGATCGTTTAAATGATCAAGCCCAACATCGCTTG
161001 CAGAAACTTTTAAGGTTAAAACAAACTAATAATGACCCTTATTTAGTAAC
161051 AAAAACTAGTCTAACCCATTCTTCAAAAAGCTTTCAAGTTGAATTTGAAA
161101 AATGTTCAGAAGAAGAGTTGAAGAAAAAAGCAACTGTCTCACTAGCTGGA
161151 AGGATCATTGCTATTAGACAAACCTTTTTAATTATTCAAGATTTTGATGG
161201 TCAAGTCCAACTTTACATCAATAAAAAAATCCATCCTAAGTTATTTGATT
161251 ACTTTAATGAATTTGTTGATATTGGTGATCAAATTGTTGTTAGTGGTAAG
161301 CCAATGTTAACTAAAACAAAGGTATTAACTTTAGCTGTTGAAGAGATGAA
161351 AATCATTGCTAAGTGTTTATTGGTTCCACCTGAAAAGTGACATGGACTTA
161401 CTGATATTGAAACCCGCGCTCGCAAGCGCTTTCTTGATCTTACCTATAAC
161451 TTAGCAATGCGTGATGTTTTCTGAAACGCACTAAGATTATTAAATCAAT
161501 CCGTAGCTTTCTTGATCAAAATGGTTTTATTGAAGTTGAAACCCCCACTT
161551 TACAAGCTGTTTTAGGAGGAGCTAATGCTAAACCCTTTAAAACCCATTAC
161601 AATGCTTTAAAAGCGGATTTTTATCTCAGAATTGCTAATGAAATAGCATT
161651 AAAAAAAACTCATTATTGGTGGATTTAACAAGGTTTATGAAATGGGTAAAA
161701 TGTTCCGTAATGAAGGGGTTGATACTACCCACAATCCTGAGTTTACCAGT
161751 ATTGAAATATATCAAGCTTATGCAGATTTTGAAGTCATGCTTGTGCTTGT
161801 TGAAAAGCTGATTCAATCACTTTGTGAAAGCTTAAACCAATTTAGCTTTA
161851 ACTGAAATAACAAAACGATTAATCTAAAAACACCATTTCATAAGATAACA
161901 ATGGTTGAACTTATTAAGAAAGTTACAGGGATCGATTTTAATTCAGTAAA
161951 AGATGATCAATCTGCCATTTTATTAGCAGAAAAACATCATGTTAAACTAG
162001 CAAAACACCAACAAATAAGCAACACATCATTAATTTGTTTTTTGAACAG
162051 TTTTGTGAACAAACATTAATTGAACCTACCTTTGTAACCCATTATCCAAA
162101 AGCAGTTTCTCCTTTAGCAAAACAAGATCCTTCAAATCCTGAATTCACCC
162151 AACGATTTGAACTTTTTATTAATGGTAAAGAGATTGCTAATGCTTACAGT
162201 GAGCTAAACGATCCTTTAGAACAAAGAAAAAGGTTTGAACAACAACTTGA
162251 AGAAAAACAGCTTGGTAATGATGAGACAAGTGAACTTGATGAATCGTTTT
162301 TAGAAGCATTAAGTTTTGGGATGGTAAACACTGCTGGGCTTGGGATAGGT
162351 ATTGATCGTTTGGTAATGTTGTTATGTGAATGTAATTCTATCCGTGATGT
162401 TGTTTTCTTCCCCCAGTTGCGTGAACATAAATAGTTTTGATATTTTAATT
162451 GTTGGTGCTGGTATTAGTGGAATAGTACTAGCTAACATCTTAGCTAATCA
162501 CAATAAAAGGGTTTTAATTGTTGAAAAAAGAGATCATATTGGTGGTAACT
162551 GTTATGATAAAGTTGATAGTAAAACTCAACTCTTGTTTCACCAGTATGGA
162601 CCCCATATTTTCCATACTAACAACCAAACTGTTATTAACTTTATCTCACC
162651 CTTCTTTGAACTAAATAACTACCACCATCGGGTTGGTTAAAATTGAAAA
162701 ATAACCTAGATTTAACCTTACCCTTTGATTTTCAACAGATCTATAAACTA
162751 ATGGGAAAAGATGGTAGAAAACTCGTTAGTTTTTTTAAAGAAAATTTCAG
162801 TTTAAATACTCATCTATCATTAGCAGAATTACAACTAATTGATAATCCTT
162851 TAGCACAAAAACTCTATCAGTTTTTAATTAGTAATGTTATAAACCATAC
162901 AGTGTCAAAATGTGGGGTTTACCATTTGCAATGATTAATGAGAATGTTAT
162951 TAACAGGGTCAAGATAGTTTTAAGTGAACAAAGCAGTTATTTtCCTGATG
163001 CAATTATCCAGGGATTACCTAAATCAGGTTATACAAACAGTTTTCTTAAG
163051 ATGTTAGCCAATCCCTTAATTGATGTGCAGTTAAACTGCAAAGATAACCT
163101 TTTAGTTTATCAAGATGAAAAACTGTTTTTTAACAATAACTTAATAGAAA
163151 AACCAGTTGTTTACTGTGGCTTAATTGACAAGCTATTTAACTTTTGCTTT
163201 GGTCATTTGCAATACCGTTCTCTTGCCTTTAGTTGAAAAAGATTTAACCA
163251 AAAAAAATACCAAACCTACCCTGTTGTTAATATGCCTTTAGCTAAATCAA
163301 TCACAAGGAGTGTGGAATACAAACAACTAACAAACCAAGGTTCTTTCAAA
163351 CCGCAAACCATCGTTAGTTTTGAAACCCCTGGCAGCTATGCAATTAACGA
163401 TCCTAGGTTTAATGAACCTTATTACCCAATTAACAATACACTAAATGATA
163451 CTCTTTTTAAAAAGTACTGAAAAAAAGCAAGTAAGTTAAAGAATCTACAC
163501 CTTTTGGGAAGATTAGCAACCTACCAATACATTGATATGGATAAAGCAAT
163551 CCTACTTAGTATTAAAAAAGCCCAACAACTGTTAAGTTAATGGAACAAAA
163601 AAACATTAGAAATTTTTCTATTATTGCCCATATTGATCATGGTAAATCTA
163651 CCTTATCAGACCGCTTGTTAGAACATAGTTTAGGCTTTGAAAAAAGACTA
```

-continued

The Nucleotide Sequence of the *Mycoplasma genitalium* Genome

```
163701 TTACAAGCGCAAATGCTTGATACTATGGAGATTGAAAGAGAAAGGGGTAT
163751 TACCATTAAATTAAATGCTGTTGAATTGAAAATTAATGTTGATAACAACA
163801 ACTATCTTTTTCATTTAATTGACACCCCTGGGCATGTTGATTTTACTTAT
163851 GAAGTGTCTCGTTCTTTAGCAGCTTGTGAGGGAGTTTTATTGTTAGTAGA
163901 TGCAACCCAAGGAATTCAAGCACAAACGATTTCCAATGCTTATCTTGCGT
163951 TGGAAAATAACCTGGAAATTATCCCAGTTATTAACAAGATAGATATGGAT
164001 AATGCTGATATTGAAACAACAAAAGATTCACTCCATAACTTATTAGGAGT
164051 TGAAAAGAACAGTATCTGTTTAGTATCTGCAAAAGCTAACTTAGGGATTG
164101 ATCAGTTAATTCAAACAATTATAGCTAAGATCCCCCCACCAAAAGGAGAA
164151 ATTAATAGACCTTTAAAAGCATTACTCTTTGATAGTTACTATGATCCTTA
164201 CAAGGGGGTTGTTTGTTTATTAGGGTATTTGATGGTTGTTTAAAGGTTA
164251 ATGATAAGGTTCGTTTTATTAAAAGTAATTCTGTTTACCAAATTGTGGAA
164301 CTAGGGGTTAAAACCCCATTTTTTGAAAAAAGAGATCAATTGCAAGCAGG
164351 AGATGTTGGTTGGTTTTCAGCAGGGATAAAAAAACTTCGTGATGTTGGGG
164401 TTGGTGATACTATTGTTAGTTTTGATGATCAATTTACAAAACCCCTAGCA
164451 GGTTATAAAAAGATCTTACCCATGATCTATTGTGGTTTATATCCAGTTGA
164501 TAACAGTGATTATCAAAACCTCAAGTTAGCGATGGAAAAGATCATAATCA
164551 GTGATGCAGCATTGGAATATGAATATGAAACATCCCAAGCGTTAGGTTTT
164601 GGGGTTAGGTGTGGTTTTCTAGGTCTTTTACATATGGATGTTATTAAAGA
164651 AAGATTGGAAAGAGAATACAACCTAAAACTCATCTCAGCTCCCCCTTCAG
164701 TTGTATATAAGGTGTTGTTAACAAATGGTAAAGAGATTAGTATTGACAAT
164751 CCCTCTTTGTTACCAGAACGCTCCAAGATTAAAGCAATCAGTGAACCATT
164801 TGTAAAAGTCTTTATTGATTTACCTGATCAATATTTGGGCAGTGTTATTG
164851 ATTTATGCCAAAACTTCAGGGGTCAATATGAAAGTTTAAATGAGATTGAT
164901 ATCAACAGAAAAAGAATCTGTTATCTGATGCCTTTAGGGGAAATTATCTA
164951 CAGTTTTTTTGATAAGTTAAAGTCGATTAGTAAGGGTTATGCATCGTTAA
165001 ACTATGAGTTTTATAACTACCAACATAGTCAACTGGAAAAAGTTGAGATC
165051 ATGTTAAACAAACAAAAGATTGATGCATTATCTTTTATCAGTCATAAAGA
165101 CTTTGCTTTTAAGCGGGCAAAAAAGTTTTGCACTAAGCTCAAAGAATTGA
165151 TTCCCAAGCATCTGTTTGAGATCCCTATCCAAGCAACAATAGGGAGTAAA
165201 GTAATAGCAAGAGAGACAATCAAAGCAGTTAGAAAGGATGTAATAGCTAA
165251 ACTTTATGGAGGGGATGTTAGTAGAAAAAAGAAGTTATTAGAGAAGCAAA
165301 AAGAGGGTAAAAAACGCTTGAAAGCAGTTGGGAGTGTTCAATTACCCCAA
165351 GAGCTATTTAGTCATTTGCTGAAAGATGAAGATTAACATTTTTATAATTT
165401 GTTATTCTTTTGTATTGGTTGATACTTTAACAAAGTATTCACAATAAAAT
165451 TTCAACACTAATATAAACAATGATAAAGGATTTTAATCCTGGTGATTTTA
165501 TTGGTAAAAAACCAACTAAAATCTATGCTTTTGGTGGTATCCAAGAAGTT
165551 GGTAAAAACATGTATGGGATTGAATATGATGATGAAATCATCATTATTGA
165601 CTGTGGCATTAAATTTGCTAGTGATGATCTACTTGGCATCAATGGGATTA
165651 TCCCTAGTTTTGAACACTTAATTGAAAACCAAAGTAAGGTTAAAGCATTG
165701 TTTATTACCCATGGTCATGAAGACCATATTGGGGGTGTACCATACCTTTT
165751 AAAGCAGGTTGATATTCCTGTTATCTACGCACCAAGGATCGCAGCATCAT
165801 TAATCTTGAAAAAGGTTAATGAGCACAAGGATGCTAAGCTCAATAAGATA
165851 GTTACTTTTGATGATTTTAGTGAGTTTCAAACCAAACACTTCAAAATTGA
165901 TTTTTACCGGGTAAACCACTCGATTCCCGATGCTTTTGGAATCTGTGTGC
165951 AAACCCCTAATGGCAACATTGTTCAAAGCGGTGACTACCGGTTTGATTTT
166001 GCTGCTGGGAGTGAGATGTTAGATGTTCATAAAGTAGTGAAAATTGCCGA
166051 GCGCAATGTCCATGTTTTTATGAGTGAATCTACTAATGCTGAAGTACCAG
166101 GTTTTTCCCAAAGTGAAAAGTTAATTTACAGAAACATCCAAAAGATCTTA
166151 AAAGAAGCAAGGGGTAGGGTTATTTTAACTACTTTTGCATCTAACATCAC
166201 ACGGATTAATGAAATTATTGAGATTGCTTTAAACAACAAACGCAAGATCT
166251 GTTTATTGGGTAAATCAATGGATGTTAATGTTAATATTTCACGCAAAATT
166301 GGATTGATGGCAATTGATAGTAATGATATTGTGGAAGTTCGTGATATCAA
166351 AAACTATCCTGATCGTAATATCTTAATCTTGTGCACTGGTTCACAAGGTG
166401 AGGAGGCTGCTGCTTTAAACACAATGGCACGTGGTAAGCATAATTGGGTG
166451 AGCTTAAAATCAACTGACACCATTATTATGTCTTCAAATCCAATTCCAGG
166501 TAATTATGCTGCAGTTGAAAACTTGCTTAATGAACTCTCTAAGTTTGGTG
166551 TTGCTATTTATGAAAATTCATCCCAACTAAAACTACATGCCTCAGGTCAT
166601 GCCACTCAACAAGAGTTACAGTTGATGCTAAATTTAATGTTTCCTAAATA
166651 CTTAATTCCTATCCATGGTGAATTTAAGATGATGCGAACCATAAAAAACA
166701 TTGCTAATGAATGTGGCATTAAAAGCGAGGATGTGGCGCTTTTAAGTAAT
166751 GGCCAAGTAATGTATTTAATTGATGAAGAACTTTATTATTCCAATGAAAT
166801 TATTAATGCTGAtCCTATTTATATAGAGAGTCATAAcTCTTCTCCTGATC
166851 TTGCAAGAATAATTAAGCAAAGACAAATCCTTAGTCGTGATGGGATGTTT
166901 GCTGTTATTGTTGTTTTTGATAAGAATAATAACATCATTGGGATTCCAAC
166951 CTTAATAACAAGGGGTTGTTTCTTTGCACTTGATTCCAATCCTTTAATGA
167001 CAAAGATAGCCCATTCTGTTAAAAGAACTTTAGAAAGTGTTATCCAAAGT
167051 AAGAAGTTTAATAGTCATGAACAACTAACAAAGGAATTGAAACGAGTTTG
167101 TAAGGAAACTGTTTCTTACTTTATCTGAAAAAATAAAAACCGTAATCCCT
167151 TAATTTCAACTGTGCTTTCCTGGATCTAATTCCCCCAACCTCTATTTTCT
167201 GTTACTAGTGCCAAAAGTGGTATTAGAGTACCACAACCTGAATAACCAAG
167251 TAGTCAAAGAGAGTTTGGAAGTGGAAGCAACCCAATCATCCTTCAACCCC
167301 ACCCAAAGGTTGAAGAGTGGGAGTCCAATGAAGGATACAGGAAAGATGGG
167351 GGAGAAACTCAGTGAAACAACTGCTTCATCCATGAGTGGTATGGCTACAT
167401 CCACTCGAGCCAAGGCCCTTAAGATAGAGGTGGAAAGGGGAGTAATGTC
167451 AATCAAGGCGAACTACAATCCAACGACTTTGCCAAAAAGCCGTTTAAAGA
167501 TGAGAGCAATAAGAAGTTGGATTCACAGAAGGAGTTTCCCCAAGGAAAGG
```

| The Nucleotide Sequence of the *Mycoplasma genitalium* Genome |
| --- |
| 167551 TTTGAAAACCGGTGTTGAGTACAGATGAGATAACAAGAGAGAGGGGATG |
| 167601 GGGGCGACTTAGACTTTCTCCCCTGAATCGGCAATGGTAAACCCTTCTCC |
| 167651 AACTCCCCCTCCCCTTCAACTTCTGCTTCCTCAACCCCCCTCCCCACTTT |
| 167701 TTCTAACATCAATGTTGGGGTTAAATCAATGATCACTCAACATTTAAATA |
| 167751 AAGAAAACACCCGGTGGGTGTTTATACCTAACTTTTCACCTGACATCTGA |
| 167801 ACAGGAGCAGGTTATAGAAAAGCTAATAACAACAATAACGGCATTCCTTT |
| 167851 TGAACAGGTGAAACCTAGCAATAGTAGTACCCCCTTTAATCCCACCTCAG |
| 167901 CTGGTGGCTCCTCAGCCAAAAAAACAACCACCTATTCCTTTTTACCCAAT |
| 167951 TCCATCAGTCCCACCAGTGACTGGATCAACGCATTGACTTTCACTAATAA |
| 168001 GAATAACCCGCAACGAAATCAACTGTTGTTAAGAGCACTGTTAGGAACTA |
| 168051 TTCCGGTCTTGATCAATAAGAGTGGGGATAGTAATGATCAATTTAACAAG |
| 168101 GATAGTGAGCAGAAATGGGATAAAACGAATGAAAAAGATGGGAATTTACC |
| 168151 TGGGTTTGGGGAGGTGAATGGTGGTTTTTATAAGATTTTTACTTATTTAA |
| 168201 TAGTTAAAAAAGTTTTGAATTTTTCTTAGTTTTTTATTTGTTTAATATTT |
| 168251 AAGAAAGTCTCAAATTTTTATCAGTTTATTGGTCAAAGAAGTCGCAAATT |
| 168301 TTTCTTAGTTTTTTATTTGCTTAATGGTTAAAAAAGCGTTAGTTTTTACC |
| 168351 TTTATTTAATTAATAAAAACATTAAACTTCGCCACCCCCATCACCGATTC |
| 168401 TAAAAGTGATCTGGTTAGTTTGGCACAACTTGATTCTTCCTATCAAATCT |
| 168451 CCGACCAAACCATCCATAACACCAACTTGTTTGTGTTGTTCAAGTCCAAG |
| 168501 GATGTGAAGCTTACATATAGTTCAAGTGGCTCAAATAACCAGATTAGTTT |
| 168551 TGATTCAACTAGTCAAGCTAACAAACCCGCCTACATCGTTGAATTTACTA |
| 168601 ATTCCACCAACATTGGCATCAAGTGAAGGGTAGTGAAAAAATATCAGtTa |
| 168651 GATGTACCGAATGTTTCAACAACCATGAACGAAGTTTTGCAAGAATTGAT |
| 168701 CCTAGAACAACCTTTGACTAAGTATACCTTAAACAGTAGTTTGGCCAAAG |
| 168751 AGAAGGGTAAGACACAAGTAGCGGTACATCTGGGTAGTGGGCAAGCAAAT |
| 168801 CAGTGAACCAGTCAACGCAACCAACATGACCTAAACAACAATCCCAGTCC |
| 168851 CAATGCTTCAACTGGGTTTAAACTCACTACCGGCAATGCGTATAGAAAAT |
| 168901 TGGATCAATCCTGACCAATTTACCAACCAATTGATGGGACCAAGCAGGGC |
| 168951 AAAGGGAAGGATAGTAGTGGGTGGAATAGTGAAGAAAACGAAGCTAAAAG |
| 169001 TGATGCGCCCCTAAGTACAGGAGGGGGTGCTTCTTCTGGAACATTTAATA |
| 169051 AATACCTCAACACCAAGCAAGCGTTAGAGAGCATCGGCATCTTGTTTGAT |
| 169101 GGGGATGGAATGAGGAATGTGGTTACCCAACTCTATTATGCTTCTACCAG |
| 169151 CAAGCTAGCAGTCACCAACAACCACATTGTCGTGATGGGTAACAGCTTTC |
| 169201 TACCCAGCTTGTGGTACTGGGTGGTGGAGCGGAGTGCACAGGAAAATGCA |
| 169251 AGTAACAAACCCACCTGGTTTGCTAATACCAATTTAGACTGAGGGGAAGA |
| 169301 CAAACAAAAACAATTTGTTGAGAACCAGTTGGGGTATAAGGAAACTACCA |
| 169351 GTACCAATTCCCACAACTTCCATTCCAAATCTTTCACCCaACTTGCATAT |
| 169401 CTGATCAGTGGCATTGACAGTGTCAATGATCAAATCATCTTCAGTGGCTT |
| 169451 TAAAGCGGGGAGTGTGGGGTATGatagTAGTAGTAGTAGTAGTAGTAGTA |
| 169501 GTAGTAGTAGTAGTAGTAGTACCAAAGACCAAGCACTTGCTTGATCA |
| 169551 ACAACAACTAGCTTAGATAGTAAAACGGGGTATAAGGATCTAGTGACCAA |
| 169601 CGACACGGGATTAAATGGTCCAATCAATGGGAGTTTTTCAATCCAAGACA |
| 169651 CCTTCTCATTCGTTGTTCCTTATTCGGGGAATCATAGTAATCAAATTTCA |
| 169701 TCAGGAACCATTAAAACTGCTTATCCTGTGAAAAAAGATCAAAAATCAAC |
| 169751 TGTCAAGATCAATTCCTTGATCAACGCTACGCCGTTGAATAGTTATGGGG |
| 169801 ATTTAAACATTAAATAAAGAGAATTCACCCAAATTATTTACTTATTTATT |
| 169851 AACTATTGTTACCCAATTTTTCTCTTTTTATTTGTTGTTTTTTTACTAAT |
| 169901 TAAATAAGCAGTCTTTCtTACAAAAAAGaAAAATTCATATATAATCTTTG |
| 169951 cGCTGTTAACACCTTTGTTAAcGCCAAAAATGTTCTTTCAAAACTGGATG |
| 170001 CAATCTGTCAATTTTTTCTGAGAGTTTGATCCTGGCTCAGGATTAACGCT |
| 170051 GGCGGCATGCCTAATACATGCAAGTCGATCGGAAGTAGCAATACTTTAGA |
| 170101 GGCGAACGGGTGAGTAACACGTATCCAATCTACCTTATAATGGGGGATAA |
| 170151 CTAGTTGAAAAACTAGCTAATACCGCATAAGAACTTTAGTTCGCATGAAT |
| 170201 TAAAGTTGAAAGGACCTGCAAGGGTTCGTTATTTGATGAGGGTGCGCCAT |
| 170251 ATCAGCTAGTTGGTAGGGTAATGGCCTACCAAGGCAATGACGTGTAGCTA |
| 170301 TGCTGAGAAGTAGAATAGCCACAATGGGACTGAGACACGGCCCATACTCC |
| 170351 TACGGGAGGCAGCAGTAGGGAATTTTTCACAATGAGCGAAAGCTTGATGG |
| 170401 AGCAATGCCGCGTGAACGATGAAGGTCTTTTTGATTGTAAAGTTCTTTTA |
| 170451 TTTGGGAAGAATGACTCTAGCAGGCAATGGCTGGAGTTTGACTGTACCAC |
| 170501 TTTGAATAAGTGACGACTAACTATGTGCCAGCAGTCGCGGTAATACATAG |
| 170551 GTCGCAAGCGTTATCCGGATTTATTGGGCGTAAAGCAAGCGCAGGCGGAT |
| 170601 TGAAAAGTCTGGTGTTAAAGGCAGCTGCTTAACAGTTGTATGCATTGGAA |
| 170651 ACTATCAGTCTAGAGTGTGGTAGGGAGTTTTGGAATTTCATGTGGAGCGG |
| 170701 TGAAATGCGTAGATATATGAAGGAACACCAGTGGCGAAGGCGAAAACTTA |
| 170751 GGCCATTACTGACGCTTAGGCTTGAAAGTGTGGGGAGCAAATAGGATTAG |
| 170801 ATACCCTAGTAGTCCACACCGTAAACGATAGATACTAGCTGTCGGAGCGA |
| 170851 TCCCTTCGGTAGTGAAGTTAACACATTAAGTATCTCGCCTGGGTAGTACA |
| 170901 TTCGCAAGAATGAAACTCAAACGGAATTGACGGGGACCCGCACAAGTGGT |
| 170951 GGAGCATGTTGCTTAATTCGACGGTACACGAAAAACCTTACCTAGACTTG |
| 171001 ACATCCTTGGCAAAGTTATGGAAACATAATGGAGGTTAACCGAGTGACAG |
| 171051 GTGGTGCATGGTTGTCGTCAGCTCGTGTCGTGAGATGTTGGGTTAAGTCC |
| 171101 CGCAACGAGCGCAACCCTTATCGTTAGTTACATTGTTTAACGAGACTGCT |
| 171151 AATGTAAATTGGAGGAAGGAAGGGATGACGTCAAATCATCATGCCCCTTA |
| 171201 TGTCTAGGGCTGCAAACGTGCTACAATGGCCAATACAAACAGTAGCCAAC |
| 171251 TTGTAAAAGTGAGCAAATCTGAAAAGTTGGTCTCAGTTCGGATTGAGGGC |
| 171301 TGCAATTCGTCCTCATGAAGCTGGAATCACTAGTAATCGCGAATCAGCTA |
| 171351 TGTCGCGGTGAATACGTTCTCGGGTCTTGTACACACCGCCCGTCAAACTA |

-continued

| The Nucleotide Sequence of the *Mycoplasma genitalium* Genome |
|---|
| 171401 TGAAAGCTGGTAATATTTAAAAACGTGTTGCTAACCTTTATTGGAAGCGC |
| 171451 ATGTCAAGGATAGCACCGGTGATTGGAGTTAAGTCGTAACAAGGTACCCC |
| 171501 TACGAGAACGTGGGGTGGATCACCTCCTTTCAAATGGAGTTTTTATTTT |
| 171551 TTATTTATCTTAAACACCCATTAATTTTTTCGGTGTTAAAACCCAAATCA |
| 171601 ATGTTTGGTCTCACAACTAACACATTTGGTCAGTTTGTATCCAGTTCTGA |
| 171651 AAGAATGTTTTTGAACAGTTCTTTCAAAACTGAAAACGACAATCTTTCTA |
| 171701 GTTCCAAAAATAAATACCAAAGGATCAATACAATAAGTTACTAAGGGCTT |
| 171751 ATGGTGGATGCCTTGGCACTAAAAGGCGATGAAGGACGTGTTAACCTGCG |
| 171801 ATAAGCTTCGGGGAGGTGGTAAAAACCTGAGATCCGGAGGTGTCCGAATG |
| 171851 GAGCAATCTGGTAGCTTGCAAAAGTTACCATTAATTAATGAATTCATAGT |
| 171901 TAATTAAAGCGATACGTGGTGAAGTGAAACATCTCAGTAACCACAGGAAA |
| 171951 AGAAAACGAATGTGATTCCGTGTGTAGTGGCGAGCAAAGCGGAACAGGC |
| 172001 CAAACCTATCTGAGGATAGGGGTTGTAGGGCTTGCATTATGGAAGTTAAA |
| 172051 AGGATAGAAGAAGCTGTTGGAAAGCAGCGCCAAAGAGGGTGATAGCCCCG |
| 172101 TATTTGAAATCTTTTTAATACCTAGCAAGAAACCTGAGTAGCTCGAAAAA |
| 172151 CGTTATTTTGAGTGAATCTGCCCAGACCATTGGGTAAGCCTAAATACTAA |
| 172201 TTAGTGACCGATAGCGAAACAGTACCGTGAGGGAAAGGTGAAAAGAACCC |
| 172251 AGAGATGGGAGTGAAATAGATTCTGAAACCATATGCCTACAACGTGTCAG |
| 172301 AGCACATTAATGTGTGATGGCGTGCGTTTTGAAGTATGAGCCGGCGAGTT |
| 172351 ATGATAGCAAGCGTTAGTTAACCAGGAGATGGGGAGCTGTAGCGAAAGCG |
| 172401 AGTTTTAAGAGAGCGTTTGTTTGTTATCATAGACCCGAAACGGGTTGAGC |
| 172451 TAGTCATGAGCAGGTTGAAGGTTGAGTAACATTAACTGGAGGACCGAACC |
| 172501 GACTCTCGTTGAAACGATAGCGGATGACTTGTGATTAGGGGTGAAATTCC |
| 172551 AATCGAAATCCGTGATAGCTGGTTCTCGTCGAAATAGCTTTAAGGCTAGC |
| 172601 GTAAGATCACAAATAAGTGGAGGTAAAGCTACTGAATATGATGGCGCC |
| 172651 ACCTAGGCGTACTGAATACAATTAAACTCTGAATGCCATTTATTTTATTC |
| 172701 TTGCAGTCAGACAGTGGGGATAAGCTTCATTGTCAAGAGGGGAAGAGCC |
| 172751 CAGATCATTAAATAAGGTCCCCAAAATATACTAAGTGGAAAAGGATGTGA |
| 172801 AAGTGCTAAAACAGCAAGGATGTTGGCTTAGAAGCAGCCATCGTTTAAAG |
| 172851 AGTGCGTAACAGCTCACTTGTCGAGTGTTTTTGCGCCGAAGATGTAACGG |
| 172901 GGCTAAGTATATTACCGAATTTATGGATAAGATATTTTTATCTTGTGGTA |
| 172951 GACGAGCGTTGTATTGGAGTTGAAGTCAAAGCGTGAGCATTGGTGGATCC |
| 173001 AATACAAGTGAGAATGCCGGCGTGAGTAACGCTTGGGAGTGAGAATCTCC |
| 173051 CAAACCGATTGACTAAGGTTTCCTGGACCAGGGTCGTCCTTCCAGGGTTA |
| 173101 GTCTGGACCTAAGCTGAGGCTGAAGAGCGTAGGCGATGGACAACAGGTTA |
| 173151 ATATTCCTGTACTTACAGTTAGACTGATGGAGTGACAAAGAAGGTTATCC |
| 173201 ACCCCCATTATTGGATTTGGGGATAAACCATAAGGTGGTACAATAGGCAA |
| 173251 ATCCGTTGTGCATAACACTGAGTGGTGATGTCGAGTGAACGAGTGATCAA |
| 173301 GTAGCGAAGGTGGCAATTAATCATGCTTTCAAGAAAAGCTGCTAGGGCTA |
| 173351 ATTTAACTGTAACCAGTACCGAGAACGAACACACGTAGTCAAGGAGAGGA |
| 173401 TCCTAAGGTTAGCGAGTGAACTATAGCCAAGGAACTCTGCAAATTAACCC |
| 173451 CGTAAGTTAGCGAGAAGGGGTGCTTATCTAAAAGTAAGCCGCAGTGAAGA |
| 173501 ACGAGGGGGACTGTTTAACTAAAACACAACTCTATGCCAAACCGTAAgG |
| 173551 TGATGTATATGGGGTGACACCTGCCCAGTGCTGGAAGGTTAAAGAAGGAG |
| 173601 GTTAGCAATTTATTGCAAAGCTTTTAACTGAAGCCCCAGTGAACGGCGGC |
| 173651 CGTAACTATAACGGTCCTAAGGTAGCGAAATTCCTAGTCGGGTAAATTCC |
| 173701 GTCCCGCTTGAATGGTGTAACCATCTCTTGACTGTCTCGGCTATAGACTC |
| 173751 GGTGAAATCCAGGTACGGGTGAAGACACCCGTTAGGCGCAACGGGACGGA |
| 173801 AAGACCCCGTGAAGCTTTACTGTAGCTTAATATTGATCAAAACACCACCA |
| 173851 TGTAGAGAATAGGTAGGAGCAATTGATGCAAGTTCGCAAGGATTTGTTGA |
| 173901 TGTGAAATGTGGAATACTACCCTTGGTTATGTTTTGTTCTAATTGGTAAC |
| 173951 TGTGATCCAGTTTCAAGACAGTGTTAGGTGGGCAGTTTGACTGGGGCGGT |
| 174001 CGCCTCCTAAAAGGTAACGGAGGCGCACAAAGGTACCTTCAGTACGGTTG |
| 174051 GAAATCGTATTTAGAGTGTAATGGTATAAGGGTGCTTGACTGTGAGACTT |
| 174101 ACAGGTCGAACAGGTGAGAAATCAGGTCATAGTGATCCGGTGGTTCAGTA |
| 174151 TGGAATGGCCATCGCTCAACGGATAAAAGCTACTCCGGGGATAACAGGCT |
| 174201 GATACTGCCCAAGAGTTCATATCGACGGCAGTGTTTGGCACCTCGATGTC |
| 174251 GACTCATCTCATCCTCGAGCTGAAGCAGGTTCGAAGGGTTCGGCTGTTCG |
| 174301 CCGATTAAAGAGATACGTGAGTTGGGTTCAAACCGTCGTGAGACAGGTTG |
| 174351 GTCCCTATCTATTGTGCCCACAGGAAGATTGAAGAGCTTTGCTTCTAGTA |
| 174401 CGAGAGGACCGGAGCGAGGACACCGCTTATGCTCCAGTTGTAGCGCCAGC |
| 174451 TGCACCGCTGGGTAGTAACGTGTCTATTAGATAAACGCTGAAAGCATCTA |
| 174501 AGTGTGAAACTATCTCAAAGATTAATCTTCCCATTTCTGTTAAAGGAAAG |
| 174551 TAAGAGCCGTTATAGACCATGACGTTGATAGGTTACAGGTGTAAGCATAG |
| 174601 TGATATGTTGAGCTGAGTAATACTAATTGCTCGAGGACTTATTGGTTGAT |
| 174651 AAAAGGTATTTATCAACTAAAAGATTGTCGTTTTTGTTTGGTGCTAATAT |
| 174701 CGCTGTGGAAACACCTGGAACCATCCCGAACCCAGCAGTTAAGCACAGTG |
| 174751 GAGCTAAATGTAGGTAGTAATACTGAGAATAGGTAAGCACCAAGCAAAAA |
| 174801 TTAAGGACTATAGGTTTAAAAACCTATGGTCTTTTTTATTTAATGAATA |
| 174851 GTTTTTATAACTAATTTATCTAAAAAAATCGAACAACCTTTGACTAAGTA |
| 174901 TACGCTCAATGGCAGTTTGGCCAAAGAGAAGGGCAAAAGCCAGATAGAGG |
| 174951 TGCATCTGGGTAGTGGGCAAGCAACTAATTGATCCACTCAACGCGCCACT |
| 175001 CCATTGGTCTGAATGACAATCCCAGCCCAAATGCTTCAACTGGGTTTAAA |
| 175051 CTCACTACCGGCAACGCTTATAGAAAATTGGATCAATCCTGACCAATTTA |
| 175101 TCAACTAATTGATGGGACCAAGCAGGGCAAAGGGAAGGATAGTAATGGGT |
| 175151 GGAATAGTGAAGAAAATACGGCAGCAGGGGATGCGCCTCTTGTTTCAACA |
| 175201 AGTGGAGGTGGTTCTTCTGGAACATTTAATAAATACCTCAACACCAAACA |

| The Nucleotide Sequence of the *Mycoplasma genitalium* Genome |
|---|
| 175251 AGCGTTAGAAAGGATCGGCATCTTGTTTGAAAGTAATGGAGAGGCGAGGA |
| 175301 ATGTGGTTAGCCTCCTTCCAACTCTACCAACCCAACAAGGTGAAGGCTTA |
| 175351 CCAAACCACTAACACCTACAACAGGTTAATTGAACCTGACAAGTGACAAT |
| 175401 CAAGTAGTGATTTGAACAATATGACCAACTTGTTAAAACTCCTAACAACT |
| 175451 AAAAACATCAAAGCGAAATTGGGGAAGGACACCCAATCAATGGGAAATAA |
| 175501 TAATGGAGGGGGTGTTAGTCAAACCTTTTCCTTTGTTGTTCCTTATTCAA |
| 175551 TGAATCATACAAATACGGGAACTAGTGGAACCATTAAAACTGCTTATCCA |
| 175601 GTGAAAAAAGATGAAGCTTCCCAAGTAGCGATCAATTCCTTGATCAACGC |
| 175651 TACGCCATTGAATAGTTAAAAACCTGATTTATTTTTATAGAAACAGTTAC |
| 175701 TTTGAAGATTCACTACTAATAATTTAAATTAAGCACTCATACTAATATAT |
| 175751 TAATCCCTTTAGATTGCTTAACTCTTTAAAACTTCCCTTTATAATCAAAT |
| 175801 ATCGCCATGAACGACTGACAGTGACTGAAAAACAGACTTGTTAATTCCAA |
| 175851 AACCAAATCTGTTAGTTTCTGATTACCACAAACCTCAAGTAATATCATTG |
| 175901 ATATTGCTGAATTAATTAAGTGCTGTAGTGAGTAAAAAACACTTCTATT |
| 175951 AATGGTTTAATTGACTTTTTGAACCAACAGGATAAACTTGAATTTAACTT |
| 176001 AACAAGATTAAAGGAGATAGATGTTGAAGATGGTAAGCAACTATTTGGGA |
| 176051 TAGAAACTAGTGTTTATAAACACTTTCAAAATGAAATTGCTCGTTTTTAT |
| 176101 AAACAAGTAAACAAACACTTTCGTGAAACAGGTAGTGAAAGTTTGTTTTT |
| 176151 AGCTTTACCAGTTATTGAAGGGATTAATGAGTTTAACGATATCTTTCGAG |
| 176201 CTCCATTACTTTATGTTGGAGTTAAACTCAAAGTTTCCCCACGCTTTGAA |
| 176251 CGTTTCTGATTAGAAATTAACAAAGAAGAGATCTTTTTAAACCCTACTAT |
| 176301 TATTGGAGTTGAAACCAACAAACGTAATAGTTTGTTTAAAAATAACTATG |
| 176351 ATACTACTAAGATAGATGTTAATGATGCTTTAAAGGTATTTAGTGAACTT |
| 176401 GAATATGAGTTTAGAATGCCTTTAACTTCTGAATTGAAGAGTTTTAGTAA |
| 176451 AAAAGCAAAGAGTGATTTTAATACTGAAAAACGAACTAACTATCTTATTA |
| 176501 ACAACGTTCTTTTGGGGATCTTTGATGTTAAGGGTGATCAGCTGTTCCAA |
| 176551 AACTTTAATGAGATTCTAAACACTGATCCTGATGTATTAGATGAACTTCT |
| 176601 AAAAGATAGAAGAGATCTGTTGTTAGAAAACCGGGAATTCCGTGAACAAT |
| 176651 TTGATTTAAAAGATACCTATCTCTTCAGTCACCTTGATATCTACCAACAG |
| 176701 TATGCAGTTAAGCAAGCTTTACTTGGTGATTTAATTATTGAAGGCCCACC |
| 176751 TGGCACAGGGAAATCTGAAACAATTGTTAATATCTTAGTTAACCTTGTTT |
| 176801 TAAACAACAAAAAAGTATTGTTTGTTTCTGAAAAAGTAACTGCACTTGAT |
| 176851 GTTGTTTACAACCGTCTTGGTAGTTTTAAACACATCGCACTTTTCAACGC |
| 176901 TAGTGTTGCTGCTGAAAAGAAACGCTTTTATAACCAGTTTGCTGAGTTTG |
| 176951 AAACTTATTTCACTACTTACTTTTCCAAGAAAGATTTGGATGCTACTTTA |
| 177001 CCAACATTTGAAGGTAAATGGGTGGATGATATTTTAGGGGCATTTCAAGC |
| 177051 ATTACAAGCTCTTTATGACACCAAGATAAATTCTGGTGAAAATCTGTTTA |
| 177101 GTTTCAAAGAGATTGTCAGTAGCTTTCAGATGTTGGATGCTAGTTACATC |
| 177151 AAGATTAAAGAATATGAACGTTTTGATGAGTGAGTGCGCGTCTTTTCAAA |
| 177201 TCCATTGTGATTAGAAAAACACTTAAGTTACCAAGAGTTGAAAAAAGAAC |
| 177251 TTAGTCAGCGCTGGAATGGTATTGATAATTTCTATCAGTTGCAATCGCTT |
| 177301 CTAAACCAAACCAAAAAACGAAAGGTCTTAAACTATGTGTTGGAACACTT |
| 177351 TGAACAGTTTAATACAGTTATCAGTCCTAAGCATGTTTTGTTCTACAAGC |
| 177401 CTAGCAATAAATCACAATTGCTCTTAAAACAACTGAAACAGGATGTTGAA |
| 177451 CAATACACTAGTTTACAACGTTTCCAATCTCCTACTAAGTTTGAAACAAT |
| 177501 CAAGTTGAATTTCATCAACCAAGTTAATGAAAACCCAACCCCATGGTTCT |
| 177551 TTTCTTGATTTATCCAATTTCATGCCAAGCCACTGTTGGAAAAACTCGTT |
| 177601 AGTTTTGAGTCAAACATTATTAAAACAAAACAAGCTTATCTTAATGGGAT |
| 177651 TGAAAGCTATGTAGCAAGTTGTAAGAAACTGCTTAAAACAACTATTTTAA |
| 177701 ACAACTTTTTTCAGCTTTATCAAACTAATAAAGATGAACTATTGGAGATC |
| 177751 TGCAGACAAGCAAAAAACCCAGTTTTAAAAGAGATTACTTGGTGGTTTAA |
| 177801 AAAACATTTTGAACTCTTAAAAAAAACTCTTTCCAGTGCACATTATGACCC |
| 177851 TTGAGTCTGCAGCAACTCTAACCCCTAACCAACGTGGTTTGTATGACTAT |
| 177901 GTGGTTATTGATGAAGCTAGTCAAGTATTTCTAGAAAGAGCAATTCCTAT |
| 177951 CTTATTTAGAGCTGATAAGTACATTATTGCAGGGGACACTAAACAGTTAA |
| 178001 AACCAGCTAACTTCTTCCAATCACGTGCTGAGTATGATGTTGATGAGGAG |
| 178051 TTTGAAGATGGCAATATAGAAGCTGCTGTTCACTCCAGTTCTCTACTTCA |
| 178101 TTTTTTAAAGAACCGTTCAAGAATCTTAACTTTACTTAAGTTCCACTACC |
| 178151 GCAGTGATTCAGCTGATCTGATTGCTTTTACTAATAACAGGATCTATGAC |
| 178201 AATGAATTAATCTTTATGAATAAAGCTAATGCTGATCAAAGGGTTTTTAT |
| 178251 TGTCCATGATGTAATAGATGGTATCTGAAAAAACAACCGGAATCTCCAAG |
| 178301 AAGCACGTGATGTTGTGCAACGCTTAGAACAACTAACAACAACCAATGAT |
| 178351 TACAAAAAGTCACTTGGTGTAATTTGTTTCAATAAAAACCAAGCAGATCT |
| 178401 AATTGAATATCTAATTGATAAACAAAACAATCCATTACTTAACGAGTGAA |
| 178451 GAGAAAGACAAAATGATGTTGGTAATATGAAGGATTATTTGTGAAAAAC |
| 178501 ATTGAAAATGTGCAGGGTGATGAAAGGGATATCATCATCTTTTCTTTAGG |
| 178551 TTATGATCGTTCAGTAAATAGTTATGGTCCTATTAGTAAGCAAGGTGGAG |
| 178601 AAAACAGACTAAATGTAGCGATAACTAGAGCTAAACAAAGAATAGAACTG |
| 178651 TTTAAGACAAATAGAGGAGAAGACTACAATGGTTTAAGCTCCAGTTCCTT |
| 178701 GGGTAGTAAACTGTTAGTTGAATATCTGCTTTATTGTGAAGCGATGGCTA |
| 178751 AAAACCAGGGTGAGAAAATCACTTTTCAAGCGGTAAAAAGAAAAGAAACA |
| 178801 AAAGCAAAGTATGAACTGGCAGTTGAAAATGATTTCTTCAACCAACTGCA |
| 178851 GGCAATTTTTGGTGGAGAGTTTGAGATTAAACGTAACGTTAATGAAGGGG |
| 178901 CTTACTTTTTCTCATTTGTCTTTTACTTTAATAATATCCCTTATCTTGCC |
| 178951 ATTGACTTTAACATCCCCATTCCCACTTCAAGAAAACAAGTTATGGAAGG |
| 179001 GATTTTATACCGTGAACAGTTTCTCAAAAAACGTCAATGGAACCTAATTA |
| 179051 ACATCTGGATTGATGAGTGAAAATTAAACCCAATTGGGGTGATTTCTAAA |

-continued

| The Nucleotide Sequence of the *Mycoplasma genitalium* Genome |
|---|
| 179101 ATCAGATCAAGTTTAGCAGTGCATCAAAACCAGCATGAAGAAATATAATT |
| 179151 AGATGAAGATAACTTTCATTTCTGGACAAGAAGTGTCGTTAGGCACTTCT |
| 179201 TTTTTATTGTTTTCAAAAAAAATAGTTATGAATGAATTAAACCAACCCTT |
| 179251 ACTTGCTATTATTAAAAATGTTGCTAAAACCAAAAACCTTTCTATAGAAG |
| 179301 AGGTGGTTTTTTGTTTGAAAACAGCTTTAGAACAAGCCTATAAAAAACAC |
| 179351 CTTAACTTTGTTAATGTTGAAGTTAACATTAACTTTGATAAGGGGATTAT |
| 179401 TAATGTTGAACAACTCTTTAATGTTGTTAGTGATGAAAATGAAGATTATG |
| 179451 ATGACTTTCTTGAAATCCCTTTACAAGCAGCTAACAAAATAAACAGTTCA |
| 179501 TTGCAATTAGGTGATGTGTTGCGAAAACCAATCCCCTTAAAAAACATTAG |
| 179551 TAGTGATCTTATCAATAAGATGATTGCTATCTTTAACCAAAAGATTAGTG |
| 179601 AAACAAACTTTAAAGCAGTAATGAGTGAGTTTAGTAGTGAGGTTGGGGAA |
| 179651 GTGATTGAAGCGAAAGTTGAAGATATTGATACTAACAAAGAAGGTGGTTT |
| 179701 AAAGGGTTATATTATTAACCTTGAAACTACAAAGGGTTATATCTCCAAGC |
| 179751 GGGAATTGTCAAAAGGGGAGCGCTTAGAGATAGGTAAAAAATACCTCTTT |
| 179801 GTTATCAAAGAAATCCAACGGCAAGCATCGTTATGACCAATTACTTTATC |
| 179851 AAGAAGTGATACCCGCTTACTACAGTTTTTGTTAACTTCAAATACTCCAG |
| 179901 AAATTGAAAATGGTACGATTGTAATCAAAAAGATTGAACGTTCCCCAGGA |
| 179951 GTGAAATCAAAGATAGCAGTTATCTCCAATGATCCTGCAGTTGACCCAGT |
| 180001 TGCTGCTATCTTAGGACCTAAGGGTGAGAAGATTAGGGGGATTAGTGAGG |
| 180051 AATTTAATGGTGAGATTATTGACATTGTCTTTTGGAATGAAGACAAGTTA |
| 180101 AAGTTCTTAATTAATGCCATTTTACCTGCAGAAGTCATTGGTTATAACAT |
| 180151 CTTGCAGGATGATGAGCGTGATACTAGTATTGAAGTTGTTGTACCTGCAA |
| 180201 ACCAAATTGCTAATGTTTTTGGTTTTAAAGGTGTAAACATTAGGTTAATT |
| 180251 AGTAATTTAACAGGTTGAAATAGTGTTGATGTTTACAGTGAAAAAGATGC |
| 180301 AAGTGAAGCCAACATTAAATTCACGAGGTTAAGCTTTGAACCTGAAGGGT |
| 180351 TGTTTGGCATCAAAAAAAGAAGGGAAAAGATCATTAGTAATGATGCTACT |
| 180401 GATAAAGTCTTTTACACCTCTAAAGACAATGTGATAGATGATGAGATTAT |
| 180451 TGTTGATTTAGCTAAAGATCTAATGGTTGATAATAAACAAAAACAACCTG |
| 180501 AGCAAGTTGCAAAGCAAGTTGTTGAAAAATCACAATTAGAAAAACAAGTT |
| 180551 ACTCCAAAAGAAAAAGAGAAAGTTCAACCAAAAGCTAAGGtTCATTCTAA |
| 180601 TAGCCATTCCAAAAAACCAGCTAAACCTAATCAGATTTTTTCTATCACTG |
| 180651 TTGATGCTAGTGATAAGAATCTTAAAAAAGATCAAGTTGATAATAACCAA |
| 180701 ACAAACCCCCAAACAAAACAAACATTTGATAGCTTTGATGATCTTTAATG |
| 180751 CAACTAATAACAAGACTTTGTTTATTAACAAGAAAACATTTTGTTAAAAG |
| 180801 AGAACTTTTACGTCTTGTAAAATTAGACAACCAACTTGAAATTGATCTTA |
| 180851 ATCAAAATCTCAAGGGCAGGGGTTATTATTTGAGTGTTTTTGGTTTAAAG |
| 180901 CTAGATAAAAAACACCTCAAAGCTGTAGTTGAAAAACACCTTAAGGTTAG |
| 180951 TTGTAATGATGCAAAGCTTACTGCAATGATTACCGCCTTACAACAATTAG |
| 181001 CACAAGATGAAAAAAAAATAGAGCTTTCAATCAGGTTAAAAAAACAAAGTT |
| 181051 TGACGGTAGGATTAAAACCAGTGCCAAACACCAGTTACGTAATGTTAAAA |
| 181101 CCGGGGTTAAAGATGGTGTTTTTATCTATAAAGGTCCTTTAACTGTTAGT |
| 181151 GAGTTTGCAAGTAAAACTAATATCGCTGTTGCTAACATTATCAAACACTT |
| 181201 TTTTTTAAATGGTTTGGCACTAACAGTTAATTCAGTTTTAACAAATGAAC |
| 181251 AGTTAGCAGATGCATGTGTTAACTTTGGGTTTGACTTTAAGATGGAAACT |
| 181301 GAAGTTACCCATGAAAATATTGTAGCTAACATCCAGTTTGAAGATAGTGA |
| 181351 TGATTTATTGCAACCAAGACCACCTATTGTTACTATCATGGGTCATGTTG |
| 181401 ACCATGGTAAAACTTCGCTTTTAGACACAATTAGAAAAACTAATGTAACT |
| 181451 GCTAAGGAGTTTGGCGGAATTACCCAAAAAATTGGTGCTTATCAGGTGAA |
| 181501 AAATCACCAAAATAAAACGATTACTTTTATTGATACTCCTGGGCATGAAG |
| 181551 CATTTACTTTAATGCGTGCAAGGGGTGCAAAAGTAACTGATATTGTGGTG |
| 181601 TTGGTTGTGGCAGCGGATGATGGGATTAAAAAGCAAACAGAGGAAGCAAT |
| 181651 TAGCCATGCTAAGAGTGCTAACACTCCTATCATTGTTTTTATTAACAAGA |
| 181701 TGGATAAACCAACTGCTAACCCTGATCTGGTGATCCAACAACTCAATAAG |
| 181751 TTTGATTTAGTTCCTGAGGCTTGGGGTGGGAAAACTATCTTTGTAATGGG |
| 181801 TAGTGCTTTAACTGGTCAAGGGATTAATGAGTTGCTTGATAATATCTTGT |
| 181851 TGCTAGGGGAAGTGGAGGGTTATCAAGCTAACTATAATGCCCATTCATCT |
| 181901 GGTTATGCAATTGAAGTACAAACTTCAAAGGGACTTGGCCCTATTGCCAA |
| 181951 TGTCATTGTAAAAAGGGGTACTTTAAAGTTAGGTGACATTGTGGTGTTAG |
| 182001 GGCCTGCATATGGAAGAGTTAGAACGATGCATGATGAAAATGGTAATAGC |
| 182051 TTAAAACAAGCAACCCCTTCAAAACCTGTGCAGATCTCAGGGTTTGACAT |
| 182101 TATGCCTGTTGCTGGGGAAAAGTTCATTGTTTTTGATGATGAGAAGGATG |
| 182151 CAAAGTTAATTGCTAACAAGTTTAAAGAACaACAAAAACAAAAAGCTAAC |
| 182201 AACTTAACAGTTAATCAAACCTTAAAAGAACAGATTAAAAACAAGGAAAT |
| 182251 TAAGATATTAAATTTGATCTTTAAAGCAGATAGTGATGGTTCATTGCAAG |
| 182301 CTATTAAACAAGCAGTTGAAAACATTAATGTTGCTAAGATCTCACTTAGT |
| 182351 ATCATCCATGCTGCAGTGGGGCAGATATCAGAGAGTGATATTATGCTAGC |
| 182401 AAAAGCATCAGGGGCTTTATTGTTTAGTTTAAACTTAGGTTTGAGTCAAA |
| 182451 CTGTAAAAAACATTGCTAGTTTACAAGGGGTAAAATTAGAAGTTCACTAC |
| 182501 CATATCCCTAAACTAGCAGAGGAGATTGAAAACATCTTAAAAGGTCAATT |
| 182551 AGATCCTGTTTATGAAGAGATTGAAATAGGTAAAGCGGAAGTTTTACAAC |
| 182601 TCTGGTTCCACTCTAAAATCGGTAATATTGCAGGAACCATTGTTAAATCA |
| 182651 GGAAAGATAAAAAGAGGGAATTTATGTAAGTTATTCAGAGATAAAGAGAT |
| 182701 TATCTTTGAAGGCAGAATTGACTCTTTAAAAAATGAAAAAACGCCTGTTA |
| 182751 ATTTAATAGAAACAGGGAAGAATTGTGGGATAGTTATTAATGGTTGCAAT |
| 182801 GATATTAAGATTGGTGATATCATTGTTGCTTATGAAAAGCAGATAGTTAA |
| 182851 AGATGGCAAGCTATAGAAAACAACGGATTGAAAATGATATCATCCGCTTA |
| 182901 ATTAATCGCACGATTATTAATGAGATCTATGATCCTGTTGTTAAGTTAGG |

-continued

The Nucleotide Sequence of the *Mycoplasma genitalium* Genome

```
182951 TCATGTTAGCCATGTGAAGTTATCAGCTGATTTTTTTCATGCAGTAGTTT
183001 ATCTTGATTGTTATGATCGTAGTCAGATTCAAACTGTAGTTAATGCTTTT
183051 AAAAAGGCTCAGGGCGTTTTTAGTCAAATGTTAGCACAAAATTTGTACCT
183101 AGCTAAAAGTGTAAAACTCCACTTTGTGAAGGATGATGCAATTGACAATG
183151 CTTTGAAAATAGAACAGATAATTAACTCTTTGAAAAACTAACAGCTTGAA
183201 GTAAAATTAATCCTAATGGACCCACAAAACAAGTCCCCAAAACCACAAGT
183251 TAAATCAACTAGATTGGTTGTCAAAAAACAACCAGCAGGTGTTGTTTTTC
183301 CCAAATTGAGTATTCCTGTTAATGATTTTGAAAAAACAGTTACTTTAACA
183351 AGAGCACAAAAAAAGGAAGCTAAACTTCTCAAAAAAGCCCAAAGGAAAGC
183401 TAATAAGCTTAATAATAAACAAGATAGTACCTTTTTCAATTCTGCTTCAG
183451 GTGAGACTAATAACACCATTCTTCCTCCTGGTGTTAAAAATCAAGCTGAT
183501 AATAAAACTAACCGTTTTAGTAAATTTATTAGTTTTTTCACTTCTTCAAA
183551 AAACAAACAACCAGATGAAATAACAGAAAGGTTAGTTGATGATCCTACTG
183601 TTAAAAACCGTTTTAGTGCTTTTAATAAGAAGCTTATTTGAGTtCTAAAG
183651 GATAAAAAACTAAGAGCAAGAGCGTGGAAGATTGTtGGTTATACCAATTT
183701 AGTTATTGTGGCATTTTTTGCTGGACTTTTAGCAGTGATGAATAAGTTCA
183751 TCACCCTTTCCTCAGTTGAATATCCTGCTATTGCTTTACAACTCCCTATT
183801 AACAATGCATTATGAGGGATTTCTATCTTTGTTATTAGCATTGTTACTTT
183851 ACCGTTTTGAACAATGTTTATCTTGTTTTTAATGGGAGTAAAGGATGTGA
183901 GAACTTCGCGTTCTATCCATTATTTTATCTGGATAGTGTTAATTATTAAT
183951 GTAGTTTTATTACTAGTTAGTTGCTTGTTGATGATTGCTGCTTATGCCCA
184001 TCTTGATGGTTATAACATCTGAAGAAACTTAGAATCACTTAACCCTAATA
184051 ACTAATGAAATCACTCTTTATTGGTTATTTTGATGGATTACATCAAGGTC
184101 ATCTATTTTTAAAGCAGAACAGTAAGTTTGAACCAATGGTGTTATTAATT
184151 GATAACCCACCTTTAAAACAAACCAACTGGCTTTATGATTTACAACAACG
184201 GGTTGCACAAATAAAAACTTACTTGAAAGCAACTGTAGAAGTATTTGATG
184251 TTGCCAAACATAACATGAATGCACTTAGTTTTTTTGAACAACAGATTAAA
184301 AGATTGAATTGTGATGAAATTATTGTTGGTACAGATTGGCATTTTGGTAA
184351 TGATCATAAGGATGGGATCTGGTTAAAGAAACTGTTTAAAAATACTGTTA
184401 TTGTTAATAAAACAAACCTATCAAGTAGTGTTATCCGTAACTATCTAACT
184451 AATAATGAACTTGAAAAAGCTAACCAACTTTTAGTGGAACCTTATTATAG
184501 AGTGGGCACAGTAGTACATGGTTTAAAAAAGGCAAGGTTGCTTGGTTTTC
184551 CAACTGCTAACATTGTTATGGATAACCACTTATTGACTTTAAATAAGGGG
184601 AGTTATATAGTAAGAGTTTTATTAAATAACCAAACTTTTTATGGGATTGG
184651 TTTTATTAGCCAAAAGGATCAGGATTTGGTGTGTGAAACCCATATCTTTA
184701 ACTTTAATAATGAGATTTATGGTTCACTGGTCAAATTTACACTGTTAAAG
184751 TTCATTAGAACAATTAGTAAGTTTTCCAGTCAAGCAGCTTTGCAAAAAGC
184801 AATTCAAAGTGATGCTAACTTTGCTTTAAAGTGGTTGGAAAACCAAAATT
184851 TAGATAAAATTTAAAATCATCCAAATATGGACAGTGCCCCCAGTGGTTTA
184901 ACTTTAACTGTTATTATCCTTAGCATCATTCTGCTTGCTTTTATCAGCAC
184951 AGTTGTATCAGCTTATGAAACAGCAATCACTTCTTTAAcCCCTTACAGGT
185001 GAAAGAACTATATCAAGACTAACAACAAGCAAGATAAACTATCAACTAAG
185051 ATAATAAACCACTTTCAAAACCACTATTCAAGTTGTTTAATTACTATCCT
185101 AATTACTAACAACATAGTGGCCATTATGGTTTCTAACATCCTTTTTTTAG
185151 CACTAGAACAAACAATTAAAAATGAGCTTTTATCAAGTGTTTTAAATTTG
185201 GTAGTTAGTGGGGTTTTAATCGTCTCTTTTTGTGAAATTCTACCCAAAAC
185251 TTTGGGCAGAATTAATGTGATTAGAACCCTGGTTCTATTTGCTTATTTGG
185301 TTTATTTTTTTTATCTGATCTTTTGACCAATTACTAAGCTAACCAGTTTA
185351 ATTCTCAAAAAGTATGAAAACCCCTTACCTGTTTCAAGGAAAGATGTTTA
185401 TTATTTTATTGATGAAATTGAACAAAACGGTTTATTTTCCAAAGAAGATA
185451 GTTTACTGATTAAAAAAACCTTAATCTTTGACCAAGTACTAGTTAAAAAG
185501 GTAATGATCAAGTGAAAAAAAGTGGCTTATTGTTATCTTAATGACAGTAT
185551 TAACTTGATTGCCAAGCAGTTTTTACAAAGGCAGTTTTCCAGAATGCCAG
185601 TAGTAGATAAAACTACTAATAAGATAGTTGGTTTTATCCATTTAAAGGAT
185651 TTTTTTACAGCTAAAGAAGCAAACCCTAAGTCACTTGATTTAAACAGTT
185701 GCTTTATCCAGTTGTTTTAGTTCAAGATTCCACCCCCATCAAACAAGCAC
185751 TAAGACAGATGCGTTTAAACAGAGCACATTTAGCAGTTGTTAATGATAAA
185801 CATGAAAAAACAATAGGGATTGTTCTATGGAGGATATTATTGAAGAGTT
185851 GGTGGGTGAAATCTATGATGAACATGATGATATCCAACCGATCCAAGTAT
185901 TGGATGAAAATGTTTGACTTGTTTTACCTAATGTAAAAGCAGCCTACTTT
185951 TTTAATAAGTGAATTAAGCCAGATTTGGTAAAATCAAAAAATATTACTAT
186001 CCAGCATTATCTCGCTTCACTAGATAATGATAGTTTTGCTTGCCAAAATA
186051 AGCTTGACACTCCCTTATTTAGTGTTGAAGTGATAGCTGATAGCGAAGAT
186101 AAAACCAAAATTCTTTACGAAATTAGAAAGAAGAGTGATGTTATTGCTTA
186151 GAGCATTATTTTTAGAGTTGAAAACCAACAAAAATTGTAAAGCTTTACTT
186201 TTGTTATTAATCCCCTTACTAGTTGGTTTAACCTTGATAATCTATGGGAT
186251 TGTCTTATTTTCCACTGAAGGGGTAATTGACCATGGTGATCATAACCACT
186301 TAAGAGCAAGGTTTCAACTCACTTTAGAGGAGATTATTGTTTTTGTTGTT
186351 GGTAGTATTATCTTGTTTTTTACTTTAGCTAGCTTTTGTGTGAGTTGCTT
186401 TATGTTAATGAGAAGTCCTAAGCAAAAACAGCTAGAGGTTGATCATGCTA
186451 ATAAAACTAATTTAAAACCAAAAGCAATAGTTAATTGTGATCTTTTTCAG
186501 TTGGGTGATTACTGTGTGTTTACATTTAAAAAACTTAGCTTTAAACAACG
186551 GTTTAAGCAAGATTTTTTTGCTAGAAGTAAGTTTTCGTTTCGCAGTGAAC
186601 TGTATCGTCTTTGTTTGGTGGGAGTGTTAATTGCTCTCAATTTAGCGTTA
186651 AGTTTGATTGAAATTCCTGGGATAGTTTTACCTTGGGGTAGTTCGATCCA
186701 ATTCCGTTTTTTTAATACGGCTATCTTGTTTATTGCTGTTAGGTTGGTGG
186751 GATTATTATCTACTTCTTTAGTGGCTTTAATCACCCCCTGATTACACCTG
```

-continued

| The Nucleotide Sequence of the *Mycoplasma genitalium* Genome |
|---|
| 186801 TTAATCCATCCTATTCACACCCCCATTAGTAGTTTGTTTTACATGGTTAA |
| 186851 TGACTTTTTGGTGCTGTGGATCTTTTATTTCTTTTTTTTCCATCTCTTTA |
| 186901 AAGCAGAGGTGAACCAAACTACTACTGTAGTTGACAACAAACCTTTTAGT |
| 186951 CAGTTAGTTAATACTAAAAAGACGAAGTGAACAAAGTTTTTTTCCTTACT |
| 187001 TGTAATTAGCTTTTTGTGTGGCTTTATTGAGGGGTTAGGTTTTTACTTTG |
| 187051 GTTATTTTTAATCCTTGGTAATGTTTCTAGTTTAGGATTGAAGATCTAT |
| 187101 TATGATGGGTTACAACAACGTGATCTGATTAACAGTAGTAATGTTTTGTT |
| 187151 CTTTTTAATGACAACAACTGCTATCTTCAGTATTAAATACATCTTTGAGA |
| 187201 TGTTATTTTCTTTAGTGTTGAAAAGAATGTAGTTAATATTGCTAACCAC |
| 187251 TTTGGTTTGTATTAATCTAAACTTTTTGCAACTAATTAATTAGTTAACTA |
| 187301 ATAATGAAGTATGTAAAAGTACAGATCATCAATAAATCAACTATTGAACT |
| 187351 GTTAGAGGATGCTAAAAAAGGGGAAAAAATTAATTTAGATTTAATTAACC |
| 187401 AAGTTGATCAGACCAACATCCTCAATACGATCACTACTAACCAAAAATTA |
| 187451 GCATGAGAAAAGGAGTTAAGTGCTCAATTTATCAATCAGCAGAATGAGTT |
| 187501 AATTAAAAACTTTGAAATTGAGATCATTAAGTTAAAAACTATGCTTAATG |
| 187551 ACAAAGAGCAAGCATTGTTGTTAAAAACCAAATTAGAATTACAAAACCAG |
| 187601 TTTCAAAAGCAGATAGAGAACTATATCAATGAGATTAACAAGCTCAAGTT |
| 187651 AACCAATAAAGAGCTTGAAATTACTAACCAAAAACAACTAGAAAGCTCAC |
| 187701 TTAAACTACAGCGAAACGAATTTGAAGAGAAAATCAACCAGCAAAACTTA |
| 187751 ACGATTGAAAAACTGAAAATTCAACAAGCAAGAAGTAGTATCTGAGCAGT |
| 187801 TGCTAAAAAAGGGAATGAACTTGAAAAGTGGTGTGAAAACCAGTATGAGT |
| 187851 CTTATGCAGATAGCTTTGAAAACTGTCAGTTTACTAGGTATAAAACTGAA |
| 187901 ATTAACTTATTAGATGAAAATGATTTTCCTAATGAAAAAGCAGATTACAT |
| 187951 CTTTAGTTTCTTTGGTGAAAAAACCAATAAAATTCCGTTTTTATCAATTT |
| 188001 GCTGTGAGATGAAAAGTGAGTTTAATGATAGTAAGCATAAATCAAAAAAC |
| 188051 AAAGATCATATTAGCAAACTGGTCAGGGATGCTAAACGTGCTAACTGCAA |
| 188101 GTATGCTTTTTTAATTAGTGAACTTGAACTGGAGACTGAAAATGACATCC |
| 188151 AAGTGCGCTTAATGCCAACATTGGAAAGTGGTGTTGAAGTCTATCAGTT |
| 188201 AGACCAATGTTTTTATCTTAATGCTTAAACTTTTCTATAAGTTAGCTAA |
| 188251 GAAGTTGTTTGCCCTTAACCGTTTTCAATCAGTTGAACTAATTGATAAAA |
| 188301 ATAAGTTAAATGAACAGTTTAAACAGTTGAAAGATAATTTTTTAACCAAA |
| 188351 ACCTTTTTAGAGATTGAAAAAGTGTGTAAAAGTAACTTAGTTGATATTGA |
| 188401 AACACTTGAAAAAGCAGTGGTGAAACTAAGGGTTAGAAACGAACGCGTTT |
| 188451 TAGATCAGTTACTTAATAAATGAACTAAGAaAATTGATAGCTTTGATTTA |
| 188501 CAGTTAACTAAGAaAATTACTAATAACTACTAGGGTTTAATTTGTTAGCT |
| 188551 TATTTAGAAAAATTCAAAATAAGCAAATTATAATTaGGTGTCTTTCTTTA |
| 188601 CTAAAAATATGAAATTATACCGATCTTTAAAAGCAGCCCTGTTACCAGGG |
| 188651 ATATGCACTAGCATTTTACTTGCTAGTTGTGCTTCAACAAATACTTATCA |
| 188701 AGACCAAAGGAATGCCTTGATTAGTTTGGCTTCTAATCGTGATACTTTAA |
| 188751 TTGCGAATGCTAAAAAATCCAAAGAAGAAGTGCAAAAAGAAGTTACCAAA |
| 188801 ATGAATAGTAGTACTTCATCAATGATGACAGCTACCCAAAGTGTTGCAAT |
| 188851 TACAACACATCAAACTACTGAAAAAACAAATAATTCTAAGTATGATCTAG |
| 188901 ACAAGCTTTTTAAGGATTACATCCTTTATGTTGTTGATAATTTTTCAGGA |
| 188951 CTTGTTTTTAAAAGAACTGGCGGTCATAGGATCCAGTTAATCGATAAGGA |
| 189001 TAAAGAGATTTTGGATGGTGGTAATCTAACTAAACATACCCACCACGATC |
| 189051 ATAACCATATGCATAATCATGAACATGAACATGAAGAACACCATGATGG |
| 189101 GAAGAGACAGAAGTAGTTGGCAGAGCACTATCTTTTACTAATGGCATCTT |
| 189151 TCTAGTGATTGACTATAAAAAAGACTCTGAAAGAAAAAATATGAGTGGTT |
| 189201 CAACTACTATGATGCACCAACACCACCATGAAGCTGAAGAACATAAAGAG |
| 189251 GAACGTAAGCTCTCTTTAAACTTAAAAGCATACAAATTTAATACCCCTTT |
| 189301 TAACATTAGTGAGTTTATTAGTGCTTGACATCATAAAGAATCTCATAATA |
| 189351 GTGACACAGAGTTCAATAACCTTCACAATAAGTATGACAAGGAAGAATTG |
| 189401 GATATTATTGACTATAACTTTGAAGAAAAGCTGTTGATGAAACAATTGC |
| 189451 TTAACTAAAAAAGATAGTTATTAACTTAATTTAGAATTAACTAATGACAG |
| 189501 TGTACACTTACACTGTTTTTTATTTAATTGAGAAAATATTGGGTTGATG |
| 189551 GAACAACAAAACCCTGATCGTTTAAAAAAAGATAGGGAACTTATTTATGC |
| 189601 AATTGTTACAGCTAAAGGTATCATTAGCCGTTTCTTTTGATCAATCCTTA |
| 189651 GTTTTTTAATTACTAACCTTATCTTCTTTTTTGCAGCTTTTGTAGCGCTC |
| 189701 TTAATTTATCTGTTAGCAAGTGTTGATAATCAGTTTGCATTTGTTTTTAT |
| 189751 TGCTGCAATTATCTTCATTATTTTTTACAACATCTTCTTTTTAAGTTACC |
| 189801 TGTTGTTTATCTATTTTAAGGGCCAGAAAGCAATTGAAAACAACTGTAAG |
| 189851 TACCTGTTAACAATCCTTGATATTAAGAGTGATGAACTGTTACCTTTTTC |
| 189901 GCTTTTAGGTAGTTTAAGAAAAGGTTATATGCTAGATGAAATGCTCTTAG |
| 189951 AACAGTAAATATTTGCTACAATCATAACGCTTTAGTTTTTAGTTGATACA |
| 190001 CCAAAATCCGTAGTCAATTTATTAACTAACTAGTGAACTAGATTTTGATG |
| 190051 AATAGCGCTGTAAAATATCCTGAGCTGAAGATCAAACTTGAGTCTTATGA |
| 190101 TAGCACCCTTTTAGATCTCACTATTAAAAAGATAGTTGAGGTTGTAAAGG |
| 190151 GTGTGAACATTAAGATTAAAGGTCCTTTACCTTTGCCTACTAAAAAGGAA |
| 190201 GTGATCACCATTATCCGCTCTCCCCATGTTGATAAAGCATCCAGAGAGCA |
| 190251 GTTTGAAAAAAATACCCACAAGCGCTTAATGATTCTTGTTGATGTTAATC |
| 190301 AAGGAGGGATTGATAGTTTAAAAAAGATTAAGATCCCAGTTGGGGTTACA |
| 190351 CTGCGTTTTTCAAAATAGGTTATGGATGTAAGGGGAATATTTGGTGTTAA |
| 190401 AGTAGGGATGAGTCAGATCTTTACTGAGCAAAATGAGTGCTTACCTATCA |
| 190451 CCATTGTTTATTGTGAAGCTAATCAGGTGGCTGGGATTAAAACGATTGCT |
| 190501 AAAGATAATTACAACGCCACTCTATTAAGCTTTCAAACTGTTGATGAAAA |
| 190551 ACAACTTAACAAACCTAAACAAGGGTTCTTTTCCAAACTTAAACTAGAAC |
| 190601 CTCATAAATATCTGAGGGAAATCAGAAAGATGCAAGGGTTTGAGTTAGGT |

-continued

The Nucleotide Sequence of the *Mycoplasma genitalium* Genome

```
190651 AAGAAGATCACCCCCCAGGAGTTGTTTAAGATAGGTGAATATGTTGATGT
190701 CACTTCACTCACCAAAGGTAGGGGTTTTACAGGAGCGATTAAAAGGTGAA
190751 ACTTTAAGATAGGTCCTTTGGGTCATGGGGCGGGTTATCCCCACCGCTTT
190801 CAGGGTTCTGTGCAAGCAGGTAGAGGTGGTAGTAGTGCGCAGCGTGTTTT
190851 TAAGGGTAAGAAGATGTCTGGGCATTATGGTCATGAACAAGTTACGATCC
190901 AAAACCTCTTTATTGTTGGCTTTGATGAAATCAATAAGTTAGTGTTAGTT
190951 TCAGGCGCAATTGCTGGTCCTGAGGGTGGGATTGTTTTAATTAAAACTGC
191001 AAAAAAGAAAACTGGCAAGATAAAAGATATAAAGTTAGCAGTACAAACTG
191051 TTAAAGCCCCACAACTAAAAGCACCAAAAAAGCAGAAAACTAAGGTTGAA
191101 ACCAACCAGGTTAACCCAAAAATTGAAGAAGAGAAAACTAAGTAATGGCT
191151 AAACTTAAAGTAATCCAGTTTGATGGTAGTTTTAAAGGTGAGATCCAACC
191201 TGCTAACCACCTCCTTTTAAAAAAAGCAGTGATCCAACCAGTGTTTGATG
191251 CTATCTTATTAGAACAAGCAGCATGTAGACAAGGCACTCACTCTACTTTA
191301 ACTAAGGGTGAAGTTAGTGGTGGGGGTAAAAAACCATATAAACAAAAGCA
191351 CACTGGTAAAGCTAGACAGGGTTCAATAAGAAACCCCCATTATGTGGGGG
191401 GTGGTGTTGTTTTTGGTCCTAAACCCAACCGTAACTACAAACTAAAACTA
191451 AACAAAAAGGCTTATCAACTTGCTTTAACTAGTGCCTTTGCACAAAAGCT
191501 TAACAACAACCAAGTGATAGTTGCTGAAGCCAAGTTGTTTGAACAAACCA
191551 ATGCCAAAACTAAAAAGATGCTGACGTTTCTCAAGAATGCCAAACTAACT
191601 GAGCAAAAACTCTTGTTTGTGATTGATACTATCTCAAAACCACTGTTGTT
191651 GAGTACTAACAACCTAAAGCAGATAGTAGTCAAACAGTTTAATAAAGTAT
191701 CAGTAAGAGATCTACTTTTAGCTAAAACTATCATCATTGAAAAAGCTGCT
191751 TTTACAAAACTGGAGGAACGACTTAAATAGGCTATGGATGTAACCAACAT
191801 ACTCTTAAAACCAGTCTTAACTGAAAAGAGTTATCTCAACCAGATGGGGG
191851 AATTGAAAAAATATGTCTTTGCAATTAACCCTAAAGCTACTAAAACCAAA
191901 GTAAAACTAGCGTTTGAAATTATCTATGGGGTTAAACCTTTAAAGATTAA
191951 CACGCTAATTAGAAAACCAGTGACCATTAGAAATGGCACTAAATACCCTG
192001 GGTTTAGTAAGCTAGCAAAACTAGCAGTAATCACCTTACCTAAGGGAATG
192051 GATATTGCCATTACTGGTGAGAAAACAACCAAGAAAGAAACAAAGGATCA
192101 ATAATGGCAATTAAAAAGATTATTAGTCGTTCTAACAGTGGGATTCACAA
192151 CGCCACTGTCATTGACTTTAAAAAAACTCCTTACCAATTCCAAACCCGAAA
192201 AGTCGCTTTTAGTTACTTTAAAAAAAACATGCAGGAAGAAACAACCAGGGC
192251 AAGATCACTGTTCGCCACCACGGTGGGAGACATAAACGTAAGTACCGTTT
192301 AATTGATTTTAAGCGTTACCACTATGACAATTTAAAAGCAACTGTTAAAT
192351 CGATTGAATATGATCCTAACCGCAGTTGTTTTATCTCCCTTTTACACTAT
192401 CAGAATGGGGTTAAAACTTACATCATTAGtCCTGATGGGATTAAGGTTGG
192451 TGATCAAGTTTATTCATCTGATCATGCCATTGATATCAAACTAGGTTATT
192501 GTATGCCCCTTGCTTTTATCCCTGAAGGAACCCAAGTTCATAACATTGAA
192551 CTTAACCCTAAGGGTGGGGGTAAGATAGCAAGAAGTGCTGGAAGTTATGC
192601 GAGGATCTTGGGTCAAGATGAGACTGGTAAATACATCATTCTCCAGTTAA
192651 TCTCAGGGGAAACTAGGAAGTTTTTAAAGGAGTGTAGAGCTACAGTTGGT
192701 GTTGTCTCTAACTTAGATCATAACCTTGTTGTAATTGGTAAAGCAGGGAG
192751 AAGTCGTCATAAGGGAATCAGACCAACGGTTAGAGGTTCAGCAATGAACC
192801 CTAATGACCACCCGCATGGGGTGGGGAAGGGAGAAGCCCAGTTGGCAGA
192851 GATGCACCAAGAACCCCTTGGGGCAAACGCCATATGGGTGTGAAAACACG
192901 TAACATGAAAAAACATTCAACTAACCTGATTATTAGAAACAGAAAAGGAG
192951 AACAATACTAATGTCAAGAAGTAGTAAAAAGGGCGCATTTGTTGATGCTC
193001 ACCTCTTAAAAAAAGTGATTGAAATGAACAAACAAGCCAAGAAAAAACCA
193051 ATTAAGACTTGGTCAAGAAGAAGTACTATCTTCCCTGAGTTTGTGGGTAA
193101 CACCTTCAGTGTGCATAACGGTAAAACCTTTATTAATGTTTATGTTACTG
193151 ATGATATGGTAGGTCATAAGTTGGGTGAGTTTTCCCCAACTAGAAACTTT
193201 AAACAACACACTGCTAACCGTTAGTTATGATTGCTTTTGCTAAACAATAC
193251 AGAGTTCACATCTCCCCCCAAAAAGCACGGTTAGTGTGCCAGTTAATTGT
193301 GGGTAAGAAGATTAATGATGCGCAAAACATCCTTTTAAATACGCCAAAGA
193351 AAGCTGCTTACTTTTTAACTAAGTTACTAAATAGTGCGATTAGTAATGCC
193401 ACTAATAACCACGGGATGAGCGGGGATCTTTTGTATGTATTTGAATGTGT
193451 TGCTAACCAAGGACCTAGCATGAAAAGAACAATCGCTAGAGCCAAAGGTT
193501 CAGGGAGTGTTTTAACCAAGCGTTCTTCAAACCTAGTTATTAAGTTATCT
193551 GATAATCCCAATGAAAGAAAATTACTCTTAACCCAACAAAAGGAACTGGT
193601 GAAAAAAAGAACAATGGGTCATAAAAAAGAGAAAGCAAAGCAAAAGCAAA
193651 AACAACAATAACTATGGGACAAAAAGTAAATTCAAACGGCTTAAGGTTTG
193701 GCATTAATAAGAACTGGATCTCACGGTGAACTGCCAGTTCCAACCAACAA
193751 ACAGCAACCTGATTAGTACAAGATGAGAAGATCCGTAACCTCTTTTTTAT
193801 CAACTATCGCAACGCTCAGGTGTCTAATGTTGAGATAGAAAGAACCCAAA
193851 CGACTGTTGATGTTTATGTCTATGCAGCTCAACCTGCTTTATTGATAGGC
193901 AGTGAAAACAAAAACATCCAAAAGATTACCAAAATGATCCAAATCATTGT
193951 GGGCAGAAAGATTAAACTTGATCTTACTATCAATGAGATCGGCTCTCCGA
194001 TGTTATCAAGTAGGATCATTGCCCGTGATATTGCTAATGCGATTGAAAAC
194051 AGAGTACCACTCCGTTCAGCAATGCGCCAAGCTCTAACCAAGGTTTTAAA
194101 AGCAGGTGCTAATGGGATTAAGGTATTGGTATCAGGCAGATTAAATGGGG
194151 CGGAAATTGCCCGTGACAAGATGTATATTGAGGGCAATATGCCTCTTTCA
194201 ACTTTAAGAGCAGATATTGACTATGCCTTTGAAAAAGCAAAAACCACCTA
194251 TGGCATTATTGGGGTGAAAGTATGGATTAACAGGGGATGATCTATGCaA
194301 AGGGTTTAAACAGAACCCCAGCACACATCCTCCATCCCCAAAAGAAACAG
194351 CTAAAAACCCCAACTATCAAAAAAACCAATTCAGTAATAGCAAAACAAAA
194401 ACTCACTGGTAGTGATATTGAAACTGCTAGTTTAAAAGCACTTACTGATA
194451 ATAATCAAAACCACGAATAGTTAAGATGTTACAACCAAAAAGAACCAAAT
```

The Nucleotide Sequence of the *Mycoplasma genitalium* Genome

```
194501  ACAGAAAACCACATAACGTCAGTTATGAAGGACACACTAAGGGCAATGGT
194551  TATGTTGCTTTTGGTGAGTATGGAATTGTTGCTACTAAGGGTAATTGGAT
194601  CGATGCGAGAGCAATTGAATCAGCGCGGGTTGCTATCTCAAAGTGCTTGG
194651  GTAAAACTGGAAAGATGTGAATCAGGATCTTCCCCCACATGTCAAAAACC
194701  AAAAAACCCTTAGAAGTGAGGATGGGTTCAGGGAAAGGTAACCCTGAATT
194751  TTGGGTTGCTGTTGTTAAAAAGGGGACAGTGATGTTTGAAGTTGCTAACA
194801  TCCCTGAACAACAGATGATCAAAGCCTTAACAAGAGCAGGCCATAAACTC
194851  CCTGTTACCTGAAAACTAATGAAAAGAGAGGAGAACAGTTAATGACAATC
194901  GCTAAGGAGCTGAAGCAAAAGAGCAACGAAGAGTTAGTGAAACTAGTAAT
194951  TAAGCTTAAGGGTGAACTCTTAGAATACCGCTTTAAACTTGCCCATGGTG
195001  AACTTGACAAACCCCATCTGATTGCCAAGGTGAGAAAGTTATTAGCAGTT
195051  GTACTTACTATTCTCACTGAACGCAAACTCAACTGACAAGTTGAAAAAGA
195101  TAAGTACAAGTTACTTTCAAGAAAAACCAATGAACTTATTGTTAACAGTT
195151  GAAAGCAAAAACTATCAACTAAACCTGAATCCAAACAAGAAACTAAAAAG
195201  GCTGAAGTTAAACCTAAGGTTGAATCAAAGCCTGAATCCAAACAAGAAAC
195251  TAAAAAGGCTGAAGTTAAACCTTTAAAACAAGAAACTAAAAAAGTTGAAG
195301  TTAAACCTAAAGTTGAACCAAAACCTTTAAAACAAGAAACTAAAAAGGTT
195351  GAAGCTAGGATTGAAACTAAGACTAAAGTTGAATCAAAACCTTTAAAACA
195401  AGAAGTTAAAAAGGTTGAAGCTAAAAAATCTGTTTCAAAACCCCAAAAAC
195451  CAGTTAAAGCCAAAATGATTAAAACAAAGGAGAAAAAACAATAATGAAGC
195501  GCAACCAACGTAAGCAGTTAATTGGCACAGTTGTTAGCACCAAAAATGCT
195551  AAAACAGCAACTGTCAAAGTAACATCACGCTTTAAACATCCTTTGTATCA
195601  CAAATCAGTTATTCGCCATAAAAAGTACCATGTCCATAACTTTGGTGAAC
195651  TTGTTGCTAATGATGGTGATAGGGTACAAATTATTGAAACAAGACCCCTT
195701  TCCGCTTTAAAGCGGTGAAGGATTGTCAAATCATTGAAAGAGCAAAATA
195751  GTTTATGGTTAGTTTTTATGACAAGATTAAATGTAGCTGATAATACAGGCG
195801  CTAAGCAAGTAGGTATTATCAAAGTTTTAGGTGCTACATACAAACGTTAT
195851  GCATTCCTTGGTGATGTTGTTGTTGTATCAGTTAAAGATGCAATCCCTAA
195901  TGGCATGGTTAAAAAGGGTCAAGTGTTAAGAGCAGTCATTGTTAGAACCA
195951  AAAAGGGACAACAACGCCAAGATGGTACCCACCTAAAGTTCCATGACAAT
196001  GCTTGTGTGCTTATCAAAGAAGATAAATCCCCAAGGGGAACAAGAATCTT
196051  TGGACCAGTTGCTAGAGAGTTGAGAGAAAAAGGTTACAACAAGATTTTAA
196101  GCTTGGCGGTGGAGGTTGTTTAATGCAAAGGATTAGAAAAGGTGATAAGG
196151  TAGTTGTGATCACTGGTAAAAACAAGGGTGGTAGTGGGATAGTGCTTAAG
196201  GTATTAACCAAGCAAAACAAAGCGATTGTTGAGGGGATCAATAAGGTTAC
196251  TGTTCACAAAAAAGAACAAGTCAACAAGCGCAGCAAACAAACAAACCCAA
196301  CTACTAAAGAAGCCCCTTTACCATTAAATAAACTTGCTTTATTTGATCAG
196351  AAGGCCAAACAGCAAACAATTGGCAAGATCAAATACCAAATTGATCCTAA
196401  AACCAAACAAAAAACAAGAGTCTTTAAGAAGACTAATAATGCCATTTAAC
196451  TGTTATGAATAACCTTGAAAAAACCTATAAACTGAGTTAGTTAATCAAC
196501  TCCAACAACAGTTGGGCTTTTCTTCCATTATGCAAGTCCCTAAGTTAACA
196551  AAAATCGTTGTTAACATGGGAGTTGGGGATGCAATTAGAGACAACAAGTT
196601  CCTTGAATCAGCACTAAATGAACTGCACCTGATTACTGGTCAAAAACCCG
196651  TTGCTACTAAAGCTAAGAATGCTATCTCAACTTACAAGTTACGTGCTGGC
196701  CAATTAATTGGTTGTAAAGTTACTCTAAGAAATAAAAAGATGTGATCCTT
196751  TCTGGAAAAATTAATCTATATTGCTCTGCCCAGAGTAAGGGACTTTCGCG
196801  GTTTATCACTGCGCTCTTTTGATGGGAAAGGTAACTATACGATTGGCATT
196851  AAAGAACAGATTATCTTCCCTGAAATTGTCTATGATGATATCAAAAGAAT
196901  TAGGGGTTTTGACATCACTATTGTCACTTCCACCAACAAAGATAGTGAAG
196951  CACTTGCTTTACTGAGAGCACTAAAGATGCCGTTTGTAAAAGAATAGATA
197001  TGGCTAAAAAATCATTAAAAGTAAAACAATCCCGTCCCAATAAGTTTAGT
197051  GTACGCGACTACACCAGGTGTTTAAGGTGTGGGCGTGCTAGAGCAGTGTT
197101  AAGCCACTTTGGTGTGTGTAGGTTGTGTTTCCGTGAACTTGCTTATGCAG
197151  GAGCAATCCCAGGAGTTAAAAAAGCATCATGATAATCAATAAAGTTCCCA
197201  AAGCCCATTTTGATCCAGTTTCTGATCTTTTCACTAAGATCAACAATGCT
197251  AGAAAAGCTAAGCTTTTAACTGTTACCACCATCGCTTCTAAGTTAAAGAT
197301  AGCTATCTTAGAGATTTTGATTAAAGAGGGCTATTTAGCTAACTATCAGG
197351  TGTTGGAAAATAAAACTAAAACCAAAAAACTAGTTAGTTTCACATTAAAA
197401  TACACCCAAAGAAGGATATGTTCTATTAATGGGGTGAAACAGATCTCAAA
197451  ACCAGGATTAAGAATCTATCGTTCCTTTGAAAAACTTCCCCTTGTTTTAA
197501  ATGGTCTTGGTATTGCAATTATCTCCACTAGTGATGGAGTGATGACTGAT
197551  AAAGTAGCAAGGTTAAAGAAGATTGGTGGGAGATTTTAGCTTACGTTTG
197601  GTAAAAAATTATGTCAAAAATAGGAAATAGATCAATCAAAATTGATCCTA
197651  GTAAAGTGAGTTTAATGCAAACAACAACACTGCTTACTATTAAAGGACCA
197701  TTAGGGGAAAACACCATTAAACTACCCAAAAACTTACCCTTAAAGTTTGT
197751  TGTTGAAAATGACACTATTAAAGTAACTAATAACAACAACTTAAAACAAA
197801  CTAAGATCTTACACGGTACTTTCAATGCGTTAGTTAACAACGCAGTTATT
197851  GGGGTTACCAAGGGTTTTGAAAAGAAACTCATCCTAGTTGGGGTTGGTTA
197901  TCGTGCTAATGTGGAAGGGCAATTTCTCAACTTACAATTGGGCTATTCCC
197951  ATCCTATTAAGGAGTTGATCCCAAACCAACTTACTGTTAAAGTAGAGAAG
198001  AACACTGAAATCACCATTAGTGGAATAAAAAAAGAGTTAGTAGGTCAGTT
198051  TGCCACTGAAATCAGAAAGTGAAGAAAACCTGAGCCTTATAAGGGTAAAG
198101  GGGTACTTTACTTTAACGAAGTAATTGTTAGAAAACAAGGTAAAACTGCA
198151  GAGGGCAAGAAATAAGATGACAAGAACGATAAAAGAAGGATTAGACACA
198201  AACGGATTGTCAAAAAGATTAGGTTAACTAACCTTAACAACAGGGTTGTA
198251  CTAATTGTTATCAAGAGTTTAAAAAACATCTCGGTTCAAGCTTGGGACTT
198301  TAGTAAGAaCGTTGTTTTAACATCAAGTTCCTCACTTCAACTAAAATTAA
```

-continued

The Nucleotide Sequence of the *Mycoplasma genitalium* Genome

```
198351 AAAATGGCAACAAGGAGAATGCTAAACTAGTGGGAATGGATATTGCAACC
198401 AAACTCATCAAACTAAACCAAAAGGATGTGGTTTTTGATACTGGGGGTAG
198451 TAAGTACCATGGTAGGATTGCTGCTTTAGCAGAAGGAGCGCGAgCTAAGG
198501 GTTTAAATTTTTAAAGCTATGAATGATCAAAAAACTACTAACACTGGCTT
198551 GTTAACTTCCACTCTTAAAACCAAGCCCAAACACAACCTTAAACCTTCCA
198601 GTGAAGCCATTAAAAAAGCAGTGTCCAAAAAGGAAGGTCATTACAAAAAC
198651 AAGCGCTTTCAAAAACATAACTTTAATAACAAAAGTGAGTTTGAAGAGAG
198701 GATTGTCAAACTCAAACGGATCTCCAAAACCACAAAAGGTGGGAGAAACA
198751 TGCGCTTTAGTGTCCTTGTTGTTGTTGGTAACAAAAAGGGCAAGGTTGGT
198801 TATGGGATTGCTAAGGCATTGGAAGTACCACTTGCCATTAAAAAAGCGAT
198851 TAAAAAAGCCCATAACTCCATTCATACAGTAGAGATCCATAAGGGTTCAA
198901 TCTACCACGAAGTGATTGGTAGAAAAGGTGCATCTAAGGTGTTGTTAAAA
198951 CCTGCACCTTTAGGAACTGGGATCATTGCTGGGGGAGCGATCCGTGCAAT
199001 TGTAGAGTTAGCTGGTTTTAGTGATATCTATACCAAGAACTTGGGAAGAA
199051 ACACCCCCATTAACATGATCCATGCCACTATGGATGGGATCTTAAAGCAA
199101 CTCTCACCCAAAAAAGTGGCATTATTAAGAAATAAACCAATTAGTGATCT
199151 ATAAAAACAATGGAACTACACCAATTAAAAAGTGTCTAAAAGCCGTAA
199201 CCACAAGTCCAAAGTGGTAGGTAGGGGCCATGGCTCGGGATTAGGTAAAA
199251 CATCATCACGTGGTCAAAAGGGACAAAAAGCAAGAAAATCAGGTTTAACT
199301 AGGTTAGGTTTTGAAGGGGGACAAACACCCCTTTACCGCCGGTTGCCTAA
199351 GTATGGGGTTGCTAACAAAGGGATCTTAAAAAAAAGGTGGGTTGTTTTAA
199401 ATTTGAACAAAGTTGCTAAACTCAATCTCAAAACAGTTACTAGAGCAACT
199451 TTGATTGAAAAAAAGGTAATTAGTAAAAAAATAACCTCCCTTTGAAGTT
199501 AATTGGGAACACAAAACTCACTACTCCCATCCACTTTGAAGTGCAAAAAA
199551 TCTCCAAAAATGCTTTAAATGCAGTGCAAACTAGCAAAGGTAGTGTGAAA
199601 ATTATCACCTAATGCAAACTGTTTCTTCACCCAAACAAAAACTTAACTTT
199651 GGTCAAAGGTTACTAACTCTATTACAGAACCGTGACTTTATGGTGTCGCT
199701 GGTTTTAACAGTGGTACTTTTAATCTTGTTTAGGGTGTTAGCAATTATCC
199751 CCTTACCAGGGATTAGGATTAATGAGAGTGTCTTGGATAGAAATTCCAAT
199801 GACTTTTTTTCACTTTTTAACTTACTTGGGGGTGGGGATTAAACCAGCT
199851 ATCGTTGTTTGCAGTTGGGATCAGTCCTTATATCTCAGCCCAAATCATCA
199901 TGCAACTGCTTTCAACTGATCTAATTCCTCCACTTTCAAAGCTAGTTAAC
199951 AGTGGGGAAGTGGGGCGAAGAAAGATTGAGATGATCACAAGAATTATCAC
200001 CTTACCCTTTGCTTTAGTGCAAGCATTTGCTGTGATCCAAATTGCTACTA
200051 ATGCAGGCACTGGTTCAAGTCCGATTAGTTTAGCTAATAGTGGCAGTGAG
200101 TTTATTGCTTTTTATATTATTGCTATGACTGCAGGGACTTATATGGCAGT
200151 GTTTTTGGGTGATACTATCTCCAAAAAAGGGGTTGGTAATGGGATTACTT
200201 TGTTAATTCTCTCAGGGATTTTATCCCAACTCCCCCAGGGCTTTATTGCT
200251 GCTTACAATGTTTTGAGTGGGATAGTAATTACTCTAACCCCACAGTTAAC
200301 TGCAGCAATTAGCTTCTTTATCTATTTCTTAGCATTCTTAGTTTTACTGT
200351 TTGCCACTACCTTTATCACCCAAGCGACCAGAAAGATTCCCATCCAACAA
200401 TCAGGACAAGGGTTGGTTAGTGAAGTCAAAACCTTACCTTATTTGCCTAT
200451 TAAGGTGAATGCTGCTGGGGTGATCCCTGTCATCTTTGCATCCAGTATTA
200501 TGTCTATCCCTGTGACCATTGCCCAGTTTCAACCCCAAACTGAGTCACGG
200551 TGGTTTGTGGAGGATTACCTATCACTTTCAACACCCGTAGGGATCTTTTT
200601 ATATGCAGTTTTGGTTATCCTTTTTTCCTTTTTTTACAGTTACATCCAGA
200651 TTAACCCAGAACGGTTAGCTAAGAACTTTGAAAAATCTGGCAGATTTATC
200701 CCAGGGATTCGACCGGGCAATGATACAGAGAAACACATTGCGCGGGTGTT
200751 AATAAGGATTAACTTTATAGGTGCTCCTTTTTTAACTGTTATTGCTATTA
200801 TCCCTTACATTGTTTCTTATTTCATTAGGTTACCTAACTCCTTGAGTTTA
200851 GGGGGGACGGGGATTATTATTATTGTTACTGCTGTAGTTGAATTTATCAG
200901 TGCACTGCGTTCAGCTGCTACTGCTACTAACTACCAACAACTAAGGAGAA
200951 ACTTAGCAATTGAAGTGCAACAAACAGCTAAACAAGATAGTCTAGAGCAG
201001 CTTCAAAAAGAAGCACCAGGGATTGGTAACCTATGGTAGCACAGTTTAAT
201051 AAGTTCATTATCTTAGGACCCCCAGGGGCAGGAAAAGGTACAGTTTGTAA
201101 ACTGCTTAGCAAAACAACTAAGTTAGTCCATATTGCTAGTGGTGATCTGT
201151 TTAGAGAAGCCATTAAAAACCAGAGTGTTATTGGTAGAAAGATTGCAGCA
201201 ATTATCAGTCAGGGTGGTTATGTTGATGATGCCACTACTAACCAGCTTGT
201251 TTATGAATATATCACTACCAATCCATTACCAAATGGTTTTATCTTAGATG
201301 GTTATCCAAGAACAGAGAACCAGCTTGATTTTCTAAATATTAAACTAACC
201351 ATTGACATGGTCTTTGAACTAGTTGTTAGTGATCTGAATAAACTGATTAC
201401 ACGGATTGATAACAGGGTTATTTGTAACAACTGTAACAGTGTTTATAACT
201451 TGCTTTTTCAAAAACCACTAGTTGAAAATAGTTGTGATCAGTGTTCAGCT
201501 AAACTAGTGAAAAGGAGTGATGATAACAAAGCAGTGGTCAAAGCAAGAAT
201551 GGAGTTATATCAACAAACAATTCAACCAATCCACACTTACTTTTTCAACA
201601 AACAACTTTTAGTACAAATTGATTGCTTTTTACCACTAGAAGAACAACTC
201651 AAGACAATCAAACAATTTATTAGATAAAGATGATCTATCTCAAATCTGCA
201701 AATGAAGTTGCAGGGATTAAAAAAGCATGTGCAATCTTCAAAGCAGTTAA
201751 GGCATATTTTACAATTGAAAAGTTACTTGGCAAAAAGTTGGTTACCATTG
201801 ATCGTTTAATCAAACAATTCATTGAACAAAAACAAGCTAAATGTGCGTTT
201851 CATGGTTATCTAGGTTTCCCTGGTTTTAACTGTCTATCGTTAAACCAAAC
201901 GGTTATCCATGGAGTTGCCGATCAAACTGTTTTTAAAGATAGTGATAAAC
201951 TAACGCTTGACATTGGGATAGACTATCATGGTTATCTTTGTGATGCAGCT
202001 TTCACTTTACTTGGTAATAAAGCTGATCCAAAGGCAGTAAAACTGTTAAA
202051 TGATGTTGAACAAGCATTTAGTAAGGTAATTGAACCTGAGCTATTTGTTA
202101 ACAATCCGATTGGTAATTTATCCAATGCGATCCAAACTTACTTTGAAAAC
202151 AAGGGCTATTTTCTTGTCAAAGAGTTTGGGGGTCATGGTTGTGGGATTAA
```

-continued

The Nucleotide Sequence of the *Mycoplasma genitalium* Genome

```
202201 GATCCATGAAGATCCTTTAATCTTAAACTGGGGAGAGAAAAACCAGGGCG
202251 TTAGGTTACAAGAGGGGATGGTAATCTGTATTGAACCGATGGTTATGACT
202301 GATAGTAGTGAGATAACAATGGCAGCTAACAACTGGAATGTACTAACTTT
202351 AAAGAGTAAGTTTAACTGTCATGTGGAACAGATGTATCACATCACAAACA
202401 ACGGCTTTGAATGTTTAACTAACTAATGAAAAACGATAAACTCTTTCTAA
202451 CAGGTAAGATACTGGAAATTATCCATGGTGATAAGTACCGGGTGATGCTT
202501 GAAAACAATGTTGAGGTTGATGCACATCTAGCAGGTAAAATGAAGATGAA
202551 AAGAACCAAGATTCTCCCTGGGGATGTTGTTGAGGTGGAATTTTCTCCCT
202601 ATGATTTGAAACTAGGTAGGATAACCCAAAGAAAATAATTAAAATATTAT
202651 GAAGGTTAGAGCAAGCGTAAAACCAATTTGTAAAGATTGTAAGATCATCA
202701 AACGTCACCGCATCTTAAGGGTGATCTGCAAAACCAAAAAACACAAGCAA
202751 AGGCAAGGATAATGGCACGAATCTTAGGGATTGATATCCCCAACCAAAAA
202801 CGGATCGAGATAGCTTTAACATACATCTTTGGGATTGGTTTGTCAAGTGC
202851 AAAAACAATCTTAAAAAAAGCAAAGATTAACCCTGATAAACGCGTTAAAG
202901 ATCTGAGTGAAGAGGAACTTGTTGCGATTAGAAACGCAGCAAGCGGTTAC
202951 AAGATTGAGGGTGATTTGAGAAGAGAGATTGCTTTAAACATCAAACACCT
203001 AACAGAGATCGGTTCTTGAAAAGGGATTAGACACAGAAAAAACCTGCCAG
203051 TAAGAGGACAACGCACTAGAACCAACGCAAGAACCAGAAAAGGCCCTAGA
203101 AAAACAGTGGCTAACAAGAAAATTGAAAGTAAGTAATGGCTAAGAAAAAA
203151 AAGATTAATGTTCCCAGTGGTTTGATCCATGTCTCCTGTTCACCTAACAA
203201 TACCATAGTATCAGCCACTGATCCCAGTGGTAATGTCTTGTGCTGAGCGA
203251 GCAGTGGTACAGTAGGATTCAAAGGTTTTAGAAAGAAAACCCCTTACTCA
203301 GCAGGGGTAGCAGCTGATAAGGTGGCTAAAACTGTGAAAGAGATGGGAAT
203351 GGGGAGTGTTAAGATGTATCTGAAGGGAACAGGTAGAGGAAAAGACACCA
203401 CGATTAGAAGCTTTGCTAATGCTGGGATTACGATCACAGAAATCAATGAA
203451 AAAACCCCTATTCCCCACAATGGCTGCAAgCTCCTAAGCGTCCGCGCTAA
203501 TCAAAACAACAACTTATGGAAAAATTTTTAAAGTACGAAATTAAGGTTAA
203551 CAACAACCAACCAACCAACACTAACCCTAACTATGGGATCTTTGAAGTAG
203601 CACCGTTAGAATCAGGATTTGGGATTACCATTGGTAATGCGATGCGCCGA
203651 GTGTTACTTAGTTGTATCCCAGGCGCTAGTGTGTTTGCCATTGCCATTAG
203701 TGGGGTAAAACAAGAGTTTAGTAATGTGGAGGGTGTGTTGGAAGATGTGA
203751 CTGAAATGGTGTTAAACTTCAAGCAACTAGTGGTGAGAATCTCTGATCTT
203801 TTGTTTGAAGATGGGGAGATGATCGAACCACCCTTAGAAAGGTGACCAGT
203851 TTTAAAAGTTACTGCTGAAAAAAAGGGTGCAGTATATGCAAAGGATCTTG
203901 AGTGTCCAGCTGGTTTTGAAGTGATTAATAAGGACCTTTATCTCTTCTCT
203951 TTACAAAAGGACATGAAACTAACAGTCAGTGTTTATGTTAAACAGGGTAG
204001 GGGCTTTACTAGCTTTCTTGAAAACAGAGAATTGATCAATTCGCTTGGCA
204051 TTATTGCTACAGATGCTAACTTTTCCCCGGTTTTACACTGTGGTTATGAA
204101 GTTCAAGAGGTGAAAACTTCCAAACAAAAGTTAACTGACCATCTCACCTT
204151 TAAGATTGCTACTAACGGTGCAATTAAAGCAGTGGATGCGTTTGCTATGG
204201 CAGCAAAGATCCTAATTGAACACTTAAACCCAATTGTAAGTGTCAATGAG
204251 TCAATTAAGAATTTAACAATTATCCAAGAGAAAGCAGAGGAAAGAAAGGT
204301 GAAATCATTTGCCAAGCAAATTGAAGAACTTGACTTTACTGTTAGAACCT
204351 TTAACTGTTTGAAAAGAAGTGGGATCCACACACTCCAAGAGTTACTATCA
204401 AAGTCATTAACTGACATTAGAGAGATTAGAAACCTAGGTAAGAAATCAGA
204451 ACGGGAGATTATCAAAAAGGTGCAAGAGTTAGGTTTAAAATTCCGTTCTT
204501 AATAAAATAGAGCTATGTCATACATTAATAAAGAGGGGAAAACCACAGCT
204551 TGAAGAGTGATGACAGTGCGTCAGCAAGTGAGTGCAGTGTTAAGTTATGG
204601 AAAGATTCAAACCACTTTAAAAAAAGCTAAGAACACCCAAAAAAGGTTAG
204651 AGAAGATTATTACCATTGCTAAAGTTGATAACTTTAACAACCGCAGGGCT
204701 GTTAAAAAGTGGTTATTAAATACCAATTCATTAGATGTAGATCAACTCAC
204751 AAACCACCTTTTTAAAAAAGTAGCACCACGTTTTTTAAAGCGTAATGGTG
204801 GTTATAGTAGAGTGTTAAAGTTGGGAGTTAGAAGGGGTGATAGTACTGAA
204851 ATGGCGATCTTACAGCTGATAGATGCTACCAACTAAACAAGCTGCTTGTA
204901 GTTTTATTAATGTTGCTTTTTCCTATAATGAACTGCCATTAATTAGGGAA
204951 CTATCTTTTAGTGTTTATGAGGGGGAATATGTTTGTATTGTTGGTCATAA
205001 TGGCAGTGGTAAATCAACCATTTCCAAACTGTTAACAGGGTTATTAAAGC
205051 CCCAGGCAGGTGAGATTAAGATCTTTGGTAAAACAGTTGATTTTGATAAT
205101 GTTAGTTACTTGAGAAATAACATTGGGATCATCTTTCAAAACCCTGATAA
205151 CCAGTTTATTGGGATCACTGTTGAAGATGACATTGCCTTTGGGCTTGAAA
205201 ACAAGTGTTTTTCAAGACAGAAGATAAAAGCCATTATTGATGAAGTTACC
205251 CTACAAACCCAAACTGATGGGTTTATTAAACAAGAACCCCATAACCTATC
205301 AGGGGGACAAAAACAACGGGTAGCAATTGCATCTGTTTTAGCACTAAATC
205351 CTGCTATTATCATCTTTGATGAATCAACTGCGATGTTAGATCCTAAAGCT
205401 AAAAAAACGATTAAGCAGTTTATGGTTAAACTAGCCAAACAGGGCAAGTG
205451 TGTGATCTCAATTACCCATGATATGGAAGAAGTTACTAAAGCTGATAAGG
205501 TGTTAGTAATGAATGAGGGCAAACTGATCAAACAAGGTAAACCTGTTGAA
205551 GTTTTCACTAGTGAACAAGAGTTACAAAAAATCCGTTTAGACATCCCTTT
205601 TTCACTCAGTCTTTCAACCAAGATAAGAGGGATCACTAGTACAATTGATT
205651 ACCAAACCCTGATTAAATCAATTGCCAAGCTGTGSAAAAAAAGATAGTCC
205701 CAATTAACCCTTTAAAAGCAGATGAGATTTTAGCAGTTAGTCACTTATCA
205751 TGTGTTTTTAACAGTAAAACTAACAATCCCATTAAGGTGATTGATGATTT
205801 TTCCTATACCTTTCAAAAGAACCAAATTTACTGTATTATTGGTGATAGTG
205851 GCAGTGGTAAATCAACCCTTGTTAACCACTTCAATGGGTTGATAAAACCC
205901 AACCAAGGTGATATTTGGGTTAAAGATATCTATATTGGTGCTAAACAACG
205951 CAAGATTAAGAACTTTAAAAAACTGCGAAAAACTATCTCAATTGTTTTCC
206001 AGTTTCCTGAGTACCAATTGTTTAAAGATACCGTGGAAAAAGACATTATG
```

-continued

The Nucleotide Sequence of the *Mycoplasma genitalium* Genome

```
206051 TTTGGTCCAGTAGCATTAGGTCAATCCAAGTATGATGCGCGCCAAAAAGC
206101 GGCTTATTATCTGGAGATGATGGGGTTAAAATACCCTTTTTTAGAACGTA
206151 ATCCCTTTGAATTGAGTGGGGGGCAGAAAAGAAGGGTAGCGATTGCTGGT
206201 ATACTTGCAATTGAACCAGAAATTCTAATCTTTGATGAACCAACTGCTGG
206251 GCTTGATCCTGAAGGGGAAAGGGAGATGATGCAGTTAATTAAAACTGCCA
206301 AACAACAACAAAGAACGGTATTTATGATCACCCACCAGATGGAAAATGTC
206351 CTTGAGGTGGCTGATGTGGTTTTGGTTTTAGCTAAGGGTAAACTAGTAAA
206401 AGCTGCTAGTCCATATGAAGTGTTTATGGACCAAACTTTCCTTGAAAAAA
206451 CAACGATTGTTCTCCCCCCTGTGATCCAAGTGATCAAAGATCTAATTGCG
206501 ATTAATGCTCACTTTAATAAGTTAATTGAGTTGCAACCAAAGAACCTAGA
206551 ACAGCTTGCATCAGCAATTAACAAGACTATAGCAAACCATGGATAACTTT
206601 ATTAATGGCTATATCCCAAGAAACAGCTTTGTTCACAAGCTGCATCCAAC
206651 TACTAAACTAGTAATCTTTTACTGTTAGTTATCTTGGTATTTGTACCAA
206701 TTGGCTTTGTTTTTCAAAGTGTTATCTTTCTTTTTGTTACCTTTGTTTTT
206751 TTTATTGCTAAACTCCCGGGGCGGTTTTACAGTTCAGCAATTAAGTCAAT
206801 TACGCTGTTATTTCTCTTGTTGTTATTTGTAAACTGGTTTACCTTTCGTG
206851 ATCCAGGGTTTTATCTTACTAGTGATCAACTTAACAGTTTACCAGCCATT
206901 GATAACAGCAAGTTTAGCTTTTGAAACATTAGTTTGTTTAACTATCAAGA
206951 TAATGTTTTTCCCAGGTTTTTGCTTTTAACAGGGTAATTTAACCAACT
207001 TAAATCAACTTGATTTTTTCTATAAAGCTAACAATGCTGATAGTTACACC
207051 AAAGTAAAGGGCATTGATAGTTTAGCAAGTATGCTAGCAAACAATGGCAA
207101 TGGTTTAAGCAAAGACAAAATTCTGAGTGCTTTTTTAGATCACAATTTAA
207151 ACCTTTATTTAGCGAGAAGTTGGGGGGCAAATTTTGCTGGGTTTGTTGTT
207201 GATTTTAACCCAACAACCCAACTCTTTAAACTCACCCCTTTTCTAGCAAA
207251 TGCTAGTTATGTTTTAACGTTAAGAGCAGTTATCTTAGCATTCTATGTCA
207301 CCCAAAAGATCCTAATTATGATCTTATTTGCAACTGTACTCACTTCCACT
207351 TCAAGTTCAGTTGAACTAGCATATGGGATTGAAAGGTTATTATGACCTTT
207401 AAAACTCATTAAAATACCTGTTAATGTCTTTGCAATGACCATTGCCATTG
207451 CCATTAGGTTTGTCCCTTCCTTGTTACTAGAATCACAACGGATCTTAAAT
207501 GCCCAAGCCTCCAGGGGTTTAGACTTTCGAAATGGGGGATTTTTAGTGAA
207551 GATGCGTTCACTCTCTTCGTTAGTAGTGCCAATGGTTTCCATTGCCTTTC
207601 GCAATGCCTCTGAACTTGCTAGTGCAATGGAAGCAAGGGGTTATCACCCT
207651 GCAAAGAAGCGCAGTAGTTATAGACAATACAAAATCACTTGGATTGATAT
207701 TTTAGCGTTATTTTTGGTTTTTGCTTGGTTTGTTGTGATTATCTTTTTAA
207751 CTATTAGAGGAGCGGTCTTTTTGGATCTAGGTACACCAGAATGGTTATTA
207801 ACAGGAAAGATTAATGAACAGGTAATCAGGGATCTGAAGGTAAGTGGCTA
207851 GGTACTTGGGGATTGTTAGTTATGATGGCAGTTACTTTAAAGGGTGAGCG
207901 ATTCAACCAAACCTAGCTACTATCCAAGGTTTATTGGAGCAAAGTTTTC
207951 ATTAATCATTGGCAGAAAGATAAAGGTAATTGGTTCAGGTAGAACTGATA
208001 AAGGGGTACATGCCATCAACCAAACCTTTCATGTTGATATTAATGGTGAA
208051 ATTAATCTCAATTTGTTAATTAGAAAAATTAACCAGTTGATTAAGCCCCA
208101 CTGTATAGTTAAAACCTTGGTATTGGTTAACGATAGCTTTCATGCGCGGT
208151 TTCAAGTTAAAACCAAGGTGTATGAATATCTGATTAACTGTGGGAATTTA
208201 AATCCGTTGCAATTTAACTATGTTTGGCAGTTAAACCAGCAATTGGATCT
208251 TGAAAAACTCAAAGCTGATGCCACTTTATTTTTAGGTAAGAAAAACTTTC
208301 TTAGCTTCAGTAGTTCGATTCACACTGATTCAATTCGCACAATTAGTAAA
208351 ATTACCATACAAAAAGAAACTAACCAACTAGTTAGACTAACTTTTTTTGG
208401 CAGTGGTTTTCTCAGGAGTCAAGTGAGGATGATAGTTGCTTGTTTAGTGA
208451 ATTTAAACACTAATAAAATGGCACTTGAAACAGTTGCAAAATTGTTTGAA
208501 CACCCCAAGAAAGGGAGTTGTGTTGTTAAAGCCCCTAGTTGTGGTTTGTA
208551 TCTGAAAACAGTGGTATATGAAAAATAGTTACAAGTGGGATCTATCAGTT
208601 TTATTAAACAACCAAAGCTTACAAGCAAATTTTTTAAAAATTCAAACAGT
208651 TAGTGAAGCGTTAATTAAAGCTTATAACAACGGGTTGTGTTTTACAAATA
208701 AAACTAGCTTTGAACAGTTTTTAGCAATCGATGATAAGTTCACTGAACTT
208751 GAAAATCGTTACACTAACTACCTTTATAACAAGCAGAATGAAAATAACTT
208801 GGATAAGGAGGTTAATGATGCAATTTTTGCATACCAGAGTTTTAAAAATA
208851 ACCATAACCTTGCTTTCAGTACACTGCAACAGGAGTTATATAACCATGAA
208901 AAACTCATTAAGGATTATTTAACTGATCCAAAGCTAGCGGTTTACAAGCG
208951 CAACTTAATGTTAGTTTTTCGCGATAAACCCCACCAACTATCTAGTCAAA
209001 CCCAGAGTTTATTGAGTCAAATTAACCCTTGTTTTAACCAAGCAGAACGG
209051 ATTTTTAACATCCTTTCAACTGCTGATTTAAACTTGCAACCTGTTGTTTA
209101 TCAAAACAAaAAATATCCGATTAACAGTGTGAGTGATTATCAGTCCTTAC
209151 TTGAAAACACTAACAGGGGGATTAGAAAAGCTTGTTATGAGAAGTGGATT
209201 GAAATTTATTGAACTAATAGAAACAGCTTAAGTTTAAGTTTGGTGGAAAA
209251 TTACATCCAACTAGAGAACTTCGCTAAACTAAAGAACCATCCTAGTTACA
209301 TTGCCCAAACTGCTTTTAATGATGAGATTGAAGTTGGTTTTATTGATTTT
209351 GTTTACCAACAAGTAGCTCAGTTTGCCAAAACCTTTCAAGCATTATTCG
209401 CTTAAAAAAACAGATTTATAAACATGTTTTAAAAGTCAATAAAGTTGAAC
209451 CATATGATCTTACCCTAACACTTTTTAAAACTAAAAAATCATCACGATT
209501 GAACAAGCTAAACAAGATGCACTAAAAGTTTTAGATCTACTTGGTGACAA
209551 CTACATCAAGATAGTTAAAAAGGCTTTTAATGAAAACTGGATTGATTGAC
209601 TAGCAGATAAAAACAAGTACACAGGGGCATATTCAATCTCCAATGTTAAG
209651 GGCTTAGAGCACTTTTTTATCTTAATGAACTTTGATAAAACCAAATCATC
209701 ACTAAATACGTTGGTACATGAACTTGGTCATTCAGTTCACTCTTGGTATG
209751 CATCACAACACCAATCCCAAAACATCGATCCTACTATCTTTTATGCTGAG
209801 ATTGCTTCTATTGCCAATgAACTGTTGTTGTGTTATTATGAGCTGCAACT
209851 TTATAAAAATAACCACAAGCAGTTAATTGCTAGTTTATTGAGTCAAATCA
```

-continued

The Nucleotide Sequence of the *Mycoplasma genitalium* Genome

```
209901 ACCATTTTTTGGCGCTACTACAAGACAAATAATGTTTTCACAATTTGAA
209951 AAAGATACGCTTTATTTAATCAGAGTTAACCAGAAACCTGACTTTAAAAC
210001 TTTGATTAAAATTTATGCAAATACTGCGGTTAAATACCAAGGTTTTAAAC
210051 CTGAAGTAGTTGCTAATAAACTAAAAAAGACCCAGTATCAAAAATCATTG
210101 TCACACATCATTGCTATCCCCCATTTTTATGCAGGTAACTTCTATGTTTA
210151 CAAGTATGCCATTGGCCAAGTTGCAGGTATTTTAGTAGCTAAAAAAATTA
210201 ATAGTGGTGATAAAAAGATGAAAGATAATTACTTTAAATTCCTCAGTTCA
210251 GGTTCTAGTTTAGCGCCACTTGAAACCATTAAACTCTTAGGGATTGACCT
210301 TACTTCACCCCAACCCTGACAAGAAGCACATAACGAAGTAAAGCGTTGGC
210351 TTAAAATTGTGAAACAAAGCTTTAAAAAACTCCAAAAATAAGTGCACCAT
210401 TTTAACCGCGCTAAAAAGGCCAAGAATAACGAGTTTTTTACTTTAATTGA
210451 TGAGATTGAAAACGAAGTAATTAACTACCAAAAGCAGTTTGCAAATAAAA
210501 CCATTTTTTGTAACTGTAATGATGGTAAAAATTCCCATTTTTTTCAGTTT
210551 TTTCAAACTAACTTTAACCAGTTACAACTAAAAAAAACTCATTGGGTTTAG
210601 TTTTAATAATCTCTCACAAGCTGACAAGTTCACTTTTGATGGAAATAAAG
210651 TAACTAAAACCAAATTAAAGGGTAATGGTGATTTTAGTTCTGATGAATCG
210701 ATTGAAGTGTTAAAACAAGCAGATATAGTTGTAACAAATCCACCCTTTAG
210751 TTTGTTTCAAAGTTTCATTGATCTGTTAATACAACACAACAAGCAGTTTC
210801 TGGTTTTAGGGTTAAATGCAGCAGTTAGCTATAACCATATTTTTACCTAC
210851 TTTAAAACTAACAAGTTGTGGTTTGGCTATACCGTTAATAAAACAATGAG
210901 TTTTTCAGTTAACAGTGACTATCAACTTTATAACCCCAAAACTAGTAACT
210951 TTTTTACAAAAAATGGCAAGTGTTTCCAAAAGATAGCAGGTATCTCTTGG
211001 TTTACTAATTTAGGAAAACCACATTATAACCCCTTTTTAAATACCAACTG
211051 TTTTTATAAAAACAACGAAAAAAACTATCCCAAGTTTGATTGGTATGATG
211101 CTATTTATGTCAACAAGATTAAAAACATCCCTATGGATTGAAATGGATTG
211151 ATGGGAGTTCCTTTAACCTTTTTAAACTGTTACAACCCCAAGCAGTTTGA
211201 ATTAGTTGATTGTCTTGCTAACCCTTATGCTACCTTAGATACATTAAAAA
211251 CAAATGCCTTTGTGAAATTAAATCAGGGTGATGTGAGAAATGTTAATGgT
211301 AAAAGAAGGTATGTAAGGGTAATAATTAAAAAACAACAAATTTAGTTTTT
211351 TCAACATTTAACAACTCTGTTTTTACAAAAGTTAGCTTAATTTTGCTAAA
211401 TTGTTTTTTGATAGCACACTGCTGTCAACGAACCATGTTGATAAATGAAA
211451 TTCAAACTATTTTTTTTATCAAGCAGTGTGTTGGGTCCAATTGCCCTATT
211501 TACAACTGCTTGTAGTGCTGTTTATAGGTTTGATCAAGTTGATGATGGCA
211551 AGATTAAACTAGCAACTGTAACTTCAGCTTCCGCTAGTGGCTCGCTTACT
211601 ACTATCATCAGTAAATATAATTCACAAAAAGATCCTAATGATTATCCAGT
211651 GGAACTGGTTTCACTTGATAGTAGGGGCAGTTATTCTAATGGCAAAAAGG
211701 ATCTGCAAGCTAAACTGCTAGCTAAGGATAAAAATAACTTTTATAACCTT
211751 ACTTTTAACTATAGTGATGTAGTTTCAATCCTCTCAAGAAGCCAGATGGA
211801 GTTGAGCTTTGATACGGTTGATACTAGTAATTTTGATCCTAGTTTTCTTA
211851 GTTTTAACAATAATATTTCCAATGTTAATCCAAATAGCATCTATGCTTTA
211901 CCTGCTACTGTATCAGGTGAAGTTTTAGTTTTAAATGGACCGGTGTTACA
211951 TTACATTTTAAGTAGTGCTAAAAAAGATAGTAACACCACCCTTTCAACCC
212001 ATTCAGCTAGCAATAATAGCAATAAGGGAACAATGGTTGTTGCTAGTGAT
212051 AGTGAAACATCAAGTTTATGAACTAAATTAGAAGCTGCAGCAAAAATGAA
212101 TGCTCAAACTAATGAAACCCAAGTTTTAAAAAGTAATTCATCAGAATCTA
212151 ACCAAACCCAAGCTAGTGATACAGAGATTAAAAAGATTTGGGGTGATTAT
212201 CAAGAAGTTGATGGAGGGTTGAAAAATTACACCTTTAAAGCTAGTGTTTT
212251 TAACAATTGAAAAGACCTAAATGACTTTGCCACCAGGATTGCAAAATCCT
212301 TTACAAAACTGCAAACTACCACTAAAAAAGGGGAGGAAGTACAAGCTGTA
212351 TTTGGGATTGGTAGTTTGGAAAATGCCTTATATACTGCTTTATTTGCTTC
212401 TGGAAAAGCTGATTACAATAACTTTCTTTTTAACATCAAAAACCAGCGAA
212451 TTAATTTCAGTAACTTTTTTAATAAATCCTCAACTGCATTTCAAAACCTT
212501 AAAACTATCTTTAACAGCTTCAAATCCTTAATTGATCAAAACGGTTTAAT
212551 CTCAAATGCACACTTTAACACCCCAGTTAATGACTATGCTAAGTTTAACC
212601 AATTAGCTTTTTACACCTCTTCAACTGCACGCTTTCCCTATTCATTTGCA
212651 AGTGATAGTGTAAAGCGTTTAATAGTTAATGACAAGACAATTGAAAACAA
212701 AAACAATAAGAGTGTTTTTGAGGTTAATTTAAGTAGTGATAGTGATAACA
212751 ACAGTAACCTAATTGGTACTGTATCACTGGAAAATAGTAAACAAGTTTCA
212801 CTCTATGAAAAGCAAGTGGATAGTAATAAACAAATTGGTGTTGATGCTTT
212851 GTTAATCAAAGATGAAACTTTAATCAACCATCTTAAGAGTTTAAAATCGC
212901 AAGTTAGTGCAAAAAGTGCTAGTGAAACTTCCCAAACAAAACAAAACAAA
212951 ACCTTTTTAGCATTTACAACTGTGAATGCAGATCAAAAAGCAATCTTTGA
213001 TGTTGGTAAACTTAATGGCAAAACTGCCAAAATCATTATTAATGCTACTG
213051 AAACAACTAATGCTAAGATTAGCACCTTACAAGAAAAAGAGGCAATAGTT
213101 CTAAAAGCACCCCAACGCTTTGAGAGCACTGATCCATTTCCTATTGCTTT
213151 AGTGCAAGGTCCTAGTTTAATAGGGATCCATGCAAATGAAAGAGAGGATA
213201 TTGAAACCAAAAAGTTTGTGAATTGGTATCTGAATACTAAAGTCCAATGG
213251 GAAGAAAATTCTATTAAAACTCCTGCAGAATATGTAGCTGATAAAGCtTC
213301 TTATCTTTTACCTTTTAAAAATAGGCTAAATAATACTAACAGTTACAATG
213351 AGTTTGTTAAAACTGCAGTTAGTCAGTTTGCTGATAAAAATGTAACTAAA
213401 TTTGCAGAACCTGCTGATTTTTTATCCAACAAAGTACGTGATGGTGTTAA
213451 GAGTAATTTAAATGCTGCAATTAACAACCACAGCATTGATTTTGATAGTT
213501 TTATCAATGATTTAACAGACTATCTTGGTAGTGATGTTAAAAACATCTAA
213551 TAATTTATTCCCCCAACCTCTATTTTCTGTTACTAGTGCCTAAGGTGGTA
213601 GTGGAGTATCACAACCTGAATAACCAAGTAGTCAAAGAGAGTTTGGAAGT
213651 GGAATCTTCTTCCTCTTTCAACCCCACCCAAAGGTTGCAAAAAGATAGTC
213701 CGGTGAAGGATTCAAACAAAGACAGTGAGAAACTCGAAACAACTGCTTCA
```

-continued

The Nucleotide Sequence of the *Mycoplasma genitalium* Genome

```
213751 TCGATGAGTAGTGGGGCTACATCTCCTCGCAAGGCCCTTAAGATAGAGGT
213801 GGAGAAAGGCAGTAATGTCAATCAAGGCGAACTAGCAAAAAACGACTTTG
213851 CTAAAAAGCCACTGAAACATAAGAACAGTAGTGGGACAGAGGTGAAGTTA
213901 GCTGCGAATGGGGAGTTTGCAGGAGACAAGGCCTGAAAACCATTGTTGAC
213951 TACCGAGCAAATAAAAGATAATAGGGGGATGGGGCTTTCTCCAACTCCC
214001 CCTCCCCTTCAACTTCCGCTTCCTCAACCCCCCTCCCCACTTTTTCTAAC
214051 ATCAATGTTGGGGTTAAATCAATGATCACTCAACATTTAAATCAGCAAAA
214101 CACCCGGTGGGTGTTTATACCTAACTTTTCACCTGACATCTGAACAGGAG
214151 CAGGTTATAGAAAAGCTAATAACAACAATAACGGCATTCCTTTTGAACAG
214201 GTGAAACCTAGCAATAGTAGTCAACAGTTTAATCCCAATTCAGATGATAA
214251 TAAAGTCACTCAAGGTGGTGGCTCCCCAGCCAAAAAAACAACGTATGACA
214301 ATTTACCAAACTCCATCAGTCCCACCAGTGACTGGATCAACGCATTGACT
214351 TTTACTAATAAGAATAACCCGCAGCGCAATCAACTGTTGCTCAGAAGCTT
214401 ACTAGGAACTATCCCGGTCTTGATCAATAAGAGTGGAGGAAGTGGGAATG
214451 AGTTTACCCATACGAGTGAGCAGAAGTGGGATAAAACGAATGAAAAGAT
214501 GGGAATTTACCTGGGTTTGGGGAGGTGAATGGTGGTTTTATTATGTTTTT
214551 ATCAAATCTTTATTTACTTTAATAGTTAAAAAAGTTTTGAATTTTTCTTA
214601 GTTTTTTATTTGTTTAATATTTAAGAAAGTCTCAAATTTTTATCAGTTTA
214651 TTGGTCAAAGAAGTCGCAAATTTTCTTAATTTATTTATTCAATAGTTAAA
214701 AAAGCGTTAGGTTTTCTTAGTTTTTTTATTTGTTTAATATTTAAAAATT
214751 TCTTGATTTTTATCCTTAATTTAATTAATAAAACCTTTACCCCTATTATC
214801 ACAAACCATCCATAACACCAACCTGTTTGTGTTGTTCAAGTCTAGGGATG
214851 TAAAAGTTAAGTATGAGTCAAGTGGCAGTAACAACATTAGTTTTGATTCA
214901 ACTAGTCAAGGTGAAAAACCATCCTATGTGGTCGAGTTTACTAACTCTAC
214951 CAACATTGGCATCAAGTGAAGCGTGGTGAAAAAGTATCAGTTAGATCTAC
215001 CAAATGTTACCAATGAGATGAACCAAGTGTTGCAAGAATTGATCCTAGAA
215051 CAACCCCTTACCAAGTATACCTTAAACAGTAGTTTGGCTAAACAAAAGGG
215101 TAAAACCCAAAGGGAGGTGCATCTCTCAAATTCAAATCAGTGACAATCGA
215151 TGCGTAATCAACATGACCTAAACAACAATCCCAGCCCCAATGCTTCAACT
215201 GGATTTAAATTAGACAAAGGCAATGCATATAGAAAACTAAGTGAATCCTG
215251 ACCAATTTACCAACCAATTGATGGGACCAAGCAGGGCAAAGGGAAGGATA
215301 GTAGTGGGTGGAGTTCAACAGAAGCAACAACGGCAAAAAATGATGCGCCC
215351 AGTGTTTCTGGAAGTGGAACATCAGACACCGCTTCAAAATTCAAAAGTTA
215401 CCTCAACACCAAGCAAGCGTTAGAGAGCATCGGCATTTTGTTTGATGGAA
215451 CAACGGCGAGGAATGTGGTTACCCTCCTTCCTCTACTTTCAACCCAACAA
215501 GGTGAAAAGTGGTCAATATCAACAAAATAACACCTACAACAAGTTAATTG
215551 AACCGGAAAGTGCAACAAGTGCAGCGAGCAGCATGACCAACTTGTTAAAC
215601 ATGTTGTCTAGTAAAAACATCAAACAGAAGTTGGGGAAGGGGGAACAGC
215651 AATGCAGGGAAGTTTCAGTGTCCAAGACACCTTCAGCTTTGTTGTTCCTT
215701 ATTCGGGGAATCATACAAATAGTGGAACAACTGGACCCATTAAAACTGCT
215751 TATCCGGTGAAAAAAGATCAAAAATCAACTGTCAAGATCAATTCCTTGAT
215801 CAACGCTACGCCGTTGAATAGTTATGGGGATTTAAATAATCACACCAAGT
215851 TAATTTACCCAAATTATTTACTTATTTATTAACCATTGTTACCCAATTTT
215901 TCAACCACTTCCCCACTCTATAAATTGTTATTTTTAACAATTTGAACAA
215951 TTAAATTGCAAAAAATAACTATATTAATGTAAATTTAGCTAACAAGCTTA
216001 ACTGGTTGTTTTTGAGATGAAAGGGTTTTTAAAACCAAATTTCTCGCTCG
216051 GTGCTTTGTTTTTAACTTTAAGCCCCATAGCCACTGCATGCATTGCTGAA
216101 AAACCAGTTAACAACCGCTTTAACTTTAATAGCGAGCAATTAGCTAGGCT
216151 AAGAAAAGCAAGGGTTAACCACTGAAGAGATGGGGATACTTTGGAAGTTA
216201 GCTTTGCAAATAACCACCAAAAACCGATCCGTATCTATGCCATTGATACC
216251 CCTGAAAAAGCAGTTTTATCTATACAACGCAAATCAGAGATAGAaCTTAA
216301 AGAAGCTAATAAAGCAACTGAGTTTGCCAAAAGCTTAATTCCCATTGGTA
216351 GTGAGGTGTGGATCTGACCACTAAATAGCTATAGCTATGATCGTGAAGTA
216401 GCTGCAGTGTTTTTCAAAACCAATCCATTGCAACTGCACTTTGAATCGTT
216451 TGCAGTTGAAATGGTAGCAAATGGTCATGCTTTACCTATTGCTGGTAATG
216501 ACTTTGATTTTGTTTTTAGTGATTTGGACCCATTTAATCCCCTAAAAATA
216551 GTAGGGATTGAACTAGCTAATGGTTTAAACAATGCTTTTAACAACAGAAA
216601 AAACATCTTTAGTTATTTAGAAAACAGTTTTCAATCAATAACAATGGTCT
216651 ATCAACAACGCGGTGTTGACCAAAGTTGAACAAGGTATTTAGCTCCTAGT
216701 AATGATTTTTCCTCTACTAAACTGGGGTTGGGATTAACCATCTATGAATT
216751 GAAACTAAACAATGGCTAACAATAAGAGTGCAATTGAGTTGAAAAACATC
216801 GTTGTTGATTTTGGTGAATCAGTTGCGATTGACAACATTAACCTTAGTGT
216851 TGAAAAACACCAACTAGTTAGCTTACTTGGTCCTAGTGGTTGTGGTAAAA
216901 CCACTACACTTGCAGTTATTGCAGGACTTATTAAACCAACTAGTGGTCAG
216951 GTGTTATTTAATGGTTATGATGTCACCAAAAAACCACCCCAAGAACGTAA
217001 ACTAGGGCTAGTTTTTCAAAACTATGCACTTTATCCGCACATGAATGTGT
217051 TTGAAAACATTGTTTTCCCCCTCTACAGTGATAACTCGTGAAAACAAGCA
217101 GTTTTGGAAARAAACAGTGTTGCAAACCATGAGATTAACTGTTTGTTACT
217151 TACTAGCAACGGTGCATCAGTTCAAGAGATTGATCAGCTCAATAAGTTAT
217201 TTCATGATAGTATTGAAAAACCCAAACAGATCCAATACCAAATTAATGAC
217251 CTTAATGTTAGTGTTTTTAAAAACTTAAATGAACTAACTGCAAACCTTAA
217301 GTTAATACCAAGTAAGCACCAGTTTGCTATTACCAATCTCAACAAACAAA
217351 CTCTAAAACAGATTAATGAACTGGAAGCTGAGTTTAAAACAAAGTGAAAG
217401 TTACAAAAACAAACCCCAATTAAGAGTGGGGTTGAACACAATGCCAAACT
217451 CCAAGCAATTAAACAACACTTTAGTTATGAAAAACAACGGTTAAAAAAAC
217501 ACTATTTCAAAACTAAAGTGGAACTAAAACAAACCCTTGTTGAAAACCTT
217551 AAGTTAGTTAAAAAAGCGATTAGTGAACAAACTAAGTTAATTAAACAGAG
```

-continued

The Nucleotide Sequence of the *Mycoplasma genitalium* Genome

```
217601 TAGTGATTACACTAAGTTAAAGCAATTAAAACGGTTAATTAAAGTTGAAC
217651 CTAACCAACTCAAAAAACAATATAAGGTTTTTCTCAATCAGTTAATTAAA
217701 AACTATTCACTTAAAACTGATAAGTTAACTGATACTCAACTTAATGAAAT
217751 TGAACAGATTAAAACCAGAATTGTTTCAATAAAACAGTTTATCAACAAAA
217801 CTGCACTTGAAGTAGCTAACAAACTAGCGATTACCAAGATTTTAACCAAA
217851 CGCCCTGATAAGATTTCTGGTGGACAACAACAACGCGTAGCAATTGCTAG
217901 AGCAATTGTCAGAAGACCTAAACTATTGTTAATGGATGAACCACTCTCTA
217951 ACTTAGATGCAAAGCTAAGGGTACAGACAAGACAGTGGATCAGACAGTTT
218001 CAACAGGAGTTACAAATTACCACTGTTTTTGTCACCCATGACCAGGAAGA
218051 AGCGATGAGTATTAGTGATGTCATTGTTTGTATGTCAACTGGAAAAGTGC
218101 AGCAAATCGGCACACCCAGTGAACTTTATTTAAAACCTGCTAATGAGTTT
218151 GTTGCGCGCTTTTTAGGCACCCCTGAGATGAACATCATTGAATGTAGTGT
218201 CAAAAACAACCAGTTGTTTTGAAACAACCATCTGTTAGTTACTGAGAGTT
218251 TTAAGCTTAATGTAGAGAAACTCTTAGTTGGGTTTAGGTATGAACAACTA
218301 GTGGTCACTACTAACAAAAGTAGTTTGCAAGCTAAACTAATTAACATTGA
218351 AAACTTAGGTAAACACTTAGTTGCTACCATTAGTTTGTTTGATACCACCT
218401 TATCAATGCGCTTAGAATTGAATAGCCACTTAAAAGTAGGTGATAGTTTA
218451 AATTTCATTATTAAAGCTAACAACCTCCATTTTTTTGATATTGATACAAA
218501 ACAACGGATTGAGATTTAACAATGTTTAAGTGGTTATTAAAACATCATAA
218551 TCAACCTCATAGCCTCCAGTTAGGGTTACTAGACCAACCATTACCGTTCT
218601 GAAAGCCCTTTTTGTTGTTCCTCCCTGCGCTTTTAACAACAATTTTGTTT
218651 ACCATTATCCCCTTCTTTTTAAGCTTACAGAAGGGTTTTAGTGCTAACAG
218701 TGATCTGTATGATCTCTCCTCCCAATCCTTTAGTTTACGAACCTTTCAGG
218751 ATCTGTTTAGTGAATCTAACTTTGTGTTGGGCTTACGCAATAGTTTTCTC
218801 TATTCACTAATCTCTTTACCCTTTAGCATTATCATTGCTATTGTTATTGC
218851 CAGTGCCATAGTATTTGTGTACAAAAAATTGTTAAGAGGGTTTTGACAGA
218901 CCGTGTTTTTTTTACCCTATGTAACTTCAGGGGTGGCAATCTCGATTGCC
218951 TTTGTATATATCTTTGATTCTGCCTCTGGTATTTTAAACACGGTGTTTAA
219001 TGTCAACACCAAGTGGCTTGATTCAGGTTCACGTGATACATTTAATGCCT
219051 TGTGGGCTATCTTAATCTTTGGGGTGTGGAAAAACTTGGCATTTAATGTG
219101 TTGATTATCTCAACAGCAATGTTAAGTGTTAATCCCCAACTTTACAAGGT
219151 AGCAAGTTTAGATAGTGCCAATCCTGTAAGACAGTTCTTTAAGATTACTC
219201 TTCCCTCCATCCGTCCTACTTTAATCTTTCTTACTACCCTTTTAATCTTA
219251 GGGGGGATGCAAGTCTTTCCGCTGGCTTTGTTTGAAAACAAACCTGAAGA
219301 AGCGGTTGCTAATGGGGGGAATAGTATCTTGCTTTACATCTTTCAACAGA
219351 TCCAAAGTGGCAATACTAACTTAGCAGGTGCTGCTACTTTAGTGTTGTTT
219401 GTGTTGGGAGTTTGTTATGGGTTAGTGTTACGTAATGGCTTTTATCTGAT
219451 TGAATGGTTGCAGTGAAAAATTAAACAGCTTTATGTTCAAAAACAACTTA
219501 CGCTTTACTAGTTGAATTAATCAACACAAGTTTTACCAACTTGATCTGAG
219551 CTTAAAAACCCGCTCGATCAAACAAATTGTTTTAACGTTGGTTTTCAAAA
219601 CATTGGTATTGGGGTTTTTTGGGTTAATTGTCATCTTTCCCTTTTATCTG
219651 ATGGTTGTGGTTAGTTTTGCTAGTGATGAAAGAGCATTAGACACAAGAAC
219701 CCCAATCCTTTGACCTGATAGTTGAAACTTTGATAACTTTAGTAGGGTGT
219751 TAAGTGATGGGAAATATCTCAATGCAATAGTTGTCAATACTTTAGTAACG
219801 GTACTTTCAGTGTTACTAACATTGTTTTTTACCATTTGCATGGGTTATAG
219851 TTTTTCACTACGGAAGTGAAAATACAAAAAACTGGTGTGGTTTTTCTTTC
219901 TTAGTGTGTTAATACTGCCTGAGTCTGCGCTTTTAATTGGTCAGTATCGG
219951 ATTGTAATAGTTGCTAACTGAAATAACCCCAACAGTCCCTTGATTGTTCT
220001 GGGACTCATTATGCCCTTTGTTAGCAGTGTTTTTAGTGGGTTTATGTACC
220051 GTACTAGCTTTGAAGCCATTCCATCTCAATTAAAAGAGTCAGCACTCATT
220101 GATGGGTGTAATGGCTTTAACTACTTTTTGAAGATTGCTTTACCAATGGT
220151 GAAATCTACCAGTTGAACAGTGGGGATTTTAACTGCATTTAGTGCTTGAA
220201 ATTCCTATTTATGACCATTACTGTTGTTGGGCAACAGGGTGGATTTAAAC
220251 ATTAACTTGTGGGTGTTACAACAAGGGATCTTGGATGCTAACAGTAGTGA
220301 TGAACAGATCAGAACGCTGTTAAATCTCAAGATGAGTGCAGCGATTCTAG
220351 CTATCCTTCCGATGTTTATTATCTACTTTTTGTTCCATAAAAGGATTATG
220401 AATGCCATTAAAAACAGAGCCAACACCATTAAGGGTTAATATGCAAAAGT
220451 TTAAACAACTGGTTGGTGCAATGCACAGATGGGTAAAACTAGCACTATTA
220501 GTAATCATTGTGTTATTAGGGATTATCTTTTGTCTGTTTGCCATCTATGA
220551 CATTGCGCAAGTGATCATTACCATTATCAATGAAGGGGCACTTTTATAAT
220601 CTTTGTTATGAAAAAAGGATCAATAACTGAAGCAATTAATGCCATTAAAC
220651 AATTTGATAAGATTGTTATCTTTCACCATGTGCGCCCTGATGGGGATTGT
220701 TTAGGAGCACAACAAGGCTTGTTTCACCTCATTAAAGCTAACTTTAAAAA
220751 TAAGGAGGTGAAGTGTGTTGGTAATAACAACAACCTGTTTAGCTTTATCA
220801 ACATGACATTTACCAACCAAATTGATGAGAGCTTTTTAAAAGAAGCACTT
220851 GCCATTGTGGTCGATGCTAATTACAAAAACAGGATTGAATTGAGAGAACT
220901 GTTAGATAAAAACCTGTTTAAAGCAGTGTTAAGGATTGATCACCATCCCA
220951 ATGAAGATGATCTAAACACTAGCTTTAACTTTGTTGAAGAAAGCTATGTA
221001 GCTTGTTGTGAGCAGATAGTGGAGATGGCCACAGTGGCGAAGTGGACCAT
221051 ACCACCAGTGGCTGCTACTTTACTATATATAGGTATCTATACGGATAGTA
221101 ATAGATTTCTATATAGTAATACATCATATAGAACACTATACTTAGCAGCA
221151 ATACTATATAAAGCTAAAGCTGATATAAGGATAGTACATGATCATTTAAA
221201 CCTATACTAGTTTAGCAGATCTTAAGTTTAAAAAGTATGTTTATAACCACT
221251 TTAAAACCCAAGGACAAGTGATCTATTTTATCTGTACTAAAAAGATCCAA
221301 AAGAGACTAAGAATGACTGCAGATCAATGTGCTAGAGTTAACTTGTTAAG
221351 TAACATAGCAGATTACAAGATCTGACTTTTCTTTATTGAACAAGCTAATA
221401 ATGAGATCAGGATAGACCTGAGGAGTAATGGGATTAATGTCAGAGATATA
```

| The Nucleotide Sequence of the *Mycoplasma genitalium* Genome |
|---|
| 221451 GCCATTAAGTATGGTGGGGGAGGACATAATAATGCAAGTGGAGCGATCAT |
| 221501 TACTAACAAAAAACAAATTAGTGATGTTGTTAGTGATTGTGTGAAAAAAA |
| 221551 TTGTTTATAATTAAGTTTGTATGCACCAACCAAAGAAAAGACTGGCTAAG |
| 221601 AAGTCTTGAGCCTTTCTAACCGCTGCACTTACCCTTGGGGTTATAACAGG |
| 221651 TGTAGGTGGTTATTTTCTCTTTAACCAAAATAAGCAACGTAGTAGCGTGA |
| 221701 GCAACTTTGCTTACCAACCCAAGCAGTTAAGTGTTAAACACCAACAAGCA |
| 221751 GTTGATGAAACCTTAACCCCTTGGACTTGAAACAATAACAACTTCTCTTC |
| 221801 ACTAAAGATTACTGGAGAGAACCCAGGATCATTTGGATTAGTAAGAAGCC |
| 221851 AAAATGACAACTTAAATATTTCAAGTGTTACAAAGAATTCTAGTGATGAT |
| 221901 AATCTCAAGTATCTCAATGCTGTTGAGAAATACCTTGATGGTCAGCAAAA |
| 221951 CTTTGCAATCAGAAGGTATGATAACAACGGTAGAGCTTTATATGATATTA |
| 222001 ACTTAGCAAAAATGGAAAACCCCTCAACGGTGCAAAGGGGTTTAAATGGC |
| 222051 GAGCCTATCTTTGATCCTTTTAAAGGCTTTGGTTTAACTGGTAATGCCCC |
| 222101 TACTGATTGGAATGAGATCAAAGGTAAAGTTCCAGTAGAAGTAGTTCAAT |
| 222151 CCCCCCATTCCCCCAACCTCTATTTTGTGTTACTAGTGCCTAAGGTGGCA |
| 222201 TTAGAGTATCACAACCTGAATAACCAAGTAGTCAAAGAGAGTTTGGAAGT |
| 222251 GAAAGCAACCCAATCATCCTTCAACCCCACCCAAAGGTTGCAAAAAGATA |
| 222301 GTCCAGTGAAGGATTCAAGTAAACAAGGGGAGAAACTCAGTGAAACAACT |
| 222351 GCTTCATCCATGAGTAGTGGTATGGCTACATCCACTCGAGCCAAGGCCCT |
| 222401 CAAAGTGGAGGTGGAAAGGGGGAGTCAAAGTGATTCACTTTTAAAAAACG |
| 222451 ACTTTGCTAAAAAGCCACTAAAGCATAAGAACAGTAGTGGGGAGGTGAAG |
| 222501 TTAGAGGCAGAGAAGGAGTTTACTGAGGCCTGAAAACCATTGTTGACTAC |
| 222551 TGATCAAATAGCAAGAGAGAAGGGGATGGGGCGACGGTGGTTAGTTTCT |
| 222601 ATGATGCACCCTACAGTGAAAACCATACTGCCTTTGGACTTGTTGATCAC |
| 222651 ATCGATCCTAAAAAGATGGTTGAAAACTACCCACCAAGTTGAAAGACCCC |
| 222701 GAAGTGAAACCACCATGGGATCTGGGATTACAACGCAAGAAACCTCTTGT |
| 222751 TACAAACAACAGGGTTCTTTAACCCAAGAAGACACCCGGAGTGGTTTGAT |
| 222801 GAAGGACAAGCTAAGGCAGATAACACTAGCCCTGGCTTTAAGGTAGGGGA |
| 222851 TACTGATCACAAAAAAGACGGGTTTAAAAAAAACTCTTCTTCTCCAATAG |
| 222901 CTTTACCATTTGAAGCATACTTTGCTAACATTGGTAACATGGTTGCTATT |
| 222951 GGTAACTCGGTATTTATCTTTGGTGGTAATGGTCATGCTACTAAGATGTT |
| 223001 TACCACCAATCCCTTAAGTATTGGGGTATTTAGGATTAAATACACTGATA |
| 223051 ACTTTAGTAAGTCATCAGTAACAGGTTGACCATATGCAGTGTTATTTGGG |
| 223101 GGATTAATTAATCCCCAAACCAATGGCTTGAAAGATCTTCCCCTTGGTAC |
| 223151 CAACAGGTGGTTTGAATATGTACCAAGAATGGCAGTTAGTGGGGTGAAAT |
| 223201 GGGTTGGTAATCAACTAGTGTTAGCAGGAACACTAACAATGGGTGATACA |
| 223251 GCTACTGTACCTAGGTTAAAGTATGATCAACTAGAAAAACACTTAAACCT |
| 223301 AGTTGCTCAAGGCCAGGGACTATTGAGAGAAGACTTGCAGATCTTCACTC |
| 223351 CCTATGGGTGAGCTAATCGTCCTGATATTCCTGTAGGAGCATGACTCCAA |
| 223401 GATGAAATGGGCAGTAAATTTGGTCCCCATTACTTCTTAAATAACCCTGA |
| 223451 TATCCAGGACAATGTTAATAATGATACGGTTGAAGCATTAATCAGTAGTT |
| 223501 ACAAAAACACTGATAAGTTAAAACACGTTTATCCTTATCGATACAGTGGT |
| 223551 TTGTATGCTTGACAGTTATTTAACTGGTCTAACAAACTAACCAACACTCC |
| 223601 CCTATCAGCTAACTTTGTTAATGAAAACAGTTATGCACCAAACAGTTTGT |
| 223651 TTGCTGCTATCTTAAATGAAGATCTGTTAACAGGGCTAAGTGATAAGATT |
| 223701 TTCTATGGTAAGGAGAATGAGTTTGCTGAAAATGAAGCAGATAGGTTTAA |
| 223751 CCAACTTTTAAGTTTAAATCCTAATCCTAACACTAACTGAGCTAGGTATT |
| 223801 TAAACGTAGTACAACGTTTTACTACCGGACCTAACCTTGATAGTTCTACC |
| 223851 TTCGATCAGTTCTTAGACTTTCTCCCCTGAATCGGCAATGGTAAACCCTT |
| 223901 TTCCAACTCCCCCTCCCCTTCAACTTCCGCTTCCTCTTCTACCCCCCTCC |
| 223951 CCACTTTTTCTAACATCAATGTTGGGGTTAAATCAATGATCACTCAACAT |
| 224001 TTAAATAAAGAAAACACCCGGTGGGTGTTTATACCTAACTTTTCACCTGA |
| 224051 CATCTGAACAGGAGCAGGGTATCGCGTTCAAAGTGCTAATCAGAAAAACG |
| 224101 GCATTCCTTTTGAACAGGTGAAACCTAGCAATAATAGTACCCCCTTTGAT |
| 224151 CCCAATTCAGATGATAATAAAGTCACACCATCAGGTGGCTCCTCCAAACC |
| 224201 AACCACCTATCCTGCTTTACCCAACAGTATCAGTCCCACCAGTGACTGGA |
| 224251 TCAATGCATTGACTTTCACTAATAAGAATAACCCGCAGCGCAATCAACTG |
| 224301 TTGCTCAGAAGCTTACTAGGAACTATTCCGGTCTTGATCAATAAGAGTGG |
| 224351 GGATAGTAATGATCAATTTAACAAGGATAGTGAGCAGAAATGGGATAAAA |
| 224401 CTGAGACAAATGAGGGTAATTTACCTGGGTTTGGGGAGGTGAATGGGTTG |
| 224451 TATAATGCCGCATTACTCCATACCTATGGTTTTTTTGGCACCAATACCAA |
| 224501 CTCTACTGATCCTAAGATAGGTTTTAAAGCTGATAGTAGTAGTAGTAGTA |
| 224551 GTAGTACACTAGTAGGTAGTGGGTTAAACTGAACTAGTCAGGATGTAGGT |
| 224601 AATCTTGTTGTAATCAATGACACCAGCTTTGGGTTTCAACTTGGTGGTTG |
| 224651 GTTTATTACCTTCACTGACTTTATCAGACCAAGAACTGGTTATCTAGGGA |
| 224701 TTACCTTAAGTAGCTTACAAGATCAAACCATTATCTGAGCAGATCAGCCT |
| 224751 TGAACTAGTTTCAAAGGCAGTTATCTAGACAGTGATGGTACCCCTAAATC |
| 224801 ACTGTGAGATCCAACTGCTTTAAAATCCCTTCCAAATAGTTCAACTACCT |
| 224851 ATGATACCAATCCTACCCTCTCACCCTCCTTCCAACTCTACCAACCCAAC |
| 224901 AAGGTGAAGGCTTACCAAACCACTAACACCTACAACAAGTTAATTGAACC |
| 224951 AGTTGATGCAACAAGTGCAGCAACTAACATGACCAGTTTGTTAAAACTCC |
| 225001 TAACAACTAAAAACATCAAAGCGAAATTGGGGAAGGGAACAGCTTCTTCG |
| 225051 CAGGGAAATAATAATGGAGGGGGTGTTAGTCAAACGATTAACACCATCAC |
| 225101 CACTACGGGAAATATTAGTGAAGGTCTAAAAGAAGAAACTAGTATTCAAG |
| 225151 CAGAAACACTTAAAAAGTTCTTTGATAGTAAACAAAACAATAAGAGTGAA |
| 225201 ATAGGGATAGGTGATAGTACATTTACCAAGATGGATGGTAAACTAACTGG |
| 225251 CGTAGTATCTACTCCCCTTGTTAACCTTATCAATGGCCAGGGAGCAACTA |

-continued

The Nucleotide Sequence of the *Mycoplasma genitalium* Genome

```
225301 GTGATAGTGATACTGAAAAAATTAGCTTTAAACCTGGTAACCAGATTGAC
225351 TTTAATAGGTTATTCACCTTACCAGTAACTGAACTATTTGATCCTAACAC
225401 GATGTTTGTCTATGACCAGTATGTACCACTATTGGTTAACTTACCTAGTG
225451 GCTTTGATCAAGCTTCAATCCGCTTAAAGGTAATTAGTTACTCAGTAGAA
225501 AACCAAACCTTAGGAGTTAGATTAGAGTTCAAAGATCCTCAAACCCAACA
225551 GTTTATCCCGGTACTAAATGCATCAAGTACAGGTCCCCAAACTGTCTTTC
225601 AACCCTTTAACCAGTGGGCAGACTATGTCTTACCTTTGATTGTAACTGTT
225651 CCTATAGTAGTGATTATCCTTAGTGTTACTTTGGGATTAACGATTGGAAT
225701 TCCAATGCACAGAAACAAAAAGGCATTACAAGCAGGGTTTGATCTTTCTA
225751 ACAAAAAGGTTGATGTCTTGACCAAAGCAGTTGGTAGTGTCTTTAAAGAG
225801 ATCATTAACAGAACAGGGATCTCTAACGCTCCTAAGAAGTTAAAACAAGC
225851 TACCCCAACCAAACCAACTCCTAAAACCCCACCAAAACCTCCAGTAAAAC
225901 AATAAGATGAAAACAATGAGAAAACAGATTTATAAAAAAGCATACTGGTT
225951 ACTATTACCCTTTCTACCATTAGCACTAGCCAATACCTTCCTTGTCAAAG
226001 AGGATAGTAAGAaTGTTACTGCTTACACCCCCTTCGCCACCCCCATCACC
226051 GATTCTAAAAGTGATCTGGTTAGTTTGGCACAACTTGATTCTTCTTATCA
226101 AATCGCTGACCAAACCATCCATAACACCAACCTGTTTGTGTTGTTCAAGT
226151 CTAGGGATGTAAAAGTTAAGTATGAGTCAAGTGGCAGTAACAACATTAGT
226201 TTTGATTCAACTAGTCAAGGTGAAAAACCCTCCTATGTGGTCGAGTTTAC
226251 TAACTCTACCAACATTGGCATCAAGTGAACGATGGTGAAAAAGTATCAGT
226301 TAGATGTACCGAATGTAAGTAGTGACATGAACCAAGTACTGAAAAATTTA
226351 ATTCTTGAACAACCTTTGACTAAGTATACCTTAAACAGTAGTTTGGCCAA
226401 AGAGAAGGGCAAAACGCAAAGGGAGGTACATCTGGGTAGTGGGCAAGCAA
226451 ATCAGTGAACCAGTCAACGCAACCAACATGACCTAAACAACAATCCCAGT
226501 CCCAATGCTTCAACTGGGTTTAAACTCACTACCGGCAATGCATATAGAAA
226551 ACTAAGTGAGTCCTGACCAATTTATGAACCAATTGATGGGACCAAGCAGG
226601 GCAAAGGGAAGGATAGTAGTGGGTGGAGTTCAACTGAAGAAAACGAAGCT
226651 AAAAATGATGCGCCCAGTGTTTCTGGAGGGGATCATCTTCTGGAACATT
226701 TAATAAATACCTCAACACCAAGCAAGCGTTAGAGAGCATCGGTATCTTGT
226751 TTGATGATCAAACCCCAAGAAATGTTATCACCCAACTCTATTATGCTTCT
226801 ACTAGCAAGCTAGCAGTCACCAACAACCACATTGTCGTGATGGGTAACAG
226851 CTTTCTACCCAGCATGTGGTACTGGGTGGTGGAGCGGAGTGCACAGGAAA
226901 ATGCAAGTAACAAACCCACCTGGTTTGCTAATACCAATTTAGACTGAGGA
226951 GAAGACAAACAAAAACAATTTGTTGAGAACCAGTTGGGGTATAAGGAAAC
227001 TACCAGTACCAATTCCCACAACTTCCATTCCAAATCTTTCACCCAACCTG
227051 CATATCTGATCAGTGGCATTGACAGTGTCAATGATCAAATCATCTTCAGT
227101 GGCTTTAAAGCGGGGAGTGTGGGGTATGATAGTAGTAGTAGTAGTAGTAG
227151 TAGTAGTAGTAGTACCAAAGACCAAGCACTTGCTTGATCAACAACAACTA
227201 GCTTAGATAGTAAAACGGGGTATAAGGATCTAGTGACCAACGACACGGGG
227251 CTAAATGGTCCGATCAATGGGAGTTTTTCAATCCAAGCACCTTCAGCTT
227301 TGTTGTTCCTTATTCGGGGAATCATACAAATAATGGAACAACTGGACCCA
227351 TTAAAACTGCTTATCCAGTGAAAAAAGATCAAAAATCAACTGCTCAAGATC
227401 AATTCTTTGATTAACGCTACGCCCTTGAATAGTTATGGGGATGAGGGGAT
227451 TGGGGTGTTTGATGCGTTAGGTTTAAACTATAACTTTAAATCTAACCAAG
227501 AACGTTTACCTTCCAGAACTGATCAGATCTTTGTTTATGGGATTGTCTCC
227551 CCTAATGAATTGCGAAGTGCTAAAAGTTCTGCTGATTCAACTGGTAGTGA
227601 TACAAAGGTAAACTGATCAAACACCCAATCACGTTACCTCCCTGTTCCCT
227651 ATAACTATTCAGAAGGGATCATTGATGCAGATGGATTTAAGCGTCCTGAA
227701 AACAGGGGTGCTAGTGTAACTACCTTCTCAGGGCTTAAATCAATTGCCCC
227751 TGATGGTTTTGCTAACTCAATAGCTAACTTCTCAGTTGGGTTAAAAGCAG
227801 GAATTGATCCTAACCCAGTGATGAGTGGTAAGAAAGCTAACTATGGAGCG
227851 GTTGTGTTAACACGGGGGGGTGTTGTTAGATTAAACTTTAACCCTGGTAA
227901 TGATTCATTGCTTTCAACAACTGATAACAATATAGCACCTATCTCCTTCT
227951 CATTTACTCCGTTCACAGCTGCTGAGAGTGCGGTGGATCTCACTACCTTC
228001 AAAGAAGTTACCTATAACCAAGAATCAGGGTTATGGAGTTATATCTTTGA
228051 CAGCTCCTTAAAACCAAGCCATGATGGTAAACAAACTCCTGTCACTGATA
228101 ACATGGGCTTTAGTGTTATCACTGTCTCAAGaACTGGCATTGAACTAAAC
228151 CAAGACCAAGCTACTACAACTCTTGATGTAGCACCTAGTGCACTAGCAGT
228201 GCAATCAGGGATCCAATCTACCACCCAAACCCTAACTGGAGTACTCCCAC
228251 TTAGTGAGGAATTCAGTCAGTTATTGCTAAAGATAGTGATCAAAATAAG
228301 ATTGATATCTATAAAAACAACAACGGGTTGTTTGAAATTGATACCCAACT
228351 AAGTAATAGTGTTGCCACCAACAACGGTGGGTTAGCACCTAGTTACACAG
228401 AAAACAGGGTTGATGCATGGGGTAAAGTTGAGTTTGCTGATAACAGTGTA
228451 TTGCAAGCAAGAAACCTAGTTGATAAAACTGTTGATGAGATCATCAATAC
228501 CCCTGAAATCTTAAACTCCTTCTTTAGATTCACCCCTGCTTTTGAAGATC
228551 AAAAAGCTACCCTTGTTGCTACTAAGCAAAGTGATACATCACTTAGTGTC
228601 TCACCAAGGATCCAGtTCTTAGATGGTAATTTCTATGATCTTAACTCTAC
228651 CATCGCTGGGGTACCTTTAAACATTGGTTTCCCTTCAAGAGTGTTTGCTG
228701 GGTTTGCAGCACTCCCTGCATGGGTGATCCCTGTATCAGTAGGTTCTTCA
228751 GTTGGGATCTTGTTTATCTTGTTAGTCTTAGGACTTGGGATTGGGATCCC
228801 AATGTACAGGGTAAGAAAACTCCAAGATGCATCGTTTGTTAATGTCTTTA
228851 AAAAGGTTGATACACTCACACTGCTGTCGGTAGTGTGTACAAAAAGATT
228901 ATTACCCAAACTGGTGTGGTGAAAAAAGCACCTAGTGCATTGAAAGCTGC
228951 TAATCCTAGTGTTAAAAAACCTGCTGCTTTTTTAAAACCACCTGTTCAAC
229001 CACCAAGTAAACCTGAAGGGGAACAAAAAGCTGTTGAAGTTAAGTCAGAA
229051 GAAACCAAAAGTTAGTTTTTAACCTTTCAATAACCTAAAACACAATCTTT
229101 AAAACAAGGTTGTGTTTTTTTGTTTTTTGTCACTTTTCACTAAACTTGCA
```

-continued

The Nucleotide Sequence of the *Mycoplasma genitalium* Genome

```
229151 ATTTAGAGAGTGGATATGAAAAGAACAGTTAAAAAAATAAAACCTGACCA
229201 CTTGTTTAATAAAAAGCAGTGGCACTTACTGAGTGAAGAGATCAGTGATA
229251 ACCCAATGATTAAGCGTTATTGACTCAAACAACAAAAGCGTCAGCTTGCC
229301 AAACTAAAAAAACGCCGTTATTTTAAAAATTAACTATGTATTCTACTTTA
229351 AGACAATATAAACCATTGAAAAGAAAGAAATGGTTAAACAAGATCTCAAA
229401 ACGGAAGTTAAAACAACTTTATAACAAAGCTTATTAGTTTTGTTTTTTAT
229451 TTTTACTAGTGCCTAAGGTGGTATTAGAGTACCACAAGCTCAGTAAGGAT
229501 GTAGTCAAAGAGAGTTTGGAAGTGGAAGCAACTGATTCTTTTGATCCCAC
229551 CCAAAGGTTGCAAAAAGATAGTCCAATGAAGGATTCAAGTAAACAAGGGG
229601 AGARACTCAGTGAAACAACTGCTTCATCCATGAGTGGTATGGCTACATCT
229651 CCTCGCAAGGCCCTTAAGATAGAGGTGGAGAAAGGTTCTTCAGGGTCTGA
229701 CACCCTCACCAAATCCGACTTTGCTAAAAAGCCACTGAAACATAAAGAAA
229751 ATAGTGGGACAGAGGTGAAGTTGGATGCACAGAAGGATTTTGCCGGAGAG
229801 AAGGCCTGAAAGCCATTGTTGACTACTGATCAAATAGCAAGAGAGAAGGG
229851 GATGGGGGCGACTTAGACTTTCTCCCCTGAATCGGCAACAACAAACCCTT
229901 CTCCAACTCCCACACTGCTTCCCTTTCTGTTAGTTCAAATACCCCCTCC
229951 CCACTTTTTCTAACATCAATGTTGGGGTTAAATCAATGATCACTCAACAC
230001 TTAAACAAAGAGAACACCCGGTGGGTGTTTACCCCTAACTCTTCACCTGA
230051 CATCTGAACTGGGGCTGGGTATCGCAAACAAGGTAACAATAATGGCATCC
230101 CTTTTGATAATGTGAAACCTAGCAATAGTAGTACCCCCTTTAATCCCAAT
230151 TCAGATGATAATAAAGTCACTTCAGGTGGCTCCTCCAAACCAACCACCTA
230201 CACCCATTTACCCAACAGTATCAGTCCCACCAGTGACTGAAGCAATGCAT
230251 TGACTTTCACTAATAAGAATAACCCGCAACGAAATCAACTGTTGCTCAGA
230301 AGCTTACTAGGAACTATCCCGGTATTGATCAATAAGAGTGGAACGGGAGA
230351 TCAATTTAACAAGGATAGTGAGCAAAAATGAAACGAAACAGATAAATTAG
230401 GAGGCAACCTCCCGGGGCTTGGGGAGGTGAATGGCGGTTTTTATCAACTA
230451 AATAAAAACTTATTAGCTTATTTTTATTAGGTTTTTACTTATTTAATAGT
230501 TAAAAAAGTTTTGAATTTTTCTTAGTTTTTTATTTGTTTAATAGTTAAAA
230551 AACACTAGGCTTTACCTTTATTTAATTAATAAAACCTTTACCCCTATTAC
230601 CAAACCATCCATAACACCAACTTGTTTGTGTTGTTCAAGTCCAAGGATGT
230651 GAAGCTTACATATAGTTCAAGTGGCAGTAACAACATTAGTTTTGATTCAA
230701 CTAACAACAAACCCTCCTATGTGGTCGAATTTACTAATTCCACCAATGTT
230751 GGCATCAAGTGAACGATGGTGAAAAAGTATCAGTTAGATGTACCGAATGT
230801 TTCTAGCAACATGAACGATGTACTGAAAAATTTAATTCTTGAACAACCCC
230851 TTACCAAGTATACGCTTAATAGTAGTTTGGCTAAAGAGAAGGGTAAGACA
230901 CAAGTAGCGGTACATCTGGGTAGTGGGCAAGCAACTAATTGACGATCGAT
230951 GCGCAACTCCATCAGTCTAAACAACAATCCCAGCCCCAATGCTTCAACTG
231001 GGTTTAAATTAGACAAAGGCAATGCATATAGAAAACTAAGTGAATCCTGA
231051 CCAATTTACCAACCAATTGATGGGACCAAGCAGGGCAAAGGGAAGGATCA
231101 AGCGAATTGGAGTTCAACAGAAGAATCAACGGCAGCTAGTGATGCGCCCC
231151 TAAGTACAGGAGGGGGATCATCTTCTGGAACATTTAATAAATACCTCAAC
231201 ACCAAGCAAGCGTTGGAAAGCATCGGTATCTTGTTTGATGGGGATGGAAT
231251 GAGGAATGTGGTTAGCCTCCTTCCTCTACTTTCAACCCAACAAGGTGAAA
231301 AGTGGTCAATACCAAACCACCAACACCTACAACAGGTTAATTGAACCTGA
231351 CAAGTGACAATCAAATAGTGATTTGACTAACATGACCAGCTTGTTAAAAC
231401 TCCTAACAACTAAAAACATCAAAGCGAAATTGGGGAAGGGAACAGCAATG
231451 CAGGGAAGCAAGACACCTTTTCCTTCGTTGTCCCTTATTCAGATAGTCAT
231501 AGTAATCAAACTTCATCAGGAACCATTAAAACGGCTTATCCTGTGAAAAG
231551 TGATCAAAAATCATCAGTAGCGATCAATTCCTTGATCAACGCTACGCCGT
231601 TGAATAGTTATGGGACAATAAAAAAACTACCTGTCAACAAAAAACAGGTA
231651 GTTAATTATTTATCCAATTAGTAAGTTGCCTATGGGTTAACAAAGAGATG
231701 CACTTAATATACGACCAACCTAATTTATTTGAAAGCGTATCTTTTATTAA
231751 TGAATGTGGAACTAAGCAACTATTTATTTAAACACAGCAAAAGCGTGTAAT
231801 TTTTTATTAAAAGCGATTTAGTGGGAACAGAAATAAAAGATTAACATGAC
231851 TTTATACAACTTCTGTTCCCATCTACTAAATTGCACAAAAAAAGCTTTTT
231901 GACAAAAAAATAGTTATTTTTGTAATTGCTTAATTTAATAACAAACTAA
231951 ACTATTATTGTTACTTAATGATTTTTTGATCTATATAGCACAATTAATAT
232001 AACTTCATGATTGATCAAAACAAGTTAATTACTAAGTGAAAAAAAGCATT
232051 TGCAAAAGCTAAGAATTTAACTACTTTAGTTAATCTTAAGAACACTTTAC
232101 ACAACAGTGATTTAAAGCCATTACTCCAAAAGATTAAAACCGCTACAAAA
232151 CTAAGTGAAAAAAGTAGTTTAGGTAAGCTTTATCAATCACTTGATATTCA
232201 ACTAACTGATCTGTTAACTAGTTACARAAAAACCTTTGAAATAAATAACC
232251 AAGTTAGTCAAAAACCTTCACTTGATGTGATGCTACCAGCAACAGAGTTT
232301 ACCAATGGTTCTAATAACGCACTATATCAGGTTATTGATAATTTAGTTGA
232351 ATACTTTAAAAGCTTTTTATTCACAATTAATTTTGATAGTGAACTGACCA
232401 GTATTAGTGACTGTTTTGATCTTTTAAATATCCCTAAAGATCATTCCAGT
232451 AGGAATGAATCTGATTCTTTTTATATCGATAAAACCAGTTTATTGAGAAC
232501 CCATTGTACTGCTACCACGCTAAAAGCAGTCAGAACTTCTAAARAAACTA
232551 ATAATCCTGATATCAGGGTTGTCTCTTTAGGAGCGGTTTTTCGTAATGAT
232601 AGTGATGATGCCACCCACTCCCATCAGTTTACCCAACTTGATTTTATGTG
232651 GATTAAAAAAGGGCTTTCATTAGCTAATTTAAAGTGGTTATTAACAATA
232701 TGATCACCCATTTCTTTGGGGAAAATACTTTTACTAGGTTTAGACTATCC
232751 CACTTCCCATTCACTGAACCCTCGTTTGAAATTGACATTAGGTGTTGGTT
232801 ATGTCAAAATGGTTGTTCTATTTGTAAGCAAACCAAGTGAATTGAGATCT
232851 TAGGGGCGGGGATCATCCATCCCCAGGTGATGAATAACATGGGAATTGGG
232901 GATACTGAAAATATTACTGGGATAGCAGCAGGAATTGGGATTGAACGCTT
232951 AGCAATGTTAAAGTATGGGATTGATGATATCCGTGATTTTTATGATAACA
```

-continued

The Nucleotide Sequence of the *Mycoplasma genitalium* Genome

```
233001  ACTTTAAGTTTTTAACCCAGTTTACTGACTAAAATATGTTGATATCAAAA
233051  AAAACACTTGGCGTTTTAATCCCTGACATCTTTAGTTTTTCTAATGATCA
233101  AATTGCCCAAAAGTTAGAACAAATGGGGATTGAAGTGGAATCAATTAAGC
233151  AGTTTAACAGCCCTGATTACCTCCAACTTGCAAAGGTTGTATCAATCCAA
233201  CCCCATCCCCATGACAACAAGCTTTTTATCTGTGAATTACAAATTGATAA
233251  AAACAAGTTTATTAATGTTGTTTCCAATGCTAATAACATTAACAATCCTG
233301  ATAATATCAACAAGTTTGTCATTGTTGCAAAAAAAGGAACTGAGTTACTC
233351  AACGGGTTAATTGTTAAAACCCAAAATATTAAAGGGATCATTTCAGAAGG
233401  GATTTTATGTAGCTATATTGACATTAACCCCTTCAGTAGACAGATCATTG
233451  AAAAAACAGAAGTTGCTGATGCGATTATCATTGATCATGTTAGCAATGAT
233501  CATGACTGAAACCAATACCTCTCGTTTTTAAGTTTGGATGATGTGATCTT
233551  TGATGTTAAAACCCCAACTAACAGAGCAGATCTTCATAGCTTAATCTTTT
233601  TAGCAAAAGAACTTGGGGTACTTTTGAAAACCAAAACCTTTTTAAAACAA
233651  AAAAGTAGTGTTGTTAACCATGACTTTTTTAAGTTTCCCCTAAATTTAAA
233701  AAACAAGTTAAAAGCGAATTATTTTGGCGGTTTGTTCTTAAGACAAATTA
233751  ACCAACATAGTTCACCTTGAACAGTTAAAGGACTGTTAATTAACCAAATG
233801  ATCAAACCAGTTAACTATTATGTTGATAAAGCTAACTTAGTAACAGTGTT
233851  CACCGCTCAGCCAATCCATTGTCATGATGCAGATAGAATTGTTGGTAACA
233901  TTGAACTTAAACAAGCAACCCATAATGAAACTTTTGTTGGACTTGATGAC
233951  AAGCAATATGAGATTGAACCAGGGGATATTGTTGTTTGTGATGAGAAGGG
234001  CATTATTGCACTGGTAGGGATCATTGGTTCAAAGCGCACAATGGTCAAC
234051  CTACAACAACTAACATCTTTTTTGAAGTTGTTAACTGTAACAGTGAAACC
234101  ATTAAACAAACTGCCAAGCGCTTTTTGATCAATAACTTTGCCAGTAAGTT
234151  TATGGTTAAACCGATTAGCTTATTAGCTACTGATAACTGTTTAAACTACT
234201  TACAAAACAGTTTACTAACCACTGATAACATTGGCAAAATTAGCCACTTT
234251  TCAAGTTCGCTTAAAGTTGAACCATTTAGTAAAAAGCTCACAGTGAATTT
234301  CCATAAGATACGCCAACTAATTGGCATTGALAAAAAGGAACTAACTGATC
234351  AAACCATTAAAAAAAGCCTCAGTCAACTAGGGTTTAAAGTTGACAACCAA
234401  CTTCTCAAAATCCCCAGTTACAGACAAGACATTAATACCTGACAAGACAT
234451  TAGTGAAGAGATTGTGAAGTTAATTGATATCAATAAGTTAAAACCAATTG
234501  GGATCACTAGTAGTTTTAACTTTGAAAAGTCCAGTTACTTTAACACTTTT
234551  AATGCTTTAACAAAACTAAGAAAAAAGCTACAAACACTTGGTTTTCACAA
234601  CGTTATTACCTACCAGTTAACTGATCAAAAAAGTGCAAAAACTTTTAATT
234651  TGTTTAACTTAGAAAATTTCATCACCATTAAAAACCCAGTGTCCCAAAAC
234701  CATTCTGTAATGCGTGTTAGCTTAATTGATTCACTGTTAAAAGTGCTAAA
234751  AACCAATAACAACTATAAGAATGAACTGGTGAACATCTTTGAGTTTTCCT
234801  TTATTAAAACCCAAAACAATAGTGAACTGCACCTGGCAGTATTATGAGTT
234851  GAAAAACTGTTTACTTCTAGTTTCAATCCTATGCAAGGGATAAGCAATGA
234901  TGTTTTTACTATGAAGGGATTAGCAAAACTCATTGTTGCTAACTTAGGGT
234951  TTAGTTGTGACTTTGAACCACTTGATGATAGTGACTATTTTGTTAATAAT
235001  CAAAGTTTAAAAATAGTAGTTTTTAACGAACAGATCGGTTTTATTGGGCT
235051  AATTAAAGAATCATTGTTAAATAACTATGATCTGAACAATAAACCCATTT
235101  ATTGTCTTGAAATCAACTTAGATAGGATGCTCTCTTCTCTAAACAGGATT
235151  GAAAAAAACTACCTTGGTTACAGTAAACTACAACCTGTTTGCAAGGaTCT
235201  TACCTTTAGTTTTACCAACCCTGCTAGTCACTTTGATCAGTTTGCTAACA
235251  TGATCAAAAGGATAACTGGCATTGAAAGTTGAAAGTTAATTAGTGTCTTT
235301  GAAACTATGCAAAACAACCAACTGATCACTAAGTACACCGTTCGTTATTT
235351  TCTGAAAAATGATGCTAACAAACCACTAACTAACCAAACAATTGAACTTA
235401  TCACTAATAACTTAAAACTCCAGTGTGAAAAACTAAAAATTAAATTAGAT
235451  ATTTAGAATTACTTATTACTATCAAGATAGTTACCAACTATTTTGTTAGT
235501  AAAACTTAATACAATTGGCACAAAACGCAAAACACCCTTCTAAAAAAGAA
235551  CAAAAACCACTCGTTAATGAACAGATTGCTTTCAATCAGTTCACTTTAAT
235601  TGATGAAAACAGTACTAATTTAGGGATAGTTAAGATGGAAAACGCTTTAA
235651  AGTTAGCACAAGAAAAACAGTTAGATCTAGTTCTAATTGCTCCAAACCCA
235701  ACCAAACCGATCGTTAAGTTGTTGGACTTTGGCAGATATACCTATGATTT
235751  AAAGCGTAAGAAAAGACAAGCCAAGAAAAACCAAACAATCATCCAAACCA
235801  AAGAAGTTGTTGTCAAACCAACGATTGCTAAACATGATTTAGAATTTAGA
235851  GCAAAACAGAGTAAGAATTGGATAGAAAAAGGTCATCATGTCAAGTTTAT
235901  AGTCCGTGCCTTTGGCAGGGTTAGCACCAGGATAGAGTTAATTGAAAAGG
235951  TGTTTGATGACTTTTACCAGTTAGTTAAAGATGTAGTTGAGATCCAAAAA
236001  CCTTTAACCGCTTCTTCCAAAACGATGTACGCTGCTCTATTAGTACCTTT
236051  AAAAAGATAGTTATGAAAACCAAAAGTGCTGCAGTAAAACGCTTTAAACT
236101  CACCAAATCAGGACAAATTAAGCGCAAACACGCTTATACTTCCCACCTCG
236151  CGCCCCACAAATCAACCAAACAAAAGCGCCATTTGCGCAAGCAAGCTACT
236201  GTGAGCAACAGTGAATTGAAAAGAATTGGTATTTAATTTAGTTATGCGT
236251  GTTAAGGGAACAAATACAACCAGGATTAGAAGAAAAAAATGGTTAAAACA
236301  AGCTAGTGGTAGCTTTGGGACAAGAAAAGCTTCTTTTAAGGCAGCTAAAC
236351  AAACTGTTATCCAAGCAAGCAAGTATGCTTACCGTGATAGGAGACAGAAA
236401  AAACGTGAGTTTCGTTCGTTGTGGATCTTAAGGTTAAATGCTGCACTGCG
236451  TGCACAAGGGATGACTTATTCAGTGTTTATCAATGAATTGAAAAAAGCCA
236501  AGATAGTCATTAACAGAAAGGTACTTTCTGAACTAGCAATTAAAGAACCT
236551  AATAAGTTAAATCTGATTATCAATACCATCAAAAAACCAACTAATAAACC
236601  AACTGTTGCAAAAACTTAGTAACGTTTTTAAAGTTAAGTTTTGCCACCTG
236651  TTTAAACTGTTCAATTTGACTAAAACCGCGTTGTTGGTTAAGAAATAACA
236701  ACGCTTGTTCAATGCCATGACTACTGCCTTTGGGTAAATCATAGTTTACC
236751  TTTTGGTTGAGTAATTGCAGCTGATTAATAAAGCTATCTCTTGCTAAGAT
236801  AGATGCAGCTGCAATCACCAGTGACTTAGTTTCACCATTAATTAGAAACT
```

-continued

The Nucleotide Sequence of the *Mycoplasma genitalium* Genome

```
236851  GATCAGGTAATAACACTGTTTTATCAGTGAAATTAGTTAGCTTATTTAGA
236901  TAGTTAACAAATAACTCTTGATTGGCAAACTGGTCAATGCTAATTGTTAC
236951  TGTTTGTCTTAATAACTGATTTTTTTCCAGTAACTTTTGGTAAAGCTGAC
237001  AGTGTAAATTGGTCAAAAGTAAATTGGTATTTTTCAGTGATTTTGTCAAA
237051  TCATTATACTGCTTGGGATCTAATGTAATTGTATGGTGATCCATTACTGT
237101  TGTTTGGATCGATTTAGCTAACAGTTTGACAGTGTGATCACTGAGTTTTT
237151  TTGAATCAGTTACTTGTAAATTTTcCAAGATTAATAAGCTGTTTTTTTTC
237201  AATTAAAACAGCACTAACACAAATCCCACCAAAACTATCACCCTTGCCAG
237251  ATTCATCACTGCCAATTAAATAAAAATCAGCTGGTTTGTAATGTTGCAAC
237301  TATCTAGTTAATTAATAAAATTATACTTACTCTGATTGATTCTTAATGGC
237351  TGAACAGAAACGTGATTATTATGAAGTGTTAGGAATAACCCCTGATGCTG
237401  ATCAATCAGAGATTAAAAAAGCCTTTCGTAAGCTGGCTAAAAAGTACCAT
237451  CCTGATCGTAACAACGCGCCTGATGCTGCTAAGATTTTTGCTGAAATTAA
237501  TGAAGCAAATGATGTTTTATCAAACCCCAAAAAAAGAGCTAACTATGATA
237551  AGTATGGTTTTGATGGGGTTGATGGTGAACCTGCTTTTAACTTCCAAGCA
237601  GATGTTTTTCAATCCTTTTTTGAAGAGATAGCAAATCAGGGGTTTTTAA
237651  CAACCAAACCAATCCTGAACAAAAAGAAAAAAAGAAACGTTACCACTGGT
237701  TCTCCAAAAAACCTAAGCAAGAACAACCTGAAATTAACTTAGATCACGTT
237751  GTTGAGCAAACCATTAAAAAGGTGCAACAAAACCAAAACCAAAACAAAGA
237801  CCCAGATGAATTACGTTCTAAGGTCCCTGGAGAGGTTACTGCTAGTGATT
237851  GGGAAGCATTGGTTGGTGATACTAGGTATGGGTATTTTGATGAAACAGGG
237901  GATTGGAGTTGAAAGGGTTACTTTTGATGAACAGGGCAAATGGGTTTGAAA
237951  CGAACCAGTTGATTCTGAAACCAGTGAGGTATCAGTTGAACCTGAACCAA
238001  CCCCAGTTGCCCCTGAAGCTAGTTTTGAAGAAGCTCAACCTGAAATTAAT
238051  GCTGAACCAGAAGCTAGTTTTGAATCAACTCCAACTCCAGAACCAGTTGC
238101  CCCAGAAGCTAGTTTTGAAGAAGCTCAACCTGAACCAACTCCAATTCCTG
238151  AACCAATCCCAACCCCAGTTCAAGTTCAACCCCTGTTGTTAGATCTCAAC
238201  CTCTTTACTATCCCAACTAAAGCTACTAAGGATGATCTTTTGTTTGACAA
238251  CATTAACCTCACTACCTATGAACAAGTTGTTGATTATCTCAACAGTCAAG
238301  CAACCCCTAATTTAGCTAAAACCGATGGTGAATTGCAAACGATTGATGGT
238351  ACCAACCCATTGTTATTAGAACAGTGCAAAAAGATCAAAAAACAAGCAGA
238401  ACAACTCTTTAAAAAACTCTTTTTAAAAAAACAACTCCCCTTCATCACCC
238451  AACCTGAAGTTGTTGAGGAAAGTAAAACCAGTTTTGATGAGAACAACGTT
238501  AACCTTGTTTACTTTGAAAAGGTCCCTGAAATCCTTTTCATTAACCAACA
238551  ACCTAAGGAGGTAAAATACACCCGTCAAGTCTTTGATGGGTTGACAAACA
238601  AAACAACTAGTGAAACGATTACACTAGAGATCCAACTCCTCCAAACCCCA
238651  AAAGAGACTGTTAGTGCCATTTTTAAAGGCTTTGGTAATGACCATGGCAA
238701  GGGCTGTGGGGATTTAAAGATTGTTTTTGAAAAGATTAAAAGCCCCTTTT
238751  TTCAAGTCAATGAGGATGGCTTGCACTCTGCTTGCATCATTGACCCTTTA
238801  GTTGCTTACAACGGCGGGATTATCGATGTGTTTGGGCCCTACACTAACTT
238851  CCAAGTTAAGGTAGATGGGGAGATAGACATCAATGCCATTATGAAGTTTG
238901  AAAAACTAGGCATTGCTAAAACCAAGCGCAAGGGCGATCTTTTTGTCCAT
238951  CTCTATTACAGTAGTGTCCCTAAAAAGAAACTCACCACTAACCCCCAAGT
239001  TCAACAGTTCTTAGAACTTTTACAAGCTGAATATGAACTGTTGCAAGACA
239051  ACATCAAGAGCTTAAAGTACTTTAAAAATAACCTAGTTATCCCCAAAAAG
239101  CCACTTGATCAACAAAGCTATCAATACCTCTCCCAAGAACCCATTAGTTA
239151  GAATTTGTTAATATGTGTGAAAAATCACAAACAATTAAAGAGCTTTTAAA
239201  CGCCATTAGAACCTTAGTTGTCAAGAACAATAAAGCTAAGGTTAGTATGA
239251  TTGAAAAGGAACTGTTAGCTTTTGTTAGTGAACTTGACAAAAAGTTCAAA
239301  CAACAACTCAACAACTTCAATGAACTACAACAAAAGATCCCACTACTCCA
239351  AAAAGCTAACGAAGAGTTTGCTTTAAAGTTTGAAAGGATGCAACGCAAG
239401  CACAAAACCAGATCCAAGCCAAACTAGATGAGTTGAATCTTAAAAATAAA
239451  AAGGAGTTAGAACAAGCCAAGAAATATGCGATTGCCAAAACCCTTGACCA
239501  ACCCTTAAACATCATCGATCAGTTTGAAATCGCGCTTTCATATGCCCAAA
239551  AAGACCCTCAAGTAAAAAACTATACCACTGGTTTTACCATGGTACTTGAT
239601  GCTTTTTCAAGGTGATTGGAAGCAAATGGGGTTACCAAGATTAAGATTGA
239651  ACCAGGGATGGAATTTGATGAAAAGATTATGTCTGCATTGGAACTAGTTG
239701  ATTCTAACCTTGCTAAAAACAAGGTAGTAAGAGTCTCAAAATCTGGCTAT
239751  AAACTCTATGACAAAGTGATCCGCTTTGCATCAGTATTTGTCAGCAAAGG
239801  TAATAAAAAATCATAATAACAACTTATGAGTGAACAAAAAAGAAGAACAA
239851  TCCAAATTGCGATAAGTGAAGACCACTATGAAGAGTTACAAAAGGCATTG
239901  GAACTACTTAAAGGGACCCAATTACCCTTTTCAACCACTGTTGAACAGTT
239951  TGTGGAGTTAATCTTATCTAACTATGTAGCTACTTCCAATAAGATTAGTA
240001  GTTTAGCTAAGAGTGGTTTTGATGTAGCTTCATTGCAGCAAGAACTTGAG
240051  AAGATAGGTAACCTTAGTGGGGTTGATGATAACCTCAAGGGTTTTCTCTC
240101  AGAACTGTTGAAAACCTCAAGGAATGGGTTTAGTAACCCCAATAAAGATG
240151  GCAAAAAAAATGATGACGATAATAACTCGTCATCAAAATCATAGTTATAT
240201  AAAACTTTAAGTGGTGCCGAATAACAGAGTCGAACTGTTCTCTGATCCTT
240251  ACCATGGATCTGTTTTGCCCCTAAACCAATTCGGCAGCAAAGCTAATTTC
240301  AATTTTAAATTCAAACTTTAGATGAAAAGTAACTACAGTGCAACTAACAT
240351  CAAGATCTTAAAGGGTTTGGATGCAGTTAAAAAGCGTCGGGGATGTACA
240401  TTGGTTCTACTGATAGTAAGGGTCTGCACCACATGCTATGGGAAATTCTT
240451  GCTAACAGTGTTGATGAAGTTTTAGCTGGTTATGCAACCAATATTACTGT
240501  TACTTTAGATCTCAACAACACCATTACTGTTAGTGATGATGGCAGGGGTA
240551  TTCCCTATGAGATCCACCAAGACAGTAACATCTCTACGATCGATACAGTT
240601  TTCACCTTTCTCCATGCAGGGGGGAAGTTTGATGATCAGTCATACAAACT
240651  AGCAGGGGATTACATGGGGTTGGTGCATCAGTGGTCAATGCCTTAAGTG
```

-continued

The Nucleotide Sequence of the *Mycoplasma genitalium* Genome

240701 ATCATTTAGAAGTAACAGTGAAAAGAAATGGTCAGATCTACCAATCAGTT
240751 TATCAAGCTGGGGGTAAGATCATCCAAAAAGCCAAAAAGATTGGTGATAC
240801 AACTAGCCATGGTACCACTGTTAGTTTCCATGCTGACCCTAAGGTCTTTA
240851 AAAAGGCTCAATTTGATAGCAACATTATTAAAAGCAGGTTAAAAGAGCTA
240901 AGCTTTCTGTTTGCTAAACTAAAGCTCACTTTTACTGATCAAAAAACTAA
240951 TAAAACCACTGTTTTTTTTAGTACCTCAGGACTAGTTCAGTTCCTTGATG
241001 AAATTAATAATACTGTAGAAACACTTGGCCAAAAAACACTGATTAAAGGT
241051 GAGAAGGATGGGATTGAAGTGGAAGTGGTTTTCCAGTTTAACCAATCAGA
241101 TCAAGAGACAATCTTATCATTTGCTAACTCGATTAAAACCTTTGAAGGAG
241151 GGAGTCATGAAAATGGGTTTTGTCTTGCCATTAGTGATGTGATCAACAGC
241201 TATTGCAGAAAGTACAACTTACTAAAAGAAAAAGATAAAAACTTTCAACT
241251 TAGTGAGATCAGACAAGGGTTGAATGCTATTATCAAAGTTAACTTACCTG
241301 AAAAAAACATCGCTTTTGAAGGACAAACTAAGAGTAAGTTGTTTTCAAAG
241351 GAAGTGAAAAACGTTGTTTATGAATTGGTCCAACAACACTATTTCCAGTT
241401 TCTGGAAAGAAACAACAATGATGCTAAATTGATCATTGATAAACTACTCA
241451 ATGCTAGAAAGATTAAAGAGCAAATCAAACAACAACGTGAGTTGAAAAAA
241501 AGTTTATCAAGTCCCCAAAAAGAGAAGATCTTATTTGGGAAGTTAGCACC
241551 TTGTCAAACCAAAAAAACCAGTGAAAAAGAGTTGTTTATTGTTGAAGGTG
241601 ATAGTGCTGGTGGCACTGCTAAAATGGGCCGTGATAGAATTTTTCAAGCT
241651 ATCTTACCTTTGCGCGGCAAGGTGTTAAATGTTGAAAAAATTAACAATAA
241701 GAAGGAAGCGATCACTAACGAAGAGATCCTCACTTTAATCTTTTGTATTG
241751 GTACAGGGATTTTAACTAACTTCAACATCAAGGACTTAAAGTACGGAAAG
241801 ATCATCATTATGACTGATGCAGATAATGATGGCGCACACATCCAAATCCT
241851 CTTACTTACCTTCTTTTATAGGTACATGCAACCCTTAATTGAACTGGGCC
241901 ATGTCTATCTAGCTCTTCCTCCTTTATATAAACTGGAAACCAAAGATAGA
241951 AAAACAGTTAAATACCTCTGGAGTGATTTGGAGTTGGAATCAGTCAAACT
242001 AAAGCTTAATAACTTCACTTTACAACGATACAAAGGACTTGGAGAGATGA
242051 ATGCTGATCAGTTGTGAGATACTACTATGAATCCAACTACCAGAAAGCTA
242101 GTGCAAGTAAAGCTTGATGATCTAATTAACGCTGAAAAGCAAATCAACAT
242151 CTTTATGGGTGAAAAGAGTGATTTGCGCAAACACTGGATTGAAGCCAACA
242201 TTAACTTTAGTGTGGAAAACTAATGGATCAAAAAAACAACAACCTCTTTC
242251 AAAAGGCAATTGAAGAAGTCTTTGCAGTTAGCTTTAGTAAGTATGCTAAA
242301 TACATCATCCAAGATAGAGCTTTACCTGATCTAAGAGATGGGTTAAAACC
242351 AGTACAAAGACGGATCTTATATGGGATGTTTCAAATGGGCTTAAAACCCA
242401 CCACTCCCTATAAAAAATCAGCCCGTGCTGTTGGGGAGATCATGGGGAAA
242451 TACCACCCCCATGGTGATAGTTCCATTTATGATGCAATTATCAGAATGTC
242501 CCAAAGCTGAAAGAACAACTGAACAACTGTTTCTATCCATGGTAACAATG
242551 GTTCAGTGGATGGGGATAATGCTGCAGCAATGCGTTACACAGAAACCCGC
242601 TTAAGCTTGTATGGATTTGAACTATTAAAAGACATTGATAAAAAGTTAGT
242651 TAGTTTTATCAATAACTTTGATGATAGTGAAAAAGAACCAACGGTTTTAC
242701 CAACCTTACTGCCTAACCTCTTTATCAATGGTGCGAGTGGGATAGCTGCT
242751 GGATATGCAACTAATATTGCTCCCCATAACACTAATGAACTATTAGATAG
242801 TCTTTGCTTGCGAATAGACCAACCTAATTGTGAACTTAAACAAATTTTAA
242851 AAATTGTTAAAGGTCCTGATTTTCCAACAGGGGGTAATGTTTATTTTGAA
242901 AAGAGTTTAAGTGATATTTATCAAGCAGGCAAAGGTAAATTTATTATCCA
242951 AGCTAAGTATGAAGTTAACAAGAACTTAAACCAGATTGAAATTACCCAAA
243001 TCCCTTATGAAACACTGAAAGCTAACATTGTCAAACAAATTGAAGAGATT
243051 ATCTTTGACAATAAACTATCTGCTATTGAAAGTGTCATTGATAGTTCAGA
243101 TCGCAACGGCATTAGGATCATTATTAAACACAAGGACTTTTTGCCTGCTG
243151 AGAAGATCATGGCCTTTTTGTTTAAACACACCCAACTCCAAGTGAACTTT
243201 AACCTTAATAACACCGTGATTGCTAACCGCTTTCCCATCCAAATTGGTTT
243251 ACTAAGTTACCTCGATCATTTTTTAAAGTTTTGTCATGAACTAATTATTA
243301 ATAAAGCTAAGTATGAACTTGAGCTTGCAAGCAAGCGCTTGGAAATTATT
243351 TTAGGACTAATTAAAGCGATTAGTATCATTGATAAAATCATCAAATTAAT
243401 TAGATCAGCAGTTGACAAAAGTGATGCAAGAGAAAAGTTAATTGATAACT
243451 TTAAATTTACTTTTAACCAAGCAGAGGCAATTGTTAGTTTGCGACTTTAC
243501 CAACTAACTAACACTGATATTTTTGAACTTAACCAAGAACAAAATGAACT
243551 TGAAAAAACTGTGATTAGTTCAGAGCAACTAATTGCTAGTGAAAAAGCAA
243601 GAAACAAACTCCTAAAAAAACAGTTTGAAGGTTATAAAAAGCAGTTTCAC
243651 CAGCAACGAAGGTCACAAATATGTGGCTTTATTAACCAAAAAAAGGTGGA
243701 GGAAAGTGAGCTAATTGAAAACAAAACTTATGGGGTTTTAATCACTAAAG
243751 CTGGTAACTACCATAAGTTTGAATCTAACCAACTATTAAAAAGCACCACT
243801 GATTTTAAAAGTGAGAGTGACACAATTATCTTTGCACAAACTATTGCTAA
243851 TACCGACCAAATTTTTATTGTCACTTCACTAGGTAACATTATTAATATCC
243901 CTGTTTATAAATTAGCTTTCAATTCCAAAAATAAACTAGCAAGTTTAGTT
243951 AGTAAAAAACCAATCCTTTTGGAGTATGAAACGATTGTTTTTGTTGGAAC
244001 AATGAACAGTGTAAACCAACCAATCCTTGTTTTAACTTCCAAACTAGGAA
244051 TGGTTAAACGGATTGATTTAACCAAACTTAACATTAAGCCACTTAAAGCT
244101 ACTTTGTGTATCTCACTCCGTGATAAAGACCATTTAGTAAGTGCATTTTT
244151 ACAACAAGATGATAAACTGATCTGTTTAGTGTCTGATCACAACTATTACA
244201 CTGTTTTTCACACCAATGAGATCCCATTAATTAGTAGTAAGGGGATGGGA
244251 GTGAAGGGGATGAAGTTAAAACTAGAGGATCAAATTAAGTTTGTTGTTGC
244301 TTTTGAAGCTAATGAACCGTTAGTGATGATATGTAGTGATGGTAGTGTCA
244351 TTAACTTAAAACAAACTGAACTAGTTGTAGTTAGCAGGATGGCAACTGCA
244401 AAAAAACTGCCTGTTAAGAAAGCAATTAACTATTGTTTTAGTGATGCAAC
244451 TAACACCCAGTTAATTAATTTTCAGGGTAAGAACGGTAGTAAATTAATTA
244501 CAACTAGTGAACTGAACCAGATGAGTAAAACTGCAATTAGTCAAACCAGG

-continued

| The Nucleotide Sequence of the *Mycoplasma genitalium* Genome |
| --- |
| 244551 TTTAACAAACTTAATTAGGTTTGGTTGTGGATCTTTTTATCATATTTTTC |
| 244601 TATCTCTTCTTTTAGAGTAGTTAATAAGGCTTTAATCTTTTGGTAGTCCA |
| 244651 TTCTGGTTGGTCCTACTATAGCAAGTTGGTGCTTGGCTTCACTGGTGGTA |
| 244701 TTGATTAAAGTAGAAGCAACTGATATCTCTTTAAAACCCAATTGATCACC |
| 244751 AAAGACAATGTTGGTCTTTTGGTTGGTTTGGTTTATGAATGCCATCTGTT |
| 244801 GTCAAACACTAGTATCTTCAAGCAGATTTAAGATTTTAGTGAGTTTCTCT |
| 244851 TGGTTAGCAAACTCGGGTTGTTTAGCAAGGTATTGGATCCCATAGATCTT |
| 244901 TTTATTTGCCTCAATTTGATCTAAATCAAATAACTTAAATAAGATCTCAT |
| 244951 CAATTACATACTGATACTCATGAACCTTGGTTCTAATGATCTCTTTTAAA |
| 245001 ACTTCTAGTTGGTTGTTAATCTCTGAAAAGCGGGTATCAATGATGCGATC |
| 245051 ATTAAAGATCCTTACACAAATAACAATGTCTTCAAACTGCCTTTGGTTAG |
| 245101 CATAGCTAATGGTTTTTTTAAAGACTTTACCACTAGCGGAGACCAATAAA |
| 245151 AATAAGGCAAATGACTTATCAAGGATGATCAGATCAATCTTTTTTAAAAC |
| 245201 TTCATCACTACTAAAGTTAGTTAACACTACTGGTAGGTTAATGATCTCAT |
| 245251 TGATAAACTTAACCCCAAGTTCAATCACCTCATCAATCGTTTTGTGTTGC |
| 245301 TGGAGAATAACACTTCTTAAGCGGGTTTTCAGATCGTTAGTGGTGTTACT |
| 245351 AACATTTAACACTTTGACATAATACTGATAACCAATTTGGGAAGGAACAC |
| 245401 GGCCTGAAGAGATGTGGTTTTTCTTTAAGAACCCTTTTTTCTCTAAAGCT |
| 245451 GCCATCTCATTTCGTAATGTTCCCCAGAGAGGTTTTTAAAATATTTTTT |
| 245501 GGTTAGTAATTTACTGCCAACAGGGATAGCATAAGCAATGTATTCATTGA |
| 245551 TAATTGCTTTGAGAATTTGGGCTTGCCGTGGCGTTAAATTCTTCATTAGT |
| 245601 TATCTAATTTTATCTTTTAACAATAACCAGCTTGACCACTAATCTAAAAC |
| 245651 AAAAGTTAAAAACTGCACCTAAAAAACCGGGGTGTTATTTGTGAAAAGAT |
| 245701 AGTAACGGTAAAGTTTTATATGTTGGTAAAGCTAGTAATATTTTCAACAG |
| 245751 GGTCCACCAGTATTTTCAAAAGAATAATCCTTATAAAACCCAGCTATTAT |
| 245801 CAAGCCAAATTAGTGATGTTGATTTTTTCATTCTCAAAGATGAAAATGAT |
| 245851 GCTTTAAATCTGGAAGCAAAGCTCATTAATCAATATCAACCCCGCTTTAA |
| 245901 CTTAGTTTTAAAACAAAACAATGGTTATCTTTATTTTTATATCACTAAAG |
| 245951 CCAAAAAACCTACCTTGGAATTAGCCAGAAAATACCAGATTAAAACCACT |
| 246001 AAGTGCTTTGGACCGTTTGCTTCAAGTAAGTTTAAGTTACGTGAGATCCA |
| 246051 TGACCTACTTTTAAAACTCTTTCCTTTAAGAAAGTGTGCACCTCACCAAA |
| 246101 AAAACCACCCGTGCTTTTATTTTCAGATGGGTTTATGTATGGGCAATGT |
| 246151 ATGCAAACTGATACTAAGGAAAAATACCAACAGGTAATTAGTAACATTGA |
| 246201 ACAGTTTTTTAATGACCCTAGTGTGGTAATTAACTATTTAAAAGCTGCAG |
| 246251 AAAAAAAGGCAAGTGATAATCAGGAATTTGAAAAGGCCCAGCAGTTTCTA |
| 246301 ACACTGCAAAAAGCAGTTTTAGAGTTAACAAAAACCCACCATACCACTAT |
| 246351 CATTAAACAAAAATCAAGCCATGATTTTATTGGGTATGTCTTTCAAAATA |
| 246401 ACGTTTTGGCCATTACCATTTTTTGTTATGAAAAAGGGGAGTTAACTGAT |
| 246451 AAAGAACAAGCAGTGTTTACCCTAGAGCAAACTGACATTGTGGAAGTTGA |
| 246501 AAGTGCTATTATCACCTTTATCTACCACCACTATAAAACTACCCCACTTC |
| 246551 CAAGTAAGATTACTGTTTCACTTGATGAAACTAACCTAAAACTTATTAGT |
| 246601 GATAGCTTAAAAATTGGTGTTTTTAAGCCCAAGAATGGTAATGAAAAACT |
| 246651 GATCTTACAAACTGTTATTGATAATGCCAAACATGCACTTGCAACCAAGT |
| 246701 GGTTGAAGTTTACTAGTAACTATGATAAAACCCAGCTCCACAAGGATTTA |
| 246751 GCACAACTTCTAAATACTGATTATATCCATAGTCTTGAGATTATTGATGT |
| 246801 GTCATTCTATGATCAAAACCATGTTGTTGGTTGCATGTTAAGGTTTGAAG |
| 246851 ATGGTAAAAAGATCAAACACTTATCAAGAAGATACAACATTAACAGTTTA |
| 246901 AAAAAAGGTGATACTAACCACATTGCTTTACTTGTTTACAGAAGGATCTT |
| 246951 AAGTGCGATGCAAACCAAAGCTAACCTCCCTTTTAGTGATCTTTTAATTA |
| 247001 TTGATGGTGGTAAAGCACAAATTAAAAGTGTTAAGCAAGTTTTTAGTCTC |
| 247051 TTCAGTAATGTTAAACCACCCATTATCATTGGACTAGTTAAAAACAAAAA |
| 247101 CCACCAAACTGATCACATTATGTTATCTGATTTCCAAGTTAAAAAGATAG |
| 247151 CAATTAACTCCCCACTCTTTCACTATTTAGCAACAATCCAAACTGAAGTT |
| 247201 GATGGTTTTGCTAAAAGAAGTGCTTTTAATAAGTTAAGTAACCACCAACT |
| 247251 GCAAAACCCGTTGCTACAAATCCCAGGAGTTGGCAAGATAACTGCCCAAA |
| 247301 TTCTCTTTGATAACTTTCAAACGCTCAATAACATAAAATTAGCTTCAGTT |
| 247351 AATGAGTTAAGCCAGTTTATTAAAAAACCATTAGCACAAAAGATTAAAAC |
| 247401 TTACTTTGCAAAACAAACTGATTAAGGTTTTGGTAATTGCTGATACCCAT |
| 247451 GGTCAAAACCAGAGGTGGATTGAACTGAAAAACTACCATAACCCTGATGT |
| 247501 GATTATCCATGCAGGAGATCACATGACCACTAAACAATTCATGGATCAAA |
| 247551 ATGCTACTTTTTGAGTGGCAGGTAACAACGATTCAATTGGCAATGAAATT |
| 247601 GAAATTTTCCAGTTAGGGCAAATTAACTTTGTGTTAATGCATGGTCACCA |
| 247651 AGCACCAAGAGATAACCTGAAAAAGTGGTACCAATTATTAGTTTTAAAAG |
| 247701 CACAACAATACCCTTGTGATGTTTTAATCTTTGGTCATAGTCACATTGAA |
| 247751 TATACCAACAAAATTAATATGATCCAGTTAATCAACCCTGGTTCTCTACA |
| 247801 ACTACCAAGAAACCAAACCAACACCCCTTCATACTGTACCTTTATTGTCA |
| 247851 ATAAAGACGAGCTAACTGATCTAACTATCCACTATTACCAAGCTTCAAAA |
| 247901 GTTAGTTAACAGGATCTTTTAGATAGATAGGTTGTAAGGTTAGAGGATCT |
| 247951 TCGATTCTTTCAAAGTGATCGATGTTGCTTAATAACAGCTTGCTATAACT |
| 248001 CTCAATGTTTTCAAAGTTTTCATACATAGGAAGTTCATTGTTTGCCTTAC |
| 248051 ATAACTTCACAAAATCAGCTTTACTAATTAGCTTTATTTCACTAGTAGTT |
| 248101 TGGCTGTATAGTCCACAATAGTTCTGATCATTACCACAACTAATCTTGCT |
| 248151 AATCCCATGTTCATATGGGATTTGAAAGCGGAGTGAATTTAAAGCATAAA |
| 248201 GTTCACAACTGGGATACAATAAACACCAGCTTTTAGCAATGATAGTTGCT |
| 248251 ATCCTCTGACCGGTGAAACTACCAGGGCCAATTGTGACATAAAACTGTTT |
| 248301 AATACTGCTTTTTTTCAACTTGTTTTTTGTTAACATTGTCTCCAGATAAT |
| 248351 AAACAGCAAGTTCAGTTAAGTTCTGTTCAACACCAATGGACAACTCATCA |

-continued

The Nucleotide Sequence of the *Mycoplasma genitalium* Genome

```
248401 ACCACTGCATTGGTTTTCATCTCTAAAATAATGATGTTAAGGGTTTTATA
248451 AGCACAGTCTAAAAACAGCTTATACTTACTTAAAAAGAACATGGAGTGGA
248501 TCGGTTAAAGATAAGTTTAAACTCTTAAGTTTCGTTGAAAACTTAGGTTC
248551 AAGTGGGGCGTGAAAGTCCATAGGTTTGTTTAAAGTGGGATGGATAAAAC
248601 AGATCCTGTTTGCATGGAGAAACTGACCATAGCTATCTTTCTTTTCACTT
248651 TTAATTCCATACAGTGGATCATTATAAACTGGATGTTGGATAAATTTCAG
248701 ATGCACTCTAATTTGGTGGGTTCTACCTGTTAACAATTCCAAGCTAATTA
248751 GTGCTGCTTTTTCATTCTGATTAATCACTTTAAACTTAGTTATTGCTTGC
248801 TTTGCTTTAGCAGTTTGGGCTATTTTAAACATTACCTTGTTGTTATTAAC
248851 CCTTGCTAAAGGTGCATTAATTGAACCAGTTAAGGCATTAAAAGGGAAGT
248901 GGACTAGTGCTACATAATAACGTTTTAAGGTGCGATTTTGCAGTTGATTT
248951 TGCAAATTTAATAAGCTTGCTTGGTTTTTACAGACAACAATTGCCCCACT
249001 AGTATCACGGTCCAATCTGTGCACTAAGTAAACAGGGTTTTTGTTGTTGT
249051 GAAAGATACAAGCAGCTAACAAGCTGGCTTTTTCATTGAAAGTGGTGGGA
249101 TGGGTTAACAAACCTGATGGTTTGTTAATAACCATCAAATCCTTGTCTTC
249151 AAAAAGAACCTCAAGCTTTAAGTTATAAGGTTCAACACTAGTAATGAAAT
249201 CACTAGTTGTCTCATCATGAATCTCAACTTTAATTACATCATCTTTTGCA
249251 ACTATTAAACTGTTTTTAAAAGTTAGTTTTTCATTAACTTTAATCTGTCC
249301 ATTCATGATCAGCTTCACTACCTTTACTCTTGAAAGGTTCAGTAAGCTAG
249351 CTAAAAGACTATCTAAGCGTTTGGTAGTTGTAACAACAAAACACTGTTTC
249401 ATTACTGGTTTTTGGAATGTTTAAACTCTTTGAACATCTGGATTAAAAAA
249451 CAAAAGAATAAACCTATAAAACCAAAGGTAATACAACAATCAGCAAAGTT
249501 AAATACTGAACTACCATTCTGAAAGATAAAGTAATCTAACACTGAATCAT
249551 TAGCTGAAGTTAAACGATCAAAGAAGTTTCCAAGTGAACCAAATGCTAAA
249601 GTTGTAATTCAAAAGATGTAACTATATTTCACCATAAAAaCAAGAAAAAC
249651 TAACGCAATTACTGATAATAATCCCTGGAGAAAGTAAACTAAGCCAGTTT
249701 GGTTTTGTAATAAGCTAAACCCTACCCCTTTGTTTCTAATCACATAGATA
249751 TTAATAAAACCACTATTTGCTACCATGGTGTTATCCATCTCACCATTTAA
249801 CGCATTTCTTAATATGAAAACTTGCAGTAAGATAATAAAGCCAACAAACC
249851 CAATCATTGTCAGTTTATAGAATAAAAATGGTTTTTGGTTTGCAGTTAAA
249901 ACCTGGTGTTTAAGTTGTGAAAAAAACTTGGTTTTTCTTAATTTCATCTA
249951 CTTGTATATTCAGTTAAAATTCACTAATTAACTAACAAAATTATTAAGG
250001 AGTATTAACACTTTTTTACTAGTTTTTAAACTAACTTTTTTAAGTGTAAT
250051 CCTAGTTTAATTTCTGGTAGTTTTCTTTACTAATAGCTACTTGTAAAAAA
250101 TTAAAAGTTAGAATTAATGGCACTATTTAGTATATAGATATCAGGCTTTG
250151 GGGAAAACAAAAAACAAATCAGACTGACAGATCTTTCTAGAAGATTACCG
250201 TTTTTATTTTGAAACAGATTTTGATTGGGTTACATACCTGAACAACTGTT
250251 TAAACAGCTATCCTGATTTTGACATCATCAAGTTCATTAAGAAGTATGGC
250301 CCTGAGTGTGAAAAGAGCTTTCTAAGCTGACAGAGCAAAGCTAAGAGTGA
250351 TGTTTACAGTGAACTGACTAACAAGATTAAAAAACAACAGTTCTCAGAAC
250401 AGTTAATTTACCAGCTAGTCCAACTTGATGCTTTACGAACTAACTATTTA
250451 ATTGGTTCGTTGTTTTCAGATAACAAAACCCAGCGCAAACTCCTGAAGCG
250501 TTCTTGAAAAAATGCTAAGAAAGAAGGTTATACAAAACAAGAATGGTTGA
250551 TGATCTTAGTTGGTTTACCCTTTGAAAAAGGTGCTTATCATAAGCAGTTA
250601 TATGACCATTCACGTCAGGAGATCTTAGATCTTACTGAAGTTATTAAAAA
250651 GCTTTATCTAAAAACAGAGACCAACAACGATAAGCTTGAGTTTGCTGCAA
250701 CTACTAGTAAAACAACAGCGCAGCTAACTAAAACTATGCCCTTAAACAGT
250751 AGTGATCTTGATAAGGATCTAATGGAGTTTAGTGGTGAGAAGTGAGGTGA
250801 TAATTAGTGCCTAAGATTGAAGTTAAAAATGATGATTTAGAGCTAGCTTT
250851 AAAAAAGTTTAAAAGGATATCACTGGAAGTACGCAGGTTAGCACAACGCC
250901 ATGAATACCACTTGCGCAAAGGGATGCGGTTAAGAGAAAAACAAAAGATA
250951 GCACAGAAAAAGCGCAGGAAGTTTCGCAGTTTAGCTAGCCATTAAGATGG
251001 ATAATAAAAACCCCCAGAAACTTATTACTAGTGAATTGTTGGCAAACCAC
251051 CGCTTTAATTTTGCTAAAGATGATAAAGGTGGGTATGATGCTAATGAAGT
251101 TGATGCATTCTTAGATCAACTAACCAAGACTTTAATCCACTATGAGGAGA
251151 TGAAAAACAACGAACAAGAATTGAAAAATGCTTATGACAAGTTGTTTTCA
251201 GATCGTGATCAGATTTTAAGTCGTTGTGCTAAATTAGAAGCTGATTTAAA
251251 CACCTTTTATGAAAATGGTTATGCAAACAAGGTGTTAATTAACCGGGTTC
251301 AGGAGTTGGAGGATAAACTTGAAAAACTACCTGATCGTTACACTGAAAAA
251351 CTAGAAAGGATTGAAAAACTGTTAAAAAAGGTCATTAAACACTGAACTGA
251401 TGGGGAGGACATTAGTAACTTTGAAGATGAGTTTTTTTAAAGATGGTTGT
251451 TGGGATAGGGATTGATGTTGTGCAATTAAAGCGCTTCTTAACTTTAGTTG
251501 AAACTAGTGATTGTTTTGCTAAACGATTGTTAACTAGCAATGAACTAAAC
251551 AGTTATTGAAAGCTAAACAATAACCAAAGAGCTAATTTTCTAGCAGTGCA
251601 TTGAACTTTAAAAGAAGCGATTTATAAAGCTACCAGTCACATCAAACCAC
251651 TTTTCACTAAACTTGAAATTTATAAACTTAACAACCAGTACCGGTGTGAA
251701 TTTATCCAAAACATCAACCTGTTGTTATCAGTTAGTTACACTAATTGCCA
251751 TGTTAGTGCTATCTGTTTAGCACAACAAATGGATAAACTATTTAAAACA
251801 AGTTTTAGATTCATAATAAGGTTTTTACAAATCCTGAGTTTACCAGTTGT
251851 TTTTCCTTACTTTTTATTAAGCTTTTTAGCTTGTTTAATTACTAGTAAAA
251901 ACTATGAATCACTCCCTTATAACTATCCCCCTGAAATCCGATTCAAAAAG
251951 GTGTATAGATTGGTATCAATGTGACTTTACATTAAGGGAATTAAAGTAGT
252001 GACAGTAAATGACAAGATTATCCCTAAAAAACCAGTTTTAGTGGTAGCTA
252051 ACCACAAATCTAACCTTGATCCTTTAGTATTAATTAAGGCCTTTGGCAGG
252101 TTGAAAAATAGTCCACCATTAACCTTTGTTGCTAAGATTGAACTGAAAGA
252151 TACAGTCCTTTTTAAACTGATGAAATTAATTGATTGTGTTTTTATTGATC
252201 GAAAAACATCAGACAAATTGCCAATGCATTGGAAACCCAACAACAACTA
```

The Nucleotide Sequence of the *Mycoplasma genitalium* Genome

```
252251 ATTCGCCAGGGCACTGCTATTGCTGTTTTTGCTGAAGGGACTAGGATTTT
252301 AAGTAATGACATTGGGGAATTTAAACCAGGAGCACTAAAGGTTGCTTACA
252351 ATGCTTTTGTACCTATCTTACCAGTTAGTATTGTGGGTAGCTTAGGAAAG
252401 ATGGAATCAAACAAAAGGCTAAAAGAACATGGTGTTAAGAAAAGTTCAAA
252451 CTATGAGGTTAAAGTAATCTTTAACAAGCTAATTAACCCAATTAGTTTTA
252501 ACCAGATTGATTCTAATAACCTTGCTAATAACATTAGAAGCATTATTAGT
252551 GATGCATACACTAGTGAAAAACCAAGCAATGATTAGTTTAATTTTTGATA
252601 AAAGCAACAGTTTTAACCCCCAACTTTGTGTTGAACTTCTCAACCACTTT
252651 AAAGTGGTTATGCTAACTAAAACCATCGTTGTTGACTATCCCAGCTTTCA
252701 AGCATGAAAAGCACAACTCAAACCGTTTAAATTAGCAGTTTTTAGTGATA
252751 ATTTGCAAACCGAATTAACCCCAAATTCAAAACTCACAGTTTTTAACAAC
252801 TACCAGCAACTTTTAGTTGATAATAATGACCTAATTATCTTTGCAAOCCC
252851 CACTTTAGTTCAGCTTTTTGATAATGAGATTGACCAGTTAATAGTTATCA
252901 ATCCCACTAGTAAATCTAAAGATCAGTTTAACTGTAATTGAAACGACTTT
252951 GTTTTAATTAAACAAACTAATTTCAAGAACCATCAAGTTGGTTATTTTGA
253001 TAAAAAAAGTAGTTATGAACCACCTTTCACTGTTGTTACAGACCACTTCT
253051 TTGGGAACCTAACTGATTTATTTAGTCTTTTAGTTGATAAAAAGGTAAGT
253101 GTAAATGATGTGGATATTGGCTTGATTTCCTTACAATATCTCAATATCAT
253151 TGCAAATTACACCAATAAAAAAGCCATTGAAAAGATCACTGATTATCTGG
253201 TGATTACAAGCAAAATTCTCGCTAAAAAAGCAGATAATCTGCTCAATGAT
253251 CATCAGGAAGAGAGTGTGTTGGAATATGATTTAGCTACTAATAACTTTCG
253301 TGATAAGATGATCGCTAACTTAGTGGAACACAAACGCTATTGTGATTCAC
253351 TGGGTGAATTTGAAAAACTCAGGGTTAACCGCTTAGCTTACTTTTCCAAA
253401 GCTAATGAGATGGAGCAATTTATCAAAACAGCTAATGATCAACTTGTTAC
253451 AGTTGAAGATCAACTCCCTAACTATATTAGTGTCTTAAAACTCTTTCATG
253501 CTATGAACAAGTTACTGGAGATGAGACTCAGCTCTCTTCTAACAAATAAA
253551 AACATCACCATTAAAGAGTTATCAGTTGAACAGGTTCAAAAGGAGTTGGT
253601 TTTAGCAATCAAACAGTTTAACTACCAAACAGTTTCTTTAAAGCGGGTGT
253651 TATTAAAACTTAACCATCCTATCTCTTTAATGTATTTtGTTACTGCTTTT
253701 GTGGCACTTTTAGTGCTATTAAACAACCAGGTAATAGGTTTGGAACAAAA
253751 AGATTATCACAGTGAACTTTACATCTTTTTACTAGATGAAAACCAACTGA
253801 AAACCTTCCAAGAATCACCAGATGAAATGGTAAAAGAATCCAAGCTCAA
253851 CAACAGCAAAACGAACTGATAATTGCTAAAAACAAGCAACTAAGAGCTAT
253901 CAAAAACAAACAAAAGCGAGCTGATTATCTAAAAAAAGAAATATGGTAAA
253951 ATTACTTAGATAAAACTAACTTAAAAGATGAAAACAACAATTAATATTGC
254001 CACCCCTACCCTAAAAAAACCTAGCAAAGAAGCTAACTTGGTTGCTAGTA
254051 TCTATGGGTTGTTATTTGTTTGTGGCGCGAAAGGGATCACTTTAAGAGAA
254101 CTAATTAGGATCTTTAAAAAAGCAGGGATTGAAAAGGTGAAATTAGCACT
254151 CTTAGCACTTGAAAGGAAGTTAGCAGATGATGAGCAATCAGGAGTGGAGT
254201 TGAAAAAATTTGGTAATAGTTTTTCTTTGGTAACAAAACCAATTATCAAA
254251 GACTATCTCCACTTATTATTGGCTCATAAAGTCAAAAATCCCCTTAATTC
254301 CAAAGCAATGGAAGTGTTGGCTATCATTGCTTACAACCAACCTTGCACCA
254351 GACCCAGAATTAATGAAATTAGGGGAGTTGATTCTTTTCAAATTGTTGAT
254401 GATCTAATAGCAAAAGAGTTAATTGTGGAGTTAGGGAGAACTGATAAACC
254451 AGGTCGACCTTTTATTTATGAAGTGTCAGCTAAGTTCTATGATTTATTTG
254501 GCATTGATAGCTTAGATCAACTCCCTAAGATTGAGCATTTTGATCTTGAT
254551 AAATTTAAGCAAGGTAGCTTTTTTGATTCCAACCGCTATGGTGATGAATA
254601 ACCTTATATAATTTACAACATGGATAAAATAGCTATTTTAACTTCGGGTG
254651 GTGATGCTAGTGGGATGAATGCCACCATCGCTTATCTAACCAAATATGCA
254701 ATTGCAAAGCAATTGGAAGTTTTTTATGTAAAAAACGGTTATTATGGCTT
254751 GTATCACAACCATTTTATCACCAGTAAGGAACTTGATTTAACTGACTTTT
254801 TCTTTATGGGGGAACAGTAATAGGATCAAGTCGTTTCAAACAGTTTCAA
254851 GATCCTAGCTTACGAAAACAAGCAGTTTTAAACCTCAAAAAACGTGGTAT
254901 TAACAACCTTGTTGTTATTGGTGGGGATGGGAGTTATATGGGTGCTAAAG
254951 CACTCAGTGAATTAGGATTAAACTGCTTTTGTTTACCTGGTACGATCGAC
255001 AATGATGTCAATTCCAGTGAATTTACCATTGGTTTTTGAACTGCTTTAGA
255051 AGCAATTCGGGTTAATGTTGAAGCAATTTATCACACCACCAAATCCCATA
255101 ACCGCTTAGCAATCATAGAAGTGATGGGCGTGATTGTAGTGATCTGACC
255151 ATCTTTGGGGGTTAGCTACTAATGCTAGTTTTGTTGTTACTAGCAAAAA
255201 TAGCTTGGATCTCAATGGCTTTGAAAAAGCAGTGAGAAAGGTGTTGCAAT
255251 TCCAGAACTATTGTGTTGTTTTGGTTAGTGAAAACATCTATGGTAAGAAC
255301 GGTTTACCTAGTTTAGAAATGGTTAAAGAGCACTTTGAAAACAACGCAAT
255351 TAAGTGTAACCTAGTTTCACTAGGACACACCCAAAGGGGCTTTAGTCCTA
255401 ATAGTATCGAACTCTTTCAGATTAGTTTAATGGCTAAACACACGATTGAT
255451 CTGGTTGTAAATAATGCCAACAGTCAAGTAATAGGGATGAAAAACAACCA
255501 AGCAGTTAACTATGATTTTAACACTGCTTTTAATTTACCAAAAGCTGATA
255551 GAACCAAGTTACTTAACCAAGTTAACACTGCAATTATTTAACGATGATTG
255601 ACCATTTAAAAAGAACAAAGATAATCGCTACCTGTGGCCCAGCTTTAACA
255651 AAAAGCTTGGTTAGCTTAAAGATGCTTGATGATAATGAGTATGCAGCTAT
255701 TAAAAAGGTTGCTTATGCCAACATTGAAGCAATTATTAAAAGTGGGGTTA
255751 GTGTGATTAGGCTTAACTTCTCTCATGGTACCCATGAAGAACAACAAGTG
255801 AGGATCAAGATAGTAAGGGATGTAGCGAAAGCAATGAACATCCCTGTTTC
255851 TATTATGTTAGATACAAATGGTCCTGAGATCAGGATAGTAGAAACTAAAA
255901 AAGAGGGTTTGAAAATCACCAAAGATAGTGAAGTGATTATCAACACCATG
255951 AGTAAAATGATCGCTAGTGACAACCAGTTTGCTGTCAGTGATGCTAGTGG
256001 CAAATACAACATGGTTAATGATGTGAATATAGGTCAGAAAATCCTTGTTG
256051 ATGATGGTAAGTTAACCCTGGTTGTCACAAGGGGTTGACAAACAACATAAC
```

-continued

The Nucleotide Sequence of the *Mycoplasma genitalium* Genome

```
256101 CAGGTTATCTGTGTTGCAAAAAACGACCACACAGTTTTCACTAAAAAAAG
256151 ACTTAACCTACCCAACGCACAGTACTCTATCCCTTTTCTCAGTGAAAAGG
256201 ATCTGAAGGATATTGACTTTGGTTTAAGCCAAGGTATTGACTATATTGCT
256251 GCCTCTTTTGTTAATACTGTTGCAGATATTAAACAACTGAGAGATTATCT
256301 GAAATTAAAGAATGCTAGTGGGGTGAAGATCATCGCTAAGATTGAATCTA
256351 ATCATGCTTTAAATAACATTGATAAGATCATTAAAGCTAGCGATGGGATT
256401 ATGGTTGCTAGGGGTGATTTGGGCCTTGAAATCCCTTATTACCAAGTCCC
256451 TTACTGACAAAGGTACATGATTAAAGCTTGTCGCTTTTTTAACAAGCGTT
256501 CTATTACTGCAACCCAAATGCTTGATTCACTAGAAAAAAACATCCAACCA
256551 ACCCGAGCTGAAGTGACTGATGTTTACTTTGCAGTTGATCGGGGTAATGA
256601 TGCAACTATGTTAAGTGGGGAAACTGCTAGTGGGCTTTACCCTTTAAATG
256651 CAGTAGCGGTGATGCAAAAGATTGATAAACAATCAGAAACCTTCTTTGAT
256701 TACCAGTATAACGTTAACTATTATTTGAAAAACTCCACGGCAAATAAAAG
256751 TAGGTTTTGACACAACGTTGTTTTACCTTTAACAAAAAAGACTGTTCCTA
256801 AAAGAAACTTGTTAACAGTGCCTTTAAGTATGACTTTATTGTCTATCCT
256851 ACTAATAACATTAACAGGATCTATGCATTATCAAACGCACGCTTAGCAGC
256901 AGCAGTTATTATTTTAACCAACAACAAACGGGTTTACACTGGCCATGGTG
256951 TTGATTATGGGATCTTCTGTTATTTAATTGATAAAAACCCCAACCAGCTA
257001 ACCAAAGCTGAACTGATTGAACTTGCTTGAAAAGCAATTAACCACTATCA
257051 GGCTTATGGTGATTTAGAAAAACTCAAACAGTGTTTAGCTGTCTATAATG
257101 AAACAATTATCAATCTTTAGATAAAAATTGGTGAGAGTTTGTAAAATATT
257151 GTACACGGTGCCTTAGCCAAGTGGACTCAAGGCCTGGAGCTGCAACCTCC
257201 ATATCGTCAGTTCGAATCTGACAGGCACCTCCATGTACATGAAAGTTAAC
257251 TACTCTCCATGTGCAAACGGGAAGTAGCTTAGTTTGGTAGAGCACTTGGT
257301 TTGGGACCAAGGGGTCGCAGGTTCAAATCCTGTCTTCCCGACCAAAAGGC
257351 TGGATACCTCAGTTGGTTAGAGGGCCCGGTTCATACCCGGGTTGTCGTGA
257401 GTTCGAGTCTCACTCCAGCCACCAAAGTTACTTAAATATTAAAGGATCTA
257451 TAGCTCAATTGGTTAGAGCCCCCGACTCATAATCGGTCTGTTACAGGTTC
257501 AAGTCCTGTTAGATCCACCACTTTGCTGTGTTAGAATCATATTTGCCGCA
257551 ATTTTGTGGAGACTTACCCAAGCGGCTGAAGGGTTCGGTCTTGAAAACCG
257601 AGAGGTGCTTTATAAGCACGCGAGGGTTCGAATCCCTCAGTCTCCGCCAA
257651 ATAATATTTAATCGCGGGATAGAGCAGTTGGTCAGCTCGTCAGGCTCATA
257701 ATCTGAAGGTCGAGGGTTCAAATCCCTCTCCCGCAACCATGGTTCCATGG
257751 TGTAGTGATAACATATCTCCCTGTCACGGAGGGGTTGCGGGTTTGATTCC
257801 CGTTGGAACCGCCATTGGTCTTGTAGCTCAGTCGGTAGAGCAACGGTCTG
257851 AAGAACCGTGTGTCGGCAGTTCGATTCTGCCCGAGACCACCATTAAAGT
257901 TTTTAAAAAAGCCCTAAAAAGGGGCTTTTTTAGTGTTACCACCAATTAAA
257951 ATATTTTATAGCAAGCAGTTGCATATTTTTAATATAAGTTAGAATTATT
258001 GGTATAGTGTCTTCAGCTGTTTAATTCATATTAAAGCGCATGGAAAAAAA
258051 TAGATCAGCTTTTCAACAAAACCAACAAGCATCAAACCAACCTTTTAACC
258101 AAGATCAAAACCAGTATTACCAAGATCCTAACCAACAACAATTTAACCAA
258151 TCTGGTTTTGATCCAAATCAACAGCAATTTAATCAACCAGGATTTGATCC
258201 TAACCAACAATATTATCAAGATCCCAATCAACAACAATTTAATCAAGCTG
258251 GTTTTGATCAAAACCAACAGTATTACCAAGATCCCAATCAACAGCAATTT
258301 AATCAACCAGGATTTGATCCTAACCAACAATATTATCAAGATCCCAATCA
258351 ACAACAATTTAATCAAGCTGGTTTTGATCAAAACCAGTATTACCAAGATC
258401 CTAACCAACAACAATTTAACCAATCTGGTTTTGATCAAAACCAGTACTAT
258451 CAAGATCCTAATCAGCAACAATTTAACCAGCCTAGTTTTGATCTAAATAA
258501 CCAACAATTTAACCAACCTGGATTCAACCAATCCCCAGCATTTGAAATCA
258551 CACCTCAAGAGCAAAAAGCTGAACAGGAAATGTTTGGTGAAGAACCACCT
258601 CAAGTAGTTAGAGAGATCCATGAACTACCATTTGAAAAGATCCGTTCTTT
258651 TTTACAAAGTGATTTTGATAGCTATAACTTTCGCTTAAACTCACTTAAAA
258701 GCAAACTGGATAATGCCTTGTATTCACTTGATAAAACAATCCAAAACACC
258751 AATGAAAACACTGCTAATCTAGAAGCAATTAGACATAACTTAGAACAAAA
258801 GATTCAAAACCAAAGCAAGCAATTAAGAACTAACTTTGATACCCAAAAGC
258851 TTGATGATAAGATCAATGAATTGGAGATCAGAATGCAAAAACTAACCAGG
258901 AATTTTGAATCTCTAAGTGAACTTTCAAAGCACAACTCTTATCCTAATTA
258951 CTATGAAAAATTGTTACCAAATGGTGGTGATAGTATGACCAATGTCTTTG
259001 AAAAAGCACTAATGATGAATTTATTGAGAACTACATTACCCCCTCAACCC
259051 CAAGTTCAATACTACCCTCAACCCTATCCATACATAAGACCTTACTATGA
259101 TGAACCTATTTACGCTGGGTTTAGAAGAAGGGGTTACCGTGATGACTTCT
259151 ATGAATAAAAAGCGTGTTTTAACTAATGAAACCATTTGATAAAAAACCTT
259201 CGCTGCAACCAATTTATGACATTGGTTTTGATGATGGTTATCTCCAAAGT
259251 GAGTATGAAAAAAATCGTTCTAAAACCGATGTTGATAAGATCGAAAACCA
259301 GCTTTTAAAAGAGATTAAAAGCCTGGAAGATGAACTTAAAAACCTTAAGG
259351 GCTTGAAGAATCAAGCAGAAGATAATCCTGAACTTGATAAAAAGATTAAC
259401 CACTTGGAAGTTGATCTAAACCGTTTGGTTAATGAATATAAAAACTTCCA
259451 GTTCCAAAAGAACCACATGGTTGATAAGGTTAGTGAACTTGATAACTTAA
259501 CCCGTTTTTATAAGAATGAACTAACCCGCTTACAACAAGAAACGCTGAT
259551 TTTCTCAACTCCAAGTATGCTAATTTAGCTAACTTCCAAGCTAACTACCA
259601 CAATAAACTAAATGATTTTCACCGCTTAATAGAAAATCAAAACCAAACCA
259651 TTAACCGCTTAAACCAAAAGATTAATGGTAACCAAAATCTGATTGATAAT
259701 AACGTTGCTTTACTGCAAAACCCCAACATCACAGTTGAAAAAAAGAACTA
259751 CTTACTAAATGTTATTGATCAACTTTACAATGAGCTTGATCAACTTGAGA
259801 ATCAAAAAAGATTATTAAGTATTGAGTATGAAAATACCTATAGAGAGTTA
259851 GTTAGTGCAGATAATGAACTGCAAAATGTTTATGAAAACATCGATCAAAA
259901 TCAGATCCAGTTTAAACACCAATACCAAACTTATAGAGATGAGTTAAGTC
```

-continued

| The Nucleotide Sequence of the *Mycoplasma genitalium* Genome |
|---|
| 259951 AACTTGAGCGCAAGATCCAGCTCACCAAACAAGAGTTAGTTGATAAAGAA |
| 260001 TCAGCACTAAGAGTAAAGATAGATGATGCTGATTTTTACATTAATGCCCG |
| 260051 TTTAGCTGAACTTGATGATGTAGCTAAACAACTTAGCTTTCAAGATGGTA |
| 260101 TTACCAAGCAAAATGCTCAACATGTTGAGGATAAGTTAGTTGCTTTAAAC |
| 260151 AAAGAAAAAGACCGTTTAAATACCCAAAAAGAGGCCTTTTTTAACTTAAG |
| 260201 ACAATCTGCTTTAATTGATATCAATAAACTCCAGCAGGAAAATGAACTGT |
| 260251 TTGCTAAGCACTTAGAACACCAGCAAAATGAGTTTGAACAAAAACAGTCT |
| 260301 GATAGCCTCTTAAAGCTTGAAACTGAATATAAGGCTTTACAACACAAGAT |
| 260351 TAATGAATTTAAAAATGAAAGTGCCACTAAGAGCGAGGAACTTTTAAACC |
| 260401 AAGAACGGGAACTATTTGAAAAACGCAGGGAAATTGACACGCTTTTAACC |
| 260451 CAAGCATCTTTGGAATATGAACACCAACGTGAGTCAAGTCAACTACTCAA |
| 260501 AGATAAGCAGAATGAAGTAAAACAACACTTCCAAAACTTAGAGTATGCTA |
| 260551 AAAAGGAGCTAGACAAAGAAAGAAACCTCTTAGATCAACAAAAAAAAGTT |
| 260601 GATAGTGAAGCAATCTTTCAACTCAAAGAAAAGGTTGCTCAAGAACGTAA |
| 260651 GGAGCTTGAAGAACTATACCTTGTTAAAAAACAAAAACAAGATCAGAAGG |
| 260701 AAAATGAACTGTTGTTTTTTGAAAAGCAGTTAAAACAACACCAAGCAGAT |
| 260751 TTTGAAAATGAATTGGAAGCTAAACAACAGGAGTTGTTTGAAGCTAAACA |
| 260801 TGCATTGGAACGTTCCTTTATCAAACTTGAAGATAAAGAAAAAGATCTTA |
| 260851 ACACTAAAGCACAACAGATTGCCAATGAGTTTTCCCAACTAAAAACTGAT |
| 260901 AAGTCAAAGAGTGCTGATTTTGAACTAATGTTGCAAAATGAGTATGAAAA |
| 260951 CTTGCAACAAGAAAAACAAAAGTTATTCCAAGAACGTACTTACTTTGAAA |
| 261001 GGAATGCTGCGGTTTTATCAAACCGGTTACAACAAAAACGTGAGGAGTTA |
| 261051 TTACAACAAAAAGAAACGCTTGATCAGCTTACAAAAAGCTTTGAGCAAGA |
| 261101 ACGGTTAATCAACCAAAGGGAACACAAGGAGTTGGTTGCATCAGTTGAAA |
| 261151 AACAAAAGGAGATATTGGGCAAAAAACTCCAAGATTTTTCCCAAACTTCA |
| 261201 CTGAACGCTTCTAAAAATTTAGCTGAACGGGAGATGGCAATCAAGTTTAA |
| 261251 AGAAAAGGAGATAGAAGCAACTGAAAAGCAACTGTTAAATGATGTTAATA |
| 261301 ATGCTGAAGTTATCCAAGCAGACTTAGCACAACTCAACCAATCACTTAAC |
| 261351 CAAGAACGCAGTGAATTGCAAAACGCCAAACAAAGGATTGCTGATTTTCA |
| 261401 CAATGATTCACTAAAAAAACTCAATGAGTATGAACTTAGCTTACAAAAAC |
| 261451 GGTTGCAAGAATTACAAACCCTTGAGGCTAACCAAAAACAACATTCATAT |
| 261501 CAAAATCAAGCTTACTTTGAAGGTGAACTTGATAAACTTAACAGAGAAAA |
| 261551 ACAAGCTTTTTTGAACTTACGTAAGAAACAAACTATGGAGGTTGATGCTA |
| 261601 TTAAACAAAGGTTGAGTGATAAACATCAAGCTTTAAATATGCAACAAGCA |
| 261651 GAGCTAGATAGAAAAACCCATGAGTTAAATAATGCTTTTTTAAACCATGA |
| 261701 TGCGGATCAAAAGAGTCTACAGGACCAACTAGCAACTGTTAAAGAGACCC |
| 261751 AAAAACTAATTGATTTAGAACGTAGTGCACTGCTTGAAAAGCAACGTGAG |
| 261801 TTTGCTGAAAATGTTGCTGGTTTTAAGCGCCATTGGTCTAATAAAACTAG |
| 261851 TCAACTCCAAAAGATTTATGAACTGACCAAAAAACAGGAAAGTGAGCAAA |
| 261901 CCCAAAAGGAAACAGAACTAAAGATTGCTTTTAGTGATCTACAAAAAGAC |
| 261951 TATCAGGTTTTTGAACTCCAAAAGGACCAAGAATTTAGACAAATTGAAGC |
| 262001 TAAGCAACGTGAACTTGACAAGTTAGCTGAAAAAAATAATCAGGTCAAAC |
| 262051 TAGAACTTGATAACAGGTTTCAAGCGCTGCAAAACCAAAAGCAAGACACA |
| 262101 GTACAAGCTCAGCTAGAACTGGAACGTGAACAACACCAGTTAAACCTTGA |
| 262151 GCAAACTGCTTTCAACCAAGCTAATGAATCACTTTTAAAACAACGTGAAC |
| 262201 AACTCACCAAAAAGATCCAAGCTTTCCACTATGAGTTGAAAAAGCGTAAC |
| 262251 CAATTCTTAGCTTTAAAAGGGAAAAGGTTGTTTGCAAAAGAGCAAGATCA |
| 262301 ACAACGCAAAGATCAGGAGATCAACTGACGCTTTAAACAGTTTGAAAAGG |
| 262351 AATATACTGATTTTGATGAAGCTAAGAAAAGGGAACTTGAAGAGCTTGAA |
| 262401 AAGATCAGAAGAAGTTTAAGTCAAAGCAACGTTGAATTAGAGAGAAAAAG |
| 262451 AGAAAAACTGGCTACTGATTTCACTAATTTAAATAAGGTTCAACACAACA |
| 262501 CCCAAATTAACCGTGATCAACTTAACAGTCAGATCAGACAGTTCTTATTA |
| 262551 GAACGCAAAAACTTCCAACGCTTTAGTAATGAAGCTAATGCTAAAAAAGC |
| 262601 CTTTTTAATTAAGCGCTTAAGAAGCTTTGCATCCAATCTAAAACTCCAAA |
| 262651 AAGAAGCGTTAGCAATCCAAAAACTAGAGTTTGATAAGCGTGATGAACAA |
| 262701 CAGAAAAAAGAGTTACAGCAAGCTACTTTACAACTAGAACAGTTCAAGTT |
| 262751 TGAAAAGCAAAACTTTGACATTGAAAAACAACGCCAACTAGTTGCTATTA |
| 262801 AAACTCAGTGTGAAAAACTTAGTGATGAAAAAAAGGCACTAAACCAAAAG |
| 262851 CTAGTTGAACTAAAAAACTTATCCCAAACCTATCTTGCTAATAAGAATAA |
| 262901 GGCTGAATACTCCCAGCAACAACTCCAACAGAAATACACCAATTTACTTG |
| 262951 ATCTGAAGGAAAACTTAGAGAGAACCAAAGATCAATTAGATAAAAACAT |
| 263001 CGTTCTATCTTCGCTAGATTAACTAAGTTTGCAAATGACTTACGTTTTGA |
| 263051 AAAAAAGCAACTGTTAAAAGCACAGCGCATAGTTGATGATAAAAACCGTC |
| 263101 TTTTGAAAGAAAATGAACGTAACCTCCATTTCCTTTCCAATGAAACAGAA |
| 263151 CGAAAACGAGCAGTTCTCGAAGATCAAATTTCTTACTTTGAAAAACAACG |
| 263201 TAAACAAGCTACTGATGCGATCCTAGCATCACATAAAGAAGTTAAAAGA |
| 263251 AGGAAGGTGAACTGCAAAAGTTACTGGTTGAATTAGAAACAAGAAAAACC |
| 263301 AAACTCAACAATGATTTTGCAAAATTCTCAAGACAACGTGAAGAGTTTGA |
| 263351 AAACCAACGCTTAAAGCTCTTGGAACTGCAAAAAACCCTGCAAACCCAAA |
| 263401 CTAATTCCAACAACTTTAAAACCAAAGCAATCCAAGAGATTGAAAACAGT |
| 263451 TATAAAAGGGGATGGAAGAACTTAACTTCCAAAAGAAGGAGTTTGATAA |
| 263501 GAATAAATCACGCTTATATGATACTTTAGAAAGATGCGTGATGAGATTG |
| 263551 AAAGAAAGGAAAGTCAGGTTAAGTTAGTTTTAAAAGAGACCCAAAGGAAA |
| 263601 GCCAACCTCTTAGAAGCACAAGCCAACAAACTTAACATTGAAAAAAACAC |
| 263651 TATTGACTTTAAAGAAAAAGAGTTAAAAGCCTTTAAAGATAAGGTTGATC |
| 263701 AAGACATTGATTCAACCAATAAACAACGCAAGGAGTTAAATGAGCTTTTA |
| 263751 AATGAAAACAAGTTATTACAACAATCACTAATCGAAAGAGAAAGGGCTAT |

-continued

The Nucleotide Sequence of the *Mycoplasma genitalium* Genome

```
263801 TAATTCCAAAGATTCACTTCTAAATAAGAAGATAGAAACGATTAAACGCC
263851 AACTCCATGATAAGGAGATGCGGGTGTTGCGCTTGGTTGATAGAATGAAA
263901 TTAGCAGAACAGAAATACCAAACAGAAATCAACCGCTTAAGAACCCAAAC
263951 TTTCGATTCTGAAAAACAAGACATTAAAAACTTCTTCCCACCGTTATTTA
264001 AAATTAACGGTAATGTATATGGCCTTTCCTTACTTGTACCCCTGACTATAT
264051 CCTCAACAAAAGCAAGATGATAATACTCTGCAAATTCGTCAGCTTTTTGA
264101 ACAGCAGCTGCAGTTCATGCAACAACGCTATGAAAATGAGTTAAATGAAT
264151 TGCGTAGACAACGTAATTTACTTGAGAAAAAACTTGATCAAATCCAACTA
264201 GAATCCCAACTTAATAATAAGCAAAGTGAGTTTAGTAAGGTGGAATCAAT
264251 GATGGAAAAACTACTTGAAAAAACTGAGAGTAGGTTAAATGATTTTGATC
264301 AGAAAATTAACTATCTCACCAAGAAAGTTAACCAACACAACACCTATCAA
264351 CCAAGTTCCTATCAACCAACTCCTTCTTATCAAGACAGTGATAAACAACA
264401 GTTGTTATTTAGAATCCAAGAACTGGAAAAACAAAACTTATTCCAACAAC
264451 AATTTCAACCTGCACCAGCTGTTGTCCAACAACCTACTAGTTTTGCAGCC
264501 CCTAACATCACCAAACAACAGCAAATTGCCCAACTTAATGCTGAAATTAA
264551 CAACATTAAAAGGTTGATTGCCCAAAAAGCAGCAAGTAAATAAAGATGGT
264601 TAATAATGAATATCAACAACTAAACACTTTAGTTGAGAGTGATGATGAAG
264651 CGGATCTTGTGATTGCTAACCTAGTTAAACAACTCAATGAACTAAAGCAA
264701 ATCCTTGTTTCACTAGATAATCAAGAAGCAAGTGCCACTGCAGTTACTGA
264751 TAAAAAGGAAGAGGAATACAACCAAAACCAATCCAGTTTCCATAACTTCA
264801 GCAAAGAAACACTGCAAAAGCAAGCAAAACGTGGTTTTCTTTTACTGGAA
264851 CGCTGTTCGTTGGTTGGGTTACAACAACTAGAGTTGGAGTATGTTAATTT
264901 GTTGGGCAGAAGTTTTGATTCTTATCAACAAAAAACAGAGCTTTTAAACA
264951 ACTTAAAGGAGCTTGTTGATGAACATTTCAGTGATACTGAAAAAATTATC
265001 AATACCCTTGAAAAGATCTTTGATGTTATTGGCGGTAGTGAATATACCCC
265051 TGTCTTAAACTCGTTTTTTAACAAGCTTTTAAGTGATCCTGATCCAATCC
265101 AACGGGAAATTGGCTTAAGACAATTTATCATCACTCTCCGTCAGCGCTTT
265151 AAAAAGTTATCACAAAAGATTGACAGTTCTCTCAAACAGATAGAAACAGA
265201 GGCTAAAATAGCCACTGAACAGGTTCAAAATAGTGAAGTGATGTTCGGTC
265251 CCCCTGATATTGCTAATGATCATGAGTTAAACCTGAACTGACCTGATAGT
265301 GAAACAGATGCTATCTTAAGTTCAATGGAAAATGAATTGGAAGCTGCTTT
265351 ATTAGCAAAACACCAAGAAGAACCACCGTTAATTGTTACCCCACCCAGCT
265401 TAATAAAACCAACTGTTAGTCAACCTGAAGTTGAAGTTGTTACACCTACT
265451 AACAACACTAATTTCCAACCCCAAGTTGATCTCAAACCTACTGATTTGAA
265501 AAAACAACAGAAGAAAAAACCACTTAACTTTATTACCCGTCCTGTTTTCA
265551 AAAGTAATTTGCCACCGAAACTAAGTAAGGATGACATAGTTCATTATGCG
265601 CACCAGTTACTTGAAAAAAATACCCATAATGAATAGTGATAGTGATCTAA
265651 AACTCCAAAAGGTGTGGATCGAGCGGCATGTTGATCAAGATGAACTTAGT
265701 TTAACAACTACTGCAGTTGAACTTAAAAAGAGTGATGAACAAAAACCTGT
265751 TGCCATTAAAAGTAGTGACTTTATTGGTCATGAAGAGTTAATCTCTGTTC
265801 CAGTTTTACTAATCCCAACCCCTGTTGTTAAAGAGATTGATCAACCAGCA
265851 GTTATTCCTCCAGTTAAAGCAAAACCAAAAGCAACTAAAAAGAAAACTCC
265901 TGTTAAATCAAAACCAACTAGTAAATCAACTAAACAAACAAAACCTAAAC
265951 AATCCAAGCCCAAATCAAAACAAGTTCAACAAACCAAAGCTAAACCAACC
266001 CAAATTCAAACAAAAAAAAGCAATAAAAAAACCAGATCTTAATCTGGTTT
266051 TTTTAGTGTTAACAACAGTAGTTTTAACTAAAAACTGGAAAGGAATAGGA
266101 AGAACTACCTGGGGTTAATCCTAGTTTAAACCGTGCGGTGTTAAAGTAAT
266151 TGCTTTTAGAGCGATAACTATTATTTTTATTCTCATTATCATCATCAGAA
266201 CCATTGGCATTAGCTGTGGTACTTTGAAAAATGTCATTTACTGCATGTGC
266251 AACCCCAGTAAGTGCATTAACTATCATAATAAGTCCTGCACTAAAAGTTC
266301 AGAAAGATAATCCACCAACAACTTGCTTAGCTTGTGCTTTTTCTAATTTA
266351 TACATATAACTCCTTTTGTCTATTAATCACATCTAAATCTAAAAGTGCCA
266401 AAGTTTTATAATTGATCAACTGTCATCATAGCTCAATAGGACAGAGTATC
266451 AGCTTGCGGAGCTGAGGGTTACAGGTTCGATTCCTGTTGGTGACGCCATT
266501 AACTTTATTTGCCTATCAGTTAAATAACTGGTAGGCTTTTTTATTGTTTT
266551 GTAGTTTATCAAGGGTTAATTTAAGTTGTAGTCATTTCATTTTGGACAAA
266601 AAGAAATTTTTATGCTAAGATAAAAGTGTTTAAAAGTGTCGCAAAGTGTG
266651 ACAAAGTGGAAAAAATGCTGCTAGGTACCTTTAATCTTACCCTTGATAAC
266701 AAGAACAGAATTAGCTTGCCAGCTAAGCTCCGTAGTTTCTTTGATAGCAG
266751 CATAGTTATTAACCGCGGCTTTGAAAACTGTTTGGAAATTAGAAAACCTG
266801 CAGACTTTGAGAGTTATTTTCAAACCTTTAATAACTTCCCTAACACCCAA
266851 AAAGACACAAGAACATTAAAACGCTTAATCTTTGCTAATGCTAATCTAGT
266901 TGAACTTGATAGTGCAAACAGAATCCTAATCCCTAATAACCTAATTAGTG
266951 ATGCTAAGTTAGATAAAGAGATCGTGTTAATTGGTCAATTTGACCATCTT
267001 GAAGTTTGGGATAAAGTGCAATATGAACAATATCTAGCTAGTTCAGAATC
267051 ACTAGAGACAGTAGCTGAAAGGATGAAAGATGCTAAATAACCAACAGATC
267101 CACCAGAGTGTACTGATCAATGAAGTGATCCATAACCTCAATATTAACCC
267151 TTGTGGTAACTATTTAGATCTAACTGCAGGGTTTGCAGGACACAGTCAAA
267201 AGATCTTAGAAAAACTAACAACAGGAACTTTAACAATTAATGATGTTGAT
267251 AAAGAAAGTATTAATTTTTGCCAAAAGCTTTTTTTTAAAAACAACAACGT
267301 TGTTATTATTCACGATAACTTTGCTAACTTCCCAGTTCATCTTAAACAAC
267351 TATCAATAACCAAGTTTGATGGGATCTTAATGGACCTTGGTGTATCAAGC
267401 CATCAACTCAACCAACCTAATCGCGGTTTTAGTTTTAAGAATGATGGACC
267451 GATTGACATGCGTATGGACCAATCCAATCAGAAAAATACCGCACTAACAG
267501 TTTTAAAAAACTTAACTGAACAAAAGTTAAGTCTAATCCTTAAAAAGTAT
267551 GGTGATATTAAACACCCTAAACCAATTGCTATTGGATTGAAAAAAGCAGT
267601 TCAAACTGAAAAAAATCTTACCACAACTCAACTAGCAAAAGTGGTAAAAG
```

-continued

The Nucleotide Sequence of the *Mycoplasma genitalium* Genome

```
267651 AATGTGCTACTGGATTTGAAAAATACCAATCAAGAAACTATCTTGCCAAA
267701 GTTTTTCAAGCAATTAGGATCTATCTTAATGATGAGATTACTAATCTGAA
267751 AACTGCGTTAACTTTTATCCCTAATCTTTTAAAAAACAACAGCAGGTTTC
267801 TTGTGATTGTTTTTCACTCCATTGAAGAAAAAATTGTAAGGAATTTCATT
267851 GCAAAACTAACCAGCTTTATCCAACCTGAAGCTCTACCCATTAAACTCAC
267901 TCCTGCTTACCAGTTAATTACAAAAAAACCAATCCTACCTTCCCAAAAAG
267951 AACTTGAATTAAACCCGCGTTCGCGTAGTGCCAAACTCTTTGTTATCCAA
268001 AAAAACTAGTATGTACAAACCAAAAAATATTAACAGCGTATTAACCTTTT
268051 ATAAGGATCAGATCCAACTGGTTGTTAGTGATGATCAAAACCAGTTCAAC
268101 ATCTTGTTTTACCAAACAATTGATAACGATGGCTTTTATTCAAAACAACA
268151 GTTGAAAAACAAACTAAGACTCAAGTTAGCATTAAACCAACTAGTTGATC
268201 AAGCTAACTATTTTCTTGGTTTTAAACTGGAAAAGGTAGTTGTTGTTCTC
268251 GCTGAACTGATTGATGATTTGAAGATCCATAATTTCAAGAGTGAGATCTT
268301 TTTTACTGGTTATGATTTTGATCATAAAGCGATGATTAAAAAAGAAAAAC
268351 AACGCTTTTGTGAGCAAAATAACCAACTAACAGTTATGGATACAATGGTT
268401 TTAAACTACCATGATGTTATTAACAATAAGATCACCAAAAGCTTTGCATT
268451 TAACAAGAGCTATGTAGCTAATTTAGTGGCATATTCCTCTAAAAGTAACC
268501 TGATCGGGGAGTTGAAGTTCTTTTTAAAAAGAAACGTTAATCTTAAGGTT
268551 AAGAAAATTATTAGTCACCACTTAGCATTAGCCAACTCCTTAAGTAAGAA
268601 ACAAAACAACATGTTTGTTTATTTAGGACAAAAAACTACTGAACTGATGC
268651 TATTTATGGACAATGCTTTAGTTGATGTTATTACCAACCAGTTTGGTAAA
268701 AACCACTTTATTGATATTCCAGCTAACCAGGAAAACAAACCACTGCTTGA
268751 GTTTTTAGTTGATAACACCACTAAGATTGGTGATTGTTATTCGCTTGGTA
268801 TGACCTATACAGATGGTGATAGTTACAAAGAGATTAAGGCTTTGACTATT
268851 GGTGATTTAATGCAAACAGTTAGTGACAAGATCAAAACCTTAATTGATTT
268901 TATTAACAGTGGTTCTCTAACTTTTTTCAACAAGTTTAAAACCTTACCTA
268951 AGCTATTGTATTTTTATACAAGATCAAAACAAATTACCAACCTTTTTCAA
269001 GCTAATGTTGCACTTATCAATCCCCAGTTTAAAACTGTTGATATTTATAA
269051 GAACAAGATCCAGTTTATTAGTGAAAACTACCTGTTAAGCTGTGAAGCGA
269101 TTAGCTTGCAGATTACCAATAGAATCAAAAACCAAATTAGTTTTGATTTC
269151 ACAAATGCTGATAATATTCAAAAACCTAAACCAAAAAAAACACTTCATGAT
269201 CTTATCAAAACACCTAACAAAGTTTGTCCAACGCTTGGTTAAATAACTAT
269251 GGATGAAAATGAAACTCAATTCAACAAGTTAAACCAAGTTAAAAACAAGC
269301 TGAAAATTGGTGTTTTTGGGATTGGAGGTGCTGGTAATAACATTGTTGAT
269351 GCATCACTTTATCACTATCCTAATTTAGCAAGTGAAAACATCCACTTTTA
269401 TGCTATAAATTCAGATTTACAACACCTTGCATTTAAAACGAATGTTAAAA
269451 ATAAACTCTTAATTCAAGACCATACTAACAAGGGCTTTGGAGCGGGGGGT
269501 GATCCAGCTAAAGGAGCTAGTTTAGCAATAAGCTTTCAAGAACAGTTTAA
269551 TACACTTACAGATGGGTATGATTTTTGTATCTTAGTTGCTGGATTTGGTA
269601 AGGGTACTGGTACAGGTGCTACCCCAGTTTTTAGCAAGATCTTAAAAACT
269651 AAGAAGATCTTAAATGTTGCTATTGTTACCTATCCATCTTTAAACGAGGG
269701 ATTAACAGTGAGAAACAAAGCCACTAAGGGGCTTGAAATTCTCAACAAAG
269751 CAACTGATAGTTACATGCTATTTTGTAATGAAAAATGTACAAATGGTATC
269801 TACCAACTAGCAAACACAGAGATAGTCAGTGCCATTAAAAAACCTAATAGA
269851 ACTAATTACTATTCCTTTGCAGCAAAACATTGATTTTGAAGATGTACGTG
269901 CCTTTTTTCAAACCAAAAAAACTAACCAAGATCAACAGCTTTTTACTGTT
269951 ACTCACCCCTTTAGTTTTAGCTTTGATAGTAAAGATAGTATAGAACAGTT
270001 TGCTAAACAGTTTAAGAACTTTGAAAAAGTTAGTTATTTTGACCACTCTA
270051 TAGTAGGAGCTAAAAAAGTGTTATTGAAAGCTAACATTAACCAAAAGATA
270101 GTCAAGCTTAACTTCAAGCAGATCCAAGATATTATCTGAACTAAAATTGA
270151 CAACTACCAACTTGAGATTAGGTTAGGGGTTGATTTTGTGACAACCATCC
270201 CTAATATCCAAATTTTTATCCTCAGTGAACACAAAAATCCAGTTTCGCTT
270251 CCCATTGATAATAAATCAACTGAAAACAACCAAAATAAGTTGAAACTTTT
270301 AGATGAGCTGAAAGAACTTGGCATGAAATATGTTAAGCACCAAAACCAAA
270351 TCTACTAATTAATTTAATTTATCGTTTAGAATTGCTATCTTAAGCAATAG
270401 TTTATGGGTCAAATCAATCGGAAGTTTAGCGAAAAGCAGTTCTTACTTTT
270451 TGTTGTTAACTATATTGCTGGATTTGGCTTTATTGCTACTGCTATCTCAC
270501 TGTTTCGCTTAGGACCTTTTTCTTGGTTAATCTTTCTGCTTGTTAGCTTA
270551 GTTAGTTTAATTGTTACCTTATCATTCGCACGGCTTTCATCAATAGATAG
270601 TCAAAACTATGGTGGGCCTTATCTTTGGGCTAAGAAAGCGGTTGATAAAG
270651 AGAAGATAGCAGGGAGAATGTTTAGCTTTTTTACGGGGTGAAATAACTTT
270701 ATCATTGGTCCTCTTTCAGCAGCAACTGCACCACTTTTTATCCTCAATTC
270751 CTTTAGTGGTATTGATGGGATTAGAGGTAACTTAGTTAACACTTGAATCC
270801 TAATTGCAATAGGTTTTTCTTTTTATGTATTACTAGCATTTATCTCAACC
270851 AAAGGAACCTCACTAAACAAGAAACTAATAGCACTATTTGCTTCAGTAAA
270901 GTGGATTGTGATCCTCTCAGCACTAATAGTAGCAATCTATGTTATTGCTA
270951 GAGATGGTAATGGTTATAGTCAAAACAATAACTTAGAAAGTGGTTTTTTT
271001 GGGAGAAGAGAGATTAGTTTTGCACAGATAGCAACGGTATTTATTACCTT
271051 CTTTTATTCTTATGCAGGGGTTGAAGATATCTCAGTGATGACTCCTGATG
271101 TTAAAACTAATAACTTTAGAAAGATATTAATTGTCTCTTTTATAGCAGTT
271151 TTCCTCTTTTATTTCATTGGGATTATTATTCTAAATGGTTTGCAAAACAT
271201 TGCTCAAAGAGGTGGGAAGCCAATTCAATTGGTAATGTAGCGGATATCT
271251 TTAAAAAAGCTGCTGGGCTTGGGACTTTAATCTTTTATGGAGTTGGAGCA
271301 TTGTTTAACAATGTCTCAACCAGACTTTCAACTATTATTGCCAACTCCAG
271351 AAAGATTCTTCCGCTTGCTTATGATAACTATTTACCTAGTTTCTTTTACA
271401 AGCAAAACAAAAAAGGTGAGTTTCAGAATGCAATTTGGTTTACCTTTGGT
271451 ACTACTTTAATTGCAATGACTTTGCTTGTCTTTATCCCTTTAGTTGCTTC
```

| The Nucleotide Sequence of the *Mycoplasma genitalium* Genome |
|---|
| 271501 TAACTTTGATTTTGATAATGCTACTGAGTATGCAGCATCTGTTGGCTCAG |
| 271551 CTGCAACTTTGCTACAATATATTTTTGTTTTTTTTATAATCTTTAAGTTT |
| 271601 ATCTATAAAAAGAACCACTCTACCAGAAAAAATGGGTTAAAACAACTGA |
| 271651 AGAATTATTGTTTTGTTTAGGAACAATTGTCATTGTTTTAATGTTGTTGG |
| 271701 TTTATCTGTTTCCTGTTATAGATGGATTTTCAAAATGGGAAACTAAACAC |
| 271751 ACATTAACAATTGTGTTATATGGGGTTTTAAGCCTGATAGGATTGGTACT |
| 271801 TTTTTTGCTCCAAGAATACAAACATAAAAACAAGCAAAATGCAAACAAAC |
| 271851 AAACAACCCAAACAACAGTTTAGTGAAAAGCAATTCATTGCTTTTGTCTT |
| 271901 TAACTATATTGCTGGATTTGGCTTTATATCAGTGGTGATGACCATGTTTG |
| 271951 ATGTTGGGCCATTTTCCTATCTTGTTTTAGGGTTAACTTCGTTTGCTATT |
| 272001 TTAGGAGTTGTGCTTTCTTTTTCTCGCCTTTCAGTTCTCTGTGGTAATAG |
| 272051 TGCTTATGGAGGGAGTTATTTAATTGCTAAAAAAGCAGTTGGTACTAACA |
| 272101 GTAAAACAAAAAGGTTTTTTGTTTTTTTAAGTGGGTGGAATGTATCGTTA |
| 272151 ACAGGATCTTTTAACGGTGTTGTTATTCCAGCAGTATTAATCTTTTCCTT |
| 272201 TGCAGATATTCCAGTAGTTAAAGCGAATAATAACATCATTATTGGCCTTT |
| 272251 TAGTAGGTGGGTTTTTGTTGTTTGGCTTACTTACTTTTATCTCGTTATTT |
| 272301 GGTTTAAAAATTAACAAGAAAGCAATCTTTTATTTTGCTGTTATTAAGTG |
| 272351 GATAGTAGTAATAGGTGGGTTTATCTTAGGGATCTATTTAATTGGTACTA |
| 272401 CCAATGGTAAAGGTTTTGTTGAAAACAATTTAATTGGGACTAGGGAAAAC |
| 272451 ATTGATTTTTCAAGATTATCTTTATTAGTCTGGCTTTAACCATTGCTTT |
| 272501 TGCAGGGACAGAGGATTTAGCTTCGATTACTCCTGATGTCAAGTCAAATA |
| 272551 ACTTAAGAAAGTGTTTTTTAATTGCCTTTGGGTGTGTTGTGTTACTTTAC |
| 272601 CTAGTTGGGTTTGTTATTATCAGTGGACTTGATGGGATTAGAGGTTATGG |
| 272651 ATTAGCATTAGGTAATAAAGATCCCAAGGCAATTAATAACTATGGATCTA |
| 272701 TCTACCGTTTGGTAGGAGGAGTTCCTTTACTTGTTATCTATGGACTTGGG |
| 272751 TTACTTGTCAATTCCTTAGCATCACGCCTATCAATGACAATTACAACAGC |
| 272801 TAGAAAATATGTAGCTTTAGCTCAAGATGGGTTTTTACCCTCTTTTTTAG |
| 272851 CAAAAACTAATAAACATAATGAGTATCATCATGCAGTTTTAATTAGTAAT |
| 272901 CTAATGACTTTATTAGTGATGCTAATTATGGTAATAATCCCCTTTTTACC |
| 272951 AGACCATAACAACAATAACAATAGTTTGTTTAATGCTATTGAACAGTTGG |
| 273001 TTACAGTTACCATTGAAATGGCTGCAGCCATTTCTTTGATCCAATACTTT |
| 273051 ATTACCTTTATCTTCTTTTTTATGATCTTTGCTAAAAAGGAAAACCAGAA |
| 273101 GTTAATTCCCTTGTGAGAAAAGGTTAGTTATGTAATTAGCTTTGCTTTGG |
| 273151 TAAGTGTGTTGTTGTTTGTACCACTTTTCCCTTTTAATCAGTGAACAGTG |
| 273201 TTTAACACCTTTAAGATAGTTGTTCTAATTTGTTTTTATCTACTTGGTGT |
| 273251 TGGTTTTTTTGGTTATGCTGAATGGAAAAATAAAAACAAATACCAATTAA |
| 273301 TGAATAACAATAGCTAATCTACAGTTCATTAAGCGAAATTGCTTTTGAAT |
| 273351 CGGCAACAACAAACCCTTCTCCAACTCCCCCTCCCCTTCAACTTCCGCTT |
| 273401 CCTCTTCTACCCCCCTCCCCACTTTTTCTAACATCAATGTTGGGGTTAAA |
| 273451 TCAATGATCACTCAACATTTAAATAAAGAAAACACCCGGTGGGTGTTTAT |
| 273501 ACCTAACTTTTCACCTGACATCTGAACAGGAGCAGGGTATCGCAAACAAG |
| 273551 GTAACAATAATGGCATCTCCTTGACCAGGTGAAACCTAGTAGTAGTAGCA |
| 273601 ACACGTTTAATCCCAATTCTTCTGATAATAAAGTCACTCAAGGTGGTGGC |
| 273651 TCCCCAGCCAAAAAAACAACCACCTATCCTGCTTTACCAAACTCCATCAG |
| 273701 TCCCACCAGTGACTGTTAAAATGTTTATTAAAAAAACAAATAAAAAGCG |
| 273751 GTTTTATACAATGTATAACCTGTCTAAAAGACAATTTCATGAAACAGTAT |
| 273801 TTAGATTTAGCTAGTTATGTTTTAGCAAATGGTAAARAAAGAAAAAACCG |
| 273851 TACAGATACAGATACTTTAAGTGTCTTTGGTTACCAGATGAAATTTGACC |
| 273901 TTACTAATAGTTTTCCTTTATTGACAACTAAAAAGGTTAATTGGAAGGCA |
| 273951 ATTGTCCATGAATTGTTGTGATTTATTAAGGGTGATACCAACATTAAGTA |
| 274001 CTTAGTTGATAATGGGGTGAACATCTGAAATGAATGACCATATGAAAACT |
| 274051 TTAAAAAATCACCAAGTTTTCAAAACGAAACACTCCAAGAATTTATCTTA |
| 274101 AAGGTTAAAACTGATAATGAGTTTGCTAAACAATTTGCTGATTTGGGTCC |
| 274151 TGTTTATGGCAAGCAATGACGTAATTTTAATGGTGTTGATCAACTCAAAA |
| 274201 AAGTCATCCAAGAGATTAAAGAAAATCCCAACTCAAGAGGCTAATTGTC |
| 274251 TCAAGCTGAAACCCTAGTGAATTGGAAAAAATGGCATTGGCTCCTTGTCA |
| 274301 TTCACTCTTTCAGTTCTATGTTGAAGAAGATAAACTAAGCTTACAGCTTT |
| 274351 ACCAGCGCAGCGGTGATATCTTTCTTGGTGTCCCATTTAACATTGCATCT |
| 274401 TACGCCTTACTTGTGTATTTAGTTGCTCATGAAACTAAGTTAAAACCTGG |
| 274451 TTATTTTATCCATACACTAGGAGATGCACATATCTATGAAAACCACATTG |
| 274501 AACAAATTAAATTACAACTAACAAGAACAACCCTAGACCCCCCTCAAGTG |
| 274551 GTTTTGAAAAGTGATAAATCAATCTTTGCTTATAGTTTTGATGATATTGA |
| 274601 GTTAGTTGGTTATAATTACCATCCATTTATCTATGGGAGGGTTGCAGTTT |
| 274651 AATGCTAATTGCTATCTGAGCGATGACAAGAAGGACTAATAGGTAATA |
| 274701 ACAACACTTTACCTTGGATGATTAAACAAGAGCTAGCTCACTTTAAAAAA |
| 274751 ACTACGTTATTTCAAGCTTTGTTAATGGGGAGAAAAACTTACGAATCACT |
| 274801 CCCCAAGGTATTTGAAAAAAGAACAATATTTCTCCTTTCAAAAGATCAAA |
| 274851 ACTACCGTTTTGAAGAAAAGGGAAGTGAAGTGAAAGTTATTAATGATTTT |
| 274901 TGACCACTAATTAAAAGTTACCAAGCAAATAAAGAAAAGGATTGTTTAT |
| 274951 TTGTGGTGGAAAAAGTGTGTATGAACAGACCATTAATGAATGTGATCAGT |
| 275001 TAATTGTTTCAATCATTAAAAAGAAGTATAAGGGTGATCAGTTTTTGAAG |
| 275051 GTTGATCTCAGTAAATTTGTACTTAATGAAGTTGTAGAGTTTGAGGAATT |
| 275101 TAATGTTAATTATTATAGAAAGAAACAACAATAAGAGATATGGCAGCTAA |
| 275151 CAATAAAAAGTACTTTTTAGAATCATTTTCCCCACTTGGGTATGTAAAGA |
| 275201 ATAATTTTCAGGGCAACTTACGTTCTGTAAACTGGAATTTGGTTGATGAT |
| 275251 GAGAAGGATTTGGAAGTGTGAAACAGGATTGTTCAGAACTTTTGGTTACC |
| 275301 TGAAAAGATCCCTGTATCCAATGACATCCCCTCATGAAAGAAACTCTCAA |

-continued

The Nucleotide Sequence of the *Mycoplasma genitalium* Genome

275351 AGGATTGACAGGATCTGATCACTAAGACCTTTACTGGTTTAACACTACTT
275401 GATACTATCCAAGCTACCATTGGTGACATCTGTCAAATTGATCATGCTCT
275451 AACTGATCATGAGCAGGTTATTTATGCAAACTTTGCTTTTATGGTAGGGG
275501 TACATGCCCGTTCCTATGGAACGATCTTCTCAACTTTATGTACATCAGAA
275551 CAGATTAACGCTGCTCATGAGTGGGTTGTAAACACTGAAAGTCTCCAGAA
275601 AAGAGCAAAGGCATTAATCCCTTACTATACGGGCAATGACCCGTTAAAAT
275651 CAAAGGTAGCAGCAGCTTTAATGCCTGGGTTTTACTGTATGGTGGGTTT
275701 TATTTGCCTTTTTACTTGTCATCAAGAAAACAACTACCAAATACATCTGA
275751 TATTATCCGCTTAATCCTTCGTGATAAAGTGATCCATAACTATTACAGTG
275801 GTTATAAATACCAACGTAAACTAGAAAAACTCCCTTTAGCAAAACAAAAG
275851 GAGATGAAAGCATTTGTTTTTGAACTAATGTATCGGTTAATTGAACTTGA
275901 AAAGGACTATTTAAAAGAGCTTTATGAAGGGTTTGGAATTGTTGATGATG
275951 CCATTAAGTTCAGTGTTTACAATGCTGGTAAGTTTTTACAGAACTTAGGT
276001 TATGACTCCCCGTTTACTGCAGCAGAAACCAGGATTAAACCAGAGATTTT
276051 TGCCCAACTATCAGCACGTGCTGATGAAAACCATGACTTTTTCTCAGGAA
276101 ACGGTTCGTCGTATGTGATGGGAGTTAGTGAAGAGACAAATGATGATGAT
276151 TGGAACTTTTAAGTTATGCATAAAGATATCAAACTAGTTAAGGAAACTGA
276201 AATTAGAAAACCAATTGGTTCTCCTTTTATTGTCTATTTTTCATCTATCT
276251 CCAACAACACCCACCGTTTTATTGAAAAACTGGGTTTTCAACACAAAAGA
276301 ATCCCAGTTGATATAACCCAAAGCATTACTGTAAGTAATGAGTATGTTTT
276351 AATCTGTCCAACTTATAGTGGTGGGGGTAACCAGGTTGAAGGAGCGGTAC
276401 CCAAGCAAGTTATCCAGTTTTTAAATAACAAGCATAACAGGGAGTTATGC
276451 AGAGGAGTTATTGCATCTGGTAACACTAATTTTGGAGATACTTTTTGTCT
276501 TGCAGGAACTGTTATTTCCAAAAAACTAAACGTCCCTTTGTTGTATCAGT
276551 TTGAACTTTTGGGAACAAAAAATGATGTAGAACAAACCCAAAAAATAATT
276601 GCCAATTTCTTTCAAAACAGCAACTAGTATTTATAGTTATCCACTATGAC
276651 ATCCAAAGAAAAAATCCCTACTTTTAATACTGAAGAAGATGTTGAAAGTT
276701 ACATTTCTTTTAATGCCCAAGCCAAAATCTATGATGATTTTGCAATCGAT
276751 TTACAAGCAGTTGAAAGCTATATTCAAGAGCATGTAAAACCCAAAACTAA
276801 GGTCTTTCATTCCACCAAAGAACGCCTTGATTTTCTGATTAAGAACGATT
276851 ATTATGATGAGAAGATCATCAACATGTACAGTTTTGAACAGTTTGAAGAG
276901 ATCACCCATAAAGCATATTCATACCGCTTTCGTTATGCTAACTTCATGGG
276951 AGCATTTAAGTTCTATAATGCCTATGCTTTAAAGACATTTGATGGTAAGT
277001 ACTACTTGGAAAACTATGAGGATAGGGTGGTGATGAATGTATTGATGTTA
277051 GCTAATGGTAACTTCAATAAGGCATTAAAACTCTTAAAACAGATTATCCT
277101 TAACCGTTTTCAACCAGCAACCCCTACCTTTCTTAATGCTGGTAGAAAGA
277151 AACGTGGTGAATTTGTTTCATGTTACCTGTTAAGGATTGAAGATAACATG
277201 GAATCAATAGGTAGAGCGATAACAACTACACTACAACTATCAAAACGTGA
277251 TGGGGGAGTAGCACTTTTGCTTTCCAACTTACGTGAAGCGGGAGCGCCCA
277301 TCAAAAAGATAGAAAACCAATCATCAGGGATTATCCCAATTATGAAATTG
277351 TTAGAGGACTCTTTTTCCTATTCCAACCAACTTGGACAAAGACAAGGAGC
277401 GGGAGCGGTGTATCTCCATTGTCACCATCCTGATGTTATGCAGTTTTTAG
277451 ATACTAAAAGGGAAAATGCTGATGAGAAGATCAGAATTAAATCACTCTCC
277501 TTAGGACTTGTGATTCCAGATATCACCTTCCAATTAGCAAAAAATAACGA
277551 GATGATGGCACTTTTCAGTCCATATGATATCTATCAGGAGTATGGTAAGG
277601 CTTTATCTGATATCTCAGTAACTGAGATGTATTATGAATTGCTTGAAAAC
277651 CAACGCATTAAAAAGACCTTTATTAGTGCTAGAAAGTTCTTTCAAACAAT
277701 TGCTGAACTCCACTTTGAAAGTGGTTATCCCTACATCTTGTTTGATGATA
277751 CAGTTAACAGGAGAAATGCCCACAAAAACAGGATAGTAATGTCTAACCTT
277801 TGCAGTGAAATTGTCCAACCATCTTTACCTTCTGAATTCTATTCAGACCT
277851 TACTTTTAAAAAGGTAGGTAGTGATATTAGCTGTAACTTGGGGAGTTTAA
277901 ATATTGCTAGAGCAATGGAAAGTGGTAGTGAGTTAGCTGAATTGATTCAA
277951 CTAGCAATTGAATCACTGGATTTAGTGTCAAGGATCAGTAGTTTAGAAAC
278001 CGCTCCTTCCATTAAAAAAGGTAATTCAGAAAACCATGCGTTGGGATTAG
278051 GAGCGATGAACTTACATGGATTTTTAGCAACAAATGCTATCTATTATGAT
278101 TCAAAGGAAGCGGTTGATTTTACTAACATCTTTTTTTATACAGTAGCATA
278151 CCATGCGTTTAGTGCTTCCAATAAATTAGCATTGGAACTAGGTAAATTTA
278201 AAGACTTTGAAAATACTAAATTTGCTGATGGTAGTTACTTTGATAAGTAC
278251 ACTAAGGTAGCTAGTGACTTTTGAACATGTAAAACAGAAAAAGTTCAAGC
278301 CCTTTTTGATAAATACCAAGTAAAAATTCCAACTCAGGAAAATTGGAAGC
278351 AATTGGTAGCAAGTATCCAAAAAGATGGACTTGCAAACTCCCATTTAATG
278401 GCTATTGCCCCAACTGGATCTATCTCATATCTCTCTTCATGTACCCCTTC
278451 ACTTCAACCAGTAGTATCTCCTGTTGAAGTGAGAAAAGAAGGGAAGTTAG
278501 GACGGATTTATGTCCCTGCTTATAAGCTTGATAATGATAACTATCAGTAC
278551 TTTAAAGATGGTGCTTATGAACTGGGCTTTGAACCTATTATTAACATAGT
278601 AGCAGCAGCCCAACAACATGTTGATCAAGCAATCTCTTTAACCTTGTTTA
278651 TGACTGATAAAGCTACCACCAGAGATCTCAATAAAGCTTATATTTATGCT
278701 TTTAAAAAGGGTTGTAGTTCTATCTATTATGTCAGAGTAAGACAAGATGT
278751 TTTAAAAGATAGTGAAGATCACACTATTAAAATCAAGGATTGTGAGGTTT
278801 GTTCTATCTAACTATTAAAGCAGTTAGAAATTTGTTAGAATTACTTGTTTT
278851 AAAACTATCTTAATCCCTAATATATAAATTAGAAAGGCAACGGTTTTGAG
278901 AAGATGCATGCTATTGTGGTTTGTGGTGCTAAGCAGTATTTAGTCCATGA
278951 AAACGAGTCTATTTTTGTTGAAAAATTAGCTGGTAAAGTTGGTCAGGAGA
279001 TCCAACTTGATAAGGTATTGATGCTTGATGAAAAGATAGGCAAACCTTAC
279051 CTTGAAAAAGCTAAGGTTGTTTGTGTGATTGAAAAACACGGTTTAAAATC
279101 GAAAATTAAACTAATTAAACACATCTCCCAAAAAACACCACCTCAAGCGTT
279151 ATGGCCACCGTCAACCCTACACCAAACTAAAAGTGGTACGCTTTATCCAT

-continued

The Nucleotide Sequence of the *Mycoplasma genitalium* Genome

```
279201 GATTAAGATTAATATCTCCCAAAACTTTCTAGTTGCAAAAGGTCATGCTT
279251 TGTTTGCTGAGAAGGGTAAGGACATAGTTTGTGCTGCAATTAGTGGAATT
279301 ATCTTTGGGGGGTGGCTTGGTTTGAACCTGATAAGATTGAATTTACTGA
279351 AAATAAATTAGTACCTAGTATAGCACTGAAACTCATTGACCCAACCCCTA
279401 ATGTAGCAGTTGCTTTTAGTGTTATTACAGTACAATTAAAAGCAATAGCC
279451 AATTCCTATCCTAATCACATAGTTATCAATGAAGAGAGTTATGAGTAAAA
279501 ACAGTTACTGCTACCAAATTAACTTACAGTTTTTCGCTTCCAAAAAAGGG
279551 GTTGGTTCCACTAAGAATGGACGTGATTCACATTCTAAGCGCTTGGGCGC
279601 TAAGAAGGCAGATGGTCAGATGATTAGAGTTTGGTCAGATTATCTATAGAC
279651 AAAGGGGAACTAAGATCTTTGCAGGACAAAATGTTGCAATGGGTAGTGAT
279701 AACACCCTCTTTGCTTTGAGCGATGGCATTGTCCGCTTTCAAAAGTTTGG
279751 TAGTAAACAAAGCAAAACCCGGGTTAACATCATCAAACACCAACTAAATG
279801 CCTAAGCTACTGGGTAGCTTTATTAGCTTTAAAGCCCCCAATTACTTTGT
279851 TCAAAGTGCTCAGGATGCAATTGCTATTGATGCAACTGCTCTAATGGTAT
279901 TTTTAGGTCCACCCCATTCTGCTTACCGTGTTCCTTTTAACAAGATGCAG
279951 TTTAGTTTGGGCTATGAGTTGTTAAAAACAAAGAATATTAATAGTAATGG
280001 TTTGGTTGTTCATGCTCCATATATCATTAACTGTGCATCAAAAGACCCAC
280051 TAAAACAGCAGAATGCTATCAGTGTTTTAACCAATGAGATTCAGCTTTGT
280101 AACTTGGCTGGTGCTCACTATTTAGTTTTGCATCCAGGTTCTGCAGTAGC
280151 CCAAACAACCAACGAAGCATTAGATAACCTGGTTAAAGTACTCAATCAAG
280201 TTATCAATAAAACCAAAACAACAGTTATTTGCCTTGAAACAATGGCTGGT
280251 AAGGGTAATGAGATAGGCAGAGACTTAACTGAGTTGAAATATGTTATTGA
280301 CAGGATCGTTGATAAAGATAGGATCGGGGTTTGTCTTGATACCTGTCACT
280351 TCCATGATAGTGGGATTGACTTTAGTGATCTAACTGGTGTTTTTAACACC
280401 ATTACAACTAAACTTGGTTTTGAGTTTCTCAAAGTAATCCATTTAAATGA
280451 ATCTAAAAATAATTGTGGTTCTAAAAAAGATAGGCATGCTAATATCAATG
280501 CTGGGATGATTGGTTTTGAGAACTTAATGAAGTTCATTAGTCACCCCCAA
280551 ATTAAGGATTTACCTATTATCTTAGAAACCCCTTCAACTAGTTTAAACTA
280601 CCCAACTATTTACCGTGAAGAGATTAGTCAAATCCGCAGCTGATTTAAAA
280651 CTTACCAACCAGATGCTAACTAGTTATGTGAAGGTATTAGAACAAAACAA
280701 TCTGCGCTTAACAAAACCGCGGATTGCTTTATTAAAGTGTTTAATTGAAC
280751 ACCAAGATTGGCATAATCTCTCCCAAATTAAAACCCACCTTGATTTAGCC
280801 AATCAACCCTCAACACTCGCTTCTATCTACAACAACTTAAGAATCCTAGC
280851 TAAACTTAAACTGATTAACATCTTTGTAGATCCAGAGCGGTTTGAAACTT
280901 ACTATTGCCTGCGCCATGCAGAGCATAACCATATCTATCTTTTTGATGAA
280951 GTTAAACAGCAGTTTTTTACCTTACCTTTAACAGATGGCCAAATTAAAAC
281001 ATTGCTTGAAACCCAAAACCATACCAGTAAGGTAAAGCTTAATGATTTTT
281051 ATATTGTTGCTAGGGGTGAGATAAACAATGATTAACAAACCAAACCAATT
281101 TTTAAACCACCTTGATGGCTTAAAGCAACATTTTTTCTGATTATGATTCAC
281151 TACAAAAATCCTTTAAGAAATATCTATCAGAAAATCAAACTGAACTTAAC
281201 AATTTCTTTTTTAACCAGTTTGAAAAGATCATTGTTCTGGTCAAAAAAAA
281251 GGAGTTTAAAACTGCTCAAGAGAGGTGTGAAGAGGAGTTAGCTACCCCTT
281301 ATTTTTCAAAGCCATTGGTTGGTTTTTTCCAATCACTATTACAACTAATT
281351 AACCATGATCTCATCGAACAGaAAAACCAACAGTTAGCTAACATGAGTTG
281401 TGAAAAAATTGTGGAGATGGTGTTAAGTGATTACCCCAATAAACTTAACT
281451 TAATCCACTATTTGTTAGCAAAAGAAGCGAGTTTTGTAAACCCTAACCTT
281501 TTACAGCGGATGACTTTTGTGTTAACTGATCTTGAACTGTTAGAGTTAAA
281551 GCGTTTCTCTTTTTTTAAAGCCCTTAACCAGATACCTGCTTTTAAAAACC
281601 ACAAAGTAACATACTTTAACAGCAAACTCAAACAGAAGTTTGTAATAACA
281651 TTAGGTGAATTTGCTTTCCCCCAAACTGATAAAACCAAACAGTTTTTCCA
281701 ACAACTAATTAAAAAAGTAAGTCAACTGTTTTTAAAAGAACCTGTTAGTT
281751 GTGAATTTGCTTATGAAATTATTGATGCATTACTCGTCAGTTTTTTTCCA
281801 CTCCATCCTAATTTAGAAGTAAACCACTTAGCTAAAAGATCCACCAGTA
281851 TGTTAGTAAGATTGTCATTAATGAAGTTGTTGATCTGAAAGATCCAACCA
281901 CTAAACTAATTGTTGATACACTTTATGAACAGTTAGATAGAGCAATTGGT
281951 GAGGAAAATTAAAATTAAGTTAGCACTAGTAGATACAAAAGATGAAGTTA
282001 TACAAAGTTCTTAACAGTAAAACAACTGATAAAAGTCTTTGTTTGGAAGT
282051 TGAGATTGAtCCAAATTACTGACAAGCTACCCAPAAAAAACTAGTAGGTG
282101 AAATGGCTAAATCGATAAAAATTAAGGGTTTTCGTCCCGGTAAAATCCCC
282151 CCTAATTTAGCCAGTCAGTCGATTAATAAAGCTGAATTAATGCAAAAAAG
282201 TGCCCAAAACGTCATGAACAGTATTTATGAATCAGTTCAACAAGAAGAGA
282251 TCGTTGCTAGTAATGATAATGTCATTGATGATTATCCTACCATTGATTTC
282301 AAAACGATCACTGAACAAAACTGTGTACTTTTGTTTTACTTTGATCTGAT
282351 CCCTAACTTTCAACTCCCTGATTACAAAAAGATAAAAGATTTAACACCAC
282401 TTACCAAGTTAACTGAAGCTGAATTTAACAACGAAATTGAAAAGCTGGCA
282451 AAAACTAAAAGCACAATGGTAGATGTTAGTGATAAAAAACTAGCTAATGG
282501 TGATATTGCTATCATTGATTTCACTGGGATAGTTGATAACAAAACTAG
282551 CATCAGCTTCAGCACAAAACTATGAATTGACAATTGGTTCAAATAGCTTT
282601 ATTAAGGGTTTTGAAACCGGGTTAATAGCAATGAAAGTTAACCAGAAAAA
282651 AACTTTAGCACTAACTTTTCCTAGTGATTATCATGTTAAGGAGTTGCAAT
282701 CAAAACCAGTTACATTTGAAGTAGTTTTAAAAGCAATTAAAAAACTGGAA
282751 TTCACCCCAATGGATGAAACTAATTTCAAATCCTTTCTCCCTGAACAATT
282801 CCAAAGCTTTACTTCTCTAAAGGCATTTAAGAGTTATTTTCATAAGCTAA
282851 TGGAAAACAAAAAACAAGAGACAATTCTCCAGGAGAATAACCAAAAAATT
282901 CGTCAGTTCTTACTTACTAATACCAAACTTCCTTTTCTTCCAGAAGCGTT
282951 AATTAACTAGAAGCTAACCGCTTGTTAAAGCTCCAGCAAAGCCAAGCTG
283001 AACAATATAAAATCCCCTTTGAAAAACTCTTAAGTGCTTCTAATATCACC
```

-continued

The Nucleotide Sequence of the *Mycoplasma genitalium* Genome

```
283051 CTAACAGAGTTACAAGATCGCAACATAAAAGAAGCTAAGGAAAATGTTAC
283101 CTTTGCTTTGGTAATGAAAAAGATAGCTGACATTGAAAAGATTAAGGTTG
283151 ATAATAACAAGATTAAAGCTGAAATTGAAAATGTTATTGCTGTTGAATAT
283201 CCCTTTGCTAGTGATGAAATGAAAAAACAACTCTTTTTTAATATGGAACA
283251 ACAAAAGGAGTTTGTGGAATCAATTATCATCAACAGATTAACAACAACTA
283301 AAATCGTTAGCTATTCAACTCATTAGCACTCAAAGCTTGTGAGTGCTAAG
283351 AAATGTGTTAAAATTTATTGAAATTCCCTAATTAACTTTTAAATATGCCC
283401 GTTACGAAGAAAAGTCAGATCTTAGTAGTTAGAGGTCAAGTCATTTTTCC
283451 TTTTGTTCCCTTTAGTTTGGATGTTGGCAGGCCCCGTTCGCGTAAGATCA
283501 TCAAAGCGCTTAAAACTCTGAAAACCAAACGTTTGGTTTTAGTAACCCAA
283551 AAGTTTACTGGTGAACAAAACCCTGAGTTTAATGACATCTATCATGTCGG
283601 TACACTCTGTGAGATTGATGAGATAGTTGATGTTCCAGGGGTTGATAGTA
283651 AAACAGTAGACTACCGTATTAAAGGCAGAGGTTTACAACGGGTTTTAATT
283701 GAAAAATTCTCAGATGCAGATATTAATGAAGTTAGTTACCAATTACTTAA
283751 CTCCACAGTTAAAGATGAAGCTAATGTTGACAGGTTCTTACAGCGAATCT
283801 TTCCTGAAAAAGAAGAAATTGAACAGTTAATGGAAGGAGCTGAGAAGTTT
283851 TTAGAACTTGAAAACATCAGCAAAACAGTTAATGTTCCTAAGGGTTTAAA
283901 GCAACTTGATATTATCACCTTTAAACTGGCTAATCTTGTCCCTAACACTG
283951 AAAGTATTAAACAAGCTATCTTAGAGGAAAATGAGATAGCAAACCGATTG
284001 GAAAAGATTATCCAAGCAGGGATTGAAGATTTACAGAAGATCCAAGATTA
284051 TGGTAGATCTAAAAACAAGGAAACTGAGTTTGATAAACTTGACAGTAAAA
284101 TTACCCGCAAAATTAACGAACAACTCTCAAGACAACAACGTGATTTCTAT
284151 CTTCGTGAAAAGCTAAGAATTATCCGTGAAGAGATAGGGATTAGTTCCAA
284201 AAAAGAGGATGAAGTTGCTAGTATTAGAAAGAAACTGGATGAAAACCCTT
284251 ACCCTGAAGCCATTAAAAAACGGATTTTAAGTGAACTTGAACACTATGAA
284301 AACTCTTCCTCCTCTTCCCAAGAATCAACCTTAACCAAAACTTACATTGA
284351 TACGCTTTTAAACCTGCCTTGATGACAAAAGAGCAAAGATAACAGTGATG
284401 TTAAAAACTTAATTAAGACGTTAGATAAAAACCACACTGGTTTAGATAAG
284451 GTTAAAGAAAGGATTGTTGAGTATTTAGCAGTACAACTAAGAACCCAAAA
284501 AAACAAAGGTCCTATTATGTGTTTAGTAGGTCCTCCTGGGGTTGGTAAAT
284551 CAAGTCTAGCTAAGTCTATTGCAGAAGCATTAGATAAGAAGTTTGTCAAG
284601 ATCTCATTAGGGGGAGTACATGATGAATCGGAAATCAGAGGTCACCGTAA
284651 AACTTACTTAGGTTCTATGCCAGGAAGGATTTTGAAAGGGATGACCCGTG
284701 CTAAGGTAATTAATCCCCTCTTTTTACTTGATGAAATTGATAAGATGACC
284751 TCCTCCAACCAAGGTTATCCTTCAGGTGCTTTACTTGAAGTATTAGATCC
284801 AGAGTTAAATAATAAGTTTAGTGATAACTATGTTGAAGAAGATTATGATC
284851 TTTCTAAAGTAATGTTTATCGCTACTGCAAACTACATAGAAGATATCCCT
284901 GAAGCTTTACTTGATAGGATGGAGATAATTGAACTCACTTCCTATACAGA
284951 ACAAGAGAAGATTGAGATAGCAAAAAACCACTTAATTAAGCGTTGCCTTG
285001 AGGATGCTGATCTTAACAGTGAAGAATTGAAGTTCACTGATGAAGCAATC
285051 AGCTACATCATTAAGTTTTACACAAGAGAAGCGGGGGTTAGACAATTAGA
285101 ACGATTAATCCAACAAGTTGTAAGAAAGTACATAGTAGCAATGCAAAAAG
285151 ATGGCATCAAACAAGAAACGATTGATGTAAACGCTGTTAAAAAATACCTT
285201 AAGAAGGAGATCTTTGATCACACTATGCGTGATGAAGTGTCTCTACCTGG
285251 AATTGTCAACGGGATGGCATACACCCCAACTGGAGGGGACTTACTTCCCA
285301 TAGAAGTTACCCATGTTGCTGGTAAAGGAGAGTTGATCTTAACTGGTAAT
285351 TTAAAGCAAACAATGCGAGAAAGCGCTAATGTTGCTTTAGGCTATGTAAA
285401 AGCTAATGCAGAGCGTTTTAACATTAATCCTAGTTTGTTTAAAAAGATTG
285451 ATATTAACATCCATGTTCCAGGTGGGGGAATTCCTAAGGATGGACCTAGT
285501 GCTGGTGCTGCTTTGGTAACTGCAATCATCTCATCATTAACTGGTAAGAA
285551 AGTAGATCCTACAGTGGCTATGACAGGAGAGATCACTTTAAGAGGCAAAG
285601 TGTTGGTTATTGGTGGGGTGAAAGAAAAAACTATCTCAGCTTACCGCGGT
285651 GGGGTTACAACTATCTTTATGCCTGAGAAAAACGAGCGCTATTTAGATGA
285701 AGTACCCAAAGAGATAGTAGATAAACTTAACATTATCTTTGTTAAGGAAT
285751 ACAGTGATATCTACAACAAGCTTTTCAGTTAGTCTTTAACTAGGTTTTGG
285801 ACATATTTTAAGGTAATTAAATAGGCCTGTTTTAAGTTGCTTTTAGCTAG
285851 TTTTACTAGTTGATCAATCTCAATTCCCCCACTCCACTGTTCCTGTTTAC
285901 GGTTAGGTTCTAGTTTATCTGCTAAATAAACAATCATATCTAGCTTGCTA
285951 ACTTGTTTTGGTGGGATGGTGTGGTTTTTGATGGCATTAATAATCATTTT
286001 ATCTTTAACACCCAAATCAGTTTTTTAAGATATAAGCCCCCACATAGCTAT
286051 GTAATACTTTTCAACTTGGGTAGTTAGTTATCTTCAGTTCACTAGTTGCA
286101 ATGTTAACTAACTGATCAACTGGTAGTTGTTTGGCCAAGTCATGATAAGC
286151 CCCAGCAACAAATGCTCTTTTAGCATCTAGTTTGTTTGCAATTGCTAGTT
286201 GTTTTGCTAGTTTACCAACCCTTAAACAGTGTTGAAACCTCTTATCATCA
286251 ACCATTGCTTTTAAAGTGGGAATTAGATAGAGGTGATTGGTATTGATGTA
286301 ATTTAAAACTGCCAGTGGTATCAGTTTTTTTCTAGGTTGATTTAAAAGTT
286351 TACTTGAAGCGATTTCAAGTGGGCATTTAGCCAAGTATTTAACATTAAAT
286401 TGGTTTGCTATTTTTTTATTAAAAGGATAAGGTTTTCGTTCATAACAAAC
286451 AAACGTGCACAAATCTTTTAACTGTTGGATGTGATCTCACTTCTCAAGTT
286501 CATTTAATTTATCACTCCCTATTAAAAAATAGATTTCACTAGTTGGATAA
286551 CAACTTTTAAAGTGGTTAACAGTATTAATTGAAAAAGCGTTTTAGTTTTT
286601 AATATCAAAATTGGAAACTAAAGCATTGTTGACTGATTTAATTGCTAGCT
286651 TTAACATAGCAATCCTATCCTTATTACTAGCATGAAAATTATTTTTAAAA
286701 ATACCATTGTAAGTTGGTACAAAAAAAAGCTTTTGCGCTTTTATTTTTTT
286751 AATTGCATGTTTAGCAATGTAGAGATGGGCATTGTGAATAGGGTCAAAAG
286801 AACCACCAAAGATAATAATTTTTTGCTTCAAAAAAGATCTTAAAACATTT
286851 AATTCTAACTAAAAATAATTGTGACACAAGAGCAATGATCCAAAAGGAGAT
```

-continued

| The Nucleotide Sequence of the *Mycoplasma genitalium* Genome |
|---|
| 286901 GGAGATCTATAACCTCTTTACTTTTCAAATTGATCTTGATAAAAAACTGT |
| 286951 TGTTTGAAAAATCAAATGATCAGAAGAATTATTCCAAGATTAGAACCCAT |
| 287001 TATTTCAAGCATAAATTCAAAAATAAAAGTGCTGTTTTTCTCAATAAAAA |
| 287051 CCTGATTAAAAATAGCTTAAATAAGGTTCTTTTAAACTTTTCTGATTTTG |
| 287101 TTAGTGGTGCTGGAATTGATACAGTTTTTAACCAAATCATTGATGAAGAT |
| 287151 CCTGAGGTTTTAAACTATTTAAAGCAAGTTAAAAAAGATCTTTCCAAAGA |
| 287201 AAACAACGCTACATCCCAACTAACCTTTAATGTAACTATTAACCCTAAAA |
| 287251 ACACCCTCGCCAATTTTTTTGAAGGATTTAATATTTATCTCCATTTTAAT |
| 287301 GAAGAAAACAATACAGTGATAGGTAGTTTCTCACTACAATGACACATCAA |
| 287351 AAAAACTGATCTGTTTTCTGAAACAAAAAACATTGCCATTAACAATTTAA |
| 287401 TTCACACTTTTTGTAAGAACAACATGCATGAAATTAGTTTTATGCAGATC |
| 287451 ATTAATTGTTTTTCCAAAACAAAAATTAATAAACATGGTGAAATTGTTTT |
| 287501 AAAAAGTTGTGCTTTTAAACAAAAATGACAAAATGTTGTTGCTGAAAAAT |
| 287551 ACCCATTCTCAACTGCATCTAAAGATTTGGAGAAAATTAATGATTTTTTT |
| 287601 GATGCTCTTTTTGTAATGCTATTATTGGTATGTCACCTCAATAAAAACCT |
| 287651 GTTATGATTATGTGAAAAAACTGATTTTTTTGAATGAAAACCAAGTCAGA |
| 287701 AAACTGCACTTTTTAAAGCTAATGATAGTGGAGCATACTTAGCTAGAATG |
| 287751 CTGCTCTTTTTAAACGATTGGTACAACGAAAATCAAGCAATAACAACTGC |
| 287801 TGACATTGAAAATGTTAATGAGGTTGAAGACATAGGAAAATTAGTTGAAA |
| 287851 AATACAGCACTAATCAACCCCAAAAGTTATCGTTAAATTCAACAGTTTAT |
| 287901 GTATTACAAACAAAACAAAAACAGTTTTTTTAAAAAATGATTTCTTTTT |
| 287951 TAATAATAACGAAGCAAAGCTGTTTTTTCTAATAACTATGAAGCCCAATG |
| 288001 TTTTTGGTCTTGATGATACAGCAATAGCAAATAACTTAAACCTTAAAAAA |
| 288051 ATTAGTGATTTTTTTAAAGAGATTGATTTTAATGATGAGGATATTCTAAA |
| 288101 TGACTTTAAACAAGAACAGGAAAAGTTATTGGTTAGAAGAACATTTAACC |
| 288151 AACTGTTATTTATGAACAAAAATACTGAAATTCTCAGTGTTGTCAATGAC |
| 288201 AAGCAAAAGTCAGTAATCCATAACATTGTTTGAACCATTACTTATAGTAA |
| 288251 AGCGATCATGTTAAAAGCCTTTGATTATTCCAAAGCCTTTGAAAAAAACC |
| 288301 GAACGAGTGATCCTTCCTTATTGCGATCTAATTTAACTGTTATCAACCGC |
| 288351 TTAAGATACCTCAGTGAATACTTTCAAAATGCCTCACTTAAGTATGATCT |
| 288401 ACTCTACACTAAGGCCAAACAATATATGCAAATTGATAAATTTATCAACG |
| 288451 ACATGATTCGCAAGGTAAACCATGAGGATGAAATCTTTGGCAAATTTAAA |
| 288501 GAAAGAATTTATTTAAGTTTGGGAATTATTAGTGCGGTAGTGTTTGGCAT |
| 288551 AGTTGAATTTTTTAACTGTGTATGGACTATCTTAACTGTTAGTCAAGAAG |
| 288601 TGGTTGATAAAAGTGTTTTGGATCCAAGGAATATTATCTTTATTAGTATA |
| 288651 GGTACTATTTTGGTTTTATTTCTTTTGGTTACTATCTTGGTTTTTATGAC |
| 288701 AAGAAGACTTTATCTGTTTGAAATTAATAAAAAGCATAAAAATTAGGAAT |
| 288751 CATGAAATTCAATAAGTTAAACCTAAGTCATTGTATCTCTTTTTACATCT |
| 288801 CAGAAGTTTCAGAAGTTTTCTTTGAAAGTATCAACCAACACCCTAGTCGT |
| 288851 GATTTTGTTAATAACATTCTTCAAAAGATTAAAACTACTTTAAGTGAAGA |
| 288901 AGAGCTTGAAAAGTTAAACAGTATTGAAGAAGTTACTAAGGATGAGAAGA |
| 288951 TTGTGATCATGCTCAACCATGTTTTGAAAAAGATTGTTTCTAAAACTGGT |
| 289001 AGTTCTAAGTGTGACTTATTTAATGTAATCAAACAAGATAGGTTTAATTC |
| 289051 TCCAGTGTATATCCAAAGTATTAATGCTTTTGAAAACAACCTTATTAACA |
| 289101 ATGAATTTGCTGAAAGAAGGTATGACTATTTGATTGAAGTTAATAAAAAt |
| 289151 TCATACCTTAAAAAATTTGTCAATTCGATCAGAATTTCCTTCTTCTTAGA |
| 289201 TTTAAGAGCACAAATTTTGTCAGGTTCATTTACCCTTAATTTAGTTAATA |
| 289251 AGTCAATTGAAAAACAAAAAAAGACAGAAATTTTTAAAGATATTTTTGTT |
| 289301 AATGCCTTAGTTAAGCATTTTATCTGTAATCAACTTTATCCTATCTCTTT |
| 289351 AAATTCCTTTATTTTTGACAGTGAAAATCCTAGCAATAAACTCGCTCTAA |
| 289401 AAGAACGGATTAAGCTTTTAAAAACAAACTGAAATTCCCTCTTTTTTGAT |
| 289451 AAGTTTTACAACTGTTTAAACAATAAAAATAAGCAGCAACTTCAAGAAAC |
| 289501 TAGTGATGAGATGTTTTATGCAGTGATTAACACTTATTTAATCATGTTAA |
| 289551 TCTCTGTTGAAGAGTTAAGGGTTTACTTTACAAGTAAAGAACCAGCACTG |
| 289601 ATTTTAAAGGTATTAGATAAAAAAAAACACACTAAGAGAAGATTCCTGATCA |
| 289651 AAACCCTGAAACTGATTTGTATGAACTAATACAGTTTATAGAACAAAACT |
| 289701 ACTTAAAAAAAGATAAAAAAACCAGCTGAAATAAAAAAAAGGTACAGGAT |
| 289751 CTTGAACAGTTACTTGAAGAGATTAACAAGATTAATTTAGAAACAAAAAA |
| 289801 TGAATCTTTAGCTTACCCTGATGAGATAACAGAATTGGAAATTGATAATG |
| 289851 ATAATTTTGTCTCTACAAAACAAGTATTTAGAAACCAATTAGAATTACAA |
| 289901 CTTTTGCATGGGATTGTAATTAATCCTGAGAAGTATGGAATTGGCATGTG |
| 289951 AAGTAGTTATTTTGCTGATTGAAGTGAGTACAAAAATTTAATAGAACAGA |
| 290001 TGCTCAATCCCAAAAGTGGTAATGATTTTTATCAGTTTGAAAAGGACATA |
| 290051 GATGAAAGCATATGTCAAATTAACAAAAAATATCTAACTTTTATTAGCAG |
| 290101 TGATAGTAATACCTTTTTAATAGTTAAAAATGATGATGTAAAAGTTATTT |
| 290151 CTAACTATGTATGAGCACAACTTTCTTTGAAACAAGAAGGTGAATTATC |
| 290201 AATGACATTGAATTTGACTTGTATGAAAAAGGATTTGATAAAAGCCACTT |
| 290251 TTCACGTAACATTGCTTTACTTGAAAGTCTCAGTTTTAGTTGATTAGATC |
| 290301 CTTTTTATGGTTTGACATCAATTAAAGAGATCATGCAGAAAATAGATAGT |
| 290351 AAAAGTAATCTTAAAACCTCGATTGAAGAGATGGTAAATAGGTTTAAACA |
| 290401 TGAGCAGCGAATTAATAAAAAGGACAATGAAAGGGTGTTGATGATTTTTG |
| 290451 CTTATATTGCTGCTTTTGTAGTAGGATTTATCAATTTTTTCTCAATGGTC |
| 290501 TTTACTATTCTCACTGTAAGTGATCTAAATGCTGGGCTTACTGTACCTAA |
| 290551 CATCATTGTAATCAGTATCGCTAGTGTTTTAGCTTTTATTTTGATTGTGA |
| 290601 TTGCTGTTTTATTTCGTTTTAAATGAAAACACATTAAGCACTAATAATGC |
| 290651 AAATTAAAGTTATTAATGAAACAAATAAAACTGTTCAAATTTTTCAATGT |
| 290701 GCTAAAGTAAAACATAGGGCATTAGCTTGATTGTGCGATGTATTTTATT |

| The Nucleotide Sequence of the *Mycoplasma genitalium* Genome |
|---|
| 290751 AGCTATTGTACTTGTGGTTATCTTTTTAATTACTCAAGCCTTTAGTGATA |
| 290801 ACCGTTTTCTTTTATTTTTAGTTTTAAGTTGTTCACAAACAATCCTGTGA |
| 290851 ACGGTTTATTTCATTTTTTTACCATTTTTTTGGGATGGTAAAACTTTGTT |
| 290901 TCGCAACCTTTTGAAGATTAAGCTATTTGCTTTTGACAAAAGGTTTTTGA |
| 290951 GAATAATGATCCATGAGTTGTTTTTATGGATTTGCTTTCAGTTTTGTTTT |
| 291001 TAGTGATTGCTAGTTATTTTTTATTAACCAAAATAGCAGCGAAGCGCTT |
| 291051 AATTTTTTCACTAATTTAGATAAGCCTAATGCAATAGCGATAACAATTAG |
| 291101 AACCATAACAATTTTGATTAGTTTTTTACAACTGATTTTATTGGTTATT |
| 291151 TTTGTTTTAGTTCTGAAAAACAAGCTTTACAAGAGATACTGTCAAACACC |
| 291201 TTTATGGTTCAAGAAAAACACACTTTAAAATCAAAACCAACTAGCTTAAA |
| 291251 AACCAACAATCAACCTGATCCAGCTAATTTACCAGGCGTAATAGCTCTTG |
| 291301 ATGAAGTGGAAAAACTCATTAATTAATAACAATGAATGAACAACAAAAAC |
| 291351 AAGCAATTAGTTGTGGAAAAGGGGTTAATGTTGTTTATTCTGGAGCAGGT |
| 291401 ACTGGTAAAACAACAATTATTACTAATCGCTTTGCATACTTGGTTAATAA |
| 291451 AGAAAAAGTTGATCCTAGCAGAATTTTAGCAATCACCTTTACTAAGAAAG |
| 291501 CTGCTAAGGAGATGCAGTTTAGAATCTTGAAACTAATAGATAGTTCTTTA |
| 291551 GCTGAGAAAACAAATATCTATACATTTCACAGCTTTTGCAATAAGTTTTT |
| 291601 AATTCAAACATTAAAAAAGCGCTTTATCATCGATGATGATATTAGCTATT |
| 291651 TCCTAAAGGAATTTTTAGCTGATTCAAAACTCGATATCAACCTAGCGAAA |
| 291701 CAAATTATTGATAACTTTAAAAATACTTTTGCTGATTTTGAAATAAATAA |
| 291751 GTTGGATCAAGATGAAAGGTTAATTAGTTTATGTGAGCATTCACTTCTAA |
| 291801 ATAAAGATGAAGAATATTCCACTTTAAAAACCCAACTGATTAATGCATTC |
| 291851 ATTAGCTATGAAAAGAATAAGATATTAAACAATAAACTTGATTTTCATGA |
| 291901 TCTTTTAATTAAAACTTGTAATTTATTGAGTAATGATAATGATTTACTTA |
| 291951 ATCAGTGGAGTGAACAGTTTCAGCATATTTTAGTTGATGAATTTCAAGAT |
| 292001 ACCAACCAAATCCAATATGAACTGATCAAGATGTTAGTAACTAAAAATAA |
| 292051 AAACTTGTTTTTGGTAGGTGATAATAACCAGATGATTTACCGCTGAAGAG |
| 292101 GGGCGGTAAACGGGATCATAACTGCTTTAAAGCATGACTTTAATGTTCCG |
| 292151 AAAAGCAATGAATTCTTTATTAATCAAAATTACCGTTGCGATCAGAATAT |
| 292201 TTTAGCAGTTGCTAACCAAATTCTTTTAAAAATTATGGCCTATGAAAAAC |
| 292251 AAGTTAAAACTGAAAAAAAATCTCTTGTTTTCAACTTTAAATTCTGATAAA |
| 292301 AAACCTGTTTATTTTCAAGCTGAATCAGTTGAAAATCAAGCCAATTGGAT |
| 292351 CTTCAATAAAATCAAAGCACTAAACCAAACAGAAAAGATTAATTTTAAGG |
| 292401 ATATGGCCATCTTGTTTAGAAAGAACAGAGATATTACTACTATGGTTGAA |
| 292451 TTGATTGAAGCGGATGGAACAATTCCCTTACCTAAACAAAAGAGTTATTT |
| 292501 TAACCAACTAGTAAAACTCCAGCGGGTTTTAATTGCGATTTCAACCAGAA |
| 292551 CAAATCTTGATATTAAAGAGCTTTGCAAGCCCTAAAAATTTGATCAAAT |
| 292601 GATTTAAAGGAATTGTGAAAACAGAGTGATAAAACAAACCTATTTGATTt |
| 292651 TCTTAAATGATCAGAATTAAATCAAAAAAACCATAGTTCAAAACTTAAAG |
| 292701 CTACTGGTTATTTTAATCTGCTGATTAAGTTAGCAGAGGATCAGCAAATT |
| 292751 AACCTTTTGTTTACTGAACTGTTTAAAAAACTCAAAGTGGATCAAACTAT |
| 292801 TGAAAATCTGCTTTGAAAAAAACTAACTGAATTTCAAAAAGATAAAACTG |
| 292851 AATTTAGCTTATCAGAGTTTATTACTAGCTTAGCATTGGAATTTGACTCA |
| 292901 ATTATTGAAAACAGCAGTGATACAATCAATTTGCTAACCGTTCATGCAGC |
| 292951 AAAAGGACTTGAGTTTGAAGCTGTATTTATTTATGGCATGAATCAAGGGG |
| 293001 ATTTTCCCTTATTTTTAAGTCAAAATCAAAATGACGAACAACATTTAATT |
| 293051 GATGAATTAAAACTGTTTTATGTTGCTATCACAAGAGCAAAACGTTTTTT |
| 293101 GTTTATCACTGCGGTTTTACAAATAAATAACAATTCTATAAAACCATCTA |
| 293151 GTTTTTTAAATTACATCAATAAAAGTGAGTATTTAGACATTGCTACTATT |
| 293201 AACTATGTATTAGAGCAGGATGATGATTTTTTTGATTCAACTAAAAAAAC |
| 293251 AGACTATACAAAGAAACTAAGAAAAGAAAGTTTAGACATTATAGTGGGTG |
| 293301 ATTTAGTTACTAGTAGATACTTTGGAAAAGGAGTTGTAGTTGAAGTGAGA |
| 293351 GACAAAGAGGTTTTAGTAGCTTTTAAAGACACACGCTATGGATGAAATG |
| 293401 GATCTTAAAAAACCATAAATCACTAACAAAAGCTTTATATTAACAATGGT |
| 293451 TGATAAAAACAGTTTAAGAAAATTAATGCTTCTAAAAAGAGCAGAACTAA |
| 293501 ATGATCTTGAAAAATCGCATTTAGATCAAAAGATTAACCAAAAATTAATG |
| 293551 GCTTTTTTAATAACAAGACCAACAATTAAAAATTTAGCACTTTACATTCC |
| 293601 CATTAAAAACGAAGTGGCTTTTTTAGATAACTTTCTAGATTTTCTTAAGT |
| 293651 TAAATAAAATTACAAGCTGTTTTCCTAGTATTGTTGATCAATTTAACATG |
| 293701 AAGTTTATTGATCAAAATAATAATGAAATTAACCCTAATGATATTGATTG |
| 293751 TTTTTTTATCCCTTTATTAGCTTTTAATAAGGCAAACCACAGGATTGGTT |
| 293801 TTGGTAAGGGTTATTATGACCGTTATTTATCATTAACTAGCAAAAAACAA |
| 293851 CTAAAAATAGGGATAGCATATGACTTTCAATATGCAGAATTCACTAATGA |
| 293901 TCCTTGGGATTATCAATTAGATTTAATTATTTGCAATGGATAACATAAAG |
| 293951 GTTCTTTTTTAGGTGATGTTTATGGCAAAGCTGGTAGAAAGATTATTAG |
| 294001 TGATCATCTTCCCATAATTAAAAAkAGTATCAGTTAAATCTAATTATTG |
| 294051 CAAATGCTGAAAACACTACTAATGGTAAGGGTTTAAGTTGAAACCACTAC |
| 294101 CAAATACTAAAACAAGCAGGAATTGATTACATCACTATGGGTAACCATAC |
| 294151 CTGGTTTCAAAAGCAAGATTTAGAACTTGTTTTAAACCAAGTTGATGTTA |
| 294201 TTCGCCCACTTAACTTAATGCAAGATTTTAACTATTTTCAGCTTGGCAAA |
| 294251 GGGAGTTATTTATTTAGCTTAAATGGTTTGAAAATAAGGATTACTAACTT |
| 294301 GTTAGGAACAAGTATTAACTTACCATTTGCAATAACAAACCCATTTGTGG |
| 294351 AATTAAAAAAGTTAGTTTTAACTAAAGATTGTGATCTTCATATCGTTGAT |
| 294401 TTTCATGCTGAAACAACTAGCGAAAAAAATGCTTTTTGCATGGTTTTTGA |
| 294451 TGGTTATGTTACTGCTATCTTAGGAACCCACACCCATGTTCCTAGTAATG |
| 294501 ATTTAAGAATCACTCCTAAAGGAAGTGTTTACATTACTGATGTAGGGATG |
| 294551 TGTGGTCCTGGATTTGGTAGTGTTATTGGTGCTAATCCCAAGCAATCAAT |

-continued

| The Nucleotide Sequence of the *Mycoplasma genitalium* Genome |
|---|
| 294601 TAAGTTATTTTGTACAGGTGAAAGACAGTTTTTTGAGGTTTCTAATTGTG |
| 294651 GTGCACAACTCAATGGCGTCTTCTTTGAAGTTTGTTCAAAAACCAATCAA |
| 294701 GTTGTGAAAATAGAACAGATTAGAATAGTTTTAGATGATGAAAAGTATTT |
| 294751 AGCTAATGACTACTTTAATTTAGTTGAGTAATCTTGCTTTCCTTACCATG |
| 294801 TAAAATTCTGATTATGTTTGCACGGTGTAATCAGAAAACAACCACAGTTA |
| 294851 AAGGTCAATATCACAAGCAAAAAAATAAAATGATATACCATTCATTTTGA |
| 294901 TAAGTAATCGACTTTAGAGGATCACTGTTAAAGAAGTATAAATAATCAAG |
| 294951 TCAGGGTATTAAGATGATTACAGCTAACACAAAGAATGTAATAAGACTTG |
| 295001 CTAAAGAAACATACTTAGTTATTAAAGTAATCATTATCCAAATTAAAAGA |
| 295051 CAGATTAAAAATCATCATAAAGATATTGCAAGTAAAGATCCACCAGTAGT |
| 295101 AGCAATTGCCTTACCACCCTTAAACTTAAAATACAGCGGAAAGATATGAC |
| 295151 CTATTGTAGCTGCAAAACaACTTAAATAACTTAAAAAATAGGTGCTTTGA |
| 295201 TACACTTTTTCTGTTAAATAACCTTGTAAACAAAACGGAATAAAATTCA |
| 295251 GGTTAATAAAAAAGCAAAAAAACCTTTAAATGCATCAAAAATAGCCACCA |
| 295301 AAAAACCAATTTTTAAGCCAAAAACACGCATTGAGTTAGTAGCTCCTGGG |
| 295351 TTTTTTGAACCAAATTCCCTGACGTTTTTCTTGAGTATTTTGCTGAAAAT |
| 295401 ATCAGCAAAAATAATTGAACCTAACAGATAACCAGAAGCTAGGCTAAAAA |
| 295451 TGACCAAAATGGCAATTGCACTAGCTTGATTCATAGCTTGTAATTATCTT |
| 295501 ATTTAATGTTTCAATTATCTTAAGATCCATCAAGCTAGGTTTTTGTTTGG |
| 295551 GTTGATAAACTCTCAATAGGCATTGGTAGTGTTTCATTAAACAGTGTTTA |
| 295601 TCTTTAAAGTTAATTAGCTTTGGTCCTAAAATAACCAATTCCTTTGTTAA |
| 295651 TTTAAACGGTTTTTTTAGTTTTTCAATAACCAAAATAGGATATATAAACT |
| 295701 CTCGATCCTGAACTAGTGTTTCATTAACAATATCCCAACTGTTTAAACTT |
| 295751 AAAAAACTACGTAATTCAATTAAATTAGATTGGGGTTGGATTACAAAACG |
| 295801 ATTAATAAAGTTTTCTTTTTGGCTAATTATGTTAATGATTTTCAATCCAC |
| 295851 CAAGTCCAGCAATTACCCCTATTTTGGGATTAATATTTAGTTCTGGAAGG |
| 295901 TTATTAAATCCATCACTAACAAAGAAGTGGATATTATTGTTATTTTTAAA |
| 295951 TTTTTGGTAATTACTTAATAAAGCATTTTTACTAATATCACTGTTAACAA |
| 296001 TGGTTAGGTTTTGATTAGTTTTTATTAGATAGGATGTTAGATAGGAATGA |
| 296051 TCACAACCGATGTCATACACTAGCTTAGGATTAAATGATTGAACTAAATT |
| 296101 AGCAATTGTGCTAATCCTTTTTTTCATTAATTCTTAGAAATGACATACTA |
| 296151 ATAGGATTGTTTCTAACTGCATGTCTCAATTTTCTAATTGCTTTGTTTTC |
| 296201 AATTTGTCTGATCTTCTCTCTAGGGATCAAAATCTTTTGACCTACTTCAT |
| 296251 CAAGTGTTTTAGGTTCATTGTAAGGGGGCATGCCAATCCGCATTCTAACA |
| 296301 ATTAACTCTTCTTGTTCAGAAAGATTATTGTTCAACAATTCATCAATTTT |
| 296351 TTCTGAATTTGAACGGCTTTCGGTAAACTCGTCAGGAGTTTGAGCGTCTG |
| 296401 TGTCTTTAACAAAATCACCAAACTGGGACTCTTCATCATGTCCAACTGTT |
| 296451 TTATCAAGCGAAACTGGATCTAAACTTAACCGTTTAATTTCAGCAATCTT |
| 296501 TTTAACATTAAATCCTTCAGCTTGTCCTCCCATCTTTTCAGCTAACTCCT |
| 296551 CATCAGTAGGTTCTCGCCCTAACTCTTGATACAAAGCCCGTTCTGCTTTA |
| 296601 GCTAAGCGGTTAATGGTTTCTACCATATGAACAGGGATCCTTACTGTTCT |
| 296651 TGCTTGATCAGCTATTGCTCTTGTAATTGCTTGTTTAATCCATCAAGTAG |
| 296701 CATAAGTTGAAAACTTATTCCCTAAAGATCAGTTAAATTTGGAAATAGCT |
| 296751 TTTAAAAGCCCCAAATTACCCTCTTGAATTAAATCATTAAAATCCAACCC |
| 296801 TCTTTCTAGGTGTTTTTTGGCAATAGAAACAACTAGTCTTAAGTTTGAAG |
| 296851 TAACCAACTGATTAATTGCATACTTACGTGACTCTTCATCAGTACTATTT |
| 296901 AAAACCTTGGCAATCCGCTGTTCAGATTCAAAATCTAACATTTTAGAAAA |
| 296951 GTCAAGTGATCCTAAAAAGAACCTAACATTATCATCAACCTTATCACGGT |
| 297001 TAGAGATGTTCTTACTTGTTAACTCTTCAATATCTTCATCAATAATTGAA |
| 297051 AGGTCTTGGTTAGCACGAAATTCATGGATGTGCTCTTCAACATCGTGTTG |
| 297101 GAGTTGAATCCCCTTATCACGTAGTTCATCCAAAACATAGATAATTTCAT |
| 297151 CTTCAGGTAGTTCAAACTTAGCGAGAACACTAATAATTTCCTTATTTGAA |
| 297201 AGCGTGATGTTTTTTTGTTTCTTTTTGCTTTTCTTTTCTCAAGCTTCTGT |
| 297251 TAGAAGGTTGATGACTGTGTTGGTGTCATCATTTTCAATGTGGCTTTTTA |
| 297301 ACGATCCTTCTAAGATATCAAATAACTTCAGATTATTTTTTCTTTTAAA |
| 297351 GGAGCGTGTTTAGGTTTTCTACCCCTTCTTTTTTTAGGAACATCACTCTC |
| 297401 CTTATTTTCATGAAGGGTTTTGAGAAAAGCGATGTTTTCATGACGGTGTT |
| 297451 TGCGTTGCACTTTATTGTCAACATAAATCATCTTTTTGTAAGGACGATTC |
| 297501 TTTTCAAGAATACGCTGTTTTTTAAGTTCAGCAATTAATTCTTCAGATAG |
| 297531 TTCTGGTTTGGTTGAATTGGGTTTTTCGCCTAGCGTTTTTTGTCAGTGG |
| 297601 ACATTTAGCTCAATGCGACTAGCATTATAATTTTAGCTTATATAACTTTT |
| 297651 ATAGCGTTAACTTTAAATTTTTTAAGCGCTGCTTTTGTTGTTTTAATAAC |
| 297701 GTTTGAAAGGTCTTTAGATAGTTTTGAAAATCATTAGCTGATAACAAGT |
| 297751 TAATTCATCTAAAAAAATATCTTTAATTTCCAATAACCTTGCTTTATTGT |
| 297801 TTAAAAGGTAATTTTGATCTAAAACACTTTCAAAACCAACTCAGTTAGCA |
| 297851 GTTTGATTTTCACTCCAATAGATCCTTGCTTTTTCAATAAAAAGTTCAAC |
| 297901 ATCAAACAAATTAAAGTTACATTCCTTAAAAACTTCATCTAGATGGGATT |
| 297951 GTTTTAATTCAACCAAAAAGCGTTTATCAATTAAAGCAAACGCAAAGATT |
| 298001 TCAGGTTTTCACAACTCATTAACTGCTTCTTCAAAAGCTGTTTGCACTAG |
| 298051 TGCTGCAGTGGTTTTTTGCAATTCTTGTGGTGGTTGAGCATGGCCTGAAG |
| 298101 TATTTATGTAAAAACGGTTGTTATCAAACTTAGATACAAGTTTTTCTTTG |
| 298151 TGTTTTAAAACTGTTTCATACAGAGTTTTTTCATCACTATATTCAAGTAG |
| 298201 TTTAACCAAATTTTTAATGAGAAAAATTAAAAAACTATGGTCGTTTAAAA |
| 298251 TTGTTTGGTTTTTTGTTAAAAAAGCAATGATTTTATTAGTAATAACCCTT |
| 298301 TGATCAAGTTGTTGCTTTTTAAAAAAACTAACAAGATATTCAATTAGATT |
| 298351 TTGTCTTTTGTTTGCTTGTAATATAACTTGCTCACTACCCTTGTTTAAAT |
| 298401 ACAGTTCATCCCAATCTTTATAGTTGTGTTCTCACTGAACAATTTCCACA |

-continued

The Nucleotide Sequence of the *Mycoplasma genitalium* Genome

```
298451 ATAAAATTGTTGTTATTAAGTTTTTCAATTAAGCTAAACACAGCATTTTG
298501 ACCACTAGCATCATTATCAAGTGCTAAAACTAAGGTTTGTAACTCCTTAA
298551 AGTGAGCTTTAATGGCTTTAATTTGCACATCATTTAATGCTAATCCCATT
298601 AATGCAACAGCTTCAAACTTGGAGTTTGTTAGTGTAAAAACATCAAAATA
298651 ACCTTCCACAATAAAGAGTTGATTGAGGTTTTTATTTAACCTGTGAAAGT
298701 TAAATAACAGCTCCCCTTTTTTAAAAAATTCGTGATCAGCACTATTTTTA
298751 TATTTCAGTTTGTTGATGTTATCAACACTTCTTGCTGAAAAACCAACCGG
298801 GTTACCATTAAAGTCATGGATAGGGATCATAATCTGGTTTTGAAAGGTAG
298851 CTTTTTTGGTATTAAAGTCAAAAAAGCCAAGACCTTGCTGGTTAGTTTTT
298901 GAAAAAAGATACAATTCACTCGGTTTTATCTTTGGATTAATGAAGGGGTA
298951 TCTTTCCATACTTTCACATAGATACTTATCTTCATTGTGAAAAGCAAGTC
299001 CTAGCTGAAACTGTTCAATTAATGTTTTATTAAGCTTTCTTTTTTCAACT
299051 AAATAATTCATCCCATTTGGGTTTGTTTCTCTTTTTAATCTGGTTTGATA
299101 ATAAGTAATTAAAGCATTGTTTATCTCCCAATATCGTTTTTGTTTTGGAT
299151 CAACTTTTGTTAGTAAATTACTGTTCCAATTTTCTAACTTAATTCCACAA
299201 ATTTCAATTGCTTTTTTAAGTGCAGTTTTTCAATCTAACTGGTCATGCTT
299251 TTGGATAAACGCTATTCCGTTGCCAGCTGCATTACAAGCCCAACACTTAA
299301 AGATGTTTTTAGAACTGGAAATGGACATAGAAGGATTTTTATCATCATGA
299351 AAAGGACATAAAGCAAGTAGACTATTACCCTTAGTTTGGATTTTAACCCC
299401 GTAGTGTTGAATAATTTCAGTAATTTTAATCTGCTTTAAAAGTTCATCTA
299451 AACTGTTGCTTTTATTGACCATTTTTCATGAATCATTGTGGTAATTCTTT
299501 GATAGCAATTCGCTGTTGAACTAAAGTATCTCTATCTCTGATGGTAACTG
299551 CATTATCTTCTAAACTTTCAAAGTCAAAAGTGACTGCATACTTTATTCCA
299601 ATTGCATCTGCTTTTCGATACCTTTTACCAATACTACCAGTTGTCTCAAA
299651 GCACACTCTTCACCTTGTTTTTGCTAGCGTTTCAAATACAGAAAATGCTT
299701 CTTTTTTAAGTTTATTTACAAGTGGTAAAACAATAATTTGTTCAGGACAT
299751 AAGTCAAATGGTAAACTCAATACTTCCCGTTCTTCCTCATTAATAATTTC
299801 TCTCCTATAACTACTGACAATTAGTGCATAAAATAACCGTTCAATGCCAA
299851 CCGCAGgTTCGATTATGAAAGGTAAGAAATGTTGGTTTAATTCGCTATCA
299901 AAAAAACTCATGCTCTTTTTTGAAAACTCTTGGTGTTGTTTTAGATCAAA
299951 ATCACCCCTGTTAGCCAAGCCTCATAACTCCTTTAATCCGTGGGGAAAAT
300001 TAAACAAAAGTCAGTAGTTTTTTTGGCATAATGAGCCAATTCTGATTGA
300051 TCATATTCATGTTTTTTTAACAATTCTGGGTTAATTTTTAACACTGTTTG
300101 TAGAAACTGTTCTACCATTATTAATTGTTTTTCAAACAGCGAATTTGCAT
300151 CATCAGGTTTACAAAACCACTCAATTTCAAACTGTTCAAACTCTCTAGTT
300201 CTAAACAAGAAGTTACCTGGGGTGATTTCATTACGAAAGCTTTTACCAAA
300251 CTGGGCAATAGCAAAAGGTAAATTACGCTTCTTAGCTTGCAAGATATTTT
300301 TAAAGTTAATAAAGCTACCTTGAGCAGTCTCAGGACGGAGAAAAACAAGG
300351 CGTTTATCGTTGTTTACAACCCCGATTTCAGTTTGAAAAAGTAAGTTAAA
300401 ATCCCTCACTTCTGATCAATTTTGGTTATGACAATTAGGACAGTTAACTT
300451 TAAAACTATTCCAATCCTTTTTAGCTTTTATTTCAGCATTAATTTGATCA
300501 ACACGAAAGCGGTATTTACAACTCTTACAATCAACTAAAGTATCAACAAA
300551 GTTAGCTAAATGTCCTGATGCTTTTCAAACCAATTCGCTGAGAATAATAG
300601 GGGTTTCAACTAAAAGAACATCAGCTTTATTTTTAATAAAAAAGTTATAT
300651 AAAGCTTGTTTGATTTGTTGTTTTAAAACTGCACCTAATGGACCAAAATC
300701 CCAACTATTGTTTAAACCGTTGTAAATTTCACTACTCTGAAATACAAAAT
300751 CATGTTGTTTGAGAAACTGAACATAAACTTCTTGGTTGTAAACTTTAGCC
300801 ATTGTTAATTAATCTTAAAAATTAGTTTTTTCAAGCAAACAAGATAATCC
300851 CTAAAGCAACACTTACATTTAAAGAATTGATCTTATTGTTCATAGGAATT
300901 TTGATTCTACAATCTGCATTCTTTGTTATTAGTTGATTCACACCCCTATC
300951 CTCATTGCCAACAATTAAGATTTTTTAGCAAAATCAACTTTGCGATAAT
301001 CAATTGGTTTTCAAATAGGATCCAGAGTTGAAACAACAGTTCAAAATCCT
301051 ATTTCTTTTAGCTTAGTGATCGTATAACTTAAGTTAGCTACTTGCACTAA
301101 GTTTTGATAAAAAACACTACCCATACTAGTTTTCATGACTGTATTGTTGA
301151 TAGGGACTTGGTTATTCTTTTTAAAGATAATTCCATCAACCTCACTAGCC
301201 AAACAAGTTCTTAGTATAGCACCAAAATTATAAGGGTCTTGGATCTCATC
301251 TAACATCACAAGTGTACTGCACtTCTTATTTTCAACTACTTTAACCAGTT
301301 GATCAAGTGGAATTAAGAGTTGGTTAGTATCTAAAACTGCTACCAATTCC
301351 TGGTGGTTAATATCTCTATACTGATTGTTAAATCAGTTAGTTGAATGGAT
301401 TTGAAAATTAATTTTTTTAGCTTCAATTAAAGGTATTAGTTTTTTGTGAC
301451 GAATGGAAATGTTTACCAATTTAATGTGAACTTGGTTATTAATCGCTTCC
301501 TCAAAGGCTTTAACACCAAATAAGCAACTTTGTTGGCGTGGTTTTTTCAT
301551 TATTACAGCAACATTTTTTAATTAGTTTTTTTCTAATTTGATCAGCTTTT
301601 ATCCATTGCTTTTTGTTTGTGTAATATTGATCACTCTTTAATTAAACGCA
301651 CATTAAGTTTAGTATGGATAGATTTAAAGCTAATTCCTAATAAATCAATT
301701 GATCATTCCAAGAAACTAAGTTGTTCTCTCAGCACACTAAAGTCCTTAGT
301751 TTTAATACTTGTATTAATTTTTTTATTAGTTTTCAGATAGCAGCAACTG
301801 CATTGGCAAAGTTGAGATTATCAAGTAAAGCTGAAAAAACTGGATCATAT
301851 TGCTTGGGACTAATCAACTCAGATTGTTCTGAATAAACTAATCAGGTTCT
301901 AGCAACATTAAGTGTTTTTGCAATCCTTTGAATATCATTATTAGCTTTTT
301951 CAATCAATGATTGGTTTAGATCAATAGGATGCAAATAGTGTTTTTGGTAA
302001 AAGATCCAACGCAAAACACGAAAATCATGAAAGTTAAGAAAATCAACTGC
302051 TAACAAGAAGTTCTGCAATGACTTTGACATCTTTTGGTTTTCAATCATCA
302101 AATGACCAATATGCATCCAATGTTTGGTAATGGGCTGGTTATATAAAGCC
302151 ATGTGTAAGGCATTTTCATTTTCATGGTGGGGAACTTTAAATCAACTCC
302201 TCCTCCGTGGATCGTGAGTTCATTTTTGAAACAATAATCAATTAAGAAGG
302251 CACATTCAACATGTCAACCTGGTCTGCCAAGTCCCCACTTACTATTTCAT
```

-continued

The Nucleotide Sequence of the *Mycoplasma genitalium* Genome

```
302301  TTAATCCCTGCAGTAGTAATCTTTCAAAGTACAAAATCCAATTTGTTCTT
302351  TTTATCAGTATCAGTTTCTTCTAAATGCACCATTCGGTTAGCTAGATAAC
302401  CATATTGCTTTAGTGAATTAACTGCAAAATAAACGTTGTTTTGAGTTGAA
302451  ACATAAGCATGGTTTTGATTTACTAATTGATCAATATAGTCAGGGATTTT
302501  ATCGATTTTTTCAGTGATTTGAATATGTTTAATAGGCAGAATATTTAGTT
302551  TTTTTAAAAGTGATTTGTAAGCAGTGATTTGTTGTTTTGTAACAACTGAT
302601  TCGCTTACTTCTTGTTGTTGAGCAATCTTGATGATCTTATCGTCAATATC
302651  AGTGATGTTTTGAACAAAATTAACGGTATATTTAGCCTTTTTTAAAACTC
302701  TATTTAAAACATCAAAAACAATTAATGGTCTGGTGTTGCCTAAGTGCAAA
302751  TCGTTATAAACTGTGGGTCCACAGAGATAAATGTTAATGGTTTTTTGAAC
302801  TAGTGTTGTTGGTTTTTGACTAACACTGTCAACAATCATAAACCTATGTT
302851  CAAATTGCTTCATTAATGATAGGAATGTTCAGTTCTTTGGCGTGATTGAT
302901  TTTTCTTAAAGTTGGTTTGTTTCCTGCAATAACAAAGTCAACTGTTGGTT
302951  TGACTTCACTTGCAAACTGGCAATCAAACTTAGCTGATAATAAAtCCTTA
303001  ATTTGGTCACGACTAATGTTAAAGCTACCGGTAATAAGAAAGCGTTTTTG
303051  aAAATAAATACTGTTAGTTTCAAAGTTAATTTTCAGTGGTAATTGATCTG
303101  TTTTTACTTGTCTTAATTCAAGTTGTTCAATTAACTGCAAATGGTTAGGG
303151  TCATGAAACCAGTTATACAATGATTCAGCTACTGTTATTCCTACATCATT
303201  TAAACTAATTAAGTTCTCTAAGCTAGCATGCTGTAATGCTTTGATATTTT
303251  TAAAATGATTAGCTAAAtTCTTAGCTAATACATTACCAACATGCTTAATA
303301  CCAAGTCCTGTTAGTAATCTAGCCATTCCTTTTTGTTTTGAATTTTCAAT
303351  GTTATCAACTAACTTGTTGAAAAGTTTATCACCAATCTTCAGATCTAATT
303401  TTAAAACTTGGTTTTTCTTGTCTTTTAAATCATAAAGATCAACTATAGAT
303451  CTAACCAAATTGTGTTCATAAAGTTTGGTAATAGTATTAATATTCAACCC
303501  GTTAATGTCCATAGCAGTTTTAGAAACAAAATAGTTAATTAACTGGATGT
303551  TTCGCTCCTTACAAGTTTCATTGGTACAATACTGATCAACTTCATCAACT
303601  ATTTTGACTAGTTTTGAATTACATGAAGGACAATATTTTTGCTCTTGAAT
303651  TATGATAGTGTCATTTTTTCTTTTTTCAAGATTTACCTTTAGTACTTTAG
303701  GGATAATTTCCCCAGCTTTATAGATAACAACAGTGTCATTGATCCTAATG
303751  TCTTTAGTTTTAATGTAATCAAAGTTATGTAAAGTAGCAGCTGTTACTTT
303801  TGTTCCATCTAAATTAACACTTTCTAATTTAGCAGTATAGTTCACTCTAC
303851  CAGTTCTACCAATCGTTATAAGAACTGCTGTTAATTTAGTTTGAACAAAT
303901  TTAGGACTAAATTTAAATGCTATTGCCCAACGTGGTGATTTACTTGTAGC
303951  ACCTAATTGTTGATAAAAAAGCAAGCTGTTTAGTTTAATAACTAAACCAT
304001  CAAGATTAAAAGTTAACTGTTCTCGTTTTTTGTCAAACGCTTCCAAGTAA
304051  TTAATTAATTGAAATTTGTTTTGAAAAACCCTGATGGTATCACTAACTGG
304101  GAATTTTCACTGCTTAAGCTGTTCTAAAACCATAGTTTGAGTAGTGATTG
304151  ACTCTTCCAAACCATTAGGGATGTAATAAAATAATGCCCTTAATTTGCGC
304201  TGTGCAGTGATTTCACTGTTTAAATTACGTATTGTACCTGCTGCTAGATT
304251  CCTTGCATTAGCAAATGGTTTTTCAAGTGATTGTTAATTGCTAAAAAAG
304301  TTTTTTTATCAACAAAAATCTCACCCCTAATCTCAATTGTTTTTGTGAAA
304351  GGGATTGTTAAAGGGATAGATTTAATGGTTTTAACATTATTTAAAACATC
304401  TTCCCCAACACTTCCATCTCCTCTGGTTAAAGCATGAACTAAAACACCAT
304451  TTTTATAAGTTAGAGAGATACTAACTCCATCAATTTTAGGTTCAACTACA
304501  AATTCATTTTTTGAGTTTGTTTGAAAGTTAATATTATCAATAAAATTAGC
304551  AATTTCTTTAGTTGAAAAAGCATTTTCCAAAGAGAGCATTGGACTGTTAT
304601  GGTTTAACTTTTTAAAACCCTTCACAGCTTCTCCTCCCACCCTTTGGGTA
304651  GGGGAATCAATTTGGATTAAATCAGGATGATCTTTTTCTAATTGTTGGAG
304701  TGACTTATACAACATATCATACTCAAATCATCAATTAAAGGTTCGCTTA
304751  AAACATAGTAGTGATAGTCATAGTTTTTTATTAAGTTAACCAGCTGTTGA
304801  ATCTTCAATTTCACATCCATCACTACTATAAATAAGAAAAATCCTGACTT
304851  AGTTGATACCAATCAGGATTTTACAAAGAAGTTTTAATTTGGAGCAGATA
304901  ACGGGAATCGAACCCGCATCTTAACCTTGGCAAGGTTATGTTCTACCATT
304951  GAaCTATATCTGCGTTGTTACTTTAATATTTAGTATATTTTAACTTGCAT
305001  GGAATCTGAAAACCAAATTGCAATCCTGGATTATATTTTAACCAAGTCA
305051  ACCAGCCCAATCAACCAAAAATAGTTTGGTTCTCTGGGGAAGGGGAGGAT
305101  GAGAAAATTAATTTTTTAATCCGCTTAAATGATTTTTTTAAACCAAAATT
305151  TGTTGAAAATACTAATGATAGTAGCTTTTTATTAAGTTTTAGAAACCATG
305201  TTGAAACTAAAAATTCAACGCCTTTAACCCAAGCTAACTTTGCTAATATT
305251  GCCAACAAATTACTAGCGGTTTTATTTGGTTCATTGCAATGAAAACAGTT
305301  AAATAAACCAACTGGAAACTGATTTCTTGTAATTTTGTTTTTAGCTTTAT
305351  TATGGTTAAGACAATGCTGACTAAAACTTCAGTTAACTAAGATAAGTAAA
305401  TTTGTAAACCAAAAGGGCATTTTGAGTTTTATTAAACAACAATGGCCTAT
305451  TCTAACAACATTGGTAACAGTAGGGACCACATTAGGTACTCCAGTATTTT
305501  CATTAACAATAGCCCAACAAGATGGTATTAAGCAAAATGCGGGGAATGAT
305551  GTCTTTATCTTTTTGATTATCTTCTCTGTTTTTTCTATTAGTTTAGGGCT
305601  TGTTTCATCACTTATCTTTTTAGTCTCCAGCTTATTTTCAATTCGTCAGA
305651  AAAAAAACGTTGGATGCTTTGGATAAAGTGTTATCAAAATTTATTGATAAA
305701  TACTTTTTTTTAGATGAAAAAGAGATCAAAAAACAACTTAAATATCAGTT
305751  TAAAAACAACGGTGTTTGCTTTTTTTATGGTTTTGATTTTGATCAGGCAG
305801  AGTTTCTTGAACAATCAATGAACTTAATGTTGTTGTTAAAGCAAACCAAT
305851  TGTTTTATTTTAGTTGGTTGTAAAGAAAGTGAAATGACGCTCATTAAAAA
305901  CAAGATAGAACCTAACATTAACTTAAAACAAAACAGTTTTTATCTGGATT
305951  TAAGCAATGAAATTTCACAAGTAGAACAGATCAGCAAATTTAACTTGTTG
306001  TTTAGGCAATTGAGGCTCAGTTCTGAACTATTTTACTTAGAAGATTTTTT
306051  TGATTATCTAACTACTGCAAAACAGATAGTTAACTTTCTTTTTTAAAACA
306101  AAACCTAACCTTGATCAATTTCAAGAAAATCAAAAGAAATTATTTGATTT
```

-continued

The Nucleotide Sequence of the *Mycoplasma genitalium* Genome

```
306151 TTTAGCGTTATGAGCATTAGTAATTGGTACTGATTTTGAGTTTAATAACG
306201 TGTTGTGATCATTTAATAACCACTTTGTAATTGATAACAGTTTTAAACAG
306251 GAATATGACAAACCCAACATTACTGCTTTCTTTAATCGTTCTTTGCAATT
306301 TTTTCAAGAAAATAGCTTGGTTTTAAAACCTGAATTGTTTAGTTTGCAAA
306351 AATACACAAAGGATGTTTATGGTTTAAATGTTATCAACCAACTAAACTTA
306401 AATAAGCACCCTATGCTAATTCCATTAACATGGGATAAAAAGCAAAAGTT
306451 TATTAGCTTTATTGAAAGCTGTGTTCAAAAATACAGTCAAGTTAAAAAAG
306501 ATAACCAGGTATTTAGTTTAACAGTTGGTAAGCGCGTCTTTTTTCTATTA
306551 TTAATAAATAAGCAGTTTAAACAAATTAAACTTGAAACAGCACTAAAGTA
306601 CCTTGGCTTTAAAACTTCCCTTGGTGCAATGGACAGCACAACTGAGTCCT
306651 AATCAGTAAATAGAGGTTCAACTCCTCTAGGGAAGGCCAATTTATGATAA
306701 AAACTTAGTTAAATTGCTAGGTTTTTATCTAGTTTTAGGGGGTGTAGTTT
306751 AGTGGTAGAACAACAGTCTCCAAAACTGTCTGTGTGGGTCGATTCCTTC
306801 CACCCCCGCCATTTACAGATGCACTTCAATTCAAACTTTAAAGAATGCTT
306851 TAATAAGATTGCAAAAAAAGTTAATTCACTGGACAGTGAATACTATGAGT
306901 TTTCTTCTTTTATTGAAAGGATTAGAACTACCTTTGGACTTTTAATTGCT
306951 TTAACTGTTTTAAGTAACCTAATCATTATTAGCTTTGTTTTAATTTGATT
307001 TTTTACTGATGGCTTTGGTCAGTTAAGGCTGTTATTCTTTACGCTTTTTA
307051 TCCCCTTTTTTATCTCTTTATTAGTAGCAATCTTTCTAATCTTTCTTAAC
307101 AATTCATTCCGTAATTTTTTTCAGATTAATGAAAAGAACTGGCTGTTCTT
307151 ATGGACCTGTGTTTTTTCCTCATTACCAATCTTTAACTTGTGGTTAATTG
307201 TGAGATTAAATAAAACTATTAAGAATTTCGCTAGTGATTATGGTTTTAAG
307251 ATTGTTAATAAATATAACAGTTTAACAAGCGGAATTTTTGTGTTTGACTT
307301 TGCTGATTATGTTAGTTTTGAAGCCAACCTGACTAATTGAAAAAACACAA
307351 ACGATAAAAATCGTAATTTTGTTAACTTCTTTGAAACAATAAGCAAAGAA
307401 AAAACTGGTGTTGTTCAAAAACCAGTTCTTAACTTTCAAAGATTATATGT
307451 TAATCGTTTGTACTATCAAAGTAAGCTAAGTGTTGGTAGCAACCAACAGA
307501 CTCCCCAAACTGCTTTTGATAACCTAAGAAACTATGTTGAAAACAAACAG
307551 CGTGAAACAGTAAGGGTTAAGCAGTATATCCTCACTTAATTAAGTGAATA
307601 TATTAATATTTATTGGTCTTTGTCAAAAAATAAGATGAAAAAGGCAATCC
307651 ACTTTCAGAGTCAACCAGTTGTTTTTAACTGTGCTTCATGCAATAGCAAC
307701 TTTACCATTGACTCCACTGCCAAACAAAAGGATCTTGCCATTGACATTTG
307751 TGGAAAATGTCATCCTTTTTACATAGGGCAATTAACCAAACAAACCGTGC
307801 ATGGACGGGCTGAAAAACTTTCTCAAAAGTTCAACGCTGGAAAGGCTTTT
307851 TTAGAAAATAAAACTAAAAAGAGTAACCAAGCTAAAGTTGAAAAACAAAC
307901 TAGGCACCGTTCTATTAACGAGCTTTAGTGGATTTTGACAAACAACTCTT
307951 TTTCAATGTTGAAAAGATTGTTGAACTTACTGAACAACTTGAAAAAGATC
308001 TCAATAAACCTAACCTTAGCTTTGAGCAGATTAAAGTTATTAACAAAGAG
308051 TTAAAACATAAACAACCTTTAATAGTTAAATTCAAGGAGTTGCAAAAGCT
308101 GGTTGAAAATGCTAATGAAGCTGAACAAATTCTTAACAATTCCAGCTTAA
308151 AAGAATTGCATGAAGAAGCTAAAAAAGAACTTGAAAAAATCAAAGCTAGT
308201 TTACCTAGTTTAGAAGAGGAAATTAAGTTCCTTTTACTACCGGTAGATGA
308251 AAATAACCAAAAGAATGTTATTGTAGAGATCCGTCCAGCTGCTGGTGGGG
308301 ATGAATCTTGCATCTTCTTAAGTGATCTTTTTAATATGTACAAAAACTAT
308351 TGTACTAGTAAAAATTGAACGGTTGAACTTAATGAAATTATCCCTGCAAG
308401 TGTGGGGATTAACTTTGTTTCTTTTGCGGTAAATGGTACTGATGTTTTTG
308451 CTAAACTCAAGTTTGAATCAGGAGTACATAGGGTGCAACGTGTTCCTTTA
308501 ACAGAAGCTAAAGGTAGAGTGCATACCTCAACAGTTACTGTTGCTGTTTT
308551 ACCTCAATTAGAAGAGGTAGAGATCACCATTAATCCTAGTGATTTGAGAA
308601 TCGATACTTACCGTGCTTCAGGAGCGGGTGGACAACATGTTAACAGAACT
308651 GAAAGTGCAGTTAGAATTACCCATCTACCTACGGGAATTGTTGTGGCTTG
308701 CCAAGAGGGTAAATCCCAGTTTTCTAACCGTGATAAAGCAATGAAAATGC
308751 TACGTGCTAAGTTATGGGAAAATGCTCAAAATAAACAACTCTCAACCCAA
308801 GCGGATTTAAGAAAAAGTCAAGTTGGTAGTGGAGAGAGAGCTGAAAAAAT
308851 TCGTACCTACAACTATCCTCAAAACAGAATTACAGACCACAGGATTAAAT
308901 TAACTATTAATAAGCTTAATACTGTTATTTTGGGAGATCTTGATGAGATC
308951 ATTGAAGCTTTACAAGCTGATGAAAAGAAACAACAGTTGGAAAAGTTTAT
309001 TAGTTAGATGACTCTGTATGAGTTTTTTTAAATCAAAAGTTAGTTTACC
309051 AATCCAGTCCCCATTTTAACGGGGTATTTTTAACAATATTGGAACACTAT
309101 GGTTTTCAATTTAAAACAATTGATAAACTCTGAAAAAGTAAGCTTCTAAT
309151 TACTAGTGAGTTAACTGATAAAATCAAACAACAATTAAAGTGTTATTTTA
309201 TTGAAAAGATCCCTTTGCCCTATTTGTTGGGAACAATTCAACTAAGGAAG
309251 CTTACTTTTAAAACTAAGAAAGGAGTTTTTATTCCTCGAATTGATAGCTT
309301 AGCACTAATTGCAAGTGTTAACTTAAAAAAAATAAAAACTGCACTTGACC
309351 TTTGTTGTGGTTCAGGTACTTTAGCCATTGCTTTAAAAAAGAAGTGTGAT
309401 ACACTTGATGTTTATGGTAGTGATATTGATATCCAAGCATTAAAACTAGC
309451 GCAACAAAATGCATTAATTAATAACGTTAGTATTAATTGAATTGAAGCAG
309501 ATTGATTTGATTGTTTTAACAAGATAAAAACTCCGATTGATTTAATTGTT
309551 ACAAACCCACCTTATCTGAAAAAAACACAACTAAATAAAACATTAAATTA
309601 TGAGCCTAAGCACAGCTTGGTTTTTCAAAATAAAAATAGTTATTTTGCAT
309651 ACAAGCAGTTGTTTAATCTATTACTAACAAAACGATCAATTAAACAGTTA
309701 ATTTTTGAATGTTCTTTATTTCAAAAAGAAAGGCTATTAAATTTGTTTTC
309751 AATCTTTAAATCAAGGCCGATTTTTAACTTTCAAAAACAGTTTATTGGTA
309801 TGAAAGTTGATAATCAAAAACTCCCAGTAGTTGATATTAAAAATACCAAA
309851 ACTATTAAGCAACTTTTAAAAATGGGGCTAGCAGGAATTGTAAATACTGA
309901 TACACAAATGGGATTAATTAGTTATTCAGAGTCTACTCTTGACAAAATTA
309951 AACAACGTGCACTTAACAAACATTATGTATCAATGTTTGGGTTAGAAGAA
```

-continued

The Nucleotide Sequence of the *Mycoplasma genitalium* Genome

```
310001 TTAAAGAAGTTACCAAAAAAACTACAACAAATTGCTAGTTACTTTTGACC
310051 AGGTAGTTATACCTTTATTAAAAATAACAAGAGCTACAGGGTTCCTAAAA
310101 ACTTGGGCTTATTAAACCTTTTTAATGCAATTGGTAGGGTTTTTTGTACT
310151 AGTGCTAATATCAGTAATCAAAAACCATACACCAAATTAAGTGATTATCA
310201 AAACGATAGTTACTGAATAAAGCAACCTTGTTTTATTATTAGAAGCACTT
310251 CTAAAGTGCAATCAAATAACACACCTTCACTTGTCTATAATTTAGATACA
310301 AAACAGTTGGTTCGCACCACAGCTAAACAAACAAAACAGTTTCATAAATT
310351 AATAACTAAACACCAGTTAGCTATCTAATACACAAACCAAAATGAAACCA
310401 AAGATAATAACAAGCTTTTCAATATAAAAATGCTTAATTCAGTTTTATTT
310451 TTGAAATAAAACTATTTTTTTTAATTAGTATATAGCATCAACTACTAAAA
310501 CATAAGGGATGAAGCTCAAAGGTTTTTTAGCTGTTGGTGTTAGTGTTTTT
310551 GGTTTTTCTGGTTTACTGATGGCTTGTAGTGTTGTAAGTCAGTTTGATCA
310601 AGTGGATGATGGCAAAATTAAGCTAGCATCTTCATTAACTTCGAAACGCG
310651 CAGCGGAAGCTTTAGAGACAGTAGTTAAAAAATATAACGATACTAAAGAT
310701 CCTGGTGATTATCCAATTGAAATAGTACAAATTGCTGGGGGTTATGATGG
310751 GGGTAAAAAGGATGTTCAAACCAAGGTTAGTACCAAAGATAAAAATAACT
310801 TTTATAACCTGATTTTAAACTATCCAGAAATAGTAAGTACCTTATCAAGG
310851 TCTAAAATGGCTTTGAATTTTGATGGGGTTAATGTTGATAAACTCCATCC
310901 TAACTTTTTAAGCTTTAACAGCAGAATAGGTGGAATTAGAGATGATGGAA
310951 TCTATGCTATTCCAATATCTATGTCCACTGATCTGATGGTCATTAATGGC
311001 CCTGTTTTACACTATATTCTAAACAGTGCTAGAAAAGAAGGTACACCAAC
311051 TAGCACTACTGTTCAAGCAACTGTCAGTTCAAGAAGTGCAGAAAAAAAAG
311101 GTACATTAGAAATTGCAAATGATAGTGAAACTACTAAACTTTGACAGAAC
311151 ATCCAAACCACTGCTCAAAACAACAGTAATGAAACAACTAAGGAGCAAAA
311201 ACAAGTAAAAAGATCTAGTAGTTCTTCATCTACAACATCTACTACTGGTG
311251 AAACTAAAGATACTACAAAATCAGATAACAAGATTAAAGAGTTTTGGGGT
311301 GAATATCAAGAAGTGGATGGAGGGTTAAAGAATTTTACCTTTAAAGCAAG
311351 CATCTTTGAAAACTGAAATGAAACGTTAGATTTTGCTACTAGAATAGCAA
311401 ACTCTTTTCCTGAAAAGGTTAAAAATATAACAAATAAAACTGGGCTTGAT
311451 TTACAAGGTGTTTTAGGAGTTGATAGTAGTTCTAATGCACTTTATGCAGC
311501 AGTTTTTGCAGCTGGTCAAGCTAACTATGATAACTTCTTTTTTAACATCG
311551 ATAAAAGAACTGGTTATGCAGATTACTCTAACTTTTTAAATAAAGATAGT
311601 TCATACCAAAATTTAGAGAGTGTTTACAATGACTTTTATAAATTAATCCA
311651 AGCTAATGGTTTGTTTGTTAACCGTGGTGGTTCCTATTCATCCAACTTTG
311701 AAAAATTTCACCAATTGGCATTCTCAGTATCTTCTTCTGGAGGATACAGT
311751 TATTACTTTGCTAAAGATAATGCTAAGCGCTTAAAGTTTAGTAATTATGC
311801 TATTGAATATCCTAGTTTTACCCAAACAATTCAAGCTCCTAATTCTTCAG
311851 AAACAGAAAGTAATTTACTTGGTACTTTTAAATTAAGTGAAAAAGATATC
311901 AATCTATATAAAGGTTCAATTCCTAGTGGAAAACAACAAGGAGTTGATGC
311951 TATCTTAATTAGTAACCCAAACTTAATTAATATTCTTGAACAAGCAAAAC
312001 AAAAAAACACTGCACAAGGAAGTGAATCAACCACTAACAAGATAATAGGT
312051 TATACCACCACTGCAAATGTTAATGTTGATAATCAAAACATCTTTTCTGT
312101 TAGCAAACTTAACAACGAACAGTTTCAAAGAAAAATCATTGTTAATGCCA
312151 CTGAAGAAACACTTGATCAATCCCAAACCTTACAGAGCAATGAATCAATT
312201 GTTTTACCAATGCCTGGTAAATACAAATCAACTGATAAAAATAAAGTAAT
312251 GATCACCCAAGGTCCTAACTTAATAGGCATCCATGCAAATGAAAAAGAAA
312301 ATATTGAAACTAAAAAATTTGTTAATTGGTTTTTAAATCAAAGTATTACA
312351 GATTGGAATAGTAATAATCAGCAAAAAAATAGTGATCAAACAACAAAAAC
312401 TGCTGCTGAATATTTCACTGATCAAGCTTCTTACATCCTTCCTTTAAAGG
312451 AAAAATTTAACAAAAGTTCAGATTTAGAATTGAAAGGCAGTAGTAGTTCT
312501 TCTAATTTAACAACCAGTAGTGCTAGCGCCTCTTTGTTAATAAGTAATAA
312551 TAGTTCAACTGCAAGTTCTCCTGCTCCTAAAAAAACAAACAATAATTCTA
312601 ATACCTTTACAGCTAAAGCACTAGAATTATTCCAACAAGCTGCTAACAAT
312651 GAAATTATTCCCTTTAGTGATCCAAGTGACTTTAGGAACGGCACATTCCG
312701 TAATAATATAAGCAGTAGTTTTAATGCTGCGGTGAATTCTAAGGTTAGTT
312751 TTAATCAATTTGTCCAAAACTTTATTAATAGTTTAGGATCTGGATTTAGA
312801 AGATAATTAGTTAACCTCCCCCAACCTCTATTTTCTGTTACTAGTGCCTA
312851 AGGTGGCATTAGAGTATCACAACCTGAATAACCAAGTAGTCAAAGAGAGT
312901 TTGGAAGTGGAAGCAACTGATTCTTTTGATCCCACCCAAGGGTTGCAAAA
312951 AGATAGTCCAGTGAAGGATTCAAGTAAACAAGGGGAGAAACTCCAAGAGA
313001 CCATGTCATCAATGAGTGGTATGGCTACCTCTACAAGAGATAAAGCCCTC
313051 AAGATTGAGGTGGAAAGGGGAGTCAAAGTGATTCACTTTTAAAAAACGA
313101 CTTTGCTAAAAAGCCACTGAAACATAAGAACAGTAGTGGGACAGAGGTGA
313151 AGTGGATTCACAGAAGGATTTTCCCCAAGGAAAGGTTTGAAAACCGGTG
313201 TTGAAAACAGATGAGATAGAAAAAAATAGGGGATGGGGCGACTTAGAC
313251 TTTCTCCCCTGAATCGGCAATGGTAAACCCTTCTCCAACTCCCCCTCCCC
313301 TTCAACTTCCGCTTCCTCAACCCCACTCCCCACTTTTTCTAACATTGGCG
313351 TAGGGGTTAAATCAATGATCACTCAACACTTAAATCAGCAAAACACCCGG
313401 TGGGTGTTTACACCTGGTAGTACACCAGACATTTGAACAGGAGCAGGTTA
313451 TAGAAAAGCTAATAACAACAATAACGGCATCCCTTTTGAACAGGTGAAAC
313501 CTAGTAGTAGTAGCAACACGTTTAATCCCAATTCAGATGATAATAAAGTC
313551 ACACCATCAGGTGGCTCCTCCAAACCAACCACCTACACCCATTTACCCAA
313601 CAGTATCAGTCCCACCAGTGACTGGATCAACGCATTAACCTTCACCAATA
313651 AGAATAACCCCAGCGCAATCAGTTGTTGTTAAGAGCGTTATTAGGAACT
313701 ATTCCGGTCTTGATCAATAAGAGTGGAACGGGAGATCAATTTAACAAGGA
313751 TAGTGAGCAAAAATGAAACGAAACAGATAAATTAGGAGGCAACCTCCCGG
313801 GGTTTGGGGAGGTGAATGGTGCTTCTTATAAGATTTTTACTTATTTAATA
```

The Nucleotide Sequence of the *Mycoplasma genitalium* Genome

```
313851 ATTAAAAAAAGTGTTAGGTTTTTTTAGTTTTTTATCTATTTAATATTTAA
313901 GAAATTCTCAAATTTTTCTTAGTTTTTTATTTGTTTAATAGTTAAAAAAA
313951 GCGTTATGTTTTATCTATTTTATTAGTTAAAAAAGTTTTGAATTTTTATC
314001 TATTTTTAGTTAATAAAAGTCTTATGTTTTTATCAAATTTTTATCTGTTT
314051 TTTGGTTAAAAAAGTTTTAGATTTTCTTTCTTAAATTTATTTATTAAATA
314101 GTTAATAAAAGTGTTAAGTTTTATCTATTTTTAATTAATAAAACCTCGAC
314151 CCCTCTTCCTATCAAATCGCTGACCAAACCATCCATAACACCAACCTGTT
314201 TGTGTTGTTCAAGTCTAGGGATGTGAAGCTTACATATAGTTCAAGTGGCT
314251 CAAATAACCAGATTAGTTTTGATTCAACTAGTCAAGGTGAAAAACCCTCC
314301 TATGTGGTCGAGTTTACTAATTCCACCAACATTGGCATCAAGTGAAGGGT
314351 AGTGAAAAAGTATCAGTTAGATGTACCGAATGTTACCAATGAGATGAACG
314401 ATGTACTGAAAGAATTGATCCTAGAACAACCCCTTACCAAGTATACCTTA
314451 AACAGTAGTTTGGCCAAAGAAAAGGGCAAAACCCAAAGGGAGGTGCATCT
314501 GGGTAGTGGGCAAGCAACTAATTGACGATCGATGCGTAACTCCATTGGTC
314551 TGAATGACAATCCCAGCCCCAATGCTTCAACTGGGTTTAAATTAGACAAA
314601 GGCAATGCATATAGAAAACTAAGTGAATCCTGACCAATTTATCAACCAAT
314651 TGATGGGACCAAGCAGGGCAAAGGGAAGGATAGTAATGGGTGGAGTTCAA
314701 CTGAAGCAACAATGGCAGCAGGGGATGCGCCCCTAAGTACAGGAGGGAGA
314751 TCATCAGATCAAAGTAATAAATTCACCAAGTACCTCAACACCAAGCAAGC
314801 ATTGGAAAGGATCGGCATCTTGTTTGATGGGGATGGAATGAGGAATGTGG
314851 TTACCCAACTCTACCAACCCAACAAGGTGAAAAGTGGTCAATATCAACAA
314901 AATAACACCTACAACAGGTTAATTGAGCCTGACAATGCAACAAGTGCAGC
314951 GAGCAGCATGACCAGCTTGTTAAAGCTGTTGTCTAGTAAAAACATCAAAC
315001 AGAAGTTGGGGAAGGGGGGAACAGCAATGCAGGGAAATAATGGTGGAGGG
315051 GGTGTTAGTCAAACGATTAACACCATTACCACTACGGGAAATATTAGTGG
315101 CAATGGAACCATTCAAACGGCTTATCCGGTGAAAAAAGATGAAGCTTCAA
315151 ATGTAGCGATCAATTCCTTGATTAACGCTACGCCCTTGAATAGTTATGGG
315201 GATTTAAATAATGCTAGTTTTTCTAAATAATTAAATTGTTAATAACAAAA
315251 AAATCTCTATTAAAAAAACCAACTTTAAAGTTGGTTTGAAATTCTAAATG
315301 GCGCGCCCAATAGGACTTGAACCCATAACCTTCTGGTCCGAAGCCAGACA
315351 CTCTATCCGATTGAGCTATGGGCGCATATATTAATAAATTTTATTAATAT
315401 AAGCAAGAACAATCTAATTCTTTATTAGAATTTAAACGATTTCATCTAAT
315451 AGTTCAAATCACATATGGCAAAAGATAAAAAAAATAAGGTTGATGGAACA
315501 GaGCAATCAGTTGATCTATTTGAACGTACAAAACTTGAAGATACACAAGT
315551 TTTAAATGAAGTTGAACTTGATGATATTAAAAAGATAACAGAGCTTAGAA
315601 AAGAACTTGAACATACTTTTGAACCACAAACAAGAATGCAAATTAAGCGT
315651 GAAATTAAAGAAATAGAACGCAAAATGAAACGTTCTAGTCGCTAATTGAT
315701 GTTTGTTAATTTACATACAAATTCATACTATAACTTTCTCAATTCTGCCC
315751 TTTCTCCTAAAAAGCTAGTTAATCTAGCAATTAATGATCAGCAAAAAGCT
315801 GTTGCTATTACAGATCCTAATCTTTTTGGCGCTGTTGAATTTTTTATAAC
315851 TTGTAAGCAAAATAATATTAAACCAATTATTGGTTTAAACTTAACTGTTG
315901 AATACCAAAAAAATGATGTTAAGTTATTACTAATTGCTAAATCAAATAAA
315951 GGCTTTCAAACGTTGAACAAAATAGCATTAATTCAACAAAAACTTGAAAT
316001 TAATTCTTTAGTTGATCAACTAACAGATATTGCAGTAATTATCTGTTCTT
316051 TAACAACATGAAAATCTACTTATAAGGATGTTTATCAAGCAAAAGGAATT
316101 GAAATAAATCAAACCCCGATTGCCATTCTTGCAAATGCTGTTAACTGTGA
316151 AAAAACTAATAGCGATCAAGTAGTTTTAACAGTTTTGAAACAAATGAAAC
316201 AAAACCAAACGGGAAAAATAACTACATTTGATTGGGATCTTAAACAAAAA
316251 TTAAATCAAATTTCAATTAATGAAAATTTAAAAGTAAAGAGTGAAATTCA
316301 ACCTTTTTTAGATCAAAAAACTGCACAACAATTATTCAGTGAAACAGAAC
316351 TTAATAATCTGAATGATCTAGTTAATAGATGTGAATTAGATTTGGAGCAC
316401 CTAAAAGCTGCTTCACTTTCTTTAACTGATAATGATGCAGCAGTTTTAGA
316451 AAGTTTGTGCCAAACCAATTTAAAACAGTTTTTAGATAAAAATCAAGATc
316501 TAAATAAAAAAGCCTATCAGCTACGTTTAGAGAAGGAATTAAATGTTATC
316551 AATAAACTTAATTTTGCTAGCTATTTTTTAGTTGTCAATGATCTTGTTAA
316601 TTATGCTTTTAAAAAGGACATCTTAATTGGTTCTGGTAGAGGTTCTGCAG
316651 TAGGATCATTAGTGGCTTTTTTATTAAACATTACCAAGATAGACCCAGTC
316701 CAACACCAGCTTATTTTCGAACGTTTTATCTCAACCCACCGTCAAGATCT
316751 ACCTGATATTGATATTGATATCATGGAGAATAAAAGACAGAAATGATAA
316801 ATTATCTGTTTGAAAAATATGGCAAAGAAAACTGTGCACAAATTGTTACT
316851 TTTCAACGTTTTAAAACCCGTTCTGCTGTTAAAGAAGTTGCTAAATTATT
316901 TAATGATTATGGCATTAGTGACATGATCCTAGGAGTGTTACCTAAAGATC
316951 AAACTATAACATTCACTGATCTTAAAGCTACTGAAGATAGTGCTTTACAA
317001 CTTTGTTTACAACAGTTTGGTTTAATTGTTGAATTAGCACTAGCAATAGT
317051 TGATTTTCCAAGACAATCAAGTATCCATGCTTCAGGCATAGTTATCGCTT
317101 CAAATTCTTTGATTAAAACCATTCCCTTGTTACAGCTTGACAATAATCAC
317151 TTTTTAACTCAAGTTTCAATGGAATGGTTAAGTTTTTTTTAATCTCAATAA
317201 GTTTGATCTGCTTGGTTTAATTAACCTTACTATGATTAGCGATGTAATTA
317251 CCCAAATTAAACCATCTAACCAGACCGTTAACCAGTTTTTAAATACCATT
317301 TCTTGAACTGATCAAAACACCTTTATAAACTTAGTAAATGAAGATACACT
317351 AGGAATCTTTCAACTTGAATCGTTTGGCATGAAAAAATTACTGGTTCAGA
317401 TTAAACCTAAAACCATTAATCAACTAGCAATTGTTCTAGCGCTTTACAGA
317451 CCAGGTGCACAGGATAACATTAACCTTTTTATTAACCGCTTGCACAATGG
317501 TTATGATCAATCTGACATTGATCCTAGGATTTTACCCATTGTGAAAAATA
317551 CCTATGGAGTTTTAATTTTTCAAGAGCAGATCATTAACATCGTTAAAGTT
317601 GTGGCTAACTACTCTTTAGAAGAAGCAGATAGCTTCCGTAGAGCCATTTC
317651 TAAAAAGGATGTTAAATTGATCCAAAAAAAATAAGCGTAACTTCTTTGAAA
```

-continued

The Nucleotide Sequence of the *Mycoplasma genitalium* Genome

```
317701  GAGCAGTTCAAAATAACTTTGATTTAAAGACTACTACCAAAATTTTTAGC
317751  TACATAGAACGCTTTGCTAACTATGGGTTTAACCTTTCTCATGCGTTGGG
317801  TTATGCACTGCTTTCATACTGAACAGCTTGACTTAAAACTAACTATCCTG
317851  TTTATTTTTATTTATGGTTATTAAACCATTTTCAATCTAGTAAAGACAAA
317901  CAAAAACTAATTATTAGAACTTTAGAAAAAAGTGGTATTGAAATTTATCC
317951  ACCTCTTTTAAATAAAGCTCAACCAAATAGTGTTATAGAAAATAAAAAAA
318001  TTTATTTAGGTCTAAACCTAATTAAGGGAATTAATGACAGGTACATCCAA
318051  AACTTACAAAAAGTGCAACATTTAATTCAAACTCAAAATAACTTACAACT
318101  AACTGATGTAGTAAGTTGGTGTTTGGATAAAACCATTGGTGATATCCCTT
318151  TAAAAGATTTACTTTTATTAAAAACTATGGGCTGTTTTGATTTTTTTGAA
318201  TACACTTATGACTTTAATGATGCAAAGGATTTTTGAATTAAAAGCGATCA
318251  CCTATTGTTTACCAGAATGCCTTTAGAAAAAAGGATAGTAATTTTTGAA
318301  TTAAACAATTTTTTACCAATTAGTTGAACATGAAAAAAGCAATCCTGATT
318351  GATGGCAATTCCTTAGCATACCGTGCTTATTTTGCAACGTGAAAACAAGT
318401  TGAATATGCTAAGCAAAATAATTTACCTTTCAATAATGCAATAAGAACAA
318451  TGTTACTAATGTGTTGGAATTTAATTAAAGCCAATGTTTATCAATATGGA
318501  ATTGTAAGTTTTGACACTAAAGCGCCAACTTTCCGTGATCAAATCTATGA
318551  AGGATATAAACAAAAAAGGGTTAAAACTCCAGTTGAACTTTTAGTACAAA
318601  TTCCTCTAATTAAACAAGCGCTTGTTTATTTAGGGTTTTTAGTTTGTGAA
318651  AAAGATGGCTTTGAAGCAGATGATTTGATTGGTAGTTATGCCAATTTATT
318701  TACAAAGCAAGAAATAACAGTTGATATTTACAGTTCAGATCGAGATATGT
318751  TGCAATTAGTAAACGCCTTTACTAATGTGTTTCTCTGTATTAAAGGTACA
318801  AAGGAGATGGTTATGTACAACAATGAAAATTTCAAATCACTTTTTTATGG
318851  TTTGGCGCCCTATCAAGTTGTTGAATATAAGGGGTTAGTTGGTGATAACA
318901  GCGATAATTTAGCAGGGATTAAAGGGATAGGTCCCATCAAAGGGATAGAA
318951  TTACTCCAACAATATGGAACCATTGATAACATCTACACTAACTTCAATAA
319001  TCTCCCCAACCAACTTCAAAAACTTTTAAATAACCAAAAGGAAATAGCTA
319051  AAACCTTTAGTTTTCTAGCTAAAATTAAAACTGATATTGAACTTGATCAA
319101  AACATAGATCTTACTGGTTTAAAACCAATCCAAAAACAAGCGTTAATTCA
319151  ACTTCTAAGTGAAAACAAAATTAATACTTTAGTTGAAAAATTTTCAAAAA
319201  TATAATGCCTGAACTTCCTGAAGTAACTACTGTTATTAATGAACTTAAAG
319251  AAACTGTTTTAAATAAACCTTTAGATCAAGTTCAAGTTAACCTAAGAAAG
319301  GTTTTGAAAAATATTGATCCTCAATTGCTGAATAAACAATTAAAAAATCA
319351  GTTTTTTACTGATATTAAGCGTAAGGGTAAATATATCATTTTTCTTTTAA
319401  GTAATGGTTTGTATTTAGTTTCGCATTTACGTATGGAAGGTAAATACTTT
319451  TTTGAAGAAGAGGTAGTAAATTTAATCAAAAGCATGTTTTAGTAGAATT
319501  TCATTTTGATGATGGTAGTCAACTCAATTATCATGACACCAGACAATTTG
319551  GAACGTTCCATTTGTATGAAAAGTTAGAACAAGCAGCACAATTAAATAAA
319601  CTTGCATTTGATCCTCTAGAAGCTGGTTTTGACTATAGGAAAATCTTCCA
319651  AAAAGCACAAAATTCAAAACGTAAAGTTAAAACTTTTATTTTAGACCAAA
319701  CAGTGATTAGTGGAATTGGCAATATTTATGCAGATGAAATCTTATTTGCA
319751  AGCAAAATTAATCCTGAAACAATGGTTGATCAACTAACAATTAAAGAGAT
319801  AGAGATTTTATGTAAAAATGCTACCAAAATTTTAGCTAAAGCAATAGTTA
319851  TGAAAGGTACTACCATCAGCAGCTTTAGTTTTAAAAAAGATCATACTGGA
319901  GGCTATCAAAACTTTTTAAAAGTTCACACTAAAAAAGATCAACCTTGCTC
319951  AGTTTGTAACCAATTAATTGTTAAAAAGAAGATTAATGAAGGGGGAGCT
320001  ATTTTTGTTTAAACTGTCAAAAAATCACAACCAAAGTTTCTACAAAACTC
320051  AATCCATAAATTTTTTAAAACTTTAAATATCTTAAAATTAACTTTTAACA
320101  AACTAATTGAAAACTTTATTTAACAAAGTAATGCTGTAATTAATCAATTA
320151  GTTAATGAACATTAAATAACATTTATGAAAAACGAAATTAAATATCTTTA
320201  TTCTGACTTGGATGGTACTATTGTTAGCTGAAATCCTAAAACAGAATTTG
320251  TTTATCAAAATAAAAGTTATAAAAATTTCCATGAAGTTAGTGATGCTACT
320301  ATTAGTGCTTTTTACCGATTGCAACAAAAGGGAATTAAGGTTGGTATTGT
320351  TACTGGTAGGGATTATTGTCGGGTGTTATGACTTGAAAAACAACTTAGAA
320401  CAGGATTGCCTACCATTACTTTAGATGGGGCTATTATCTTTTATCAAAAC
320451  GAAATCTTAAGTCAAACTTATTTAGATGATAGATTTATTGAAGGGATTAA
320501  TAACATAGTAAAGCGCTTTCCTGAAGCTGCTTATAAACTTAACAGTGGTT
320551  GAATTAGTTACTTTACTAAAAACCCTTCTGTTATCTTTGAAATTGATTAT
320601  GCTTTTCTTGGCTATTTCAACCCTAACACCAAACTACAAAAAAAGTTTAT
320651  AGACAGTACTGAAAATTGAGATCTTAATAAACTAAAAGTTAATCAGGTTT
320701  ACTTTGATATTGATACTTGCCCCTTAGCAATGCAAAAGGAAATAATTGAA
320751  CTAATTAGTGTTAGTGATGTAAATGCCAAAATCTATGAGCACTCTATGTA
320801  CATTATTAAAAATGGTGTTTCTAAAGCTAGTGCATTGCAAAGCCTTAACC
320851  AGTTTGCAATTCCAATAACAAAAGATAACACTATTGTTTGTGGGGATGGA
320901  GATAATGACATTGAAATGATGCAGTGAGCTAAACACAGTGTCTCACTAAT
320951  CGGTAGTAATCCCAAATGCTTTGCTCTAGCAAAATACCACACTGATAGTG
321001  TTGACAATGATGGTATTGCTAACTGGATTGAAAAAAACTTGTTATGTTAA
321051  TTGCAATCGTAGGTAAACCAGGTGTTGGTAAAACCAGTCTATTGCAATAT
321101  CTCAAAGATAACTATCACTTTTCAGTTTTTTATGCAGATAGTTTTATCCA
321151  TGAACAGTACCAAAAAAACAATCCAGGTTATCAATTAATCATGGATCATT
321201  TTGGCAAAGAGTTTGTCAATCAAACTGAAGTTGATCGTAAAAAACTAGCA
321251  AACTATGTTTTTAGTGATGATAAGTTAATCGAAAAACTTTCACTAGTAAC
321301  AAAACCGCTGTTAATAGCGTGAATCAAATCCTTAAAAACCCAGTTTCAAA
321351  AAAAGCTAGCACTAATAGAGATTGCTGTGATGCTTAACTATTGAAATGAA
321401  TATAGATCGTTGTTTGATTATGTGATTAAATTAGAAAGGGATGATCAGCT
321451  AGTTAACTTAGCTTTACAACAACGTAATAGTCATAAAAAAGTTAAGGATT
321501  TGATTAAAGAGCCTAATTGCAAAATAGATACAATTTTCAACAACGATTCG
```

-continued

The Nucleotide Sequence of the *Mycoplasma genitalium* Genome

```
321551 ATTGCAACAGCTGCTTTAAAGCTAATTAAGTTGCTAGAAACTTTTTTAGA
321601 AAGAAATAAATGCCGTTGTGATTGTTGTCATATTCAGTAATAAACTTAGC
321651 ATTTTTTTTAGCTAAATCAGTGCCATTAACCAAAGCaACTGGCCATTTAA
321701 CACTTTGAAATATTTCAACATCATTATCAGCATCACCAAAGACCATAGTC
321751 TTTTCAGGATCAAGATTATAATTATCAACTAATACTTTCAATCCATAAGC
321801 CTTATTAACATCTTTTTGCATGATATCAAGAGCAAATGTCATTGAACTCA
321851 CATAGTTAATATCTTGAATTTGATCTAGTTGTTTTGCTAGAAAAGGAACT
321901 TTTTCTCTGTTTTTAGTTACCAGTAAGATCTTTGTAATAGTATGTTGCTT
321951 AAAATCAAAATCCAAAGCTTTTTCAAACTTGTTAACTATGTAGTTATTTT
322001 CAATGAGATCAATTCCTACTATTTGACTTCTAGTTGAAAGAATTTTAGCT
322051 GAATCAAGCTCATGTGTAAAAGCAAAAACCTTTTTATCTGTATAGAAATA
322101 AAATGTTTCTTGAAATTCCAACAACATTTGCATAATTGCAGGTATTACTT
322151 TATTATCAATAGGTTTGATATGAACTGGTTTTTCACTAGCAAATCATAA
322201 ACAAGTGCACCATTGGAAGAAATTACAGGTAGATTTGGTGTAATAAAGGT
322251 AGCTGTGTTTCTAATTAAAATATGGCTTCTACCACTAGCAAAAGTGATTC
322301 TAATCCCTTTTTTCTGTAAATCCTTTAAAAACTCAACTGTTTGTTCTAAT
322351 GGAATTTGGTTGCTTGAAAGCAAGGTACCATCAAGGTCAAAAATAATGTT
322401 TTTCAGTTCCATTTAGCTATATACTTTTATCTATTTTTTTAAAAGAACAT
322451 TAATAATTCGATCCTGAACATAAACTACCCTCTCAATCGGTTGGTTGAGA
322501 ATGTCATTTATCTCTTTATCCTGTTTAAATGATTCTAAAACATCTATCTC
322551 TAAACTACCTTTAGTAAATTCTTTAGCTGCTTTAAATTTGCCATTAATTG
322601 AAAGAATAACCTTAGTTTTAGCAGTCTCAAAAAGTTGATAATCAACTAAA
322651 GAAATCGCTTGTTTAACAACAAATGGTTCAAGTCCACATTTTTCATTCAA
322701 TTCTTCAGCAAGAAAGGGCGCAAAAAACGACAGTACTGTTAAAAATCCCT
322751 TTGCATAATTTAAGCTAATTTTTTTGGTTTTATAGAGAAAGTTTAAAAAG
322801 ATCATCATTTCACTAATCACCAGATTTAGTTCATGTTTGTCAAGATGACA
322851 ATAACTGTTTTTTAAAAACAAATTGTAAGCAAAGATTGTCTCTTGACTAA
322901 CTTGATCAGTAACAACAGCATGATTAAAAAAGAAGTTATAAACTCGATCC
322951 AATCACCTTCTCATCCCGTTTAACCCTTCATCATTTCAAGTTAAACTAGC
323001 ACTAATTGGGCCCATAAACATTAAGTACAACCTTAAAGCATCTGCTCCAT
323051 GTGAATCAACAAGTGGTGTGGGGTTAATGGTATTACCTTTGGATTTGGAC
323101 ATCTTTTTACCATCAGGACCTAACACCATACCCTGATTAATTAATTTTTG
323151 AAATGGTTCTTTTGTTGATACTAGCTTCTTGTCAAACAAAAATTTGTGTC
323201 AAAAACGGGCATACAAAAGGTGTAAAACTGCATGTTCCGCACCCCCAACA
323251 TAAAGATCAACTGGAAGGTATTGATCAAATAATTTCTTCGCTTCTTTTGA
323301 ATCAATTGGTCAAAAATTAGGGTTTTTAATCAACATTAAATAACCCAGAT
323351 AATACCAACAAGAACCAGCTCATTGGGGCATGGTATTAGTTTCCCTTTGG
323401 TAATGGATGTTATCTTTGACTATGTTTACCCAAGCTTGATTTCTCATTAG
323451 TGGAGAATTACCACTTCCATCTGGTTTGTAATTCTCAAGTAAGGGTAATT
323501 CAACAGGGAGTTGTTCTACCAAATGAGGAGTGTTATTTTCATCAAAAATA
323551 ATTGGAAAAGGTTCGCCCCAATAACGCTGTCTACTGAAGATCCAATCACG
323601 CAGTTTATATACAGTTGTTAATTTCGCTTTATTTTGTGAAATTAACTCAT
323651 TAGTAATAGCTACTTGTGCTTCTTTAGTTGTTAATCCGTTATATGCAAAT
323701 GAATTTTGCAGCCGTTCTTTTTTATCAATGACGTTGATAATTTTCAACTT
323751 TTGTTTACGTGCGAAGAAGTTATCATTTTCATTGTGTGCTCCAACACCCA
323801 TAATAGCATCTGTTCCATATCCTTCAATTACATAGTTAGCAACATAGACA
323851 GGGATCAATTCATTTGTAAGAGGGTGAATAGCATTTGTTAATAAATCTAT
323901 CCCATCATATAAAGTTGCTTTTTGCTTTAAAGTTGTGGTTTTCTGGAGTT
323951 GTTTTTTTAAAAAACTAGCTACTTTTTTATTTGTTTCTGCTATCTTTTTT
324001 GCTAACCAATGGTTGGTTGAAACTGCAAGAAAACTAACCCCAAAAATTGT
324051 TTGTGGTTTAGTTGTAAAAATTGCAATAGCTTCCTTATGATCTTTTAGTT
324101 GAAAGTTAATAGTAACACCTTTACTTTTACCAATTCAGTTCCGTTGCATC
324151 TCTTTAATTGGTTCAGGTCAATCAAGTGTATCTAAGCCTTCAAGAAGTGC
324201 ATCAGCAAAAGTAGTGATTTTCAAAACTCACTGTTTCATCTTGCGTTTTT
324251 CAACTGAAAATGAACCCCTTTCACTAACTGCGTTGCCATTACTATCAATT
324301 AAAACTTCTTCATTAGCCAATACAGTACCTAGCTGTTCACACCAATTAAC
324351 ATCAATATCAACTAATTCCGCTAGGTTTGCTTTAAACAGCTCACTGAAGA
324401 TCCATTGTGTGTATTTGTAATAACGTGGATCAGTTGTTTTGAGACTTAAA
324451 TGATAGTCATAATCAAAACCAAAACTAGTTAATTGATTAATAAAGTTATT
324501 AATGTTTTGATCTGTTCAACTGCCAGGGTTTTGATTAGAGTTAATAGCAT
324551 ACTGTTCAGCAGGTAAACCAAAAGCATCAAAACCAATCGGATGGATCACA
324601 TTAAATCCTTTAGCTTTGTAATACCTACTTATTACATCAGTGATAGTATA
324651 AGCTCTAACATGTCCTAAATGTAATCCTGCTGCTGAGGGATAAGGGAACA
324701 TGTCAAGGACATAATATTTCTTTTTGTTACTATCGCTTTCAAAGCGGTTA
324751 ACATCTTTGTTTTTTCATTTTTTTAACCACTTTTCTTCAATTAAATTGTG
324801 ATTGTACATCTAATTGCTTTGATAAGAACGCTTGATTGCATATTTAGTTA
324851 AGCGATAGAGTATGTCAACAATAATCGCAATAATCAAACCAAATAACAAC
324901 CCAAAGCCAACAGGGATAAAAAAGTGAACCATTGTTTTAAATAAGACTGG
324951 TTGGTTTGCAACTGTGGCATTAAACCAACTGTTAATGTTGGGAAAAATCG
325001 TTAAAATAATCCCACTAGCATCACTGGAAGCGAGTAAATCAGCCCACTGA
325051 GCTGTTTGGTATGTATTAAGTCAAAAACTACCAATAAAAATAAAAAACCC
325101 AATTACCATCAAAAAAACTAGGATTGCAATTTTCACTAGTTTAAACAAAA
325151 GTGTCATTGTAGTTTTCAGTAAGTGTATTTCAATTATAAAGTTAGATAAAT
325201 TTTCAATCTAACTTTTGTAACTTTAATTTTTCAAGGATCATTTTAATAAT
325251 AGTTACTATTGGTAGTTTTGCATCTATAATACAGTAATTAATCCCAAAAT
325301 CATTACAAACCGCTTCCATAAATCCAGTGTAAACCCTGTGTAAATTTTGA
325351 AAGTAAAGTTGATTTTTAGTAAAGTTATCAATCTCTACTTTGCGGTTACG
```

-continued

The Nucleotide Sequence of the *Mycoplasma genitalium* Genome

```
325401 CATAAATAGTCTTTTTTCAAATAATTTTCAATCCCCATCCAAAATGACAT
325451 ATAAATTAGGAACCCCATGCTTATTAACTAGTTCTTTTGCTAATCTATTT
325501 CACAGTTGGTTATAGTATGAAAAGACTGCAGGACGAATGATGTTGTGCTT
325551 AGCAAACAACCAGTCTTCAAAGATAGAACGATCAAAAATGGTTGGATTGA
325601 TAGTGTTGCAATTGTTCTGGTATTTACCAAAGCGATTAAGCGTAAAATAA
325651 AGCTGAAACAAAGGTGAATAGAGCAATTCATCACTACGTTCATACATCTT
325701 TGCTAGTAAAAGTTCAACCAACTGGTCATTAGTTTCCAATTCACAAACAA
325751 CTTTTGCAGCTTGAATGTGGTTAGCTAATGTATTAGCAATGGTGGTTTTT
325801 CCTAAAGCAATCATTCCCCCGATCACAATACAATTAGCAATTTTATTTGG
325851 TTGAAAATGGGGCTTTTTTAGTTGCATATAAACACTTTTTAATATGTTGG
325901 GTTAAGGTTTATTTTTAATAAAAAACCATCACACTCACTGACAAGTCTTA
325951 ATGCTGCTCCATTTCTGGCCTGACATGATTCGACTCTAATGATGTGATGG
326001 TTCTAAATTCTAACAATTATTTAAATCTTAATCAATTAATTTACTAACCC
326051 TGTTAATAGAATTGGATTTGGGTTGTGTAGTGCCTCTAGGCAATGAACTT
326101 GAATTTGATTTTTAGATGGTTTGATCGGTTCATTCTCTTGATCTAATTG
326151 CTGTTGTGACGCTGGAGTTTCTTGTTGATAATTTGTTGGCGTTGAATGAT
326201 CAAGTTTAGTAATTTCAGCTATCTTTTTGTTAGTTTTGCTTTGGTTTTT
326251 TCAAACTGCTTAATGAAGTTAGTAAAGCCAGTCTTTGGATTCTTAGTTTC
326301 ATCAAAAATGGTTGCAATAATCTCATCAAGCTTGGTGAAATCAATTTCTA
326351 TTTCGGTGGTGAGCTTTTGGTGTTTTGAAGCGAATTTACAACTAACTTA
326401 TATGCTTTTTTAATGCTTGCTTTTCTTTTTCAGCGGTTTTTAAAAGTGA
326451 TTGGGTTTCACTAATTTCCCCATCTTTAAGTGCTAACTTGTCTTCAAATA
326501 CGGTTTGGATGTGTTGATCACGTTTATAAATTGCTTCATTACACTGCACT
326551 TCATATTCCTTTAACAATTCCTCTACATTAATACTTTCATGTTCTTCAAT
326601 TAGTTTCTTATTGGCTTCTTTTATTGCATGTAACTGTTTATTTAATGCTT
326651 CAATTTGGTGTTCTTTTGCTTCTACCAGCTGCTGCATTTGGATAATTTCA
326701 CTTTCACTTTGTTTGAGTTGTGAGAAAAGTTCGCTGTTCTGTTGAACTTG
326751 ACGGTTAATCTCTCCTTCCAAGCGTACCTTAAGTTGTTCTTGCAAACTTA
326801 AGATCCTTTTTAAACGTTCTTTTTCACTTCTCGCTTCAGGACCAAACTTT
326851 TTTAATAACAAAACAAGCATCTGGTTCCAATCAACATTTTTTGGGTTGCT
326901 TGTTCGTAGTTTGACATAAGCAGTTTTTGCTTGTTCTARAAAAACATCAA
326951 GCTGGGCTTTGGAAGCAAAGGGAAACTTGGCTAAAAAGAAGTTAATAGTT
327001 TCTCTTCTTTGAAAGTCATCAAAGTCTCTATAGTAATCAAAATTATTCAT
327051 GGAAAGCTAATTCTCTAAAGAAGCTAATGATAGCATCAGGATCATTAAAG
327101 TCTAAATCATAATGGTGTCTAACATAAACACTAACAAAACTAAAGATTGC
327151 TAAAACAAAACTAGTAAAGAGGAAAAAACGGGAGTTTATTGCCATGGTTT
327201 TTAACAAACAAATCTAACTTTTCATTAGCAATTTTTTTAAAACTAACTAC
327251 ATCACTAAACTGGTTAGGATCTAGTAAATAGTTGTTAAGATCACTAACTT
327301 TACTTTCAACCCATTCCAAGTTAGCTTGGTTATATTGAAATTCACTTTTA
327351 ATAGTTGCAAAATCAGTTTTTTCAACCTTGTTCAAAATTGATTGAAGCC
327401 ATTTGTGTATTTTTGAACAAAACTATCCATTTTACTTGTTATCAAATATT
327451 ACTCCTAAGAGTTGCTCAGGTTTTAAACTGCCAAAGTAATCACTAAAATG
327501 ATCAAGTTCATTGAAGAGTTTTTCAAAGGTTTTATAATCGTACTTCTGAC
327551 CAATTAGTTTTTTGTTACTGGGGTGATATCAACAACACTTAAAAAGTCC
327601 CCATAAAACTTAATATCAACAACTGTTCCTTTCTCTACTTGAACATTGCA
327651 CTCAAATAAACCAGCATTATTAAAATAACGCTTGTTTTAAAGTTGTATT
327701 CATAAGTTTTACCAAAGTTTCACTCCCATGATTGAAAGTGTTCTTTTGCT
327751 CTTTTTTCAACCTTTGCTAGTGCATCTTTAGTTAAAACAATTGTTTCTGC
327801 TTTTTCAGTAACAGTGAAAAAATTAATCATCTCTTCTAAAAATTTTGCTG
327851 TTGTTCAATTTGGTAAATACTCCTTTACATTAACAACGCGCTTAGCAACA
327901 CTGTCAACACCCTTACTTGCTATCTTGGTCTTATCAACATTTAAATACTT
327951 TGCTAACTTAGAAAAGTCAGTGTCAAACAATAATGTTCCATGGACTAATA
328001 ACCTGTCTTTAGCGATATATTCAGCTAACCCAGAAAACTTCTTGTTATTA
328051 ATCTCAAGGTCATTACGACCATGAAATACAGCAGGTACATTTAAGCTATT
328101 TAAGAACTTCACCACATTTCTTGTAGTTTGTTCATAAGCATTTTCCATCA
328151 CTTTACCTGTTCTTGGCAAAATAATAGAAAAACAGATGTTACCAAGGTCA
328201 TGAAACACCGCTCCCCCGCCTGAAAAACGTCTAAACAAGTTAACCTTATC
328251 ACTTTCCAACTCCTTTAAGTTAACCTCAGCATAAGTATTTTGGTTTCTTC
328301 CCACCACAATAGTGTTAGCGTTCTGCCAAAAGTAGATGACCTTAACTAAC
328351 TCATTTTTTCTAAATTCAGTTAGCAATCACTCCTCTAAAGCTGCATTAAA
328401 ATACGGATTGAAAACAGGGGAAGTAATAATGAAAGTTTGCATCAACTACC
328451 AATTAACTAAAGTAATCAAAGATCGCTTTTTTACAAACATCAGTTACCAT
328501 TTCATTCATGGTAGGATGGGTGAGATAGAATTGGCAATATCAAACACAG
328551 TGAGGTTGTTTTCCATCACCAAAGCAAGCTCAGCGATAATATCACTAGCA
328601 GTGCTAGCAATAATACATCCACCTAAGATAGCACCAGTTTTAGGATTAAA
328651 CATCATCTTGACAAACCCATTGGTTTCATGATCTGCAATTGCTTTACCAC
328701 TATAAATAAATGGCAAGGAAGATTTGACATAATCAATCTTTTCTTTTTGC
328751 AATTCCATCTCACTATAACCTACAAAAGCAACTTCAGGATTTGTGTAAAT
328801 ACAAGCAGGACACTTGTTTTTTTCAGCAGGCTTTACCTGGTTTTGGTTCA
328851 AAATTTGATCAACAGCATATCTGCCCTGTTGGTAAGCGTAGTGTGCCAAC
328901 ATCATTTGCGTGTTAACATCACCTATTAGATAGATGTTTGTAGTTGATGT
328951 TTGTAGTTTTTCATTTAAAACAATTTTGTTGTTATGGTCACGTTTTAAAT
329001 CAAGTTGATCTAAACACTCTGTGTTAGCAATTCTTCCTATAGAAACTAAG
329051 ATTTTATCACCAATTACAGACTGTTCAACTCCATTAACTGTGTAAAACAG
329101 TTGGTTGTTTTCAGCTCTAACAACATGAGCATTGGTAATAATCTGAACTC
329151 CTTTGTTTTTTAAGGTTTTACTTATCAGTTCAGAAACATCACTATCACAA
329201 ACCTCCAAAATCCTATCAACACCTTGGATAATGGTCACTTCACTCCCTAA
```

-continued

| The Nucleotide Sequence of the *Mycoplasma genitalium* Genome |
|---|
| 329251 TGAAGCAAATAAAAAAGCAAACTCAACCCCAATCACACCTCCCCCAACTA |
| 329301 CAACAAACTTCTTAGGTACTCCCTCTAAAGCCAAAGCTTGGGTTGAGTCA |
| 329351 ATGATAAACCCAGCTTGTTGTGCTTTTTCAAACCCTGGTAAAGTTAAGTA |
| 329401 TCTTGGTCTTGATCCGGTTGCAACAATAATGTTGTTAGTGGTGTAAGTTG |
| 329451 TGTTGTTTACTTGCACCTTGTTTTTATCTATAACAGTAGCTTCACCTTCA |
| 329501 ATACTTTCTACCTTAGCACCCTTAATAATTGTTTTTACCCCTGCAACTAA |
| 329551 TTTATCAACTACTTCCTGTTTTTGTTTTAACAGTTGTTTTCAATCAAGTT |
| 329601 TAGCTTGACCATTAATAGTGATACCATAATCTTTGGCATGAACTAAATAA |
| 329651 TCAATAATCTTTGCTCTTTTTAACAACGTTTTAGTTGGGATACACCCAAC |
| 329701 ATTTAAACACACCCCACCAAAGTATTGCTTTTCAATCACTAGGGTTTTAA |
| 329751 GTTTATGTTTGCCAGCATACTCCGCAGCAATATAACCAGCAGGGCCAGCA |
| 329801 CCCAAAATAATTAGATCATAATCCATAAATTAAGCTACTGTAAGATCAAT |
| 329851 TAATTCCTCAATTTGTTTTGCAATCTCCTTACCAAACCTACCAACATCCG |
| 329901 CCCCATCAACCCAGCGGTGGTCTGCAGCTATTGTTAAAGGTAAGATGGTA |
| 329951 TGAACTGCAATTCCATTTTCCACTTTAACAATGCGTTCTTCTAAATTACC |
| 330001 AGTAGCAACAATACACATCTCAGGGTACTTAATAATAGGTGTACCTACAG |
| 330051 CTGCTCCTAATGAACCGAAGTTAGTAACTGAAATAGTACCTTTATTCAAA |
| 330101 TCAGTCAACTTAATCTTTTTTGTTCTAGCTTTGTTAGCTAAATCAACAAT |
| 330151 TGCTTGGGCAATTTCAACCACAGATTTGGTTTGGGCTTGCTTAATGTTAG |
| 330201 GGACAATTAAACCTTCTTCAGTATCAACAGCAATTCCTACATTAATGTCA |
| 330251 TCATTTAAAACAATTTCGTTTTGATCAGGATCATAACTAGCGTTAAAAAC |
| 330301 AGGGAACTTCTTAAGCGCATTAACAATTGCTTTAACAAAGAAAGCAAAGT |
| 330351 AAGAAATTTTCATGGAATACTTACTTAAAGCATAACCATTAACACTTTCA |
| 330401 CGATATTGTTTTAACTTGGTTGCATTAACATAAAAAGTTAATACAGTGGT |
| 330451 TGGGATAATTGCGTGCGACTTTGTCATTGCTTCTGCAATCGCTTTACGCA |
| 330501 TTGTTGAGATAGCAATGGTTTTCTGTTCAGTTTTACTTTCTGGTTTTTGG |
| 330551 GTTGTTTCTACAGTAATGTTAGTACTACTTGCAACTTTAGTGTCTTTAAC |
| 330601 AGCTGGAGTTGCATGAGGTTTTACTCCAAAGATAGGAAAGAGGTTATCAG |
| 330651 AAACCTTAATTTCCCCTACTACTGAAGCCCCCGCTTCTTTTACCTTAGCT |
| 330701 ACTTCTTCAGTTGGTTGAGGTTTTGGTTCAACAAGTGGTGTACTAGTCTT |
| 330751 TTCACCAATAACTGCCATCACCTGACCAATGCTAACAACATCACCAACTT |
| 330801 TAACATTAATAGCACTAATTGTACCTGCAAAAGGAGAAGGTAGTTCAGTT |
| 330851 GTAACTTTATCAGTTTCAACAACAAATAAAGCTTCATCTATCTTGATCTG |
| 330901 ATCACCAACTTGTTTTAAGATTTCAGTTACTTTTCCTTCATGTAAACCCT |
| 330951 CACCAACATCAGTGAATTTAAACTCATTTGCCATATCGTATTGATAGTAC |
| 331001 TTAAAGTTTAAATTTAATAGTAGTGATCTATAACAAATAAAAAAAGCCAG |
| 331051 TTTAGTTACTGGCTTTTTAGTTGTTAGACAAAAATTTTGTCTTACTTTTT |
| 331101 ACAGCAGCTGTTGCACTTAGCGCATTCGCACTTGCATTGGCAGCATTTCT |
| 331151 TGTTGTCTTCCATCACTTTAATTTATGAAATGAGGTACCTAGCTCTAAAA |
| 331201 AATAAAGCTAGGTAACTATATTTTAAAAAAGTGTTATTTTAAAAGTTGAT |
| 331251 TAACTGCATCAATAACCCGTGCATTAATTTCAAACTGGTATTTTTCACCT |
| 331301 CTAGCTAAAGGCACAACAATATCAAACCCAGTTACCCGTTGTGGGGCTTT |
| 331351 TTTGAGATAAGTGAATAGTTCTTCAGTTACTGAAGTGATAATCTCTGCAC |
| 331401 TTGTAGTGAAACTTTTCACCGCTTCAGTCACTACAAGTAGTCTTCCTGTT |
| 331451 TTCTTCACTGAGTTAAATACTGTTTGTTTATCTCAAGGGGAGATAGTACG |
| 331501 CAAGTCAATTAACTCAATTCCCTTATCTTTCAATTCCCCGCTGTAAACTA |
| 331551 AGTTAATTAAATCAAACATTGTAGGACCATAGCTAACTATTGTAAGTTCA |
| 331601 CTACCTTCACTAATCAAGTTGGCTTCACCAATAGGGACAGTGTAATAATC |
| 331651 ACTAGGAATCTCCTGACGAAAAGCACGATAAAGCTTCTTTGGTTCAAAAA |
| 331701 AGATAACAGGATCAGGTGATTCAATAGCAGCTAGAAAAAGTCCTTTGGTA |
| 331751 TCATAAGGATTTGATGGCATCACTGTTTTAAGCCCAGCAATCTGTGCATA |
| 331801 AATTGCTTCCAATGTTTCACTGTGGTGTTCCAATGCTTTAATCCCCCCAC |
| 331851 CCATTGGCATCCTCACTACTAGTGGAGCGGTATATACACCACGAGAACGG |
| 331901 TTTCTAATCCTAGCAGCATGGACAAAGATTTGAAACATAGCTGGGAATGA |
| 331951 AAAGCCTGAAAACTGGATCTCTACAATAGGTTTAAGACCACCTATAGCAG |
| 332001 CCCCAACCCCAATACCAGCCATAGAGTTTTCTGCTATAGGACAATCCCAT |
| 332051 ACCCTTTCACTCCCATACTTTTGTTGTAAGCCTTTAGTTGCACGGAACAC |
| 332101 ACCCCCTTCAAAACCAGCGTCCTGGCCATAGAGTACAACGTTTTGATCTC |
| 332151 TTTCCAGTGCAAGATCCATTGCGTTGTTTAACGCTTCAATGTTATTTACT |
| 332201 TGGATTTTTGACATAGTTATCTTTTTTTAAATTAGTCTTTAAAGTATTTT |
| 332251 TTTGCAATCTGTTTCTGTTCAACTAGTTCAGGGGTTAATTCTTGATAGTT |
| 332301 GTAATCAAACACCTCATCTACTGATACAGGAGTATCTAGTACCATCTTTT |
| 332351 CATAAGCAGCTTGGATTTCCTGTTCAATTTTGCTGAACATCTCTTCTTCT |
| 332401 TGAGCTTGGTTAAGAATTGATCTATCAAACAAGAAGTTTCGCAACCGCTT |
| 332451 CACTGGATCACTCTTCATTCCCTCCTCCTCTTCTTGTTTGGTTCTGTAGA |
| 332501 TAGAAGGGTCATCTGAAGTGGTGTGAGGACCTTGCCGGTAGCTGAAGAAC |
| 332551 TCAATTAAGACTGGTCCATTACCACCTCTAGCGTAATTAGCAGCATCTTG |
| 332601 CATCGCTTCATAACTAGCAATTAGATCATTACCATCAACCCTTACCCTTG |
| 332651 GGATCCCACATGCTATTGCTTTAACGCTTAGATCACTAACAGCAGATTCA |
| 332701 AGTTTAGTTCTTGTTGAGATAGCAAACTGATTGTTGTTAATACAAAAAAC |
| 332751 AGTGTTTCACTTGTGGATGCTTGCAATGTTCATCGCTTCATAAAATTCCC |
| 332801 CTTCAGCTGTACCTCCATCACCAATCATAGTAACAGCAACATTAGGTTGC |
| 332851 TTTTTATAGTGCAACATGTAACCTAATCCAGCAGCATGGGAATACTGAGC |
| 332901 ACCAATGGTGATGTTAATAGGTAAAGTTTTGTATTTAGCATCTATCTGAC |
| 332951 TACCTTTTTCATTACCATTTCAGTAGAGTAAAAGTTGTTCTGGTTTTACC |
| 333001 CCACGATACAACATTAAAGCCCCACTACGAAACGTAGGACAAACCCAATC |
| 333051 ATTTTCATTTAAACCTAATCCCATTCCAACCTGTAAAGCTTCCTCTCCCA |

-continued

The Nucleotide Sequence of the *Mycoplasma genitalium* Genome

```
333101 AATTAGGAGCGAAGTTTAACATCTTACCAGCACGCTGTCAAACTAACATC
333151 TTTTTGTCCATCATTCTACTCAAGTTCATTAAGTAATAAGCGTGTTTTAA
333201 CTGTTCATCAGTTAGGGTAATTTTGTGGTTAGGATCAATTAATTTACCCT
333251 CATTATCATAAACCTGATAAAGGGTAGTTGGAACTTTATTTTTAATCAAG
333301 ATTGCCATATATtTCTATGCTAATTTAAAACTAAGCTATTTTTTAGGAAT
333351 GTAATAGCTAAAACCAAGTGCTTGTAAAACAGTTGCTAACACAAAGTTAA
333401 ACGGTTTGTTGTAATGTGGAAGAAAATAAACATCCACTAAACCCAGTTCA
333451 GTTAGTAACATCTGCTTTTGGATTGCAAGTGCAATATAGAAAATAATCTC
333501 ACTGTGATTGGTATTCCAAGAAAGGAGTTGTGCTCCTAAAATTCTTAGGG
333551 TTTTCTTGTCATATACAAGTTTAAAACGCACCTTGTCATAACTGCCCATA
333601 AACTCAGGACGATCATTGTCATCAACAACTGATATGCCAACATCAAAACC
333651 TAACTTCTTAGCACGCTGTTCAGTTAATCCACATGCTGCTAAATTTAAAC
333701 CAAAGATATGGAGTGCATTGGTGCCAACGATAGATTGGAGTTTAACTTGG
333751 TTACTACCAATGATATGCATCGCAGCTACTAATCCACTCTTTACTGCATT
333801 GGTAGCAAGATCGATGTTTTCATACTGTTCACTAGCAGCATTGTAAATAG
333851 CAGCACAACCCCCAATGACATAAACATCCTTATGATTTAGTGCTTGGAGA
333901 AATTCATTAACTTTAATTGAACCGTTGTGAATAAACTCAAAGTTTTGATC
333951 TTTAGGAACAAACTTAGTGCTAGGTCTAAACCCAATTGATTGGTTCACAA
334001 GGTCTGCATTTACTATTCCCTTATCAGTTTCAACTCCTTTGACAACGTTG
334051 TTTGTACTATCAACAACAAAGCCCTTAACACTGCAACCCATCATTAGTTT
334101 TAACCCATCTTTTTGCATCACTTTTTCAAGTTCATCAGTAAACTCATGAT
334151 CAAAGTTATTACCAGCAGGCTTATCAAGTAAGTCAATTACTGTTACTTGC
334201 TTTTTGCATAACCAAGCTGCTTCAGCAAGTTCCAAGCCAATGTAACCAGA
334251 ACCAACAATAGCAACTGATTTAATGGTTTTATCTTTACGAAAACTATCGA
334301 TTAAGGTAAGTGCATGTTGGTATAACTTACAGCTAATTAAGTTCTTAACA
334351 TTACCACAATATTTGTCAGTGTAGTTAAACTCCAAAGGCTTGTGTGTCAC
334401 CTTGTTTTCAACATTCATACATATAGGTCATGCTCCTGAAGCGATTACTA
334451 GTTGATCAAACTGATCAGTGAACTCTTTATTTGATGTTAAATCTCTAACT
334501 GTTACCTGTTTTTTGATTAGATCAATGTTAGTAACATCATGACTCATAAA
334551 GATGTTAGCGCCCATCTGTTTCAACTCCTCAGGGTTGGAATAGAAAAGAT
334601 CATCAGTGTTTTTAACAACACCACTAACAGCAAGTGCAATTCCACACCCC
334651 AGAAACGAGATGTTTGTGTTTCTATCATAAGCGTTAACCTTAAAGTCCTT
334701 ACTTTTTGAAAGTAAAGTTCTAATAAAACTAGTACCAGCGTGATTTATTC
334751 CAATCACAATCACTTTTTTCATATATCTTAGCTGCAGTAATTTTTTAAGC
334801 TATTTAAGGATAATTTGTGCAGTAGTGATTCGAtCTTTTAAAATTAAGCT
334851 TTTGCTAGTAATGTAATAAAATCTTGCTAACCACATTTGGTTGTAACTTA
334901 GCTTTACCATTGAGTTTTTTCAGCTCAATTAAAAAGCAATATCCCACAGT
334951 TTCACCATTTAACTGTTTAAGTAATTGGTCAATAGCAGCAACTGTTCCAG
335001 CAGTGGCAAGTACATCATCAACAATAACACACCTTTTAGCATTATTAGCT
335051 TGGATTAATGAAGTGGTTGACATCTCCAATACAGCATGTTTTCTGTACTC
335101 CAAATCATAGCTAGCACTAATTAATTGCCCTGGGAGTTTATTGGCTTTTC
335151 TAACCAATACTAACGGGAGTTGGGTTTTAGAAGCTAATGCTCCCCCAAAG
335201 ATAAAACCCCTCGCTTCAGGACATACTATCGCTTCTGCATTAATAGCTTT
335251 AATAAACTGTGCCATTTGGGTTAGCACAAAATTAAATAGTTGGGGATTGG
335301 AAAATACTGGGGTAATGTCATAAAACAATGTACCTTGGTTGGGAAAATTT
335351 TCAAAGCGCTTGATTGCTTGATCAAGCAACTTAAAGTTTTGATCCATAAA
335401 TATCTTTTTTTAAAAACTGTTAATTCCTGCAATTAACTGCTCTTCAATC
335451 TGATCAATCTCTTTAAAAGGATGTTTTTTGTGTTTTAAGCTCAAACGGGA
335501 ATGAACATAGTTGAAAGGACTGAGTCAACCATTGATTAAACCAAAGCAAA
335551 ACATTGGTAAAAAAGCAGTTGCAACATCAAATAAACCAACAATAGCAATT
335601 AGATAAAAGATCACAAGGTTAAAGTTGCCATCAATCCCACCAAAGTTAAA
335651 ACCACTGTAGATAATAAAAATGAAAACTAAGCTAGAACTTTCAATCAGAT
335701 CTATCTTCCACTGCGAGTTGAAGTTATCGTTAAATAAGTTTTTGATAAAT
335751 ACCTTGTCCTTTAAGCTCCTTTTAAACCAGTAAAAGTAAGTCCAAGTTGT
335801 TGTTTGTGATACCTTAGCTGCAAAAAAGAGCCAAAACAGATAAACAAAGG
335851 TAATTAACTGGATTGTTGATTGGTCTATACTAAACAGATAGTTAGTTAGA
335901 TACATCACTGCAAACAAACCACTACATAACAAGATAAAGCTAACCAAATA
335951 ACTTAAACAATAAGCAACACCATATCTAATCAAACAATAAGCTAAGTACA
336001 GTAAACTAACTATTCCTATCCCAGCAATAATCCCGTTACTTGATTCAACA
336051 TCTGCTGCTAAAAATTCTCCTAACAGGTTAGGTTGAACAAGATATAAAAC
336101 TAGCATTACAACTCCTATAGCTAACAAGATTAGCCATACAAACAAAACT
336151 TCCAGTTGTTTTTCAAAAAGAAATCATGTTGGTTTTTGGTTATAAAAAAG
336201 TCTGTGTTCAAGTCACTAGTTGAACTTAAAAGTGAATAGTTACTAGAAGT
336251 TTTAGTTAGTGCTTTTGCATCCTTCTGATAGAGAAAAAGCTTTCAGTTTG
336301 CACCTGATTCTGAACTGACAAACAGTGAGATTAAAACGATGCTGATTCCA
336351 TAACTAAAAAAGTAAGAAGTAATGGCTGATATTGCCATCAAATTAGCTAG
336401 TTGTTGGACCTGATAATTAGAAAGATAGATAACAACTAAAGCACTAATTA
336451 ACCAGGTAATGTGAAACTCAAGATTAGCAAAAAAGCTTCTTTTTAAACAC
336501 AGTTTTCACGATTCGATAATAGAAGCATTATTTCTAATATTTCTTAAGAA
336551 TAACTCTCCTAAATTCAAGAGATTAATTAGGTTGATGGCAATAACAAAGA
336601 AGATGCCCACAAAAGAAAAGACATCAACAACTCCACCAACTGCACTAAAG
336651 ATAACCAGTGATGACACCACACTTAACCCTAAAGCTAATGCTTTGTATAA
336701 CCCTAAGAGCTTGTATCGTAGTGTTAATAGAACAGCAGCAATAAGAACGA
336751 TGATACCAAACGCAATAAAACTAGAAGCAAAATTAGAAACATCTGTGATG
336801 GTATTTGCAAGTGGAGCGTTAACCAGACTTGTTTTTGCAGTTGCAATGGT
336851 AGCTGCTGTGGGAAATGGATTTGTTAAAAGCTCTTTAACAGTAGCTGCTG
336901 TTACAAAGTTTGGTGGGGTGTATGTACCATCACTACTCAAGAAATTACCA
```

-continued

The Nucleotide Sequence of the *Mycoplasma genitalium* Genome

```
336951 ACTTGAAACTTAATATTACCACCATATTCTATCCGTTGGTTGTTAGTGTC
337001 TAAAAAGCTTTGTAGAGTAGGATTAATCTTAACAGGATCACCGGTTTTGC
337051 TAACCGGATCTTCAGTTCTAATTTCACTGATAATATAGTTATGGAATAAC
337101 CCTGAAAAACCACTGCTATCTGCACTCCTTAACTTTCTTGTATCAGCACT
337151 ATTTGAAACTGTAATTACATCTGAACTATTGTTGTTATTGTTATTATTCT
337201 GGTTATTATTGTCATTACTGTTGCTAGCAACCGCTGAAAAGTGGTTAGGA
337251 GCAGCGTAGATATAATAAAGGTTTTTGAGAGTAATGTCACTTGCTTTTTT
337301 AATAGGAGATGCCCCATTAGCATCAGTGTTTAAAAACAGATTATCACCAC
337351 TAGCAAAGCTACCCTTTGCATGTAAAAATTCCCAGAGACTCTTCTCTCTT
337401 TCATTAAAGGTGAGATAATCACTACTACCCTCAACTACATTAAAGATATT
337451 ACGGACATAGTTTAATGCGCCTTGTTTATCTTTTCACAATACTAAAGTTT
337501 TATTACCACTACTTGAAGTTCCATTCGCATTTTGCTTAAAAAATTTACCA
337551 TTGCCCTCAACACTAGCTTGCCCATTACCAGTATTATAATCAGAACTTGA
337601 TAAGTTTTTAGAGTTGATAAAATCAAGAAAATCGGTGTGTAAACTTTCTT
337651 TGGTAACTACATTTTTATTTAACTTGTATTCAAAGGTTAAAGCACTGTTT
337701 ACAGAAGTGTTTTGGGGAACAACTGCCCTAATGGAAGCATTAATAAAATT
337751 ATTATCCAGTGAATCAAATAAAACCACTCCATCAGTTGTTTCAAGTGAAA
337801 GTTGGTAGTTGTGTTCAACTGAACTAATTGCATTTCTTCTAACCTGAGCA
337851 TCAACTTGTCTTTTTCTTTGGCGGGTTTTGGCTTGCTCACGGTTTTGTTC
337901 AAAGGTGAGAGTAACAGAAGGTAATCCCCCATTAACCAATCAGGACTTGT
337951 CAATGTTGTCAAGTTCACTAGCAGTTTTATCATTAGTGTTTTTAGTAATG
338001 TTTACAGAAGAAAAGCCCTGAATGAATAAACTGTTAGCATAACTTTTTTC
338051 AACACCATCTAAAAAGCTATCAATGTTAGTGATGTTTTCAATCCCGTTGG
338101 TTGGTTTTGTTTGCTGAGGATCTAATGAGGTATTGTTAGTTGACTTATGG
338151 TTTAAAAAGTAAACAGTTGTAGTGGTAGAACCGTTGAAAACAGCACCTAA
338201 CCTGCTGTCATTTAACAGTTTGTAACTCCCAAAAATAACACCAAACAAAC
338251 CCAGACAAACAAGTCCAAGAATAGTTCCTATTTTTAGGATTCAGTCCAAA
338301 GAAAAGCGCTTTTTGAACCTCACTAACTATTTTTAATAACTTAAATTTTA
338351 TATAAATATTAAGTAATGGCAACCATTCAGGAAATCGAGTGTGATTTTTT
338401 AGCTAAAATAGCACAAAAATTTACTAATGCAGAGATTGAATTAATTAACA
338451 AAGCATTCTATCACGCTAAAACTTGGCATGAAAACCAGAAACGGCTTAGC
338501 GGTGAACCTTTTTTTATCCATCCTTTAAGAACGGCATTATCACTAGTTGA
338551 ATGGAACATGGATCCTATCACTATTTGTGCTGGTTTGTTACATGACATCA
338601 TTGAAGATACAGACCAAACCGAAGCTAATATAGCAATGATTTTTAGCAAA
338651 GAAATTGCTGAGCTTGTCACTAAGGTTACAAAGATTACCAATGAATCTAA
338701 AAAGCAACGTCATCTCAAAAATAAAAAGGAGAATCTTAACTTAAAAAGCT
338751 TTGTTAACATTGCAATCAATTCTCAACAAGAGATAAATGTAATGGTACTA
338801 AAACTAGCAGATCGACTTGATAACATCGCTTCCATTGAGTTTCTCCCCAT
338851 TGAAAAGCAAAAGGTAATTGCAAAAGAAACTTTAGAACTTTATGCAAAGA
338901 TTGCTGGGAGGATTGGGATGTATCCTGTTAAAACAAAATTAGCAGATCTT
338951 TCATTTAAGGTGTTGGATTTAAAAAACTATGATAACACCCTGTCAAAGAT
339001 TAACAAGCAAAAGGTCTTTTATGACAATGAGTGGGATAACTTCAAACAAC
339051 AATTAAAAAAAATCTTAGCGCAAAATCAGATAGAATACCAACTTGAAAGT
339101 CGGATTAAAGGCATTTACTCTACATATAAAAAACTAACTGTTCATGAACA
339151 GAACATCAGTAAGATCCATGATCTTTTTGCTATCCGCTTAATTACTAAAT
339201 CAGAACTTGATTGTTATCACATCCTTGGTTTAATTCACCTTAATTTTTTA
339251 ATTGACAGTAAATACTTCAAAGACTATATTGCCTCACCTAAACAAAACCT
339301 TTACCAATCAATTCATACCACTGTTCGTTTAAAAGGGTTAAATGTTGAGA
339351 TCCAAATTAGAACCCAACAGATGGACAATGTTAGTAAGTTTGGCTTAGCT
339401 AGTCACTGGATCTACAAAGAACAGAAAGAGGGATTGTTAGCACCTGCTTT
339451 GCAACTTAATTACCTAGTGACAAAACAAAAACACTCACATGATTTTCTAA
339501 AAAGGATTTTTGGGACTGATATTATCAAGATTAATGTTAGTGCTAGTCAT
339551 GAACCTAATGTAATTAAGCAAATTAATGTTGATAGCAACAATAAACTCCT
339601 TGATATTGCTTTTGAAAACTATCCCAAGCAATTTGCTAAATTAACCAAAA
339651 TTGAAATTGATGGGGTTGAGATCAATTCTTTTGATACTAGTGTTGAAAAT
339701 GAGATGCTGATTGAATTTTACTTTGGCAAGAATAACAATTTGAAATCAAA
339751 GTGAATTAGGTATATGAATAACCCTATATACCGTGAAAAGGTAAAAAAGA
339801 GCTTGGCTAAACTAGCTAAATCTGGTAGATACAGTGAGTTAGCTTTTTAT
339851 GAAAAAGAACTGGGTGAAAAACAGTTAAAACTTGCTAGTGAAACTGAAAT
339901 CCAAAAACGCTTAAACACCCTAAGAATTAAAAAAAATGAGTGATTACTTAG
339951 CGTTAATTGAGTGTACTAACTTTACTAATGATGAACATTTGTTGTTTCTA
340001 GCTAAAAACAACGACAAGTGAAATAAACTAACAAAACCACTTAAGTTTGC
340051 TTTTTCAAAAGTAGTTTTTCACAACTCTTACTTTGAACAAATTGAAGGTA
340101 TTTTTATCACCAAAATAGTGATTGAACCATGTTGTAGTAAGATCCCTGAT
340151 ATGCCTGAACAAGTAACTGGTATCTTAACTAAAAACATTTTAAGTGTTCA
340201 CCGTTATGGTTGTAAGAATTTACAAAATAAAAAGCAGTTAAAAATTATCC
340251 CGTTATATTGAAATATCCAGCAGTTAAAACTAAAACCACGTAAGTTTCGC
340301 AGTTACATTAACATTAACGGAGTGTGGAGTGAAAAAACCATTAATAAAAT
340351 CTGTCAAACAATTATTAATGGTGATGGTTATATTGAAAAAATAATTCCCA
340401 AGATCAACAAACAAAAAGATGAATTTGATTTAAACATCACCCTTTTTGTT
340451 AATAACTACCAACAACTTCTCACCTTAATGGACCAAATTACCACTAAGAA
340501 TATCAGCTTTAGTTGAAAATACCTTTAGTTACCAAACACCGCATCATACA
340551 CTTCTTCATCTCTTAAAAGTAAAACTAAGTGCTTTTTTAGTAGCCGTTGT
340601 GGATTGAAACGTGATACTCTCACTCCATAAACTTTCTTTGTAAATAAAAT
340651 TAATAAAAAACCAGAAACAAAAAATGCCCCAATAATTGAGATTCCTGTAT
340701 AGAAAAGGATTTGGGAAACTTCAGTTAAATACCGCTTAAAATCATCATTT
340751 TGGTTTGGATTTGGGAACTTTTCTAGCATTTGATCAACAAAGCTAGTTAT
```

-continued

| The Nucleotide Sequence of the *Mycoplasma genitalium* Genome |
|---|
| 340801 GTTATTTAATGTGTGTTTAATTTGGGTAAAAGCAGCATTACTATCAAAGT |
| 340851 TATTAATTTTTTTCAATGAACCTTCAAGTGCATTTAAAGAACTATCTAAT |
| 340901 CCTGATGCAAATGAATTGTTTTGCGTTAATTTTCGCCCTTCGTTTAAAGA |
| 340951 TTTTTCAACTTCTGAAAGTGTTTTAACTAGGTTATTTTGGAAGATATTTT |
| 341001 GGGAGATCTTTTTAATTTCAGTGTTATATTCACTAATCTTGTTATATCCC |
| 341051 TCTTTATAGTAGTTGTTAATAGGTTCACGGTAAGTAAAAGCAAAATAACC |
| 341101 AGCAGTAGCAATTCCACCTAACAATAAAATCCCTACCAAAATAATAAGAA |
| 341151 AAACTGCAAGTTTTTTTAATAGTCTAATCATGGTCTAATGCTGTTATCAC |
| 341201 TTCCTCTTCCAAATCAGGATAACGATCTAAGATATCATTAACATGATCAG |
| 341251 CTAACTGTTCAGTACTAATAAATCTTGAAAACCTGATCAATCCTCTTTTT |
| 341301 TTAGAAGTTAAAAAGGAAAAGACAATGGTTGTAATCAAAATTGCTAACAT |
| 341351 CCCACCTGATACAGCAACAATGGTTATCATTGTGACATCATAATAATTAT |
| 341401 TGAACTGTTCAGAAGAAGGGATGTTGTTTTTGATCTTTTCATAGCTACTA |
| 341451 ACAATGCTTTGTGCTTGTGTAGAAAACTCACTAACTGCACTAATTACACC |
| 341501 ATCAGCTGTTGCTTGTTTTTTTACAGATGGAGATGAACTAGCAGTACCAT |
| 341551 TTTTATCAAGATTATTTTTAAAGTTGTCTAATTGTGTTTTACTGTTTTCC |
| 341601 AAGTCTTTTTTGGTTGCATCAAGTTCCCTAATCTTTTCTTGACTAATATT |
| 341651 ACCTAGATTGTTCTGACTCTCTAAGTTCTTTTTGTATTCATCCACTTTTT |
| 341701 GTAAAGATTGCTCTAAGTCTTTTTTAACTTGATCTAAATTGTTAGTAATG |
| 341751 GAACTTTTGCTAAATTGGTTAGCACTATTTGCTAAAGCATTAGCAAAGGC |
| 341801 TTTAGCAGAATTGAAAGAACTATCAATGGAATTACGAGCTTGAACATAAA |
| 341851 GGTTAGCTGCTGTACTACGAAAATACAAAGCAGTAATACCAAACCCTAAC |
| 341901 AGAAATACAAAAACCAACATTCCAAAGAAAAGCAAGATGGTTTTCGAAAA |
| 341951 CCGATTAATAAAAATAACCATTTAAATACTTGTACTTTTAACCAAACTAA |
| 342001 TGGTTATAAAAGTGTTTTGAAAACAAAACTACTAGAGTTTAAGTTTAACA |
| 342051 CCCAATGCGTTGGTTTTAAGTTCTTTTGCTAGTGATTTAACTTCATTTGT |
| 342101 ATCACTGGAAACACCAGTAATATCAACTGTTTCAAACTTTTCTTCACCAA |
| 342151 TTACAGTAACCAACCCTTCAACTGCTTTAGTCATTCTTTCAAGACTACTA |
| 342201 TCTGTATCATTTTCTAGTTTTTGGAACTGTACACTGTATTTACCACTAGC |
| 342251 AGTAATTCTTTTGATGTTTTCATCAAATGTTACTCCgTTTTGTTCAGCAC |
| 342301 GTTTTAAGATTTCATTTTGAAACTCGCTGTCTCTGCTTGCGCGTTCATTT |
| 342351 TCATAGATGCTAGCACCAGGGTAATAGTTTTCATTAACCCTGTAATAGGT |
| 342401 GTTATCTCCTTCTCTGTAAGCTTCTTCTAAGTGGAGGTTAAGTTCTTTTA |
| 342451 AAGAACGGTACACCAAATCATCATCACTATCCTTGTTGGTATTAACATTC |
| 342501 TTAACTAAGTaCTTGTCAATGTATCCCCCAGCAAAATAACCTTGGAACTG |
| 342551 TCTTTCAAACCTTCTGTAGTTGTAAATATCACCAACTGCTTGTTTGAGCT |
| 342601 TATTAGCATCAATGGCTGAATTATCACTGTTTTGGAGTGTAACTTGGGTT |
| 342651 AAATCAATGTGGGTAAATGGTTTTGAGGCAAACAGATCATAGATAACATT |
| 342701 AGTTTTACTTCCCAATACTAATGGGTTAAAACCAAAACTATTTGCTTTAC |
| 342751 TGGTGGAATAAAATTCCAACTCAACTACGTTTGCAAAGATTTGTTTAGCT |
| 342801 ACATTAACACCAGTGTAATCACCATAAAGTGAAACTTTTTTAACTGATTC |
| 342851 TGGTAATTGCAATTCATTAAGTTGTGAACCATTACCACTTAAACCTCTAA |
| 342901 TAATTAGGTAAGTAGGTTTTTCTGAATCTATTGTTGTTTTTAAAGCACTG |
| 342951 ATATCTTTAGCATCAATTGCGAGTGTTTTAACATCTTCAAAGAAGTGGTT |
| 343001 TGGGTATGAGTCATAAAGTGGTGAACCTTTAGCAGCAAAATAAGTTCACT |
| 343051 TATCATAAGTAAGGTTATTACTAGTTGAAACAGTTGTTGCTTTTGTGTTA |
| 343101 CTCCATCCGCTGAAACTAGGAACTTGTCTAAACACATCATCATAACCACG |
| 343151 GTTGTTTGCCATGAGAGTACCGTTAGTTGTTTGCAAGATTGGCATCAACA |
| 343201 CGCGGTTATTGAAATATTCAGTTGATTGGTAATAGCTAAGCAGTGAACCA |
| 343251 TCACTAGCAACATGATCATAATAACCAGCTTTAAAACTAGGAGTAATAAA |
| 343301 GTTATCACCTGTTTTAATTAAGCCACTAATTTCAGTTTTAGGAACAGGAC |
| 343351 GGTCTAAACCCTTTGGACTGTTAGTGATCGCTTCTGATAACTCATTAGCA |
| 343401 AAGTTTCTAAATTTCTCACGGAAGTTAGCACCACCAGATAAATCAATCTC |
| 343451 ACTCTGATAGCTACCATCGTTTAAAGAAAGTGATTTCAACTTTACTTCTG |
| 343501 CACTAGGAGATTGTGTTGAGAACAACTTAAAACCGAGGTTACCACTCCTA |
| 343551 CCTGATGCAACCAAAGCATAACCACTTTGATTAACTAGGTTAGTGATCAT |
| 343601 AACTGCTGAGAATGTGGTTAACGCTCCAGCACCTAAAACACCAATAGTCC |
| 343651 AAAATAATTTACGCTTAAATTTCACACTATTTTTATGTTTTTTAAATTGC |
| 343701 ATTATTTTTTGTATTATTAGAAACTTTTAATTTGTAAACAGTAGTCTACT |
| 343751 TATCAATTTTAAATTAAATCCACTAGTAAACTTCAATAACCCTTTCTCTG |
| 343801 AAAGAGCTTGGTAATTTATTAAACAAATAAAAAACACCCTTAAATTGCTT |
| 343851 TAAGGATGTAATGAGTTTAAATCTTTAATTTTTGGAGCGAGTAATCGGAA |
| 343901 TCGAACCGACACGATCAGCTTGGAAGGCTGATGTTCTACCATTAAACTAT |
| 343951 ACTCGCACAAATTTGGTGCCCAAAGCCGGACTTGAACCGGCACACCATTA |
| 344001 CTGGCGTGGGATCTTAAATCCCATGCGTCTACCATTCCGCCACTTGGGCT |
| 344051 GGTGACCCACCCGAGGATCGAACTCGGGACCCTTTGATTAAAAGTCAAAT |
| 344101 GCTCTACCGCTGAGCTAGTGAGTCTTTTTGATAGGGAGTTAACCCTATCT |
| 344151 TTAGAAATTTAAGCTTTAACTGGCTGGGATGGATGGGATCGAACCATCGC |
| 344201 ATGATAGAGTCAAAGTCTATTGCCTTACCGCTTGGCTACATCCCAAAAAT |
| 344251 GGTGGACAGGGAGAGATTCGAACTCCCGAAACCATAAAGGTGTCTGATCT |
| 344301 ACAGTCAGAAGCGTTTAGCCACTTCGCTACCTGTCCATTACTACCAGCAA |
| 344351 GATATTTTACAAATTATCTGTTGCTGATCTTCAGGATTTTAACACGATAG |
| 344401 GGAACTTCAATACCAACAACATCACATTCATCACCAATTAAACGCCCATA |
| 344451 GATTGCAAGGGCAAGGGGTGATTCATTGGAAATTTTGTGTTCTTCAGGAT |
| 344501 TTGCTTCAAGTGTACCTACAATTGTGTATTTTTCGTTCGATTTAGAACTG |
| 344551 TAATCATAGATCTCAACAGTGCTCCCTAAGCTAACTTTTGTTACTTTGGT |
| 344601 TTTTGCTTGGTGGTCACTAATTAACTTAGCGTTGGCTAATATATCTTGAA |

-continued

The Nucleotide Sequence of the *Mycoplasma genitalium* Genome

```
344651  TTTCAGCAATCCTAGTTTCAATCTCACCTTGCTGTGCTTTAGCTGCATCA
344701  TAATCAGCATTTTCACTTAAATCACCCTGATCACGTGCTTCTTGTAAGAG
344751  TCTGATAATCTCAGGACGTTTAACTTGGATTAGGTTTTCAAGTTCTTTTT
344801  CCAGTTGCTTAAATCCTTCTTGAGTTAGGTAATTTTTATTTAGTTCCATG
344851  ACAAAATTAAAAGCAGCAAAAACACTTTTATTATTTAATTATTTCCCCTT
344901  TTTTTGCCAATTTTTGCTAAAAAAATAGAAAATCAGTATTGCAGTAATAT
344951  AGATATTAAATAGTAAATTTCTATTTAACTTCGAAATAATAAACTCAAGA
345001  TCAACAGAAGATTGTGAGTTTTAATACAGATGAGAGAAAACAATAGTAAT
345051  GCTCAAAACAAAAAGAAGATCCGCTTTTTAGCTTTGGGCATCATTATTCT
345101  AATCGTACTAATTGCTTTAATTACTATGCTTTTTATCACTGGAGTAATTA
345151  GTCGCAACCGTTAAGATTACTTTTTGCTAGATGACAAAAAAAACACAAGA
345201  TCTCACTAGTTGGTATGACCAACTGCTAGTTAAAGCAAAGTTAATTTGTC
345251  ATGGTGAAGTTAAAGGTACAGTTTGTTTTTTAAATAACAGTTGAGGCTTA
345301  TGGATGGAAATCCAACAGCTTTACAATGATGCAATTGCAAATAAAAATCA
345351  ATTGTCTGCAATTGCTCTAACTAAATTCCAACCAACTACTAGTTTTTGTT
345401  ATCAAGTATTCCAAGTACAACTCCCTACCCTTTCTTTTTACAGTGAATAT
345451  CAAAAGGAAAAAACCCATATCAAAGGTTTTAATCCTGAGCTTTTTTTAAT
345501  TAATCAAGTTGGTCAAAAACAACTCAATGATCCTTTGGTTTTACGACCTA
345551  CTAGTGAGATTGCTTTTTGCAACTTATGGAAAAAACAAGAGTTATCTTAC
345601  CATGATCTACCTTTAATTTATAACCAGTGAACTCAGGTTTTTCGTGCAGA
345651  AAAAAACACCAGACCTTTTTTGAGAAACAGTGAGTTTTACTGACAAGAAA
345701  CTCATGGGCTTTTTGTGGATCAGAGCCAATCTGAACAAGCTGCTATTAGC
345751  TTTTGAAATTTATATCAGGATTTAATTATTAACAAACTTTGTATCCCTGC
345801  TTTTGTTGGTTTGAAAAGTGAAAGTGAAAAATTTGCAGGTGCTAAAAACA
345851  CATGGACAATAGAAGCAATTATGCCTGATGGACAAAGTTTACAATGTGCC
345901  ACTAGCCATGATTTAGGTGACACTTTTACAAAGAGTTTTACTATCAGCTA
345951  TCAGAGTAAAACTAACCAAAAAATGACTCCAAGTAGTTTTAGTTGTGGGA
346001  TGTCAACTAGGATCTTAGGAGCAATTTTTTTAACCCACAGCGATGATTAT
346051  GGTTTGGTTTTACCTTGGTATCTAGCAAGTAAACAAGTCAAGTTATACCT
346101  GTTTGATAAAAACAATAACCCTAAAACAAGAGCTTTAGCTTTTTTAGTGA
346151  AGGATTTTTTAGAAAAACTCAAAATTCGCTTTAGTTTTATAGAAATTAAC
346201  AATCAACTAGGTAAACAACTTTTAAAAGGAGAAATAGAAGGTATTCCATT
346251  ACAGATGATTGTTGATAATGAAAAAACTATTAACATCTTCAACCGCTTAA
346301  CACGTTTAAAAACCAGCTTAACATTTGCAAATCTQCAAACTGAATTTGTT
346351  AATTTAGTTAACAACTACCATACAGAGATGTATAGAAAAGCAAATGATTT
346401  AGTTGAACAAAAACTAGCAAGAGTACAAACTTTAAAGGAAATTGAACAAG
346451  CATTCAAAAATAAAAAGGCTGTTTTATGTACCGTGAAGTTAACTGGTGAA
346501  CTTGAACAACACTTAAAGACAAAATACCAAGTTAGTGTTAGGTGTGTTTT
346551  TAAAAAGTCAGATGTAACACAAAACTGTCCTTTTACAAATCAACCTTGTT
346601  TTGATTCAGTTTTAATTGCACGTGCTTACTAACAAAGTACTGTCAATCAC
346651  TACCCAATAAAACCCTTGATTATTTGGTTTTATTTAATTTATTTCTAAAT
346701  ATTTTTTACCAGTAATTTTTGTTTAAAAACAAACTCGTTTTGTAAAAGAA
346751  AAAAGTTAGAGTTGTTGTATTTCAATAACGATTATTTAGCCTCTAAAATC
346801  GATTAGACGATCTTCTGATCGTTTAAGATTTATTCAAATTCAACATGACT
346851  TTATGACTTTTACAAACAAAGAAAAAAATTGCAAACAAAGCAAATCATTA
346901  GCAGCGTTGATGACAAAATTTAAGCGCTCGCAATTAATCTTGAAACACCA
346951  AGCTAATAACATAGCACTGGAGTTGTGAAATGAAAATGATATTAACCTAT
347001  CAAAACAGCTTATTGAGTTAATAGAAGATACTTTTTCAATGCTTAAAAAA
347051  GAAACTGTTGATTTTATCTATGACATCTATATTTATGGCAAAAAGCCGTG
347101  TGATATTGGTTATTCTAATTCCACCTATTACAAAAAACTAAACAAAGCAG
347151  CTAATAGTTTTTTTGACCATTTTGTTTGAGATTCGTCAATATTAGACAAA
347201  AGGATCATAACTAATGGCAGCAATTCTCAACGTACAACGAATTCAAAATA
347251  ACCAAGTCACTGAGTACACAATGAGTCCAGTGCGTAATTTTGCAAACACA
347301  AAAGATGTATATTTTGATGCGCAATTAACAAATATAGAAAGCAAATTGA
347351  TAGTAGTAGGGCTCAAATTCACCTTACTATTGCACTAAAATACAACACTA
347401  ATCTCCCTGATAATATCTTTCAAGCCCACTTCAGTTTAGGCAATTGACAA
347451  AGTGATAAGATTCAACTTCAAAAAGCTCCTGATAAAAAACACGATAGTTT
347501  AAACAGCATTAAATATTTTATGCATTTCTAGATGTACCCCGTTCAGCAC
347551  TAGCAAAAAAAGAAATTAATAGGTTTAGTAATGTGGTTGCTAGAGTATTG
347601  AGAATAAGTTTTCGCTTGCAAGATCAATCTGAAAAAGGGAATTGAAGTGA
347651  CTATCATTTGTTTGATACTGTAGCTAGTGAATTGTATGCAACAGTAATTA
347701  AAGAAACAATCAACTTTGGCAACATGATTAAGATTAATGCACTTGATGGT
347751  AGTAAACAGCTAACTAGTAGCCAAGGAAGTTTTAAATACAGTTGAACAAT
347801  GTATGACTATAGGAATTTAGAACAACTTGATGAGGTGAGAAACTTGATCA
347851  ATATCAGTTTTGACAAACCAGTTCAAATAGTAAATGTTGATGTCAAAATT
347901  CACTATGTTCCAACTAAAGGTAGGTTACAAGAGATAAAACAACAAGGTGA
347951  GTTTGAAAATAACCTTGATGTTAATGAAAAGCTTAAACTCAATTTAATAG
348001  GCAATTGAAATTTGACAAACATAACAAGAAGCTAATCAGTGATATTTCA
348051  GGTACTGGAATCTTTTTACCCCAGGGTGGTTATGGAAGTTATGAAATAAT
348101  GATTGGCGCTACAGTAGGTAATGATTTCTACACAATTATAGCCAACAACC
348151  AGTTTAAGTACGAAACACCTTTAGATGATCTTGAACAAAATGACTTTTTT
348201  GAGGTAAATTATTTACCTGTTTACAGTACATACAACTTTAGTGATTTAAC
348251  TCAGTAAGTATGATTTTTTCAATTAGTAAACGAAAGTTAATTTGCGGATT
348301  TTTGCTAGTTATTTTAACAATAGGTGGGGTTTTGGGTGGTGTTTATTTAG
348351  TTACTAAAAACAACAAGGATAACTACCAAAATGAAAGTAATTTCAACAAT
348401  CAAGAACAAATTAGTAAAATCCCTAATTTCAAAGCTATTGGTCCTGAAAC
348451  ACAACGTATCTTAAGAGAAAGAAACTATCCTTTAGATGATAGTGGTTATT
```

-continued

| The Nucleotide Sequence of the *Mycoplasma genitalium* Genome |
| --- |

348501 ATGTTTATAAGTATGGTGAAATTAATAGGTATCTAAGAAATGAAAGTGAA
348551 CTAGATGAATTAATTAACTATAGAGTGATGGTACCTTCACTTAAATTACA
348601 TCACAAAAGGGTTAATTTTGATAAGGCATTTCTTGAAAGTAAATTAAGAA
348651 AATGGATTATCAAAGCAATTAAGCAACATAACTATTTCCAACACTTTGAA
348701 AATGAACCAAATTTAAGAGTTCAATATAACATGAATATTCCAGCACAAAA
348751 AATTGATGTTAATGCTGTTTGATCTTATAAAAAAGATAATGATGCTGCTA
348801 CTGGTAAGCCAATCCGATATTGAGATCAATTTGAGCTTAAACTTAAATAA
348851 TAAATCTTTATAATTTTTACTAGATTTACTAATGCAAACGCATGAAATTC
348901 TTTTAAAAATTAAAGAAATTGCTAAATCAAAAAACTTTAATCTTAATTTA
348951 GATGAAAAGACAATAAATCAACCACTTCGTGAGTTGAAAATCGATTCACT
349001 TGATATGTTTAGTATTGTTGTTAGTCTAGAAAATGAATTTGGGATTAGTT
349051 TTGATGATGAAAAGTTAATGAATCTAAAAAATCTTGCTGACTTGGTTTTA
349101 GAAGTTAAAAACCTTTTAGCAAAAAAAGGGGTATAGTTCAAAGGTAGAAC
349151 ATCTGTCTTCAAAATAGAGTGTTGTGGGTTCGAGTCCTGCTACCCCTGCC
349201 ATAAAATATAAAAGCTTAGTAAGTTTTTACTAAGCTTTTTTCAATCCCCC
349251 CATTCCCCCAACCTCTATTTTGTGTTACTAGTGCCTAAGGTGGTATTGGA
349301 GTATCACAACCTGAATAACCAAGTAGTCAAAGAGAGTTTGGAAGTGGAAG
349351 CAACTGATTCTTTTGATCCCACCCAAAGGTTGCAAAAAGATAGTCCAATG
349401 AAGGATACAGGARAGATGGGGGAGAAACTCCAAGAGACCATGTCATCAAT
349451 GAGTGGTGGTGGGGCTACATCTCCTCGCAAAGCCCTCACCATTGAGGTGG
349501 AAAGGGGGAGTCAAAGTGATTCACTTTTAAAAAACGACTTTGCCAAAAAG
349551 CCACTGAAACATAAGAACAGTAGTGGGGAGGTGAAGTTGGATGCGAGTGG
349601 GGAGTTTACTGAGGCCTGAAAACCATTGTTGACTACTGATCAAATAGCAA
349651 GAGAGAAGGGGATGGGGGCGACTTAGACTTTCTCCCCTGAATCGGCAACA
349701 ACAAACCCTTCTCCAACTCCCACACTGCTTCCCTTTCTTCTTCTTCTTCT
349751 tCCCCACTCCCCACTTTTTCTAACATCAATGTCGGGGTTAAATCAATGAT
349801 CACTCATCTCAACAAAGAAAACACCCGGTGGGTGTTTACCCCTAACTCTT
349851 CACCAGACATTTGAACGGGAGCAGGTTATAGAAAAGCTAATAACAACAAT
349901 AACGGCATCTCCTTGACAAGTGTGTTGCCTAGTAGCAATAGTAGTCAACA
349951 GTTTAATCCCAATTCAGATGATAATAAAGTCACTCAAGGTGGTGGCTCCC
350001 CAGCCAAAAAAACAACCACCTATTCCTTTTTACCCAATTCCATCAGTCCC
350051 ACCAGTGACTGGaTCAACGCATTGACTTTTACTAACAAAAATAACCCGCA
350101 GCGCAATCAACTGTTGCTCAGAAGCTTACTAGGAACTATCCCGGTATTGA
350151 TCAATAAGAGTGGAACGGGAGATGAGTTTACCCATACGAGTGAGCAGAAA
350201 TGGGATAAAACGAATGAAAAAGATGGGAATTTACCTGGGTTTGGGGAGGT
350251 GAATGGTGGTTTTTATCAACTAAATAAAAAACTTATTAGCTTATTTTTAT
350301 TAGGTTTTTACTTATTTAATAGTTAAAAAAGTTTTGAATTTTTCTTAGTT
350351 TTTTATTTGTTTAATAGTTAAAAAACACTAGGCTTTACCTTTATTTAATT
350401 AATAAAACCTTTACCCCTATTACCAAACCATCCATAACACCAACTTGTTT
350451 GTGTTGTTCAAGTCTAGGGATGTAAAAGTTAAGTATGACAGTTCAAGTGG
350501 CTCAAATAACCAGATTAGTTTTGATTCAACTAGTCAAGCTAACAAACCCG
350551 CCTACATCGTTGAATTTACTAATTCCACCAACATTGGCATCAAGTGAAGG
350601 GTAGTGAAAAAATATCAGTTAGATGTACCGAATGTTTCTAGCAACATGAA
350651 CGAAGTACTGAAAAATTTAATTCTTGAACAACCTTTGACTAAGTATACCT
350701 TAAACAGTAGTTTGGCTAAAGAGAAGGGTAAAACGCAAAGGGAGGTGCAT
350751 CTGGGTAGTGGGCAAGCAAATCAGTGACGATCGATGCGTAATCAACATGG
350801 CCTAAACAACAATCCCAGTCCCAATGCATCAACCGGATTTAAACTCACTA
350851 CCGGCAACGCATATAGAAAATTAAATGAGTCCTGACCAATTTATCAACCA
350901 ATTGATGGGACCAAGCAGGGCAAAGGGAAGGATAGTAGTGGGTGGAGTTC
350951 AACAGAAGCAACAACGGCAAAAAATGATGCGCCCAGTGTTTCTGGAGGGG
351001 GATCAGACACCACTTCAAAATTTAAAAGTTACCTCAACACCAAGCAAGCG
351051 TTAGAGAGCATCGGCATCTTGTTTGATGGGGATGGAATGAGGAATGTGGT
351101 TACCCAGCTCTATTATGCTTCTACTAGCAAGCTAGCAGTCACCAACAACC
351151 ACATTGTCGTGATGGGTAACAGCTTTCTACCCAGCTTGTGGTACTGGGTG
351201 GTGGAGCGGAGTGCAACAACTGATTCATCATCAAAACCCACCTGGTTTGC
351251 TAATACCAATTTAAACTGAGGGGAAGATAAACAAAAACAATTTGTTGAGA
351301 ACCAGTTGGGGTATAAGGAAACTACCAGTACCAATTCCCACAACTTCCAT
351351 TCCAAATCTTTCACCCAACCTGCATATCTGATCAGTGGCATTGACAGTGT
351401 CAATGATCAGTTGATCTTCAGTGGCTTTAAAGCGGGGAGTGTGGGGTATG
351451 ATAGTAGTAGTAGTAGTAGTAGTAGTAGTAGTACCAAAGACCAAGCACTT
351501 GCTTGATCAACAACAACTAGCTTAGATAGTAAAACGGGGTATAGGGATCT
351551 AGTGACCAACGACACGGGGCTAAATGGTCCGATCAATGGGAGTTTTTCAA
351601 TCCAAGACACCTTCAGCTTTGTTGTTCCTTATTCGGGGAATCATACAAAT
351651 TCAAGTGGTTCATCAGGAACCATTAAAACGGCTTATCCGGTGAAAAACAC
351701 AGAAAAATCAACTGTCAAGATCAATTCTTTGATCAACGCTACGCCGTTGA
351751 ATAGTTATGGGGATGAGGGGATTGGGGTTAGAAATATTTTTATGAGTTTA
351801 AAACAAGGTAATGCAGATAACTAGCTAAATCAACAACTGGAGGTTTTGTA
351851 GCCCCATTTCTTAAATCCAAATTATGTAAGTTTTGCTGTTTAAGTAAATC
351901 CATAAATTTACCATCTTGAACTTTTATCTGTTCTTTTACGTGTAAAGTGA
351951 AAAGTAGTTGATTGTCTTTAAATTGAAATAGAGAACCTGGATAATCAGTA
352001 TTTTGAACTAAGTTATAATCCAAATCACCATCAACTATGAACTTGACATC
352051 CATTTCACCATTTCATGATGAAGGGATACCAGAAAAAGGTGCAAATCAAC
352101 TAAATAACCCAGTTAATTTGTATCCACCTTGGTACTTTATGTCAATTTCA
352151 AATTTAAATTTGTATGGATAATGTTGCCTAAATTCAATTCCATTATTTTT
352201 TCAATCAATGGTTGGATTATTTCCTTGTTTTCAATTTTTATGCTTGTTA
352251 AGTTTAGTTTTATGTCAGTATAGGAAGTTAGCTTTCCTCTTAATCAGTCA
352301 GACATATAAAGACCTTCAAGCCCTTGTCTAGGAACTGAATTCCTTTTTC

-continued

The Nucleotide Sequence of the *Mycoplasma genitalium* Genome

```
352351 ACTAAAGGCTTTCTTTGCATTTtCACTTTCATCTTTTTTATTATTTTTGT
352401 AATAATCTGACGTTGCTTTAGTAAAGCTATTAATTAAAAGTGAAAAAGTT
352451 TTATTTTTATCAGCAGCAAAAGAAGTTTTTAGAGCATCTATTAGTTGAGT
352501 CTTATCAGTAACATCTTTCTTTTGATTTTTTCAATAATCTTTAAATTCTT
352551 TAGCATTTTCAAATGATTTATTAAATTGTTCTTGTTGTTCTTTTAAGCGC
352601 TTAGCTTCCTCTTCTTTTCGCTTAAGTTCTTCTTCTTGTTTTCTTCTTTC
352651 CTCAGCTAAAATTCGTTGTTGTTCTTCATAATCAGCTTTAGCTTTTTCAC
352701 GTTCTTTTTTGAATGGTTCAATTATTTCTTTTTCAAATTTTGTTTTAGCT
352751 AAATCTAGTTGTTCATCAATTTTTAAAACTGAATTAAAGATATTTGTATT
352801 GGAAAGAAAAAGTGAATCACTTACAGCAGTTTTAGCTATTGAAGTGAGAT
352851 CATTTTGATTTTTATCAACAAGTTTATTAATTAGAGGTTTTCAAAACAAT
352901 TGGGTATTTAGATCGTTACCATTAAAGCTATTTTGCAACTCTTGTAAATT
352951 CAAAAAATTAGAAGTTTGGGCTTTTAAATCAAATTGCAAGTTAACAGTGT
353001 TGTTACCACCTTCATAATCAACTTCAAAATCCATTTTGATTTCAAAGCTA
353051 TAACGAATCTTATCTTTAATAACAATGTCATTTTTTTAACCAATTCAAGA
353101 TTAAAGTCTTTTAATTGAATTTTCTTTAAGTTGTATTGATTAAATATTTC
353151 AACAATACTTTCGGTAATGTTTAAACCTTTTGGATGCAATTGTGGAAAGA
353201 AATTTTCATTAAGGAATTTAAAAAAATTCTGTGGAACTTTAGGCAATTTA
353251 TCTTCATCATTAATTGGAAAAATTTTGTTAGTTTCATTAATGCTTGATTA
353301 CAGCCTATTTAATAAATCAACTGTTTTTTTAATACCTGATTTAAAACCAC
353351 TTAAAAGATGAAAAATATCTATAACATTAAAGTTCCTAGGATAAAATTCA
353401 TTCTTAAATTTCTCTTGAAATAAGTCAAAGTTTTTATCATAATCTTTCTC
353451 TTTAGCAATATAGTTTTCTTCTTGCTCTGTTATAGCTGTTTGCTGTTGGA
353501 GTAGAATACTATTTTCTCTACTATTTGTTGTACTTGATTTTCTTAGACTA
353551 GGTTGACTTAAATTTGCAGCTGAGCCATTATAGATAGAAGGGACAATAAG
353601 TACACCAGCAGTTAAAGTTGATGCAAAAGAGACAAAGAGAAAAGTTTTAA
353651 TTTTAAAACGAGATTTTTTGATAGCTTTCAAAGTTAATAATTAATATTGA
353701 AAATAATTAGCTAAAACTAAAAAAAGTTACAAACGAAATTGAATTTGTTTA
353751 AAACTAAAACAGACAGGGAAAATTTAACATTATATTCTAACTCTGAATAG
353801 CAAAAAATATAAGAATAGCTTTAATTCAAAAAAGTAATTCGGATCTTALA
353851 AAATATTTTTTAATAAAGATTAATTGCCAGCAACTTGAATCTAAGTAATA
353901 AAGTGAATATTTATTTTTATTAAAAACTTATATTCAAATTTGTAGTCTAT
353951 TTTTAACTAATATAAAAAAGTTGAATATTTAAAAACAATTAATTTTGATA
354001 ATTAATAATCCAGGATTAATAAGTGCTTTTCAAAAAATTTACTTGGGTCA
354051 TTCCAAGTTTGTTTTTAACAATTATTTCAACATCTTTACTTATTAGTTGT
354101 GCAACTAAAAGCGATAACACCTTAATATTTAATATTTCACTTGATCATAA
354151 CGCTGATACATCAATAGAAAAATTCTTTACTGTTTTTTCAAAAAAACTTA
354201 GTGGAAAATTGAATAAAAAAATTAATGTTAACTTTAATATAGTTGATGAT
354251 TCCTTTACAAAAATTAACAATATTCAAGCTAATAAAGCAGATTTTGCTTT
354301 TGTTAATTCACAAGCTATTGCTTCAAATAATTGGTTTGGCTATACGCCAT
354351 TGATACAAACTTTAACAACAGCTTTTAAAGAAGATTTGGAGCTTGATTAT
354401 TATGAAGATGGTAATTTACAAAAAAAAGCTGAAAAAACGAATTTGCTTTT
354451 TCTAAGTCCaCCTTACAAAGAATGAGATGATATCAAACAAAAATGAACTG
354501 GAAATCGTTATGACTTTCTTTATGAACCTTCGAAGTTAGTTTCTTTTTAC
354551 AGATCAATGATTTTAATAACTGGTTCAGCTAGTGAAATTACAGCTATTAA
354601 AAAAGCGTGAAATGAAAAAAACTGAAATCAGTTTATGAAATTTGGAATTG
354651 GTCATGGACAAACAAATTCAGCTTCACGTTTTGAGCTACCTGATCTTTTA
354701 TTTAGAAAACATTTTGCTAAAAATTATCCCGGATTACAAAATGCAATTAA
354751 TTCTGATCCCGATAAATTTGCCGTAGTTAGAGGAAGAGAGATAGGTATAA
354801 ATAAAAACATCAAGATTGTTTTTGATGATGCTAATTCATTTTCTTGAACA
354851 CAAAATATTAAAGGTTCAAAAAGACCTTTTTACACTCCAATTGATCCTAA
354901 CGATAGATTAGAAATTCTCACTTATAGTGATCCGCTTTTGTATGACATTG
354951 GTATTGTTAGCAACAATTTATCAAGGATATATCAAAAAGCTATTGGTGAA
355001 ATTTTTATTGAGTTAGCACAATCAAGTGAAGATCTATATGGGCCTTCAAT
355051 TGGTTATAACGGCTATAAAATGATTAATGATTTTGAGAAAGAAGTTGTTG
355101 AAATAATTGAAAAAACCTATGGAAAATAAACCAATTCTTTCTTTTGAAAA
355151 AGTATCAATAATATACAAAAAAGCTCCACTTTTGCAAAACATTAGTTTTA
355201 AAGTAATGGCAAAGGAAAATGTTTGCTTATTAGGTAAGTCTGGAGTTGGA
355251 AAATCGAGCCTTTTAAACAGTGTTACTAATACAAAAATAGTTAAAAGTGG
355301 GTTAGTTTATTTTGATGGTGTTGCTTCAAACAAAAAGGAATACAAAAAAC
355351 TGAAAAAACAGTGCAGTTATCTGGATCAAATACCAAATTTAATTGACACT
355401 GATTATGTATATGAAGCAATTTTAAGATCTGCTAAACAAAAATTAACTTG
355451 ATTACAAAAATTAATTTGTTTTGAACCTAAATGAATTAAAGATAAGATCT
355501 TAGCAATACTAAAAGAAGTTAATCTTAATGATTATGTTAGTTGTATTATT
355551 AAAGATCTTTCTGCTGGACAAAAACAAAGAGTTGAAATTGCTAAGCTTTT
355601 TTTTAAATCACCAAAGCTACTTTTAGTTGATGAACCAACCACAGGATTAG
355651 ATCCTTTAACCGCTTCTAAAATAATGGATTTAATTACTGATTTTGTGAAA
355701 AGAGAAAAAATAACTTTGGTTTTTGTAACACATGATATAGATTTAGCACT
355751 GAAATATAGCACCAGAATTATAGCACTTAAAAATCATGCTTTAGTGTTAG
355801 ATAGATTAACAGAAAAACTAACAAAAGAACAACTTTATAAAATTTATGAT
355851 AACTAAGTTGTTTTTTCACCAAGTTGGCGATAATAAAAAACGCTTAATTT
355901 GGTATTGAAAACTATTAATAATAATTGCTGTTTTGGCTATTGTCATTTAC
355951 AGTTGAATAGATAACTTTTCTAGCTTTAATCAGTTTGGTTTAAATGTTTT
356001 TATTAATAACATTACAAGCTTATTTACCCCCAATCTTAACCACGAATATA
356051 CACTAGTAAGATTCCTAGCACAAACTGCTTTTTTGTTACAGGAGGTAGC
356101 TTTTTAGGATTTATTTTTGCGATCCTATTTTCCTATTGAACTGCATTTAA
356151 AATTCAACCCTTTTACATTGCTCTACCGATCAGGTTAATAACTATAGTTT
```

-continued

The Nucleotide Sequence of the *Mycoplasma genitalium* Genome

```
356201 TAAGAGCATTTCCCGTACTTTTATTTGGTTTTTTATTTAGTAATTTATTT
356251 AATAAACAACTAGCAGCTACACTAACGATTAGCTGGTTTAGCTTTTTATG
356301 GAATACAAAATACATTACTACATTTTTTGAAAACAGCAATTTAAAGTATT
356351 TTTTTAACAAAAAAATTAGAGAAGGAAGTGGTTTTAAAGCTTTTTGAACT
356401 ACTATTTTTCTTAGTGAAAATGAGCGACTATGGTTGTTTTTCTTTTATAG
356451 TTTAGAAGCAAATTTTCGTTGAACTACGCTTCTAAGTATATTTGGCATTG
356501 GTGGCATAGGACAACTAATTGTTGATCCTTTAAGTATAAGGGTGCAGTTT
356551 GATCTTGTATTAATTCCATTAGTTGTTTTAATAACCTTTCTAATTTTTAT
356601 AGAAGTTGTTGTTTTTTATTATCAAGTTTTGTTTTTGAGAAAAATAGTG
356651 AAGATTTAAGACCAATTTTAAAAACAACAGTTATTGAAAAACGAAAGTGA
356701 AAAAGAATTATATTTATTTTGTTATTGTAGTACTAATTAGTCTTAGTTT
356751 AGCCAATTTAGTGACTATTGATTACAGAATTAACGATGCTGAATTTTTAC
356801 AAGATTTTTTTAACCAGTTTTTTCAGTTAAAAAGTAATCTTTTTTCAAGT
356851 AATGATCCTAATATAaCCCAATTTTAATGTTAGTTAAACTTACAACTCA
356901 AGCTATTAGTTTAATTAGCTTGGTTGTAATCTTTTCTATTCTCTTTGGTT
356951 TTATATCATGTAATTTATTTAAAAAGAGATTTTCAATTAGTTTTAAGATC
357001 TTATTACTTTTTGTTAGAGTAGTTCCTAGTATTCTGTTGTTTAGGCTACT
357051 AGATCCTTTATTTCTAGAAGCAAAAACAACTATTATTTTAGTCTTACTAA
357101 TTAATCATGGTTCAAGTTATGGCCAATTGATGTCAATTAACTTTAATAAG
357151 GCAAATCAAhATATCATCAATAACTATAAAAATCATGGTATGACAkAAGG
357201 TTTTATTTTATGAAACTATTTGTTAGTTGAAAATAAACCTAATTTAATAA
357251 ACATTACCAGTGATGCTTATGATAGTGTAATTAGGGATTTAATTTTGTTT
357301 GGTAGTTTTGGCGGTTCAATTATTGGTAGTAGAATTACTAATTTTTTTGA
357351 AAGAGCTCAATTTGATAATCTAGGTTCTGTTACAATCCCATTAATGGTTT
357401 ATCTAATTGCAATAGAAATAATTTTCCTTTCAGTTAGATTAACTAGAATT
357451 TCAGTTTTTAAGAACTACCTTTACTAATGATAGTTTTGAAAGAAGCGCTC
357501 TAATATTAAAACTGCAGCTAATGTATCTTTAGCCTTTTTAAAATCCTTAT
357551 GTTTTAAATCCATTGTTATAAGCTTATCTTTAACAGCACTTGTAGTATTA
357601 CTTTCATCAACCAAAATTATTGGCAAATTAAAACGTTTTTCTAAAAGTTG
357651 TTTAAATGATTTAATTGCCTTTTGAATATCAGAATAATAGTGAAATTTGG
357701 GAAAACCTATCACTATTTTTTCAAGTTCATACCCATCGTTTTTAATTCGC
357751 AAAAATAAGTTGTTAACAGCAGTTTTGAAATTATTTTTTACTTCAAAAAC
357801 ATGAAATGCAGAAGGATATTTATCTAGTGTATTGGCAATTGCTGTACCTA
357851 TTTTTTTCAAGCCAAAATCAATTGCTAATATATATTTCACTATTTATTTT
357901 GAAACAATTCATTAAGCTTTTGAGGGGTAACATTATCCTGAAAAGAACCT
357951 CTAAATAACTTATCATTGCCTCCGCCCTTTAAATTAAAACTATTTCTTAA
358001 TTTTTCAATAATGGTGGTAGTTTTATTTCCTATAACAATAAATGAATTAC
358051 TTTCATTGAATTGATTAATTATCAAGAAATTTTTAGTTTGATTTTGATTG
358101 AAAACATCATGTAGTGTTTGTAGCAATAGTTTAGGTTCTACGTCATTAAA
358151 AGTGGCAATTACATAACTTTTATTTTCATCTACTAAGGATAATAATTGCT
358201 TTTTAATTGATAAAGCTAAAGCTTGCTGTGATACTTTATAGTTTTTGTT
358251 TTTAACTGGTTAATATCATTTTTTAAAGCTAATAAAGTATCAGATGCATT
358301 TCTTAATTGGGTAATTTTTTCAGGTAAGATAAATTTATCTAGCCTTTGTT
358351 GCAATTCTTTTAACTCAACTTTAAAAATTGAACTATCAATCAAAGATAGA
358401 ACTTTTTCAAGTTCTGATTTTAATTGGATTAATTTTTGATTTTCTGCTTT
358451 TAAAATAGTTGTTAATAGTTTCATTACTGCTAATGATTTCAATCCTTCATC
358501 TTCCAGCTCCTAAAGAATAGAAATCAGTAATAAAACAATCTTCAATTGAA
358551 GCAGTGTTAGCTACATGAGTGCCACCACACAACTCAACACTATAATCACC
358601 AAAGCGGATCACTCTTAATATTTCATGTTGAGAATATTCCTCTTCAAAAT
358651 AAGCAATTGCATTTAGTTTTTGACTCCCTTCAAAATCAGTAAAAATCTCT
358701 TTTGAGCTTATTTTTTGTTTAATCAAAGAGCGAATTTTATTTTCTACTTT
358751 CTCAAGTTCATTTCTTGTTAAATGACGATTCAAATTAAAGTCAATAGTTG
358801 CTTTTTGCGCAGATTTAAAAGCACCACTTTGTTTAATAAGTGGATCAATT
358851 TCTTTTTGTAAAGCTGCATGTAAAAGGTGTTCTAAACTATGGTTGTTAGC
358901 AGCAAGTTTTCTTCAAGTTTCATCATGTGATAAAGTTACTTGATCATTGA
358951 GTTTAhAACTACCTACTAAAAAGTAGTGGAAGTGTTGTTTATTAGGTCCT
359001 TTAAATACACCTTGAAAACTGATTTTTTGATCATTATTATTAGAATGATT
359051 AAtGCAACTtCCTTCATCATATCTCTGTCCTCCAGAAGTAGCATATAAAA
359101 CTGTTTGGTCAAAAACTACATAACCACTTTGATTATTAAGTTCTTTAACT
359151 GGTAAATAATTTTCATCAAAAAGACCAATTACCTTAGCATTAATTTTATT
359201 TTTGTGATAaAAAAAAGTACTTTTAGTTTTGAAATTAACTAAATTAATAT
359251 TTTGTTTTTCAAAATTTATAGTTTGGTTATTTTGCTTAGAGATAGAACGA
359301 TGTTTGGCCATTAACTGATCAAATACTGTTCAATCAATAGTTAAACCTTT
359351 TTGATTAACTAGTTCTCTTATTATTTCAACAGGAAAACCGTATGTTTCGT
359401 TCAATTGAAATGTTAATTGGGGAGTTAGAGTATTGTTTTTAACACTTTTT
359451 TCAAACAGCACTAAACCTAAATCAATCGTTTTATTAAATGCATTAATCTC
359501 TTTTAAAACTACCTGTTTAACAGTTTCATTTTTAGCTTTTAAATGTTGAT
359551 AATAATTCTCATATGAAGCGATGATTTCATCTATTATCTTTTCAATAAAT
359601 GCTAAGTTTAATTGCAATTCTTACAAGCTATTAAAGCACGTCTTAAAAG
359651 TCTTCTTACTACATAATTTCTCTCATTAGGACCAGGTAAAACTCCTTCTG
359701 AAATGGTAAAAGTGATTGCTTTAAAGTGATCAGCAATAATCCGAAAATAA
359751 CTCTGTTCTTTCACTTTTTGAGGATCGAATGTAAAGTAAGAGTTGGGATC
359801 ATATTTAAATGGACAAAAAGCTTCAATTATTTTGATTAGCTTTAAAAAGA
359851 TGTCAGTATCAAAATTGGTTGGACTATTTTGTAATACTGAAACAAGTCTT
359901 TCTATTCCAGCACCTGTATCAATATTTTTTTGAGCAAGTTCTGTATAGTT
359951 GCCATTACCATCATTATTAAATTGACTAAAAACAATGTTTCATATCTCAA
360001 CATAACGATCATTTTCAATGTCCTCAAAGAAAAGTTTTTCACCAATTTTT
```

-continued

| The Nucleotide Sequence of the *Mycoplasma genitalium* Genome |
|---|
| 360051 TTAGGATCAAATTTCTCACCACGATCATAATAGATTTCAGTGCAAGGTCC |
| 360101 ACAAGGTCCTAAACCTAAGTCTCAAAAGTTACGACTTTTGTCACACTTAA |
| 360151 TAATGTGATTTTTATCAATTTTATGCTTAATTCATCTTTTATAAGTAGTT |
| 360201 TCATCATCTTCATAAACAGTGATATAAAAACGCTTAGGATCTAGCTGATA |
| 360251 ATAATTAACTAAAAGATCAAAAGCAAAATCAATTGCTTCTGTTTTAAAAT |
| 360301 AATCACCGATTGAAAAATTTCCAAGCATCTCAAACAAAGTTTGATGTCTT |
| 360351 GAAGTAAAACCCACATTTTCAATATCATTTACCCTTAAACATATCTGTGC |
| 360401 ATTAACAAGGCGTTTAGATGGTGGTGTTTTTCTAGCACTGAAATAATCTT |
| 360451 TTAAAGTAGCAACTCCTGAATTGATTCATAATAATGATGGGTCGTTGATC |
| 360501 GGAATTAGTGATTTTGAAGCTAAAACCAGATGGTCTTTCTTTGCAAAATA |
| 360551 ATCTAATCAGGTTTGCCTTACTTTATCAGTTGTTCAATTCATTGCTTAAT |
| 360601 TTTAAATGCAATTTACCAGTGATAAAAATAACTATAGTTCTTTTATTTGC |
| 360651 TAATTTATTTTTATTTCAAACTTTTTGTTAGCAATTTGTGCATAAACATG |
| 360701 ATTATCAGCTAAGAACTGCTGAAACTTATTTTGACTGTTTACTGTTCATA |
| 360751 AATTTAAAGGTAAGTTAAGTTTTTTGATCATTTGGGGATACTTTTCATAT |
| 360801 ATTTTGGTTCATGGGTGGAGGAATTGACAAATCTTTTGGATTCTAGCTGT |
| 360851 ACTAATTGTTTCAAACTGTTTTTTAGTCCAAAATAAAAAACCTTTTTTGT |
| 360901 AACTATTATCTAAATCATAAACTTTTTGCAAAGATTCAAAGTTAAAGGAT |
| 360951 GAAAACAAGATCTTATCTATTGCTTTTTTACCATAACCTTTAACTAGGTC |
| 361001 AACAAGCTTCTTTTCAATTCCTAAATATGGTTTTTGATCAGTTTTAATCT |
| 361051 CAATATTGATTAACTTAAATTTATCTAAATAAAGATCTAAGAACTCTTTT |
| 361101 AAAGTTAGGATCGATTGAAATTGAATTTTAAGGTGAAAAAAAGCACTATG |
| 361151 ATCATCTCTTTTTAAACTAACTAATGATTCAAACTCAACCTCCTTATTAA |
| 361201 CTAATGCGGTTCTCAATGTTGTCTCATCATGAATGATAACTAACTGTTCA |
| 361251 TCTTTAGTTAAATGAACATCAAGCTCTATTCCATCAAAACAATATTCAAA |
| 361301 AGCTAAATCAAATGCTAGTTTGGTGTTTTCTGGAGCAATGAATGAATAAC |
| 361351 CCCTATGTGCTAAAAGCAATTGCTTGTTATGCATTATCAAGATCTCTTCA |
| 361401 ACGGTATGAAGCTTTATTTAATCGTTTAATTTCCATGCTATTTGAGATAA |
| 361451 AAACAATTGATCCACATATCAAACCAAACAAAGCAATGGATAAACAAATA |
| 361501 GCAGCGATAATTTGATAACCAGTGTTACTAGTATTACTTTGTCCTGCAAC |
| 361551 TGTATATTTCTTACCAACTTCAGCAGTCACAGTGTAAAGTCATCCATCAG |
| 361601 TAGAAAAACCAATAAAACTAAGTAAACCAACACTAGATGCATAGTTATTT |
| 361651 TTACCAATATCAATTTCACCTATTTGGTTATATCTGACTGTAACCATTCC |
| 361701 CCATGATAAGATACCAGTAAAGATATAGAGAATGGAAGAGAAGTAATTA |
| 361751 AAGTGATGTTAGCAGAATTTGTTTGTACAAAACCAAGTAGAATAuATGCT |
| 361801 AGAACAAATACAATACCAAGAACAGTACATATCATTAAAAACAAGATATA |
| 361851 GCTTTTACACTTATCTGCTAATCTACAAAGATAAACACTAACAGCACTTC |
| 361901 TCAGTGCATAAGTTCTAATTCCCCCAATTACAGTTACTAATACTACAGGC |
| 361951 GCTAAAAATGCATTTTGCAACATCTGTAAAAGGTAATAAGCAAAAGTGCT |
| 362001 TTGAAACACATACATCCCCATTAAAAAGAAGGATAGTAACCATAACTTTC |
| 362051 AGTTTTTTAAGGTCACTAAAATCTGGTTTAAATTGCGTTTAAAACTTACT |
| 362101 AAAGTGGTTTGACTTTGTTTTTCAATTGGTTTTTCCTTAACAAAAAACAA |
| 362151 AACTGTAAATCCAGTAATTACTAGCATTATGGCAATGATAAAAGCGTATG |
| 362201 CAGCAAATGGTTTTGAATCAGCATTCTCACTACCTCCTGATGGATAGAAA |
| 362251 ATGCTGGTAATTATCAATGCAATTAGAAAGATAAATATTAAACCTCATAT |
| 362301 TCCATTAGCAGCTCCCTGAATTCCAAAACCAAGTGCTTGGTTTTCTTTTG |
| 362351 TTGCTTGTTGACTAGCTAGTTTTCATAATGGTGTTCAAAAGATTAAAGTA |
| 362401 CTTGTTATCCCTCATAACCCTCATATTACACAATACTGAATAAATAAAGC |
| 362451 ATCATGGCTTTGTTGGTTTTTAGTTAAGATGTTGGCTGCTAATCAAAAAG |
| 362501 TAATTGCTCCAGTAGTAATTGCTGATAGAAATAACAATTTTCTAGAACTG |
| 362551 AAGCGATTTGTTAAAAACCCTCCTGGTAGTTGAGTGGCAAGTGTTACATA |
| 362601 ACCAATGATAGAAGTAACAGTAGCAACTTCATCCTCTGTAATTCCTAAGT |
| 362651 ACAAGTGGAGGTTAGGAACAACATTCTTAACATAATAGGGTGCAGCAATT |
| 362701 ACAAATACATCAATTGCTCCCAAAATAATTAAGGCAAGAATTTGTTGTTT |
| 362751 TGAAAAATCCTTTAAGCGTTTTTAAATCCTTTTTTTGTTGTCACTATCA |
| 362801 CTAATGATAAAGTGGGATAAATTAAATATACATCTAATAATAAAAGTGGA |
| 362851 TGGAAGTGAAACGTTCTTCACTTACTTTTAAAAAGAAAAATAATGTTTAC |
| 362901 TAGAAAAACTATTTTTTCTTAAATTAATCCTGCTCCTAAACARATTTGAT |
| 362951 CAAGTGTATATAATACACCAAACTGTCCAGATGCAACACTTATAACAGGA |
| 363001 TTTTTAAATGTTATTTCCAGTTTATTATCTGATAATAATTTCAACTTTGC |
| 363051 AATTTCTGGTTTTTGAGCATGTCTAATTCTTACCAGAACTTGACTAGGAA |
| 363101 GTTGCTTTGGTGTATACAACCAGTTAAATTGATCCAATAAAATTGTTGTT |
| 363151 TTCAATAATTCTTCTTTGTCACAAGAAACAAATAATTCATTAGTTTCAAT |
| 363201 ATCCTTAGCAACAACAAAATGACGTTGTTTTAACCCCCCTAAATTTAATC |
| 363251 CACTGCGTTGACCAATCGTATAAAACCAAACACCATCATGTTCACTAATA |
| 363301 GTTTGTTTGGTTTTTCAATCCTTAATTAATCCTTTTTTTACAGGTAAATA |
| 363351 GTTTTTTAAAAAATCACTGAAATGTCTTTCACCAATAAAACAAATTCCAG |
| 363401 TTGAATCTTTTTTATCTGCAACTTCTCAATTATTTTCTCTAGCAATATTT |
| 363451 CTCACTGTTATTTTTTTAAATCTGCTAAAGGAAAAATAACATTCTGAAA |
| 363501 TTGTTCTTTTTTAACATTTGCTAAAAAATAAGTTTGATCTTTATTGGTAT |
| 363551 CTTTAGGAATAGAAAGCAAAGGCTGATTTTCTATCATGTTTATTTTGGCA |
| 363601 TAATGACCAGTTGCAAAAAGAGAATTAGGGTTAATTTGCTTACAAAAATC |
| 363651 ATGCAATAAACCAAACTTAATAAAACGATTACACCAGATGTCTGGATTTG |
| 363701 GGGTTAACCCTTTTTTGAAACTTTGAATCATAGGTAAAAAAACTTTGTTT |
| 363751 CAATAAGCTTCAATTAAGTTTTTTTTATTAACTTAATTCCTAAAGAATT |
| 363801 AGCGATTTTTTTAGCCTGTTGGAAGTCTTGAAAAGATGAACAACCTGATT |
| 363851 TGTTATTATTTATTTTCTTATGACCATAAAAATCATTATTAAGTGTCTCA |

-continued

The Nucleotide Sequence of the *Mycoplasma genitalium* Genome

```
363901 TCCCAACATTCCATAAAAACACCAATAACTTCTTGGTATTGCTTTTTTAA
363951 AAGTAAAGCACTAACAGCAGAATCAACACCACCGCTTAAACCTATAAAAA
364001 CTGTTTTTGCAATAATTGACATTTTTAATAAACAGCGTGAATaGCARACC
364051 TGTTTACTAATCTTTGGTGAAATCTATTAGGATTAATGCCTTTTGTAATA
364101 GCAAGTGCAGAAATAAACACTATTAATGCTTCATAAAAATTTTGACAGCA
364151 CTGTTGATCACTATCTTTAGGATTTTCTACAACTTTTGCTAGATAATCTA
364201 GCTGTTTAATTACTTCAGTTTGGATAAAAAAACCATCACTTAACATTGGT
364251 TTGAAAAAAAATGGTTGGTCATCATAATCATCATCTTCATAAATAACAAT
364301 ATTGTCTTGTTCTCGTTTTAAACACAAATTAAAGTTAATGCGAAAAGTCT
364351 CAAAATCAACCGCTTGAAATTCAGTTTGTAAAAATTTTTTAAAAGCTATA
364401 AGTTGTGGTTTCATTACACCAGTCTAAAAAGTTTTAACACTTCTTGTTCA
364451 AGATAGCAATCCTTAAACAGTTTATTTCAGTATTACTTAAATAAACTACT
364501 AACCAAAATACTGTAAAAGGTTTAATTTAAAAACTAATTTTCTTTATTAT
364551 CTAAGTTTAAGTTATTAAGTAAACCTAAAACATATTTTTCCAGATCAAAG
364601 ATAGCTAAATCACTAGTTTTTTCACCAAAACCTATCAGTTTAACAGGCAG
364651 GTTAAACATATCTTTAATAGCTAAAATAATTCCACCCTTAGCAGAACCAT
364701 CCATTTTAGTTAAAACAATCCCTGTTAGTTTGGAAAATTCATTAAATACC
364751 TTTGCTTGTGATAGTCCTGTTTGACCTACTGTACCATCTAAAACTAAAAG
364801 TGTTTCACTAGGTTCACTTCCACTTACCTTTTGAATAATTTGATAAATTT
364851 TTTGCAATTCATTCATTAAGTTAAGCTTGTTTTGCAATCTTCCTGATGTA
364901 TCACATAAAACAAAGTCATATTTATCATCAATCCCTTTCTTTACGCCACG
364951 AAAGATAACAGCTGGAGTTTGTTCTTTAGGGTTTGGAAGTACAATGTCAC
365001 AGTTTAACAGCTTTGCTCACTGATTAAGTTGTTCAATGGCTCCTGCTCTA
365051 AAAGTATCACCTGCAACAAGTAGAACACGTTTATTTTGTTTTATGAAAAA
365101 ATCCGCTATCTTAGCTAAAGTAGTTGTTTTACCAACTCCATTAACACCAA
365151 CAAAGAGATAAACATTTGTAAAGTTAGGTTTAACTATTAAATCAGTATCA
365201 AAGAGTTTATCTTGGATGTAATAAACAATAATTTGGTCAATAATTAGCTC
365251 TTTAATGAGCTGAAAATCTGTAATTCTGTTTAGCTTGATCTGTTCAATAA
365301 TAGCATCACAAATTTTGTTTGCAGCATGATAACCAACATCAAGCAAAACT
365351 AGCCCTTCAAATAGATTTTCTTTAAACTGTTCGTCAACATTAACATATCG
365401 TTTTGACAGTTCATTAATAGTTTTAGCGAAAGTTGTAGCAGATTTTTTCA
365451 AACCCTGATAGTAAGTTTTATTATTGGTTTGAAAAAGGCTTTGTTTTTCA
365501 ACTTCTTCTTTAAGCTGTTTAGCAACTGATTTTTTTGGTTTTAGTTTGGC
365551 AATTAACTTGCTTAAAAAGCCCATTATTAGTTAATTAGAATCATTTTCAG
365601 ATACATATTTTTCAGCATTTTCAAGTTCAACTGCAAAGGTTTTAGTTACA
365651 CCTTTAGTTTGCATTGCAGCACCCAATAACATGTCACATTTCATCATTGT
365701 ACCTTGACGATGGGTAATAATTAAAAATTGGGTGTTTTTGCTAGCAGTTT
365751 TAATGATGTTAGCAAAGCGCTCCACATTAGCAGGATCAAGTGCACTTTCC
365801 GCTTCATCTAAAATAACAAGTGGAAAAGCACTTACTTTCAAAATACTAAA
365851 TAAAACAGAAAGTGCAACTAAAGTTTTTTCCCCGCCTGATAACAACATTA
365901 AGTTGGCAATATTTTTACCAGGAGGATTTGCAAAGACATCTATCCCTGAA
365951 ACCAATACATTACTAGGATCAGTGTAACGAATTTGGCAAGAACCACCACC
366001 AAATAGATATTTGAAAGTTTTTGGCAACTCTTGATTTAATTTTTGGATCA
366051 GTTGATCAAACTCATTGCTAGCAATTTCATCAATTTCAGTAATAGCTTTT
366101 TGCAAATTTTCAACTGCTTGTTGAGCTGATTCATATTCAGCGTTAATATC
366151 ATCAAAGCGCTTTTGCTTTTCACTTATCTCAGCAATTGATTCCATGTTAA
366201 TTACCCCCATTTCATTCAATTGATTTTGTAGTTTAGCAATCTTGTTATGG
366251 GCTTGCATAGAAGAGAGTTTAACTGGTTTGTTGTGATTAGCAATAGCAAA
366301 CTCCATTGTCATTTTGTAAACACTGTTAATCTTTTCAGTGATATTTTGGA
366351 TTGTATTTTCAAACCTAATTTTTCCTTCCCGCGCTGAAACTAATTTAGCA
366401 CGTTGTTCATCTAACAATGCCCTAAGATCAACTATCTTCTCTTCACTTTG
366451 TTTAATTGTTTTTGCTAGTTGTAACTTAAGTTCTTGATTAAGCTTTAACT
366501 TAGAGTTAATTTCATCACGTTTAGCTCAAGCACTATTTAATGAATGGATT
366551 AATTCAGCTTCACTAGCAACAGCTTTTTTACCATCAAAAGTTGTGTTAGT
366601 AAGTTGTTCATATTCCATTTTGAGCTCTAAAATAATTTTTTTAATTTGAA
366651 CAATACGCTCTATAAACTTGGCTTGTAACAACTCTTCATACTTGAGTTTT
366701 CTGTTCATTTCATCTAGCTTTACTTCTAGTTCTGTAAGCTCCTTTTTTAA
366751 CTCTCGTTCGTTGTTTTCTAGTTTGTTAATGTTCTGTTCATTATCAAGTG
366801 AAGCTGATGATAAATACCCATCACTAAGATTTGTTTTTTCAAATCCACCA
366851 TTGATAATTCCCCCTGCATAAACTGTCTCACCATCTAAAGTAACGATCCT
366901 ATATAACTTGTAAGTATAGTTAGAAAGGTTAATGGCACTATTTAAATCTT
366951 TAGCAATAATAACTTGTGCTAAAAGAGTATTTACAACTGGTTGAAACAAT
367001 GGATCACACTTAACATGATCACTACAAACACCAAGAAAACCATCAAGCTG
367051 CTTTAAAATTTCCATGTGTTCGTTTGTGATTTTAGTATCACTAGCAACAT
367101 CATCTAAAGGTAAAAAGTTACTTTACCTATCTCATTTTTGACTAAAAAA
367151 TCTATTGCTTGGATGGCAGCATTATTGTTGTTAACAACTAGGTAACCAAT
367201 TGATTTTCCAAGTGCTTTTAAGATAGCTTTTTCATACTGCTTATCAAATT
367251 TAAGAAATGTTCCTAGTGTATTTAAAATTCCTGTTAAAGCATTAGCATTT
367301 TTAACTAAGATATTGGCATTGTTAGTTTTTTAAGCTCATTAGTTTGGAG
367351 TTCAATAATTGTTTTTAAGGAACGTTGGTAAATTAAATCAGCAGTATTTT
367401 TTTCAATCTGTAACTTTATCTGATCAACAAGTGATTTTTGTTCGTTAATT
367451 AGTTTTTCAAGATCAGTGATGGTTGTTTTGGAATTTGATAGTTGGTTTTC
367501 AAAACCATCAAGCTGGGTTTGATCAACTAAAATTAGTTTTTTTAAAGCTG
367551 CAGCTTTTTGCTTTTCATCTTTTTGTGAAAAACCTTGTCTTAACTGCACA
367601 TCAATAATGACTTTACGTTGTTCCAATTCATTGATCTTTTGGTAAATATC
367651 TTGTAACTCTTTTTGCAATTCATTAGATTGCATATCAGCACTATGAAAGC
367701 GACTATTAAAGATAACAATCTGTTCTTCTAACAACTCTAGTTGGGGTTCG
```

-continued

The Nucleotide Sequence of the *Mycoplasma genitalium* Genome

367751 TGTATTTTAAAGTCATGTTCACTACTGTTAATCTGAAAATTAAACTTATC
367801 AAGTTCAGTTTGTGCTTGGAGATATTCCCCAACCAAAACAGCAAGTTCCA
367851 ACTCTTTCAATTCGTTTTTAACCCTAATGAATTGTTGTGCTTTTTCAGCT
367901 TGTAATGTAAGCTTTTTTAAATCTTTTTTCAGTTCATTTAAAACAACGCT
367951 AACTTGTTTTAAGTTAATTAAGGTTCGATTTAACTGGTTAACAACTTCTT
368001 CTTTACGCTTGGTATATCTACCAATTCCCGACGCATCTTCAAAGATCTTT
368051 CTGCGTTCTTCTGGCTTAGCTTCTACAAATCAAGAGACACTCCCTTGTGA
368101 AATAATTCCAAGTGAACCTTTTTCAAGACCAATATCAGCAAAAATACCGC
368151 TAATTTCTTTTAAAGTTGCTGGATTGGAGTTAATAAAATATTCACTCTGG
368201 CCACTCCCTCTATAAACCCTACGCATCACGCTTATCTCTTTTCTTGAATC
368251 ATGTAATAAACGGTTGGAATTATCAAAGGTTAGCTCTATTTCAGCTAACT
368301 TACTAGCAGGTTTGTCTTTAGAGCCAAAAAAGATCATATCATCACCTGAT
368351 TTACTACGGAGATGTTTCATACTTCTCTCCCCTAAAACCCACTTTAATGC
368401 ATCAACAACATTGGATTTGCCCGATCCATTAGGACCAACAATACCAGTCA
368451 TTGAATGGGTAAAATCAATTGTGATTTCATCAGCATATGATTTAAAACCA
368501 TATGCGCGAAAACGTTTTAGAAAAACCATTTGTTCTAAAAAGCTTTAATT
368551 TGGATGTTGTTATTAGATTATACTAGTTGAAGTAAACTAAACTAGGCTAA
368601 TTATTAGGTTACTAAAAAATAAGCTAATAACGCTTCATTTAAAAAAGCTT
368651 CTATGTTTTAATAGTAACTAGTTTATTTAATTTAAAAATTACATTAATTG
368701 CTTTTAGAAAAGCAATATCATTTAAAAGTTTTTATTTAATTGCTTGAGCG
368751 GCAGTGATAATTCCAACATTAAAAATGTCACTGACACTAGCTCCCCTTGA
368801 AAGATCATTCACTGGACTTGAAAGTCCAAGAACAATAGGACCAATTGCAT
368851 CATACCCTCCAAGTCTTTGGGCGATTTTATAAGCAATGTTACCAGCATCT
368901 AAATTAGGAAAAACATAGATATTAGCACTATTTTTTCAAGTTAGTTGAGG
368951 TGCTTTTTGTAACCTAACCTTTTCAACAAAAGCAGCATCAAACTGGAGCT
369001 CACCACAAACACTTTGATGCAATTCAGGGTGTTTTTCTAAAAATAGTTTA
369051 GTTGCTAAAACAACTTTATCCACCATTTCACCCTTACCACTGCCAAGCGT
369101 TGAATAGCTTAAAAAAGCCATTTTTATCTCATCCTCATTTAAACTTTTGG
369151 CAAAATTGAAGGTGTTTTCAGCAATTGTTGCTAACTCTTGGGAGTTAGGA
369201 TAAACAGCAAAAGCACAATCAGTGAAGTACAAACGTTCTTCACCTTTTTC
369251 CATGATGAAAACACTAGAAACAAAATTACCAGTTGCTAGTAACTGTAAAG
369301 CTGGTCTTAAAGTATCTTTTGTAGCATATTCTTTACCACAAACCTCACCA
369351 TCAACAACCTTTAGAGCAACTAAGGTAGCAGCTAAAGAACTAGGATCACG
369401 TACAAACTTTTGTGCTTCTTTTAAATCCATCCCCTTATGCTTACGTTTTT
369451 CATAGACAAAGTTAGCATAGCTAGTTAAATCCATCTCATCAATCACATAA
369501 TGAGTTATTTTTTTATCAAAATTTGCAGGGATTTCCTGACGATTATGAAA
369551 GATAACTGCAGGTTGGATCAGCTTAGATTCATTAAGCATTTCAACTGCTT
369601 TTAAAACACTTGCTGATCAACCTTCTGGAAAGATAATTACAGGTTTTTTA
369651 CTAACAGCTTGTAATCGTTTTTTAAAAATATCAATAACACTCATTGTTTT
369701 ATTAATTTGGTTTAAGAATTTTTTTGAATATCGCTAATACCTACTAACTC
369751 TTCCCCACCAATTAGTGCTAAAGAAGCACCACCACCAGTGGAGATAAAAC
369801 TAAACTGATCAGATAGTTGCATTTGCTTAACTGCTGCAGCTGAATCCCCA
369851 CCACCAATAACGCTAAAAGCAGTTTTATTTTTAGCAATAATCTCACCGAT
369901 TTTTGAAGTTCCTTTAGCAAAGTTAGTAAATTCAAAAACTCCAAGGGGAC
369951 CGTTTCAAAAGATAGTTTTGGCTGTTTTTAAATAACTTTCAAATAAAGCA
370001 ATTGTTTAGATCCAACATCTAGAGACATATAGGATTGATATTGTTCTTG
370051 AATTTTGTCACTAACATCTAAAGTAATGCCAGTTTGATCTTTAAATTCAG
370101 AACCCATTACCTGATCAATTGCCAGCACAATCTTATTATGAGTATCTTTA
370151 TCCAAGATTTGCTTAGCAACATCAATTAACTCTTTTTCAACTAGGGAATT
370201 AGCAGTAGCTTTGCCTTTTGCTTTAAGAAAGGTATTTACCATCCCTCCGC
370251 CAATTAAGATATTATCAGCAAGTTTTAGTAAGTTTTCAACTACCTTTAGT
370301 TTATCTGATACTTTCGCACCACCCAAAACAACAACAAAGGGTTTTTGTGG
370351 GCTTTGAATTAGGTAAGAGAGGTTCTTTAGTTCTTTTTCCATTAAAAACC
370401 CAATACAGGATTTTGCAACATACTTTGCAATTCCTGCATTAGAAGCATGT
370451 TTTCTATGGGCAGTACCAAATGCATCATTAACAAAAATTTCCCCTAAACT
370501 AGCCCAGAATTTCGCTAGTTCAGGATCATTTTTACTTTCTAATTTAACAA
370551 TTTCTCCTTTATCGTTTACATCACAATAGCGAGTGTTTTCAAGGAGAAGG
370601 ATTTCACCGAATGCTAATGCTTGCACTTTTTGTTTAACTTCAGCACCAGT
370651 GTTTTTACAAGAAAATTGAACCTTTACAGTTGGTAAGAGTTGTTGGAGTA
370701 ATTCAGCAACCGGCTTTAAAGATTTTTTGTTGTTTAGTTTATCTTCTAAA
370751 CTCTTAATCCTTGAAAGGTGTGATAGTAGCACTATCTTGCAGTTCTTTTT
370801 AACTAAGAACTTAATAGTATCCAAACCAGCTAAAATTCTTTCACTATCAC
370851 TAATAACCCCATTGATCATTGGGACATTAAAATCACTTCTTAAAACAACG
370901 GTTTTGTTTTGAAAATCAATTGCTTGGAGTGTTTTGAAATTAAGCATATT
370951 AGAGCTTAGCACAATAGCTAACTACTCTCACTAGTTGGTGTACATAGGAA
371001 GATTCATTATCATACCATGCATACACCTTATAAAGTTTCATGCCATCAAC
371051 TTCAACAATATTGGTTAGTTTAGAATCGAAAATTGAACCATATTCAGAAC
371101 TTACCACATCGCTAGATACAATAGGATCTTCACAATATTTAAAAGAAGCG
371151 GAAGCAAATCGCTTCATGGCTTGATTTACTTGTTCAACAGATGGACTTTT
371201 TTCAAGTACAACACTTAACTCTACAATAGAACCAGTTAACACTGGAACAC
371251 GGAGTGACATCCCATTAAGTTTGCCATTTGCTTCTGGAACAACAAGCCCA
371301 ATTGCTTTAGCTGCTCCTGTTGTTGTTGGCACAATGTTAACAGCTGCAGC
371351 ACGAGCACGACGTAAGTCATTATGAGGAGCATCTTGTAAGCGTTGATCTG
371401 CAGTATATGCATGAACTGTTAGCATCGTTCCATAAACAATCCCAAAGTTC
371451 TTTTCAAGTACATGAACTAATGGTGCTAAACAGTTAGTAGTACAGCTAGC
371501 TGCTGAGATGATCTTATCATCGCTACTAATGGTTTTGTGATTAACATTGT
371551 AAACAACTGTCCTGATAGTTTTTTCTTTAGCGGGTGCGGAAATAATTACT

-continued

| The Nucleotide Sequence of the *Mycoplasma genitalium* Genome |
|---|

```
371601 CTTTTAGCACCTGCTTTTAAATGGAGAGAAGCACCCTCTTCACTTACAAA
371651 CCTACCAGTTGATTCAATTACTACATCAATATCATGTTCATCCCAAGGTA
371701 AATTTTGGGGATCTTTTTCACTAAAAACATAAACCTTTTTTCTATCAATT
371751 TGCAAGATGTTTTGTTTAACAGTAATCTTTCTTTTCAATTCACCATGAGC
371801 TGAATCATATTTCAACAGGTGCGCTAAAACTTCAGGTTGGGTCAAATCAT
371851 TAATTGCTACAACTTCAACATTTGCCTTACTGAGAAGAGAACGAAAAACA
371901 AGTCTTCCAATTCTTCCAAAACCATTGATTGCAACCTTAATGGTTCTATT
371951 CTTTGCTGCCATACTTTAATTTAATAATTAGATTTTAATACTTTaGCCTA
372001 TTGCAATTAATTCTATCTGTCAAAAATACAgCAAATTATTGCTATTAATT
372051 GCTCTtAAABAAATAAAGTTTTGCTTATCAAAATTGAAACTATAATTAGG
372101 ATTTTCTCAGTAAACTAAATTCCAGTTATTAGCAATTAATAAAATACTAA
372151 ATAAAAGTAAACCCACTAATAAAAATACCCCGTTTAATAAGTTGTATTTT
372201 AAAGGATAATGAGTTCTGTTAGTGTTATTTAAATCATAACCTTTAGCTTG
372251 TAGAGCAAACGCTGTTGTTTCTGTTTTTTAACTGTTGAAAGTAATACGG
372301 GAATAAAAAGGGTTTTAATCTTGAAAGGATTTAAAAACGAACACTTGTTA
372351 TAGATAAAACCTCTAGTAGCTTGAGCTTGTTTAATTCTTATAATTTCACT
372401 TTTAACAGTTGGGAGTAATTTAAATATAACTGCAAGCAAGATACTAATTG
372451 GTTGAACCTTAATATGAAATAACTTAAGAAACTTAAAAAACCTCTCAACT
372501 GCTCAAGCCAATTCATAGATAGAACTTGAAGTTGTCAGTAAAAAGAAGC
372551 ACTGAAAAGCATACTAATCCTTAATGCAATTACAAAGGATCGTAAAAATG
372601 AACGTAGATTAAAACTTCACCAGCTAACACCACCAAAATTATTACCACCT
372651 GAATAGATAAAACTTCCTAAAAAATTATGGTTCTGATCAACGCTTAAAGC
372701 AGTATTTGGTAAAAAGATAAAACCGTTAACAATTACATTAAACCACAAGA
372751 AAAATAACATCCAACTCAAAATAATTAATGCACTTTTAACCCTTTTCTCA
372801 CTAATTACAACTAGGGTTAAAAAAACTAAGTTAATAATTACAAGACCATA
372851 TAATCCTAGCGGTAGAAAAGCAACAACTAAACTAATTAGTCAAAACCACA
372901 ATTTTAGAAGTGGGTCAATTTGTTTAAAAAACTGGTTTTTGCATGAAA
372951 ATAAGTTTTTTAGTTCACTAATAAGATCATCAAGGTTTTTAATTTCTGCT
373001 TGGTTTTTAAAAGCTATTCCCTTTTCATTAAACATCTTAACTGCTTGGAT
373051 AATTACTGGAGGGGTGATTCCATATTGCATCAACCAACTGGTGTTTGAAA
373101 AAAAATCATTAACAGTGGTTTGATGAATTATCTTTCCCTGGTGGAGATGG
373151 ATGATTTTATCAGCAGTTTCAAAGATAAAATCAACATCATGGCTAACAAT
373201 AACAATCCTTGTTGTTTGTTTCATTGCTACTAGCATTTTGCTTAAGTTGC
373251 TAATCGCCATTTGATCTAACCCAACAGTAGGTTCATCAAGGATTAAAAAC
373301 TTAACTTGCATTGCTAACACACTAGCTAATGCCAAACGCTTCTTCTGTCC
373351 ATCGCTTAATTCAATGGGATTTTTTATTAACGGGATGTTTTCCAATCCAC
373401 ATAGATCAAGGTATTTTTTGGCATAATTAACATCTTTTTTATGACAAAGT
373451 TTAAGGTTCACTGCTCCTGTTAAAACTTCTTCTAAAATAGAATCACAAAA
373501 AAACTGATCTTCTGCTTTTTGCAAAATATAACCAATTTTTTGCTTAAAGT
373551 TTTTTGTTATCTTTTGTTGGTATTGGTTTGCAAAATAACAATAATTAGCA
373601 CAATTTATATAGCCAAAACTAGGTTTTTCAAATAAACCTAACTGTTTTAT
373651 TAGTGTAGTTTTACCACTACCACTTTCACCAAAAATAACTGTAATTTTAT
373701 TAGGtTCTATTACCCCTGAACaACATTTAATGATCTGACCATCATTATGC
373751 TTATTGACAAAGCACACTAATATTGTTAAAAAACAATGGATCTTGTTCAAT
373801 GTTCAGTAATTTGCTATTAAAAAATGGAATGCTTTTTTACTGTTTAAAA
373851 AGTAAAAAGGATTAATGATTTTATCAACCTTTTTATAAAAAGAAACAGT
373901 TTTTTTGAATCTAATTTTGCTAGTTTAAGATTCGCTTTTTGAGCTTGAAG
373951 ATGGTATTTTGTTCAATTAAATCTAGTTTTATTTGAGGTGTTTGCATAT
374001 CCAGTTAACTACATCATTCAATTCAAAACTTAAACTTGGTGTTTTTTTGT
374051 TTATTTGTTTAGCCACCTTATGGGCCAATAAAAGTGGAAAAGGGAGATTA
374101 AAGTGGTGGTTATGAAACAAATCAAGCTGCTCATATATCGCTTCAGGAGC
374151 AAACTTTTTAATTAGCGATCCTTTACTTAAAAAGATAATCTCATCTGCTA
374201 GAAACAGATCATTAAAATCATGGGTAATATTGATAACTATTTTGTTTTGT
374251 TTTTTGATGGTATCAAACACAAATTTTTAAGTTTATTGCTGATCTTATT
374301 ATCAAGCATACTAAATGCCTCATCAAGCAGATAAATTTGTGGTTTGACAG
374351 CCAATAAACAAGCAAAAACAGCACGTTGTTTTTCACCAAATGAAAGTTTT
374401 TTAAGTGGTGTAAATTGTTTATCTTTCAATTCAACAACAGTTAAAACTTC
374451 ATTAATAATCTTATCCATTTCACTAGCTAAAACTCCATGGTTTTCCAAAG
374501 TAAAAATCAATTCCTGGTGGAGTGTATCAGCAAGTAATTGCACATCAGGG
374551 TCTTGTAATAAGATTCCAATCTTATTAAAACCAACAGAAGTCAACTCCTT
374601 ATCATTGAAAAAGATAGTTCCTTTTTTAGCTTTTAGAAATCCGCCAAGGA
374651 GTTTAACTAGGGTTGATTTACCTGAACCGTTATGACCTATTACTGCTAAA
374701 TGACACCCATCTTGAACATTAAAACTAATCTGATTTAACACATTGTTTTG
374751 GTGTTTTGGGTATTTAAAACTGAGGTTTTAACTTGTAGCAAACTAAGCT
374801 TATTTATAAATTTTAAAAATAAGTCAGAGCTAAAAATCTGTTTTTTGGTA
374851 GATAAAAAACAAAAAAGCAGCTGTTGTGCTGCTCTTTTTTATTTGGAATA
374901 TGTTCTATATGAACAGGTTATTTTGCTTGTGGACCTTGTTCACCAGTTGG
374951 GTTATATTTTTTTGCCATCTCTTCTCTTCACTTCTTAAAGTTTTCAATTT
375001 CCACTTTGAGTTTGGCATAGTCATTAGCTTTAATAGCAGCATCAATGTTA
375051 CCTGTTAGCTTTTCTAACTTCTCTTTTTCTTCTTTAGGGAAATTCTTAGC
375101 ATCAGGACTTGCTAATATCTCTTTGATGGTATTAACAATACCTTCCCCTT
375151 CATTACGTAATTCAATACGTTCACGGATGATGTTATCCCGTTCCTTGTTA
375201 GCTTCAGCATCACGGATCATCTTTTGGATCTCCTCCTCAGAAAGATTACC
375251 GTTGTCACTAATGGTAATACTGTTTTCCTTTTGCGTGGTTAAATCCTTAG
375301 CTTTAACATTTAAGATCCCATTGGCATCCAAACTAAAGGTAATCTCAATT
375351 TGGGGTTTACCCTTTAGGTGCTGGTTGAATACCACCTAAGTTAAATCTTCC
375401 TAATGACTTATTATCTCTAGACATTGGTCTTTCCCCTTGACATACAACCA
```

| The Nucleotide Sequence of the *Mycoplasma genitalium* Genome |
|---|
| 375451 CATCAACTGATTCTTGGTTATCTTGAGCAGTTGAAAAGATTTGACTTTTA |
| 375501 CTTACTGGGATAGTTGTATTTCTCTTAATTAAAGGAGTAGCCACACCACC |
| 375551 TAAAGTTTCAATAGAAAGGGTTAATGGAGTTACATCTAAAAGTAAAACAT |
| 375601 CCTTAACATCACCACGTAAAACCCCACCTTGAATACCAGCGCCAATAGCA |
| 375651 ACAACTTCATCAGGATTAATAGAACGGTTTGGTTTTTTACCTGGTACCAT |
| 375701 TGATTCAACTAGCTTTTGAACTGCAGGCATCCTTGTAGAACCACCAACTA |
| 375751 AAAGAATTTCATTAATCTCTTCAGGTTTAATCTTAGCTTCCTTGATAACA |
| 375801 TCTGAAATAGGGTTTCTTGTTCTTTCAAGTAGTGGTTTTGTTAACTCCTC |
| 375851 AAACTTAGCACGGGTTAGTTTTAACTCAACGTTAACAGGACCTTTTTGGG |
| 375901 TAACAGTTAAAAATGGTAGAGAAATAATCGTTTCAAGTTGAGCGGAAAGT |
| 375951 TCAATCTTAGCACGTTCAGCTGCTTCTTTAAGCCGTTGCATTGCCATCTT |
| 376001 ATCTTTTGATAAGTTTAAACCCTGGTGTTCTTTGGCAATGTAGGCTGAGA |
| 376051 TATATTCAATGATCTTGTTATCCCAATCATCACCTCCCAAACGGTTGTCC |
| 376101 CCAGCAGTTGCAAGTACTTCAAAAGTACCTTCTGCAATGTCAAGTAAAGA |
| 376151 TACATCAAAAGTTCCACCACCCAAGTCATAAACCAAGACTTTCATCTCTC |
| 376201 TTGATGCTTTATCAATCCCATAAGCTAGAGCAGCAGCAGTTGGTTCGTTA |
| 376251 ATGATCCTTTCAACATTTAAACCAGCAATCTTACCTGCGGTTTTAGTAGC |
| 376301 GTTTCTTTCCGCATCATTAAAGTATGCAGGAACAGTAATAACTGCTCTTG |
| 376351 AAATCTTTTTACCAATCTTTTTTTCAGCAAAGTCCTTAAGATAACTAAGG |
| 376401 ATTTGCGCTGAAACTTGTTCAGGACTTAATTCCTTAGTTGTACCATCAGC |
| 376451 ATTTTGGACTTTTACTTTATTTGAGGTACCCATCAACCTCTTGATGGAGA |
| 376501 CAATGGTATTTGGGTTTGTAACCATCTGTCTTTTAGCAGCATCACCTACT |
| 376551 ATAATTTCATTGTTTTTATAGGAAACAATGGAAGGTGTTGTTCTTTTACC |
| 376601 TTCAGGATTTTCTAATACAACAGGTCTCCCACCTTCCATTACAGAAACAC |
| 376651 AAGAATTGGTAGTTCCAAGGTCAATGCCAATAATTAAACCATTGTCTGCA |
| 376701 CTCATACTTTTTTTTTAGATCAATAACAATTACTCAGTAATTATAAACAA |
| 376751 AAATTAGCACTCAAACACTAAAAGTGCTAATTAAAGTTTGTTTTATTTAT |
| 376801 CTTTTTTAGTTTCTAAGCTAACAGTGTTAACTGTTTTCAACGGTACATTA |
| 376851 ACGGTCTTTTTAAATTCCCATATAACTTGAACAATTCACACAACAAACA |
| 376901 AATCCCAGTGAAAATAGCAGGTAGATAAACAGATAAAAGTCTTCATAAAA |
| 376951 AAACACCATCTTTAATCTGATCATGGAGGAATTGATCAGTTGGTTTGAAT |
| 377001 GCATTGAGAAAACTAGTCATCACAAATTGTGTTGCACCTTCCCCACTAGC |
| 377051 AACTGGAATAAAGTTAGAAGCGGTAACAGCAATATTAGTAATGTTAAAAA |
| 377101 GATCAATTAAGCTGTATTGATCAATAACGTTATTAGTTGTGTTGACAGTT |
| 377151 TTTGTGATCATAAAAACACCAAACAAACTAAAGTAGGAaACAATTGCTAC |
| 377201 AACCATGTTAGCTAGTAATTTAAAGATTGTTAACCCTCACCTTCGCATCT |
| 377251 CAATTCCATACAACTTATTAAATTCAGCTTTTTcTATAAAAcGTTGGTAG |
| 377301 ATCTGCTCTTTAGTTAAATAAGGACGTTTAAGTCACTTTCGAAACTGGTT |
| 377351 TACAAGTGAATAGATCAAAACATGCATCTTTTTATTGAAAGCAATAACAA |
| 377401 TAAATAAGATAGCAACAACAACATCAAAGATCATCCCAGTAAGACTTAGT |
| 377451 CAGTAAGAGACAAAGCTATTATGGTTATTTGCTAACAATTGATAGTTTTT |
| 377501 AGAAAGAACAAAAAAAGAAGGTCAAGTTATTAACGCTTGCGATAGATTTC |
| 377551 AAAATGCTCCTGTAGAAGTGACAATTAAAACTGCAGTTTGTTTTTTCATC |
| 377601 CCCTTTTTAATGAATCAATACAAGCGAAATGGATCTTGTCCTAGTGATAA |
| 377651 GGGGGTTACAATTTGAAAAAACTGTACTACAAAACCAAATAATAACCACT |
| 377701 CTCACCAACTAGCATAAAAACAAAATCTCCTTGATACCCACCAATTAATG |
| 377751 ATTACATTCCACAAAACTGAAACTAAAAACCCTAAGATAACAACAAATAT |
| 377801 CCAACCCCAATTCTGATAGTTAATTGCAGTGATAATAGTTTTCACATCAT |
| 377851 CAACACTAACACCTAAAAAAAAGATAGTAACAATAACACTAATAACGATT |
| 377901 AGAAAAACCAAAAAAAAGCTAAAAGCAACGATGTTTTTAGTGTTAAAAAA |
| 377951 GGTATTGGTGGTTAACTTTGCCATTACTTAAGCAAGTTTAAGCCTGATTG |
| 378001 AATTCTTTTATCACCAATCCTAAATTGGGGTTTTTCAATTGCACTTAAAG |
| 378051 CAAGTTGTTGGGTGCCTGTATCACTAGCTTGAAATAAAACTAAAGCTGCT |
| 378101 ACTATATCACTTTCAATATTGGTAGAACTTGTTAAACTAAGTGAATCAAT |
| 378151 GTCACTTTTAGTGAACTGAAGATAGTTGTAACTATCACCACCAAAGTTAA |
| 378201 ATTCACTAAATTTTTGGTTGGTTTGGGTACTTCTTTTTGAAATACTTGGA |
| 378251 CTATTTGATGAATTAAAATAACTGGAATATTGGTCTAAAACAGCTAATAA |
| 378301 CAACGCTTGTTTAGCTTTGAAATCTAAAGCAGAATTGTTAATTGCATCGA |
| 378351 CCTGAAAATAAGCTGAAAGTGTTTTGCCATTACTACTACTACTTGGA |
| 378401 GTTAGTCTACTTAGCTGTCGGGCAATGTTATCTAAAACTAATTGGTCTTT |
| 378451 TGTTTCACTAATAAATTTTTTAAGATCATCCTTTGAACCATATTGTTTTA |
| 378501 AGGAATTGGCAGCGATATGGTTTAAAAGTGCCTGGTTAGTATTGTTTTCT |
| 378551 AACATGGAACTGTTAGTTGTATTCAAACCAGTAAAACCATAAGTACCATT |
| 378601 ATTACTTGTTGATACTGCTTGTCTGGTGCTTAACATCGTAGTAGCAGGTG |
| 378651 TAGTGTTAGGACTTGTTTTGGTTTAAAAAAGAAATTATTAGGATCAATA |
| 378701 GTTTGGTTGGCATTAGCTGTTGTAGCATGTTCATCATTTTCATAGTTAAA |
| 378751 AACAGAGCCAAATATTCCCTGAGGATTATTGGTGTTGTTACTGATAATAT |
| 378801 TCTTATCATAAGCAATATAGGCAATTTCACCATACTTTAAGTTAGCTTGT |
| 378851 AAAAATATCTTTAAAGTTTTTTAGGTTGTTTTCAATTAACCATTGCAAAGT |
| 378901 AAAAATGAAGCGATAATGGTCAATAACTGCTTTAAAGTTAACATTAAAAC |
| 378951 CTGATTCATCAACACTCTCTAAAAAAAGCTTTTTTAAACAATTCATCAATA |
| 379001 TTGCCATTATTAGGATTACCATACATGGCTTTATTGGTTAATTTGCTTCA |
| 379051 TGTCATGTAATAGTAATTGCTAATTACTTTAGCTAAACTATCTGCATCAC |
| 379101 TACTTGATGAAGTTGATGAAGATCCATTTTTAGATTTAATCTCTTCAAAT |
| 379151 AACTTTTTAGCTTTTTCAAACTGTTGATTGCTAGTAAAAGCATTTTTTAA |
| 379201 CAATGCAAAGGAAAGAGGGTTTACAGTTGTTACATCTAACAACGCATTTA |
| 379251 AACTCCAATTGGCACTGTTAGTAAGTGATTGATCATTGTTAATATCAACT |

-continued

The Nucleotide Sequence of the *Mycoplasma genitalium* Genome

379301 AGAATAATGTTGCTAAAGTTAGGTTTTGATTTTTCTGTAACTTTCAATTG
379351 GTTAACAAATTCTGTTACTTTGTTATTTATGTCGCTCAGAATTTCATCTC
379401 TTATCTTATCAACATCAGCTTTTGTAGTTTTTAACTTATTGTTGTTTTCA
379451 CTAATATTTATTTTTTCACTACCTACTTTTTTCCAAAGTGTTTTAGTAAT
379501 TAAAAACAAGAAATAGTTATTGAGTTTTTCATAATGACCAGACTTGCGAA
379551 CATATGGCAAATGGGAAGATAAGCCATTTAACCAAGGGGTTGGATTAATT
379601 TGGTTAACATTGGTATTAAGTTCAGTTGTTCTACTTGTTAGTTTGTTATC
379651 TAATGCATCCATTTGTAAAAACAAATCTCTGATTACATTTGTTGCTAATG
379701 CAACTGGTGCAhATTTTTGCATTAGTTCTTTGTAATQATTGAATGCTTTT
379751 TGCATCGCATCACTACCTTTATCTTTTTTTTGAAAATCAGTATTTATTAG
379801 TGCGTTTACTAATATTAATTCCTGATTTTTTTCAAACCAAGTTTTCAGTG
379851 TTTCATTTAATGGAAAACTAAAGGAATATAAACTGTTTTTAAAGGTGTTT
379901 GTTTTGGCTTGAAAAGCTCTTCACATTAAAAACTGCTTTTGCTTTTCAAT
379951 GTCTCTTTCAGTTTTGCTACTACTATTTTTTGTCAGATAATAACTACCTC
380001 CATCAATTCCAATTACAGCAACTCCCTCTCCGTTTCTAACTAGTCTTAGC
380051 TTCAATTGGTTATTAGAGTTATGGCTTGTATTTGAACAGTAGCATTTGC
380101 ACAGTTTGCACTAACAGTGCTAGCACCATTATTTGTTTTGTTATTAGGAA
380151 TAGCTGCATCCCAAACAAGATAACTGCTTGTTGTTGATGAACTAGCTTTA
380201 GTTGAAACCATCATATCACTTGTAGTTGTTTGGTGGATTTGCTTTGCTAG
380251 TTTTCCTAAATTGGAACTATCATTAGAACTTATAAAAGCATCTTTAATAA
380301 GACTCTTTAAATTGTTTTGTGAACTGTCTGTTGTATTGTGTTCACAGAAC
380351 AATGTATTACTCTTAGTATGGTTTTCAATTTTAGTTGATTCAACAACAAT
380401 GGTATTGTTAAGTTCTTTATTAAGCTCTTTAATTGTGGGAAGTTGATCTT
380451 TATCTTGATTTAAAAGATCTAGTTTTAAATTTAAACTAGCACCTAAATTA
380501 GCTGCTTCTAGTTGATCAACAATGTTTAGACTATCTACTATTTGCTTGGT
380551 TTGAGTGTTATCAGAAAGAGTTGTTGGAAAATCAATCAGGTTGCCTTGAT
380601 TTTGATCTAAGATGTATTTTTCTAAACCTGTTTTTGCTGTATTTAATCCG
380651 TCTTTTCCCTCAATTAACTGCTCTCAGCGTTTGTTGCCAACATTCTGGTT
380701 CTGAGGAATTTCCCCATCTTTAGGAAAGAAAGGAAACGCATAAGAAGGGG
380751 TTAATTTATCTTTTAGTTTTTCAGTGTTGTAAACTTGACCCAAACCTTGT
380801 TGTGGTGCTGCATATTTAAAAGTAGCTTGACTGATTAAAGTAGGATCGGT
380851 ATATTCAACCCAGAGATTAAAGATTTGTGCTTGTAACTTTGCAAACAATG
380901 CATCATTAGTTTCACTAAAACGTGGTTCTTGAAaACCAcAGTCCTTTCAT
380951 TTTTCAGGTTGGGATAGTTCATCATAGATATAAGGACCAGTTGAGAGTTG
381001 TCCATTAGGTTTATAAACTAAGAAATCCTTAGCGAATAATTTAGCGGTAA
381051 AATCACTAATAAGTTGATTGAAAAGTTGTTGGGATTTTCAACTAGCCTCA
381101 CTGCCACCACTTTTATCTAATAGATCTTGTTGAATAAATACTGCTCTGTT
381151 TCTGGGTGGTGATATTAACCCATTAACAGTATTTTTATATTGATCATCAA
381201 CATTCTTTTTAGTGTCTTTTAAAAACTTGTTTATGGCTTTGTCTTCATTG
381251 TTTTCATACCAAGCCTCAAGTGCTTTTAAAAGTGGTCCTATAACAAAATG
381301 TTTGTTTGCTGAAGGAGTTTTTAAAGCAGTAATAAGTCCTTCTTTTAAAC
381351 TACCCTTTTGACCATGAAAAAAATTAGTTGAGGTTGGTGAAAAAACTGTT
381401 TGCAAAGCACTGTTTGTTGGAGTTGAACAAGCTACAAGTATTGTGCTTAC
381451 TGACAAACCACAAAGTAAAAACCACCAGAACTTTGATTTTTTTAAAAGtT
381501 TTTTCATGATCTTGGTTTTTTCTTATTAATTAAAAGGTTTTGAATCTGTT
381551 GTTTTTGGTATTTTTTGTAGTTAGGTTTAACCTTTTTATATTTAGCTTTG
381601 ATAGCTTTAATTTTCTTAATTTGTAAAGTTGAAAGCGGTTTTTTGGTAGT
381651 TTTTTGGTTATTTTCAGTCAAAAACTTCAAATCACCATTACTAGTTAAAC
381701 TAACGTTTTGAAATTTAATTCCTTTTGCTATTAGTTTATTTAATTTACTT
381751 TGATTTTGGTCATTTCAAAAAAGATATGATCTGCCCCAACTGTTAAGTCG
381801 TGCTACACGACCAGAACGGTGGATGTAAAAACTATCAATTTTAGGTAGAT
381851 CTCAAGAAATCACCACACTGAAATAATTTAAATCTATCCCACGTGAAAAT
381901 AGATCAGAAACAACTAGTAATTTCAATTTATTATTAGTTGCTTTTGTGAA
381951 ATTATTTTTACGTTCTTGATAGGTTAAACTACCATAAATTGAACCAAaAC
382001 TAATATTGTTATTTGAAAGCAATTGTGTTAATTGTTTTAAAGATTTTTGA
382051 TTAGAACAGAAAACAATAATTTGCTGATTTTGGTGGTGTTTTAATAAGGC
382101 TAATAAACCAGAAAAAACGGTTTTCAGTATTGAGATGAACAACAAAATGCT
382151 TAACTAAGGGGTGAATCCATTGCTTTGGATGGAGATTAATAACTTTAGTA
382201 TTAATTACTTGTTTTTTAATTATTTGGAGTTGTTGATTGAATAAAGTAGC
382251 ACTAAAAAAGGCAAACAAGGGCTTTGCTTTTTGAAAAAGATGAACACATT
382301 CAAGTCACTGCTGGATTGAACTTTGCTCTAAAAACATGTCAATTTCATCA
382351 AAAACAACGTATCTAACTTTGCTAGTAAAAAGGTATTTTTCGTTTAGTAA
382401 ACTAACAATTAGTTGTGCTTTTGAACTAAATGAAGTGGCAAAAGTAAAGG
382451 TTTTAAAGTACTTTTTGATTTCAGTTAAGATGTTGATAATTTGTCATTGT
382501 AACTCTTTGGTTGGTACAAAAATAACTGCTTGAGGTTGATCTAAACTGGT
382551 GTTAATCTTATCTAATAGAGGTAAAAGATAAGCAAAGGTTTTGCCACTAC
382601 CAGTTTCAGCAATACCAATGATATTTTGGAATGGTCATAATTTAAAAACT
382651 GCTTGCTGAATTTTGGTAAATTCAACAATGCGTTTCTTATCTAAAAACTG
382701 CCTAATAGAAGAGGAAAATTGCATCTTAAACTAGAATTTACGCACTCACT
382751 GTGAACTGATTGCTGAAAACAATCTGTTATCACCAACTCTAACTAAGCCA
382801 TTTTTGGCATTTGCTATCAATGCATTAATAGCTTGGGTTTGATTATTAGG
382851 ATTAAGCGCTTCAAGCGCAACTGTACTTAAAAATTCTTCAAGTGAAAGAT
382901 CAAGTCTTTTTGAATTATTTGAATCTGTACTATTCAAACTATCACTACCA
382951 AGCATACTTACATCTTCAAGGTTAATCTGTTTTGCATAAACTGCATGATA
383001 GATCTGGTTATCTTGTAAAAAGTTATAACTGCTATAATTACTGGTTTTAT
383051 TTGTACCTATATACCCTTCAAACCTACTAAACACATCATTAAAGTTACTA
383101 TTATTAGTTTTACTTTGAGCTTGTTTTAATTGAACAGTTTGAGTATTGTT

-continued

The Nucleotide Sequence of the *Mycoplasma genitalium* Genome

```
383151 AAAGTTTGAATTAGCAAAATTCTTCAAATTAGTTTTTTGTTCTTGTAAGG
383201 ATTTTGATCTATCAACACCAGTAACGTTAATATTAAGGTTACTTGTTAAA
383251 TGGTTATAAAGTGCATCAAACTCAGCTTGGGTTGGGATGTTATCAATTGT
383301 TTCTATAAGTTTTGTTAGAGAACCAAAACTAAATAAAGCACCTTTGTAAA
383351 TTGTTTCATTACTACCACTTGATTGAGTAGATTGTAATTGTGCTTGACCA
383401 CCATTAGAACTTGATTTTTCAGATTGGGAAACAAAACTTGTAAAGAGGCG
383451 ATTTCTAACTGCATCTGGTAAGTTGTTGGATGAAGTGTTGGTAACAATAC
383501 CATGGAAACCAAACCTTCTTTGCTGGTTATTGGTTTGCTGTGCACTTTTT
383551 TGCATTAAAGTTAATGATGTACTGCTACTACCATTGTTCTTTGTATAGTA
383601 AAGACTTGAAATATCATTTGCAGCACTGTTAACTGTTGGGGTTTTGTTGT
383651 TGGTTCAATTATAAGCACTCGAACCAAATACATAGTTAGGATTTTGTTGT
383701 TCTTGCTTGGTAAAGTCTTGATTAGTTTGAGAAGCAACGTTGTTAGCCAT
383751 TTTTACTAATACAGATTTAGAAGAACTTACACTCATTGCTTGACTAGCAG
383801 TATTATTTCTGTCTTTATCACTAGCTAAACTTCAAACCAAGAAACTATTT
383851 GTTGTTCTTGATAGTTTAGCTTGCAAGTCCTGTTTTAGGTTTTTAAGGTT
383901 ATCTTTTAATAGCCATTGAACTGTATAAAGATAAGAATAGTAATTGATTA
383951 AGTCATTGCTATCCAAGCGTTCTTCTAAGTTTAAGCTGTTGTATAAACTA
384001 TCTAAAACCCCATTAATTTTGGGTTTATTATCAGTTGAACTTTCATTAAC
384051 ACCATTACCAAAAATAGAAGGATTAGCTTGTTTTTGAAAAAGATCAAATA
384101 GGTAGGTATATTTAAAGATATTTCAGTTTTCATTATTGAGACTGTTTCAG
384151 TTTTTAAAAGTTAATTTATCTAAATCAATCGCTTGTTTAAACTGATCATC
384201 ATTGACAAAATAATCTCGTCTAATGGTATTTTGTAACTCATCACTTGATA
384251 AAACAGCATTTAAAGCTAAATTAAGTGCTAGAGAAGTGTTTCTAGGATCA
384301 GATGAAAGTTTGGTATCAACAAGGATAATTTGTGAATATTGCGGTGAGGG
384351 AATTACCGAAACTTTTAGTTCATCAACATGCTTTTTAACTGCTGCTTCAA
384401 CTTTCTTTTTATTCTCTTTTAACTTGTCAATTATCTTTTTTGAAAAAGGA
384451 TCACTACTACTACTATTACTATTACTATTACTATTACTTGTATTTGAACT
384501 AACTTTATCAATGATGTCTTTATAGTAAATACCAAGTTCATTGTAGTGTC
384551 CTGTTTTACTATCTTGTTCATAAGGTAAAACAGCAGCTAAACCGTTCATC
384601 CATATTTGTTTATTTCGCTCATTATCAATGAAAGGTTGGTTACGTTCTGC
384651 TAGTTTTAAAGCAACTTTGTTTTCTGCAGTAGCAACTTCATTAAAAACAA
384701 TTTGTTGATATTGACTTTCAACTAAATCCTTCAACTCGTTTTTAACAGTG
384751 ATAATGCTATCACTAAACTTTTTAAACTGAGGGAAACTTAAAAAGTTACT
384801 TTCTTTGCTGTCTACTAATTTAAAAAGGGCATTAAATAAAAATAAAACTC
384851 TGTTCTTATCAAAGTGTTTTTTCACTTCATCAAACAACTTAAAGTCATAA
384901 GTAGTGTTTGTATCAATTAAGCCATATTTGGTTTGTAGTGCACGGAATAA
384951 TAAGAATTGTTTTGTTTATTTACATCACGTCCTGATTCAGAGAGATAAT
385001 AACCACCACCATCAACACCCATTAGATGGATACCATCTTTACCACGTGCT
385051 AAGATTAAATCAGGTTGACTATTGTtATCTTTTTTAAGTTCTTTTAGATC
385101 AACGATTGCAGAATTATTACTACTATCACTGTTACTTGTACTAGTAGCAT
385151 TACTGAACTTTTTTTGATATTCACCTTTAAAAACATCTGTTGATTTAGTA
385201 GTTTCATTTTCTTTAAAGATCTTAGCTAGATCTGTTTTATGAACAGTAGT
385251 TGTTTGTGAACTACTACTTGCACTTTTCATTGCAGCCTTAGCTGAATTAT
385301 TTTCAACAAAGAAATTTTCAATGATTGATTTATCTTTTTCTAATTTAGTG
385351 TATTCAGTTTGTTCTGCACCTTTGGATTTTTTTTGTAAAGCTAAATAGCC
385401 CTGGATAAAAGCTGCTGAAAAGCTAGGATCAAAGGTATCAAACATATCAC
385451 TAGCTTTTAACAACAATTTACCACCACTATCACTAGAAAACTTATTAGGG
385501 ATGTCAATGGTTTTATTGTTAGTATTTACATAGCTTTGTAAATTACTAGC
385551 TAGGATATGAAAACCATTTGCTCCTTTTATGGAGTTATCTTGTTGGTTAT
385601 ATTTGTTAAATACTTGAAATTGATAGGAAGGGGTTGGAGATTTAATTAGA
385651 TCAGGATTAAAATAGTTATCAAACCCATCATTAGGAGTTTCATTAGTAAA
385701 TACTACTCTTGAAACTAAGTTAGGGTTTTCATTAGTAACGAACTGATCTA
385751 ATAATTTATCTTGAATGGCAGCATAAACTGCATCATTATTGATCCTAAGT
385801 CTTTTATTTTTATCAACAAACTTAGCTTGTATTTTGATATTATTCCAATT
385851 ACTTTGGTTTTCAATTAAACCTTTTAATGGAGTTGATAATACGCCAACAC
385901 TTTTATCAACATATTCAACAAAGTTCTTTGTAAAAAGCTTATTGATAAAA
385951 TCATCAACAATTTTGTTGTTAACATCACGGAGCTTTCAGTTGGCTTGATT
386001 TCCACCAGTGTTATCTAAAATATCAGTTTGTAACCTAACTAAATAATCAC
386051 CCCGATACTGATTTCTTAAGTTTTGTTCTTGATTAACAAAACTATTGTCT
386101 GTATCAGTATTAAAAGtTCTTAAATTTCTCTTAATGTCATCATCAACATT
386151 TTCTTCATAAAAATTGCGCAATACTGGCGCTAGGCGCATCGTTAAATATT
386201 GCGTTAGTCCTTCTCTATTTTCAAGTGCTTTATAAAGTGTGGCATTAATA
386251 CTACCATCATTTTTATCAGTAAAAGCACTACTGGGTCTAAAGAGATTTTC
386301 AATGGTTCTGGAGTTTGGTTGTGCACAGGCAACAGCAACAATTCCCAAAC
386351 TTACAGCTATGCTTGAAAGCAGCAATGGTCATTTTACTCGGTGTAAAAAA
386401 CGTTTCATTGCACAGTCAAAAATTTCAATAATTTTAAAATTTATATTTTT
386451 ATTATTACCACATGCGACTTGAAATAGAAAACGGGCTTGAATTTGTCAAT
386501 GATCCTGTGGTAAATGAACTTGGCAAGATCTGTTTTTTTCATCCTTTTAC
386551 AGGTAATTTAACAAACAAACTTAGTTTCAGAAGTCATTTCAATAGATACA
386601 GTTTTTATGCCATTAACTACCCAGGGCATGGTAATAGTGTTATTAACAAT
386651 CCAAAGCAACTTGAATTTAGTTACTGATTGGAAATTACAAAACAGTTTTT
386701 TGATAAACATAACTTAAAGGATGTAATCTTATTTGGTCATTCTATTGGCG
386751 GTGGTTTAGCAGTTGCTTTAACTAACTATTTAAGCAGTGATCAATATAAA
386801 GCAGTCTTGTTAGAAGCACCATTAAATCCTGCTATTGTTGAAACTCCTTT
386851 AAATATTGTTCAAAATCTCATTCCTGATCCTGATAGTGATTTTGCTGTTA
386901 TTCAAAAGTGTCTTGTTTTACAATATTGAGAAAAAACTTGGGGCAAACTTT
386951 AAAGAATATTGTGAAAGAGAAAAGCAAAAATCAATTCACCAAAACCAACG
```

-continued

| The Nucleotide Sequence of the *Mycoplasma genitalium* Genome |
|---|
| 387001 CCTTAAAGTGATGTTAGAACCTTCTACACTCAAACAAAACATAGTTTTAA |
| 387051 TCAATGCAGCTTTTTTAAAGTTAAATTGTCCTGCTTTGTGAATCCATGGT |
| 387101 AAGCAGGATGGAATTATTAAGTACCTTCCATCCAAGGCTTATTATGAATC |
| 387151 ATTAAACAATAAGCAAATTCAATTTAAAGCCATAGAAGCAGCGGCTCATA |
| 387201 CCCCTTACTTTGAACAACCACAAAaGtTTTTAAGTTTAGTTAATGATTTC |
| 387251 TTTCAATTAATAAGTTAAAGCAGTTTATTTAACTAAACGCTTGTATCACT |
| 387301 CAACAACGTAAGATTCATTTATTCCAGCAGGTAGTTCGCTACGCTCTGGG |
| 387351 AATCTTATATAAGTACCTTCAAATGCCTTTTTGTTGGTTTCCACAAATGA |
| 387401 TGAGATAACACTGTTTTCAATAAAATTTTTAACTAATGGGGATTTAGTTA |
| 387451 TTCTTGCTTTTAAACGGACTTTATCCCCGGGATTAATGATGATTGAAGGG |
| 387501 GTGTCAACAGTTTGATCATTTAAAATCACATGACCGTGGTTTACCATTTG |
| 387551 TCTTGCACTCTTTCTTGTTGGTGCAAAACCCATTCTGTAAACTATGTTAT |
| 387601 CCAAACGTGATTCTAAAACTCTAAATAAATTAACTGTTAAGTTACCTTTT |
| 387651 TGTTTTAAAACAAAGCGAAATAACCTACGAAATTGTTTATCAGTAATACC |
| 387701 ATACATGTATTGCATCCTTTGTTTTTCTTGGAGTTGTTGGGCATAACCTG |
| 387751 ATAAAGTTGAGGAACGAAACCTATTTCCATGTTGACCGGGAATAGATTTA |
| 387801 CGTTTTTTTCCTTTGGAAAACTCTTTGTTGTTTTCAAGTAAAGAAAAACC |
| 387851 TAAACGTCTTGATCGTTTGAAAATACTACCAGTATATTTCATGTGTTTTC |
| 387901 GATTTTAAATTATCTTAATAATCAAGGCTAAAATCACCACTGCTTTCAAA |
| 387951 TAAGTCTTCATCTAATAATGAACTGAAATTGGAAGTACGATCAGGAACTA |
| 388001 GTGTTTCTATATCCAAATCATTAACACTAAAAGCACTCATTGAATCCATT |
| 388051 ACTTTGGCATCAATGTCAACAAAATCATTGTTAAAACCTTCAAATTCAAA |
| 388101 ATCGATGTTACGATCCATGTTTTCATAGATAAAATCATCTAACTGTTCAT |
| 388151 TGGAGATGTTATCAAAAGTGTTGGAAAAATCTATTAAATCATCCATTAAC |
| 388201 TGATTAGGTTCTACTAACCCATTATCTGTTACACTATCAAAATTGCTTAA |
| 388251 AAGTAAAGGATCTTTTTCTTTCTTTGCAAAGCGGAGCGTATTATCAAGCT |
| 388301 TATTAATGTTGTTCATAATAGTTTCACAACAAGAGTTATAAACAGTTTTA |
| 388351 AGTTGTTTTAAACTACCTTGAATGCTTTCTATCTTCTTTTCATTTTCAGT |
| 388401 GATAGCACGTTGAACATGACGCATAATTTCTCCAGATTTTTGCAGTTGTT |
| 388451 CATAACTATTACTTGGTTTGTAAGCAATAGCAAAATCACTAGCTAATGAT |
| 388501 CTGATCATTTCTTCTTTTTGAAGTGTTGTTAGATTCTTAGCGTTATTAAA |
| 388551 TTGAACGTTAAGGTTCTCATTTTGATCAATTAAACGGGAAAGTTCACTTT |
| 388601 GTAATTCCTTTTTAATTATTAAGTAACGtTCACTAATTTGGTTCTTATAG |
| 388651 TTGGTAACAAAATCATTGAGATGGATAAATGATTGTTTAACAGACATCTG |
| 388701 ATAATCATTCATTTGAAAGATTGCATCAAAGTTAATTGTAGGGTTTAATT |
| 388751 CACCACGTTTCAATTCACTAATAATCTTGTAAAGATCTGATTTTTTATTG |
| 388801 ARATTATCAAGTTCACTTTTATCTTCAACCGATTGCTTATTTTGAGTAAT |
| 388851 TGAGTGTTCTTCAACAGGTTCTTTTGCTTTGACAAAAACTTCAATTTTAG |
| 388901 GTTGTTGGTCTTCGCTATTAACAGTATTGATAGTTAGTTGATCATCTTTT |
| 388951 TTATCGAGTCTTACTGATTCACTAGTAACAATTGATTGATTATTTAAGCT |
| 389001 ATTAATTTGTTGCAATTGGACAGATAATGTTTTTGCAAGTGTTTTGGAAT |
| 389051 CTTCAGTTATGGAATTAATGGTAATTTGTTCTTGCTGACTTTCTTTATTA |
| 389101 TCTAAAGCTAAAGTTTCAACTGGTTTATATTCAATACGGTTGGATACAAA |
| 389151 ACTAATAGGTAAAGTTGTAGGGATTTGGGGTGAACTTTTTTTGGTAGTGA |
| 389201 TAGTTATCTTATTATCAGACTGAATATCAAATTTCTGTAAATTATTAGTG |
| 389251 TAGTTACTAGTTTCAACTACATCTTGTTTATTGAAACTACTTTCTAAAAC |
| 389301 TGGCTCCTTAGTTATTTCAGGTTTGAATTGATCGTTAACTTCGCTATTTA |
| 389351 CTTGATCAAACTGCTCAACTGTTGGTTGAGTTTCAAATGAAGAAGAAAAA |
| 389401 GTTGTTTGGTCTTGTTGATCTGTATCAATTGGTAATTGGTAACTATCAAC |
| 389451 TACTTGGGCTTGTTTACTTTCAAAATCAGTAGTTACTTCTTTTTCAGCAG |
| 389501 TTGGTTGTATTTCCTCATTATTATCAAGATTAGCTTGAACTTGATCAAAT |
| 389551 CCAACTTGATAATTATTTTGTTCTTCAGCAACTGGTTTGAGCTCTTCATG |
| 389601 GTGATCAAAGTTGTACTGAACATGATCATCTAAAGAAGGTTGGTCAAGGG |
| 389651 TTGGTTGAGGTAAATCACTGTCAAAGCTGTAGCTATCAGTTGTTGATTCA |
| 389701 GGTTGTTTTGCAAAATGATCATCTGAAGAAGGCTGGTCAACAACTGATTC |
| 389751 AGGTTGTTTTACTTCTGGTGGTAGGTCGTTATCAAAACCATAGTTTTCAT |
| 389801 CAGTTGGTTGTTTTGCAAAATAATCATCTGAAGAAGGCTGGTCAAGAGTT |
| 389851 GGTTTTAGCTCTTCATTTTGATAAATGTCGTATTGAACTTGATCAACTGG |
| 389901 TTCAGATTGACTTTCAAAGTGTGCATCAGGTGCAgtTTCACTATTAAACT |
| 389951 TAACAGGTTCAGACTCTAACGAATTATTGCTGTTTGATTGAGATAAATCA |
| 390001 CTCCCAAATTTATAGTCATGAATTGGTTCAGATTTACTTTCATAATGCAC |
| 390051 ATCATCAGATGCAGTTTCACTATTACTATTAAGTTGAATGAATTCAGAAT |
| 390101 TTAATGAATCATTGTTAGTTGCATCTTTGTTGTTTTCAGAGTAAAGATTA |
| 390151 GATTCAGAATTTAAGTCACTAGTTTCAACTACATCTTGTTTATTGAAACT |
| 390201 ACTTTCTAAAACTGGCTCCTTAGTTATTTCAGGTTTGAATTGATCGTTAA |
| 390251 CTTCGCTATTTACTTGATCAAACTGCTCAACTGTTGGTTGAGTTTCAAAT |
| 390301 GAAGAAGAAAAAGTTGTTTGGTCTTGTTGATCTGTATCAATTGGTAATTG |
| 390351 GTAACTATCAACTACTTGGGCTTGTTTACTTTCAAAATCAGTAGTTACTT |
| 390401 TTTTTCAGCAGTTGGTTGTATTTCCTCATTATTATCAAGATTAGCTTGA |
| 390451 ACTTGATCAAATCCAACTTGATAATTATTTTGTTCTTCAGCAACTGGTTT |
| 390501 GAGCTCTTCATGGTGATCAAAGTTGTACTGAACATGATCATCTAAAGAAG |
| 390551 GTTGGTCAAGGGTTGGTTGAGGTAAATCACTGTCAAAGCTGTAGCTATCA |
| 390601 GTTGTTGATTCAGGTTGTTTTGCAAAATGATCATCTGAAGAAGGTTGGTC |
| 390651 AACAACTGATTCAGGTTGTTTTACTTCTGGTGGTAGGTCGTTATCAAAAC |
| 390701 CATAGTTTTCATCAGTTGGTTGTTTTGCAAAATAATCATCTGAAGAAGGC |
| 390751 TGGTCAACAACTGATTCAGGTTGTTTTACTTCTGGTGGTAGGTCGTTATC |
| 390801 AAAACCATAGTTATCTTCAACTGATTCAGGTTGTTTTACTTCTGGTGGTA |

-continued

| The Nucleotide Sequence of the *Mycoplasma genitalium* Genome |
|---|
| 390851 AATCGTTATCAAAACCATAGTTATCTTCAACTGATTCAGGTTGTTTTACT |
| 390901 TCTGGTGGTAAATCACTGTCAAAACCATAGTTTTCATCAGTTGGTTGAGA |
| 390951 TTCTTTAGTGGAGATCCACTGGTCATTTTCAAAGTAACCAGATCAAACCC |
| 391001 ACTCACCATTTTCATCATAAGAACCATAGTCAGGGTTACCAACATACTTT |
| 391051 AAATAATCATTCTCTTCTTGCTTTTCATCAAAAACAAACGGATTCCCATT |
| 391101 TTCATCAAAGAGTTGGGAGATATCATATTCAGTATCTCCATAAGGATCAT |
| 391151 AGTAAACCCCTGTTTCTTTGTTAAAAGCTATATAATAGCCATTACCATCA |
| 391201 GCATCATATGCTACCTTAATATTAGGGTCTTCTTCAACAGTGGATTTACC |
| 391251 ATCATAAAGATCACCAAAAATGTTTTCAGGTTCGGTTTGGGTATAGTTTT |
| 391301 TTTCTTCAAAAACCGATTGCTTGTTTTTAGCCATCAAGAAAAGTTATTTA |
| 391351 TGCCAGTTTAGTCAAGCTTGATTATAAAACTTATCGCTTCGCTCTAACTC |
| 391401 TTCCATGAAAGCGTAAATAGTAATAAATAATTTTTTAAATTATTTTCCAC |
| 391451 AATCCCTATTAAAGGGTAAAACAAAGCTACATAGATAGGTAATAATAACG |
| 391501 CTTGCACCAATACTCTTGGTAAAAGAAAGAAATAAACCCCATACAAAACA |
| 391551 AAGTTATTACTTGGTCTGCCATTATTAATAAAAGTAATAAACTCAATGGC |
| 391601 AGCAATTGTCCCCAAAAGGATAGAAACAACTACTGACATTAAAACCATTA |
| 391651 GAACCAAGCTATAAATAGTTAAAAGTGCTTGTTCTTTATTTCTCTTTTTT |
| 391701 ACATAAACAAACCCTAAAAATCCTTCTGTTACTAAAAAGAAAATAACAAA |
| 391751 GCTAACTAAAGTTATGATTTGTAAAACAACAACATTAACACTAAGATCAG |
| 391801 CAGTTTGAAAATTTTTTGTTCCAATTTGCTGAAACTCATTATTAGTTAGA |
| 391851 TAAAGTAAAAGCAGTGTtACACTAACAACAAAAAAAGTTACTAATAGTGT |
| 391901 TTGTAACACCCAAAAATCAACCTTGTAATTACTGGCATTTTTTCTAACTA |
| 391951 GATAAATCCCTTTAACTATGCCAGCAAGaAAAGCAAAGAGTGGCTTTTGC |
| 392001 AATGCAAACATCCAAAACCACACATAACCCTTTGTTAACCAATCAATAGT |
| 392051 ATCAGATAAAAATCCAAAATAAAACCCCAAATAGGACCAAAGATCCATC |
| 392101 CGAACAATGCAAAGGGAATCCTTAGAAAACTAATGCTTAATACATTAGTA |
| 392151 ACACTAATTGAAAAGATAGAAAAGATAAAGGTTAGTGCTAATAAAACACT |
| 392201 AGCTCAAACTAACAGTTGTAAACTCTTTAAAAGTCTCAACGGATAGTAAG |
| 392251 GAAACAAAAAGTTTCAAAACAGTTTTTTAGATTGAAGCTTGAATGTGAAT |
| 392301 TTTAACCAAAAATAGTAGGTGGGGGGATATCTAAAGTAGTTTTACTTTCA |
| 392351 TCACTAGTAATTGGTTTTGCCAATTCCTCTTGAAAGTACTTATTAAATAT |
| 392401 CTCATTAGTTTGTTCTAAGTTTAATTTAGGACTTAATGAAAAAGCAATTA |
| 392451 CACTAATGATGCTAAAAGGAACAATGCTAAAAACAAACAATCAGGCGATT |
| 392501 CCTATCAGATAACTTGCAAATAATGGTGAAACACTAATTAGTTGGTTTTC |
| 392551 ACTAAATAAGCGGATGATTAAAGCTGCATTTCAAAAGCCACTTCTTACTA |
| 392601 TATTACCAGGGATACAATTTAAAAAGACAAAGATAAAGATAGTCCAAAAG |
| 392651 ATCCATTTTATTCTTACCTTATAACGGTAGTTATCATTAATTTTGGGAAA |
| 392701 CTCTTTGACCCCAAATTCACTACGTAAATACCGACATTGCTCTATTGGTTT |
| 392751 GACCTCTAGTTGCAAAGCTATAGGGTTTACCCTGAAAAGCAAAGAAAAAA |
| 392801 GAAGCACCACCAAAAGCCAGGAAGATCATGGTAATCAAGTTAGATGAACT |
| 392851 TAAAGCAAAAAAGCGGTTTAGATTTGTTGTATCTGCATTACTTTGCTGAA |
| 392901 CAGTATTTTGGTCATTATTAACATTGAAAAGTGGACTGCTGTTCTTATCAACA |
| 392951 AAGTGGGTAAAAAAGACATTGACCATCACAACGTATGCTATCGAAATGAA |
| 393001 AAAGATGGCAATCATAGAGATGAAAATCGCTAGTTGTGCTCATTTAATCC |
| 393051 ACTGACTCTTAAACTGAAACTCAAAGATCTTACCAACTAGTTTTTCAGAG |
| 393101 GTAAACCTACCAAAGGCACGATCTCTGGCACGAACTTGGAGGGTTTGTTG |
| 393151 CAAAATATTATTCTCAAGTCCTGAGTTTAGCTGTTGAGAATTGTTTATAG |
| 393201 TTTGAAAACTTGGGTTATCTTTAACTGTTTTATTGTTTTCTTGTAACTCA |
| 393251 CTAACGGGTTTAACTTGAGTTTCAGCAAGTTTGGTAAAGCTATTCAACTC |
| 393301 TTTATTAAACAAGTTTTTAACAGCAACATTAAGATAATTAGCTAAATCTA |
| 393351 ACGCATCAGTTAGATCAAACTTAGCAGCTTTAAGTTCTTTTTCACTTAAT |
| 393401 TGGTTTTGCCCTAATTGGATAAACTTATCATGAAAACTACCAAAAAGAAA |
| 393451 GTGGTCTGGTTTTTTTGTTTAACTCTTTTTTGTTTTTCCTCTAAAAAAT |
| 393501 AAAGTAATTTGAGTTGTGCCAAAATTGTTTTGGCAAAATCACTATCAGTT |
| 393551 TTTATCCTTGTTCTTAAAGTTTCGTTATTAAAAACAATGTCAAGATTATT |
| 393601 TTGTACCTTAGTTAGAATTTCACTAAACGTCATTTTGATAAGTAATTTTA |
| 393651 GAGAGGTTAGTTAGTAAAAAAGCTTAAAGCAAAGTTTTTTAACAACGGAA |
| 393701 TGGCAAAGCCATCATTGTGCTTTAATTTAATATCCAATTTTTGAATTGCA |
| 393751 TTAATTATATTTACTAAAACTTTGCTAGTAAAGTTATGGTACTGACTTTG |
| 393801 AATAGCAATTAAGCGAAACTGATTAACATTTAGATTAATGTTAGTTAGTT |
| 393851 GCTTTGGATTACAACTTTTAACCATCAATGCTAATAACAACTCCCCACTA |
| 393901 AAAAATTCTAAAAATTGGGTGGCAAAATTTGGTTTTGTACTTGCCAATTC |
| 393951 ATCAATATATTTAAATGCCTTTACAATTTGTGAATTTGTTAGAGCTTTGG |
| 394001 TTAATTTGTAAATTTGAACAGGTTGATAATCACAAATAACTGTTTCAACT |
| 394051 AATTTGTTATCTTTGATTTCATTTTTACCTAACAAGCTAAGTTGTTAAT |
| 394101 TTCTTGGTAAATTACCCCCATATTTAAAGGTAAAGCATTCGCTAATCAAT |
| 394151 CAATTATTTCCAAATCAAGTTTTAAGTTAAGTTCTCTACAAACTTCACCA |
| 394201 ATTGCTTTATGCATTGATTTTCAATCCAATTTATCACAAAAAACAGTTGT |
| 394251 GATTGATTTAATGGTTTTAATCCCACTAAAAGGATTGTCAGTATAAACAG |
| 394301 TTAAAACTACATCAGTTGTTTTTAGTTTTTCTAAACACAAGTTTTCTTGT |
| 394351 CTAGTTAAGCTTGTTTTTTCCAAAAAACTGCAATTATTGACAATAAACTT |
| 394401 TTCATTATTAGAACCAAATAATGGTTGTGAAAAGAGATCATAAAGTTGCT |
| 394451 TAAGATCTTTAAACCAAATAGTTTTATATGGAGAATTGCTTTTGATTTGA |
| 394501 CTTAATTTTTGGTGAATTAGCCCAATATCTTGACCATAAATTATTGTCAT |
| 394551 AATAAGCTACTGTAAAAATAGTATATAAAAGTCCCAATAAGCCATAATAA |
| 394601 ACAAAAAAGAAAATCAGATTAGGTTTAGGTATTTGTAGAAAAACTGTTAC |
| 394651 TTTTAATGATCATTCACTTAGCATTTTAAGTGGGAGATAAATACCAAAAC |

| The Nucleotide Sequence of the *Mycoplasma genitalium* Genome |
|---|
| 394701 TAGCTTGACCAAAAACACCAATAAAGGGTAAAATAATTCAACTAACACAA |
| 394751 AAATAAAATAAGGCAATTGGGCTAAACAAAAGGTTAAACAAGACACTAAA |
| 394801 AGCATTTAGTCTTGAATTTAAATACAAGCTTAAGGGGCTGATAACAATCA |
| 394851 AGATTAAACTAGAACTGACAAGCGGTTTTAAAGCTTTTAATAACTTTAGT |
| 394901 TTGTTGACAAATAACAATACAAAACAAGCTAGAAAAGAAAAATTAAAACC |
| 394951 AAAGTTATTTAAAGCATGGTTACTAATAAGAATGATTAAAAGTGCAGTTA |
| 395001 AACTTAAGTTATCTTCTGGTAACTGTTTTTTAAAAACCTGTTTTAACAGT |
| 395051 GTTGAGATAAAAACTCTTAGTGCTGaAAAGGCAAATCCTACTAAAAACAG |
| 395101 GTAAATCAATAAAACAGCAAAACCACTAAGTTTGTTTAAGTACCATCTTT |
| 395151 TTCATAAAAACCGTTCCATTAAATTAAACAAGAAACTTAAGTGAAAACCA |
| 395201 CTGATAACAAACAAATGGACAATGTTTAGTTTTAAAGCATTTTGGTACAA |
| 395251 ATTGTTTTTAGTGGTTTCATTAATTAAAAATAGTTTTAAATACTGATTTA |
| 395301 ACTCACCTTTAGTGGTCTGATCAATTCAATTAATGAAAGGGGTACGAATA |
| 395351 AAGTTATTTTTAACAATTTGATTTATCTTGACTGCTGGAACAAAATAACA |
| 395401 AAAAGCAATAAAAAAACCAACAATTGTTAAGTTCAATAAACAAAACTTTC |
| 395451 AGTCATACCAAAGACTAAAAAGCGTTATCAAAATGATCCAAATTGACAGT |
| 395501 GCAACAAACTGTTCTTGTTGTACTAAAAAGAAGCCTGGGATAAAACTGAG |
| 395551 TAAAACAAAAAAATAAAACAGCTTTGTTTGCATGCTGTTTTATTAATAGA |
| 395601 TTTATTTTGAACTTTTTAACAAATTAAAAGtCCTTAGATCAATATGATCT |
| 395651 TGATGGATAACGTCTAAGTCCATCATAGCTAGAACTAAATGGTAAACTAG |
| 395701 TTCTTCTAAAACTTGATAGTCTTGTTGGTGAATGGAATGATGAACGGTAT |
| 395751 GAACTGATATTAGTTAATCTTCATGGTCTTCTTGTTAAGGGATAATAACT |
| 395801 ACTTGGTGTTCTGCTAAAACGATAGTTAGAAATAGCATTATTTTGGAAAT |
| 395851 TAGTTGATCTTAATGGTGTGTAATTGTTGACTCTAGATTTTGGTGTGTAG |
| 395901 TCAAAATCAAGAGAAAAACGATCACTAGTTAAACTTTGATTGGTATCGCT |
| 395951 GTAAAGTGGATCACTGTATTTAGTTGCAACATACTCATTTTCAGGATAAA |
| 396001 AACGGCTGAAATTGCTACTTTTTATAGTGTTATCACTCTTTAGAGCAATA |
| 396051 TCACTCATTATCCTTTGGTGGTTTAAAGCATTAATTTTCTCTAGAAGAGA |
| 396101 AGCGTGGGAAGAGACACTAACAGTGATATCTGAATCAGTTGTGCGTTCAA |
| 396151 CTTGTCTAGGTTGAAAACCAGTGTCTAATTTTGATTGAAGTAAAGCTGCT |
| 396201 GATCTTGGTACAACTTTAATTTGTAAACCTGAAGTTGGCAATGGTTGTTG |
| 396251 GGGTTGATATTCAGTTTTTACTTCTGGTTTTCAGTGGTGAACTTCAACTT |
| 396301 GAGGAGTTGATTCTACTTGAGGGATGTATTTTGTTTCAGGTTTTGGTTCA |
| 396351 ATTCTTGGTTCAACCATTTGAGCTTTCGGTTGAACTTCAACTTGAGGAAT |
| 396401 ATGTTTTATTACTTCTGGTTTTGATTCAATTCTTGGTTCAATCCTTTGAG |
| 396451 GTTTTAAATCAACAACAGGTTTTGGTTGAACTTCAACATGTGGTACATGT |
| 396501 TTTACTTCAGGTTGTTTAACTTCTGGTACTGAATCAACAACAGGTTTCAC |
| 396551 TTCTGGTTTTGGTTGAATTTCAACATGTGATACATGTTTCACTTCTGGTT |
| 396601 TTGGTTCAATTTTGGGTTCAACTATTTGAGGTTTCGGTTGAACTTCAACT |
| 396651 TGAGGAATATGTTTTACTTCAGGTTGAACTAACTTTGCTGGTTTATTAAC |
| 396701 TAGTGGTGGTTTTAAAGAAGGGGAATTATTAAAACTATGGTTTTGAGATC |
| 396751 CACTATCAACTTGAACGGGTTGTTGGTGGACTAAATCCTGATGGAGCTGT |
| 396801 TGAGTAGGTGGCACTTCTTTTTCAACAAACTGGTCATCACCCAAGTTTTC |
| 396851 TGTAGGTTGTTGGGGTTGATTTAAACTGTCATTAATTCAAAGACATCAG |
| 396901 GTTCACTTTCAGTTTCTAGAGTAGTGTGTTGAGCTGCTTTTGGTTGGTCA |
| 396951 TCAACTTCTATCTTAGGAAGACCTGCATCAATACTAGGATAATCTTGTTG |
| 397001 GGTTGGTTGTTCTTGAGAAGTTTGAGTACTGCTTAAATAGTTAATTAAAG |
| 397051 GGACCTTTTTCTCATCAGTATAGCTAGAAACATCCAAAACATTACCATTT |
| 397101 TGGTCATAGAAAGTGTTGTTATCCTGATCATATTGAACAGTTACCAAGTT |
| 397151 GTTCTTATCATCATAAGCATTTAAGCTAACAATGTTATTTGTAAAGCTAA |
| 397201 TAGGGTTATCTGAAGTTAATTCAAACAAAGGATAGTTACTAGCTAACTGC |
| 397251 TTTCTTTTTTCTAAAGAGAAGATATTACCTGATTCAGGATCTTGGTATAG |
| 397301 AGCATGAACCTTATTTTTATGATCACGGGCATAAACAACACTAACATCAG |
| 397351 GATATCTTTTGTTAATCTTTTTAAAAGCTTGTTATAGGCTTTGTTTATT |
| 397401 TTAGCTTTCTGTTTATCGTTCATAAAAAATTACTAAATTAGGGTTTTAAA |
| 397451 CCGCCTTTTGGCATCAATTGTGATGGGTTAGGACGTTGTTGCATATTTGG |
| 397501 ATTAAACCCAGGGCGTTGTTGCATGTTTGGATTAAAGTTATTTGGTTGTG |
| 397551 CAAATTGGTTAGGATGGGGTTGGTTAAATCCAGGGCGTTGCATGTTTGGG |
| 397601 TTCATCCTTGGGTTGAAATTATTGTGTGGTTGGAACTGTTGGTTTGGTTG |
| 397651 GTTAAAACCAGGGCGTTGTTGCATGTTTGGATTAAACCCAGGGCGCTGCA |
| 397701 TGTTTGGGTCATCCTTGGGTTGAAATTATTGTGTGGTTGGAACTGTTGG |
| 397751 TTTGGTTGGTTAAAACCAGGGCGTTGTTGCATGTTTGGATTAAATGCAGG |
| 397801 TCTTAAAAGCGGAACACGCTGTTGAAACTGTGGTTGAAGGGGTTGTTGAA |
| 397851 CTTGGGGTTGGGAAGGCTGAGCTTGGGATTGTTGAGGATCAATTTCAACT |
| 397901 GTTTGTTGTTCTTGTTGATCTGAGATTCTTTGTAATTGCTCAGCAATCTG |
| 397951 TTCTTGGCGTTCCTTCTCTTCAAGTAAACGTTTTTCTTTGCGCTTTACAA |
| 398001 TAGGTAAACCTATCGCAAGTCCAAGGATAATAGCTAAAGCACTAAAACCA |
| 398051 AATGAACCTGCTACTGTAGGGATAAATCAGGGCTGTTCAACAATTGATCT |
| 398101 GCCCTGAATTACAGTTGTATTATCTTCTGTTTGATGAAAAACAACCCCTA |
| 398151 GTTCACTACCATTAGTTTTCACAACAAGTGCAAATGCTAGTAACGATAAA |
| 398201 CTAACAATTAGGATTGTTGTAAAAAGTAAAGCAAGAACTATAAAAAGTTT |
| 398251 TTTGTATCTCAAAAATCCATTTAACTCCATCCATCTTTATCAAAACTTAATTAG |
| 398301 TTCCTTTTTCTTCTTGATCTTGAATCATCATAATACTCTTCTTGTTCTTG |
| 398351 CTTTTTCATGTTCCTTTTTCTTCTTTTAATTGAACGAGTGATTTTATTGA |
| 398401 GAAAGAAGTTAACAATTAAAGTACCTATTAAACCACTAACAAATGCCATT |
| 398451 CCTAGGGGAATTACATACTTAGTTAGATAAGGTGTAAACTGTTCAACAAA |
| 398501 TCCAGGCAACTTAGCATTTTTCAAAAAATCTACATATCCTGGGATAGCAT |

-continued

The Nucleotide Sequence of the *Mycoplasma genitalium* Genome

```
398551  AAAATGCACTTTTTTCAGTTGGAAAACGGTTATCCAAACCATTACTTGAA
398601  CCTTCTAAAAGTTGTAATAAGCTACTTGTTTGAGCAGTTGCAGTTGCACC
398651  ATTGTTTGAAGAGATGTTATCCAACGCTTCTTTTGAAAAGAACCTGTTGA
398701  AAACATCCATTGGTTGTGCTAACTCAAATGGGTTTAGAGAACCAAAGTAA
398751  AAGATAGCTAAGAAAAGATAAGCAAAGCCTACCAATACCAATAAAAGAAA
398801  GCAAAGCTTAAAGAGAAATCGAAACAAGCGCATTTGTATTAGTCAAAAAT
398851  AAAACTACTCTGTGAATTTTAACTTTATTTAGTTAAGCAAATGGTTTATG
398901  TAATTAATTAAATTAACTATAGAGCTTTAGAAAGCTCTAAACTCTAGAAA
398951  AATTTTTAGTAATTAGGATGATTCTTAGGATGAAATAGACCAAATTCATG
399001  AAGCTGCTAATTAATCAAGCCCCAAAGAATAAAGCAGATCTTCAGCTCTG
399051  TCTTCTTGCCATTTCATAATCTTCACTTTCATAGTATTTAATCAAATCTT
399101  GTTCATTACGGATCTGTAAACTCACAAAATAAACTGAAATTAATGAAAAG
399151  ATTCCCCCTACTATTAAAGATAAGCCAGGGATAATTCTATCAAGTAGGTT
399201  TGTTGTAGAAGCAAACACTGTAAAGTTCAAAATAAAGCTCAATAAGCTCG
399251  CTACAATACTAATTACAAAAGCCCATAATAAGATGTGaAACAAAGTTTGG
399301  GTTTGTTGATATCGCCTTTTTTGACTTGGTAGCGCACTTAATCCTCACAC
399351  TGAACCAAACACCAAACTAGCACCTAAAAAAGCATAAACAATGTCATTAG
399401  CTTCAAAGTTAACTTGTTTTGAAAATGTCGTTGCTAAAGTTAATAAGATC
399451  CCAAGGGTTATCCCATAACTAATCACATCAGTAATGATTAAGGCCCAAAA
399501  CCATGTCAAACTAGTGTTGGGATTCCTTAATTTAAAAGCAGTAACAAAAT
399551  AAAGAATTAAAGAGACAAAACTAGTAATAACTGCAATAGTACTAAGTGTT
399601  CTAAAATCACTAGCTAAATCAATTAGTGTGCTTCTTGAAAGCAATTGTTG
399651  TACTGTTAATGCAACAAGAAAGATAAAAAAGATCCCAAAAGCAGCTACCA
399701  TAAAAGTTAAACGGATTACAGAAAGCTGTTTTGTTTGTACAAACTGCTTT
399751  GCTGCTAAACCGTTTTGATCAATATAGCCTTTTGTTGAATTAATCATGAC
399801  AATTTGACTTGTTAAATTTTAATTTGTCAATATAAAAAAACTAATAATTG
399851  CAAAATATATAGATAAGGATACTTACCCAAGTGGCTGAAGGGGTAGGCTT
399901  GGAAAGCTTATAGATGGGTAAAACCATGCGAGGGTTCGAATCCCTCAGTA
399951  TCCGCCAGGGAGATTTACCCAAGTGGCTGAAGGGGGCGCTCTCGAAAAGC
400001  GTTAGGTGGTTATCCACGCGTGGGTTCAAATCCCACAATCTCCGCCAAAT
400051  TCTTAACTGTATAAACAAAAAACACACCATTTTGGTGTGTTTTTTTATGT
400101  CCATAAGTTAGTTGAATTTACTCATCAATGTAACCTGAATCACGCATTGT
400151  AGCAATCCCTGAAGGGGCATTACGGAGTGAAAATCATGGTTTTAAAAGCG
400201  AAGGAATAGTTTCATTTAACCCAGGAGCGGAGACTGGTAGAACAGGAAAG
400251  TAACTATCTACTACAGTAATTAAGAACTTAGCATTATCAGTGTCCTGTTC
400301  AGCTCAAATGCTGTTAAATCGGTTAAGTTGAGCAGCGTTGTCATAAAGAT
400351  CTTTCAATTCATAACCAATGTGGATATCTGATACATTTGCTGGTTTGTTG
400401  TCATCTATCTTGCTTCTTTTTGATAGATATTTATCAGGATCTTTAATTGC
400451  TTCTTTAACTTTTATCAGCTTTCAATACCTTATTATCAACTAAAAATTTCA
400501  GTAAGCTTAATGCtTTTTTAGTGAATGCTAATGAAGCGGATGTACCGTTA
400551  TTACCATTAGTACCAAAGTTCTTAATGACATAGGGATCATCTTTAAAAAG
400601  ATCAGCACTTGTTATGCAACTACACCAGTCTTTTCCGTTAGTTGTTGTGT
400651  TATTTTGAAGTTTATTTTCAATTTGATTAAAGACATTGTTTTGGGATGCA
400701  GCTAACAATAAAGTTCTGACAATATGACTACCTGAATTGTAAGTAATTAC
400751  TTCACCAATACCCTCACTGTTAAGCTGTGTAGCAGCATCAAGTCAGGTAC
400801  CAACCCCATCATAATCAGGACTCCAATAAGAAAAACCAAGTACACTTGAT
400851  AAACCTATGTATCATTCGTTTCTTGTTGGACCTTGTGCATCTCCTAAGAT
400901  AATCTCAGGGATAATTAAATTTTCACCATTATCATTACCAAGTTCAGTTA
400951  AAGCTTGTTTTAAAGCGTTATAGTAATCAACTTGGTTAGAGGAGAGTGAT
401001  GCATTTCCTAGTTTAATGTTGAAGTGTAATGGATTGTTACCAGTAAACCC
401051  AACTTTTTTTAATGCACTGATAAAACTTTGCTTGGTAACACTTACTTGTT
401101  TTGAAGAAACTTGACTAGTTTGACTACTGCTGCCACTAGTAGAAGCTGTT
401151  CTTACTTGAGCACCATTAGTTTTTGTAGAGCTATAGTAACTTAACTTAAC
401201  AGTTGCAGTATCAAGAACATTCTTATCCTTTTGAAAAGTTCAGTTTGTT
401251  CAGGGATTAAACCAAGTCTTTGGTTGTTGTTAATCTTGTAATAATAATCA
401301  TTCTCAATTCCATCTGTATTTGTACCACTACTAGTTCCATTTGCTGGTTT
401351  TTCTTTAAAGATCCCAAAAGGAACAGTAGAATAGTTAACATCTCCTGAGT
401401  TGGGCAGATCAATGATTGCTAAGTTCTTTCAGTTGATCAAACCATTAATT
401451  CCAGCACGGATAGTCAACGCTTCTTCAGATTCACTGTTATATAAGAACTT
401501  AGCTTCTGTCTCAGTGATGTTTGCATTTAGTTGAACAGTACTGTCATTAG
401551  CAACATAAGGTTTACCTGAATAAGTTACTTGAGCACTTTGCGCAGTTTTT
401601  TGGATTTTTAATCACCTCAGATCCCCTGTACCATTAAACCTTGATCTTGC
401651  ATCTTGTTGTTGGAATAGGGAACAGCTGAAGCTGATAAGCCCCCAGCGA
401701  TATAACTAGAATAGAACACTTCAGGAGTAGCTCCTGGTTGGAAATAACTA
401751  ACTATAGCAGGGATAGGTTTTTCGTTTTCTTGTCTTGTTTTAGGAAGATT
401801  AGGGGTGATAATTGCATCATAAATCTGGTTGCGTTTAAAGACAATTTGTG
401851  CTTGGTTAAAACTCTCAACATAGTAAGGGCCAACTGATCAAGTGTCTTTT
401901  CAAGCATTAACACCCCCTCCATAGATACCATCAAAGTTAGTATTTGCTTG
401951  ATCTAAAATCTTTCTGTTGTTATTTTGGTTATATTTAAGCGGTGAATCTT
402001  TACCTAGTTTAAGGGCTTTTACCTTAGGATGGGTGTGAGGAATTGGAAAG
402051  AAGAATTCCTTTGACATCATTGATAGAAAGAAAGGAAAAGGAGAAGTTAG
402101  ATAAACATTAAACTTGTTATCATCTAQACTTCTATAGTTTTCAACATCAT
402151  AATTTTCATCAGTGATCTCAATACCTTTACCATTGCCATCACTAGAACCG
402201  TTGGTTTTATCCATACCAACGGTTTTTTCAACATCAAGACCCATTAGGTC
402251  AATGAAATAACCATTCCGGTTAAAACCTAAGTTAGAAGAGAGAATATAGG
402301  TCTCAAAACCCCTTTCAAAGTCTTTAGAGGAGAGTTTAACTGGTTGGTTG
402351  TTTTGTTTGACTTCTCTACCAGCATTATCAACCCAGCTCAAACTAGTGTT
```

-continued

**The Nucleotide Sequence of the *Mycoplasma genitalium* Genome**

```
402401 AATGGTAAATTCATATCTGGTTGCTTCTTGGGTTATCTTGTGATAGTTAG
402451 GATCTTCAGTAATAGACTTTGAACTATCACGATAAATTGTGCCTATTGCA
402501 TCCCACTCATTGAACTTAGTGTAATCATTCTTACTAGATCCATCAGAAGA
402551 ATCTGTTGAACCGTTTTTTGTGCTCTACCTTTAAGGCCACTGTGTGTTG
402601 TCTTTTTATAGCCAGTAACTGATAAAGCAAGTTCTAACACTAATTTTTCT
402651 TTAATTTGGTCAGTAACATTAACCCCATCATCACGGTTTGTACCAGTAGC
402701 AACATAGTTAGTTAACCCTGCATAAGCATTACCAAAAAAAGATGAAGTGG
402751 GTGAAACGTTAAACATGCTCAATGGAACAGAGTTGTTCTTTAACAAATCT
402801 GCTGAAGAAGAGGTGAAAAACACCCCTTTGTTTAACTGTGAGGATGCACA
402851 AGCACTTAGGATTAGTGCTGCACTAACTGTCAGTGTAGAACCGAGCAACA
402901 AGTATCTTTTTTTAATTTCATTGTGTTCTTTCATAAATAAATCGGTTAA
402951 TTGATTGCTGATTAGTAAAAAAGAGTTAAAAAACAGCAATTTACCCTTAG
403001 TTAAAAACTAAAAGTAGTTTTATTCTAGTTTGCAATCACATTAGATTGCA
403051 AAATCAAAAACTAATGTTTTTATCAATTGCTCACTTTTTAAACAAGAAAA
403101 TGCTTAATACAAAGTTAGCAAAACTAAAAACATGGTGCACCCGAAGGGAC
403151 TTGAACCCCCACTTCTAGATGAAACTAGATCCTAAGTCTAGCGCGTCTAC
403201 CATTCCGCCACGAGTGCATTATTGGTGCATCTTGAGGGGATCGAACCCAC
403251 GACCCAATGATTAAGAGTCATTTGCTCTACCAACTGAGCTAAAGATGCAG
403301 ATAGTGGTGCCGACTATAGGATTTGAACCTACGACCTATTGATTACAAGT
403351 CAATTGCTCTACCAACTGAGCTAAGTCGGCATGGTGGATTGTGAGGGGAT
403401 CGAACCCCCGACCCTATGCTTGTAAGGCATATGCTCTCCCAGCTGAGCTA
403451 ACAATCCATCACTTATGGTGCCGAATACAGGAATTGAACCTGTAGCCTAT
403501 GCATTACGAGTGCATCGCTCTGCCCTTGAGCTAATTCGGCATTGGTGACG
403551 CGTACGGGATTCAAACCCGTGAATGCACGCGTGAAAGGCGTGTGTGTTAA
403601 GTCTCTTCACCAACGCGCCAAATAATGGCGGCCACAACAGGGATCGAACC
403651 TGTGACCAACCGGTTAACAGCCGGTTGCTCTACCGCTGAGCTATGTGGCC
403701 TGAGAATAAATTCTAGAATTTCTAGCCAATTTTAACAGCTTCCTTAGGAT
403751 ATGAATAACTATTTGCTTTGGGATGTTTTCTAACAAAAGTTAGCACAGAA
403801 CTGGACACACCAACCTGTCCCATAACCATTAATAGACATAAAGCAAGGAA
403851 ATTAAAGGTATTTCTATTTGGATCTAAAGCAATGTTAACAGTAGCTCCAC
403901 TTGAAAGTCCAACTGTTCCAAAAGCACTAGTTGTTTCAAATAAAGCATCA
403951 ATGAAACTAACTGGTTGTTCCATACTTAAAGGTAGAAGAACAGCTGTTAG
404001 TAAAACTGCAATTAAGCTTATGATTAGTACTAAAAAAGCATCTATTACTG
404051 TAGTTTGATCGATTGAACGCTTAAATGCTTTTACTTCCTTTTGACCTTTA
404101 AACTTAGCAACTAGAGCTAAAAAGATTACTGCTAGCGTAGTTGTTCTAAT
404151 CCCCCCAGCAGTAGAAGAGGGACTAGCACCAATAAACATTGCCAATGCAA
404201 TAATTATTTTTGTAGTTTGAATCTCACTAGCAACAGGGAAAACACTAAAA
404251 CCTGCTGAACGGGATGAAATAACCATAAAAAAGAGCTGCATTACCCTACT
404301 TGCATTAGGGTTATTACCAAAAACTGACGCATGGATTGCTTGGTTAGATT
404351 GTGATTGCAATTGGGTATTTATTAAACTCTTTTTTTCATCACTAAAATTA
404401 ACAATAGTGTTAGTTAAACTATCACTAGCAATAAATTCCACCATTAAAAG
404451 TAAGGTGAAAAAAAGCAGGATTACAACGATATTAGTAATTACTGTCAACT
404501 TGGTAAATAGACTAAATTGGTGTTTTGTGTGTCTACCATACTTAATCTTT
404551 TTTTTAATGGCTTCAAAGCCATCAAACAAACAAGGATAACCAATTCCCCC
404601 AAAGATAATTTGGCTAATAGTTAACCACTGAATAATAATACCAAGTCCAT
404651 TTCTATAAGGAACAAAAGAACTACCCCCTATCAGATCTATCCCAGCATTA
404701 TTAACTGCTGATAAGGAATGGAAAAAACCTGCTTGAAAAGCCTTATTAAT
404751 ATCATTAAAAGCTGCTATTGTTTGGTTTGAATCAACTACTAAAGCTTTTA
404801 ATTGAGTTGAAACTTTTGCATGATCTGCAAACAAGTTAGCAGGTTCAAAG
404851 CCTGGGATGAAATAAAACaAAATACCATATAAAAATCCATAAATTAGTTC
404901 AACGATAAAAAGAAAGATGATAGATACTAAGATCATCTCACTAGTATTAC
404951 CTAGCTTAGAACCACCTCGTTCTGATTGCAACATTAACTTTTCATAAAAA
405001 CTGTATTGTTCCTTCTTGTGAAAGTTAAACAATCGTCATGCTAAAAAAGC
405051 AATAACAACAAATCCAATCCCTCCTAACTGGAGTAATACTGCTAAAACTA
405101 TCTGGCCAAAGATACTGTATGTTTTTGATACAACAACAGTAGAAAGTCCT
405151 GTATCACTAAAAGCACTGGTTGATAAAAATAATGCATCTAAAAAGTTGTA
405201 ATCAGTTTTCTGTTCAAATCTTTTTCCCTGTCAATCAATTCCATAACTAA
405251 CCACTTTTTGGTAGTTATCTTGGAGTGCAATTGGCAAAAATAACAGCAAA
405301 CTTCCAAACAAGATGCAATAGATATAAAAACAAAAAATTCGTTGGGTAAT
405351 AGTCTCACCTCAGCCAATTTTTTTTAACCAAGTGGTGAGTTTTACCATCT
405401 GGTTTTGTCTTCTTGTCATTAAAAGAACGCTATCAAATATAATTTTACCA
405451 AGGTATGAAACGTGCAGATTTTTGCATTATTGGTTTAGGTAGATTTGGGA
405501 TGCAGGTTGCACAATCACTAAAAGAAAACAACTTTAACTTACTTTTAATT
405551 GATCTTGATGATAAAAAAACTGACACCGCCTCGCAACAGTTTGATTATGT
405601 TATTTGTTGTGATGCTAGTAATCTAACTGCTTTAGAAGAGTTACAAATTG
405651 ATGAATTTGCTGGGGTTATTGTTGGGGTTACCAACATAGAAGCGAGCATC
405701 ATGATATGTGCTAATTTAAGGGAATTAGGACAAAAAAACATTATTGCTAA
405751 AGCCAAAAATGAAGTACATAAAAGGGTGTTAAGCACAATGGGAATTACAG
405801 AAGCTTTGATCCCTGAAAAGATTGTTGGTAAAAATCTGGTTATCCGCTTA
405851 ATCCATGGGCTTGAAAATGAAATTATCAACCTTGGTAATGAGATAATTTT
405901 CATCCGTTCAGCAGTTAACAACAAGGCTTTTTTAACAAAAGGTTAGAAG
405951 AGATTAACTTTAGGCAAAACACCGATGCTAACATTATCTCCATCATGCGC
406001 AGTAATAAAACTGTTGTTTTTCCTTTAGGACCAAATACTGAGATCCAACC
406051 AGGGGATATTATCACTGCAGTTTGTCAACAAAAAAGTTTAAATAAGTACT
406101 TAAATTACATCAATCCTAAAACCAAAAATAAAAATTAAAAAAAGGATCAT
406151 CATGATCCTTTTTTTAGATAGCATGCTGTCAATAAGCCATGTTCTGTTTT
406201 AAAGTCAGTTATTTATCTACAGCAATTGCTGTCATTACTTTAATTATTTG
```

-continued

The Nucleotide Sequence of the *Mycoplasma genitalium* Genome

```
406251  TTCTTAAAGCAACATTCCCTTACCAAAATTTAGGTTTCTTGCTTGTGGAG
406301  TTTACCGCGTTTCATACCTGGTTTTCACCAAGCTCGTCTCTGTGGCACTT
406351  TCAAAACATCATCATAGTATTAACCTTAGACTAGTTATGTCGTTATGGCT
406401  ATCACATCCTAAATCTTATCGCTTTGATTTACACAAACACTACTTGCATT
406451  CCAGCAAGTGCAAGCATGGACTTTCCTCTACTTTAAATATATCTTTAAAG
406501  CAGCAACTAACCGACAGCGTCAAAATTATAATTTGGTGTTGGGGATGTTT
406551  TGGGTTTGACATAATGCTGATAGACAAACAGTAGCATTGGGGTATGCCCC
406601  TTACAGCGCTAGGTTCAATAACCGACAAAGAAAATAACGAAGTGTTGGTA
406651  GAACCAAATTTGATCATTAACCAACAAGCAAGTGTTAACTTTGCTTTTGC
406701  ATAAGTAGATACTAAAGCTACAGCTGGTGAATAGTCATAGTTTGCTAGCT
406751  GTCATAGTTTATGACTCGAGGTTAAATCGTTCAATTTAACCTTTAAAAAT
406801  AGAACTTGTTGTTTCCATGATTGTTTTGTGATCAATTGGAAACAAGACAA
406851  AAATCCACAAAACTAAAATGTAGAAGCTGTTTGTTGTGTCCTTTATGGAA
406901  ACGGGTTCGATTCCCGTCATCTCCACCATTTATCAACTTTAAGTTGGCCT
406951  TACACTCCCCTAGTTGGGAGTTTTTATTTTGCCTTACTCTTTTTAAAGAG
407001  TTGTTTTAATTTGGTTTTGTTGTAATTAAAAGCAAAGATAGCTATAAAAA
407051  AGAAAGAATAAAAAACTAAGCTAATCGCTCAAGCGGTAGCAAATACACCA
407101  AAACTATTTAATTTAGAGAGATAAACACCATTGTTATTTTCAACATTAAA
407151  AAACAAGCTAAACCGCGTTGCTGATTGAATTTTTTGTGTATCTCTTTCAA
407201  AAAACTGTTGGTCTAATAACACCAAAAATAAAACCATTAGCAAGATCCAT
407251  AAGAGATAAACAACAATACTGATAAAAAATCCAGTAGTATAGCCAATGCG
407301  CTCTCACTTAGTAGTCTGACTTTTAAAAAATAATGAAACAGTTCATCTAA
407351  AACTTAGaAAAACTAATAATGCTAAACTAATTAACCCAAAAACTAAGTTA
407401  GCAATTCCATATTGACTAATCTGATAAGTAATACTAGCTTGAATAATATC
407451  AGTTGGTTTTTCAACAGTTCAAAAAAGGTAAAACTGATTAAAGCCGTTAA
407501  CTTCGTTAAAAGTGAATTGTTTAGTGTGAAAAACGCCAGCTAAAACAAA
407551  ACGTTGTTTAGAAARAAGCAGAGAAAAAATAAAAAGTAAACAAAAGTATC
407601  AAGTAAGCCAAACCTGCTGTAAAACAGATAGTTACTGTGTTTGGAAACAA
407651  CTTGATACTCAGCGACATTTATTTCACTGAGTTTATCAGATATCTTATTA
407701  ATCCAACCACCACCACTATTTTTCTTTTTAGAAAGCACGTGGGATAGATT
407751  TAGATAATCAAACTGATTTTTCTTTTTTAACAAGTACCATATCTTCTATC
407801  CTAATTCCACCAAGGTTAGGAATATAGATCCCAGGTTCAATGGTTACAAC
407851  CCCATTTTCACACAATAACTTGTTGTAAGATTGGGAAACATTTGGCATTT
407901  CATGGATATCaATACCAACGCCATGACCAGTACTATGCACAAAAAAGTCT
407951  TTAAACTCAGAGTTTTCAATAATATCGCGGCACACCTTATCAACTTGTGA
408001  ACCTGTTAAAGTAGTGTTTACTGCATTTATACCAGCCAAATTAGCCTCTT
408051  CAACTTTTTTGTATGCAGATAATAACTTTGCACTTTTAGGTTTTTTACCA
408101  ACTAAAAAGGTTCTTGTAATATCAGAGCAATAACCGTTGTAAATGGTGCC
408151  AAAATCACAAGTGATAAAATCACCTTCCTTAACTATTGTTTTGGTTGGTT
408201  TGTGATGTGGGTTAGCACCGTTTTTACCAGTAGCTACTATAGGATCAAAT
408251  GAGTTTTTAGCCCCACCCTGCTTCACAAGCTCATTAGTAATCCATTGTGA
408301  AATGAAAAGCTCAGTCATTTTTGGTTTAATAAAACGCTTTAACTTAACTG
408351  CTACTTTTCTTGTAATATCAACTGCTTTTTCAATGGCTTGAATCTCACTA
408401  GGCAACTTTACTCTTCTAATCTCTTGGGCATTAATTACTGTGTATTGTTT
408451  ACAAATAGCTTGAATTCAATCCTGATAGTTAAAGGTAAGATAGTCACCCT
408501  CAATTAAAAGGTGATTGATACCATTAGATTCACAAAAAGCTTTAACTTGT
408551  TTAAAACTAACAAATAATTCAACTTCAACAATAGGATTAATAAAAGTTCCT
408601  TGCTGCTTCATAATACCTACCATCAATAAACAATTTTGCTTTATTGCTGG
408651  TGATGATTAACCACCCTGCACTACTTGGAAAATTAGTTAATCAAAAGCGG
408701  TTTTGATCAGAACCAATTAGGATAGCATCAGCTTTATTGGTTTTTAAAAG
408751  ATCTTTAAGAACTGTAATTTTTTGTTGTAATTCACTAATCATTATTTACG
408801  TTTTACCTCTTTGTGCAATACTACCTTACGACAACGTGAACAAAACTTAT
408851  TAAGTGCTAGTTTTTCTGGATTTTTCTTGACGTTTTTAAAGGTTAAATAA
408901  TTAATCTCAGAACATTCATTACAACCTAGTCGTGTGCTTCTTTTAACAGC
408951  CATAATTAAATTATCTTAATTATTTATTGTCAATAAGTAAACTAATAGAA
409001  AAAGCATCAATGCCAGTGTGAACAATAATCACACTTGTAATGAAAGCATT
409051  TTCAATTTCATTTTGAAAGTTAATCTTATTATGCTCAATGAAATCAGTAA
409101  TTATTTTTTTAATTTCATTAGCGTAATTTTTACAAAAAGAATAGCAAAAA
409151  CCGATCCGTTTAATTTTGTAGTTATCACCAAACTTAGTTTTAACAAAACC
409201  AAATATCTTCTCAACCGCTTGACTAAAACTAAAAACTTTTGCTCCTAGAG
409251  TATTAACTCCCTTGTCAAACAAGATAATAGGTTTAACTCTTAGTAAAGTA
409301  GTAATGAACTTTTTCAAACCAGAGATTCTCCCACCTTTACGCATTTGCAC
409351  TAGGTTTTTTAAAGTAACTGCAGAAAGGATATTTTGTTTATGTGATTCAA
409401  CCTTTGCTTTAATTGTTTGATTATCACAACCCTTGTCAACCAATGCCTTT
409451  ATATCTTCGACCAATCATTTTAGAGAAATAGCAATATCACTAGTTTCAAA
409501  CACTAAAAATTCTTTGTCTTTATTTTGTTCACTAAGCTCTTTTGCTAATT
409551  GAACCAACATATCATAAGTACCACTTAAACCTTTACTTAAAGGCAGAAAA
409601  ATAAAGCGATCATACTTAGTTTTAATCTCTTCAAAGATCTTAAGAAGATC
409651  ACTTTGACGTGGTAAGGAAGTTGAGATGTTAAGTCCATGTGGGTTTTCTT
409701  TTAGAAGTTTATGAACATGATCATAATCAATTTCTATCCCATCACGAAAG
409751  CTTTTTTCACCATCAACAATTACTTGTAAAGGCAAGATGTAAACGCCGTT
409801  AATCTCCCCAGGTTTAATAGAAGCAGTTGAATCAGTGATGATAGCTGTTT
409851  TCTTCATGAATTAATCTCCTTAGTACCTTTGTTTCTTTAAATTATCTAGA
409901  AACTCTAGCACATAATCAAAAAAAAGTTTAGGCGCTGAGTCGTGTGGTGA
409951  ATGACCAACACCATCAATAACCTTAAAAATAATCTTGTCACTTTTATTAG
410001  CTAGATAGTCTACAGAAGCTTTGGTTGGCGTGACAATATCATTAGCTCCT
410051  AAAATAACTAAGGTAGGTTTATTACCAATCATTTCATAAGCCCTTTCAAG
```

-continued

The Nucleotide Sequence of the *Mycoplasma genitalium* Genome

```
410101 TGAGTCATTACCATATTTAGCGTTTTGAACCATATCACTGTAAAGTGTTT
410151 TAAAGGTAGTTCTTTTTTTAAATGCATTGATAGCTATTTTCAAAAGTGAT
410201 TTACGTTTTTCTTCATGTTCAACAAAATCCTTATGGTTGCTGTTATTACG
410251 CTTAAAAAAAGTATCTAAAATCCGCTTTTTATTAACTGAGAAAGAAGTTT
410301 GATTCATAGGAGCTACTAATATTAAAGCCTTAATTTTTAGTGGTATAACT
410351 TTGTTAACTAAAACAGCCACAGCACCTCCCATACTATGACCTATTAAAAT
410401 GACGTTATTTAGTTTTTTTTGAACAATAAAATCACAAACCAAATCAACAA
410451 AGTGGTTTAGTTTTAATTGATCTGTATCTGTTGATTCATTGTCTCCATGA
410501 CCGGGAAAATTAAAAGTAAAGAAAGGCCACTTTTTCTTTTTAAACAAGCT
410551 AAAAATACGACTAAAACTGGCATATTCGCTTCCAAATCCATGTAAAAAAA
410601 TAAAAACGTTTTTtCTTTTTTTAGGTTTAAAGGCAAATATTGAGTTAAAA
410651 AGAGTATTTTTATTACTCGTTAGCATTGATTTTAGCTAAACGTTCTGCAT
410701 ATGCTTGGATGCGTTCTTTCTTAGAAAGTTTAGCGAGTTTATCATCCTTA
410751 TTTTGGATAACAAAATCACGTTTTTTAATTCGTGGTTTTTTTATTTCAAC
410801 TGGTTTATCTTCATCACTAGCTTCTTTGATCTCTTCAGTTTGATTAGCAC
410851 TAATGTCATTGAAATATTGCAACTGATTTTGCAGTGCTTGGTTTTCTAAA
410901 AAAAGTTGTTCTTTTTCAATTTTTAATGTTTCTAGTTCATCAAGATGTTC
410951 ATCACTGGTAACTGGAGTAAATTGAAGTCTTTTTTAGCATTTTCAAGTG
411001 AATTTATTTGTTGTTTTAACTGATTATTTTCACTATCAGATGCACTTAAA
411051 CTTTGCTTGGCTTTCTCCAATTCACTGTTTGTTTCTTCAAAAGCAGAGAG
411101 TAAATCTTGGTATTGTTCATTAGCATCATTCAATTTATTCTTTTTAAGCT
411151 TTTCAAAATCAGTTTTTAATTTGCCATAGCTTTCTTGTAAGATTTCATGA
411201 TCAGCTTGGAGCTTTGCTAATAAGTTATTGCTATTCTCAGAGCCTGATAA
411251 TTCATCTTCTAAATCATTAATTTTTTCATTAAGTGCTAAATTAACTTCTT
411301 CAAGCGTGGCTAATTTATCTTGAGCAACATTAAAAAGATTTTGAGAGTCT
411351 TTGAGTTGCTGTTGGAGATTTACTAACTGATTGGTATTTAAATTACTCTT
411401 CTCTTCATTCCATTCTTCTAACTCTGCAATTTTGTCTTGCAGTTGTTGAT
411451 TTTGAATTGTTAAACCATTAAGTTTTTCATCGAGTGCTTTTTTCTGTTCT
411501 TCAAATGAATTTTTAGTGTTATTGAAGTCATTATCTTTAGACCTTGTTCA
411551 CTCAATTTCATCTAATAAAACATCATTTTCATGTTTAAGTGCTGAAATTG
411601 TTTTTTGATAATCTAAGTTTAGCGCTTGTTGTTTCACTTGCAATTTATCA
411651 AATTTTGTTTCATTCTCATCAAAAGTAGTTCATACTGATTAAAAGATC
411701 ATCATATTTTTCATTCTCATCATTAGATGTGTTGTCATGGAGTTTTTTCA
411751 GTTCATTTTTCAAAAAATCATTTTCTTGTTCAACTAGATCCAATCTTTGG
411801 TTTGCTTCTCTTGCTGTTAGTAACTGGTTTTGAAGTTCGTTTATTTGGTT
411851 GTTTAAAACTGGTAATAAAGCTAATTGTTGTTGAACATTACTGCTCTTAT
411901 TTTTCAATGCATCTAATTGATCTGAAAGCAAAGCTTTTTCTTGTTTTAAA
411951 TTCTCCAACTCTTCATTAACTTCATCACTTAAAGGATTAATAGCAACTGG
412001 TTTATTTTGCAGTTGCTCATATAAATCCCTATTTTCTTGCAAAAGATCAT
412051 CCTGTAATTTCTTGGTATGTAAGTGCTTACTTTTTTCCTCAGATAACCTC
412101 CTTTTAAGATCATCGATTTCCTGTTCTAAATCAAATATTTGATCATTATT
412151 ATTCTCTTTAAGATCATCGATTTGTTTTTTTAAATCAGCATTTTCCAATA
412201 AAAGCTCTTTGTTATTATAGTCATCCAATTCATCAACTTTTTTTGTTGGA
412251 TGTTGCTCTTTTAAGATCCTTTTAACAACAAAAGGTTGATCATCATTCTG
412301 ATCATATTGGATCGTTTTATGAACTGGATTGATAGCTTTGGTTAAATTTT
412351 CAATGGAATAGAAATCATCAAATTGTTCAGGTTCTTTAACCTTATCAGTT
412401 GAAAATATTTGAACTTCTGGTTTTTTTGTTTCATTAATCTCTTCACTAGG
412451 TTGGTTAAACAACTCTTCAAAAGATACTTGTTTAGTAGCTTCTGGTTTTA
412501 TCTCATCCTTATCATCTTCAGCAGTAATCACTGATGGTTTTAGTTCCTGA
412551 AAACCAGTTTTAATTTCCTTGGTTAAAACTGATTGATCATCAACTTCTTG
412601 AAAAGCCATAGTTTGATCAACTGTCTGTTGCTCTTCCTCTCTAGTTTTAA
412651 GTTGATTTGCATAATGATTTAAAACATTCTTATCCCATTTTTTATCTAAA
412701 ACCTTTAAATCTATCATCCAATTAAAAAAAGAAACTATTGACTTTTCTTT
412751 CTCAGCTTCATCAACAGTACCAAAAAATGTTTTCTCCAATAAATTTCTTT
412801 CAAAGGGAATAGCAGTAATTTTAGATGGTGAAAAAAGGATATTATTAGTT
412851 CTTTGTACTAATTCTTTTAAAAGTGTTTTTTCATCAAGCTCATTATCAAA
412901 ATCACTAATTTCAAGTTCCTTATCTACTGCCATGGATTATGTTGGAATAT
412951 TAGATAAATAAGTATATTATCTTAAACTTCTGGCTTTGTTCTTATCCGTG
413001 CGTTTTTTGATTTAAAGTAAAGGCTAATAGGTACAGAATTAAAACCAAAG
413051 TTTTCTCTAATCTTATTCTCTAAAAAACGTGCATAAGAAAAATGAAGATA
413101 CTTAGGGTCATTGCAAAATAAAACAAAATGGGGAATTTGACTTTTGGTTT
413151 GTACTGCGTAAGTtATCTGCAAACGCTTGCCTTTAAAAAGTGGAGGTTGA
413201 TTGTAAAGTTGTGCTTGCTGAATAACATCATTTAAAAGTGGTGTTGCAAC
413251 CTTAGTTTCAAGTTGGCTTTGAATAATTTTAAGTTGTTCAAAAATAGTAT
413301 TTAAGCGCTGATTTTTCAAAACACTAATAAACAAAACAGGCGCAAAATCG
413351 AGGTGTTTAAAATGCAATTTCAGCATTTTTTTATATGCATTTGTGGTGTT
413401 ATTGTTTTTAAAACTAGATCCCATTTATTCACAAGAATAATAACAGGGA
413451 TAAGTGCAGCTTGTGCCAATCCACCAATCACTTCATCTTGTTCACTAATA
413501 GGTTTTGATCCATCTACCATCAAAAGGATAACGTTACTACGGGCAATAGC
413551 TAGCTTTGTTTTGATGTAAGATGCGGTTTCAATTCCCATGTTAATTTTGC
413601 CTTTTCTTTTAATACCAGCAGTATCAATCAAAAGAAATTTTTCACCATTA
413651 ACTTTTAAAGGAACATCAATAGCATCTCTAGTTGTACCACTCTCATTTGA
413701 AACTAAAACACGATTTTGTTTTACAAGTTGATTAATAAGTGAGCTTTTAC
413751 CAACATTTGGTTTGCCAATTACACAAAACCTTATTTTTGCTAAATCATCA
413801 TTATTTTCATTAGGGAGTAATTGATTTTGTTTAACTAAGAGATCCATTAA
413851 ATCACCAATTCCAATTCCATGAGCAGCACTAATAACAACTGGTCTTCCAA
413901 ACCCTAAGCTGTAATAATCTTTTAATGTTTCTTCAGCAGTTTTAGGGTTA
```

-continued

The Nucleotide Sequence of the *Mycoplasma genitalium* Genome

```
413951 AAATTTTCAGCTTTATTTACCACTAGTATTACTGGTTTATCCTTATTTTT
414001 TTTAAGAACCTTAGCTACATAAAAATCATCGCTATTTAGTTGTTCTTGTA
414051 GTGACACTAAAAAAATAATAGCTTTGGCTTGACTAAGTGCTGCTTGTACT
414101 TGTAATGCAATTAGTTGTTGCAAGGGAGTTTGTTTTGCAATTAATCCACC
414151 TGTGTCAATAAAAGCTATCTTTCTTTTTAACCATTCACCAATTCCAAAGA
414201 TCCTATCTCTTGTCGTGTTAGGAGTATCTGAAACAATAGCCATTGGCTTT
414251 TGAATTAAGCGATTAAATAAAGTTGATTTACCAACGTTTGTACGACCTAT
414301 TATTGCAACAGTAAACACAAATTAAAGTTTAAAAACCTTCTTTGCTTCTT
414351 TGAGGGTTTGTTTTACTACTGCATCAAAACTTAGTTCAGAAGTGTCAAGA
414401 TAAATAGCGTCCTGGGCTTTTTTTAATGGGTCTGCAGTTCTAGAACTATC
414451 AATTTGATCACGTTGCTTTAATTCTTGAATTAGTTCCTTTAGTTTTTTTT
414501 CATTTGATAGAGAAATTCCCATATCTTGTAATCTTCGCTGCGCTCTAATT
414551 TCAACTTTAGCATCTAAAAAAAACTTCAATTGAGCATTTTTTAAAACTAC
414601 TGTTCCTATGTCTCTACCATCCATCACTATGTTTTTATTTTCTGCTAGTT
414651 TCTGTTGTTTAATAACTGCAATTTTTCTAATGTTAGGATCAACAGCTATT
414701 TTACTAGCAATGTTAGCAACTGATTGGGTTGTAATAACTGTTGTAATATC
414751 AGCATTGTTATAATACACAGCATCTTTCTCAAAGCGTCAGTTAATTTGAT
414801 TAATGATTTTTAAALAAAGATCAATATTTAATCTATTCACTTGCATTACA
414851 TAGGCAAAGGCACGATACATTTTTCCACTAGAAAAATATAAAAAATCAAG
414901 TTCTTCAGCTATTTTTTTAGCAACACTGGACTTTCCAGAACTACTTGGAC
414951 CATCAATTGCTATTTGTCAATTCATAACTAAATTTAAACAAATGAAACAA
415001 AACTAACAATCAAARAAATAAGAAAAAACAAAATGCTAAACAGCATGAAA
415051 CTTATTAAAGTTATCACTAAGTTCTTAAAAATAGCCTTATTAGCATTAAA
415101 CAAATTAGGTTCGATGTTATCAATGCTTTTTTTAAAAGCAAAACTtTCAG
415151 TTGAAAAAACTGTTAGTATCTTGTTGTAtTCTTTTAAATCACTAGTTAAA
415201 TTGCTTGTTTTTtTTAATCATTGTTTCTCATTAGCTTCATAAAATTTACT
415251 TAAGTGGTTAATCTTTTCTATTCCCTTATCATCACTAATTCAGCTTTCAT
415301 AACCGCTAGAAGTTTGGTTATATGCTGCGTTTAACCACATCCTATCAACT
415351 TTTTCTTCTAATAATTTAAAGTCAGTATTTTTTAAATCAACTATTAATTC
415401 CTGAAGTGTTTTAAACAGTTTATTTGGTTCAGTGTGATGTTTAACTGGAT
415451 TTTTATTAAATTCACTAAAAGGATGGTAATTAATCAAGATTTTCTGATTA
415501 ATTTTATTAAGCTGTTTTTTTCAGCTTTCAGTGTTCTTCTGAGCGTTAAT
415551 TARAGCTTTTTTAACTATCTTATTGTTATCAAAACTTTGTCTATAAAAGC
415601 GAAATTTTTCTACTCTTCCCATGGGTTGGCATTATGAACAACAAACTGAA
415651 TGTCATCATCTTCCTCACAAGCATTGAGAAAACGTGATAATAAAGTTTGC
415701 TGATTTCTATCTAAATCAACAGTTAAAAGAGGTACCAATTTAATTTCACT
415751 ATCTACTATTGAAAAATTGTTTTTTTTCAACAGCTCCTTTGCATGAAAAT
415801 AACTATTTGAATGCAAGCTAATTTCAAAACACTCTTCATCATAATCAACA
415851 TCAATTAAGTTAATATTGTCCAAAATTAATAATTCAATTAGATCATCTTT
415901 CAAATAGTTATTTTTATTAACAAAGATAATCCCTTCTTCTTGAAAATTAA
415951 TCTTGACGCTATTTGGCTTGGCTAATTGTCCTTTTAGTTTAGCTAAATAA
416001 CCGTTTAAACTACTGAGTAAACGGTTAGGATTATCAGTTAGTCCAAACAC
416051 AATAATTCCAACACCATTTGGTCCAAAAATCTCATAACAAAACTCGCTAA
416101 TTTTAGTTGTATCTTTTTCACTACCATGGATATTTCTTTTAATTGAATCC
416151 ATGCTTAGACCCTTAGCTAAAGCAAGATCAACTGCAACTTTTAGATGTGG
416201 ATTTGACTGGATATTAGTTCCACCTTTTTTAACAGCTGAAGCTATTCTTT
416251 TTGCTAGTTTTTGAAGTTGTTTTGCACTTGTTTGTTGTTTTTTATTAGTT
416301 TGATTAGCAATTAGATGCTTACGTGGCATGTAAGATTAAAAATTATTAGC
416351 AACTTGGTCAACTTTGTGTGCAAACAGATCAACTACCTCTTGCTTGTTTT
416401 TATCTTTGTAAAGAATTTTAGTGTCATCAATTAAAACACTCTCAAAATGT
416451 GTAACACCTGCAAAACCAAACAAGCCCTTTAAATTACTAACATGATCAGC
416501 TCAAGGGTATCATCCTAATGGTGCACCTTGTGACGCTAAAACAACTACCT
416551 TAAGATTAGTAAGTAATCCCTTAGAAGCACCTTTAGTAACATATTTGTCT
416601 TGAAAGGTTTTATTAGCTACAAAGACATGATCAATAAAGTTTTTTAAACT
416651 AGCAGGATAATTAAAGTTGGTCATTGGTGCAAGGATAACAATTCCATAAG
416701 CTGTTTTTAGGAGCATCAATATAATAATCACTATTTTCAAAACTAAAAAA
416751 ATTACTAGCGTTTTGGGTATTATAAGATATCTTACCTACTGGTAATTCAt
416801 TTAAATTTCAATCAATAAATTCAACACTACTATTTTGTTTTTTATAAGTT
416851 TGAAGGAAACGATCTAATAAAAGGTGGGTGTAAGAACCAGAAGGGGTTAC
416901 AGAAGCATCAACAATAATAACTTTCTTCATAGCTAATAATTAAAAGTCTA
416951 ATTTTTATTGTTAATTCTAATGAGCTTTAGTTAATTTAGCAATTAATTGG
417001 TTGGTTTCAGTAAGTTTTTTTTGATATTCTTCCAATTTTAAAAATTCACT
417051 TTTTACCTTTTCTTTGGGTGCTTTTTCTAGAAAGCTTTTATTTTTAACAA
417101 TAGCTTGGCTACGTTTTACTTCACTTTCAAAAAAAGCTTGTTGCTTCTGT
417151 AGAGATTTAAGTCTTTGGGTTGTATCATCAACAATTTGGTATTTAAACT
417201 AACTTTTTTATTAGTTTCAATTTTCAGTTCAATTCAACTAAAGTTAAAGT
417251 ATTGTTTAACATCAACAGCATTTTTACCAGATAAGATAACAACTAGTTTT
417301 TGTTGTGAATTAAGCATGTACTGTTTTCTGTAATTGCGTAAGTCATTAAT
417351 AGCAGCTAAAACAAGATCAAAAAGTTTGGGAATTTTAATTTTAGTTGCAA
417401 GAGGTCATGTTGCTTGCATAACACTTTTATTGTTAAATTGCTGATAAATA
417451 CGCTCAGATAAAAAAGGAACAGTGATACTAAGCAAAATAGCAATATTAGA
417501 TAAAACTGATTTAGCAGTATAAAAAAGCTGTGGTTTTAGTTGATTTGGTT
417551 CTTTTTTAATTGCTTCAATGAAAGTATTGCAAAAATCATCCCAAACAAAT
417601 TTAACAAGAATTTGGTTTGCTAATGCTAACTGGAATTTATCTAGTAGCTT
417651 AGTTATTTTTGAATTACTTTATCTAATTTAGCTAAGATTCAAGTTTCAC
417701 TTAATGAAAGTTTGTCCAAGTCATAACTAATTTCTTGATCATTTTCTAGT
417751 TGGATAACAAACTTAGTAACATTCCACAATTTATTTAAAAAATTTCATGC
```

-continued

The Nucleotide Sequence of the *Mycoplasma genitalium* Genome

```
417801 ACTTTTTATTTTTTGTTCGCTGAAAATTAGATCATCTCCTGGAGTGTGAT
417851 TTGAACACAAAAATAAGCGCACTGCATCCGCTCCATAATTTCTAATAAGA
417901 TCAACAGGATCAATGCCATTATTCAGTGATTTTGACATCTTACGATTTTG
417951 TTCATCGCGTACTAAACCGTGGATTAAAACAGTTTTAAATGGCAGTtTTt
418001 TAGTTTCAAAAAAGGAGTTAAATAACATTCTTAAAACTCAGAAAAATAGA
418051 ATATCATAACCTGTAACTAAAAGCTCAGTTTCATGAAAAGAGTCATCCTG
418101 TTCTCAATTCAAACAAATTAAAGGTCAAAGCGAAGAAGAAAATCAAGTAT
418151 CAAGTACATCTTTTGATCTAGTGTAGTTTTGTAAATTTTTTGAAGGTTTT
418201 TCACCAACAACTATTTCACCTGTATTGTTTTCAAATCAAACAGGAATTTT
418251 ATGACCCCAAATTAACTGTCTTGAAATACACCATGGTTTGAGTTTATTCA
418301 ACCAATTTGACACTTGCTTATTAAAGCGTTTGGGAATAAAATCAGGATAT
418351 TTTTTTAAATATAAGTGATCTTTTAACTTTGGTAAATCAACAAATCACTG
418401 TTTTGAAAGCATGGGTTCTACAACAGTGCCACTGCGTTCAGAAAAACCAA
418451 CATTACTAGTTAATGGTATTGATTTAACAAGTAATTTATTTTTTTCTAAT
418501 CATTTAACAATTTTATTTCTTGCTTGTAAAACACTAAGGCCTTGAAATTT
418551 ACTTGCATTTTGATTGAGAATACCGTTACTGTCAATGCAGCTTAGAAAAT
418601 CAAATTTATATTTAGTGTTGATTTCATAGTCATTAAAGTCGTGTGCAGGA
418651 GTACATTTCAATATTCCTGTACCAAATTTAATGTCAACATAGCTATCTGT
418701 TACAACAGGAATTTGTTTTCCTGTTAAAGGGTTAACTACTAATTTATTTC
418751 AGAAATTAGTATAGCGCTTATCTTTTGGGTTTACCAATAGACAAACATCA
418801 GCAAAGATAGTTTCTGGTCTTGTTGTTGCAACTATTAGTTCTTGTTTACT
418851 ATCATTCGCTAGTTTATAAACAACATAATGAAGATGTTGATTAACAGGTT
418901 TATTGATAACTTCAATATTTGATATAGCAGTATTCAATTTTGTATCTCAA
418951 TTAACAAGCGTGTATGCTTGATAAATAAAACCGTTTTCATAAAGGTTTTT
419001 AAAACAATTGTTAACAATTTTATTAGCTTGTTCTGAAAGCGTGAATTTAG
419051 TTTCAGATCAATTTAAGCAAACTCCTAAACTCTTTAGTTGATTTTTAATT
419101 ATTTCGCTTTGATTTAATGCCCAATTCATGATCATTTCAGATTTTTTATC
419151 ATCATCTGCATCAAAATATTTTTGATTTTCTTTTAATGCTATTTTTTCAT
419201 ATTTCGTTTGAGTAGCAATGCCAGCATGATCAAAGCCAGGAATTCAGTTA
419251 ATACTAAATCCCTGCATCTTTTTAAAACGCATGATTTGATCAGTAATACT
419301 AACCTCAAAAGCATGACCAATATGAAGAGTACCTGTTAGATTTGGAGGGG
419351 GAAGAATTGCTGTAAAAGAATTGTTTTTATCTTTAGGTTTAAAAAAACCA
419401 GCATTATTTCAAATTTCATAAAGCCCATCACTAACTAAGTTGAAATCATA
419451 GTTTTTTTGAAAACTAAATTTATCTTTCATCTTCAACGAATAATTCGAAA
419501 ATTTTTTTGTGAACTAAAGCAAGATTATGATGTGTTTtGTACTTGCAAA
419551 AACACATTTATCAAAATTAACTTTTAAAAAATTTGCAATATTCTTAAGCG
419601 AAAAATATCTTTCACTTTGATTTAGTTTGTCAAATTTATTAGCAACAATC
419651 AAAAAGTTCAATCCTGTTTGCAAAATAATTTTAACCACTTCCTGATCTTG
419701 AACAGTAACAACTCCACTATCTACTATCAAAACAACACCAACTAGATTAC
419751 TACGAAAATTTAAAAATTGGGTAAGTAAATTAGTAATAAAATCTTTCTTA
419801 TTTTTGTTTATTTTAGCAAAGCCATAACCTGGTAAATCAACAAATCTTTT
419851 GTCTTTATATTCAAAGTAATTTAGTAATTGTGTTCGACCTGGTGTTGCTG
419901 AAGTTTTAGCCAGTTTCTTTTTAAAAAAAGCATTAATCAAACTTGATTTA
419951 CCAACATTACTTCTTCCCATGAAACAAATCTCTGGGATATTATCTTGAGG
420001 ACAATCTTTTAAATCACTTGCACTCTTCAAAAAATGTGCATCCATGTGTA
420051 TTTTATTTTTGGTTTTTAATGGAGCGCATTATCTCTTTTACCTGGGTTTC
420101 AGATAATTTTCTACCCATTTTTGCATACATTGCTTTAATTTGATTTTCAG
420151 TAATAGGTGGATTGTCACGCATCTGTTTTTTAAAGATTTTTATAGAAATA
420201 AAATAACCAAGAATCATTCCCACCAAAAGCGAAAGAGGGATACCTAAACC
420251 TAATGCAAGTGCTAGATCATTCATAGCTATATATTAATAATTAAACATTT
420301 TAAAAGTCTTATAAAATTAAATAATCGAATTAATGGATAAACTTGTTAGT
420351 ATATTAGTTCCTTGTTACAAATCAAAACCTTTTTTAAAACGTTTTTTTAA
420401 TTCACTTTTAAAGCAAGATCTTAATCAAGCTAAAATTATTTTTTTCAATG
420451 ACAATGTTGCTGATGAAACCTATGAAGTTTTGCAAAAATTCAAAAAAGAA
420501 CACAATAACTTAGCAATTGAAGTCTATTGTGACAAACAGAATGAAGGTAT
420551 TGGAAAAGTGCGTGATAAGCTAGTGAATCTAGTAACAACACCTTATTTTT
420601 ATTTTATCGATCCTGATGATTGTTTTAACAACAAAAATGTCATAAAAGAG
420651 ATTGTTGAATCAATTAAAAAAGAAGATTTTGATCTTGGTGTATTAAAAAG
420701 TATGGTCTATTTATGCTTCTTAAAACATGATTTCATTATTAAATTTTTGC
420751 CTTTAAAAGGTATTTTTCaAGGCAGAGTAAAATTAATTAATAATAACaAT
420801 GTTAATAAATTAAATTACATCaAAAATAATGATCaATATATTTGAAATAT
420851 TGTTATAAACACAGATTTTTTTAGGAAGCTAAATTTAACTTTtGAATCAA
420901 GGTTATTTGAAGATATACCAATCTGATATCCGATGTTTTTTCATCACAA
420951 AAAATTGTTTTTATTGATGTGATAGGAACaAATTATTTTATTCGTAATGA
421001 TAGTTTATCAACTACTATTAGTGCTCCACGCTACTTAAATTTAATCCAAT
421051 GTTATGAAAAGCTATATGTAAATCTCAGCCAAAATGGTTCTCTTGCAAGT
421101 TTTATTGATCCAAATCATAAGATTGAAGCTAGGTTTTGAAGAAGGCAAAT
421151 GTTTGTTTGATTTGCACTTTTCAGCTTTGAATACTTTAAGAAAAATTTTT
421201 CTGAATCAAAAAAAATTCTTGAAAAACTATTTGTTTTTTTGGAAAAAAAT
421251 GGAGTTTATGAACGTGTTTTTCAAACAAAAAATCAAGGTATTTACTATAT
421301 TTGGGTACAGCGACTAAAATATTTTAAACATGTTTTGGAATCTAAATCAG
421351 ATAACTAATTAAGTTCTCTTTAAAAAATCAATGAGATTAAAGTTATTTAA
421401 AGCTTATTGTTTAATTTACTTAAATTAAGAATCTTTATCTTGTTAAATTA
421451 ATACTTAACTGGTTTAATGTCTGCAATTAAATTTAATCCTAGTTCATTCA
421501 GAAAAAACTTTAAATGGTTTGAAAATAACAAAAATTGGATTAATTTGAT
421551 AATGCTGCTACTTCCATTGCACTTGATGTTGTGGCTGAAGCAAGCAAAGA
421601 ATATTACCAGTATTTTTGTGTCAATCCTCATAACAAAAATCCTGAAATTA
```

-continued

The Nucleotide Sequence of the *Mycoplasma genitalium* Genome

421651 ACCAAAAACTTATTGCTATTATTGAAGAAACAAGAGATTTATTAGCAAAA
421701 TTTTTCAATGCTAAAAAAAATGAAATAATTTTTACAAGTTCTGCAACTGA
421751 ATCGCTTAACTTATTCGCCTTTGGATTAAGCTCTTTAGTAAAAAGTAATG
421801 ATGAAATCATTCTCAAAGAAGATGAACATGCTGCTAATGTTTTTCCCTGA
421851 GTAAATCTAGCAAAAGAAAATAAAGCCAAACTAAAAATAATTAAAAAAAC
421901 ACCAAATAAATCTTGAACTGATGCTTTTTTAAAAGCTTGTACACCATCAA
421951 CAAAACTATTAGTTATAACTGCAACATCTAATCTTTTTGGAAATAGTATT
422001 GACTATGAAAAAATTTCTAAACACTTAAAAAAAATATCACCAAATAGCTT
422051 TATTGTTGTAGATGCAGTACAAGCTGTACCACACCATAAAATCGATATTA
422101 CAAGTGCTAATATTGATTTTTTAACTTTTTCTACACATAAATTTTATGGA
422151 CCTACTGGTCTTGGCATTGCCTTTATCAAAAGCGAATTACAATCACGACT
422201 AAAACCCTTTAAATTAGGTGGTGATATTTTTAAATCATTGGATAATAACT
422251 TTAAGATAATTTTTAAAGAAGGTCCTTCCAAATTTGAAGCTGGAACGCTA
422301 AATATTATGGCTATTTATGCTTTGAATAAACAGTTAAAATTCATGCAAAA
422351 AGAATTTAATTTCAGTGAAATGGTGTTTTACAGCAAACAATTAAAAAATT
422401 TAGCTTATCAACTGCTAAGTCAAAATCCTAATATCGTTTTAGCTAATCAT
422451 GATCAAGATGTTCCTATCTTTGCTTTTAAGCATAAATATATTAATTCTGC
422501 AGATCTAGCAACTTTTTTAAACATTAAAAAAATAATTGTTAGACAAGGAT
422551 CCATCTGTGTTGGTAAATTTAAAAATAAAGAGAGTTTTTTACGTGTTTCT
422601 CTACTCCATTACAACACAAAAGAGGAATTACTTTATTTAGAAAAATTATT
422651 AAAAACTAGTAAGAATTCCATTATTAATGAACTAATATATTAGCTAATGG
422701 ATATTAGAGCAAGAACAAAAATTATTGATATTTATTCAAATTTAAAATAC
422751 AAAAAACCTCTCAAAAGTTTTCAAAAAATTTTAACAACAAGTGATAGTGA
422801 TAATTGTGAAGACTTTTTTAATATAGGTTTAAATATTGATAAAAATAAAA
422851 TTACTGCAATTGGTTTTGATGGTGATGGTTGTATTATCTCTACAATTGCA
422901 ACTGAATTAAGTATTAAAGCAATTGAAAATAAAACTATTAACCAAGCAAA
422951 AAAAATATTATCAGATTTAATTGCAACTTATAAAGATAAAAAATTCAGCAA
423001 ACCAAGTTGTTGAAGAATTAAAGCTTTTAATTGAAATGAATGTAACTGAA
423051 AAAAGGTTACAGTGTTTGCTTTTAACACCAAGCAACTTATTGCAATGGTT
423101 TAAAAATTTTTAGCATTAATAGCTAACGTTTGTCCTAGGATATCATATAA
423151 GCGTTTATCACCAACTAAAATCTGTTGATGTTCTCTTTGGTGTTGCTTTT
423201 GATTTTCACGAATTAAATCTAAAAATGCCAACTCTTGAGTGCCTTCATCT
423251 AAAGCTTGTTCAATAAGTAAAGACATAAAGATCTCTTTCTTTAAACCTAA
423301 TGAATTAGCTTTATTATTTTTTCAATTACTAGAAATCTTATTTACATCAT
423351 CATTTGTTATCTGAATAACATAACTAAGAGTCTGGATACTAGAGTCATTT
423401 GTTAATGGAACTGTTTGCACAGTTTTATATCCTTCTGTATTGGAACCATC
423451 TGTATTTGCAGCTTTAGATAAACCAACATAACCTTCAAATTTATGAAAAT
423501 AAAGATCATCTAGTCTATCAACTACATTTAATAAAAACTTTTTTTTATTA
423551 TCAAAACTTATTAAAGGTTCACCTCTAGAGTTAAAGCGACTTAAATTATT
423601 TGTATCAACATTAACTGAGCGATGTAATAACTCACCAAAAGCATTAAGTT
423651 CAGCATCAGAACTGGTTTTATTAATCAAGCTTCACAAGGTAAACTTATCC
423701 TTATATTGACTTAAAGCGCCTGCTTTATCAGTTGCTGTAATTAACTGTCC
423751 GTAATTATTAAAAAGCTGTTGTGTTAAACCAGCACTAGCTGTTGAAATAC
423801 TTTGATTGGAATTAATTGTTAAACCATTAAATCCATAAAAATATTTTTTA
423851 TCACTTGATCCTTGTGATTTATTAGATAAAGCTACAGAATTATTAAACGG
423901 TTCATCAGTAAATCTATAAGTGTTTTCACTTTCAAGCAATGAATCGGGTT
423951 GAATTGGTGTTTGTTTATCATTGAATCAGTTTATTTCAGAACCTTGAGTA
424001 TAGTTAGGATTTTGTAAAAACCTATTAAAAGGGTTTTCATTAGCTGATGA
424051 AGTACTGGATTTTGTTTTTTGACTAACAGTAGCGCTAGGGTTTTTATCAT
424101 ATCCTACTGTTCATGAAACAAATGCTCTAGTGCCAATTGGAATTGCTTGT
424151 TGTAAAAGATTCTTATAGTTTTGAGCACCATTTTTAACAAGTCACATTAA
424201 CGCTTGCAAAAAGCGCATGTATTTGTACTCAGCATCCTGATTAGGATCTT
424251 CCAATTCCTTTTCAAATGCTTTCTTTGCTAAATCTAATAGGGTTTGATTA
424301 ACACTACTAGAAGTATGAGATTGGGCAGCTTTATTTTGCATTTGCAACAT
424351 AGTTGAAGTTGAATTTACACTACCCAAATCCTTATAGTAACCAAAGCGTT
424401 CTTTACTAGTTAAATTTTGTCAAGAACGGATATAAAGTGCCTGTTTAACA
424451 AGATCATTAAAATCAGAAAATTCACCTTTTAATTCTTTATTTGAAGTATC
424501 AAAATTATTAGTGAATGAATTAGTGTTTTTAAAGTACCAATTTTTAAAGA
424551 TGTTTGCAACAGTACCTGTTCTAATTCCTGAATCAGTTAAAAGTGATAAT
424601 ATAAGATCAAGATCCAAGTCATTTAATTGTGATGATTTTAGGGTAATAAT
424651 CTCTGAATATTGACTAGAAGAATAAGTTGTAGCTTTTCATTTTTCAACTA
424701 ATTCTTTGGCTTTATTTTCTACTTCAGTTGTTAAAGTCTTTAAAGTTTGA
424751 TTATTTTTTTCACGAGTTGGTTCATTATCAGAAGTAATAGCTGCAGCAGT
424801 GGTTTTCAAAGTTAAAGTTTGAGCACTACTTTGATCAGAGTTGTTATTAA
424851 AAAATTTTGCTAATGAAGGATAACTACCATCATTTGCTCTTTTATATGGA
424901 AGAGGTTGACCCCAACCAATTGAACTTTCTTTAGCTTCCTTTTGAAGTTT
424951 AATGTAGTTGTTAGCACGATCAACAATTGCTTGTTCTAGTTTTTCTATAT
425001 TAGCTAAATCTGTTCTAAAGTTATTAAGTTTATTAGCAGCTTTAATATAA
425051 GACTCATAACTTGATTTTATTTGTGAAAGTGAATTATTAAAATCTTGTTG
425101 TTTTTTAATAGTTTCAGATAAATTGGTATTGTTTTTTAAAAGTTTTTTAG
425151 CTAAATCACATACATCTTTTTGACCGTTATTATTAGAAGTTCCATTTTCT
425201 AACATAGTTGTTAAAGCTGTGTAAAGTTTTAGTGTTGTATTTCTATTTGC
425251 TCAACTTCTAAATTCGCTGTTAGAACCAAATAAATCAACTGAAAAACTGA
425301 CATTATCTTTAGAGAAATTATTAGTTTGTCCTTGTAAAAATCGCATTAAT
425351 AAAACTTCTGCTTGTTTTTCAAAATTACGTTTGTTAGGTGATGAATTCTC
425401 TAAAAAATAATTACCTCCATCAATATGAAATGCATATATGGCATCATCAC
425451 CTCTAACATAAACAGGTTTCTGTTGCTGTTTTTGAGTTGTCTTTGAACTT

| The Nucleotide Sequence of the *Mycoplasma genitalium* Genome |
|---|
| 425501 AGACTAACTAATAAATTACTTGTTACTACTTGTGCTTGAGATGAATTTGA |
| 425551 TTCCATTCTAACTGCATCAAAAATAGTTGCAGTTTGACTACTATTATTA |
| 425601 AAGCTTGTACTTGTTTTCAAAAAGACTGCGTGTTACTACTATTATCACTA |
| 425651 CcAGAAGAAGAAAGCGAGGGATTAATTTTTAAAAATTCACTTTTAACATT |
| 425701 AAAACCATTATTGTCTGAAGTAACTTCTTGACTTTTTGTCATAGCACTCT |
| 425751 TCATCATAACTGTTGTTGCACTTGAACTTTTAATAAATTTATCAAGAGGA |
| 425801 TTTAAATTGCTACTAGTTCCACCTGTTGTTGTTGTTGTTGTTGTTGTTGT |
| 425851 TGTTGTTAATTCTGTTTTATTATTCAGTAAGTAATGGTATTGATCAATAA |
| 425901 CTGCAGCAGATAAGTTAACAGTTTTTAAAACAGAGAGAATGTTATTTTTA |
| 425951 CTAATTAAAACTTTGCTTGCACTATACTTGTTTTCAAAGTCAAGTAAATC |
| 426001 ATTTCTGGTATTAGTAGCAGCTGAACTTTGTGATGAACCACTAGAATTAG |
| 426051 CAGTTTGTAATTGTTTATCAAACTCTTCAAATAATTTTGCAGAGTTTGTT |
| 426101 TGACCACCACTTTCACTAGGATCTTGAAAAGCAGGAAAGTTATAAGAAAG |
| 426151 ATTTAGATTGGAAGCTCCAATTGCATTTTCATCATAAATACTGCCAAGTC |
| 426201 CAGCAATTGGAGATTGGTAATTGAAAGAAGCTTGATTTAATAAAAATGGG |
| 426251 TTTTCTTCTATTAATCACTGTGAAAATAAATAAGCTTGAAGATTAGTAAA |
| 426301 AAAATCACCATTTACATCATTTAAATTGCTGTTAATAAACTTAAGTTTAT |
| 426351 TTTCTGTTTTTTCAATGTTTTCTTTAGTTGTTGCAACGCTTGTATCACTT |
| 426401 GAATTCACTAAACTAACATTTGCACTAATGTTATTGAATATTAAAGATTG |
| 426451 AAAATCAGTAATTAATCTATCATAGAGTTTAAGTTTTTTTCAACTTTCTT |
| 426501 GATTACCACCGAACTGATCATATTCTTTTTGTACTTCAATAGGTCACTTT |
| 426551 ACTCTATCAGCACGTTTCTTTTCATCTATCAAGTTATCATGTTCATCTTC |
| 426601 AACATTTTCTTCAAATATCTTTAATCGATTAGAGATGTTTCTATCTGCAT |
| 426651 TTGCTTGGTATCATTTTTGTAATGCTGATCCAAAACTAACACGTAAGATA |
| 426701 GAATCAACACCACTACCATCATTTAAAGCAGACTTTAAAACTACATCTGG |
| 426751 GTTTATGATATTTTGATCACTAAAACCAATTAGTTTTTGGGATCGATTGA |
| 426801 GAGTAGGAAAAAGATTAGCAGTGTTTATTGTGGAACAGGCTGTAATTATT |
| 426851 GCTGTTGCACCCACTCCACTAAATGCTAAAGCAATTAATGATCAGCGCTT |
| 426901 AAAACGATGAGCCATCTTATACTAGCAGTTTGATAATTATCACATTTAAA |
| 426951 AATCTAGCTAATATAATTGCAAATCTAGATTATTaAAAAATGTATATTAA |
| 427001 TTATAAATAAGTTAATTTTTCTAATTTAAGCATTAAAAAAGCTTAAATCT |
| 427051 CTCTAATTAAAATGCTTTACCAGAAAATCAAAAAATTAGTTTTTAGCTAG |
| 427101 CTGTTTGTTGAAATGAATTTTTATTAGCCAATTGTTGAACAGTTAGTTCT |
| 427151 TTTATTTGTTCAAATAATGCTGGCTTTTCTGATAAAACATTTAATAATTT |
| 427201 TTCTTTACCAACAGCAATGCTTTCATTGTTAAAAGAATAAGAATTTCCAG |
| 427251 CTCTTACAACAACATTAAATTTAAGTGCTAAGTCAATAACTTCATGTTCA |
| 427301 TGTACAAAACCACGGTTAAACATGATTTCTAATATAGCAACACCAAAAGG |
| 427351 TTTAGCAATCTTATTTTTAGATACCATTACTTTTGTTTTTATGCCAACAT |
| 427401 AATTGTTGAATTTATCCTTAAGTAATTCAACACGCTTAGCTTCCATTCTT |
| 427451 AATGAACTATAAAATCTTAGAGCTTTTCCTCCTGTTGTAACTTCGTTATT |
| 427501 TCCAAACATCACTCCTGGTTTTTCGCGTAACTGATTAATGAATAAAACAC |
| 427551 AAGTTTTAGAATCTGGTAATATCGATTGTATTCTTCGCAAACCTTTTGAC |
| 427601 ATCATTCTTGCATGCAAGCCAATAGTTTGTTCTTCAATTGTGCCTTCTAA |
| 427651 CTCTTGTTTAGGAATTAACGCTGCTACAGAGTCAATAACAATTAAAGATA |
| 427701 TCTTGTTTGTTTTAATTAATGATTCGATAAGAGCAAAAGCGTTTTCACCA |
| 427751 TGCCTAGGATGAGCAATCAAAAGTTTATTTAGATCAATACCAATTGATTT |
| 427801 AGCATATGCTAAATCAAGTGCACCTTCAGCATCAATATAACATGCTGTTT |
| 427851 TACCTGCTTTCTGAAAACTAGCGACTGCATTTAGTGCAATAGTTGTTTTT |
| 427901 CCAGATGATTCATTTCCATATAGTTCTACTATCCTACCTAAAGGTAGACC |
| 427951 ACCAGACCCTAATGCTTCATCTAAATTTAAACTTCCAGTTGAAATTGTTT |
| 428001 CAATTTCACTGTTTTTCTTTGCATCAAAAAAATCAAAACTTGTCAAATTA |
| 428051 TTACTTTCAATAAAACTACTATTTTTTTGAGTATTTTTCTTATTAATTAT |
| 428101 TTCTtTTTGAGCCATCTTTCATTACACCTTATAAATAAGTGCAAAAAAAT |
| 428151 AAAAATGACATTTTTTTATTAGAAATTTTGTTTATTTTTTAATTTTCTT |
| 428201 AAAAAAATCTCTTTTTAGGAGTTTATTTTTTTATATTAGTTAACTTGTTT |
| 428251 GGTTTGTTGACATAAACACTCCTAAAACTCCTATATATTATTAGTAAATA |
| 428301 TATAGATTTTTGTTCAAGTCTACTCAGGTGAAGCTTACATACAACAGTTC |
| 428351 AAGTGGCTCAAATAACCAGATTAGTTTTGATTCAACTAGTCAAGGTGAAA |
| 428401 AACCATCCTACATCGTTGAGTTTACTAATTCCACCAATGTTGGCATCAAG |
| 428451 TGAACGATGGTGAAAAAGTATCAGTTAGATGTACCGAATGTTTCTAGCAA |
| 428501 CATGAACCAAGTGTTGCAAGAATTGATCCTAGAACAACCTTTGACTAAAT |
| 428551 ATACCTTAAACAGTAGTTTGGCCAAACAAAAGGGCAAAAGCCAGATAGAG |
| 428601 GTACATCTTGGTTCAAATTCAAATCAGTGACGATCGATGCGCAACTCCAT |
| 428651 TGGCTTAAACAACAATCCCAGCCCCAATGCTTCAACTGGATTTAAACTCA |
| 428701 CTACCGGCAATGCATATAGAAAATTAGATCAATCCTGACCAATTTACCAA |
| 428751 CCAATTGATGGGACCAAGCAGGGCAAAGGGAAGGATAGTAATGGGTGGAG |
| 428801 TTCAACTGAAGAAAACGAAGCTAAAAATGATGCGCCCCTAAGTACAGGAG |
| 428851 GGGGAACATCAGACAACGCTTCAAAATTCACCAAGTACCTCAACACCAAA |
| 428901 CAAGCATTGGAAAGGATCGGTATCTTGTTTGATGGGGATGGAATGAGGAA |
| 428951 TGTGGTTACCCAACTCTATTATGCTTCTACTAGCAAGCTAGCAGTCACCA |
| 429001 ACAACCACATTGTCGTGATGGGTAACAGCTTTCTACCCAGCATGTGGTAC |
| 429051 TGGGTGGTGGGAGCGGAGTGCAACAACTGATTCATCATCAAAACCCACCTG |
| 429101 GTTTGCTAACACCAATTTAGACTGAGGGGAAGACAAACAAAAACAATTTG |
| 429151 TAGAGAACCAGTTGGGGTATAAGGAAACTACCAGTACCAATTCCCACAAC |
| 429201 TTCCATTCCAAATCTTTCACCCAACCTGCATATCTGATCAGTGGCATTGA |
| 429251 CAGTGTCAATGATCAAATCATCTTCAGTGGCTTTAAAGCGGGGAGTGTGG |
| 429301 GGTATGATAGTAGTAGTAGTAGTAGtAGTAGTAGTACCAAAGACCAAGCA |

-continued

| The Nucleotide Sequence of the *Mycoplasma genitalium* Genome |
|---|
| 429351 CTTGCTTGATCAACAACAACTAGCTTAGATAGTAAAACGGGGTATAAGGA |
| 429401 TTTGGTGACCAACGACACGGGATTAAATGGTCCAATCAATGGGAGTTTTT |
| 429451 CAATCCAAGACACCTTCTCATTCGTTGTTCCTTATTCGGGGAATCATAGT |
| 429501 AATCAAATTTCATCAGGAACCATTAAAACTGCTTATCCAGTGAAAAAAGA |
| 429551 TGAAGCTTCCCAAGTAGCGATCAATTCCTTGAATCAACCTACGCCGTTGA |
| 429601 ATAGTTATGGAAGTGGAATCTTCTTCCTCTTTCAACCCCACCCAAAGGTT |
| 429651 GCAAAAAGATAGTCCGGTGAAGGATTCAAACAAAGACAGTGAGAAACTCA |
| 429701 GTGAAACAACTGCTTCATCCATGAGTGGTATGGCTACATCTCCTCGCAAA |
| 429751 GCCCTCAAAGTGGAGGTGAAAAAACAAAGTGGATCAAGTGACACCCTCAC |
| 429801 CAAAAACGACTTTGCTAAAAAGCCACTGCAGCATAAGAACAGTAGTGGGA |
| 429851 CAGAGGTGAAGTTAGATGCGAGTGGGGAGTTTGGTGACAACAAAGCCTGA |
| 429901 AAACCATTGTTGACTACCGAGCAAATAGCAAGAGAGAAGAGGATGGGGAT |
| 429951 GCCAACTCCCCCTCCCCtTCTTCTTCTTCTTCTTCTTCTTCTTCTTCTTC |
| 430001 TTCTTCTTCTTCTTCTACTACTACTACTACTACTACTACTTCTACTTCCT |
| 430051 CAACCCCCCTCCCCACTTTTTCTAACATCAATGTTGGGGTTAAATCAATG |
| 430101 ATCACTCAACATTTAAATAAAGAAAACACCCGGTGGGTGTTTACACCTGG |
| 430151 TAGTACACCAGACATCTGAACGGGAGCAGGGTATCGCGTTCAAAGTGCTA |
| 430201 ATCAGAAAAACGGCATTCCTTTTGAACAGGTGAAACCTAGCAATAATAGT |
| 430251 ACCCCCTTTGATCCCAATTCAGATGATAATAAAGTCACTTCAGGTAGCTC |
| 430301 CTCCAAACCAACCACCTATCCTGCTTTACCCAACAGTATCAGTCCCACCA |
| 430351 GTGACTGAAGCAATGCGTTGACTTTCACTAACAAGAATAATCCGCAGCGC |
| 430401 AATCAACTGTTGCTCAGAAGCTTACTAGGAACTATCCCGGTCTTGATCAA |
| 430451 TAAGAGTGGAACGGGAGATGAGTTTAACCATACGAGTGAGCAGAAGTGGG |
| 430501 ATAAAACTGAGACCAAGGAAGGCAACCTCCCAGGGTTTGGGGAAGTGAAT |
| 430551 GGGTGAAAAATAGTAACTATTTTTTTAAATTAATACTCTTCAGCAACTGT |
| 430601 TTTGCTACCTAAGAAAGTTAACTCTTCATCAGTTAAAAATCCTGTTCCTG |
| 430651 CTGGAATTTTTCCACCAATAATAACATTCTCTTTTAAACCTAAAAGATAG |
| 430701 TCTACTTGGTTCTTAACAGCAGCATCAGTTAGGATTTTTTTGGTATCTTG |
| 430751 GAAGGATGCAGCACTTAAAAAGGAGTTAGATTTACTTGCCGCTTCATCAA |
| 430801 TTCCAAACACCTGATTAATTGCAATAACAGGCATCTTTCCAGCTAAAAGT |
| 430851 AAGCTCTTATTTAGTTCATTGAGATAATGGCTATGCACTAACTGACCAAC |
| 430901 AAATAAATTGCTGTTACCTGCATCTGTTACTTGCAACAAATTAGTTAGTT |
| 430951 GTCTGATAATAATTTCTACATACTTATCAGCAATATCTATCCCTTGAATC |
| 431001 CTATACACTTTTTGGATCTCTACAATCATGTATTGTCTTACCCTTTGGAT |
| 431051 ACCTGCAATTCGCAAAAGTTGTTTAATATCAACAGAACCTTCTGTAATCT |
| 431101 TAGAACCTGGTGAAACTTGATCACCAACATGAACACGTATTTGAGCACTG |
| 431151 AAAGGGATAGTATAAATCCTCTCATCAACGTTTGATTTAATCACTACTTC |
| 431201 CTGAGCGTTTTGAACAGTAGTAATTGATTTAACTGTTCCTTTCACTTCAG |
| 431251 AGATAACTGCTTTTTCAAAATCTTTAGGAGTAACTACTTCAAAGATCTGT |
| 431301 TTTAAACGTTCAAAGCCTTGTGCTAAGTTGTTTTCAGTTGAAACTCCCCC |
| 431351 AGTATGGAAAGTACGCATTGTCAATTGGGTCCCAGGTTCACCAATTGATT |
| 431401 GAGCAGCAATCACCCCAACAGCAGTTCCCAATTCCACCAACTTACCAGTT |
| 431451 GACAAGTCAATGCCAAAGCAGTATTGACAGATACCATTTTCCCTTTCACA |
| 431501 ATAGATAACAGATCTAACTAAAACTTCTTTAATAGATGTTGCACAAATCT |
| 431551 GTTTAGCTAATTGCGTTGTAATAAGACTGTTAGCTTCTACAATAGTTTTT |
| 431601 TGTGTTTCAGGATCAACTATAGGAGTAATTGAGTAGCGATTAACAATCCT |
| 431651 GTCAAATAATGATTCAATCAAGGATTTGGTTTTGGTTTCAACAATTGCTT |
| 431701 CAACAACAATTCCTTTTCTTGTTCCACAATCATCATGGTTAATAATTAAT |
| 431751 TCATGAGTAGCATCTACTAGCTTTCTTGTCATATAACCAGACTTTGCTGT |
| 431801 TTTCATTGCAGTATCTGTCATCCCTTTTCTCGCTCCATAAGAAGAGTTGA |
| 431851 AGTATTCATTAATGGTCAAACCTTCAAAAAAGGAGTGTTTAATAGGAACT |
| 431901 TCTATCGTATCTTTAATGATCTTAGATTGGTTATTTCTTTCATAGTTAAA |
| 431951 GCTTTTAGACATTAAGCCTCGCATCCCAAATAACTGGGTAAAGTTAGAAA |
| 432001 TGTTACCTCTAGCACCTGAATCAGCCATTACCACAATGGAATTATCACGG |
| 432051 TACTGTTCTTGTTTAATTAAGTTTTGGATCTCATCAGATACTTTTTCTTT |
| 432101 CACATTGTTTCATAACTTCACAACGCGTTTATAACGTTCATCATCGGTTA |
| 432151 ACAAACCCTTGTTATAAAACTGTTTGTATTTCAGCACCTGTTGATCAGCA |
| 432201 CTATCAAAGTAATTTTGTTTATTGGTGTACTTAGGGATATCAAATACTGA |
| 432251 AACAGTAGTTGAAGAAAAAGTAGAGTACTTAAAGCCAAGTGCTTTGATAT |
| 432301 TATCAAGTGTTTTAGGAAGGTCTTTAAATTCCAATAAAAGATAGAGTAGA |
| 432351 TCGATTAACTTGGAAATAACCTTTTTGGAAAATGCAGGGATAATTTGATG |
| 432401 CTTTAAAATTGATTGTCTTACATCTTCTCCCTGTTTCACAATGAACTTTT |
| 432451 CGGGACATGCATTTTCATCAAATTCCCCGTCATTAATATAAGGAACATTA |
| 432501 TTGCCTAAAACATCATTAAAGATAATCTTACCAACTGTTGTTATTAAAGT |
| 432551 TCCTTGGCATGCAAACTTCTTGTTGGGAAATGCTTTAGTACTTATCCCTA |
| 432601 CAATAGCATGTAAATGAACCTTTTGACTTTCATAAGCAGCACGTGCTTCA |
| 432651 TAAACTGTGCTGAAGATAATCCCCTCTCCCAACTGTCCTTTTCTCTCTGT |
| 432701 GGTTAGATAATAGTTACCTAAAACCATGTCCTGAGTAGGAGTTACAATAG |
| 432751 GTCTTCCATCTTTCAAACCTAAGATATGTTTTGATGCAAGCAGAACAGCT |
| 432801 CTTGCTTCATTAACTGCATTCTCACTTAAAGGAACATGAACTGCCATCTG |
| 432851 ATCACCATCAAAATCAGCATTAAATGCAGTAGTTACTAATGGGTGTAATC |
| 432901 TAATTGCTTTACCATCAACAATTCTTGGTTCAAATGCTTGGATCCCTAAC |
| 432951 CTATGTAGGGTTGGAGCACGATTTAGTAAAACGGGACGATCTTTGATAAC |
| 433001 ATCATAAACTATTCCCCAGATAAGATCATCCTGGTTTTTAATCATATCTT |
| 433051 CAGCTTGTCTGATGGAAGCGGCAATTGGTCTAATCTCATTACCATTTTCA |
| 433101 TCAAACTTATTGATCAATCCATGGATAATAAAGGGTTTAAACAGCTTTAA |
| 433151 GATCATTAGTGCTGGGATCCCAACTTCATACATCTTCAATTCAGGGCCAA |

| The Nucleotide Sequence of the *Mycoplasma genitalium* Genome |
|---|
| 433201 CCACAATTACACTTCTACCTGAATAATCAACTCTTTTACCAAGTAAGTTG |
| 433251 TGTCTAAATAAACCTTGTTTTCCTTTTAAACGATCTGTTAAAGATTTCAA |
| 433301 TGACCGTTTGTCTTTGGAAAGTGATGGTTTATGACGTGAAGAGTTATCAA |
| 433351 ATAAAGCATCAACAGACTCTTGTAAAAGTCTTTTTTCATTGTTAACAACA |
| 433401 ATAGAAGGTACAGTACCATCTTCCAAAATCCTTCTTAATCGGTCATTTCT |
| 433451 AATGATTACCCTGCGGTAAAAATTGTTGATGTCACTGGTGGTAAACTTAG |
| 433501 CACCATCAAGTTGGATAATAGGTCTGATATCAGGGGGGATAACTGGAACA |
| 433551 GTATGTAAGATCATGTTTTTAGGATGAAGCTTAGAATTTCTAAACCAACT |
| 433601 AATAGTTTCCAGTTGTCTTAAGATCTTCTTAACTTTAGCATCTTCAACAC |
| 433651 TATCTTTCTTGGCTTTTCTTAAAGCATCATTTAACCTGCTAAATTCCAAG |
| 433701 TTAAGATCGATTTTATTAAGCAATTCCAAAATTGCTTCAGCCCCTATTCC |
| 433751 AACCCTAAAACCAGTGTACTTCTTAATGTAATTAAAAGCATCATTTAGAG |
| 433801 AAAAGGGGAGAGAGCTGTTTTTTAAACTTTCATAAAAGATTTTTCCCTTA |
| 433851 CGGTAATCTTCACTACTCTTACTTTTAATGAGATTTCTGAAGATATAACC |
| 433901 TATCACACGACGCATTTTTTGTCGTGTTGAAAGTGAACCCTTACCAGTTA |
| 433951 AGTCCAAAACTTCTTTGAACTTAAAAGGCATGATTTTATCATCTTTGATC |
| 434001 TTACCTGTATCAAGTACTATGTAGTTAACAAAGTACAAAACCTGTTCAAC |
| 434051 CTCTTTGTAAGAGATGTTTAAAACTAATGATATTTTGGAAGGAGATGGTA |
| 434101 ATTCTTTTGACATCCAAATGTGAGCTACAGGACTCACAAGTGCAATATGT |
| 434151 CCCATCCTTTCTCTACGTACAATAGATTCAGTAACTCACACCCCACAGCG |
| 434201 ATCACACCTCACACCACGGTATTTAATCTTTTTGAACTTGCCACAAGCAC |
| 434251 ATTCATAGTCCTTAACAGGTCCAAAGATTGCTTCATCAAACAAGCCTCCA |
| 434301 GGTTCTGGTTTTAATGATTTATAGTTAATGGTTTCAGCTTTTGTAACTTC |
| 434351 CCCTTCAGATCAGTTCAAAATGGTGTCATTGGAAGCGATGGAAAGTTTAA |
| 434401 TTGCTTTAATGTTTTTATAAAGCTTGTTATTTCTTTTATTACGTCTTGTT |
| 434451 GTTGTCATTGTTAATTTCTAATAACCCTCAGTGTCAAATTCAAAATCATT |
| 434501 GAAAAATTCATCTTGTTCCCCATCACTTTGCAAGATGGAAACATTATTGG |
| 434551 AGTCTTGTTGGGTGTTGTCATCATAGATAAATGAAACAGATAAAGCCAAG |
| 434601 CCCTGTAATTCTTTTGTCAATAATTTAAATGATTCAGGGATACCAGGCTC |
| 434651 TGGGAAAGCTGCACCTTTAACAATAGCAGCATAAGCCCTATTTCTTCCTT |
| 434701 GTACATCATCAGATTTAATGGTTAAAAGTTCTTGCAAGTTATAAGCAGCT |
| 434751 CCATAAGCTTCTAATGCTCACACTTCCATCTCACCAAACCGCTGTCCACC |
| 434801 ATTTTGCGATTTACCACCTAATGGTTGTTGAGTGATCTTAGAATAAGGGC |
| 434851 CAACAGCACGAGCATGGATCTTATCATCAACCATGTGATTCAGCTTCATC |
| 434901 ATGTACATAATTCCAAGTGAAATAGGTCTTTCAAATGGCATTCCACTCCT |
| 434951 ACCATCAATGAGTTTAAACTTACCCTGATTTTTTTGGGGATCTAATCCTG |
| 435001 CTTCTTGCATAACATCTTGGAGATCTAAGAAGTTCACTCCTTGGAAAATA |
| 435051 GGGGTTGCAATTTTGTAAATAAGATCATCAAAAGACATCCCTATCTCTTT |
| 435101 CAAAACTAAACTAATGTCACTGTTATCGAGTTTTTCAAGTGCTTCTTTTT |
| 435151 CACTTTTAATATTGCGATCATTGATTTGGTTTTTTAAACCTTTAATTAAT |
| 435201 CTTTCAACCCTTGCTTGAGGTTGATTGATTTCAATGGCAAACTCCTTAGC |
| 435251 TTTATTTTGATCAAAACAACTACTAATTAAAGAACGAACTGCTAGCTTGT |
| 435301 GTGCTGCATAACCCAAGTGGGTTTCAAAAATTTGTCCTATGTTCATCCGA |
| 435351 CTAGGAACACCAAGGGGGTTGAGCAGAATATCAACTGGGGTTCCATCTTC |
| 435401 TAAATGGGGCATATCTTCAATAGGCACCACTTTAGAAATAACTCCTTTAT |
| 435451 TTCCGTGTCTACCAGCTAATTTATCACCAATTTGAATCTTACGTTTTTGA |
| 435501 ACCACATAAACCTTGATCATTTCAATCACACCATCATTAAGTTCATCACC |
| 435551 ATTAGCAATTGAAAAACGTTTTACAGCTGAAACAATACCATCCCCACCAT |
| 435601 GGGAAACTTTAAGTGAAGAGTCTCTCACGTTTTGAACACTTTCAGGGAAG |
| 435651 ATGGCTTTAAATAGCTTTTCTTCAGGAGAGACTTCGACTTGACCTTTAGG |
| 435701 GGAAACTTTACCAACCAAAACATCCCCTTCTTTAACTTCAGCACCCACCA |
| 435751 TAATGATGCCATTCTCATCAAGATAGCGTTTGTTTGCATCACTAACATTA |
| 435801 GGGATATCACGGGTAATTTGTTCATCACCATTTTTAGTAGACAAACATTG |
| 435851 AGCAACATACTCATTAATGGTTAATGAAGTGAGAATATCTTCCTTAACTA |
| 435901 ATCGTTCTGAAATGACAATTGCATCTTCATAGTTATAACCATTTCAAGTT |
| 435951 GTAAAAGCAACTAAAACATTCTGTCCTAATGCCAACTCACTCTTATTAAC |
| 436001 AGCAGGGCCATCAACAATGATTTCATCCTTATTAACCCTTTGGCCTATTT |
| 436051 CAACAATTGGTTTGTGGTTATAACAAGTATTTTGGTTGGAACGTTCAAAT |
| 436101 TTAACTAGGTTAACTGTCTCTTTTTTAGAACTATCACTTGTAATAATAAT |
| 436151 CTTACTGTTATCAACATAACTAACAACACCTGAGCAAGGAGAGGACATTG |
| 436201 TTAAACCTGAATCACTAGCAATTTTGTGTTCTTGACCAGTACCTACTGCA |
| 436251 GGAGCATATGGCTTTATTAAAGGATAGGCCTGACGTTGCATGTTGGTTCC |
| 436301 CATTAATGCTCTAGCTGAATCATCATTTTCCAAAAAGGGGATTAAAGAAG |
| 436351 AACCAATGGAAACAACTTGGTGTGGTGCTACATCAATGTAATCAATCTTT |
| 436401 AAAGGATCATARAGtCCTTGCATAGATCGATACCTACCAATAATTTCCTT |
| 436451 ATCTAAGATCTTGTTATCGTTACTAATATTGACAAGTGAAGAGATCTCAG |
| 436501 CAATAATATGTTCATCTTCTCTAAGCGCAGTTAAAATATTCCACCTCATCA |
| 436551 GTAATTACCCCAGCTTTGATTTTGCGATAAGGTGCCATTAAAAATCCGTT |
| 436601 TTCATCAATCTTAGCAAAGCTAGCTAAAGACATGATCAACCCTATGTTCA |
| 436651 TCCCTTCAGGTGTTTCAATAGGGCAAATTCTACCGTACTGAGAATAATGC |
| 436701 ACATCACGGATATCTAAATTAGGGTCCTCTCTTGATATTCCCCCAGGTCC |
| 436751 CATTGCTGAAATCCTTCTTTTATTACTCAATTCTGATAAAGGGTTTTGGT |
| 436801 GGTCTAAAAATTGGGTTAATTGGTGGGTATTGAAGAAGTCTTTAATCACA |
| 436851 ATTTGAATTGGTTTTGAGTTGATTAAAGATTTAATAGTTAATTCCTTTTT |
| 436901 TTCACCTTGTTCAATAACCTGACCCTCTTCATTAATTTGCTGGCCACGGT |
| 436951 TAACTCCATCAGCAATAGTTAACTTTTCTTTTAAAAAGCGCTCCATTCTA |
| 437001 GTGAAGCCGCTTTCTAATTTAGCAGTAATTAATTCATTAATTAACTTAAC |

-continued

The Nucleotide Sequence of the *Mycoplasma genitalium* Genome

```
437051  CCGCTTATTACCAAGGTGATCAATATCATCATATTTACCAATTCCATAAG
437101  GTAAATTAATCACATAACTAATTGAAGCGATGAAATCACTGAGAGTCATT
437151  GCTTTGTTCAGATCATTTTCGTTATGGATCCCTATAACTGGTACTGAAAC
437201  ACTAAGATTATCATTAGTGATATATACATCTATCGTTTCATAAAAGAGTG
437251  ATTCTTTTGCTAAATCAACAGCCTTACCATCAGTTGTAAGTTGCATTTTA
437301  TTAACAAAACTAATTTCATTGTTCTTAGCAGCTTGTTTGATTTTGTCAAT
437351  CTCTTCTTTTAAAAGTAAAGTACCTTTTTTTAAAAGTAGCTTGCCATCTT
437401  TTAAGAACAAATCACATGCCAGAGTTTTTTGATAAATACGTTCTGTTAAA
437451  CGTAACTTTCTAGATACTTTGTATCTCCCTGCATTAGAGAGGTTGTACCT
437501  CTTGTTTCTAAAAAAACGCGCACATAAAAGTGCATGGAAACTCACTTCAT
437551  GACACTCTTCAGTGTTTTCAATATCACGCAGTGAAATAGAAAGTTCATTG
437601  ACAATGTGTTTAGCAGCTCTTTCAGTAATAACACTATCCATTTTGTTTTC
437651  CATTTCCAGTTCAAGTGCAGTTAAACTAGAATCATTTGGACTTGTTTGTT
437701  TTAGCGCATTATATTGTTTCTCAAGCGTTACATATTCATTAACAAGTGAT
437751  CTTAATTTCTGATCAGAAGCGATCCCTTTTCTTCTTAAATCAGTTTTACC
437801  ATCTCTAAATTCTTTTAAAAGGTTTTTGATTTCAGGATCAACATTGCTTA
437851  AAAAATCCTTAGCATTGTAAATTTCCGCTTCCAATGAACGTTTGATAAAT
437901  TCATTGTTTTTAAAGATTTTAAGGATCTCACGATTATTTAAACCAAACGC
437951  TTTTAAAAGTGTTGTAATAGGGAAAATCTTAGCACCTTCTCTTACCGCAT
438001  CTCTTAAAAGAATTTGTACAAAAGCATCTTCAATCTTTTTTTATTGGAG
438051  ATGTATATAAGCATCACTGAACCATTAGCAGGTAAAACCTCACAAACATA
438101  ACCTTCCTGTACTCTTTTACGGGAGTTGGATAGTTTTAGTTGGGATTTTG
438151  TTAGCATGTATATCCCTGGAGAACGGGTTATTTGGGAAATAACAAACTTT
438201  TCTATCCCATTGATAATAAAAACCCCATCATGGGTTATTAAAGGCATGCT
438251  AGCTAAAAATACACCATTTGTATTGCTAGCAATATTTTTCTTTGATTTCC
438301  GTGCTTTTTTAACTGTTCCTTTATCATTATCAACTAATTCAAGATCAGCA
438351  TAAATACCAACTTCATAAGTTTTAGATTGAGCACGTGATTGTGCTTCATC
438401  ACGTTCTGGTTCAGTTCTGTGTAATCCCCTAAAATTGATAGTGTAGCGAT
438451  CATTAGGGGATTTGATTGGAAAATATGAGGCAATTAATTTTTCAAGATCA
438501  TGATCTAAGAATTTTTGGTAGCTTTTAATCTGAATATCAGCTAAATTTGG
438551  TTGGATAAAATTGGTCTCAATTTTGCCATAATACCTTCTGGTAGCTGTAG
438601  GGGAATAACGTTTTTGAAAGAAATTAGATTTTTGTGACATTTGTGGGGTG
438651  AAAAGCGGATCAAAACATTAAAAAGCCACTAACAGCGTTATAAAACGCAT
438701  GCTAATGGACTTAATCACAGTTCGCTAAATTATATTAATTTTTTAACTTG
438751  TTCAATAAAAGGCTTAAAATCAAAGTTCTCATGATAACCGTTGACTAAAA
438801  CTGTTCCTTTAACATTAAGACCGCTAAAACTTAAAAATTTATCTAGTAAT
438851  TCTAGAACAGTTTTACCCCCACCCGCAGTTGCTGGAGTTACACAACAAAT
438901  AACTCCATTAAGACCTTTTAAAAATTGATTTCTACCATACTGCTCATCAC
438951  GAGTCATCCAGTCAATGATGTTTTAGCAAAAGCAGGGATAAAACCGTTG
439001  TGTTCAGGGGTAACAAAAATTAAATTGCTATGTTCTTTGATTTTTCTAAC
439051  TAAAGTTTTAATTTTGTCAGGAAAGTTAGTTGCTTCTAAATCAACAGAAT
439101  AAAAATCAACTTGATAGTCTTTTAACTCAATCAATTCACAACTTAAAGAA
439151  TGTTTTAATTCATTAGCAAATTTCCTGTTAATGGAATGTTGCGAATTGGA
439201  GAGCATTAAAATTAATGACTTTTGATCTTTTGACATAAATTAACACTTAA
439251  ATTTTAAATAAAAAGTATTTAAAAACAATTTAATAGAAGCGTATAGCTAT
439301  TTTTTTCAATGTTGTTAATTATTGAGAAAATAGCAACCTTGATAAGTCTT
439351  AATATCAGCAACCTTAGTATCTAAACTAACGGTTGGTAAATTGGGGTTTT
439401  GTTCTTTATTTCCTTCAAGTAAACAGATACAATTCTCATCAAAATTAAAA
439451  CCTTTCATTATTTCAACAATTAAGTGGAATTCCAAATCAAAAATCAAAGC
439501  ATCAACTTTTAATTTAGTAGGAGAATTTGAAAATACTTGTAATTTGGAAT
439551  AATGCAGTAAAAACTGCTGATTAAAATCTTTAACAGTTTGTTGTCAAATT
439601  AAGTTCTTTTGCTCAAAGTTAGGATGCTTAATGTTTTCTAAATTTTTTAA
439651  CAAGTATTTATGAGGCAAGATAAAATGGCTGGTGATTTTTAACTTTTTTT
439701  CAATTGTGAATCTGTCTTGAAAACTAGTGAAACTAAAATCAATGTTACTT
439751  TTTTCAAAGTTAGTTTCATAACCAAACACACCGTTTAGTTCAACAAACAT
439801  TACGTTATTTTTAGACTTGTGCTTTTTTTCTAATTTTCTAACTAACTTAA
439851  AAAACTTATTTTGAAATGATCTTAAAGAATAAACTTCATGTTTTATTTTT
439901  TGTTTTTTAATTTCTTTAATTAGCGAATCAGAAAGCTTAATAGTTGTTTT
439951  TTCTTCTGGTGAATTAATTAATAAAAAAACTATTTTCAAACCCTTAAAAG
440001  TTTTCAGTATTTTTAAAAACTTATTAATTTCTGTATCTGTATTTTTGGTT
440051  TTTTCAACAAAAGCAAATACAGTATCGTTTTGACTTTTATTTCTTAATGC
440101  TAAACCAAATGCACTTCACAAGTTATTATCAAAACCTAAAAAAGGGAAGT
440151  TATCAAAATAAATCTTTTGATATATTGGAAGACTTACTTTGTTAACAAGC
440201  AGATAATTTACTTTTTTAGATCTAACTAAAAAATTAACAAAATCTAGATA
440251  TTGTAATGTTGATAAAAGTCCAACCTTATTGCTATTTTGAAAAAAATCAT
440301  AAGCTAATAGGCGTTGCTCATTAACGAGGGTTTGATCATTAATTTTATGA
440351  GACATTGTTTAATAAATTTTACTTAGTTTATTATGATTCAGGATATCATC
440401  CATTGCTTTACAAAAGCTTTCATATTTACTATTAAACATTTGGTGTTCAC
440451  TGTTTAAGATAACAGATGATTGCAAATTATTGTTCTTAATTAGGTATTTA
440501  TTGAAATAGCTTAATGTTAATTTTGTTGGCATAAATAAATCATTTTGAGC
440551  TAAAACCAAAAACACTGGTAACTTTAAATTTTTATAAGTCTTATTTAAAA
440601  CTGGTAGTTCTTTCAAAATATTATTAGAAAGCTTTTTAGCCATTTTACTG
440651  TGTTTTGACAGCTCATTTTCTCAGCTGTTTTCATCAGTTAAATTACTAAA
440701  TTTAGTTTGAAACATTGCTTTAAAATTAGCCATTCTTTCTGCCTTATCTT
440751  TTTTAAAAGAACTTTTAATTTTGAAATATCTCAATAAGTTACAGTATGAA
440801  AGAGGTGCTAAAAGTATGAGTTTTTCAACACGTTTAGCATTTAATAAATT
440851  CATGGCATAACTACAAACAGCAGCACCCATACTGTGTCCTATTAGAACGA
```

-continued

The Nucleotide Sequence of the *Mycoplasma genitalium* Genome

```
440901 TGTTTTCCAGATCCTTATTTTCTATAAAAGCAGCTAATAGTTCTCCATAA
440951 TGGATTGGAGATAATTCCTTATAATCAAAACCATTTACATTATGACCAGG
441001 TCAAAGTGGAGCGTAATAGTCATAATCAGTAAGGGTTTTATAAAAACTTT
441051 GAAAGTAGCTATGAAAAACAGAAAATCCATGTGCAAAAACAACCGTTTGT
441101 TTTTTTGTTTTTTTGCTGGCTGAAAGAAAACTTCAAGCTTAGAAATATC
441151 AATCTGATTAAGATCTGAAAACCTTTTCACAATTATTTTTTTAACACACT
441201 TTAAAACAACGTGAGCACAAATTATGATCTAATTTTTGCTTAATGATTGT
441251 TTGAAAATTTCAGCATCTTTCACACATTGTTTTTTAGTTTTTTTAACTT
441301 TAATTTCATTTTCATTATTTGTTAAATTAACACTGTTTACATTAAGTCAA
441351 AGTGCGAGATTATCCTTTAATTTTTTGGGTATTTTTTATTAATTCCAAC
441401 GGTTAATTCAATTTGATTATTTTTAGAAATCAACCCTTCTTTTCTTAGCT
441451 TTTCAATTTCTTTGAAAGCAGCATTTTTAATACTAGTAAAAGTTTTATAG
441501 ATATTTCCTAAATTCTTAGAGTTAGCAACTTTAAAAACAGTCGGTTTTGT
441551 AAAGAGGTTCACACTTATTGGTTTTTTATTGAATGAATAGTTTTTTCAAG
441601 CATCTTCTGCAGTGTGGGAATAAAGATATTTAAAAAACTGATTAGTTGT
441651 GTAAAAATATAGTTTAAAACAGCTTGTTTAGCTAAACGATTAGGATTATT
441701 TTTAGCATCACAATATAAGGTGTCTTTAATTATTTCAAAGTATCAGCTTG
441751 ATAGTCATAAAACAAACTTATTAATCACTTTTAGGCAACCTAAAAAATTA
441801 TATTTCTCTAAAAATTTCTCAATTTGTTCTACTAGTGAATTAGTTTTATG
441851 GATAACTATTTTGTCTTCTAGTGAAAACTTATAATCATCCATTGATGTAA
441901 AGTTAAATCCATTAATATTACCCAAAATAAAACGTAGTAAACTATTTCTA
441951 ATTCTGCGGTATTGTTCAGCAACTTGTTTAAGAATATTAACACCTATTTT
442001 GTTATCAATTTGTCAATCAGTATTAGCAACTCACAACCTTAATATATCCG
442051 CTCCATATTGATCACAAATTTTTAAAGGATCAACTATGTTTCCTAATGAC
442101 TTTGACATTTTATTGCCATTTTCATCAAGTGTAAAACCATGTGAAACAAG
442151 TGATTTAAAAGGGATTAAATCATTTTGAATAATTCCGCAATTTGAAGAAG
442201 AGTTGAACCAACCCCGATATTGATCAGAACCTTCAATATAAAGATCAGCT
442251 ATTGAACCATATTTATTTATTTCCAAAACATTATAGGAAGAACCTGAGTC
442301 AAATCAAACATCTAATGTATCAATCTCCTTGTGATACTTAACTCATTTTT
442351 TGGTTTTATCAGGTTTTAAAAAACAAGTTACATCTTTTTCAAATCAACTA
442401 TCAATACCATGCTTTTTCAATTGTTTAATTGTGTATTGAATTGTTGAAAA
442451 ATCTAACAATGGTTTGTTATTTGCATAAACAATTGGTATAGGCAAGCCCC
442501 ATACTCTTTGACGTGAGATACATCATTCATCACGTTGTAAAAGCATCTCT
442551 TTTAATCTCAATTGATTTTTTGAATTTAAAAAATTAACTTGATTAATTTG
442601 TTTTTTTAACTGCTTTTTTTATTGATTTAGTTTTAATGAATAATTGTTTGG
442651 AAGCACGGTATATAACTGGAGTTTTTGAGCGTCAATCATGTGGTTCGCGG
442701 TGGGAAATAACTTCAGAAAAAATAAAGCTATTGTTTTGTTTTAAACGATT
442751 AATAATTAGATCATTTGCTTTAAGATAAAAACAATTCTCAAGTTCTTTAT
442801 CATTAAGTAAGTTATTAAATACACCTTTCTCATCAATAGAAATCAAAACT
442851 TCTTTAATCTTGTTTTTTTGACAAAGATAAAAATCATCAATTCCAAATGC
442901 AGGGGAGCTGTGAACAATACCTGTTCCCTCATTATCAACAACATGTATTC
442951 CCATTAGAACTGGTAAAACCTTGTTATAAAAACAATGAGAATAGCTTGAA
443001 TTTTTTAAATTTGAACCCTTGAATTTTTTTAGTTTAATTGCATTTGTTCA
443051 ATTTAACTTATTTGTAAAAACTTCAAATAATTTTTCCAAGATAACAAATT
443101 TTTGTTGGTTATATTCAAAAAGAAGATAATCAAAATCAGGATGAATGGCA
443151 ATtGCTTGATTAGTTGGTAGTGTTCAAGGAGTTGTTGTTCAAACTAATAA
443201 ATTAGCATTTTCATCTAAAAAATCACTTTTAGAAACTTTAAAAGTTAAAT
443251 AAAGTGCAATTGAATTAACTTCTTTATATTCAATTTCCGCTTCAGCAAGT
443301 GAAGTTCTTGAAATTGGTGATCAATAAGTTGGTTTTAAATCTTGAAAAAT
443351 GAGCCCTTTTTTAATTGCTTGTAAAAATAGTTCAAGTTCCTTAAATTGAA
443401 AACTCTCATCTATTGTGTAATAACAGTTTTGAAAATCATTTAAAAGTCCC
443451 AGTCTTTGAAATTGTTCTTTTTGAACTGCAATTTGTGAAAGTGCAAACTG
443501 ATGACATAATTTtCTTTTTTCAACAGTTGAAAGATTGCTATAACTACTAG
443551 GGTTTTTCTTACTAACTGCATGTTCTATTGGTAGTCCATGACAATCCCAA
443601 CCAGGAATAAAAACAACATCATATCCtTCATATAACCAACTACGTAAAAT
443651 GAAGTCTTTTAAAATCTTGTTAAGAGCATGTCCCACATGAATACTACCAT
443701 TTGCATAAGGTGGTCCATCATGCAGTATTTTTATCTGTTTTCCTTTATTC
443751 TGTTTTTTTAATTTTTGAAAGACTTTTTTATCTTTTCAAAAATCATGAAA
443801 ATTCTTTTCACTAGTAGATAAATTTGCCTGCATCGCAAAGGATGTTTTAG
443851 GCATTAACAATGTCTTTTTTAAGTCCATTAAATCAGAGTAATTTTATTAA
443901 TATTTATCTAACTTACATCTGATGTATAAATCAGTAATAAACATAGTTTT
443951 ATTTTGTCCAGAAATTCCTAATAACACTGGCAACATCGTACGTAGTTGCA
444001 CTGCTTTTAAAGCTAATCTACACTTAATTAAACCTTATGGCTTTTCTTA
444051 AATGATAAAAGGATGGTTAGAGCTGGTTTAAATTGTTGAGATAAAATTCA
444101 ATTATTTGAACACAAATCATGAGAACATTTCTTACAAGCAACCACTGAAA
444151 ATAAAACTATTTGGCTTTTAACTAAAAGTGGTGATAAAACTCCTGATCAA
444201 ATTTGCATGACAAATAAATTACCAAACGAACTTTACTTTGTTTTGGTCA
444251 GGAAACAAAGGGATTACCTAAAACAATCATGGATAACTTTAAACAAAACC
444301 AAATTAGAATTCCCATTTGAAATAGTGTTAGAAGTATTAATCTTGCTAAT
444351 GCAGTTGTCTGTATTTTGTATGAATATTCAAAGCAAAATCAATACTCTAA
444401 TTTAGATAAACAGTGCGCTTAAGAAAAGTTAAAAACGCTCTTTTAAAAAT
444451 TAATCAAAGTCCTTATTTTTATTCAAAAGATAAGTTTGCTAAGTTTACTA
444501 AAAAACAATTAGTGCTGGAATTGGGTTGTGGTAAGGGTACTTTTTTAATC
444551 AAAGAAGCACAAAAAAATAACAATTTTCTTTTTATAGGAATTGAACGTGA
444601 ACCTACAATTGTTTTAAAAGCAATTAACAAAATTAACAAGTTGGATTTTA
444651 ATTTGGAAAATATCTTATTGTTGTGTACAGATGCAAAACAACTTGATGAT
444701 TATTTTCAAGCTGAATCTGTTCAAAAAATCTTTATTAATTTCCCTGATCC
```

-continued

The Nucleotide Sequence of the *Mycoplasma genitalium* Genome

```
444751 TTGACCTAAAAAGCGTCATATACAAAGACGTCTAACAAGTCCAGATTTTT
444801 TGAAACTTTTTTGAAATTTACTAGTAAAAAATGGCTTAATTGAGTTTAAG
444851 ACTGATAATGATAAGTTATTTGAATATACTTTAACAACATTGCAAGAAAA
444901 TAGTCAAATTTTTGAAATTATCCATCAAATAACTGATCTTAACAATTCTG
444951 AATTCAGTTTTCAAAATAGTATCACTGAATATGAACAGCGCTTTATGGAA
445001 TTAGAAATTCCAATTAAAAAACTAGTGATTAAGAAAATAATTTAATTAAA
445051 GTTATTAGAATAATTATTAGCTTGATGGCGATTGTGGCGAAGTGGTTAAC
445101 GCACCTGATTGTGGATCAGGCATTCGTGGGTTCAATTCCCATCAGTCGCC
445151 CCATTAAAGATTCAAAGAGCAGCAGTTAGCTGCTTTTTTTTATTAGCTAG
445201 TTTAGTGGAGTATAAACACTATCCAAGAAATTTAAAAAATCAACACTAAC
445251 TCTTACTGCGTGTTGTTTAATTCCATAAGATTTTTGTGATCTTTGAACTG
445301 CTGGTTGAGAAGATTGTGGTGAAGTAGGAGTAGTATTTTGTCCATTACCA
445351 CTACTTGAGTCACCACCTGAACTGCCATCACTACCGCCCCCTTCACCACT
445401 TGAAGCTGGTGGGGTTGAATCACCCTGACCTGATCCAGGTGCATTAGGAT
445451 TTGTAGAGTTATCCARACCATAAAAATTAGCTCTTATCTTATTAAGGTTA
445501 TCTTTTCTAAAAGCAATCACAATTGCTTTAGTTACATCATTACCAACTGT
445551 TTGAGCATGCACATTTGATTGATTGATTAAGTTAGCTACATTACCACCAT
445601 AAGTACGTTGAATAAAATCAACTATTTCTCTATAGCGAACTGCAGAAGCA
445651 TCTGATCTTCTTAACTTATTGGAATTGTCTTTATCTTCTTGACTTGCAAG
445701 TTCGTTTTTTCTATCCACAACAGGAAAACGTGCATATGGGTTTCACTTTA
445751 CTGAACCAGGAGCAATATCATTCCAAATTAAAAATTTAACTCCGTTTGGA
445801 TAAGTAGAATAACGGTTTTGCACCTGTCTGATGGTGGTACCCAAGGTACC
445851 TCCTCAACTAAGAGAACTTGTACCTTGATTAGTAGAACCGTTTAGAAAAT
445901 TAATTTGGGAACTATCTGTTTCGGTTGCAATAACAACCACATAATTACCA
445951 TCGTTATATGATCTGGTTCCAAAAACTAAGTTTCTAAATGTTGTACTGTT
446001 AACAGGCAATTGGTTGTAAGCTGTATTTTTTCCACACTTTCAACAGAAA
446051 GTTCACGAAAAAAAGACTGATCGATGTTACTACAAGAACTTAAAATCATT
446101 CCTGTTCCTAGTAATAAAACTAACCATGCTTTTTTATGTTTTAGATTTCA
446151 AAAAAGACGCTTCATTTCTAAATTGACTGGTGTCGGAGACCAGACTTGAA
446201 CTGGCACAGTCTTTAACGACCACAAGCACCTCAAGCTTGCGTGTCTACCA
446251 TTCCACCACTCCGACTATTTGCTTGTAGTTAATATTGTTTATATTAATAA
446301 AAATTTTAATACAAGAGTTAACAAGGCTATTAGCTTGTACTAGCTTAAAC
446351 TAGGAATATAAAGGTGTTATTTCAAGCTAAATTCCCGCTTTTTTCTCCTT
446401 AAATTCAACTTTTTTTATCCGATTATTGGTAAATAAATCAGTTTAAAAAG
446451 TTATTAACAAAATGTTTATAAGTCTCAAAAAAGGGTTGTTTTAGACTGTT
446501 TTTAATGTCAATAAGTTGTAAATAAATGGCAGAAAAATCTTTTTTTAGCC
446551 TTTTAATGCAAAGTAATTTCAATAAATGGAGGATAGCGTCTTATACTCTT
446601 TTTACTTTTGAACGTATATGCAACCCAACTATTACCGTGTGATCAAAAAA
446651 GCAACATCATTTTCTGGATTAGAAATGATCTCTCATGCTTATGGTCAAAT
446701 TGCGGGAGTGGAAGTTGTTGGGTTTATTTATGACTAATAACAGAAGCTA
446751 ATATTCAGGCGTTCAACAGTGAAATTAGAACCCCCATTTCACGATTACAA
446801 AATGCCTTTAATCCTTTTGAAATTAAAAAAAACCAAGTCTCTGAATGGAT
446851 TTATAAAACTATTAGCAAATTAGAGAGTCTTGGTTTAGTGAGAACTTTTT
446901 TTTCACCAAAACGCTCTGAAATAACTTTTTGTATTATTGATCCTTTAGAT
446951 TGGAAAGAATTTAAGCAAAACAAACAATTAAAAGAAAAACTAGTTGAGGC
447001 AATGGGAAAAGTTGAATATGACCGAAACTGCTTAGCTTTTGATCAAATCG
447051 ACAATCTTCAATTTGATAATGCGCTTGAAATCTCTGCTAACTTTGAAGTT
447101 AATTTCACTGCAAACCAAAGCGATGTTTGATTTAGCTTTAACTTCGAGGA
447151 ACTACATAAAGAACTTGTAAAAAACAAACTTTTAATTTCTTTAGATGAAA
447201 AAGCTAAGACTTTAATTAATGGTTATTTTGAAAAATACAAGCTTTCATTG
447251 CAACAAATTACTGATTGCATCATCAACAGTAGTACTCAAGAGATAGCT
447301 TGATTTTCAAAAGTTAGAAATGATGTTTTTTCAAATAGTAAAAAATGATA
447351 CAGCTCCCATTTTAGAAACAGTTTCAAACAACAAAGACTTTTTTTATAAG
447401 AATGAAATTTTAGATGAATCAACAAAAAAAAGCAATAACAGACTGTCATGT
447451 AAACTTCAATTCTGAAAAATACCTTTTTCTTCTATATGGAAAGATAGATG
447501 AATCGCAATTGCAATTAGTTAGACAATTGAGAAGTGATTATCAACTATTA
447551 GATAAAGTAATTAATTTAGTATTAGACTTTTCCTTTTGAAAAAATAACGG
447601 AATGTGAAGAGAAAATACATTCTAAAAATTGCCCAATCCATCAAAATTA
447651 ATAACAGTCAAAACAGTTATGAAAAAACCCTTAATAATTTTATTAGAGCA
447701 CTAACTTTAAATAAAAAGCATTCTTTAAATAATATAAAACCAGTTGAAAA
447751 AACAATTTCCTTTACTGAGTATTTTGAATTTATTAAATAATGAAAATTTC
447801 ACCAGATCAAAAAGATAAAAAGTCATTATTTAAAAAACATTTTGCTTATT
447851 TGAAATTAACTGAAAAAGAACTTAATGATCCTAAGATACAAACACTTTTA
447901 GAAGTTGCGTGGAATCATTTTGATCAGTGTAGAAAAATTAAAGAAAGAAG
447951 ATGTAGTAATAAAGGTGTATATCCATCTTCAAGCTGTTAGAGAGTGGTTAC
448001 CTTGAGAATTTAACGCTAATCAACTTAAAAAAAAATAGTACAAAAGAAACA
448051 ACGCAAGTTAGTGAAAATGAATTTATGGGTAATGTTATGCTCATGCAAAC
448101 TATTTGTCCTAAATTAGTTAATAAAGCAAACTGATTTGATTTAACTTATG
448151 AGCGTTTTATTGTTACAAAACCAAACTGATTTAAATACATGGATTTGATT
448201 CCAATGATCCAAAATTTACCAGTAACTCCAAGTGATAAAAATAGTTTTGG
448251 TTATGCATACAAAAAGATATCTAATCTTTTTGAAACTGAAAAGAAAACAA
448301 AGAAAAGGATATTTTTTTCAATTTACAAAAGAATAACATTAACAATATG
448351 GCAGCTTGTATGTTAACTTGTGAAATAGCTAAGAAAAATATAAAAGTTGC
448401 TTTAATTTATTGTGAAGAATTTGTTAGCAGATATGACAAAAGTTATTGAA
448451 AGGTAGATGATGATTTAAATTTACTTGATGAGGCAAAAGTAATCATATTC
448501 ATTGGTTTAGGTCAGGAAAGTTTTCATAACAAAAACTATATCTTGTTTAT
448551 GACAAGGCTTTTTATAAATTGTTTTTTGAAAAGAAAAGATGTTTTCTTTT
```

-continued

The Nucleotide Sequence of the *Mycoplasma genitalium* Genome

```
448601 TTAGCACTACTTATAGTGATGGTAATGGATTAATTCAAACATTTAAAAAC
448651 CAAATTATTAGTAGTGCAAATTGAGTAAAACACTTTTTTGAACAACTTAA
448701 TGATTTATTAATGATTAATATTTAAAAATTACATTCTTTCACCAATAAAT
448751 AGCTAAGTTTATGTAAAATTTATCTTGTATTACCTGGAGTGGCGGAATGG
448801 TAGACGCGGTGGACTCAAAACCCACTAGGAAACTGTAGGAGTTCAAGTCT
448851 CCTCTCCAGGACCATAATTAAATACTTAAATTTACACTACGAAATTACAA
448901 GCTCAGTTTAAAGCTGAGCTTGTTTTATTTTTATAGTGATTTCTATTTAG
448951 CTAATGCTCTTTTTCAATAAAACTTTTGAAAGGAACGCATAATTGGCACT
449001 CCAAAACAACTAACAAGTCCAAATTTCACCAAATTAAAAAACGAATATAA
449051 ACAGAAAATTCCCAGCCAATAGTTATTAATTCCAAAGAAAAAGAAATGAA
449101 AATCAGTGTTCTTGTTATATTGTTCAGCAACTATTAAAAAGTTAGGTGTT
449151 TGAACATAACCAAAGTAGTATCAAAACAAAGGTGTTATCAAAATACCGTT
449201 AAGCGTTGTTAGTAATAAAGCATTGGATAAGGTTGTAAATAAAAACACAA
449251 AGATTCAACAAAATCTTCTTTTTGAAAATAAACAAAAATAAAGCCTTGTA
449301 AATAAGATAGTCGATAAGTTAGCTAAAGTTACAGTTAGAACACCAATAAC
449351 ATTATTAGTATTTCAAAAAAAACTAGTTAAAGCAGAAGCTAATGTAATTG
449401 TTAAGCTTCAACCTAGTGACACAAAAAAAGCACATGCAACTAAAAAAACA
449451 ACGGAAATATCAAAAGTTAGTTTTAGTTGTGAGAAAAAAGGAATACTAAT
449501 AAATTCACTAATTAATGATGTAATGATGGCCAAAGCAAGCATCATTGCAC
449551 TAAAAGTAATATTAAATAACTGATGGTATGATTTTTTTGGCAAAAAAACC
449601 AGTTTATTACCATTCATTATTTAAAAGACTCTTGAATTATTAGTTAATAA
449651 TAATATTTATTGATATGGACAAATTTTTAATTGATGTTATTGTAGAAATC
449701 CCTAAAAACAGCAAAATAAAGTATGAGTATGATCGTCAAACTGGTCAAAT
449751 TCGCGTTGATAGAATCCTATTTGGAAGTGAATCATATCCACAAAACTACG
449801 GTTTTATTAAAAATACATTAGATTGAGATGGGGATGAACTTGATTGTTTT
449851 ATCTTTGCAGATCAACCATTTTTGCCTGCAACAGTTGTGCCTACAAGAAT
449901 TGTAGGAGCACTTGAGATGATTGATGATGGGAAATTGATACTAAGTTAT
449951 TAGGAGTTATTGATTGTGACCCTAGATATAAAGAAATTAATCAAATTAGT
450001 GATTTACCTAAACATAGAATAGAAGAAATTCTTATCTTTTTAAAAACTTA
450051 TAAATTACTTCAAAAAAAAGACTGTAATTATTAAGGGTTTAAAAGATGTTT
450101 GTTGAGCTAAAAAAGAATATGAAATTTGTTTGCAATTAATGAAAGATTAT
450151 GGTCATTTATCAAAAGATCAATTTATCCAAAAAATGCAAATTCTTCATCC
450201 AGAACATTACCAAAAGTAAATATGATAAATGCCAATCGCGGAATGCTTTT
450251 AGAGACAATTGTTAATCAAACAATTGCTAGGTTAAAGGATCATCCAGATA
450301 TTTGACTGGAAAAGCGGTTCTTACCTATTAAGCCTATAGCTTTTCGTCAT
450351 GCTCATGTATCTGGCAACGTATCACAAAAATCAAAAACTGATTATTATGG
450401 AATTTACAAGGGAATGTATTTTGATTTTGAAGCAAAACAAACAAATAAAA
450451 GTAAATTTTCCAATTGCTCAAATAGCAGAACACCAATTAAATCATTTGAAA
450501 AGAATTGACCAAATTGGAGGAGTTAGCTTCTTGCTAATTTACTTTCAAAC
450551 TAAAGATCAAATTTTTGCATTTCACACTAAGGATCTTCTAGAAACAATAA
450601 AAAATCAAGAAAGCAAACAATTAAAAGGGAATTGATAGAACAAAAATCT
450651 CAGAAAGTTCCACTATTGTATCCTGGTATTATTGATTTAATTTCAATAAT
450701 TCAAAGCTTTAAAAATTATTAGTCTGCGTACTTTCAACGCACTTTAGCTG
450751 CAGTTTCTTTGATCGTTTTGCTTGGACTGTAGCGCACTAATGGTTTTGGT
450801 GGGATATGTCTAATCTCACCTGTTTGCATATCCTTCTGATAACGTGCATT
450851 TCTAATAGTAATCCTTAATTTACCTAAATTTTCAGGTAATATACAAACAC
450901 TTCTACTTACCAATTCATTTAGTAACAATGTGTTAAGGTATTTAAAGATT
450951 TCCTTAATTTTTTTTTCTTTTATACCAGTAGCAACTGCAATTATTTTATT
451001 GATTTCACTACGAGAAAGTGGCTTACTTGTATTTGATGTTTTTTCCATAT
451051 AATTATTTTTTAAAACTTTATTAGCTCTGTTATTGCTAAAAACAAAAGAG
451101 AAACAATTTAACGCATTCTATTTTATTATTGATTCAACAATTAAATTAAA
451151 ACACTTATAAAGTAAATTTTTAGACAATTATTTCTATTCTTAAGACATGG
451201 AACAAAACAATATTAAAGAACAACTTATTTCTTTCTTTAATCAAGCATGT
451251 TCTACCCACCAAGAAAGACTTGATTTTATCTGTTCTACAAGAGAAAGTGA
451301 TACTTTTTCTAGTGTTGATGTACCACTTGAACCCATTAAAAATATTATTG
451351 AAATAACTAAAGATGAAAATCAACAAATTGAAATTACAAAAATAGCTGTT
451401 AATAACATTAAAACATTATCTTCTGTTGGTGCAACCGGTCAGTATATGGC
451451 ATCTTTCTTTTCAACGAATAGTGAGCCAGCTATAATATTTTGCGTCATTT
451501 ATTTTTTATATCACTTTGGTTTTTAAAAGATAACAATAAAAAACAAATA
451551 ATAAAAAAGGCTTATGAAACTATTGCTGATAACATTGCTGACTATTTAAA
451601 TGAAAATTAGGTTTAAGACTTATTATTTTGTGTAATGGTAATATTGTCTT
451651 TAACAACTGCAATGTTGTATCCAACACCTTTTTTATCTTTCCCTGAAGG
451701 ATATATTTAGCTATTAAAGTTGCAACACTATGATCAATAAAGCGCTTAAT
451751 TGGTCTTGCACCCAAACTGTTGATCAAAACTACTTTTATAGATAAACTCTG
451801 TTAGATTTGAAtCAAAATTAAAAAATAAATTTTGTTTATTCAAGCGTTTT
451851 GAAAGTTGTGCCAACAAGCTGTTGATTATCGATAAAACTGTATCTTTCTC
451901 AAGAACATTGAAAAATACTATCTCATCAATACGATTTATAAATTCAGGAC
451951 GGAAATGTTTCTTTAGACTTTGAATGGCCAAATCTTTTTTTCCTTCTAAA
452001 AGAAAAATTTGAACCTAGGTTAGAAGTCATAATTATCAAAGTATTTTGAA
452051 ATTAACAACCCTTCCTTGTGAATCTTTTAAAGTACCATCATCTAAAACTT
452101 GTAATAAAACATTAGTTACATCAGGATGTGCCTTTTCAATTTCATCAAAT
452151 AACAAGACGCTATAAGGTTTTCTTCTAACCGCTTCAGTTAGCAAACCTGA
452201 TTGTTCATAACCTATGTACCCTGGGGGTGCACCAATTAATTTAGCTACTG
452251 AATGTTTTTCCATATATTCACTCATATCAAAACGAATCAGAGCTTTTTCA
452301 TTGTCAAAAAGAACTTCTGCTAATGATTTGGCAAGTTCAGTTTTACCAAC
452351 ACCAGTAGAACCTAAAAAGATGAAAGAACCAATAGGTTTGTTTGGGTCAT
452401 TTATATTTACTCTACCTCTAATTACAGTGTTAACAACAGCATCGATGGCT
```

-continued

| The Nucleotide Sequence of the *Mycoplasma genitalium* Genome |
|---|
| 452451 TCATCTTGTCCTTTAACTCTTTTTTTGATTTCATCACCTAAGTGCAAAAG |
| 452501 TTTATCCTTTTCACTTTCTAATAGTTTTTAAGTGGAATTCCTGTTGTTT |
| 452551 GTGAAATAACTTCAGCAATTTCATTTTCAGAAACTTCAGTTTTAAATAAA |
| 452601 TCGTGCTTAGAAGTTGCATATTTTTGTTGTGCACTTTCCAGTTCTTTTTT |
| 452651 AAGTCTTGGGATATCAGAGTACAGAATTTTAGATGCACTTTCATAATTTC |
| 452701 CTTCACTTTGGTATGTCTCTAGTTTGGTTTGAAATTCTTCAATCTCTTTT |
| 452751 TTGAGCTTATTAATGTTTTCAAAATCAGCCTTTTCCTTTTTTCATTCATT |
| 452801 TATAAGTGAATCACGCTTTTGTTTAAGAGCATCTAATTGTTTTTTTAGTT |
| 452851 TCTCTAAATATTCTTTCTTTGATTGTTTGTTATCATTTTCCTTATCTTGT |
| 452901 TTAAGAGCTGCATACTCTGTCTCAAGATTGATTATTTCACGTTTAAGACT |
| 452951 ATCTATTGCAACTGGTTCAGATGACATTTCTGTTTTGATCTTAGCAGCAG |
| 453001 CCTCATCAATAAGATCAATGGCTTTATCAGGTAAATTACGTTCATTAATA |
| 453051 TAACGAGTTGACATTTCAACAGCAGCTACTAAAGCACTATCAAAAATAGT |
| 453101 GATGTTATGAAAGAGTTCTCAACGTGTTTTTAAACCACGCATAATTGTTA |
| 453151 GTGCCTCTTGACTACTAGGCTCGTTAATAAGAATTTTTTGAAATCTACGT |
| 453201 TCTAAAGCGCCATCTTTTTCAATGTATTCCCGGTATTCTTTTAGAGTAGT |
| 453251 AGCGCCAATTACTTTTATTTCTCCTCGAGCTAGCATCGGCTTTAATATAT |
| 453301 TGGCAATATCCATTGCACCACTGCTAGAATTACGTCCTAATCCAACTATT |
| 453351 TGGTGAATTTCATCAATAAAAAGaATAATCCTGCCATTTGAtTCTTTTAC |
| 453401 TTGCTTAAGAATGGTATTAATTCTTTTTTCAAATTCACCTTGGAATTTAG |
| 453451 TGCCAGCAATTAATCCAGAAAGAGATAGTTCATAAATTTCTACATCCCTT |
| 453501 AAATTTAAAGGTACATCATTACTAACAACTCTTCTAACAAAACCTTCTAC |
| 453551 TATTGCGGTTTTACCAACTCCAGGTTCACCAATTAAAACAGGATTGTTTT |
| 453601 TGCTTTTACGACTTAATATCTCAATTAAACGACGAATTTCGTTATCTCTT |
| 453651 CCAATAATAGGATCGACCTTATTTTTTAATACTTCATCGTTAATATTACG |
| 453701 ACCAATTTCTTGCAAAAAATTACGATTTTCACCAGCAGGTGTGAAATTAA |
| 453751 TATTCATTTTAATTGCTCACTCCTTTTAATGCAAAAATTATATAAAATTA |
| 453801 GCACTCAAGGCATTCGAGTGCTAATTAAAAACTAGGTTTTTTGTTTATCT |
| 453851 CTAATTTATCTAATCAGAGTTGATATTTTTGTCAAAATAATTAGAAACCT |
| 453901 AAAATAACTATTAACTATTTTTTTGTGCTTGTTTTCAAATTGAGGGAAAT |
| 453951 AATGCTTTTAAAAAGTATTCTAATCGTTTTTCAACTCATTTTCGATAGTT |
| 454001 TAAAATTGCTTCTGTTTGGGGCATAATCTCAGTTCATTGAAAAGCAAATA |
| 454051 ATAAAACATAAATAACTGTTTCAAAAACAAGCTTACGCTTAAGTCCACCA |
| 454101 TAAATATCAATAAGTTTATTTGCTGTTTCTATGGTTAGTTCTTCACGAAT |
| 454151 AATATTAGCTATTTCATAATAAGGATTATCAACACAAGATCATTCAAAAT |
| 454201 CAATAAGGATTACTTGCTTTTTAGGTGTTCAAACCAAATTATCAAAAGTA |
| 454251 GCATCATGATGACAGAGAGTTTTTGGTATGTCAATATGCTTCTTAGTTAA |
| 454301 ATTAAGATATAACCGTTTATAAAAAGCGGAAAGCTTAGTTTTTTCAAAAT |
| 454351 AAACCAAAGGATCAAATATTAAAAGTTCATTAGCAAATGGTTTTCAGTCA |
| 454401 ACTGAATGAACTTTTTTTAAAGATTCAACCAATCTGCATAAAAATAGATC |
| 454451 AGTTGCTCTTTTAGGTTGAGTGCCTTCTATCCACCTTTTTATAGCATTAC |
| 454501 CTGTTGTTACATCAAAATAAACAAATGGGTTTGAAAAAAAAGGTTCTACT |
| 454551 AGTTGCAAAATAATTTGTTCATTTCTTCTGTCTAAAATAACATCTTTTCT |
| 454601 TGAAAGTCTTATTTGAAATTTACTATGATCTTTCAATTCACAAAAAAAAG |
| 454651 AAAAATTAGTAAAACCAGAATGAATTTGCTCTATCTTGAAAATATCTGTT |
| 454701 TCTACAACTTGAAGTTTTTCACAAAGAAAAGCAACCGCTTTTTTTAAATC |
| 454751 CATTAATTTTGATGATTATTTTTTAATGTTTGTACTTACTCTCAAAGCAT |
| 454801 CTTCTACAATCATCAATTCCTCATTTGTACGAACTCTAAAAATTTGATAC |
| 454851 TTGCTTTCATTTGTTGAAATTAGAGAACTATCTTGATAATTTCCAAATAA |
| 454901 ATTACTGTTAGTTTTAAAACCAAGTGAAGCAACTTTTTCAATTATTAATT |
| 454951 GCACACAATAACTAGCATTTTCACCAACTCCCCCAGTAAATACCAAGCTA |
| 455001 TCAATTTCACCTGAAAGTTGATTTAGGTATTTAGCAATATAGTCAGCAAC |
| 455051 ACGATTAACATACATTTTTATAGCAATATCATTAATTTCTGGTTTATCAA |
| 455101 AAATATCACGCATGTCAGAACTACCTGTTATAGCAAACATTCCACTCTTT |
| 455151 TTATTTAATTCATTTACAACATCATTACATGAAAGCTTTTGCTGTTCAGC |
| 455201 AATGTAACTAACAATGGCAGGATCAATATCACCACTACGTGTTCCCATTA |
| 455251 TTAATCCTTCAAGGGGAGTGAATCCCATCGATGTGTTTAGTGATTTGCCT |
| 455301 TGTTTAATCGCACAAACACTTGCACCATTACCAAGATGACAAACAATTAA |
| 455351 ATTAAGTGGTTTTTTATTAAACTTTTTTTCTAAAAACTCGTTAATGTATT |
| 455401 TATAAGAAGTTCCATGAAAACCATATCTTCTTACTAAGTTATTTTTCTCT |
| 455451 CAATTTTCAGGAACTGCATAAAGATAATTTTCCCTTGGAATAGTAGTGTG |
| 455501 AAAAGTGGTATCAAATACAGCAACATTCTTAGCAGTTTTTATCTCTTTTA |
| 455551 GAAAAATTTCAATAACATCTGCTTCTGGTTTATTATGAAGCGGTGCTAAC |
| 455601 TTAATGAATTCTTTTATTTTTGCTAGTGAATGTGTATCAACAAGAACTGC |
| 455651 ATCTGTAAAATAATTTGCTCCTTGTACTACTCTATGCCCTATTAGCCCAA |
| 455701 TTTCTGAAAGTTCAGTAATAATTTtGTTTTTTTTAAGCGCATTTAAAAAA |
| 455751 TGCTTAACAGCAAGATTATGATCATTAAATTGAACCTTTTCTTCTATCTT |
| 455801 TTTTTGATTAAATTCAAGCTTAAAAAAACCATCAATGAAAATACGTTCAC |
| 455851 AAAGTCCTTTAGCTAGTACTTGTTTTTTATCATTAAAAAGTTGAAATTTA |
| 455901 ATTGAACTGCTACCTGCATTAACAACCAAGATTTTGTGACTTTGCATTTA |
| 455951 ACCGAAGAATATTTACCTTATTTATTAAAAAATAATACTAAATTAATATA |
| 456001 GTGTGGAATAATTAAATGTTTTAACTAAAAAGAAATATTATTAAATCTTA |
| 456051 AACAATGAAAATTAAAAAATGCTATATTATCGCTGTTATTTCAGCTTTTA |
| 456101 TTGGTTTTCTTTTTTACTTTTTATCTTCACTTATAGGGATAACAGATGTT |
| 456151 AATAATGCAAAAACAGTAGCAACTGTATTTTTTGTATTAGCAACATTAAT |
| 456201 AGTTGTTAATGCTATTGTCTTCTGGATTCTTTATCTATTCAAAAAAAAGA |
| 456251 ACGTAGTTAAGTAAATTTATTTGTCACTAATAGTTTTTTAGCACATTAAT |

-continued

The Nucleotide Sequence of the *Mycoplasma genitalium* Genome

```
456301 TTGATAGAAAACAAATTGAATGTAATATGGAAACTATCAGAGAAACACTT
456351 TCTTCTATACAAAGAAGCAATTTTTTATTAAATGAAAGCGCACAAATTCT
456401 CAATACGTGTGTAAACAAGAACACATTGCTTGACGATAAGCTGCGCAATT
456451 CGATTAATTTTGCACTTAGCATCATTAAGCTAGCAGACTTTTGTCTAAAG
456501 GATGATACTGAAAAAATTAATCAATTCTTAGGTAAAACATATGATTTACC
456551 ATGAGAGTTTCAATTTAACCAAAAAGACAAGCATATAGAATGCACTGTCA
456601 AAGACAATTTTGGTCGTGAGAAACTAATAAATTTGATTTTTCAAATTGGT
456651 GATGCTATTGAAACTTATCATACTACTTTAATAAGATTCAAAATTCCCAA
456701 GCATTGTTTGAATGCAAGGGATCAAATCAAAAAAATAATGGAGGGCAAAT
456751 AAAAATGATTACATCTATCTTTGGAAAAGTTACTTTTGTAGGCAAAAGAA
456801 AAATAATTGTTGAGCACAACTGGATTTCATATTGATTTAATACAAAAGAA
456851 AACCATAAATTTGAAAAAAATTTGGAAAAAAATAAGCAAATTTTTTGTCA
456901 TATTATTAAAAAAATTGTCGCTAACCAAATTATAGAAGAGGCTTTTGCCT
456951 TTAATACTCTAGAAGAAAAAGAGTGGTTCTGTAGATTAATAGAACTCAAT
457001 GGTATTGGTAGTAAAACTGCACTTAATTTGCTCAATAATGACCTTGAGGA
457051 AATTAAACAATACATTCTGGAAAATAACTACAGTGCATTATGTGGTATTA
457101 ACGGTGTAAATAACAAAATAGCTCGTGCACTTTTATCACTTGAAATATTT
457151 GAAAAATCTGAAAATAATAAAAATATTAAAGGAGTTCAAGTTGCTGATGG
457201 TTATGATGAATTGTTTGAAACACTAAAGTCACTTGGTTACAAACAACAAG
457251 AAATTCAGGATGCACTAAAAATGATAGAAGTAAAACCTGATTTTGATATA
457301 AGTCAGTTAGTTGCAGAAGTAATTAAATTAATGTCTTTTAAGAATAATGA
457351 AATTACAAATAAAACCGCCTAATACCTTTGATGAATTTGTAGGAAAACAA
457401 GAAATAATTAGTCAAATTCAATTAAGTATTAAAGCATCTAAATTAAATAA
457451 AACACAACTAGATCATATCTTGTTATATGGCCCACCTGGTGTGGGTAAAA
457501 CTACTTTAGCCAGATTAATAGCAAATGAATTGAAAACAAAGTTGCAAATT
457551 ATTCAAGGTGGACATTTACAAAAACCAAGCGATTTCTTAAACGCAATTTC
457601 ACTCATTAAAAAAGGTGATGTTCTTTTTATAGATGAGATCCATGCCGTAG
457651 CACCTAATGTCATGGAACTAATGTATCCAGTTATGGATGTGTTCAAAATA
457701 CAAGTATTAATTGGCAAGGATTTTAATTCCAAGATAGTTGAAATGAAGGT
457751 AAATCCTTTTACTCTAATTGGTGCAACTACACAACTTGGTAAAATCATCA
457801 ATCCTTTAGAAGATAGATTTGGCGTTATCTTAAACATTAACTATTATTCA
457851 AATGCTGAAATTGAAAAGATGGTAAGTATCTATGGAAAGCAAATGAAGTT
457901 AGAGCTAAATTCAAATGAAATTTCAGCTATCACTGAACATAGTAAACAAA
457951 CACCAAGAATTGCAATTAGAATAGTTAGAAGAATATTTGAACAAAAAATT
458001 GTTAATAAAAAAATAGACCTTGAGGGTTTGTTTAAGAATTTAATGATTTA
458051 TAAAAATGGTCTGCAAAGTATTGATGTCCAATATCTTGAGGTTTTAAATC
458101 GCCAAAATGAACCACAAGGAATTAAGTCAATTAGTTCCATGTTAGGTATA
458151 GACAGACACACTATAGAAAATAAAATTGAACCTTTTTTGTTGCGTGAAAA
458201 TATGATTCAAAAAACCAAAAAAGGCAGGATTATTACAAATAGCGGAAGAG
458251 AATATTTAGTTAACTTTTAAGCTTATTAGCTCTTTTAATAATTTCAAAAC
458301 CAAAACTTTCATTAATATCAAAAATTAATTTATCAAGTGAAGATCTTCG
458351 CTTAATTTGCTAATTGATTTTGGTATGAATTGATAAAATAAAGATTTTTT
458401 CTGTCCTTCATCTGTATCTATCTTTTTTAAATCAAAAAAACTAATACCTA
458451 TTAATCGAACGTTCTTTTCAGTATTAATTAATAGTCTGTTGAATAATCGT
458501 TTTGTTATTGACAGTAGTTTTCTATAATCGTTTGAATATTTTTTCATTTT
458551 ATTTGAATGAGAATTAACAATAAAATCATTGCTTTTCAATTGCACAACTA
458601 TCCCTTTACACACTTGTGAAGAGAGTTGTAATCTTATAAAGAGCTGATCA
458651 AATATTTGCGTTAACTTTTTATTTAACTGATTGTTTGAATAATTTAAATC
458701 TTCTAACGTTTCACTGACTGCAAAAGAGCGAGACTTAACCTGATTGTTAT
458751 TATCTGTATATCATTTGCCTAGTGAAACTGCTTTTAAAGATTCTCAAAAA
458801 TTACCAAATACTTTTTTTAAAAGCGAAGCATCTTCACAAACTGCTAGATC
458851 ATTTATTTTGTAAAAATTATTTTTAAAAACTAAATCAATATGTTTTTCTC
458901 CTATCCCTGGAATTTCAGTAATTGGTAGTGGTCAAAGTTTTTTTTTAATA
458951 TCCTTAACTGAACAACTTTTAATTCCAAATGGTTTTGCTTGATTGAAAA
459001 AATCTTAGCAATTAAAAAATGATCTGAGATGCCAATTGAAATTTTGATTC
459051 TCAAGTTTTGAAAAACAAAATTTTTTATTTTTTTCGCTATTAAAAATGCC
459101 TTTTTAAATGAAATGTTTTGAAAACAAGCAACCCCTTCATCAACAGAAAG
459151 AACATCAATTTTTAATGAAAAAGTGCTTTCAATAACTGAAAAAATACGTT
459201 TAGAATGTTTTCTGTAATTACGAAAATTAGAATGTGCAAAAATAGCATTT
459251 GGACATAGTTCTAATGCTTTTAAAATAGACATTCCAGATCTAATTCCATA
459301 ACTACGAGCAACATAGTTACAAGTTGAAACTACACTTCTTGAAAAGCGAT
459351 TACCAACTATTAAGGGTTGATTAACTAATTCTGGATTTTCTAATTCTTCA
459401 ACAGATGCAAAAAAAGCATCAAAATCAAAATAAAGAAAAATTAAATTTTT
459451 ATCAATTAAATATTCTGGTTCAAAATATGTAAAGGTGTTAATCATATTTA
459501 TCAAGTTATGTTATTATTTACTTGCAATAAAACCAAAGAAAATAACGAGT
459551 TTTTAACTTTAATAAAGTTATCGAGGATTTATCATCGTTTGTGCTATTGC
459601 GAATATTGTAGTTAATGGTAGATAGTAAGAAAAATAAAAAACAGCAGGTT
459651 ACGGATTTTTCTAATTTACTCTCTCAAAGTAAAGGATTTGTTATTTTTGA
459701 CTATTCAGGAATGTCTGCTGTTGATGCAACTTTAATGAGAAAAAAGTTGT
459751 TTAATAAGGGTAGTAAGATAAAAATTGTTAAAAACAATATCTTAAGACGT
459801 GCTTTAAAAACTAGTAATTTTGAAGGTGTTGATGAATCGGTCATCAAAGG
459851 AAAAATTGCAGTTGCTGTTGGTATTAACGAGATCTTAGAAACCTTAAAAG
459901 TTGTTGATAGTGTAGTTAAAGAAAAAGAGTTAATGAAATTTGTTTGTGGT
459951 CATTTTGATAACCGTATTTTTAATAGTGATGACTTACAAAAAATAGCAAA
460001 ACTCCCTGGTAGAAATGAACTTTATGGAATGTTTCTTTCAGTTCTACAAG
460051 CACCATTACGAAAATTTCTCTATGCTCTTCAGGCAGTAAGGAATGCTAAG
460101 TAAATTAAATAAATAGaAAAATATTATGGGAAAACTAGATAAAAACAAT
```

-continued

| The Nucleotide Sequence of the *Mycoplasma genitalium* Genome |
|---|
| 460151 TAATTGAATCTCTAAAAGAGATGACTATAGTTGAAATTGATGAAATAATC |
| 460201 AAGGCTGTTGAAGAAGCATTTGGTGTAACTGCAACTCCAATAGTAGCTGC |
| 460251 TGGCGCAGCTGGTGCTACACAAGAAGCTGCTAGCGAAGTTAGTGTAAAGG |
| 460301 TAACAGGATATGCTGATAATGCTAAGTTAGCTGTTTTAAAACTTTATCGT |
| 460351 GAAATTACTGGAGTTGGTTTAATGGAAGCTAAAACTGCAGTTGAAAAATT |
| 460401 ACCTTGCGTTGTAAAACAAGATATTAAACCAGAAGAAGCAGAAGAaCTTA |
| 460451 AAAAGCGTTTTGTTGAAGTTGGTGCAACTGTTGAAGTTAAATAAAGATGG |
| 460501 CAGTACAACAACGGCGTTCTAGTAAACACCGTCGTGATAAAAGACGTTCT |
| 460551 CACGATGCACTTACTCTACAAACTTTAAGTGTTTGTAAGAAATGTGGTAA |
| 460601 GAAGAAGTTATCACATCGTGTGTGCTCTTGTGGTATGTACGGTGAACTAA |
| 460651 GAGTTAAAAAAGCTCACTAATTCACAGATAAATATTATTGTTTTTTTGCA |
| 460701 GTTGAATTTGTATTACTTTTATGCAAAATAACAGCATTTTTTGATTTTAA |
| 460751 ACGCTTAGCTCTGTTTAAAGAAATAATCCCTTTTCTGGCTAAACGATCTG |
| 460801 CTTGAGAATAAACAGAACTGAGATTATCTAAATTAATCTCTTTATTAAAT |
| 460851 TTTTTAACATTAGTTTTTAGTTTAGTTTTTTGTCCTTTATTATTTAAATT |
| 460901 TCTCTTAATGTCTTGACGTAATCGTTTTTCGTTAGATTTAATATTAGCCA |
| 460951 TTTAGGTTATTAATTAGTTTTAGAGTATATTATTATCTTGATTATATTGT |
| 461001 AACTAGAACCATATATGGATGGTGGACAACAAGGGAGTTTTTTTGGGCTT |
| 461051 TTAGTAATTGTTATTCCAATAATTTTGTTAATTGTTTTTTTTTCCAAGAA |
| 461101 AAAAGGGGCACAAAAAAATGATTTTAGTGGTGAAGGAGGTAATCGATCAT |
| 461151 CAAGAAAAGATGAAGTGTGAAAAACAATTAAACAGTTTTTGCAAGAAAAG |
| 461201 AATGAACGTGGTAAAGAAATTATTAAAACTTTTGTAGCTAAAAAACCAAA |
| 461251 CCCTTTACATTCAAAAAAAGACCGCAAGCTTTTCAATCAAGAGATACAGG |
| 461301 CATATATTACTAGTAATAACTTAGGAAAAAGCGAAGCAAAACGTTATAAA |
| 461351 AATGAGCAAACTCGCTTAATGCAAAGAGAACTTTATTGTATTTATTTTGT |
| 461401 TACAAAAGATGCTAAATCAACTGAAGTTGATGATGCTAGGATTATAGAAG |
| 461451 CTGAGGTTTATCAAAAACCTACAAAAACCAAAAGTACTCCAGAGCGGCTA |
| 461501 ATTCGTATACTTGGTTTAAAAAATTTTGAAACTGAAATGCAATGAATTCA |
| 461551 ACCATTAATGGTTCGTGAAGAAAAGAGAAAAGAAAAAGAAGAACAGAAAA |
| 461601 AACTTAAATTAGCTGCAAGAGAACTAAAAAAGAAGAAAAAGAAGAAAATA |
| 461651 AAAAAACCAAAAGAAATCAGAAATCAGAAAAATGTTTAAAATTGTTTTCT |
| 461701 TTGGTACTTCAACGCTTTCAAAAAAATGTTTAGAACAACTTTTTTACGAT |
| 461751 AATGATTTTGAAATTTGTGCTGTTGTAACTCAGCCAGACAAAATTAATCA |
| 461801 TCGTAACAATAAAATAGTACCTTCTGATGTTAAGTCTTTTTGTTTGGAAA |
| 461851 AAAACATAACTTTTTTTCAACCAAAACAAAGCATAAGCATAAAAGCTGAT |
| 461901 CTAGAAAAATTAAAAGCTGATATTGGTATTTGCGTTTCATTTGGTCAGTA |
| 461951 TCTTCATCAAGATATTATTGATCTTTTTCCAAATAAAGTAATTAACTTAC |
| 462001 ATCCTTCTAAGTTACCACTACTTCGTGGTGGTGCACCATTACATTGAACC |
| 462051 ATTATTAATGGTTTTAAAAAATCTGCATTGAGTGTAATTCAATTGGTTAA |
| 462101 AAAAATGGATGCAGGTCCGATTTGAAAACAACAAGATTTTTTAGTTAATA |
| 462151 ATGACTGAAATACTGGTGATTTAtCCATATATGTAGAAGAACATTCACCC |
| 462201 TCTTTTTTAATTGAATGTACTAAAGAAATTCTCAATAAAAAAGGGAAATG |
| 462251 ATTTGAACAAATAGGTGAACCTACTTTTGGATTAAACATAAGAAAAGAAC |
| 462301 AAGAACATCTTGATCTTAATCAGATTTACAAGAGTTTTTTAAACTGAGTA |
| 462351 AAAGGTTTAGCTCCCAAACCTGGTGGTTGGTTAAGCTTTGAAGGAAAAAA |
| 462401 CATCAAAATTTTCAAAGCTAAATATGTTAGTAAAAGTAATTACAAACATC |
| 462451 AATTAGGAGAGATAGTTAaTATATCTCGAAAAGGAATTAATATTGCTTTA |
| 462501 AAAAGCAATGAAATTATTTCAATTGAAAAAATTCAAATACCTGGAAAAAG |
| 462551 GGTGATGGAAGTAAGTGAAATAATAAACGGAAAACATCCTTTTGTTGTTG |
| 462601 GTAAATGTTTCAAATAGAATGATTACAAAGAGTTTTTTCCTTAAAAATTT |
| 462651 TGATCGCTCTAAAGAATTAATTCCTCTTTCTATATAACGATGTTTTTAGCG |
| 462701 CTGTTAATCAGTTTCTGAAAAGCTATACTGACGTTAATGATATTGATATT |
| 462751 ATTGAAGAAATTTGATTGAAGATCCAGTTTTTTGAACTTGATGTTTTAGA |
| 462801 ACTTTTAAACGAGGATCCAATGCTATTATTGGACAGTAAAAATCCCCGTG |
| 462851 TTCAAGAAGCTAAAATTATTGCTAATAAAGCAAAAAAAAAATATTAAAGAT |
| 462901 TATTTTAATCTTCCCATTTTTTTTGATACAGATAGTTTAGATAAAAATGT |
| 462951 TTCTGTTTATCAAAAAGCTGAGCTTACTGAAAAGAAAATTCAAGAAATAA |
| 463001 TAACATCAAAAAAATCAGCTATTATTTTTAAACCTATTTTTGAAATAGAA |
| 463051 GATTGCTTAATTCAACCAGATGCTATTATTGTTCATGAAAAAGGACTTTG |
| 463101 TGAATTGTTGTTATAAAAGCTACAACCAATACAAAAAGAAAATATTTTT |
| 463151 TGGAAATAATTTATGACTTTGTGTTATTAAAAAAATAGGTAAGTATAAA |
| 463201 CTTTTAAACTATTATTTTTGTACTGTTAAATACGAATTACAAAATAAAAA |
| 463251 TAATGTTTCTTTCTTTTTAAATACTGAAATAAAAACATCAAAAAACAGTT |
| 463301 TTAGTTTAAGTTCAAAAGAAAAAGATTATTTTAAGAATAAACCTTTTAAT |
| 463351 TGGTTTTTTGATTGTAAAACTCATTGATAACCTTATTAAAAACAATATAG |
| 463451 TTGATTTAAACAAAATAAGTGATTTTGTTACTAAAGAAATTGACAGTAAA |
| 463501 AGTGTTCGTAATATTCAACCACTTATTAAAAATGCGGCTAAAATACAAAT |
| 463551 TAATTTTTGAGATCAAATACAAGATATAAAAAAAATATCAAGAACTCAAAA |
| 463601 TAAATCAAATTGTTTTTAATTACAGTGAAAATTTTGATTCTTTTTGGAGT |
| 463651 AACTATTTATTAAGAAATTTAATTAAATTAGTTTTTGCTCATAAATACAA |
| 463701 TGAAATTTTTAAATTATCTGGTAAATTAGCTAATTGAAGTCaATTAACAT |
| 463751 ATGCATATAAAGAAAATAAATCAATaACTATAAATCAACTGCTTCACGAA |
| 463801 TTAAATCAGAAAAAAAGCAAGGCTAATTTTAATAACTCAACTAATAAAAT |
| 463851 AAGTTTTTTTCTTGAAGCGTGAAATAGTGAAAAAGGTTTTGCAATTGGCA |
| 463901 ATAAATTTAAAAATACTTGAAATAAACTTAAAAAAAAGAAAGTTTATTTT |
| 463951 GATTTTGAAACAATTAGTTCATCAATCAGAATCATAAATAATTCATTACC |
| 464001 ATTTAGTCAAATTGTTACCCAATGCTCATTAATAGTTGATAAAAATGAAA |

-continued

The Nucleotide Sequence of the *Mycoplasma genitalium* Genome

```
464051 TAGATGATAAAAGAAAACTTAATTGTGAAAATCTAATTTTTGATCCCTTA
464101 TTTATTAGCGTTAATGACTTTAAAAAAGTAATTGATTCACTCTATCAAAA
464151 CAATTGCAGTGATTATAGTTTTGTTGTTTTAATAAATCTTTTGAAAAAA
464201 ACAGATTATTGGAAATGGCTACATTGATTAATGAACAAATATATAAAGAA
464251 AAAGTAAAAGCTATTGTTGACAATCTTTTTGACTTAGCTGATATTTTTAC
464301 TATTGAAAATAACTGTTTGGCTTTCAAACAGCTAAACGGTTTTTCCTCTA
464351 TCAAAAAGGTTTTAACTATTATAGATGAAAGCTTTTTAAAGGCAAGTAnA
464401 TCAATTGGTTATCAAAATTTAAAAATCCAAAAAGGTGATGTAGCACAAGA
464451 AGTTGCTTTATCGCGTTTTCTAAATTGCTTAAATAAAAATGAATGAAATC
464501 AAGTAGCTTTTGAATTAAAAAAATATTGTGAAAATGATGTCAGAGCGATG
464551 ATTTCAATTGTTTTATTTATCCAAGATTTAATCAAAAAAAATGATCTATT
464601 TACTTTTTATTCAGAAAATTAGAACCTGCTTTTCTACTATTTCACCTAAT
464651 TTTTTTTAGGTTTAATAGCTAGTTTCTTACACATCTTTTGATTTTCTATC
464701 TTCTCTTTTAAATCACTAAAAAAATGGCTTCCTTTACTACTTTTTAAAAA
464751 ACTTGTAAAAGAAGCCATTGCGTTGTGCTCTAAAACACTTTTATCATCGT
464801 AATTTTTGTTATTTGGGATAGCTTGTGATCAAATAATATCACCATCAAGT
464851 TCAATTATACTAAGTACCAAATTATTTGAAGTTAAGCTTACCCTAACTCT
464901 TGGTTCAGGTAATTTTTGCTCTTGAAAAAGTGAAAAGAAATCGTATTTTA
464951 AAATCTCAGAAAAAGTTCTTTCAAAAATATATTTTTCAACAAATTCAGTT
465001 GCTTTTTTCATCCCCATATCTTCATAAATGGCGCCAACCAAAGCTTCAAG
465051 TACATCACCAACAGTGTTTTCAGTTAGTTCAGCACCATTGCTTAACTTAA
465101 CAAAATCACCTAATTTTAGCTCCATACCAATACGATTAAGATTTTCACCC
465151 TTAACAATTTCAATCTTAGTTCTTGTTAAAAGACCTTCGTTATATTTAGG
465201 ATAAAGTTCAAATAGTTTTTTAGCAACAACAAAGTCAATTAAAGCATCAC
465251 CTAAAAACTCTAAGCGATCGTAACTTTCACTAACATCTTCATGTTCATTG
465301 ATGTAAGAAGCGTGAATAAAAGCTTTTTCAAAAAATTCTCAATTATTAGG
465351 AAAAATATCTAAATTCTTTAAAAAAGTTGCTAGTTTTTTATCAAAAATCT
465401 TATTATTTTTTAGTTTCAAAACTTTATTCTTCATAGTTATTCAAGAAGT
465451 TTTAATTGCATTAATAAGATCAGATTTTAAGCTTAGATGTGCTAATCTAA
465501 TCGTGCTTAAAAATTGTTGTTTATCAGCAGAACCGTGAGTTTTTAAAGCT
465551 AATTTATTTAAACCCATTACAACAGCTCCAGCGTTATTTTTGTAATCAAA
465601 TTTTTTGGCTACACTTTTGATAATACCTAAGCTAAATAAGCCAGCAAGAG
465651 GATTTCTTTTATAACCCCTCTTAAGAATCCGTGCTATCGTTTTAAAGTA
465701 CCTTCCATTGCTTTTAAAACTAAATTGCCGCTATATCCATCAGCTATCAA
465751 AATATCACATATTCCATCCAGTAAAAACCTTGATTCCACAAATCCTAAAA
465801 AGTTAAGATTTTTATCAGCTTTTAAAAGCTTAAATGCTTCTTGATGATAA
465851 TCAAAACCTTTATTTTCTTCTGTTCCTATATTCAATAGTCCAATTTTAGG
465901 AGTTTTTTTGTAGTTGTTTTTTAACAAAAATATCAGCCATTAAACCTA
465951 AAAAATAAAGTTCTTTTCCTGTGAAATATTTATTAGCTCCAACATCCAAA
466001 AAATAAAACCAATTATTGTTATCTGTCGGTACATAAGACATAAAAGCACT
466051 CTTAGTATTTTTATTAATTTTGCCAAAAGCATCATTTGTTAAAGAAGCAT
466101 AAACTGCTGAAGAGCCTGCTGAAATTACAACATCAGCATTACCTTCACGA
466151 ACTAAGTTTATGGCTATTTGCATTGAACTGTTAACTTTTCTTCTTGCACT
466201 TAGTGGAGTGTCGGTCATTTCAATGAAAGAATTAGCAAGTTTTTTTGTAA
466251 TATTTTTTGGAAGTATATCAAGACCATCAAAAGCCTTTTCATCACCGATC
466301 AGAATGAAATTTAAGTCCTGATGAAAACTCCAATATTTCAATACTGCTTC
466351 AATTGCTTCACTAGGTTTGTTTTCAAAACCTAAACAATCAACTGCAAATC
466401 TAAAAGCCATTACTGTATGCCTATTATGTAAGAACACTTTTTGTTCTC
466451 CAGGTGAAAATTCACAAAACAATTTATATTTTTTTCAACTAAAGCTTGC
466501 ATTTTTTTCGCATCTTGTTCAGTGATGTCTTTGCCATAATAAGCCAAAAG
466551 GAACTCAGGTTTTTTCACTTTTTTTGAAAGGTATATCAATTGTTTTAAAAA
466601 AACAGTCTGTAAGTTGAGATTCACTAGCAATAATACTTTTATTTGTAACA
466651 GCAATAAAATCATTTTTATTCACCATTACTTTGTTTTCTTTATATGACTT
466701 TGAAGCTTGTGTTATCGTAGCGGAAGCAAACTCTTTAATAAAGCGCTTCA
466751 TTGCTTTCACATTAGTGTGAATAGAAAGATCACTGTTAAATACAGTTAAA
466801 GCAGCAATTGACTCCACAGGATTTGCTGTAATAACATAATCTGCATTAAT
466851 CTTTTGGTGTTTTAACTGTTTAATTGTTTCATTGGCAGATAGAAAATAGT
466901 TTTTATCATGTAACAAAAAGATTACATTACTAGAATTGGTTAACTTAACA
466951 GCCTCAAGTAAAGAAAAAACAGAAGGAGCCCCAGTATCATCAGTACATAA
467001 TATGGCGTTAATATCATGATCTTCACGAATTCTTTCAGCAAATGCTTCTG
467051 TAGGTACAGTAGCTACTATAGCAGGTTTTAAAACTCTTTTTGTTGGTGAG
467101 TTATTCTTGTTATTAACCTGTAAATTCATGTTATCAATTTTGACAAATTC
467151 AAATTCACCATAATTAAGACCCATTTCTAATAAAAGATGTGGTTTTAAAG
467201 TATGAGCATGAACTTTAACAAAACCATTGTCTTTATCACTAGCAATTACT
467251 ACAGAATTGGCAATTCTATTTACTTTACTTTCAAACTTTTTTTGATGAAA
467301 TTTTTGCTTTTCAACTGTCTGATTTATTTTTAAACCTAGTCTTAAAACAT
467351 ATTCTGTACAATAACCAAATTCATCTTCATTAGCATGTTGTTCTTTAAAC
467401 TTGTTAAATTTAATTTCTATAGTTGATAAAGTATTGTCATCTAAATTAGA
467451 TTCGCCCCCATAATATGACAACATTCCTTCAAGAAAACAAGCAAAACCAT
467501 AAGCACCTGAATCAACCACACCTGATGCTTTTAATACAGGTAACATTTGG
467551 GGAGTTTTTTTCACTGCTTGTCAAGCTACTTTAACAGCTTGTTCAAAAAG
467601 TTTTTCAAGTGTTTTAGGACGATTTTTTTGACTCTTAAACTCATTGCTTA
467651 TTAAACGAGCAACTGTTAGCATAGTTCCTTCTACTGGTTTTGATACGTTT
467701 TTATAAGCCACTTCTTGAGCAACAATGAATGCATTTGCAACATCTTCTAT
467751 ACTCAACTCTGAATTATTGCTTGTTTTATTTACGATTATGTTACTGAAAA
467801 ATCCTTTCATTATTTGTGAAAAGATAACCCCTGAATTGCCACGTGAAAAC
467851 AAAAGTAAATCTCTAGTAAAGTTTTTACCAAGTTCACTAAAGCTTTTTAT
```

-continued

| The Nucleotide Sequence of the *Mycoplasma genitalium* Genome |
| --- |
| 467901 ATGACTTTTTCATTTTCTAGTTTCTTGATGGCTTCTGTTATTGTTACTT |
| 467951 TCATGTTTGTTCCAGTGTCACCATCAGGAACAGGAAAAACATTCAACTGG |
| 468001 TTTATGTATTCATAATTTTTAGCGATGTTATTACAGCCAAGGCGTAACAT |
| 468051 ATCGATAAAAGAAGATAAATTTACTGATGACATCTAAAGTAAAACCCTAG |
| 468101 CTTATAAGGGATAAAAAAGAAGTTTATAACCACAATAATTTTAAATTTTA |
| 468151 ACTATTGAATTAAATATTCAAACCAAGGTACTATTTTACTCTTGAATTGC |
| 468201 ATTAATGAATAATTTGTTAAAATGGGAAACTTGCTCGTTTCTAGTTTAGG |
| 468251 AAAAACTAATTCATAAGCGTGAAGTGCTTGATGCTTATATTTATTATTAC |
| 468301 GATTTTTAAATTGAATCAAGCTGTATTTTTTATCACCAACTAGTTGATTT |
| 468351 GAAAATAAATTTAAACACGCACGAATTTGGTGAGTCCTACCACTAATTAA |
| 468401 TCTAATTGTTATTAAAGACATATCTTTTTGAGCTATGTATGAAGAATTTT |
| 468451 CAAAAAAGTGCTTATCTTTTTGCTTCTGGAAAAGGTTTTCATTTTACT |
| 468501 GTTACAATGCCATTATTGTTATCTTTTTTCAATAAGCAGTTTGTAAGCC |
| 468551 AAGATGGTTAAATTGACCAAAAACTAAGCCTTTATATCTTTTGGTTAAAT |
| 468601 GGTTATTTTTAAAAACTTTGTTCAATTCTTTTAAAGCTTTGTTTGTTTTA |
| 468651 GCACCAATAACAATTCCAGAAGTATTACGATCAATACGATGTGCAAACTG |
| 468701 GGGATAAAAGTTAAGTTTATTACTGTCAAATTGTCTATATCCACAGTGTT |
| 468751 TTAAAAGCATATTTGATAAATTAATAATGCTATGTTTTTTATCAGGTTGG |
| 468801 CAAACTATTCCAGTTGGTTTGTCAACTACAATAATATTTTCATCCTCAAA |
| 468851 TATAATTTTTAGCTTATCTTTTACCAAATCTAGAGATAAATAGTCATTAT |
| 468901 TAGTTTGTAAATAGGGATTTATATCAAAAAGAAAAGCTATCTCATCTTTA |
| 468951 GTTTTTAATCTTGTGTTGACCTGTGGTTTTGTTTTATTTAACAAAACCTT |
| 469001 TCCTAAGCGTAAATACTTAAAAAAGTCACTTCTTTTAATTAAGGGAAGGA |
| 469051 TTTTTAAACAAAATTGGTCAATTCGTTGGTTTTCACTTTCTTTAGGAACT |
| 469101 AAAAATTTATTAGCTATTCTCATTTTGTTTGGCAAGAAAATCATCCATTA |
| 469151 TCTGTACTAATTTCATAAATTGATTTTTTTCATCCAAAACAAAAGCAGCT |
| 469201 GCATATTTATGTCCACCACCATTGAACATTTGTGCAAAGTTATTAATTGG |
| 469251 AATATTACGTGAGCGAATGGAACCAATTCATTTTTTAATGGACTCGTTAA |
| 469301 AGTAAACAGTAGTCCATATTTTTACTCCTTTTATGTTATTCAAAGCATGA |
| 469351 ACCATTGGTAAAGGAGAGACAACACCAAAATGTTTATATGCTCCTTTTTT |
| 469401 AATCAATGCATAAGCTAACCCATTTTTAGTTATTTTGGCTTTGCTAAGTA |
| 469451 CATAGCTAAAGTACTTATGTTCTAGTAATGGCTTTAAATAAACTGCATCA |
| 469501 TGAACCTTATTGCGGTTAAAACCAGTTTCCATCAATTTTGCTGTTAGGGC |
| 469551 AAATGTTTGGGGTGTAGTAGTTGGACCTCAGAATCGCTGTGTATCAGTAA |
| 469601 TTATTCCTGCATAAAGATATGATGCAATCTCATCATTTAATTTGTAACCC |
| 469651 ATCTGCAAAATTAAATAACCAATCATCTCAGCAGTTGCTGAAAAAGAAGA |
| 469701 ATCAATTCATTCCATATCAGCAAATTTTTCAGTTCTAGGATGGTGATCTA |
| 469751 TCCTAACTGTCTCTTTTGCCAACTTATGTTTTTGAGTTAAAACTCTTTCT |
| 469801 TGGTTGGAAGTATCAAAAATAATAGCTAAAGATTCTTTTTACAAAATCATC |
| 469851 ATTTATGTCAGTTTGCTCAAAAGGAAAAAGTTCTCTACCGTCTGCATTAA |
| 469901 TATTGTATGAACCCATAACATAAGCTTTTTTTTCACTGAAAAAAGTATTT |
| 469951 AGGAAAGTTTTGAAAGCAAAAGCAGATCCAAATGCATCAAAGTCTGGGTT |
| 470001 TACATGTACAAATAAACTGAACTTATCAAACTGTTTAACCTTTTTTGAAA |
| 470051 AATTCTTAATGAATTGTGGATCGATACTAATCATTGCTTAATTCACTTAC |
| 470101 TCCCTTTTCAATTAAATCATTTAAAAAAATAAGCTCACTTTCAAGCTTTT |
| 470151 CAACATTTATCAATTTAGCTTTCGTTGTAGGATTTTTGGGAGAAAACTCA |
| 470201 CTACAAGTATCTAAATGTTGTTCAATAGAAATATCAAAAGTATTAAAAAA |
| 470251 TTTAGCTAATTCAATAATTTTTATCTTTACTAAAGCCAATTAAGGGGCGAA |
| 470301 CTATAAATGTATCTGGTGTTGCTGATTGAATAACTTTTAAATTTTCAATG |
| 470351 GTTTGGGATGCAACTTGTCCCAAAACCTCACCTGTAACTAGACAATCATA |
| 470401 CTTAAACATACTAGCAGCTTTATAAAAAACACGACGCATTAAACGATAC |
| 470451 GATAAGATTCATTACTAATATGAATTAACTCTTTTTGAATTGCAGTGAAA |
| 470501 TCAAAAACTAATAATTTACCACTACAAATCGTTTTATTAAAAGAAATTAA |
| 470551 ATTTGCTAACCTTGTGATTTTTTCAATTGTTTTTTGATTCTTATTTGGTT |
| 470601 CATTAATAAAGGTGATAAAATCAATGTTAAAACCACGTTGCATTACAAGT |
| 470651 GAAGCTGCAACTGGGCTATCAATTCCTCCTGAAAGTAAGACTAAAGCTTT |
| 470701 ACCACTACTATAAACAGGTAATCCACCTTTACCTTTAAAACGTTCTGTAA |
| 470751 AAACAAGAAAATGCTCCTTCAAAATCTCTATATTAGCTATTATTTCAGGG |
| 470801 TTATTAATTACTCCTTTTAATTGGTATTTTTCAAATAGTTTAACTGCTAA |
| 470851 ATACTTCTTAAAATTACTTGAATTTTCAGCAAAATTTTTATCACGTCTCT |
| 470901 TAACTTCTAATTTAAAGGAATTAAAATCTTTAAATAAATTAAAAAGAAGA |
| 470951 TCTAATAGTTTGTTTTCTTCCCTTACTATCTGTGATGCAAAAAAGAACAA |
| 471001 ACTAATTCCAGGCAAAAAACTGAATAATTCTTGGAGAATCGCTCTTTGTT |
| 471051 CTTTTTTAATATCAAAGACAACAATTCTATCAAATTCATAAACAATACTA |
| 471101 TTGTTAATTTCCAGTTTTTTAAAAGCTTTTTTGATGTTAATTTTAATTG |
| 471151 TTTTGTGAAATAAGAACGGTTTTTTCCTTTTAAAACCAATTCACCATAAC |
| 471201 GCGCAACTAATACATCTTCACTATTCAATTCCATTTTCCTTTAATCATTG |
| 471251 AATATCACTTTCTGTTAGTTTAGGACTTTTACCAGTTAATATGTAATTTT |
| 471301 CATATCAAATTCTCGCCTTATCAACTAAAACACTAAATCCCTTATGATCT |
| 471351 ATCTTGATAGGAATTAACCTAATTTCTCTATTGCTAGCATTAAATTGTTC |
| 471401 TGGTAAGACATAATCTTCTGGTTTCAAAAAGGCAATTGCAAAAAGTCCTT |
| 471451 TATTTACATTGCGCAAATATAGATAAAGACCAATTTGACAATAATATAAA |
| 471501 GTACTGATAATAATTTTTCCATTACTGTCAAATCAACTATCTTTTTTGCC |
| 471551 ATCTTTCTTTTTAACAATAGGCATACCATTTTCATCAAGAATCATCTTGA |
| 471601 GATTTCCATTGATTTTTTATAAATAAGACTATCGCAAGAAGTTGTTTTA |
| 471651 ATCTCTAACATAGGAAGATCATTTTGATAAGCTAATTCACCATTTTCATC |
| 471701 AAGAGGTTCACCATCAGGTATCCCACCAAAAACACTATCATCCTTAAATA |

-continued

The Nucleotide Sequence of the *Mycoplasma genitalium* Genome

| | |
|---|---|
| 471751 | AATCAAATTGAACTTTTTTAGGATCATAAGAATGAAAATTAAAACCAGTT |
| 471801 | TTTAAATTGACATAATCACGTATTTTAGGTTCTATTATGTTTCCAGCTTT |
| 471851 | TGCCAGTGTTTCATCAAATTCATCTTCATAAATTTTGACCATATTAGCTC |
| 471901 | AAGTTTTAAATGATGACTCATATTCAGATAAACCTAAAACCTTGCCAAAG |
| 471951 | CGAGTACCGGTTATTTTTTAAATAGAGCTTTATTTCTTAAAAAATACTG |
| 472001 | TTCTGATAGAACAATTTGATTATCAACTATATCAAAATCAGTTTTATATT |
| 472051 | GCTTTATAAATCCCATTTATTTCATCAACTGTTCACAAATTCCTTTTAAA |
| 472101 | ACAATTGATATTTCAGGATTATTAAATTCCTCATCATTATCTGGTTGTTT |
| 472151 | TTTGCTTAAAAATACAACACTTGCTAATTGATTAATGTTATTAATTGGAA |
| 472201 | CTTCTGTCACATTTAAATAATGAACATCTTTTAAAGAGCAATTCTTGCTT |
| 472251 | TTAACATATGTTTCTAAAGCACTAAACTTGGAATTTTTTGTGCTAGTAAA |
| 472301 | TAAAAAATTTTCGTTATAAAAATTGCTGTAATGAAACTTAGGCTGACCAC |
| 472351 | TAGAAATATGTTCCATAAGTTGAAAGTCTAAATGATACTGAGGACTAAAT |
| 472401 | ACATAAATAGAACTAACATCCATTTCACTGAGATTTTTTAAGAAATTTTG |
| 472451 | GTACTTTAATGTTTGGTCAAATTCCGTTAATCAAATTAATTTGAATTGCT |
| 472501 | TATATTTTTCTAATGAAATAAAGTAATTAATTGTTGTATTAGGTTCCTCA |
| 472551 | CTAATCTTGCTTTTtCCAATTGCAAAAACACCAGAATTAGTAATAATAGC |
| 472601 | ATGGTGTACAATAGTGTCTATACTAACAGAATCTAAAARAGATTGATAGA |
| 472651 | TAAATTCATTGGTTTTGCTAATTCATATAATCGCGCCTGATTCTGCAATT |
| 472701 | ATATCAACATCATCTAACGAGAGTAAATCAAGTAAATAAAGCACTGCTTG |
| 472751 | TTGTCAACAACTTGACATAAAAACAAGTTGATGGTTATTCGCTTGAATGA |
| 472801 | AATTAAAAAAGTTTTTTCATACTTCTAAATCCTTTGTAGTGTTAAAAAAA |
| 472851 | TTTGCTGTATTAATATCTAAAACAACTATTTTTCTATCCATCTCTTCTAA |
| 472901 | CTCTTTTAACAAAATTATTAAAGCTAATTCTGGTGATTTTTTCACCTTTA |
| 472951 | AAACCACGGCATGTCAACTTCTCTAAATTCTCTATTTCTTTATCTCCAAC |
| 473001 | AATAAGTTGTAAAGGAATTTTTTCAATGATTGCTTGTCTAACTTTTTTAG |
| 473051 | CTAAGCGATCTTGATTATCATCTAAATTTACACGGATGTTTTCTTTTAGC |
| 473101 | AATTTGTTATAAAGTTTTTTTGCTGCCTTTAAATGCTTTTGGATATTAAC |
| 473151 | AGGAATAATTACGGCTTGAACAGGTGCTAACCATAAAGGAAAATTACCAC |
| 473201 | TTGTTTTTTCAAGTAAAGCAGCAATAAACCTTTCATAAGTTCCAATAATT |
| 473251 | CCAACATGGATAATAACTGGTTTTTTTAGTGTATTTTTTTTATCTATATA |
| 473301 | AGTTAGATCAAATTTTTCTGGTAGTAAAAAATCTAGTTGAATGGTGGCAA |
| 473351 | TAGTAATCATTTTTTTAAAGATTGTTTTGAACTGAAAATCAATTTTTGGT |
| 473401 | CCATAAAAAGCAGCAGCTCCTATCTCTTTTTGATATTGGATATTTAAATC |
| 473451 | TTTTAAAACATTCTCCATTTGGCTTTCAGATTCTCTTCATAAACCAGGAT |
| 473501 | TATCAATAAATTTTGATTGATTTTTAGGATCATGTAGAGAAAGATCTATC |
| 473551 | CTATCAAATATAAATCCAATTTTTTATTAACTTTTTGAATTAAATTAAA |
| 473601 | TGCGTTTTTAATCTCACTTTTAATTTGATCTGCACGACAAAAAATGTGAT |
| 473651 | TATCAAGTAAAGTCATGCACCTCACTCTTTCTAATCCTATTAATCCTCCA |
| 473701 | GAGGCTTCAAAACGATGCAAAATAGAATCTTCTGAAAAGCGCTGTGGCAT |
| 473751 | TTTTTTATATGAATATCGTTTTTGTTTGAAAATCAGACAGTGATGAGGAC |
| 473801 | ATGTCATAGGACGAAGCATCATTGCTTGACTATCAAGTTTAATAGCAGGA |
| 473851 | AACATATCTTCCTTATAGTGCTGATAGTGGCCGCTAATTTTAAAAAGCTC |
| 473901 | TATGTTAGCTAATACAGGAGAACAAACAGTATTAAAACCAAACAATAGTT |
| 473951 | GCTGGTGATGCACAAAATTACCGATTATATTCCTTAGTGTTGTACCCTTT |
| 474001 | GCTAATCAAATAGGAAGACCTGCACCGATCAGTGGGTCAAAGCTAAATAA |
| 474051 | CTCTAATTGTTTACCTAAAGATCTGTGATCCTTCTTCAAGCGTTCTTCAT |
| 474101 | TTTCTTTTATTAATTGTTCTAATTCTTTTTTTGATTGAGCAAAAATGCCA |
| 474151 | TTAATCCTCTGAAGTTGTAATTGTGAAGGATCTCCCAAAAAATAATTTAC |
| 474201 | GCTTACATTTAATAGCTTAATAAAACTTTTTTTAATAAAAGTTAAAGTTA |
| 474251 | AATCTTCTATTCAAAAATGTTTATTTTCAAAAAAAGGTGATTTTAAATTTG |
| 474301 | TTTAAGTTGCTTTTTTTTAATAAGTTTTTTGTAAACTGATCATTTTCAAA |
| 474351 | AAAACTTAATGCTTCATCTAAAGAAACAAATTTTTGAGAAATCCCTTCTA |
| 474401 | GTTTACTAGAAAGAGAGTTTAAATCAGATTCTATTTTTGCAAACTGTTTT |
| 474451 | GTAGAAAAATTCTCATTTATATAAAAATCTAAATAAAATTCATCTCCATT |
| 474501 | AAAACCATGTTCACCAAACTGAACATTAGCATATTTGCATTTTAACCATA |
| 474551 | TTTGTAATAAAAGAACTCCTGCAAGCATTAAGATTCTTGATAATCAATCA |
| 474601 | TTACTTTTGAATTTGGTTTCATAATTTTGACAACTTCGATTGTTGTTTTT |
| 474651 | CAAATTCCACTGCGTTTTTCTAGGTAAGTGCGCAGAATACCTTCGATGCT |
| 474701 | AATTGTTTTAAATTTTTGAGTATATGCTTCAAGTTCAAATGCTAATTGAC |
| 474751 | CATTTGCATAAAAAACAAAAAAATCAGTAAAACTTCGTTCACCAAACAAA |
| 474801 | CGTTTCTGCTTAATAGTTACTAAAAATCCTGTCTTTTTGTGGCTTCACTT |
| 474851 | TGTGCTTTCTATTTCACCTTCCAAAAAAACGCAATTTAACATGCTTTTA |
| 474901 | GCTAGGTAATTGACCTGTTAAGTTGAAATGAAATTTAAAGTGGTTAATTG |
| 474951 | TTTCTAAAACCATTCTTTCTTCTATTAATGCAGTTCTAATACCTTCAAAC |
| 475001 | TTTTGTTTATCATCAAGATATTCTCTAACATTCTGATTAGTTTTTTCATA |
| 475051 | ATACAAGCTAATAACTCTTTTAACAATATCATCACTAACTTCAACCTTTC |
| 475101 | ATTCCTTTTGTAAGAAATTAAATACTAAAGCTTTTTTAATGATTTTTTCA |
| 475151 | GCTATTGATTGAATTGTTTTTTCATCAGCATCTTTAACAACATCTCTTTT |
| 475201 | CAAGCCTTCAACAACATTTTTTAACTCTTCAGGGTTAATTTGAAATTCAA |
| 475251 | AATAACTAACAATTTCATTCATTGCTGCTGAAAACAAATTATCTTTAATA |
| 475301 | ACAATATGAGTTAGTTCGTGGTAAAGAGCACTTTCCTTAGCATCTTTAAA |
| 475351 | AGAAGCTAAAATTCTTTGCCGATGTTGCTCAATAAAAGCAGGATCTGCAA |
| 475401 | AAATACGATCAACTTCAATTACCTTATCATACTGAATAGGTTTTTGCAAC |
| 475451 | TTTGCAATAGATTTAAGATTAGTAGCCATATTTTTAGAAACTTATTAAAT |
| 475501 | TTTAATTCCTATATGCGTGAAGAATTTACATTTGTTGTGGTGTTGAAATC |
| 475551 | TTCAAAACATCAAGGATTTGTTTAACTATAAAATTGTAATGATCTCAATAA |

-continued

| The Nucleotide Sequence of the *Mycoplasma genitalium* Genome |
|---|
| 475601 AGCAAGTCTTTGTGCTGATAAAAGTGAATTTTTATCATCATTAATTTTGC |
| 475651 AAACTTTATACCAGGAATGAAATAAACTAGCAGTTTCATATAAAAAGTTA |
| 475701 GTTAATAAGTGCAATTCGCCTGTTTCCATAGCTTTTTGCAACATAAAAGG |
| 475751 ATAATAGACAAGTTGATTTAAAAGTGATATCTCTTTTTCATTAATCAAAA |
| 475801 GACTGCAATCAGTAATTTCTTTTAATTGATCAGAATTTGCAATTCTAAGA |
| 475851 ATACTATTCATTCTTGCAAACGCATATTGAACATAATAAACTGGATTAGC |
| 475901 AGAGTTTTGCAAATTAGCTATATCTAAATCAATTTTGATAATTGTGCCAT |
| 475951 TATTTTGAGATAACATAAATCATCTAGCAGCATCTTCACTAATCATTGAA |
| 476001 AGCATTGTTTCAATTGTGATTACATTTCCAGCACGTTTTGACAAACGTAC |
| 476051 TAGCTCTTTATTTTTATAGAGAGTAACCAGTTGTAATGCAAAAATTTTTA |
| 476101 AAGAAGTTTTAGTGGTATTTTTTAAAGCATCAAATGCACAATACATCCTT |
| 476151 TTAATATGTCCTTCATGATCAGTGCCTCAAACATTAAATAGAATGTCAAA |
| 476201 GCCACGTTGTAATTTTTCTAAGTGATAAGCAACATCAGTTCCAAAATAAG |
| 476251 AAGCTCTTTTATCACTTCTAATTAAAACTCTATCCTTATCATCTCCATAA |
| 476301 AGCGTAGTTTTTAGTCAGAGTGCATTATCTTGATAAAAATAACTATTTGG |
| 476351 TTTAAGTTGTTCTAAAAGATCATTAAAATTTGTTTTTTTAACAATTTCGC |
| 476401 TTTCAAATTTTCAACTATCAATAAAAACATGGATTTTATTCAAATCACTT |
| 476451 TTAATTAAAGACAAAACTTTTTGGGTGCAATTAACTAAAAAATGATCTAA |
| 476501 GAATGATGTTTTACAAAACTCTTCAAAATTTAAATTATCAACTGGAAAAT |
| 476551 TTTCAATTTCACTAGCAATTTTATCTATTACTATTCCACTATATCCATCA |
| 476601 GGATGTTGCTGGATAGCAATATTTTTTTTAACTGCAAACTTTGATAAAC |
| 476651 ACTAAAGCTAAAAACTCGTGCTTGTTGTCCATAATCATTTACCCAATATT |
| 476701 CACAGACTGTTGTATAACCCAACAGCTTGGCTAAATTGTTTAAAACATCA |
| 476751 CCAAAAAAAGCTATTCTCACATGACCTAAATGGATCCTTCCGGTAGGATT |
| 476801 TGCTGATACAGATTCAATTAAAATCTTTATATTTTTCTTAGTAAAGCAAG |
| 476851 GTGTTTTTATCAAGTATTCTAAGTACTTTTGATAGCTAATTTGAAAGTTT |
| 476901 ATAAAATTATTGTTAGCAATAAAAACATTTTGGTAGTTATCCTTTTTATT |
| 476951 TTTTAAAAATCACTCAACAATACTATCTGCAATTTTTTTATGATTTTCAC |
| 477001 TTTTTAGTTGGAAAATAATAGTTGAAGAAAAACCATTAAAACTATTATTT |
| 477051 TTAACTAGTTTAACAAGTTCCTTTTGGTCATCAAATTTAAGCTTTAAAGC |
| 477101 GCTAATGCATTCTTTTAAATCATTGATGATAAAAAACATTACTTTAAATT |
| 477151 ATATTTAATGATGCAAAATGTCTTTTATCATAACAGTAATAGGTGCTGGG |
| 477201 CATGCTGGATTGGAAGCCGCTTTCATTGTAAGCAAATTCAACATCAAAGT |
| 477251 AAACCTTTTAGTTCTTGATATAAATCATTTAGGTTCTTGTCCATGTAATC |
| 477301 CTTCAATTGGTGGACCTGCTAAGGGAATTGTTACTAGGGAAATTGATGTT |
| 477351 TTAGGAGGTATGCAAGCAATTGCTGCTGATAACAATGCCTTACAATATAA |
| 477401 ATTACTAAATAGTTCAAAAGGACCTGCTGTGCAAGCTATCAGAGCACAAA |
| 477451 TTGACAAAATAGGTTATAAAAACTGGTTTCAAAGTCAAGTTAAATTAAAT |
| 477501 AAAAACATTAATCTAATTCAATCTGAAGCAATCAATTTAATTGTTAGAAA |
| 477551 TGAAAAAATAAAAGGCGTTATTTTAAAAGACGGAAGTGAACTTTTAAGTG |
| 477601 ATGCGGTTATTATCACTACCGGAACGTACCTAAGATCAAAAACATACTGT |
| 477651 GGTAATACAGTTAAAAATCAAGGACCTGATCAATCTAAAAATAGTGAAAA |
| 477701 ATTAAGCACAAACTTAATTAACAGAGGTTTTAAAACAATTCGTTTAAAAA |
| 477751 CAGGAACTCCGCCAAGAATTTTAAAAACTTCACTTGACTATAATCAAATG |
| 477801 GAATTAGAAATTAATAATAATCAkAACCTTGCTTTTAGTACTACAAATAA |
| 477851 AAATTTCTTACCACTTGAAAAACAAATACCTTGTTACTTAGTTCATACCA |
| 477901 ATCAAAAAATTCACGATCTAATCCTTAAAAACTTAAAAAAATCTGCAATG |
| 477951 TTTAATGGTAGTATTTCAGCACAAGGACCACTTTATTGTCCAAGCATTGA |
| 478001 AGACAAAGTTTTTAAGTTCTCTCAAAAACCTCGTCACCAAATTTTTGTAG |
| 478051 AACCTGAATCATTGAGTCTAGATACTATTTATTTAGCAGGATTATCAACT |
| 478101 TCTTTTACACCAGAAATTCAAAAAGAAATCATCCAGCTTTTACCTGGTTT |
| 478151 TCAAAATGCAGAAATTAAAAAGTTTGGTTACGCTATTGAATATGATGCTT |
| 478201 TTCTATCTAATCAACTAAAACCAACACTTGAAACGAAGTTAATAGAAAAC |
| 478251 TTGTATTTTGCTGGACAAATTAATGGCACTAGCGGTTATGAAGAAGCTGC |
| 478301 TGGTCAAGGTTTGATGGCAGGAATTAATGCTGCTTTAAAATTATTAAAAA |
| 478351 AACCACCATTTATTTTGCAACGTAATGAGGCTTATATTGGGGTTATGATT |
| 478401 AATGATTTAGTTACTAAAACAATCAGTGATCCATACCGTTTGTTAACATC |
| 478451 CAGAGCAGAATATAGACTATGATTGAGAAATGACAATGTTCAAGAACGGC |
| 478501 TCATTAAAAAAAGCTTTGAACTTGGTTTAACAGATAAAAAAACATATGAA |
| 478551 TTGTTCCTTAAAAAGGAAAAGAAAAAACAGGAATTAATTTCATTTTTAAA |
| 478601 AAACACTCAAGTAGGCAAGGTTAAAGCATTGAAATTCACTAATAAAAATA |
| 478651 CCGCTCAATCACTTTATGACTTCAACAAACGAAGTGAAATAAATTTAGAT |
| 478701 AAATTGATCAAAGATCTTCCTGAAAAATACCAATTAGATTCAGAAACACT |
| 478751 TAAACAAATTGAAATTGAAATTAAATATGAGGGTTACATAAAGAAAAATG |
| 478801 AAAAGTATTTTAAGGGTTTAGATAAATTAAGCAAAATTAAAATTCCTCAT |
| 478851 ACTTTTGATTACCATAAGGTTAAGAATTTAGCTAGTGAAGCTATTTTTAA |
| 478901 ACTATCTAACTTTAAGCCTAGTAATTTAGCAATTGCAAGTCAAATAGCTG |
| 478951 GAGTGAACTTTAATGACATTATAGCCATAAAACATTTTTTAAAAACTTAT |
| 479001 GAATAATGCTAATTTTGAAAAATATGTTGATTTAGTTTTTGAAGCAAACA |
| 479051 AAAATTTCAACTTAACAGGATTTAAAACAAAAGAAGCTATTTATCAGAAT |
| 479101 TTAGTTATAGAAATATTGACATTATTTAAAGGATATGAAAAATTTTTTAT |
| 479151 TGACAAAACTGTAGCAGACTTGGGAAGTGGAAATGGTTCGCCTGGGATAA |
| 479201 TATTAAAACTGTTATTTCAAAAAAATAAAGAAGTTAGTTTTAATTGATAGT |
| 479251 AAACACAAAAAAATTAGCTTTTTAAATAAATTAACTAAGCAACTAAATCT |
| 479301 GGAGAAAACTGTTGCAATTTGTGAACGAATTGAAGTACATAAAAATCACT |
| 479351 ATGATGTTATCTGTTCTCGTGGTCTAAGTACGATTATTAAAGTTAATGAT |
| 479401 TTAGCATTTTCCTTGCTTAACTCAAAAGGTATTATTTTTCATATAAAACA |

-continued

The Nucleotide Sequence of the *Mycoplasma genitalium* Genome

```
479451 AAGCTTAGACCAATACATTGAATTTGAAAAATCAAATCAGAAGAATCAAT
479501 TTAACTTGTTATTTATAAAGCACTTTACTAGTCAGAATAAAAAACTAATT
479551 TTGATAGCTTTACAAAAAAATGATTAAGTTAGGTTGAGCGTCTTTTAGTA
479601 ATACAGAATTTGCTCAAGATATCTTTATAAAGTTTGCCAATCAATTCTAT
479651 AAACAAGATGATGCTGGAACAATTTTATTTGAACTAAAAAAAACATTAGG
479701 AGTTAATCAACTAGATGARATTGAAAAAAATAAAAAAGTTATTATTGTTA
479751 ATCAGTTTCAAAATAGCTTAGGCAAATTTTTACTTTTTAATAAAGAAAAT
479801 ACTAAAAGAATAAACAGTTTAGCTAATGAACATATAAGTTCTTTTTTAAA
479851 AAAAATTTTCAGATTATCTGGATTTAAAGATATGTTGATTGATGTTCAAC
479901 ATCATAAAAAGTTACAAAAATGTTTATTAAGAGAAATTCATCTTTTAGTT
479951 TGTTTAATTAATAGCAATCAATTTAGTGATGAATTAATGCAAATTATTGA
480001 GTGGTATCAGTATTTAAAAAAACACTCTAGTAAACTTTTTGTTATTACTG
480051 CAAGTAGTGATAAAAAACCAGTAATAGAGCCAACTATAAATGAATATAAA
480101 GCTATTTTTGGAGAGTATTTATCTTCATTTCACCTAGATCTAAAAAATAA
480151 TCAAAGTAATGATTTATTCCAGAAATTACTTGATCAGATCAAAATAAAAG
480201 CTACCTCAAAAACTAGTTTGAGATAGCTAAAAATATAAATGGCGCATCGG
480251 GAGGGATTTGAACCCACGACAACACGCTTAGAAGGCGTGTACTCTATCCA
480301 CTGAGCTACCGACGCATTTCTTTACTAGAAACTATCATATGAATCTTCAA
480351 TAAGACTCTAATAAAAGTTTAGATGATTTTTAACTTTTTTATTGTATTCA
480401 TGCAATAAAAATTAATTTAAATAAAAGAAATTTATTAAAAAATCCTTAAA
480451 GCACAAATATCAATAATTTCCTTTTCTATTGATTCTTAACTATTTTTAAA
480501 AAAATAGTCAATTTATTTAGTCACAAAAACCTTAGTTAAAAATAAATTTA
480551 AGTTGCAATTGGATTGAACATATTATTTAAACTTTCTTTTAAATTAAGTG
480601 TTTTAAAAGTTGATTTTTAATAAATTAATTAACAAAATAAGATAAATAGT
480651 TAAAAACTCAATAATAAACGCTTTAAAATATTTCACTTTGATGGATGAAA
480701 AAGGGATTTTAGTTGCAATTAGTGGTGGTAGTTGCTCAGGAAAAACTACT
480751 GTTGCTGAAATGATTTATCAACTTTTAAGTAAAAAATTAAAAGTTGCGAT
480801 CATCTGTCAAGATAACTATTACAAGTCCTATAAAAATAAGCCATTATTAA
480851 AAAGAAAAACAATAAACTTTGATCATCCTGATGCTTTTGATTGAAAACTT
480901 TTAAGATCACACATTGAAGATCTTCTAAACGGTAGTATAGTTAATGTTCC
480951 TTTATATGACTACATTAACTATACCAGAGCTAAAAAAACAGCAAAAATTG
481001 GTCCAATTGATGTTGTTATTCTAGAGGGTTTAATGCCATGATTTGATGAA
481051 AAATTATCAAGACTTTCTAAGCTAAAAATATTTATAGAAACAAATGGGGA
481101 AGAACGTTTAATTAGAAGAATAGAAAGAGACTGACAAAGGGAAGAAATA
481151 TTGATTCTATTATTAAACAGTGACGCGAAATAGTAGCACCAATGTATGAA
481201 ATATTTGTAGAAAAAATGAAGCGAAATGCTGATTTAATTCTGCCTTGAAG
481251 TCAACGCAGAGAAGTAAGTACAAGTGTATTGGATGTCGCAATTGAACACT
481301 TATTTCACAAAACTGTTGAAAAAAATAATTAGTTCTGGAAATTATAGAGA
481351 TGTTTAAATTTCAAAGGTGAATTATGTTTATGCTCTGCTTTTGCTTTCAA
481401 ATCTAAAACAATTTTTTGCTTTTCTGAACTAAGTATTAAATCACCTTTTA
481451 AATATTGATCAAGTTCCTTATAAGTAATGCCCATCTCTGTCTCATCAGTT
481501 TGCCCTTCAAAAAGACTAGCAGTTGGCGCTCTTGTGATTACAATTTCAGG
481551 AATATTAAAATGCTTAGCTAATTTGTAAACGTCCTCTTTTAAAAGCCATG
481601 CTAAAGGAGCAATATCACAAGCTCCATCTCCTCATTTTGTGAAATAACCA
481651 AGTGTATACTCTACAAAATTACCAGTACCTAAAACTAAGAAGTTGTGTTT
481701 TTGAGCATAAGCATATAAAGTTATCATCCGTAAACGTGCTTTAATGTTAC
481751 CAGCTGTTAAAAAATCTTTTTTTGGATCTATTCCAAGGGTTTTTACTAAC
481801 AGATTGAAACTCTCTTCCAGTTCAATGTTAATACTATTAAATTGCATTTT
481851 TTTAACAAGTTCACTAGTTGCTTGAAAATCAAGTTTTGAATTATTAATAT
481901 GCATTATTAAAGCTAAATGGTTTTCAAAACCAAAAGTTTCTTTAGCAATA
481951 GCAGCAACAACTGCTGAATCAATTCCTCCAGATAAGCCAAAAATAACACC
482001 TTTAGCTTTAGATTTTTTTACATAATCAAACAGCCAGTTTTGGAGTTCTT
482051 TTAAATATTTAATTAAATTAGTCATTAATTACAAATTCACAACCATCAAA
482101 GAAAATAATATCACCTTTTTTAGCACCAACGGATTTAATTGATCTTCAA
482151 TACCGATTTCTTTAATTTTATTTCCTAAGCGACGAATGTTATCAAGCGTA
482201 GTTTGTGGAATTTTATCAAATCAATATCTTAGACGTTTACAATTAACAAT
482251 TCATCTGTTTAAACTATCTTTTTCAATATTTAAAGGGTCGTTATTATTTT
482301 CATTGGTATTTTGAAAAACATAATGCTTCTCAAGTTCCATTGGCAAACTA
482351 AACTTATTAGCTCCAAATTGGGAAATTGTTTTATTGTAAAGTTCAAAAAC
482401 TCTATCAAGTAAATTGCCTAATTCTTTCTTTAAAGCAGAAATTTTTAATA
482451 CAGAAATAGATTTTTTTTGAAGAAATTTTTCTAATTTTTTAAACCGTTTC
482501 TCACCTTCATTAACATCAATTTTATTAGCTACAACAAGCATCTTTTTTTT
482551 AACTAGAAGGGGAGAATATTTTGAAAGTTCATCCATTATTTGTAAATATG
482601 CTTTGCAAGGATCATCATTATCTACAGGATCAAGTGAAATTAAATGAATT
482651 AATATTTCACACCTCTCTATATGCCGTAAAAAATCATGTCCTAACCCACT
482701 TCCTTCACTAGCATTTTCAATCAAACCAGGAATATCAGCAAAAACTAAAC
482751 TATTATTTTGATATTTAACTACACCAAGTACGGGTATTAAAGTAGTAAAG
482801 CGATAGTTTGCAATTTTAGGTTTGGCATTTGAAAGTTTGGAGATTAGTGT
482851 TGATTTACCTGAATTTGGAAAACCAACAATTCCTACATTAGCTAAATATT
482901 TAACTTCCAAACTAACGTTTAAAATCTCTCCTTTATCACCATTTTCATAT
482951 AGATTAGGAGCACGCATAATTGGGCTTTTAAAAGCAGCATTTCCTTTTCC
483001 GCCTTTTCCGCCAAAACAAAAATAAAACTCTGTTTATCATGAACAAAAT
483051 CCACCAATACACTATTATTTTCTAAGTTTTTAACTGTTGTTCCTATTGGC
483101 ACTTTAATTAAAAGATCTGAACCATTTTTACCATGTGCTAAATCTGGTTT
483151 ACCATTTTGTCCATCTTCTGCAAACAGGTGTTTTTTATTCTTCAAGaAAA
483201 AAAGTGAATCGCAGTTATGATCAGCTTGCAAAATAACATTACCACCATTA
483251 CCACCATTACCACCACCAGGACCACCTTTATCATAATGTGCTTCTCTTTt
```

-continued

The Nucleotide Sequence of the *Mycoplasma genitalium* Genome

```
483301 TCATGCTATGATTCCATTACCACCATTTCCAGCAGTAAAGCGACACTCAC
483351 AATAATCTGTAATAGCCATTATTTTGGTTTCTTTTTCTTTATTTTAAAAA
483401 CGATTTCTGCAGATTTTTTCTTTCTAGATCACTTTGAATTTGTTGCAAC
483451 TTTTGTCGATTTTTAGTTTTAGATTTACCTGTCTTTAAGAGATTTTCAGC
483501 AATTATTATTGCATATTTTGATCTGATTApAAAAAAGTTAGTCATTTTAT
483551 TCAAAAGAAAAAAACTTAGCATTAATGTTATTAGAACTAAAAAAAATCGA
483601 AGTAAGATAATTCAACTATTTCAAGCCATTGGTATTATTCCTGATAAAAA
483651 AAGaACTATTAAAGTAAAAGCAGTAGAATAGCAAAAAGGAATTAATTCCC
483701 AAATAATGTATTTAGTAAAAGCAAATAAAAAAAAGGCTAPAAAAAGATAA
483751 ATTAGTAAAGGAACAAATAAAAATCACAACAAAACTAAGTCAAAAATGGG
483801 CTCTATTTCCTTACCCATAAATGTTCTGTTTTGTGCTGCAATTAAAAAAT
483851 TAAAGCCTAGTAAATTGATTTCACCAAAAAGAATTCAAATCAAAAGATAA
483901 TAAATAAAAACTAAAAAGAAACTAAAACTTCCTATTAGTCAATTAGGGGT
483951 TTTAGTTTTTTTATTTGACTTGAAAAAATAATTCAAAACTAATAAATTTG
484001 TGCAGTAATTTGAAATTTCACAAAGCGATCGTTTTCATAAAATTGATAAC
484051 GAAGAAGACCCTTGATAACTCAAAGAATAACTGGTAATCCCAGGTTTTGA
484101 ATTTCTTTGCAGTTCTTATGATAAAAACTCTCGTTTGGCACTAAAAAACG
484151 GCAATATCTCATTAATTCGTCTCTAGAAGCTACTAATAAAGCTTTTTTGT
484201 TTGCAATTACAAAACCGGTTTTAAAGCCTTTGAAAGTCTCATTTATTAAC
484251 TTAATGATATGAAAATTACTACTTAACAAAATCATTTTTTCTTTAGCTAA
484301 GACAAAATCTTTGCAAAGCAAATTCAACTGTTCTAATAATGAATTGTTAT
484351 TTTCTTTATCATCTTTAATATGAATCAGCAAATATTTAAAGGGCTGAATA
484401 AATTGCGTTAAAACTTCCTTTAAAGTTTGAATTTGTTGTGAAGTTACCTT
484451 AAGCTTAAATTCACTTGCAAGGTTAACCTTTTTAAGATCAACTAAATTAA
484501 TTTGGTTTAAATTCAAGTTTTTATTAGAAACTTTAAAGTTTTCTTTATGA
484551 GTTACTACTATTTGTTTATCTTTGGTTAATTGAATATCAATTCAAATACC
484601 ATCAAAATCAAAAACTTGGGCTGCTTGAAATGCTAATTTGGTGTTTTCTG
484651 GTGCAATAGAACTATAACCGCGATAAGCTATTAAAAACTGTTTTCGCATT
484701 ACTATTTTTATCATTACTGCCAAAAACATCCTTAGCATCATCTGCTGAA
484751 AATTGACTAAGTCATTCATCTGCGTCAATAGAGTCAATATCATAACCTTC
484801 AAGAGCAGGAATATCCTTAGTTATATCTTCATTTAAATTCTCAGTTTCCT
484851 CAGACTGGAATACTAATCAGTTACCTTCACTATCAAATTCCCCATCATAT
484901 CAGTTTCATTCATTGTCTTCATAGTAACCATATTCTTCATTTCCGATTAA
484951 TTTCTCTCAAAACTTAGGTGCCTCGTTAATTCGTGGTTGACGATTCTTTC
485001 ATTGTTCATCAACAAGAACTCAGTCTCCAGATTCATCATAGAAACCATAT
485051 CAAATCCACTCACCTTTATTGTTGTACCTACCATAAACTTCATCACCAAT
485101 AAGTGGTAAATAATCTCTTTCTCTAGCTCATTTAACAGTTGCATCCTTAT
485151 TTCATTTTTGATCATCACCAAAGAATCCTGCTCAAACTCATTCTCCATCA
485201 GGTTCATAATGACCATAACTATTGTTACCAACTAATAATTCTCAATCAAG
485251 TGATTCTTCTTCACTAGCTTCTGGTTGAATTTCATCAGCTTGAGGTTCTT
485301 CCAATACTGTTTCAGGTTTTCGTTCTTCAAAGTTAGGTTGAACAACTACT
485351 TCAGGTTCACTAGAAACTTGAGGTTCTTGAATAGTTTCAACTGGTGAATC
485401 AAATTTAGCTTCTTGAGGAGTTTGTTCAGGTTGAACAGTATCAAAAGTAG
485451 CTTCTGGTTGAGATTCTACAGGTTGAATTTCTGGTTGAGTTTGAACTTCT
485501 TCAAGGAGAGGTTCAGGTTGTGAATCTTGAACCGATTCAACTGGTGAATC
485551 AAATTTAGCTTCTGCAGATGGTTCAAAAACTGCTTCTCCAGGTTGTTGTT
485601 CTACTTGAGGTTCAAATTGTGGCTCTGATGGTTTTGATTCAATTTCATAA
485651 TTTGGTTCATCAAAGTCATAATTAGGTTCATCTACATCATATTGAGGTTC
485701 TGATGGTTGTAGATCTGAATCATAACTAGGTTGATCAAAATCATAGTTAG
485751 GTTCATCAAAGTCATAATTAGGTTCATCAAAACTAGCTTCTGATTCAACA
485801 TGTTGTTGAGTTGGTTCACTACTAAATTCAGGTTGTTCAACAGTTTCAAC
485851 TGGTGAATCAAATTTAGCTTCTTGAGGAGTTTGTTCAGGTTGAACAGTAT
485901 CAAAGGTAGCTTCTGGTTGAGATTCTACAGGTTGAATTTCTGGTTGAGTT
485951 TGAACTTCTTCAAGGACAGGTTCAGGTTGTGAATCTTGAACCGATTCAAC
486001 TGGTGAATCAAATTTAGCTTCTGCAGATGGTTCAAAAACTGCTTCTCCAG
486051 GTTGTTGTTCTACTTGAGGTTCAGAAATAACTTTTTGTTGATTTTCAACA
486101 TCATCAAACTTAACTTCAGTAGTTTTTTCAGGTTGAACATCAAAAACTGC
486151 TTCAGGTTCTCCAACAGTATCAGTAGTTGTTTGATCAACTACTTCAGCTT
486201 CACTAGAAACTTGAGGTTCTTCCAATCCCTCAGTTTGAGTTTGATTTTTA
486251 TCAAAAACTGCTTCATGTTTAACAGTATCAAAGCTAGCTTCAGTTATTAA
486301 TTGATCAACTGGTTCAGATTTAGGTTCCTCTTCTAATATTTTTTCAGTCT
486351 GTGTTTCTAATTGAGGTTTTTCAAAAACTGCTTCTGATTCAGCTTCAGAT
486401 ACATTATCAAAAGTAGCTTCAGATTTTAATTCTTCTGTTGATAATGGTTC
486451 AGAGGAGGTTTCCTGTTGAAGTTCTTTAGTTTCATCAAAAGTAATTTCAG
486501 CTTCTGTTTCTTTAGGTTGAACTTCATTATTTTCAACATTATCAAAGTTA
486551 GCTTCCTCTAGTTTTAAATCTTCTAACTTAGTTCCATCAAAGATTTGTTC
486601 AACTTCAGCAGTAACAATTTCTGGATGATTTTGATCTAATGCAGGTTCAG
486651 ATGGTTGATCTTCAGAGCTAGGTTCTAATTGGGTTTCAATTGTTTCTGGT
486701 TCAAAAGCAGTAACTTCAGTAGGTGTAACAACTGTTTCTTCAGACTGATT
486751 TTCTAATTGTTGATGATCAAAAACTGCTTCAGTTTTTTCTTCTAATTTAA
486801 TTTCATCAGAGATTTGTTCAGCATGAAATTCAGCTTGCGATGATTCTTGG
486851 GGAATTTCGACTGGTGAATCAAATTTAGCTTCTTGAGGAGTTTGTTCAGG
486901 TTGAACATCTGGTTGAAAATGATCATCAAAAACAACTTCAGTAGTAGCTT
486951 CAGGCTGTAGTTCTTGAGTTTTAATTTCATCAAAAACTGCTTCTGGTTGA
487001 ACAGTATCAAAAGTAGCTTCAACTTGTGATGATTCTTGAGGAACTTCAAC
487051 AGTTGAATCTAATTTAATTtCTTTGAAAGTAGGTTGGAGTTCTGAATCAG
487101 AACTCTCTTTTTCGTCTGGTTTTGAATCAAATAAAGCATTTGATTCAATG
```

The Nucleotide Sequence of the *Mycoplasma genitalium* Genome

```
487151 ATTTCAGTTAAATCAAGCGGTAGAGGAGTGAATAAGTTATTTTCATCTTG
487201 ATGTTCAAATAATTTTGTTTCTTGTTCAACTGTGGGTACATTTGATTCAG
487251 AAGTCTCAACCTCTTGAGTTTGACTAATGAATTCAAGCGTATCTTTTTGT
487301 TCAGATGAAAATTCATTAGGAGTTTCAGCACTTTCAGTGAAACTGTCTTC
487351 AACTATTTGATATGTTGGTAATACGAACTCACTATCAGTTTCTAGTTGTG
487401 TTGTTGGTTGTTCTTGAACTTCTTTTTCAGAAACATCTAAATTAATAAAT
487451 TCATTACCAATTTCTTCATGATTTAATTCAACAGATGTAGTTTTAGTTTC
487501 TAATGATTTATCAACATCATTTACAGAATCTAATTCAAGTGATAGGTCAG
487551 GTTGAATGAAAGGTGGTTCACTTTCTACAACTATTGTTGTTTTTTCATCA
487601 AATAATGATTTTGGTTCAGTTTCAAGGAAATCTACTTTATATTCCAATCC
487651 TTCTTGAGGTTTTGGATCATTATTAATAAAAGTTATTTCATCAACTAGTT
487701 CACTTTTGGGAAGTTCACTTGAAACCTTAACTTCTGTTTCTGTTGAAAAA
487751 GGAGCATTAACATCAACATATTCATTTGTTAAGAGTACCTCATTAACAAG
487801 TTTTTCACTAAATAAAGCAGTTAAATCAGTATTAACACTTTCATCACTGT
487851 TTGTTTCTTTTATCTTTTCATCTGAAACAACAGGTTCGCTAAATTCTTGT
487901 TGAAATTCATTAACAGAATAAGTAGGTTCAAATTGTTGTTCTGAAACTGT
487951 TTCATTTATTTGAGAATCAATATTATTAACAACTTCATCTCTAAAAAGGG
488001 ATTCATTAATGAAATCATTATTAGCATCTAAAATAATTTCATCTACTTGT
488051 GATTTTCTTCTACACTTTTTTGTGTTTCATCAGTAAAAGAACCGAATTC
488101 TTTTCAAACTGAATCAATATCATCAGAAATATTAGATAAATCTGCTTTAG
488151 CACTATCTTTTATTTCTTTAGAATAATCTTGACTTAAATGTTCAACATGT
488201 TTAGCAATTTCATCATGTTGTTGGTCGTCTTTAATAATAGAATCTAAGCC
488251 TTTAAGATCATCTTCGTAAACAAAAACGGTCTCAACTTCTGGAACATTTC
488301 CTGCTTGAGTTTGATTGGAATCTAAGCCCTTAAGATCATCTTCGTAAACA
488351 AAAACAGTCTCAACTTCTGGAATAGTAGTTTCAGGTTCACAAGCTGCTTC
488401 AGGTTCAATTTCAACAGGAGCCTCAACTTCAGATTCAACCTTAACTTCCT
488451 CTTTAACGATTTCAATTAAAGGGATGGTTTCATTAGTTTCTTTAACTGGA
488501 TTTAAGAATTCAAATTTTTCTTTTTCAAAATGTAATTTAGTTACTGGATT
488551 ACGGAAGATAACTTCATTTCTTCTTGGTTTAACTTCTTCAATTACCGGCT
488601 GCTCTTCACTTGAATTTTCAAGTAATAGTTCGTTTTCTAGAGAAGAAGCT
488651 AAGCTCTTGGTATTAAATACTGTAACAACAATGTCATTTTCCTGTTCTCA
488701 GTATGGTTGTTCAGAAATAGTCTTTTTCTCTATTTCATCAACTAAGCTAT
488751 CAGTATGACCAAGTGCTTCTTCAGTAAAGCGAACAGGATCAGGGATCCAA
488801 TTTAGTTTCTTGTCAAAAAATCCTTTTCAGATCCATGTATTATTTTGAAC
488851 AAAACCATAGTTAGGGTTGCCTACAAGTGGTCTTCAAAAATCAATATCAG
488901 CTGGTCTTTGTTTAATGAAAGCTGCATGTTCTTGAGGAACTTCAACTGTT
488951 TCAATTACCTTAAAGTAGTTTCATCTTTGTAATTGGTCAAAATAACCTAG
489001 TCAAACTCAAGTATGATTTTTTCAAAAACCATATTTTCTATCACCAACAA
489051 AGATATATCAGAACGCTTGTGAATCTTCTGGATTTAATTTTTTTTCTCTA
489101 ATAGTTGTTGTAAAACTATCTTTTTTTGTTTCTAGAACTTTGGTTTCTGG
489151 TTGATTGTTTAATTCAACCAACTTATTTTCATTAATGGTTGGATAACTGC
489201 TTGTTTGATTTGGAACTGTATTAACAACAGTTTTTTGATTAAGTTCTCTT
489251 CTACTTAAGATATCTGTTTCAGGTGGAACAATAAAAACACCGCGCTTGGT
489301 TTCATCARAAAAATCTATAGGTGATTTGCTCTTTGATTTAACTGTTTCCT
489351 TTTTCTTACTATTAAAAGACTTTGTTTTCTTGAGAATGTTTTTTTTGATT
489401 TCACCTAAAAAAGGTTGATCAAAAAGATTTTCAACTTTATCTTGTTCTTT
489451 TTTTGGTTTAGTAACACTCTTCTTGTTAGCTGATTCTAAATACTTTTTGG
489501 TTTTTGATTTAGGGGTGGTGTTTTTGTTTTTATTCTTTGTTGTTTTTGGC
489551 ATTAATAAAAATACTTAGCACTAGTGACTAAAGTTATCTGACTCACTAAA
489601 TTGTAATTTTTAATATCAAGATAACAAAAGTTAGCTATATATGCTAAAAA
489651 ATAAATAGATTTTAATTACTATTTATATTAATTTATTTAATGTAGATTTA
489701 ATAGTGTTTCAGCTTCTTTTTGCAAAAGAAAAATAGTTATAAhATCAAAA
489751 ATTAATCACTTTAATTTCAAAAAAATTTGACAGCTAAAGCTTTACATTTT
489801 ATTAACAACAGaACAAATAATTTTTAGCTTTTAAAAATTTATTTAGAAAG
489851 AAAACTATAAACAGGCAATTTTTGTTTTTCTGTTTTTACAAAAATATCAA
489901 TAAAAATATCACAGTCAAAATGATTTAATAGTTTTTTGCGAGTTGCTATC
489951 CCAATTGCTTTGATCATTTCTGCATTTTTTCCAATGATAATCTTTTTTTG
490001 GCTTAATTTTGGAACACTAATTACTAGGTGAATTTTTAACAAGTTTTTTT
490051 CTTTATTGAAACTCTTTTCAATAATTTCAATTCTTGCTATATGGGAATT
490101 TCGTTTTTGCAATAAAAAATTATTTGTTCACGTAATCCTTCAAGAATCTT
490151 AAAGTCATCGTTGTTTGCATCAATAAAATTGATATCTTTACGAAAGATAT
490201 TATACCTAAGTTCAACTTGTTTAAAAATTGATCAAAAGAGGTTTTTATCA
490251 AACTTAAGCAAGTTTATTTCAATTGTTTTTTGTGGTTTAAACTCTTCTAA
490301 AATAATTGCTTTATTAACTTCACTTAAACTTTTTTGATGAAATTTATTAA
490351 TTAAAAAAATTCTTGTTAAATTTTGATAGCGCTTTAATTGTTGTAATTGA
490401 GTTTTTAAAAATTCTATCTTGTTATTCTGATCACTTCTAACAACTAAAAG
490451 TAATACATCAATTCCACTTAATGCTTTGCGAATTTCTTTAGTTATTAATT
490501 CATAATTTGAATGTTTTTTCTCAGTAAAACCAGGGACATCAATAAAAACA
490551 ATATTTTTATTAGCTTGGTTAATTACCTCAGTGGAAATAGAAAGAAGCGT
490601 TGTGTTATTCATGGATGATACCATCAGACTATCATCGTTATGTAAAAAAT
490651 TAATTAGCGTTGATTTTCCTGCATTAGTAGGTCCTAAAACACCAACTTTT
490701 AAAACTTTCATACTGATAAGATCTCTTCATGAATTGCATCTTGAAAAAAC
490751 ATAGTAACGCTTTCAAATGCTTCACTTTCTTCATGATTAAATTCAAAGAG
490801 GTGTAAAATGCCGTGTATTAAGCATCTAGTTAAAAGAAATCAATTGTTAC
490851 AACCAATCTCTTTAGCTTTTTAAAGATGTATTTAGGACACAAAAAAATT
490901 TCGCCGATTGCTAGTGAAAAACCGGTTTCAGTTTCGTTATAGCACAAACT
490951 AATTACATCAGTACAACCTCTACGTTTTAAAAACTGTTTGTTCAGTTTTT
```

-continued

The Nucleotide Sequence of the *Mycoplasma genitalium* Genome

```
491001 TCATTTTTGAACAGGAAACAATTAAAAGCGCAAATTCTGGGTCAAACGAT
491051 AGGTTTAAACTGCTTTTAATAATTTGGAAACAAAGTTCGACTCCTGCTTG
491101 GTAATTTTTACCAAAAAAGCGCTTAAAAAGGCGGCTTGAATTAATGCTAA
491151 AAGATGACTTCAAACAAATCTTTTGATGGTAACATGATAGTAATATTATA
491201 TCAGCCCTGTTCTAGAGTAACACTTAAATCTACCTTTACTAGATTTTTGT
491251 TCAATTCTGATGAAATTTCTGATGTAGAAATTTTCTTTTTGTAAAGTCTA
491301 AAAGCTTTTTTGCTGATTTTTCTGTTGTTTCTGCTTGAAAATTAGTCCA
491351 TGAAACGTTGTTAAAAAGATTTTCATCTTTTTCATTTTTAAACATTAAAA
491401 AATTTTGTTGTTGCGTAGTTCAAAGATTTACATTAAGATATTGTTTTACC
491451 TTTACTGAAAACAAGATAGCAACTGTTGTTAAAAGCAAAATAATAAAAGC
491501 AATTGTTATTCCTAAAATTTTCTGCTTCATAATTTAACTATTTCTTAAGT
491551 AATTAGTTAGGTTAATCTTGTTTTGAGCTTCACTTGCAAAACTCAGATCA
491601 TGCTCAACTAAGACTACAAAATTATTTAAAGTAAGTGGTTTTACTAATAG
491651 CTGATAAACACGGTTTTTAATTTCAGGTGCTATTGCATTCATGCATTCAT
491701 CAAGTAAGATCACCTTATTCTTAATGTTGCTAAGTAAGAATAGTTGTAAA
491751 ATTTGTTTTTGTCCTGAACTTAACTTTGTTTGATTTTGAACACCTGCATC
491801 AAAAAGTAACTGATAGATATGTGGATTCTGATTATTAAATAAAGCCTCAC
491851 TAAAGCCAAAATCATTTGCTTCTGTTTGCATTAAATTTTGACCCTTTAGA
491901 TAATAAACGTTTTCAAAAAGCTGTTCTTTTGAACATCTTTTTAAATCGAC
491951 GTTATTAAATTTAATATTGCCCGTATATTCAAAACCTCTACCAGTTAATA
492001 TTTTTAAAAAAGTAGATTTACCACTACCATTTTGTCCAAAAATAACTGTT
492051 TCATTTTTGATTTTTAAACTAAGGTTAGCTAAATCAACGTGTTGATTAAG
492101 TGTAACTGATAAATTTTCTAGACTAATTTCATCAGGACACTGTCAATTTA
492151 CTTTAATACCCTCATCCTTTTTGGTTTCTATAAACAAGTTAACTAATTTC
492201 TCACGACAATAGTGATAAATGTTTATTGCAGCACCAAATTGAACAATTCT
492251 TGTAGCATAAGTTGAAAAAAGTGATTGGATACCAAAAACATAGAATAAAA
492301 AGCTCAATTGATAACGCTGTTCAATAATACCAATCACCCCCAAACCTAAT
492351 ATAGCAAAATCAAAACCTTGTTGGAAGAAGCTTTTAATGTTTTCTATAGT
492401 TAGACGATTAATTTCCTTCTGGTTGTTAATGTTTTGATTTTGTAAAAGTG
492451 CTTTACGAAAATTCAACATTAAGAAATTAAAGCGCTTTTTATTTTGTTCT
492501 TCACGCAAATTTTCATCTAGCTGTAAACTAATTTTGTTTTGCAATTCAAC
492551 ATAAGGAATTTCCTTCTTTGTAATTTTTTTAGTAAAAAAGAAGTCATAAC
492601 AAAATAAGCCAGCATTGACTACTATTTGTGCAATGGCAATCAATAAAAAT
492651 TCTAATTGATTAATTCCTATTAAAACACCGATAATTAGTGCAACAACACA
492701 ACTAATAATTAAaTTGGGAATATAAAAGTTAAAAAAGGAAAGAACTTCTT
492751 TTAAATAAAATTGTCGTTCTATTAATTGATTTGGTGATTATTACTAAAG
492801 TAAACAAAGCTTTTTTGTTGCAAACTTTGAATAATTCAACCCAAATATCC
492851 ACGGTATTGTTTTCAAAATAAAAAATTCCTAATTAGTTGCAAAATAACTT
492901 GCAAAAGCAAGTTTAATCCCTTTAGACATGAAAAATAAACTACCAAAACA
492951 ACTAAATTAACTGCAGTTCCAAAATCAACAGTATTAGTTATTATGGTACG
493001 CGATGCTGTTGCTAATAATGTAGAGATACCAATAATAATCAGTTCAATAA
493051 AAACATAAAAAGTGACTAAATTAAAATCAAAAAAGTTACTGAAAAAATTA
493101 CTTTTATTTACTGGTGGAATCTCTTTAAATGCTTTTGCAACAGTTGCTGC
493151 ATAACCCGTTCAGAGTTTTTCTAGCTTTTCATCAGTTAAAAGGTATTtC
493201 CTTTTGCAGGATCATATACCTCTCAACTATTTTCATGTTTGTTTTTAACT
493251 ATGACAAAGTGATCTTTAAAATGAACTATTATGAATTTGCTATCAAGTTC
493301 TTTTAGTTCTTGAAATGTTAATTGATAACTGTTGATTTCAAGACCAAACT
493351 TTTTGCCATAACTTTCCATTTCAAATAAGCTTAAGCCATTTGGTGGTAAG
493401 TTAATTTGTTCTAGTAATTCATCATGAACATACTTTTCATCATGGATTGC
493451 ATTGGCAAGCATACCAATTACGCAAATTCCACACTCATTCTGTTGTTCTT
493501 GATAAATGATTTTCATCGCCTTTGTTTTGTCTTATTAATAGCAATGAAAA
493551 GTGAAAAATGACAAATTTGTAAGCTGTTACAAACACTACAAACTGTTTTA
493601 TTAGTTAAAAATAAAGTTACTTATTATTTATTTGCAAGCTGACTAGCACG
493651 TTCGTACAAGGTTCTCACTAAAACACCTTGTCCAAGGTTCTCAATGGAAG
493701 CAGTTGATGCAATATCACAATGGATCAAAGATACACCTTCTCTAAATTCT
493751 GCAAGGAAACAAGCTGCTCTTGAAGAtCCAGCACCTCTTGCACTAGTAGA
493801 ATTTTGCAAATCAGCAAGTTTTGTTAGCTGTAAAGGTTTTAAATAATCAG
493851 GGTGCATAGGTAATCTTCATACAGGTTCACCTGCACTACATGCTGCTTTT
493901 TTAAAAGATTCTCACTGGTGATCACAAGTACTGAAAATACCTGTATAGGT
493951 AGTACTCAATATGTATGACATTAAACCAGTAAGGGTTGCTACATCAATAA
494001 TATGTGTAGCAGCTAAATCCTTAGCAGCATATGTAATAGCATCAGCTAAA
494051 ACCAATCTTCCTTCAGCATCAGTGTTATCTATTTCAACACTTTTACCATT
494101 GTATGCTATCTTAATGTCATCAGGACGTTGCGCCTTAGCACCAGGAAGAT
494151 TTTCAGTAAGAGCTGCTACTGCAACAACATTGGTTTTAACCTTGTTTTTA
494201 GCTAATGCCAAAACAGTAGAACATACTATAGCCGCACCACTCATGTCATA
494251 TTTCATGCCACGCATATAATCACCTGTTTTAATGTTCATTCCGCCTGAAT
494301 CATAAGTAATTCCTTTCCCTACAAAAGCAAGTTTTTCTTTGGAATTTTTA
494351 TTAGCTTGATAACTAATAACAAGTAAACGTGCTTCTCTTTCAGAGCCTTG
494401 ATTAACCCCTAAAAGTAAACCCATTTTTTTCTTAATTAGATCTGATTGTT
494451 TAAGAACTTTTATTTTTACAGGCAATTTACTTGCAGCCTTTTCAAAATGT
494501 TTAACAAATACTTCTGAATAAAGTAGATCTGAAGGAGTGTCTTGTAATTC
494551 TCTTGCTAGGTTAACATATTCGCCTACTGTTTCATATTCTTTAACTAAGT
494601 TGTGATATTCAACAGCACATTGAACAGCAACTTCAACATTTTTTTCAGGT
494651 TTGGTTTTCATTGTGAAAGGAGTAGTTTCACAAAAAGTAACACTTGTAAT
494701 AACAGTTTTTATCGCAGTATGAAAACAACCACTATTTTCATTTTTCTTAT
494751 AAAGTTCTATAAGACTGTCAAGATTAATGTTTAATTTGGTTTTCTTTCTT
494801 TTAAGAAATTGAACTAAAGCACGGTTGAAAGCAGGAAAATCAGTTGGTAA
```

-continued

The Nucleotide Sequence of the *Mycoplasma genitalium* Genome

494851 AACAACACCAAATTCAACATTAGGATTATGTGCAGCTTCTTCTTTTACAC
494901 CATATGTTTTTGAACTCACAAAAACAACTGTGTTGCTATCATCACTAAAA
494951 GGTTTATTTATTCTCATTCTATATCTCTATTTATTATTCTGAAAAGGAGT
495001 TATCTTTTCTCTCTTTAACATCATACACAGCAACATTAGTAGTAATTAAT
495051 GAACTAGCTACAGAAGCAGCTTTTTCAAGTGCAGTTTTAGTTACTTTGGT
495101 GGGATCAATGATTCCATTTGCAATCATATCAACCTTCTTTTTAGTCTCAG
495151 CATCAAAGCCAACACCAGTTTTTTCATTTTTCAATTCACTGAGAATTTTA
495201 ACTGGGTCAACTCCTGAGTTTTGAATAATTTGACGCGCTGGTGCTTCTAG
495251 AGACTTTTGCACAATTTCAAAACCAAGTAGGATTTCTTTAATGTTTTCAA
495301 CACTAGTTTCATTTTCATATCGTTCTTTTAGTTTACTGTTAGTTAAAACA
495351 CAAGAAGCATTTAATAAACCAACACCACCTCCAGCGATAATCCCTTCTTC
495401 AACTGCAGCTTTGGTGGAATTTAAAGCGTCTTCGATTCTGAGTTTTAATT
495451 CTTTTTGTGCGAGTTCAGTTGCACCACCAACACGGATAACAGCAACACCT
495501 TGACTTAAATAAGCAATTCTTTCTTTAATTAAATCAGAATCATACTTGTC
495551 AGTGGTTTGTTTAATCTTCCGTTTAGAAGTTCAACATGCTTTTTGATTT
495601 TATCCTTATTGCCTTTACCACCAATAACAGTAGTTTTTcCTTTAGCTATT
495651 TGAACCTTTCTAGCATCACCTAAATTATCAACAGTAACATCTTTAAAACC
495701 ACTATTAATTTCGGTATTATATGCTAAGGTTCCACTACTAATTGCTAAAT
495751 CTTCTAAAGCTGCTTTTTGACGTTCACCATATTCATTACATTTAACAGCA
495801 ACAACATTAATGGTGCCCCTGAGTTTATTAACTGCTARAGTAGTAACAAC
495851 TTCTTCTGCAAAGTCAGGTGCAACAATTAATAATGGATTACCATTTTCAA
495901 CACTACCTTCTAAAAGCGGAAGAATTTCTTTAATTGTGTTAATTTTTAAA
495951 GAGCTTACTAAGATTTTAGGTTGTTCTAAAACAACTTCCATTTTTTCTTG
496001 ATCACTAACCATATAAGGTGATGCATATGTTCCTTTAAATTCAATTCCTT
496051 CAGTGGTTTCTAATGTTGTATTAATGGTTTTTGCATCATCAGTTGTTATC
496101 ACGCCATTTTTACCAACTAAAGCCATTGCTTGAGCGATCAGTTTACCAAT
496151 TTCTTTAGAACCTGAAGAGATAGCTGCAACTTGTTCTATCTCTTCGTTAG
496201 TATTAATTTTTTTAGAGTACTTTTCAAGTTCTTTAATAATAAGTAAGCTT
496251 GCATCTTCAATACCCCTGCGGATGTTAACAGGATTAGCACCTTTATTGAT
496301 AATTTCAATACCACGGTTTGTCATTTCTTGTGCTAATATGGTAGCTGTTG
496351 TTGTACCATCCCCAGCAATGTCATTAGTTGACACTGCAGCAACTGAAATA
496401 ACCTTAGCACCAATATTTTCAACTGGATCACTAAGTTCTATTTCTTTTGC
496451 GATTGTAACCCCATCGTTAGTAATTAATGGGTTTGCAAATTTTCTCTCTA
496501 AAATAACATTTTGGCCTTTAGGACCTACTGTTACTTTAACAGCATTTGCT
496551 ATCTTATTAATACCCTGCAACAAGCGGGTTCTCGCATCTTTACCAAAGAT
496601 TAATTCCTTTGCCATAATTGTTTAATTTTATCTTTTTCTTTGCTTACCAC
496651 TTTCTGGTTTTTCAAAGGCAAGTACATCCTCAAATCCAATAATTTTGTAC
496701 TTGTTTCCCTCATTCTCAAAAGAGATACCACTATACTCCTTAAAGTAAAT
496751 AATATCACCAACACCAAAAGCATATTTTGGTTTTTCTGTTTTGCCATATG
496801 CAGGACCAGCACCAAGAGCAATTACAATCCCTTTATTAGCATTAGCATCG
496851 CTTTTATCATTACTTGCCAATGAGGTAATAATCCCTTTTTTTGAGACTTC
496901 TTCTTTGTTTGATTCCACAAGTGAAACCAAGACGTTGTCATGAATTGGCG
496951 TTATGTTCATAATAAAAATATTTTAATAATTAAAAACTAATTTAAAAGAA
497001 AGTAAAAGTTATCTTAAATTTATCTGATATTAGCGCTAAACATTAATTAA
497051 TATTTAGTGAGATATTGTTAATTTTTAAATACAAATTAATAAGCTAAACC
497101 CTTATAGAGCGGAAAGCGTTTTAAGAGATTTAAAACAGCTGTTTTTGTTT
497151 GACTAATTACCTTTTGATTACCATTACTTTTAATAACCTTATCAATCAAA
497201 CTGGCAACAAAAATAAAGTCATTAGTTTTAAAACCTCTGGTTGTCATTGC
497251 AGGAGTTCCAAGTCTAATACCTGAAGGACTAAAAGCAGATTTTGTTTCAA
497301 AAGGGATTGTATTCATATTCAAAACAATGTTAGCTTTTTGTAACCACAAC
497351 GCAACATCTTTACCATTACCAACCACTAATGAAAATAAGTGGGTTCAGT
497401 ACCTTTTGACACAACACGATAACCCTGCTTTAAAAATCAATTTGCCATTG
497451 CTAAAGCATTATCTTTAACTTGTTGCATATACTGCTTAAACTTTGGATTC
497501 AAAGCTTCTTTAAAACAAACATATTTAGCTGCTATCACATGTTGTAAAGG
497551 TCCACCCTGACATCCAGGAAATACTCCACTATCAAGCTTTTTGATAATTG
497601 CTTGGTTGTTAGACATAATGATACCCCCCCTAGGACCACGCAAAGTTTTA
497651 TGAGTTGTTGAAGTGACAACATCCACAAAAGGCAAAGGGTTTTGGTGCAA
497701 ACCTGCAGCGATGAAACCAGCAATATGGGCAATATCAGCTAAAAGATACG
497751 CATTAACTTGTTTTGCAATTGCACTAAATTTTTTAAAGTCAACAGTCCTA
497801 GAATAGTTAGAAAAACCACAAATAATTAACTTTGGTTTGTGTTCGAGAGC
497851 AATTTGAAGAATTGCATCATAATCAAGAGTTTCTGTTTCAAAATCTAACG
497901 AATAAGTTACTGCTTGATATTGCTTACCTGAAAAATTAACGGGGCTACCA
497951 TGGGTTAAATGACCACCACAATTAAGATCTAATCCTAAGATAGTATCTCC
498001 TGGTTTTAACAATGCTAAGTAAACTGCATAGTTAGCAGATGATCCAGAAT
498051 GAGGTTGGACATTAGCCCATTGTGCTCCAAATAAAGTTTTGCAACTTTCA
498101 ATGGCTAAGTTTTCAGATTCATCAACAACTTCACAGCCTTGATAAAAACG
498151 TTTACTGGGATAGCCTTCTGCATATTTATTTGTTAATACTGAACCAGTTA
498201 CAGCTAATATGTCTTGGCTAACGTAATTTTCTGAAGCAATTAAACAAATG
498251 TTTTCTCTTTGACGTTGTAACTCTTTATTAAGTAAAAGTCTTACCTTTGA
498301 AAACATTCAACTTAATTAACGTAATAAAAACGGTGTTTTTTGATTGTTCT
498351 TATCAACATATTTAAATTCTTCCTTTTCACTACTTTTAATTTGGTCGTAC
498401 AAGTGGGTATTGTGCTTTTTAGCAAATTGTGCATAGAAAGATTTTGTGTT
498451 ACTGTCACCAAAAATTAAATCATAGTGCTGAAATTTATCCCTATTATTAG
498501 TAGTTCTGGTTTTATTTTTTTCACTTTCACGTTTAGAAGTTCTTAAAAGT
498551 TGAGACATACCAATGTTATCTTTATGTGTTTTGGAATTCTTATATACCTC
498601 TAAAACACCAAAATAAATACTGTTAATTTTTTGGTTGTTGTTAAATATAG
498651 CACTTCCAGAAGAACCACCAGGGAGATTGGTATCATCAAGCATTAAACCA

-continued

| The Nucleotide Sequence of the *Mycoplasma genitalium* Genome |
|---|
| 498701 TATCCATACTGTTGGTACTCTTTGTCATGATATTTAAGTTTAAAGTTTTT |
| 498751 GAAGTTTTGAAATGTAACAATCCCTTTTTCGTGTTTAATAACTTTATCAA |
| 498801 CATGACTGTCTTGGGTTTTTTTGGAAAATATTTCACTACCTATTTGACCA |
| 498851 TCTTTTCTGGCATTTTTTGTAATTACAGGGATCTCTTTAGCAGTTGAAAC |
| 498901 TAAATATGTGTTTTTACTCCATAACTGACTTTTTTGATTAAAGTTATGAG |
| 498951 TTCTAGCAAACTCTTCTTTTTGTTCTAATAAGCGGTTTTGATCATAACCT |
| 499001 CTTTCAAGTACAGGATAACCCAAAAGATAGTGGCTATGGTTTCAATGTTG |
| 499051 TTCTAAATCTTTGGTTTCAAATATATTAGTGCTATCACCCAAACTTTTAT |
| 499101 AAGTATTAATTGCTGGCTTAATGAATTCATTGAAGATTTGTCAATCACGA |
| 499151 AGATTTTCTAAATTAAGTTCCAGTTCTATAACAGCAAAGTCTGCATAAAC |
| 499201 AGGCTTAATACTGTTAACACCTTTCAAGAAATTAGTTGCGGTATACGCAG |
| 499251 TTTTAGGAATATTTGATGTTTGAATAGAAAGCAGTGAATCATTTACCTTT |
| 499301 CTTTGTTCTAATTTTTCTTCTTGATAGAGTTTTGTAATATCTGTTTTGTT |
| 499351 AGTGTATTTACCAATTGAAAAATAAACAGTTGATTCATATTCATTAAACT |
| 499401 CCCTTTGATCATCTGTTTTGCTGTAAGGTCAATGATCACCGATATTTCTC |
| 499451 AACCCATCAGCAACATGCAAATTGGTTGCAATGTAAGCGAAAAAAGAACC |
| 499501 TTGCTTTTGGGTTGTGTTTTCATCACCTTTTCAGTCAATTAATCAACCAG |
| 499551 TGCCATAAGAGTCATTACTAAAGCTAGTGAAATTTAAAGTAAAAGTTAAA |
| 499601 TCATATCCTTTTCTGTATATATCACTTTCTTCTGGGATAAAACTTGTATT |
| 499651 AAATTTAAAGTTTCTGTTGTAAACCTTCTGTTCTACCTTAGGTTGCTGAT |
| 499701 TTACTTCTGTTCCTTGATCAGATTGTTCATCTTTAAAAGGAGTAGCGTTG |
| 499751 TTATCTGTTGTGCTGTCGTTTTTTTCTTCTATAGGAACAGGAACAGGTGA |
| 499801 AACAGCAGAACAAGAAGCTAAAAGTGCTTGTAATGAAATTAGTGAAAAAC |
| 499851 CTAAACTTTTAGTTTAAACCACATATCAATCTTTAACATTTTAATACAA |
| 499901 AAATATTTCAAAACCTTTAATTAATGAAGTTAAGAAGCACTTGTTAAACT |
| 499951 TAGGCTTTAGCTTCAAAAATAATTGAGTTCATCTTTTCACTGATAAATTT |
| 500001 AATTATTTTTATTCTGCTTAGTTTTAGATGCAATTAAAAAGAAGAAGCTA |
| 500051 ATGAAAAAACTAATGAAAGCAAATGCAACCATCAAAAAAGTTAAAAATGA |
| 500101 AAATAGAACTACTATTGACTCAGGTAAACTAACTAAATTAAAACCAAAAA |
| 500151 AATTAATCCCGTTAGAATTTGCATTGGCTTGATAACTACTATCTAAAGCT |
| 500201 AGAAAGCCAACTACAAAGCTACCAATTAGAAGAATTAAACCAAAAATAAA |
| 500251 TCAAAAAACACTATTCAGTTTCTTTTTCATATCGAATAATCTTATCTATC |
| 500301 CGTCTTTGGTGTCTACCACCTTCAAAATTAGCTTTGAGAAAATCATCCAC |
| 500351 TATTTTAATGTTTTCACTGTCAGTTACAAAACGACTGGAAAGACATAAAA |
| 500401 CATTGGCATTATCATGTTGTCTAGCTAAAGCTGCTGTTTTCTCACTAACA |
| 500451 ACCAAAGCCGCTAATACTCCTTTTACTTTATTTGCTGCCATACAAACCCC |
| 500501 AACACCAGTACCGCAAATTAGTATCCCAAGATCTTTATCAGAATTTTTCT |
| 500551 TGACCTTATCAGCTACCAAAAAAGCAAAGTCAGGATAATCATCATTAGCA |
| 500601 TCAAAATAATTAGGGCCAAGATCAACTACATTAAACTGCTTAGTCTTTAG |
| 500651 GTGTTCACTAATAATTTTTTTAAGAGTTAAACCGGTATGATCAGAAGCAA |
| 500701 TAAAGATATTAAAACTCATTTAATTCAGTTCCAGATAGTCTTGTTTTGTA |
| 500751 TTGGTTTTAATTTTAGTTAAAAGATTAATTAATCCTTCTAATGTATCAGG |
| 500801 ATAGTTTTGTCGATTGTATAGTTTTGTTAACTGTTCTAATGATCTATCGA |
| 500851 TATGACTACTCTTTTGACGATATTTATTTGCAAAAAGAAAAGCTTGTTTG |
| 500901 CACATTAGCCTTAAGTTAACTAAACTAACAACATCACAAATAACTTCAGT |
| 500951 CAATTGAATTTGCAATAAATCTATCTTTTCACTAAACAAATTAAAAGTAC |
| 501001 CTAAATAGTTATTATTAGCTTCAGTGAAGATGTTATCAAGTTCTAATTTC |
| 501051 GATTTATTAATTACTTGCAATGTTTTAGCAGGAACCTTTAAATCTTGATC |
| 501101 GCTAATTAAATTTTCAATCTGAAAAAATTTAAATCGGAAATCATCTAAAG |
| 501151 TATAGACAAAAAAGCGATAGTCATCAAACTTATTAACTGCTAAATTAAGT |
| 501201 AAATCAGTTAGTGAATTTTTCAGTTTTTCTAAAGCTTGATTTGTTTGACT |
| 501251 CATCAAGTAAAACAGTTTTTCATAATTGATTTGATTCTGAGCTAAACTTT |
| 501301 GATGGTTTAAGTTATTAATATTTTTAGTAATTAGATCGCAGTTCTCATTA |
| 501351 AGCTCAATAATTAAATCATGCACATCTGTTTCATTTTGGAACACTAATTC |
| 501401 AATGGCTTTAATTGTTGTTTTTAAAAGCTCATTTTTCTTTTCATATTGTT |
| 501451 GAATTTGATTACGAAAATCATCAATATTTTCAACCACTAAATTAATGCTT |
| 501501 TTTTCTTTGGAACTAACTGCTTGAAAAAGTCAACTAATCGCCTCTTGAAC |
| 501551 TTCATCCATATTCCTTTCGCATAGCATTAAATTTAAGTTATTAAGAAAAT |
| 501601 TGGTACAATCCTTTAATTTAATGGTAATGTTATTAATCAATTCATGAAGT |
| 501651 TTTAAGAGATCTTGACTGTTAATTACTTTATTCTTCATTAATTCCATTTG |
| 501701 TTTTACCTTTTGAATTAAAACCTTAAAGTGATGGGTTAAATAACTTAACT |
| 501751 TAATATCAAACATATATTGCCTGTTAGCAGTAATAATTGTTTGACTGAGA |
| 501801 ATGTTATGTAATTTGTTTAAAAAAGCAATTTGCTTTTCTACATCTTTAGC |
| 501851 TTGAATACAATTTTCTATCTCTTTAAACAAGAGCGAAATCCTGTTAAGAA |
| 501901 CATTTAAATAGAAAAGCGAATCATATTTTTCAATTAAAAAATTATTAATA |
| 501951 AATTGGTTTAAAAAACAGAAAGCCTGACGATAAAAAACTAAACAATCATA |
| 502001 GCTATTGTTGAAATAAACAATTGCGTTCTTAGTTAGATTAATGTATTCTT |
| 502051 GTTGTTTTGTATATAGATGTTGAAGATTTTTATTTAAGAGCTTAATATTT |
| 502101 CTATTAAATCAGATGAAACGATAAATATTATTTGGTTTACTGTAAACTGT |
| 502151 TAGTTGCTCAAAAGCTGAATTGATTTCATTATCAAATTTGATTTGAAACT |
| 502201 GTTTTAAAACTTTAATGGATTGTtCTAACGCTTGTTTTTCATTTCTTAGT |
| 502251 AATTGAAATGGACTAATCACACAATTGAAATTGCTTAATTTCAAGTTATT |
| 502301 ATAGAGTTGTTTGGTTTTTTTTAAAAGTAAGTTATTTTGTCTAACAAAAA |
| 502351 GACAAACTAATAGATAAGCACCAAAAATTACTAGTAGTAAGAAAGGGAGC |
| 502401 AAGATTAGAAAAACCAGCATTTTATTTTTtCTTACTTGAAAGTTTTAATA |
| 502451 GTTCAAACATTAAATTTTGTTCAATTTTAACGTTTAGCTTAGCATCCTTG |
| 502501 ATATGGTGAATTTTTCTTTCAAGTTCTGTTTTTCTTTTTAAGGTTTCATT |

-continued

| The Nucleotide Sequence of the *Mycoplasma genitalium* Genome |
|---|
| 502551 AATATCAACTTCATCAGCAAAAACAAAATTTTCTGTGAAAATCTTAGCTT |
| 502601 CTGTTTTTTTAATAAGCATTAAACCAGCACCAATAATTGCTTCTCTTTTT |
| 502651 GTTTGATCAGCAAAAATAATTTTGCACAGATGGGATTGAATAGCAGCAAT |
| 502701 CAAAGGAGCGCGATTAAAATTTAATCCTATGTAACCTTCAGTAGTTTTAA |
| 502751 CTTGCGCACTAATAATGGTTTTATCTAGTTTTATGCCACTAGGACTAAGT |
| 502801 ACCAAAAAGCGCAATAACTTCATAAAACTATTTAGTTTTATCAAACTCTT |
| 502851 GATTTAATCTTTTTGCTTTTTCAACAGCCTCTTGAATGGTTCCAACATAA |
| 502901 AAGAATGCTTGTTCAGGCAAATGATCATGCTTACCTTCCAAAATTTCTTT |
| 502951 AAAAGATTGAACAGTATCATTTAAAGATACATATTTACCTGCAATACCTG |
| 503001 AAAACTTTTCAGCAACAAAAAAAGGTTGGGATAAAAAGTTACGTATCCTT |
| 503051 CTTGCTCTTTCAACAATAATCTTATCTTCATCAGACAATTCATCAATCCC |
| 503101 TAGTATAGCAATGATATCTTGTAATTCTGCAAAACGCTGCAAGATATTTT |
| 503151 GCACTCCTAAAGCGACTTTATAATGGTTGATACCAACAACACTAGGATCT |
| 503201 AATAAACGACTTGTTGATTCTAAAGGATTAATTGCTGGAAAAATACCTAG |
| 503251 TGCTGCAATATTACGATCCAACACTGTTTTAGCATCAAGATGGGTAAATG |
| 503301 TTGTTGCAGGTGCTGGGTCTGTTAGATCATCTGCTGGAACATAGATAGCT |
| 503351 TGAACAGATGTAATAGAACCTGTTTTGGTAGAAGCAATTCTTTCTTGTAA |
| 503401 CTTACCCATTTCAATAGCTAAAGTTGGTTGATAGCCAACAGCAGATGGCA |
| 503451 TTCTACCAAGTAATGCTGAAACCTCACTACCTGCTTGAGTAAAACGAAAA |
| 503501 ATATTGTCAATGAATAACAGCACATTCTGATTATCATGATCACGAAAATA |
| 503551 TTCTGCCATTGTTAAAGCAGTTAAAGCAACTCTCATTCTAGCTCCTGGTG |
| 503601 GTTCATTCATTTGGCCAAAAACTAAAACTGTTTTATCAATCACCCCACCT |
| 503651 TGAATCATTTCATAGTAAAGATCATTACCTTCTCTTGTTCTTTCACCAAC |
| 503701 TCCAGCAAATACACTTAAACCAGAATGTTCTTTGGCAATGTTATGAATTA |
| 503751 ATTCTTGCACCAAAACAGTTTTCCCAACACCAGCTCCTCCAAATAAACCA |
| 503801 ATTTTACCCCCCCTAACGTAAGGAGTTAAAAGATCAATTACTTTTATTCC |
| 503851 TGTTTCAAAAATATCAACAGTATTTGGTTGTTCATCAAAAGCAGGTGGGT |
| 503901 TACGATGGATTGATAGCTTTGGTTTTTTTGGTAATGGTTCTTTTCCATCA |
| 503951 ATGGGTTCACCTAAAACATTGAACATCCTTCCCAATACATTTTTGCCAAC |
| 504001 AGGTACCTCTATTGGATGGTTATAGTTAGTAACTTTAACATTACGTGCTA |
| 504051 ATCCTTCTGTAGGACCTAATGCAATGCAACGAACAATGTCATCACCTATT |
| 504101 AATTGGGTTGCTTCTAAAAAAAGCTCACTTTTTTTTAGTTGTACACTCAA |
| 504151 ACAATCATAAACTCTAGGTAATTGTTTACTTTCTGAAAAGATAACATCAA |
| 504201 CTACAGGACCAATGACTTGGTGAACTTTACCATATGTTAGGTTTTCTTTT |
| 504251 TTTATCAATTTAATTCATACCTCCTATAACTTCAATAATCTCTTCTGTAA |
| 504301 TAGAGTTTTGTCTTAGCTTGTTAAATTGTAAAGTGTATTTATCAAGTAAA |
| 504351 TCTTTAGCATTCTTTGTAGCAGCTTCCATTGCATTTTGTCTAGAAGCTGA |
| 504401 TTCACATAACTTAGTTTCAACAAGGCCACCATACAGAGCCACATCAAAAA |
| 504451 ACTGTGGAGTAATTAAATTAATTATCGTGGCTTGATCTGGCTCAAAATCA |
| 504501 AGTTGTTGATCAGTTACAACCGGATTTAAAGTTTTAAAAGTTTCAACATC |
| 504551 GAAAGGAAAAACTTGAAAGAGCTGAGATTGTTGGATTAATGAGTTTTTAA |
| 504601 ATTTAGTGTAAACCATACAAATTCGATCAAGTTTAAACTCTTTAAATGCA |
| 504651 TCCATAATCTGATCAAATATCGTTTGACAATAATCAAAATTAATATCACG |
| 504701 ATCTTGGATATCAATAAATCCAACAGCAGGATTATATTGACTATTTTTAT |
| 504751 TTCAAAATGATTGGTTTTTTCTACCTAAAAAAAAGATTTTATCATCAGCT |
| 504801 TTAAAATTAGCTTTTAATAACTTATTCATGTTCGAATTATGCTGTCCACA |
| 504851 AAGTCCTAAAGAAGAACTCATCATTATCCATAAAGTTTTTTGGTTATCTG |
| 504901 GTTTCTTTTTTGGTTCTTTTAAAGAAACAACTACTTGGCCAACAGCTTTA |
| 504951 TAAAATTCATTAAAAAACAAACTAATTTCTTGAAACTGTTTTTTGAACTT |
| 505001 AATAAACTTAGCGCGTGACACCATTTTCATTGCATTAGTTATCTTAATGG |
| 505051 TGGATTTTACTGTATTCATTCTGCGCTTAATTTCTTGTATAAAAGCCATT |
| 505101 AATTAAGTTCCTCAATACTACCAAATTTGGTAATATCATAATCTGTTAAT |
| 505151 GTACTGATAAAACGTTTCACAAGCATTTTAAAAGCGGTTTTAGTTTTACT |
| 505201 TTCTAAATCCTCAGTAAATTCTTTTTTGTTAGATAACTCTTTAAACAGAG |
| 505251 GATGGGAACCATTAAATTCTTCTGTTATCCTTTGTTTAAATTTAGCAATT |
| 505301 TCATCAACTGGAATAAACTTAATGAAAGCTTTGTTAATAGCAAATAAAAA |
| 505351 TAATGCTTCATGGACTTGAGAGTAAGGTTTACCATTTGGTTGTTTAATCA |
| 505401 TTTCCATTACTCTTTTACCATGCTCTAAAACCTTTTTTGTATTTTCATCA |
| 505451 AGATCACTACCAAATTGACTAAAACTATCAAGTTCACTATACTGAGCAAG |
| 505501 TTCTAGTTTTAAACTGCCAGTTTGCTGTTTAATCGCTTTTGTTTGTGCTG |
| 505551 CACTACCAACCCTTGAAACTGATAAACCAATTTGAATTGCAGGGCGTTGT |
| 505601 CCAGCGTTAAATAGACTACTAACCATAAACAGTTGGCCATCAGTAATTGA |
| 505651 AATAACATTTGTAGGAATATATGCAGAGATATCACCAGCTTGAGTTTCTA |
| 505701 TAATTGGTAAAGCTGTAATTGAGCCACCACCATTTTCATCATTTAACTTG |
| 505751 CATGCACGTTCCAAAAGTCTTGAATGTAAATAAAAAACATCTCCTGGAAA |
| 505801 AGCTTCTCTACCAGGTGGTCTTTTTAACAAGAGTGAAAGAGTTCTGTAAG |
| 505851 CAACAGCATGCTTAGAAAGGTCATCAAATACAATCAAAACATCCTTTCCT |
| 505901 TTTTTAAGTCAATATTCAGCAATAGTTATTCCTGTAAAAGGACTTAAATA |
| 505951 AACCATGGAATCAGAGTCACTAGCTGTAGCACAAACCACTGTAGTGTATT |
| 506001 TCATTGAATCATTAACTTCAAGTTGGTGTACAATTTGTGCTACTGATGAA |
| 506051 TTTTTTTGACCAATTGCTACATAAACACAATAAACATCTTTATCTTTTTG |
| 506101 ATTAATGATAGTGTCAATCGCAATAGCAGTTTTACCTGTTTGTCTATCAC |
| 506151 CAACAATTAATTCACGTTGTCCTTTACCTATAGGAAATAAAGCATCAATT |
| 506201 GTTAAGATTCCAGTTTCAAGTGGTTGGTTAACACTTTTCCTTTTCATTAC |
| 506251 ACCTGGAGCAATTTTTTCTATTTGATCATATTCAGTAGCTTTAATATCAC |
| 506301 CTCTACCATCAATTGCTTCACCAAGTGCATTGACGATTCTACCAAGCATA |
| 506351 ACATCACCAACAGGAGTTTTCATTACACTGTGGGTTCTTTTAGCGGTACT |

-continued

| The Nucleotide Sequence of the *Mycoplasma genitalium* Genome |
|---|
| 506401 GCCTTCTCGTAACGAAGAATAGTCACCAAAAAGTGCTATTCCGACTGTAT
506451 TTTGTTCAAGGTTTAATACTATTCCTTGAATATTATTTTCAAATTGAATT
506501 AACTCATTTAATAAAGCATTTTCAAGTCCACTAACCTTGGCAATTCCATC
506551 AGCAACACTAATGACTTGACCAATTTCACTGTTAAATATTTTTTGGAAT
506601 ACTTTTTAATTTCAGTTTTGATTAATGCTACGTATTCATTTAGTTTATCT
506651 GCCATAACTTCTCAATTAACTTAAATAAAATGGGCCATTATGCGTTTTAA
506701 TTCATCACGCACATTTTTTTCAAATAAATGGGAACTTGATTCTATCCTAA
506751 TTCCTGAAATTAAACTGCGATCAATCTCAGTTTTATAAACAACCTTTGTT
506801 TTAAAACGTTTTTCCATTATTGCAATAATTTTGTTAAGTTGTTTTGAGCT
506851 TAATTCAAAAGCAGTAATTATTTTGATAAATTGAATGTGTTTTTGACTTT
506901 CAACATTATCAAAAAAATACTTAATTGCCTGTTCAACTAAAGTAAAGTAA
506951 CCCTTTAAAATAATTACTTTTAAAAAATCAACAAAAACTTGACAAAAATG
507001 ATTTTTAAACAACTTATCAACAAGTCTTATTTTATCTGGTTTTGTTAGTG
507051 TATAAGAATTAAGTAAGAACGATAATGAACCATCTTTAAAATTACGCATT
507101 AATTTCAGAAAAAAATGGCACTCTTCATAAATTTTCTTTACTTGTTTTTG
507151 CTCTTCACTTAATTGAAAAAGTGCAGTTCCAAATGCTTGTGCATTAATCA
507201 TCTTCTGTTTCGTTAGCTTCTAAATCTCTAATAAACTTATCAATAAATTC
507251 TCTATCTGATTTTTGATCTATTTTCTTGAGAATTAGTTCTTGTGCAGCCA
507301 ACATAGCCAATTCCACACTCTCTTTAATAGATTGTTCTTTAAGAGAACGT
507351 CTTTCTTTTTCAATTTCCTGACGAGCTTGAAAAATCATTAAGTTAGCTTG
507401 GCGATTTGCTGTTTTTTCTATTTCACTTTTTAATTGCAAAGCTTCATAGT
507451 TAGCTTGATCAACAATTTCTTTAGAAACTATTAGTGCTTTTTCATGCCTT
507501 TGATTAGATTCTTCAAGTAGATTTCTTGCTTGTTTTTCTAATTCATTAGC
507551 TTGTTTGATTTGTGCTTCTAGTAAATTTTTACGGTTATTTAAAAACCTTT
507601 GAGTTGGTTTTCAAAACAAGAAAATCATCAGTGTTAGTAAGATGAAAAAT
507651 GCTAGTAAATGAGTAATAAATACCCAAAAGTTAGGAAAAAGTTCATTTAT
507701 TACTGAACTACTCTTAATTTCTCTAACATTCTCAGTACAAGAAACCAAAA
507751 ATAAGCTGAGTGTAAAAAAGCTAAAAACTAATAAGCTTCATTTAAAGACA
507801 AGTTTTTTTGCCTTTACCATCCTTAAGCTCCTGCTACAAAAATTAAGATA
507851 AAGGAAATTAAAAGTCCATAAATTGCTGTAGATTCAGAAACAGCAGAACC
507901 AATGAAAATTAGTTTAAAAACCTGTTTTTCAACTTCAGGATTTCTTGCTA
507951 TTGCCTCAACAGCTTTACCAAAAATATAACCTTGTCCAATCCCTACAGTT
508001 GAACCTGCAATCATAGTAACACCAGCACCTATATAAGCACCTAGCTTAGC
508051 ACTAGCGTTAACATCCTGGGTAGTTTGAGTTTGTTGTAATATAACACCAA
508101 CTGTAGCTAAAATTTCATTAACATGTTCCATAACTAAATATTTTCTTGAA
508151 TTACCTTTATGCCTTTAAAGTGTAATTCACTTGCATTATTATTTTCCAAA
508201 CCTTGATTGCGCATTTTAGCCCAATAATTATAAGTCAACATTACAAAAAC
508251 ATAACCCTGCAATACACCTGCAATTACATCAAAATAGATGTGTAATACTG
508301 GGGTTATTAAACCTGCAAAAACTGTTCCTAAGCTAAGTGCTAATGGTTGG
508351 TTATTAATACTTGAAAAAATAAAAATTCAAAAGTTATAAAAAAGCGCCAA
508401 AATAACTGTGCCCGCTAATATGTTTCCCCATAACCTTAATGAAATAGAAA
508451 AAAGCGGTGCAAATCCACTCAATATACTAAAAGGATTTGGAATGAAAGTA
508501 GAATACTTTTTTCCTTTAACAGTAATTCCAAAGGCAAACTCTTTAAAAAA
508551 ATTTCATCTTTGGTATCTAATCCCCATAACAACAATCCCAATAAAAGTTG
508601 CAAGTCCTAAAGAAAAAGTAAATGTTAAAGATGATGTTGGTGGTGAAATA
508651 CCACCAAGCAAGCTAACTAAGTTGCTTGATACTATGTACAGAAGCAACAT
508701 TAAAAAGTAGGGAGCAAATTTCTTATTTTCCTCTCCTAAAAGATCTGCTG
508751 TTGTATCTTGTACCCAAACAAACAACATTTGAAATAAAAGCAAAAAATAT
508801 GAATTATTTTTAAAGAATCTGCTTTTTTTAACTTAAGCTTATAAAAAAT
508851 AAAAAAAGTTAGAAGCAGTACAAAAACAATAAAAATACCAAGAAATTTGAT
508901 CAGTAGGGGCAAATGGTTTTCAACCGCTAATTGGTGAGATATCAAAAATA
508951 CTTTGATTGGAAATGAAATCTATTTGATTAGTTTCTTTTAAAACTATCTC
509001 CCGTGGCGACATGTTTTCTTTTCGATTTAGATATTAAATTGATAAAAAAA
509051 TATTCTAAAGGTAACCAAACAAATGATAACACTAAATTTAGTATTGGAAA
509101 AAACAATGTTGAAATTATTGTTGCAATAGTGTTAAAAATTGACGGAGTGA
509151 CAACAAAAGAAATAATCACAGGAATTAAATAAATTAAATATCTAGCTGTG
509201 AAAAAAAATGCAAAGAATGAAACTGCTTTTTGCTTTTTGACATTTTTCAA
509251 ACTTGCAAAGAAAGATGCTAATCTTAAAACTGATAGTGAATTTAAAACAG
509301 CAAAAGGTAATGGCAACATTCAACCAAATAAAATGTCCAAATTATTGCCT
509351 TTTGTTAAAACAACAACTGCTATTAAAATTAGTACAAATAACCAAGCTAC
509401 AAAAATAATTAAGGTAATAATTTTTGCAACCTTTCTATTGTTTCAATTGA
509451 ACAAAACTTTTAGATGTTAAAGTTTTTAGGTTTAATGTTTGTAAAGGTAT
509501 TTCAACCTAAGTATTTTCCTTTATCACCAAGTTCAATTTCTATGTACAAC
509551 AAACGATTGTATTTAGCTATTCTTTCTGAGCGTGACATTGAACCGGTTTT
509601 AATTTGACCAGTTTGGGCAGCAACTGCCAAATCAGCAATAGTTGTATCTT
509651 CTGTTTCACCACTGCGATGTGAAATTACTTGACTCCAGTTAGCTTTTTTT
509701 GCAACTTCAATTGTTTGAATCGTTTCACTAATAGAACCAATTTGATTTAA
509751 TTTAATCAATATCGAGTTTGTTGTATTTTGTGCAACACCTTTTTTAGCAA
509801 GTTCTGCATTAGTACAGTAAGTGTCATCACCAACAATTTGAATATGGCTA
509851 CCTATGGTTTTAGTTAATTGGTTCATCCCTTCTCAATCATTTTCACTCAA
509901 ACCATCTTCTATTGAAATAATTGGATATTTTTTGTTAATTTTTCTAAGT
509951 AAGCAATCATTTCTTTGCTTGTTAAACTCCAATCCTTTGCATTAAGGATA
510001 TTAGCTTTTATTCCTTTCTTGAAAACATAAAGTTTTTTATCTTCGTCATA
510051 AAACTCACTAGCAGCAACATCAATGGCAATAGCAATATCATCTCAAGGCT
510101 TATATCCAGCTAATTTAATGGCTTCAACCATGATGTCAAGTGCATCTTCT
510151 GCAAGTTTTAAGTTAGGCGCAAATCCACCTTCATCTCCTTTATTTGTGTT
510201 TAATCCACGCTTTTTTAAAAGATTTTGTAAAGCATGAAAAGTTTCACTAG |

-continued

The Nucleotide Sequence of the *Mycoplasma genitalium* Genome

```
510251 CCATTTTTAAAGCTTCATGCATCTTTTTAGCACCTAAAGGCATGATCATG
510301 AACTCTTGAAAATCAATATAGTTATCAGCATGAGCACCACCATTAATTAC
510351 ATTTAACATTGGCACAGGTAAAACAAAATTTGTTGTATTTAATCCAATTA
510401 ATTTATTTGAAATGTATTGAAATAATGAGCTGTTTTGTGCTTTTGCTGCT
510451 GCTTTTGATACTGCAAGTGAAACAGATAATATAGCATTTGCTCCTAATTT
510501 TGCTTTGTTGGGAGTATTGTCTAGTTTAATCATTGCTTGATCCACTGTTA
510551 ATTGATCAAATGCATTTAAGCCAATAAGCTTAGGGGCAATAACTTTATTA
510601 ACGTTATCAACGGCTTCGTTAACGCCTTTACCAAAATAATTTTTTGGATC
510651 ATTATCACGTAATTCAATTGCTTCTTTCTCACCTGTAGAAGCACCTGATG
510701 GAACCATCGCTTCACCTACATGACCAGATGCCAATTTAACAACACAAGCT
510751 ACTGTTGGAACACCCCGAGAATCAAAAACTTGATAAGCAAAAATATCGGT
510801 TATTTTTGAATTGATGTTTAGATTTGAACTTCCCATATTAAATAGAAAAA
510851 TATTGTTAATAAAATTATTATATGTTTTAAGATTTCTATTAATTCAAGTA
510901 ATATGAAAGAAATTTATTTTGGTGGTGGTTGTTTTTGAGGAATAGAAAAA
510951 TATTTTCAACTTATTAAGGGTGTTALAAAAACATCTGTTGGTTATCTCAA
511001 CTCTAGGATTAGAAATCCTAGTTATGAGCAGGTTTGTTCTGGTTATACTA
511051 ATGCTGTTGAAGCTGTAAAAGTTGAATACGAAGAAAAAGAAATTTCTCTT
511101 TCAGAATTAATTGAAGCACTTTTTGAAGTTATTGATCCAACTATAAGAAA
511151 TAGACAAGGTAATGATATTGGAACACAATATCGTACTGGTATTTATTGAA
511201 CTGATAGCAGTGATGAAAAAATAATTAATGATAAGTTCTTAAAACTTCAA
511251 AAAAACTACAGTAAACCAATTGTTACAGAAAATAAAAAAGTAGAAAATTA
511301 TTATCTTGCTGAAGAATACCATCAGGATTATTTAAAAAAGAATCCAAACG
511351 GTTATTGCCACATCAAATTTGACTAATTAAATATTTCAGGATTTTTAATA
511401 AATAAAAAGGATTTAATGATGTTATAGCaATAATCATTAATCCGTTCAAT
511451 ATGTTTAACAGAAGCTACAAGATCAATTAAGAAAATCCTTTCAGTAACCT
511501 CATTTTTATTAATGGTTTCATAGTATTTTGTTAATACAAGGCGATATTGG
511551 TGCTCAAATTCAATAATAGTTTTGGTTGCATTTTCAAATTGTAATGTAAG
511601 TGGCTTTTCTTTATCTTGTAAACTTTCAAAGGTTTTCTTAAGGTTATTGA
511651 GCGCACTTTGATGCAAAGTAACTAGATTATTARAAATCTTTATATCAAGA
511701 TGCARATAATGTTCTATAAACTTAGTTAAATTATTAGCATAATCACAAAT
511751 GCGTTCCAAGTCACGACTTGACATAATTATTGTGATTGTTAGGCGTAAAT
511801 GGCTAGCTAATGGAGAATTTTTAGAGATTGTCCAAATTGATTCATTAATT
511851 AATTTAAATTCAGACCTATTAGATTGGTCCTCCATTTCATAAATAGTTTT
511901 AATCAGTTCTTTGCGTTTTTCTAAATTATCTTCACAAAGTAATTGATTTA
511951 ATGTTTCATGTGCATTGATTACGTGCTTAAAATACTCAAAAAAAAGCTTT
512001 AATAATTTCTTTTCTGAACGCTTTAAAATTTGGTAATTAATGTTTTCCAT
512051 AGCTAATTTTTCCCACTTATATAACTATTTGTTGCTTTTTGCTTAGGCTT
512101 TGTAAATATCTGtTTTGTAGTGCCTTGTTCAATTACTCTTCCATCAGCAA
512151 AAAAAATCGTTTCATCAGTTATTCTAATTGTTTGAGCCATAGAGTGAGTA
512201 ACAATAACAATTGTGAATTTTTCTTTTAGTTGTTGAATTAGAAGTTCAAT
512251 AGAGTTTGTGGCAATTGAGTCTAAAGCACTGGTAGGTTCATCCATCAAAA
512301 GAACATCTGGTTGTAAAGCAATAGCACGCGCAATACACAAGCGTTGTTGT
512351 TGTCCACCAGAAAGGGTGTTTGCATTCCTATGTAAATTATCTTTCACTTC
512401 ATCTCACAATGCTGCTGATATCAATGCCTGTCTTACTATTTCATTGATAG
512451 CATTTTTATTGTGAATACCATGTGCTCTTATGCCATAAGCAATGTTTTCA
512501 AAAATAGAAAAATTAAAAGGAGTTAATTTTTGAAAAACCATGCCAACACT
512551 AGTGCGCAATGTTAAATCATTAATAATTCCTGAATTGATATTCTTACCAA
512601 GAAAATATATGTCACCTGTTCAACGTGTGTTTTCATTTAAATCATTTAAT
512651 TTATTTAAGCACCTAATAAAGGTGGATTTACCGCATCCTGATTTACCTAT
512701 TAAAGCAGTTATTTTATTGCGTTTAATGTCAAGATTGATATCAAATAATA
512751 CTTGTTTGTTTTTGTTATATCAGAAGTTGAAATTTCGAATTTCAAATACA
512801 TTTTTTTCATCAAAATCCTTTTTAATGACATTATCTTTGGTGTTTTTAAT
512851 CTTTATTAGACGGTTTAAAATTTCAATTTCATTCTTAATACGGGAGATTT
512901 CATTTGCATCTGTTTCATTATTTAAACCAGTAATTTTCTTTTTATATTCT
512951 TTGATTTGTTGTTCATAAAGCTTTCGGTAATGCTTAATTTTTTCAAGCTT
513001 CAATTGAAAATTTTTTCAAAGTGCTTTTATGTTCTTTTCCATAATTTAAA
513051 GGACTGAAATTTACTTTTAATTACTAGCCATTTTTTGTTTATTTAACAAAA
513101 ATAAACTCGGGATTAAATAAGAACTGAAAAAGATTAAAAGAATTAAGAAA
513151 ACAACAGAGACCAATGATGTTTCTAACATAACACTTATTGCATTGCTATT
513201 AATAGAAAATAACTGTCCATATATCCTTGTTGTTAGTGTTTGACCTGGCA
513251 ATGACAAATGAAATAAATTACTAGATGATAACCCTGAAGTGATAAAGAAG
513301 GGTGCAGTTTCAGCAATAATTCTGTTGATTGACAAAATTAATGCAACTAT
513351 TAATCCTTTCAAAGCACTAGGTAAAACTATTTTGAAAATAACTTCACGTT
513401 TACTTATACCTAAAGCAAAAGCACTAATTCTTAAATCCCAACTGACATTA
513451 TTTAGTGCTTGTTGACAAGtTCTTATAAGGAAGAGTAATATAACAACACT
513501 AATAGTTAGAATGCCTGCTATTAAACTAGTACCATTAGCTCCTCCAGCAC
513551 TTAACTGCAAGACTCTTAAAAAGAAAGAAAGTCCAAATAATCCATAAATA
513601 ATAGATGGCATTGAACTTAGTGAATCAATTACAAAGTTAAAAACATTTTT
513651 AACCACTTTTGAATTATTGTACTCGTTAAGTCAAATTGCAATTAAAAGTG
513701 CTAGTGGAAAAGTAATGGTGATAGTAATCAAAATAATTACTAGAGTATTT
513751 ACTAGTGCTCTGCCAGTTGAATCAGCTTCAAATGAAAAACAGTAGAACC
513801 ATTATTATTAATAGCAACACTTCCATTAATAAATACAAACAGCAAAATTG
513851 CTAACACAAATCCAAAAGCTAAAAAAGTACAAATTAATTCCTGGAATATT
513901 TTTAAAAAATAATTAAGTTTTATTCAAACAACACTTTGAAGCCTTTCTTT
513951 AAAAAAAAGTGAACGTTCATTGATGTTGTTTACTTTTATTTTTTAACAC
514001 TTTGTCTTGTTGATGTTAAATCAACAAAAAGTGCACTAATATTATTGGGA
514051 ATGAATCACACAACTTGATAAATAAAATTACTAATCTTTTTTAAAAAGGG
```

-continued

The Nucleotide Sequence of the *Mycoplasma genitalium* Genome

```
514101  ATAGCGTTCCAGTGTTTTTGGATTAGCTGATCAAATGGCAAAGAAATTTA
514151  ACAATGAAACTAATATCAAAATTATGATTCCAAAGATATATAAAACACCA
514201  TTAATCTGTTCATCTCCATTTTCTGAAAAAATAAAAGTGGAAATAACTGA
514251  TCCCAGTGTTTTTAAATCAGAAGTAAAAAAACGATTGTTGTTAATTACCT
514301  CTTGATAGTTAACACTCTGCAAAACAAAGTTAACAGCCATTGTTTCACTA
514351  ATTGCTCTCGCAAAGGCTAAGGTCAAAATAACTGTTAATTGTGGTTTAAT
514401  TTCTTTTTTAATAATTTTGTAGATCGCACTTGTTTTATTTTCCCCTAAGG
514451  AAACAACAACACTAATTAGATCGTTATTTACATAAGTTAATGTATTTGTT
514501  GTTAATGAAATAACAATAGGAATGATCATAAAAGAAAGCATAGCTATCAC
514551  ATTTAAAAGTGAAAGCGGCGGTAATTTCAAGATATCCCGAAAGAAAATGC
514601  TTAATATTTGTGATGCAAATAATCCAAAAATTACAGATGGTATTCCTGAA
514651  AGGATATCAATAATAAGTGAAAGTTTTTTCTTATTTTTGGTTTGCATCG
514701  ATAAACAAGGAAAAATGAAGTTCTAACCCCTATATAACTAGCAATAATTA
514751  AAGCTCCTATTGATACAATAAAACTTACCAATAAGGGGAATCAAATTCCT
514801  GCCTGTTTATTACCTAAATTAAATTCAAGATTAAACAAGGACTTTGCAAA
514851  ATCAGGTCCAATTTTTGTTGCTTCTGTTAAAAGAAAAACAAAAAAACTTA
514901  TAAATAAAACTAAAAACAAGAATGCTAAAGTCTTTGAAAAGATTCTTAAA
514951  AGATTCTCTTTTTTTAAACGTTTTTTAATCTTCTTTTGCACTAAAAAGCT
515001  CCAAAGATAGGATTACtAAAAGCAAAGTCATCAACTCAAAAATTTTCTAA
515051  ATTCATTGGTGATGAGTCATTTGTTTTAAACATCTTCTTTTTCTCATCTT
515101  CAGTTAATTGCAAAATACCAAATTCATCATAAATATTTTTAATTACATCT
515151  TTTTTTCCATTAAAAAATAATCAATTAAARAAAGTTTTAATTTCATCAAT
515201  ATTCTTATTCTCTTCAGAAAGTGAAACTATTGAATTTAAAGGACGTACTC
515251  ATTTATACTCATTTTGGGAAACAGTTTGATTAGAAGGCAAAACTTCCTTA
515301  TTCTCATATTTAATTGGTAGTATCTCAAAACCATTATTTTTAATAGCTTG
515351  AAGGTTGTTTTGAATAAATCCTAAACTAAGGTAAATCATCCCGAAAAGAT
515401  TAGGATCTTGTAAGTTAGTTACAAAAGTATTAAAAGCTTCAATATTTGTT
515451  TCACTAGTAGGTTTAGCAAGAGGTCCATAATTAATAATTCCTTTCAAAAT
515501  ATCTCTAGTTTGAGAATCTAAAGTTTTATCTGATTTTAAGGCGGAAAAAT
515551  TTAAAAAAGCTTCTGCTGTTCCTGAAGCAAATGACCCACCAGTTCTTGGA
515601  AAACTTGTTAAAGGGTAATCTTTTTCATTTGACATATTTTTTGTATCCTT
515651  TTTTACAAACTTATCAATGTTAATTGTTTTAACACCAGCAAATAAGTCGT
515701  AGAGATCATTTATATTATCTTTTGTTAAAAGTAACTTACCTTTTAACTCC
515751  TGTGGTGCCTTATAAATTACTGCAATAGCATCTTTGCCAATAGTTAAAGT
515801  TTTCAGCTTTTTATCTCTTCATTTTTTTTCATTCTCTTTTGCATATTCCT
515851  TAGGGTTTTTAGAGACATTTCCGATATCAGCAAAGCCGTTAATGATTGCT
515901  CTGATTCCAGCATTTGATCCGCCTGCTTGCACACTAATTTCAACAAGCTT
515951  ATCATTGTCATTATTTTCATTTAGAACATAATAAGAACTTAATTTATTTA
516001  GTAAAGGTTGAACTGAAGAAGAACCAACAGCACTAATCAGGTTTATGTTA
516051  GCACAACCACTAAGAAAAAAAGCAGATGCTAATGTTAGTAGCGTCAATTT
516101  AAAGAAATTTCTAAACTTTAGCACTTTTTAAACAGATTAAATCTTTTCTA
516151  AAGAGAATTCGAATTGACACTCAGGTTATTATTTAGTCTAGTTTTTTCAC
516201  AAGCCAATTAATTTAAATGAAATGCATTTTTATTAATTGCAAATTTAATT
516251  TCTTTTCTTAACAATTTTCTTTTTTCTTCATTTTAAAAACAAAACAGCAG
516301  AACTTATCATTAAGCTAATGATAATTCCAAAAATGACTCATAATATTAAC
516351  TCAACATTTGTATCTTGTTTTTTAATTTCATTTTTTTCTAACTTATCAAC
516401  TTCATAGGATTTATCTTGAGATTTAAGATTAAAATCTGGAACTCTCTTGA
516451  ATTGCAGGTTATTTTGTTTTAGATAAAATGATAATGCTTTGAAAAGTTGT
516501  GTTTGATTTTCACTAGTAATATCAAATCAAATAGAATTATCAAAACCATT
516551  GGCATCTACAATTAAAAGTGTTTGATTATTTGTTATTTTTAAATCATAGC
516601  TAATACTAAATACTTGGTTATCATTATTAACACCTTTAATAAATAATTTT
516651  TTTGATCTAACATCGACATCAAAAACTAAATTAAATTGATTTTTATTTTC
516701  TACTAAATGGATGTTAATAAATTTATTCTTTAGGTTAAAGCGGACGTTTT
516751  TAGTTGTTTGCAATCTTTTTTCACTTAGAGTAATATTGAGTTTATCAACT
516801  AGTAATTGTTCGTCATTTAAACTAAAAGGTTCATGAAAATCAAGTTGATA
516851  ATCCTCTAGAAATTTAAATGAAGATGACTTTAAATCTAATTCAGCAATTT
516901  TTAAGTTATCAACTGATAAAAATACCTTGTCTTTTTCTAACTTAAATCCC
516951  AGGTCATTTTTATCAACAAAAAGTTTGTTAGTATGAAATTTAAATAAATA
517001  TGTTCTTAATTTAGGGTTTTTTGATTTTGTGATAGAAAATACATTTTGT
517051  CTTTAATAATTTCAGAATCACTTTCAGAACCATATTTGAATAGTTCATTG
517101  CTATTATTTATTTCTGCTAAAACATAAAATATACCTTTCTTTTCATTAGT
517151  AGGCTCTAGATGTTTGAAATATTTTTAGGGTTATCCACAAATGTTAAAG
517201  AGTTACTGTTGATATCTAAATCAATATTCTTATCCTTAGATTTAAAACTA
517251  TTTTTGATAATGAAAGCCATTTGTCTTTTTTCATAATCATTAAACTTTTC
517301  ATTACGTTTTTAAGTTCAGCAACATTAAAGTTTTGAACATTTTTATTTA
517351  GTGGAATACGAAAATCTTTAGCAATTCAACGCTGTTCATTAAAATCTTTT
517401  CTATATTTAAATTTGTATTCAAAACCATCCTTAGTTCTTTTGATAGTTGA
517451  AAGTTTTTTAATACTGTCAAACAGTGGTTCAACACTATAGTTACTAATAT
517501  TTTCTGATTCATATCCATCTACAAAAAAATTAAGTGCTAAAAATTCAATA
517551  TTCATTTCATTATCTGCTTTCTGTTTTTCTGTTAAAAACTCCTCAATTGA
517601  ACTTAAATCAAAATAATTCTTGTTATTCTTAACAATGTTATTTCATTTA
517651  CAGAATTACCAATTTTTACTTTAACAGTTAATGTTGATCTATCAAAAATG
517701  GTTTTGACCATTCTTGGTAAATTTCTAATAAAGAATAGTTCTTCTTTATT
517751  GTTTGGTGACATTTGCAATAGGTTGTATAAATAATCTAAATTTGGATAAA
517801  AATTACTTTGATTATTGGTTGAAATATTAAAGCTTTTTAACGCTTCATTT
517851  TTATCAATTGATTCATCAATTCTTTGATTAATTAAACTAACTTCTTTAAT
517901  TGCATTTATGAATTTATCTTTAAATTTAATAGTTGGTTTAATTTTTGTAC
```

-continued

The Nucleotide Sequence of the *Mycoplasma genitalium* Genome

```
517951 CTATTGTTTCTTTATTTAGAGTTTTTTCAGTTTGACTAACAAGCGAATTA
518001 ATATCAAATTCCAACTGTGAAATTCAAAGCTTTGAAAGATTACTGAAACT
518051 AATTGGTAAAACTTCATCAGGATTATTTTGCCTTAGATAAAAACTTATTT
518101 GATGATGAACAACTTCTTGTTCAGGTAATATAGGTGTATGTTAAAAATA
518151 TCCCATTTACTGTTGAATGCTTCACGTCTACTATCTTCAGTTTCTGGTCT
518201 AACTACTAATCCATTACCTAGTCTTAATATCGTTTGAGTTATTTCACGAT
518251 TATTAGTAAATGCTTCAATGATTTTTCTATCCTTTTTCATTTTCTCTTTA
518301 AACTCATTTATACTCATCCAATGAGCATCAACTTGTTTGTTGCTGTTAAT
518351 AGAAAAAAATCAACTGCTTCTACCAGGAAAAGGTTCGTTTCACTGAGCGT
518401 TATTCTGTTCAAAAACTGGAGGAACTTTCACTAGTTCTAAATCTCATCAG
518451 AAACGATAAGCTCTAATTGGTGTCATTGCTAAACCTCATCAGAAATCTGG
518501 AGCTACAAAAATATTATTTTTTCAGTCAGCAAAAAATCCTCTTGATTCTT
518551 GGCCAAGATAATATCACATAGGTGCATTAAAATCAATTACATAATTACCA
518601 TTATTACCTTTTCTTAATCATTTAATATTTCTAATAACATCTTCTGGGGT
518651 TGGTTTAATCATTCTTAAAGTCGATCCTCACATGTGAACAAACTTAGCTT
518701 CAATAAAATATGCTTTTTTATGACTGGGCTTTGTAAGGTCTCAAAAATAA
518751 GGATTATCAGGTTTATATCAACTTTTGTTTCAAGAACCATCTGGATTTGT
518801 ACCAGTTATTTCTATATTCCTAGAAGGAACTTCGGTTCATTTTTCATTAG
518851 TATGACCATCTCTTGGAAAAAAATTAGAAATTGCTTGACTATGAAAATAA
518901 AATCTCTGCTCACTATGGATATCAGATGACCATGAGTTTCTAATTCCAGG
518951 GTATCTAAATGTAGATGAAAATGCATGTGCAATATAACTACTCTCAATTT
519001 TTAACTTTATGTTCTTTAGATAATAAATATTGTTGTATCAGTGAAAGTTA
519051 TTATCTCTAATAATTTGTTTGTAATTATCACTATATTTATTAACTAATTC
519101 ACTTCATTCATTCGAATAAGTTTTTGCAAAATAATTATTTTGATTAGGTC
519151 TTTGAATTACTTCCATTATCAAAATTAAAGCTTTTTCGAAAATAATCGTTT
519201 TTTAAATTAAATCCAGCTGTATAGCTTCTGTTTTGAATTGTGTTTGGAGA
519251 GAGATAAAGATTAGTATCTACCAAGTTTTTTTCAAGTGAAGCATTAGCTA
519301 AAGCAACGGGAAAAGAAAAGAAACTAATAAAGGAATAAAAAGATATGAA
519351 CGCATAATTTATCTCATTAAATAAATGTGTATTTAATGAAATATTGACAA
519401 TTTTTATTGCTAGTTCTTGTTAAAAATTATCTCTTGTTTTATTTTTTATC
519451 ATCTTTTGTTTTTTATTTCACTTATGAAAGTAAATAAAAACAGTGATAAA
519501 CAAAACTAAAACACTAAAACCAATAATCAAATATACTATAATATCTGTTT
519551 TTTTATCTTCACTATTAGATTGAATAATTTTGTCTATTTGAAAACTATAG
519601 CTGTTTTTCTTTAAGCTAAAATTAGGTTCTTTTTTAAATTGAAATTTTTT
519651 TAATGAGAGAAATAACTTAAGCTCATTTTTCAGTTTCTGATTATTTTTCT
519701 TATCAAGATCAAACCAAATATATTTATTTAAGTAGTTATTTGTTGTTCTA
519751 ATTTGCAATTCATTTTCATTTTTGATAGCAATATCATAAACAAGGCTAGT
519801 TAATCTATTTTTACTTATATTAACTTCAATATTGAGCTGATTTTTAATTG
519851 CATCAACATTTAAATAAAAATGAAGCGAACTATTTATCTTTAGAGTAGTT
519901 AATTTGATCTCTTTAGGAAAAAGATCTAAGCTAGATTTCTTTTTATCTAT
519951 TAAAAGATTCATTTCACTTAAAGCCAAATTTAGTTTTTTAATTAATAGTT
520001 CTTTATTAGCTAAAGAAAAATAATCATTTATATGAACTTCATAACTTTCA
520051 AAAAATGAGGTATTATTTTCTTTTGGATTAAATTCATCTATTTCAACATT
520101 ATTAACAATTACCCTTAATTTATCACCGCTTGATTTAAATCAAATATCAT
520151 TAACATTTAAAACTAACTTTTTGGTTCTCATTTGAAAAAGATAAGTTCTT
520201 ATTGCAGGAAAGTTTTTATTTTGTTCTAAGAAATACATCTTATCTTTAAT
520251 GATTTCGCTATCATTTTTAGAACCCCATTTAGTTAAATCATTACTGTTAA
520301 TTATTTGTGCTGAAACATAGAATATACCATTTTTAACACTGGGCTTAATT
520351 AAAGATTTTTTAATTAATTTCTCAGGATCTTTTATGTATTTTATTGTAGC
520401 GGATGAAATATTTAAATTGTTTCTTTTTGAGAAGTAAAACTATTTTTAA
520451 TTGCATATGTAATTGGTTCTCTTTGATAACTATTTAATCCGTTTTTTCA
520501 ATGTCATTAACACTGAAATTTTTCTGATTTGTAACAATAGGAATTAAAAA
520551 ATGATCTTTTAAAATATGATGTTCATTGTATTCAGATCTAAACTTTAAAC
520601 TATATTGAAAACCATTTTTAGTTTTCTGAATAGAAGGCAAATTTTTAACT
520651 GACTTAAAAAAGAATCAACTGGTTGATTTTTTAATGTTCATCCTGTTTT
520701 ATTCACAACAATAAAATCAAAAGTTAAAAACtCAATTTCATaAAAATTAA
520751 TACCAGTTTGATCAGCATTTAAGAAATTTTCAACATCACTTAATAAAAAA
520801 ACGTTACTGCCATTTTCTATAAAAGTAATTACTTTATTTTTGCCACCTAT
520851 CTTTATATTTATCGTGATGGTAGTATCTTTAAAAATACTTTTAATTAGGT
520901 TGGGTAATATCCGAATAAAATTTAATGTTTTCTCTTGTTTTGGATTAATG
520951 TTAATTAAATTACTTAAGAAAAATATTGCATCAATTCTTTCATCTTTTGG
521001 TTCAAAATCAAATTTAGATTCTTCCTGTTTTTCTAATAAATCTAAAGCAA
521051 ATTGAAAAAAAGTTTTATCTTTATTTGCTAATTGATCAAACTCTTGATTT
521101 AGCTTACTTACCATTTCAATTGCATTAGAAAATTGATCACTAAATTTCAG
521151 CTTTGGTGTTATTTTTGATCCTATTAGTTCTTTGTTTAAAAACAGTAGTTG
521201 GATTAGCTATTAAAGAATTTGAATCAAATTCAATTTGGTTAACAATGATC
521251 TTAGCAAGTTGATTTGTTGCTATAGTTAATTGATTTTGTGATTAAAATC
521301 ATCTTTAACTAGATAAAGATTAGTATCAATCAACTTACTTTTTATGGAAG
521351 TGTTAGCAAATAATAAGGGAATTATCGCAAAGGAAACTCACTTTAAATAG
521401 CGTTTTCATGACATAATAAGCTTTATATTCCATAAATTAAATAAAACTTA
521451 TTAAGTGACAGTTTTTTTACTAACGCTTAGTAAATTGTGGTGCACGTCTA
521501 GCACCATATAAACCAAATTTTTTGCGTTCCTTAGCACGCTTATCACGTGT
521551 TGTTAATTTTTTGGTTTTAATAACTTTTTAAGATCTGGATTAAATTTTA
521601 TTAAAGCACGAACAATACCTAATCTAATGGCTCCTGCCTGCCCAGTAAAT
521651 CCTCCACCTTTAACAACAACATTGATATCAAAGTTATCCTTAAGTTTGGT
521701 TAACTCTAAGGGTTGTTCCATATCTTGAATCACCAATTTATTTGGAAAAT
521751 AATCGCTAGGATTACGATGATTAATGGTTATTTTACCCTTATCTTTGCTT
```

-continued

The Nucleotide Sequence of the *Mycoplasma genitalium* Genome

```
521801 TGATATAAATAAACTTTAGCAGTAGAAGATTTACGACGACCAAGTCCATA
521851 AAAAGATTTTTTATCCATATCTTTTAACTTCAATTAAGTAATGTTGGTTT
521901 TTGTGCTTCCATGTTGTGCTTATCATTCTTAAAAACATGTACTTTAGTTA
521951 TTAATCTTCTGCTTAAACGATTATCAGGTAACATTCCCTTAACAGCATTG
522001 AAAACAAGTTTATCTGAATTTTTGTTTATCATATCCCTTCCACTAGtTTT
522051 TTTAATTCCACCCATGTATTGAGAGTGATGATATCAAAACTCATTGTCTT
522101 TTTTATTTCCAGTTAAAACCACTTGATCACTGTTAATAATTATTAGATGA
522151 TCTCCACAATCTTGATTAGGAGTAAAATTAGCTTTATTTTTTCCTCTAAT
522201 TAAATTTGCAGCTTTAACTGCTAATTTGCCTAAAACCAAACCACTAGCGT
522251 CAACAAGATACCACTTCCTGTTTTAATGGCTTCTTCCTTTGTAAGCATC
522301 GATGTTTTTGCATATATTTAGATACAAAACCGCATTCTATTTAATATT
522351 ATTACTTTTCTTCAAAAAGTCCTTTAAAGTATTTATCCACCATTTTTGT
522401 GATAAAGAGCGTTTCTTTTCTTTTAAAAAAGGCTTAGCTAAGTTTTCCAA
522451 TTGGGTTAAGTTCAACACTTCAGTTTGATACTTTTGATTTTTTGTTTCTT
522501 CAGTAATTGTTGTTTATATTGATGCTCACTAAAAGATGCTAAGAATAAA
522551 TTTTGGTTAAAAATCTGAAATATAGTTGCTTGTACATTACCTTCTTCTAT
522601 TGCCTCTTTTCAAAGTCTCATAGCAATTTTTTGATCTTCAAATAAGATAA
522651 CTATCCCAAATGAAGAAGCTTTTACTATTTTGGTTGCTTTCACTATATCA
522701 CGAGCACTATATTTGTCTATAAAGTTATTGAAATAACTTAAATTATTCTG
522751 TTTATCTTTATCATTAAATTTAGTTTGAAAAACACTTAAAAGATTTTGAA
522801 AATGATTAATTCATTTATTGTCATTAAATGCATTAATTGCAAGAGCAATA
522851 TTGGCAAGATTTAGTTTGCTTGTATCTAAGAATTTGTTATTAGTAACTTC
522901 ATCATTTTTAGGTGTCTTTTCTGATTTATCTATAAAAGATTTTTCAAATA
522951 AAGAAAAGTGCTTTTGGTCTTGTTTGTGATTTGATTTTTTATTTTTTC
523001 TTTTCCAAATATTCAGTTTCTAAGTGTAGAGATTTTTCATTACTTGGTGA
523051 GCTTATTGTTAAAGGTTTTTGATTAAAAAATTCATTATAGCTAATAACAA
523101 TAGCTTTTAGCCTATCAATTAAAGTTAATTGACTTAAACCAAAATTAGTA
523151 TTTTCTTCAATGGCCTTAATTAAAAACGCATAATGCTGCTTTTCAAAATT
523201 AAGTGTTTCTATCATTGTTTTTTCAGTTGAATCTAAAACATTAATATTTT
523251 TTAGTTTTGCATACGCATATAAATTAACTGTTAGCGCAAACAACTCTCTT
523301 AAGAAGTAAGTGAAATTTAGACCATTACTTTCAAAATCATCAAGCAAGTT
523351 AAATGCTTCTTTTATATCTCCTGATAAAACTGCTTTAATAAAAGTAAATT
523401 TTGCATTTCTATCAACGATATTAAATGTTTTTCAACATCAGTAATACTA
523451 ATTTTTTCACTATCAGAGAAATTGCTAaTTGATCTAGTAAGCTAAGCCCA
523501 TCACGCAATGAACCTTGGGATAAATCAGCAATTTTTATTAATGCATCTTT
523551 CTCTATCTTAATCTTTTCTTTTTTTGCTATATCATTTAATCTTTCAAGGA
523601 TTAAATCACTAGTTATTTTTTAAAAAAGAAGCTTTGACATCTGGACAAA
523651 ATTGTTAATGGAATCTTGTTAAATTCAGTAGTTGTAAAAATAAAAAGAAC
523701 ATAAGGTGGTGATTCTTCTAAAGTTTTTAACAAGCCACCCCATGATTGGG
523751 TGGTTAACATGTGTGCTTCATCTAAAATATAAACCTTTTTTTAAATGTG
523801 AAGGGATGATTGAAAACATTTTCTACCAACTCTCTAATATCATTAATACC
523851 ATTTTTAGAAGCTGCATCTATCTCAACTATATCAATGGCACTATTAGTGT
523901 TAATACTTTTACACACATCACAACTATTACAAACATCAATTTGATCTCAA
523951 TTTAAGCAGTTTATCGCTTTTGCTATTATCTTTGCAAAAGTAGTTTTACC
524001 TGTTCCTCTTTCACCTGAAAAGATATAACCATTAGGTAGTTTATCCCTGT
524051 TAATAGCATTCACCAAGATTTTTCTTATCGATTCTTGTCCTAGGGTTTGT
524101 TTGAAATTGATTGGCCGATATTTTTGATAAAAAACTTGGTGCATAATTTT
524151 TAAATTGAATCTGGTTTTAAAATTTTGGACAAATATTGGGCAGTATAAGA
524201 TTTATTAACTTGGTTTATAAGTTGTTCAGGTGTTCCTTGAGCAACAATTT
524251 GACCACCATTGTCACCACCTTCAGGACCTAAATCAATGATATAGTCAGCA
524301 ACCTTAATAATATCTAAGTTATGTTCTATAACAACTACTGTATCACCATT
524351 CTTAATGATTCTTTGAATTATTGTTAATAGTTTGTTTATATCTTCTAAAT
524401 GTAAGCCAGTAGAGGGTTCATCTAAAACAAACAAAGTTTTACCAGTAGAT
524451 TTTTTTTGTAAAAACTTAGATAACTTAATTCTCTGTGCTTCCCCACCTGA
524501 AAGAAAAGTGACATTAATACCTAATTGCAAATATTCTAAACCAACATCAC
524551 ATAACAACCTTAGTTTACGTGATATATTTGGGATAGCTTTAAAAAATTCA
524601 TAAGCTTCTTTACAAGACATTTGTAAAACATCAAAAATTGATTTTCCCAA
524651 ATATTTAATTTCCAGTGTTTGTGAATTGTACTTCTTGCCATTACATACTT
524701 CACATTTGACATAAACATCAGGTAAAAAATGCATTTCAATGCGAATCACA
524751 CCATCACCAAAACACTTATCACACCTACCACCTGGAACATTAAAAGAAAA
524801 TCGTGAATTTGTATATCCTCTTGCTTTAGCTTCTTTTGTGTTGGCAAATA
524851 AATCACGAATATCATCAAAAACACTAATATAGGTTGCAGGATTAGAACGT
524901 GGTGTTCTACCAATTGGGTCTTGAGAGACAACAATTATCTTATCAATGTT
524951 GTTAGCACCAATTATTTCCTTATATGTATCTTTTTTAACACCTTTACGAT
525001 AAAGAATTCTTTCTAAAGCTGGAACTAATGTTTGATTAATTAAAGAGGAT
525051 TTTCCAGAACCTGAAACCCCTGTTATCAAAACCAATTTATTTAAAGGAAT
525101 GGTGACATTAATATTTTTCAAATTATTAACTTTAGCACCCTTGATAATAA
525151 TTGTTTTACCATTACCACTATGTCTATTTTTTGGAATGGAGATTTGTTTT
525201 TTACCACTAAGATATTGTCCAGTAATTGAGTTTGAGTTTTCCATTACTTG
525251 TAAAGGTGTACCGCAAGCAACTAATTCACCACCTTCATTACCTGCTTTAG
525301 GACCAATATCAATTAAATAATCTGCCGCTAACATTGTTTCACTGTCATGC
525351 TCAACTACTAATAAGGTGTTACCTAAATCACGCATTACCATCATTGTTTT
525401 AATTAAACGCATATTGTCTTTTTGATGCAATCCAATAGAAGGTTCATCCA
525451 TTACATATAAAACACCAGTAAGTTGAGAACCAATTTGGGTAGCTAATCTA
525501 ATTCTTTGTGCTTCTCCACCTGACAGCGTAGAAGCTCTTCTTGCAAGATT
525551 AAGATAATCTAAACCAACATTTTTAAGAAAAGAAAGACGATTAATAATCT
525601 CTTTTAAAGCTAATTCACCGATCTTCTTTTGCTCATCATTTAACTCTAGT
```

-continued

The Nucleotide Sequence of the *Mycoplasma genitalium* Genome

```
525651  TTTAATAGAAAATCAATACTTTTATCAATGGAAAGTTCAGTAAAGCTAAT
525701  AATGTCAATTCCTCCTAACTTAACACTTAAAGCGTCTTTTATTAATTTTT
525751  TTCCATGACACTTTTTACATGTTATTTCAGACATGTATGCAGAATATCAT
525801  TCTCTACTTACTTGGCTGTTTGTTTCTAGGTGTCTTCTTTTAATTAAATT
525851  AGCTATCCCTTCATAATGCTCAAAGCGGATATTCTTAGCACCTGAATTGG
525901  AAATTGTTTTTATTTCAATAGGTTCATCACTTCCTTCTAAAATTAAATTA
525951  AGTTGTGACTTATCTAACTGTTCAATTGGTTTATCTAATGGAATTTTATA
526001  GTGATTAACTAAAGATAAAAAGCGCTGTCAATCCAAAGAAGTTCCATGCA
526051  CAATATTTTTAAAAATATCAATGGCTCCTTGGTTAATAGAAAGTTTAGAA
526101  TCAGCAATTATCTTGTCTACATCAGGTTCATAACTAAAACCAAGTCCTTT
526151  GCAATATGAACATGAACCTAAAGGGGAGTTAAAGGAAAATAATCTTGGTT
526201  CCAATTCACTAATAGAAAAACCACATTTATCACAACCATGATTTTTGCTG
526251  AAATTTAATATTGTTCCATCTTCCTTAAGAACTTCTATCTTGCCATTAGT
526301  TAACCTATCAATGGTTTCAATGCTATCAACTATCCTTGAATAAGTTTGAT
526351  TATCTTTATTGATGATAATTCTATCGATCACTACACTAATGTTGTGTTTA
526401  GTATTTTTATCAAGTTTAATTTCATCATCTAAGGTGTAAATCTGGCCATC
526451  AACTAAGACTCTAAGAAAACCTAATTGCTTGTATTTAATAAATTCATTTG
526501  TAAAAATGCCGCGCTGATTTTTAACAGTAGGTGCTAATAATTGCACCTTT
526551  GATTTATTAGGTAAATCAAAAATCTGATTAGCAATTTGGTTAATTGTTTG
526601  CGTTTGAATAGAACCATGACCATTAGGACAATAAGGGGTCCCAATTCTAG
526651  CTCATAAAAGTCTTAGATAATCATAGATCTCAGTTACTGTACCCACAGTT
526701  GAACGTGGGTTATGTGAAGTGGTTTTTTGATCAATGGAAATTGCTGGTGA
526751  TAATCCTTCTATAAGATCAACATCAGGTTTATCACTGTTACCTAAAAATT
526801  GGCGTGCATAAGAAGATAGAGACTCTAAATATCTTCTTCTCCCCTCAGCA
526851  TAAATTGTGTTAAATGCTAAGGAAGATTTACCTGATCCTGATAGACCAGT
526901  AATAACAACAAATTGATTTTTAGGGATATCAATGTTAATGTTTTTAAGGT
526951  TATTTTCTCTAGCACCTTTAACCCTTATAAAATCATTATTTTTTCATTCC
527001  GGTTTCAAAGTCAATGTTTTTAATTGAAAAATTTTTAACTAACTTATTAT
527051  TAGGATCATTGAAAATAAGCGCAATACCTTGTTTATTTTGATATGAGATC
527101  AAAAGTCCACGAATGAAATTATAAGCGTGGTTAGTGAAATCATTGCAGCA
527151  GTTTATCATTAGTAACTTAGGATTTAACAAAAGTTTAAATAGCAAGTAAA
527201  GCTTTAGACTTTCATTTTTGTTAATTTTGTTTAAATCACTAAATAACATT
527251  CAGCTGCTAATACCATTCTTTTTGGTTTGATTTATCAATAAATTAATGTT
527301  GTTAATAAAGTTAAGTTTTTTAAGATTTTTTTGTGATCTTAAAAAGAAAT
527351  TAATTGTTTTTAATTGTGAATTCAAAACATTAAGATAAAGCTTATTTGAA
527401  GCTTCTAAACGATTGATATTGCACTCTTCTGAATCAATAAAAAAAGTTCT
527451  CTTAATTTTCTTGTTTGTTTTTTTAAGTCTTAAGTGCAATGTTTTGTTTA
527501  AAATACAATATCTTTTCATGATGAATTTAATCTTTTGTAACTTTTGATTT
527551  GTTTCATCGCGAAAAATTCACTTAACTAAATTAATGTCTTTTAAAAGTAA
527601  TTTGTATTTTGTTTGCATTTTTTTAGCTTTTGTTTTAGATCATTCTTGG
527651  TTTCTTTATTTGTTGTATCTGTTGTTGAAGAAAAACCGCGTGATGCTAAC
527701  AGGAAACTAACAGGGGTTTCAAAATTTAGATCTAAATATTTATTAATAAC
527751  TTTGTCAACTAGAAAATTTCACTTTGGGGAGTTTAAATCATTTTTTAACT
527801  TATCTTTTAGCAAACTAAAATGTGGTTCACTACGTCCTTCATTTCAAATA
527851  AAATCATTAGAACCACAACTTAAAAACTCATATTTATTAAAGAATTGTTG
527901  AAATTTTTACTTAGGCTATTTCAAAGTGAAATAAGAACAAAATACAAGT
527951  TATTTAACTCATATTTTTGTCAGTTAATTTTTTGATAATTAGCTAATAAG
528001  CTTTCATAAAAATATTGCTTTATTTGAAATGCAAAGTTAAAAGTCTCCAA
528051  ACTTTTTCTCATGCTGATTAAACCAATTGCATAtGCACTGTATCAATAA
528101  ACTGTTTGAAAACTGTTTTTTGGATTAGAACTGAAAAACTGTTATTATGC
528151  TTACCTCTATAATGATTTTGATTTAATAAGATGTTTTCTTTTAGTTCATT
528201  AACCAATTTTTCATGAACATACAAATTGTTTGATTGTTTAACAAAATTTT
528251  TAATAAAAGATAAACGTGCTTTGATCAAAAATTCATGAACCTCTTTTTTC
528301  GTTAGAATGAAACGTGCAGACATTATTTTAAGTTCTTGATTAATTGTCTG
528351  GTACTTTCAGtTCAAATTAGGACCTGATTTTAAGCTGATAATTTCTTGAT
528401  AAAGATTTTGAATATTAGCAAAGATTTTATTGACTAAATTAATACTTTCA
528451  TCAATAGTTTCTACAAGTAATTTTGGAGAAAGTAAATCCATTTTCTTAAT
528501  TTCTTTCAAAAGTAAAATTCTTGTTTTAATCCGCTTAGATACAATCTTTT
528551  TTTCTAAAATTCTTTTTCTATAAAAATTAAAAAAACTTCTTCACTTAATC
528601  TTTCAACCACTAAAAATTAAAGAAAAGGTGAATGAATTAATTAATTGCAA
528651  AGCATTTTTATGTTGTTTTGAGAATGTTTTCTTAGCATCAAAAAGTCTTT
528701  GTTTAGCTCTTTCAATTTGCAATTTTTCAAAATAACTGTTATCTCGTGAT
528751  TTAGCTTCATAAGCAGCTATTTTCAGTTTGTTTTTTAAGTTATTTTTTG
528801  TTCGTTCAATGCATAGTAACGCTCAAAAAAACTTTTTATTACTTTGTTAT
528851  TAAAAGTAAATAATTGATTGAAAAACATGCAATTAAAATCAACAAGTTCT
528901  CTTTCGTTTTTTTCAATTAAAGTTAAAAAATTATTGTATTCAAAATCAAC
528951  TTGTTCAAAGTAGATTGAATTAATAAATTTTGATGTAAAAAACTGATTAA
529001  TGACTTTACTAGTTTTTTGATTAACATTTTCAATTTTCAAAATTGAAAAC
529051  CTAAATAAATCATTAAGCGCATTAAAACCTAAAAATCACTTTAACTGTTT
529101  AGGTATATTCACTAAATTAAAGTAATTTTGATCTTTTTTATAACTTAAAT
529151  CTTGTTTTAGAAAAATGCTAAATGAATTAGGAAATAACCACTTATTTTTA
529201  TTTCTTAAATCTATCTCTTCACATAAATTAAACTTAATTTTTTGAAGCGG
529251  TAAATATTGATGGTTATTAACAAGCAAAAACCCAGAATAGGGTTGTTTAT
529301  TTAACTGTAAAACTTGTGAAAGGGTTTTTCATTGTGCTTGATTTAAATTA
529351  TCAATGAGATAGTTACCATACTTAAATAATGATAGCTTTGCAACCCCAAA
529401  ATAGTTAGCATCTAAAAAGGAGGTACGAATCATTAATAATGACAAATCAA
529451  CCCACTGTTCTAGATTATCAAAAAGAGATATTTTCTTTAGCATGTACCTT
```

The Nucleotide Sequence of the *Mycoplasma genitalium* Genome

```
529501 TCAAATTTTAATTGCTAATCTTTAAGGTACTTAAATAGAAATAATAGTTG
529551 AAAGAATTAAGGGTGCTTTTGATGTCATCTTGGTGAATAAATTCATTACT
529601 GCTCGTTTAATAGAAACCTTCAATTCTTTTGAAATTTCTTTACCTATTCG
529651 TTTTTTAATCGTGGTGAAATCCTTAATATCATTAATTTGTTTTTAATTA
529701 ATTCTTCCATTTTTGTTTTTAGTTTATCTTTTTCTGGTACATCTAAAGAT
529751 ACTCCTAAAAAAGAATAAGTTATCTCATTTAAGAATTCACTCTTTTTTG
529801 ATCAAAATAAATGATTATGATCACAACTCCAGATTCTGACATTTGATCAC
529851 GTTCAAACATAATGCTAGCTCCAATTTCTTGTAATCCAGCAGAATCAACA
529901 CACTTAGGATTTAATTTCAATTCATTTTTTTGCTATCTAGTTTTTTGTT
529951 TTCAATAGTTAAAACTTCACCGTTAAAAAGAATTAAGATTTGATTTTGCT
530001 CAGCGCCAGCTTGTTTTAAAACCATTGTGAAGTTTATAAAATCCCTATAA
530051 AGTCCACCAGTTGGAATAATATATTTTGGTTTTAAAGAACTAACTAAAAA
530101 CTTCATATCTTCATCACTTGCTTGGATAGAAAGGATTTCTCTACCTAAGT
530151 TGTAATAACTAACTTCATTACGTGCAATATCATCAAGGATTTGTGCTTCT
530201 ATCTCTTCATAGCCAGCAACTTTAGGAGTCATAAAGATAAAGTATCACT
530251 CTTACGATAACGAATTCTTTCATCTTCGTTCATTCCAATTTTGAATAATT
530301 TAGCATACAACTTATCAGGTGGTGAGGTGAGAACAACAATACTGTTGGTT
530351 GAATTGTTAATCTCCTCAATAGAAATGGTATTTAAATGCGTGTTATTAAA
530401 CAATTTTTGACGCACAATTGTGTTAAAGAGATGCACAAATGATTGTGAAT
530451 AGATAATAAAAGGACGATTTTGCATCCTTGCAATCTGGGCAAGAGTCATA
530501 ACACTGTAAGCATTTGAATCATAACAAGCTACAAATATTCTGCCTTTGGC
530551 TGGAGTTATGATCCTGTTTAACTGTTCTAATGACTTGTGTTTAGGTGTTG
530601 TAAAACCACTGTTTCTACCAACTAAACCAACTCCTGTTATTAATAACAAT
530651 GTATTGTCAGAAAGTTTAGGGATAATTTGATTTAGTTGATTTTCAAAGC
530701 AATGTTCTTATCATTTAAAACAATGAAATCATCAATAAAAACGATGTAAC
530751 CATTATCAGTATTTAAAGCAAATCCAAATGATGATGGTAAAGAACtTGAT
530801 ACTTTAAAAGGGGTAATAGAATGATTAGAAATTTCGATTGTTTCAAGTGG
530851 TTTTAATTCATGAATTTCCAATTTATCACGTGCAATATTAAGTTTGTTTT
530901 CATTAATTTTGCTTTTAATTATAGAAGCGCCTATTGAACTTGTGTAAATA
530951 GGAAAAAATCCTACTGTATGGaACAAAAATTCTAATGATCCTAAGTTTTC
531001 AGTAATGGCATTACCTATAAAAATACCTTTAACTCTTGCTTGATTTTCTT
531051 GAATTCAACTAAAATCAGGAATAATTTTTTTAACACCTAAAACTGCTGTT
531101 GTTGGTGTTAAGCTACCAACATTAAAGATAAACACATCATTGTCAATTTC
531151 AAGCACATAGCAATTTTTACCACGTTCATCTTGACCGCCGAGCGCAAAGA
531201 ATTTAATCTTAGCCATTTTTAACCCCGGAGGTTTAAATTTTTAATCAAAT
531251 CACGGTAGGTTTCAATATTACGTTCTTTTAGATATTTAAGTAGCCGTTTT
531301 CTTTTTGATACCTTTGTATATAAACCACGCTTAGAAATAAAATCCTTTTT
531351 GTTTGCTAACAGGTGGTCTGTTAATTTTTTAATCTGATCTGTTAATATAG
531401 AGATTTGTACTTGCACACTGCCAACATCGTTTTTGTGAAGTTGATGAGCC
531451 TTAATGATTGTTCTTTATCAATTTTCATTAATTAATAAACACGTTGAAT
531501 TATAACAAAATTAGAAAACGGCTCATTGCCAAGGTTAGAAGTAATAAATT
531551 CTCCTACTTACTTATTACTTATAATAAATATAGTTTTTATTTTTATTAAT
531601 AAATTCTCTCGATATTTTCGATATTTAAATCTATACATCTAAACAAATTA
531651 ACAAAGCCATTTAACTTATGGACTCAACCTTTCATGAGCTTGGGATCTCT
531701 CAAACTTTAATTGAAACGCTTAATGCGCTTCATATTAATAAGCCAACAAA
531751 AATTCAACAAATCTCTATCCCTCAGTTTTTATCAGAAAAAAACTTAATAG
531801 TTCACTCGCCAACAGGAACTGGTAAAACTGCTGCTTTTGCAATTCCCATA
531851 ATTGAGAAGCTATTAAAAGAAGATCAAACAGCAAAACCAACTTTAGTAAT
531901 TGCTCCAACAAGAGAATTAGTAGAACAGATTAAAACCACATTTTCAAATA
531951 TTGCTAAAAATAAAAAACTAAGAATTATTAGTTTAATTGGTGGTGTACCT
532001 GCTTGAAAACAAATCAAAAAAATCAAAACAAATCCCCAAATAATAGTTGG
532051 TACTATGGGTAGAATTATGGATCTTTTAGAGCGTAAAGCAATTCATTTTA
532101 GCGATTTAGAACACCTAATTATTGATGAAGTTGATTTAATGTTAGACCGT
532151 GGTTTTAAAAAACAAATTTTTAATTTACTAGAACAAATCAATTCCTTTAA
532201 ACAAATTGCTGTTTATTCAGCTAGTTACAACCAAGAAGCTATTAACATTG
532251 CCAAGCAAATTACTAATAATGGGATCTTTATTGGATCACCTGAATTTAAT
532301 AAAGACGCAAATACCAATAATGATAAACTAATCAAACAATTTGTTTGTTA
532351 TCTATTTTCAGATCAAAAAAAGCAAGCTTTATACAGCCTTATAAAAACAG
532401 CACAAGTTAAGTCAATCATTGTTTTTTGTGCACACTAAAAAACTAGTTGAT
532451 GATCTTCATGTATTTTTAAGAAAAAATGAATTAAGAaCTTTTGCACTTCA
532501 TGGTGATAAAAAACAATTTATTAGAGAGAGAAATCTTAAAATCTTTGCCA
532551 ATACAAAACAACCCACGATTCTAGTAACTACTGATCTTATTGGTCGTGGT
532601 ATCCATGTTGAAGCAATCGATATGGTTATCAATTATTCAGCTTGTTTAAA
532651 TCTAGAAGCTTATATAAATAGAATGGGAAGGACTGGCAGAAACAATCATA
532701 AAGGGACATGTGTAACTTTCTGCACCTCACAAGAAAAGAAAGTCTTTCTG
532751 AAAATGGTTGAGAAAATCACTGATAATCGAATAGCTGAATGTAAACAAAT
532801 GGAAATAAAGTTAATTCCTTTAAAAAATAAAGCTAAAACTAAAAAAGGTG
532851 GTATTTCACTTGATTGTGTTCAGAAAATATATGCCAATGCAAAACCATAT
532901 GACCGTAATAAACGTGTCCCTTTAGCAAGTGATCTTTTCAAAAGTCGTAT
532951 GCGCCAGCCTGAAAAAGCTATGCAAAAGCAAAAAATTCATGACAATGACT
533001 GACAAAGTAATATGTAATAACAATTTATAAAATACTTGTATGGCAAAAAA
533051 AGACCaACTTACCTTAAGAGGGCCTTTGTATGGCAATAATCGTTCTCATT
533101 CCAAAACTATTACAAGAAGAAAATGGAATGTAAACCTTCACTCATGCAAA
533151 ATTAAAGATACTAATGGTAAAGTAACACGGATTCTAGTTTCAACTAAAAC
533201 AATTCGTACCCTTAAAAAACAAATCGTTTCTAATTTAAATTTAAGTTAA
533251 ACTTAATCCATAAGCATATATGGATAAAAAATACGATATCACAGCTGTTT
533301 TGAACGATGATAGTTCTATTAATGCAGTAaGCGATAACTTCCAAATAACA
```

-continued

| The Nucleotide Sequence of the *Mycoplasma genitalium* Genome |
|---|
| 533351 CTGGATGCACGACCAAAAGAAAAATCTAAAGGCATTAATCCTCTGTCAGC |
| 533401 TTTTTTGGCTGGTTTAGCTGCATGTGAACTTGCAACTGCTAATGCGATGG |
| 533451 CAGCTGCTAAGATGATAACTTTGAACAAGGCACTGATTAACATCAAAGGT |
| 533501 TATCGTTTAACAAATCCTAGTGATGGTTATTTTGGCCTACGTGAACTTAA |
| 533551 CATTCACTGAGAAATTCACTCTCCTAATGAGGAAGAAGAGATTAAAGAAT |
| 533601 TCATTGATTTTGTAAGTAAACGTTGTCCTGCTCATAACACTTTGCATGGA |
| 533651 ACTAGCAATTTTAAGATAAATATTAGCGTTACTTTAGTCCACTAAAACTT |
| 533701 ATTAAAAAAGCGAAAAATACCTGTAATTTTGCAGGTATTTTTTATTTAA |
| 533751 AAAAAGGATAAATTTAAGAAATTAAATTTCGCTTTAGCAGTCGATAATTG |
| 533801 ATCATATGAAAAATAATATTAGTGATGTAAAGTTGGGACTGTTAGCAGCA |
| 533851 AAAATTTATTGAAAATCTTGACGCTTTTTAGAGTTAACAGAAGATGACAT |
| 533901 TATCTCTATTGCACTTCATGCAGAGCAAGATTCTAAGAAGCGTTTTAATC |
| 533951 CTGAATTTGGCTTAAGTTTTGACAACTATCTCAAATTAAATGGAGCAAAT |
| 534001 TTCATTAGATCAAGTTTTAGAAGTATGGTGAATAAAGTTGAATTGCTTGA |
| 534051 TTCTAAAAGTAAATACTCATTAGAAAAGCAAAACACAGTTCTAAATACAC |
| 534101 CTGAAAACTATTTACGGAGTTTAGAATTTAAAGAAATTATTACTAAAGCT |
| 534151 TTTAATAAAGCTAAAAACGATCAAGAGAGAAAAGTTTTTTCTTTATATGT |
| 534201 AAAGGGCTATAAAAACTTTGAGATAGCAAAAAAGCTCAATATTAGTCCTA |
| 534251 GAAGAGTGAGATATTTATTAGATCTTTTTAAAAGCTACATCAAATTGCTA |
| 534301 ACAGAAAGATATGGATATTAAATAAAGATATTTTCTTTTTAAAGAAATT |
| 534351 TTCTACTAGTTTTCTAACAGCACTATCACTAGTTAATTTCAATGCTTTTT |
| 534401 CAACTAATGATTTACATTCATTAATTGTTATTTTAGCAATAACCATTCTT |
| 534451 GCTTTAAACATTGAACTTGCACTCATTGATAACTCTGTTAACCCTAAACC |
| 534501 TAAAAGCAACGGTATTGCATATTGATCACTGGCCATTTCACCACACATTC |
| 534551 CAGTTCAAACATTATTTAATTTACCACCTTCTACAACTAGTTTAATTAAG |
| 534601 CGTAGTAATGCTGGATTTAATGGTTGGTATAGATAACTAACGTTTTTATT |
| 534651 CATCCTATCAGCAGCAAAACTATATTGGATTAAATCATTGCTACCTATTG |
| 534701 AGAAAAAATCAACATGTTTTCCTAAGCAATCAGCTGCTAATGCTGCTGAT |
| 534751 GGAATTTCAATCATTATTCCTAATTTAAATTTCTTAGTTTCATTAAATTC |
| 534801 TTGTTGAACTTTTGTTAAAAGTTGCTTAACTTGAACTAATTCATCAAGAG |
| 534851 TTGCAACCATTGGAAACATAATTCCTAAATTTCCATAATCAGAAGCTCTT |
| 534901 AATAAAGCACGAAGTTGGGTCTTAAAAACAGCTTGTTTATCTAATGTTAA |
| 534951 ACGGATAGCACGATAACCTAAGAAAGGGTTATCTTCATGAGGAAATTGAA |
| 535001 AATAATTTAGTTTTTTATCTCCACCAATGTCTAATGTTCTAATTATTACC |
| 535051 AAATCATTTTTAGCTTTTTGTAAAACAGTTTTATAAGCTTCAAATTGAAC |
| 535101 TGATTCATCAGGTCAATCTTGACTACTCATATAGAGAAATTCAGTTCTAA |
| 535151 AAAGACCAATTCCATTCGTGTTATACTCAACTGCTAAATCCATATCTTTT |
| 535201 ACATTACCAATATTAGAAGCGACAATAACTTCATATCCATCTAAGGTTTT |
| 535251 TACTAATTTATTGGTATATTGTTTAATTCATTTTGAAAGTTGGATTCCA |
| 535301 ACTCTTTTTCTTGTTTTCATTGAGTTATGTCTTTACTTGAAAGTCAAAA |
| 535351 CCCACAATACCTTTTCTACCATTGATACCAACTGTTTTGCCATCTTCAAC |
| 535401 TTTACTGGTAATATTTTTAAACCAACTATGGCAGGAATTTCCATAGAAC |
| 535451 GAGCCATAATGGCAGCATGACTTGTTTTACCACCACTCTCAGTTAAAAAA |
| 535501 CCCTTGACATACTTTTTATTAAGAGTTGCTGTTTGACTTGGTGTTAAATC |
| 535551 ATTAGCTACTATAATGACATCACTTTTAATCCTGATTAAATCATTAAGTT |
| 535601 TTACTCCAGTTAAATAACTTAAGAGCCTTTGGTGTAAATCTAATATATCA |
| 535651 CTGGCACGTTCTTTAAAATACTTATCATCCATTTCACTAAACATTAAAGC |
| 535701 TGTTTGTTGAAAAACATTATCAACAGCAATAACAGGATGGATGTTTTTAT |
| 535751 TTAGTTGTTGTTCTAATTGCTCAGTGATAGTAGGATCATTAAGAATTTGG |
| 535801 ATGTGTGCATCAAAAATCATTCCTGCTTCTTGATTAATATTCTTAACAGT |
| 535851 AATTGTCTTAATCTCTTCAAGGTCTTTTTTTGCTTTTTGAAAAGCACTGC |
| 535901 TTAAAAGCTTTTTGCTTGGGTGGGTGTCATTTTGACATTTGTGTATTTT |
| 535951 TTAACGTCAAATTGAGGTGTTTGAATAATGAAAGCTTTTGCAACAGCAAT |
| 536001 GCCATCTGAAACACCAATCCCAATTATTTTTTTCATAGGTTAATTGTTAT |
| 536051 TTTTTAATAAGGATTTTGCAGTCATCTCTTTTGGTTTGCTAAGGTTAAGA |
| 536101 TATTCCAAGATAGTAGGAGCAATATTAGCTAAAATTCCAGTTTGATTAAA |
| 536151 GTTAACATTTTTGTCAGTACATACAAATGGTACAGGATTAATAGTGTGTT |
| 536201 TAGTAACTGGATTGTTATTATTATCAATCATCACTTCTGCATTCCCATGA |
| 536251 TCTGCCAGTTAAAAACATAGTTATTTGATTAGCTTTACAAAAATCAACTAT |
| 536301 TCGTTTAATTTGAACATCGAGTGCTTCAAGAGCTTTAATGCAAGCTTGAT |
| 536351 AGTTACCAGTATGACCTACCATATCAGGATTAGCAAAATTTAAAACAGTA |
| 536401 AAATCAAAGTTATTAAGCTTTTCTAGTAGTGCATCAGTAATAGCTTTACA |
| 536451 TGACATTTCGGGAGCTAAATCATATGTAGCAACTTTTAAAGAAGGAATTA |
| 536501 ATGTCTTTGTTTCATTGCTGAGATTAACTTCAAAACCACCATCAAAAAAG |
| 536551 AAAGTAACGTGAGCATACTTTTCAGTTTCTGCAATCCTCAATTGCTTCAA |
| 536601 ATTATTATTAGCAATTACTTCACCAAGACTATTTTTAATGGTTTGAGGTG |
| 536651 GAAAAGCAAATTCGCTAGGTACAATTCCCTCATAATTCATCATTGTTACA |
| 536701 AAAAATAAATTTTCTTTTCGTTTCAATTCAGGTTGATAGTTGTAATAATT |
| 536751 GCTGTTAAAGATCAAATGGGACATTTGTCTTGCrCTATCAGGTCTAAAAT |
| 536801 TAAAGgAAATAACTCCATCATTATTGTTTAATGCAAACTGATCAGAATTT |
| 536851 AAATTGGCATTAATTGCAGGATAAATAAATTCATCAGTAATTTGGTTCTG |
| 536901 ATATTGCGTTTCAATATAACCAATTGGGTCATTGAATTTATTTTTTGAAA |
| 536951 CTCCTAATAAAGCTTTATAAGCAATCATTTCACGATCCCAGCGTTGATCA |
| 537001 CGATCCATTCCATAGTATCTTCCCCCAATAGTTCCAATAACAACATTAGG |
| 537051 ATAGTTTTTTAGAAATATCATTAATTTCTCAAGATCTTGTTTTAAGCTAC |
| 537101 AAGGTGCTACATCTCTACCATCACCAAATAAATGTAATACTACCTTTGCA |
| 537151 TGTTTTGAAAACAATTCAATGAGTGCTAATAGATGTTCATTATGACTATG |

-continued

The Nucleotide Sequence of the *Mycoplasma genitalium* Genome

```
537201  CACTCCTCCATTGGAAAATAACCCAATTAAATGGATTTTTGAATGGTTTT
537251  TTTCTACATGTTCTATGGTTTTTAAAAAAGCTTTATTTGCAAAAAAACTA
537301  CGATCCTTAATATGTTGATTAATCAAAGAAAGTCCAGTATAAACAACTCG
537351  ACCTGCCCCAATATTTAGATGACCTACCTCAGAGTTACCTATTTGACCCA
537401  TAGGCAATCCAACTGCTTCCCCAGATGCATCTAAAAGTACACAAGGATAT
537451  GAATTGATTAATTCATCTAGCATTGGGGTATTTGCATTTTGTACTGCATT
537501  ACCATAAATAGCATTTGAGATCCCATAACCATCAAGGATTGCTAATAAAA
537551  CTTTTTTATGCATATACCCTAGCCATTTCTAAAAAGTTTTTAATTTCTAA
537601  AGATGCTTTACCAACTAAAAATCCATCAATTTGTTCCATTATTGCTAGTT
537651  TTTGGATATTATTATGATCAACTGATCCGCCATATAGAATTGAGATATTG
537701  TTAGCAACATTTTCATCATATAAGTCATTAATATATTCCCTAATGGTTTT
537751  AATGGTTTGATTTGCAACTTCAGGAGTTGCTGTTTTACCTGTCCCAATTG
537801  CTCACAAAGGTTCATAAGCAATAACTAAATTTTTAATTAAGCTTTTGTCA
537851  ATCGTATCTAAGCAATTAGTAAGATCAGTTTTAAGAAAGCTAATCTCTTG
537901  TCCTAAAGCCTCACCAATACATAAAACTACTTGCATGGATGCTTTTAGAC
537951  AAGCAAAGAGCTTTTGATTAATAACTGCACTGGTTTCGTTATAGTATTTT
538001  CTTCTTTCAGAATGACCAATAATACTGTTGTTAACACCAATGTCTTGAAG
538051  TTGAGTAAAGCTTACAGTTCCAGTATATGAACCACTTTCAATAAAGTTAG
538101  CGTCTTGGGCAAATAAAAGGAGACTATCACTAATTATTTTTTTATTTCA
538151  GTGAGATGAACATAAACAGGTGCTATCCCAATTTTGGCATTGTAATTAAG
538201  TTTATTTTGTTGAAATTGTTCAACAAAACTAACTGCGTCTTTTAAATTTT
538251  TATTTGTTTTCCAATTGCCAATTAAATACCTTGTGCGCATATGAAAGATT
538301  TTATAAGTTTTCAAAAACCATTTTCTTTTCCAACTAATTGATCATTAAGT
538351  TATGACTTGTTTTCAGTTCCATGTTTTGTTTGCTTATTGGTACGTCTATC
538401  ATAGATATAGCCATCAAGCTTTTTAATAAAAGTAATGOAAAACAAAGCAT
538451  CACGATCAAACTTTCTCACATCTTCTAAAAGCTTAGCAGCTTTAATAAGC
538501  AAACAATTAGTTACAAGCACTTGGGTTTTTTGGCGTGAATATCCTCCTTC
538551  AGCTTCAAACATTGTGATTGAAAATCACTGTTGATTATCAAGTAGATAGT
538601  TACGAATTTTTCTATGTGCTTACCATAAACTTCTACTTTTACAAATTGA
538651  TACTTAGGGAAATAAAAAGAAGTAAATAATCCCAACACAATGTTCATCAA
538701  TAGAGTAAAAACGAGGTTTGGAGATAAAAAGAAAGCAACTCCAAATGGCT
538751  GGTGTTTATCATCACCAACATAAGATTGCACTGATAAACTACCAGTTAAA
538801  TAAGTACCAATTACATAGCCAATAATAAAGCTAACTGTATTAATTAGCAT
538851  CAAAATTCCACCAATGTCTTTGTATTTTTTTTCAGAATATCAGAATGCTA
538901  AAAAGTCAAGACCGCCTGTAGAAGCGTCAATAATTAAAATAACTGAATAA
538951  AAAACTGCTTGTAAAAACCCCCAAATAAGTCCATAAAAAAGTAAAGATAC
539001  TTGTTTTTCAGCAGATTTTTCTCAAAATATAAGTTGTACTCCCTTTTCAT
539051  TAATTAAATTTTCAAATCCACCATCTTTTGCTGTAGTTAAATTTGCAAAC
539101  AAAAAGAAGTTATCTATTCCAGGGATGTATGAAAAGAAAAAACCAAAAAG
539151  ATTTGAAACAGCTACAAAATAAAGGGTTAATAGGGTAAATTTTTTGGAGA
539201  TTTTAAACCATCCAAAAATAAAGAAAGGAACATTAAAAAGAATTTGTGTT
539251  AACCAAAAAATAGCATTAAATATAGTTGCTGAATCAACATTAATATTTTG
539301  TGAAGTAATAAAAAAATTAACAAGACGAGCTAATCCTTGGCTAATGGAAG
539351  CCATACCAATGTCATAAAGTCCTGAAAACTGAACAAAAATAACACCAAGT
539401  AATCCTCAAAAAAAAGCAACTATTGTCAAAATTACAAGTTGTAAATAAAG
539451  CTTTTTAAGGTTGTATATAGATTGAAACTTAAGAaATGATCCAGAAAGAT
539501  GAATCCTTACAAAATTACCTGAAATTTTGATGTTTTTATCTTTCATAGTT
539551  AAGAACAATTATTTTAATAATTTTGGTAATTAATAATTTCTTATTTACTA
539601  TCTTATTAGTAATATTAAGCTTAGTGCAATAATGGCAACGAAAATAGAGC
539651  TAATAAAAGAATTGCGTAAATCAACACAAGCAAGTGTTATGGATTGTAAA
539701  CAAGCTTTGGAAAAAAATAATGATGATTTTGAGAAAGCTGTTAAGTGATT
539751  AAGAGAAAATGGCATTGTTAAATCAACCAAAAAATTAAATAAGGTTGCAA
539801  GTGAAGGAATTATTGTTTTAAAAAGCAATTTACACAAGGCAATTATGGTT
539851  GAGATAAACTCACAAACTGATTTTGTAGCCAAAAATCAAGAGTTAAAAGA
539901  ATTTTCAGATTTAATGCTTGAAAAAATATTTGAAAAAGTAAATCCAAAAA
539951  CAGAATTAGTTGAAATTGAAAAAATTCAAATTAATAATGATGAAAAAGTT
540051  TAGAAGAGTAGTTGTATTTGAAACTAAAACTAATCAAATTTTCACCTATT
540101  TACATGCCAATAAAAGAATTGGGGTAATTATTGAGATTCAAGGAAAACTC
540151  AACGAAGATGATGGTAAGCATTTAGCAATGCATATTGCTGCTAATTCACC
540201  ACAATTTATTGATCAAAGTGATGTTAATCAAACATGACTTCAAAATGAAA
540251  GAAATTATTCCGTTCCCAAGCAGAATTAGAGGTTAAAGaAAATCCTAAA
540301  AAAGCAATTTTTTTAGAAAAAACTATTGAAGGTAGAGTTAACAAATTACT
540351  AATTGATACCTGCTTAATTAACCAAAAATACTTAATTGATGAAACTAAAA
540401  CAATTGGTCAATTTTTAAAAGAAAAACAAGCTAAGGTTCTTAAATTTATT
540451  AGGTATGAAGTGGGAGAGGGATTATAAAGGAAACTGTTGATTTGTTAG
540501  TGAAGTAAATGCACAAATCAAACAATAAAATCCGCCAAAGAATAATCATT
540551  AAACTTAGTGGTGCTGGGCTAACCAAAGAAAATTCTCAACCCTTTCTAA
540601  TGATTTTTTTGAaACTATTATTAATCAATTAAAAGTTTTAAAAGAAAGCT
540651  ATCAAGTAGGAATTGTTATTGGTGGGGGTAACATTATCAGAGGTAATAAT
540701  TGCCAAGAATTTAACATTGCTGAATACCATGGTCATCAACTTGGTATTAT
540751  AGCaACAGTAGTTAATGGCTATTTTTAAAAGCAAAGTTAGATGCACATA
540801  ATTTGAAAAGTGCTTTACTAAGTGCAATTAGTTGTCCTAGTTTAGCAGTG
540851  CAAATTCTTTCACAGCAAACTATTGATAAAGCTTTTGAAGAGAATGACTT
540901  TGTCATTTTTTCAGGTGGCACTGGTAATCCTTATTTTTCCACTGACACTG
540951  CATTAGCTTTAAGAGCAGTGCAAACAAAAGCAGTTGCTATTCTGATTGGA
541001  AAAAATGGTGTTGATGGTGTTTATACAGCTGATCCTAAAAAAGATAAAAA
541051  TGCAACCTTTTTACCAACACTCAACTATGACCATGCCATTAAAAATGATT
```

-continued

The Nucleotide Sequence of the *Mycoplasma genitalium* Genome

```
541101 TGAAAATTATGGATATTACTGCTTTTACTATGTGTAAGGAAAATAATCTG
541151 AAAATAATTATTTTTAACATTAATGCTGAGAATGCATTATTAGATGCATT
541201 AAACAAAAAAGGTCGCTTTACTATAATTGAAAATAACTAATGACAAAAGC
541251 ACATTACATTGATTTTTTAAACAAGCAGCTGATAAAAAAATTCAATGAT
541301 TAAAAGAAGAGTTAACAAAGATTAGAACAGGTAGGCCAAATCCTAAAATC
541351 TTTGATAATCTTTTGATTGAAAGTTATGGACAaAAAATGCCTTTAATATC
541401 TTTAGCTCAAGTGACTATTAATCCGCCAAGAGAAATAATCATAAAACCAT
541451 TTGATCCTAAGAGTAATACTAATGCTATTTACAGTGAAATTCAGCGGGCA
541501 AACATTGGTGTTCAACCAGTTATTGATGGTGAAAAAATTCGTGTTAATTT
541551 TCCCCAAATTACTCAAGAAACTCGCTTAGAAAATATTAAGCACGTTAAAA
541601 AAATAATAGAGCAAATTTATCAAGAACTGAGGGTTGTAAGAAGAGATGCA
541651 TTACAAATGATTAAAAAAGATAATCACAATGAGGATTTAGAAAACTCTTT
541701 AAAAGCTGAAATAGAAAAAATTAACAAAAATTATTCTAATCAATTAGAAG
541751 AGATTCAAAAAGACAAAGAAAAAGAATTGCTAACAATTTAAATGAATGAA
541801 AAAGCAAAACAATTCATCAAAAAGCGAACTTCAGTATTCATTGCTTTATT
541851 AGTTGTATTTTGCTTTTtCTTTTAATTAGCGCATTTGCTGATGGTTTTAA
541901 CTTTTGATCACCGTGATCAGCAGATTTCAATTCAAGAACATTAAAAGTAG
541951 AACAAGCAAGTGGTGTTACTAGTGTTATTAGTACTGAGATTAATGAAAAC
542001 TTTAAAGCTGTTCGTTTCAGCTTTAGCATAATCATTATTTTAATTGTTGG
542051 GGTAATTGGTTCTCTGATGATTTGAGAGTTGTTCACAAACATACTAAAAA
542101 ATAAACCAAAACTAAGCTTAAGTTTAACGTTGTTAAATGCTGGAATAATT
542151 ATTTTTGGGATGATTGGTACTTTTGTTGTTGTTTATTTTTACAAATGAAA
542201 TGCAACTGTTAATGGTATTTGAACATTAAGTTTTACTCTTTCTGTGGTTT
542251 TACTTTGAATAATTTACATTGCTTGCATGAGTAAAACAAGAATTAAGTTT
542301 AGCTTACAACTTTCATATAGCTTAGGAGCTATTGCTTGCTTTATTGCTAG
542351 CATAGGTACTATTTACTTTTCTGTTATCAGGGGTTGAACTACAATCTTTT
542401 TATTGATGAGTTTAGCAGTCAGTGTTGATACATTTCCTTTTCTTTTTGGA
542451 AAGCGCTTTGGTAAAAaTCCTTTAATTAAAATTTCACCATCAAAACATG
542501 AGAAGGAGCTTTTTTTGGCATCATTAGCACCATTGTTGTTGTtGCTTTAC
542551 TTTGTGTTTTATATTCAATTCCTTTCTTTGTAGCAAAGCCTACTTTTAAT
542601 CAAACAAATGGAATAGCGCTCAATACACCCCAAAATTATGATAGCCATAA
542651 TCTTATTACCAATATTTTTTAATTGCCTTTATCTCTGGAGGAAGTAGTT
542701 TTTATATCTACTGGTGGGTAAGQACTTTAGCTTTAATTTTTACAGGATCT
542751 GTTTTTGCAATAGGCGGTGATCTTTTTTTTAGTTATATTAAACGCTTAAT
542801 TAGTATCAAAGATTTTTCTAAGGTTTTAGGTAAACATGGGGGAGTTTTAG
542851 ATCGATTTGATTCAAGTTCTTTTTTAATTAGTTTCTTCTTTGTTTATCAT
542901 TTAATAGCAGGAACCATTTCCAACCAAAGGTTGTTGATGGAACCTAATAC
542951 TTATTTCAGTGCAATCACTAGTATTCAAAGCTAGTATTTAGAATTAATAA
543001 AGTATGACTCCAAAACTAAAGCTAAATAACAACATAAACTGAACCAAAAG
543051 AACAATTGATTCTTTGTTTGATTTAAAAAAAGGTGAAATGCTTGAAAAAG
543101 AGTTAATTACACCTGAGGGAAAATATGAATATTTTAACGGTGGTGTAAAA
543151 AATTCAGGAAGAACTGACAAGTTCAATACTTTTAAGAACACTATTAGTGT
543201 AATTGTTGGTGGATCTTGTGGTTATGTAAGGCTAGCTGATAAAAATTTCT
543251 TTTGTGGTCAAAGTAATTGCACATTAAATTTGTTAGATCCGCTTGAACTT
543301 GATCTTAAATTTGCTTACTATGCTTTGAAATCACAACAAGAAAGAATAGA
543351 GGCTTTAGCTTTTGGGACCACGATTCAAAACATTAGAATTTCAGATTTAA
543401 AAGAATTGGAAATTCCTTTCACATCAAATAAGAATGAACAGCATGCTATT
543451 GCAAATACTTTAAGTGTTTTTGATGAGAGACTAGAAAACTTAGCTTCTTT
543501 AATTGAGATTAACAGGAAACTAAGAGATGAATATGCTCACAAACTCTTTA
543551 GCTTAGATGAAGCTTTTCTAAGTCATTGAAAACTAGAAGCATTACAAAGC
543601 CAAATGCATGAAATTACTTTAGGGGAAATATTTAATTTCAAAAGTGGTAA
543651 ATATCTAAAGAGCGAGGAGAGATTAGAAGAAGGGAAATTTCCTTATTATG
543701 GAGCGGGAATTGATAACACTGGTTTTGTAGCTGAACCTAATACTGAAAAA
543751 GACACAATTTCTATTATTTCTAATGGTTATTCACTAGGTAACATCAGGTA
543801 TCATGAAATTCCTTGGTTTAATGGCACAGGTAGCATTGCATTAGAACCCA
543851 TGAATAATGAAATCTATGTACCATTCTTTTACTGTGCTTTAAAGTATTTG
543901 CAAAAGATATTAAAGAAAGAATGAAAAGTGATGATTCACCTTTTTTATC
543951 CTTAAAACTAGCAGGTGAAATTAAAGTGCCTTATGTTAAGTCATTTCAAC
544001 TGCAAAGAAAGGCAGGAAAAATCGTCTTTTTGTTAGATCAAAAATTAGAC
544051 CAATATAAAAAAGAACTAAGTTCTTTAACAGTGATTCGTGACACTTTGTT
544101 AAAAAAATTATTCCCCGATATGACTGAAAGAACTAAATCTATTAAGGATT
544151 ATTAATCAAAAACTTAATTCTTTCTTTCTAAAATTACTTTAATATCTCTT
544201 TTCTTGCAAAATTAGATAATCTTTTCACACCAATTGAATAACCTGATTCA
544251 AAATATCCACCATTATTTTGATAGATAAAATTAACAAATACAAAAATTTA
544301 CTTTCTTTATTTTTAATTTATCGATAAACAGTTCTTACAGCGCCAATATT
544351 AGTAACACTTTTTTGGTTTAGCATTTACTTAATTTTTAGTTTCTTTAAC
544401 AAATTGAATTGTTATAAAAATGCGATTATTTTCTTGGATTTTAACTGCTT
544451 AACTTTTTTTATTTTGATATAAAGTTAACTAATAGAAAAGTATTTATCTT
544501 CTTTAGTTTTAAGATCAAAATATATCAGGTTTTATTTTTAAAAAAATTAA
544551 AAAATCTTATTAAAGCAATGTGTAATAAAAAAACGGTAAAAGATCGATTG
544601 ACTTTCCCTTAAAAGTTCTTGTTCTAATTTTCTTCACTTGTTCATTTGTT
544651 GAAAGTAATAAATTCAACTTTTCATGAGAAGTACTCATGTCAATTTTGAT
544701 ATCAAAAGGAAAGTTAATTGAAGCAGGTATACTACTAAAAGTACTTTCAC
544751 TTACCCTCCTATTATCTGTTGGAGGAGTATAAGTAAAGATAACATCACCA
544801 TCAAAATTAGCTTTATCACCAGTAAAATCACTTTCACTTACACCACTTGT
544851 ACTAGCTAAAAAGGATTTGATTAATGAAGTACTAGTATTGTCACTACCAA
544901 CTATACCAGTCATTTTTAAGTGAATTTGAACTTTAAAATCTAAGTTATTT
```

-continued

The Nucleotide Sequence of the *Mycoplasma genitalium* Genome

```
544951  TTTCAACTGTATTGAAAATTAACTACCTTTTGACTTTTAACTCCTAAAAC
545001  TAAGGCGATTTGACCACTTATACCTGGATAAGTTTCATCAAAATATAAAC
545051  CTTTTGCACTGATGTTAGGAGTAACATCTTCCTTTGATTTATTAACTCCA
545101  AATGCTTTAGCAAATCTGCTATAATCAAGTGGTTTTCTAATAGTTGATA
545151  ATCTAATAAAGTTGTTTTTCAACTGGCAAATACAGTATTAATTACCTCTT
545201  CCTTATCAGAACTATAACCCTTTTTTAAAAAAGTAACAGCATTATTTTTT
545251  GAAAGTTCTATATTGTTTCTCTGAAAATAAGCTTGTGCTTTTTCTAAACC
545301  AGGATCAGTTGATGAACAGGCTACAGATAAAGTACTAAGTGAAATTAATG
545351  GTAATAAAAAGATCTTTCTGAGTTTCATTACAAAATGGAATAAAGCACAT
545401  ATGGTAAAAGATCGATAGTTTGATCTTGGAAGTTTTGATCAGCTAATTGA
545451  CCTACAAAATTACTTTGTAATAACTTTTGCATCAATTCATCTTTACCAAT
545501  AATTTGTAACCTTAAATTGGTATTAAAATTAATTTTTCTCAATAGAGTAT
545551  CAAAACTAGATTTGGAAAATAAATTACTGGAAGGTGGAGTATAAGTAAAA
545601  ATTAAATCAGCTGAAATAGAATTTTTATCTTTTATATCACTATCACTTAA
545651  TCCTATTTGACTCAAATATGATTTTGCTTGAGCACTGTCAAAAGTTCCAG
545701  TAGCTTGTAACCTTATTTGGACTTTGAAATCACGAGAACTGTTATAGTAA
545751  AAACTAAAATCTGTAACTGTTTGACTACTCAATTTAATTACATTATTAAT
545801  AATACTTGCAACATTTTGCGTGTATCTTTCAACTAAACGTAAGCCTTTAA
545851  CACCAGTGCTCGGTTCAACATCTTCCTTACTCTTACCACTGCCAAATGCT
545901  TTTACAAATCTACTTGGGTCTTGTTTTTCAAGAATCTTTTCGTCTTGCAA
545951  ACTAAATCTTCAAGCATCTAATAGAACGTTTGTAGCACTTTTTGAATCCA
546001  CTTCAAAACTATCTCTTAGTGAAGTAACTAACTCTTTCTTGTCTTGATTT
546051  AATTCACTATTTTTACTGAAACTATTTCTAAGTtGGTTTAAACTGGAAAA
546101  ATTTGTTCCACTGCTTAAGTTAGAGCATGCTGTAATTAAAGAACCTAATA
546151  CCATTAAAGAAGAAATGATGCCAGCTTTTGTTCAAAATTGTTTTTTTTAA
546201  CATTGTTTAAGTTAACAGATTTtCTTATTTGTAATTTTTTGATCATTAAT
546251  AGAGGTAAACTTCAACAACAATCATTTAGAAGTTTTGTTTCTATTTTTAT
546301  CAATTAACAAATAGAAGGTTTCTATACTTAAAAAAACAAAAATAATCACT
546351  TAATTTTGAATTAATAACTTCTTGTTCTTGCAAGCCTAGATTATTGACAT
546401  GAAACAGTTTTACTGCTTGAAAAGTTTCATTGGAAATCGATTCTCTACTT
546451  AATCTAATTCCAAGATTTTGAATTTGTGTTTTTATAAAAAAATGAATATT
546501  AGCAATTAAGTTTCAAACTATTTCTGTTTTTTGAAAAAGTCTAACTAAAA
546551  GATATAAAGAAGTCTGATTAAACAAAAAATGCTTAAATCTTTTTCCAAAG
546601  TTTCTAAATAAAACTAATATTATTTTTAAACAAAAAAGAAACAGTACAAA
546651  AAATGCAAATACTGATGCTTTTAAACTAAATTTAGATCTAAGAAAACTAA
546701  CACTCATTGCGTTTTAAGCAAACTAAAAACAACAATTAAGAATGATTTTT
546751  CAAAAGTTGCAACTATAATTTTAAAACTTTTATTGATTTCTTTTGTATTA
546801  AAAACATTTGCACAACTTACTCTAAATTAATATCTTTTTACTAATAATAA
546851  GAGATTTTTTAAAACTAATGGAATTACTAATTAAGTTCATAACTTAATT
546901  TGCCATATTTCCCATTAATAAGTTCATTAATAAAAATTTCACATGCTAAG
546951  TTAGTGTTTAGTTCATTAGCTTTCTTAATTAAGCCTCTCACTTTAGCAAA
547001  TTTTTCCAAAAAGTTAATAAAGCTATCCGCTTCAAATGGTAAAAGCTGTT
547051  TGTAATGTTTCTTAAGATAATTAAAAGCAAACATTCCCACTTCTTCTATA
547101  TTAACTACTTCTCTTCTAATAACATTAGTCAAAACTAGTTTATATCCAAT
547151  TtGAATTTCATCAATTCTTTTCAAAAAAACTCCTGGGGTAtCACTTAATA
547201  ATAATTCAGGGCTAATTTGAATCCAATTTAATGATTTAGTAATACCAGCG
547251  CGGTTAGCTACTTTTAAGTGATTTTTATTTATCAAAAGGTTAATTAAACT
547301  AGATTTACCTACATTGGGCATGCCAATAACTGCTAATCTAAATTGTTTGA
547351  TTAATAAGCCTTTTGCTTTTAATTGTTGTCTTTTATTTGCAAATAAAGTT
547401  GTTAATGTCTTTAGAACTTTTTTTTTGAGTTTAAAAGGTTCTTTTAATGA
547451  ACCAAATAAGATCTTTTTATTTGGTTTGTATTGTGCTAAATCTGTCTTTA
547501  ATGCCAGTATTAATTTTGGTTTATTTAAAAAATAACTAATTATTTCTGAA
547551  TTATGAGTTAAAGTTGGTGCTCTAGCATCTACTATCTCAATGATGCCATC
547601  AATTTGACTAGATAACTTTTTTAATTGATCATGGATCTTTTTCATGTGAC
547651  CCGGGAACCAATTAATTTTGGCGGAGGTATATGTGTCCATCTATTCCCCT
547701  GATTCTTGTAATAGATACCAAACAATCCTTGTCAATTTGTCTAATAATCT
547751  TAATTAAATGGGGAATTTCTACATACATGGAAACAGAAACTATCATCTTC
547801  TTTTTGAGTAAAGAATAACCACCAAGCGTTTCTTGAATAGATAAACTGTG
547851  ATTAGCATTATCACTTAACAATGCTTTTCTAACTTCTTCAAGCTTATCAG
547901  TAAATACTTTAATTTCAGCAAAATTATAACGAGGGAAAAGATAACTAACT
547951  ACTGTTCCTGTTAACAAAATTGAAAAAAAAGTTGCAATTAAATTAGGTGA
548001  GAAAAATAAACTAACTTCCCAAGCAGAATCACGATAATTATTGACATCTT
548051  GCAACAATAAACTACCAGCAACAAAAGAACCAATTAGAATAGCAATAATC
548101  AGAATAAAACTATTTACATAAAAAAGAATTGATCCTACTGATCTATTTTT
548151  CTTACGAGCATAATATTGGGTTAAGAAGTCCGCTCCCCAGCAGAACCAC
548201  CTAGTATGTAAAGTAATGAAACTGATATGCCATTATAAAAACCATAAATA
548251  GCTGCATAAATAAATGTGGAAATAATTACATTACCTTGGGAAGTATCACT
548301  TCATAAAAAAGGGACAAAACCGGCACTTTGATTTAAATCTTTCGCTGCTT
548351  TTCAAAAGTTAGTATCTGTTATAGAAGCTAACATTGGTGGTAAATTATCA
548401  GAACCTGGAATAATACTGATTAAAAAACCAAATACGTTAGATGCAACAAC
548451  AAAATGGGTTGAAAGAATAGTAAAGTTTTTACCTATTTTTTTATAAGAAA
548501  AAATAATTAAAGGGATGTTGATAAAGACATATAAAAGCCAGTAAAGGATG
548551  TTAAAAATTAATAATCTTTGAGTTTCATCAAAACTTTTTAACAAAACAAA
548601  CACTAATCTAGCAAAACCTTGAGTTAAAGAACTAATTCCAAAGCTATATA
548651  AACCTGTTTTTGAATAAAAATAAGTAAAAGAAAAGCATTAATAATTGAT
548701  AGTAAGTAAACTAATACATACTTTAATGGTTTTTTAGCCTCATAAAGATT
548751  GCTAAACATCAAAAAAGAGTTAGAAATCCTTACGCGTTTAGAACCAGATG
```

-continued

| The Nucleotide Sequence of the *Mycoplasma genitalium* Genome |
|---|
| 548801 CGACTGTTATCTTTGATTCTTTTTTAAATAAGTTGTTAAAAAATTTCATT |
| 548851 TGTAACAAACTTTTTTAAGACTTTTTTTCTTTAATTTTTGCTGACTTACC |
| 548901 AGATCTTTCACGCATATAAGAGATGTATGCTCTTCTTACTTTACCCCTGC |
| 548951 GTTTTACTTCTATGTCTATATTAGGGTTGTGGATTTGAAAGTTTTTTTCA |
| 549001 ATAGGAATTCCATCAGTGGTTTTtCTTACCATGAAAGTTTCGCTAATCCC |
| 549051 TCTTCCCCTTCTTCTTAAAACAGTTCCAGTGAAGTTTTGAACTCGAACTT |
| 549101 TTTCTTTTTCACGTAACTTAATAGCAACATTAACTTCATCTCCTGCTCCA |
| 549151 AATTCAGGAACATATTCCTTTAACTGTTTTTGTTCTACTGCATCAATTAA |
| 549201 TGCTTGTTTATTTATTTTTTTCATTTTTATTTTCTAAGTATTTTTTGTAT |
| 549251 AAATCAGGTCTGTATTTTGCAGTTTTTAAGATTTGCTGTTCTTTACGAAA |
| 549301 TGATTCAATCTTTTGGTGATCTCCTGAAAGTAAAACTTCAGGAACTTTAT |
| 549351 CGCCTTTTAAATCGTATGGCCTTGTATAAACAGGAAAATCTAATAGATTA |
| 549401 TCATTGAATGATTCACAAATAAGACTCTGATCATTAATAACTCCTTTAAT |
| 549451 TAATCTAACAGTAGCATCAATAACACTTAGTGCTACAAGTTCCCCACCAC |
| 549501 TTAAAACAAAATCACCTAAAGAAACAATTTGATCAATATATTTATAAATT |
| 549551 CTTTGATCAAAACCTTCATAGTGACCAGATAACAAAATTAAGTGTTCGTA |
| 549601 TTTTGTAAGTTTTTTAGCACAATTCTGAGAAAATTGTTCACCTTCTGGGG |
| 549651 AGAGTAAAACTACATGAGAATTTGGGGCTTTATAAAAATTTAAACAATTA |
| 549701 ATAATAGGTTCAGCTTTTAAAACCATGCCACTTCCTCCACCATAAGCCAT |
| 549751 ATCATCCACAGTTTTATGTTTATCATTGCAAAAATTTCTTCAATTTACTA |
| 549801 CTTCAAATTGAACTAAATTTGCTTTTTGAGCTTGTAACATAATAGAACTA |
| 549851 TTTAAGTAAGGCCAAATAGTGTTTTCAAAAAGTGTTAAAACAGTGATTTT |
| 549901 CACTACTTTTTAGGACTTGTTTCTTTCTTATTTTTACTTTCAATAAATTT |
| 549951 CTTCCACAAACCAGATTCACTAAATAAAGAACGGACTGTATCAGTTGGAA |
| 550001 TTGCCCCTTTATTAAGTCAATCTAAGGCAACAGTTTCATCTAATTTACAC |
| 550051 TTATTTTCCTTTAAAGCTGGATTTAGATGTCCAATTAAAGCGATATACTT |
| 550101 TCCATTACGCTTTACTCGCGAATCAACCGCTACTATTCTATAAAGCGGAT |
| 550151 AGTGTACTCTTCCCATCCGCATCAATCTTATTTTGACCAATGATTTTTTT |
| 550201 CTTAATAAAGCGGCTAATTATAACTTTTTAAAGTTCTATTTTATCTATGC |
| 550251 TTAAGAATAACTTAATCAGCTATTTTTTATTCGTCTAGTTAAATAAATTTA |
| 550301 ATCATCCAATAAGGCCCGATTTTCATTTTGCATGTCATCTGCAAACTCAT |
| 550351 TATTTTTTTAGATAAATAAGTTCTTATCTTTATATCTAACAAAGTCTTAA |
| 550401 TTATTTTCTGTTGTTTAGCATATTATTTTAAGGCGTTAAACTTGTTTTCA |
| 550451 GAATTAATGATGAAATAGTTGTTTTGCTATTCACAATAGCAAAACTTAAA |
| 550501 TTTGAATTATGTTTTTGTTTATTAATCTGTTCAATATGTTCTTCTCAAAT |
| 550551 TAACCTATATTTTATCGGTTAATTCTTTTTTAATTTCATATAAGTAGAT |
| 550601 TAATGTAGTTCCACTATTAACAAATTTTTGTTTATTTTTAAGGAATTCCA |
| 550651 ATAGTTTTTGTCACTTTCATTTGGGAGGAGAGATTTACCATTTTTAATTG |
| 550701 AATTAATTACAAAATTTTTTTTAACAAATAATTAGTTGTTTAATAATCGA |
| 550751 AATTATTAATTAGTTTTTTTAGCATTCATACTGTAATTGGATTTTTCTAA |
| 550801 TTATGAGTACTTTTCAATAAATTTGACCAACTTATTTTGTGGTGGATTAG |
| 550851 CGAAATATTTATCCATAAACAGATTAGTGTGAATTTGACCAAAAGCAATA |
| 550901 TTAATTAAACCTGCTAAGGCAGCATTTGCAGTTAACAATCAAATAAAAAC |
| 550951 TTCAATGTTATTTGTTTGAAGTGTTATTGCTTGAAAAATAAAAAGTAAAG |
| 551001 GAATAAATACAAACAATCCGTGTGTTAAAGAGACAATTCAAGAATAAAGC |
| 551051 ACTCTGTTAGTATTTTGAAAATATTGTTGACTATTAGCGCCTGTGGCTAC |
| 551101 AAAGAAAACTTGTGCTTGCACTATTAATGAAAAGTAATTTGCTAAATCCA |
| 551151 AATTTtGATCTGAAACATCAAAAAAACTAGATAAGATCTGTTTTCCAAAA |
| 551201 GCAACTGCTGTTAACAAATAGATTAAACTACCGAAcGATATACAGATAAT |
| 551251 AACTGTATAAATGTTAATTTTTTAATTTCATCATATTTTTTTGTCCAA |
| 551301 ACTTATATGATGAAACTGTTCTAACTCCTTGTAATAAACCAAAAATAGCT |
| 551351 GCTGAAGCTAAATTACTAATAGCAATAGGTCCAGTTAAAAGTGTCAGATA |
| 551401 AAAAACATCATTTTTATCAGTAGTTGCTTTTGTCAAATTAACCAAAAAAC |
| 551451 TCTCATAAAATGTAGTAACAATAGAAAGTGATCCATTTCTAAAAAAGGAT |
| 551501 GCCATTCCTATTAATGAAACTACAACTAGTAGATTAAAGTCAATTTTGTT |
| 551551 TAATTTAATAGTTTTAAAAGTTAAATAAGTAAGATTTCTTTTGTTTAAAT |
| 551601 AAATTAGATAAATAATATAAGCTAAAAAATTAATTAAGTATCCTAGTATT |
| 551651 CCAGCCACAGCTGATCCTATTACTCCTAAAGAAGAATATCTAACTAATAA |
| 551701 AAAAACTATTAATATGTTAATCAAATTAGCAATAGGCGGAACAATTGCAA |
| 551751 TAAAAAGTTGTCTTCCCTCTGATTGTGCTAAATAAAAAAACAACCTTGAA |
| 551801 AGCATAGGAATGATGTTAAGACCAATCAAAATATAAACATATTCAGATGC |
| 551851 TACATCAATAGCCTTTTTGTTAAAAAACTGTTGGAAGCTATTAGCTTGAA |
| 551901 AATTTTGTTCAAAACTTGATTGATCAAGATTATAATGCAACCATTCTTTT |
| 551951 GCAAAAGATAAAACCAAAAATTGGGTAATTAGTCCAAATACAGTTGTTGA |
| 552001 TATTAATCCGGTATTTCAAGCTTCCTGAATTTTATTTTGATCATTTCTAC |
| 552051 CAATTGCTTTAGAAAAAATAACTCCAGTTCCTAGAGGAATAAAAATATTA |
| 552101 ATGGCGTTTAACAAAACAATCAAAGGTTGACTAATATTTAAAACAGTTTT |
| 552151 AATAAAATTGTTTAATATTAAGTCCAGAGCTTAAAAAAACTATCACTTTTAT |
| 552201 AAAAAGCAGAATTTTTAAATTCATCAATTAAACTCTGATCAGTAAAAATA |
| 552251 GAATCAGGATTAAGTTCACTTCTAGGAACAAACTTAATCACCATGATTTG |
| 552301 ATCTATAAATACATAAGCAGCACTAAAAAGTGCAAAGAAAAAAGTTGGAA |
| 552351 CAGTAAATCTAAGAATAGTTAGAAAAAAGCTGTTTTGATTCAAAAACATTT |
| 552401 TTAATTAGGAGTTGTTTTTCAAAACGATCCCTTTTACTGTTCACTTATTT |
| 552451 ATTTTTAAAAAGATGGATGTAATCCTTGTATCCTAATTTTTCCATCTCTT |
| 552501 CAAAAGGAATAAATTTTAAAGCTGCAGAATTAATACAATAGCGCAATCCA |
| 552551 CCTAATTCACTCGGTCCATCATTAAAAACATGTCCCAAGTGGCTATCACT |
| 552601 GTTTTTAGCACGAACTTCAGTTCTTATCATTCCGTGAGATTCATCACGGT |

-continued

The Nucleotide Sequence of the *Mycoplasma genitalium* Genome

```
552651 AGTTAGCAATTAAATTTTTATCAATGGGTTTTGAAAAAGCAGGTCAACCA
552701 CAACCAGATTTAAATTTATCAGTTGAAATAAAAAGTGGTTCACCAGATGT
552751 TATATCAACATAAATTCCCTTTTCAAAATTGCGGTTATATTCATTAATGT
552801 AAGGTGGCTCAGTGTGAGCATTTTGCGTTACATCAAACTGGAGTTTGGTT
552851 AAAGTACGTTTTAGCTCAGCTTCACTCTTTTTTGGTATTTACTCATTTG
552901 GAATGTTGTTTATTTAAATATACATCAATAAATGGTTTTCCTACTTTGAT
552951 CTTAGGATTAATCTCAATTATACCCTCATTTTTCTGTTTTAAATTAAGTT
553001 CTTTTTCAGAACATAACATGCCAACTGAATCAAAACCAGCTATTTTAGTT
553051 TTTTTGATAACTGTACCGCTAGGTAACACTCCACCTACTTGTACTAAAAC
553101 TGTTTTCATACCAACTCTAACATTATTAGCTCCACAAACAATATCCAAGC
553151 TTTTTGTCAAACCAGTGTTAACTTTACACCTTTTTAGATGGGTGTTTGCA
553201 ATAGGAATAACTGAAACAACTTCACAAACAACAAAAGGAACTTTATTTGC
553251 TAATGAAATAAGATCATAACCTAAAAGCTCACTTATTCTTTTCATTATTT
553301 TTAATGAAGGATAGTTTAGACCTTCATTAAAGCGGTGTGATAAAAAAACT
553351 TCTTAAACTTTTTTTGATATTAAAAAGTTAAAACCAGTAATTCTATTT
553401 GCATCATTAACAAAAAAACTTCAGTCTTTGTCATTTTGTTGGCGTAAAGT
553451 TGTTTCACTTCTACTTCCTATGATGCCAAACATACAGTTTTTTAATGTTT
553501 CTTTACGATAAAAGATAGAAACAAAATCTTTAGATATATCAAACATAAAA
553551 GTTAGTTATTCTGTTTGTATTAAAAAGGCATAACTATTGATACCTGTGTG
553601 TGTACAAATTACAGGTGAAAGCAAGTGCTCACTTACATCAACTGCATTGT
553651 TGAGAAGCGTAACAAATTCTTGCTTTATGAGTTGATTTTTATCAGTTTCA
553701 AACATTGTTGTCAACAAAGCCGCTCTTCTGAAATTAACTTCTTTTTTTAA
553751 TAGCTTTTTTTCTAAAAATTGAACTGCTAACTTATGAGCACTGCTAGCAG
553801 ATTGTGCTTTGTTAAAAAACTGCAATTTGCCTGTTTCACCAAGGAAACTA
553851 ATTAAGAGATGAAATTTAAAGCTTTTGATAATAAATGACTTTAAATTAGA
553901 TAATCTTCCTCCAGCTACTAACGGTTTTGTATCAGTTACAAATAAAATTG
553951 CACCGCACTTATTACGGAAGTTATAAACAAATTCATCTAAGCCTGCTCTT
554001 AGTGAAAAACTAGCATTAATTGCTTCTAAAACTGATGAGAAAATAGTACT
554001 GAATACTGGTTGTTTTAAGTCAAACCTTAATATCACTAATCAATCAAGC
554051 TATTAAAACTTCAACTATTCTGCTATCTAAAACATGAAACTTGTCTTCAA
554101 ATTCCTTTTCAACAATCTTTCAATTTAAATAGGAGGTTGAGATCTCTTTA
554151 TCAATAGGGATTCCTATGATAAGATCATAATCATTAATTATGCTCTTAAC
554201 TTTGTCACGAACCTCTTCTTCAGAAGTTTGTGATGTTGAAAACTTAACAC
554251 CTTTAGGGGCGTTAATCATCTTATCAGTTAAGGTTTTAAGATCAATGTTA
554301 AAACCTGATTTGAATGTTTCTTGGTGTTCAGCAATTGTTTCAATAATATA
554351 AAGCGGTAAAACATAGAGATGACTATTTTTATCTTCCTTTAGATTACTGA
554401 CAGAATCAACTAAAAAAGCGATCCTCACTATTCTAGAACTTCTGTTACAG
554451 TGCCTGCCCCTACAGTTCTACCACCTTCACGAATTGAGAACTTACTACCT
554501 TTTTCACAAGCGATAGGAGCAATTAACTCAACAGTAATAGAAGCATTATC
554551 ACCAGGTAGAACCATTTCAGTATTTTCAGCTAAAGCAATAGAACCAGTTA
554601 CATCAGTGGTACGGAAATAGAATTGAGGACGGTAACCGTTTAAAAAACCA
554651 GTGTGTCTACCACCTTCTTCTTTCTTTAAAGCATAGATCTCAGCTTTAAA
554701 TTTCTTGTGCGGTTTAATAGAGCCTGGTTTTGCTAAAACTTGACCTCTTT
554751 CAACTTCTTTACGTTCAACACCACGTAATAATACCCCAGCATTGTCACCA
554801 GCCATTGCTGAATCAAGTTCCTTTTTGAACATTTCAATTCCAGTAACAAC
554851 TGCTTTTCTAATTGGTTTTAAACCAACAATTTCAACTTCTTGACCTACTT
554901 TGAGTTCACCTCTTTCAACTCTTCCTGTAACAACTGTACCTCTACCAGTA
554951 ATGGTCATCGTATCTTCAATTGCTAATAAGAAAGGTTTATCTACTTCACG
555001 TGTAGGAGTTGGAATCCATTCATCAACTGCTTTAATCAAATCATGGATCT
555051 TAGCCTCCCACTTTGGATCACCTTCCAATGCTTTTAAAGCTGAGCCATAA
555101 ATAATAGGAGTGTTCTTACCATCAAAACCATAGGAAGTTAACAGATCACG
555151 TACTTCTTCAGCAACAAGTTCTTGTACCTCTTCATCACTAGCAATATCAC
555201 ACTTGTTTAGAAAAACTACCATTTTAGGAACCCCTACTTGGCGGGCAAGT
555251 AAGATGTGCTCGCGGGTTTGGGGCATCACACTATCAGTTGCTGAAACAAC
555301 TAGAATAGCTCCATCCATTTTGTGCAGCACCTGTGATCATATTTTTAATGT
555351 AGTCAGCATGTCCAGGACAGTCAACATGGGCATAGTGACGTTTGTCAGAA
555401 GAATATTCTACGTGTGCAGAGTTAATTGTGATTCCCCTTGCTTTTTCTTC
555451 AGGGGCTTTATCAATTTCATCATAACGCGTTGCAGCTGATTTTCCTTCCT
555501 TTGCTAAAACTGTACAGATAGCAGCTGTTAAAGTGGTTTTACCATGGTCA
555551 ATGTGACCAATGGTACCAACATTGACATGTGGTTTGGAACGGTCAAATTT
555601 CTCTCTTGCCATTTGTTTAAATTATGTTGTTAATTTTAAATAAGTTTAAG
555651 ATAAGCTGGAGATAATGCTTATAATCTTCAAGGACTTAAATTTAGTGAAA
555701 ACAAACAATTGCCAAATTATTGGCTGATGAAAACAACTTTCCTTACCACA
555751 AAAGACATTCTTAAGTTTCATTCCCTTATTTTTGGTCACTAGTGCTTTTG
555801 TTTTAACTGGAATTGTTGAAAGTCTTTTAACATTTGGAACTATTATTGAA
555851 CAAATTGATAAATTCACTGATCAGACTAATGTGATGTTATTAATTTATGC
555901 AGTTATCTACACTTTTAATCCAAAAAGTTGATTGTTAAAAAACCAACAAT
555951 TCTTTTTAAGTGCATTAGCTTATATATTATTTACTTTTATTGGCTATAAC
556001 CTAATTTTGTCAATAGCTGGTATAGCTTATAAATCAACAAATCCATATAA
556051 GTTAACAAGTAGTATTTTTCTCCATGTAATTGCACCAATAGCATTCTTCA
556101 TAGCAAGTTTTATCAAAATAAAACATGAGAAAGATGTCAATATTAACATG
556151 TTCTTTAAAAGCCTATTATTATTCATGATCTATCCTTTAATATATGGGCT
556201 TTATTTAGTAACTATTCCATATGTAAGGCATTATCTTTTTAATGGTAGGC
556251 CATCTACTTATACCATTTATGGCAGCATTACAAATACTAAAAATAATCCT
556301 TTTGCTTGATTAGTTGTATTTGCAGTTTTATTTATCTATTTCCCCTTGAG
556351 TTACTTAGCTATATATCTATTACAACTTAAGTTAATAAAAAAAGCCATAC
556401 AACCGCAATTTAATTTGCCTTTTACATTAAATAAATGAAAACAAAAATAA
```

The Nucleotide Sequence of the *Mycoplasma genitalium* Genome

```
556451 GAAAAGCAGTTATTCCTGCTGCTGGGTTGGGTGTTAGGTTACTACCAGCA
556501 ACAAAAGCAATTCCCAAAGAGATGTTACCATTGGTAAATAAACCTACTAT
556551 CCAATACATAGTAGAGGAAGCAGTTAAAAGTGGCATTGAACAGATTCTTG
556601 TCATTGTTTCATCCAAAAAAACAGCTATATTAGATCATTTTGATTATGAT
556651 CTGATCTTAGAAAATGCCTTAATTCAAAAAAATAAATTGCAGGAGCATAA
556701 AGAGATTGAAGATATTGCTAATTTAGCACATATCTTTTTTGTTAGACAAA
556751 AAAATCAAGATGGTTTGGGAGATGCAATCTTGTTTGCTGAATCTTTTGTT
556801 GGTAATGAAGACTTTGCAGTATTGTTAGGTGATGATGTTGTTTTTAGTAA
556851 AGAACCTGCTTTAAAACAATGCTTGGAAGCTTATTATGAAACTAATTGTC
556901 AAACAATCGGTGTACAAGAAGTAGATCCTTGTCATGTTGATAAGTATGGA
556951 ATTATCACCCCTGAAGGTGATTACAAAAATAAAGATCTTATTAAGGTTTT
557001 AGCAATGACTGAAAAACCTAAACCAAAAGATGCTAAAAGTAATTTAGCAA
557051 TCTTAGGGCGATATGTACTCAAACCATCTATTTTCAAAGCACTTAGAAGT
557101 GTACCTTATGGAGTTGGTGGTGAGTTGCAACTAACTGATGGTTTAAATTT
557151 TTGTTTGAAAAATGAAAACTTTTATGCAAGAAAGTTTACTGGTACTAGGT
557201 TTGATGTTGGCACAAAGAGTGGTTTTATTAAAGCAAATTTATTTACTGCT
557251 TTAAACAATAAAGATATTAGTAAAAAAGAAGTTTTAGAACTTTTAAATTT
557301 AGTTAAAGCTTAATACCCATTTAAAGTTAAACCAAGGAAGTTTTCATTTCT
557351 AATCAATCGACTAAAAGGACACATTTCATGGGCTTTTTGAATTAGTTTTT
557401 TACCAACTTCTTGGTCATTACTATTAGTAGTTAATTCAACACCAGCCTTA
557451 ATGTGAAATAGTCCATTTTCTTGATGGAGTTCTACTTTAACACTTACAAC
557501 TGGTTTTTTTGAAAAACTAAATTGATGTTGTTGCATAACAACAATTACTG
557551 CTTGAGAAAAACAACTTGCATAAGCAGATGCAAATAACTGCTCAGGATTA
557601 TTTTCTGTTTGAACTGATAAATCAGGTTTGGGAAAACTAAGTTTTGTTTG
557651 AAAACCATCTAAAGTTTTAACACTACCTTCTCTGCCAGTTTCAGTTTGTG
557701 CAACAGTTTTATAAATCAATGCCATGTTAATTAATATAGATAATATTTTA
557751 GTAAAAATGTTAAATAACATATTGCAATTTCTCAAAGAAAGAGAACTTTA
557801 TTCACAAGCTAATTTTGAAACAGAACTAGATAACCATTTAAAAGAGAAAA
557851 AAAATAACTTTTATGTTGGTTTTGATCCAACTGCTAATTCTTTACATATT
557901 GGCAATTATGTTTTAATTCACATTGCAAAATTATTAAAAGACATGGGGCA
557951 TACTCCGCACATAGTTCTAGGGAGTGCAACTGCTTTAATTGGTGATCCTA
558001 CTGGCAGAATTGAATTAAGGAAAATTTTAGAAGAAAAGAAATTGTAAAA
558051 AACACCAAAACAATTAAAAAACAAATCAAACAGTTTTTAGGTGATGTAAT
558101 TATTCATGAAAACAAAGTTTGATTAGAAAAACTTAATTACATTGAAGTTA
558151 TCCGTGAATTAGGTGCTTTTTTTCAGTTAACAAGATGTTAAGCACAGAC
558201 GCATTTAGTGCTAGGTGAGAAAAAGGACTAACTCTAATGGAATTAAACTA
558251 TATGATCTTACAAGCATATGACTTTTATTATCTACATAAAAACCATAATG
558301 TCACTTTACAAATAGGTGGAAGTGATCAGTGGGCTAATATTTTGGCTGGT
558351 GCTAACTTAATTAAAAGAAAAAATAATGCTAGTGTTTTTGGATTAACTGC
558401 TAATTTATTAGTTAAAGCTAACGGAGAAAAAATGGGTAAAACTAGTAGCG
558451 GAGCATTATGACTTGATGAAAATAAAACTAGTGTTTTTGATTTTTATCAA
558501 TACTGGATTAACCTTGATGATCAAAGCTTAAAAAAGACTTTTTTAATGCT
558551 AACAATGCTTGATAAAAAAGTAATAGATGAATTGTGTAATTTAAAAGGCC
558601 CAAAAATTAAACAAACCAAGCAAATGCTAGCCTTTTTAATTACTGAATTA
558651 ATCCATGGCACTAAAAAAGCAAAAGAAGCACAACAACGATCTGAACTAAT
558701 ATTTAGTAATCAACCAGATCTTGATATTAAGTTAGTAAAAACAAGCACTA
558751 ATCTAATTGATTATTTAGTTGAAACTAAATTTATTAAAAGTAAATCAGAA
558801 GCAAGAAGATTAATTAGTCAAAAAGGTTTGACAATTAACAATAAACACGT
558851 TTTAGACTTAAACCAAATAATTGAATGAAAAGAAGAGTTACAAATTATTA
558901 GAAAAGGTAAAAAAAGTTTTTTAACAATTAAAACTGTTAATTCTTAGCTA
558951 ATTTATCTTTAACTTCTTTTTCTATTTCAGTTTCAACACTTTTTTGACTA
559001 GAGCTTTTACTTTCTGGTTTTTTGATTAATTTGTTATGAAGTAAATCAAC
559051 AACTTTCTGCATTGAATTAATGTTTTGAAATCATAGCTTGCTTGGAGTT
559101 TAATGTTTGTAACTAGATCATCAAATGCTTCATTCACTTTTAGTTTAGTA
559151 TCCATAAAGGTTGTAGGCACACTCATAAACAAGTAAGTATGAACTGTGTC
559201 ATTATAGACATTAAATTTGGCATATACATTCAAAGGATTAAAAAGCACTT
559251 TATTTAATACCTCTGTATCTAAATTCTGAAAAGAAAAATTTGAATCTTTT
559301 TCAACAAAAAGTGAGATGTTTCTTGCTTTTTGTTTTCAGTAAGTGCTTC
559351 AAACTGAGCCACATTCTTATTTAAAGAATAGTTAGCATCAGTTAAAAAGA
559401 AATGATTTTCACTATTAATTGCTGGTGTAATAGCAATCAAGCAAGCTACT
559451 TTTTCTGTTTTATTACTGCTTCTTTTAATTGCATAAATATGACCAAAAAC
559501 AAATTCACTACCATCTTTATAAGTAACTTTAAATTGTCTTGGAAGTGGTT
559551 CAAAATTGTAAAGAGCAGTTGGATAAAAACTTGGTAATATATCGCTGCTT
559601 ATAGGACCTTGTTCAAAAAATTCAAATGATTCTATTGCCTTGAAATTACC
559651 CATCTCTTTTTGTCATAAATTAGTTCTGTTTTCTTTGTTAACTTTTTTTA
559701 ATAGCTTGTTTCTTTAAAAAGAGCAGCAAAATGGATAACAAATGCTAAA
559751 AACAAAACAACACTACCTAAAACAATTAAAAAAAAGTGATGCTATATTTGG
559801 TATTTCATTACGTGTATAACTATAAATACCAAATGAGATAGCAATAACAC
559851 TAAAAAGACCACAAAGTCCAATTACTCTTAGAAAAGCATTGAGTTTATTT
559901 GGTGTCAAAAAGAACTTGTTAAATTTAGTTAGATCTGACATATTTGTATA
559951 AAAGATTGTATGAAAATATAAACCAAAGCAAGCTCAACAGTTGTTTTATT
560001 ACAAGATCTTTTTCCTAAAAACTGCAAGTTGCCAAACTTAGCACGCATCT
560051 TTATTAAACGAAGATAGAGCTCATCAAATTTTATATCAAGTATTTTGTAT
560101 CTTTTGTTTGTTTTGGAAATAAAAGTGCAAAAGTACTTTAGAAAATAAAA
560151 AATCAGATCCCAAATTCGTTTTTGTCCTAAACTAATAGTTTTGTTTTTA
560201 GTAATACTTCAGTTTGCTTTAAAACATTTTTAAAAGTAATAACAAGATCA
560251 TCATTACTGTCATTTAAATAAGTTTGTATGTTTTCAATTCAAATCAAAAT
```

-continued

The Nucleotide Sequence of the *Mycoplasma genitalium* Genome

```
560301 GTAGTGATATTCACTGTCAAACAATTGGGGATTATTTTTAATTACTGTAA
560351 AAAAATCAGTAATTGTTTTACTTTGATCATTTAGTACTTTAAAACAATTC
560401 CAAGCTTCATTACCATAACCAACTTCTATTGCATTTAATTCTTGCTTAAA
560451 TGATAGTAAGTTAACCAAGAAGTTATCAATAAAATCAACAACACTAACTG
560501 TTTGTTTCACTTTCTGGTTTTACTTCAGATTTATTTAGTTTTTGCTTTGC
560551 TTGTTGTTCTTGCTTTTGCAATAAGATTTCTGGTGGTAGTTTAGTGTTTT
560601 TATGGATGAAGTCAATATCACTTTTCAAAATAGTTTCAGCAATTAAAAGT
560651 GCTTCTACAAGCAATTCTAGTTCCTTACGGTTACTCTTAATGATTGTTTT
560701 TGCTTTCTTATACTGTTCTTCAATAATGAAATTAATCTCATTGTCAATAT
560751 CTTTAGCAGTTTGTTCTGAATAAAGTTTTACATTAGAAGGGAGTGTCCCT
560801 TGACTTGGTACATATTGCACTTGACCTAATTTAGACATCCCAAGCTGGGT
560851 TACCATTGCTCTTGCAATATTAGTTGCTTTATAAAAATCGCTAGAAGCGC
560901 CAGTAGTAATTTCTAAATTACCATAGATTTCCTCTTCAGCAGCTCTACCG
560951 CCCATAGCAGTTGCTATCATTGCAAGTAAATCAGATTTTCTTTTTAGGTT
561001 AAGATCACCACTCTTAGGTGTTGAAAGTGTGTAACCCCCTGCTTGACCAC
561051 GAGGAATAATGGTAATCTTTTGTACTTCATCATTACTGTGGACATGTAAA
561101 CCAACCAAGGCATGACCAGCCTCATGATAAGCAACTAGTTTTCTATCTTC
561151 ATCACTAATTACACGTGACTTTTTAGCAGGACCAGCTATTACTCTATCAA
561201 TTGCTTCATCAATGTCATTAATGTTAATTGTGGTACGGTTGTCTCTAACT
561251 GCTAACAATGTAGCTTCATTGATAACATTTTCTAATTGAGCACCTGAAAA
561301 CCCAGGAGTTCTCTTAGCAACATCTAAAAGACTTATCTTAGAAGAGAGAT
561351 TTTTATTTTCAGCATGAACTTTTAAAATCCCTTCCCTTTCTTTAATATCA
561401 GGGAGATTGATTTGAATATGTCTATCAAATCTTCCAGGTCTTAATAATGC
561451 ATCATCTAATACATCTAACCTATTTGTAGCTGCCATTACAACAACACCTG
561501 TTCTGCTTGTAAATCCATCCATTTCAGCTAACAATTGGTTTAAGGTTTGC
561551 TCAACAACAGAATAAGAAGAGAGTTCAACTCTACCCCGTTTAGAACCAAC
561601 TGAATCAATTTCATCAATAAAAATAATACAAGGAGCAGCCTTTTTAGCTT
561651 TATTGAAAAGATCTCTAACTCGTTTAGCACCAACACCAACAAGCATATCT
561701 TCAAATCCAGAACCCGTTGATTGAAAGAAAGGAACACCAGCTTCACCAGC
561751 TACTGCTTTAGCTAATAATGTTTTACCTGTCCCAGGTGGACCGTATAAAA
561801 TTACCCCACGTGGGGATCTTGCTCCCATCTGGGCATATTTCAATGGATTT
561851 TTTAAATAATCAACTATCTCAAGCAACTCATGCTTTTCCTCTTGAAGTCC
561901 AGCAATATTGGTAAATTTCACAGTTGACTTAGCCAACTTAGCTTGGGTTT
561951 TGCCAATAGAAAAAATATTATCTTCTTCTCTGCCCCCTGCAGATATACCC
562001 CTAGCACTTCTTCAAAAGAGTAAAAAGAAAACTACAAAGATAATAATTGG
562051 TAGCAAGCCAAACAAACCATTTAATACATCTCTAGCTCTAGTATCAGGAG
562101 CAATGAAAGTACCAAGGGTTTCAAAACCTGCAATACTCTTTGTGTTATTA
562151 CTAGAACCACCATTCATCATGGTTCCATTACTATTAACGGTAATCTGACC
562201 ATTACTTTGGTTAATTGATAAGTTAGCAATATTAAAGATAACATTGCCAT
562251 TACTATTAACAGTTTTGTGAGCAGTAACAGTTAATGGACTATTTAAACCA
562301 TCAAAGGTAATGGAAACTTGGAGAATGGTATCAGTAACATAAGTTGAACC
562351 ATTTATTTGTTTAAATGTCAGTTCATTACTAAAACCGCTTACTTTTGCTG
562401 TTAAAGTGCTGTTACTACCTCCATTTAATTTTCAGCTTTCAACTACTGCA
562451 GTAGCAGCTCTTGGACTGAAAATATAAGCTAAAACACCAATAACAACAGC
562501 TAAAATGATGACTCATCAAAAGACTTTTCAAGCAGTTTTACGTGAAAAAT
562551 TATTTTTTTCAGTAGTTGTTTGTTCTACTAAACCCTTATTTCTTTTTTTC
562601 ATCTATGTTAGTTTTTGACCGATTTGGGTTTTTTTGGTTTGAACTACATT
562651 AACTGTAATTATACTGCCAATGGTAATGAAACTAATAAGTGTTAATAAAG
562701 TGACGAAAATTATCTTTTTATGTTTACTTAAAAGTGCAATAAAAGCCTTG
562751 AACCAACGCATAAAATTTTAATATCTGTTTTAGGGATTGTCTGGTTCAAA
562801 CACACCAACATAAGGTAGGTTACGATAAAAACCATCATAGTCAAGACCAA
562851 AGCCAACCAAAAAATTATCTTTTACTTTAAAACAAGAAAAATCAATATTA
562901 ATATCAAAGGCTTTGGGTTTAATCTTTTCAATTAAGCTAATTAAAGTTAT
562951 TGATTTAGCATGCCTTGTTTTTAGAAGATCAATAACTAATTTAATAGATC
563001 TACCACTATCAACAATATCTTCTATTAAAAGGATGTCTTTATCTTTAGGG
563051 TCATGGGACATATCAAGCACAATCTTAGGTGGTTGTTTTTGTACATGTGA
563101 ACCATGATAAGAAGCAACTGCCATAAAATCTAGTTGGAGGTCAAAACTAA
563151 ATTTACTTATCACTTTGCCAAGGAAAGGGATGCAACCTTTTAGAATGCCA
563201 AGAACAATTACCTTTTTATTATTAAATTTAGCATTGCACCAATTAACTGC
563251 TTTTTGACAGCCTTCTTCTATCTGTTGTTCATTAATAACAATAGATTTAA
563301 TACCCATCTTATTTAGTTTTTTGACGTTCTACTAAAACAACAGCTAAGCA
563351 ATTAATTTCATTACTGTCTAAAGGTTTTCTAACTTTGAGATTAATTGTTA
563401 ATTCTGAAATTCTTAAAGCACTACAAATAAAAGCAAAGATAGCGTGTTTA
563451 TAATCATCAACCTTTTGCTCTTGAGGAATCTCTAAGGAGATATCAATATT
563501 ATTGATAATTCAGTTTTTTCTGATGAAATTGTAAGTTCTTGCTAAGACTC
563551 TTGGTGCTTCTTTTTTTGCAGTACCTTTAAATTGGACTGTTGATTTTCCT
563601 TTATTGAAAACAATATGACCATCACCTAATGCAGTTGCACCAAATAAAGC
563651 ATCAGCAACTGCTAATTGGATAACATCACTAACTTCATCACTGTTTTCAA
563701 GATCATAAATATATTTAGAATTCTCAAAATCAACACCGCCTAACCAAAAT
563751 TTATTTTTACTTTCTTTCCTTAATTTTATGTGGTATTTTTTGCTTCCTAG
563801 GCCAACTCTTAACTGCATTGTTACAAATAATTATAATATCGCTCATCTTT
563851 AAATAACAGTGTTGTTTTGTAATCCAAAAAAAGTAAATTCAGGCAACAGT
563901 TTTTTGACTTCAAATATCCTTATTTAGACAAAGCAAAATTTATTAAAGTG
563951 AACCAAAATAAAATTGAAGTATATCTCTAGATAAATAAATATGAAAGGAC
564001 CTAAAATTGCAATAGTAGGATCAGGTGCTGTTGGTACTAGTTTTCTATAT
564051 GCTGCAATGACTCGTGCACTTGGTAGTGAATACATGATTATAGATATCAA
564101 TGAAAAAGCTAAAGTTGGTAATGTATTTGATCTTCAAGATGCTTCCTCAT
```

-continued

The Nucleotide Sequence of the *Mycoplasma genitalium* Genome

```
564151 CATGCCCAAATTTTGGCAAAGTAGTTGCTGGAGAATACAGTCAATTAAAA
564201 GATTATGATTTTATTTTCATTAGTGCAGGAAGACCTCAAAAACAAGGTGG
564251 GGAAACTAGGTTGCAGCTACTTGAAGGCAATGTAGAAATTATGAAAAGCA
564301 TTGCCAAAGAAATCAAAAAATCTGGTTTTAATGGAGTTACATTAATCGCT
564351 TCAAACCCAGTTGATATCATGTCATATACATATCTTAAAGTTACTGGATT
564401 TGAACCTAATAAAGTAATTGGCTCTGGTACTTTACTTGATAGTGCAAGAT
564451 TAAGATATGCAATTGCAACTAAGTACCAAATGAGTTCAAAGGATGTACAA
564501 GCATATGTTATTGGTGAACATGGTGATAGTTCAGTAAGTATTATTTCATC
564551 AGCTAAAATTGCAGGACTATCACTAAAACATTTTTCTAAAGCTAGTGATA
564601 TTGAAAAAGAATTTGGTGAAATTGACCAATTTATCAGACGCAGAGCTTAT
564651 GAAATTATTGAACGCAAAGGTGCTACTTTCTATGGAATTGGTGAAGCTAG
564701 TGCTGATGTAGCTGAACAAATTTTGAAAGATACTAAAGAAGTTAGAGTAG
564751 TGGCTCCTTTACTTACTGGTCAGTATGGAGCGAAGGATATGATGTTTGGA
564801 ACTCCTTGTGTACTTTCAAGAAAAGGTATTGAAAAGATCTTGGAAATAGA
564851 ACTTTCAAATACTGAAAAAGTTGCGCTTGAAAATTCAATTAAAGTTTTGA
564901 AAGACAACATTAAACTAGCAAAGCTTTAGTTTTGATAGAAAACATTAGCT
564951 CATCTATAAAAGAGTTTTCAAAAAATAACTCGTTACTTCTCTTAACAAG
565001 CATACTAATTTCACTGAGATTTTTAATCTTGTTTTGAGAAGTTTTTATTT
565051 TTAATTCATTTTTGTGCTTATTTCATCCTTCATAAAAACCCTTAAATTGG
565101 TTATTGAATTTAGTAATGAAATAACTAGGAGTTTGATATTCTTTTACTTT
565151 TAATTCAAAATCAAGATCACGTTTTTCACAACTTTCATAAAACTTTACTT
565201 GAAATTTCAGAGTGTTAAGATAACTATCTAGTAAGGTTTTTAATATTGCA
565251 TCTTTAGTTGTTTCAAATGTATTAACTAAAAATGAGTGAAAAACATAATC
565301 ATCTAACTTCACAAAACAAGTTAATAAACTTTTTTTAAACAACTGGTTTT
565351 TTAAAAGCGGTTTAATTACACTTTCAACATTCTTAAAGTTATGAAAATTA
565401 AAGTTGTCTTCTTCAATTAAAGCTTTAATCCGTTGAAAAACAAATCATAA
565451 GTTAAGTTCTGTAGCAATACTTCTACCATCACTGTAGATTGATTGATACA
565501 TGTGGTGTCTTGTTATCAAGAAGTTTTCAATGAAAGGCAAGCATTTTTCT
565551 TGAAAAACAATTTTATAAGTGCCCTGATTATCTACACATTCCATTCCATT
565601 GATAATTGATTGATAATCAACTAATGAGTGACTGGTACCTGTAAAATAAG
565651 CATCACGTAATAAATAATCCATTCTGTCTGTGTCAAGATCTGAAGAGATT
565701 AGCTGTCTCATCCACCAGTTAATAGGTTGAATATTTTGATTTTCATCAAT
565751 TAAAGCGCCAATCAGATTTGGATCTATCTTATTAGCTTTTAAGATAGAGA
565801 CAATAGGTTCACTATTAACTAACATTGAAGTAACCTTTTCATGAATAAAA
565851 AGTTGTTTTTTAAAATCAGGATTTTTAGCAAAATAGATTTCAAAAGCATG
565901 AGAATGAGGTCCATGACCAAGATCATGCAACAAACCAGCTACTAAAACAG
565951 TTTGTTTTTAATTTGATCAATATTTAAAAATGCAGAACTATTTAAGATC
566001 CTTCTTATCAGTTCATAAACTCCTAAAGAATGGGCGTACCTAGTGTGAAC
566051 TCCACTAGGATAAAAATGGAAGTTAATTCCTAATTGTTTGATGTTTCTTA
566101 ACCTTTGAAAAGCTTTTGTATTGACCAATTCATACATCCACTTTGTGTTT
566151 TCATCAAAAATAATTTCTCCTAAAATAGGATdTTTAAAAAAGGTTTGTTG
566201 CATTAATAAATTGCTTAATTAAGTTTATTGCACTTTCTTTATCAAAAATT
566251 TCAATAATATGTGCTAAATCAGGTCCATGCTCCTTATTTGTAAAAATTAA
566301 CCTTATTGGCATAAAAAGTTGTTTACCTTTTAAGTTAAACACTGCTCCTA
566351 CTTTGTTAATAGTTGTTTTAATTTGCTCAGCTTTTCATTCTTCCAACCCT
566401 TGTAAAGATTTGGCAAGCTGTTCTAAAAAAAGTTTGATGTTTTTAAACAA
566451 AATATGACTTTTCTTAGCTAAGTTTTCAACACCTATTTTAGTGGCAAAAG
566501 ATTCTCTTATCAATTCGTTTATTTGAACACCATGGGTTATTTGATTTTTA
566551 AAAAGTAAACTTATTTCCCTGTTTTTATCTTTTAAATAATCAACCTTAAC
566601 ATCCAAGTAATTATCAATGAAATTGAAATAAGCATTATCAGTTAATTGTT
566651 TAATGTAATTAGCATTGATTCATTGCAGCTTTTTAATATCAAAAAAAGCA
566701 GGAGCACTAACAACTCTACTTAAACTAAAGTTTTCAATTAACTGTTTCAA
566751 ATTAAAAAACTCCTGGTTGTACTGTGGATGTCAACCTAAGAGTGCTAAGA
566801 AATTTAATAATGCTTCAGGTAGATAGCCTGTTGTTTAAACTGCTCAATA
566851 AACTGAGTAGTTTtCTCATCACGTTTAGAAAGTTTTTTGCCACTTTCATC
566901 AACAATAACTGAAAGATGACCAAAGCGGGGAATTCTTTTAAAACCTAATG
566951 CTTGATATATAGCAAGTTGGTATGCAGTGTTAGAGATGTGCTCAGCTCCC
567001 CTTAAAACATCAGTAATTTCCATATCATAATCATCAATAACAACTGCAAA
567051 GTTATAAGTAGCAACACCATTAGCTTTAAGAATAACTATATCTGTTAACG
567101 CACTGCCGGGAATAGTAATTTGTCCCCTAACCAGATCATTTCAACTATAT
567151 TCAGCTTCATTGTTTATTTTTAAGCGGATAGTAAAAGGATCATTTTTTTC
567201 TAAGTGATTAGTAATTTTCTTGGAATGTAAATTACGACAATGACCTAAGT
567251 ATTTAGGGGTTTTGTGGTTATTAATGGCTTGTTTTCTATCTGACTCTAAT
567301 TTTTCTTTGCTACAGAAGCAACGATATGCCAGATTTTTTTCAATTAAATC
567351 AAATGCTAGTTTTTTATAAACTGCTAGTTTTTGTGATTGCAGATATGGAC
567401 CATAATTGCCAGGGTTATAAACCGATTCATCTGCAATGACTCCAAGCCAA
567451 CGCAAGTTATCAAATTGTGAATTAATTCCTTCTTTTATGTTTCTTTCAGT
567501 ATCAGTATCTTCTATCCTGATAATAAACTCACCATTAAAGTGCTTGGCTA
567551 GTAAAAAGTTAAAGATTGCTGTTCTTGTACCACCAACATGCAGATATCCT
567601 GTTGGGGATGGTGCATAACGTGTTCTAATTTTTTCCATTACAAATGTTTT
567651 GGTAAAGATTAAAGAGTTGACAAGGACTCAACTCTTGCGCTCTAATGCTA
567701 GTCTTTAAATTTTGCTTTTGAATAATGTTAAGTAAATAATCAACTGCAAA
567751 AAAATGCTTTAAGTTATTAATTAACATCTTCCTTCTTTGATTGAAACATT
567801 GCTTTAAAAACAGACCAAACTTAAAGTCATAACTAACCGATTTATTTTTt
567851 TCTAATAATATTAAGGTTGAATCCACCTTAGGTTTAGGTTTAAAAGCATG
567901 CCTATCAATTTTAAAAACTGTTGTAATAGTCAAATAGTATTGACAAAAAG
567951 CACCAAAGGCACTATAATCACTAGAATTAACCTTTGCCAGAAGCCGATTA
```

-continued

The Nucleotide Sequence of the *Mycoplasma genitalium* Genome

```
568001 GCAAACTCTTTTTGTGTCATTAAAACAAAGCTTCGAAGCTTTGATTCTAA
568051 AAACTTATTGATTATTGGAGATGTAATGCTATATGGGATATTACCACACA
568101 ATAATGGACTTAAATTTTCAAAAAAACTATTAAAGTCCTTTTTGAGAATA
568151 TCGCCTTTAACTAGTTGGTCTTCAGTTAATATCTTTtCAACTAGAAGATA
568201 TTCAATTAAGCGTTTATCAATTTCTATCCCCTTGTAAGGTATTTTGAGTT
568251 TTAACAAATAATTTGTTAACGCTCCTTTACCAACACCTATTTCAACAATT
568301 GCTTGTGGATTTAAATTTTTAACAAAAGCAAAAATTCTTTTAATGACGCT
568351 TAAATTAACCGTAAAATTTTGACCTAATTTACGTGAAGGAAAAAAACTAT
568401 TCACGCTCTAAAATCAAATCTAATTTGGAATAATTTTGCTTTCTTTTTTC
568451 CCTTCTTTTGACAATGAAAACATGGGTTAAATAAGATTGTAATAAAGTAA
568501 ACAAAGCATTTAAAAACCAATAAACACCAACTCCAGCAGCACTAAATGCA
568551 GTAATAGCAGCAAACACAAAGTAAAAAATTAATTGCATCTTTTTAGTTTT
568601 GTTGAGTTGTTCAATACTTTTTGAGAATGGGCTTTCGCATTCTCATTAC
568651 GCTTACTTGCCCACACTTGAGGAAGTTTTTGAGAGAGAAATTGGACTGGT
568701 AAAACAATCACTAAAAAGATGATGAAAGGTCAACCAGTTGTAGTGAAATT
568751 AGAGAAAATTTCTGTTAAAGGTACTTTTGAAAGATCCCAAAAGTTAAATA
568801 AGATGATTGCTTTAATTGGTCTTAAAGTAGTAACAATCCTATAAATAATT
568851 AAAAAGATAGGTAAAGTTACAAAAACTTGAACAAAAGCAGCAGATGATTT
568901 AATGTTGTGTTTTTTATAAAGTGACATTATCTCTAACTGTCTGTTTCTTT
568951 TACTTTGTAAATCTATTGCCCCTTTATATTTAGCGTTAATTTCTGCTAAT
569001 TTACCTTGCACTTCATTCATCTTTTCAAGTGCTAAAGTAGAGTTTAAGGT
569051 AATCACAATAGTTATCAAGCGAACTAATAGTAAAAGTACTATTAATGAAA
569101 GAATCATGTTAAACCCAAGTTCCACCCCGCTACCTAGTGGAACTCTGGTT
569151 GCATACATAATTGGTAAAACTATTTGCGCTGCAGGCCAGACAAATCATCC
569201 ATAAAAAGGGCCATATGCTAAGGTGTAATCACTAAAGGTGAAATAAGGGC
569251 CAAAGTTATTTGAAATCAAATCATACCTATAATCACCAGTAGTACCAAAT
569301 TTATAACCTATCTCAAGTCCTGAACCTAAGACTTGATTAGTACCTGTTCA
569351 GGGTTGTGCTAAGGTTTGAGTACAGCCCCAAAGCCCAACAATAGTTAAAA
569401 AAATAAAGATAAAAACCTTAATAACCTTTATGAAAATAGCTGAAAACTTT
569451 TTGAAGTTTTTTCAGTTGTTTTTTTCATTAACAACTGCTGCTGATCAAAA
569501 AGGATTAAAGGTGGTTTTTATCTCTTTATTTGTTTGCGCTAGTTTGATAG
569551 GCATCTACTTCTTTTATCCGCTTTAATAGTTGCAAAAAAAGTTTTTGTTT
569601 TTCTTTAAATGTTAATTCAATAAAGCCTTTGTTGACAATAACTAAAATAT
569651 CTCAAGGTTCTAAATTATTACTAATTTGTTGAAAGATACTACGGTCTGA
569701 CGCTTAATTAGGTTACGTTGTACTGCTAGCTTATATTTAGTTTTTGCAAT
569751 TGATATTGCAACCCTTCAAGTAGAATGATTATTCTTAATAAAATAAGCGT
569801 TAATAAAGGTACCAAAGAACCTGGTTTTACTTTGAAGAATGGTTGTAAAA
569851 ACCTTGCGTTCTCTTAAGCTGTGACTCTTTTTAACGCTCACTGGAAACCG
569901 TGAGTTGAGCACGATTTTTAAAACGTCTTTGCCTTAAAACTTTACGTCCT
569951 TGTGCAGTTGCCATCCTAGCCATAAAACCATGGGTTTTAGCACGCTTTAA
570001 TTTGCTTGGTTGGTATGTTCGTTTCATGAAACAATTAATCAGGTGATTAT
570051 AACTAAACTAAGGGTCTGACTAATTGGTTAGATACTATTTTACCATCTGA
570101 AATTTTAATGATTCTATTAGCTATCCTTGTTAGGCTTACATCATGGGTAA
570151 CCATTAGGATGGTTTGCTTATATGTTTTGTTAATTGTTTGTAATAAATTA
570201 ATGATATTTTCCGCAGAATTACTATCAAGTGCACCAGTAGGTTCATCACA
570251 AAGTAATAGTTTAGGTTCTTTAATAATAGCACGGGCGATGGCCACTCTTT
570301 GTTTTTGCCCACCTGACATCTCATAAGGAAATTTATACAAGATTTCTTTA
570351 ATATCTAATTTTTCAGCCAACTCTTCTATATCAAGTCGTCTTTGATATTT
570401 GGGAATTAAGTTTTGTGAAATGGCAATATTATCATAAGCACTTAACAATT
570451 CAATCAGATTATAACGCTGATAGACATAACCAAGGTTATTCTTTCGATAA
570501 GTTAAAAGTTGTTCACTAGTACATTTTTCTAATGGACAGTTTGCTACGAT
570551 ACAACTCCCTAACGAGATAGAATCATAACCACCTATCAGGTTTAAAAGGG
570601 TTGTTTTACCTGATCCTGAAGAACCTAAAATGATTACTATTTCACCATAA
570651 GCTATCTGTAAAGAAACATCTGAAAGGATAGAAATCTCTTGCTTTGAATC
570701 ATCATTATGAACATTTTTTCACATCTTATTGATGGTAATAACAATTCCCT
570751 TAGCTTGTTGAGCAAAAGGAGGGATATATAAGGTATTGGCTTTTTGCTTT
570801 TTATTAGCTTTCTTTTTGAGCTTTAGCTCAGCTTTTTTAATGTTATTTAA
570851 AACTTTTTTATTCTTCTTAGGAGGTTTAGATTTACTCTTTTTGAAATAAT
570901 CATCGAAATTGGCACTAAAAGAAGGACTTTTAACGTTATCTAAGATATCA
570951 ATACATTCATTTCAAACAGTTTTATTGCCTTTTTTCATTAACTAAAACCC
571001 TTCCTTCAGTTCAGCTGAGCGTAACTTAATTCAAAAGTAAGAACCAATTA
571051 CAAAGATAGTAACACCAAATAATACTATCCCTACCATGTATGGCAAGAAC
571101 TCAAATACATTAGTTAAAAAGACTTGTGCAACATTGAAAACAACCGCTTG
571151 GATACCAATTAAAACACCAGCTAAAACTCCAATAGAAATTAGTAATGCTA
571201 AAACAAATGCAGGGATAAAGAAGGTAAGTAAACTAATTAAATTTTGTACA
571251 TCTCTATAGCCAATAGCCTTAAGTGAAATAAAGATTCTTTTCATCTCTTC
571301 TAACATTGAGATACCAAGTACAACACAAGTAATGAAAATGAAAGGAATAA
571351 TAGTTCCTAAAAGAAACGCATCTACTTGATTCACAGTGTTAAACAAAACT
571401 TCAGCATTATTTCTAATGATCTGAGCACTAGTTCCAGCTGCATCAATATT
571451 GAGTACAGGAGCAATAATGTTATTACCAAAAATACTACTTGCATTTTGGG
571501 AAAGTAAATTAACACTATTTCATTCTGTTTTGTATTTATTAACTAGTTCT
571551 TTACGAAGCGATTCATAATTCATTGAAGTAGTATTAATAATCTGTTTTTC
571601 TTGTGCTAACTTATTAATAATTTCAGGATCAGTAGGTAGTATGGATGTAA
571651 TAACTTTATCAAGTTTATTCCTTACTAAATTTTGGAAATTATTACCAAAG
571701 TCAGTGAAATTACCCCAAACACCAATTATCGAGTTTAATACTAATGCCTT
571751 ATTTAATAAAGAAGGTTTTAATTCTTTGGAAAATACACCATTAAAAGGAA
571801 CATAACCGTTTGGTTTTACATAATCAATTTCATATTCATCACTACTTTGA
```

-continued

The Nucleotide Sequence of the *Mycoplasma genitalium* Genome

```
571851 GATTGGCCATTTGTCTTTTTAATAACATCTCTAATAATACCTCTGCCCTG
571901 ATTACCACTTAGTTTTAATAAGTTATTAGCAATGTGTTGGTTAATATAAA
571951 GTTCTTGTCCAAAAGCATCAGTAGAAACACCAACAACTTTAAATGCTACT
572001 GTTGAATTATTTAAGGGTGCTTTTAGAAATTTTTCAGAGTATCTTGTGGC
572051 AGTATTTTTCGGTTTTATATAAACATAATCACCAATATTAATGTTGTTAG
572101 CATATTGAAAACCAGCATTAACAATTACATTCATTTCCTGATCAGAACTA
572151 ATTAAATTTCTTAAAGAGTTACCACTACCATCTATCAGATTAACAAAACT
572201 TGATTCAGGGTTAATCCCTGTTAAAGTGTATGGTGAATTCTCATCAAGAT
572251 TATCTTCTTGAAAACCAAATGGGCCTTCAACATAAGTGTAGGTTTCTTCT
572301 ATGGCAGGGTCAACAGGAACAATCCCAAAATTTAACTTAGAATCTTGTTT
572351 TGCAAGTTCAAAATCCCCATAAACTTTCAACATAAAACTAAGAAAGCTAT
572401 CATTAAATTTAACCCCACCAGGATTAAATACATCAATTGTAGTTAGTACC
572451 CTACTAGCATCTAACTGAATTTGATTAGTTCTAGGGTTTCTAATTAAAAA
572501 CCCATTAGCATTTAAGTTATTGAAAAAGTCATCAGTTAATACTGAAATTA
572551 AAAACTGATCACTAGATGCTGAAAGTAACTGAGTAATCTGTTTAGGAATT
572601 GATTTTTCAACAATTTCCCAAGGGTTAATGTTAGAACCGCCAACCCTAAT
572651 AGGAAAGTCAATAATCCATTTTGATAGAGAGGCATGCCTAAAGAAATTCT
572701 CATCAGTGTTTAACTGTTGAGCACCACCATAACTAGGCAAAAGTAAGTtG
572751 CCCAATTCAAGCTCAGTTCCATCTGCTGCTTTTATTGGTTGATCCTGGCG
572801 GTTTTTAAGTTTTAAATTACTTGGTTTATAAGGGTGCTCATTTTGAGAAT
572851 TTGCTTGAACACTTTCGTTATACAAGGTTTTAATACCATTATTATTATCA
572901 GTAACTCCAAAGTGTGAATAGGGTTGAATTGCATACCATCCAGATTGCTC
572951 TGTTGGTGTTTGTAAATTCAACTTATAGTTAAAGTTTCTATTTAAGGAAG
573001 TGCTTGTTTGTGCTGCACTAAATTTTTGGGGAATAGTACCTGCAATCCCA
573051 ATTAATAAAAGTGCAACTGAACTCAATCCTACATAGGTAAATAAACGTGA
573101 AAAACGTGAAACGATTAATGAAACCCTAAACTTGGTCAAGGGTGACATTG
573151 TATGACTTTTATGTTTTAAAAGATGAAGAAGAACTGAAAACTTGGTCTCA
573201 TTGCCTTGATCAATTAAGACATTAACAGGTTTACTAAACAACTGTTTAAA
573251 GGCAATTCAACTAATAAATTCAAAAACAAAAAAGGTTATAAAGAAAGAAC
573301 CAAAAAACGATAACCAGTTAAAGCTATTTTCAGGTAAAGCAATAAACCAA
573351 TACCTATTTATGATTCCCTTTACTTGTCCTTCTAGAAGAAAGGCAAATAA
573401 AACTCCTAAAAAACTAGAAACAATTGCAACAATACCAGCAAACACACTCA
573451 TTCCAACAATAAATTTAGTTGTTGAAAATCCCCCTGCTCTGATAATAGAA
573501 AACTCAGTTTGATTCTTTTTAATAAATGACTTAATTAAAAGAATAATTAA
573551 ATAAAGAGCAAGAATAATCAAAAATATAGCAATAACAGTACTTACTATTG
573601 CCAAATAGCTTTGCACTAAATCAGGAAAATAGTTTCTTGCTGTTGTCAGA
573651 TAATTAAACTTAGAAATATCTTTAACATTAAATGCTAAATCACTTCTAGG
573701 AACATCTAGATATCCCTCTAATCTATTAGCAATAAACTGCACTGGGTCTT
573751 GGTCAGTGTGCTGTTTTAAATCTGTTGACTTAAAAGCATAATAATTTTCT
573801 TGGTTAGCTGCTGGTACAGCAAACAGAATACTTCTGTAAGCTTGATCATT
573851 AACAAAGATTAACGCTTCATCTTGGGTATTAGGCAACGGAGATTGTAAAG
573901 ATAACACTGGGTAACCAGTTTCTACTGATTCACCTATACCTAAAATTGCA
573951 AATGTTAGTCCGTTAATACTAAATTTATAACGATCAGGTAGATCATTTAA
574001 CCAGTTAGGGAAATTGTTTGGTGTTTGCAATGCAGTTTTTCAAGCATATT
574051 CCCCTTCCTGGGGAAGAATTTCTTTATTGTGTCTAAACAACCATTGTTGA
574101 GAAACAACCGCTCCGTGTGCTTCAGGGGTTTGCACAACTAAATTTTGTTG
574151 ATCAGTAGGTAATATTAATGGATTGACCCCATTTTTAACAGTAATAGGGA
574201 TCTCAAGCATTTGGCGATTTGTCTCTATTAATTCATTAGGATCTTGAAAA
574251 GCAGGAGTAAAATAACTTAAAAGTGCAAGATAATTATTAGCTGCTTTTCG
574301 TTTATCTTCTTCCTTAAGATTATTAAATCCATTGGCATCTAAATTAGTTC
574351 ATTGTTTTAAAGCATCTAAAGCAGTAGTTGGGATATTAGTAGCTTCTGGT
574401 AATTGGGCTTGAGCAATAATATTTGCTAACTTTGGATAAATGGGAAATTT
574451 AGTAGATTTTGGACTTAAAGCTTGGGTATTTTTTAAACTAGCAGTCATTC
574501 CACCACTACTGGTGCTTGGTTTAAATTCATAATCAATTTTTTGTAAAAAT
574551 CCATTATTAGCATCTTGACCACCATAAATTGTGTCTAAAGGGTTTGATTC
574601 ATTTTGCTCAGGTTTAAATAACCAAGATTTAAGATCAACGCCATCAATTA
574651 AAGAAAGATCGTTGTATCTCTGTTCATCTTTGTTGGAAACTAAAAAACTT
574701 GCTGACTCTGCTGAACTAACATTGTTAGCTATTGCGATATTTTGCTTTGA
574751 ATAATCAATGTTATTGAAAGCAGTGGCTTTTAAAAAATGATCACGGTACT
574801 TTTCTAAAAGATCAACTGTTTTTTTAACAAGATCCTCTTGAAAGATACTA
574851 CGTCATTGATCAAGTACTGCTGCATAAACTGCATCAAGGGTTTTTCAGG
574901 AGTGTTATTGGACTGGTGAATTTTATTGTATGCAGTTTGAACATTTGAAA
574951 AGTTAGGATCAGCTATTCCATTACTTGCTTGACTGTTTTGATTTTGAACT
575001 AATTGGAGATTGTTGCTTGAAGGTTGAAAAGAAAGATTATTATTTCTTAC
575051 CATCATTCCATTCTGAGTTTTAAAGATTGTGTCTTTATCACTATCACTAA
575101 AACCTGGTAAGGAATTGAGAATTGTATCTTTCTCAGATTCAACTTTCTTT
575151 TTAAGTCAATCTTTATTAATTTTTAGTTCAAATTTCTTAAGTTGCTTAAG
575201 TTTATTTTCAAGATCTCAATCTCCAAAAGAGGAATTATTGGCTATAGTTT
575251 TAGCATTAGTTTCTAACCACTTTAACTGTTCATTATCTAGCTTATTTAAT
575301 TTAGAAATATCTAAATTAAAAGTTAATGTAAAACTTTGATTATCTTTACT
575351 TTCTTTTTGGGTTTGAAATTCTTCAACAATTTCTTTAAAAGGATTGACAT
575401 CTTTCCAAAATTGAGAACCAGGATCGATTTCTAAATCAATTGGGATGTTT
575451 GCATAAAGATTGGGAAATCAGTTAGCAGCTTCATTACCACCTGTAAATAG
575501 ATAGTTAGCAGATATATCAGTATTATCTGCTTTGGTCTCATCACTCTTAA
575551 ACCAAACTTTATCTTTGTTATTGGTTTTATAAAGTGAATTAACAGTACTG
575601 TCTTTTTGTGGATCATTGTTTGTTTGTTGCTTTTGTGTAATTTTTACTTG
575651 TGTTCCTGTGCTTTTTCCTTTATCACCAGGAAAACGCGCAATGCCAGCAC
```

-continued

The Nucleotide Sequence of the *Mycoplasma genitalium* Genome

```
575701 GCAATGAGATAGTTTCTTTAATTAAACCATCAGCAAAATAACCTAGAAGG
575751 TTACCACTAGCATCATAAATAAGGTTTTGAGGGTCTGATATTATGTGTCT
575801 ATTTGTAATGGAATCACTAATATCACTACCATTAAAAGAATCAGTATTAT
575851 TAAAAGAAACTGCTAACCCTTTATAAATTCTTTTTTCAGCAATATTGGCT
575901 TCTCCATATGCTTTTAAAATACCTCTTTTTCTTGCTAAAAAGAGTTTATC
575951 TTTTTCATTAACATCGCCTTTGCGGGGAATGGTTTTGTTTTGGTTATCAC
576001 CACTACCATTACTTTGTCCTGAATCACTTCCAAAATCATTTTCTTGATAA
576051 GGAAAAAGATAGTTAATTTTTTTATCATCTATCTTTATTTTGGAAAAATA
576101 ACCACTATCATTAGTTAAACTGGCTATATAAACAGGATTAGCTTCCTTTA
576151 AAATAGCAGGAGCTACTATATCAGAAGAGTTAGTTTTAGATACTAATGTA
576201 GTGTAGGTACTAACTAAGTTGTTACTTAACTGAACAATAGATGTTTCAAG
576251 GAAAATAATGCTAAATAAAACAAAGATAATTCCAAATAATAAAAAGAAGA
576301 ACTTTTTAAGCGATTTAAATATCTGTTTAAAAAAAGAAAACATCTCAATT
576351 AAACTCAGTTAATTTGTTCGATGGTTTTTGGATTCTGATTTAAATAATCA
576401 ACGATTATCTTGCCATCATGGATTTTAATTACCCGTTTAGCTAATTCCAC
576451 TATCTTTTCGTTGTGGGTAACTATTACTATAGTAGTACCTTTGTCACGAT
576501 TATATTCCACAAAAAATTGCAATATTTTTTGGAAATATCAATATTAACT
576551 GCTCCAGTAGGTTCATCACCAAACAAAATTTTAGGTTCTTTAATTAAAGC
576601 CCGAGCAATAGCAACACGTTGTTGTTGTCCACCAGAGAGTTTATGAACTT
576651 TCTTATGTCTATGTTCTTTTAATTCCAAGCGTTCTAATAATTCTTCAAGA
576701 TTATTATTAAACCTTTTTTTTAATGGTAGAGCAAGCTTAATATTATCATC
576751 AACGTCAAGATCACGCAATAAACCATATTGTTGAAAAATATAACCAACGT
576801 TTTTATTTCTTAACGCGGTTAGTTTTGCATCACTACAACATATGGTGTTA
576851 GTTCCACAAACAAAACTATCGCCGCTAGTTGGTCGATCTAATGCGGAAAT
576901 TAAAGAAAGTAAGCTGGTTTTACCACTACCAGATTTACCAAGAATAACAA
576951 CAAATTCTCCTGGAAGAATTTTTAAATTAATGTGGTTACAAATAAGTTGg
577001 TGTTAATGCCATTTGTAACAGCTTTACAAACTTCTTTGAAGTAAATATCA
577051 TACTTTTTAGCTTCAAATGAATTAAGTGATTTTCTTTTGGGGTGCTTTTT
577101 ATTTAACTTTTTAATTAATTTAGATGCTTTTTTACTAACAGCAAAATCTG
577151 ATGATTTTAAGTAAATATCAAACTTTTTGTTCTCTTTTGTTTTTAAAACC
577201 ATAAACAATCATTAAGTCATCTAAAAAAATACCCTGAGAACACTATTAGA
577251 AAATTTTAATTTTGCTAAATTACTAATGATGTAATTACATCCCGTAATGA
577301 ACTGTCATTTTCAATCATTTTAGCAACTCTTTTAACTGCCATTAATACAC
577351 TTGAATGACTTCTCTTAAATATTTTGCCAATTTGTTGAAATTGCATGTTG
577401 TACTTTTGACGCAAAAGGTAATTACACACATCACGAACACGGACAAGTTC
577451 TGCTTTACGATTTTCTGAAAGTACACTGTCCATAGGAACATTAAATCTAC
577501 GGCAAACGTTCTCTATTAATAAATAAGGATCAAAGCTCTTTTTATGAAAC
577551 TTCTCAAATTCTTCAAAAAGAATTTCTTTTAAATTTTCAGTATTTATTAA
577601 ATTTTGTTTTGAAGTTTTAGCAAAAAATAATAACTTTGTTGCAATTCCAT
577651 TTAAAGCACGCACATCGTTACCTGAAATTTGTGCTGCATCATGTCTTGCC
577701 TCATTAGTTATTTGGATGTTAGGATCTTTTTCTTTTAATTTAACAGTAAG
577751 TATTTCACAAAGTGAAGACAAATTATGCTTTTCTATCTTTAGTAATAATC
577801 CTGATTTAAAGCGAGAAATCATTCTTGCATCAATATCAATTAGTTCATCA
577851 GGAGCCTTATCAGAAACTAAAACAATTTGTTTTTTATTTAGAACTAGGTT
577901 ATTAAAAATATTGAAAAGAATTTCTAAGGTTTTTTCTTTTCTGCCAAATA
577951 TTTGAGTGTCATCTATTAAAACTAAATCTAAATTTTCATAATTTTTTTTT
578001 AGTTTTTCTATACCTTTATCCCTTTGATAAAAAGCATCAACAACTTCTTG
578051 GGCAAAATCACTTGAAACAACATACTTTACTCTGGCATTTGGAAAATTAC
578101 GAAATTTTTCATTTCCTATTGCTTGTAGTAGGTGAGTTTTACCAAGACCG
578151 GTTTCTCCGTAAATAAAAAGCGGTGAAAATTCGTTATCTTGAGTTTCAGC
578201 TAATCTAACGCCTGCTTCATAAGCTCTTTTATTTCCTTCACTAATTACAA
578251 AGTTTTGAAAAGTATAGTTTTTACTCAATCCAGAATTTTGATAAAGAGTA
578301 TCACGACTATTTTCTTCTAATTTTGCTAAGTTAAAAAAGAAATCTTGCTC
578351 ATTAACAAAATTAACACTTTTAATTCCTTCATACAAACTTTCAGCTAAAT
578401 GAATAATTTCAGAATTATCATTTAAGGAATTACGAGCAAATTCATTTTCT
578451 AAAAGAATTAAAAGAACATTATTTTTAAATACGAAACGATTAATGTCTTT
578501 AATGTATTTATCATGAAAACCTATTGTTTTTCATAATGCTTTTTTAATA
578551 GAGATTTAAAGGCATTAAATTGTTCCATTATTCTTCTATAACATTGTCAA
578601 GAATGATAGTTAAAATTCTCGAAATTGGGATATTAACTGCTTTGGAGTAA
578651 TTTCTAACTTTTTGTCATACTCTTTGACTTGTATAGAAGTGTACACCTGT
578701 ATCTAGTTTTTCTTGGCGTTCAACAGGAACTATTCCTGGTATTTTTGTTT
578751 TAGGTTGGGGAGGAATAGGCTGTGGTGTGTGAATTGTTGTTGAAAATTT
578801 TGATTTTTTTGCTGTAAGAAACCATTATTATGATATTGAAAATTTTGTTC
578851 CTCTTGAAAATATCTCTCTTTTTTGGTTTTCCAGAAAAATTTGATGAAA
578901 AAGATTTTCCTTCATTTCAATTTTCAAGATTATTTTCATTTTGTTGATTT
578951 ATTTGCTCAGGCTGTTGAAATGAATTATTTTTTGATCAAAAAGATTTTGG
579001 AAAGGTTTTTCAAAAGCAGATAAAGGTCCAAAATCAAATGAAGATGAAT
579051 CTTTGTCAAAAGATGTTTCTTCTCTTTTTGACAAATTTTGTTTTTGATTA
579101 AACTTATTTTATTTGGGGTGTTACTTTTTCTTTTATGGAAAACAAATC
579151 TTCTTCTAAAAGACTTTGTTCTGGGTCATCATCTTGTGCTAAATCAAAGA
579201 AAAAACGTTTCTTTTTGTTATTAATGGACATTGTAATTTGCTAAATTTAG
579251 GATTTCTTTTGTTATTTCTAAATACTCATTTAGATATTTTTTACTTGGTG
579301 ATGATACTAATGATATTGGCAATTTTTCATAACCTACAGCTGCTGATGAT
579351 TTTGATGTCAGAGAAACAAAATTTTTAGAAAAAGCTACATTATTTTTTTT
579401 AGCTTTTGTTTTAGCTAAATCTATTACTTCATTATGAAGACGAGTACGAA
579451 CGTTAACTTTTGTAGGAACTAAAATAGTTTTAAGATTTGTATTTTTTTCC
579501 TTAAATGTATCTATTGTTTCAACTATTCTCATCAAACCTAGCATCGAATA
```

```
-continued

The Nucleotide Sequence of the Mycoplasma genitalium Genome

579551  TTGATCTGGTTCAAAGGGAATAACTATGACATCTGATAAACTCATTGCAG
579601  TAGAAACTAAAGTTGCCATATTTGGTGGTGTATCTAATAAAACAAATTCA
579651  TATCTTTTTGCTAGTTGCTTAACTATTTCTGCTATATCTGAGGCCTTATA
579701  TTTTTTACGTGATATGTCTATATCAGCAAAATTAAGTTCAAAATTACAAG
579751  GAAGAATATCAAGTCCCTCATATACAGATAGCAAGCAATCATCTATTTCA
579801  ATGAAATTATTTGAACCACTGAATTTTGGAACCTTCAACAAAATGTCAAT
579851  TAACGTGTTATTCAATCTTTCAGGGTTTTGTCCAAATGATGCAGAAACAT
579901  TCCCCTGCCCGTCAAGATCAAGAATGACTTTTCGCCTTTCTGGACAAAGT
579951  TTAACCAATGATCCTGCAACATTAGTTGCCATTGTAGTTTTTAATACGCC
580001  GCCTTTATTATTTACAAAAGAAATGATCATATATTTAAATGATTATAATA
580051  TTTCTTTAATACTAAAAAAATAC
```

While the present invention has been described in some detail for purposes of clarity and understanding, one skilled in the art will appreciate that various changes in form and detail can be made without departing from the true scope of the invention.

All patents, patent applications and publications recited herein are hereby incorporated by reference.

TABLE 3

Whole Genome Sequencing Strategy

| Stage | Description |
|---|---|
| Random small insert and large insert library construction | Randomly shear genomic DNA on the order of 2 kb and 15–20 kb, respectively |
| Library plating | Maximize random selection of small insert and large insert clones for template production |
| High-throughput DNA sequencing | Sequence xxx,xxx templates from both ends (>99% genome coverage) |
| Assembly (TIGR Assembler, GRASTA) | Assembly of sequence fragments into contigs |
| Gap closure | |
| a. Physical gaps | Order all contigs into a circular genome and provide templates for closure of all physical gaps |
| b. Sequence gaps | Complete the genome by primer walking |
| Editing | Visual inspection and resolution of all sequence ambiguities when possible, including frameshifts |
| Annotation | Identification and description of all ORF's, putative identification, role assignments |

TABLE 4

Computer simulation of random sequencing experiments where L = 580,000 and w = 400.

| Clones sequenced (n) | Percent of genome unsequenced | Base pairs unsequenced | Number of double strand gaps | Average gap length (bp) |
|---|---|---|---|---|
| 1000 | 50.18 | 291014 | 501 | 580 |
| 2000 | 25.18 | 146016 | 503 | 289 |
| 4000 | 6.34 | 36759 | 253 | 145 |
| 6000 | 1.60 | 9254 | 97 | 96 |
| 7250 | 0.67 | 3886 | 48 | 80 |
| 8000 | 0.40 | 2330 | 32 | 72 |
| 10000 | 0.10 | 586 | 10 | 59 |

TABLE 5

Mycoplasma genitalium - EcoRI fragments

| 5' Enzyme | Start Res | 3' Enzyme | End Res | Length | M W |
|---|---|---|---|---|---|
| EcoRI | 572231 | EcoRI | 1530 | 9367 | 5763365 |
| EcoRI | 1531 | EcoRI | 6723 | 5193 | 3195384 |
| EcoRI | 6724 | EcoRI | 15283 | 8560 | 5266795 |
| EcoRI | 15284 | EcoRI | 25781 | 10498 | 6459359 |
| EcoRI | 25782 | EcoRI | 35532 | 9751 | 5999831 |
| EcoRI | 35533 | EcoRI | 39821 | 4289 | 2639037 |
| EcoRI | 39822 | EcoRI | 43179 | 3358 | 2066196 |
| EcoRI | 43180 | EcoRI | 43707 | 528 | 324906 |
| EcoRI | 43708 | EcoRI | 49410 | 5703 | 3509174 |
| EcoRI | 49411 | EcoRI | 62708 | 13298 | 8182420 |
| EcoRI | 62709 | EcoRI | 71387 | 8679 | 5340230 |
| EcoRI | 71388 | EcoRI | 80769 | 9382 | 5772840 |
| EcoRI | 80770 | EcoRI | 84845 | 4076 | 2507946 |
| EcoRI | 84846 | EcoRI | 89622 | 4777 | 2939580 |
| EcoRI | 89623 | EcoRI | 93383 | 3761 | 2314332 |
| EcoRI | 93384 | EcoRI | 94573 | 1190 | 732268 |
| EcoRI | 94574 | EcoRI | 102229 | 7656 | 4710994 |
| EcoRI | 102230 | EcoRI | 107347 | 5118 | 3149292 |
| EcoRI | 107348 | EcoRI | 110797 | 3450 | 2122895 |
| EcoRI | 110798 | EcoRI | 114909 | 4112 | 2530290 |
| EcoRI | 114910 | EcoRI | 116440 | 1531 | 942140 |
| EcoRI | 116441 | EcoRI | 137514 | 21074 | 12967294 |
| EcoRI | 137515 | EcoRI | 144092 | 6578 | 4047534 |
| EcoRI | 144093 | EcoRI | 155336 | 11244 | 6918646 |
| EcoRI | 155337 | EcoRI | 162136 | 6800 | 4184109 |
| EcoRI | 162137 | EcoRI | 163907 | 1771 | 1089750 |
| EcoRI | 163908 | EcoRI | 169816 | 5909 | 3636217 |
| EcoRI | 169817 | EcoRI | 171885 | 2069 | 1273325 |
| EcoRI | 171886 | EcoRI | 176630 | 4745 | 2920129 |
| EcoRI | 176631 | EcoRI | 221880 | 45250 | 27844584 |
| EcoRI | 221881 | EcoRI | 225692 | 3812 | 2345923 |
| EcoRI | 225693 | EcoRI | 228254 | 2562 | 1576700 |
| EcoRI | 228255 | EcoRI | 277826 | 49572 | 30503951 |
| EcoRI | 277827 | EcoRI | 282740 | 4914 | 3023818 |
| EcoRI | 282741 | EcoRI | 285470 | 2730 | 1679928 |
| EcoRI | 285471 | EcoRI | 292152 | 6682 | 4111409 |
| EcoRI | 292153 | EcoRI | 293879 | 1727 | 1062607 |
| EcoRI | 293880 | EcoRI | 312725 | 18846 | 11596154 |
| EcoRI | 312726 | EcoRI | 347231 | 34506 | 21232617 |
| EcoRI | 347232 | EcoRI | 352330 | 5099 | 3137714 |
| EcoRI | 352331 | EcoRI | 362310 | 9980 | 6140434 |
| EcoRI | 362311 | EcoRI | 377990 | 15680 | 9648201 |
| EcoRI | 377991 | EcoRI | 390080 | 12090 | 7439090 |
| EcoRI | 390081 | EcoRI | 402043 | 11963 | 7361170 |
| EcoRI | 402044 | EcoRI | 408452 | 6409 | 3943775 |
| EcoRI | 408453 | EcoRI | 419230 | 10778 | 6631662 |
| EcoRI | 419231 | EcoRI | 422653 | 3423 | 2106066 |
| EcoRI | 422654 | EcoRI | 425383 | 2730 | 1679735 |
| EcoRI | 425384 | EcoRI | 426391 | 1008 | 620235 |
| EcoRI | 426392 | EcoRI | 439467 | 13076 | 8046286 |
| EcoRI | 439468 | EcoRI | 444297 | 4830 | 2971763 |
| EcoRI | 444298 | EcoRI | 444940 | 643 | 395631 |
| EcoRI | 444941 | EcoRI | 452525 | 7585 | 4667018 |
| EcoRI | 452526 | EcoRI | 455595 | 3070 | 1888976 |
| EcoRI | 455596 | EcoRI | 461533 | 5938 | 3653550 |

TABLE 5-continued

Mycoplasma genitalium - EcoRI fragments

| 5' Enzyme | Start Res | 3' Enzyme | End Res | Length | M W |
|---|---|---|---|---|---|
| EcoRI | 461534 | EcoRI | 467016 | 5483 | 3373523 |
| EcoRI | 467017 | EcoRI | 483871 | 16855 | 10370549 |
| EcoRI | 483872 | EcoRI | 487269 | 3398 | 2090889 |
| EcoRI | 487270 | EcoRI | 488085 | 816 | 502090 |
| EcoRI | 488086 | EcoRI | 488496 | 411 | 252914 |
| EcoRI | 488497 | EcoRI | 498574 | 10078 | 6201025 |
| EcoRI | 498575 | EcoRI | 499113 | 539 | 331666 |
| EcoRI | 499114 | EcoRI | 516146 | 17033 | 10480304 |
| EcoRI | 516147 | EcoRI | 524998 | 8852 | 5446303 |
| EcoRI | 524999 | EcoRI | 527362 | 2364 | 1454583 |
| EcoRI | 527363 | EcoRI | 529777 | 2415 | 1485826 |
| EcoRI | 529778 | EcoRI | 530256 | 479 | 294749 |
| EcoRI | 530257 | EcoRI | 531045 | 789 | 485489 |
| EcoRI | 531046 | EcoRI | 533591 | 2546 | 1566584 |
| EcoRI | 533592 | EcoRI | 549000 | 15409 | 9480966 |
| EcoRI | 549001 | EcoRI | 550638 | 1638 | 1007852 |
| EcoRI | 550639 | EcoRI | 563713 | 13075 | 8045103 |
| EcoRI | 563714 | EcoRI | 566925 | 3212 | 1976345 |
| EcoRI | 566926 | EcoRI | 572230 | 5305 | 3264227 |

TABLE 6

| MG# | Identification | MatchAcc | % ID | Length |
|---|---|---|---|---|
| *MG394 | uridine kinase (udk) {Escherichia coli} | SP:P31218 | 34.5 | 204 |
| Purine ribonucleotide biosynthesis | | | | |
| *MG107 | 5'guanylate kinase (gmk) {Escherichia coli} | GP:L10328_14 | 42.6 | 183 |
| *MG175 | adenylate kinase (adk) {Bacillus stearothermophilus} | GP:M88104_2 | 32.2 | 210 |
| *MG058 | phosphoribosylpyrophosphate synthetase (prs) {Bacillus subtilis} | GP:D26185_114 | 44.4 | 310 |
| Pyrimidine ribonucleotide biosynthesis | | | | |
| Salvage of nucleosides and nucleotides | | | | |
| *MG284 | adenine phosphoribosyltransferase (apt) {Escherichia coli} | GP:M14040_1 | 34.1 | 163 |
| *MG052 | cytidine deaminase (cdd) {Mycoplasma pirum} | GP:L13289_4 | 38.2 | 121 |
| *MG340 | cytidylate kinase (cmk) {Bacillus subtilis} | SP:P38493 | 40.4 | 215 |
| MG276 | deoxyguanosine/deoxyadenosine kinase(l) subunit 2 {Lactobacillus acidophilus} | GP:U01881_2 | 29.5 | 164 |
| *MG470 | hypoxanthine-guanine phosphoribosyltransferase (hpt) {Lactococcus lactis} | SP:Q02522 | 38.4 | 170 |
| *MG048 | purine-nucleoside phosphorylase (deoD) {Escherichia coli} | GP:U14003_295 | 44.3 | 228 |
| *MG034 | thymidine kinase {Bacillus subtilis} | GP:M97678_5 | 48.1 | 187 |
| MG051 | thymidine phosphorylase (deoA) {Mycoplasma pirum} | GP:L13289_3 | 52.7 | 416 |
| *MG030 | uracil phosphoribosyltransferase (upp) {Mycoplasma hominis} | GP:Z27121_3 | 44.9 | 206 |
| Sugar-nucleotide biosynthesis and conversions | | | | |
| *MG119 | UDP-glucose 4-epimerasa (galE) {Escherichia coli} | SP:P09147 | 34.1 | 322 |
| *MG465 | UDP-glucose pyrophosphorylase (gtaB) {Bacillus subtilis} | GP:L12272_1 | 48.0 | 277 |
| Regulatory functions | | | | |
| *MG396 | GTP-binding protein (obg) {Bacillus subtilis} | GP:M24537_2 | 39.6 | 426 |
| *MG399 | GTP-binding protein era homolog (spg) {Streptococcus mutans} | SP:P37214 | 27.4 | 273 |
| *MG460 | pilB homolog transcription repressor {Mycoplasma capricolum} | GP:Z33052_1 | 53.5 | 128 |
| *MG420 | PILB protein MOTIF {Neisseria gonorrhoeae} | SP:P14930 | 49.2 | 127 |
| *MG105 | virulence associated protein homolog (vacB) {Escherichia coli} | GP:U14003_91 | 29.2 | 560 |
| Replication | | | | |
| Degradation of DNA | | | | |
| MG032 | ATP-dependent nuclease (addA) {Bacillus subtilis} | GP:M63489_1 | 26.8 | 706 |
| MG240 | endonuclease IV (nfo) {Escherichia coli} | SP:P12638 | 29.4 | 267 |
| DNA replication, restriction, modification, recombination, and repair | | | | |
| *MG481 | chromosomal replication initiator protein (dnaA) {Spiroplasma citri} | SP:P34028 | 30.9 | 432 |
| *MG210 | DNA gyrase subunit A {Mycoplasma genitalium} | GP:U09251_4 | 37.4 | 782 |
| *MG004 | DNA gyrase subunit A {Mycoplasma genitalium} | GP:U09251_4 | 99.9 | 835 |
| *MG003 | DNA gyrase subunit B (gyrB) {Mycoplasma genitalium} | GP:U09251_3 | 99.2 | 645 |
| *MG249 | DNA helicase II (mutB1) {Haemophilus influenzae} | GP:M99049_1 | 36.0 | 715 |
| *MG259 | DNA ligase (lig) {Escherichia coli} | GP:M24278_1 | 38.2 | 657 |
| *MG269 | DNA polymerase I (polI) MOTIF {Mycobacterium tuberculosis} | GP:L11920_1 | 29.9 | 837 |
| *MG031 | DNA polymerase III (polC) {Mycoplasma pulmonis} | GP:U06833_1 | 38.1 | 1352 |
| *MG001 | DNA polymerase III beta subunit (dnaN) {Mycoplasma genitalium} | GP:U09251_1 | 100.0 | 97 |
| MG007 | DNA polymerase III subunit (dnaH) MOTIF {Bacillus subtilis} | GP:D26185_83 | 22.7 | 142 |
| *MG432 | DNA polymerase III subunit (dnaH) {Bacillus subtilis} | GP:D26185_83 | 49.1 | 224 |
| *MG268 | DNA polymerase III, alpha chain (dnaE) {Escherichia coli} | GP:M19334_4 | 31.9 | 843 |

TABLE 6-continued

| MG# | Identification | MatchAcc | % ID | Length |
|---|---|---|---|---|
| *MG010 | DNA primase (dnaE) MOTIF {*Clostridium acetobutylicum*} | SP:P33655 | 25.7 | 174 |
| *MG255 | DNA primase (dnaE) {*Bacillus subtilis*} | GP:M10040_1 | 27.3 | 587 |
| *MG123 | DNA topoisomerase I (topA) {*Bacillus subtilis*} | GP:L27797_2 | 38.9 | 658 |
| *MG433 | excinuclease ABC subunit A (uvrA) {*Escherichia coli*} | SP:P07671 | 47.8 | 842 |
| *MG075 | excinuclease ABC subunit B (uvrB) {*Escherichia coli*} | SP:P07025 | 48.0 | 662 |
| *MG270 | formamidopyrimidine-DNA glycosylase (fpg) {*Bacillus firmus*} | SP:P19210 | 37.6 | 272 |
| *MG391 | glucose inhibited division protein (gldA) {*Escherichia coli*} | GP:L10328_106 | 40.3 | 600 |
| *MG392 | glucose inhibited division protein (gldB) {*Escherichia coli*} | GP:L10328_105 | 24.8 | 143 |
| *MG370 | Holliday junction DNA helicase (ruvA) {*Escherichia coli*} | GP:M21298_1 | 26.2 | 153 |
| *MG371 | Holliday junction DNA helicase (ruvB) {*Escherichia coli*} | GP:M21298_2 | 34.7 | 297 |
| MG187 | methyltransferase (ssolM) {*Shigella sonnei*} | GP:M97479_2 | 42.5 | 314 |
| *MG349 | recombination protein (recA) {*Staphylococcus aureus*} | GP:L25893_1 | 46.6 | 292 |
| *MG095 | replicative DNA helicase (dnaB) {*Escherichia coli*} | SP:P03005 | 33.1 | 439 |
| MG450 | restriction-modification enzyme EcoD specificity subunit (hsdS) {*Escherichia coli*} | GP:J01631_1 | 24.6 | 390 |
| *MG047 | S-adenosylmethionine synthetase 2 (metX) {*Escherichia coli*} | SP:P30869 | 43.6 | 363 |
| *MG092 | single-stranded DNA binding protein (ssb) {*Haemophilus influenzae*} | GP:U04997_2 | 21.8 | 162 |
| *MG209 | topoisomerase II subunit B (topIIB) {*Mycoplasma gallisepticum*} | GP:L35044_2 | 52.4 | 630 |
| *MG098 | uracil DNA glycosylase (ung) {*Escherichia coli*} | GP:D13169_3 | 32.6 | 217 |

Transcription
Degradation of RNA

| MG# | Identification | MatchAcc | % ID | Length |
|---|---|---|---|---|
| *MG379 | ribonuclease III (mc) {*Escherichia coli*} | GP:X02673_1 | 30.2 | 118 |
| *MG477 | RNaseP C5 subunit {*Mycoplasma capricolum*} | GP:D14982_2 | 40.0 | 78 |

RNA synthesis, modification, and DNA transcription

| MG# | Identification | MatchAcc | % ID | Length |
|---|---|---|---|---|
| *MG319 | ATP-dependent RNA helicase (deaD) {*Escherichia coli*} | SP:P23304 | 23.1 | 369 |
| *MG437 | ATP-dependent RNA helicase (deaD) {*Escherichia coli*} | SP:P23304 | 32.4 | 390 |
| *MG352 | DNA-directed RNA polymerase beta chain (rpoC) {*Escherichia coli*} | SP:P00577 | 44.5 | 1348 |
| *MG018 | helicase (mot1) MOTIF {*Saccharomyces cerevisiae*} | SP:P32333 | 36.5 | 502 |
| *MG145 | N-utilization substance protein A homolog (nusA) {*Bactillus subtilis*} | SP:P32727 | 30.9 | 360 |
| *MG180 | RNA polymerase alpha-core-subunit (rpoA) {*Bactillus subtilis*} | GP:M26414_5 | 39.4 | 295 |
| *MG353 | RNA polymerase beta-subunit (rpoB) {*Bacillus subtilis*} | GP:L24376_3 | 46.5 | 1144 |
| MG022 | RNA polymerase delta subunit (rpoE) {*Bactillus subtilis*} | GP:M21677_1 | 28.7 | 152 |
| *MG254 | RNA polymerase sigma-A factor (sigA) {*Clostridium acetobutylicum*} | SP:P33656 | 43.7 | 370 |
| *MG054 | transcription antitermination factor (nusG) {*Bactillus subtilis*} | GP:D13303_4 | 30.9 | 171 |

Translation
Amino acyl tRNA synthetases and tRNA modification

| MG# | Identification | MatchAcc | % ID | Length |
|---|---|---|---|---|
| *MG303 | alanyl-tRNA synthetase (alaS) {*Escherichia coli*} | GP:J01581_1 | 33.8 | 795 |
| *MG390 | arginyl-tRNA synthetase (argS) {*Corynebacterium glutamicum*} | SP:P35868 | 33.6 | 431 |
| *MG114 | asparaginyl-tRNA synthetase (asnS) {*Escherichia coli*} | GP:M33145_1 | 41.5 | 449 |
| *MG036 | aspartyl-tRNA synthetase (aspS) {*Thermus aquaticus*} | SP:P36419 | 40.9 | 563 |
| *MG258 | cysteinyl-tRNA synthetase (cysS) {*Bacillus subtilis*} | GP:D26185_156 | 34.3 | 437 |
| *MG474 | glutamyl-tRNA synthetase (gltX) {*Bacillus stearothermophilus*} | GP:M55072_1 | 42.9 | 480 |
| MG256 | glycyl-tRNA synthetase {*Bombyx mori*} | GP:L06106_1 | 35.9 | 574 |
| *MG035 | histidyl-tRNA synthetase (hisS) {*Mycobacterium leprae*} | GP:U00011_2 | 30.7 | 395 |
| *MG357 | isoleucyl-tRNA synthetase (ileS) {*Escherichia coli*} | SP:P00956 | 33.3 | 921 |
| *MG274 | leucyl-tRNA synthetase (leuS) {*Bacillus stearothermophilus*} | GP:M88581_1 | 43.4 | 799 |
| *MG137 | lysyl-tRNA synthetase (lysS) {*Bacillus subtilis*} | GP:D26185_144 | 45.6 | 490 |
| *MG377 | methionyl-tRNA formyltransferase (fmt) {*Escherichia coli*} | GP:X63656_2 | 24.1 | 304 |
| *MG021 | methionyl-tRNA synthetase (metS) {*Bacillus subtilis*} | GP:D26185_101 | 37.5 | 515 |
| *MG085 | peptidyl-tRNA hydrolase homolog (pth) {*Borrelia burgdorferi*} | GP:L32144_1 | 38.2 | 154 |
| *MG201 | phenylalanyl-tRNA synthetase beta chain (pheT) {*Bacillus subtilis*} | SP:P17922 | 26.0 | 677 |
| *MG200 | phenylalanyl-tRNA synthetase beta-subunit (pheS) {*Escherichia coli*} | GP:V00291_5 | 35.1 | 320 |
| *MG292 | prolyl-tRNA synthetase (proS) {*Escherichia coli*} | GP:M97858_1 | 22.7 | 438 |
| *MG005 | seryl-tRNA synthetase (serS) {*Bacillus subtilis*} | GP:D26185_77 | 42.6 | 416 |
| *MG387 | threonyl-tRNA synthetase (thrSv) {*Bacillus subtilis*} | GP:M36594_1 | 38.7 | 556 |
| *MG457 | tRNA (guanine-N1)-methyltransferase (trmD) {*Salmonella typhimurium*} | SP:P36245 | 40.8 | 223 |
| *MG127 | tryptophanyl-tRNA synthetase (trpS) {*Bacillus subtilis*} | GP:M24068_1 | 41.2 | 324 |
| *MG466 | tyrosyl tRNA synthetase (tyrS) {*Bacillus stearothermophilus*} | GP:M77668_1 | 38.5 | 418 |
| *MG344 | valyl-tRNA synthetase (valS) {*Bacillus subtilis*} | SP:Q05873 | 38.5 | 867 |

Degradation of proteins, peptides, and glycopeptides

| MG# | Identification | MatchAcc | % ID | Length |
|---|---|---|---|---|
| *MG334 | aminopeptidase P (pepP) {*Escherichia coli*} | GP:D00398_1 | 30.5 | 254 |
| *MG403 | aminopeptidase {*Mycoplasma salivarium*} | GP:D17450_1 | 44.6 | 303 |
| *MG244 | ATP-dependent protease (lon) {*Bacillus subtilis*} | SP:P37945 | 43.6 | 753 |
| *MG367 | ATP-dependent protease binding subunit (clpB) {*Escherichia coli*} | GP:M29364_2 | 47.7 | 709 |
| MG067 | glutamic acid specific protease prepropeptide {*Staphylococcus aureus*} | GP:D00730_1 | 28.8 | 250 |
| MG224 | IgA1 protease {*Haemophilus influenzae*} | GP:M87491_1 | 32.2 | 675 |
| MG186 | oligoendopeptidase F (pepF) {*Lactococcus lactis*} | GP:Z32522_1 | 30.0 | 442 |
| MG321 | proline iminopeptidase (pip) {*Bacillus coagulans*} | GP:D11037_1 | 29.2 | 209 |
| MG020 | proline iminopeptidase (pip) {*Neisseria gonorrhoeae*} | GP:Z25461_2 | 37.5 | 281 |
| *MG046 | sialoglycoprotease (gcp) {*Pasteurella haemolytica*} | GP:M62384_1 | 38.4 | 313 |

Nucleoproteins

TABLE 6-continued

| MG# | Identification | MatchAcc | % ID | Length |
|---|---|---|---|---|
| Protein modification and translation factors | | | | |
| *MG090 | elongation factor G (fus) {*Thermus aquaticus*} | SP:P13551 | 59.2 | 683 |
| *MG026 | elongation factor P (efp) {*Escherichia coli*} | GP:U14003_62 | 26.4 | 162 |
| *MG445 | elongation factor Ts (tsf ) {*Spiroplasma citri*} | GP:M31161_2 | 39.1 | 294 |
| *MG463 | elongation factor TU (tuf) {*Mycoplasma genitalium*} | SP:P13927 | 100.0 | 393 |
| *MG176 | methionine amino peptidase {*Bacillus subtilis*} | GP:D00619_5 | 36.3 | 245 |
| *MG263 | peptide chain release factor 1 (RF-1) {*Escherichia coli*} | GP:M11519_1 | 43.2 | 320 |
| *MG108 | polypeptide deformylase (formylmethionine deformylase) (def) MOTIF {*Escherichia coli*} | SP:P27251 | 36.9 | 107 |
| MG109 | protein phosphatase 2C homolog (ptc1) MOTIF {*Saccharomyces cerevisiae*} | SP:P35182 | 27.5 | 141 |
| MG110 | protein serine/threonine kinase MOTIF {*Arabidopsis thaliana*} | PIR:S36944 | 33.7 | 242 |
| *MG146 | protein synthesis initiation factor 2 (infB) {*Bacillus subtilis*} | GP:M34836_1 | 46.0 | 619 |
| *MG447 | ribosome releasing factor (frr) {*Escherichia coli*} | GP:D26562_57 | 34.9 | 189 |
| *MG291 | transcription elongation factor (greA) {*Rickettsia prowazekii*} | SP:P27640 | 40.1 | 135 |
| *MG202 | translation initiation factor IF3 (infC) {*Bacillus stearothermophilus*} | GP:X16188_1 | 31.3 | 133 |
| Ribosomal proteins: synthesis and modification | | | | |
| *MG084 | ribosomal protein L1 (rpL1) {*Bacillus stearothermophilus*} | SP:P04447 | 48.2 | 221 |
| *MG373 | ribosomal protein L10 (rpL10) {*Thermotoga maritima*} | SP:P29394 | 29.8 | 162 |
| *MG083 | ribosomal protein L11 (RPL11) {*Thermotoga maritima*} | SP:P29395 | 51.8 | 140 |
| *MG430 | ribosomal protein L13 {*Escherichia coli*} | SP:P02410 | 39.9 | 137 |
| *MG165 | ribosomal protein L14 (rpL14) {*Bacillus stearothermophilus*} | SP:P04450 | 63.1 | 121 |
| *MG173 | ribosomal protein L15 (rpL15) {*Mycoplasma capricolum*} | SP:P10138 | 41.9 | 144 |
| *MG162 | ribosomal protein L16 (rpL16) {*Mycoplasma capricolum*} | SP:P02415 | 63.5 | 136 |
| *MG181 | ribosomal protein L17 (rpL17) {*Bacillus subtilis*} | GP:M26414_6 | 34.8 | 115 |
| *MG171 | ribosomal protein L18 (rpL18) {*Bacillus stearothermophilus*} | GP:M57624_1 | 43.0 | 113 |
| *MG456 | ribosomal protein L19 (rpL19) {*Bacillus stearothermophilus*} | SP:P30529 | 49.1 | 111 |
| *MG158 | ribosomal protein L2 (rpL2) {*Bacillus stearothermophilus*} | SP:P04257 | 58.4 | 273 |
| *MG238 | ribosomal protein L21 (rpL21) {*Bacillus subtilis*} | SP:P26908 | 37.9 | 98 |
| *MG160 | ribosomal protein L22 (rpL22) {Mycoplasma-like organism} | GP:M74770_4 | 49.0 | 103 |
| MG157 | ribosomal protein L23 {*Bacillus stearothermophilus*} | SP:P04454 | 38.7 | 89 |
| *MG166 | ribosomal protein L24 {*Bacillus stearothermophilus*} | SP:P04455 | 44.6 | 83 |
| *MG239 | ribosomal protein L27 (rpL27) {*Bacillus subtilis*} | GP:K02665_2 | 64.4 | 86 |
| *MG163 | ribosomal protein L29 {*Thermotoga maritima*} | SP:P38514 | 41.7 | 59 |
| *MG155 | ribosomal protein L3 (rpL3) {*Mycoplasma capricolum*} | SP:P10134 | 42.6 | 213 |
| *MG335 | ribosomal protein L33 {*Bacillus stearothermophilus*} | SP:P23375 | 58.1 | 42 |
| *MG478 | ribosomal protein L34 (rpL34) {*Escherichia coli*} | GP:L10328_67 | 67.4 | 45 |
| *MG156 | ribosomal protein L4 (rpL4) {*Bacillus stearothermophilus*} | SP:P28601 | 39.2 | 205 |
| *MG167 | ribosomal protein L5 (rpL5) {*Bacillus stearothermophilus*} | SP:P08895 | 57.5 | 178 |
| *MG170 | ribosomal protein L6 (rpL6) {*Mycoplasma capricolum*} | SP:P04448 | 46.4 | 179 |
| *MG374 | ribosomal protein L7/L12 ('A' type) (rpL7/L12) {*Bacillus subtilis*} | SP:P02394 | 47.5 | 118 |
| *MG094 | ribosomal protein L9 (rpL9) {*Bacillus stearothermophilus*} | GP:M57623_1 | 32.9 | 148 |
| *MG154 | ribosomal protein L10 (rpS10) {*Thermotoga maritima*} | SP:P38518 | 48.9 | 91 |
| *MG179 | ribosomal protein S11 (rpS11) {*Escherichia coli*} | GP:X02543_2 | 47.8 | 112 |
| *MG088 | ribosomal protein S12 (rpS12) {*Bacillus stearothermophilus*} | SP:P09901 | 75.4 | 133 |
| *MG178 | ribosomal protein S13 (rpS13) {*Bacillus subtilis*} | GP:M26414_3 | 63.3 | 119 |
| *MG168 | ribosomal protein S14 {*Mycoplasma capricolum*} | GP:X06414_15 | 70.0 | 59 |
| *MG436 | ribosomal protein S15 (BS18) {*Bacillus stearothermophilus*} | SP:P05766 | 48.1 | 60 |
| *MG458 | ribosomal protein S16 (BS17) {*Bacillus subtilis*} | SP:P21474 | 48.8 | 81 |
| Amino acid biosynthesis | | | | |
| Aromatic amino acid family | | | | |
| Aspartate family | | | | |
| Branched chain family | | | | |
| Glutamate family | | | | |
| Pyruvate family | | | | |
| Serine family | | | | |
| *MG406 | serine hydroxymethyltransferase (glyA) {*Salmonella typhimurium*} | SP:P06192 | 55.3 | 397 |
| Biosynthesis of cofactors, prosthetic groups, and carriers | | | | |
| Biotin | | | | |
| Folic acid | | | | |
| *MG013 | 5,10-methylene-tetrahydrofolate dehydrogenase (folD) {*Escherichia coli*} | GP:D10588_1 | 33.0 | 238 |
| *MG234 | dihydrofolate reductase {*Lactococcus lactis*} | GP:X60661_1 | 33.1 | 166 |
| Heme and porphyrin | | | | |
| *MG264 | protoporphyrinogen oxidase (hemK) {*Escherichia coli*} | GP:D28567_2 | 30.6 | 160 |
| Lipoate | | | | |
| Menaquinone and ubiquinone | | | | |
| Molybdopterin | | | | |
| Pantothenate | | | | |
| Pyridoxine | | | | |
| Riboflavin | | | | |
| Thioredoxin, glutaredoxin, and glutathione | | | | |
| Cell envelope | | | | |

TABLE 6-continued

| MG# | Identification | MatchAcc | % ID | Length |
|---|---|---|---|---|
| Membranes, lipoproteins, and porins | | | | |
| MG328 | fibronectin-binding protein (fnbA) {*Staphylococcus aureus*} | GP:J04151_1 | 24.6 | 913 |
| MG040 | membrane lipoprotein (tmpC) {*Treponema pallidum*} | SP:P29724 | 30.9 | 248 |
| *MG087 | prolipoprotein diacylglyceryl transferase {*Salmonella typhimurium*} | GP:L13259_2 | 29.1 | 261 |
| Murein sacculus and peptidoglycan | | | | |
| Surface polysaccharides, lipopolysaccharides and antigens | | | | |
| *MG368 | lic-1 operon protein (licA) MOTIF {*Haemophilus influenzae*} | GP:M27280_1 | 27.8 | 152 |
| *MG060 | lipopolysaccharide biosynthesis protein (rfbV) MOTIF {*Salmonella typhimurium*} | SP:P26401 | 36.1 | 185 |
| *MG277 | surface protein antigen precursor (pag) MOTIF {*Streptococcus sobrinus*} | GP:D90354_1 | 25.5 | 797 |
| Surface structures | | | | |
| MG196 | attachment protein (mgpA) {*Mycoplasma genitalium*} | SP:P20796 | 100.0 | 1443 |
| MG190 | attachment protein repeat (mgpA) {*Mycoplasma genitalium*} | SP:P20796 | 36.6 | 903 |
| MG267 | attachment protein repeat (mgpA) {*Mycoplasma genitalium*} | SP:P20796 | 38.0 | 963 |
| MG188 | attachment protein repeat (mgpA) {*Mycoplasma genitalium*} | SP:P20796 | 61.8 | 943 |
| MG069 | attachment protein repeat (mgpA) {*Mycoplasma genitalium*} | SP:P20796 | 76.4 | 760 |
| MG189 | attachment protein repeat (mgpA) {*Mycoplasma genitalium*} | SP:P20796 | 77.9 | 763 |
| MG232 | attachment protein repeat (mgpA) {*Mycoplasma genitalium*} | SP:P20796 | 78.2 | 86 |
| MG297 | attachment protein repeat (mgpA) {*Mycoplasma genitalium*} | SP:P20796 | 80.2 | 756 |
| MG141 | attachment protein repeat (mgpA) {*Mycoplasma genitalium*} | SP:P20796 | 80.3 | 753 |
| MG198 | attachment protein repeat (mgpA) {*Mycoplasma genitalium*} | SP:P20796 | 81.3 | 753 |
| MG266 | attachment protein repeat (mgpA) {*Mycoplasma genitalium*} | SP:P20796 | 82.2 | 753 |
| MG351 | attachment protein repeat (mgpA) {*Mycoplasma genitalium*} | SP:P20796 | 84.3 | 734 |
| *MG398 | cytadherence-accessory protein (hmw1) {*Mycoplasma pneumoniae*} | GP:U11381_1 | 34.1 | 876 |
| MG323 | cytadherence-accessory protein (hmw1) {*Mycoplasma pneumoniae*} | GP:U11381_1 | 39.3 | 1015 |
| *MG327 | cytadherence-accessory protein (hmw3) {*Mycoplasma pneumoniae*} | GP:M82965_1 | 41.1 | 669 |
| Cellular processes | | | | |
| Cell division | | | | |
| *MG469 | cell division protein (ftsH) {*Bacillus subtilis*} | GP:D26185_132 | 49.7 | 627 |
| *MG308 | cell division protein (ftsY) {*Escherichia coli*} | GP:U00039_18 | 38.1 | 323 |
| *MG229 | cell division protein (ftsZ) {*Staphylococcus aureus*} | GP:U06462_1 | 30.9 | 274 |
| Cell killing | | | | |
| *MG150 | hemolysin (tlyC) {*Serpulina hyodysenterlae*} | GP:X73141_2 | 26.3 | 234 |
| MG225 | pre-procytotoxin {*Helicobacter pylori*} | GP:Z26883_1 | 36.1 | 789 |
| Chaperones | | | | |
| *MG404 | groEL protein {*Bacillus stearothermophilus*} | GP:L10132_2 | 51.5 | 524 |
| *MG206 | heat shock protein (dnaJ) MOTIF {*Coxiella bumetii*} | GP:L36455_1 | 33.6 | 349 |
| MG002 | heat shock protein (dnaJ) MOTIF {*Lactococcus lactis*} | SP:P35514 | 40.0 | 80 |
| *MG019 | heat shock protein (dnaJ) {*Lactococcus lactis*} | SP:P35514 | 34.0 | 357 |
| *MG207 | heat shock protein (grpE) {*Bacillus subtilis*} | GP:M84964_2 | 31.7 | 158 |
| *MG405 | heat shock protein 60 (GroEL) like protein (PggroES) {*Porphyromonas ginglvalis*} | GP:D17398_1 | 39.6 | 87 |
| *MG316 | heat shock protein 70 (HSP70) {*Staphylococcus aureus*} | GP:D30690_3 | 57.3 | 580 |
| Detoxification | | | | |
| *MG008 | thiophene and furan oxidizer (tdhF) {*Bacillus subtilis*} | GP:D26185_60 | 31.9 | 456 |
| Protein and peptide secretion | | | | |
| *MG139 | GTP-binding membrane protein (lepA) {*Escherichia coli*} | GP:K00426_1 | 47.5 | 589 |
| *MG182 | haemolysin secretion ATP-binding protein (hlyB) MOTIF {*Proteus vulgaris*} | SP:P11599 | 34.6 | 236 |
| *MG074 | preprotein translocase (secA) {*Bacillus subtilis*} | GP:D10279_2 | 43.7 | 764 |
| *MG174 | preprotein translocase secY subunit (secY) {*Mycoplasma capricolum*} | SP:P10250 | 38.8 | 449 |
| MG215 | prolipoprotein signal peptidase (lsp) {*Staphylococcus aureus*} | GP:M83994_1 | 32.4 | 145 |
| *MG049 | signal recognition particle protein (lfh) {*Bacillus subtilis*} | SP:P37105 | 43.0 | 439 |
| *MG243 | trigger factor (tig) {*Escherichia coli*} | GP:M34066_1 | 24.6 | 391 |
| Transformation | | | | |
| MG326 | competence locus E (comE3) MOTIF {*Bacillus subtilis*} | GP:L15202_4 | 30.5 | 239 |
| Central Intermediary metabolism | | | | |
| Amino sugars | | | | |
| Degradation of polysaccharides | | | | |
| *MG222 | bifunctional endo-1,4-beta-xylanase xyla precursor MOTIF {*Ruminococcus flavefaciens*} | SP:P29126 | 37.6 | 240 |
| Other | | | | |
| *MG369 | acetate kinase {*Bacillus subtilis*} | GP:L17320_2 | 42.7 | 391 |
| *MG038 | glycerol kinase (glpK) {*Escherchia coli*} | GP:L19201_68 | 46.8 | 496 |

TABLE 6-continued

| MG# | Identification | MatchAcc | % ID | Length |
|---|---|---|---|---|
| MG304 | glycerophosphoryl diester phosphodiesterase (glpO) {*Bacillus subtilis*} | SP:P37965 | 30.4 | 235 |
| *MG310 | phosphotransacetylase {*Clostridium acetobutylicum*} | SP:P39646 | 44.7 | 320 |
| Phosphorus compounds | | | | |
| *MG363 | inorganic pyrophosphatase (ppa) {*Thermoplasma acidophilum*} | SP:P37981 | 38.9 | 156 |
| Polyamine biosynthesis | | | | |
| Polysaccharides - (cytoplasmic) | | | | |
| Sulfur metabolism | | | | |
| Energy metabolism | | | | |
| Aerobic | | | | |
| *MG039 | glycerol-3-phosphate dehydrogenase (GUT2) {*Saccharomyces cerevisiae*} | PIR:S48379 | 43.2 | 212 |
| *MG472 | L-lactate dehydrogenase (ldh) {*Mycoplasma hyopneumoniae*} | SP:P33572 | 50.3 | 312 |
| MG283 | NADH oxidase (nox) {*Enterococcus faecalis*} | SP:P37061 | 39.2 | 433 |
| Amino acids and amines | | | | |
| Anaerobic | | | | |
| ATP-proton motive force interconversion | | | | |
| *MG410 | ATP synthase epsilon chain (atpC) {*Mycoplasma gallisepticum*} | SP:P33255 | 36.9 | 129 |
| *MG411 | ATP synthase beta chain (atpD) {*Mycoplasma gallisepticum*} | SP:P33253 | 81.0 | 377 |
| *MG412 | ATP synthase gamma chain (atpG) {*Mycoplasma gallisepticum*} | SP:P33257 | 37.9 | 285 |
| *MG413 | ATP synthase alpha chain (atpA) {*Mycoplasma gallisepticum*} | SP:P33252 | 63.4 | 517 |
| *MG414 | ATP synthase delta chain (atpH) {*Mycoplasma gallisepticum*} | SP:P33254 | 33.9 | 168 |
| *MG415 | ATP synthase B chain (atpF) {*Mycoplasma gallisepticum*} | SP:P33256 | 36.6 | 192 |
| *MG416 | ATP synthase C chain (atpE) {*Mycoplasma gallisepticum*} | SP:P33258 | 50.0 | 77 |
| *MG417 | adenosinetriphosphatase (atpB) {*Mycoplasma gallisepticum*} | GP:X64256_2 | 35.7 | 292 |
| Electron transport | | | | |
| Entner-Doudoroff | | | | |
| Fermentation | | | | |
| Gluconeogenesis | | | | |
| Glycolysis | | | | |
| *MG063 | 1-phosphofructokinase (fruK) {*Escherichia coli*} | SP:P23539 | 26.3 | 266 |
| *MG220 | 6-phosphofructokinase (phosphofructokinase) (phosphohexokinase) {*Spiroplasma citri*} | SP:P20275 | 39.4 | 321 |
| *MG419 | enolase {*Bacillus subtilis*} | GP:L29475_4 | 54.1 | 425 |
| *MG023 | fructose-bisphosphate aldolase (tsr) {*Bacillus subtilis*} | GP:M22039_4 | 46.0 | 282 |
| *MG312 | glyceraldehyde-3-phosphate dehydrogenase (gap) {*Clostridium pasteurianum*} | GP:X72219_1 | 56.1 | 329 |
| *MG112 | phosphoglucose isomerase B (pgiB) {*Bacillus stearothermophilus*} | SP:P13376 | 34.8 | 424 |
| *MG311 | phosphoglycerate kinase {*Thermotoga maritima*} | SP:P36204 | 51.3 | 383 |
| MG442 | phosphoglycerate mutase (pgm) {*Bacillus subtilis*} | GP:L29475_3 | 45.2 | 510 |
| *MG221 | pyruvate kinase (pyk) {*Lactococcus lactis*} | GP:L07920_2 | 35.3 | 467 |
| *MG443 | triosephosphate isomerase (tim) {*Thermotoga maritima*} | GP:L27492_1 | 39.8 | 247 |
| Pentose phosphate pathway | | | | |
| *MG272 | 6-phosphogluconate dehydrogenase (gnd) {*Escherichia coli*} | GP:M64324_1 | 29.9 | 440 |
| *MG066 | transketolase 1 (TK 1) (tktA) {*Escherichia coli*} | SP:P27302 | 32.6 | 647 |
| Pyruvate dehydrogenase | | | | |
| *MG280 | dihydrolipoamide acetyltransferase (pdhC) {*Acholeplasma laidlawii*} | GP:M81753_3 | 45.2 | 524 |
| *MG279 | lipoamide dehydrogenase component (E3) of pyruvate dehydrogenase complex (dihydrolipoamide dehydrog | SP:P11959 | 38.4 | 453 |
| *MG282 | pyruvate dehydrogenase E1-alpha subunit (pdhA) {*Acholeplasma laidlawii*} | GP:M81753_1 | 43.0 | 341 |
| *MG281 | pyruvate dehydrogenase E1-beta subunit (pdhB) {*Acholeplasma laidlawii*} | GP:M81753_2 | 55.0 | 317 |
| Sugars | | | | |
| *MG113 | D-ribulose-5-phosphate 3 epimerase (ctxEc) {*Alcaligenes eutrophus*} | GP:M64173_3 | 33.1 | 175 |
| *MG050 | deoxyribose-phosphate aldolase (deoC) {*Mycoplasma pneumoniae*} | GP:X13544_1 | 83.0 | 223 |
| MG408 | galactosidase acetyltransferase {*Streptococcus mutans*} | GP:M80797_2 | 40.3 | 135 |
| *MG053 | phosphomannomutase (cpsG) {*Mycoplasma pirum*} | GP:L13289_5 | 38.6 | 534 |
| TCA cycle | | | | |
| Fatty acid and phospholipid metabolism | | | | |
| *MG217 | 1-acyl-sn-glycerol-3-phosphate acetyltransferase (plsC) {*Borrelia burgdorferi*} | GP:L32861_1 | 32.1 | 119 |
| *MG448 | CDP-diglyceride synthetase (cdsA) {*Escherichia coli*} | GP:M11330_1 | 38.0 | 120 |
| MG380 | fatty acid/phospholipid synthesis protein (plsX) {*Escherichia coli*} | GP:M96793_1 | 29.0 | 327 |
| MG066 | hydroxymethylglutaryl-CoA reductase (NADPH) {*Nicotiana sylvestris*} | PIR:S24760 | 23.3 | 502 |
| *MG115 | phosphatidylglycerophosphat synthase (pgsA) {*Escherichia coli*} | GP:M12299_2 | 29.3 | 156 |

TABLE 6-continued

| MG# | Identification | MatchAcc | % ID | Length |
|---|---|---|---|---|
| Purines, pyrimidines, nucleosides, and nucleotides | | | | |
| 2'-Deoxyribonucleotide metabolism | | | | |
| *MG237 | ribonucleoside-diphosphate reductase (nrdE) {*Salmonella typhimurium*} | GP:X73226_1 | 54.1 | 703 |
| *MG235 | ribonucleotide reductase 2 (nrdF) {*Salmonella typhimurium*} | SP:P17424 | 50.0 | 313 |
| *MG125 | thioredoxin (trx) {*Bacillus subtilis*} | GP:J03294_1 | 36.1 | 96 |
| *MG103 | thioredoxin reductase (trxB) {*Escherichia coli*} | GP:J03762_1 | 38.6 | 299 |
| *MG233 | thymidylate synthase (thyA) {*Staphylococcus aureus*} | SP:P13954 | 56.6 | 311 |
| Nucleotide and nucleoside interconversions | | | | |
| *MG164 | ribosomal protein S17 {*Mycoplasma capricolum*} | SP:P10131 | 51.2 | 82 |
| *MG093 | ribosomal protein S18 (rpS18) {*Escherichia coli*} | GP:U14003_114 | 45.5 | 64 |
| *MG159 | ribosomal protein S19 {*Escherichia coli*} | GP:X02613_6 | 58.6 | 88 |
| *MG072 | ribosomal protein S2 {*Spirulina platensis*} | SP:P34831 | 34.8 | 247 |
| *MG161 | ribosomal protein S3 (rpS3) {*Mycoplasma capricolum*} | SP:P02353 | 46.7 | 212 |
| *MG322 | ribosomal protein S4 (rpS4) {*Bacillus subtilis*} | GP:M59358_1 | 43.0 | 197 |
| *MG172 | ribosomal protein S5 {*Bacillus stearothermophilus*} | GP:M57621_1 | 56.0 | 157 |
| *MG012 | ribosomal protein S6 modification protein (rimK) MOTIF {*Escherichia coli*} | SP:P17116 | 31.5 | 127 |
| *MG091 | ribosomal protein S6 {*Escherichia coli*} | SP:P02358 | 23.9 | 87 |
| *MG089 | ribosomal protein S7 (rpS7) {*Bacillus stearothermophilus*} | SP:P22744 | 64.9 | 153 |
| *MG169 | ribosomal protein S8 {*Mycoplasma capricolum*} | SP:P04446 | 46.9 | 125 |
| *MG429 | ribosomal protein S9 (rpS9) {*Bacillus stearothermophilus*} | SP:P07842 | 52.0 | 125 |
| Transport and binding proteins | | | | |
| Amino acids, peptides and amines | | | | |
| MG231 | aromatic amino acid transport protein (aroP) {*Escherichia coli*} | GP:D26562_11 | 24.6 | 389 |
| *MG314 | membrane transport protein (glnQ) {*Bacillus stearothermophilus*} | GP:M61017_1 | 32.0 | 219 |
| *MG183 | membrane transport protein (glnQ) {*Bacillus stearothermophilus*} | GP:M61017_1 | 37.4 | 210 |
| *MG081 | oligopeptide transport ATP-binding protein (amiE) {*Streptococcus pneumoniae*} | SP:P18765 | 47.9 | 336 |
| *MG082 | oligopeptide transport ATP-binding protein (amiF) {*Streptococcus pneumoniae*} | SP:P18766 | 46.6 | 250 |
| *MG060 | oligopeptide transport system permease protein (dciAC) {*Bacillus subtilis*} | SP:P26904 | 33.5 | 269 |
| *MG079 | oligopeptide transport system permease protein (oppB) {*Bacillus subtilis*} | SP:P24138 | 28.1 | 306 |
| *MG042 | spermidine/putrescine transport ATP-binding protein (potA) {*Escherichia coli*} | GP:M64519_1 | 41.9 | 262 |
| *MG043 | spermidine/putrescine transport system permease protein (potB) {*Escherichia coli*} | GP:M64519_2 | 26.5 | 221 |
| *MG044 | spermidine/putrescine transport system permease protein (potC) {*Escherichia coli*} | GP:M64519_3 | 29.5 | 252 |
| Anions | | | | |
| *MG422 | peripheral membrane protein B (pstB) {*Escherichia coli*} | GP:L10328_89 | 50.8 | 244 |
| MG421 | peripheral membrane protein U {*Escherichia coli*} | GP:L10328_88 | 27.0 | 169 |
| *MG423 | periplasmic phosphate permease homolog (AG88) {*Mycobacterium tuberculosis*} | GP:X75297_1 | 30.8 | 254 |
| Carbohydrates, organic alcohols, and acids | | | | |
| *MG192 | ATP-binding protein (msmK) {*Streptococcus mutans*} | GP:M77351_7 | 40.5 | 357 |
| *MG062 | fructose-permease IIBC component (fruA) {*Escherichia coli*} | SP:P20966 | 42.7 | 416 |
| *MG033 | glycerol uptake facilitator (gfpF) {*Bacillus subtilis*} | GP:M99611_2 | 35.9 | 189 |
| MG061 | hexosephosphate transport protein (uhpT) {*Salmonella typhimurium*} | GP:M89480_4 | 30.9 | 158 |
| *MG193 | membrane protein (msmF) {*Streptococcus mutans*} | GP:M77351_4 | 22.5 | 263 |
| MG194 | membrane protein (msmG) | GP:M77351_5 | 27.1 | 272 |
| *MG120 | methylgalactoside permease ATP-binding protein (mgIA) {*Escherichia coli*} | GP:M59444_2 | 33.2 | 487 |
| *MG441 | PEP-dependent HPr protein kinase phosphoryltransferase (ptsI) {*Staphylococcus carnosus*} | GP:M69050_2 | 46.5 | 570 |
| MG041 | phosphohistidinoprotein-hexose phosphotransferase (ptsH) {*Mycoplasma capricolum*} | GP:L22432_2 | 48.9 | 86 |
| *MG071 | phosphotransferase enzyme II, ABC component (ptsG) {*Bacillus subtilis*} | SP:P20166 | 43.2 | 620 |
| MG130 | PTS glucose-specific permease {*Bacillus stearothermophilus*} | GP:U12340_1 | 25.5 | 108 |
| *MG121 | ribose transport system permease protein RBSC {*Bacillus subtilis*} | SP:P36948 | 27.5 | 199 |
| Cations | | | | |
| MG073 | cation-transporting ATPase (pacL) {*Synechococcus sp.*} | SP:P37278 | 34.4 | 887 |
| Nucleosides, purines and pyrimidines | | | | |
| Other | | | | |
| *MG301 | ATP-binding protein P29 {*Mycoplasma hyorhinis*} | SP:P15361 | 32.3 | 227 |
| *MG402 | lactococcin transport ATP-binding protein (lcnDR3) {*Lactococcus lactis*} | SP:P37608 | 22.3 | 654 |

TABLE 6-continued

| MG# | Identification | MatchAcc | % ID | Length |
|---|---|---|---|---|
| MG332 | Na+ ATPase subunit J (ntpJ) {*Enterococcus hirae*} | GP:D17462_11 | 31.1 | 436 |
| MG300 | protein P37 precursor {*Mycoplasma hyorhinis*} | SP:P15363 | 35.8 | 331 |
| *MG014 | transport ATP-binding protein (msbA) {*Escherichia coli*} | SP:P27299 | 28.1 | 518 |
| *MG015 | transport ATP-binding protein (msbA) {*Escherichia coli*} | SP:P27299 | 32.2 | 482 |
| *MG418 | transport system permease protein P69 MOTIF {*Mycoplasma hyorhinis*} | SP:P15362 | 40.0 | 252 |
| MG302 | transport system permease protein P69 {*Mycoplasma hyorhinis*} | SP:P15362 | 27.9 | 524 |
| Other categories | | | | |
| Adaptations and atypical conditions | | | | |
| MG467 | osmotically inducible protein (osmC) {*Escherichia coli*} | SP:P23929 | 28.4 | 88 |
| MG640 | phosphate limitation protein (sphX) {Synechococcus sp.} | GP:D26161_1 | 30.9 | 271 |
| MG482 | SpoOJ regulator MOTIF {*Bacillus subtilis*} | GP:D26185_55 | 27.5 | 245 |
| *MG285 | spore germination apparatus protein (gerBB) MOTIF {*Bacillus subtilis*} | GP:L16960_2 | 31.2 | 128 |
| MG395 | sporulation protein (outB) MOTIF {*Bacillus subtilis*} | GP:M15811_1 | 36.4 | 235 |
| Colicin-related functions | | | | |
| Drug and analog sensitivity | | | | |
| *MG475 | high level kasgamycin resistance (ksgA) {*Bacillus subtilis*} | GP:D26185_105 | 35.6 | 224 |
| Phage-related functions and prophages | | | | |
| Radiation sensitivity | | | | |
| Transposon-related functions | | | | |
| Other | | | | |
| *MG309 | 115 kDa protein (p115) {*Mycoplasma hyorhinis*} | GP:M34956_1 | 33.4 | 975 |
| *MG065 | heterocyst maturation protein (devA) {Anabaena sp.} | GP:X75422_1 | 35.3 | 221 |
| *MG479 | heterocyst maturation protein (devA) {Anabaena sp.} | GP:X75422_1 | 39.9 | 198 |
| MG100 | hydrolase (aux2) {*Agrobacterium rhizogenes*} | GP:M61151_1 | 32.1 | 456 |
| *MG223 | macrogolgin {*Homo sapiens*} | PIR:S37536 | 25.3 | 3055 |
| *MG337 | magnesium-chelatase 30 kDa subunit (bchO) {*Rhodobacter capsulatus*} | SP:P26174 | 26.7 | 245 |
| *MG315 | membrane associated ATPase (cbiO) {*Propionibacterium freudenreichii*} | GP:U13043_1 | 30.0 | 227 |
| MG376 | mobilization protein (mob13) MOTIF {*Leuconostoc oenos*} | GP:M95954_1 | 30.9 | 161 |
| MG372 | mucB protein (mucB) {*Salmonella typhimurium*} | SP:P14303 | 22.1 | 331 |
| *MG346 | nitrogen fixation protein (nifS) {*Mycobacterium leprae*} | GP:U00013_6 | 26.2 | 368 |
| MG296 | nodulation protein F (host-specificity of nodulation protein A) {*Rhizobium leguminosarum*} | SP:P04686 | 34.9 | 86 |
| MG299 | protein L {*Peptostreptococcus magnus*} | GP:L04466_1 | 31.1 | 863 |
| *MG338 | protein V (fcrV) {Streptococcus sp.} | GP:X62467_1 | 28.3 | 476 |
| *MG149 | protein X {*Pseudomonas fluorescens*} | GP:M35367_1 | 29.1 | 280 |
| MG132 | protein X {*Spiroplasma citri*} | GP:M31161_3 | 21.6 | 86 |
| *MG288 | sensory rhodopsin II transducer (htrII) MOTIF {*Natronobacterium pharaonis*} | GP:Z35088_1 | 15.7 | 208 |
| *MG059 | small protein (smpB) {*Escherichia coli*} | GP:D12501_1 | 32.6 | 128 |
| Hypothetical | | | | |
| MG142 | hypothetical 130K protein (P1 operon) MOTIF {*Mycoplasma pneumoniae*} | PIR:JS0069 | 55.4 | 512 |
| MG199 | hypothetical 130K protein (P1 operon) {*Mycoplasma pneumoniae*} | PIR:JS0069 | 45.2 | 570 |
| MG195 | hypothetical 28K protein (P1 operon) {*Mycoplasma pneumoniae*} | PIR:JS0068 | 61.7 | 239 |
| *MG342 | hypothetical protein (GB:D10165_3) {*Escherichia coli*} | GP:D10165_3 | 26.9 | 233 |
| *MG227 | hypothetical protein (GB:D10483_63) {*Escherichia coli*} | GP:D10483_63 | 35.2 | 304 |
| *MG476 | hypothetical protein (GB:D14982_3) {*Mycoplasma capricolum*} | GP:D14982_3 | 32.0 | 377 |
| MG455 | hypothetical protein (GB:D16311_1) {*Bacillus subtilis*} | GP:D16311_1 | 26.2 | 267 |
| MG383 | hypothetical protein (GB:D26185_10) {*Bacillus subtilis*} | GP:D26185_10 | 25.8 | 221 |
| *MG009 | hypothetical protein (GB:D26185_102) {*Bacillus subtilis*} | GP:D26185_102 | 35.4 | 249 |
| MG057 | hypothetical protein (GB:D26185_104) {*Bacillus subtilis*} | GP:D26185_104 | 28.9 | 175 |
| *MG024 | hypothetical protein (GB:D26185_50) {*Bacillus subtilis*} | GP:D26185_50 | 51.1 | 363 |
| *MG006 | hypothetical protein (GB:D26185_92) {*Bacillus subtilis*} | GP:D26185_92 | 41.5 | 176 |
| *MG056 | hypothetical protein (GB:D26185_99) {*Bacillus subtilis*} | GP:D26185_99 | 29.3 | 275 |
| MG333 | hypothetical protein (GB:D37799_6) {*Bacillus subtilis*} | GP:D37799_6 | 27.6 | 211 |
| MG459 | hypothetical protein (GB:L08897_1) {*Mycoplasma gallisepticum*} | GP:L08897_1 | 34.1 | 138 |
| MG218 | hypothetical protein (GB:L09228_16) {*Bacillus subtilis*} | GP:L09228_16 | 27.1 | 238 |
| MG219 | hypothetical protein (GB:L09228_17) {*Bacillus subtilis*} | GP:L09228_17 | 34.9 | 174 |
| *MG273 | hypothetical protein (GB:L10328_61) {*Escherichia coli*} | GP:L10328_61 | 27.2 | 267 |
| *MG271 | hypothetical protein (GB:L10328_61) {*Escherichia coli*} | GP:L10328_61 | 27.8 | 250 |
| MG126 | hypothetical protein (GB:L10328_61) {*Escherichia coli*} | GP:L10328_61 | 31.9 | 252 |
| MG140 | hypothetical protein (GB:L18927_2) {*Buchnera aphidicola*} | GP:L18927_2 | 28.6 | 68 |
| MG152 | hypothetical protein (GB:L18965_6) {Thermophilic bacterial sp.} | GP:L18965_6 | 25.3 | 170 |
| MG305 | hypothetical protein (GB:L19201_18) {*Escherichia coli*} | GP:L19201_18 | 23.1 | 328 |
| MG029 | hypothetical protein (GB:L19300_1) {*Staphylococcus aureus*} | GP:L19300_1 | 27.0 | 109 |
| MG425 | hypothetical protein (GB:L22432_4) {*Mycoplasma capricolum*} | GP:L22432_4 | 25.0 | 94 |
| MG250 | hypothetical protein (GB:M12965_1) {*Escherichia coli*} | GP:M12965_1 | 33.8 | 64 |
| *MG135 | hypothetical protein (GB:M38777_3) {*Escherichia coli*} | GP:M38777_3 | 28.6 | 98 |
| *MG358 | hypothetical protein (GB:M65289_3) {*Bacillus stearothermophilus*} | GP:M65289_3 | 38.0 | 155 |

TABLE 6-continued

| MG# | Identification | MatchAcc | % ID | Length |
|---|---|---|---|---|
| MG211 | hypothetical protein (GB:M84964_1) {Bacillus subtilis} | GP:M84964_1 | 30.7 | 341 |
| MG124 | hypothetical protein (GB:M91593_1) {Mycoplasma mycoides} | GP:M91593_1 | 24.0 | 249 |
| MG245 | hypothetical protein (GB:M91593_1) {Mycoplasma mycoides} | GP:M91593_1 | 27.8 | 130 |
| MG131 | hypothetical protein (GB:M91593_1) {Mycoplasma mycoides} | GP:M91593_1 | 30.7 | 246 |
| *MG400 | hypothetical protein (GB:U00016_19) {Mycobacterium leprae} | GP:U00016_19 | 30.9 | 106 |
| *MG129 | hypothetical protein (GB:U00021_19) {Mycobacterium leprae} | GP:U00021_19 | 27.7 | 152 |
| *MG454 | hypothetical protein (GB:U00021_5) {Mycobacterium leprae} | GP:U00021_5 | 26.9 | 150 |
| *MG339 | hypothetical protein (GB:U00021_5) {Mycobacterium leprae} | GP:U00021_5 | 32.9 | 430 |
| MG364 | hypothetical protein (GB:U11883_2) {Bacillus subtilis} | GP:U11883_2 | 33.3 | 167 |
| MG230 | hypothetical protein (GB:U14003_71) {Escherichia coli} | GP:U14003_71 | 22.0 | 481 |
| *MG111 | hypothetical protein (GB:U14003_76) {Escherichia coli} | GP:U14003_76 | 28.6 | 230 |
| MG473 | hypothetical protein (GB:X73124_94) {Bacillus subtilis} | GP:X73124_94 | 40.0 | 68 |
| MG265 | hypothetical protein (GB:Z32651_1) {Mycoplasma pneumoniae} | GP:Z32651_1 | 57.1 | 41 |
| *MG257 | hypothetical protein (GB:Z33078_2) {Mycoplasma capricolum} | GP:Z33078_2 | 37.7 | 210 |
| *MG147 | hypothetical protein (SP:P09170) {Escherichia coli} | SP:P09170 | 24.1 | 109 |
| *MG128 | hypothetical protein (SP:P19434) {Streptomyces viridochromogenes} | SP:P19434 | 26.0 | 106 |
| *MG226 | hypothetical protein (SP:P22188) {Escherichia coli} | SP:P22188 | 28.9 | 148 |
| *MG382 | hypothetical protein (SP:P23851) {Escherichia coli} | SP:P23851 | 27.0 | 253 |
| *MG214 | hypothetical protein (SP:P23851) {Escherichia coli} | SP:P23851 | 30.5 | 296 |
| *MG306 | hypothetical protein (SP:P25745) {Escherichia coli} | SP:P25745 | 34.7 | 123 |
| MG444 | hypothetical protein (SP:P27712) {Spiroplasma citri} | SP:P27712 | 28.4 | 231 |
| *MG252 | hypothetical protein (SP:P31056) {Escherichia coli} | SP:P31056 | 33.0 | 180 |
| MG116 | hypothetical protein (SP:P31131) {Escherichia coli} | SP:P31131 | 32.6 | 45 |
| *MG359 | hypothetical protein (SP:P32049) {Escherichia coli} | SP:P32049 | 28.5 | 128 |
| MG480 | hypothetical protein (SP:P32049) {Escherichia coli} | SP:P32049 | 28.5 | 128 |
| *MG133 | hypothetical protein (SP:P32083) {Mycoplasma hyorhinis} | SP:P32083 | 30.1 | 102 |
| *MG122 | hypothetical protein (SP:P32720) {Escherichia coli} | SP:P32720 | 30.9 | 132 |
| MG138 | hypothetical protein (SP:P37747) {Escherichia coli} | SP:P37747 | 34.1 | 363 |
| *MG345 | hypothetical protein (SP:P38424) {Bacillus subtilis} | SP:P38424 | 33.9 | 167 |
| *MG136 | hypothetical protein 4 {Trypanosoma brucei} | PIR:E22845 | 30.8 | 302 |
| *MG286 | stringent response-like protein (rel) {Streptococcus equisimilis} | GP:X72832_5 | 29.1 | 713 |
| MG336 | U3 protein {Bacillus subtilis} | GP:Z18629_1 | 27.1 | 272 |
| MG278 | yjjF protein {Escherichia coli} | GP :U14003_297 | 38.3 | 302 |

TABLE 7

Summary of gene content in H. influenzae and M. genitalium sorted by functional category

| Biological role | H. influenzae | M. genitalium |
|---|---|---|
| Amino acid biosynthesis | 68 (6.8%) | 1 (0.3%) |
| Biosynthesis of cofactors | 54 (5.4%) | 3 (0.8%) |
| Cell envelope | 84 (8.3%) | 21 (5.8%) |
| Cellular processes | 53 (5.3%) | 21 (5.8%) |
| Cell division | 16 | 3 |
| Cell killing | 5 | 2 |
| Chaperones | 6 | 7 |
| Detoxification | 3 | 1 |
| Protein secretion | 15 | 7 |
| Transformation | 8 | 1 |
| Central intermediary metabolism | 30 (3%) | 6 (1.7%) |
| Energy metabolism | 112 (10.4%) | 31 (8.5%) |
| Aerobic | 4 | 3 |
| Amino acids and amines | 4 | 0 |
| Anerobic | 24 | 0 |
| ATP-proton force interconversion | 9 | 8 |
| Electron transport | 9 | 0 |
| Entner-Doudoroff | 9 | 0 |
| Fermentation | 8 | 0 |
| Gluconeogenesis | 2 | 0 |
| Glycolysis | 10 | 10 |
| Pentose phosphate pathway | 3 | 2 |
| Pyruvate dehydrogenase | 4 | 4 |
| Sugars | 15 | 4 |
| TCA cycle | 11 | 0 |
| Fatty acid and phospholipid metabolism | 25 (2.5%) | 5 (1.4%) |
| Purines, pyrimidines, nucleosides and nucleotides | 53 (5.3%) | 20 (5.4%) |
| 2 Deoxyribonucleotide metabolism | 8 | 5 |
| Nucleotide and nucleoside interconversions | 3 | 1 |
| Purine ribonucleotide biosynthesis | 18 | 3 |
| Pyrimidine ribonucleotide biosynthesis | 5 | 0 |
| Salvage of nucleosides and nucleotides | 13 | 9 |
| Sugar-nucleotide biosynthesis and conversions | 6 | 2 |
| Regulatory functions | 64 (6.3%) | 5 (1.4%) |
| Replication | 87 (8.6%) | 32 (8.8%) |
| Degradation of DNA | 8 | 2 |
| DNA replication, restriction, modification, recombination and repair | 76 | 30 |
| Transcription | 27 (2.7%) | 12 (3.3%) |
| Degradation of RNA | 10 | 2 |
| RNA synthesis, modification and DNA transcription | 17 | 10 |
| Translation | 141 (14%) | 90 (24.7%) |
| Transport and binding proteins | 123 (12.2%) | 34 (9.3%) |
| Amino acids and peptides | 38 | 10 |
| Anions | 8 | 3 |
| Carbohydrates | 30 | 12 |
| Cations | 24 | 1 |
| Other transporters | 22 | 8 |
| Other Categories | 93 (9.2%) | 23 (6.3%) |
| Unassigned role | 736 (43%) | 178 (37%) |
| No database match | 389 | 117 |
| Match hypothetical proteins | 347 | 61 |

What is claimed is:

1. An isolated polynucleotide fragment comprising a nucleic acid sequence selected from the group consisting of:
   (a) MG318, represented by nucleotides 398280–397441 of SEQ ID NO:1;
   (b) MG217, represented by nucleotides 258040–259155 of SEQ ID NO:1;

(c) MG368, represented by nucleotides 466410–465427 of SEQ ID NO:1;

(d) MG313, represented by nucleotides 392023–391397 of SEQ ID NO:1;

(e) MG315, represented by nucleotides 394550–393660 of SEQ ID NO:1;

(f) MG317, represented by nucleotides 397423–395627 of SEQ ID NO:1;

(g) MG344, represented by nucleotides 441180–440362 of SEQ ID NO:1;

(h) MG327, represented by nucleotides 410676–409870 of SEQ ID NO:1; and (i) MG109, represented by nucleotides 136179–137267 of SEQ ID NO:1.

2. An isolated polynucleotide complementary to the polynucleotide of claim 1.

3. The isolated polynucleotide of claim 1, wherein said polynucleotide comprises a heterologous nucleic acid sequence.

4. The isolated polynucleotide of claim 3, wherein said heterologous nucleic acid sequence encodes a heterologous polypeptide.

5. A method for making a recombinant vector comprising inserting the isolated polynucleotide of claim 1, into a vector.

6. The isolated polynucleotide of claim 1, wherein said polynucleotide is DNA.

7. A recombinant vector comprising the isolated polynucleotide of claim 1.

8. The recombinant vector of claim 7, wherein said polynucleotide is operably associated with a heterologous regulatory sequence that controls gene expression.

9. A recombinant host cell comprising the isolated polynucleotide of claim 1.

10. The recombinant host cell of claim 9, wherein said polynucleotide is operably associated with a heterologous regulatory sequence that controls gene expression.

11. An isolated polynucleotide fragment comprising a nucleic acid sequence which hybridizes under hybridization conditions, comprising hybridization in 5×SSC and 50% formamide at 50° C. and washing in a wash buffer consisting of 0.5×SSC at 65° C., to the complementary strand of an ORF selected from the group consisting of:

(a) MG217, represented by nucleotides 258040–259155 of SEQ ID NO:1;

(b) MG313, represented by nucleotides 392023–391397 of SEQ ID NO:1; and (c) MG315, represented by nucleotides 394550–393660 of SEQ ID NO:1.

12. An isolated polynucleotide complementary to the polynucleotide of claim 11.

13. An isolated polynucleotide comprising at least 50 contiguous nucleotides of an ORF selected from the group consisting of:

(a) MG217, represented by nucleotides 258040–259155 of SEQ ID NO:1;

(b) MG313, represented by nucleotides 392023–391397 of SEQ ID NO:1; and (c) MG315, represented by nucleotides 394550–393660 of SEQ ID NO:1.

14. An isolated polynucleotide complementary to the polynucleotide of claim 13.

15. An isolated polynucleotide comprising at least 100 contiguous nucleotides of an ORF selected from the group consisting of:

(a) MG217, represented by nucleotides 258040–259155 of SEQ ID NO:1;

(b) MG313, represented by nucleotides 392023–391397 of SEQ ID NO:1; and (c) MG315, represented by nucleotides 394550–393660 of SEQ ID NO:1.

16. An isolated polynucleotide complementary to the polynucleotide of claim 15.

17. The isolated polynucleotide fragment of claim 1 wherein the selected ORF is (a).

18. The isolated polynucleotide fragment of claim 1 wherein the selected ORF is (b).

19. The isolated polynucleotide fragment of claim 1 wherein the selected ORF is (c).

20. The isolated polynucleotide fragment of claim 1 wherein the selected ORF is (d).

21. The isolated polynucleotide fragment of claim 1 wherein the selected ORF is (e).

22. The isolated polynucleotide fragment of claim 1 wherein the selected ORF is (f).

23. The isolated polynucleotide fragment of claim 1 wherein the selected ORF is (g).

24. The isolated polynucleotide fragment of claim 1 wherein the selected ORF is (h).

25. The isolated polynucleotide fragment of claim 1 wherein the selected ORF is (i).

26. The isolated polynucleotide fragment of claim 11 wherein the selected ORF is (a).

27. The isolated polynucleotide fragment of claim 11 wherein the selected ORF is (b).

28. The isolated polynucleotide fragment of claim 11 wherein the selected ORF is (c).

29. The isolated polynucleotide of claim 13 wherein the selected ORF is (a).

30. The isolated polynucleotide of claim 13 wherein the selected ORF is (b).

31. The isolated polynucleotide of claim 13 wherein the selected ORF is (c).

32. The isolated polynucleotide of claim 15 wherein the selected ORF is (a).

33. The isolated polynucleotide of claim 15 wherein the selected ORF is (b).

34. The isolated polynucleotide of claim 15 wherein the selected ORF is (c).

35. An isolated polynucleotide fragment comprising a nucleic acid sequence encoding an amino acid sequence encoded by the ORF MG344, represented by nucleotides 441180–440362 of SEQ ID NO:1.

36. The isolated polynucleotide of claim 35, wherein said polynucleotide comprises a heterologous nucleic acid sequence.

37. The isolated polynucleotide of claim 36, wherein said heterologous nucleic acid sequence encodes a heterologous polypeptide.

38. The isolated polynucleotide of claim 35, wherein said polynucleotide is DNA.

39. A method for making a recombinant vector comprising inserting the isolated polynucleotide of claim 35 into a vector.

40. A recombinant vector comprising the isolated polynucleotide of claim 35.

41. The recombinant vector of claim 40, wherein said polynucleotide is operably associated with a heterologous regulatory sequence that controls gene expression.

42. A recombinant host cell comprising the isolated polynucleotide of claim 35.

43. The recombinant host cell of claim 42, wherein said polynucleotide is operably associated with a heterologous regulatory sequence that controls gene expression.

44. A method for producing a polypeptide, comprising:
   (a) culturing a host cell under conditions suitable to produce a polypeptide encoded by the polynucleotide of claim 35, and
   (b) recovering the polypeptide from the cell culture.

* * * * *